US012729205B2

(12) United States Patent
Mittapalli et al.

(10) Patent No.: US 12,729,205 B2
(45) Date of Patent: Sep. 8, 2026

(54) 4-ALKOXYPYRROLO[2,1-F][1,2,4]TRIAZINES AND PREPARATION AND USES THEREOF

(71) Applicant: TenaRx, Inc., San Diego, CA (US)

(72) Inventors: Gopi Kumar Mittapalli, San Diego, CA (US); Chi Ching Mak, San Diego, CA (US); Lewis Daniel Turner, San Diego, CA (US); Brian Joseph Hofilena, San Diego, CA (US); Ramkrishna Reddy Vakiti, San Diego, CA (US); Brian Walter Eastman, San Diego, CA (US); David Mark Wallace, San Diego, CA (US)

(73) Assignee: TenaRx, Inc., San Diego, CA (US)

( * ) Notice: Subject to any disclaimer, the term of this patent is extended or adjusted under 35 U.S.C. 154(b) by 390 days.

(21) Appl. No.: 18/340,543

(22) Filed: Jun. 23, 2023

(65) Prior Publication Data

US 2024/0002391 A1 Jan. 4, 2024

Related U.S. Application Data

(60) Provisional application No. 63/458,808, filed on Apr. 12, 2023, provisional application No. 63/427,322, filed on Nov. 22, 2022, provisional application No. 63/355,076, filed on Jun. 23, 2022.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ....... C07D 487/04; C07D 519/00; A61P 3/00; A61P 25/00; A61P 35/00; A61P 3/10; A61K 31/53
See application file for complete search history.

(56) References Cited

U.S. PATENT DOCUMENTS

| | | | |
|---|---|---|---|
| 4,164,559 | A | 8/1979 | Miyata et al. |
| 4,474,752 | A | 10/1984 | Haslam et al. |
| 6,120,484 | A | 9/2000 | Silverstein |
| 6,377,849 | B1 | 4/2002 | Lenarz et al. |
| 6,440,102 | B1 | 8/2002 | Arenberg et al. |
| 6,648,873 | B2 | 11/2003 | Arenberg et al. |
| 6,911,211 | B2 | 6/2005 | Eini et al. |
| 7,709,645 | B2 | 5/2010 | Arnold et al. |
| 9,428,509 | B2 | 8/2016 | Calabrese et al. |
| 10,160,755 | B2 | 12/2018 | Lin et al. |
| 12,134,625 | B2 | 11/2024 | Mittapalli et al. |
| 2006/0264897 | A1 | 11/2006 | Lobl et al. |
| 2016/0008305 | A1 | 1/2016 | Rublinstein et al. |
| 2016/0008365 | A1 | 1/2016 | Zhu et al. |
| 2018/0179199 | A1 | 6/2018 | Dreas |
| 2018/0273538 | A1 | 9/2018 | Fiumana et al. |
| 2020/0039989 | A1 | 2/2020 | Hulme et al. |
| 2022/0062240 | A1 | 3/2022 | Tam et al. |
| 2023/0000842 | A1 | 1/2023 | Deshmukh et al. |
| 2023/0167133 | A1 | 6/2023 | Mittapalli et al. |
| 2023/0192686 | A1 | 6/2023 | Mittapalli et al. |
| 2023/0312605 | A1 | 10/2023 | Mittapalli et al. |
| 2025/0129104 | A1 | 4/2025 | Mittapalli et al. |
| 2025/0206746 | A1 | 6/2025 | Mittapalli et al. |

FOREIGN PATENT DOCUMENTS

| | | | |
|---|---|---|---|
| CN | 202106538094 | * | 6/2021 |
| WO | WO 1987/005297 | | 9/1987 |
| WO | WO 2005/095400 | | 10/2005 |
| WO | WO 2010/003133 | | 1/2010 |
| WO | WO 2011/018894 | | 2/2011 |
| WO | WO 2014/093383 | | 6/2014 |
| WO | WO 2014/100620 | | 6/2014 |
| WO | WO 2016/164641 | A1 | 10/2016 |
| WO | WO 2017/040993 | | 3/2017 |
| WO | WO 2019/074962 | | 4/2019 |
| WO | WO 2019/169306 | | 9/2019 |
| WO | WO 2019/238067 | A1 | 12/2019 |
| WO | WO 2020/006115 | | 1/2020 |
| WO | WO 2020/069418 | | 4/2020 |
| WO | WO 2020/081689 | | 4/2020 |
| WO | WO 2020/150552 | | 7/2020 |
| WO | WO 2021/257863 | | 12/2021 |
| WO | WO 2022/020342 | | 1/2022 |
| WO | WO 2022/053838 | | 3/2022 |

(Continued)

OTHER PUBLICATIONS

Yongling Xu, Discovery of highly potent small molecule pd-1/pd-l1 inhibitors with a novel scaffold for cancer immunotherapy, 2024, 67, 4083-4099 (Year: 2024).*

Galeta et al., Regio- and diastereoselective 1,3-dipolar cycloadditions of 1,2,4-triazin-1-ium ylides: a straightforward synthetic route to polysubstituted pyrrolo[2,1-f][1,2,4]triazines, ACS Omega 2022, 7, 21233-21238 (Year: 2022).*

Abbassi et al., "DYRK1A in neurodegeneration and cancer: Molecular basis and clinical implications," Pharmacology & Therapeutics, Jul. 1, 2015, 151:87-98.

Ackeifi et al., "GLP-1 receptor agonists synergize with DYRK1A inhibitors to potentiate functional human β cell regeneration," Science Translational Medicine, Feb. 12, 2020, 12(530):13 pages.

Ackeifi et al., "Pharmacologic and genetic approaches define human pancreatic β cell mitogenic targets of DYRK1A inhibitors," JCI Insight, Jan. 16, 2020, 5(1):e132594, 17 pages.

Arbones et al., "DYRK1A and cognition: A lifelong relationship," Pharmacology & Therapeutics, Feb. 1, 2019, 194:199-221, 78 pages.

(Continued)

*Primary Examiner* — James H Alstrum-Acevedo
*Assistant Examiner* — Allen Chao
(74) *Attorney, Agent, or Firm* — Fish & Richardson P.C.

(57) ABSTRACT

4-Alkoxypyrrolo[2,1-f][1,2,4]triazine compounds for treating various diseases and pathologies are disclosed. More particularly, the present disclosure concerns the use of 4-alkoxypyrrolo[2,1-f][1,2,4]triazine compounds or analogs thereof, in the treatment of disorders characterized by overexpression of DYRK1A (e.g., cancer, Down syndrome, Alzheimer's disease, diabetes, viral infections, and osteoarthritis).

24 Claims, No Drawings

(56) References Cited

FOREIGN PATENT DOCUMENTS

| | | | |
|---|---|---|---|
| WO | WO 2023/064361 | 4/2023 | |
| WO | WO 2023/064366 A1 | 4/2023 | |
| WO | WO2023196975 A1 * | 10/2023 | ............. A61P 29/00 |
| WO | WO 2023/250156 A1 | 12/2023 | |

OTHER PUBLICATIONS

Bai et al., "The USP22 promotes the growth of cancer cells through the DYRKIA in pancreatic ductal adenocarcinoma," Gene, Oct. 20, 2020, 758:144960, 8 pages.
Becker et al., "Activation, regulation, and inhibition of DYRKIA," The FEBS Journal, Jan. 2011, 278(2):246-256.
Bhansali et al., "DYRKIA regulates B cell acute lymphoblastic leukemia through phosphorylation of FOXO1 and STAT3," The Journal of Clinical Investigation, Jan. 4, 2021, 131(1):e135937, 19 pages.
Boni et al., "The DYRK family of kinases in cancer: molecular functions and therapeutic opportunities," Cancers, Jul. 29, 2020, 12(8):2106, 26 pages.
Booiman et al., "DYRKLA controls HIV-1 replication at a transcriptional level in an NFAT dependent manner," PloS One, Dec. 7, 2015, 10(12):e0144229, 16 pages.
Chou et al., "Quantitative analysis of dose-effect relationships: the combined effects of multiple drugs or enzyme inhibitors," Advances in Enzyme Regulation, Jan. 1, 1984, 22:27-55.
Dirice et al., "Inhibition of DYRK1A stimulates human β-cell proliferation," Diabetes, Jun. 1, 2016, 65(6):1660-1671.
Feki et al., "DYRKIA protein, a promising therapeutic target to improve cognitive deficits in Down syndrome," Brain Sciences, Oct. 16, 2018, 8(10):187, 13 pages.
Fernandez-Martinez et al., "DYRKIA: the double-edged kinase as a protagonist in cell growth and tumorigenesis," Molecular & Cellular Oncology, Jan. 2, 2015, 2(1):e970048, 12 pages.
Ferrer et al., "Constitutive Dyrk1A is abnormally expressed in Alzheimer disease, Down syndrome, Pick disease, and related transgenic models," Neurobiology of Disease, Nov. 1, 2005, 20(2):392-400.
GenBank Accession No. NM_001396, "*Homo sapiens* dual specificity tyrosine phosphorylation regulated kinase 1A (DYRK1A), transcript variant 1, mRNA," Sep. 20, 2020, 10 pages.
GenBank Accession No. NM_005910, "*Homo sapiens* microtubule associated protein tau (MAPT), transcript variant 2, mRNA," Sep. 26, 2021, 6 pages.
Guard et al., "The nuclear interactome of DYRKIA reveals a functional role in DNA damage repair," Scientific Reports, Apr. 25, 2019, 9(1):6539, 12 pages.
Gurbatri et al., "Engineered Probiotics for Local Tumor Delivery of Checkpoint Blockade Nanobodies," Science Translational Medicine, Feb. 12, 2020, 12(530):eaax0876.
Hadigal et al., "Heparanase-regulated syndecan-1 shedding facilitates herpes simplex virus 1 egress," Journal of Virology, Feb. 28, 2020, 94(6):e01672-19, 12 pages.
Iness et al., "Oncogenic B-Myb is associated with deregulation of the DREAM-mediated cell cycle gene expression program in high grade serous ovarian carcinoma clinical tumor samples," Frontiers in Oncology, Mar. 4, 2021, 11(637193): 14 pages.
International Search Report and Written Opinion in International Appln. No. PCT/US2022/046395, mailed on Mar. 27, 2023, 22 pages.
International Search Report and Written Opinion in International Appln. No. PCT/US2022/046409, mailed on Mar. 30, 2023, 20 pages.
International Search Report and Written Opinion in International Appln. No. PCT/US2022/046416, mailed on Jan. 24, 2023, 14 pages.
International Search Report and Written Opinion in International Appln. No. PCT/US2023/026100, mailed on Sep. 13, 2023, 13 pages.
Jin et al., "Truncation and activation of dual specificity tyrosine phosphorylation-regulated kinase 1A by calpain I: A molecular mechanism linked to tau pathology in Alzheimer disease," Journal of Biological Chemistry, Jun. 12, 2015, 290(24):15219-15237.
Kovacs, "Tauopathies," Handbook of Clinical Neurology, Jan. 1, 2018, 145: 355-368.
Kumar et al., "DYRK1A inhibitors as potential therapeutics for β-cell regeneration for diabetes," Journal of Medicinal Chemistry, Mar. 8, 2021, 64(6): 2901-2922.
Laham et al., "DYRK1A: A down syndrome-related dual protein kinase with a versatile role in tumorigenesis," Cellular and Molecular Life Sciences, Jan. 2021, 78:603-619, 44 pages.
Lee et al., "An ID2-dependent mechanism for VHL inactivation in cancer," Nature, Jan. 14, 2016, 529(7585): 33 pages.
Li et al., "TROAP switches DYRK1 activity to drive hepatocellular carcinoma progression," Cell Death & Disease, Jan. 26, 2021, 12(125): 15 pages.
Lindberg et al., "Dual-specificity, tyrosine phosphorylation-regulated kinases (DYRKs) and cdc2-like kinases (CLKs) in human disease, an overview," International Journal of Molecular Sciences, Jun. 3, 2021, 22(11):6047.
Luna et al., "DYRK1A modulates c-MET in pancreatic ductal adenocarcinoma to drive tumour growth," Gut, Aug. 1, 2019, 68(8):1465-1476.
MacDonald et al., "A Systematic Analysis of Negative Growth Control Implicates the DREAM Complex in Cancer Cell Dormancy," Molecular Cancer Research, Apr. 1, 2017, 15(4):371-381.
Malinge et al., "Increased dosage of the chromosome 21 ortholog Dyrk1a promotes megakaryoblastic leukemia in a murine model of Down syndrome," The Journal of Clinical Investigation, Mar. 1, 2012, 122(3):948-962.
Marcotte et al., "Functional genomic landscape of human breast cancer drivers, vulnerabilities, and resistance," Cell, Jan. 14, 2016, 164(1-2):293-309.
Melchior et al., "Tau pathology reduction with SM07883, a novel, potent, and selective oral DYRK1A inhibitor: A potential therapeutic for Alzheimer's disease," Aging Cell, Oct. 2019, 18(5):e13000, 14 pages.
Nalls et al., "Identification of novel risk loci, causal insights, and heritable risk for Parkinson's disease: a meta-analysis of genome-wide association studies," The Lancet Neurology, Dec. 1, 2019, 18(12):1091-1102.
Pathak et al., "DYRK1A kinase inhibition with emphasis on neurodegeneration: A comprehensive evolution story-cum-perspective," European Journal of Medicinal Chemistry, Oct. 5, 2018, 158:559-592, 2 pages (Abstract Only).
Pozo et al., "Inhibition of DYRK1A destabilizes EGFR and reduces EGFR-dependent glioblastoma growth," The Journal of Clinical Investigation, Jun. 3, 2013, 123(6):2475-2487.
Pucelik et al., "Diabetic kinome inhibitors—a new opportunity for β-cells restoration," International Journal of Molecular Sciences, Aug. 23, 2021, 22(16):9083, 53 pages.
Radhakrishnan et al., "A dual specificity kinase, DYRK1A, as a potential therapeutic target for head and neck squamous cell carcinoma," Scientific Reports, Oct. 31, 2016, 6(36132): 15 pages.
Roewenstrunk et al., "A comprehensive proteomics-based interaction screen that links DYRKIA to RNF169 and to the DNA damage response," Scientific Reports, Apr. 12, 2019, 9(1):6014, 14 pages.
Shen et al., "Inhibition of DYRK1A and GSK3B induces human β-cell proliferation," Nature Communications, Oct. 26, 2015, 6(8372): 11 pages.
Stotani et al., "DYRK1A inhibition as potential treatment for Alzheimer's disease," Future Medicinal Chemistry, Apr. 2016, 8(6): 681-696.
Xu et al., "Inhibition of DYRK1A-EGFR axis by p53-MDM2 cascade mediates the induction of cellular senescence," Cell Death & Disease, Mar. 25, 2019, 10(4):282, 18 pages.
International Preliminary Report on Patentability in International Appln. No. PCT/US2022/046395, mailed on Apr. 25, 2024, 12 pages.
International Preliminary Report on Patentability in International Appln. No. PCT/US2022/046409, mailed on Apr. 25, 2024, 11 pages.

(56) References Cited

OTHER PUBLICATIONS

International Preliminary Report on Patentability in International Appln. No. PCT/US2022/046416, mailed on Apr. 25, 2024, 6 pages.
International Preliminary Report on Patentability in International Appln. No. PCT/US2023/026100, mailed on Jan. 2, 2025, 8 pages.
Office Action in Mexican Appln. No. MX/A/2024/015663, mailed on Jan. 13, 2025, 8 pages (with English translation).
International Preliminary Report on Patentability in International Appln. No. PCT/US2024/023387, mailed on Oct. 16, 2025, 7 pages.
International Search Report and Written Opinion in International Appln. No. PCT/US2024/023387, mailed on Jun. 19, 2024, 12 pages.
International Search Report in International Appln. No. PCT/US2024/061313, mailed on Mar. 20, 2025, 14 pages.

* cited by examiner

4-ALKOXYPYRROLO[2,1-F][1,2,4]TRIAZINES AND PREPARATION AND USES THEREOF

RELATED APPLICATIONS

This application claims the benefit of U.S. Provisional Application Nos 63/355,076, filed Jun. 23, 2022, 63/427,322, filed Nov. 22, 2022, and 63/458,808, filed Apr. 12, 2023, which are incorporated herein by reference in their entirety.

BACKGROUND

Technical Field

This disclosure relates to inhibitors of dual-specificity tyrosine phosphorylation-regulated 1A kinase, and compositions comprising the same. More particularly, it concerns the use of a 4-alkoxypyrrolo[2,1-f][1,2,4]triazine compounds or salts or analogs thereof, in the treatment of disorders characterized by the abnormal expression and/or activity of DYRK1A (e.g., cancer, Down syndrome, Alzheimer's disease, diabetes, viral infections, and osteoarthritis).

Background

Dual-specificity tyrosine phosphorylation-regulated kinases (DYRK1A, 1B, 2-4) comprise a family of protein kinases within the CMGC group of the eukaryotic kinome. These protein kinases are involved in multiple cellular functions, including intracellular signaling, mRNA splicing, chromatin transcription, DNA damage repair, cell survival, cell cycle control, differentiation, homocysteine/methionine/folate regulation, body temperature regulation, endocytosis, neuronal development, synaptic plasticity, etc. Abnormal expression and/or activity of some of these kinases, DYRK1A in particular, is seen in many human nervous system diseases, such as cognitive deficits associated with Down syndrome, Alzheimer's disease, and related diseases, tauopathies, dementia, Pick's disease, Parkinson's disease, and other neurodegenerative diseases, Phelan-McDermid syndrome, autism, and CDKL5 deficiency disorder. DYRKs are also involved in diabetes, abnormal folate/methionine metabolism, osteoarthritis, several solid cancers (glioblastoma, breast, and pancreatic cancers) and leukemias (acute lymphoblastic leukemia, acute megakaryoblastic leukemia), viral infections (influenza, HIV-1, HCMV, HCV, CMV, HPV), as well as infections caused by unicellular parasites (*Leishmania, Trypanosoma, Plasmodium*) (*International Journal of Molecular Sciences* (2021), 22(11), 6047). DYRK1A has also been identified as a critical stabilizer of EGFR (*Cell Death & Disease* (2019), 10, 282) which is a crucial factor contributing to the keratinization, cell hyperproliferation, abnormal differentiation and inflammatory infiltration during the progress of psoriasis.

SUMMARY

The present disclosure provides methods and reagents, the method involving contacting a cell with an agent, such as a 4-alkoxypyrrolo[2,1-f][1,2,4]triazine compound, in a sufficient amount to antagonize DYRK1A activity, e.g., reduce the proliferation of head and neck squamous cell carcinoma, luminal/HER2 breast cancer, (Cell (2016), 164(1-2), 293-309) or pancreatic adenocarcinoma, as well as impair the self-renewal capacity of glioblastoma and compromise ovarian cancer spheroid cell viability (*Molecular Cancer Research* (2017), 15(4), 371-381).

The present disclosure also provides methods and reagents, the method involving contacting a cell with an agent, such as a 4-alkoxypyrrolo[2,1-f][1,2,4]triazine compound, in a sufficient amount to antagonize DYRK1A activity, e.g., i) to normalize prenatal and early postnatal brain development; ii) to improve cognitive function in youth and adulthood; and/or iii) to attenuate Alzheimer's-type neurodegeneration.

Some embodiments disclosed herein include DYRK1A inhibitors containing a 4-alkoxypyrrolo[2,1-f][1,2,4]triazine core. Other embodiments disclosed herein include pharmaceutical compositions and methods of treatment using these compounds.

One embodiment disclosed herein includes a compound having the structure of Formula I.

I

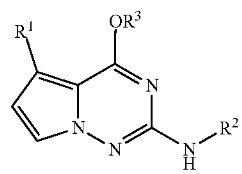

or a pharmaceutically acceptable salt thereof, wherein, $R^1$ is heteroaryl optionally substituted with 1-10 $R^4$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^5$, —($C_{1-5}$ alkylene)$_p$heterocyclyl optionally substituted with 1-10 $R^6$, -heteroaryl optionally substituted with 1-10 $R^7$, and —($C_{1-5}$ alkylene)$_p$carbocyclyl optionally substituted with 1-12 $R^8$, wherein each —($C_{1-5}$ alkylene) is, independently, optionally substituted with 1-5 halide and/or 1-3 unsubstituted —($C_{1-3}$ alkyl);

$R^3$ is selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^4$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^9$, —($C_{1-5}$ alkylene)CN, —($C_{1-5}$ alkylene)$_p$heterocyclyl optionally substituted with 1-10 $R^{10}$, -carbocyclyl optionally substituted with 1-12 $R^{11}$, —($C_{1-5}$ alkylene)$_p$heteroaryl optionally substituted with 1-10 $R^{20}$, —($C_{1-5}$ alkylene)$_p$C(═O)N($R^{12}$)$_2$, and —C(═O)$R^{13}$, wherein each —($C_{1-5}$ alkylene) is, independently, optionally substituted with 1-5 halide and/or 1-3 unsubstituted —($C_{1-3}$ alkyl);

each $R^5$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{16}$, —($C_{1-5}$ alkylene)$_p$OR$^{21}$, —SO$_2$R$^{23}$, and —C(═O)R$^{24}$, wherein the —($C_{1-5}$ alkylene) is optionally substituted with 1-5 halide and/or 1-3 unsubstituted —($C_{1-3}$ alkyl);

alternatively, two $R^6$ attached to the same carbon atom are taken together to form a carbonyl group;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^8$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$N(R^{14})_2$, —($C_{1-5}$ alkylene)$_p$OR$^{15}$, —($C_{1-5}$ alkylene)$_p$heterocyclyl optionally substituted with 1-10 $R^{16}$, —C(═O)$R^{22}$, and —NHC(═O)$R^{23}$, wherein each —($C_{1-5}$ alkylene) is, independently, optionally substituted with 1-5 halide and/or 1-3 unsubstituted —($C_{1-3}$ alkyl);

each $R^9$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{12}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$-carbocyclyl optionally substituted with 1-12 $R^{17}$, -heterocyclyl optionally substituted with 1-10 $R^{18}$, and -heteroaryl optionally substituted with 1-10 $R^{19}$, wherein the —($C_{1-5}$ alkylene) is optionally substituted with 1-5 halide and/or 1-3 unsubstituted —($C_{1-3}$ alkyl);

each $R^{13}$ is -heterocyclyl optionally substituted with 1-10 $R^{18}$;

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{15}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{21}$;

each $R^{16}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{17}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-19}$ haloalkyl);

each $R^{21}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{22}$ is independently selected from the group consisting of -heterocyclyl optionally substituted with 1-10 $R^{18}$, —$N(R^{12})_2$ and —OR$^{21}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{24}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —OR$^{23}$, and -carbocyclyl optionally substituted with 1-12 $R^{25}$;

each $R^{25}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl); and each p is independently 0 or 1;

wherein each H atom is optionally, independently replaced by $^2$H (D) (deuterium).

In another embodiment disclosed herein, included is a compound having the structure of Formula I.

I

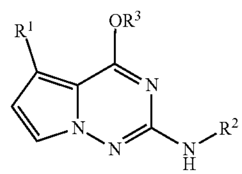

or a pharmaceutically acceptable salt thereof, wherein, $R^1$ is heteroaryl optionally substituted with 1-10 $R^4$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR, —($C_{1-5}$alkylene)$_p$heterocyclyl optionally substituted with 1-10 R, —($C_{1-5}$ alkylene)$_p$aryl optionally substituted with 1-10 $R^{26}$, —($C_{1-5}$ alkylene)$_p$heteroaryl optionally substituted with 1-10 $R^7$, and —($C_{1-5}$alkylene)$_p$carbocyclyl optionally substituted with 1-12 R, wherein each —($C_{1-5}$ alkylene) is, independently, optionally substituted with 1-5 halide and/or 1-3 unsubstituted —($C_{1-3}$ alkyl);

$R^3$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and heterocyclyl optionally substituted with 1-10 $R^{18}$;

each $R^4$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^9$, —($C_{1-5}$ alkylene)$_p$CN, —($C_{1-5}$ alkylene)$_p$heterocyclyl optionally substituted with 1-10 $R^{10}$, -carbocyclyl optionally substituted with 1-12 $R^{11}$, —($C_{1-5}$ alkylene)$_p$heteroaryl optionally substituted with 1-10 $R^{20}$, —($C_{1-5}$ alkylene)$_p$C(═O)N$(R^{12})_2$, and —C(═O)

$R^{13}$, wherein each —($C_{1-5}$ alkylene) is, independently, optionally substituted with 1-5 halide and/or 1-3 unsubstituted —($C_{1-3}$ alkyl);

each $R^5$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{16}$, -carbocyclyl optionally substituted with 1-12 $R^{17}$, —($C_{1-5}$ alkylene)$_p$OR$^{21}$, —SO$_2$R$^{23}$, and —C(═O)R$^{24}$, wherein the —($C_{1-5}$ alkylene) is optionally substituted with 1-5 halide and/or 1-3 unsubstituted —($C_{1-3}$ alkyl);

alternatively, two $R^6$ attached to the same carbon atom are taken together to form a carbonyl group;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^8$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N(R$^{14}$)$_2$, —($C_{1-5}$ alkylene)$_p$OR$^{15}$, —($C_{1-5}$ alkylene)$_p$heterocyclyl optionally substituted with 1-10 $R^{16}$, —C(═O)R$^{22}$, and —NHC(═O)R$^{23}$, wherein each —($C_{1-5}$ alkylene) is, independently, optionally substituted with 1-5 halide and/or 1-3 unsubstituted —($C_{1-3}$ alkyl);

each $R^9$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{12}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^{21}$, —($C_{1-5}$ alkylene)$_p$carbocyclyl optionally substituted with 1-12 $R^{17}$, -heterocyclyl optionally substituted with 1-10 $R^{18}$, and -heteroaryl optionally substituted with 1-10 $R^{19}$, wherein the —($C_{1-5}$ alkylene) is optionally substituted with 1-5 halide and/or 1-3 unsubstituted —($C_{1-3}$ alkyl);

each $R^{13}$ is -heterocyclyl optionally substituted with 1-10 $R^{18}$;

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{15}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{21}$;

each $R^{16}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, two $R^{16}$ attached to the same carbon atom are taken together to form a carbonyl group;

each $R^{17}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{22}$ is independently selected from the group consisting of -heterocyclyl optionally substituted with 1-10 $R^{18}$, —N(R$^{12}$)$_2$ and —OR$^{21}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{21}$;

each $R^{24}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —OR$^{21}$, and -carbocyclyl optionally substituted with 1-12 $R^{25}$;

each $R^{25}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{26}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl); and each p is independently 0 or 1;

wherein each H atom is optionally, independently replaced by $^2$H (D) (deuterium).

In another embodiment disclosed herein, included is a compound having the structure of Formula I:

I

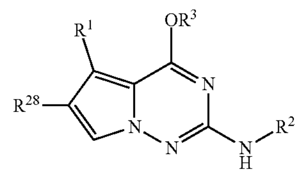

or a pharmaceutically acceptable salt thereof, wherein, $R^1$ is heteroaryl optionally substituted with 1-10 $R^4$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR, —($C_{1-5}$alkylene)CN, —($C_{1-5}$ alkylene)$_p$heterocyclyl optionally substituted with 1-10 $R^6$, —($C_{1-5}$ alkylene)$_p$aryl optionally substituted with 1-10 $R^{26}$, —($C_{1-5}$ alkylene)$_p$heteroaryl optionally substituted with 1-10 $R^7$, and —($C_{1-5}$ alkylene)$_p$carbocyclyl optionally substituted with 1-12 R, wherein each —($C_{1-5}$ alkylene) is, independently, optionally substituted with 1-5 halide and/or 1-3 unsubstituted —($C_{1-3}$ alkyl);

$R^3$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and heterocyclyl optionally substituted with 1-10 $R^{18}$;

each $R^4$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), unsubstituted —($C_{2-9}$ haloalkenyl), —($C_{1-5}$ alkylene)$_p$OR$^9$, —($C_{1-5}$ alkylene)$_p$CN, —($C_{1-5}$ alkylene)$_p$heterocyclyl optionally substituted with 1-10 $R^{10}$, -carbocyclyl optionally substituted with 1-12 $R^{11}$, —($C_{1-5}$ alkylene)$_p$heteroaryl optionally substituted with 1-10 $R^{20}$, —($C_{1-5}$ alkylene)$_p$C(═O)N($R^{12}$)$_2$, and —C(═O)$R^{13}$, wherein each —($C_{1-5}$ alkylene) is, independently, optionally substituted with 1-5 halide and/or 1-3 unsubstituted —($C_{1-3}$ alkyl);

each $R^5$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{16}$, -carbocyclyl optionally substituted with 1-12 $R^{17}$, —($C_{1-5}$ alkylene)$_p$OR$^{21}$, —($C_{1-5}$ alkylene)CN, —SO$_2$R$^{23}$, and —C(═O)R$^{24}$, wherein the —($C_{1-5}$ alkylene) is optionally substituted with 1-5 halide and/or 1-3 unsubstituted —($C_{1-3}$ alkyl);

alternatively, two $R^6$ attached to the same carbon atom are taken together to form a carbonyl group;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^8$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{14}$)$_2$, —($C_{1-5}$ alkylene)$_p$OR$^{15}$, —CN, —($C_{1-5}$ alkylene)$_p$heterocyclyl optionally substituted with 1-10 $R^{16}$, —C(═O)R$^{22}$, and —NR$^{14}$C(═O)R$^{23}$, wherein each —($C_{1-5}$ alkylene) is, independently, optionally substituted with 1-5 halide and/or 1-3 unsubstituted —($C_{1-3}$ alkyl);

each $R^9$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{12}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^{21}$, —($C_{1-5}$ alkylene)$_p$carbocyclyl optionally substituted with 1-12 $R^{17}$, -heterocyclyl optionally substituted with 1-10 $R^{18}$, and -heteroaryl optionally substituted with 1-10 $R^{19}$, wherein the —($C_{1-5}$ alkylene) is optionally substituted with 1-5 halide and/or 1-3 unsubstituted —($C_{1-3}$ alkyl);

each $R^{13}$ is -heterocyclyl optionally substituted with 1-10 $R^{18}$;

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{15}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{21}$;

each $R^{16}$ is independently selected from the group consisting of halide, —CN, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{27}$;

alternatively, two $R^{16}$ attached to the same carbon atom are taken together to form a carbonyl group;

each $R^{17}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{22}$ is independently selected from the group consisting of -heterocyclyl optionally substituted with 1-10 $R^{18}$, —N($R^{12}$)$_2$, and —OR$^{21}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^{21}$, and -carbocyclyl optionally substituted with 1-12 $R^{25}$;

each $R^{24}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —OR$^{21}$, and -carbocyclyl optionally substituted with 1-12 $R^{25}$;

each $R^{25}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —CN;

each $R^{26}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{27}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

$R^{28}$ is independently selected from the group consisting of H and halide; and each p is independently 0 or 1;

wherein each H atom is optionally, independently replaced by $^2H$ (D) (deuterium).

In another embodiment disclosed herein, included is a compound having the structure of Formula I:

I

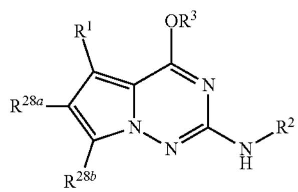

or a pharmaceutically acceptable salt thereof, wherein, $R^1$ is heteroaryl optionally substituted with 1-10 $R^4$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR, —($C_{1-5}$alkylene)CN, —($C_{1-5}$ alkylene)$_p$heterocyclyl optionally substituted with 1-10 $R^6$, —($C_{1-5}$ alkylene)$_p$aryl optionally substituted with 1-10 $R^{26}$, —($C_{1-5}$ alkylene)$_p$heteroaryl optionally substituted with 1-10 $R^7$, and —($C_{1-5}$ alkylene)$_p$carbocyclyl optionally substituted with 1-12 R, wherein each —($C_{1-5}$ alkylene) is, independently, optionally substituted with 1-5 halide and/or 1-3 unsubstituted —($C_{1-3}$ alkyl);

$R^3$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and heterocyclyl optionally substituted with 1-10 $R^{18}$;

each $R^4$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), unsubstituted —($C_{2-9}$ haloalkenyl), —($C_{1-5}$ alkylene)$_p$OR$^9$, —($C_{1-5}$ alkylene)$_p$CN, —($C_{1-5}$ alkylene)$_p$heterocyclyl optionally substituted with 1-10 $R^{10}$, -carbocyclyl optionally substituted with 1-12 $R^{11}$, —($C_{1-5}$ alkylene)$_p$heteroaryl optionally substituted with 1-10 $R^{20}$, —($C_{1-5}$ alkylene)$_p$C(=O)N($R^{12}$)$_2$, and —C(=O)$R^{13}$, wherein each —($C_{1-5}$ alkylene) is, independently, optionally substituted with 1-5 halide and/or 1-3 unsubstituted —($C_{1-3}$ alkyl);

each $R^5$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{16}$, -carbocyclyl optionally substituted with 1-12 $R^{17}$, —($C_{1-5}$ alkylene)$_p$OR$^{21}$, —($C_{1-5}$ alkylene)CN, —SO$_2$R$^{23}$, and —C(=O)$R^{24}$, wherein the —($C_{1-5}$ alkylene) is optionally substituted with 1-5 halide and/or 1-3 unsubstituted —($C_{1-3}$ alkyl);

alternatively, two $R^6$ attached to the same carbon atom are taken together to form a carbonyl group;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^8$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{14}$)$_2$, —($C_{1-5}$ alkylene)$_p$OR$^{15}$, —CN, —($C_{1-5}$ alkylene)$_p$heterocyclyl optionally substituted with 1-10 $R^{16}$, —C(=O)$R^{22}$, and —NR$^4$C(=O)$R^{23}$, wherein each —($C_{1-5}$ alkylene) is, independently, optionally substituted with 1-5 halide and/or 1-3 unsubstituted —($C_{1-3}$ alkyl);

each $R^9$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{12}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^{21}$, —($C_{1-5}$ alkylene)$_p$carbocyclyl optionally substituted with 1-12 $R^{17}$, -heterocyclyl optionally substituted with 1-10 $R^{18}$, and -heteroaryl optionally substituted with 1-10 $R^{19}$, wherein the —($C_{1-5}$ alkylene) is optionally substituted with 1-5 halide and/or 1-3 unsubstituted —($C_{1-3}$ alkyl);

each $R^{13}$ is -heterocyclyl optionally substituted with 1-10 $R^{18}$;

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{15}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{21}$;

each $R^{16}$ is independently selected from the group consisting of halide, —CN, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{27}$;

alternatively, two $R^{16}$ attached to the same carbon atom are taken together to form a carbonyl group;

each $R^{17}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{22}$ is independently selected from the group consisting of -heterocyclyl optionally substituted with 1-10 $R^{18}$, —$N(R^{12})_2$, and —$OR^{21}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$$OR^{21}$, and -carbocyclyl optionally substituted with 1-12 $R^{25}$;

each $R^{24}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$OR^{21}$, and -carbocyclyl optionally substituted with 1-12 $R^{25}$;

each $R^{25}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —CN;

each $R^{26}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{27}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

$R^{28a}$ is independently selected from the group consisting of H and halide;

$R^{28b}$ is independently selected from the group consisting of H and D; and each p is independently 0 or 1;

wherein each H atom is optionally, independently replaced by $^2H$ (D) (deuterium).

Some embodiments include stereoisomers and pharmaceutically acceptable salts of a compound of Formula I. Some embodiments include pharmaceutically acceptable salts of a compound of Formula I.

Some embodiments include pro-drugs of a compound of Formula I.

Some embodiments of the present disclosure include pharmaceutical compositions comprising a compound of Formula I and a pharmaceutically acceptable carrier, diluent, or excipient.

Other embodiments disclosed herein include methods of inhibiting DYRK1A by administering to a patient affected by a disorder or disease in which DYRK1A overexpression is implicated, such as Alzheimer's disease, amyotrophic lateral sclerosis, CDKL5 deficiency disorder, Down syndrome, frontotemporal dementia with parkinsonism-17 (FTDP-17), Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

Inhibitors of DYRK1A can also be used to treat tauopathies. Tauopathies are neurodegenerative disorders characterized by the deposition of abnormal tau protein in the brain. The spectrum of tau pathologies expands beyond the traditionally discussed disease forms like Pick's disease, progressive supranuclear palsy, corticobasal degeneration, and argyrophilic grain disease. Emerging entities and pathologies include globular glial tauopathies, primary age-related tauopathy, which includes neurofibrillary tangle dementia, chronic traumatic encephalopathy (CTE), frontotemporal lobar degeneration with tau inclusions (FTLD-tau), and aging-related tau astrogliopathy. Clinical symptoms include frontotemporal dementia, corticobasal syndrome, Richardson syndrome, parkinsonism, pure akinesia with gait freezing and, rarely, motor neuron symptoms or cerebellar ataxia (*Handbook of Clinical Neurology* (2018), 145, 355-368 and *Aging Cell* (2019), 18(5), e13000).

Inhibitors of DYRK1A can also be used to treat disorders associated with abnormal folate/methionine metabolism.

Non-limiting examples of diseases which can be treated with the compounds and compositions provided herein include a variety of cancers, diabetes, psoriasis, knee osteoarthritis, tendinopathy, human immunodeficiency virus type 1 (HIV-1), human cytomegalovirus (HCMV), hepatitis C virus (HCV), and herpes simplex virus 1 (HSV-1).

Some embodiments of the present disclosure include methods to prepare compounds of Formula I.

It is to be understood that both the foregoing general description and the following detailed description are exemplary and explanatory only and are not restrictive of the disclosure, as claimed.

DETAILED DESCRIPTION

Provided herein are compositions and methods for inhibiting DYRK1A

Some embodiments provided herein relate to a method for treating a disease including, but not limited to, neurological diseases or disorders, cancers, cognitive deficits, knee osteoarthritis, tendinopathy, viral infections, unicellular parasite infections, and motor deficits.

In some embodiments, non-limiting examples of a neurological disease or disorder which can be treated with the compounds and compositions provided herein include, but are not limited to, Alzheimer's disease, amyotrophic lateral sclerosis, Down syndrome, frontotemporal dementia with parkinsonism-17 (FTDP-17), Lewy body dementia, Parkinson's disease, Pick's disease tauopathies, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

In some embodiments, non-limiting examples of cancers which can be treated with the compounds and compositions provided herein include solid cancers (e.g., glioblastoma, ovarian, breast, and pancreatic cancers) and leukemias (e.g., acute lymphoblastic leukemia, acute megakaryoblastic leukemia, and chronic myeloid leukemia).

In some embodiments, pharmaceutical compositions are provided that are effective for treatment of a disease of an animal, e.g., a mammal, caused by DYRK1A overexpression. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, isobutyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched or straight chain chemical group containing only carbon and hydrogen, such as methylene, ethylene, n-propylene, isopropylene, n-butylene, iso-butylene, sec-butylene, tert-butylene, n-pentylene, iso-pentylene, sec-pentylene and neopentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "alkoxy" means an alkyl-O— group in which the alkyl group is as described herein. Exemplary alkoxy groups include methoxy, ethoxy, n-propoxy, i-propoxy, n-butoxy, s-butoxy, t-butoxy, pentoxy, hexoxy and heptoxy, and also the linear or branched positional isomers thereof.

As used herein, "haloalkoxy" means a haloalkyl-O— group in which the haloalkyl group is as described herein. Exemplary haloalkoxy groups include fluoromethoxy, difluoromethoxy, trifluoromethoxy, and also the linear or branched positional isomers thereof.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that none of the rings in the ring system are aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched alkyl, alkenyl or alkynyl substituted with one or more chloro, bromo, fluoro, and/or iodo atom(s). In some embodiments, a haloalkyl is a fluoroalkyl, wherein one or more of the hydrogen atoms have been substituted by fluoro. In some embodiments, haloalkyls are 1 to 3 carbons in length (e.g., 1 to 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings such as bicyclic and spirocyclic heterocyclyls. Heterocyclyls may be substituted or unsubstituted with one or more substituents. In some embodiments, heterocycles have 3-11 members. In six membered monocyclic heterocycles, the heteroatom(s) are selected from one to three of O, N and S, and wherein when the heterocycle is five membered, it can have one or two heteroatoms selected from O, N, and S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N and S, and wherein when the heterocycle is five membered, it can have one or two heteroatoms selected from O, N, and S. Examples of monocyclic heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N and S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N and S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxy) optionally substituted with one or more of halide, hydroxyl, —$NH_2$, —NH($C_{1-3}$ alkyl), and —N($C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —$OSO_2$(OR); a sulfonate [such as —$SO_2$(OH) and —$SO_2$(OR)]; —$SO_2$NR'R"; and —$SO_2$R; in which each occurrence of R, R' and R" are independently selected from H; —($C_{1-9}$ alkyl); $C_{6-10}$ aryl optionally substituted with 1-3 R'"; 5-10 membered heteroaryl having from 1-4 heteroatoms independently selected from N, O, and S and optionally substituted with 1-3 R'"; $C_{3-7}$ carbocyclyl optionally substituted with 1-3 R'"; and 3-8 membered heterocyclyl having from 1-4 heteroatoms independently selected from N, O, and S and optionally substituted with 1-3 R'"; wherein each R'" is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formula I wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^{2}H$ (deuterium) and $^{3}H$ (tritium), isotopes of carbon, such as $^{11}C$, $^{13}C$ and $^{14}C$, isotopes of chlorine, such as $^{36}Cl$, isotopes of fluorine, such as $^{18}F$, isotopes of iodine, such as $^{123}I$ and $^{125}I$, isotopes of nitrogen, such as $^{13}N$ and $^{15}N$, isotopes of oxygen, such as $^{15}O$, $^{17}O$ and $^{18}O$, isotopes of phosphorus, such as $^{32}P$, and isotopes of sulfur, such as $^{35}S$.

The term "administration" or "administering" refers to a method of providing a dosage of a compound or pharmaceutical composition to a vertebrate or invertebrate, including a mammal, a bird, a fish, or an amphibian, where the method of administration is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The terms "pharmaceutically acceptable carrier," "pharmaceutically acceptable diluent," and "pharmaceutically acceptable excipient" include any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (2010); *Goodman and Gilman's: The Pharmacological Basis of Therapeutics, 12th Ed*., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age, and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing, or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom overtime into the surrounding body tissue.

"Drug-eluting material" and/or controlled release material as used herein refers to any natural, synthetic, or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used to inhibit DYRK1A for treating a disorder or disease in which DYRK1A overexpression is implicated, such as in neurological diseases or disorders, cancers, cognitive deficits, knee osteoarthritis, tendinopathy, viral infections, unicellular parasite infections, and motor deficits.

Some embodiments of the present disclosure include compounds of Formula I:

I

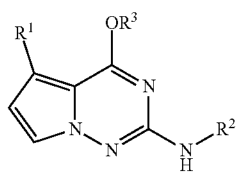

or salts, pharmaceutically acceptable salts, or prodrugs thereof.

Some embodiments of the present disclosure include compounds of Formula I:

I

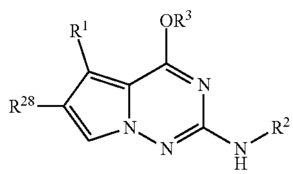

or salts, pharmaceutically acceptable salts, or prodrugs thereof.

Some embodiments of the present disclosure include compounds of Formula I:

I

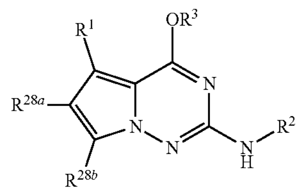

or salts, pharmaceutically acceptable salts, or prodrugs thereof.

In some embodiments of Formula I, $R^1$ is heteroaryl optionally substituted with 1-10 $R^4$. In some embodiments, $R^1$ is heteroaryl optionally substituted with 1-10, 1-9, 1-8, 1-7, 1-6, 1-5, 1-4, 1-3, 1-2, or 1 $R^4$.

In some embodiments of Formula I, $R^1$ is selected from the heteroaryl group consisting of:

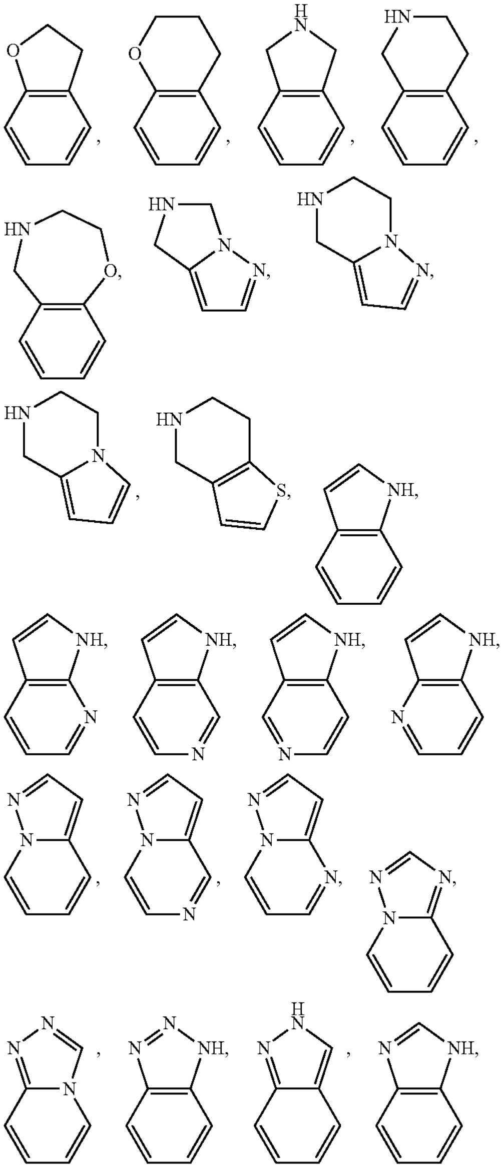

-continued

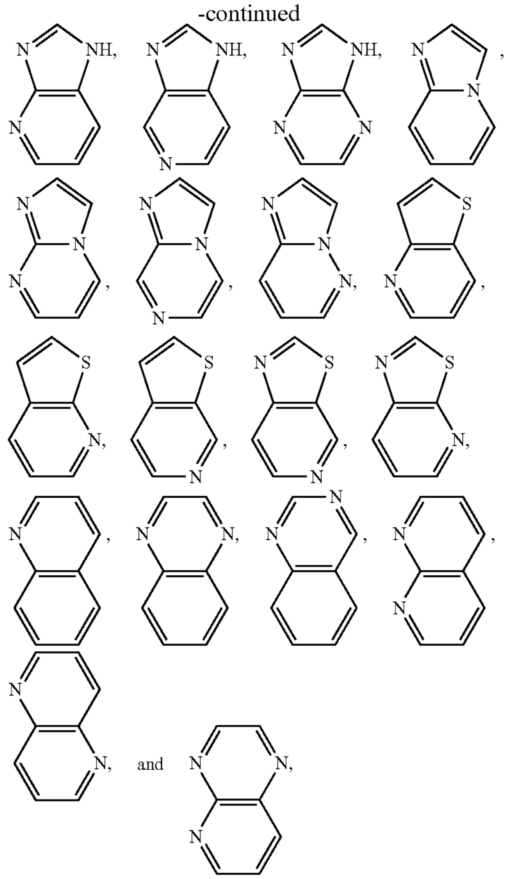

optionally substituted with 1-10 (e.g., 1-9, 1-8, 1-7, 1-6, 1-5, 1-4, 1-3, 1-2, 1) $R^4$.

In some embodiments of Formula I, $R^1$ is selected from the heteroaryl group consisting of:

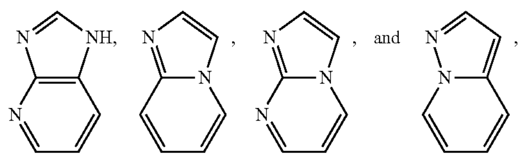

optionally substituted with 1-10 (e.g., 1-9, 1-8, 1-7, 1-6, 1-5, 1-4, 1-3, 1-2, 1) $R^4$.

In some embodiments of Formula I, $R^1$ is selected from the heteroaryl group consisting of:

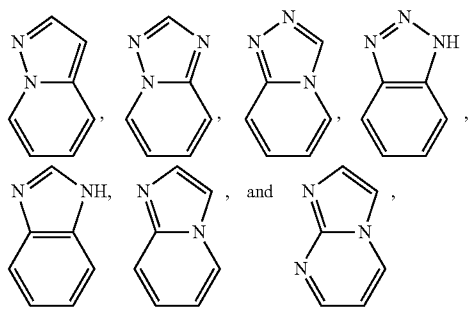

optionally substituted, 1 with 1-10 (e.g., 1-9, 1-8, 1-7, 1-6, 1-5, 1-4, 1-3, 1-2, 1) $R^4$.

In some embodiments of Formula I, $R^1$ is selected from the heteroaryl group consisting of:

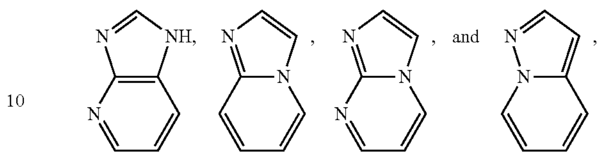

optionally substituted with 1-3 (e.g., 1-2, 1) $R^4$.

In some embodiments of Formula I, $R^1$ is selected from the heteroaryl group consisting of:

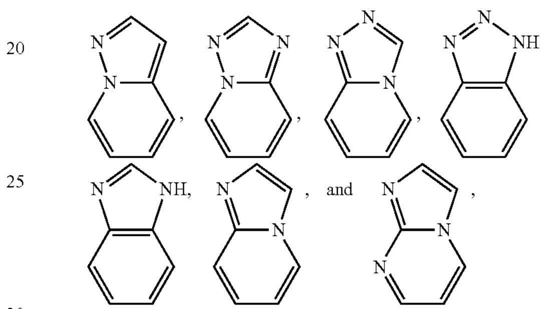

optionally substituted with 1-3 (e.g., 1-2, 1) $R^4$.

In some embodiments of Formula I, $R^1$ is selected from the group consisting of:

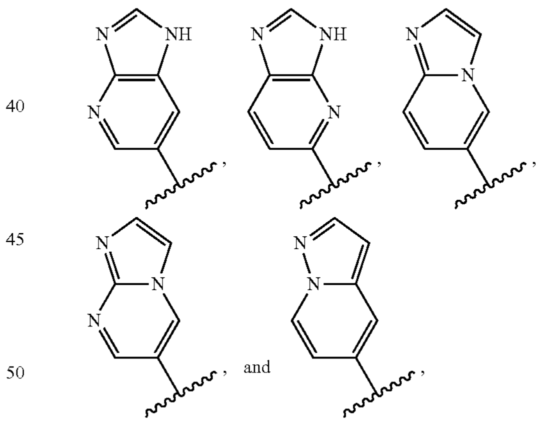

optionally substituted with 1-3 $R^4$.

In some embodiments of Formula I, $R^1$ is selected from the group consisting of:

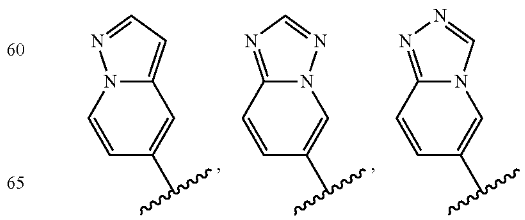

-continued

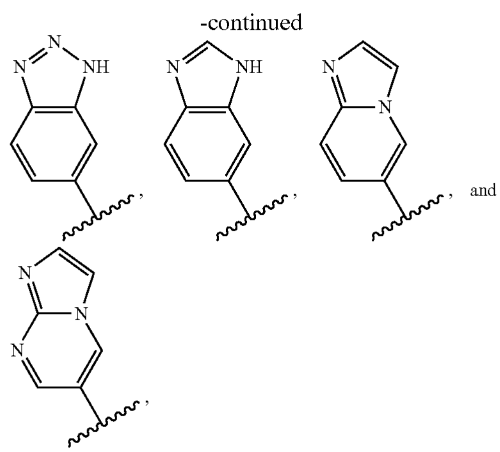

, , , and , optionally substituted with 1-3 $R^4$.

In some embodiments of Formula I, $R^1$ is selected from the group consisting of:

unsubstituted

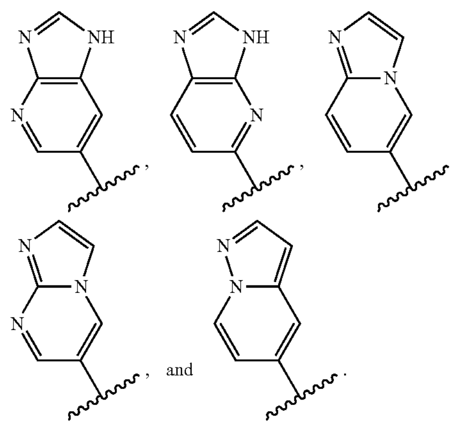

, , , , and .

In some embodiments of Formula I, $R^1$ is selected from the group consisting of:

unsubstituted

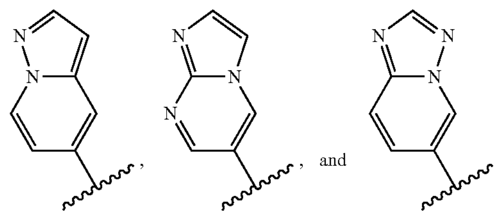

, , and .

In some embodiments of Formula I, $R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR, —($C_{1-5}$ alkylene)$_p$heterocyclyl optionally substituted with 1-10 (e.g., 1-9, 1-8, 1-7, 1-6, 1-5, 1-4, 1-3, 1-2, 1) $R^6$, -heteroaryl optionally substituted with 1-10 (e.g., 1-9, 1-8, 1-7, 1-6, 1-5, 1-4, 1-3, 1-2, 1) $R^7$, and —($C_{1-5}$ alkylene)$_p$carbocyclyl optionally substituted with 1-12 (e.g., 1-11, 1-10, 1-9, 1-8, 1-7, 1-6, 1-5, 1-4, 1-3, 1-2, 1)R, wherein each —($C_{1-5}$ alkylene) is, independently, optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, $R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR, —($C_{1-5}$ alkylene)$_p$heterocyclyl optionally substituted with 1-10 (e.g., 1-9, 1-8, 1-7, 1-6, 1-5, 1-4, 1-3, 1-2, 1) $R^6$, —($C_{1-5}$ alkylene)$_p$aryl optionally substituted with 1-10 (e.g., 1-9, 1-8, 1-7, 1-6, 1-5, 1-4, 1-3, 1-2, 1) $R^{26}$, —($C_{1-5}$ alkylene)$_p$heteroaryl optionally substituted with 1-10 (e.g., 1-9, 1-8, 1-7, 1-6, 1-5, 1-4, 1-3, 1-2, 1) $R^7$, and —($C_{1-5}$ alkylene)$_p$carbocyclyl optionally substituted with 1-12 (e.g., 1-11, 1-10, 1-9, 1-8, 1-7, 1-6, 1-5, 1-4, 1-3, 1-2, 1)R, wherein each —($C_{1-5}$ alkylene) is, independently, optionally substituted with 1-5 halide (e.g., F, Cl, Br, I) and/or 1-3 (e.g., 1-2, 1) unsubstituted —($C_{1-3}$ alkyl).

In some embodiments of Formula I, $R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^5$, —($C_{1-5}$ alkylene)CN, —($C_{1-5}$ alkylene)$_p$heterocyclyl optionally substituted with 1-10 (e.g., 1-9, 1-8, 1-7, 1-6, 1-5, 1-4, 1-3, 1-2, 1) $R^6$, —($C_{1-5}$ alkylene)$_p$aryl optionally substituted with 1-10 (e.g., 1-9, 1-8, 1-7, 1-6, 1-5, 1-4, 1-3, 1-2, 1) $R^{26}$, —($C_{1-5}$ alkylene)$_p$heteroaryl optionally substituted with 1-10 (e.g., 1-9, 1-8, 1-7, 1-6, 1-5, 1-4, 1-3, 1-2, 1) $R^7$, and —($C_{1-5}$ alkylene)$_p$carbocyclyl optionally substituted with 1-12 (e.g., 1-11, 1-10, 1-9, 1-8, 1-7, 1-6, 1-5, 1-4, 1-3, 1-2, 1)R, wherein each —($C_{1-5}$ alkylene) is, independently, optionally substituted with 1-5 halide (e.g., F, Cl, Br, I) and/or 1-3 unsubstituted —($C_{1-3}$ alkyl).

In some embodiments of Formula I, $R^2$ is selected from the group consisting of unsubstituted —($C_{1-5}$ alkyl), unsubstituted —($C_{1-5}$ haloalkyl), —($C_{1-2}$ alkylene)$_p$OR, —($C_{1-2}$ alkylene)$_p$heterocyclyl optionally substituted with 1-3 (e.g., 1-2, 1) $R^6$, and —($C_{1-2}$ alkylene)$_p$carbocyclyl optionally substituted with 1-3 (e.g., 1-2, 1)R, wherein each —($C_{1-5}$ alkylene) is, independently, optionally substituted with 1-2 halide.

In some embodiments of Formula I, $R^2$ is selected from the group consisting of unsubstituted —($C_{1-5}$ alkyl), unsubstituted —($C_{1-5}$ haloalkyl), -heterocyclyl optionally substituted with 1-4 $R^6$, —($C_{1-2}$ alkylene)$_p$aryl optionally substituted with 1-2 $R^{26}$, —($C_{1-2}$ alkylene)$_p$heteroaryl optionally substituted with 1-2 $R^7$, and —($C_{1-2}$ alkylene)$_p$carbocyclyl optionally substituted with 1-4 $R^8$, wherein each —($C_{1-2}$ alkylene) is, independently, optionally substituted with 1-2 halide.

In some embodiments of Formula I, $R^2$ is —($C_{1-2}$ alkylene)$_p$carbocyclyl optionally substituted with 1-3 R, wherein the —($C_{1-5}$ alkylene) is optionally substituted with 1-2 halide and wherein the carbocyclyl is selected from the group consisting of cyclopropyl, cyclobutyl, cyclopentyl, cyclohexyl, and spiro[3.3]heptanyl.

In some embodiments of Formula I, $R^2$ is —($C_{1-2}$ alkylene)$_p$carbocyclyl optionally substituted with 1-3 R, wherein the —($C_{1-2}$ alkylene) is optionally substituted with 1-2 halide (e.g., F, Cl) and wherein the carbocyclyl is selected from the group consisting of cyclopropyl, cyclobutyl, cyclopentyl, cyclohexyl, bicyclo[3.1.0]hexane, bicyclo[2.2.1]heptane, and spiro[3.3]heptanyl.

In some embodiments of Formula I, $R^2$ is selected from the group consisting of unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), —($C_{2-4}$ alkylene)OR, —($C_{2-4}$ alkylene)CN, —($C_{1-2}$ alkylene)$_p$heterocyclyl optionally substituted with 1-3 $R^6$, —($C_{1-2}$ alkylene)$_p$aryl optionally substituted with 1-2 $R^{26}$, —($C_{1-2}$ alkylene)$_p$heteroaryl optionally substituted with 1-2 $R^7$, and —($C_{1-2}$ alkylene)$_p$carbocyclyl optionally substituted with 1-3 R, wherein each —($C_{1-2}$ alkylene) is, independently, optionally substituted with 1-2 halide (e.g., F, Cl).

In some embodiments of Formula I, $R^2$ is selected from the group consisting of unsubstituted —($C_{1-5}$ haloalkyl), —($C_{1-4}$ alkylene)OH, —($C_{1-4}$ alkylene)OMe, and —($C_{1}$_4 alkylene)CN.

In some embodiments of Formula I, $R^2$ is selected from the group consisting of:

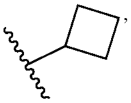,
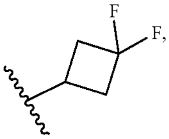
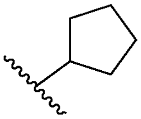,
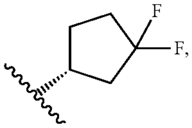
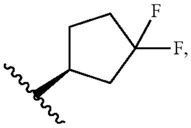
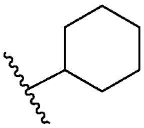,
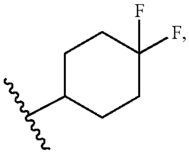
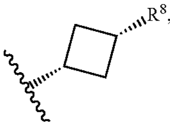
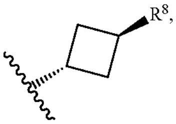
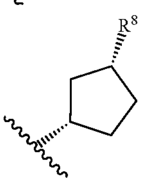,
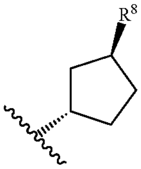,
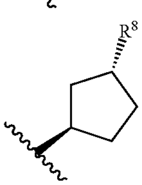,
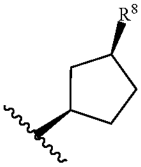,
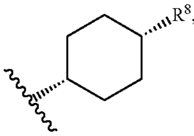
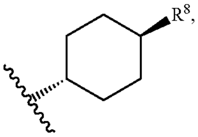
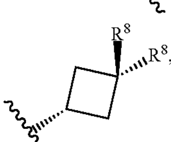
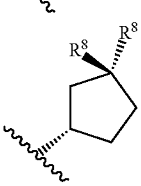,
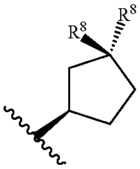,
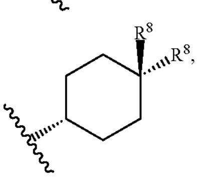 and
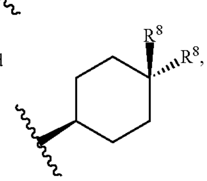

wherein each $R^8$ is independently selected from the group consisting of F, Me, —$CH_2F$, —$CHF_2$, —$CF_3$, —$CH_2OH$, —$CH_2OMe$, —OH, —OMe, —OEt, —$OCD_3$, —$OCF_3$, —$OCH_2CH_2F$, —$OCH_2CHF_2$, —$OCH_2CF_3$, —$OCH_2CH_2OMe$, —$OCH_2CH_2OH$, —$NH_2$, —NHMe, and —$NMe_2$.

In some embodiments of Formula I, $R^2$ is selected from the group consisting of:

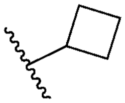,
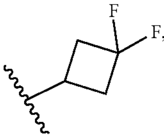
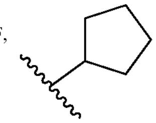,
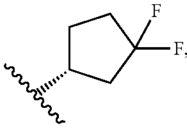
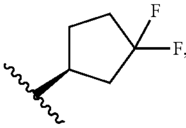
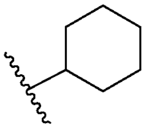,
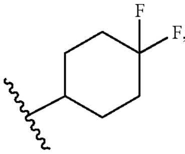
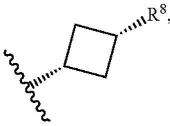
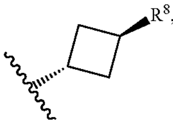
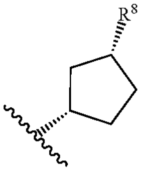,
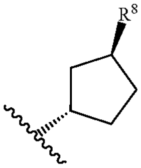,
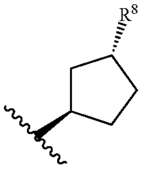,
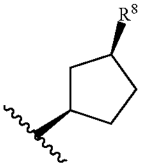,
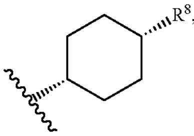
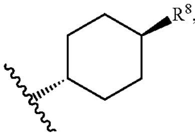
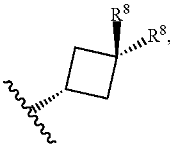
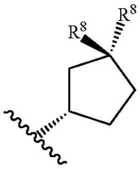,
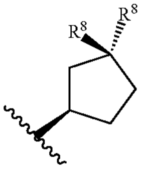,
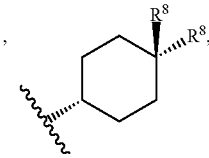
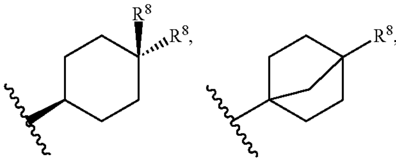 and -continued

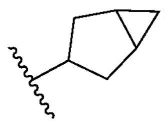

wherein each $R^8$ is independently selected from the group consisting of F, Me, $—CH_2F$, $—CHF_2$, $—CF_3$, $—CH_2OH$, $—CH_2OMe$, —OH, —OMe, —OEt, $—OCD_3$, $—OCF_3$, $—OCH_2CH_2F$, $—OCH_2CHF_2$, $—OCH_2CF_3$, $—OCH_2CH_2OMe$, $—OCH_2CH_2OH$, —CN, $—NH_2$, —NHMe, and $—NMe_2$.

In some embodiments of Formula I, $R^2$ is selected from the group consisting of:

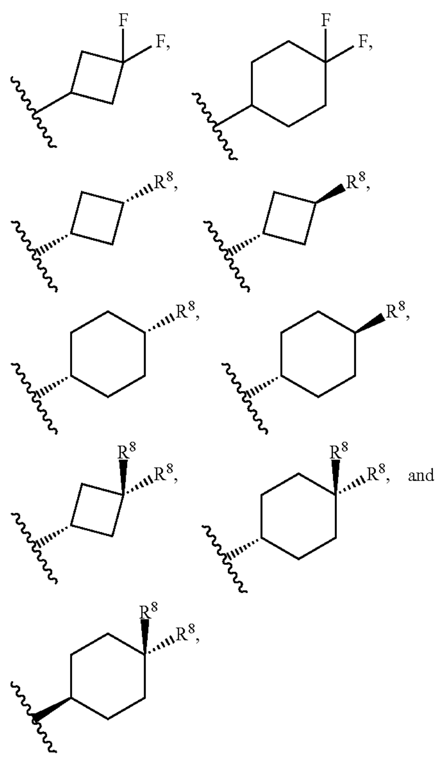

and wherein each $R^8$ is independently selected from the group consisting of F, Me, $—CHF_2$, $—CH_2OMe$, —OH, —OMe, $—OCD_3$, $—OCH_2CHF_2$, and $—OCH_2CH_2OMe$.

In some embodiments of Formula I, $R^2$ is $—(C_{1-2}$ alkylene$)_p$heterocyclyl optionally substituted with 1-3 $R^6$, wherein the $—(C_{1-5}$ alkylene) is optionally substituted with 1-2 halide and wherein the heterocyclyl is selected from the group consisting of oxetanyl, tetrahydrofuranyl, tetrahydropyranyl, azetidinyl, pyrrolidinyl, piperidinyl, morpholinyl, piperazinyl, oxaspiro[3.3]heptanyl, and oxaspiro[3.3]heptanyl.

In some embodiments of Formula I, $R^2$ is selected from the group consisting of:

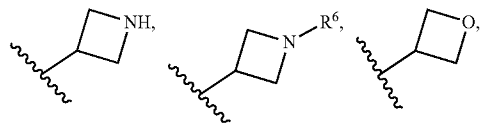

-continued

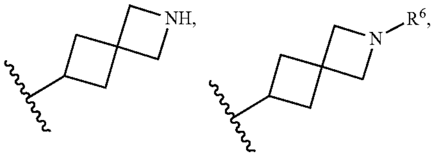

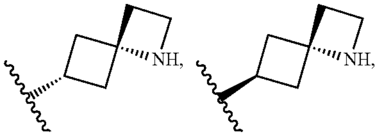

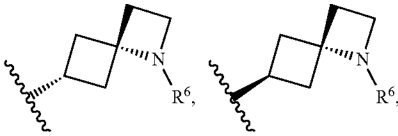

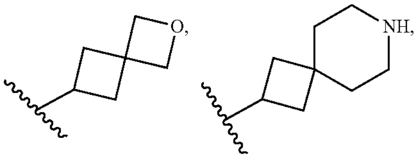

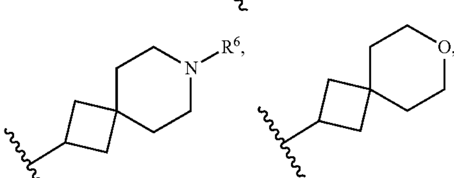

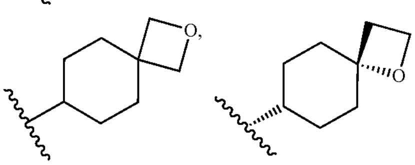

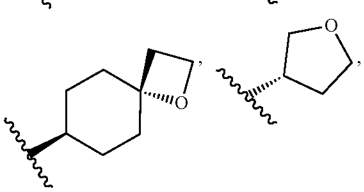

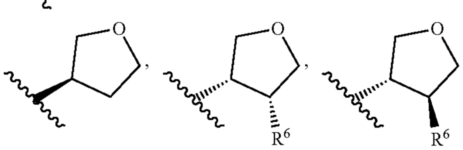

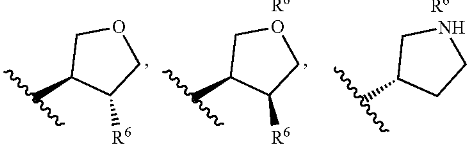

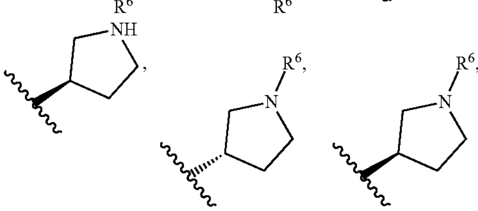

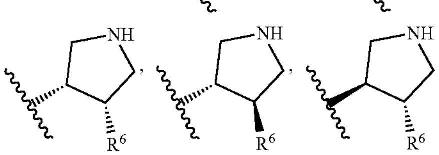

-continued

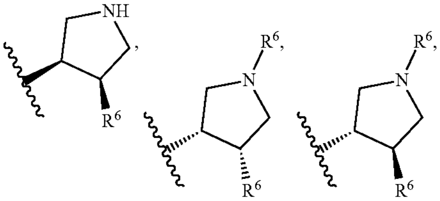

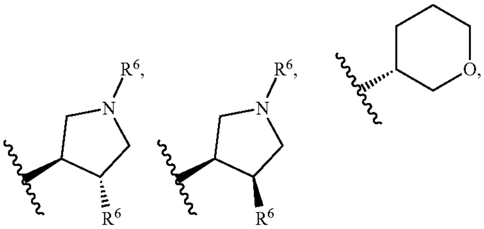

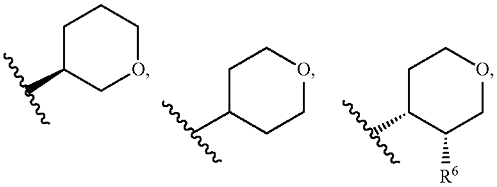

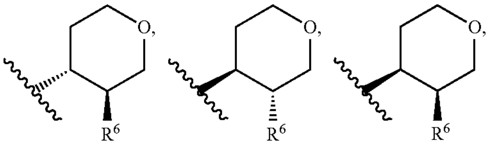

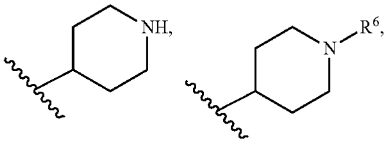

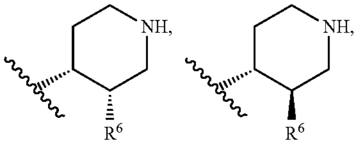

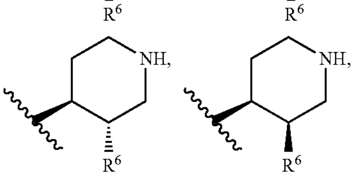

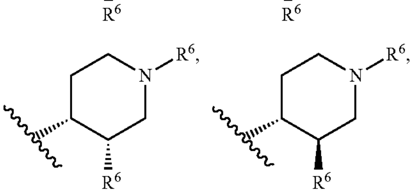

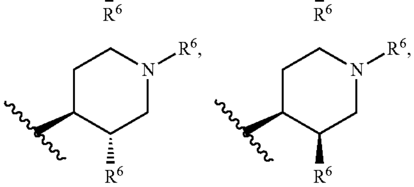

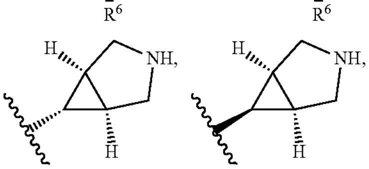

-continued

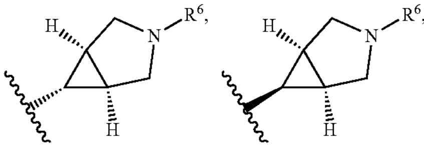

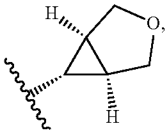 and 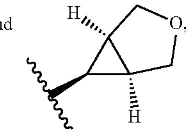

wherein each $R^6$ is independently selected from the group consisting of F, Me, Et, iPr, iBu, $—CH_2F$, $—CHF_2$, $—CF_3$, $—CH_2OH$, $—CH_2OMe$, —OH, —OMe, —OEt, $—OCD_3$, $—OCF_3$, $—CH_2CH_2F$, $—CH_2CHF_2$, $—CH_2CF_3$, $—CH_2CH_2CF_3$, $—CH_2CH_2OMe$, $—CH_2CH_2OH$, —C(═O)Me, —C(═O)Et, —C(═O)iPr,

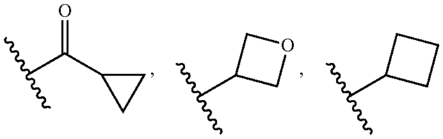

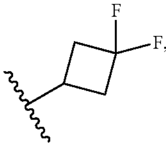

and $—SO_2Me$; with the proviso that F, —OH, —OMe, —OEt, $—OCD_3$, and $—OCF_3$ are not attached to N.

In some embodiments of Formula I, $R^2$ is selected from the group consisting of:

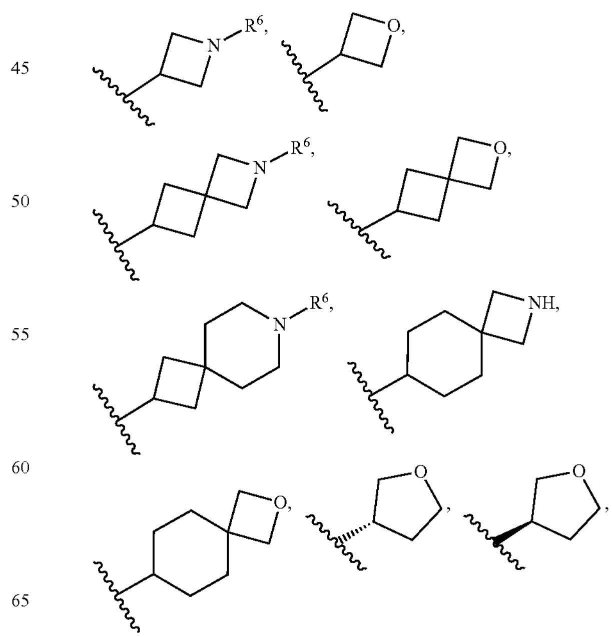

-continued

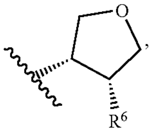, 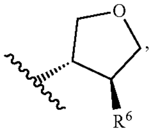, 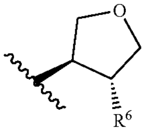,

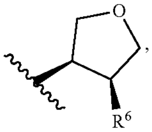, 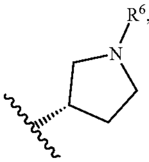, 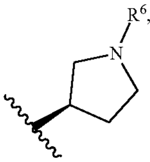,

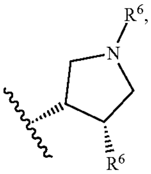, 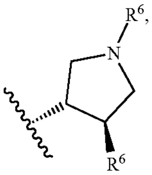, 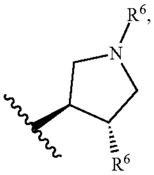,

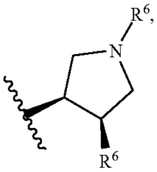, 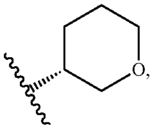, 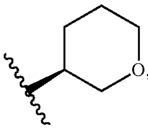,

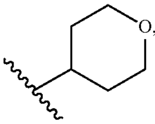, 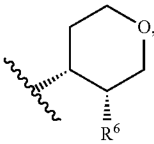, 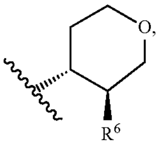,

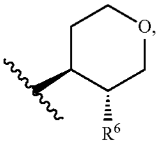, 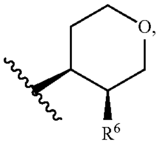, 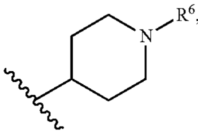,

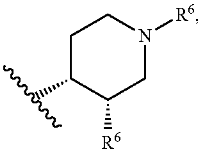, 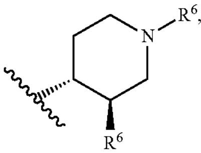,

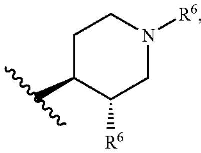, 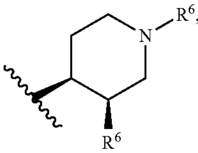,

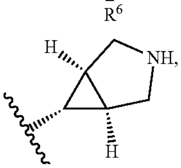, 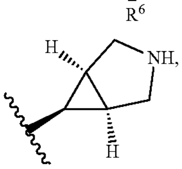,

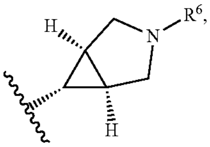, 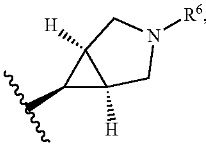,

-continued

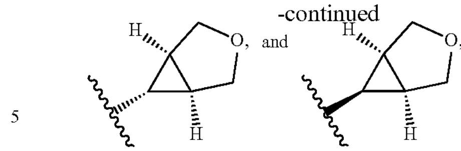

and wherein each $R^6$ is independently selected from the group consisting of F, Me, iBu, —OH, —OMe, —$CH_2CH_2F$, —$CH_2CHF_2$, —$CH_2CF_3$, —$CH_2CH_2CF_3$, —$CH_2CH_2OMe$, —$CH_2CH_2OH$, —C(═O)Me, —C(═O)Et, and —C(═O)iPr; with the proviso that F, —OH, —OMe are not attached to N.

In some embodiments of Formula I, $R^2$ is -heteroaryl optionally substituted with 1-2 $R^7$, wherein the heteroaryl is pyrazolyl.

In some embodiments of Formula I, $R^2$ is —($C_{1-2}$ alkylene)heteroaryl optionally substituted with 1-2 $R^7$, wherein the heteroaryl is pyridine.

In some embodiments of Formula I, $R^2$ is —($C_{1-2}$ alkylene)aryl optionally substituted with 1-2 $R^7$, wherein the aryl is phenyl.

In some embodiments of Formula I, $R^3$ is selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, $R^3$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -heterocyclyl optionally substituted with 1-10 (e.g., 1-9, 1-8, 1-7, 1-6, 1-5, 1-4, 1-3, 1-2, 1) $R^{18}$.

In some embodiments of Formula I, $R^3$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-9}$ haloalkyl).

In some embodiments of Formula I, $R^3$ is selected from the group consisting of unsubstituted —($C_{1-5}$ alkyl), unsubstituted —($C_{1-5}$ haloalkyl), and -heterocyclyl optionally substituted with 1-2 $R^{18}$.

In some embodiments of Formula I, $R^3$ is selected from the group consisting of H, unsubstituted —($C_{1-3}$ alkyl), and unsubstituted —($C_{1-3}$ haloalkyl).

In some embodiments of Formula I, $R^3$ is unsubstituted —($C_{1-3}$ alkyl).

In some embodiments of Formula I, $R^3$ is Me.

In some embodiments of Formula I, $R^3$ is unsubstituted —($C_{1-3}$ haloalkyl).

In some embodiments of Formula I, $R^3$ is selected from the group consisting of —$CH_2F$, —$CHF_2$, —$CF_3$, —$CH_2CH_2F$, —$CH_2CHF_2$, and —$CH_2CF_3$.

In some embodiments of Formula I, $R^3$ is an unsubstituted -heterocyclyl.

In some embodiments of Formula I, $R^3$ is an unsubstituted -(3-4 membered heterocyclyl).

In some embodiments of Formula I, $R^3$ is an unsubstituted -(4 membered heterocyclyl).

In some embodiments of Formula I, each $R^4$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$O$R^9$, —($C_{1-5}$alkylene)CN, —($C_{1-5}$ alkylene)$_p$heterocyclyl optionally substituted with 1-10 (e.g., 1-9, 1-8, 1-7, 1-6, 1-5, 1-4, 1-3, 1-2, 1) $R^{10}$, -carbocyclyl optionally substituted with 1-12 (e.g., 1-11, 1-10, 1-9, 1-8, 1-7, 1-6, 1-5, 1-4, 1-3, 1-2, 1) $R^{11}$, —($C_{1-5}$ alkylene)$_p$heteroaryl optionally substituted with 1-10 (e.g., 1-9, 1-8, 1-7, 1-6, 1-5, 1-4, 1-3, 1-2, 1) $R^{20}$, —($C_{1-5}$ alkylene)$_p$C(=O)N($R^{12}$)$_2$, and —C(=O)$R^{13}$, wherein each —($C_{1-5}$ alkylene) is, independently, optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, each $R^4$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$O$R^9$, —($C_{1-2}$ alkylene)$_p$O$R^9$, —($C_{1-4}$ alkylene)CN, —($C_{1-2}$ alkylene)CN, —($C_{1-2}$ alkylene)$_p$heterocyclyl optionally substituted with 1-2 $R^{10}$, -carbocyclyl optionally substituted with 1-2 $R^{11}$, —($C_{1-2}$ alkylene)$_p$heteroaryl optionally substituted with 1-2 $R^{20}$, —($C_{1-2}$ alkylene)$_p$C(=O)N($R^{12}$)$_2$, and —C(=O)$R^{13}$, wherein each —($C_{1-2}$ alkylene) or —($C_{1-4}$ alkylene) is, independently, optionally substituted with 1-2 halide.

In some embodiments of Formula I, each $R^4$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), unsubstituted —($C_{2-9}$ haloalkenyl), —($C_{1-5}$ alkylene)$_p$O$R^9$, —($C_{1-5}$ alkylene)$_p$CN, —($C_{1-5}$ alkylene)$_p$heterocyclyl optionally substituted with 1-10 $R^{10}$, -carbocyclyl optionally substituted with 1-12 $R^{11}$, —($C_{1-5}$ alkylene)$_p$heteroaryl optionally substituted with 1-10 $R^{20}$, —($C_{1-5}$ alkylene)$_p$C(=O)N($R^{12}$)$_2$, and —C(=O)$R^{13}$, wherein each —($C_{1-5}$ alkylene) is, independently, optionally substituted with 1-5 halide and/or 1-3 unsubstituted —($C_{1-3}$ alkyl).

In some embodiments of Formula I, each $R^4$ is independently selected from the group consisting of halide (e.g., F, Cl), unsubstituted —($C_{1-4}$ alkyl), unsubstituted —($C_{2-4}$ alkenyl), unsubstituted —($C_{2-4}$ alkynyl), unsubstituted —($C_{1-4}$ haloalkyl), unsubstituted —($C_{2-4}$ haloalkenyl), —($C_{1-4}$ alkylene)$_p$O$R^9$, —($C_{1-2}$ alkylene)O$R^9$, —($C_{1-4}$ alkylene)CN, —($C_{1-2}$ alkylene)CN, —($C_{1-2}$ alkylene)$_p$heterocyclyl optionally substituted with 1-2 $R^{10}$, -carbocyclyl optionally substituted with 1-2 $R^{11}$, —($C_{1-2}$ alkylene)$_p$heteroaryl optionally substituted with 1-2 $R^{20}$, —($C_{1-2}$ alkylene)$_p$C(=O)N($R^{12}$)$_2$, and —C(=O)$R^{13}$, wherein each —($C_{1-2}$ alkylene) or —($C_{1-4}$ alkylene) is, independently, optionally substituted with 1-2 halide (e.g., F, Cl).

In some embodiments of Formula I, each $R^4$ is independently selected from the group consisting of F, Cl, unsubstituted —($C_{1-5}$ alkyl), unsubstituted —($C_{1-5}$ haloalkyl), —($C_{1-4}$ alkylene)$_p$OH, —($C_{1-2}$ alkylene)$_p$OMe, —($C_{1-4}$ alkylene)CN, —($C_{1-2}$ alkylene)CN, —($CH_2$)$_p$heterocyclyl optionally substituted with 1-2 $R^{10}$, -carbocyclyl optionally substituted with 1-2 $R^{11}$, —($CH_2$)$_p$heteroaryl optionally substituted with 1-2 $R^{20}$, —($CH_2$)C(=O)N(Me)$_2$, and —C(=O)$R^{13}$, wherein each —($C_{1-2}$ alkylene) or —($C_{1-4}$ alkylene) is, independently, optionally substituted with 1-2 halide.

In some embodiments of Formula I, each $R^4$ is independently selected from the group consisting of halide (e.g., F, Cl, Br, I), unsubstituted —($C_{1-4}$ alkyl), unsubstituted —($C_{1-4}$ haloalkyl), -heterocyclyl optionally substituted with 1-3 (e.g., 1-2, 1) $R^{10}$, and -carbocyclyl optionally substituted with 1-3 (e.g., 1-2, 1) $R^{11}$.

In some embodiments of Formula I, each $R^4$ is independently selected from the group consisting of halide, unsubstituted —($C_{1-3}$ alkyl), unsubstituted —($C_{1-3}$ haloalkyl), —($C_{1-3}$ alkylene)$_p$O$R^9$, -heterocyclyl optionally substituted with 1-2 $R^{10}$, -carbocyclyl optionally substituted with 1-2 $R^{11}$, and —C(=O)$R^{13}$.

In some embodiments of Formula I, each $R^4$ is independently selected from the group consisting of halide, unsubstituted —($C_{1-3}$ alkyl), unsubstituted —($C_{1-3}$ haloalkyl), —($C_{1-3}$ alkylene)OH, —($C_{1-3}$ alkylene)OMe, —CN, and —C(=O)N($R^{12}$)$_2$.

In some embodiments of Formula I, each $R^4$ is independently selected from the group consisting of chloro, methyl, ethyl, isopropyl, 2-fluoroethyl, 2,2-difluoroethyl, methoxy, methoxymethyl, tetrahydropyranyl, difluorocyclobutyl, and (pyrrolidin-1-yl)methanone.

In some embodiments of Formula I, each $R^5$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^5$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments of Formula I, each $R^5$ is independently selected from the group consisting of H, unsubstituted —($C_{1-3}$ alkyl), and unsubstituted —($C_{1-3}$ haloalkyl).

In some embodiments of Formula I, each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 (e.g., 1-9, 1-8, 1-7, 1-6, 1-5, 1-4, 1-3, 1-2, 1) $R^{16}$, —($C_{1-5}$ alkylene)$_p$O$R^{21}$, —SO$_2$$R^{23}$, and —C(=O)$R^{24}$, wherein the —($C_{1-5}$ alkylene) is optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, each $R^6$ is independently selected from the group consisting of each $R^6$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 (e.g., 1-9, 1-8, 1-7, 1-6, 1-5, 1-4, 1-3, 1-2, 1) $R^{16}$, -carbocyclyl optionally substituted with 1-12 (e.g., 1-11, 1-10, 1-9, 1-8, 1-7, 1-6, 1-5, 1-4, 1-3, 1-2, 1) $R^{17}$, —($C_{1-5}$ alkylene)$_p$O$R^{21}$, —SO$_2$$R^{23}$, and —C(=O)$R^{24}$, wherein the —($C_{1-5}$ alkylene) is optionally substituted with 1-5 halide (e.g., F, Cl, Br, I) and/or 1-3 (e.g., 1-2, 1) unsubstituted —($C_{1-3}$ alkyl).

In some embodiments of Formula I, each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{16}$, -carbocyclyl optionally substituted with 1-12 $R^{17}$, —($C_{1-5}$ alkylene)$_p$O$R^{21}$, —($C_1$-s alkylene)CN, —SO$_2$$R^{23}$, and —C(=O)$R^{24}$, wherein the —($C_{1-5}$ alkylene) is optionally substituted with 1-5 halide and/or 1-3 unsubstituted —($C_{1-3}$ alkyl).

In some embodiments of Formula I, each $R^6$ is independently selected from the group consisting of F, Cl, unsubstituted —($C_{1-4}$ alkyl), unsubstituted —($C_{1-4}$ haloalkyl), -heterocyclyl optionally substituted with 1-2 $R^{16}$, —($C_{1-2}$ alkylene)$_p$O$R^{21}$, —($C_{1-2}$ alkylene)CN, —SO$_2$$R^{23}$, and —C(=O)$R^{24}$, wherein the —($C_{1-2}$ alkylene) is optionally substituted with 1-2 halide (e.g., F, Cl).

In some embodiments of Formula I, each $R^6$ is independently selected from the group consisting of F, Cl, unsubstituted —($C_{1-5}$ alkyl), unsubstituted —($C_{1-5}$ haloalkyl), -heterocyclyl optionally substituted with 1-2 $R^{16}$, —($C_{1-2}$ alkylene)$_p$OR$^{21}$, —SO$_2$R$^{23}$, and —C(═O)R$^{24}$, wherein the —(C$_{1-2}$ alkylene) is optionally substituted with 1-2 halide.

In some embodiments of Formula I, each R$^6$ is independently selected from the group consisting of F, Cl, unsubstituted —(C$_{1-5}$ alkyl), unsubstituted —(C$_{1-5}$ haloalkyl), -heterocyclyl optionally substituted with 1-2 R$^{16}$, —OH, —OMe, —SO$_2$Me, and —C(═O)R$^{24}$.

In some embodiments of Formula I, each R$^6$ is independently selected from the group consisting of each R$^6$ is independently selected from the group consisting of F, Cl, unsubstituted —(C$_{1-5}$ alkyl), unsubstituted —(C$_{1-5}$ haloalkyl), -heterocyclyl optionally substituted with 1-2 R$^{16}$, -carbocyclyl optionally substituted with 1-4 R$^{11}$, and —C(═O) R$^{24}$.

In some embodiments of Formula I, two R$^6$ attached to the same carbon atom are taken together to form a carbonyl group.

In some embodiments of Formula I, each R$^7$ is independently selected from the group consisting of halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), and —OMe.

In some embodiments of Formula I, each R$^7$ is independently selected from the group consisting of F, Cl, Me, CF$_3$, and —OMe.

In some embodiments of Formula I, each R$^8$ is independently selected from the group consisting of halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —N(R$^{14}$)$_2$, —(C$_{1-5}$ alkylene)$_p$OR$^{15}$, —(C$_{1-5}$ alkylene)$_p$heterocyclyl optionally substituted with 1-10 (e.g., 1-9, 1-8, 1-7, 1-6, 1-5, 1-4, 1-3, 1-2, 1) R$^{16}$, —C(═O)R$^{22}$, and —NHC(═O)R$^{23}$, wherein each —(C$_{1-5}$ alkylene) is, independently, optionally substituted with 1-5 (e.g., 1-4, 1-3, 1-2, 1) halide (e.g., F, Cl, Br, I) and/or 1-3 (e.g., 1-2, 1) unsubstituted —(C$_{1-3}$ alkyl).

In some embodiments of Formula I, each R$^8$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —N(R$^{14}$)$_2$, —(C$_{1-5}$ alkylene)$_p$OR$^5$, —CN, —(C$_{1-5}$ alkylene)$_p$heterocyclyl optionally substituted with 1-10 R$^{16}$, —C(═O)R$^{22}$, and —NR$^{14}$C(═O)R$^{23}$, wherein each —(C$_{1-5}$ alkylene) is, independently, optionally substituted with 1-5 halide and/or 1-3 unsubstituted —(C$_{1-3}$ alkyl).

In some embodiments of Formula I, each R$^8$ is independently selected from the group consisting of halide (e.g., F, Cl), unsubstituted —(C$_{1-4}$ alkyl), unsubstituted —(C$_{2-4}$ alkenyl), unsubstituted —(C$_{2-4}$ alkynyl), unsubstituted —(C$_{1-4}$ haloalkyl), —N(R$^{14}$)$_2$, —(C$_{1-2}$ alkylene)$_p$OR$^5$, —CN, —(C$_{1-2}$ alkylene)$_p$heterocyclyl optionally substituted with 1-2 R$^{16}$, —C(═O)R$^{22}$, and —NHC(═O)R$^{23}$, wherein each —(C$_{1-2}$ alkylene) is, independently, optionally substituted with 1-2 halide (e.g., F, Cl).

In some embodiments of Formula I, each R$^8$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —N(R$^{14}$)$_2$, —(C$_{1-2}$ alkylene)$_p$OR$^5$, —(C$_{1-2}$ alkylene)$_p$heterocyclyl optionally substituted with 1-2 R$^{16}$, —C(═O)R$^{22}$, and —NHC(═O)R$^{23}$, wherein each —(C$_{1-2}$ alkylene) is, independently, optionally substituted with 1-2 halide.

In some embodiments of Formula I, each R$^9$ is independently selected from the group consisting of H, unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{10}$ is independently selected from the group consisting of halide (e.g., F, Cl, Br, I), unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{11}$ is independently selected from the group consisting of halide (e.g., F, Cl, Br, I), unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{12}$ is independently selected from the group consisting of H, unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl), —(C$_{1-5}$ alkylene)$_p$carbocyclyl optionally substituted with 1-12 (e.g., 1-11, 1-10, 1-9, 1-8, 1-7, 1-6, 1-5, 1-4, 1-3, 1-2, 1) R$^{17}$, -heterocyclyl optionally substituted with 1-10 (e.g., 1-9, 1-8, 1-7, 1-6, 1-5, 1-4, 1-3, 1-2, 1) R$^{18}$, and -heteroaryl optionally substituted with 1-10 (e.g., 1-9, 1-8, 1-7, 1-6, 1-5, 1-4, 1-3, 1-2, 1) R$^{19}$, wherein —(C$_{1-5}$ alkylene) is optionally substituted with 1-5 (e.g., 1-4, 1-3, 1-2, 1) halide (e.g., F, Cl, Br, I) and/or 1-3 (e.g., 1-2, 1) unsubstituted —(C$_{1-3}$ alkyl).

In some embodiments of Formula I, each R$^{13}$ is -heterocyclyl optionally substituted with 1-10 (e.g., 1-9, 1-8, 1-7, 1-6, 1-5, 1-4, 1-3, 1-2, 1) R$^{18}$.

In some embodiments of Formula I, each R$^{14}$ is independently selected from the group consisting of H, unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{15}$ is independently selected from the group consisting of H, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), and —(C$_{1-5}$ alkylene)$_p$OR$^{21}$.

In some embodiments of Formula I, each R$^{16}$ is independently selected from the group consisting of halide (e.g., F, Cl, Br, I), unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{16}$ is independently selected from the group consisting of halide, —CN, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), and -carbocyclyl optionally substituted with 1-12 R$^{27}$.

In some embodiments of Formula I, two R$^{16}$ attached to the same carbon atom are taken together to form a carbonyl group.

In some embodiments of Formula I, each R$^{17}$ is independently selected from the group consisting of halide (e.g., F, Cl, Br, I), —OMe, unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{18}$ is independently selected from the group consisting of halide (e.g., F, Cl, Br, I), unsubstituted —(C$_{1-9}$ alkyl), unsubstituted —(C$_{2-9}$ alkenyl), unsubstituted —(C$_{2-9}$ alkynyl), and unsubstituted —(C$_{1-9}$ haloalkyl).

In some embodiments of Formula I, each R$^{19}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{20}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{21}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{22}$ is independently selected from the group consisting of -heterocyclyl optionally substituted with 1-10 (e.g., 1-9, 1-8, 1-7, 1-6, 1-5, 1-4, 1-3, 1-2, 1) $R^{18}$, —$N(R^{12})_2$ and —$OR^{21}$.

In some embodiments of Formula I, each $R^{23}$ is independently selected from the group consisting of unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$$OR^{21}$, and -carbocyclyl optionally substituted with 1-12 $R^{25}$.

In some embodiments of Formula I, each $R^{24}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$OR^{23}$, and -carbocyclyl optionally substituted with 1-12 (e.g., 1-11, 1-10, 1-9, 1-8, 1-7, 1-6, 1-5, 1-4, 1-3, 1-2, 1) $R^{25}$.

In some embodiments of Formula I, each $R^{25}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{26}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{27}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, $R^{28}$ is independently selected from the group consisting of H and halide (e.g., F, Cl, Br, I).

In some embodiments of Formula I, $R^{28}$ is independently selected from the group consisting of H and halide (e.g., F, Cl).

In some embodiments of Formula I, $R^{28}$ is independently selected from the group consisting of H and F.

In some embodiments of Formula I, $R^{28a}$ is independently selected from the group consisting of H and halide (e.g., F, Cl, Br, I).

In some embodiments of Formula I, $R^{28a}$ is independently selected from the group consisting of H and halide (e.g., F, Cl).

In some embodiments of Formula I, $R^{28a}$ is independently selected from the group consisting of H and F.

In some embodiments of Formula I, $R^{28b}$ is independently selected from the group consisting of H and D.

In some embodiments of Formula I, each p is independently 0 or 1.

In some embodiments of Formula I, each H atom is optionally, independently replaced by $^2H$ (D) (deuterium).

Illustrative compounds of Formula I are shown in Table 1.

TABLE 1

1

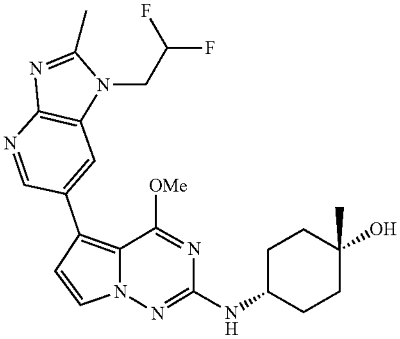 [SMILES: COc1nc(N[C@H]2CC[C@@](C)(O)CC2)nn2ccc(-c3cnc4nc(C)n(CC(F)F)c4c3)c12]

2

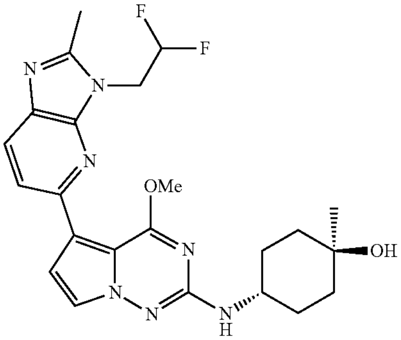 [SMILES: COc1nc(N[C@H]2CC[C@](C)(O)CC2)nn2ccc(-c3ccc4nc(C)n(CC(F)F)c4n3)c12]

3

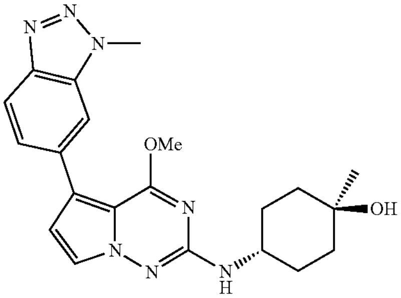 [SMILES: COc1nc(N[C@H]2CC[C@](C)(O)CC2)nn2ccc(-c3ccc4nnn(C)c4c3)c12]

4

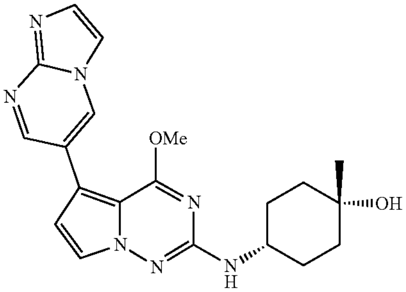 [SMILES: COc1nc(N[C@H]2CC[C@@](C)(O)CC2)nn2ccc(-c3cnc4nccn4c3)c12]

TABLE 1-continued
5
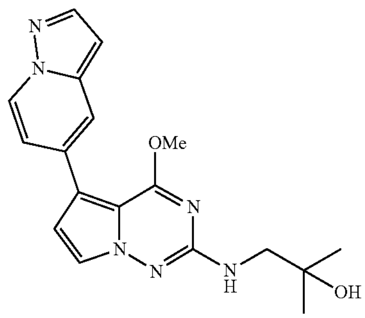 [SMILES: COc1nc(NCC(C)(C)O)nn2ccc(-c3ccn4nccc4c3)c12]
6
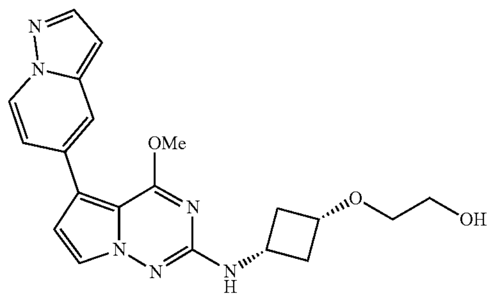 [SMILES: COc1nc(N[C@H]2C[C@@H](OCCO)C2)nn2ccc(-c3ccn4nccc4c3)c12]
7
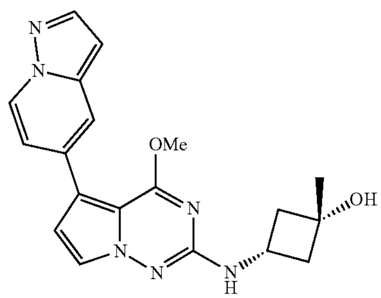 [SMILES: COc1nc(N[C@H]2C[C@@](C)(O)C2)nn2ccc(-c3ccn4nccc4c3)c12]
8
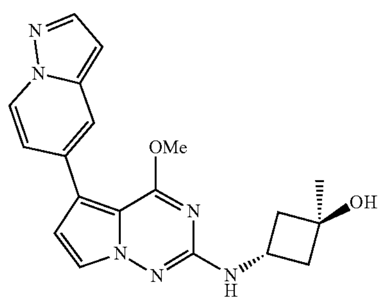 [SMILES: COc1nc(N[C@H]2C[C@](C)(O)C2)nn2ccc(-c3ccn4nccc4c3)c12]
9
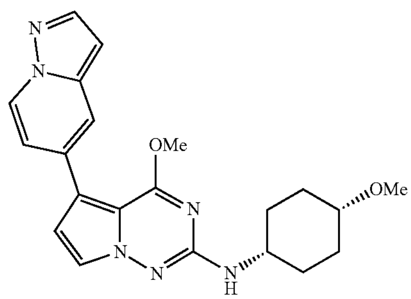 [SMILES: COc1nc(N[C@H]2CC[C@@H](OC)CC2)nn2ccc(-c3ccn4nccc4c3)c12]
TABLE 1-continued
10
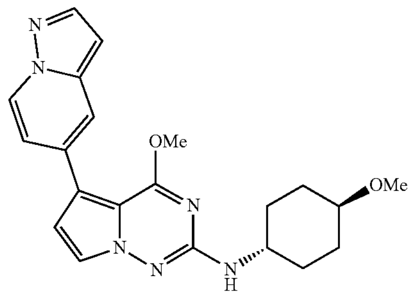 [SMILES: COc1nc(N[C@H]2CC[C@H](OC)CC2)nn2ccc(-c3ccn4nccc4c3)c12]
11
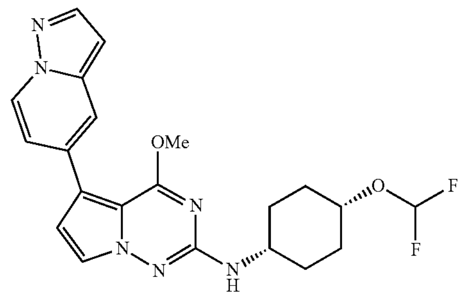 [SMILES: COc1nc(N[C@H]2CC[C@@H](OC(F)F)CC2)nn2ccc(-c3ccn4nccc4c3)c12]
12
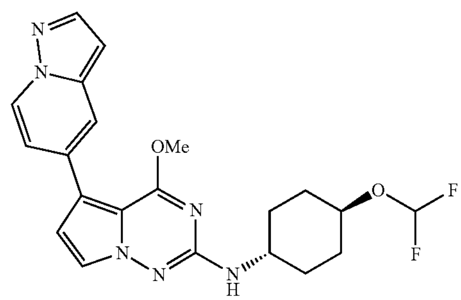 [SMILES: COc1nc(N[C@H]2CC[C@H](OC(F)F)CC2)nn2ccc(-c3ccn4nccc4c3)c12]
13
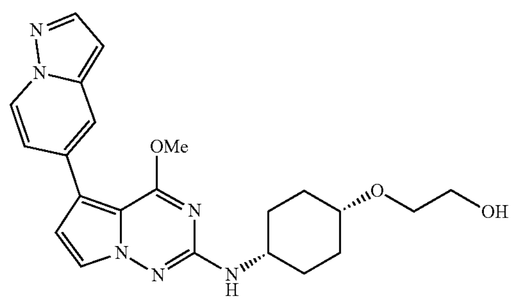 [SMILES: COc1nc(N[C@H]2CC[C@@H](OCCO)CC2)nn2ccc(-c3ccn4nccc4c3)c12]
14
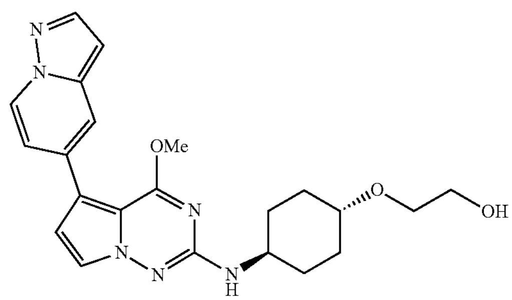 [SMILES: COc1nc(N[C@H]2CC[C@H](OCCO)CC2)nn2ccc(-c3ccn4nccc4c3)c12]

TABLE 1-continued
15
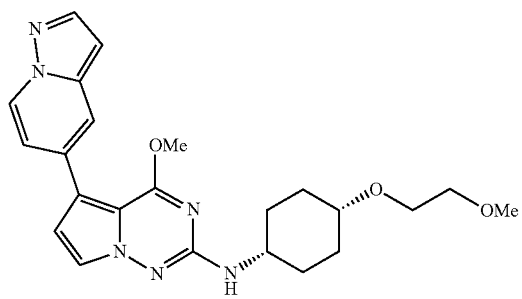 [SMILES: COCCO[C@H]1CC[C@@H](Nc2nc(OC)c3c(-c4ccn5nccc5c4)ccn3n2)CC1]
16
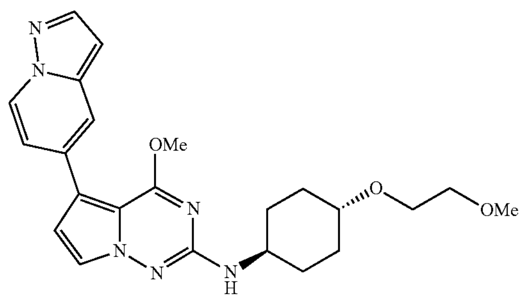 [SMILES: COCCO[C@H]1CC[C@H](Nc2nc(OC)c3c(-c4ccn5nccc5c4)ccn3n2)CC1]
17
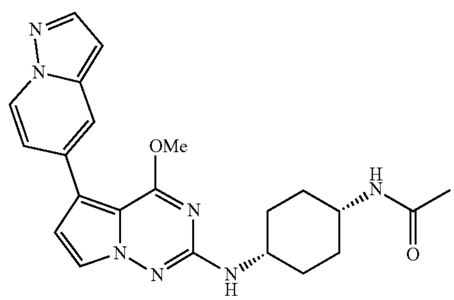 [SMILES: COc1nc(N[C@H]2CC[C@@H](NC(C)=O)CC2)nn2ccc(-c3ccn4nccc4c3)c12]
18
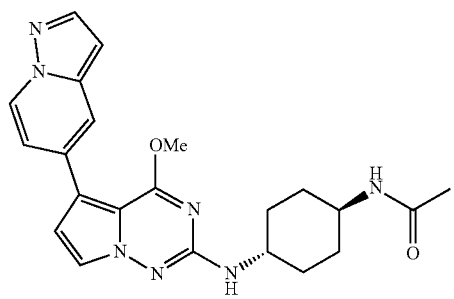 [SMILES: COc1nc(N[C@H]2CC[C@H](NC(C)=O)CC2)nn2ccc(-c3ccn4nccc4c3)c12]
19
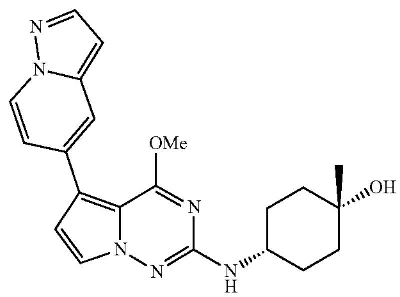 [SMILES: COc1nc(N[C@H]2CC[C@@](C)(O)CC2)nn2ccc(-c3ccn4nccc4c3)c12]
TABLE 1-continued
20
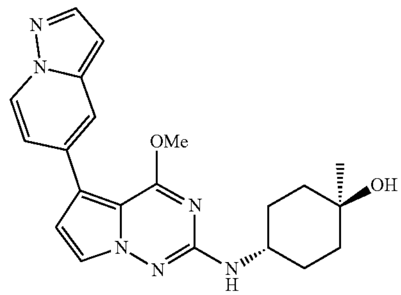 [SMILES: COc1nc(N[C@H]2CC[C@](C)(O)CC2)nn2ccc(-c3ccn4nccc4c3)c12]
21
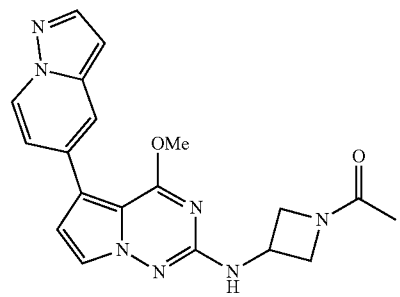 [SMILES: COc1nc(NC2CN(C(C)=O)C2)nn2ccc(-c3ccn4nccc4c3)c12]
22
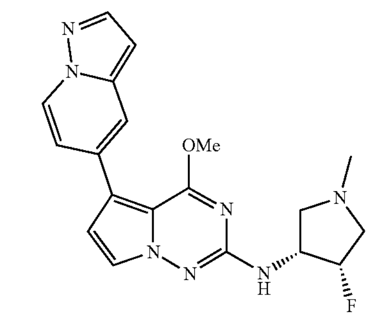 [SMILES: COc1nc(N[C@@H]2CN(C)C[C@@H]2F)nn2ccc(-c3ccn4nccc4c3)c12]
23
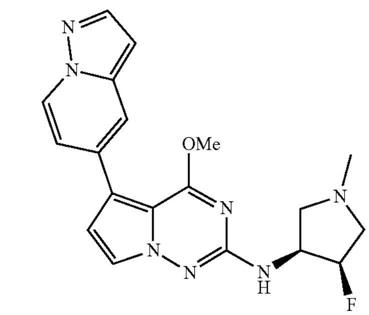 [SMILES: COc1nc(N[C@H]2CN(C)C[C@H]2F)nn2ccc(-c3ccn4nccc4c3)c12]
24
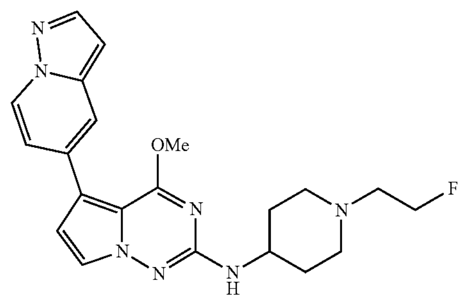 [SMILES: COc1nc(NC2CCN(CCF)CC2)nn2ccc(-c3ccn4nccc4c3)c12]

TABLE 1-continued
25
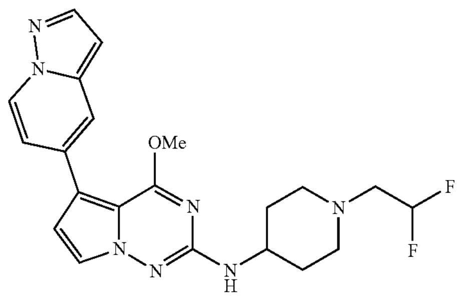 [SMILES: COc1nc(NC2CCN(CC(F)F)CC2)nn2ccc(-c3ccn4nccc4c3)c12]
26
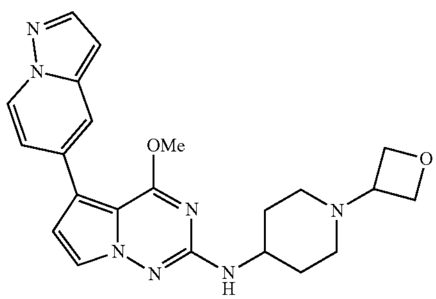 [SMILES: COc1nc(NC2CCN(C3COC3)CC2)nn2ccc(-c3ccn4nccc4c3)c12]
27
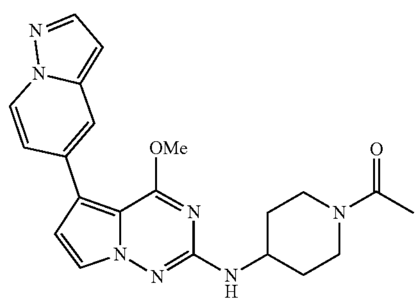 [SMILES: COc1nc(NC2CCN(C(C)=O)CC2)nn2ccc(-c3ccn4nccc4c3)c12]
28
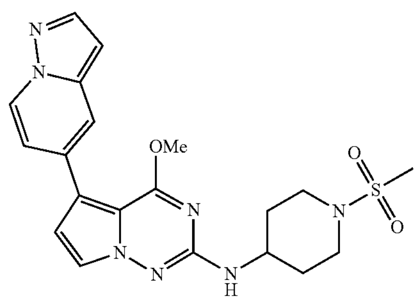 [SMILES: COc1nc(NC2CCN(S(C)(=O)=O)CC2)nn2ccc(-c3ccn4nccc4c3)c12]
29
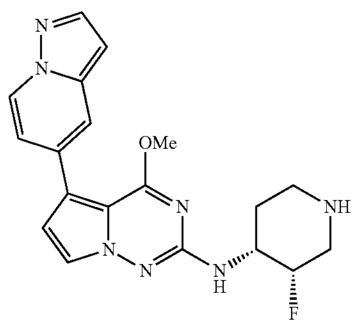 [SMILES: COc1nc(N[C@@H]2CCNC[C@@H]2F)nn2ccc(-c3ccn4nccc4c3)c12]
TABLE 1-continued
30
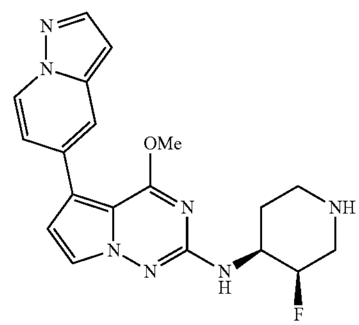 [SMILES: COc1nc(N[C@H]2CCNC[C@H]2F)nn2ccc(-c3ccn4nccc4c3)c12]
31
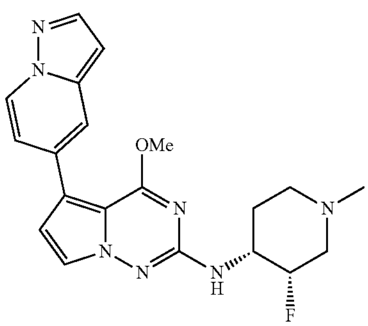 [SMILES: COc1nc(N[C@@H]2CCN(C)C[C@@H]2F)nn2ccc(-c3ccn4nccc4c3)c12]
32
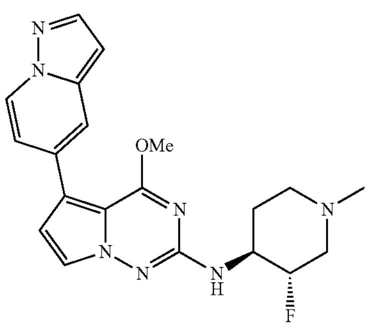 [SMILES: COc1nc(N[C@H]2CCN(C)C[C@@H]2F)nn2ccc(-c3ccn4nccc4c3)c12]
33
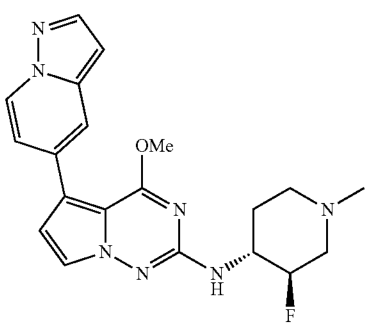 [SMILES: COc1nc(N[C@@H]2CCN(C)C[C@H]2F)nn2ccc(-c3ccn4nccc4c3)c12]
34
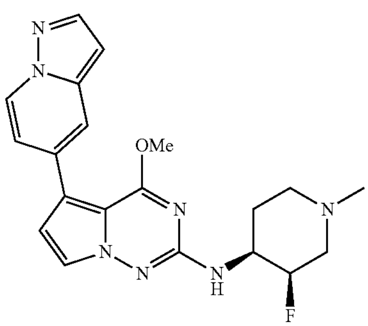 [SMILES: COc1nc(N[C@H]2CCN(C)C[C@H]2F)nn2ccc(-c3ccn4nccc4c3)c12]

TABLE 1-continued
35
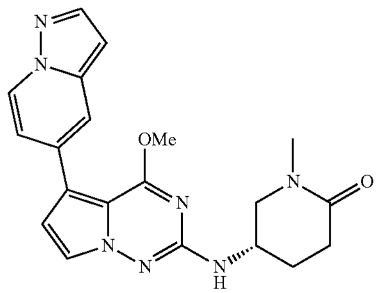 [SMILES: COc1nc(N[C@H]2CCC(=O)N(C)C2)nn2ccc(-c3ccn4nccc4c3)c12]
36
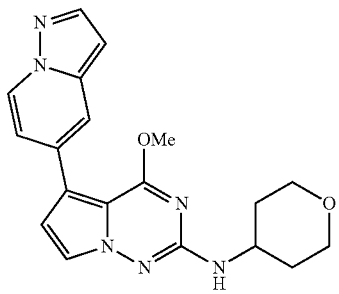 [SMILES: COc1nc(NC2CCOCC2)nn2ccc(-c3ccn4nccc4c3)c12]
37
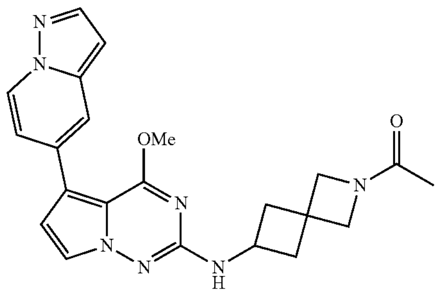 [SMILES: COc1nc(NC2CC3(C2)CN(C(C)=O)C3)nn2ccc(-c3ccn4nccc4c3)c12]
38
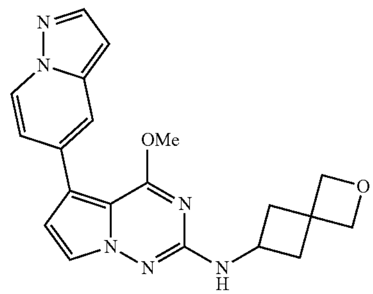 [SMILES: COc1nc(NC2CC3(COC3)C2)nn2ccc(-c3ccn4nccc4c3)c12]
39
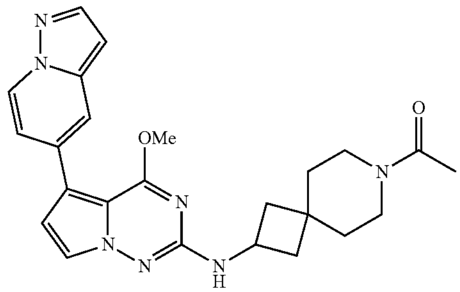 [SMILES: COc1nc(NC2CC3(CCN(C(C)=O)CC3)C2)nn2ccc(-c3ccn4nccc4c3)c12]
TABLE 1-continued
40
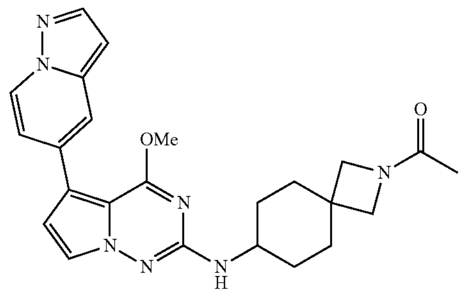 [SMILES: COc1nc(NC2CCC3(CC2)CN(C(C)=O)C3)nn2ccc(-c3ccn4nccc4c3)c12]
41
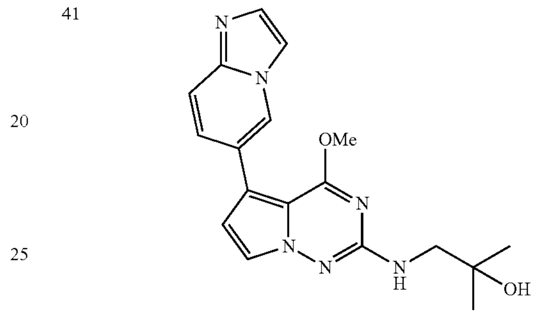
42
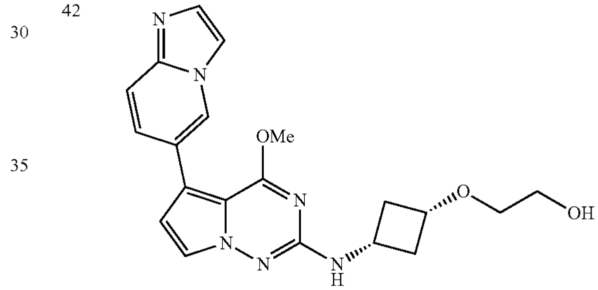
43
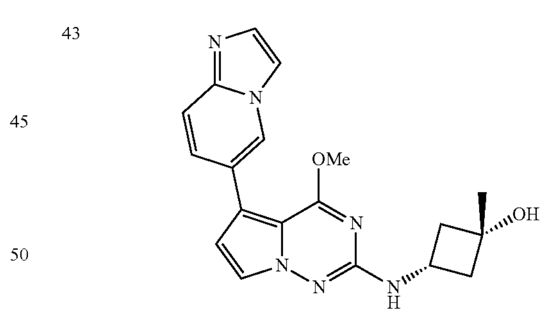
44
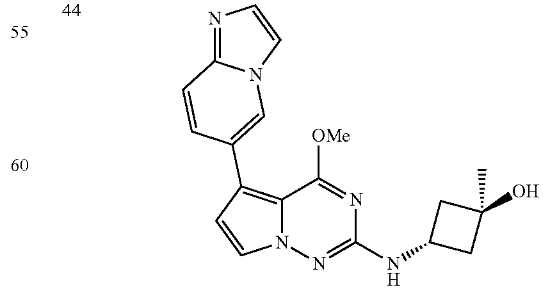

TABLE 1-continued
45
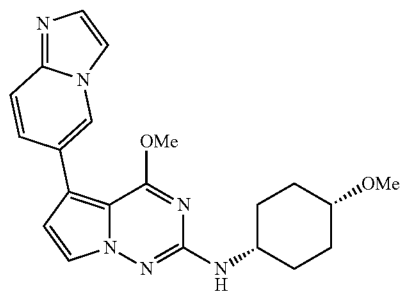 [SMILES: COc1nc(N[C@H]2CC[C@@H](OC)CC2)nn2ccc(-c3ccc4nccn4c3)c12]
46
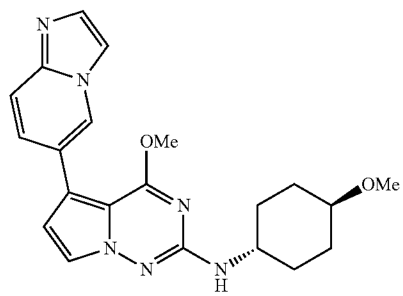 [SMILES: COc1nc(N[C@H]2CC[C@H](OC)CC2)nn2ccc(-c3ccc4nccn4c3)c12]
47
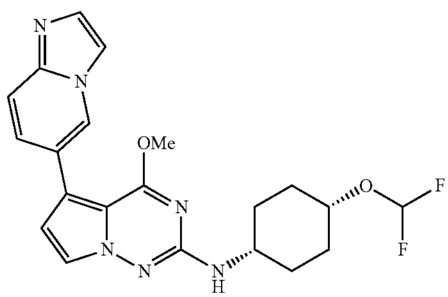 [SMILES: COc1nc(N[C@H]2CC[C@@H](OC(F)F)CC2)nn2ccc(-c3ccc4nccn4c3)c12]
48
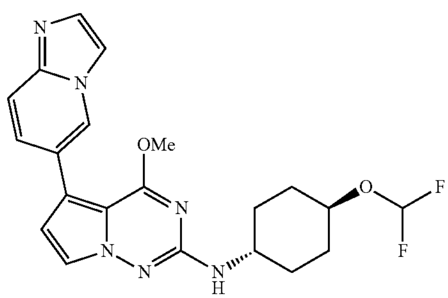 [SMILES: COc1nc(N[C@H]2CC[C@H](OC(F)F)CC2)nn2ccc(-c3ccc4nccn4c3)c12]
49
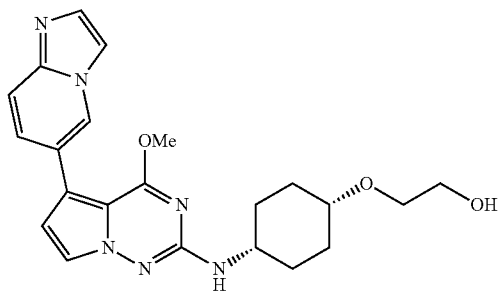 [SMILES: COc1nc(N[C@H]2CC[C@@H](OCCO)CC2)nn2ccc(-c3ccc4nccn4c3)c12]
TABLE 1-continued
50
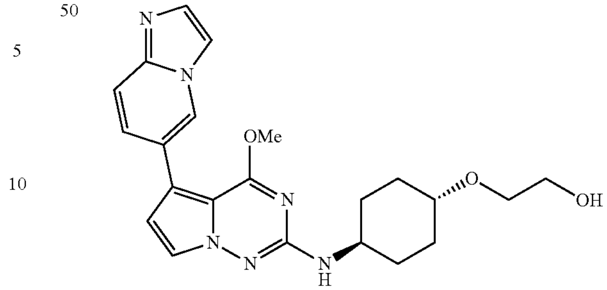
51
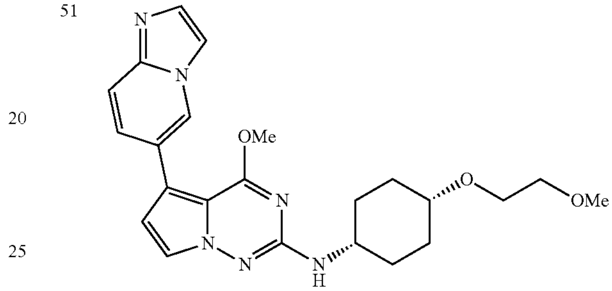
52
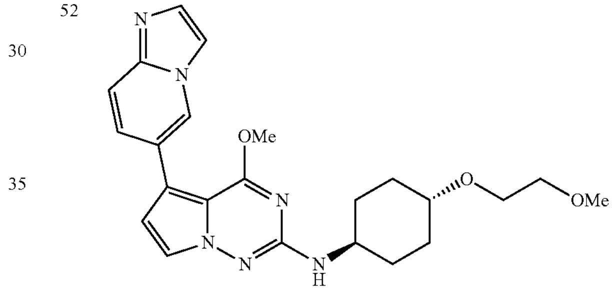
53
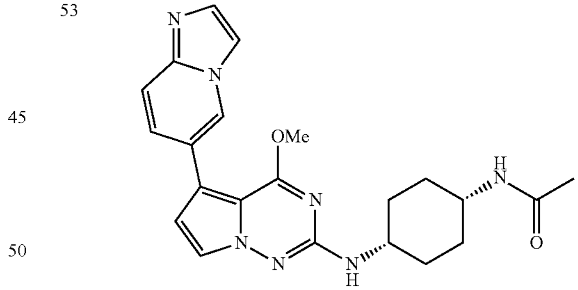
54
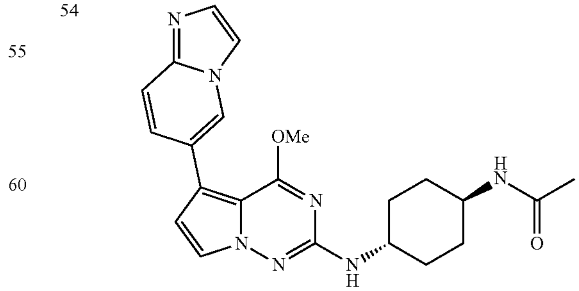

TABLE 1-continued
55
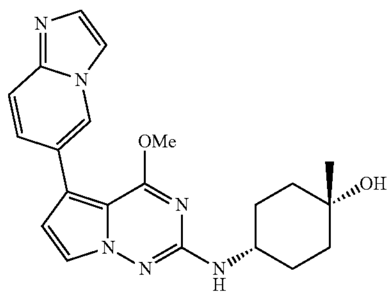 [SMILES: COc1nc(N[C@H]2CC[C@@](C)(O)CC2)nn2ccc(-c3ccc4nccn4c3)c12]
56
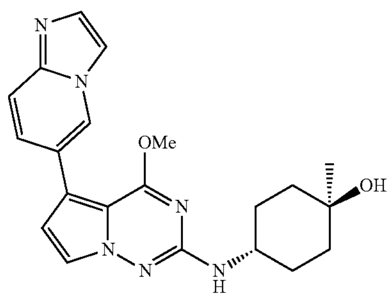 [SMILES: COc1nc(N[C@H]2CC[C@](C)(O)CC2)nn2ccc(-c3ccc4nccn4c3)c12]
57
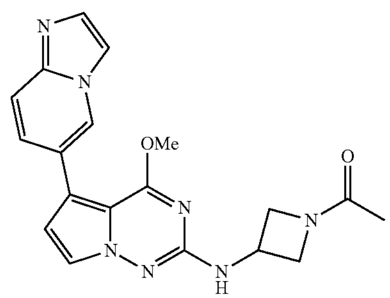 [SMILES: COc1nc(NC2CN(C(C)=O)C2)nn2ccc(-c3ccc4nccn4c3)c12]
58
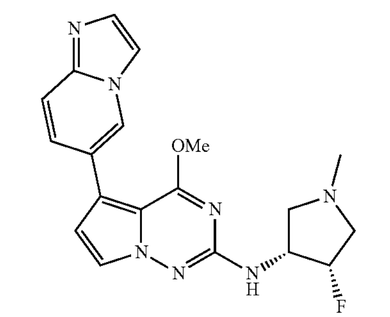 [SMILES: COc1nc(N[C@@H]2CN(C)C[C@@H]2F)nn2ccc(-c3ccc4nccn4c3)c12]
59
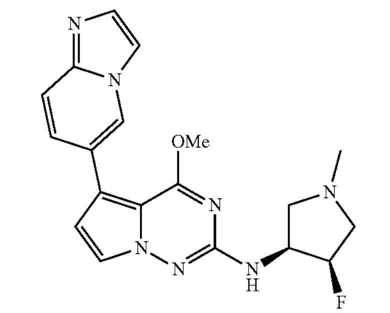 [SMILES: COc1nc(N[C@H]2CN(C)C[C@H]2F)nn2ccc(-c3ccc4nccn4c3)c12]
TABLE 1-continued
60
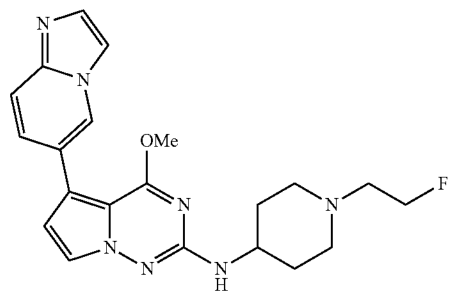 [SMILES: COc1nc(NC2CCN(CCF)CC2)nn2ccc(-c3ccc4nccn4c3)c12]
61
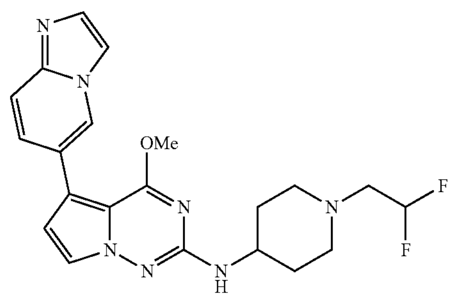 [SMILES: COc1nc(NC2CCN(CC(F)F)CC2)nn2ccc(-c3ccc4nccn4c3)c12]
62
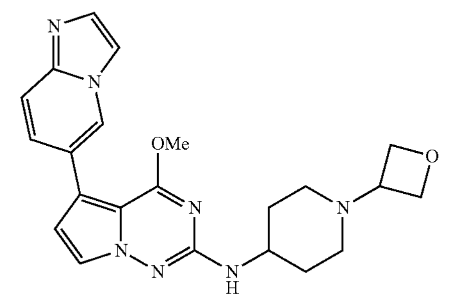 [SMILES: COc1nc(NC2CCN(C3COC3)CC2)nn2ccc(-c3ccc4nccn4c3)c12]
63
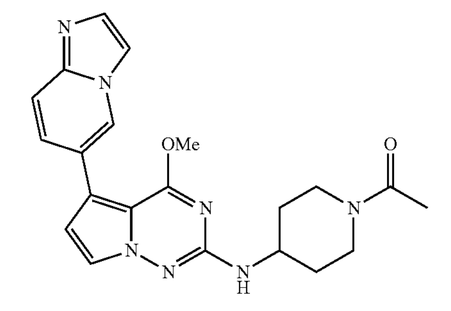 [SMILES: COc1nc(NC2CCN(C(C)=O)CC2)nn2ccc(-c3ccc4nccn4c3)c12]
64
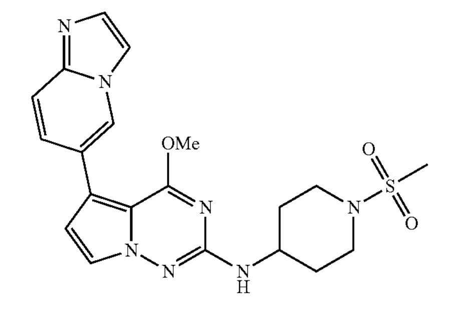 [SMILES: COc1nc(NC2CCN(S(C)(=O)=O)CC2)nn2ccc(-c3ccc4nccn4c3)c12]

TABLE 1-continued
65
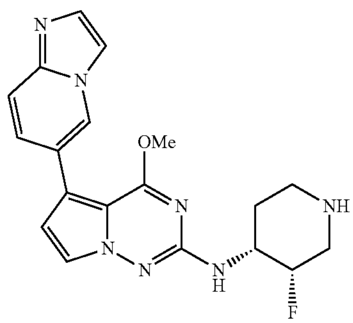 [SMILES: COc1nc(N[C@@H]2CCNC[C@@H]2F)nn2ccc(-c3ccc4nccn4c3)c12]
66
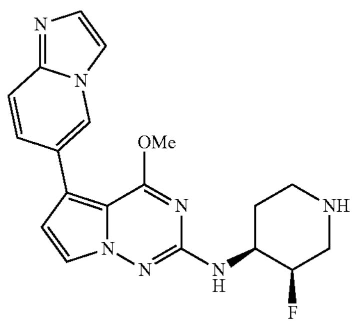 [SMILES: COc1nc(N[C@H]2CCNC[C@H]2F)nn2ccc(-c3ccc4nccn4c3)c12]
67
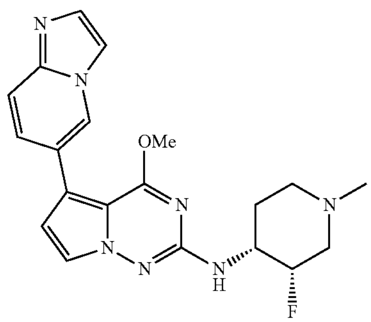 [SMILES: COc1nc(N[C@@H]2CCN(C)C[C@@H]2F)nn2ccc(-c3ccc4nccn4c3)c12]
68
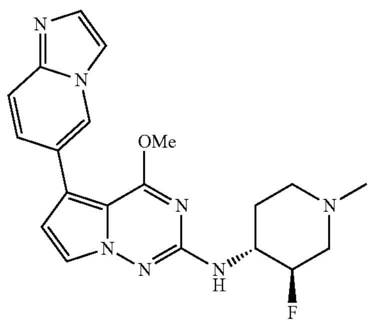 [SMILES: COc1nc(N[C@@H]2CCN(C)C[C@H]2F)nn2ccc(-c3ccc4nccn4c3)c12]
69
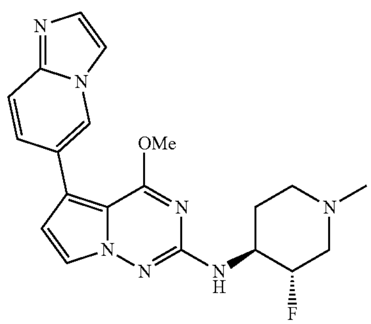 [SMILES: COc1nc(N[C@H]2CCN(C)C[C@@H]2F)nn2ccc(-c3ccc4nccn4c3)c12]
TABLE 1-continued
70
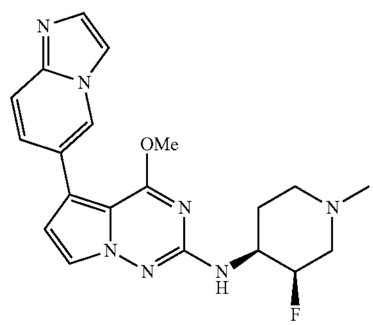 [SMILES: COc1nc(N[C@H]2CCN(C)C[C@H]2F)nn2ccc(-c3ccc4nccn4c3)c12]
71
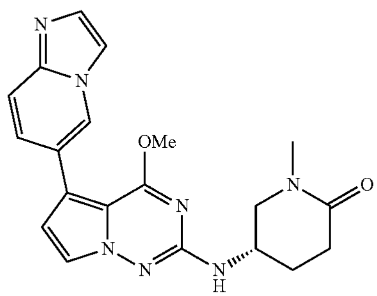 [SMILES: COc1nc(N[C@H]2CCC(=O)N(C)C2)nn2ccc(-c3ccc4nccn4c3)c12]
72
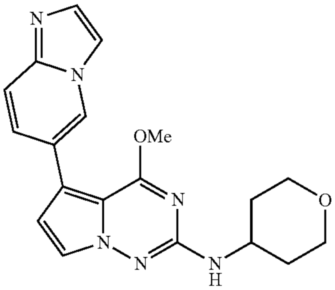 [SMILES: COc1nc(NC2CCOCC2)nn2ccc(-c3ccc4nccn4c3)c12]
73
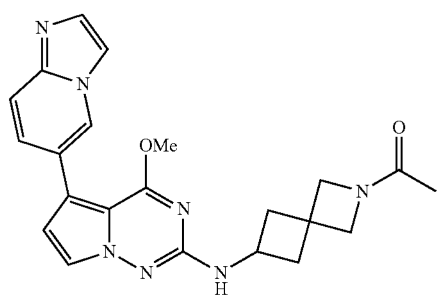 [SMILES: COc1nc(NC2CC3(C2)CN(C(C)=O)C3)nn2ccc(-c3ccc4nccn4c3)c12]
74
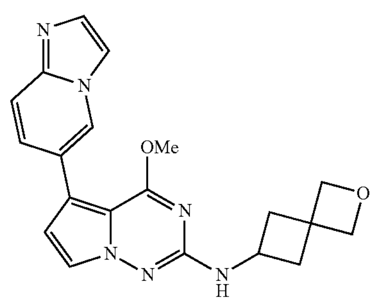 [SMILES: COc1nc(NC2CC3(COC3)C2)nn2ccc(-c3ccc4nccn4c3)c12]

TABLE 1-continued
75
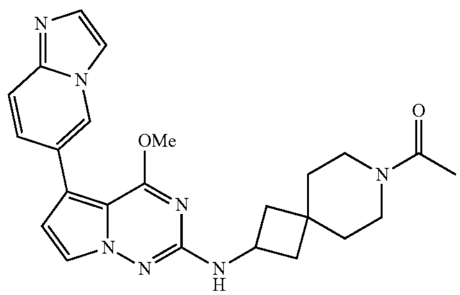 [SMILES: COc1nc(NC2CC3(CCN(C(C)=O)CC3)C2)nn2ccc(-c3ccc4nccn4c3)c12]
76
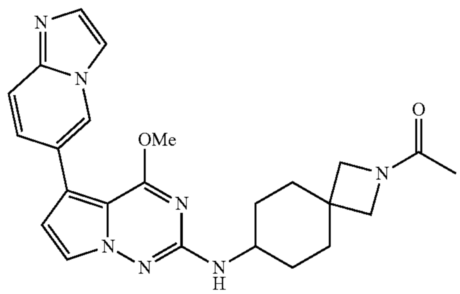 [SMILES: COc1nc(NC2CCC3(CC2)CN(C(C)=O)C3)nn2ccc(-c3ccc4nccn4c3)c12]
77
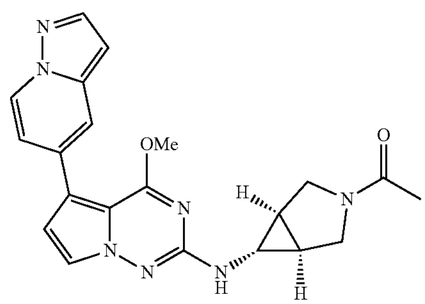 [SMILES: COc1nc(N[C@H]2[C@@H]3CN(C(C)=O)C[C@@H]32)nn2ccc(-c3ccn4nccc4c3)c12]
78
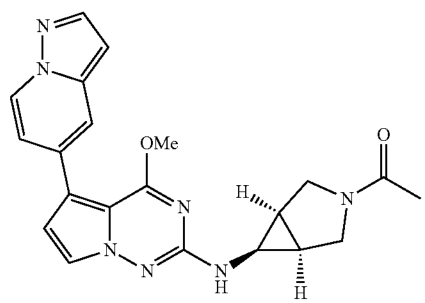 [SMILES: COc1nc(N[C@@H]2[C@@H]3CN(C(C)=O)C[C@@H]32)nn2ccc(-c3ccn4nccc4c3)c12]
79
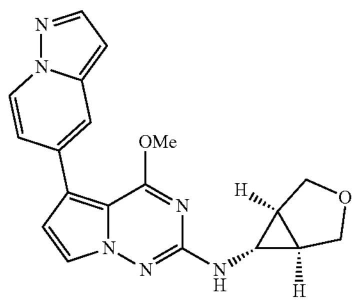 [SMILES: COc1nc(N[C@H]2[C@@H]3COC[C@@H]32)nn2ccc(-c3ccn4nccc4c3)c12]
TABLE 1-continued
80
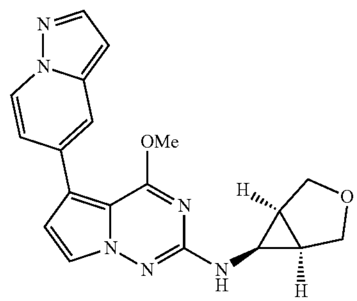 [SMILES: COc1nc(N[C@@H]2[C@@H]3COC[C@@H]32)nn2ccc(-c3ccn4nccc4c3)c12]
81
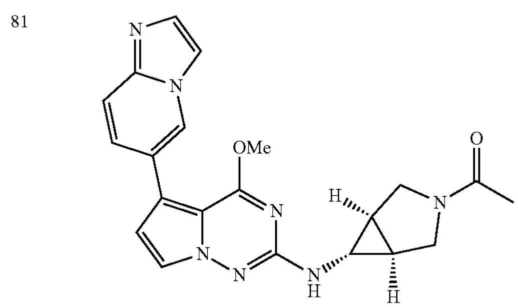
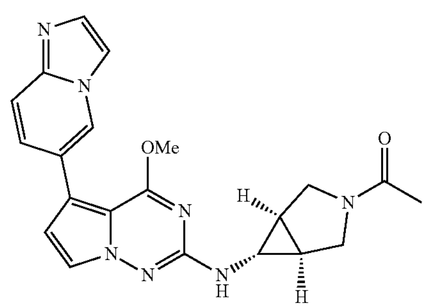 [SMILES: COc1nc(N[C@H]2[C@@H]3CN(C(C)=O)C[C@@H]32)nn2ccc(-c3ccc4nccn4c3)c12]
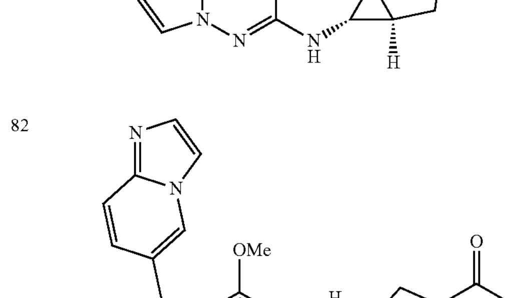
82
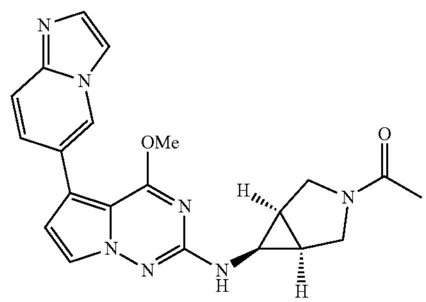 [SMILES: COc1nc(N[C@@H]2[C@@H]3CN(C(C)=O)C[C@@H]32)nn2ccc(-c3ccc4nccn4c3)c12]
83
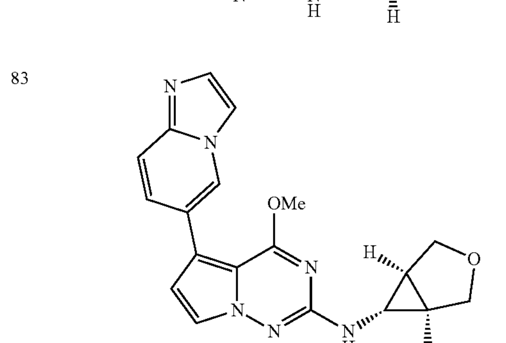
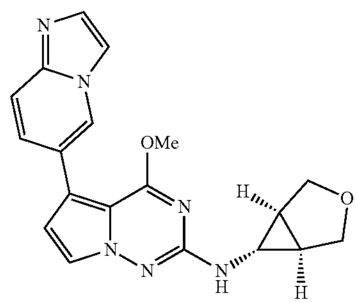 [SMILES: COc1nc(N[C@H]2[C@@H]3COC[C@@H]32)nn2ccc(-c3ccc4nccn4c3)c12]
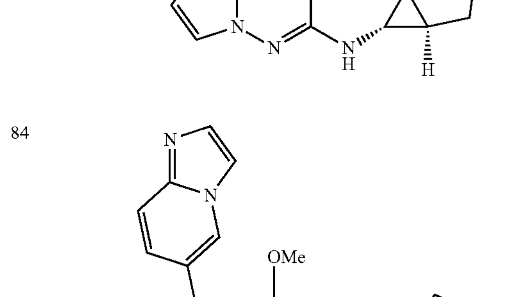
84
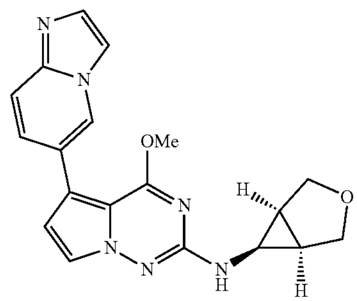 [SMILES: COc1nc(N[C@@H]2[C@@H]3COC[C@@H]32)nn2ccc(-c3ccc4nccn4c3)c12]

TABLE 1-continued
85
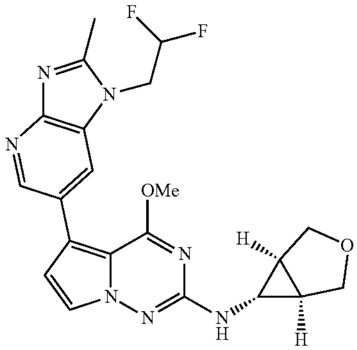 [SMILES: COc1nc(N[C@H]2[C@@H]3COC[C@@H]32)nn2ccc(-c3cnc4nc(C)n(CC(F)F)c4c3)c12]
86
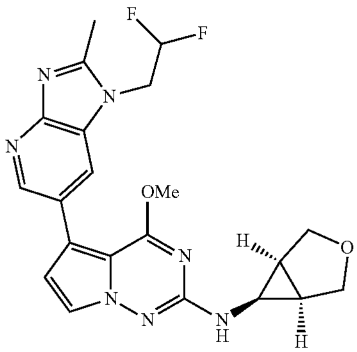 [SMILES: COc1nc(N[C@@H]2[C@@H]3COC[C@@H]32)nn2ccc(-c3cnc4nc(C)n(CC(F)F)c4c3)c12]
87
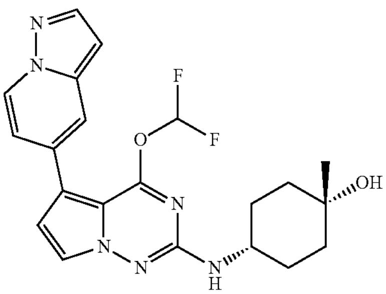 [SMILES: C[C@]1(O)CC[C@@H](Nc2nc(OC(F)F)c3c(-c4ccn5nccc5c4)ccn3n2)CC1]
88
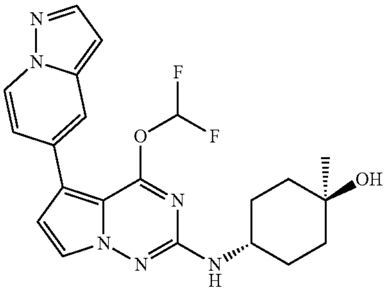 [SMILES: C[C@]1(O)CC[C@H](Nc2nc(OC(F)F)c3c(-c4ccn5nccc5c4)ccn3n2)CC1]
89
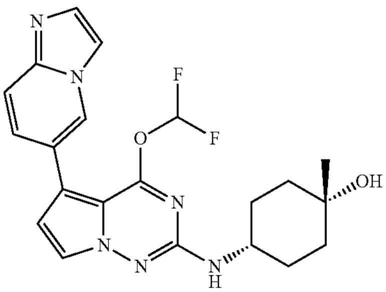 [SMILES: C[C@]1(O)CC[C@@H](Nc2nc(OC(F)F)c3c(-c4ccc5nccn5c4)ccn3n2)CC1]
TABLE 1-continued
90
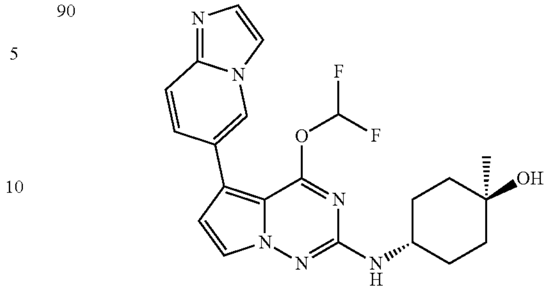
91
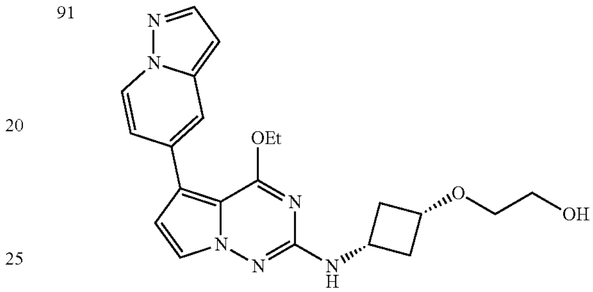
92
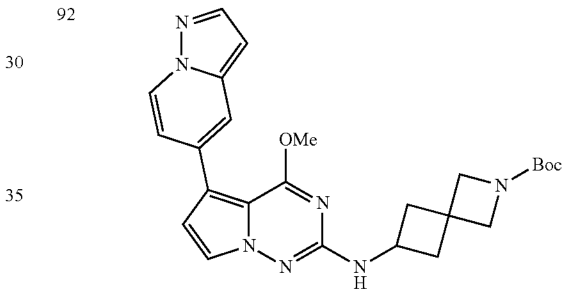
93
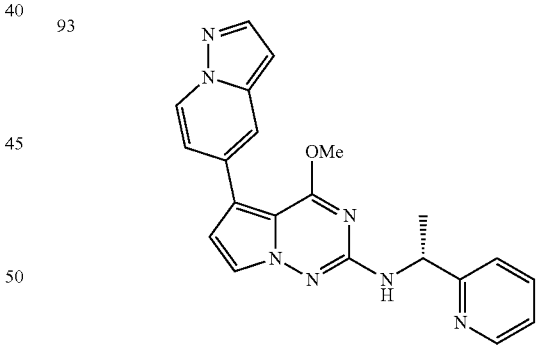
94
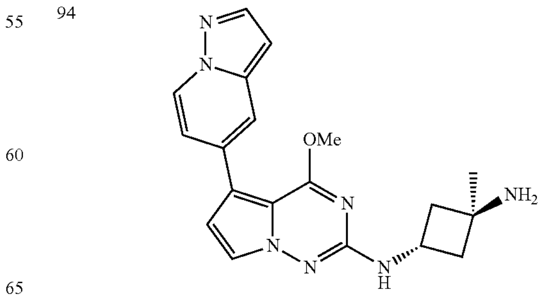

TABLE 1-continued
| | |
|---|---|
| 95 | 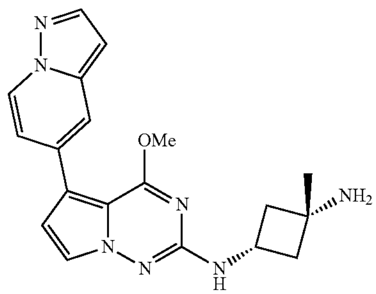 [SMILES: COc1nc(N[C@H]2C[C@@](C)(N)C2)nn2ccc(-c3ccn4nccc4c3)c12] |
| 96 | 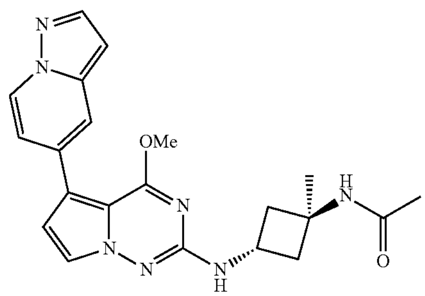 [SMILES: COc1nc(N[C@H]2C[C@](C)(NC(C)=O)C2)nn2ccc(-c3ccn4nccc4c3)c12] |
| 97 | 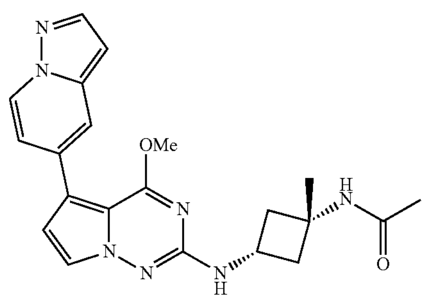 [SMILES: COc1nc(N[C@H]2C[C@@](C)(NC(C)=O)C2)nn2ccc(-c3ccn4nccc4c3)c12] |
| 98 | 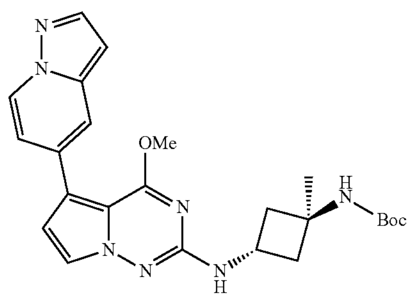 [SMILES: COc1nc(N[C@H]2C[C@](C)(NC(=O)OC(C)(C)C)C2)nn2ccc(-c3ccn4nccc4c3)c12] |
| 99 | 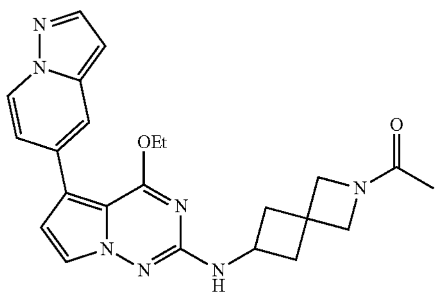 [SMILES: CCOc1nc(NC2CC3(C2)CN(C(C)=O)C3)nn2ccc(-c3ccn4nccc4c3)c12] |
TABLE 1-continued
| | |
|---|---|
| 100 | 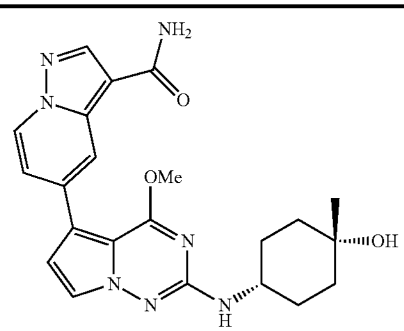 |
| 101 | 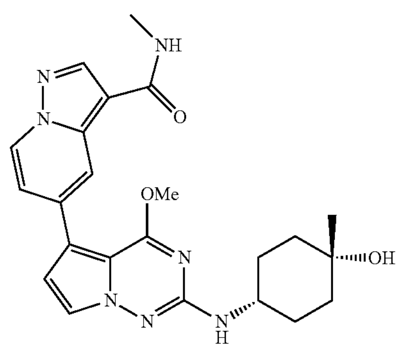 [SMILES: CNC(=O)c1cnn2ccc(-c3ccn4nc(N[C@H]5CC[C@@](C)(O)CC5)nc(OC)c34)cc12] |
| 102 | 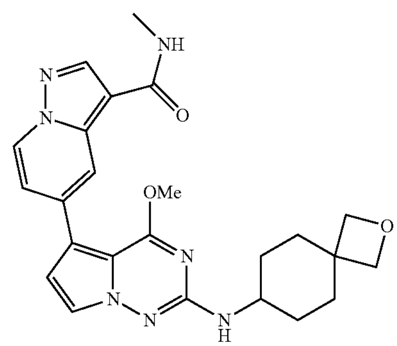 [SMILES: CNC(=O)c1cnn2ccc(-c3ccn4nc(NC5CCC6(CC5)COC6)nc(OC)c34)cc12] |
| 103 | 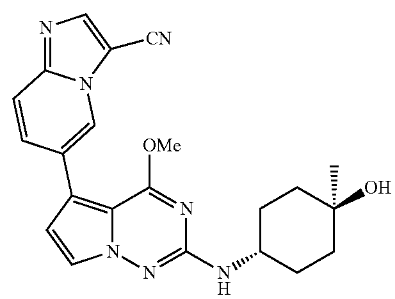 [SMILES: COc1nc(N[C@H]2CC[C@](C)(O)CC2)nn2ccc(-c3ccc4ncc(C#N)n4c3)c12] |
| 104 | 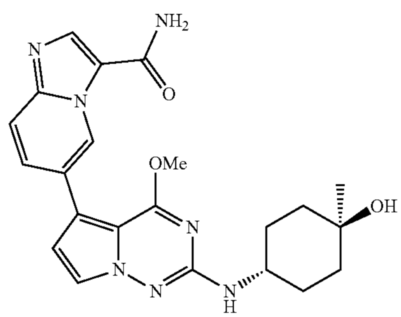 [SMILES: COc1nc(N[C@H]2CC[C@](C)(O)CC2)nn2ccc(-c3ccc4ncc(C(N)=O)n4c3)c12] |

TABLE 1-continued
105
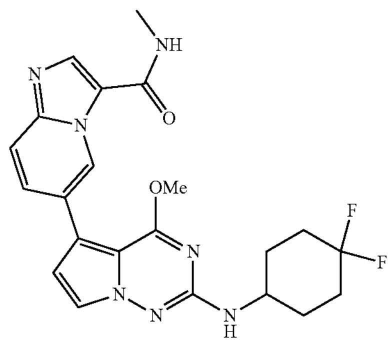 [SMILES: CNC(=O)c1cnc2ccc(-c3ccn4nc(NC5CCC(F)(F)CC5)nc(OC)c34)cn12]
106
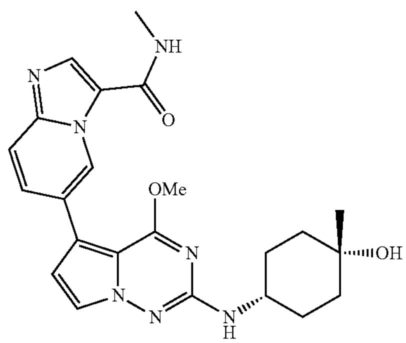 [SMILES: CNC(=O)c1cnc2ccc(-c3ccn4nc(N[C@H]5CC[C@@](C)(O)CC5)nc(OC)c34)cn12]
107
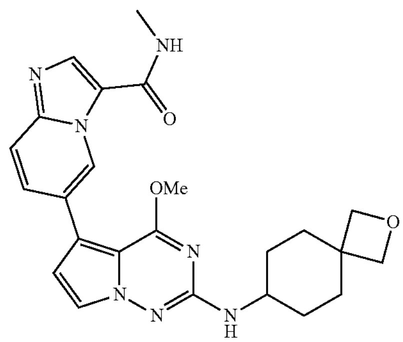 [SMILES: CNC(=O)c1cnc2ccc(-c3ccn4nc(NC5CCC6(CC5)COC6)nc(OC)c34)cn12]
108
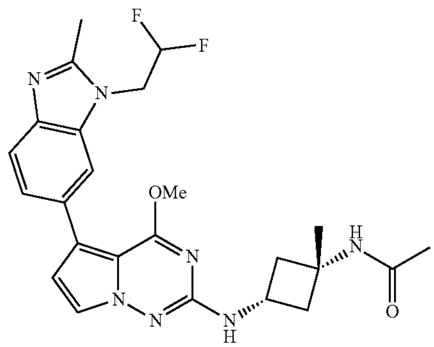 [SMILES: COc1nc(N[C@H]2C[C@@](C)(NC(C)=O)C2)nn2ccc(-c3ccc4nc(C)n(CC(F)F)c4c3)c12]
TABLE 1-continued
109
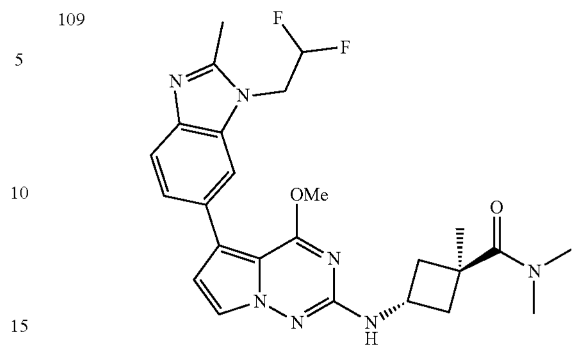
110
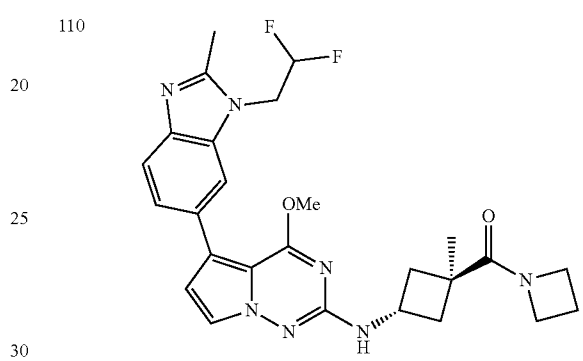
111
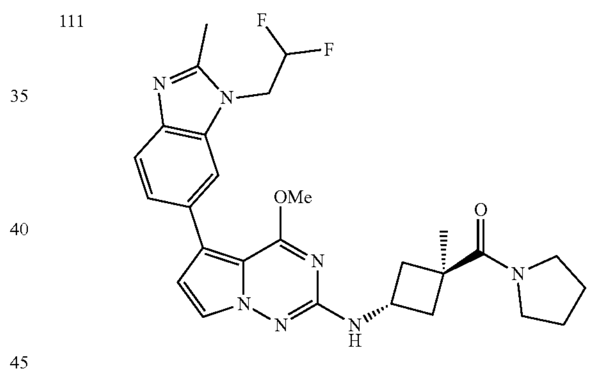
112
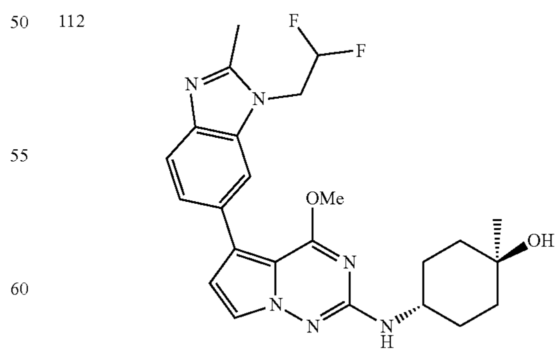

TABLE 1-continued
113
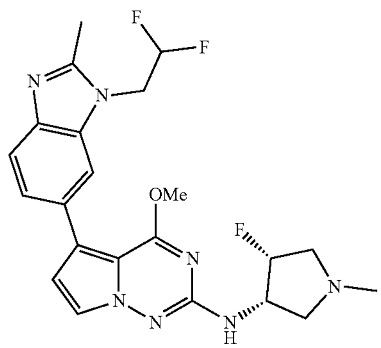 [SMILES: COc1nc(N[C@H]2CN(C)C[C@H]2F)nn2ccc(-c3ccc4nc(C)n(CC(F)F)c4c3)c12]
114
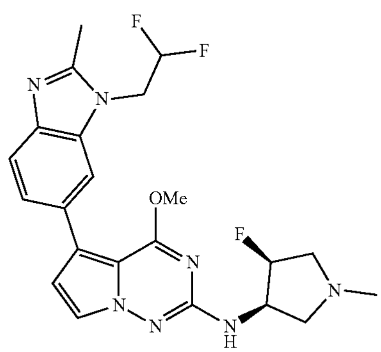 [SMILES: COc1nc(N[C@@H]2CN(C)C[C@@H]2F)nn2ccc(-c3ccc4nc(C)n(CC(F)F)c4c3)c12]
115
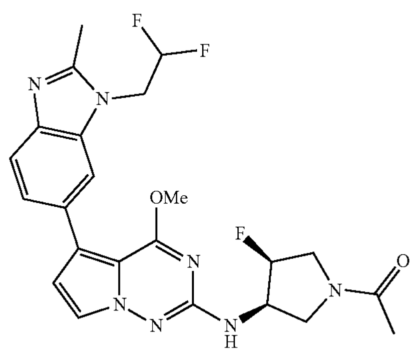 [SMILES: COc1nc(N[C@@H]2CN(C(C)=O)C[C@@H]2F)nn2ccc(-c3ccc4nc(C)n(CC(F)F)c4c3)c12]
116
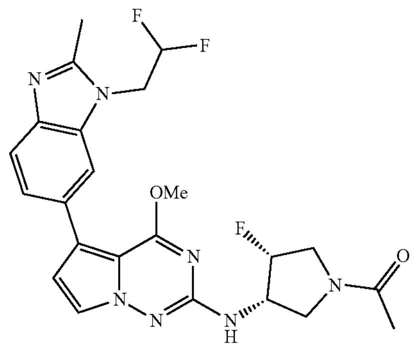 [SMILES: COc1nc(N[C@H]2CN(C(C)=O)C[C@H]2F)nn2ccc(-c3ccc4nc(C)n(CC(F)F)c4c3)c12]
TABLE 1-continued
117
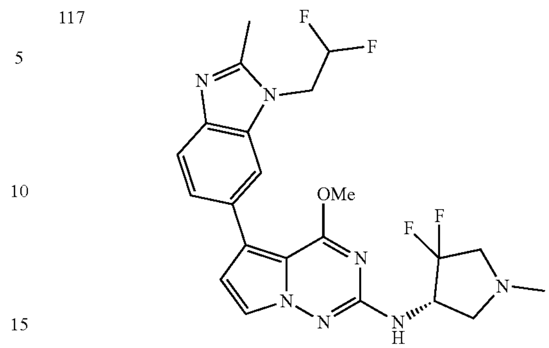
118
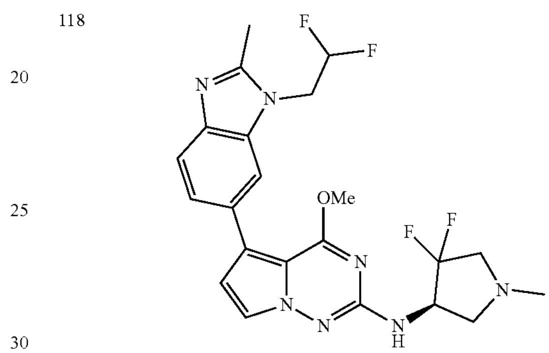
119
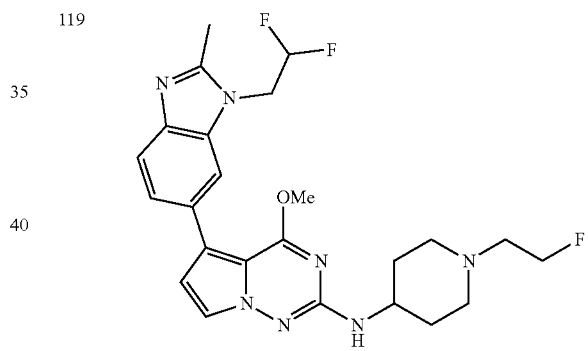
120
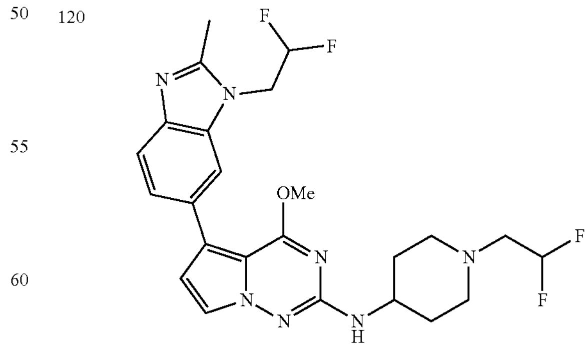

TABLE 1-continued
121
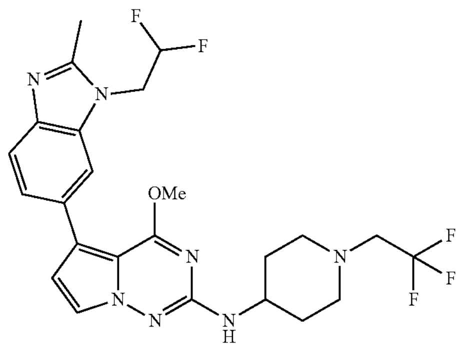 [SMILES: COc1nc(NC2CCN(CC(F)(F)F)CC2)nn2ccc(-c3ccc4nc(C)n(CC(F)F)c4c3)c12]
122
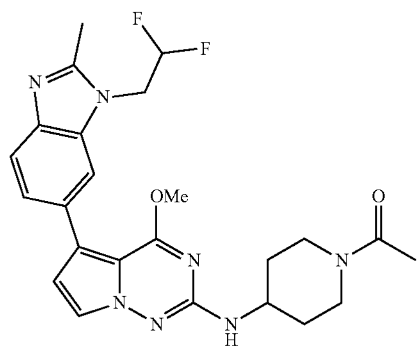 [SMILES: COc1nc(NC2CCN(C(C)=O)CC2)nn2ccc(-c3ccc4nc(C)n(CC(F)F)c4c3)c12]
123
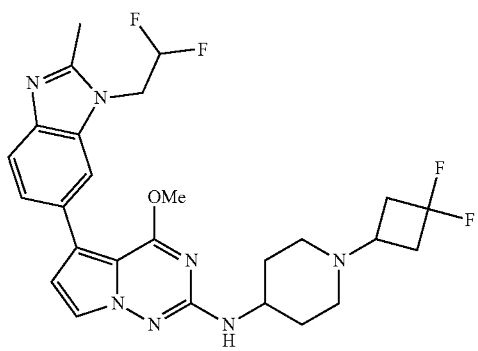 [SMILES: COc1nc(NC2CCN(C3CC(F)(F)C3)CC2)nn2ccc(-c3ccc4nc(C)n(CC(F)F)c4c3)c12]
124
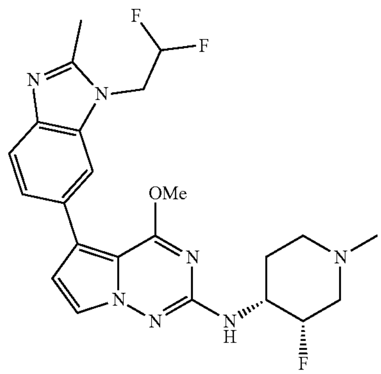 [SMILES: COc1nc(N[C@@H]2CCN(C)C[C@@H]2F)nn2ccc(-c3ccc4nc(C)n(CC(F)F)c4c3)c12]
125
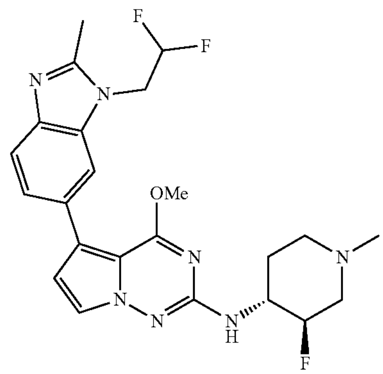 [SMILES: COc1nc(N[C@@H]2CCN(C)C[C@H]2F)nn2ccc(-c3ccc4nc(C)n(CC(F)F)c4c3)c12]
126
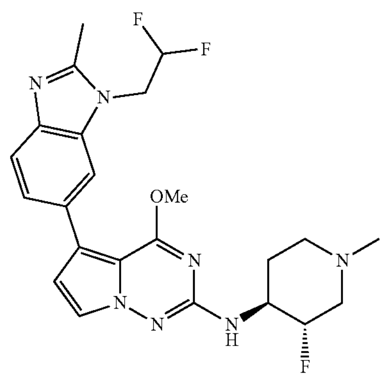 [SMILES: COc1nc(N[C@H]2CCN(C)C[C@@H]2F)nn2ccc(-c3ccc4nc(C)n(CC(F)F)c4c3)c12]
127
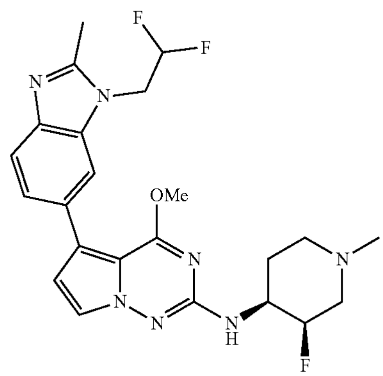 [SMILES: COc1nc(N[C@H]2CCN(C)C[C@H]2F)nn2ccc(-c3ccc4nc(C)n(CC(F)F)c4c3)c12]
128
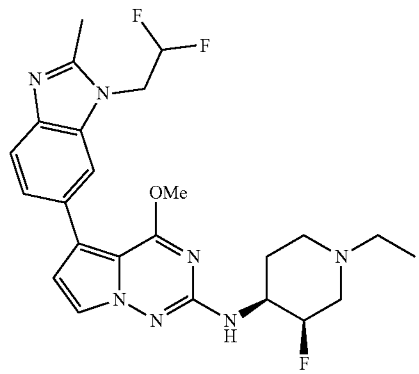 [SMILES: CCN1CC[C@H](Nc2nc(OC)c3c(-c4ccc5nc(C)n(CC(F)F)c5c4)ccn3n2)[C@H](F)C1]

TABLE 1-continued
129
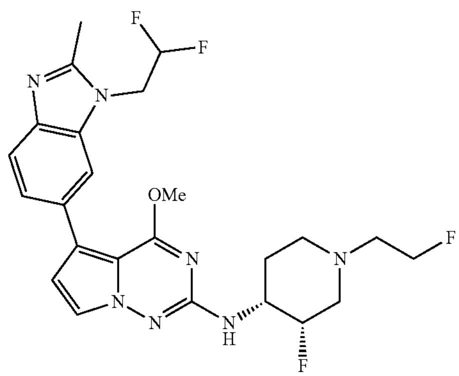 [SMILES: COc1nc(N[C@@H]2CCN(CCF)C[C@@H]2F)nn2ccc(-c3ccc4nc(C)n(CC(F)F)c4c3)c12]
130
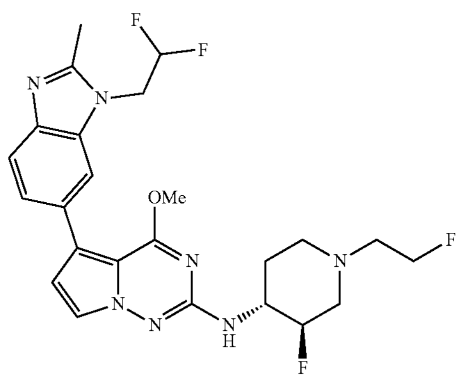 [SMILES: COc1nc(N[C@@H]2CCN(CCF)C[C@H]2F)nn2ccc(-c3ccc4nc(C)n(CC(F)F)c4c3)c12]
131
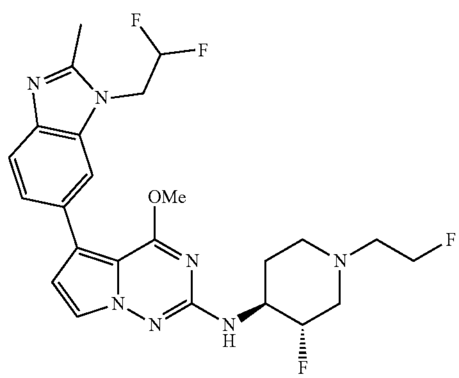 [SMILES: COc1nc(N[C@H]2CCN(CCF)C[C@@H]2F)nn2ccc(-c3ccc4nc(C)n(CC(F)F)c4c3)c12]
132
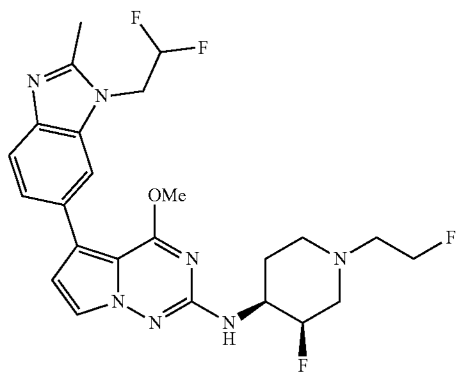 [SMILES: COc1nc(N[C@H]2CCN(CCF)C[C@H]2F)nn2ccc(-c3ccc4nc(C)n(CC(F)F)c4c3)c12]
TABLE 1-continued
133
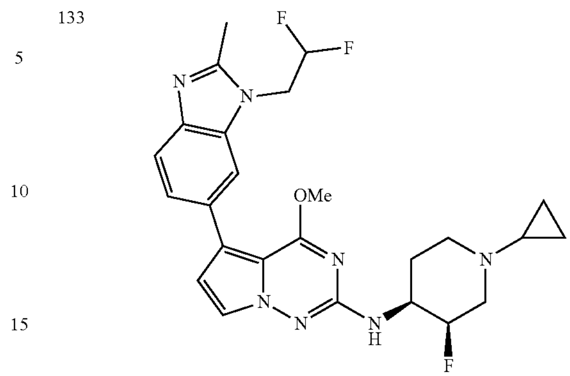
134
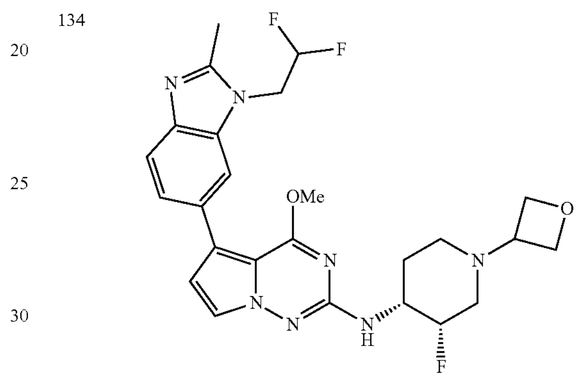
135
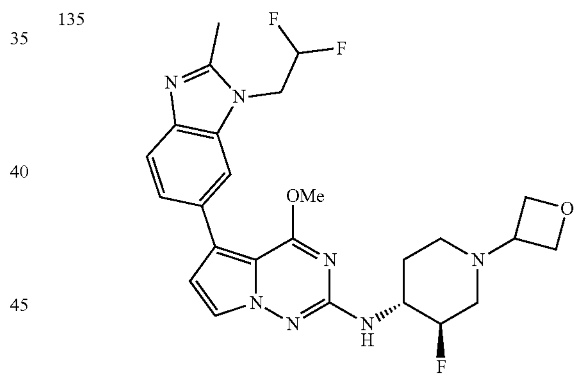
136
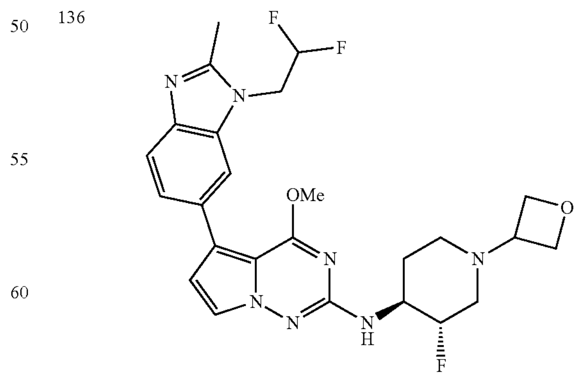

TABLE 1-continued
137
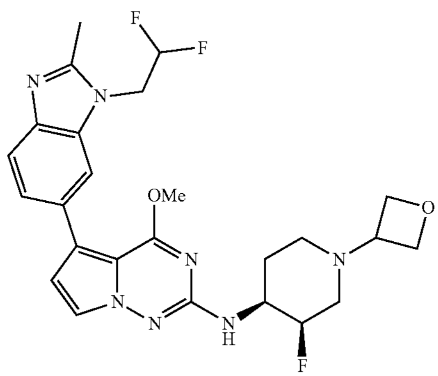 [SMILES: COc1nc(N[C@H]2CCN(C3COC3)C[C@H]2F)nn2ccc(-c3ccc4nc(C)n(CC(F)F)c4c3)c12]
138
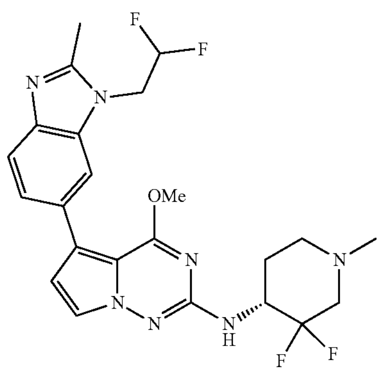 [SMILES: COc1nc(N[C@@H]2CCN(C)CC2(F)F)nn2ccc(-c3ccc4nc(C)n(CC(F)F)c4c3)c12]
139
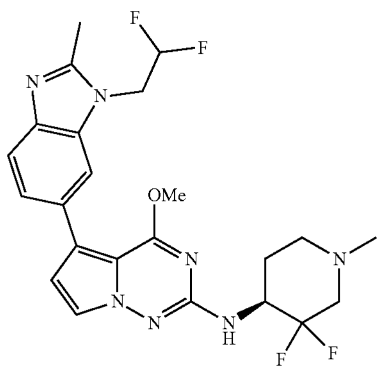 [SMILES: COc1nc(N[C@H]2CCN(C)CC2(F)F)nn2ccc(-c3ccc4nc(C)n(CC(F)F)c4c3)c12]
140
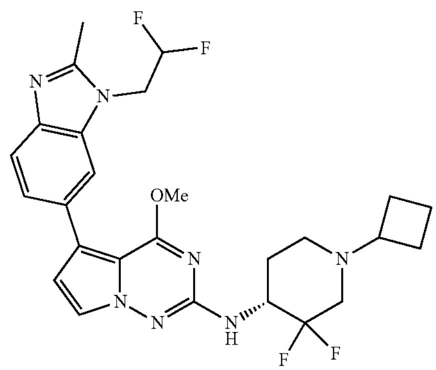 [SMILES: COc1nc(N[C@@H]2CCN(C3CCC3)CC2(F)F)nn2ccc(-c3ccc4nc(C)n(CC(F)F)c4c3)c12]
TABLE 1-continued
141
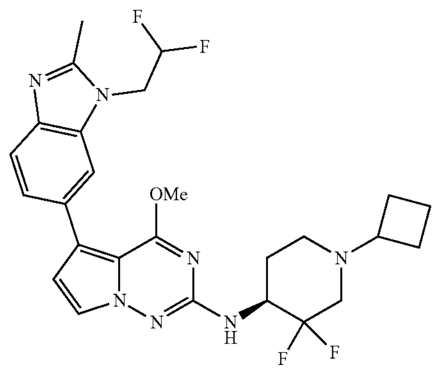 [SMILES: COc1nc(N[C@H]2CCN(C3CCC3)CC2(F)F)nn2ccc(-c3ccc4nc(C)n(CC(F)F)c4c3)c12]
142
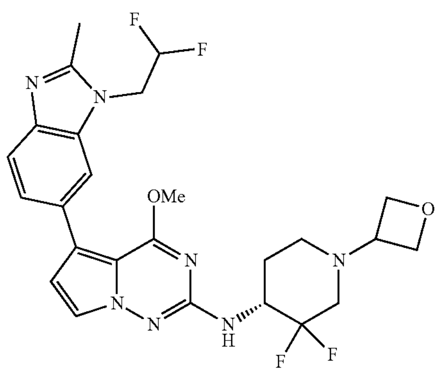 [SMILES: COc1nc(N[C@@H]2CCN(C3COC3)CC2(F)F)nn2ccc(-c3ccc4nc(C)n(CC(F)F)c4c3)c12]
143
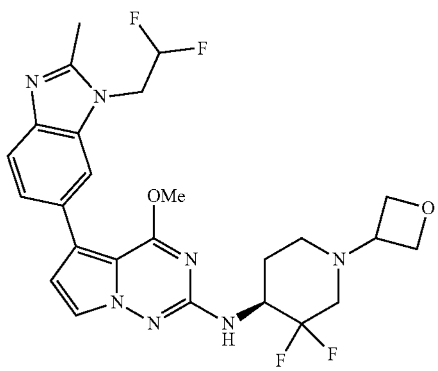 [SMILES: COc1nc(N[C@H]2CCN(C3COC3)CC2(F)F)nn2ccc(-c3ccc4nc(C)n(CC(F)F)c4c3)c12]
144
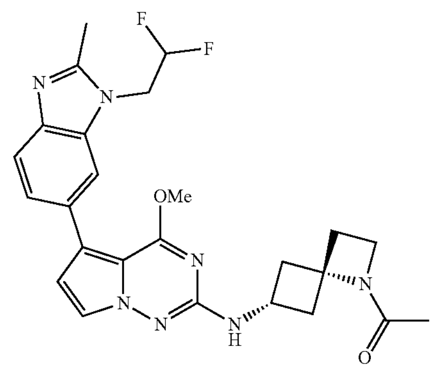 [SMILES: COc1nc(N[C@H]2C[C@]3(CCN3C(C)=O)C2)nn2ccc(-c3ccc4nc(C)n(CC(F)F)c4c3)c12]

145
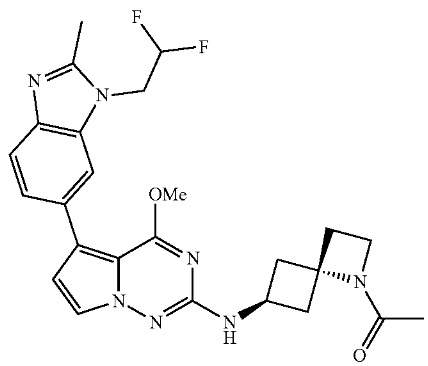 [SMILES: COc1nc(N[C@H]2C[C@@]3(CCN3C(C)=O)C2)nn2ccc(-c3ccc4nc(C)n(CC(F)F)c4c3)c12]
146
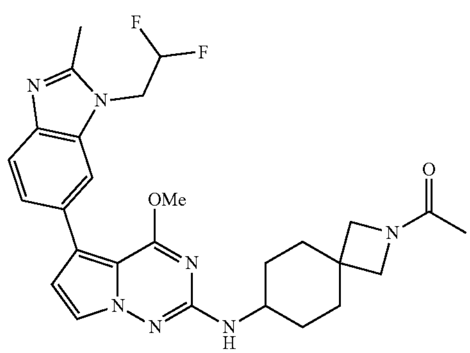 [SMILES: COc1nc(NC2CCC3(CC2)CN(C(C)=O)C3)nn2ccc(-c3ccc4nc(C)n(CC(F)F)c4c3)c12]
147
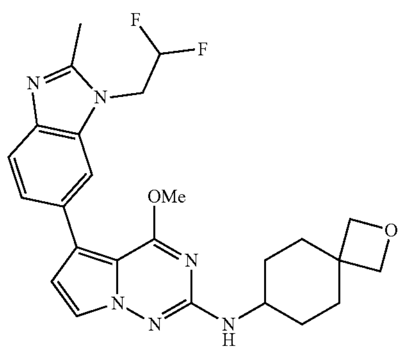 [SMILES: COc1nc(NC2CCC3(CC2)COC3)nn2ccc(-c3ccc4nc(C)n(CC(F)F)c4c3)c12]
148
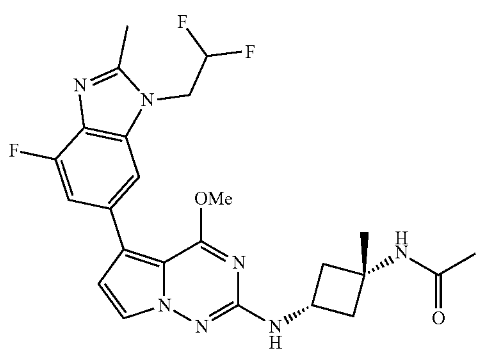 [SMILES: COc1nc(N[C@H]2C[C@@](C)(NC(C)=O)C2)nn2ccc(-c3cc(F)c4nc(C)n(CC(F)F)c4c3)c12]
149
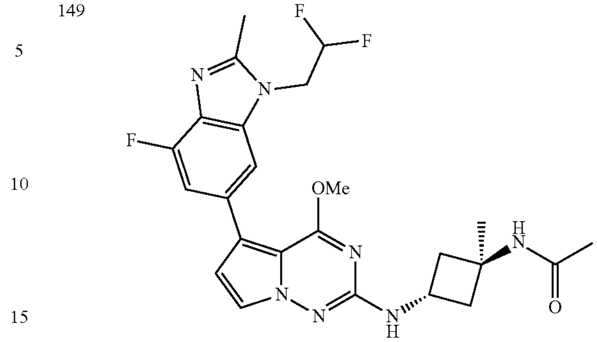
150
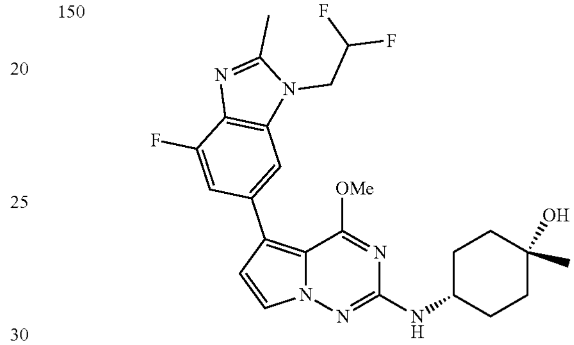
151
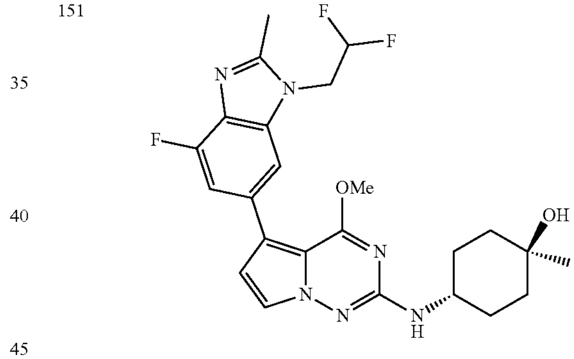
152
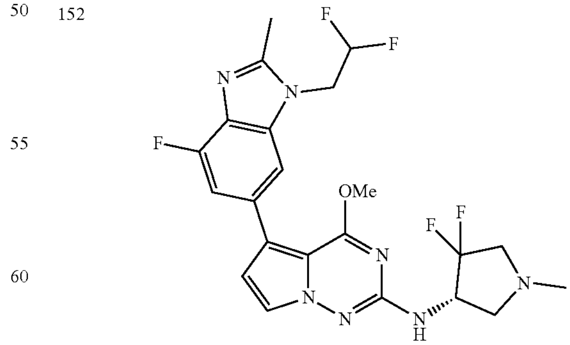

TABLE 1-continued
153
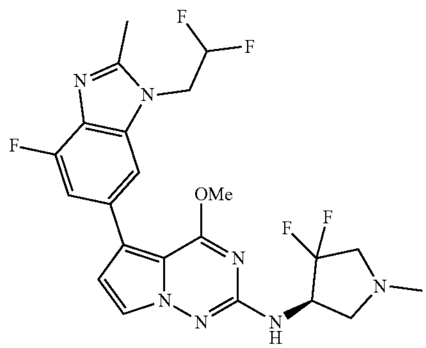 [SMILES: COc1nc(N[C@@H]2CN(C)CC2(F)F)nn2ccc(-c3cc(F)c4nc(C)n(CC(F)F)c4c3)c12]
154
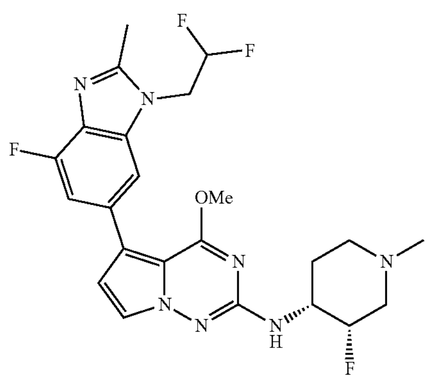 [SMILES: COc1nc(N[C@@H]2CCN(C)C[C@@H]2F)nn2ccc(-c3cc(F)c4nc(C)n(CC(F)F)c4c3)c12]
155
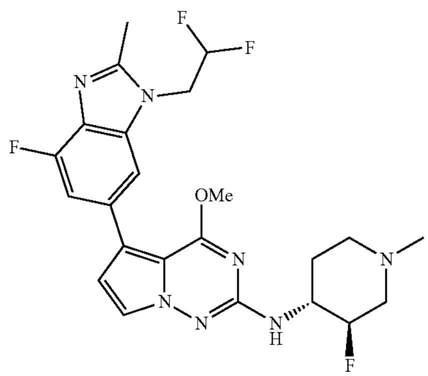 [SMILES: COc1nc(N[C@@H]2CCN(C)C[C@H]2F)nn2ccc(-c3cc(F)c4nc(C)n(CC(F)F)c4c3)c12]
156
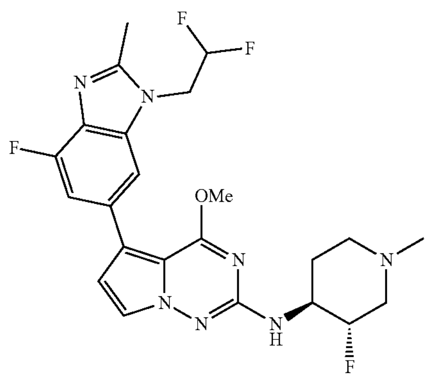 [SMILES: COc1nc(N[C@H]2CCN(C)C[C@@H]2F)nn2ccc(-c3cc(F)c4nc(C)n(CC(F)F)c4c3)c12]
TABLE 1-continued
157
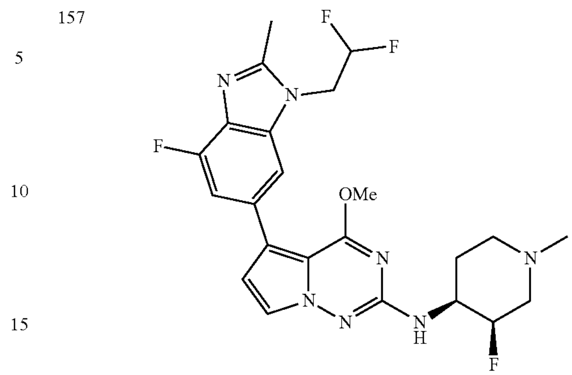
158
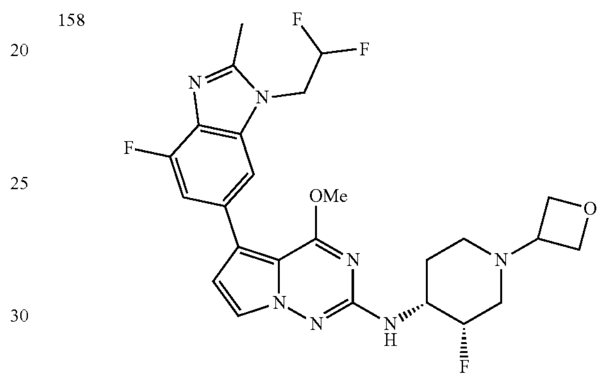
159
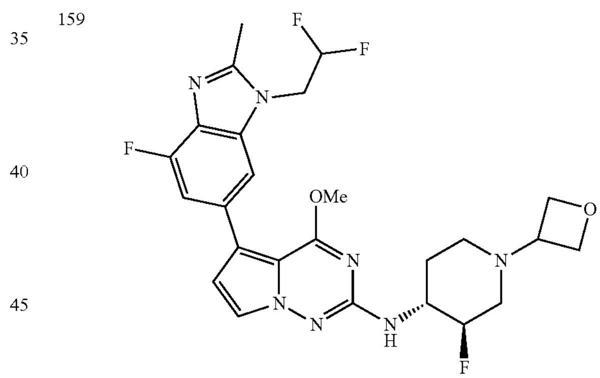
160
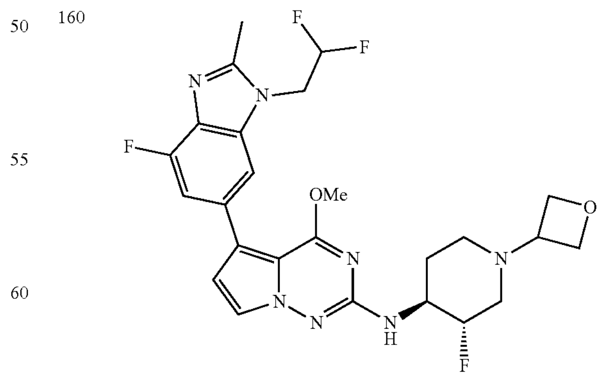

TABLE 1-continued
161
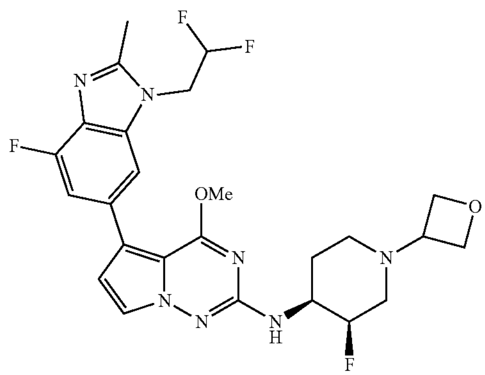 [SMILES: COc1nc(N[C@H]2CCN(C3COC3)C[C@H]2F)nn2ccc(-c3cc(F)c4nc(C)n(CC(F)F)c4c3)c12]
162
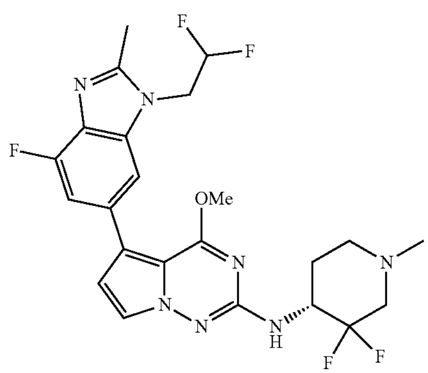 [SMILES: COc1nc(N[C@@H]2CCN(C)CC2(F)F)nn2ccc(-c3cc(F)c4nc(C)n(CC(F)F)c4c3)c12]
163
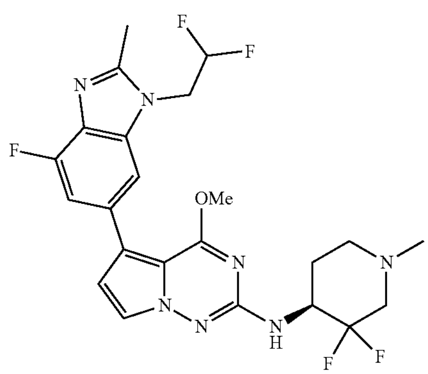 [SMILES: COc1nc(N[C@H]2CCN(C)CC2(F)F)nn2ccc(-c3cc(F)c4nc(C)n(CC(F)F)c4c3)c12]
164
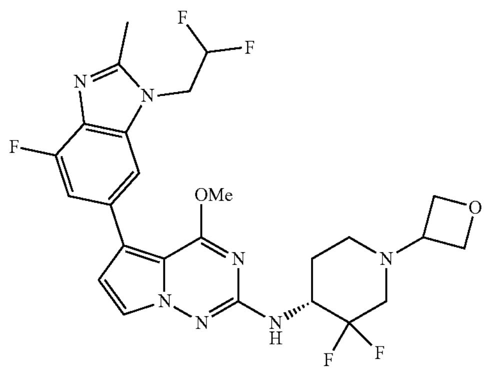 [SMILES: COc1nc(N[C@@H]2CCN(C3COC3)CC2(F)F)nn2ccc(-c3cc(F)c4nc(C)n(CC(F)F)c4c3)c12]
TABLE 1-continued
165
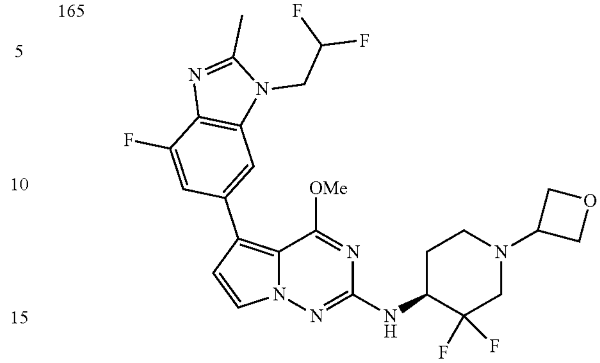
166
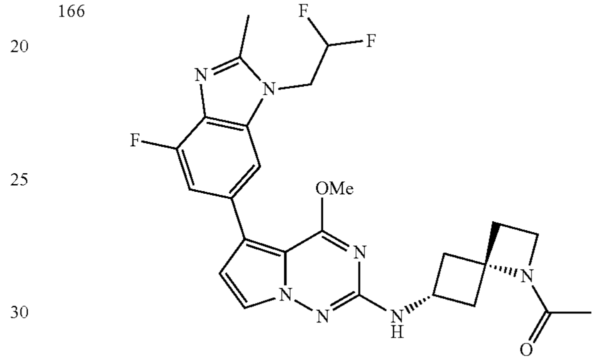
167
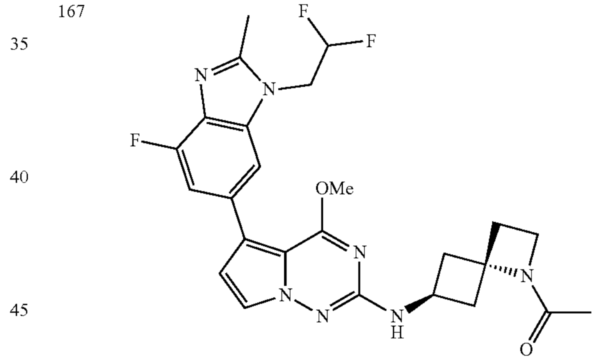
168
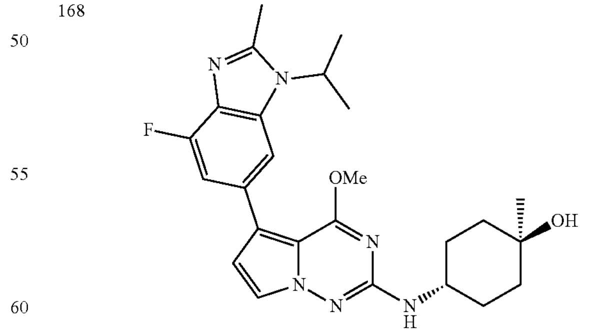

TABLE 1-continued
169
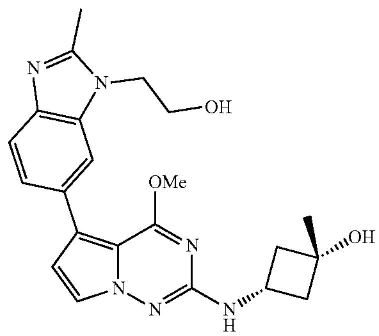 [SMILES: COc1nc(N[C@H]2C[C@@](C)(O)C2)nn2ccc(-c3ccc4nc(C)n(CCO)c4c3)c12]
170
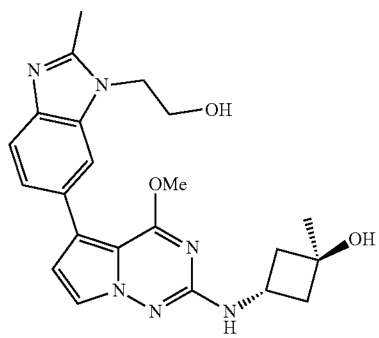 [SMILES: COc1nc(N[C@H]2C[C@](C)(O)C2)nn2ccc(-c3ccc4nc(C)n(CCO)c4c3)c12]
171
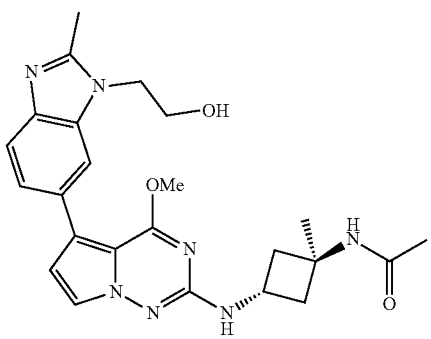 [SMILES: COc1nc(N[C@H]2C[C@](C)(NC(C)=O)C2)nn2ccc(-c3ccc4nc(C)n(CCO)c4c3)c12]
172
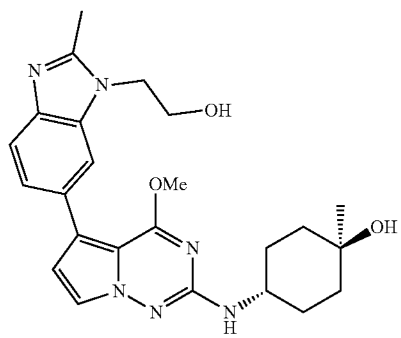 [SMILES: COc1nc(N[C@H]2CC[C@](C)(O)CC2)nn2ccc(-c3ccc4nc(C)n(CCO)c4c3)c12]
TABLE 1-continued
173
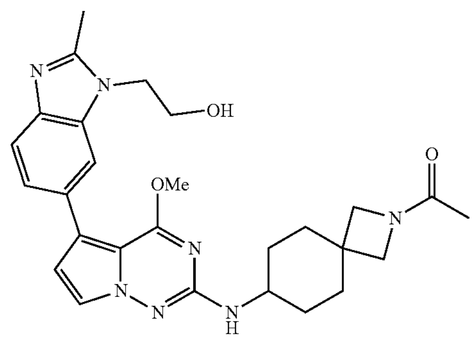 [SMILES: COc1nc(NC2CCC3(CC2)CN(C(C)=O)C3)nn2ccc(-c3ccc4nc(C)n(CCO)c4c3)c12]
174
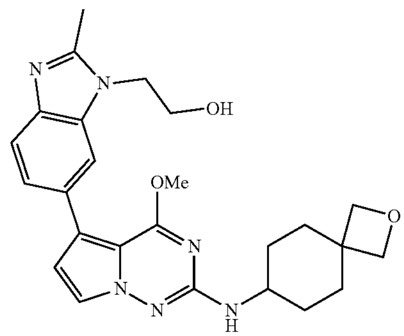 [SMILES: COc1nc(NC2CCC3(CC2)COC3)nn2ccc(-c3ccc4nc(C)n(CCO)c4c3)c12]
175
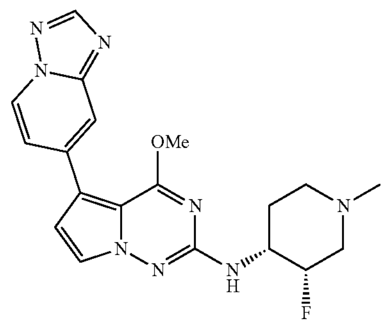 [SMILES: COc1nc(N[C@@H]2CCN(C)C[C@@H]2F)nn2ccc(-c3ccn4ncnc4c3)c12]
176
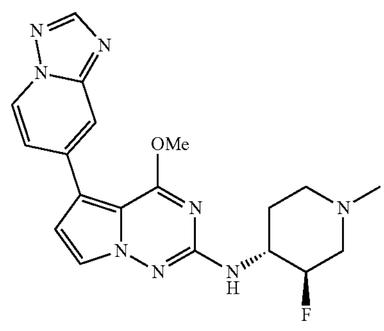 [SMILES: COc1nc(N[C@@H]2CCN(C)C[C@H]2F)nn2ccc(-c3ccn4ncnc4c3)c12]
177
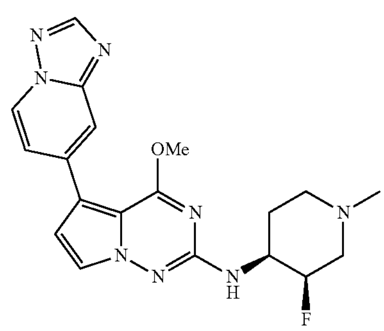 [SMILES: COc1nc(N[C@H]2CCN(C)C[C@H]2F)nn2ccc(-c3ccn4ncnc4c3)c12]

TABLE 1-continued
178
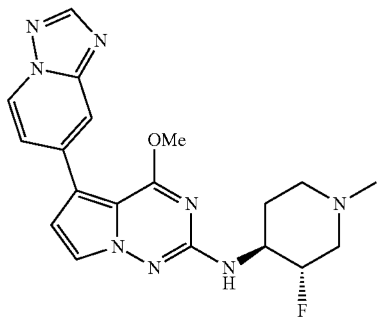 [SMILES: COc1nc(N[C@H]2CCN(C)C[C@@H]2F)nn2ccc(-c3ccn4ncnc4c3)c12]
179
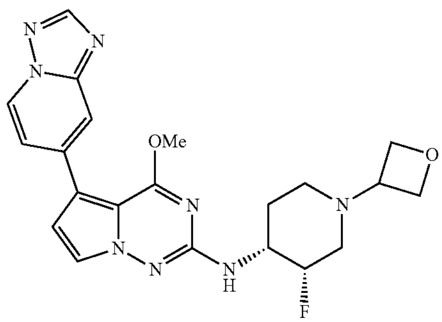 [SMILES: COc1nc(N[C@@H]2CCN(C3COC3)C[C@@H]2F)nn2ccc(-c3ccn4ncnc4c3)c12]
180
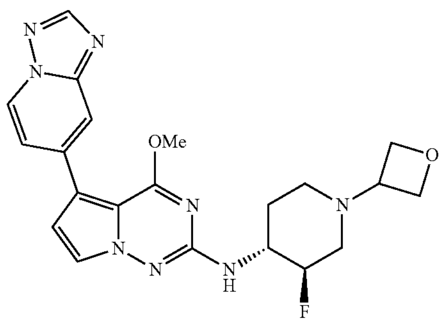 [SMILES: COc1nc(N[C@@H]2CCN(C3COC3)C[C@H]2F)nn2ccc(-c3ccn4ncnc4c3)c12]
181
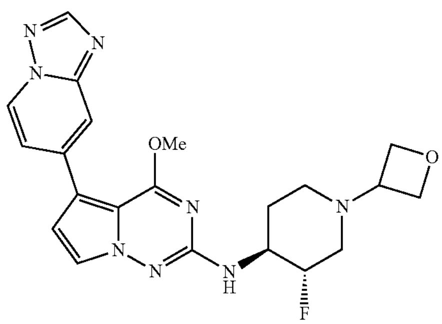 [SMILES: COc1nc(N[C@H]2CCN(C3COC3)C[C@@H]2F)nn2ccc(-c3ccn4ncnc4c3)c12]
182
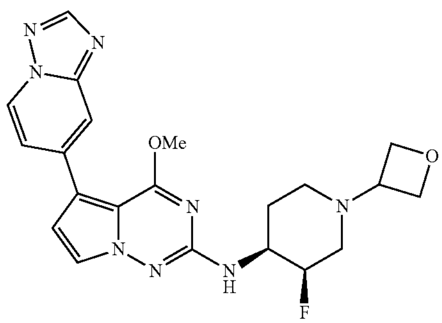 [SMILES: COc1nc(N[C@H]2CCN(C3COC3)C[C@H]2F)nn2ccc(-c3ccn4ncnc4c3)c12]
TABLE 1-continued
183
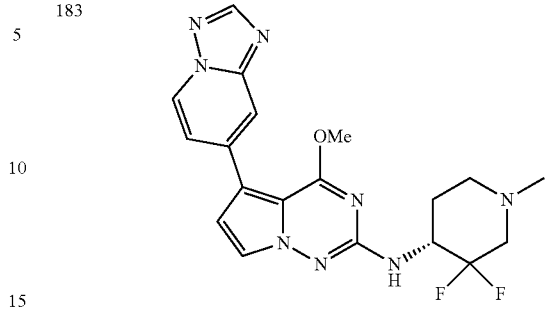
184
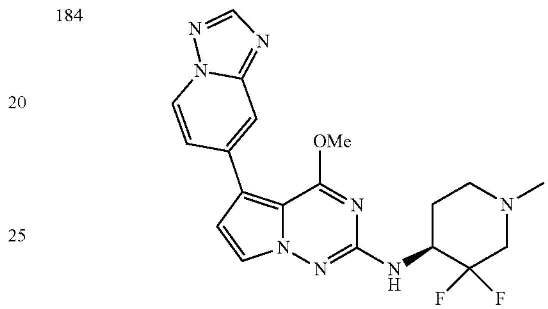
185
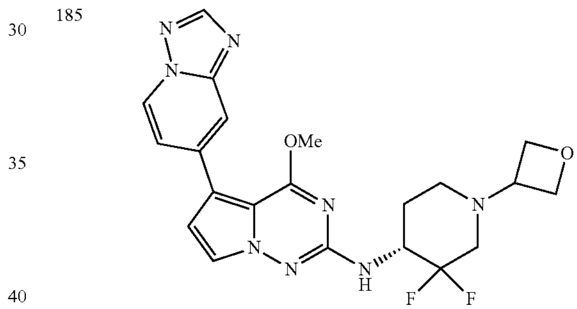
186
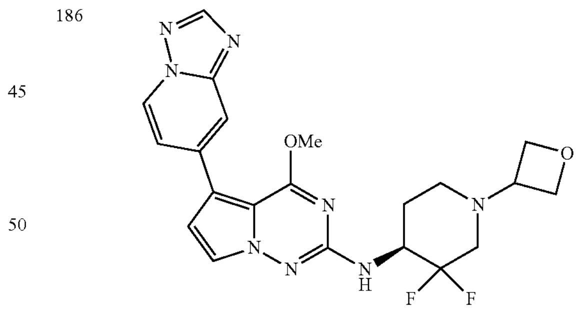
187
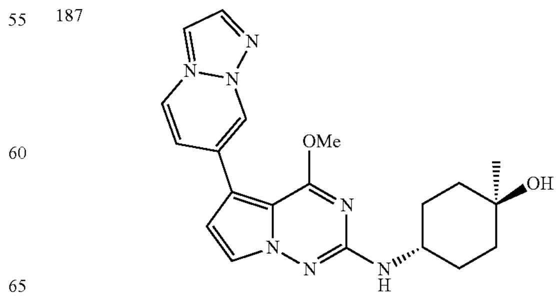

TABLE 1-continued
188
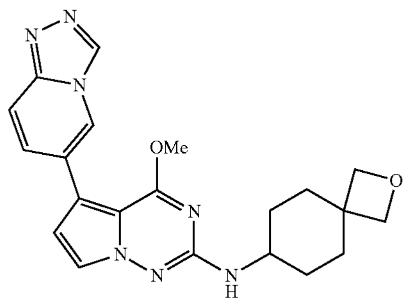 [SMILES: COc1nc(NC2CCC3(CC2)COC3)nn2ccc(-c3ccc4nncn4c3)c12]
189
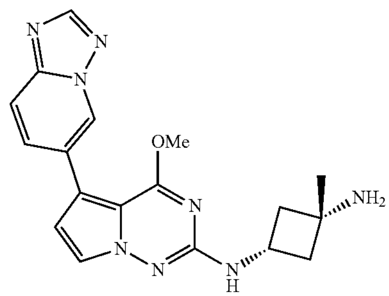 [SMILES: COc1nc(N[C@H]2C[C@@](C)(N)C2)nn2ccc(-c3ccc4ncnn4c3)c12]
190
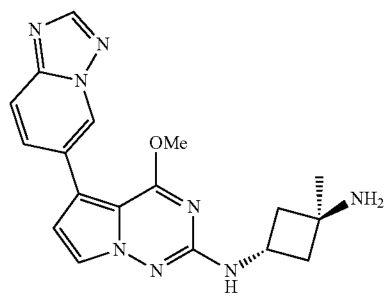 [SMILES: COc1nc(N[C@H]2C[C@](C)(N)C2)nn2ccc(-c3ccc4ncnn4c3)c12]
191
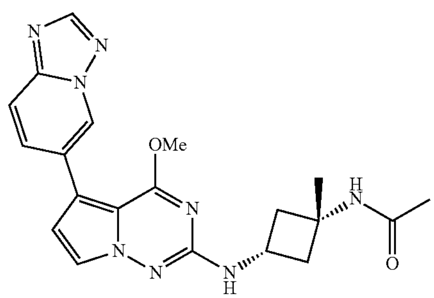 [SMILES: COc1nc(N[C@H]2C[C@@](C)(NC(C)=O)C2)nn2ccc(-c3ccc4ncnn4c3)c12]
192
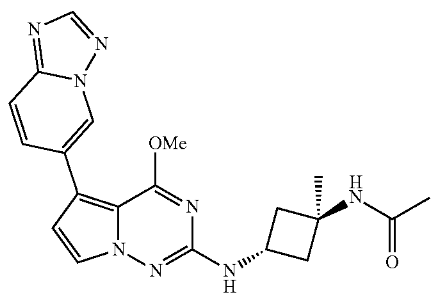 [SMILES: COc1nc(N[C@H]2C[C@](C)(NC(C)=O)C2)nn2ccc(-c3ccc4ncnn4c3)c12]
TABLE 1-continued
193
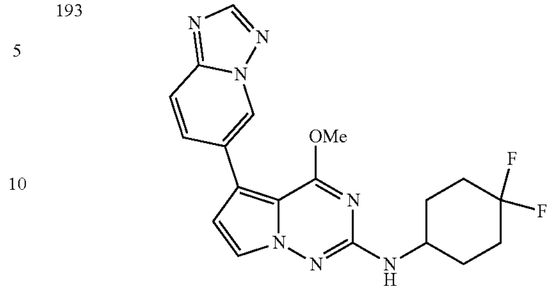
194
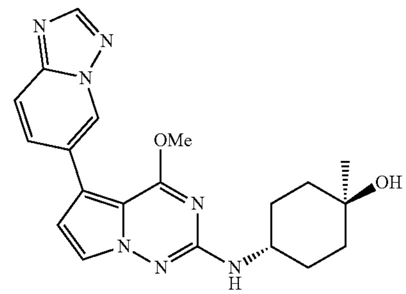 [SMILES: COc1nc(N[C@H]2CC[C@](C)(O)CC2)nn2ccc(-c3ccc4ncnn4c3)c12]
195
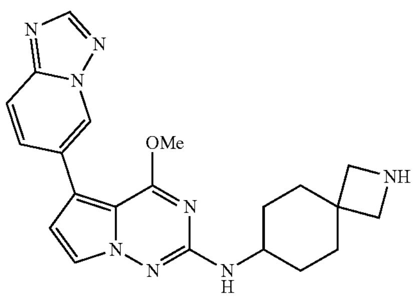 [SMILES: COc1nc(NC2CCC3(CC2)CNC3)nn2ccc(-c3ccc4ncnn4c3)c12]
196
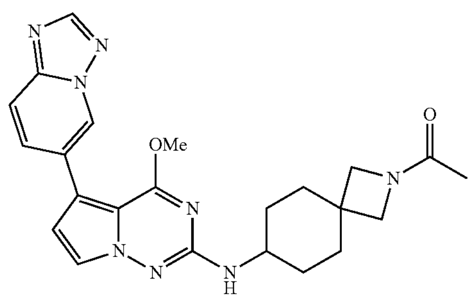 [SMILES: COc1nc(NC2CCC3(CC2)CN(C(C)=O)C3)nn2ccc(-c3ccc4ncnn4c3)c12]
197
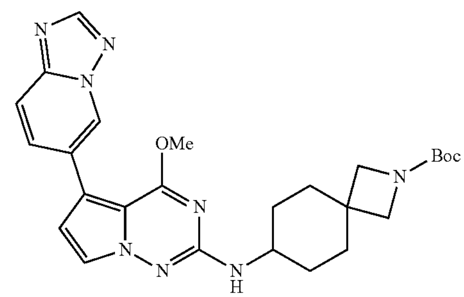 [SMILES: COc1nc(NC2CCC3(CC2)CN(C(=O)OC(C)(C)C)C3)nn2ccc(-c3ccc4ncnn4c3)c12]

TABLE 1-continued
198
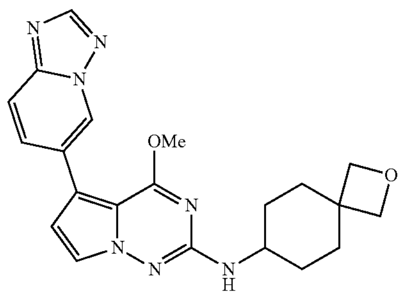 [SMILES: COc1nc(NC2CCC3(CC2)COC3)nn2ccc(-c3ccc4ncnn4c3)c12]
199
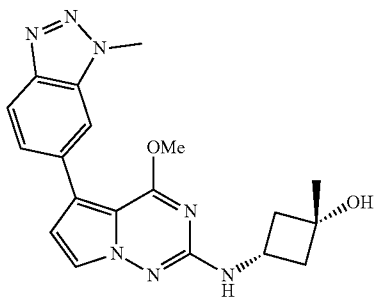 [SMILES: COc1nc(N[C@H]2C[C@@](C)(O)C2)nn2ccc(-c3ccc4nnn(C)c4c3)c12]
200
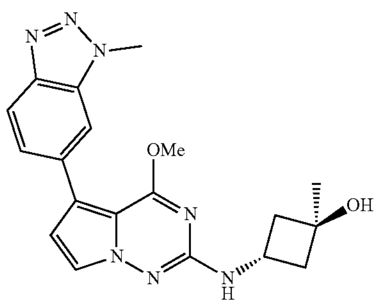 [SMILES: COc1nc(N[C@H]2C[C@](C)(O)C2)nn2ccc(-c3ccc4nnn(C)c4c3)c12]
201
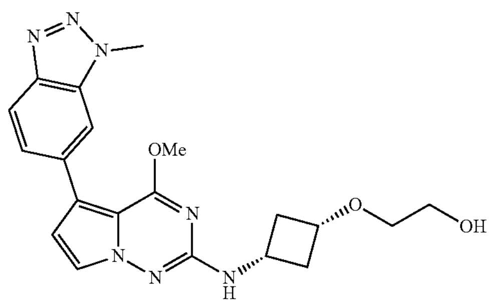 [SMILES: COc1nc(N[C@H]2C[C@@H](OCCO)C2)nn2ccc(-c3ccc4nnn(C)c4c3)c12]
202
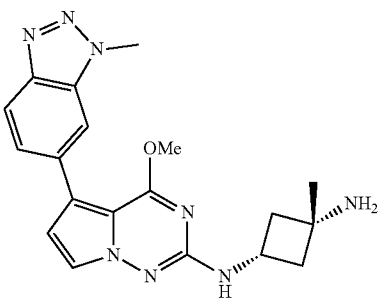 [SMILES: COc1nc(N[C@H]2C[C@@](C)(N)C2)nn2ccc(-c3ccc4nnn(C)c4c3)c12]
TABLE 1-continued
203
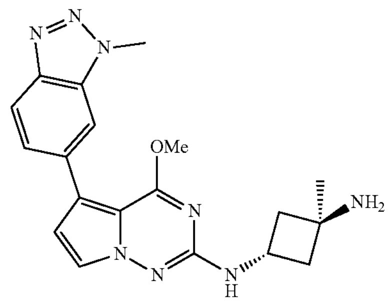 [SMILES: COc1nc(N[C@H]2C[C@](C)(N)C2)nn2ccc(-c3ccc4nnn(C)c4c3)c12]
204
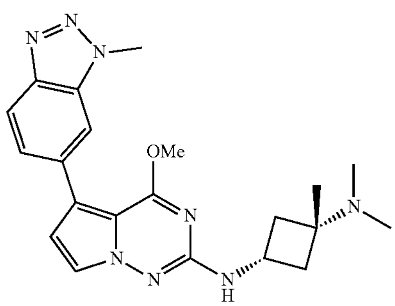 [SMILES: COc1nc(N[C@H]2C[C@@](C)(N(C)C)C2)nn2ccc(-c3ccc4nnn(C)c4c3)c12]
205
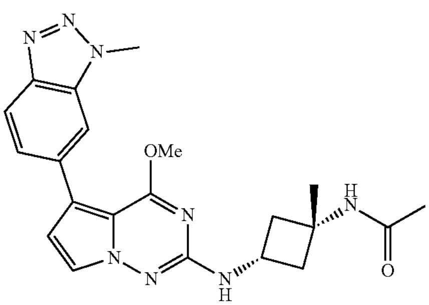 [SMILES: COc1nc(N[C@H]2C[C@@](C)(NC(C)=O)C2)nn2ccc(-c3ccc4nnn(C)c4c3)c12]
206
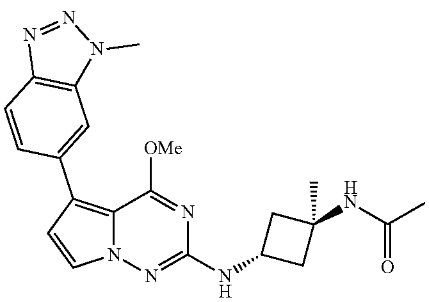 [SMILES: COc1nc(N[C@H]2C[C@](C)(NC(C)=O)C2)nn2ccc(-c3ccc4nnn(C)c4c3)c12]
207
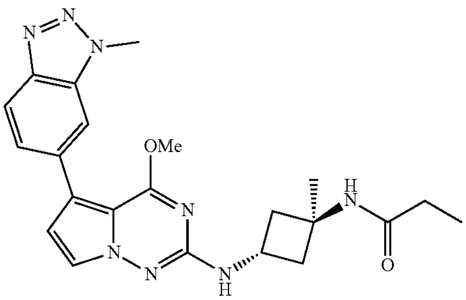 [SMILES: CCC(=O)N[C@]1(C)C[C@@H](Nc2nc(OC)c3c(-c4ccc5nnn(C)c5c4)ccn3n2)C1]

TABLE 1-continued
208
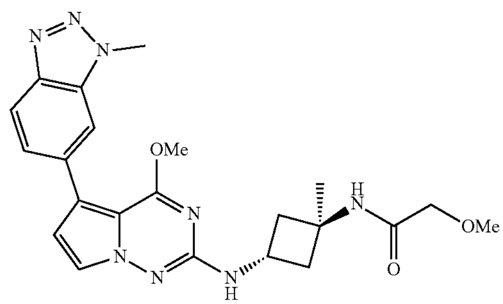 [SMILES: COCC(=O)N[C@]1(C)C[C@@H](Nc2nc(OC)c3c(-c4ccc5nnn(C)c5c4)ccn3n2)C1]
209
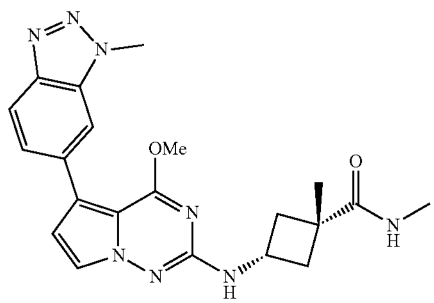 [SMILES: CNC(=O)[C@]1(C)C[C@H](Nc2nc(OC)c3c(-c4ccc5nnn(C)c5c4)ccn3n2)C1]
210
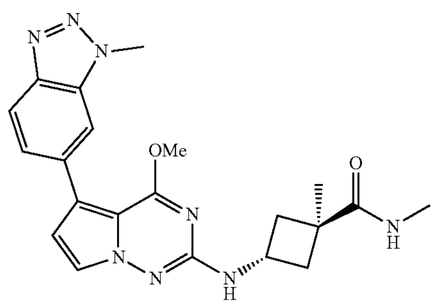 [SMILES: CNC(=O)[C@]1(C)C[C@@H](Nc2nc(OC)c3c(-c4ccc5nnn(C)c5c4)ccn3n2)C1]
211
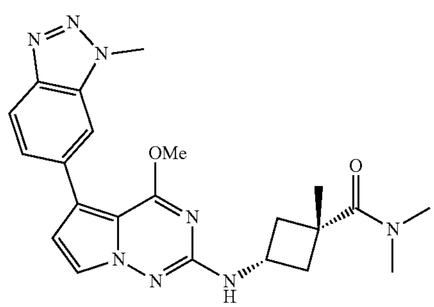 [SMILES: COc1nc(N[C@H]2C[C@@](C)(C(=O)N(C)C)C2)nn2ccc(-c3ccc4nnn(C)c4c3)c12]
212
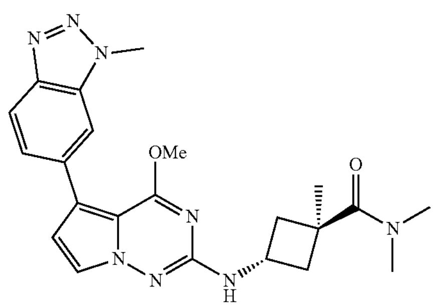 [SMILES: COc1nc(N[C@H]2C[C@](C)(C(=O)N(C)C)C2)nn2ccc(-c3ccc4nnn(C)c4c3)c12]
TABLE 1-continued
213
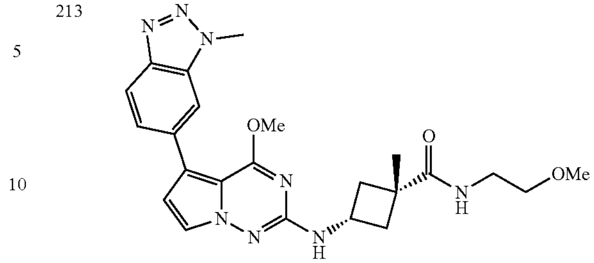
214
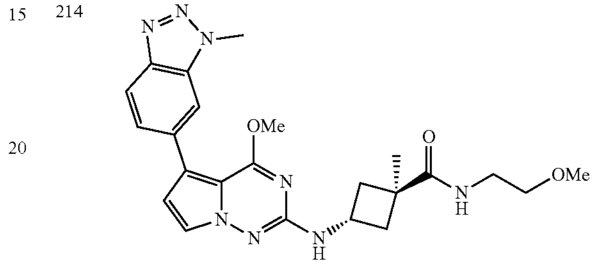
215
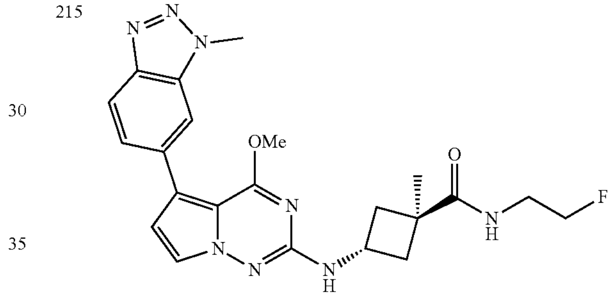
216
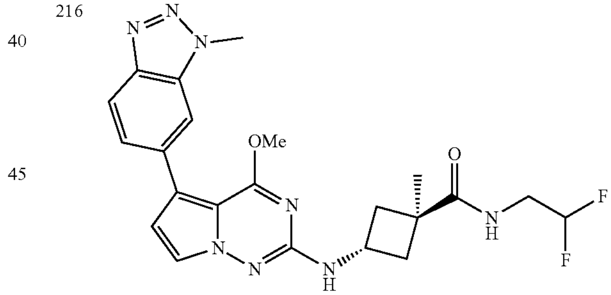
217
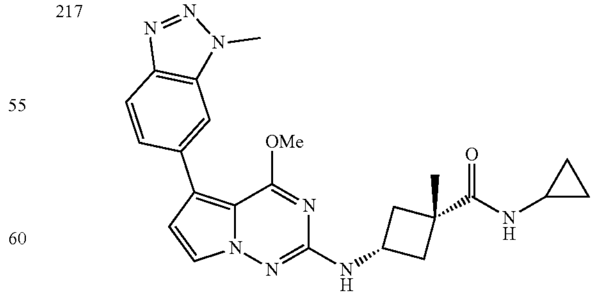

218
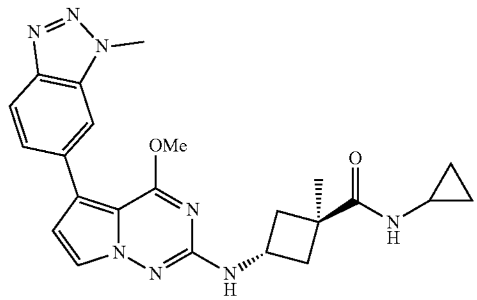 [SMILES: COc1nc(N[C@H]2C[C@](C)(C(=O)NC3CC3)C2)nn2ccc(-c3ccc4nnn(C)c4c3)c12]
219
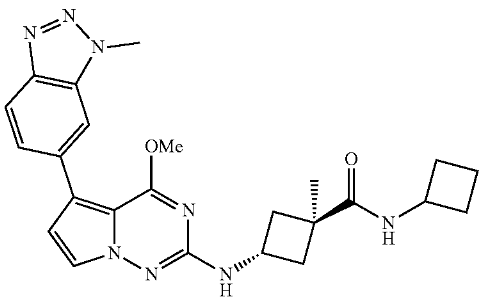 [SMILES: COc1nc(N[C@H]2C[C@](C)(C(=O)NC3CCC3)C2)nn2ccc(-c3ccc4nnn(C)c4c3)c12]
220
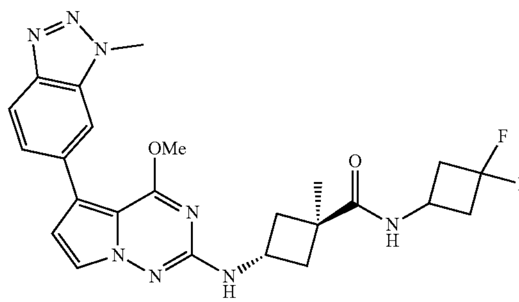
221
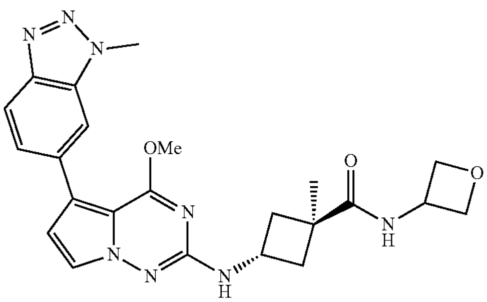 [SMILES: COc1nc(N[C@H]2C[C@](C)(C(=O)NC3COC3)C2)nn2ccc(-c3ccc4nnn(C)c4c3)c12]
222
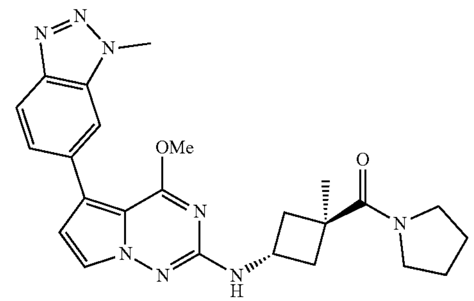 [SMILES: COc1nc(N[C@H]2C[C@](C)(C(=O)N3CCCC3)C2)nn2ccc(-c3ccc4nnn(C)c4c3)c12]
223
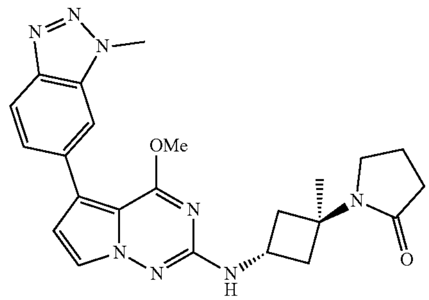 [SMILES: COc1nc(N[C@H]2C[C@](C)(N3CCCC3=O)C2)nn2ccc(-c3ccc4nnn(C)c4c3)c12]
224
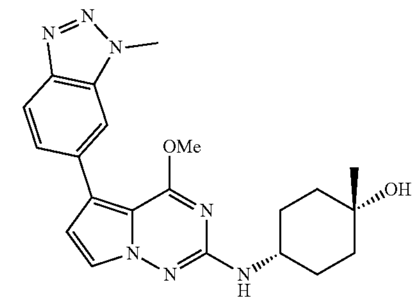 [SMILES: COc1nc(N[C@H]2CC[C@@](C)(O)CC2)nn2ccc(-c3ccc4nnn(C)c4c3)c12]
225
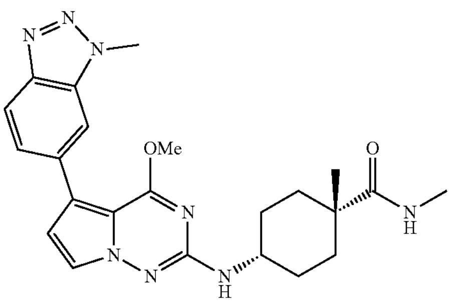 [SMILES: CNC(=O)[C@]1(C)CC[C@H](Nc2nc(OC)c3c(-c4ccc5nnn(C)c5c4)ccn3n2)CC1]
226
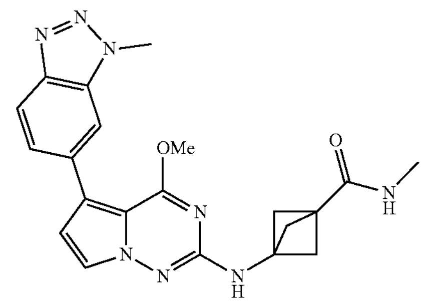 [SMILES: CNC(=O)C12CC(Nc3nc(OC)c4c(-c5ccc6nnn(C)c6c5)ccn4n3)(C1)C2]
227
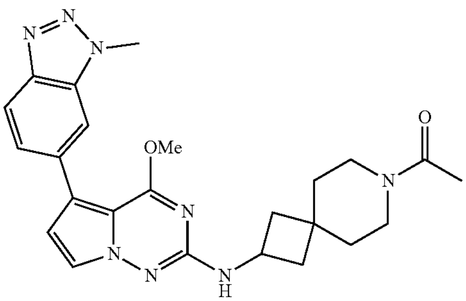 [SMILES: COc1nc(NC2CC3(CCN(C(C)=O)CC3)C2)nn2ccc(-c3ccc4nnn(C)c4c3)c12]

TABLE 1-continued
228
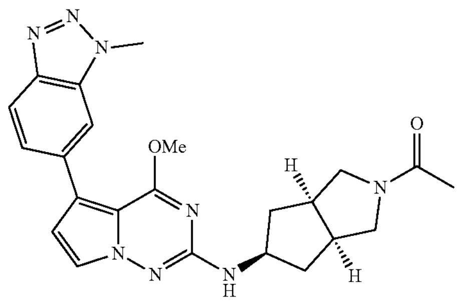 [SMILES: COc1nc(N[C@@H]2C[C@@H]3CN(C(C)=O)C[C@@H]3C2)nn2ccc(-c3ccc4nnn(C)c4c3)c12]
229
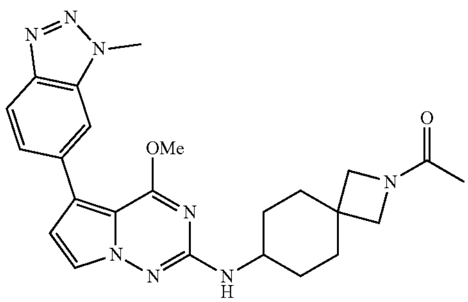 [SMILES: COc1nc(NC2CCC3(CC2)CN(C(C)=O)C3)nn2ccc(-c3ccc4nnn(C)c4c3)c12]
230
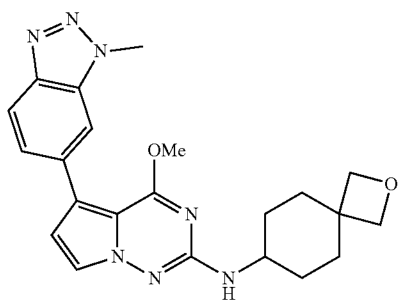 [SMILES: COc1nc(NC2CCC3(CC2)COC3)nn2ccc(-c3ccc4nnn(C)c4c3)c12]
231
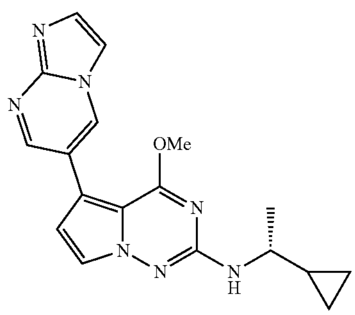 [SMILES: COc1nc(N[C@H](C)C2CC2)nn2ccc(-c3cnc4nccn4c3)c12]
232
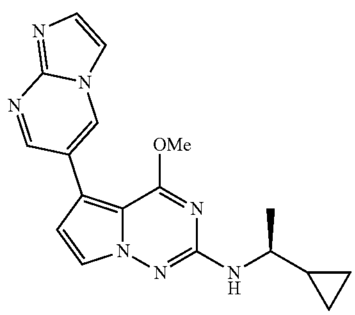 [SMILES: COc1nc(N[C@@H](C)C2CC2)nn2ccc(-c3cnc4nccn4c3)c12]
TABLE 1-continued
233
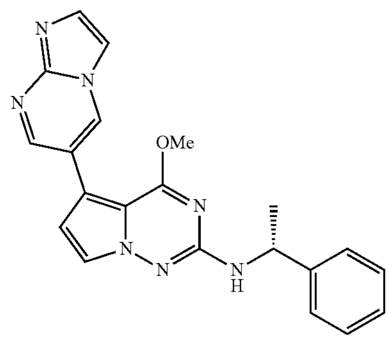 [SMILES: COc1nc(N[C@H](C)c2ccccc2)nn2ccc(-c3cnc4nccn4c3)c12]
234
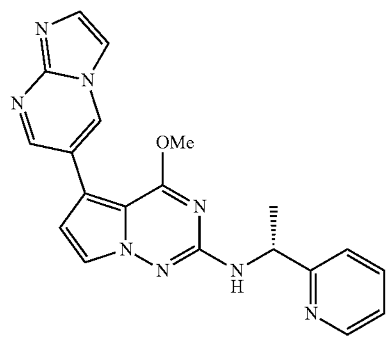 [SMILES: COc1nc(N[C@H](C)c2ccccn2)nn2ccc(-c3cnc4nccn4c3)c12]
235
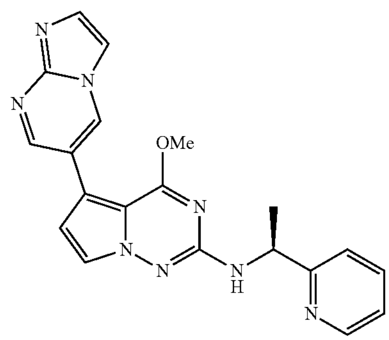 [SMILES: COc1nc(N[C@@H](C)c2ccccn2)nn2ccc(-c3cnc4nccn4c3)c12]
236
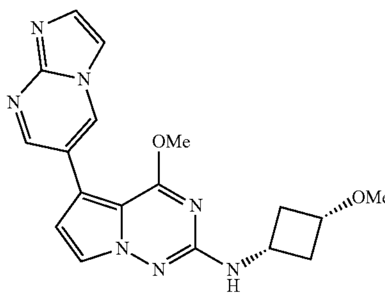
237
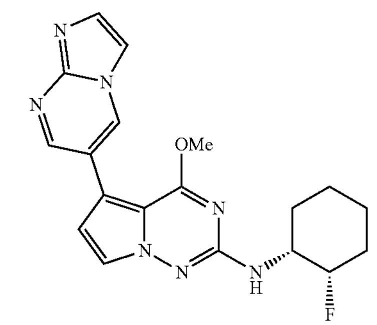 [SMILES: COc1nc(N[C@@H]2CCCC[C@@H]2F)nn2ccc(-c3cnc4nccn4c3)c12]

TABLE 1-continued
238
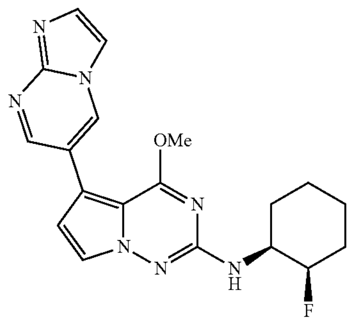 [SMILES: COc1nc(N[C@H]2CCCC[C@H]2F)nn2ccc(-c3cnc4nccn4c3)c12]
239
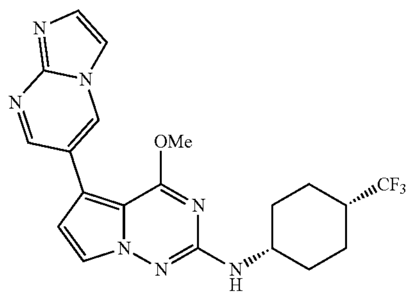 [SMILES: COc1nc(N[C@H]2CC[C@@H](C(F)(F)F)CC2)nn2ccc(-c3cnc4nccn4c3)c12]
240
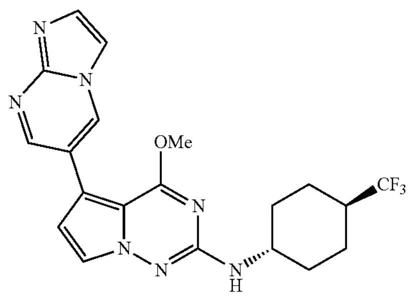 [SMILES: COc1nc(N[C@H]2CC[C@H](C(F)(F)F)CC2)nn2ccc(-c3cnc4nccn4c3)c12]
241
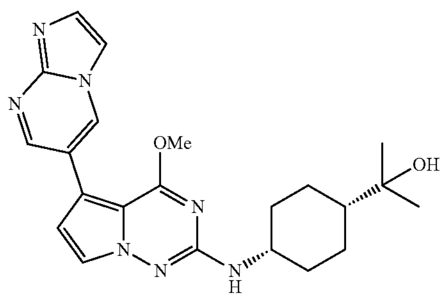 [SMILES: COc1nc(N[C@H]2CC[C@@H](C(C)(C)O)CC2)nn2ccc(-c3cnc4nccn4c3)c12]
242
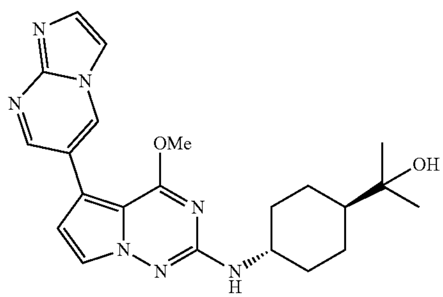 [SMILES: COc1nc(N[C@H]2CC[C@H](C(C)(C)O)CC2)nn2ccc(-c3cnc4nccn4c3)c12]
TABLE 1-continued
243
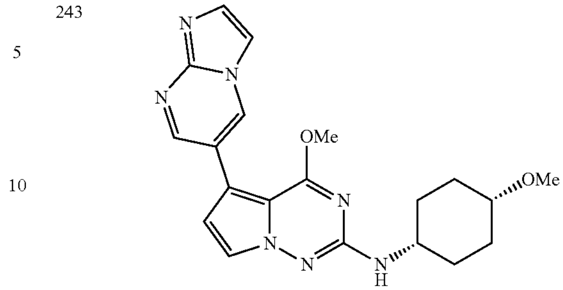
244
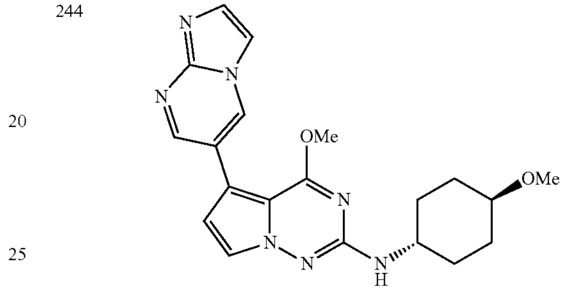
245
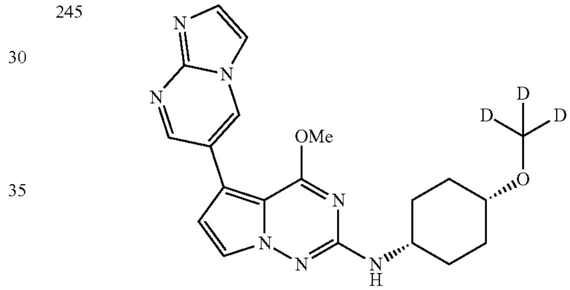
246
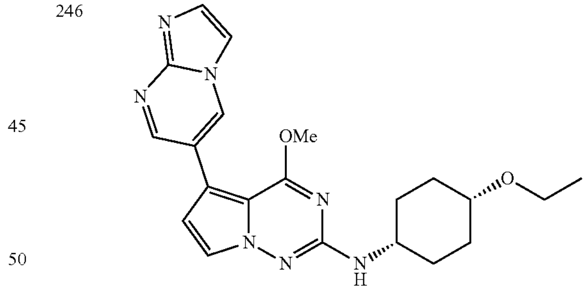
247
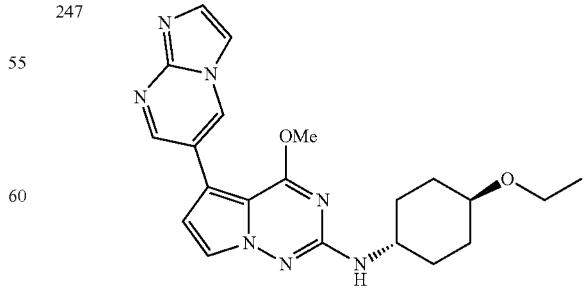

TABLE 1-continued
248
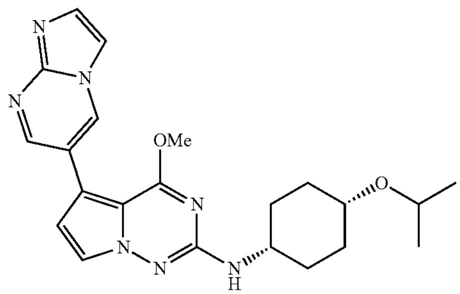 [SMILES: COc1nc(N[C@H]2CC[C@@H](OC(C)C)CC2)nn2ccc(-c3cnc4nccn4c3)c12]
249
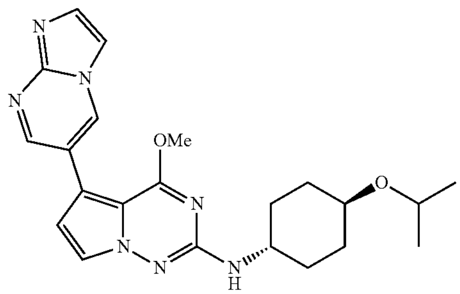 [SMILES: COc1nc(N[C@H]2CC[C@H](OC(C)C)CC2)nn2ccc(-c3cnc4nccn4c3)c12]
250
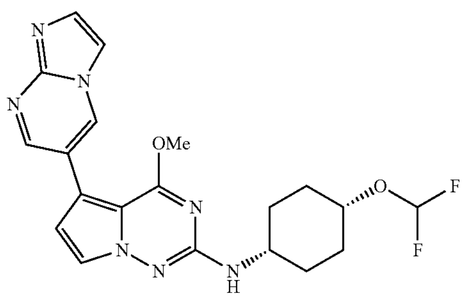 [SMILES: COc1nc(N[C@H]2CC[C@@H](OC(F)F)CC2)nn2ccc(-c3cnc4nccn4c3)c12]
251
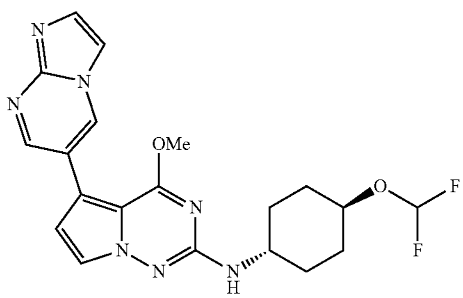 [SMILES: COc1nc(N[C@H]2CC[C@H](OC(F)F)CC2)nn2ccc(-c3cnc4nccn4c3)c12]
252
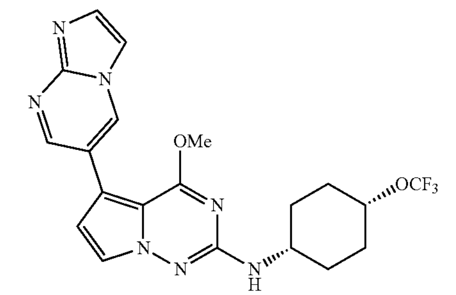 [SMILES: COc1nc(N[C@H]2CC[C@@H](OC(F)(F)F)CC2)nn2ccc(-c3cnc4nccn4c3)c12]
TABLE 1-continued
253
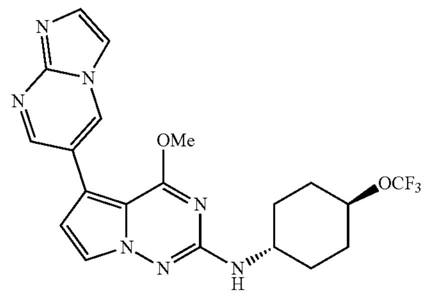 [SMILES: COc1nc(N[C@H]2CC[C@H](OC(F)(F)F)CC2)nn2ccc(-c3cnc4nccn4c3)c12]
254
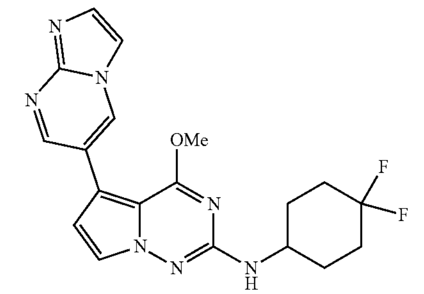 [SMILES: COc1nc(NC2CCC(F)(F)CC2)nn2ccc(-c3cnc4nccn4c3)c12]
255
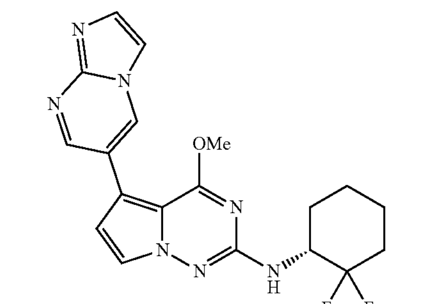
256
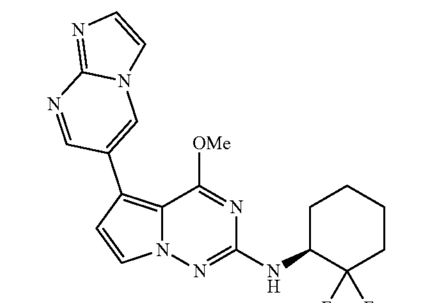
257
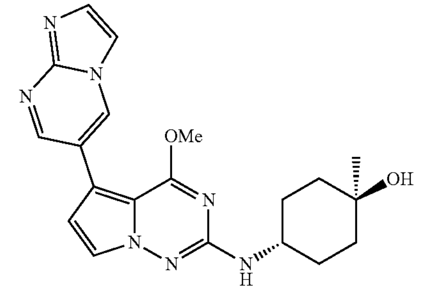 [SMILES: COc1nc(N[C@H]2CC[C@](C)(O)CC2)nn2ccc(-c3cnc4nccn4c3)c12]

TABLE 1-continued
258
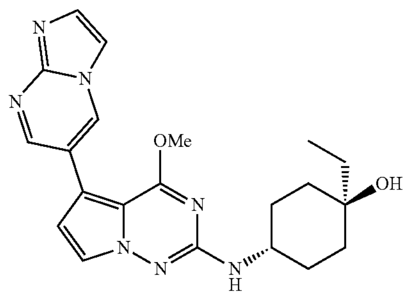 [SMILES: CC[C@]1(O)CC[C@H](Nc2nc(OC)c3c(-c4cnc5nccn5c4)ccn3n2)CC1]
259
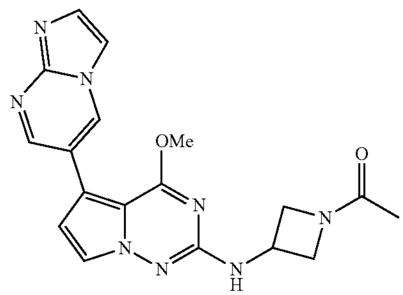 [SMILES: COc1nc(NC2CN(C(C)=O)C2)nn2ccc(-c3cnc4nccn4c3)c12]
260
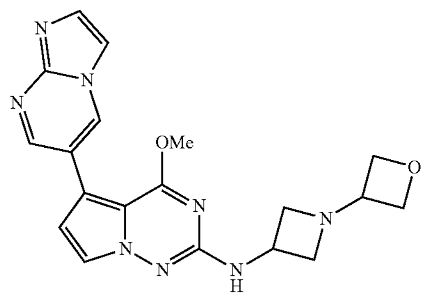 [SMILES: COc1nc(NC2CN(C3COC3)C2)nn2ccc(-c3cnc4nccn4c3)c12]
261
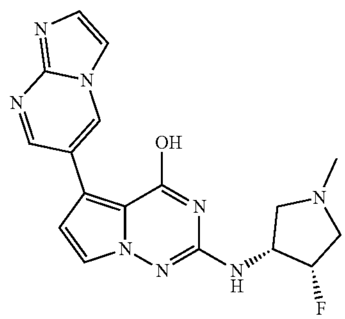 [SMILES: CN1C[C@H](F)[C@H](Nc2nc(O)c3c(-c4cnc5nccn5c4)ccn3n2)C1]
262
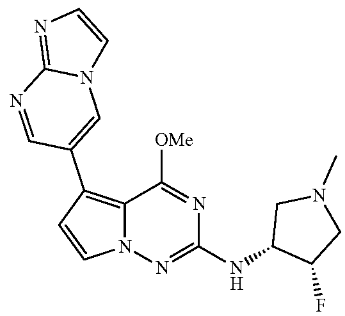 [SMILES: COc1nc(N[C@@H]2CN(C)C[C@@H]2F)nn2ccc(-c3cnc4nccn4c3)c12]
TABLE 1-continued
263
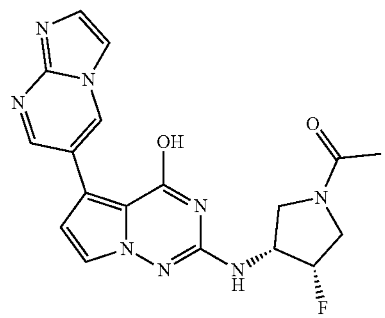 [SMILES: CC(=O)N1C[C@H](F)[C@H](Nc2nc(O)c3c(-c4cnc5nccn5c4)ccn3n2)C1]
264
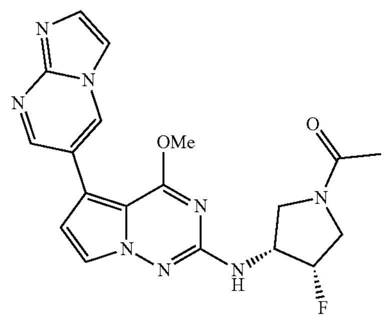 [SMILES: COc1nc(N[C@@H]2CN(C(C)=O)C[C@@H]2F)nn2ccc(-c3cnc4nccn4c3)c12]
265
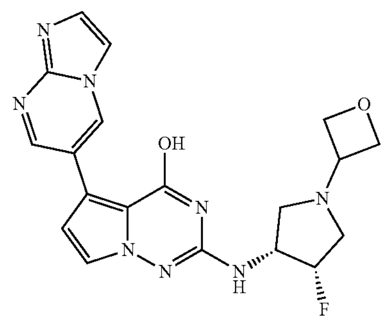 [SMILES: Oc1nc(N[C@@H]2CN(C3COC3)C[C@@H]2F)nn2ccc(-c3cnc4nccn4c3)c12]
266
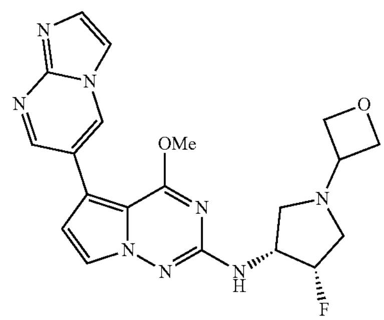 [SMILES: COc1nc(N[C@@H]2CN(C3COC3)C[C@@H]2F)nn2ccc(-c3cnc4nccn4c3)c12]
267
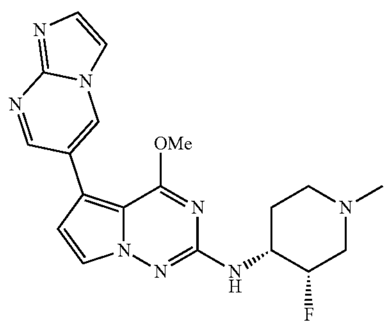 [SMILES: COc1nc(N[C@@H]2CCN(C)C[C@@H]2F)nn2ccc(-c3cnc4nccn4c3)c12]

TABLE 1-continued
268
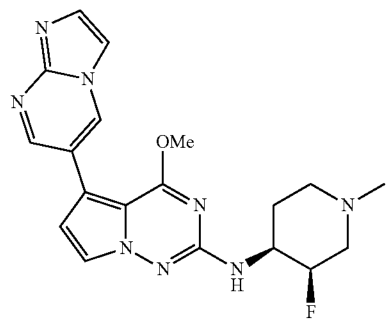 [SMILES: COc1nc(N[C@H]2CCN(C)C[C@H]2F)nn2ccc(-c3cnc4nccn4c3)c12]
269
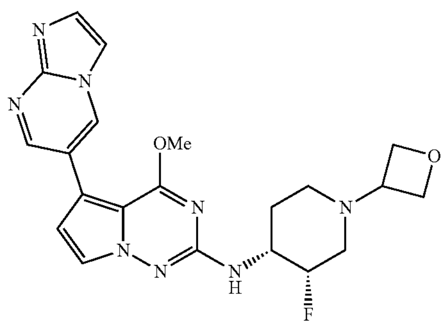 [SMILES: COc1nc(N[C@@H]2CCN(C3COC3)C[C@@H]2F)nn2ccc(-c3cnc4nccn4c3)c12]
270
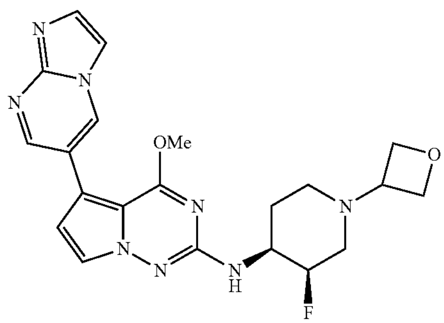 [SMILES: COc1nc(N[C@H]2CCN(C3COC3)C[C@H]2F)nn2ccc(-c3cnc4nccn4c3)c12]
271
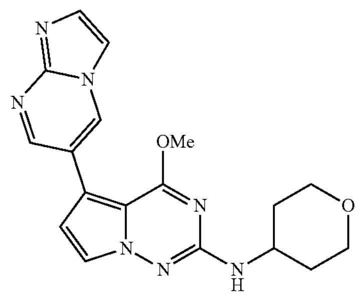 [SMILES: COc1nc(NC2CCOCC2)nn2ccc(-c3cnc4nccn4c3)c12]
272
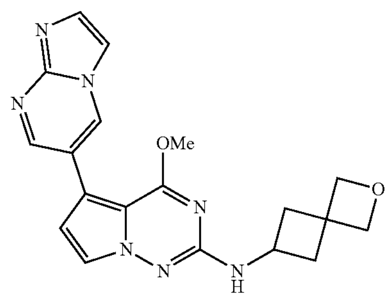 [SMILES: COc1nc(NC2CC3(COC3)C2)nn2ccc(-c3cnc4nccn4c3)c12]
TABLE 1-continued
273
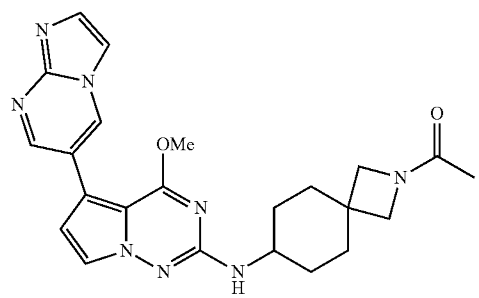 [SMILES: COc1nc(NC2CCC3(CC2)CN(C(C)=O)C3)nn2ccc(-c3cnc4nccn4c3)c12]
274
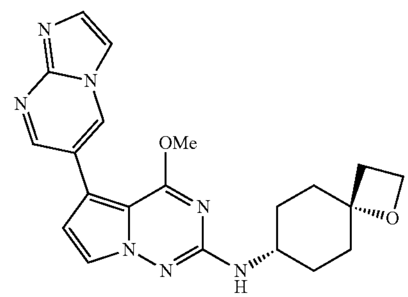 [SMILES: COc1nc(N[C@H]2CC[C@]3(CCO3)CC2)nn2ccc(-c3cnc4nccn4c3)c12]
275
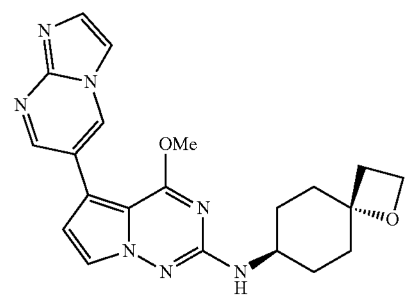 [SMILES: COc1nc(N[C@H]2CC[C@@]3(CCO3)CC2)nn2ccc(-c3cnc4nccn4c3)c12]
276
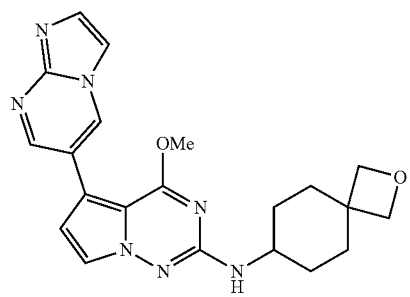 [SMILES: COc1nc(NC2CCC3(CC2)COC3)nn2ccc(-c3cnc4nccn4c3)c12]
277
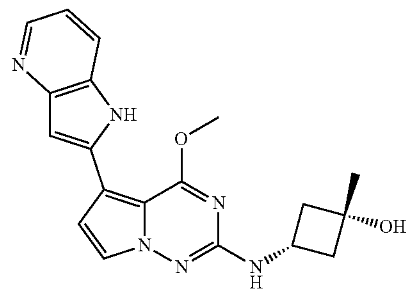 [SMILES: COc1nc(N[C@H]2C[C@@](C)(O)C2)nn2ccc(-c3cc4ncccc4[nH]3)c12]

TABLE 1-continued
278
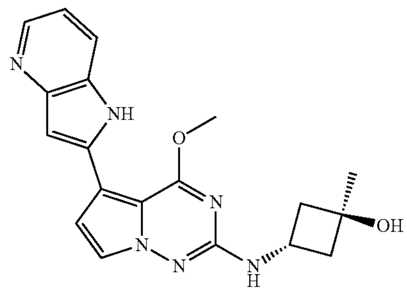 [SMILES: COc1nc(N[C@H]2C[C@](C)(O)C2)nn2ccc(-c3cc4ncccc4[nH]3)c12]
279
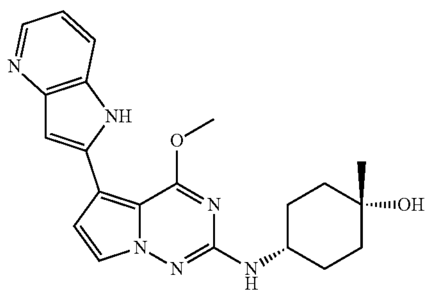 [SMILES: COc1nc(N[C@H]2CC[C@@](C)(O)CC2)nn2ccc(-c3cc4ncccc4[nH]3)c12]
280
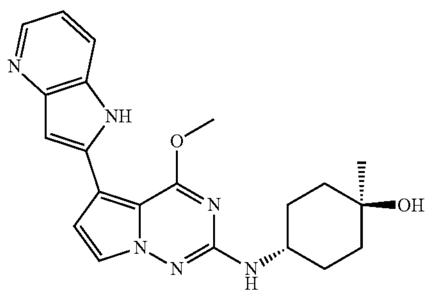 [SMILES: COc1nc(N[C@H]2CC[C@](C)(O)CC2)nn2ccc(-c3cc4ncccc4[nH]3)c12]
281
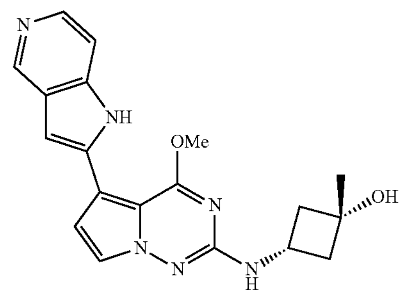 [SMILES: COc1nc(N[C@H]2C[C@@](C)(O)C2)nn2ccc(-c3cc4cnccc4[nH]3)c12]
282
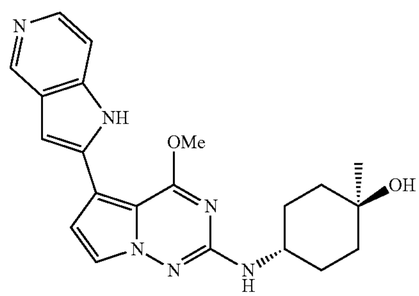 [SMILES: COc1nc(N[C@H]2CC[C@](C)(O)CC2)nn2ccc(-c3cc4cnccc4[nH]3)c12]
TABLE 1-continued
283
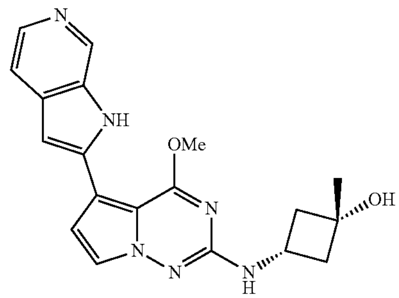 [SMILES: COc1nc(N[C@H]2C[C@@](C)(O)C2)nn2ccc(-c3cc4ccncc4[nH]3)c12]
284
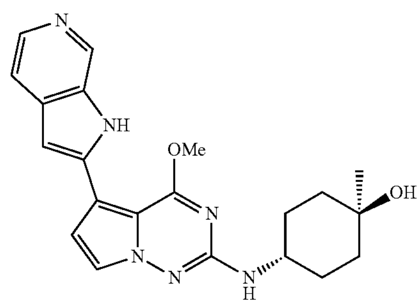 [SMILES: COc1nc(N[C@H]2CC[C@](C)(O)CC2)nn2ccc(-c3cc4ccncc4[nH]3)c12]
285
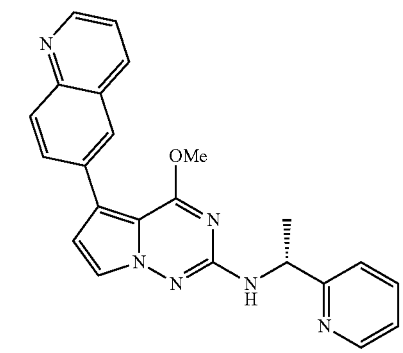 [SMILES: COc1nc(N[C@H](C)c2ccccn2)nn2ccc(-c3ccc4ncccc4c3)c12]
286
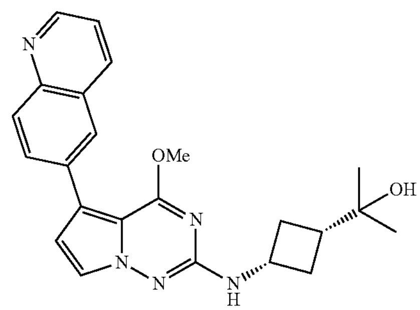 [SMILES: COc1nc(N[C@H]2C[C@@H](C(C)(C)O)C2)nn2ccc(-c3ccc4ncccc4c3)c12]
287
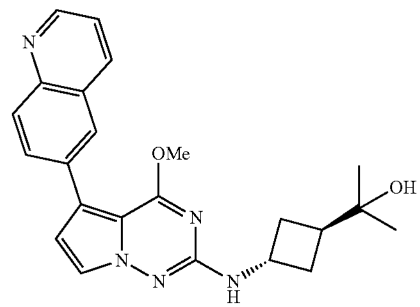 [SMILES: COc1nc(N[C@H]2C[C@H](C(C)(C)O)C2)nn2ccc(-c3ccc4ncccc4c3)c12]

TABLE 1-continued
288
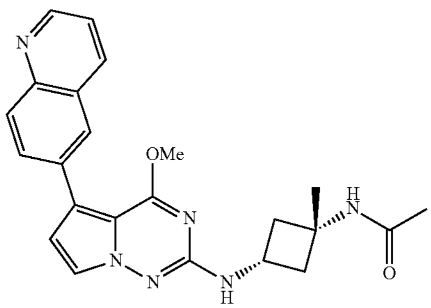
289
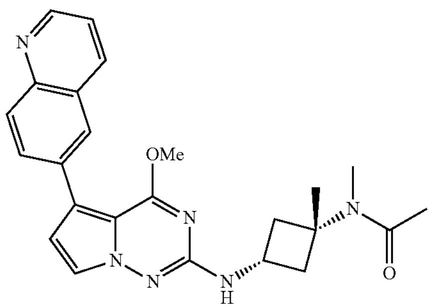 [SMILES: COc1nc(N[C@H]2C[C@@](C)(N(C)C(C)=O)C2)nn2ccc(-c3ccc4ncccc4c3)c12]
290
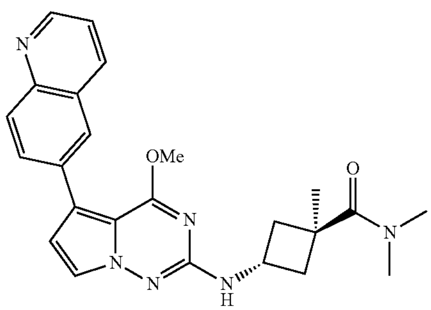 [SMILES: COc1nc(N[C@H]2C[C@](C)(C(=O)N(C)C)C2)nn2ccc(-c3ccc4ncccc4c3)c12]
291
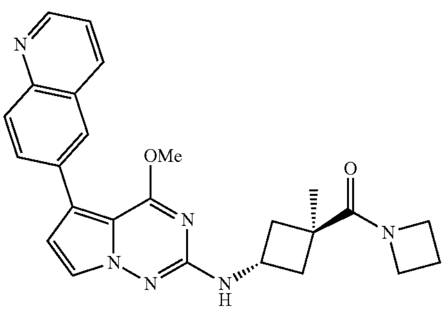 [SMILES: COc1nc(N[C@H]2C[C@](C)(C(=O)N3CCC3)C2)nn2ccc(-c3ccc4ncccc4c3)c12]
292
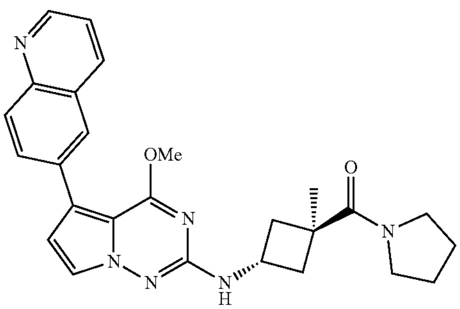 [SMILES: COc1nc(N[C@H]2C[C@](C)(C(=O)N3CCCC3)C2)nn2ccc(-c3ccc4ncccc4c3)c12]
TABLE 1-continued
293
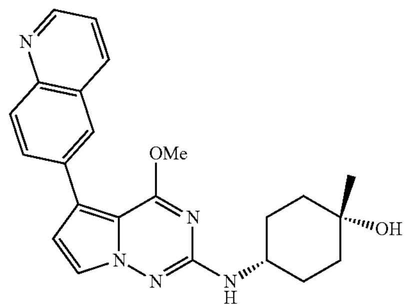 [SMILES: COc1nc(N[C@H]2CC[C@@](C)(O)CC2)nn2ccc(-c3ccc4ncccc4c3)c12]
294
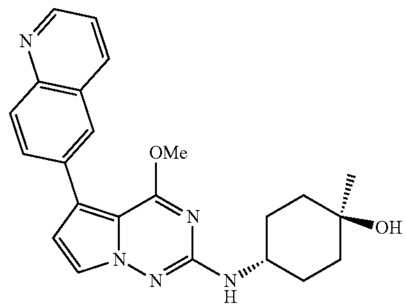 [SMILES: COc1nc(N[C@H]2CC[C@](C)(O)CC2)nn2ccc(-c3ccc4ncccc4c3)c12]
295
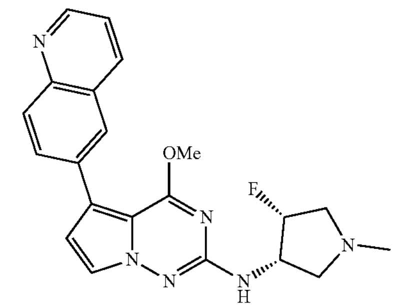 [SMILES: COc1nc(N[C@H]2CN(C)C[C@H]2F)nn2ccc(-c3ccc4ncccc4c3)c12]
296
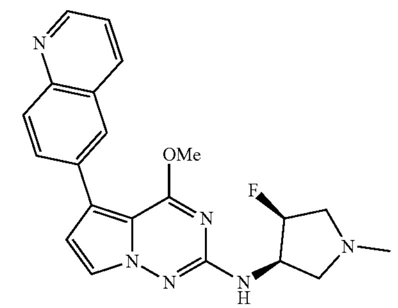 [SMILES: COc1nc(N[C@@H]2CN(C)C[C@@H]2F)nn2ccc(-c3ccc4ncccc4c3)c12]
297
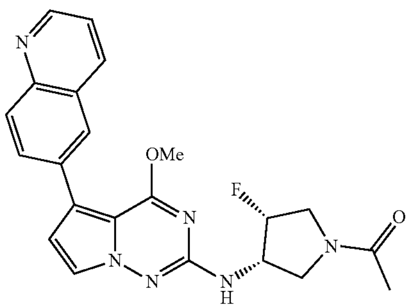 [SMILES: COc1nc(N[C@H]2CN(C(C)=O)C[C@H]2F)nn2ccc(-c3ccc4ncccc4c3)c12]

TABLE 1-continued
298
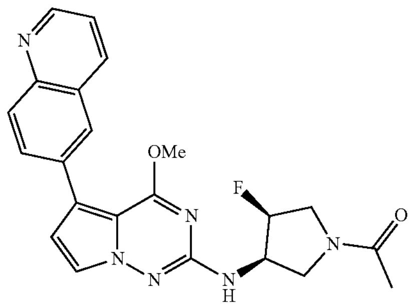 [SMILES: COc1nc(N[C@@H]2CN(C(C)=O)C[C@@H]2F)nn2ccc(-c3ccc4ncccc4c3)c12]
299
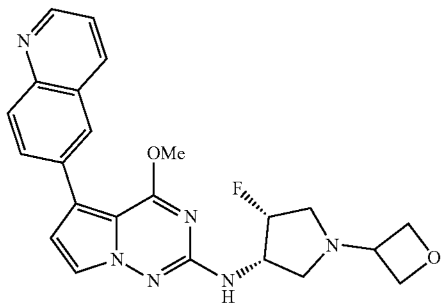 [SMILES: COc1nc(N[C@H]2CN(C3COC3)C[C@H]2F)nn2ccc(-c3ccc4ncccc4c3)c12]
300
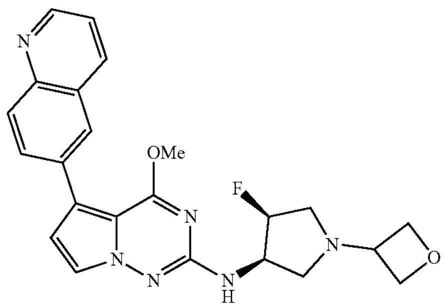 [SMILES: COc1nc(N[C@@H]2CN(C3COC3)C[C@@H]2F)nn2ccc(-c3ccc4ncccc4c3)c12]
301
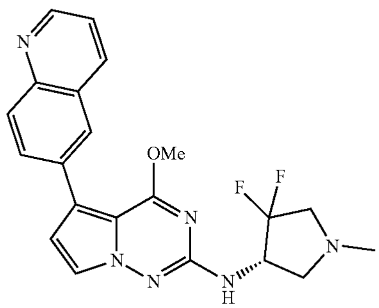 [SMILES: COc1nc(N[C@H]2CN(C)CC2(F)F)nn2ccc(-c3ccc4ncccc4c3)c12]
302
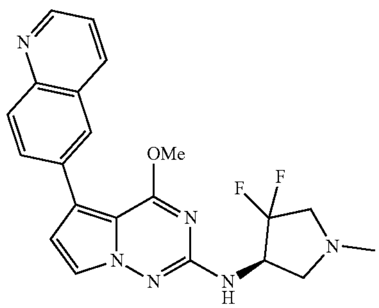 [SMILES: COc1nc(N[C@@H]2CN(C)CC2(F)F)nn2ccc(-c3ccc4ncccc4c3)c12]
TABLE 1-continued
303
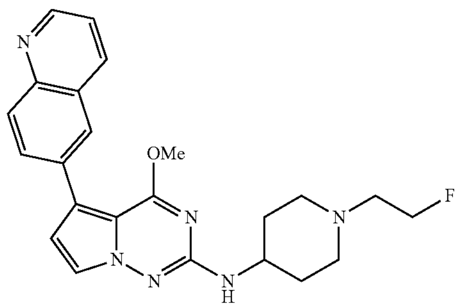
304
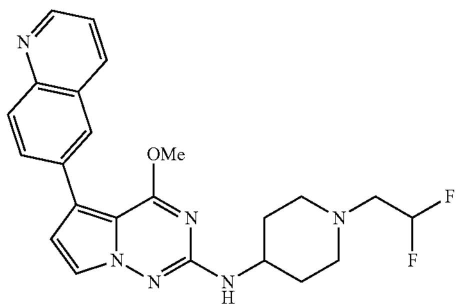
305
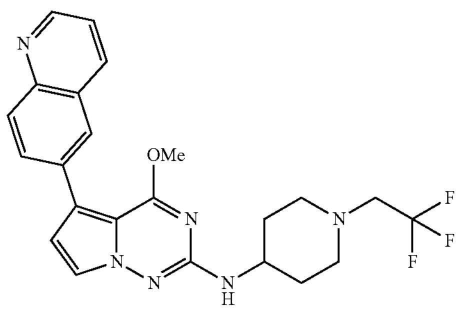
306
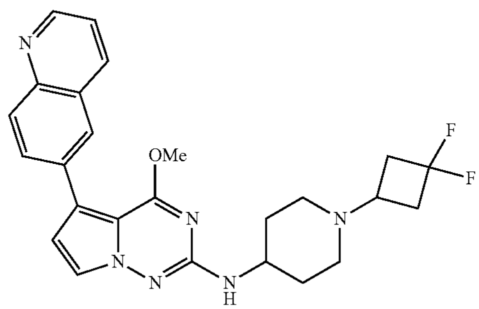
307
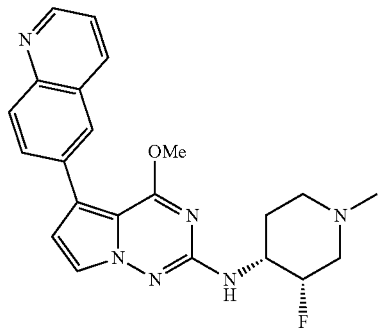

308
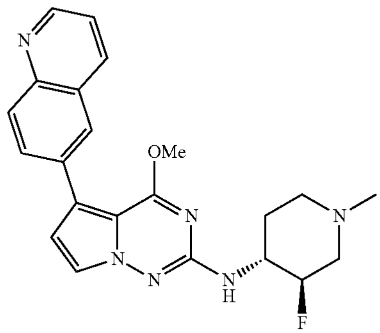 [SMILES: COc1nc(N[C@@H]2CCN(C)C[C@H]2F)nn2ccc(-c3ccc4ncccc4c3)c12]
309
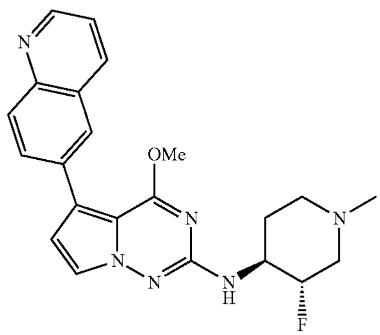 [SMILES: COc1nc(N[C@H]2CCN(C)C[C@@H]2F)nn2ccc(-c3ccc4ncccc4c3)c12]
310
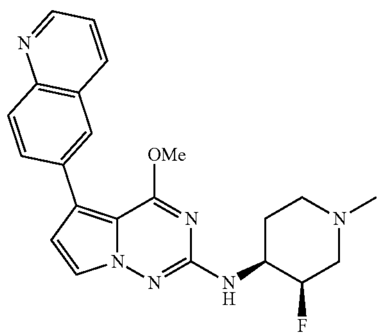
311
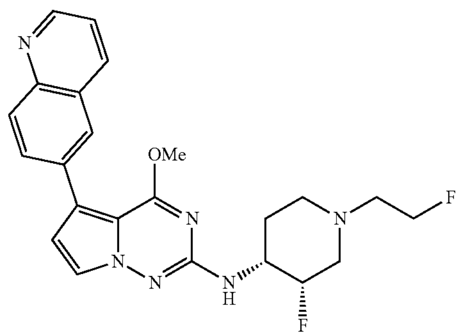 [SMILES: COc1nc(N[C@@H]2CCN(CCF)C[C@@H]2F)nn2ccc(-c3ccc4ncccc4c3)c12]
312
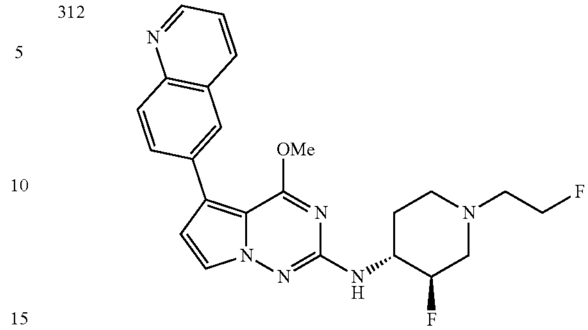
313
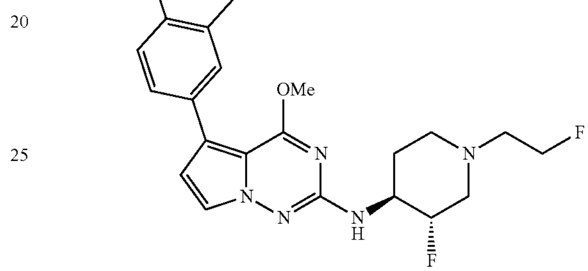
314
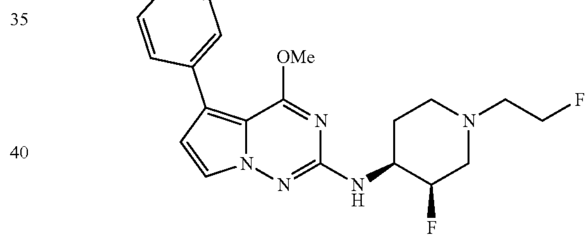
315
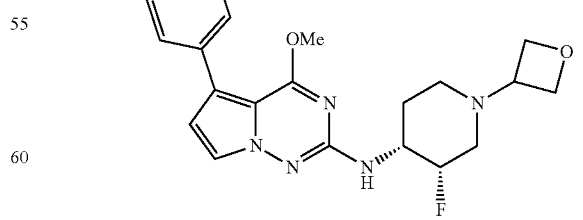

TABLE 1-continued
316
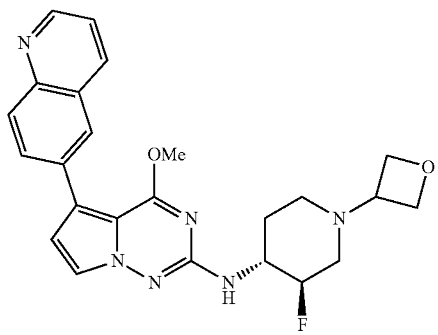
317
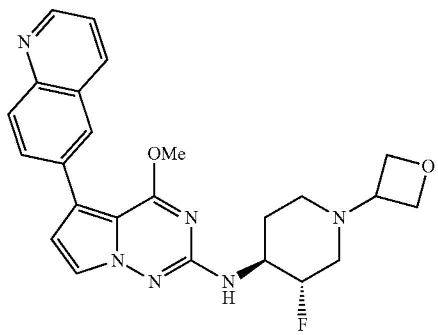 [SMILES: COc1nc(N[C@H]2CCN(C3COC3)C[C@@H]2F)nn2ccc(-c3ccc4ncccc4c3)c12]
318
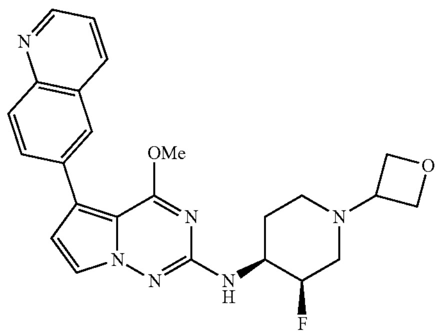
319
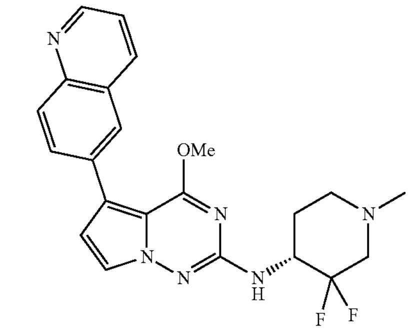
TABLE 1-continued
320
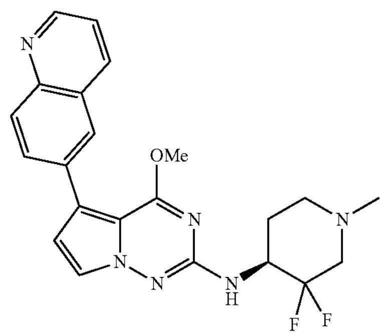 [SMILES: COc1nc(N[C@H]2CCN(C)CC2(F)F)nn2ccc(-c3ccc4ncccc4c3)c12]
321
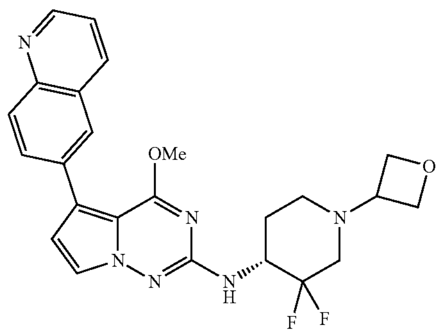
322
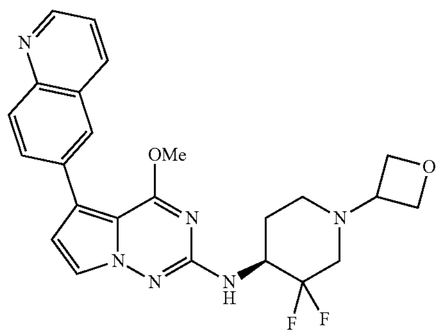
323
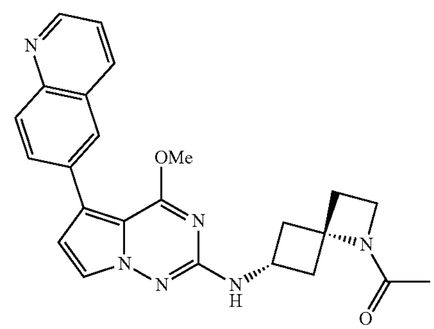
324
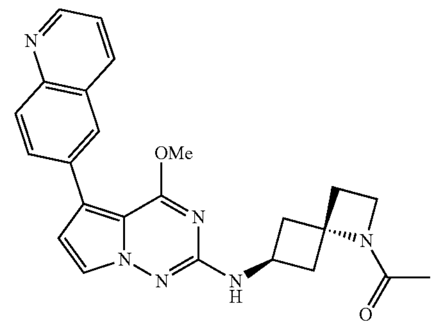

325
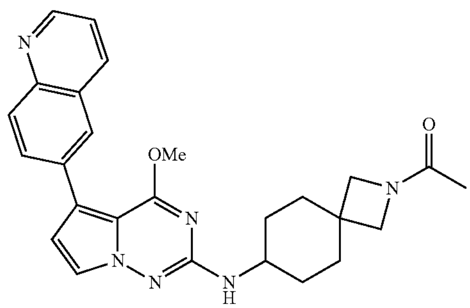
326
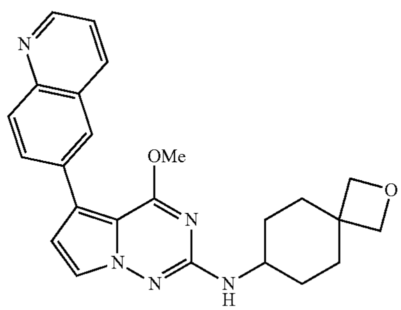 [SMILES: COc1nc(NC2CCC3(CC2)COC3)nn2ccc(-c3ccc4ncccc4c3)c12]
327
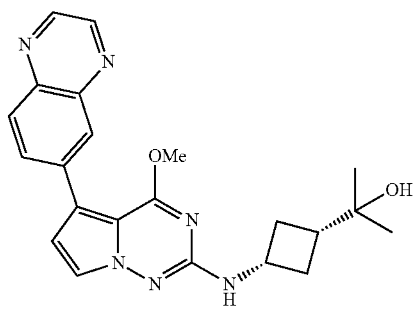 [SMILES: COc1nc(N[C@H]2C[C@@H](C(C)(C)O)C2)nn2ccc(-c3ccc4nccnc4c3)c12]
328
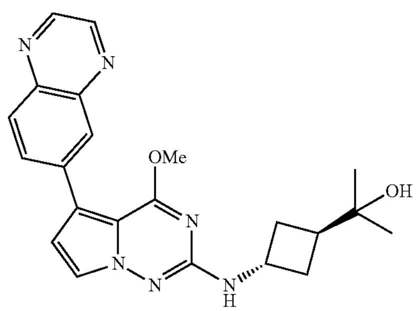 [SMILES: COc1nc(N[C@H]2C[C@H](C(C)(C)O)C2)nn2ccc(-c3ccc4nccnc4c3)c12]
329
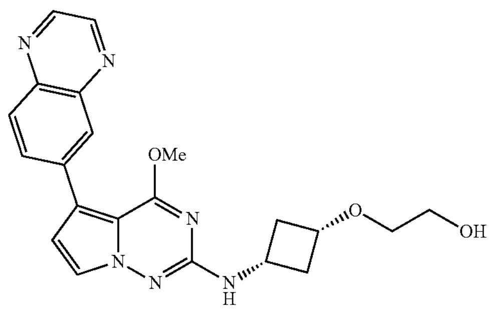 [SMILES: COc1nc(N[C@H]2C[C@@H](OCCO)C2)nn2ccc(-c3ccc4nccnc4c3)c12]
330
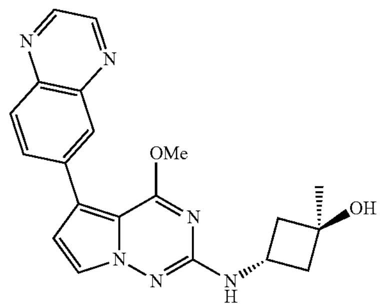 [SMILES: COc1nc(N[C@H]2C[C@](C)(O)C2)nn2ccc(-c3ccc4nccnc4c3)c12]
331
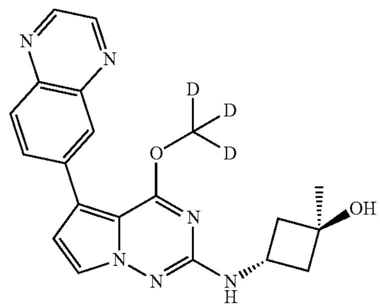 [SMILES: [2H]C([2H])([2H])Oc1nc(N[C@H]2C[C@](C)(O)C2)nn2ccc(-c3ccc4nccnc4c3)c12]
332
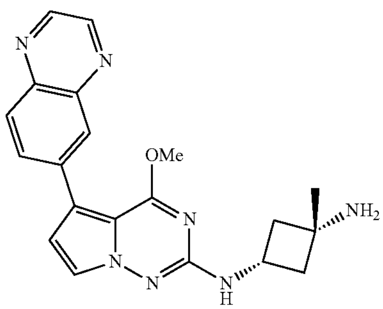 [SMILES: COc1nc(N[C@H]2C[C@@](C)(N)C2)nn2ccc(-c3ccc4nccnc4c3)c12]
333
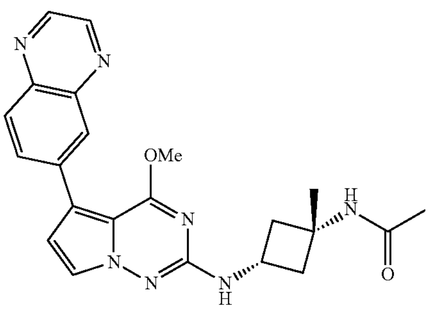 [SMILES: COc1nc(N[C@H]2C[C@@](C)(NC(C)=O)C2)nn2ccc(-c3ccc4nccnc4c3)c12]
334
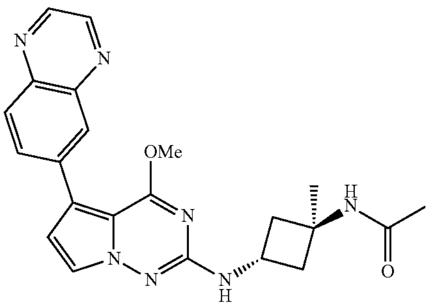 [SMILES: COc1nc(N[C@H]2C[C@](C)(NC(C)=O)C2)nn2ccc(-c3ccc4nccnc4c3)c12]

TABLE 1-continued
335
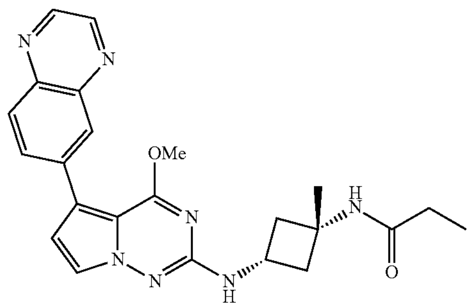 [SMILES: CCC(=O)N[C@]1(C)C[C@H](Nc2nc(OC)c3c(-c4ccc5nccnc5c4)ccn3n2)C1]
336
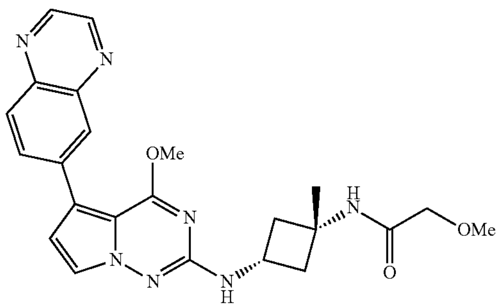 [SMILES: COCC(=O)N[C@]1(C)C[C@H](Nc2nc(OC)c3c(-c4ccc5nccnc5c4)ccn3n2)C1]
337
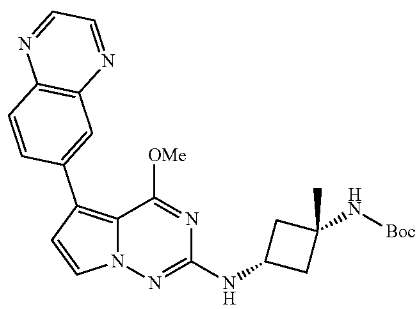 [SMILES: COc1nc(N[C@H]2C[C@@](C)(NC(=O)OC(C)(C)C)C2)nn2ccc(-c3ccc4nccnc4c3)c12]
338
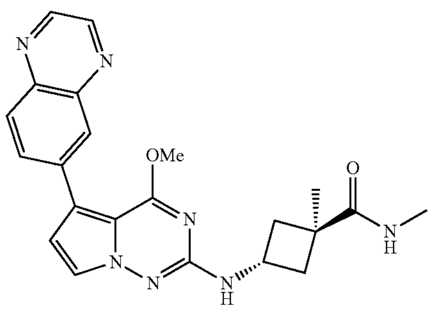 [SMILES: CNC(=O)[C@]1(C)C[C@@H](Nc2nc(OC)c3c(-c4ccc5nccnc5c4)ccn3n2)C1]
339
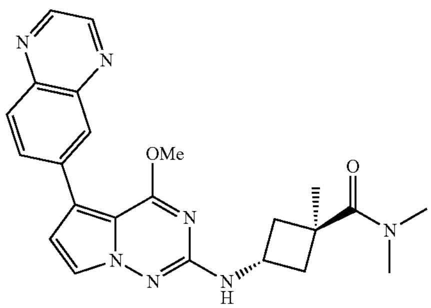 [SMILES: COc1nc(N[C@H]2C[C@](C)(C(=O)N(C)C)C2)nn2ccc(-c3ccc4nccnc4c3)c12]
TABLE 1-continued
340
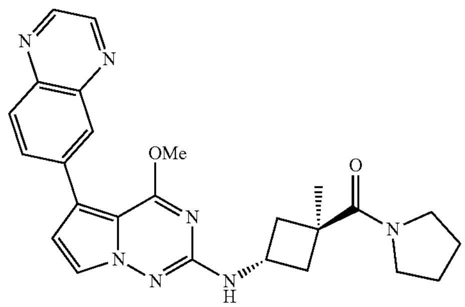 [SMILES: COc1nc(N[C@H]2C[C@](C)(C(=O)N3CCCC3)C2)nn2ccc(-c3ccc4nccnc4c3)c12]
341
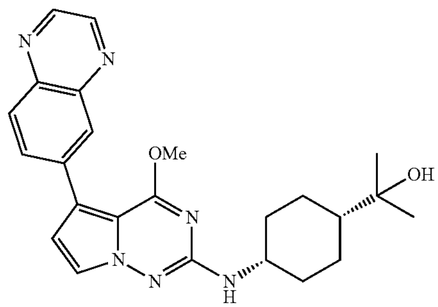 [SMILES: COc1nc(N[C@H]2CC[C@@H](C(C)(C)O)CC2)nn2ccc(-c3ccc4nccnc4c3)c12]
342
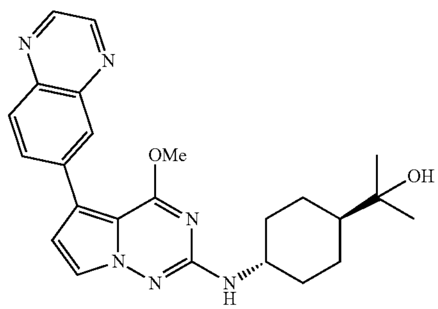 [SMILES: COc1nc(N[C@H]2CC[C@H](C(C)(C)O)CC2)nn2ccc(-c3ccc4nccnc4c3)c12]
343
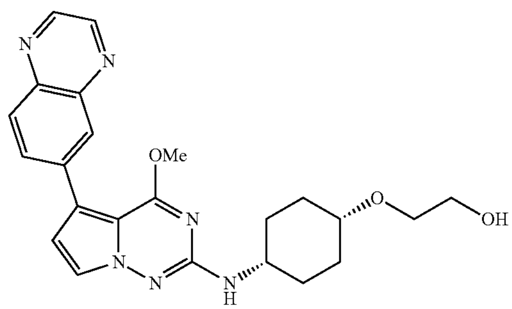 [SMILES: COc1nc(N[C@H]2CC[C@@H](OCCO)CC2)nn2ccc(-c3ccc4nccnc4c3)c12]
344
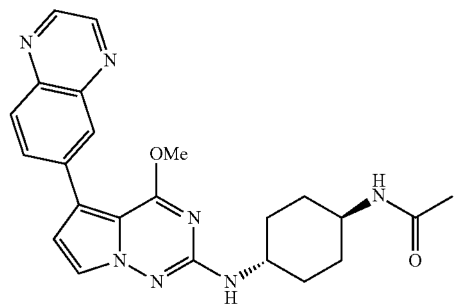 [SMILES: COc1nc(N[C@H]2CC[C@H](NC(C)=O)CC2)nn2ccc(-c3ccc4nccnc4c3)c12]

TABLE 1-continued
345
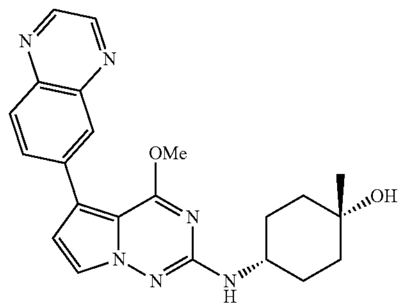 [SMILES: COc1nc(N[C@H]2CC[C@@](C)(O)CC2)nn2ccc(-c3ccc4nccnc4c3)c12]
346
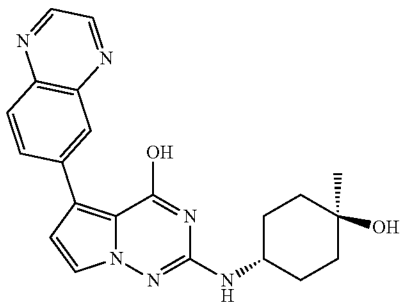 [SMILES: C[C@]1(O)CC[C@H](Nc2nc(O)c3c(-c4ccc5nccnc5c4)ccn3n2)CC1]
347
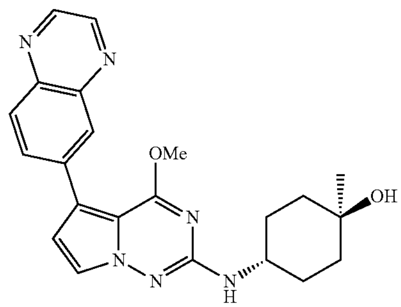 [SMILES: COc1nc(N[C@H]2CC[C@](C)(O)CC2)nn2ccc(-c3ccc4nccnc4c3)c12]
348
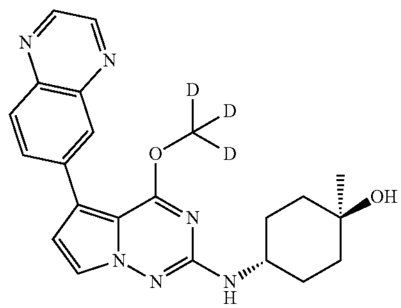 [SMILES: [2H]C([2H])([2H])Oc1nc(N[C@H]2CC[C@](C)(O)CC2)nn2ccc(-c3ccc4nccnc4c3)c12]
349
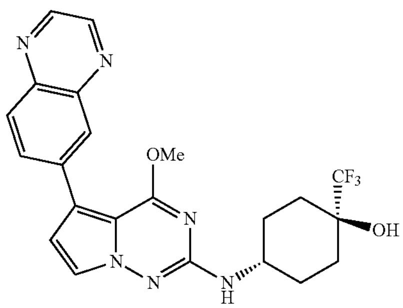 [SMILES: COc1nc(N[C@H]2CC[C@@](O)(C(F)(F)F)CC2)nn2ccc(-c3ccc4nccnc4c3)c12]
TABLE 1-continued
350
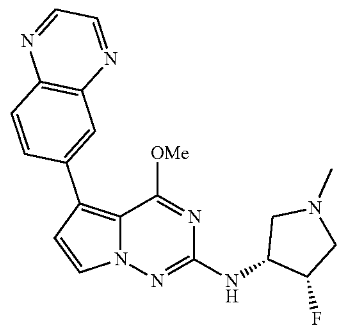 [SMILES: COc1nc(N[C@@H]2CN(C)C[C@@H]2F)nn2ccc(-c3ccc4nccnc4c3)c12]
351
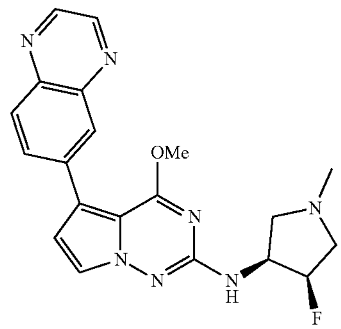 [SMILES: COc1nc(N[C@H]2CN(C)C[C@H]2F)nn2ccc(-c3ccc4nccnc4c3)c12]
352
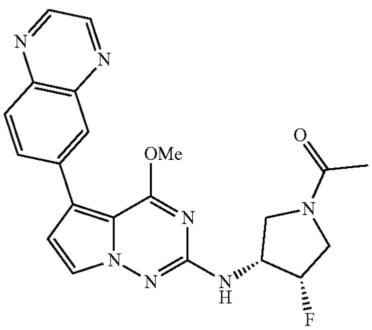 [SMILES: COc1nc(N[C@@H]2CN(C(C)=O)C[C@@H]2F)nn2ccc(-c3ccc4nccnc4c3)c12]
353
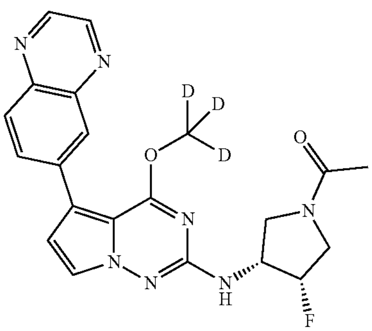 [SMILES: [2H]C([2H])([2H])Oc1nc(N[C@@H]2CN(C(C)=O)C[C@@H]2F)nn2ccc(-c3ccc4nccnc4c3)c12]
354
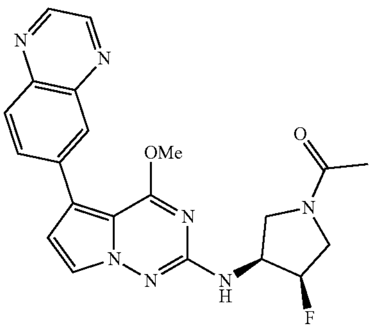 [SMILES: COc1nc(N[C@H]2CN(C(C)=O)C[C@H]2F)nn2ccc(-c3ccc4nccnc4c3)c12]

TABLE 1-continued
355
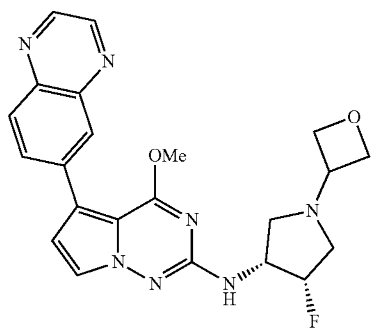 [SMILES: COc1nc(N[C@@H]2CN(C3COC3)C[C@@H]2F)nn2ccc(-c3ccc4nccnc4c3)c12]
356
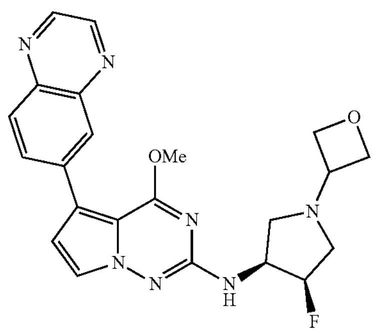 [SMILES: COc1nc(N[C@H]2CN(C3COC3)C[C@H]2F)nn2ccc(-c3ccc4nccnc4c3)c12]
357
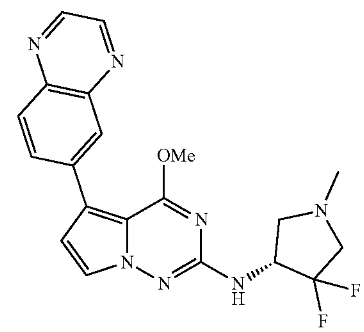 [SMILES: COc1nc(N[C@@H]2CN(C)CC2(F)F)nn2ccc(-c3ccc4nccnc4c3)c12]
358
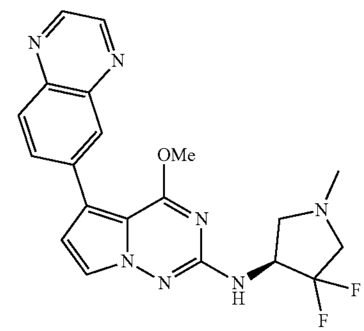 [SMILES: COc1nc(N[C@H]2CN(C)CC2(F)F)nn2ccc(-c3ccc4nccnc4c3)c12]
TABLE 1-continued
359
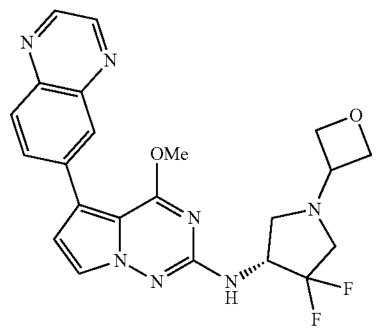 [SMILES: COc1nc(N[C@@H]2CN(C3COC3)CC2(F)F)nn2ccc(-c3ccc4nccnc4c3)c12]
360
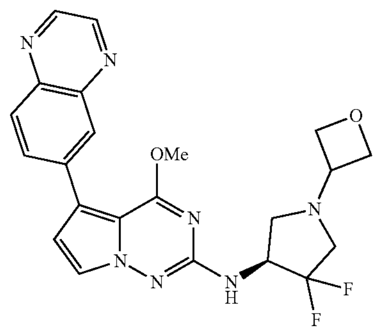 [SMILES: COc1nc(N[C@H]2CN(C3COC3)CC2(F)F)nn2ccc(-c3ccc4nccnc4c3)c12]
361
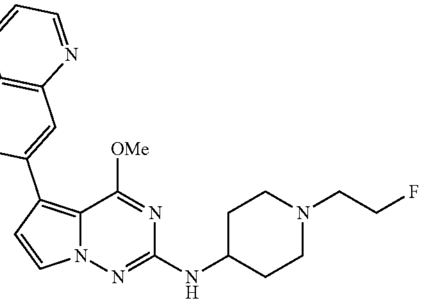
362
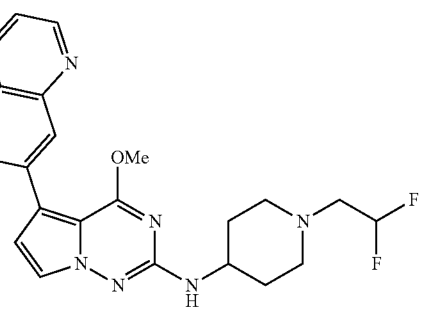
363
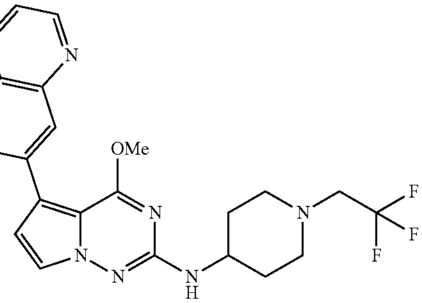

TABLE 1-continued
364
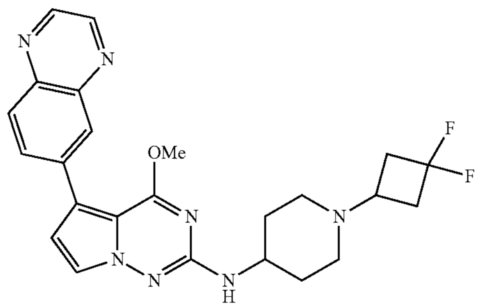 [SMILES: COc1nc(NC2CCN(C3CC(F)(F)C3)CC2)nn2ccc(-c3ccc4nccnc4c3)c12]
365
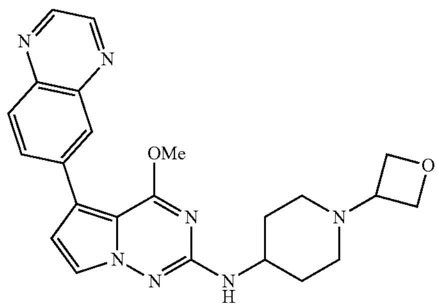 [SMILES: COc1nc(NC2CCN(C3COC3)CC2)nn2ccc(-c3ccc4nccnc4c3)c12]
366
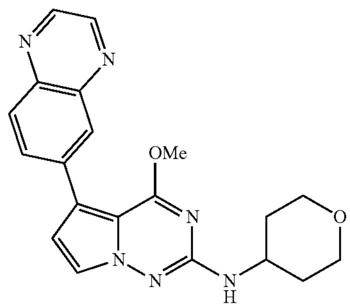 [SMILES: COc1nc(NC2CCOCC2)nn2ccc(-c3ccc4nccnc4c3)c12]
367
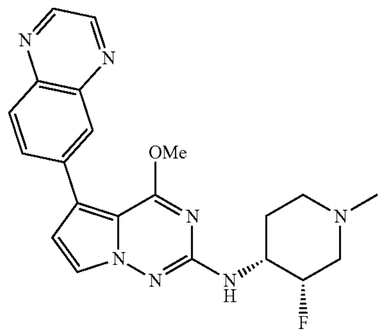 [SMILES: COc1nc(N[C@@H]2CCN(C)C[C@@H]2F)nn2ccc(-c3ccc4nccnc4c3)c12]
368
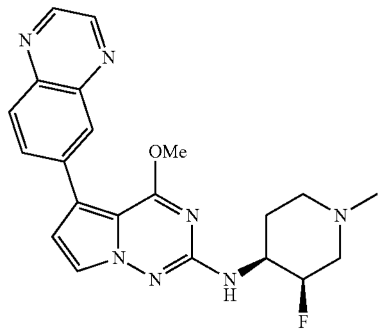 [SMILES: COc1nc(N[C@H]2CCN(C)C[C@H]2F)nn2ccc(-c3ccc4nccnc4c3)c12]
TABLE 1-continued
369
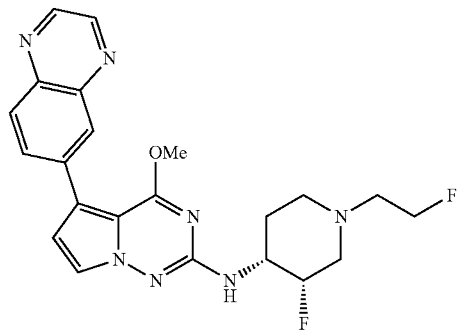 [SMILES: COc1nc(N[C@@H]2CCN(CCF)C[C@@H]2F)nn2ccc(-c3ccc4nccnc4c3)c12]
370
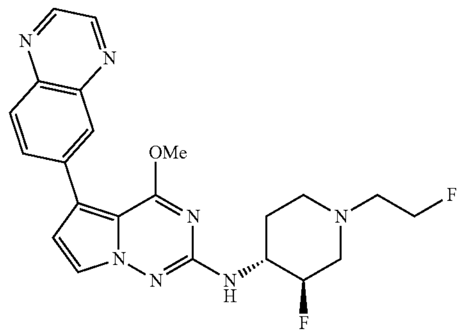 [SMILES: COc1nc(N[C@@H]2CCN(CCF)C[C@H]2F)nn2ccc(-c3ccc4nccnc4c3)c12]
371
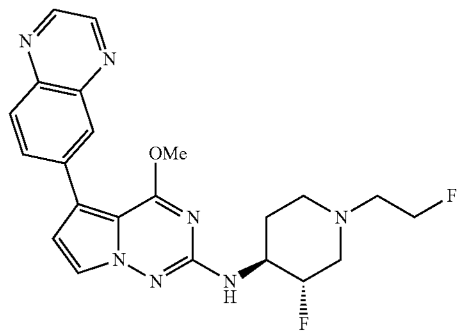 [SMILES: COc1nc(N[C@H]2CCN(CCF)C[C@@H]2F)nn2ccc(-c3ccc4nccnc4c3)c12]
372
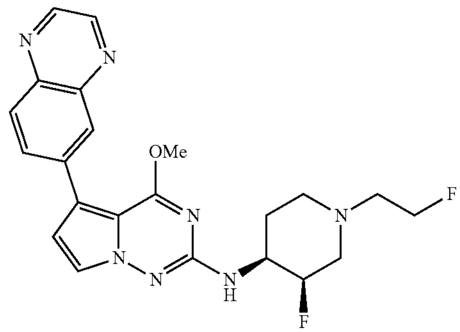 [SMILES: COc1nc(N[C@H]2CCN(CCF)C[C@H]2F)nn2ccc(-c3ccc4nccnc4c3)c12]

TABLE 1-continued
373
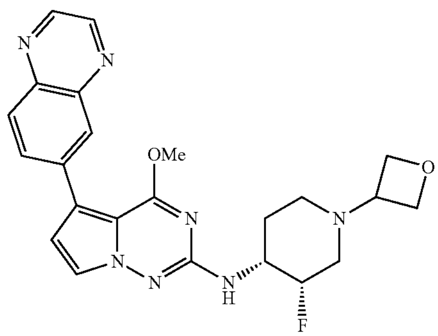 [SMILES: COc1nc(N[C@@H]2CCN(C3COC3)C[C@@H]2F)nn2ccc(-c3ccc4nccnc4c3)c12]
374
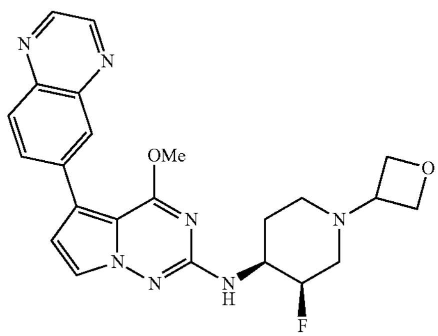 [SMILES: COc1nc(N[C@H]2CCN(C3COC3)C[C@H]2F)nn2ccc(-c3ccc4nccnc4c3)c12]
375
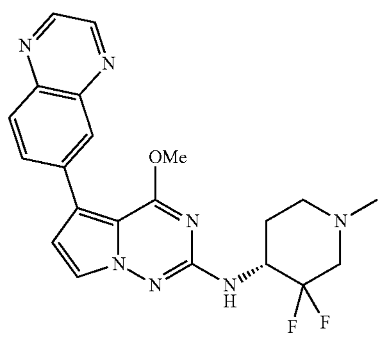 [SMILES: COc1nc(N[C@@H]2CCN(C)CC2(F)F)nn2ccc(-c3ccc4nccnc4c3)c12]
376
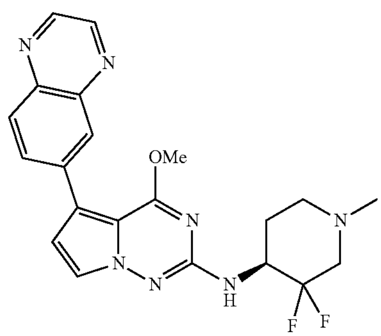 [SMILES: COc1nc(N[C@H]2CCN(C)CC2(F)F)nn2ccc(-c3ccc4nccnc4c3)c12]
TABLE 1-continued
377
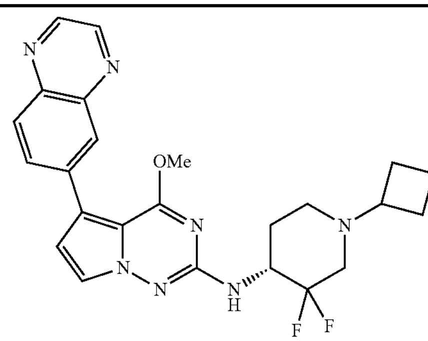
378
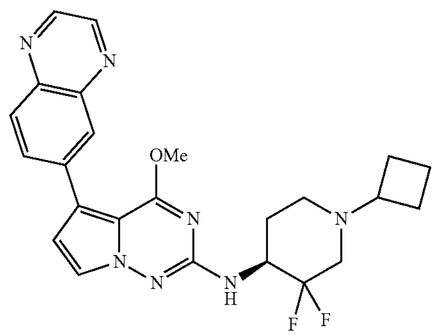 [SMILES: COc1nc(N[C@H]2CCN(C3CCC3)CC2(F)F)nn2ccc(-c3ccc4nccnc4c3)c12]
379
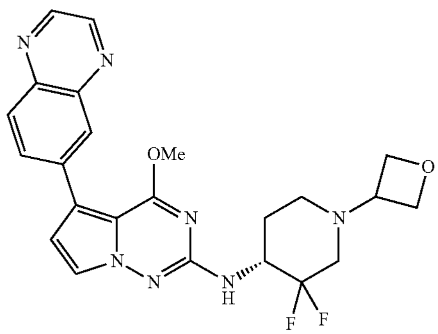 [SMILES: COc1nc(N[C@@H]2CCN(C3COC3)CC2(F)F)nn2ccc(-c3ccc4nccnc4c3)c12]
380
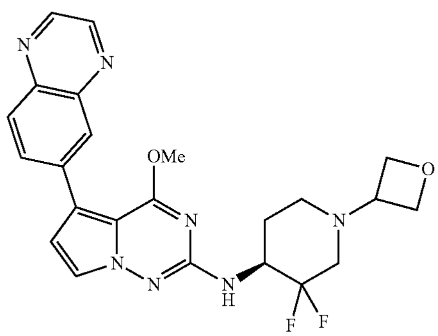 [SMILES: COc1nc(N[C@H]2CCN(C3COC3)CC2(F)F)nn2ccc(-c3ccc4nccnc4c3)c12]
381
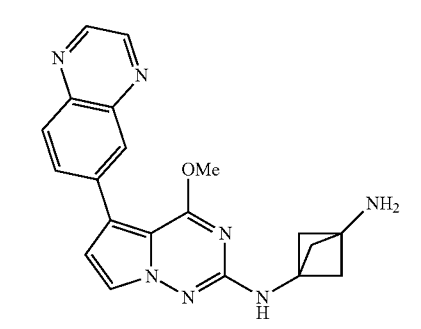 [SMILES: COc1nc(NC23CC(N)(C2)C3)nn2ccc(-c3ccc4nccnc4c3)c12]

TABLE 1-continued
382
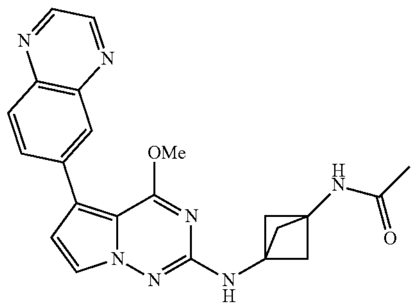 [SMILES: COc1nc(NC23CC(NC(C)=O)(C2)C3)nn2ccc(-c3ccc4nccnc4c3)c12]
383
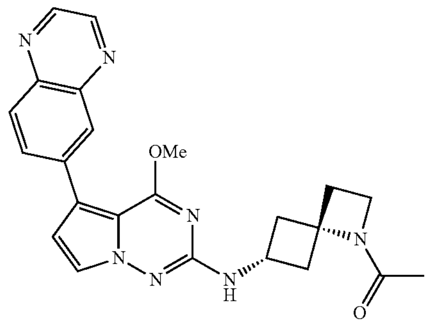 [SMILES: COc1nc(N[C@H]2C[C@]3(CCN3C(C)=O)C2)nn2ccc(-c3ccc4nccnc4c3)c12]
384
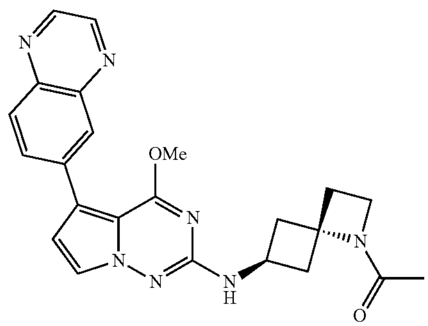 [SMILES: COc1nc(N[C@H]2C[C@@]3(CCN3C(C)=O)C2)nn2ccc(-c3ccc4nccnc4c3)c12]
385
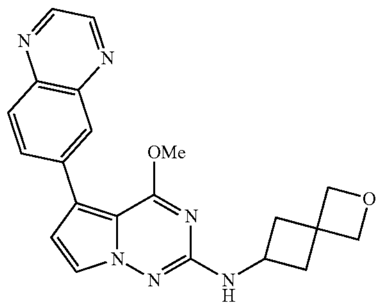 [SMILES: COc1nc(NC2CC3(COC3)C2)nn2ccc(-c3ccc4nccnc4c3)c12]
386
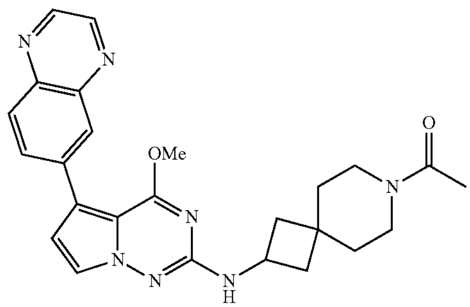 [SMILES: COc1nc(NC2CC3(CCN(C(C)=O)CC3)C2)nn2ccc(-c3ccc4nccnc4c3)c12]
TABLE 1-continued
387
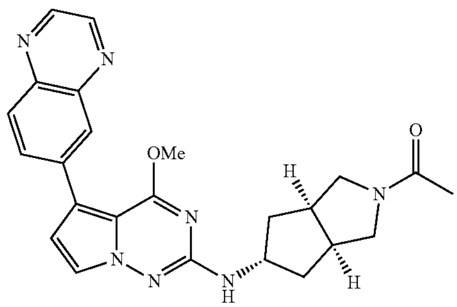 [SMILES: COc1nc(N[C@H]2C[C@@H]3CN(C(C)=O)C[C@@H]3C2)nn2ccc(-c3ccc4nccnc4c3)c12]
388
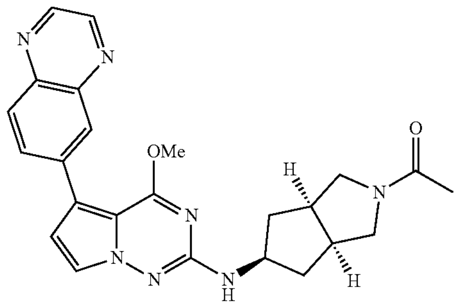 [SMILES: COc1nc(N[C@@H]2C[C@@H]3CN(C(C)=O)C[C@@H]3C2)nn2ccc(-c3ccc4nccnc4c3)c12]
389
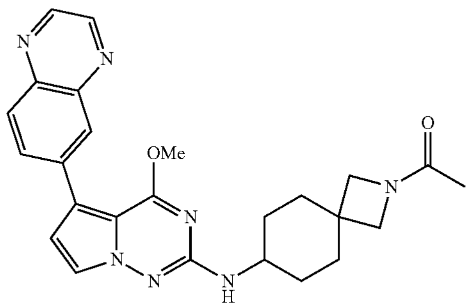 [SMILES: COc1nc(NC2CCC3(CC2)CN(C(C)=O)C3)nn2ccc(-c3ccc4nccnc4c3)c12]
390
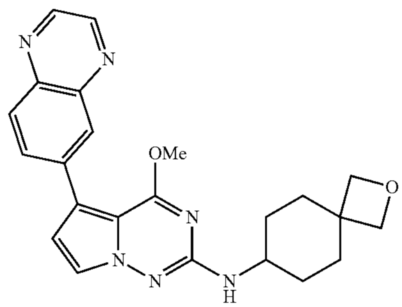
391
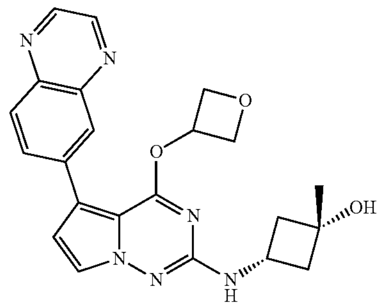 [SMILES: C[C@]1(O)C[C@@H](Nc2nc(OC3COC3)c3c(-c4ccc5nccnc5c4)ccn3n2)C1]

TABLE 1-continued
392
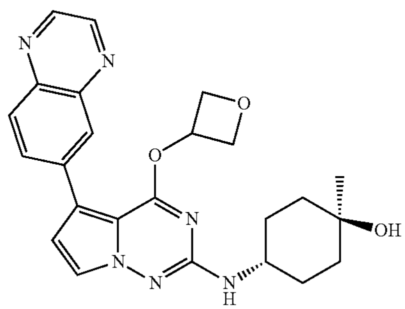 [SMILES: C[C@]1(O)CC[C@H](Nc2nc(OC3COC3)c3c(-c4ccc5nccnc5c4)ccn3n2)CC1]
393
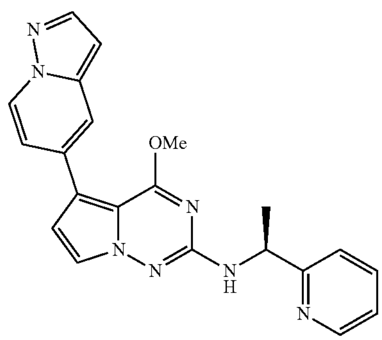 [SMILES: COc1nc(N[C@@H](C)c2ccccn2)nn2ccc(-c3ccn4nccc4c3)c12]
394
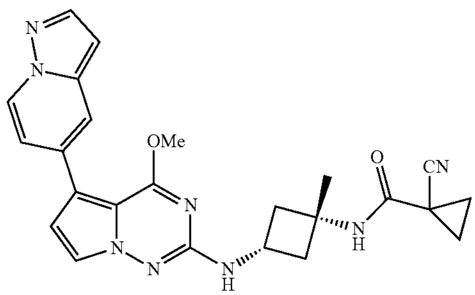 [SMILES: COc1nc(N[C@H]2C[C@@](C)(NC(=O)C3(C#N)CC3)C2)nn2ccc(-c3ccn4nccc4c3)c12]
395
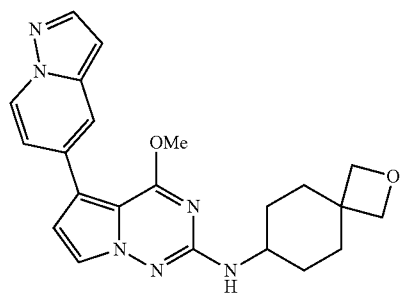 [SMILES: COc1nc(NC2CCC3(CC2)COC3)nn2ccc(-c3ccn4nccc4c3)c12]
396
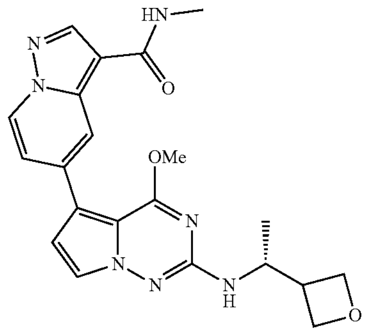 [SMILES: CNC(=O)c1cnn2ccc(-c3ccn4nc(N[C@H](C)C5COC5)nc(OC)c34)cc12]
TABLE 1-continued
397
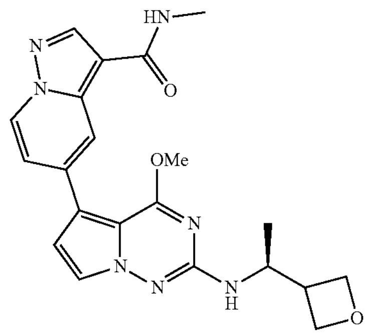 [SMILES: CNC(=O)c1cnn2ccc(-c3ccn4nc(N[C@@H](C)C5COC5)nc(OC)c34)cc12]
398
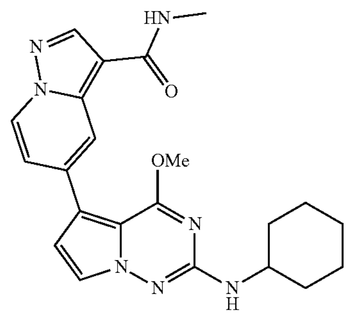 [SMILES: CNC(=O)c1cnn2ccc(-c3ccn4nc(NC5CCCCC5)nc(OC)c34)cc12]
399
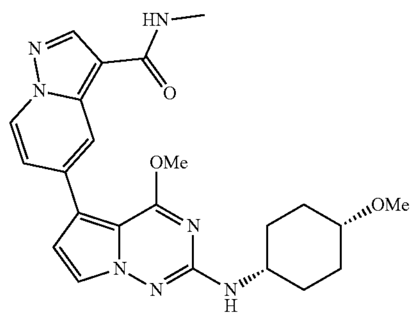 [SMILES: CNC(=O)c1cnn2ccc(-c3ccn4nc(N[C@H]5CC[C@@H](OC)CC5)nc(OC)c34)cc12]
400
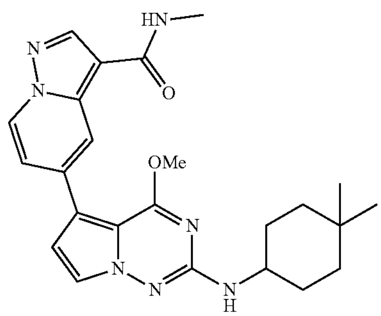 [SMILES: CNC(=O)c1cnn2ccc(-c3ccn4nc(NC5CCC(C)(C)CC5)nc(OC)c34)cc12]
401
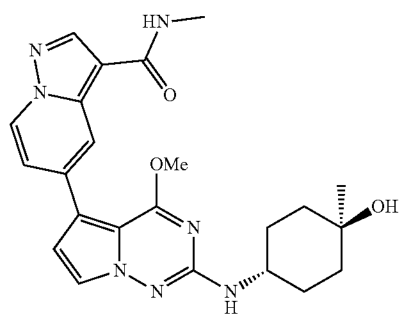

TABLE 1-continued
402
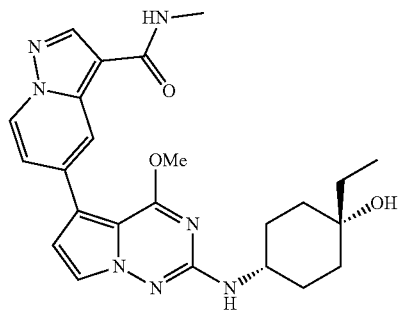 [SMILES: CC[C@]1(O)CC[C@@H](Nc2nc(OC)c3c(-c4ccn5ncc(C(=O)NC)c5c4)ccn3n2)CC1]
403
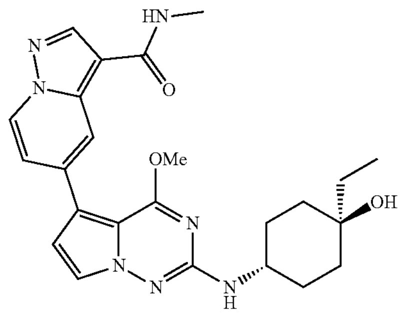 [SMILES: CC[C@]1(O)CC[C@H](Nc2nc(OC)c3c(-c4ccn5ncc(C(=O)NC)c5c4)ccn3n2)CC1]
404
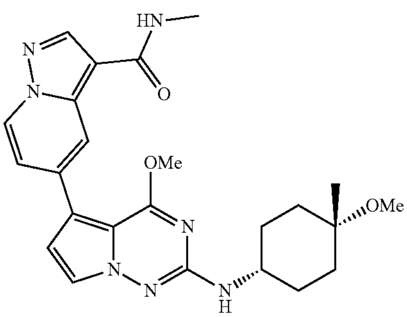 [SMILES: CNC(=O)c1cnn2ccc(-c3ccn4nc(N[C@H]5CC[C@@](C)(OC)CC5)nc(OC)c34)cc12]
405
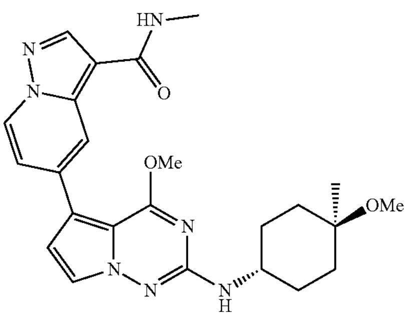 [SMILES: CNC(=O)c1cnn2ccc(-c3ccn4nc(N[C@H]5CC[C@](C)(OC)CC5)nc(OC)c34)cc12]
406
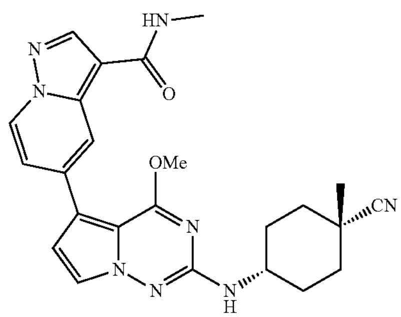 [SMILES: CNC(=O)c1cnn2ccc(-c3ccn4nc(N[C@H]5CC[C@@](C)(C#N)CC5)nc(OC)c34)cc12]
TABLE 1-continued
407
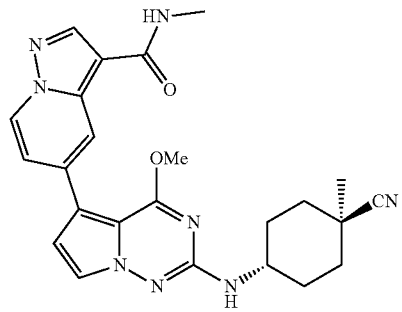 [SMILES: CNC(=O)c1cnn2ccc(-c3ccn4nc(N[C@H]5CC[C@](C)(C#N)CC5)nc(OC)c34)cc12]
408
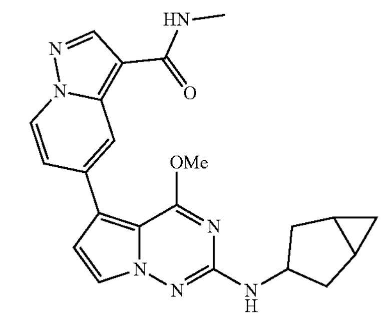 [SMILES: CNC(=O)c1cnn2ccc(-c3ccn4nc(NC5CC6CC6C5)nc(OC)c34)cc12]
409
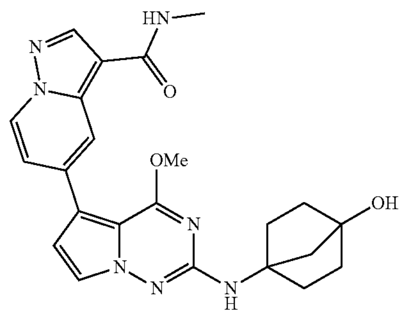 [SMILES: CNC(=O)c1cnn2ccc(-c3ccn4nc(NC56CCC(O)(CC5)C6)nc(OC)c34)cc12]
410
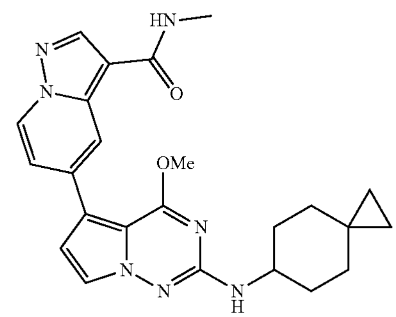 [SMILES: CNC(=O)c1cnn2ccc(-c3ccn4nc(NC5CCC6(CC5)CC6)nc(OC)c34)cc12]
411
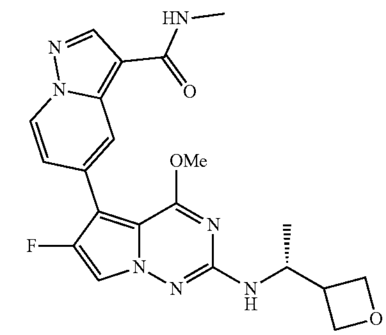 [SMILES: CNC(=O)c1cnn2ccc(-c3c(F)cn4nc(N[C@H](C)C5COC5)nc(OC)c34)cc12]

TABLE 1-continued
412
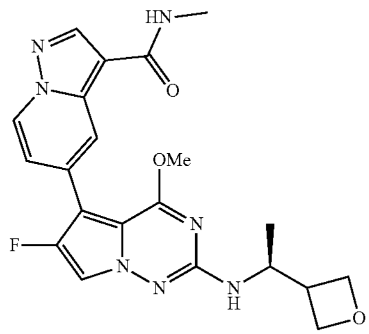 [SMILES: CNC(=O)c1cnn2ccc(-c3c(F)cn4nc(N[C@@H](C)C5COC5)nc(OC)c34)cc12]
413
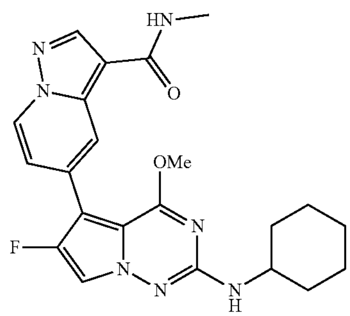 [SMILES: CNC(=O)c1cnn2ccc(-c3c(F)cn4nc(NC5CCCCC5)nc(OC)c34)cc12]
414
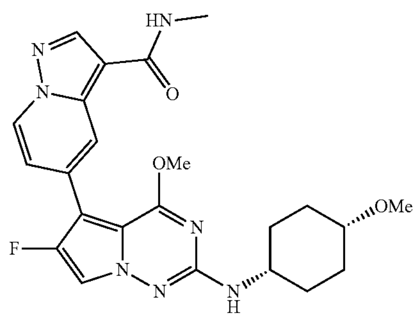 [SMILES: CNC(=O)c1cnn2ccc(-c3c(F)cn4nc(N[C@H]5CC[C@@H](OC)CC5)nc(OC)c34)cc12]
415
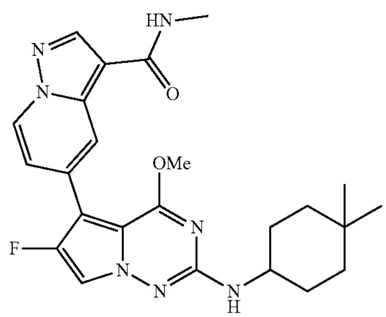 [SMILES: CNC(=O)c1cnn2ccc(-c3c(F)cn4nc(NC5CCC(C)(C)CC5)nc(OC)c34)cc12]
416
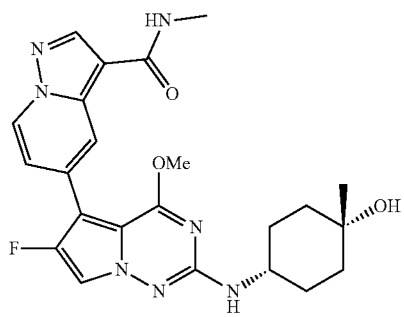 [SMILES: CNC(=O)c1cnn2ccc(-c3c(F)cn4nc(N[C@H]5CC[C@@](C)(O)CC5)nc(OC)c34)cc12]
TABLE 1-continued
417
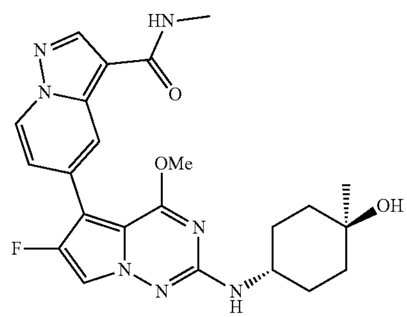 [SMILES: CNC(=O)c1cnn2ccc(-c3c(F)cn4nc(N[C@H]5CC[C@](C)(O)CC5)nc(OC)c34)cc12]
418
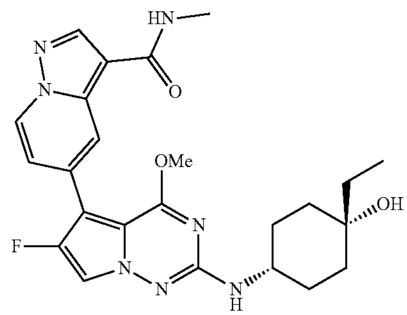 [SMILES: CC[C@]1(O)CC[C@@H](Nc2nc(OC)c3c(-c4ccn5ncc(C(=O)NC)c5c4)c(F)cn3n2)CC1]
419
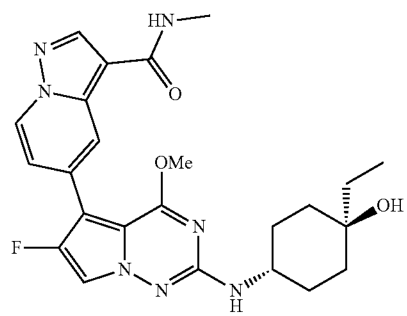 [SMILES: CC[C@]1(O)CC[C@H](Nc2nc(OC)c3c(-c4ccn5ncc(C(=O)NC)c5c4)c(F)cn3n2)CC1]
420
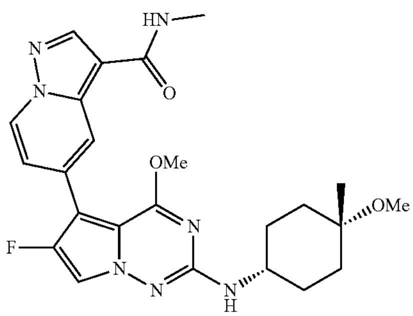 [SMILES: CNC(=O)c1cnn2ccc(-c3c(F)cn4nc(N[C@H]5CC[C@@](C)(OC)CC5)nc(OC)c34)cc12]
421
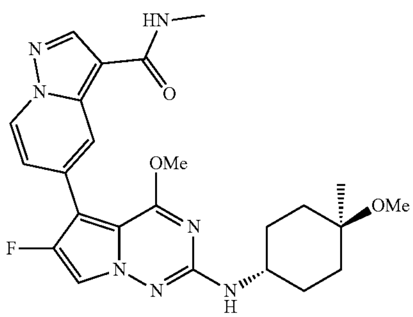 [SMILES: CNC(=O)c1cnn2ccc(-c3c(F)cn4nc(N[C@H]5CC[C@](C)(OC)CC5)nc(OC)c34)cc12]

TABLE 1-continued
422
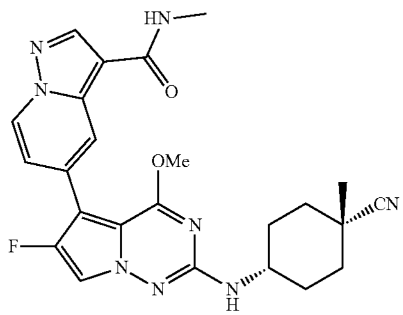 [SMILES: CNC(=O)c1cnn2ccc(-c3c(F)cn4nc(N[C@H]5CC[C@@](C)(C#N)CC5)nc(OC)c34)cc12]
423
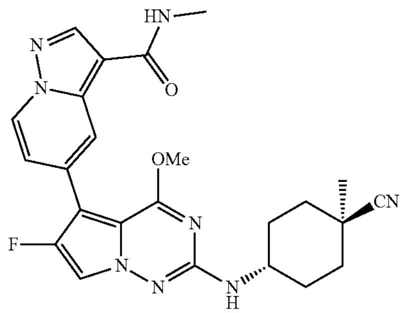 [SMILES: CNC(=O)c1cnn2ccc(-c3c(F)cn4nc(N[C@H]5CC[C@](C)(C#N)CC5)nc(OC)c34)cc12]
424
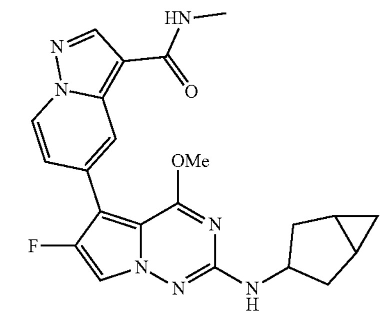 [SMILES: CNC(=O)c1cnn2ccc(-c3c(F)cn4nc(NC5CC6CC6C5)nc(OC)c34)cc12]
425
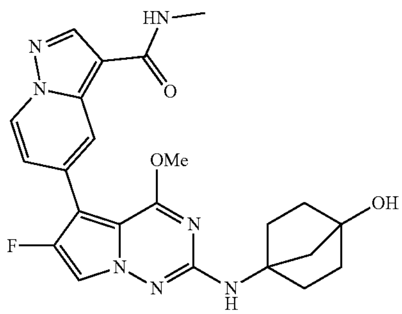 [SMILES: CNC(=O)c1cnn2ccc(-c3c(F)cn4nc(NC56CCC(O)(CC5)C6)nc(OC)c34)cc12]
426
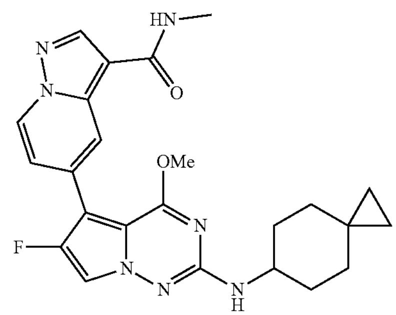 [SMILES: CNC(=O)c1cnn2ccc(-c3c(F)cn4nc(NC5CCC6(CC5)CC6)nc(OC)c34)cc12]
TABLE 1-continued
427
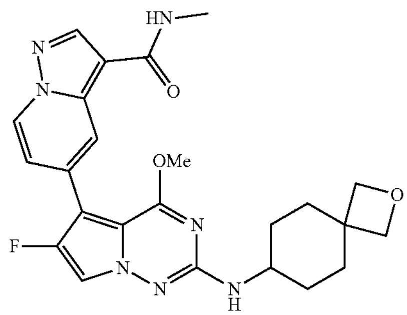 [SMILES: CNC(=O)c1cnn2ccc(-c3c(F)cn4nc(NC5CCC6(CC5)COC6)nc(OC)c34)cc12]
428
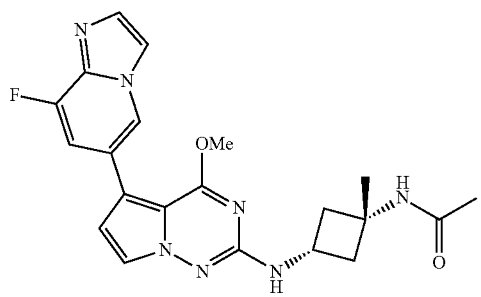 [SMILES: COc1nc(N[C@H]2C[C@@](C)(NC(C)=O)C2)nn2ccc(-c3cc(F)c4nccn4c3)c12]
429
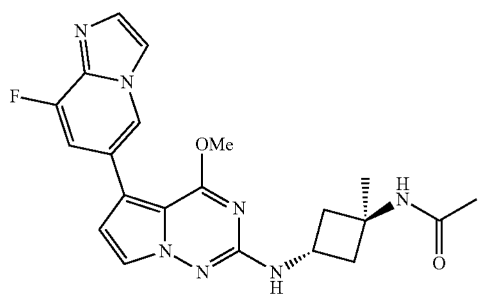 [SMILES: COc1nc(N[C@H]2C[C@](C)(NC(C)=O)C2)nn2ccc(-c3cc(F)c4nccn4c3)c12]
430
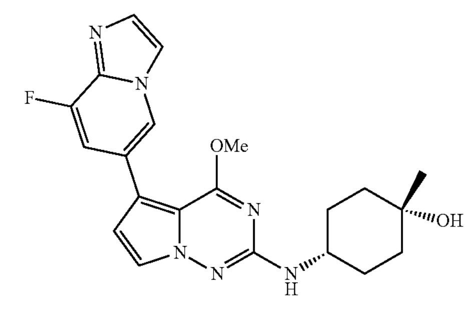 [SMILES: COc1nc(N[C@H]2CC[C@@](C)(O)CC2)nn2ccc(-c3cc(F)c4nccn4c3)c12]
431
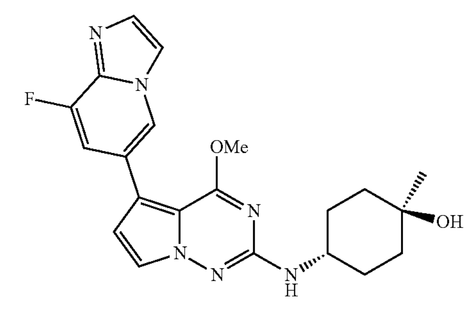 [SMILES: COc1nc(N[C@H]2CC[C@](C)(O)CC2)nn2ccc(-c3cc(F)c4nccn4c3)c12]

TABLE 1-continued
432
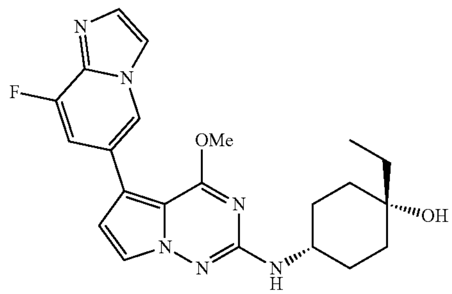 [SMILES: CC[C@]1(O)CC[C@@H](Nc2nc(OC)c3c(-c4cc(F)c5nccn5c4)ccn3n2)CC1]
433
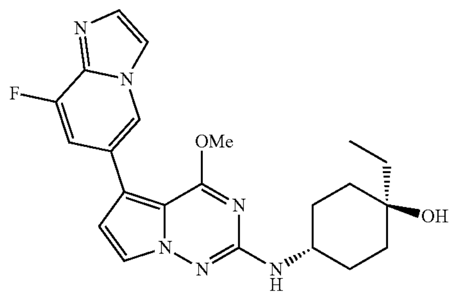 [SMILES: CC[C@]1(O)CC[C@H](Nc2nc(OC)c3c(-c4cc(F)c5nccn5c4)ccn3n2)CC1]
434
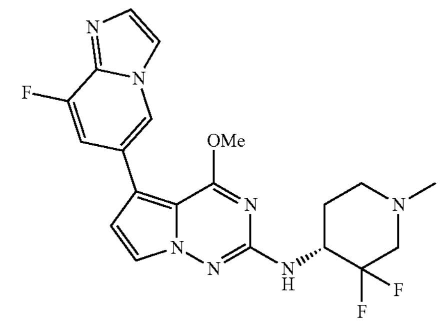 [SMILES: COc1nc(N[C@@H]2CCN(C)CC2(F)F)nn2ccc(-c3cc(F)c4nccn4c3)c12]
435
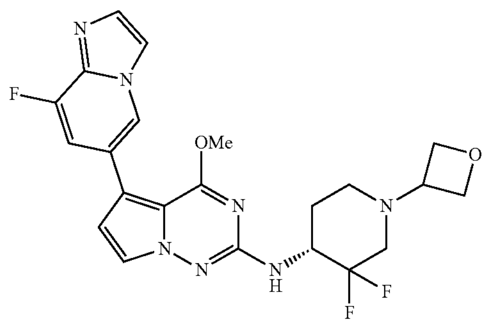 [SMILES: COc1nc(N[C@@H]2CCN(C3COC3)CC2(F)F)nn2ccc(-c3cc(F)c4nccn4c3)c12]
436
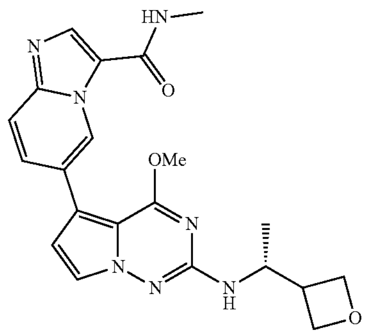 [SMILES: CNC(=O)c1cnc2ccc(-c3ccn4nc(N[C@H](C)C5COC5)nc(OC)c34)cn12]
TABLE 1-continued
437
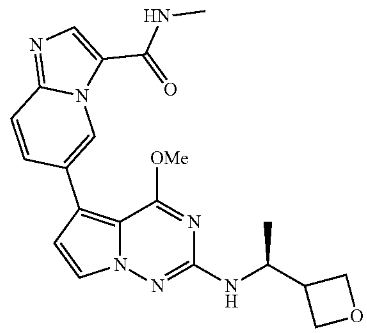 [SMILES: CNC(=O)c1cnc2ccc(-c3ccn4nc(N[C@@H](C)C5COC5)nc(OC)c34)cn12]
438
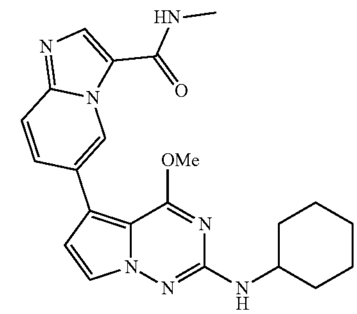 [SMILES: CNC(=O)c1cnc2ccc(-c3ccn4nc(NC5CCCCC5)nc(OC)c34)cn12]
439
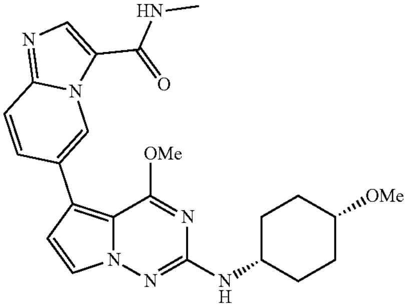 [SMILES: CNC(=O)c1cnc2ccc(-c3ccn4nc(N[C@H]5CC[C@@H](OC)CC5)nc(OC)c34)cn12]
440
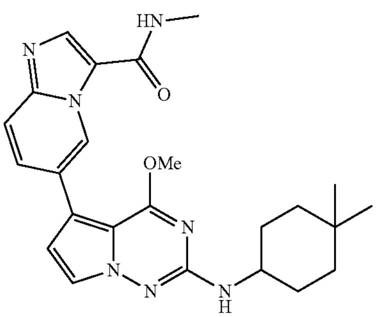 [SMILES: CNC(=O)c1cnc2ccc(-c3ccn4nc(NC5CCC(C)(C)CC5)nc(OC)c34)cn12]
441
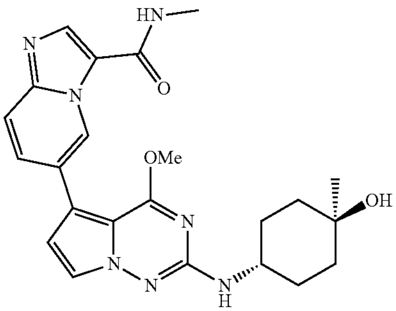 [SMILES: CNC(=O)c1cnc2ccc(-c3ccn4nc(N[C@H]5CC[C@](C)(O)CC5)nc(OC)c34)cn12]

TABLE 1-continued
442
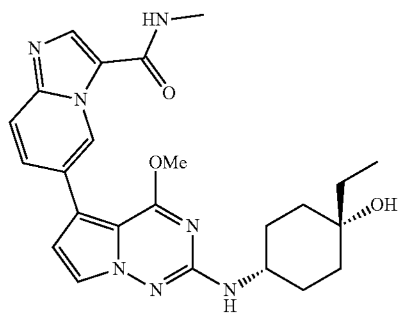 [SMILES: CC[C@]1(O)CC[C@@H](Nc2nc(OC)c3c(-c4ccc5ncc(C(=O)NC)n5c4)ccn3n2)CC1]
443
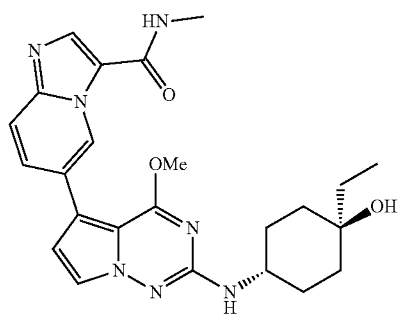 [SMILES: CC[C@]1(O)CC[C@H](Nc2nc(OC)c3c(-c4ccc5ncc(C(=O)NC)n5c4)ccn3n2)CC1]
444
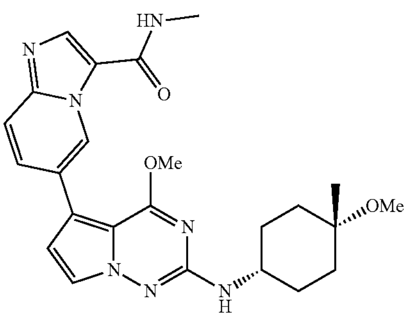 [SMILES: CNC(=O)c1cnc2ccc(-c3ccn4nc(N[C@H]5CC[C@@](C)(OC)CC5)nc(OC)c34)cn12]
445
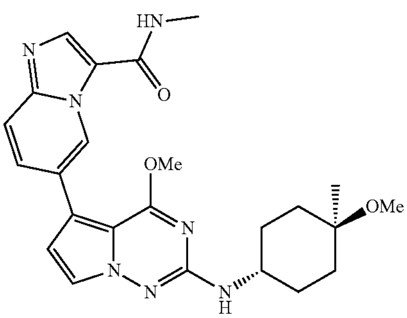 [SMILES: CNC(=O)c1cnc2ccc(-c3ccn4nc(N[C@H]5CC[C@](C)(OC)CC5)nc(OC)c34)cn12]
446
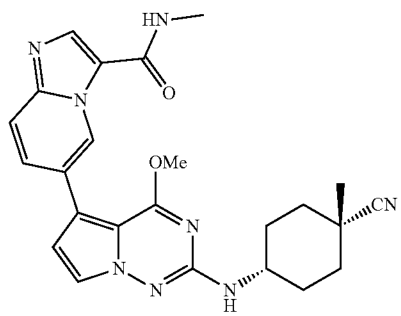 [SMILES: CNC(=O)c1cnc2ccc(-c3ccn4nc(N[C@H]5CC[C@@](C)(C#N)CC5)nc(OC)c34)cn12]
TABLE 1-continued
447
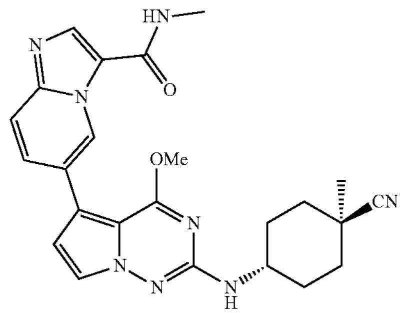
448
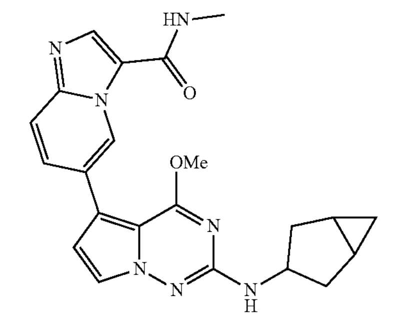 [SMILES: CNC(=O)c1cnc2ccc(-c3ccn4nc(NC5CC6CC6C5)nc(OC)c34)cn12]
449
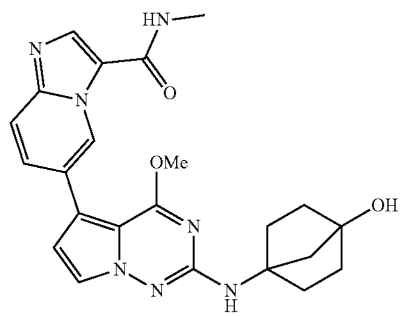 [SMILES: CNC(=O)c1cnc2ccc(-c3ccn4nc(NC56CCC(O)(CC5)C6)nc(OC)c34)cn12]
450
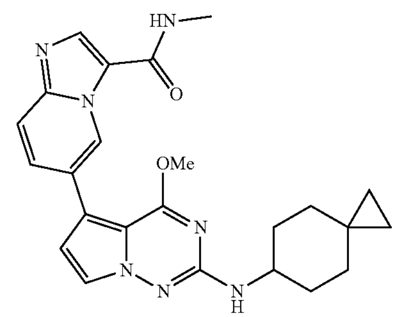 [SMILES: CNC(=O)c1cnc2ccc(-c3ccn4nc(NC5CCC6(CC5)CC6)nc(OC)c34)cn12]
451
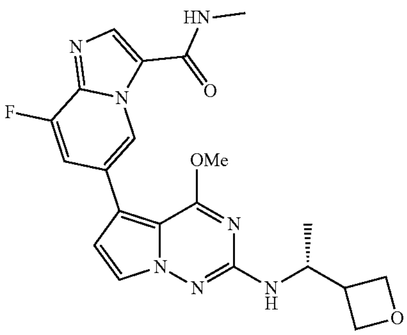 [SMILES: CNC(=O)c1cnc2c(F)cc(-c3ccn4nc(N[C@H](C)C5COC5)nc(OC)c34)cn12]

TABLE 1-continued
452
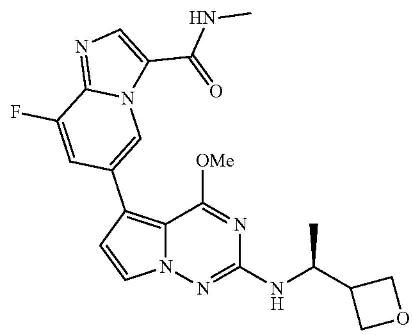 [SMILES: CNC(=O)c1cnc2c(F)cc(-c3ccn4nc(N[C@@H](C)C5COC5)nc(OC)c34)cn12]
453
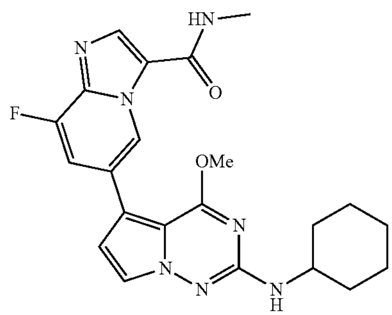 [SMILES: CNC(=O)c1cnc2c(F)cc(-c3ccn4nc(NC5CCCCC5)nc(OC)c34)cn12]
454
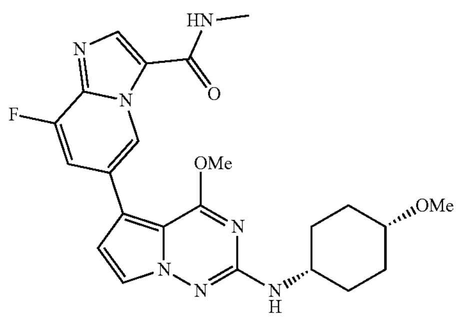 [SMILES: CNC(=O)c1cnc2c(F)cc(-c3ccn4nc(N[C@H]5CC[C@@H](OC)CC5)nc(OC)c34)cn12]
455
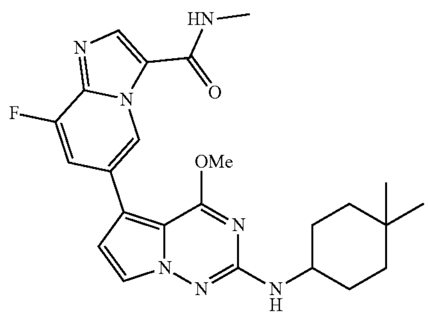 [SMILES: CNC(=O)c1cnc2c(F)cc(-c3ccn4nc(NC5CCC(C)(C)CC5)nc(OC)c34)cn12]
456
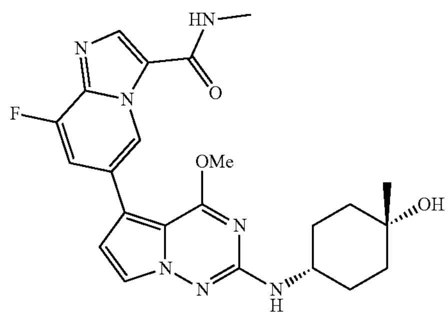 [SMILES: CNC(=O)c1cnc2c(F)cc(-c3ccn4nc(N[C@H]5CC[C@@](C)(O)CC5)nc(OC)c34)cn12]
TABLE 1-continued
457
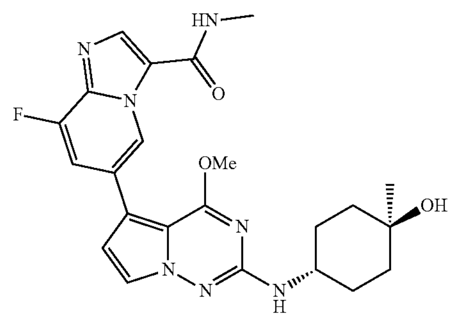
458
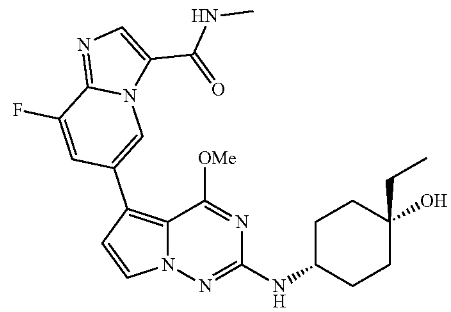 [SMILES: CC[C@]1(O)CC[C@@H](Nc2nc(OC)c3c(-c4cc(F)c5ncc(C(=O)NC)n5c4)ccn3n2)CC1]
459
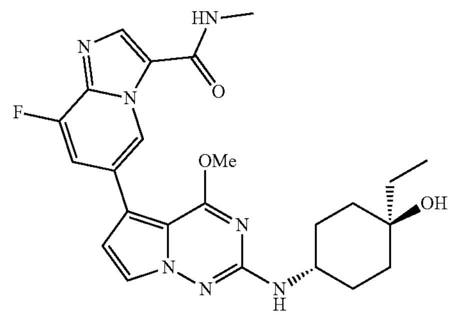 [SMILES: CC[C@]1(O)CC[C@H](Nc2nc(OC)c3c(-c4cc(F)c5ncc(C(=O)NC)n5c4)ccn3n2)CC1]
460
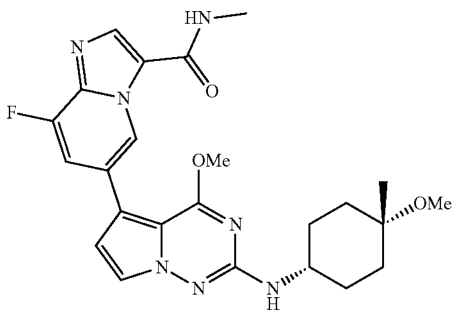 [SMILES: CNC(=O)c1cnc2c(F)cc(-c3ccn4nc(N[C@H]5CC[C@@](C)(OC)CC5)nc(OC)c34)cn12]
461
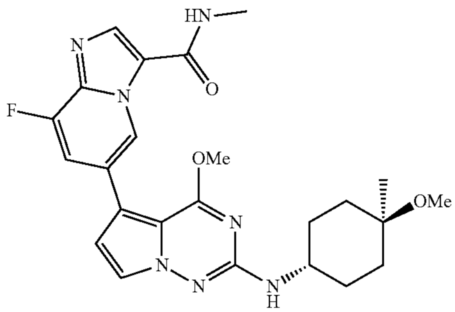 [SMILES: CNC(=O)c1cnc2c(F)cc(-c3ccn4nc(N[C@H]5CC[C@](C)(OC)CC5)nc(OC)c34)cn12]

TABLE 1-continued
462
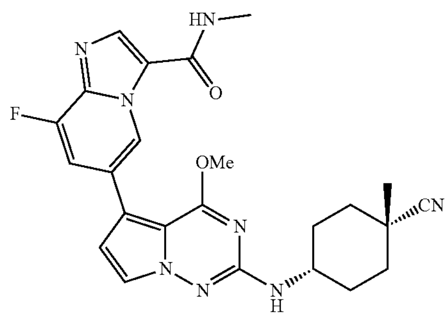 [SMILES: CNC(=O)c1cnc2c(F)cc(-c3ccn4nc(N[C@H]5CC[C@@](C)(C#N)CC5)nc(OC)c34)cn12]
463
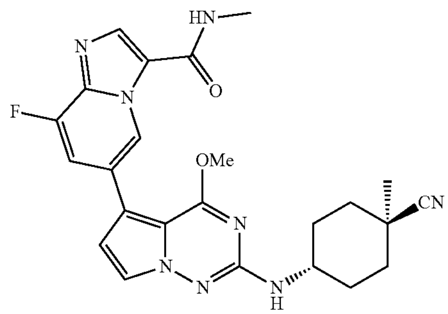 [SMILES: CNC(=O)c1cnc2c(F)cc(-c3ccn4nc(N[C@H]5CC[C@](C)(C#N)CC5)nc(OC)c34)cn12]
464
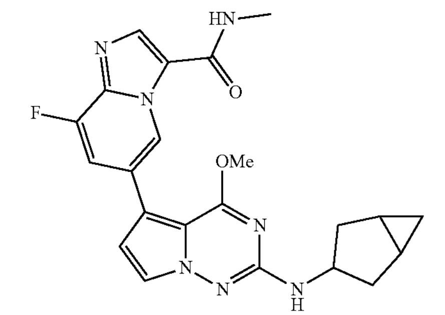 [SMILES: CNC(=O)c1cnc2c(F)cc(-c3ccn4nc(NC5CC6CC6C5)nc(OC)c34)cn12]
465
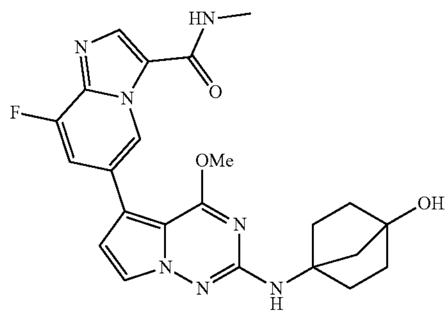 [SMILES: CNC(=O)c1cnc2c(F)cc(-c3ccn4nc(NC56CCC(O)(CC5)C6)nc(OC)c34)cn12]
466
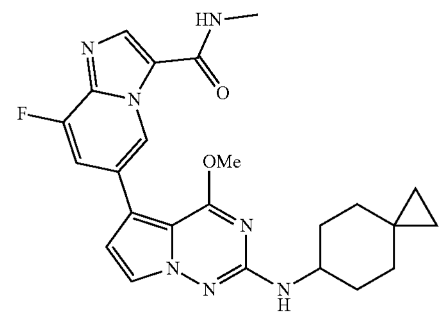 [SMILES: CNC(=O)c1cnc2c(F)cc(-c3ccn4nc(NC5CCC6(CC5)CC6)nc(OC)c34)cn12]
TABLE 1-continued
467
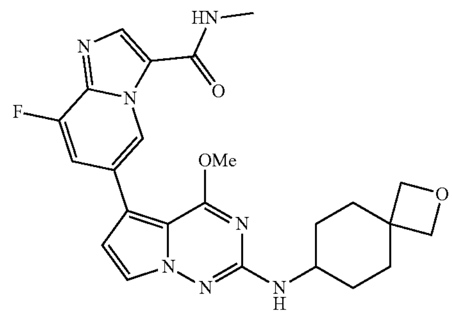 [SMILES: CNC(=O)c1cnc2c(F)cc(-c3ccn4nc(NC5CCC6(CC5)COC6)nc(OC)c34)cn12]
468
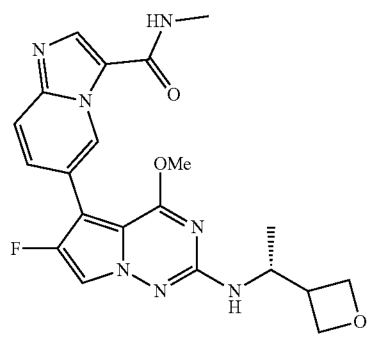 [SMILES: CNC(=O)c1cnc2ccc(-c3c(F)cn4nc(N[C@H](C)C5COC5)nc(OC)c34)cn12]
469
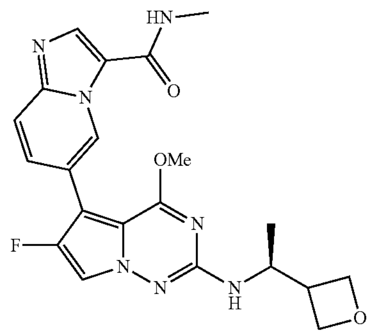 [SMILES: CNC(=O)c1cnc2ccc(-c3c(F)cn4nc(N[C@@H](C)C5COC5)nc(OC)c34)cn12]
470
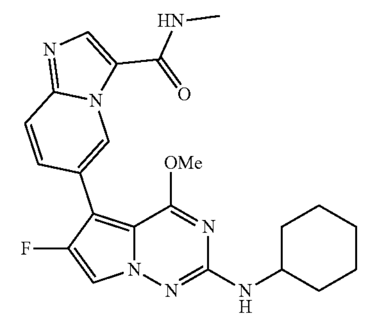 [SMILES: CNC(=O)c1cnc2ccc(-c3c(F)cn4nc(NC5CCCCC5)nc(OC)c34)cn12]
471
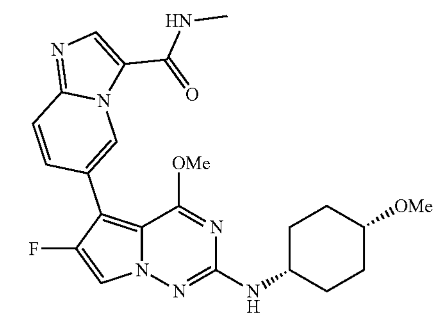 [SMILES: CNC(=O)c1cnc2ccc(-c3c(F)cn4nc(N[C@H]5CC[C@@H](OC)CC5)nc(OC)c34)cn12]

TABLE 1-continued
472
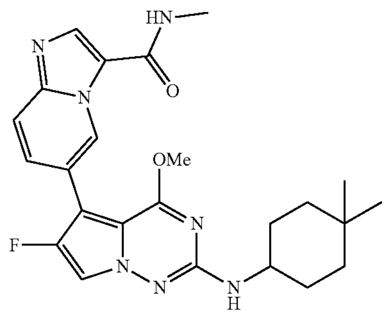 [SMILES: CNC(=O)c1cnc2ccc(-c3c(F)cn4nc(NC5CCC(C)(C)CC5)nc(OC)c34)cn12]
473
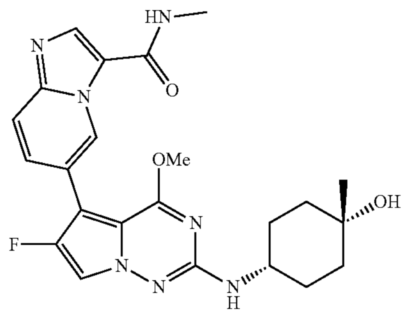 [SMILES: CNC(=O)c1cnc2ccc(-c3c(F)cn4nc(N[C@H]5CC[C@@](C)(O)CC5)nc(OC)c34)cn12]
474
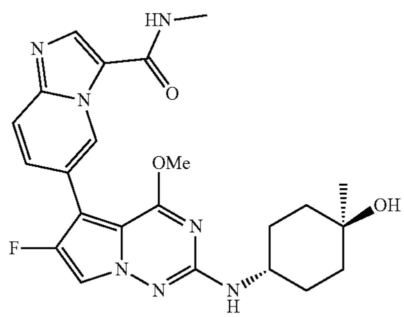 [SMILES: CNC(=O)c1cnc2ccc(-c3c(F)cn4nc(N[C@H]5CC[C@](C)(O)CC5)nc(OC)c34)cn12]
475
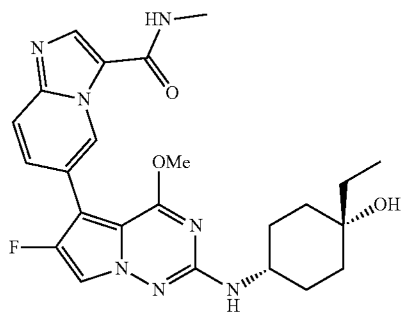 [SMILES: CC[C@]1(O)CC[C@@H](Nc2nc(OC)c3c(-c4ccc5ncc(C(=O)NC)n5c4)c(F)cn3n2)CC1]
476
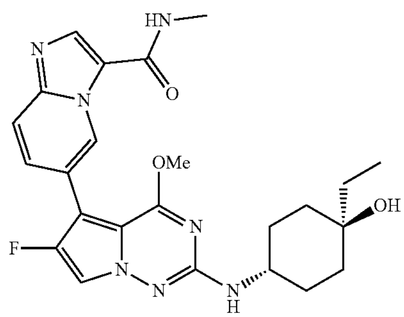 [SMILES: CC[C@]1(O)CC[C@H](Nc2nc(OC)c3c(-c4ccc5ncc(C(=O)NC)n5c4)c(F)cn3n2)CC1]
TABLE 1-continued
477
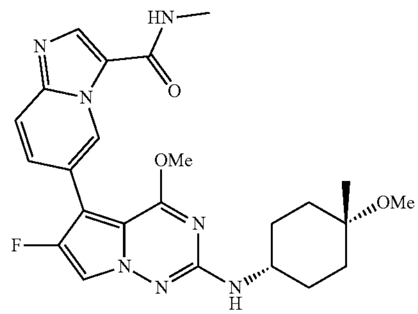 [SMILES: CNC(=O)c1cnc2ccc(-c3c(F)cn4nc(N[C@H]5CC[C@@](C)(OC)CC5)nc(OC)c34)cn12]
478
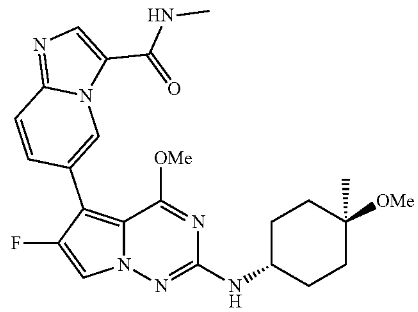 [SMILES: CNC(=O)c1cnc2ccc(-c3c(F)cn4nc(N[C@H]5CC[C@](C)(OC)CC5)nc(OC)c34)cn12]
479
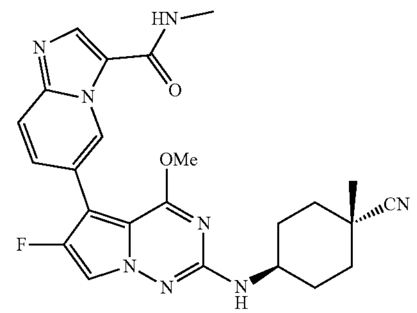 [SMILES: CNC(=O)c1cnc2ccc(-c3c(F)cn4nc(N[C@H]5CC[C@](C)(C#N)CC5)nc(OC)c34)cn12]
480
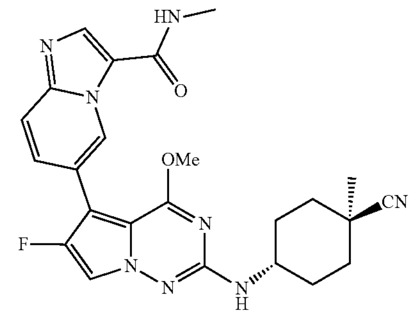 [SMILES: CNC(=O)c1cnc2ccc(-c3c(F)cn4nc(N[C@H]5CC[C@](C)(C#N)CC5)nc(OC)c34)cn12]
481
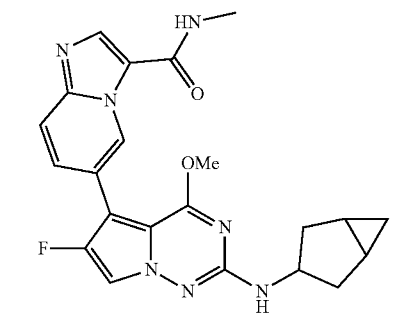 [SMILES: CNC(=O)c1cnc2ccc(-c3c(F)cn4nc(NC5CC6CC6C5)nc(OC)c34)cn12]

482
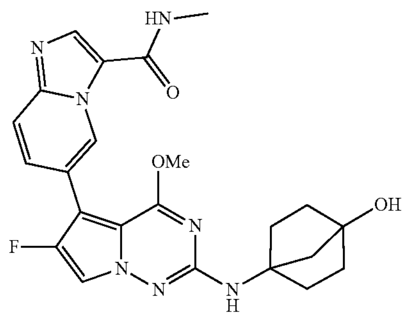 [SMILES: CNC(=O)c1cnc2ccc(-c3c(F)cn4nc(NC56CCC(O)(CC5)C6)nc(OC)c34)cn12]
483
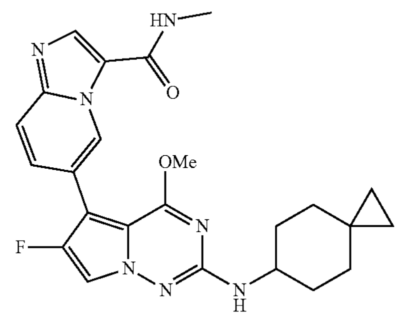 [SMILES: CNC(=O)c1cnc2ccc(-c3c(F)cn4nc(NC5CCC6(CC5)CC6)nc(OC)c34)cn12]
484
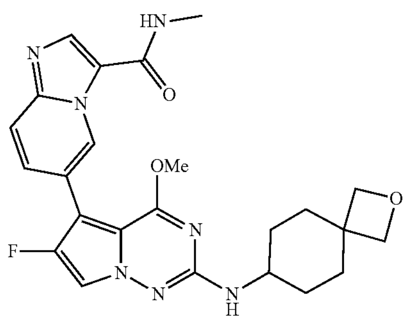 [SMILES: CNC(=O)c1cnc2ccc(-c3c(F)cn4nc(NC5CCC6(CC5)COC6)nc(OC)c34)cn12]
485
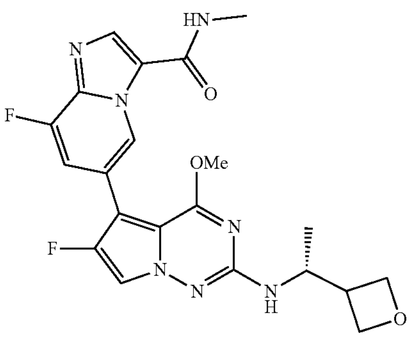 [SMILES: CNC(=O)c1cnc2c(F)cc(-c3c(F)cn4nc(N[C@H](C)C5COC5)nc(OC)c34)cn12]
486
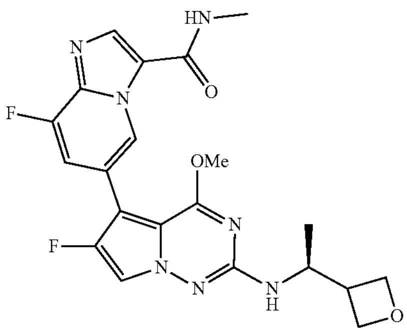 [SMILES: CNC(=O)c1cnc2c(F)cc(-c3c(F)cn4nc(N[C@@H](C)C5COC5)nc(OC)c34)cn12]
487
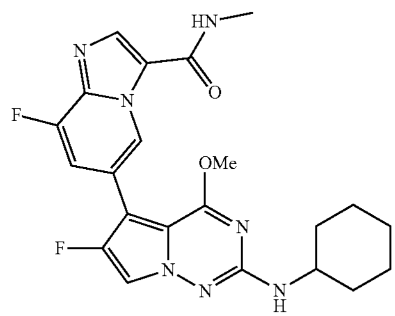 [SMILES: CNC(=O)c1cnc2c(F)cc(-c3c(F)cn4nc(NC5CCCCC5)nc(OC)c34)cn12]
488
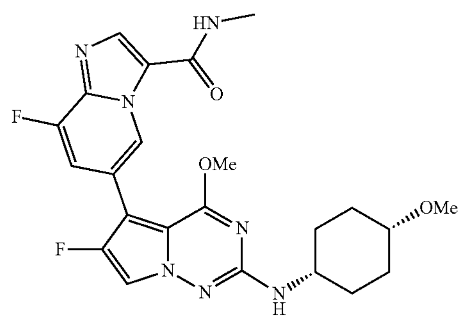 [SMILES: CNC(=O)c1cnc2c(F)cc(-c3c(F)cn4nc(N[C@H]5CC[C@@H](OC)CC5)nc(OC)c34)cn12]
489
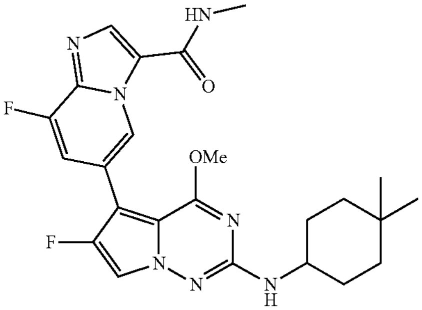 [SMILES: CNC(=O)c1cnc2c(F)cc(-c3c(F)cn4nc(NC5CCC(C)(C)CC5)nc(OC)c34)cn12]
490
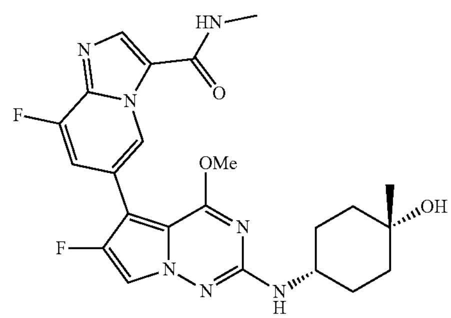 [SMILES: CNC(=O)c1cnc2c(F)cc(-c3c(F)cn4nc(N[C@H]5CC[C@@](C)(O)CC5)nc(OC)c34)cn12]
491
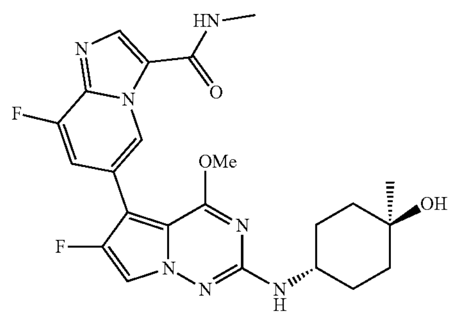 [SMILES: CNC(=O)c1cnc2c(F)cc(-c3c(F)cn4nc(N[C@H]5CC[C@](C)(O)CC5)nc(OC)c34)cn12]

TABLE 1-continued
492
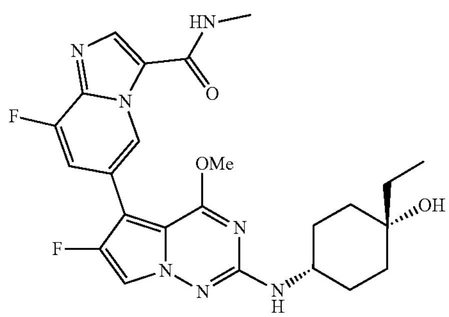 [SMILES: CC[C@]1(O)CC[C@@H](Nc2nc(OC)c3c(-c4cc(F)c5ncc(C(=O)NC)n5c4)c(F)cn3n2)CC1]
493
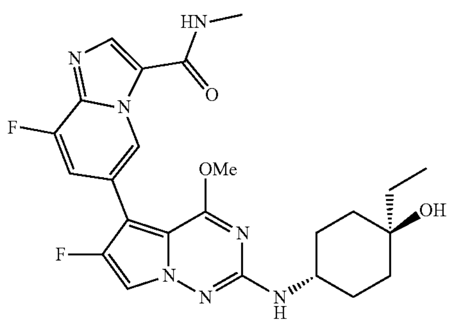 [SMILES: CC[C@]1(O)CC[C@H](Nc2nc(OC)c3c(-c4cc(F)c5ncc(C(=O)NC)n5c4)c(F)cn3n2)CC1]
494
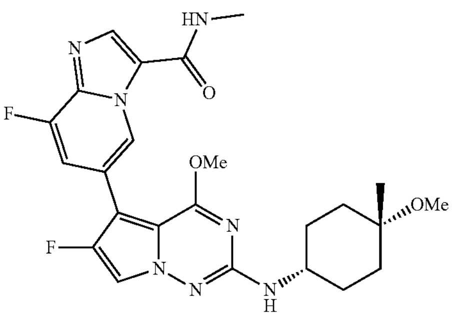 [SMILES: CNC(=O)c1cnc2c(F)cc(-c3c(F)cn4nc(N[C@H]5CC[C@@](C)(OC)CC5)nc(OC)c34)cn12]
495
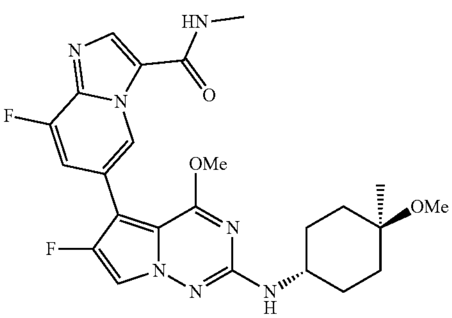 [SMILES: CNC(=O)c1cnc2c(F)cc(-c3c(F)cn4nc(N[C@H]5CC[C@](C)(OC)CC5)nc(OC)c34)cn12]
496
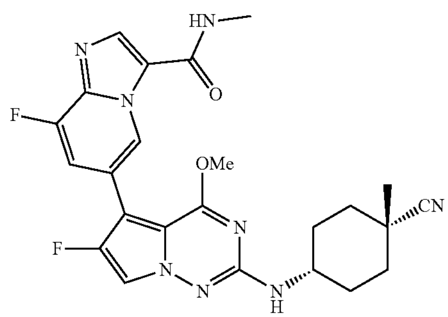 [SMILES: CNC(=O)c1cnc2c(F)cc(-c3c(F)cn4nc(N[C@H]5CC[C@@](C)(C#N)CC5)nc(OC)c34)cn12]
TABLE 1-continued
497
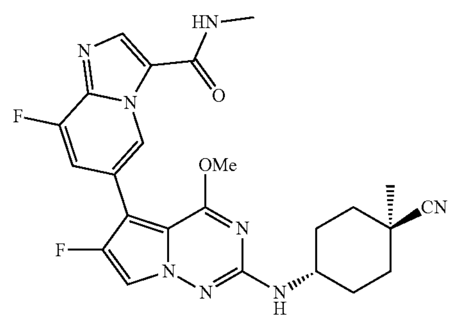 [SMILES: CNC(=O)c1cnc2c(F)cc(-c3c(F)cn4nc(N[C@H]5CC[C@](C)(C#N)CC5)nc(OC)c34)cn12]
498
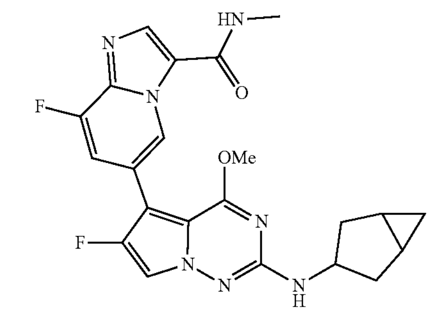 [SMILES: CNC(=O)c1cnc2c(F)cc(-c3c(F)cn4nc(NC5CC6CC6C5)nc(OC)c34)cn12]
499
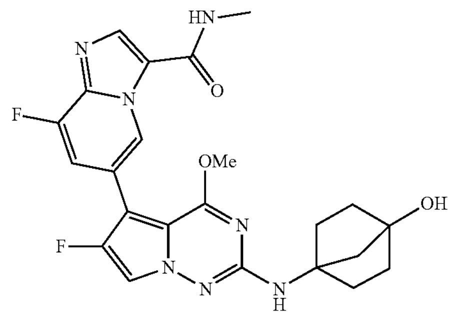 [SMILES: CNC(=O)c1cnc2c(F)cc(-c3c(F)cn4nc(NC56CCC(O)(CC5)C6)nc(OC)c34)cn12]
500
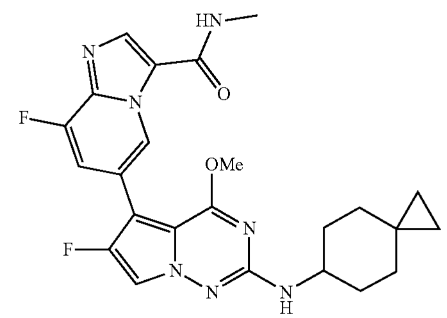 [SMILES: CNC(=O)c1cnc2c(F)cc(-c3c(F)cn4nc(NC5CCC6(CC5)CC6)nc(OC)c34)cn12]
501
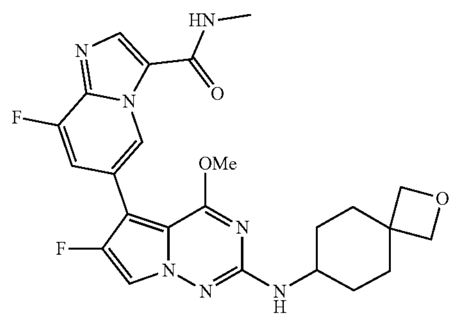 [SMILES: CNC(=O)c1cnc2c(F)cc(-c3c(F)cn4nc(NC5CCC6(CC5)COC6)nc(OC)c34)cn12]

TABLE 1-continued
502
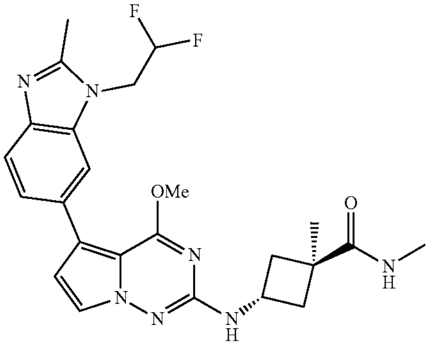 [SMILES: CNC(=O)[C@]1(C)C[C@@H](Nc2nc(OC)c3c(-c4ccc5nc(C)n(CC(F)F)c5c4)ccn3n2)C1]
503
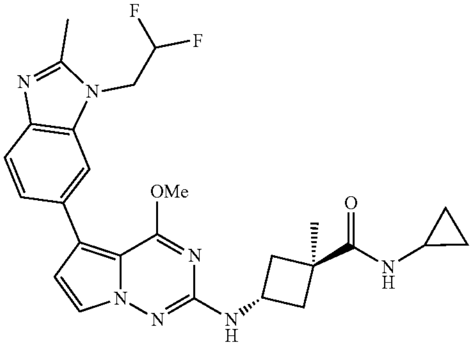 [SMILES: COc1nc(N[C@H]2C[C@](C)(C(=O)NC3CC3)C2)nn2ccc(-c3ccc4nc(C)n(CC(F)F)c4c3)c12]
504
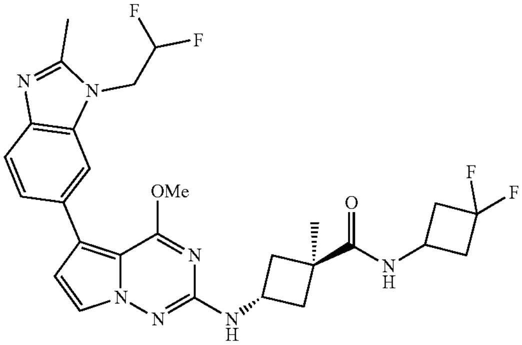 [SMILES: COc1nc(N[C@H]2C[C@](C)(C(=O)NC3CC(F)(F)C3)C2)nn2ccc(-c3ccc4nc(C)n(CC(F)F)c4c3)c12]
505
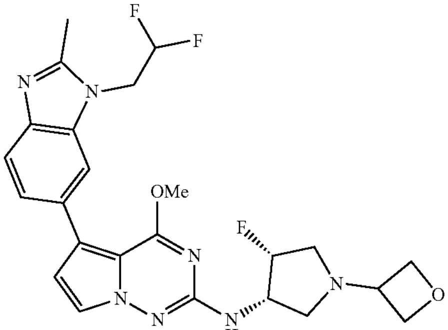
TABLE 1-continued
506
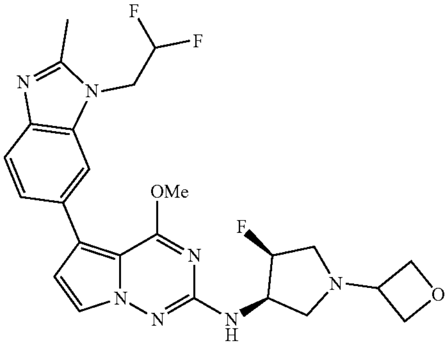 [SMILES: COc1nc(N[C@@H]2CN(C3COC3)C[C@@H]2F)nn2ccc(-c3ccc4nc(C)n(CC(F)F)c4c3)c12]
507
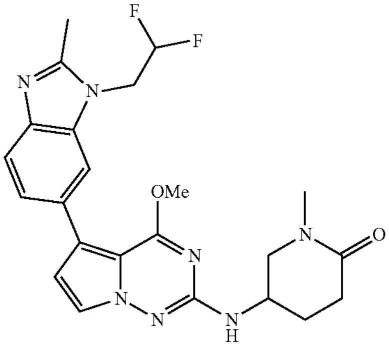 [SMILES: COc1nc(NC2CCC(=O)N(C)C2)nn2ccc(-c3ccc4nc(C)n(CC(F)F)c4c3)c12]
508
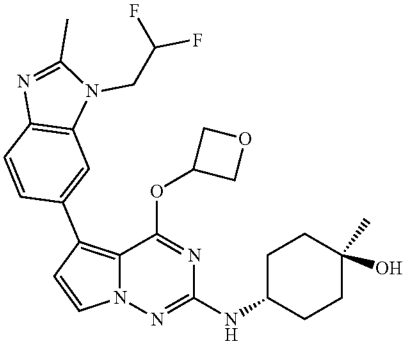 [SMILES: Cc1nc2ccc(-c3ccn4nc(N[C@H]5CC[C@](C)(O)CC5)nc(OC5COC5)c34)cc2n1CC(F)F]
509
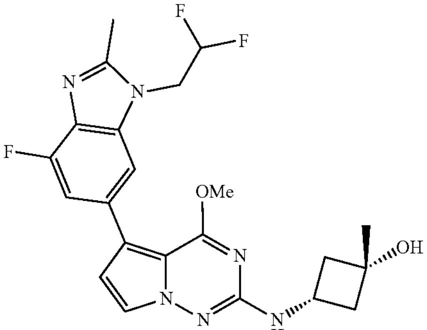

TABLE 1-continued
510
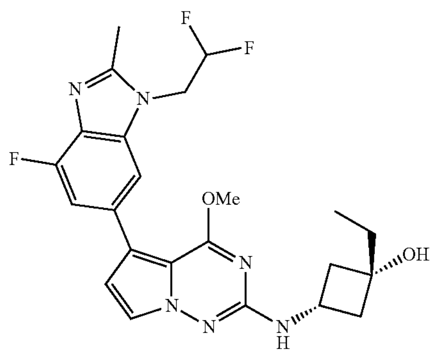 [SMILES: CC[C@]1(O)C[C@@H](Nc2nc(OC)c3c(-c4cc(F)c5nc(C)n(CC(F)F)c5c4)ccn3n2)C1]
511
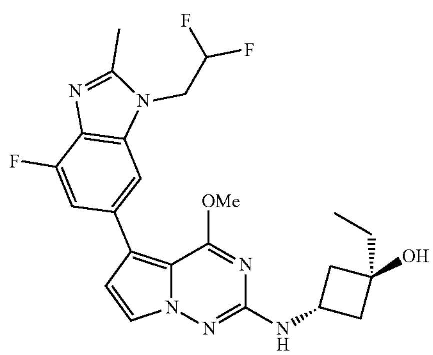 [SMILES: CC[C@]1(O)C[C@H](Nc2nc(OC)c3c(-c4cc(F)c5nc(C)n(CC(F)F)c5c4)ccn3n2)C1]
512
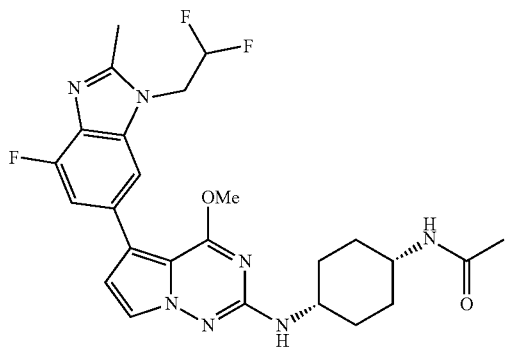 [SMILES: COc1nc(N[C@H]2CC[C@@H](NC(C)=O)CC2)nn2ccc(-c3cc(F)c4nc(C)n(CC(F)F)c4c3)c12]
513
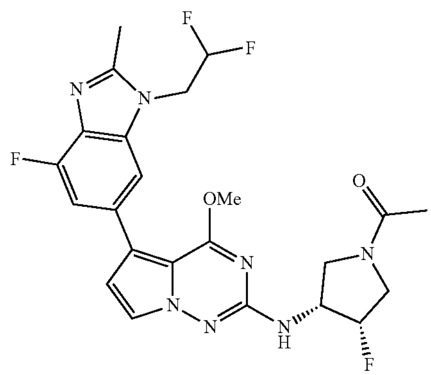 [SMILES: COc1nc(N[C@@H]2CN(C(C)=O)C[C@@H]2F)nn2ccc(-c3cc(F)c4nc(C)n(CC(F)F)c4c3)c12]
TABLE 1-continued
514
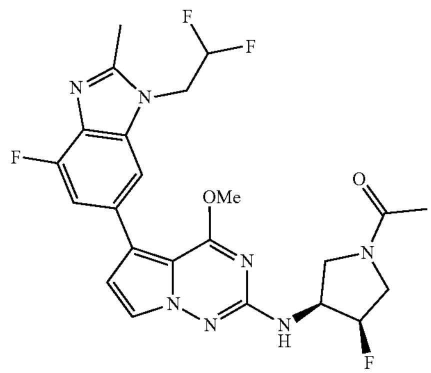 [SMILES: COc1nc(N[C@H]2CN(C(C)=O)C[C@H]2F)nn2ccc(-c3cc(F)c4nc(C)n(CC(F)F)c4c3)c12]
515
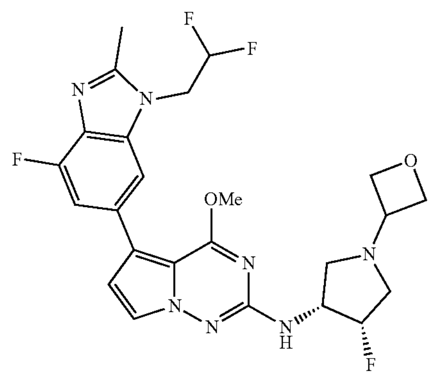 [SMILES: COc1nc(N[C@@H]2CN(C3COC3)C[C@@H]2F)nn2ccc(-c3cc(F)c4nc(C)n(CC(F)F)c4c3)c12]
516
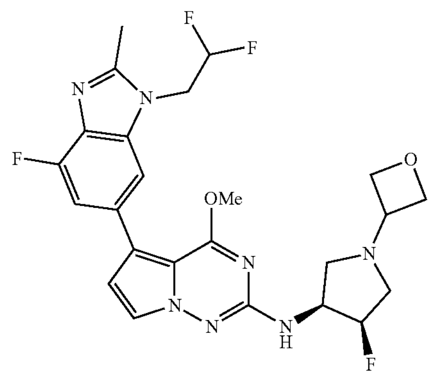 [SMILES: COc1nc(N[C@H]2CN(C3COC3)C[C@H]2F)nn2ccc(-c3cc(F)c4nc(C)n(CC(F)F)c4c3)c12]
517
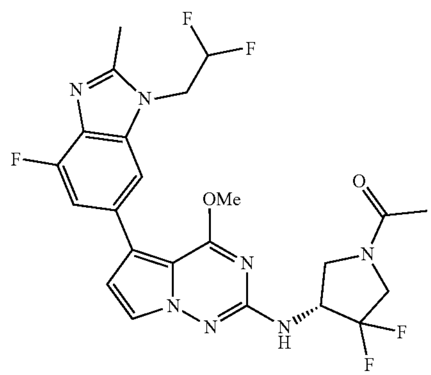 [SMILES: COc1nc(N[C@@H]2CN(C(C)=O)CC2(F)F)nn2ccc(-c3cc(F)c4nc(C)n(CC(F)F)c4c3)c12]

TABLE 1-continued
518
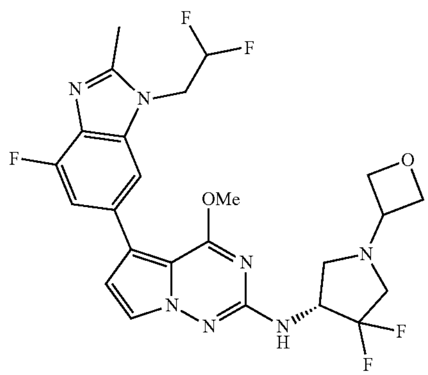 [SMILES: COc1nc(N[C@@H]2CN(C3COC3)CC2(F)F)nn2ccc(-c3cc(F)c4nc(C)n(CC(F)F)c4c3)c12]
519
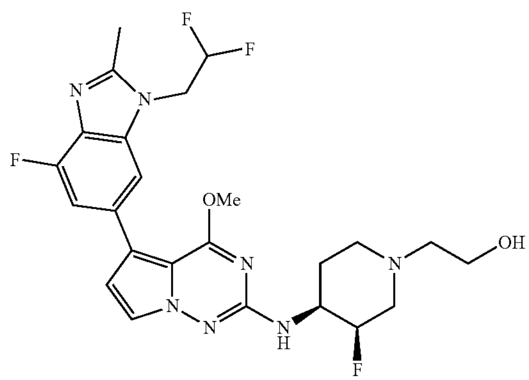 [SMILES: COc1nc(N[C@H]2CCN(CCO)C[C@H]2F)nn2ccc(-c3cc(F)c4nc(C)n(CC(F)F)c4c3)c12]
520
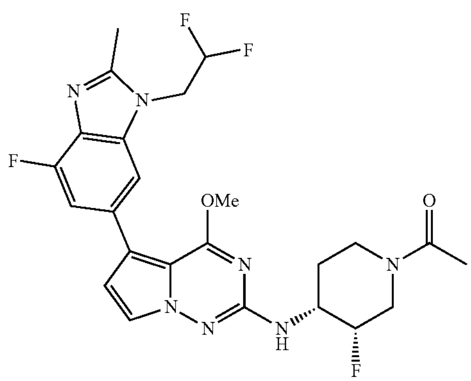 [SMILES: COc1nc(N[C@@H]2CCN(C(C)=O)C[C@@H]2F)nn2ccc(-c3cc(F)c4nc(C)n(CC(F)F)c4c3)c12]
521
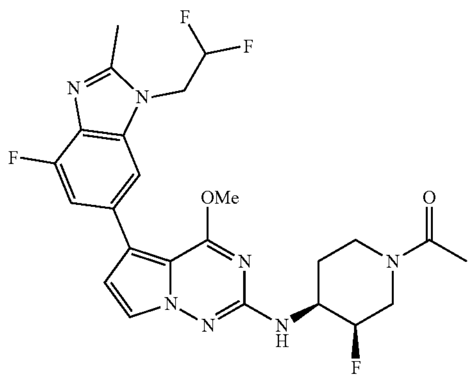 [SMILES: COc1nc(N[C@H]2CCN(C(C)=O)C[C@H]2F)nn2ccc(-c3cc(F)c4nc(C)n(CC(F)F)c4c3)c12]
TABLE 1-continued
522
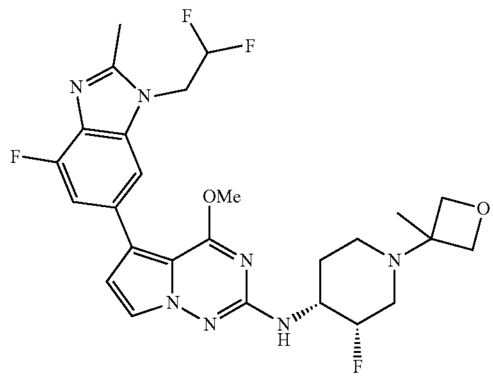 [SMILES: COc1nc(N[C@@H]2CCN(C3(C)COC3)C[C@@H]2F)nn2ccc(-c3cc(F)c4nc(C)n(CC(F)F)c4c3)c12]
523
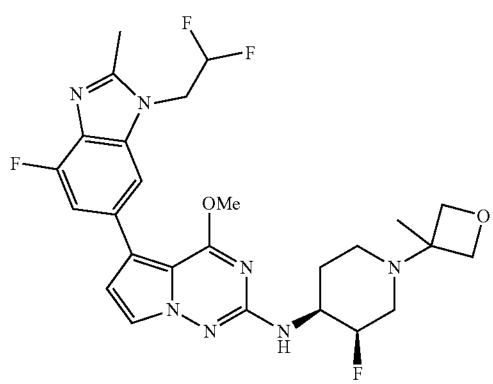 [SMILES: COc1nc(N[C@H]2CCN(C3(C)COC3)C[C@H]2F)nn2ccc(-c3cc(F)c4nc(C)n(CC(F)F)c4c3)c12]
524
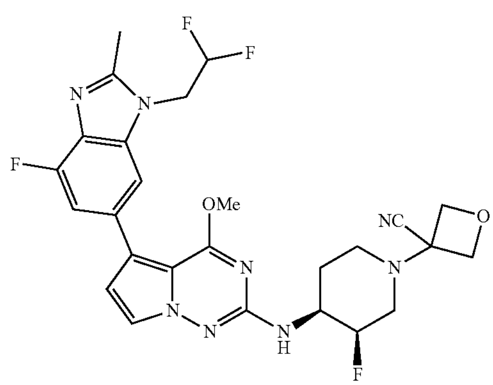 [SMILES: COc1nc(N[C@H]2CCN(C3(C#N)COC3)C[C@H]2F)nn2ccc(-c3cc(F)c4nc(C)n(CC(F)F)c4c3)c12]
525
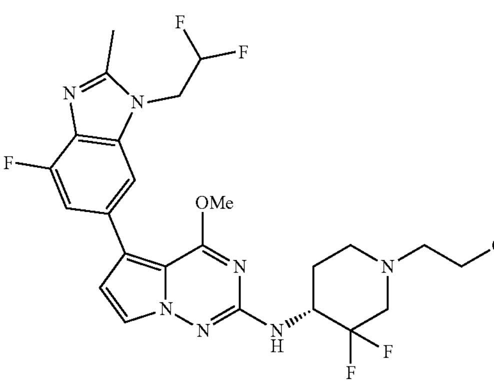

526
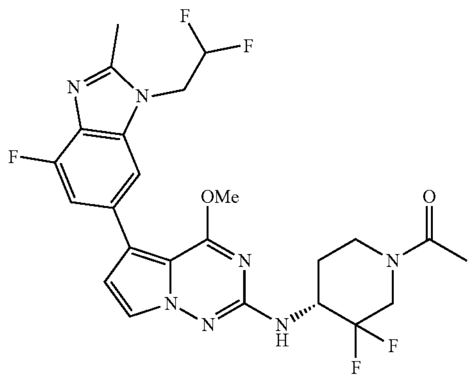 [SMILES: COc1nc(N[C@@H]2CCN(C(C)=O)CC2(F)F)nn2ccc(-c3cc(F)c4nc(C)n(CC(F)F)c4c3)c12]
527
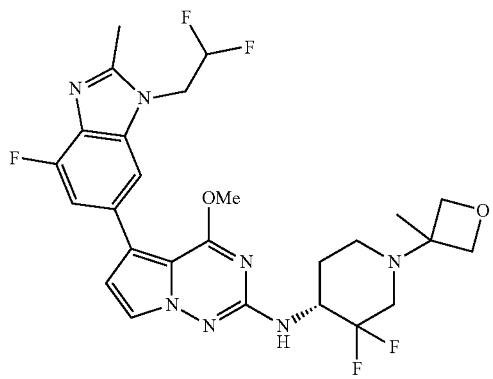 [SMILES: COc1nc(N[C@@H]2CCN(C3(C)COC3)CC2(F)F)nn2ccc(-c3cc(F)c4nc(C)n(CC(F)F)c4c3)c12]
528
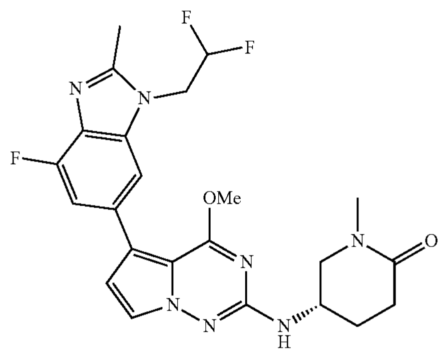 [SMILES: COc1nc(N[C@H]2CCC(=O)N(C)C2)nn2ccc(-c3cc(F)c4nc(C)n(CC(F)F)c4c3)c12]
529
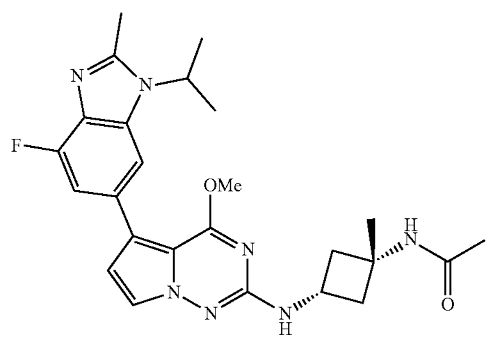 [SMILES: COc1nc(N[C@H]2C[C@@](C)(NC(C)=O)C2)nn2ccc(-c3cc(F)c4nc(C)n(C(C)C)c4c3)c12]
530
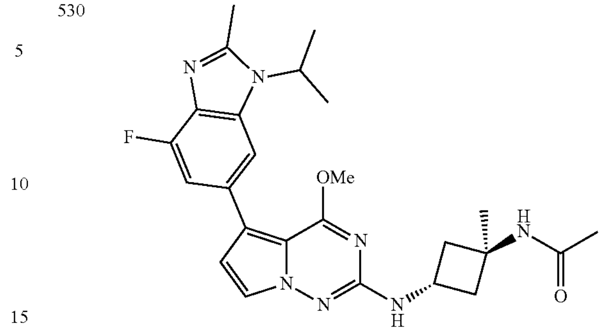
531
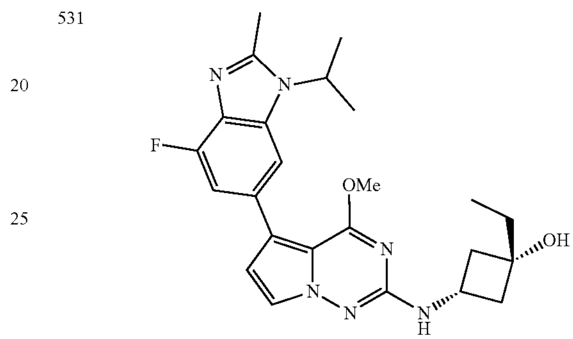
532
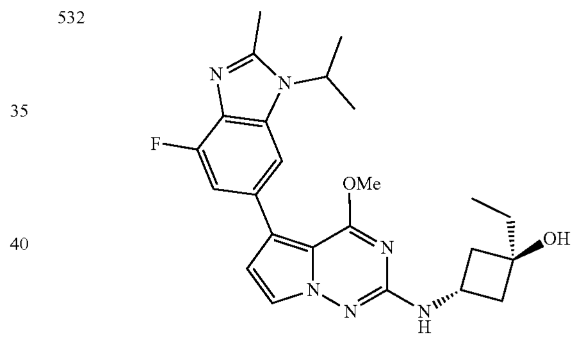
533
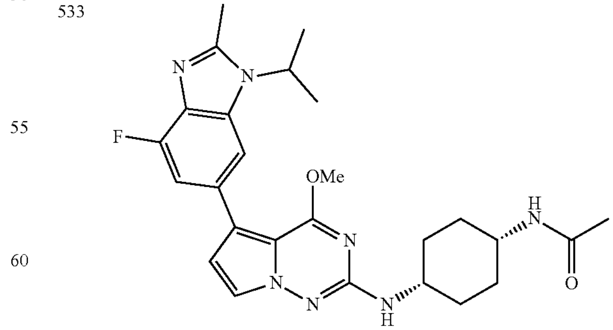

534
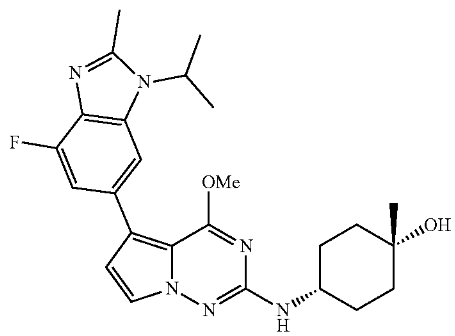 [SMILES: COc1nc(N[C@H]2CC[C@@](C)(O)CC2)nn2ccc(-c3cc(F)c4nc(C)n(C(C)C)c4c3)c12]
535
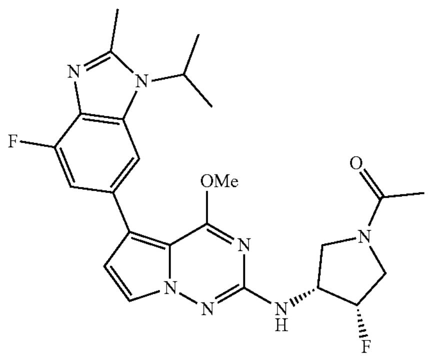 [SMILES: COc1nc(N[C@@H]2CN(C(C)=O)C[C@@H]2F)nn2ccc(-c3cc(F)c4nc(C)n(C(C)C)c4c3)c12]
536
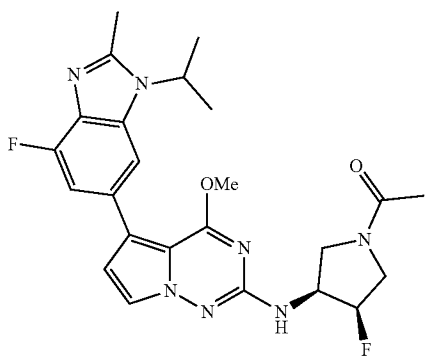 [SMILES: COc1nc(N[C@H]2CN(C(C)=O)C[C@H]2F)nn2ccc(-c3cc(F)c4nc(C)n(C(C)C)c4c3)c12]
537
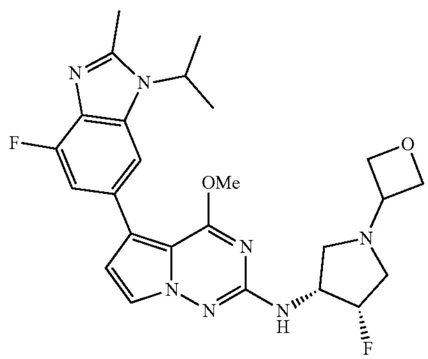 [SMILES: COc1nc(N[C@@H]2CN(C3COC3)C[C@@H]2F)nn2ccc(-c3cc(F)c4nc(C)n(C(C)C)c4c3)c12]
538
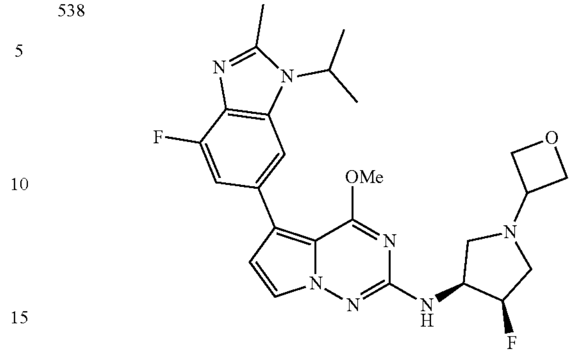
539
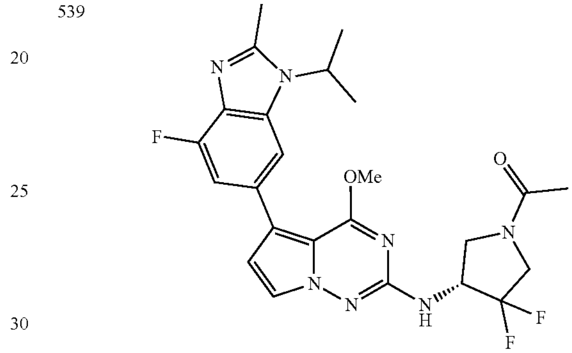
540
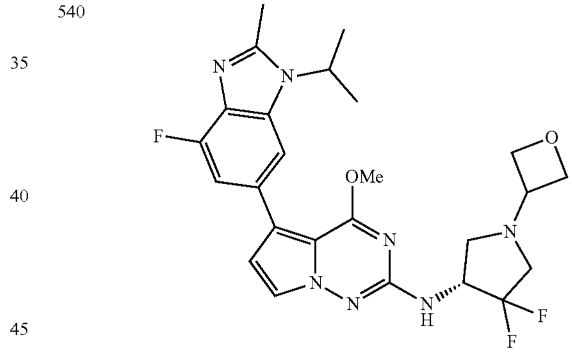
541
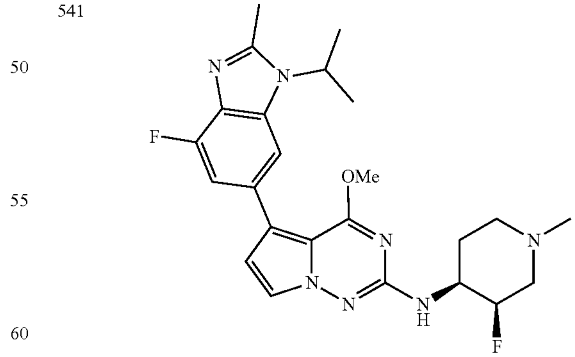

TABLE 1-continued
542
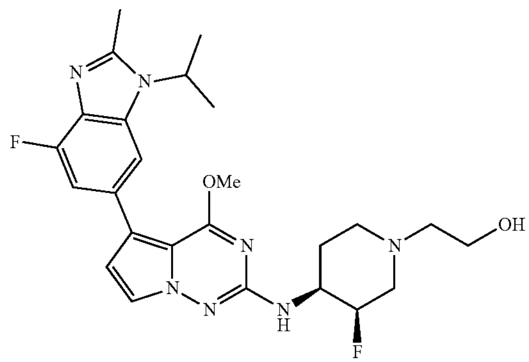 [SMILES: COc1nc(N[C@H]2CCN(CCO)C[C@H]2F)nn2ccc(-c3cc(F)c4nc(C)n(C(C)C)c4c3)c12]
543
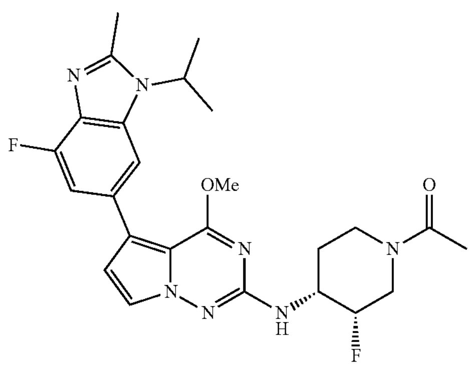 [SMILES: COc1nc(N[C@@H]2CCN(C(C)=O)C[C@@H]2F)nn2ccc(-c3cc(F)c4nc(C)n(C(C)C)c4c3)c12]
544
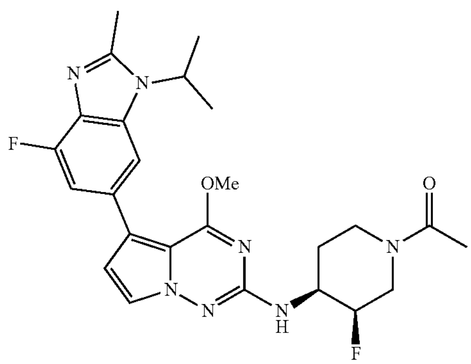 [SMILES: COc1nc(N[C@H]2CCN(C(C)=O)C[C@H]2F)nn2ccc(-c3cc(F)c4nc(C)n(C(C)C)c4c3)c12]
545
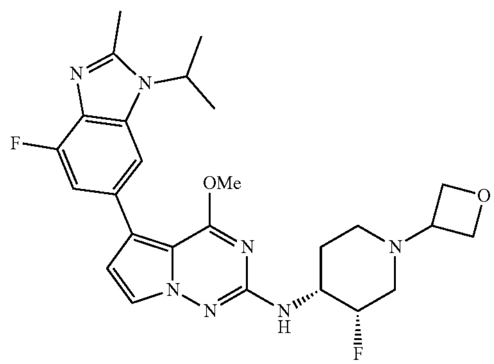 [SMILES: COc1nc(N[C@@H]2CCN(C3COC3)C[C@@H]2F)nn2ccc(-c3cc(F)c4nc(C)n(C(C)C)c4c3)c12]
TABLE 1-continued
546
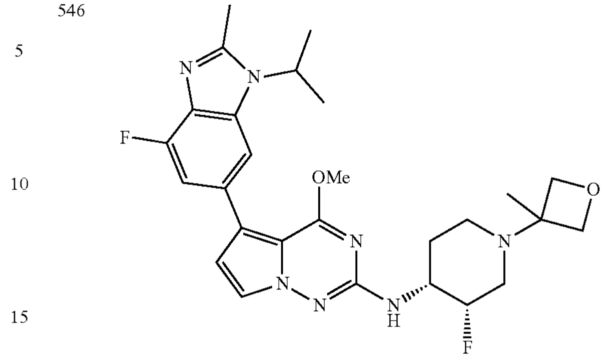
547
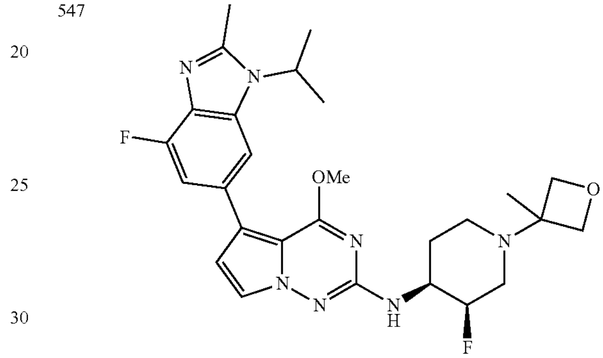
548
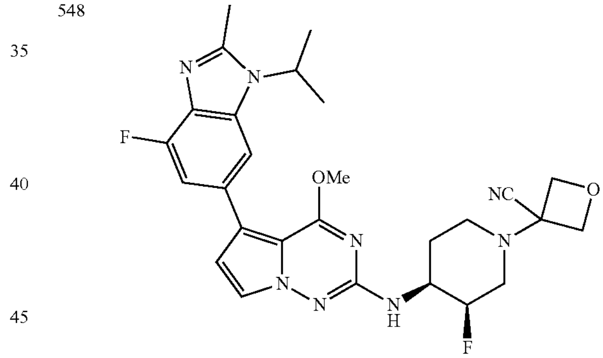
549
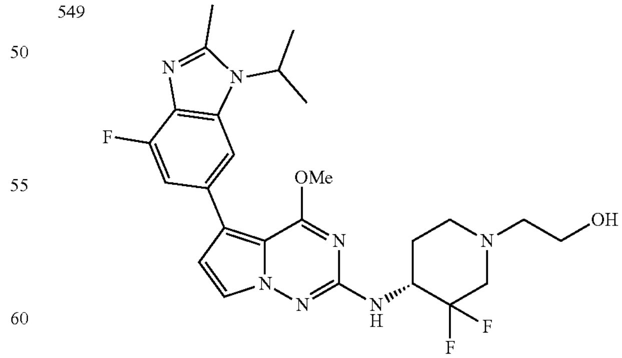

550
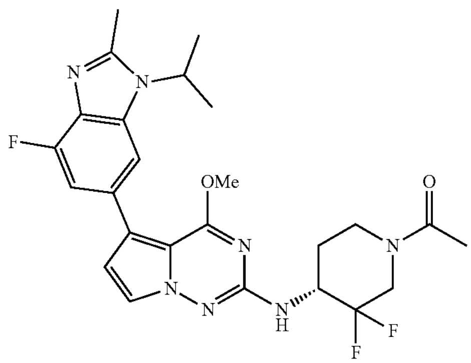 [SMILES: COc1nc(N[C@@H]2CCN(C(C)=O)CC2(F)F)nn2ccc(-c3cc(F)c4nc(C)n(C(C)C)c4c3)c12]
551
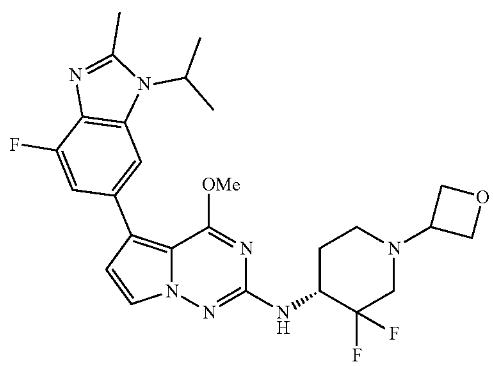 [SMILES: COc1nc(N[C@@H]2CCN(C3COC3)CC2(F)F)nn2ccc(-c3cc(F)c4nc(C)n(C(C)C)c4c3)c12]
552
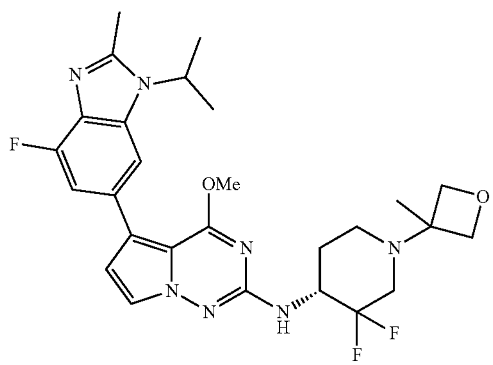 [SMILES: COc1nc(N[C@@H]2CCN(C3(C)COC3)CC2(F)F)nn2ccc(-c3cc(F)c4nc(C)n(C(C)C)c4c3)c12]
553
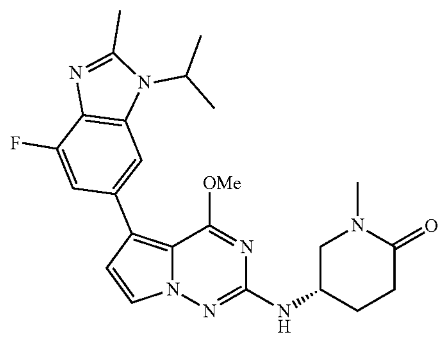 [SMILES: COc1nc(N[C@H]2CCC(=O)N(C)C2)nn2ccc(-c3cc(F)c4nc(C)n(C(C)C)c4c3)c12]
554
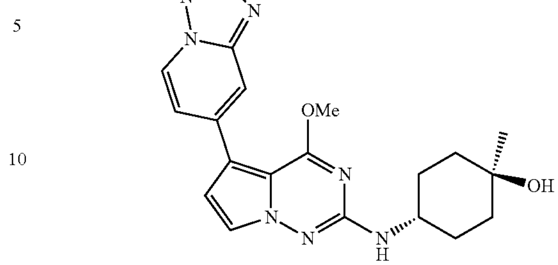
555
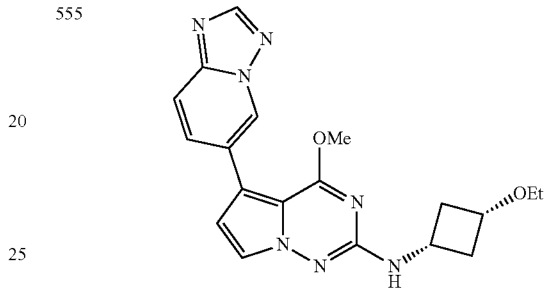
556
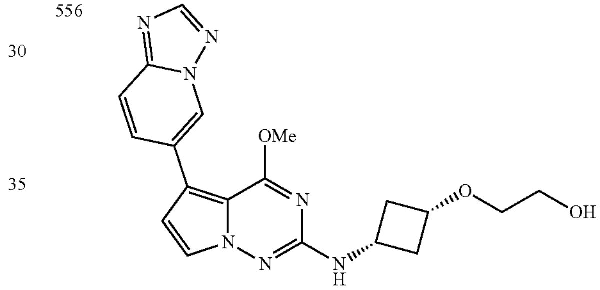
557
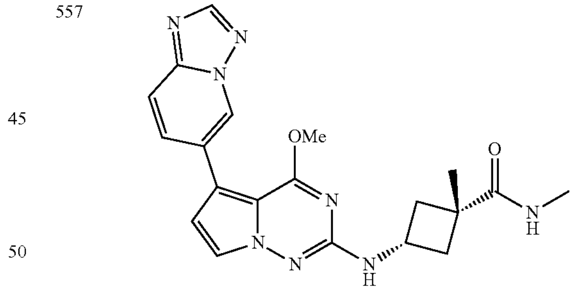
558
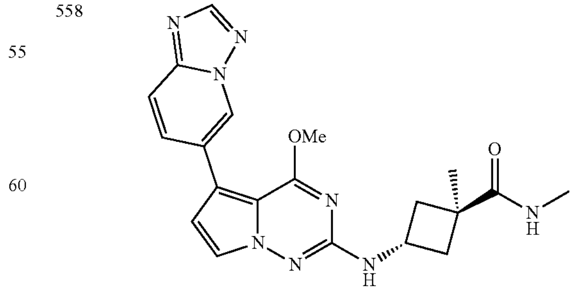

TABLE 1-continued
559
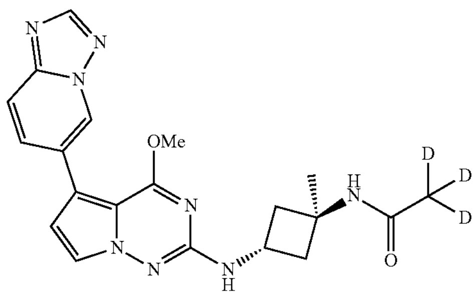 [SMILES: [2H]C([2H])([2H])C(=O)N[C@]1(C)C[C@@H](Nc2nc(OC)c3c(-c4ccc5ncnn5c4)ccn3n2)C1]
560
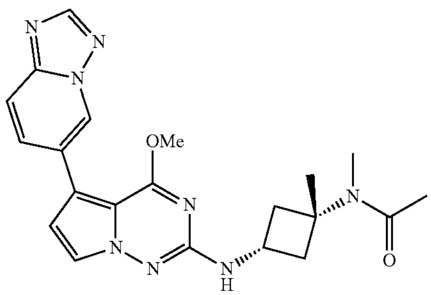 [SMILES: COc1nc(N[C@H]2C[C@@](C)(N(C)C(C)=O)C2)nn2ccc(-c3ccc4ncnn4c3)c12]
561
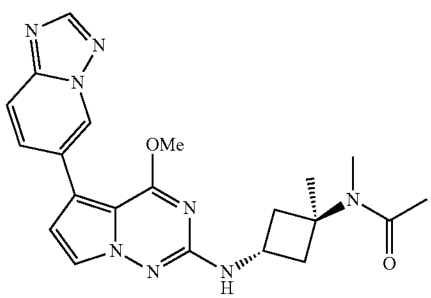 [SMILES: COc1nc(N[C@H]2C[C@](C)(N(C)C(C)=O)C2)nn2ccc(-c3ccc4ncnn4c3)c12]
562
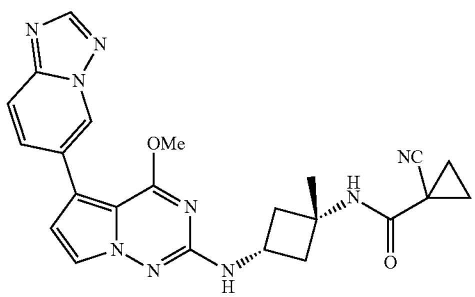 [SMILES: COc1nc(N[C@H]2C[C@@](C)(NC(=O)C3(C#N)CC3)C2)nn2ccc(-c3ccc4ncnn4c3)c12]
563
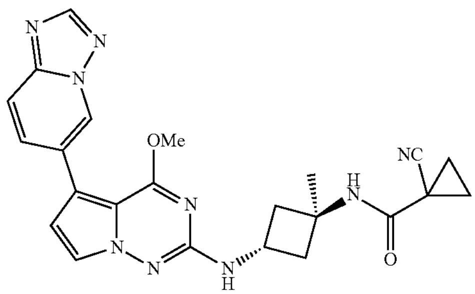 [SMILES: COc1nc(N[C@H]2C[C@](C)(NC(=O)C3(C#N)CC3)C2)nn2ccc(-c3ccc4ncnn4c3)c12]
TABLE 1-continued
564
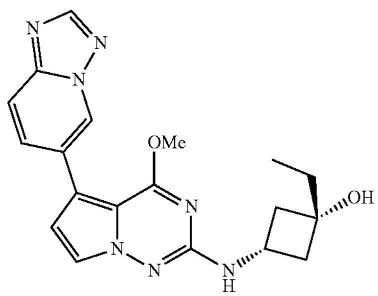 [SMILES: CC[C@]1(O)C[C@@H](Nc2nc(OC)c3c(-c4ccc5ncnn5c4)ccn3n2)C1]
565
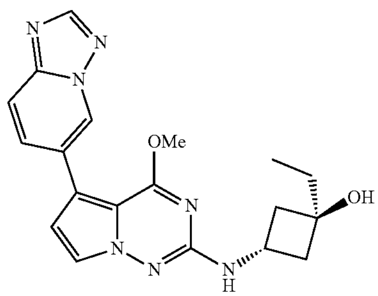 [SMILES: CC[C@]1(O)C[C@H](Nc2nc(OC)c3c(-c4ccc5ncnn5c4)ccn3n2)C1]
566
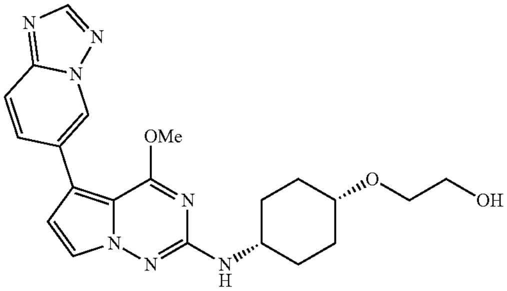 [SMILES: COc1nc(N[C@H]2CC[C@@H](OCCO)CC2)nn2ccc(-c3ccc4ncnn4c3)c12]
567
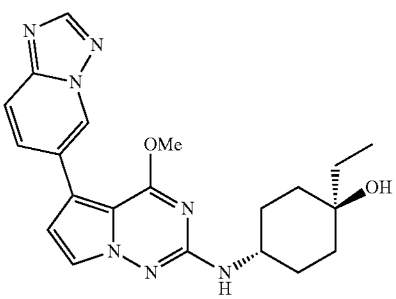 [SMILES: CC[C@]1(O)CC[C@H](Nc2nc(OC)c3c(-c4ccc5ncnn5c4)ccn3n2)CC1]
568
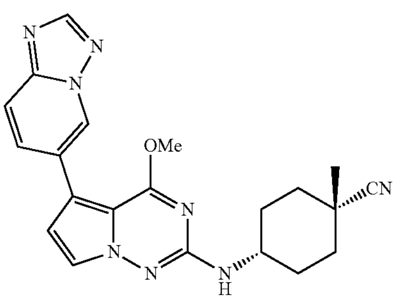 [SMILES: COc1nc(N[C@H]2CC[C@@](C)(C#N)CC2)nn2ccc(-c3ccc4ncnn4c3)c12]

TABLE 1-continued
569
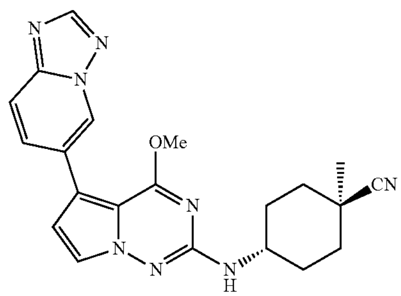 [SMILES: COc1nc(N[C@H]2CC[C@](C)(C#N)CC2)nn2ccc(-c3ccc4ncnn4c3)c12]
570
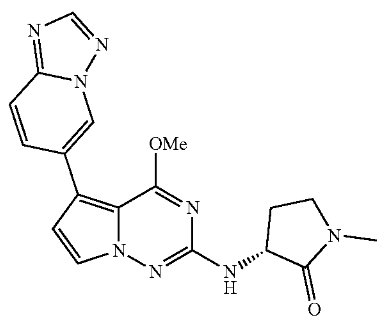 [SMILES: COc1nc(N[C@@H]2CCN(C)C2=O)nn2ccc(-c3ccc4ncnn4c3)c12]
571
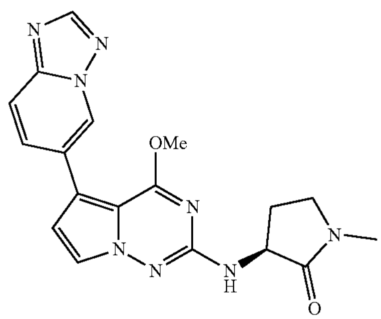 [SMILES: COc1nc(N[C@H]2CCN(C)C2=O)nn2ccc(-c3ccc4ncnn4c3)c12]
572
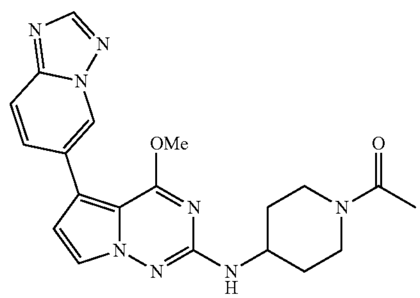 [SMILES: COc1nc(NC2CCN(C(C)=O)CC2)nn2ccc(-c3ccc4ncnn4c3)c12]
573
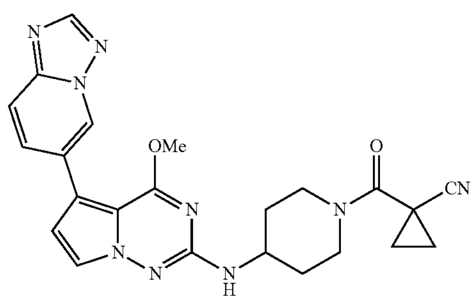 [SMILES: COc1nc(NC2CCN(C(=O)C3(C#N)CC3)CC2)nn2ccc(-c3ccc4ncnn4c3)c12]
TABLE 1-continued
574
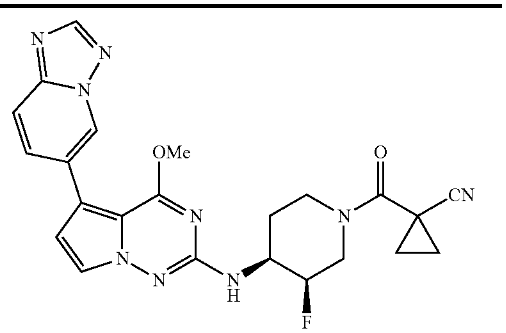
575
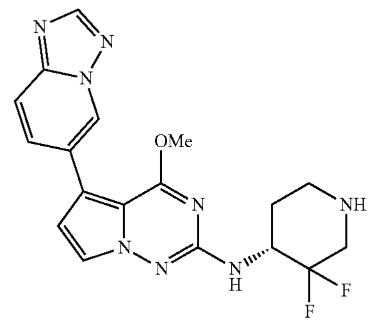 [SMILES: COc1nc(N[C@@H]2CCNCC2(F)F)nn2ccc(-c3ccc4ncnn4c3)c12]
576
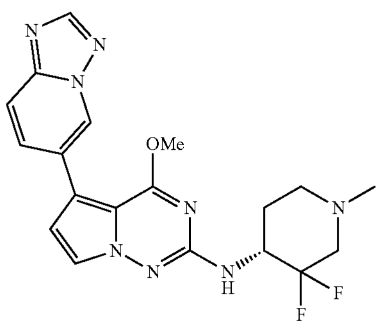 [SMILES: COc1nc(N[C@@H]2CCN(C)CC2(F)F)nn2ccc(-c3ccc4ncnn4c3)c12]
577
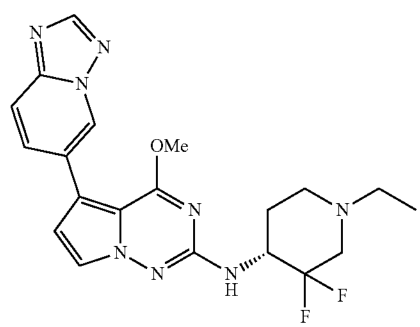 [SMILES: CCN1CC[C@@H](Nc2nc(OC)c3c(-c4ccc5ncnn5c4)ccn3n2)C(F)(F)C1]
578
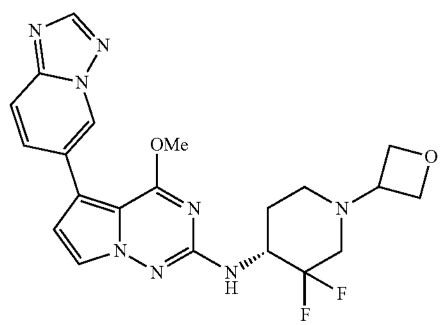 [SMILES: COc1nc(N[C@@H]2CCN(C3COC3)CC2(F)F)nn2ccc(-c3ccc4ncnn4c3)c12]

TABLE 1-continued
579
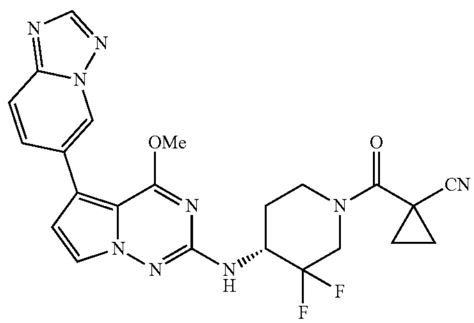 [SMILES: COc1nc(N[C@@H]2CCN(C(=O)C3(C#N)CC3)CC2(F)F)nn2ccc(-c3ccc4ncnn4c3)c12]
580
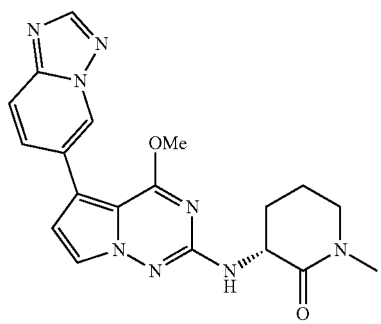 [SMILES: COc1nc(N[C@@H]2CCCN(C)C2=O)nn2ccc(-c3ccc4ncnn4c3)c12]
581
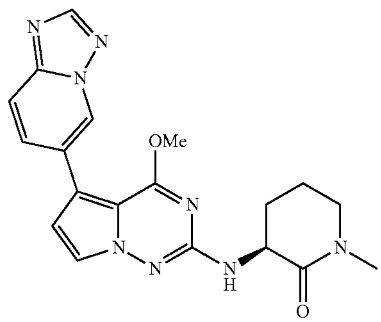 [SMILES: COc1nc(N[C@H]2CCCN(C)C2=O)nn2ccc(-c3ccc4ncnn4c3)c12]
582
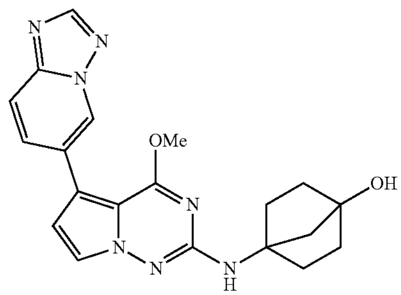 [SMILES: COc1nc(NC23CCC(O)(CC2)C3)nn2ccc(-c3ccc4ncnn4c3)c12]
583
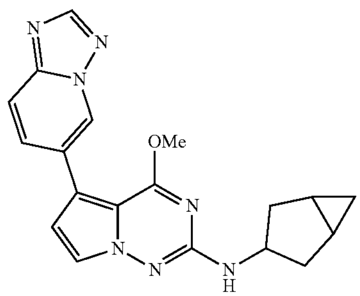 [SMILES: COc1nc(NC2CC3CC3C2)nn2ccc(-c3ccc4ncnn4c3)c12]
TABLE 1-continued
584
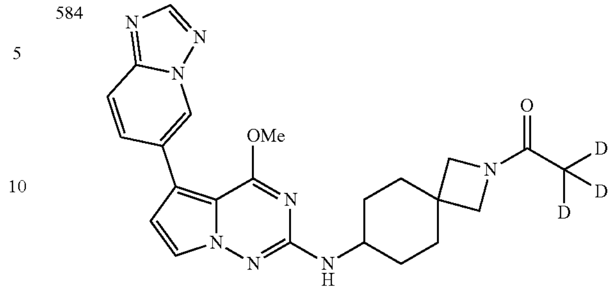
585
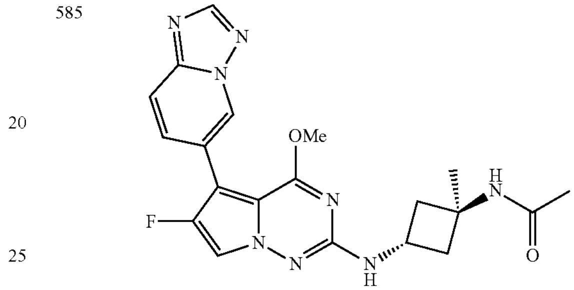
586
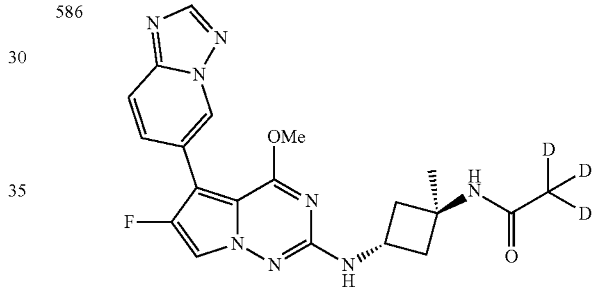
587
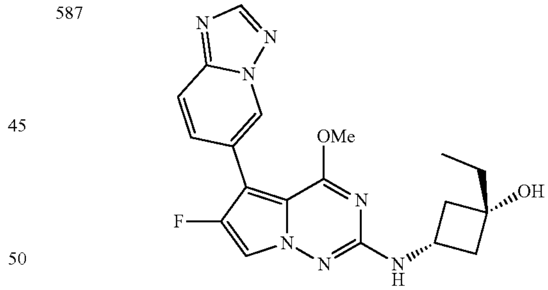
588
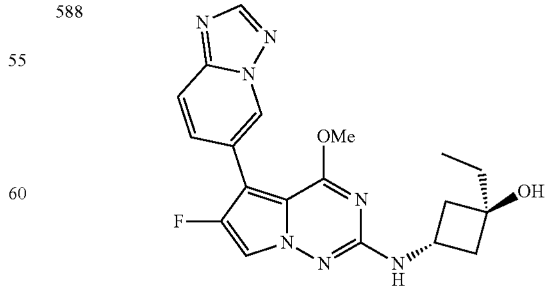

TABLE 1-continued
589
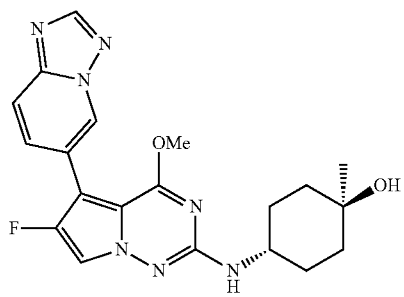 [SMILES: COc1nc(N[C@H]2CC[C@](C)(O)CC2)nn2cc(F)c(-c3ccc4ncnn4c3)c12]
590
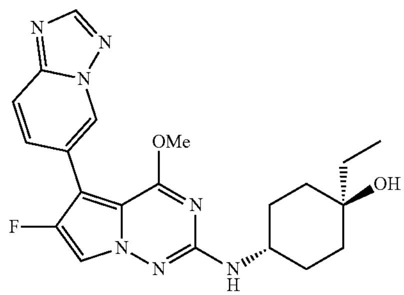 [SMILES: CC[C@]1(O)CC[C@H](Nc2nc(OC)c3c(-c4ccc5ncnn5c4)c(F)cn3n2)CC1]
591
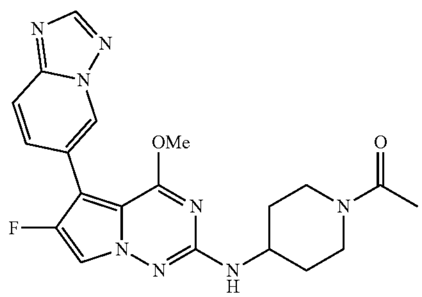 [SMILES: COc1nc(NC2CCN(C(C)=O)CC2)nn2cc(F)c(-c3ccc4ncnn4c3)c12]
592
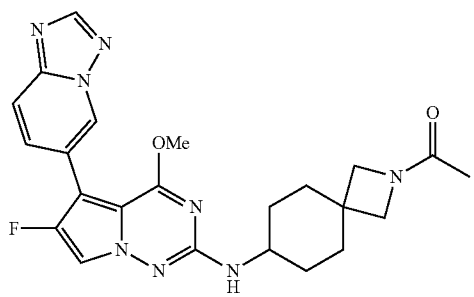 [SMILES: COc1nc(NC2CCC3(CC2)CN(C(C)=O)C3)nn2cc(F)c(-c3ccc4ncnn4c3)c12]
593
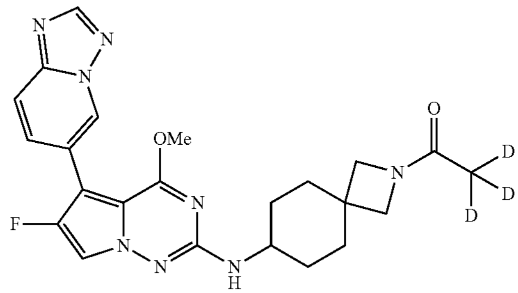 [SMILES: [2H]C([2H])([2H])C(=O)N1CC2(CCC(Nc3nc(OC)c4c(-c5ccc6ncnn6c5)c(F)cn4n3)CC2)C1]
TABLE 1-continued
594
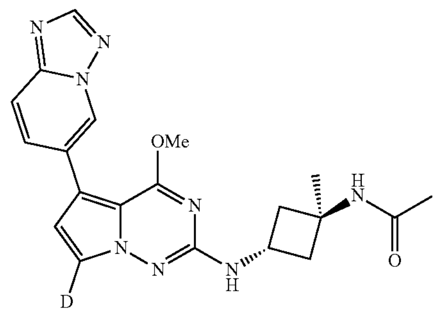 [SMILES: [2H]c1cc(-c2ccc3ncnn3c2)c2c(OC)nc(N[C@H]3C[C@](C)(NC(C)=O)C3)nn12]
595
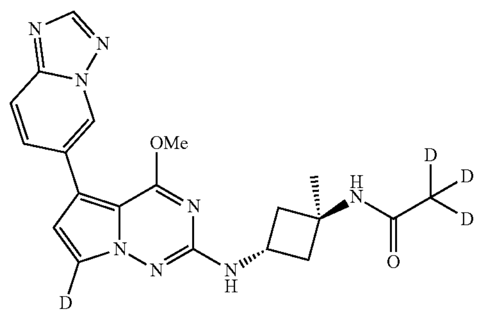 [SMILES: [2H]c1cc(-c2ccc3ncnn3c2)c2c(OC)nc(N[C@H]3C[C@](C)(NC(=O)C([2H])([2H])[2H])C3)nn12]
596
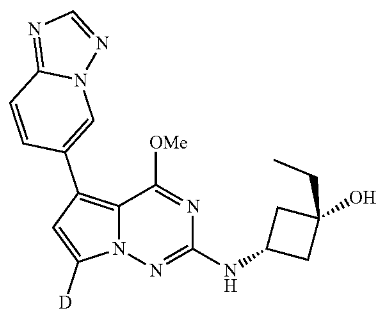 [SMILES: [2H]c1cc(-c2ccc3ncnn3c2)c2c(OC)nc(N[C@H]3C[C@](O)(CC)C3)nn12]
597
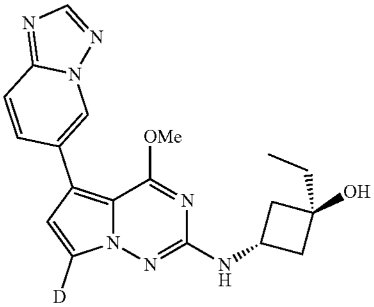 [SMILES: [2H]c1cc(-c2ccc3ncnn3c2)c2c(OC)nc(N[C@H]3C[C@@](O)(CC)C3)nn12]
598
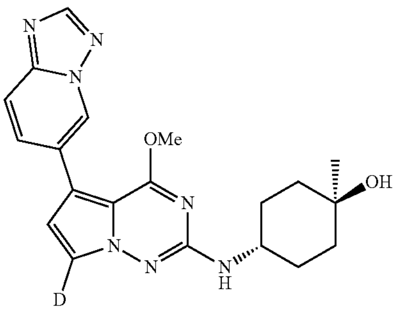 [SMILES: [2H]c1cc(-c2ccc3ncnn3c2)c2c(OC)nc(N[C@H]3CC[C@](C)(O)CC3)nn12]

TABLE 1-continued
599
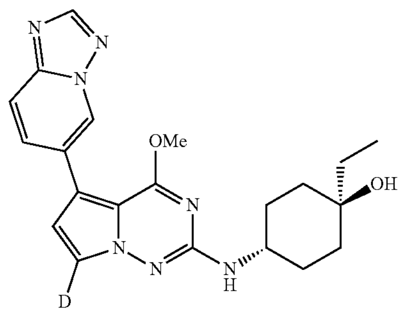 [SMILES: [2H]c1cc(-c2ccc3ncnn3c2)c2c(OC)nc(N[C@H]3CC[C@@](O)(CC)CC3)nn12]
600
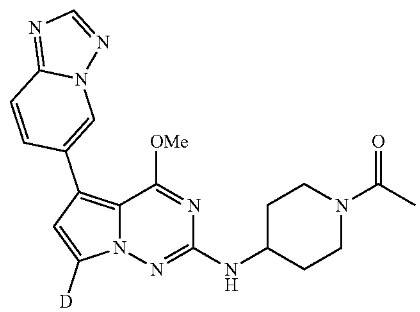 [SMILES: [2H]c1cc(-c2ccc3ncnn3c2)c2c(OC)nc(NC3CCN(C(C)=O)CC3)nn12]
601
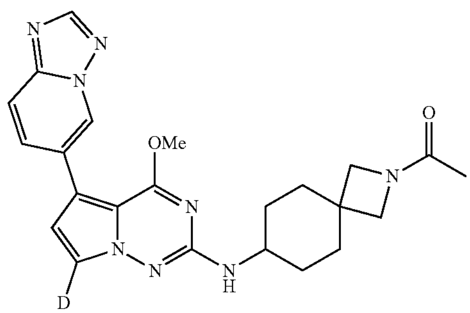 [SMILES: [2H]c1cc(-c2ccc3ncnn3c2)c2c(OC)nc(NC3CCC4(CC3)CN(C(C)=O)C4)nn12]
602
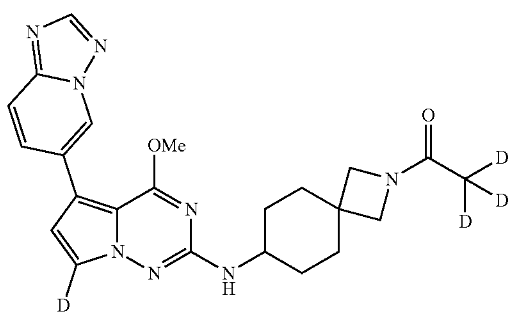 [SMILES: [2H]c1cc(-c2ccc3ncnn3c2)c2c(OC)nc(NC3CCC4(CC3)CN(C(=O)C([2H])([2H])[2H])C4)nn12]
603
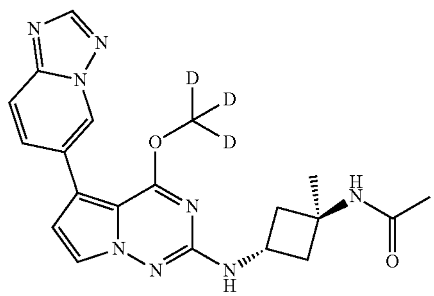 [SMILES: [2H]C([2H])([2H])Oc1nc(N[C@H]2C[C@](C)(NC(C)=O)C2)nn2ccc(-c3ccc4ncnn4c3)c12]
TABLE 1-continued
604
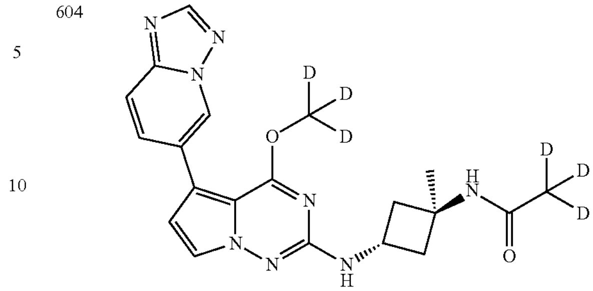
605
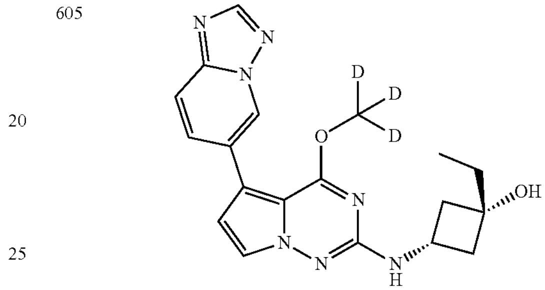
606
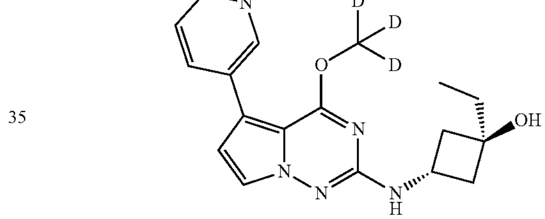
607
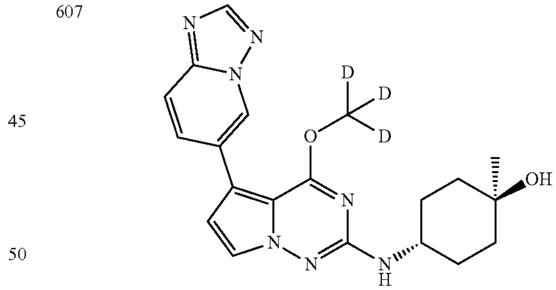
608
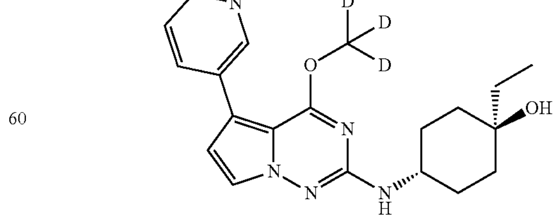

609
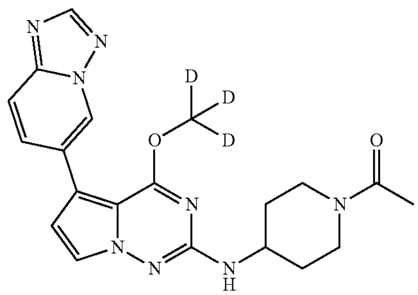 [SMILES: [2H]C([2H])([2H])Oc1nc(NC2CCN(C(C)=O)CC2)nn2ccc(-c3ccc4ncnn4c3)c12]
610
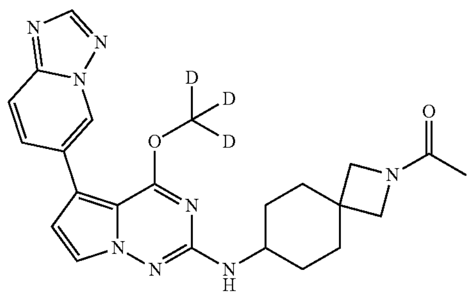 [SMILES: [2H]C([2H])([2H])Oc1nc(NC2CCC3(CC2)CN(C(C)=O)C3)nn2ccc(-c3ccc4ncnn4c3)c12]
611
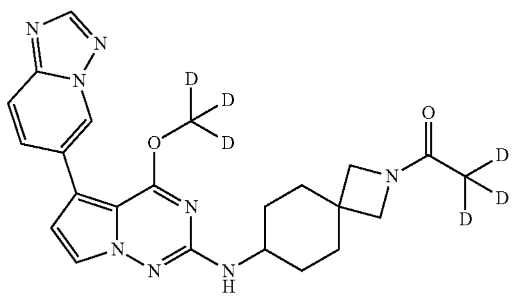 [SMILES: [2H]C([2H])([2H])Oc1nc(NC2CCC3(CC2)CN(C(=O)C([2H])([2H])[2H])C3)nn2ccc(-c3ccc4ncnn4c3)c12]
612
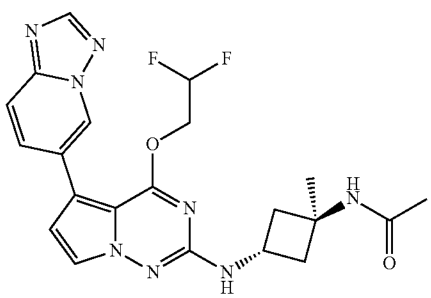 [SMILES: CC(=O)N[C@]1(C)C[C@@H](Nc2nc(OCC(F)F)c3c(-c4ccc5ncnn5c4)ccn3n2)C1]
613
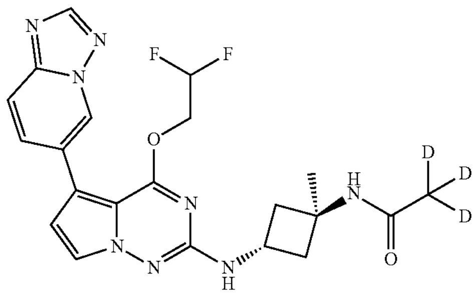 [SMILES: [2H]C([2H])([2H])C(=O)N[C@]1(C)C[C@@H](Nc2nc(OCC(F)F)c3c(-c4ccc5ncnn5c4)ccn3n2)C1]
614
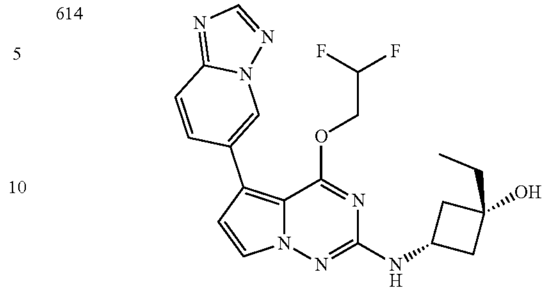
615
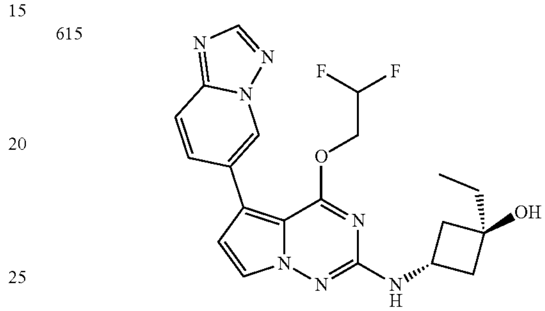
616
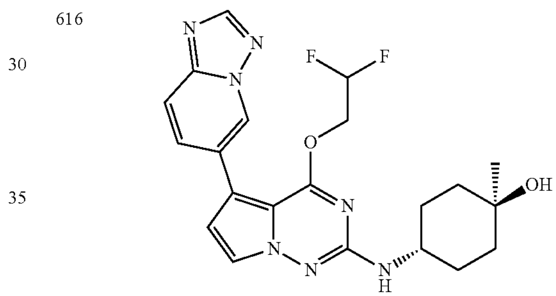
617
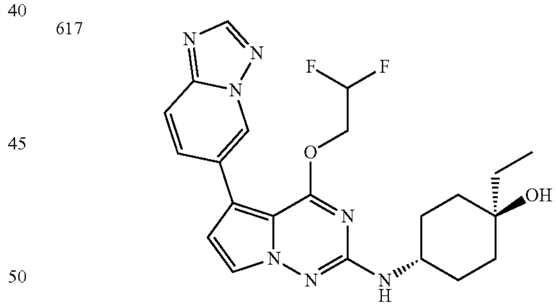
618
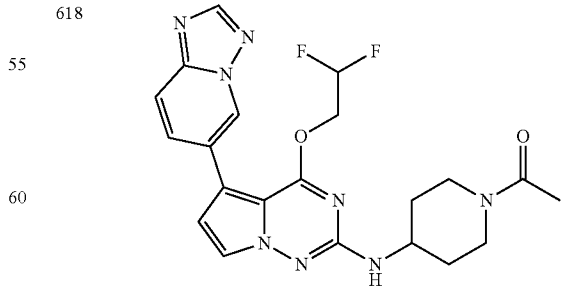

TABLE 1-continued
619
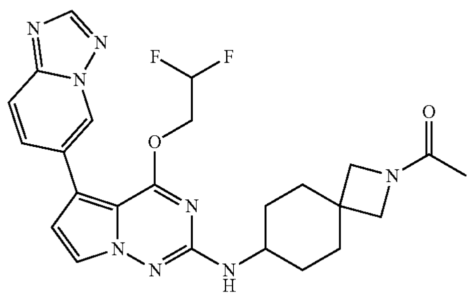 [SMILES: CC(=O)N1CC2(CCC(Nc3nc(OCC(F)F)c4c(-c5ccc6ncnn6c5)ccn4n3)CC2)C1]
620
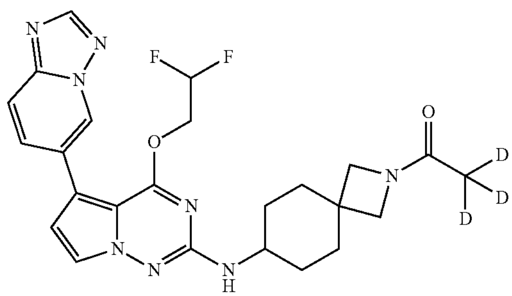 [SMILES: [2H]C([2H])([2H])C(=O)N1CC2(CCC(Nc3nc(OCC(F)F)c4c(-c5ccc6ncnn6c5)ccn4n3)CC2)C1]
621
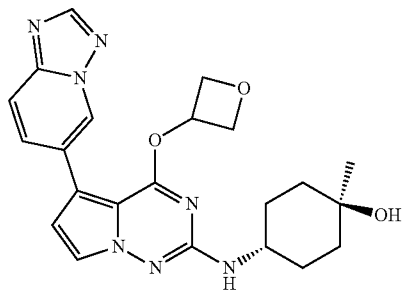 [SMILES: C[C@]1(O)CC[C@H](Nc2nc(OC3COC3)c3c(-c4ccc5ncnn5c4)ccn3n2)CC1]
622
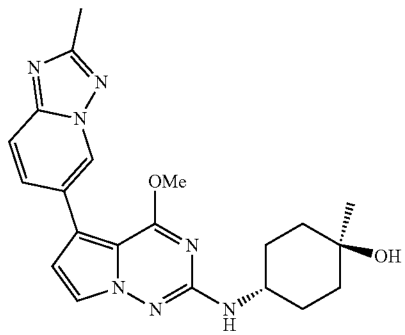 [SMILES: COc1nc(N[C@H]2CC[C@](C)(O)CC2)nn2ccc(-c3ccc4nc(C)nn4c3)c12]
623
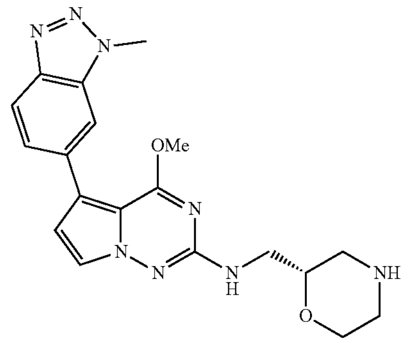 [SMILES: COc1nc(NC[C@@H]2CNCCO2)nn2ccc(-c3ccc4nnn(C)c4c3)c12]
TABLE 1-continued
624
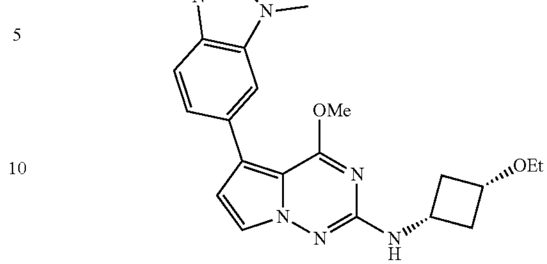
625
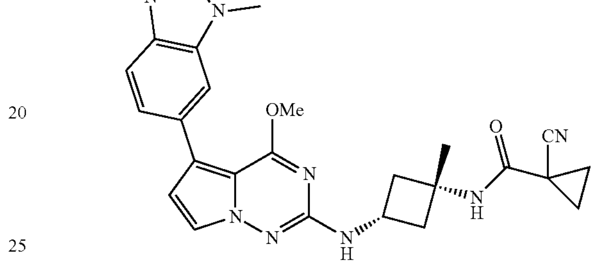
626
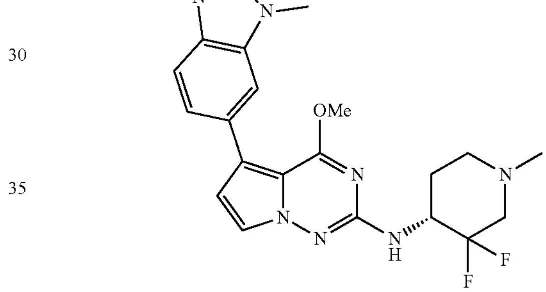
627
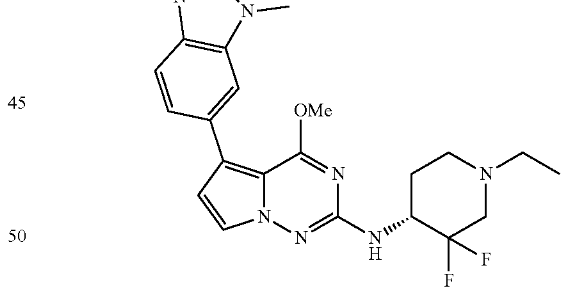
628
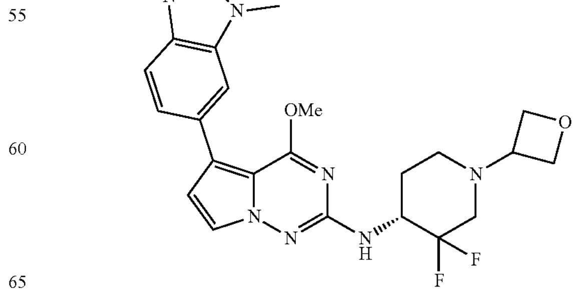

TABLE 1-continued
629
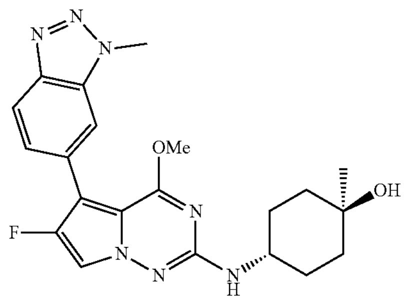 [SMILES: COc1nc(N[C@H]2CC[C@](C)(O)CC2)nn2cc(F)c(-c3ccc4nnn(C)c4c3)c12]
630
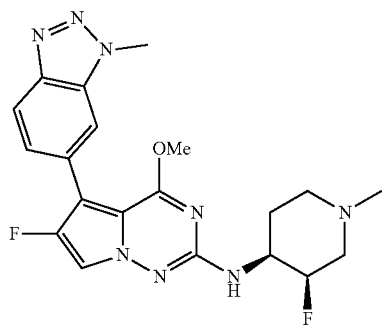 [SMILES: COc1nc(N[C@H]2CCN(C)C[C@H]2F)nn2cc(F)c(-c3ccc4nnn(C)c4c3)c12]
631
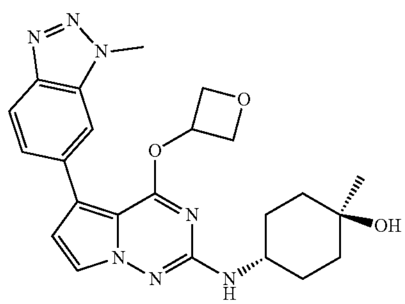 [SMILES: Cn1nnc2ccc(-c3ccn4nc(N[C@H]5CC[C@](C)(O)CC5)nc(OC5COC5)c34)cc21]
632
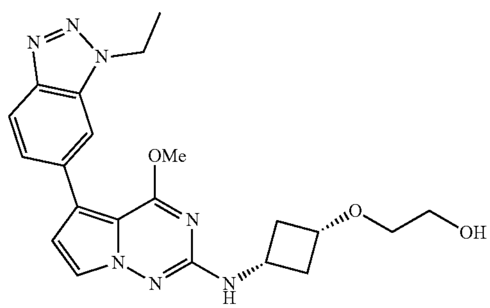 [SMILES: CCn1nnc2ccc(-c3ccn4nc(N[C@H]5C[C@@H](OCCO)C5)nc(OC)c34)cc21]
633
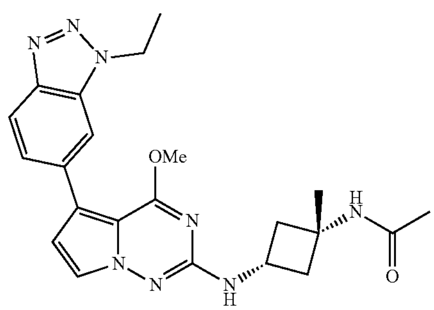 [SMILES: CCn1nnc2ccc(-c3ccn4nc(N[C@H]5C[C@@](C)(NC(C)=O)C5)nc(OC)c34)cc21]
TABLE 1-continued
634
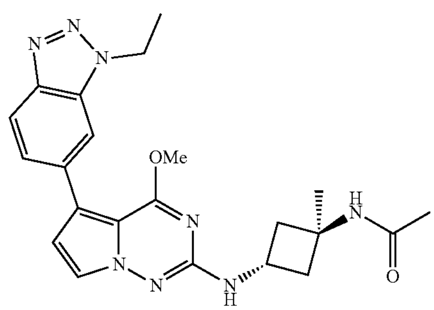 [SMILES: CCn1nnc2ccc(-c3ccn4nc(N[C@H]5C[C@](C)(NC(C)=O)C5)nc(OC)c34)cc21]
635
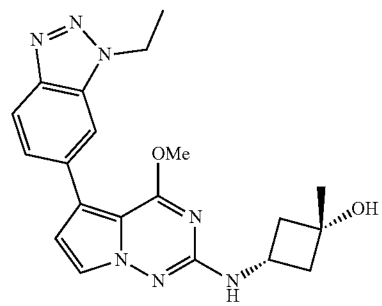 [SMILES: CCn1nnc2ccc(-c3ccn4nc(N[C@H]5C[C@@](C)(O)C5)nc(OC)c34)cc21]
636
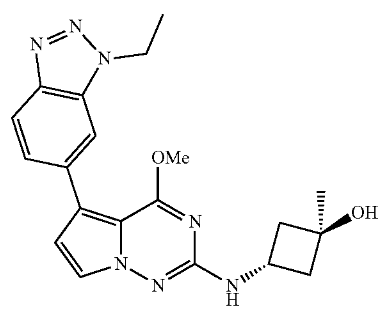 [SMILES: CCn1nnc2ccc(-c3ccn4nc(N[C@H]5C[C@](C)(O)C5)nc(OC)c34)cc21]
637
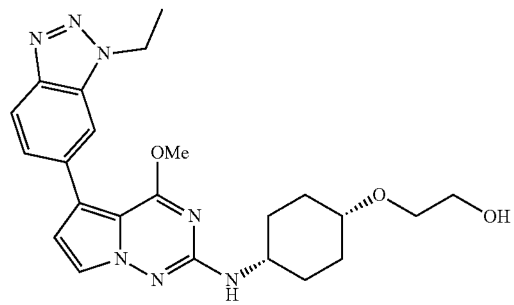 [SMILES: CCn1nnc2ccc(-c3ccn4nc(N[C@H]5CC[C@@H](OCCO)CC5)nc(OC)c34)cc21]
638
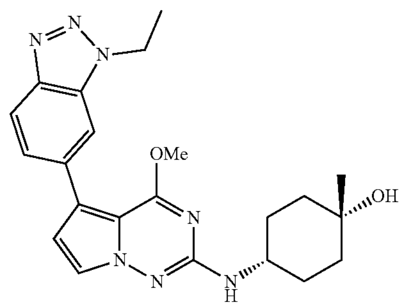 [SMILES: CCn1nnc2ccc(-c3ccn4nc(N[C@H]5CC[C@@](C)(O)CC5)nc(OC)c34)cc21]

TABLE 1-continued
639
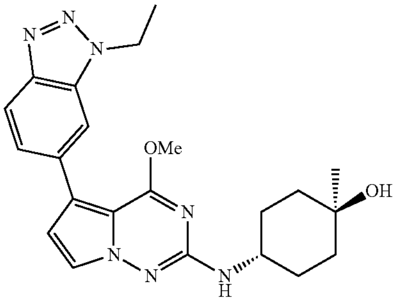 [SMILES: CCn1nnc2ccc(-c3ccn4nc(N[C@H]5CC[C@](C)(O)CC5)nc(OC)c34)cc21]
640
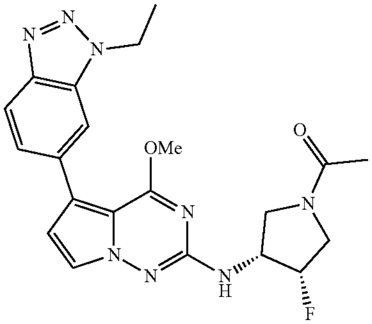 [SMILES: CCn1nnc2ccc(-c3ccn4nc(N[C@@H]5CN(C(C)=O)C[C@@H]5F)nc(OC)c34)cc21]
641
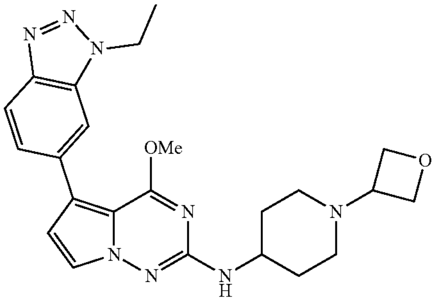 [SMILES: CCn1nnc2ccc(-c3ccn4nc(NC5CCN(C6(C)COC6)CC5)nc(OC)c34)cc21]
642
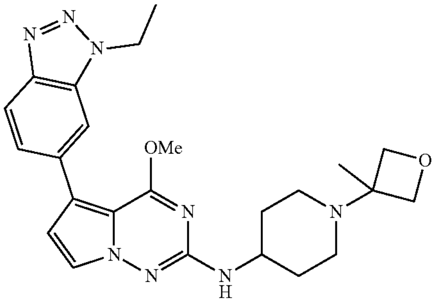
643
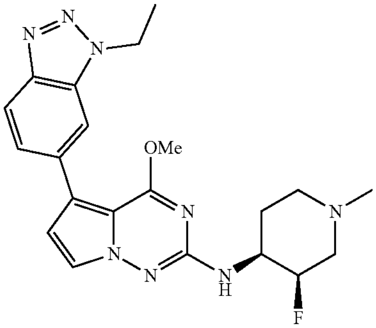 [SMILES: CCn1nnc2ccc(-c3ccn4nc(N[C@H]5CCN(C)C[C@H]5F)nc(OC)c34)cc21]
TABLE 1-continued
644
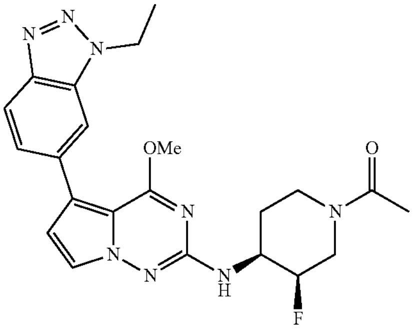 [SMILES: CCn1nnc2ccc(-c3ccn4nc(N[C@H]5CCN(C(C)=O)C[C@H]5F)nc(OC)c34)cc21]
645
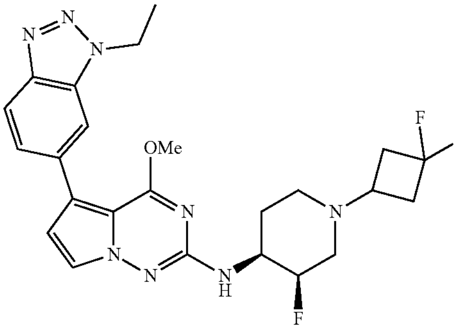
646
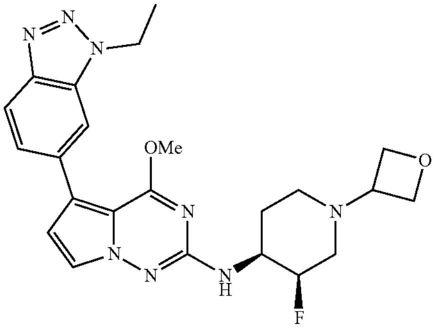 [SMILES: CCn1nnc2ccc(-c3ccn4nc(N[C@H]5CCN(C6COC6)C[C@H]5F)nc(OC)c34)cc21]
647
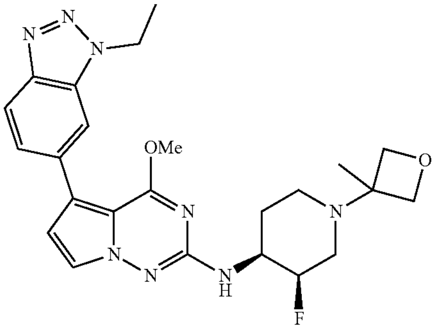 [SMILES: CCn1nnc2ccc(-c3ccn4nc(N[C@H]5CCN(C6(C)COC6)C[C@H]5F)nc(OC)c34)cc21]

TABLE 1-continued
648
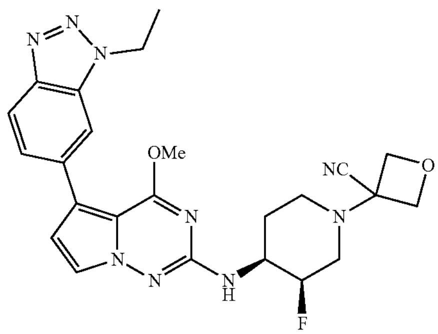 [SMILES: CCn1nnc2ccc(-c3ccn4nc(N[C@H]5CCN(C6(C#N)COC6)C[C@H]5F)nc(OC)c34)cc21]
649
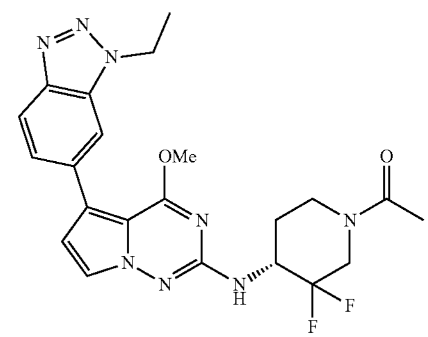 [SMILES: CCn1nnc2ccc(-c3ccn4nc(N[C@@H]5CCN(C(C)=O)CC5(F)F)nc(OC)c34)cc21]
650
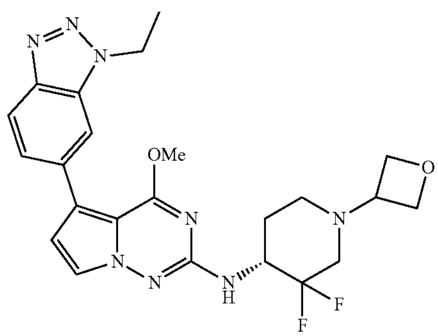 [SMILES: CCn1nnc2ccc(-c3ccn4nc(N[C@@H]5CCN(C6COC6)CC5(F)F)nc(OC)c34)cc21]
651
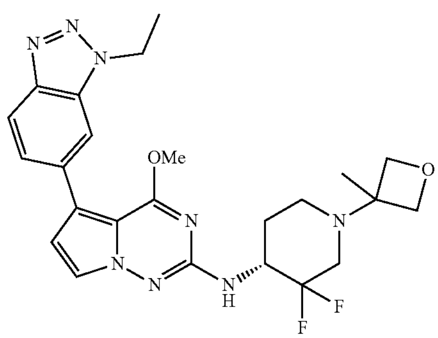 [SMILES: CCn1nnc2ccc(-c3ccn4nc(N[C@@H]5CCN(C6(C)COC6)CC5(F)F)nc(OC)c34)cc21]
652
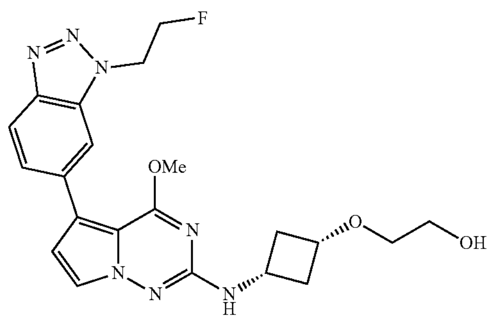 [SMILES: COc1nc(N[C@H]2C[C@@H](OCCO)C2)nn2ccc(-c3ccc4nnn(CCF)c4c3)c12]
TABLE 1-continued
653
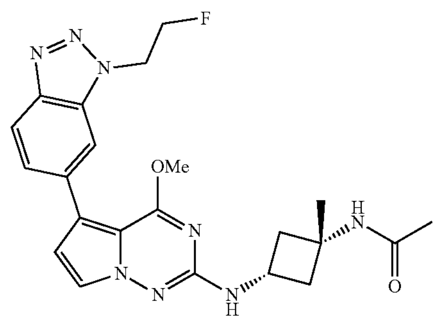 [SMILES: COc1nc(N[C@H]2C[C@@](C)(NC(C)=O)C2)nn2ccc(-c3ccc4nnn(CCF)c4c3)c12]
654
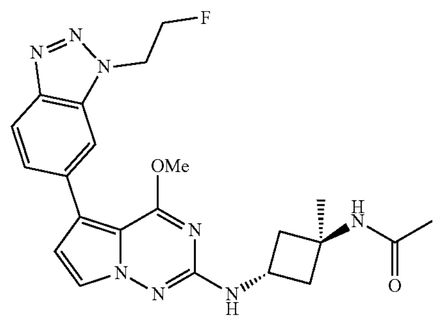 [SMILES: COc1nc(N[C@H]2C[C@](C)(NC(C)=O)C2)nn2ccc(-c3ccc4nnn(CCF)c4c3)c12]
655
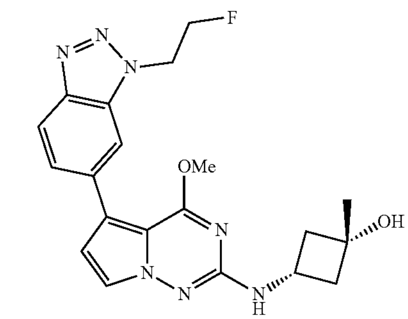 [SMILES: COc1nc(N[C@H]2C[C@@](C)(O)C2)nn2ccc(-c3ccc4nnn(CCF)c4c3)c12]
656
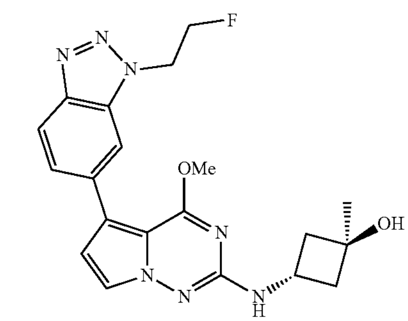 [SMILES: COc1nc(N[C@H]2C[C@](C)(O)C2)nn2ccc(-c3ccc4nnn(CCF)c4c3)c12]
657
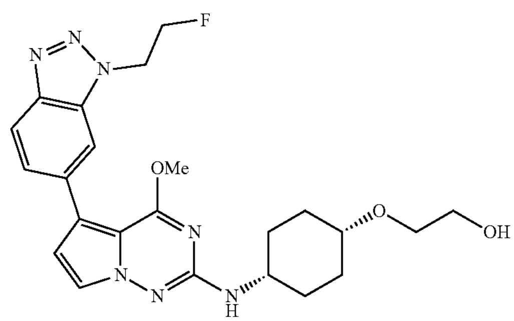 [SMILES: COc1nc(N[C@H]2CC[C@@H](OCCO)CC2)nn2ccc(-c3ccc4nnn(CCF)c4c3)c12]

TABLE 1-continued
658
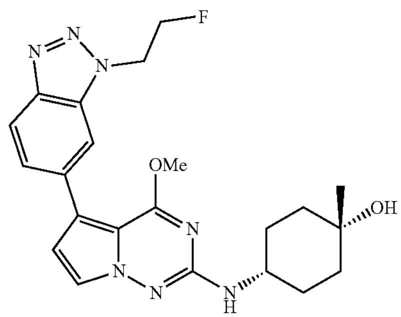 [SMILES: COc1nc(N[C@H]2CC[C@@](C)(O)CC2)nn2ccc(-c3ccc4nnn(CCF)c4c3)c12]
659
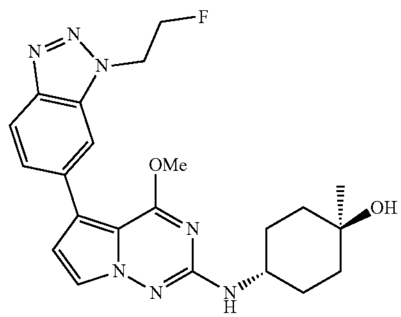 [SMILES: COc1nc(N[C@H]2CC[C@](C)(O)CC2)nn2ccc(-c3ccc4nnn(CCF)c4c3)c12]
660
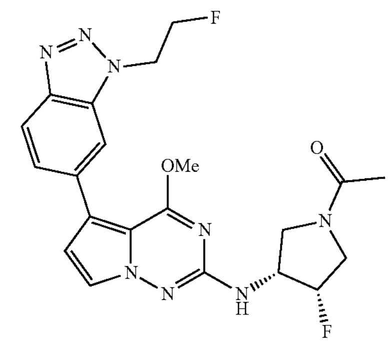 [SMILES: COc1nc(N[C@@H]2CN(C(C)=O)C[C@@H]2F)nn2ccc(-c3ccc4nnn(CCF)c4c3)c12]
661
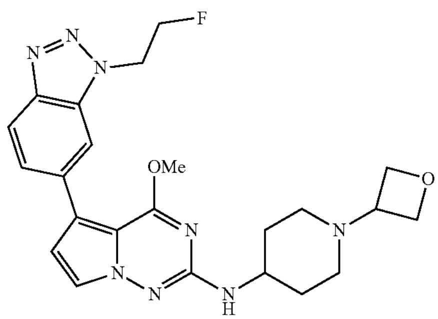 [SMILES: COc1nc(NC2CCN(C3COC3)CC2)nn2ccc(-c3ccc4nnn(CCF)c4c3)c12]
662
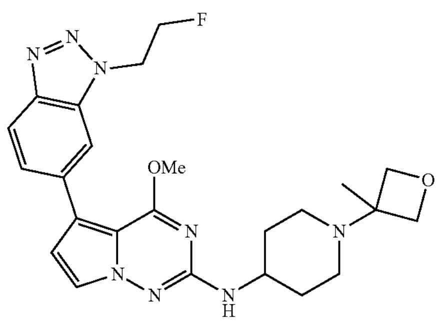 [SMILES: COc1nc(NC2CCN(C3(C)COC3)CC2)nn2ccc(-c3ccc4nnn(CCF)c4c3)c12]
TABLE 1-continued
663
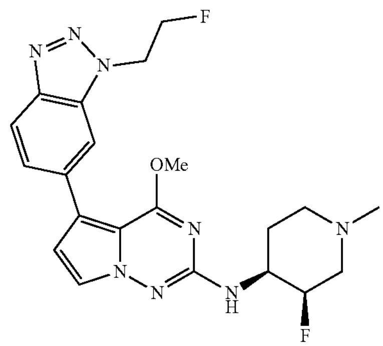 [SMILES: COc1nc(N[C@H]2CCN(C)C[C@H]2F)nn2ccc(-c3ccc4nnn(CCF)c4c3)c12]
664
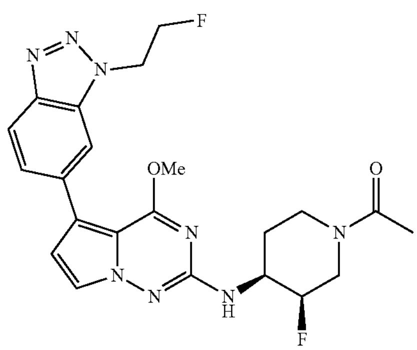 [SMILES: COc1nc(N[C@H]2CCN(C(C)=O)C[C@H]2F)nn2ccc(-c3ccc4nnn(CCF)c4c3)c12]
665
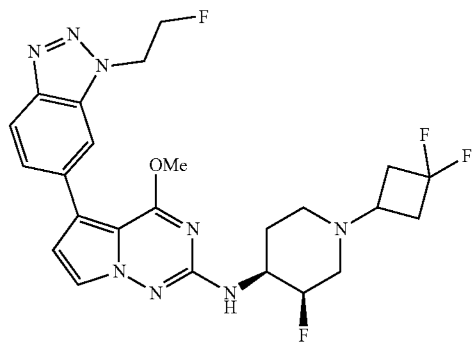 [SMILES: COc1nc(N[C@H]2CCN(C3CC(F)(F)C3)C[C@H]2F)nn2ccc(-c3ccc4nnn(CCF)c4c3)c12]
666
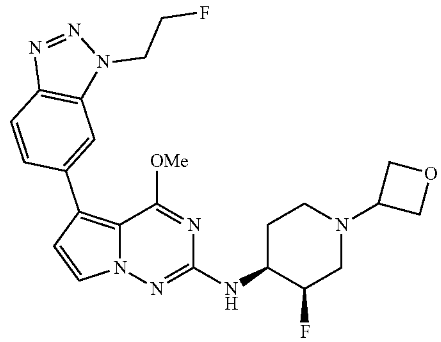 [SMILES: COc1nc(N[C@H]2CCN(C3COC3)C[C@H]2F)nn2ccc(-c3ccc4nnn(CCF)c4c3)c12]

TABLE 1-continued
667
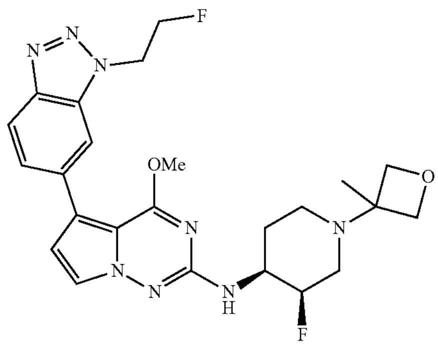 [SMILES: COc1nc(N[C@H]2CCN(C3(C)COC3)C[C@H]2F)nn2ccc(-c3ccc4nnn(CCF)c4c3)c12]
668
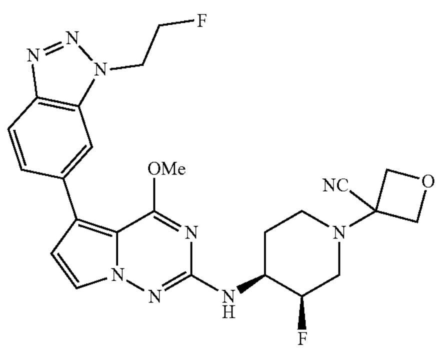 [SMILES: COc1nc(N[C@H]2CCN(C3(C#N)COC3)C[C@H]2F)nn2ccc(-c3ccc4nnn(CCF)c4c3)c12]
669
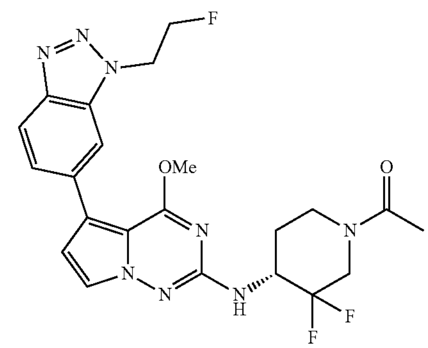 [SMILES: COc1nc(N[C@@H]2CCN(C(C)=O)CC2(F)F)nn2ccc(-c3ccc4nnn(CCF)c4c3)c12]
670
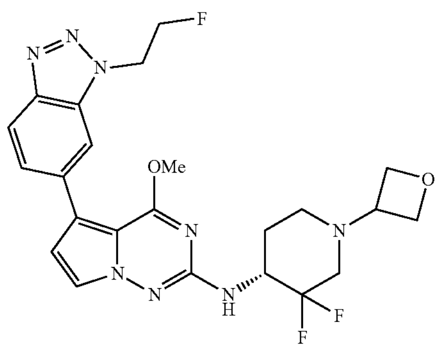 [SMILES: COc1nc(N[C@@H]2CCN(C3COC3)CC2(F)F)nn2ccc(-c3ccc4nnn(CCF)c4c3)c12]
TABLE 1-continued
671
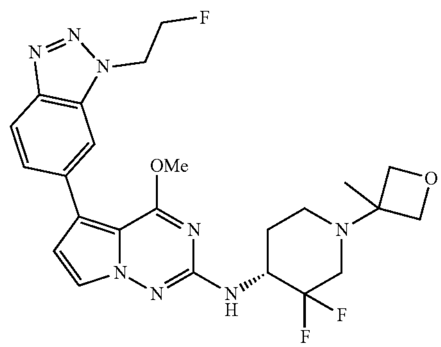 [SMILES: COc1nc(N[C@@H]2CCN(C3(C)COC3)CC2(F)F)nn2ccc(-c3ccc4nnn(CCF)c4c3)c12]
672
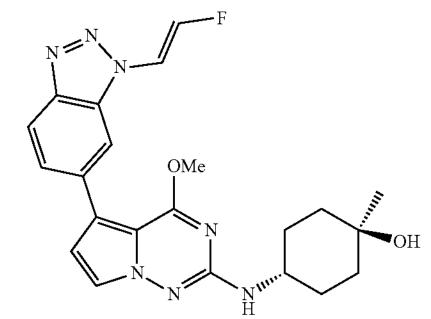 [SMILES: COc1nc(N[C@H]2CC[C@](C)(O)CC2)nn2ccc(-c3ccc4nnn(/C=C/F)c4c3)c12]
673
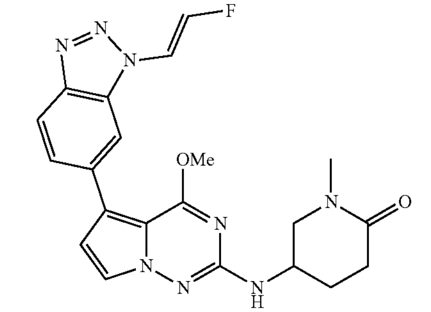 [SMILES: COc1nc(NC2CCC(=O)N(C)C2)nn2ccc(-c3ccc4nnn(/C=C/F)c4c3)c12]
674
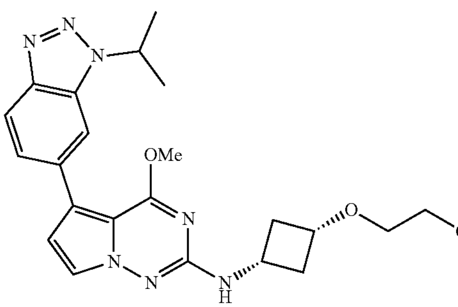
675
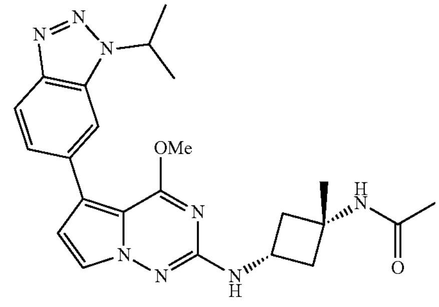 [SMILES: COc1nc(N[C@H]2C[C@@](C)(NC(C)=O)C2)nn2ccc(-c3ccc4nnn(C(C)C)c4c3)c12]

TABLE 1-continued
676
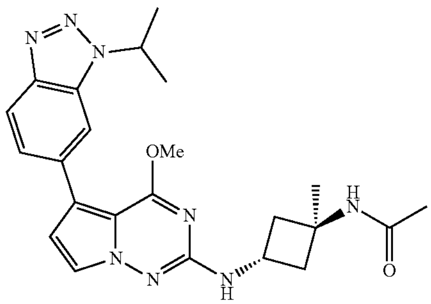 [SMILES: COc1nc(N[C@H]2C[C@](C)(NC(C)=O)C2)nn2ccc(-c3ccc4nnn(C(C)C)c4c3)c12]
677
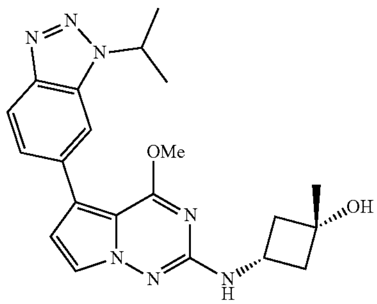 [SMILES: COc1nc(N[C@H]2C[C@@](C)(O)C2)nn2ccc(-c3ccc4nnn(C(C)C)c4c3)c12]
678
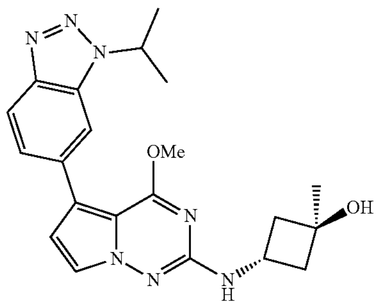 [SMILES: COc1nc(N[C@H]2C[C@](C)(O)C2)nn2ccc(-c3ccc4nnn(C(C)C)c4c3)c12]
679
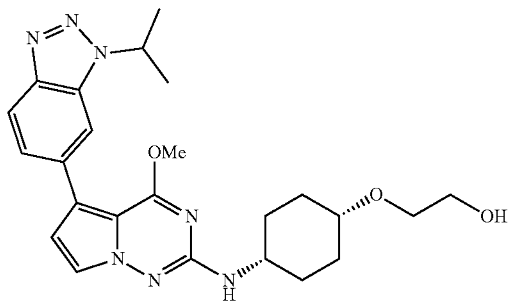 [SMILES: COc1nc(N[C@H]2CC[C@@H](OCCO)CC2)nn2ccc(-c3ccc4nnn(C(C)C)c4c3)c12]
680
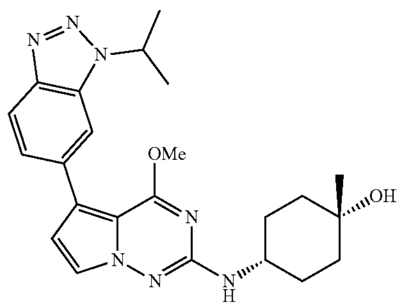 [SMILES: COc1nc(N[C@H]2CC[C@@](C)(O)CC2)nn2ccc(-c3ccc4nnn(C(C)C)c4c3)c12]
TABLE 1-continued
681
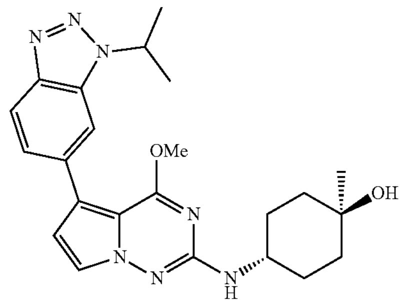 [SMILES: COc1nc(N[C@H]2CC[C@](C)(O)CC2)nn2ccc(-c3ccc4nnn(C(C)C)c4c3)c12]
682
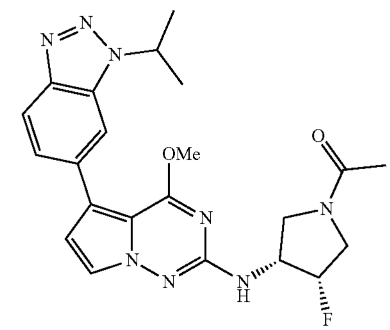 [SMILES: COc1nc(N[C@@H]2CN(C(C)=O)C[C@@H]2F)nn2ccc(-c3ccc4nnn(C(C)C)c4c3)c12]
683
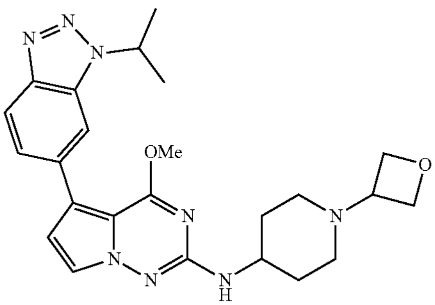 [SMILES: COc1nc(NC2CCN(C3COC3)CC2)nn2ccc(-c3ccc4nnn(C(C)C)c4c3)c12]
684
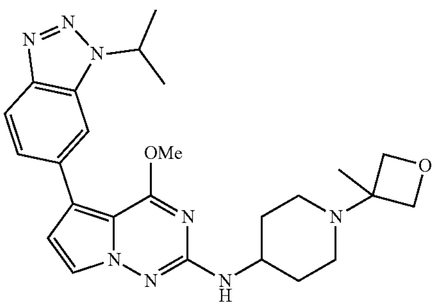 [SMILES: COc1nc(NC2CCN(C3(C)COC3)CC2)nn2ccc(-c3ccc4nnn(C(C)C)c4c3)c12]
685
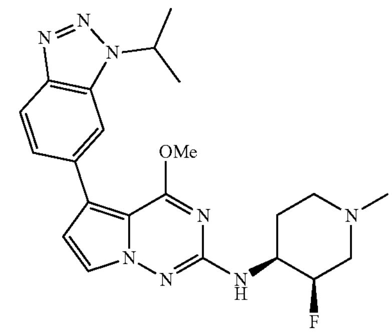 [SMILES: COc1nc(N[C@H]2CCN(C)C[C@H]2F)nn2ccc(-c3ccc4nnn(C(C)C)c4c3)c12]

686
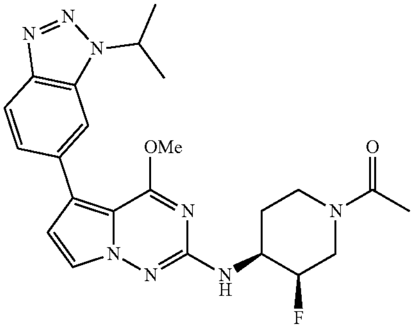 [SMILES: COc1nc(N[C@H]2CCN(C(C)=O)C[C@H]2F)nn2ccc(-c3ccc4nnn(C(C)C)c4c3)c12]
687
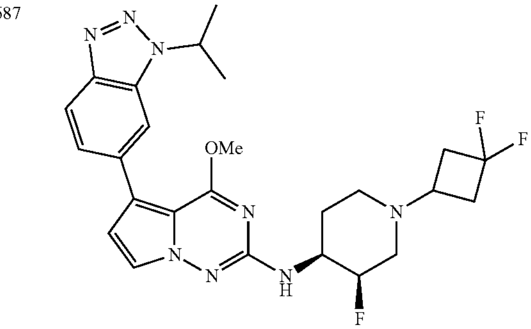
688
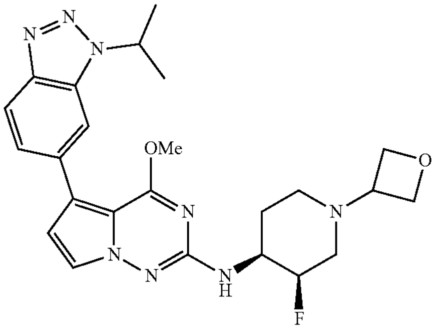 [SMILES: COc1nc(N[C@H]2CCN(C3COC3)C[C@H]2F)nn2ccc(-c3ccc4nnn(C(C)C)c4c3)c12]
689
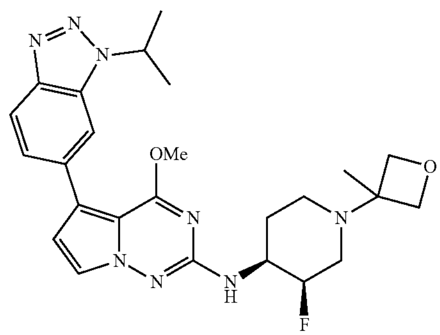 [SMILES: COc1nc(N[C@H]2CCN(C3(C)COC3)C[C@H]2F)nn2ccc(-c3ccc4nnn(C(C)C)c4c3)c12]
690
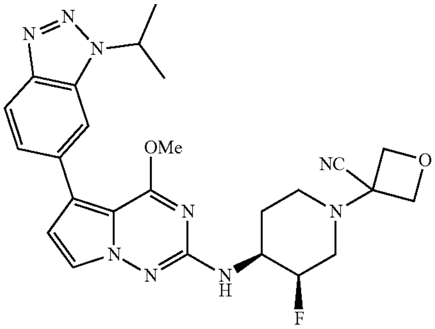 [SMILES: COc1nc(N[C@H]2CCN(C3(C#N)COC3)C[C@H]2F)nn2ccc(-c3ccc4nnn(C(C)C)c4c3)c12]
691
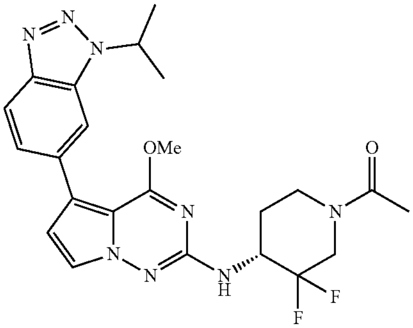 [SMILES: COc1nc(N[C@@H]2CCN(C(C)=O)CC2(F)F)nn2ccc(-c3ccc4nnn(C(C)C)c4c3)c12]
692
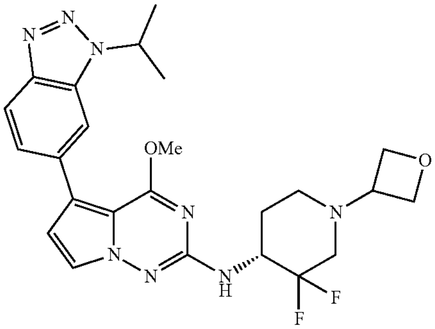 [SMILES: COc1nc(N[C@@H]2CCN(C3COC3)CC2(F)F)nn2ccc(-c3ccc4nnn(C(C)C)c4c3)c12]
693
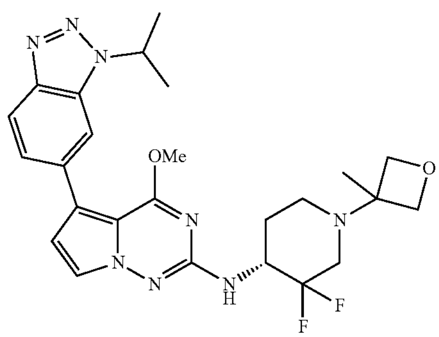 [SMILES: COc1nc(N[C@@H]2CCN(C3(C)COC3)CC2(F)F)nn2ccc(-c3ccc4nnn(C(C)C)c4c3)c12]

694
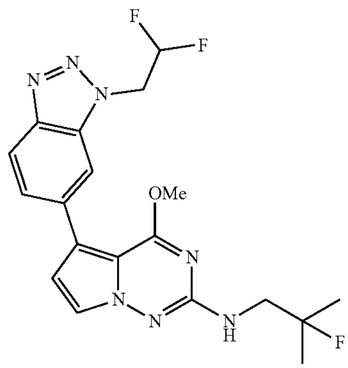 [SMILES: COc1nc(NCC(C)(C)F)nn2ccc(-c3ccc4nnn(CC(F)F)c4c3)c12]
695
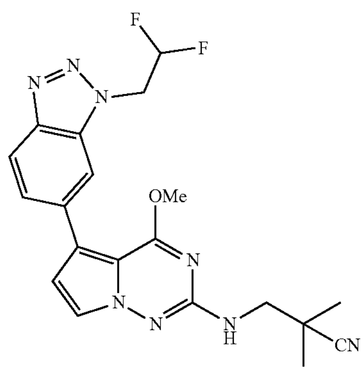
696
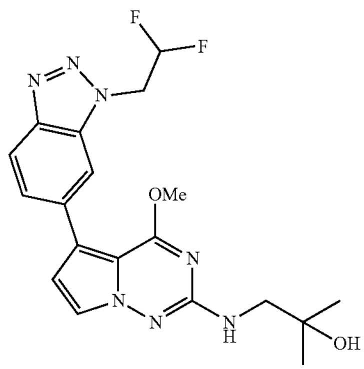 [SMILES: COc1nc(NCC(C)(C)O)nn2ccc(-c3ccc4nnn(CC(F)F)c4c3)c12]
697
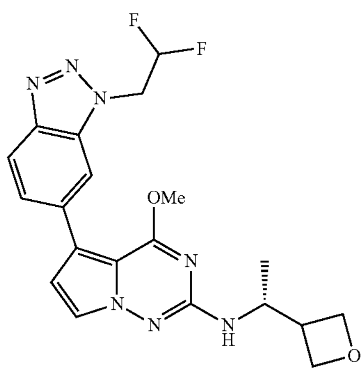 [SMILES: COc1nc(N[C@H](C)C2COC2)nn2ccc(-c3ccc4nnn(CC(F)F)c4c3)c12]
698
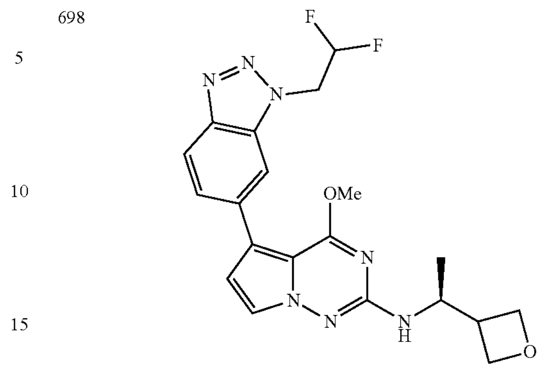
699
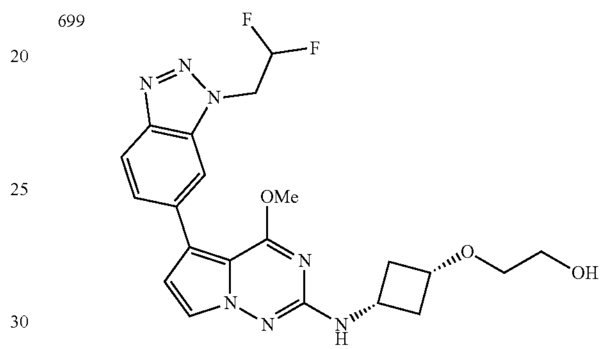
700
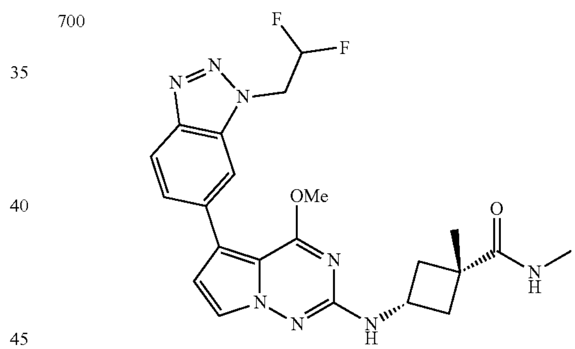
701
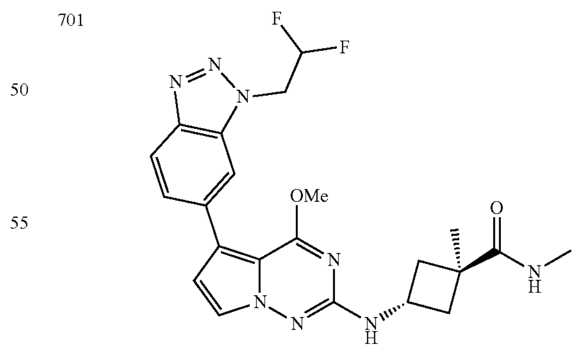

TABLE 1-continued
702
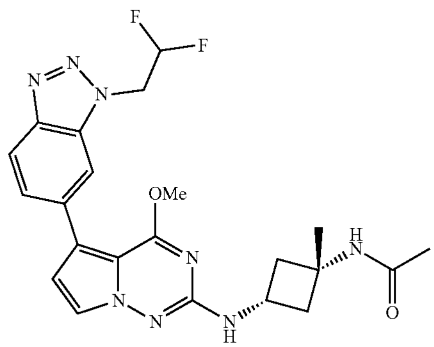 [SMILES: COc1nc(N[C@H]2C[C@@](C)(NC(C)=O)C2)nn2ccc(-c3ccc4nnn(CC(F)F)c4c3)c12]
703
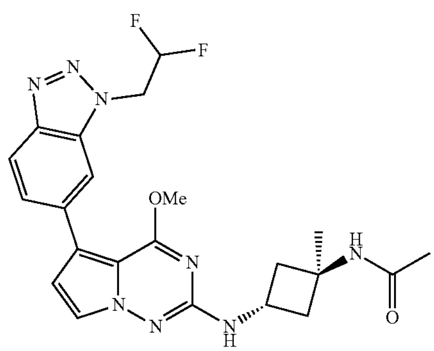 [SMILES: COc1nc(N[C@H]2C[C@](C)(NC(C)=O)C2)nn2ccc(-c3ccc4nnn(CC(F)F)c4c3)c12]
704
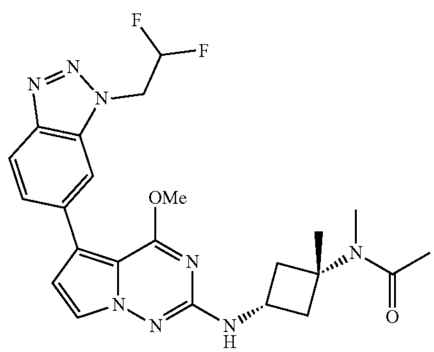
705
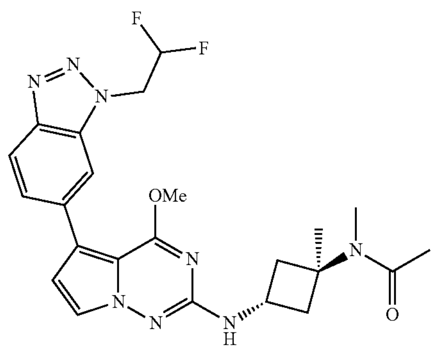
TABLE 1-continued
706
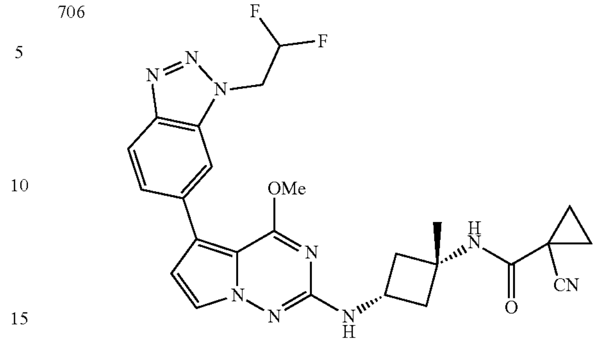
707
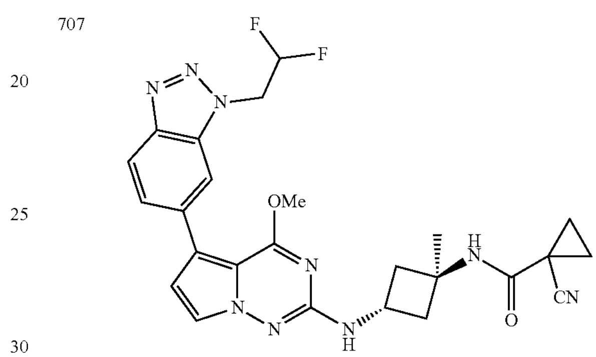
708
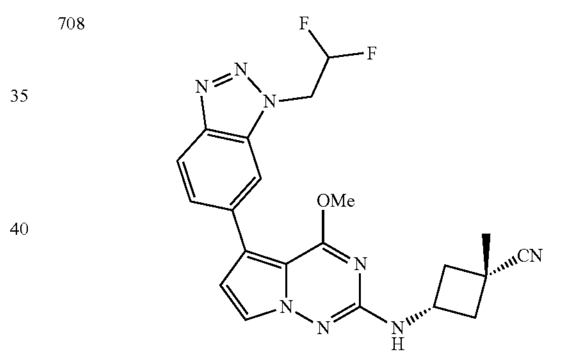
709
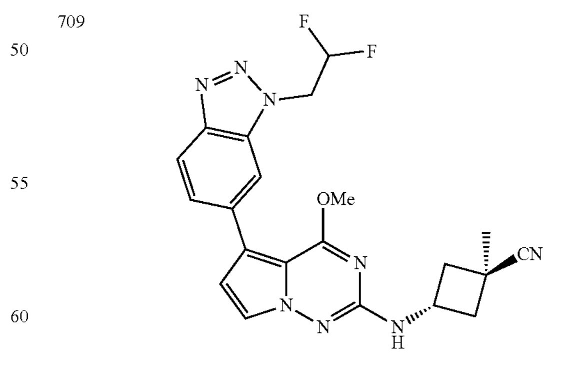

710
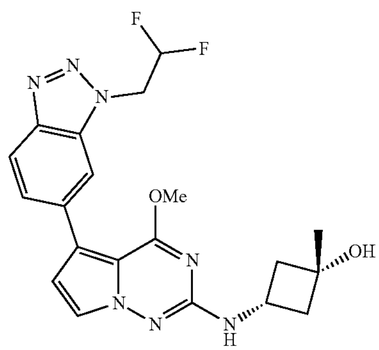
711
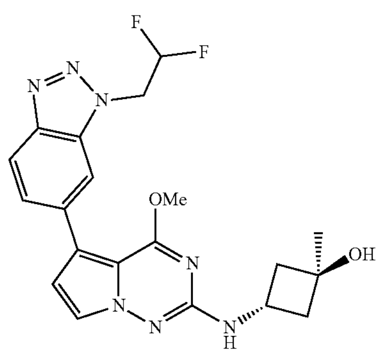
712
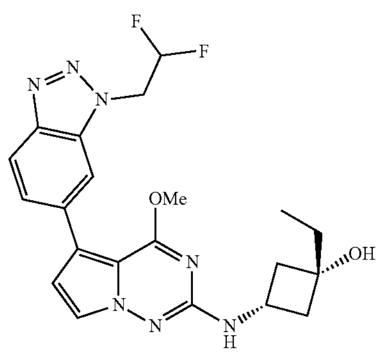
713
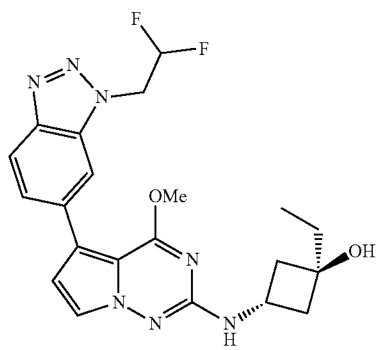
714
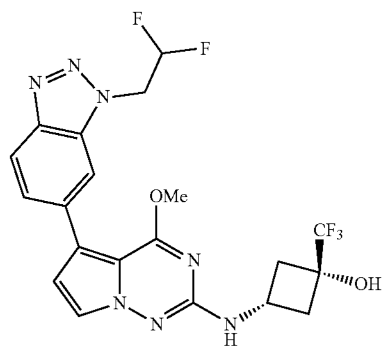
715
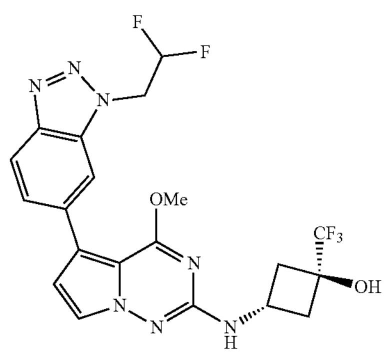
716
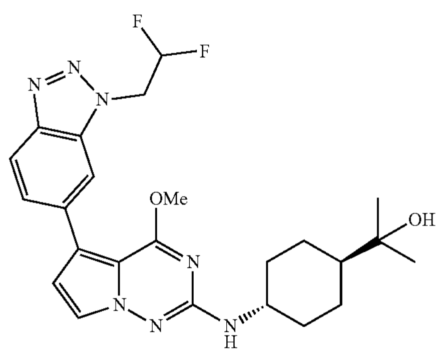
717
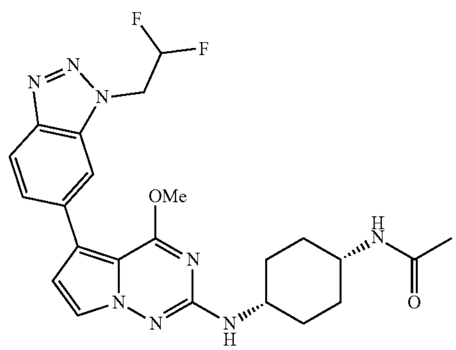

TABLE 1-continued
718
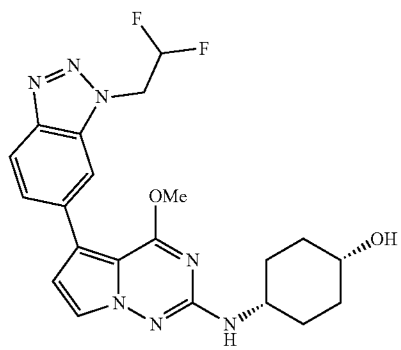
719
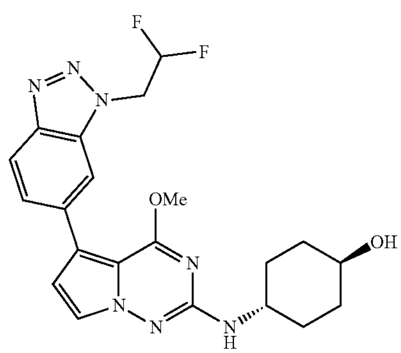
720
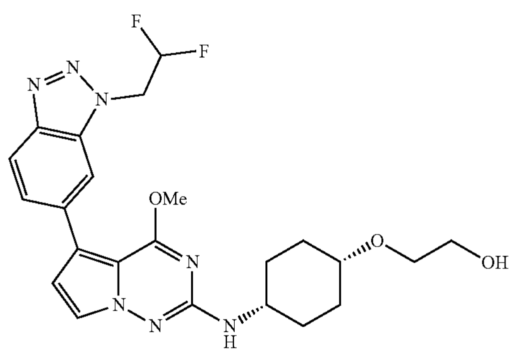
721
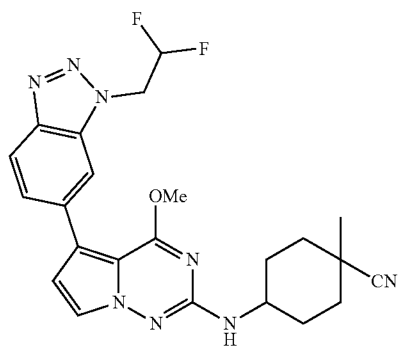
TABLE 1-continued
722
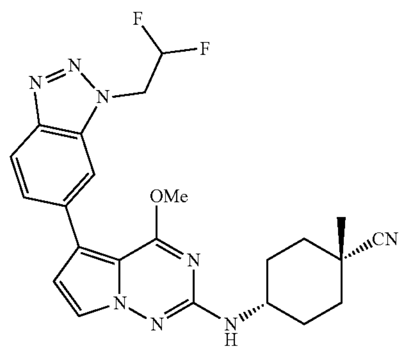
723
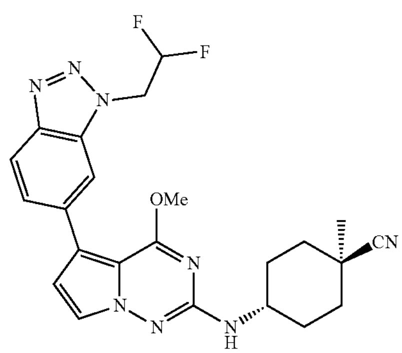
724
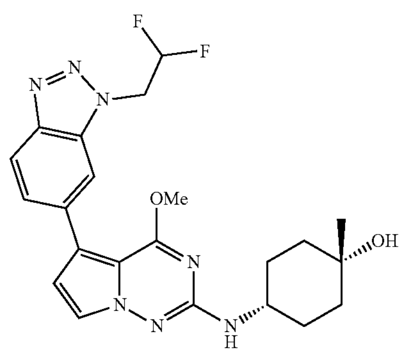
725
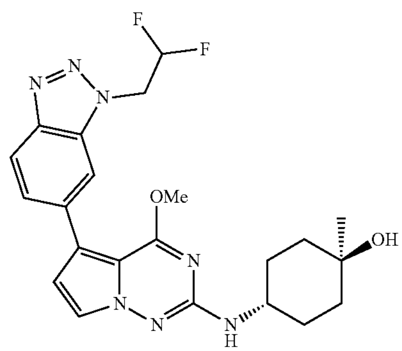

TABLE 1-continued
726
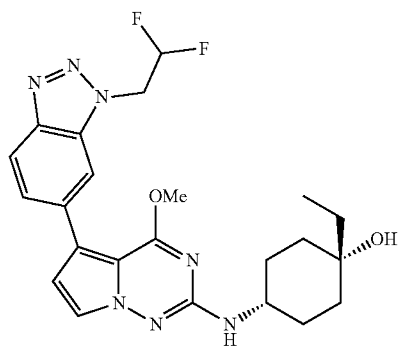
727
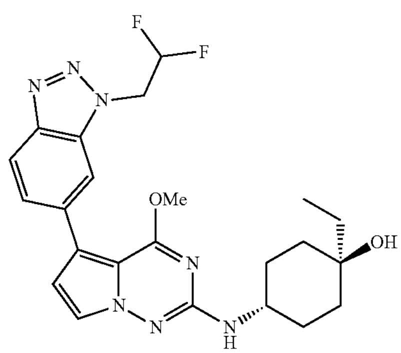
728
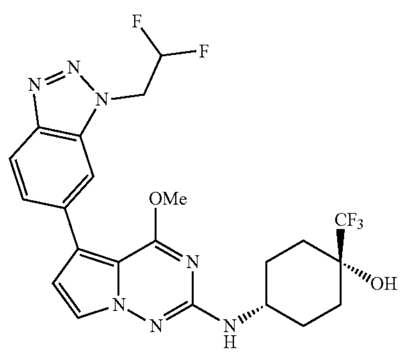
729
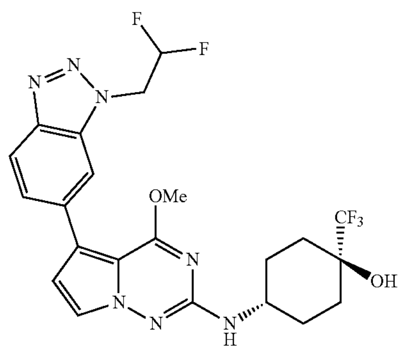
TABLE 1-continued
730
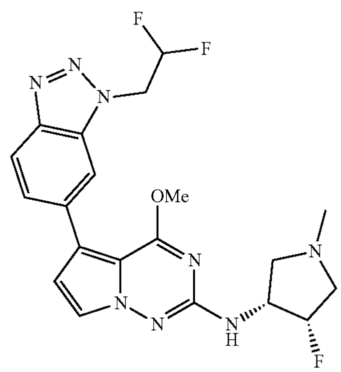
731
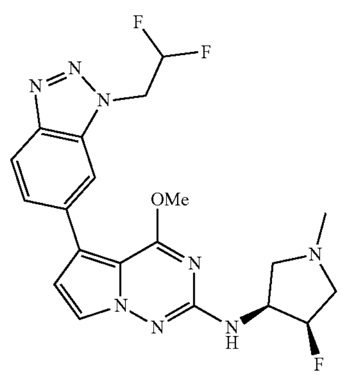
732
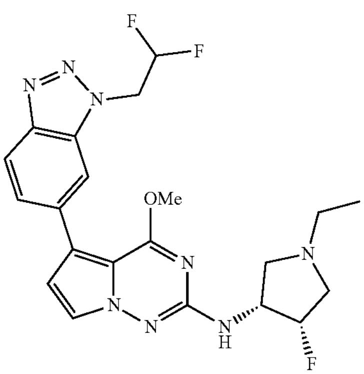
733
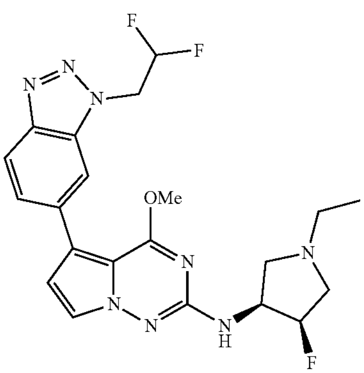

734
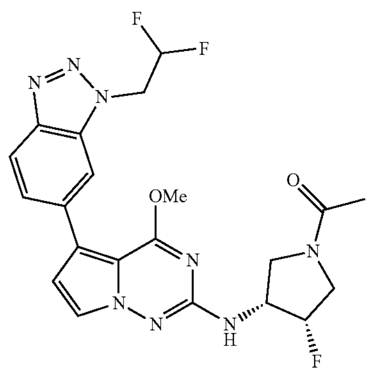
735
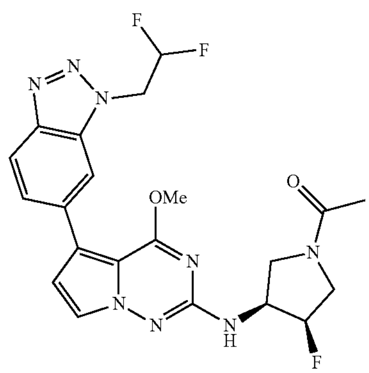
736
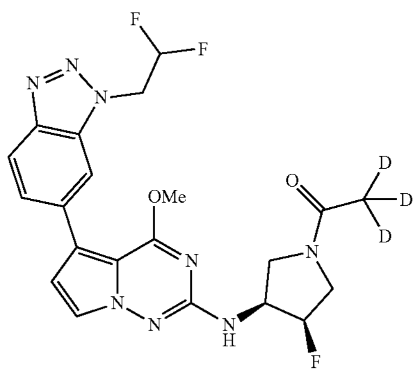
737
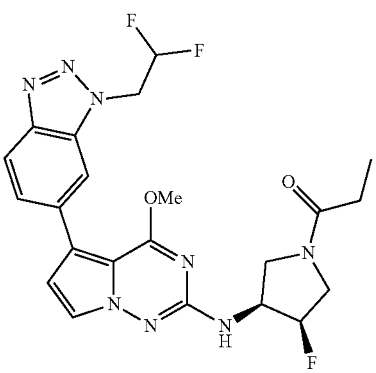
738
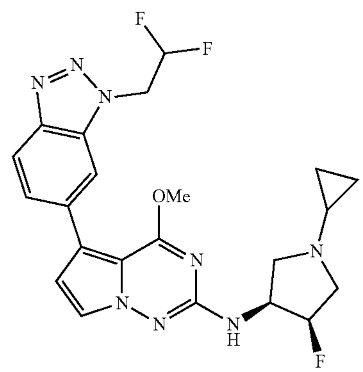
739
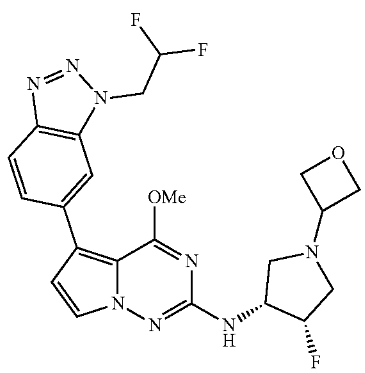
740
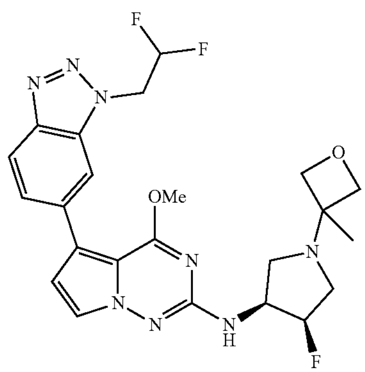
741
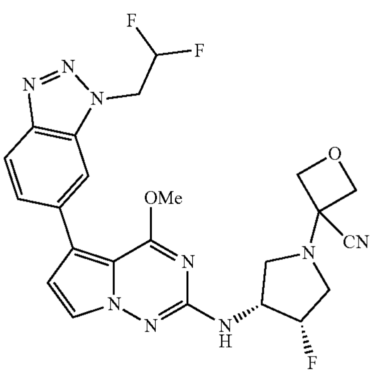

TABLE 1-continued
742
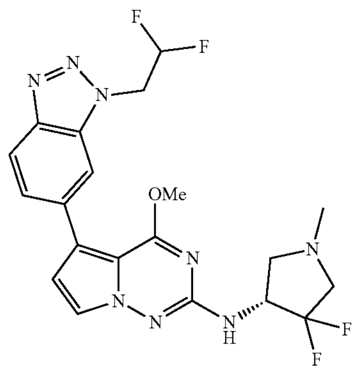
743
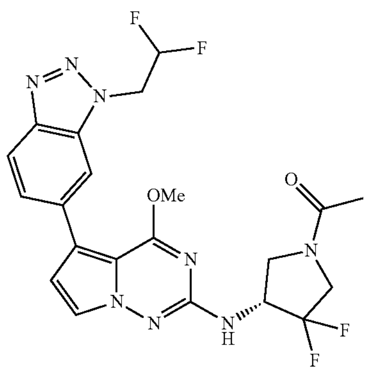
744
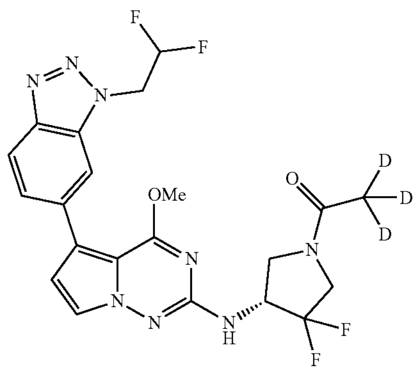
745
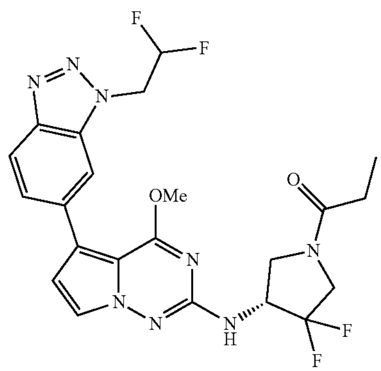
TABLE 1-continued
746
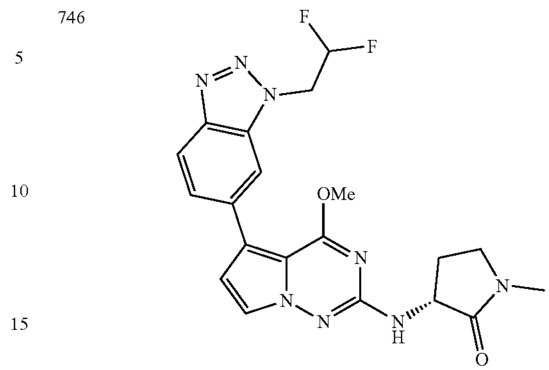
747
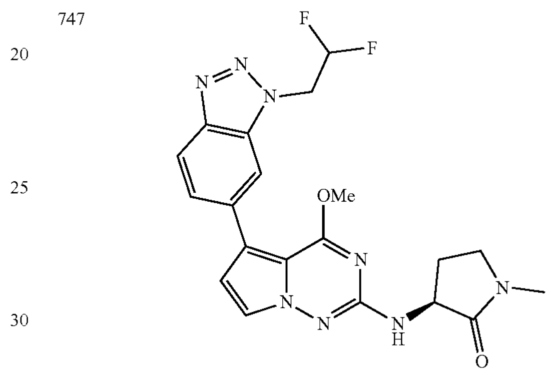
748
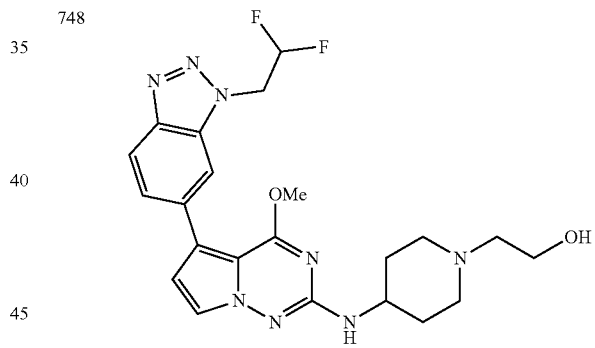
749
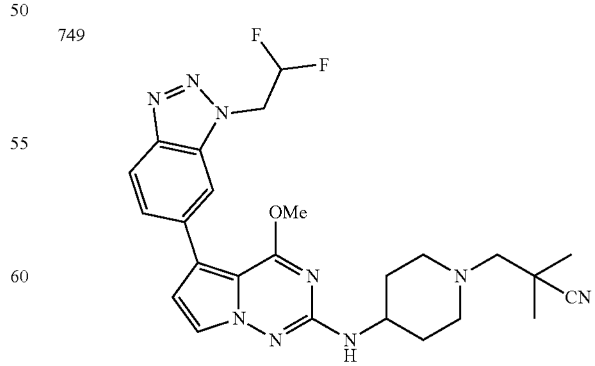

750
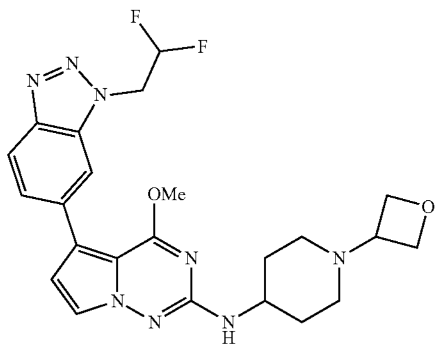
751
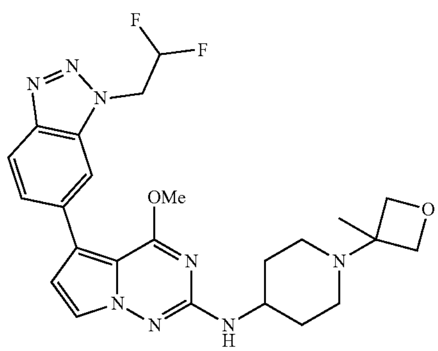
752
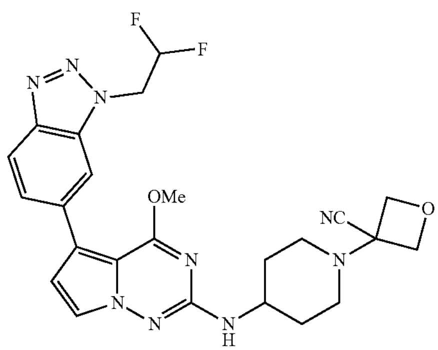
753
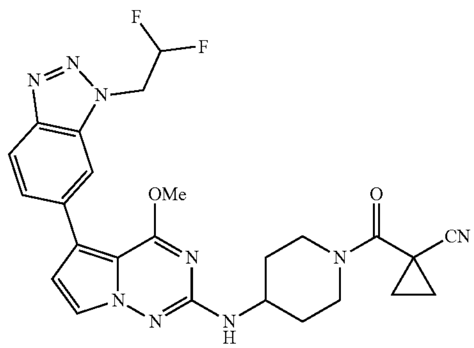
754
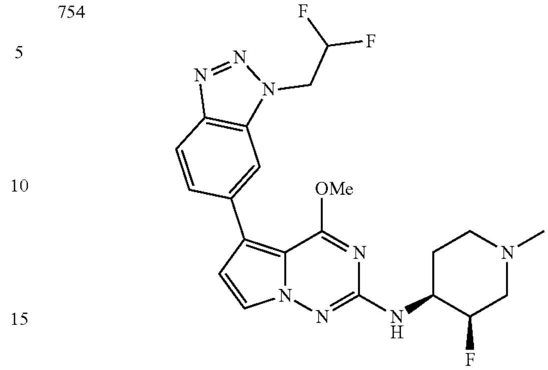
755
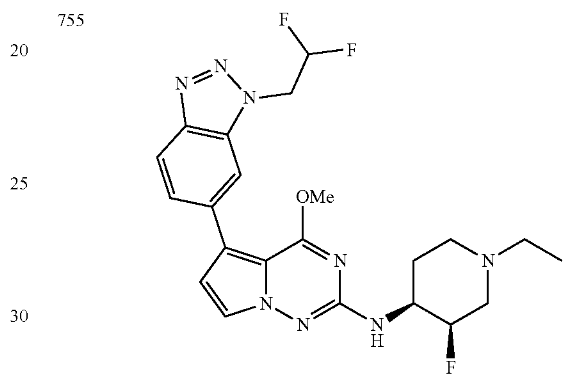
756
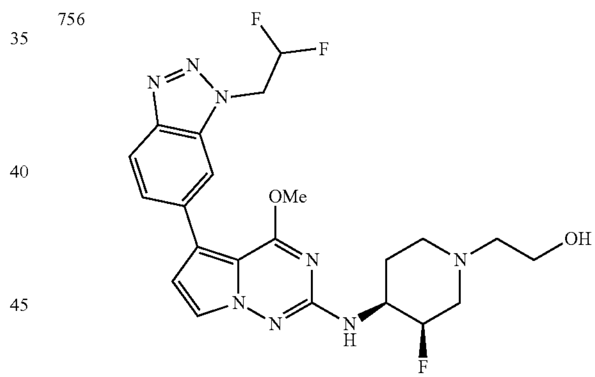
757
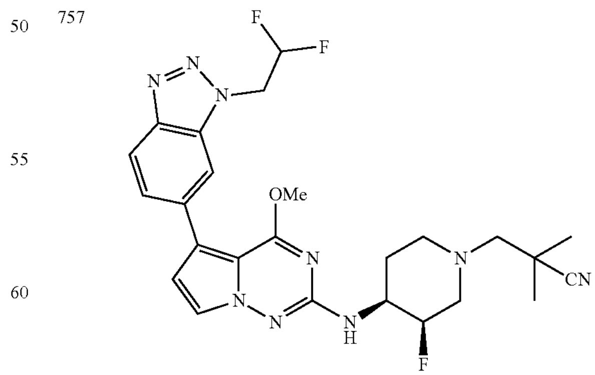

758
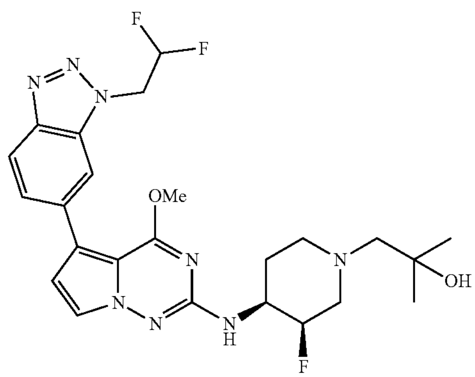
759
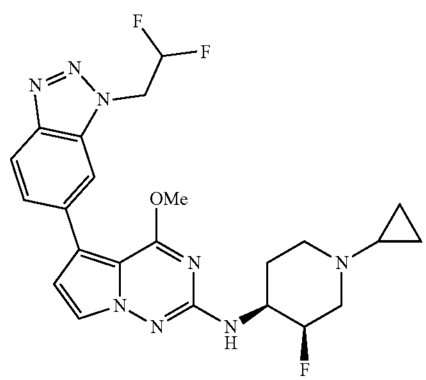
760
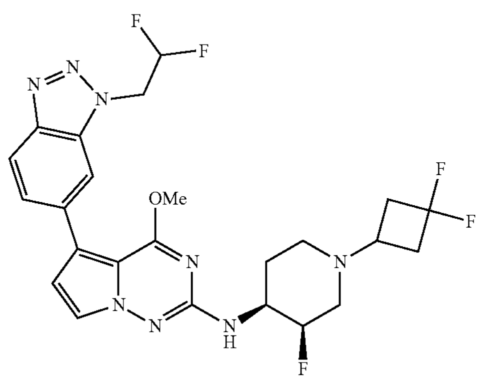
761
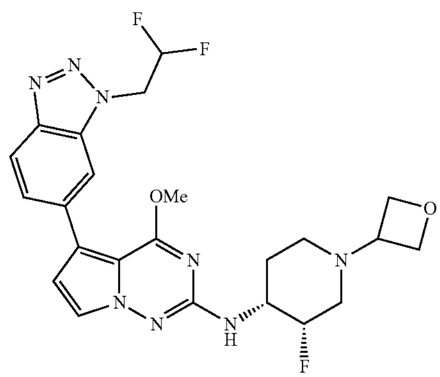
762
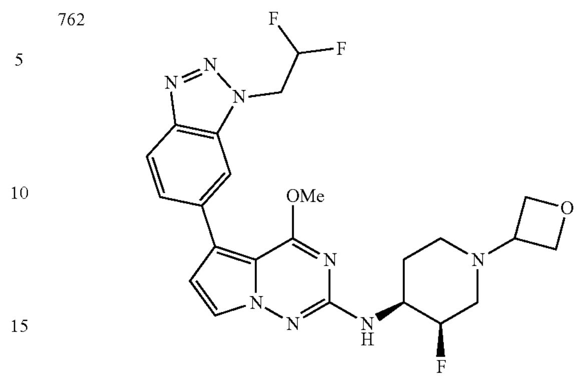
763
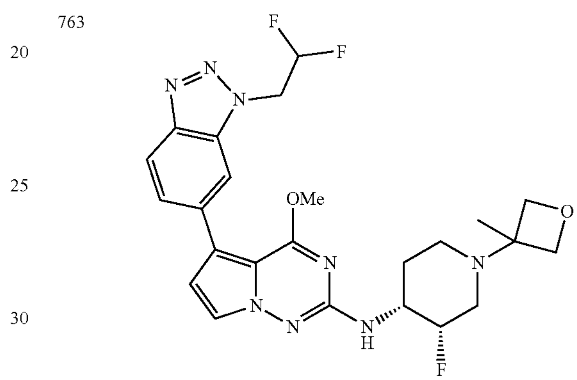
764
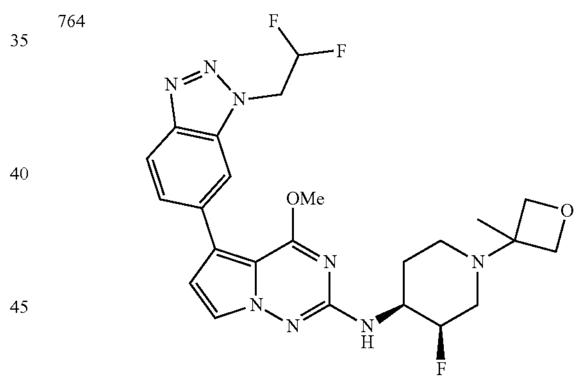
765
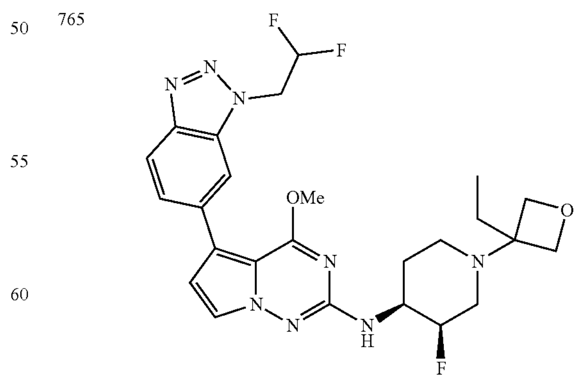

766
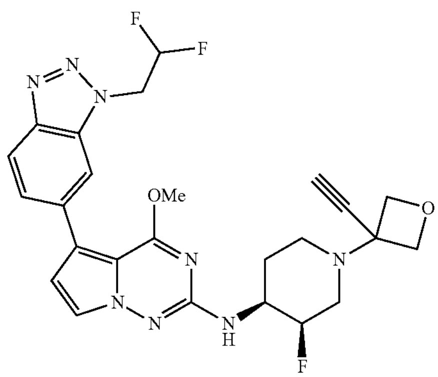
767
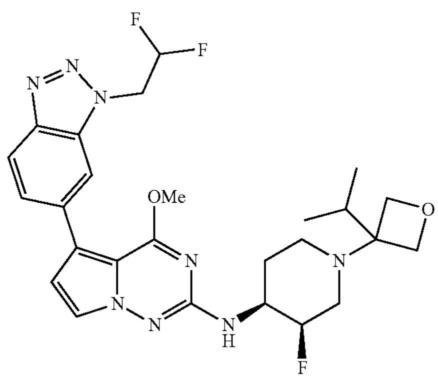
768
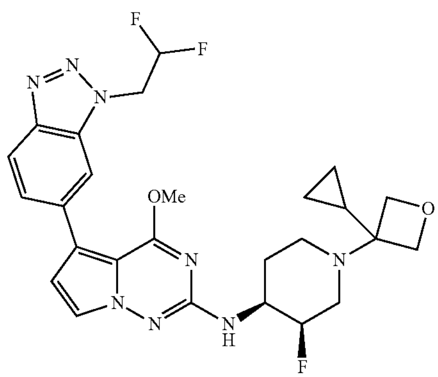
769
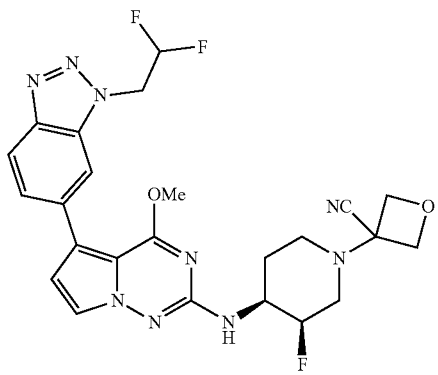
770
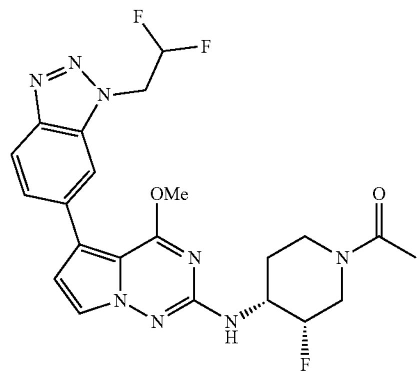
771
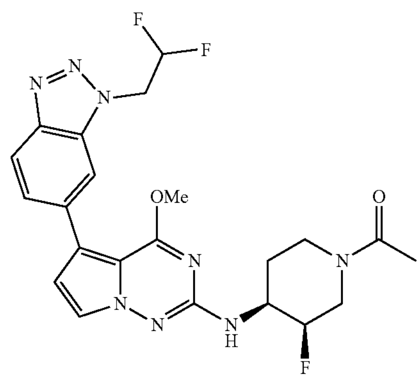
772
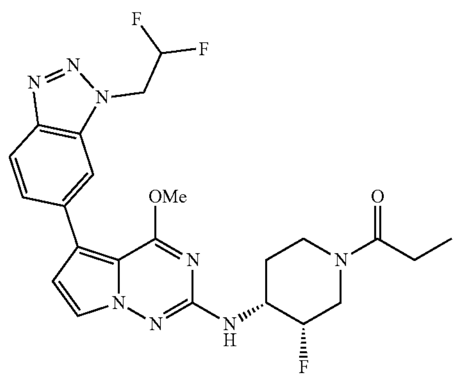
773
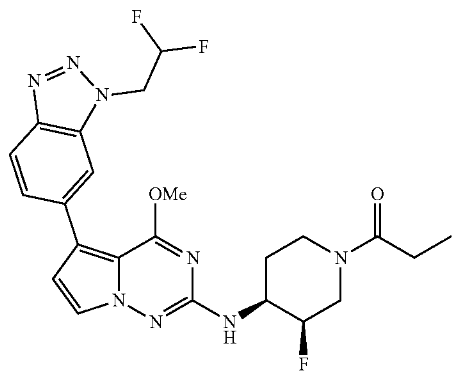

TABLE 1-continued
774
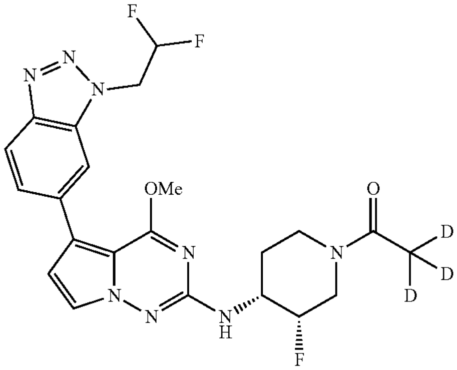
775
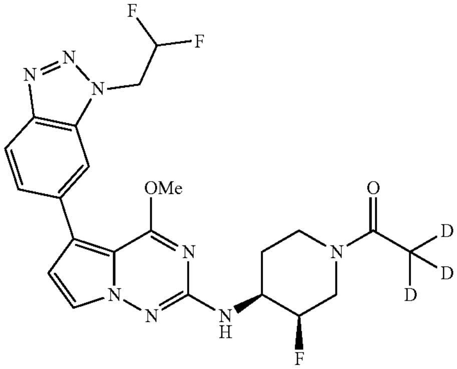
776
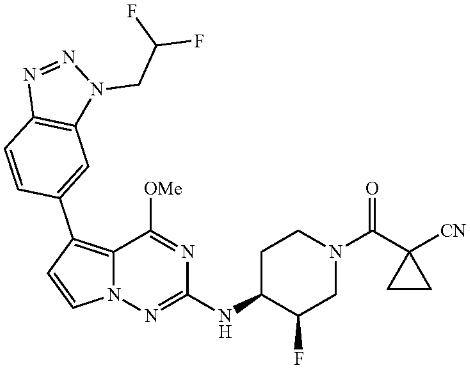
777
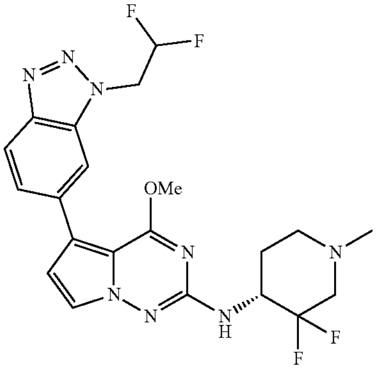
TABLE 1-continued
778
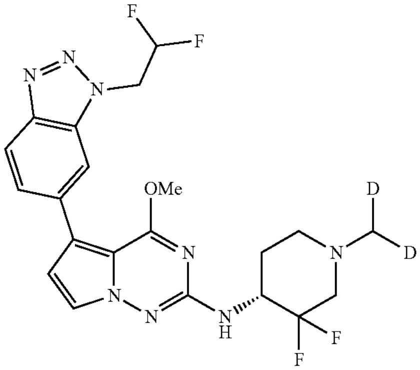
779
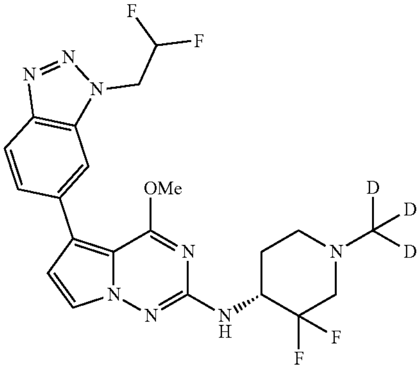 [SMILES: [2H]C([2H])([2H])N1CC[C@@H](Nc2nc(OC)c3c(-c4ccc5nnn(CC(F)F)c5c4)ccn3n2)C(F)(F)C1]
780
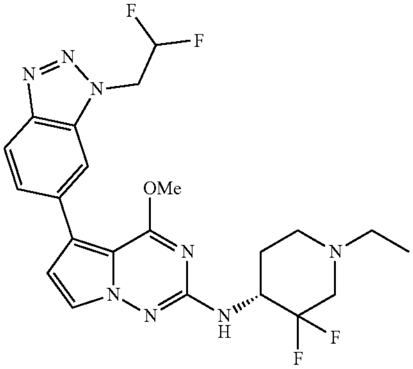 [SMILES: CCN1CC[C@@H](Nc2nc(OC)c3c(-c4ccc5nnn(CC(F)F)c5c4)ccn3n2)C(F)(F)C1]
781
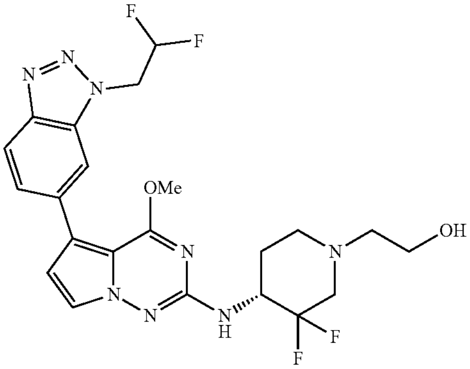 [SMILES: COc1nc(N[C@@H]2CCN(CCO)CC2(F)F)nn2ccc(-c3ccc4nnn(CC(F)F)c4c3)c12]

TABLE 1-continued
782
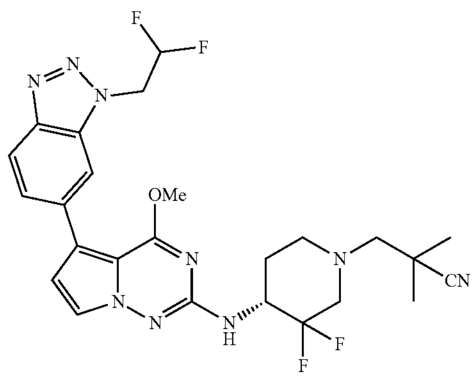
783
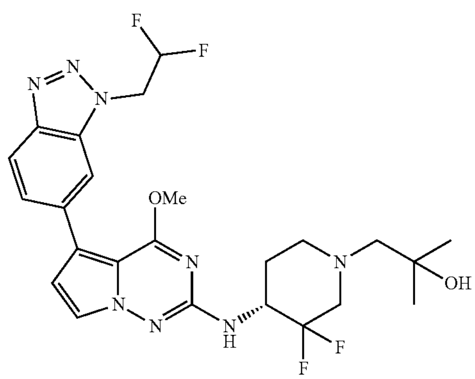 [SMILES: COc1nc(N[C@@H]2CCN(CC(C)(C)C#N)CC2(F)F)nn2ccc(-c3ccc4nnn(CC(F)F)c4c3)c12]
784
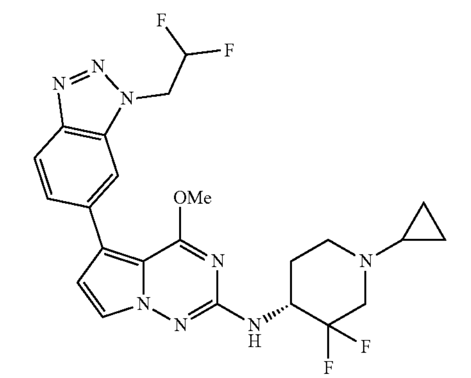 [SMILES: COc1nc(N[C@@H]2CCN(C3CC3)CC2(F)F)nn2ccc(-c3ccc4nnn(CC(F)F)c4c3)c12]
785
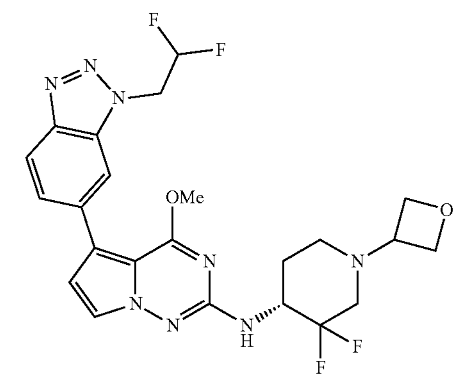 [SMILES: COc1nc(N[C@@H]2CCN(C3COC3)CC2(F)F)nn2ccc(-c3ccc4nnn(CC(F)F)c4c3)c12]
TABLE 1-continued
786
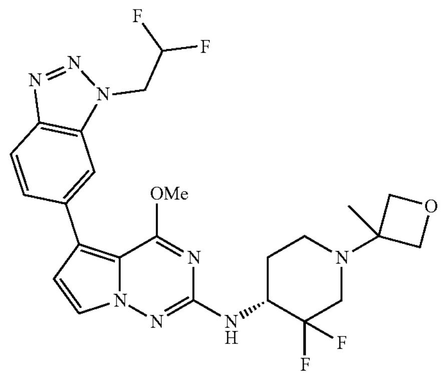 [SMILES: COc1nc(N[C@@H]2CCN(C3(C)COC3)CC2(F)F)nn2ccc(-c3ccc4nnn(CC(F)F)c4c3)c12]
787
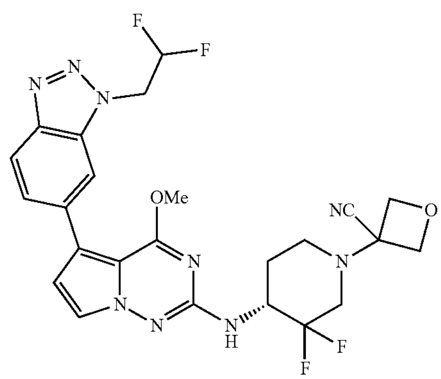 [SMILES: COc1nc(N[C@@H]2CCN(C3(C#N)COC3)CC2(F)F)nn2ccc(-c3ccc4nnn(CC(F)F)c4c3)c12]
788
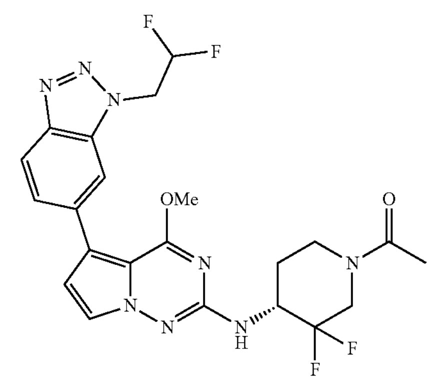 [SMILES: COc1nc(N[C@@H]2CCN(C(C)=O)CC2(F)F)nn2ccc(-c3ccc4nnn(CC(F)F)c4c3)c12]
789
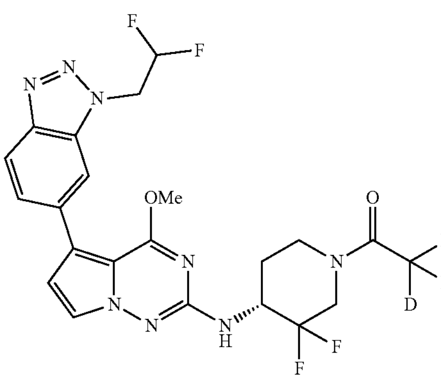

TABLE 1-continued
790
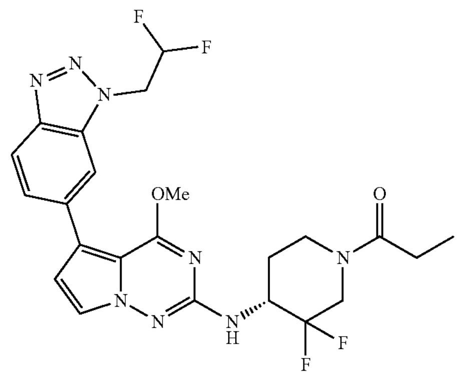 [SMILES: CCC(=O)N1CC[C@@H](Nc2nc(OC)c3c(-c4ccc5nnn(CC(F)F)c5c4)ccn3n2)C(F)(F)C1]
791
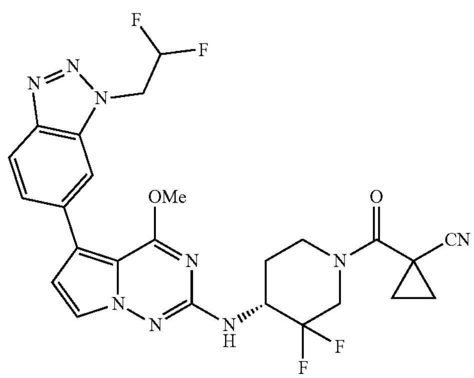 [SMILES: COc1nc(N[C@@H]2CCN(C(=O)C3(C#N)CC3)CC2(F)F)nn2ccc(-c3ccc4nnn(CC(F)F)c4c3)c12]
792
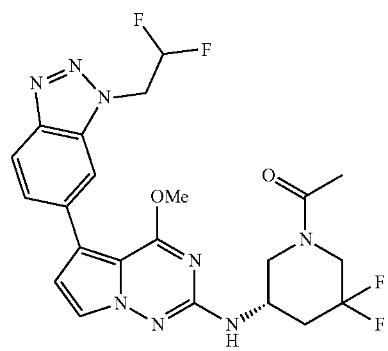 [SMILES: COc1nc(N[C@@H]2CN(C(C)=O)CC(F)(F)C2)nn2ccc(-c3ccc4nnn(CC(F)F)c4c3)c12]
793
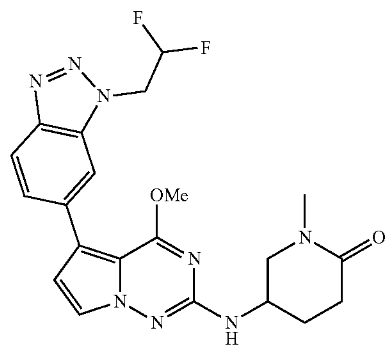 [SMILES: COc1nc(NC2CCC(=O)N(C)C2)nn2ccc(-c3ccc4nnn(CC(F)F)c4c3)c12]
TABLE 1-continued
794
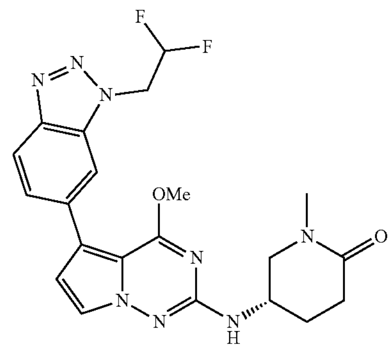
795
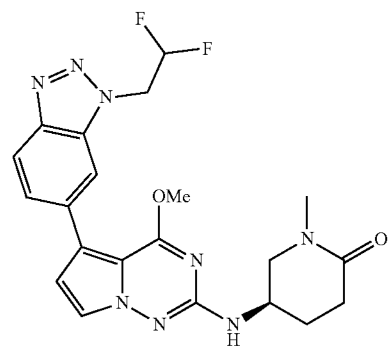 [SMILES: COc1nc(N[C@@H]2CCC(=O)N(C)C2)nn2ccc(-c3ccc4nnn(CC(F)F)c4c3)c12]
796
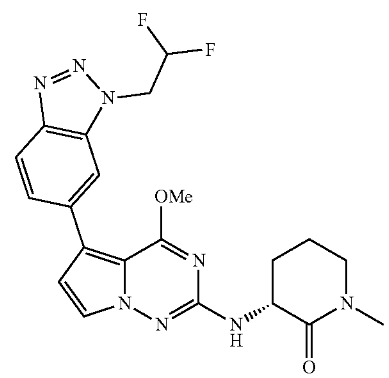 [SMILES: COc1nc(N[C@@H]2CCCN(C)C2=O)nn2ccc(-c3ccc4nnn(CC(F)F)c4c3)c12]
797
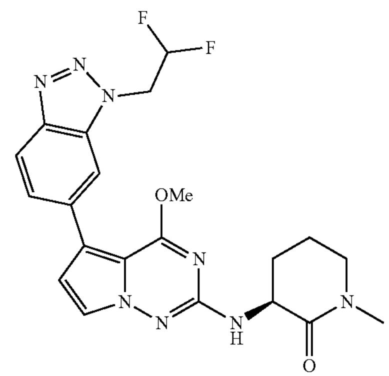 [SMILES: COc1nc(N[C@H]2CCCN(C)C2=O)nn2ccc(-c3ccc4nnn(CC(F)F)c4c3)c12]

798
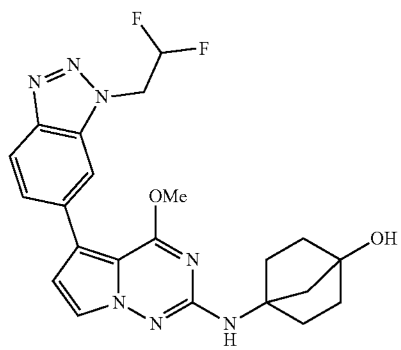 [SMILES: COc1nc(NC23CCC(O)(CC2)C3)nn2ccc(-c3ccc4nnn(CC(F)F)c4c3)c12]
799
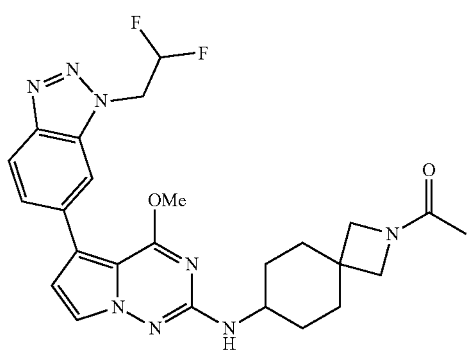 [SMILES: COc1nc(NC2CCC3(CC2)CN(C(C)=O)C3)nn2ccc(-c3ccc4nnn(CC(F)F)c4c3)c12]
800
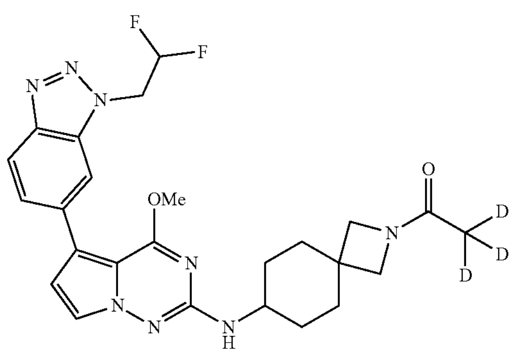 [SMILES: [2H]C([2H])([2H])C(=O)N1CC2(CCC(Nc3nc(OC)c4c(-c5ccc6nnn(CC(F)F)c6c5)ccn4n3)CC2)C1]
801
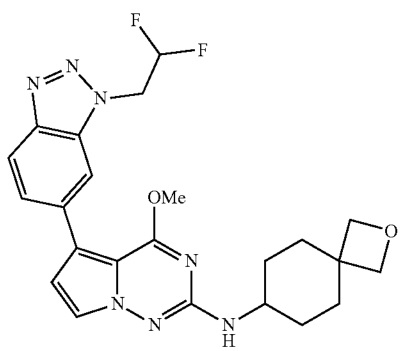 [SMILES: COc1nc(NC2CCC3(CC2)COC3)nn2ccc(-c3ccc4nnn(CC(F)F)c4c3)c12]
802
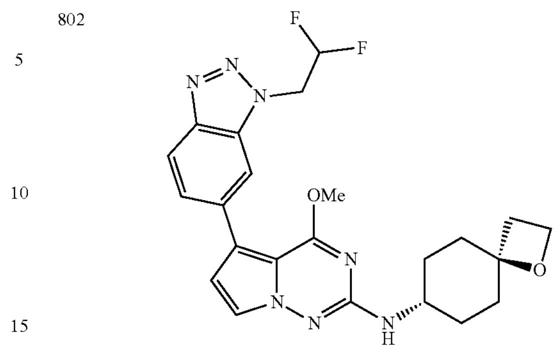
803
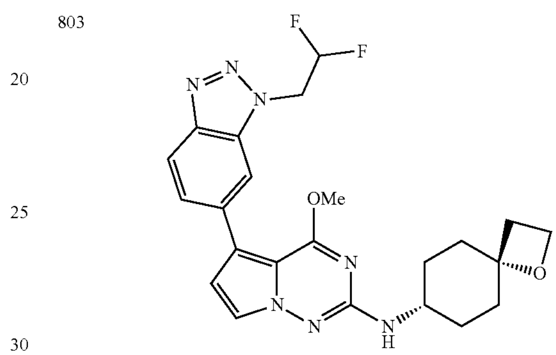
804
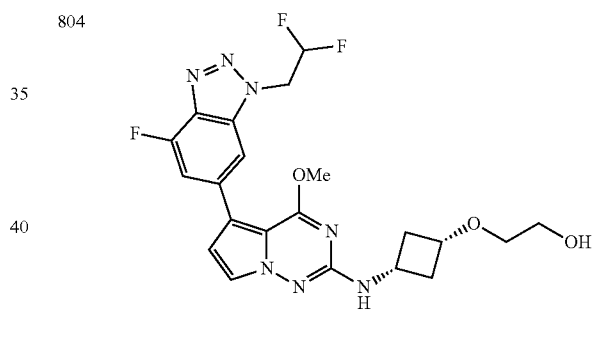
805
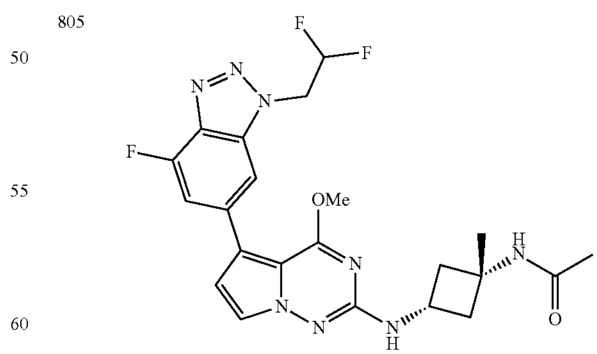

TABLE 1-continued
806
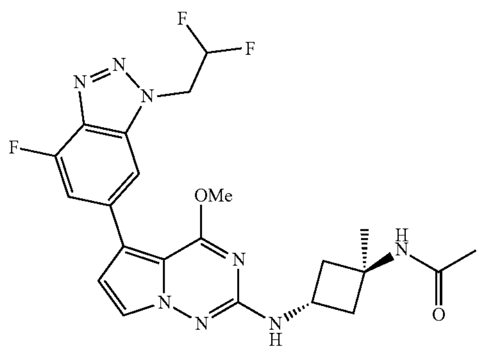 [SMILES: COc1nc(N[C@H]2C[C@](C)(NC(C)=O)C2)nn2ccc(-c3cc(F)c4nnn(CC(F)F)c4c3)c12]
807
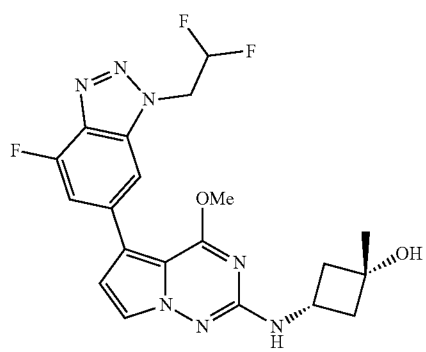 [SMILES: COc1nc(N[C@H]2C[C@@](C)(O)C2)nn2ccc(-c3cc(F)c4nnn(CC(F)F)c4c3)c12]
808
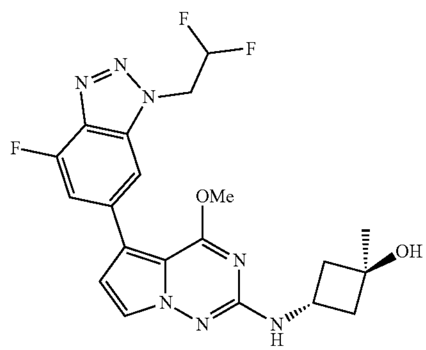 [SMILES: COc1nc(N[C@H]2C[C@](C)(O)C2)nn2ccc(-c3cc(F)c4nnn(CC(F)F)c4c3)c12]
809
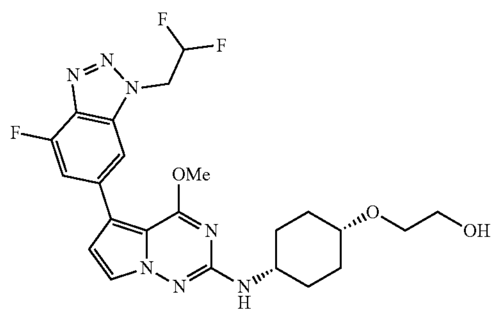 [SMILES: COc1nc(N[C@H]2CC[C@@H](OCCO)CC2)nn2ccc(-c3cc(F)c4nnn(CC(F)F)c4c3)c12]
TABLE 1-continued
810
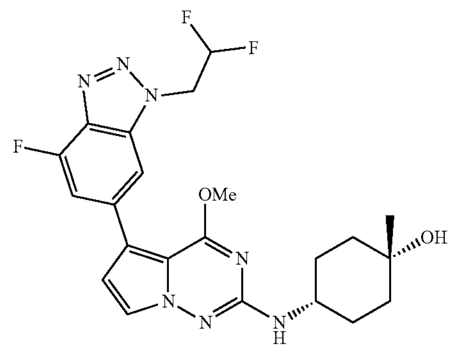 [SMILES: COc1nc(N[C@H]2CC[C@@](C)(O)CC2)nn2ccc(-c3cc(F)c4nnn(CC(F)F)c4c3)c12]
811
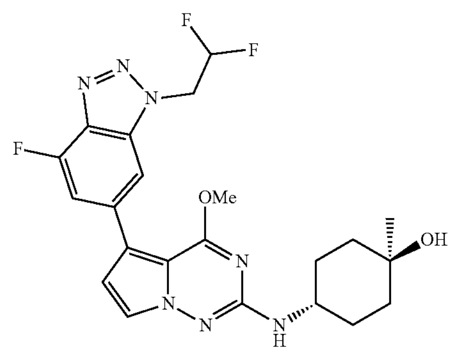 [SMILES: COc1nc(N[C@H]2CC[C@](C)(O)CC2)nn2ccc(-c3cc(F)c4nnn(CC(F)F)c4c3)c12]
812
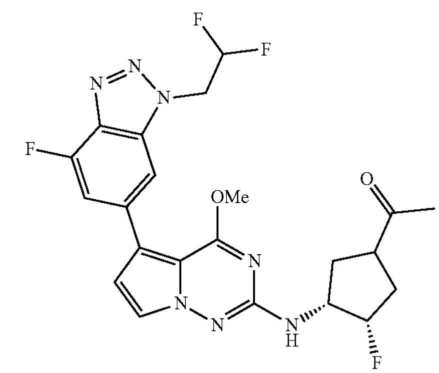 [SMILES: COc1nc(N[C@@H]2CC(C(C)=O)C[C@@H]2F)nn2ccc(-c3cc(F)c4nnn(CC(F)F)c4c3)c12]
813
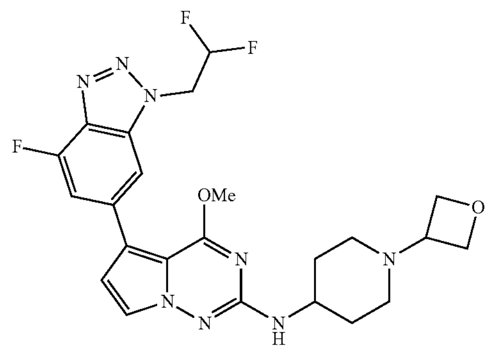 [SMILES: COc1nc(NC2CCN(C3COC3)CC2)nn2ccc(-c3cc(F)c4nnn(CC(F)F)c4c3)c12]

TABLE 1-continued
814
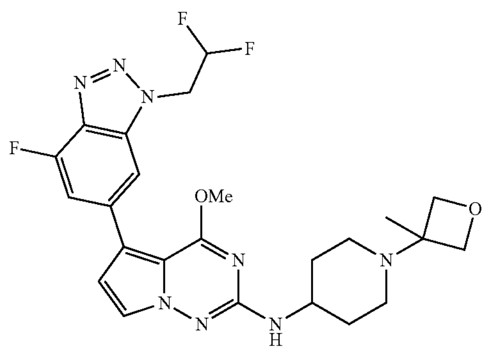 [SMILES: COc1nc(NC2CCN(C3(C)COC3)CC2)nn2ccc(-c3cc(F)c4nnn(CC(F)F)c4c3)c12]
815
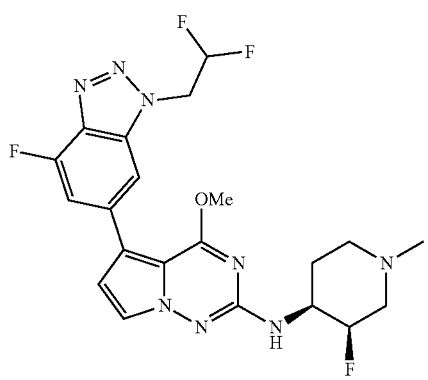 [SMILES: COc1nc(N[C@H]2CCN(C)C[C@H]2F)nn2ccc(-c3cc(F)c4nnn(CC(F)F)c4c3)c12]
816
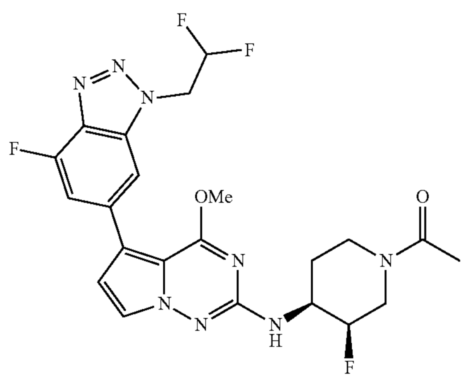 [SMILES: COc1nc(N[C@H]2CCN(C(C)=O)C[C@H]2F)nn2ccc(-c3cc(F)c4nnn(CC(F)F)c4c3)c12]
817
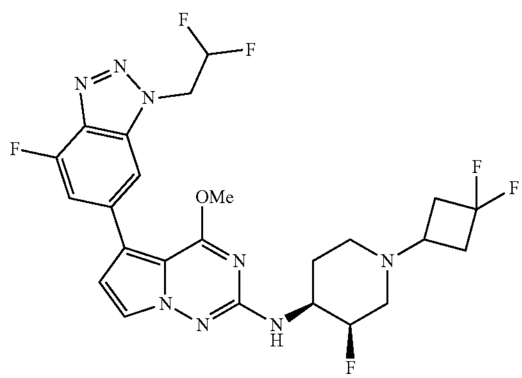 [SMILES: COc1nc(N[C@H]2CCN(C3CC(F)(F)C3)C[C@H]2F)nn2ccc(-c3cc(F)c4nnn(CC(F)F)c4c3)c12]
818
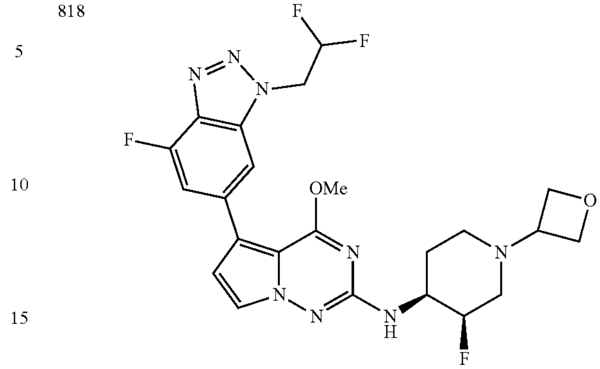
819
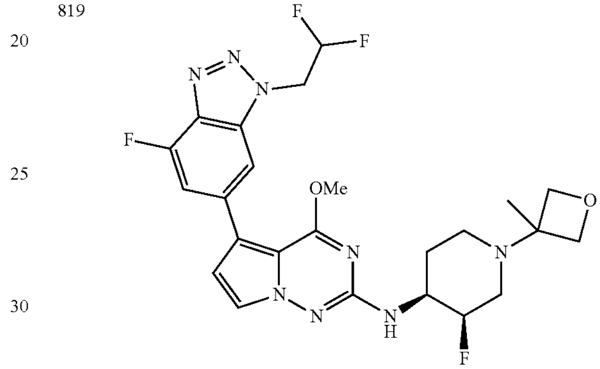
820
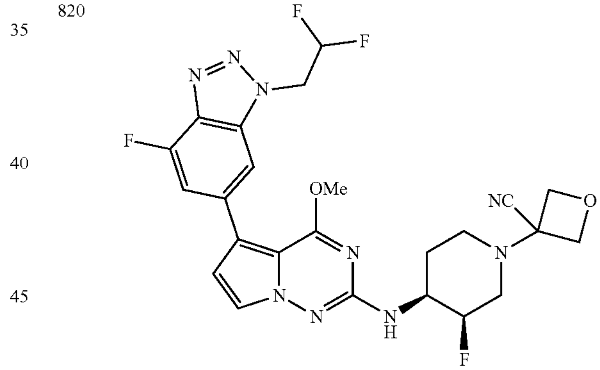
821
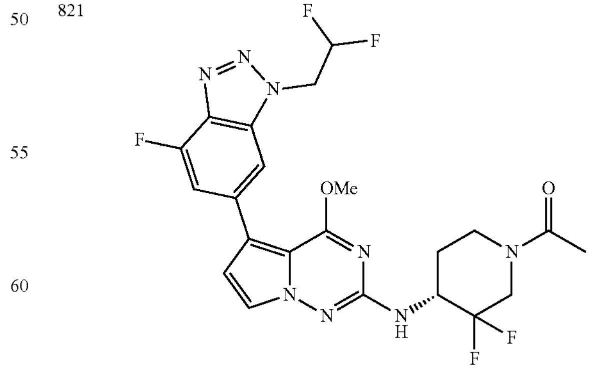

TABLE 1-continued
822
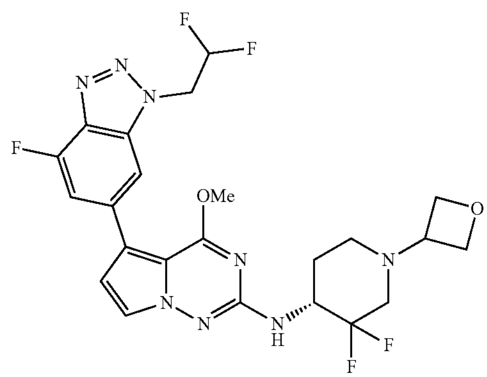 [SMILES: COc1nc(N[C@@H]2CCN(C3COC3)CC2(F)F)nn2ccc(-c3cc(F)c4nnn(CC(F)F)c4c3)c12]
823
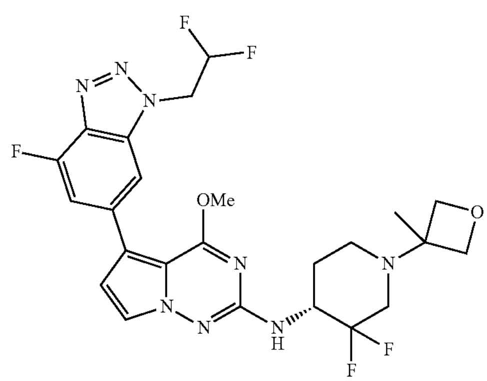 [SMILES: COc1nc(N[C@@H]2CCN(C3(C)COC3)CC2(F)F)nn2ccc(-c3cc(F)c4nnn(CC(F)F)c4c3)c12]
824
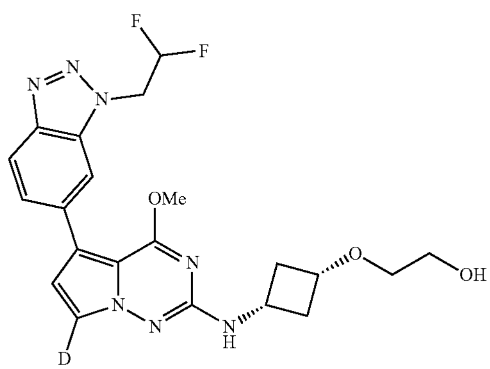 [SMILES: [2H]c1cc(-c2ccc3nnn(CC(F)F)c3c2)c2c(OC)nc(N[C@H]3C[C@@H](OCCO)C3)nn12]
825
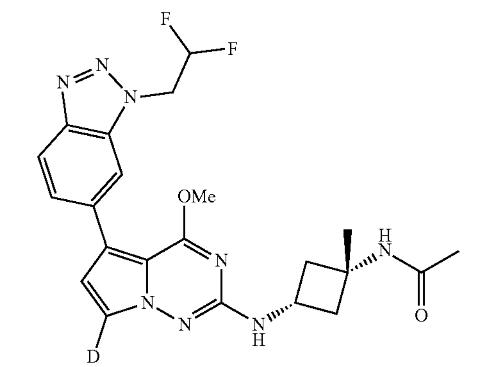 [SMILES: [2H]c1cc(-c2ccc3nnn(CC(F)F)c3c2)c2c(OC)nc(N[C@H]3C[C@@](C)(NC(C)=O)C3)nn12]
TABLE 1-continued
826
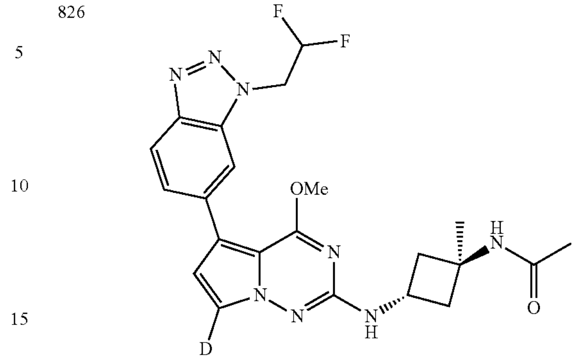
827
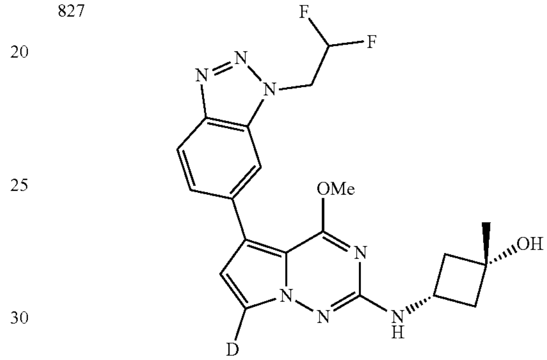
828
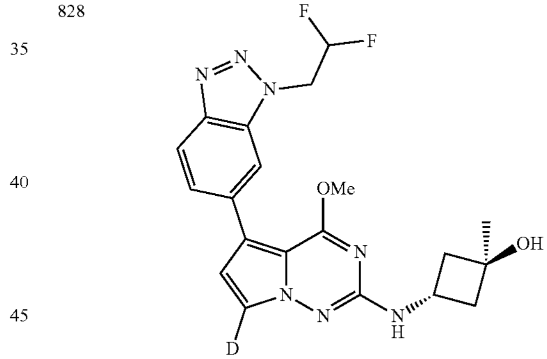
829
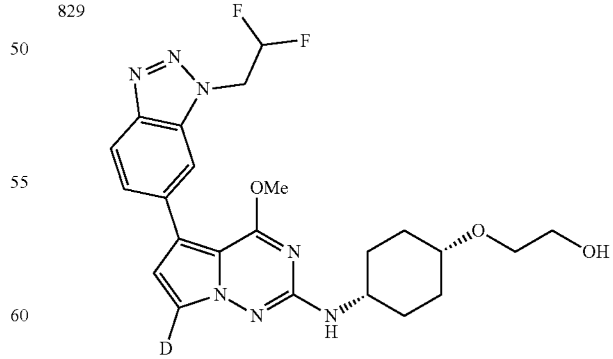

830
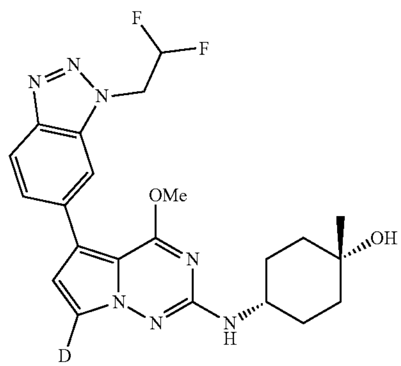 [SMILES: [2H]c1cc(-c2ccc3nnn(CC(F)F)c3c2)c2c(OC)nc(N[C@H]3CC[C@@](C)(O)CC3)nn12]
831
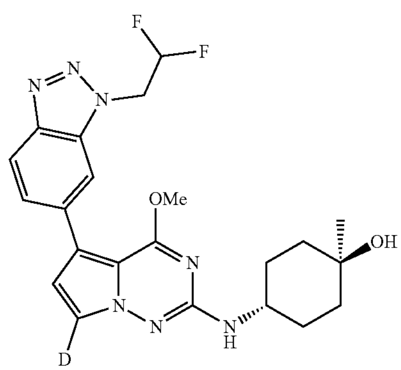 [SMILES: [2H]c1cc(-c2ccc3nnn(CC(F)F)c3c2)c2c(OC)nc(N[C@H]3CC[C@](C)(O)CC3)nn12]
832
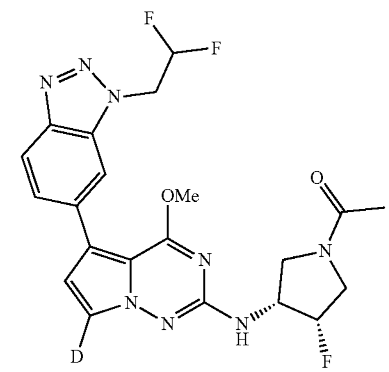 [SMILES: [2H]c1cc(-c2ccc3nnn(CC(F)F)c3c2)c2c(OC)nc(N[C@@H]3CN(C(C)=O)C[C@@H]3F)nn12]
833
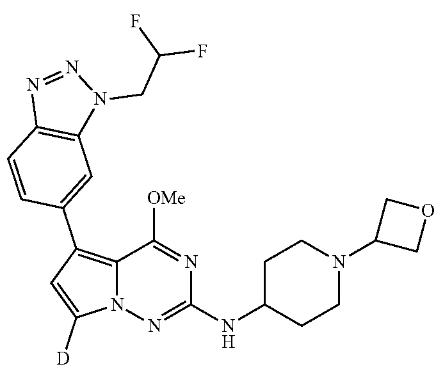 [SMILES: [2H]c1cc(-c2ccc3nnn(CC(F)F)c3c2)c2c(OC)nc(NC3CCN(C4COC4)CC3)nn12]
834
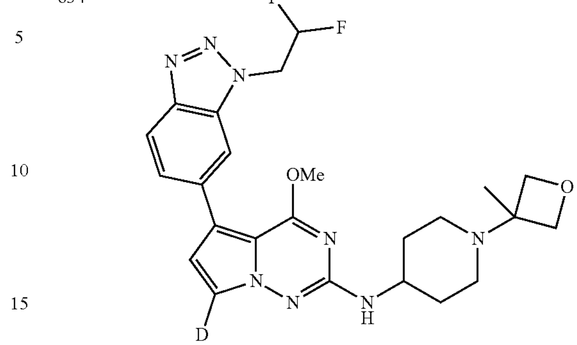
835
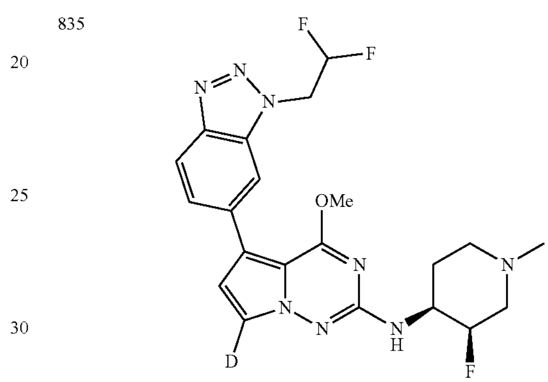
836
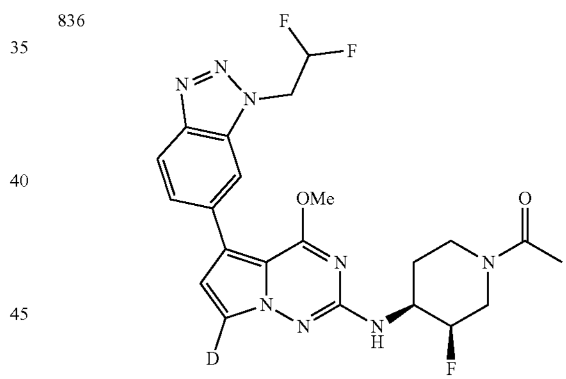
837
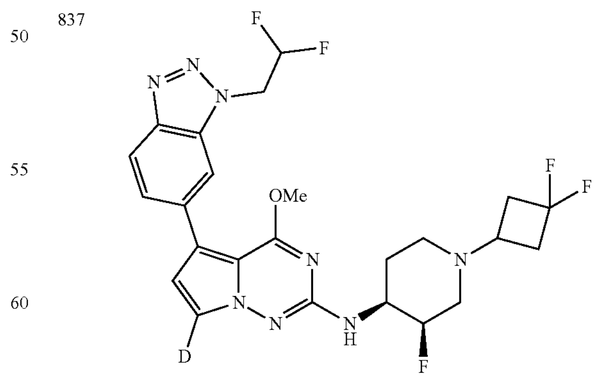

TABLE 1-continued
838
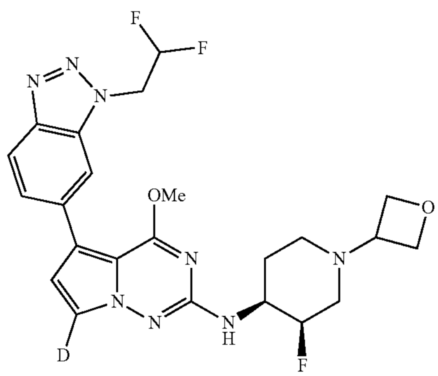 [SMILES: [2H]c1cc(-c2ccc3nnn(CC(F)F)c3c2)c2c(OC)nc(N[C@H]3CCN(C4COC4)C[C@H]3F)nn12]
839
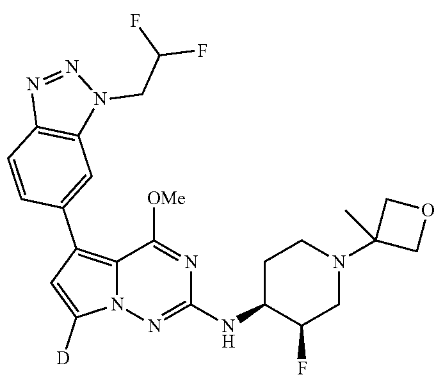 [SMILES: [2H]c1cc(-c2ccc3nnn(CC(F)F)c3c2)c2c(OC)nc(N[C@H]3CCN(C4(C)COC4)C[C@H]3F)nn12]
840
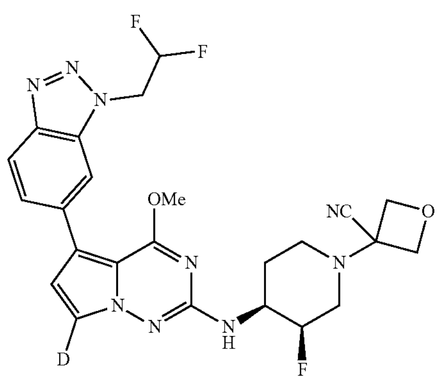 [SMILES: [2H]c1cc(-c2ccc3nnn(CC(F)F)c3c2)c2c(OC)nc(N[C@H]3CCN(C4(C#N)COC4)C[C@H]3F)nn12]
841
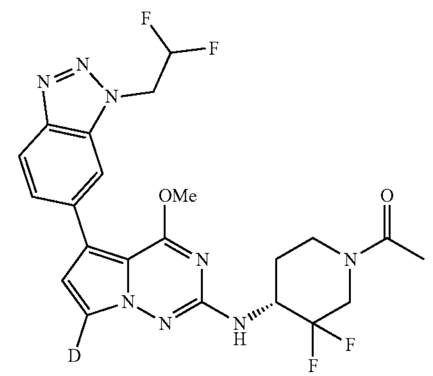 [SMILES: [2H]c1cc(-c2ccc3nnn(CC(F)F)c3c2)c2c(OC)nc(N[C@@H]3CCN(C(C)=O)CC3(F)F)nn12]
TABLE 1-continued
842
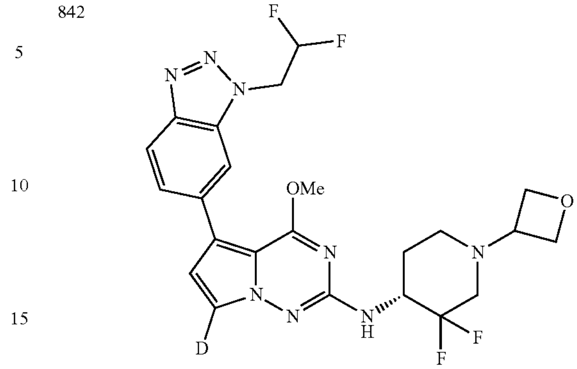
843
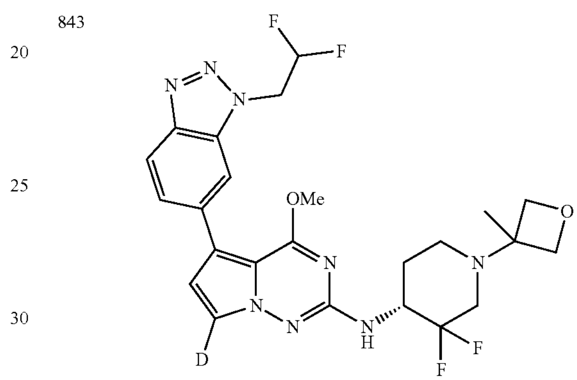
844
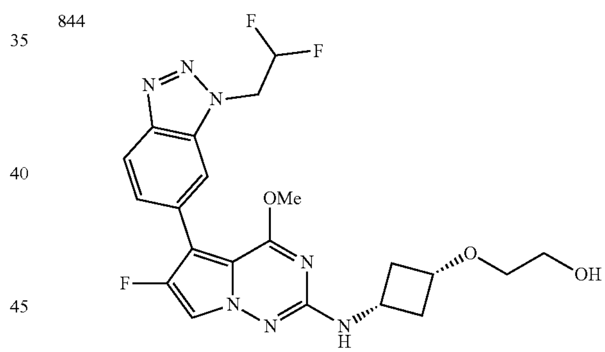
845
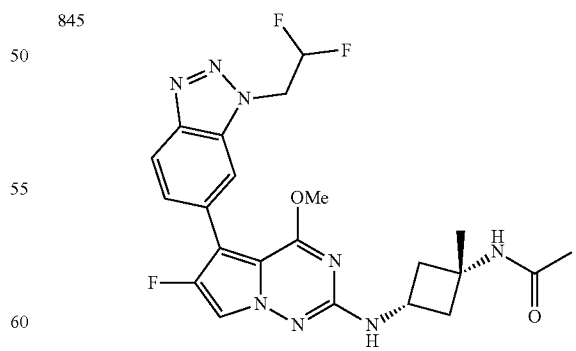

TABLE 1-continued
846
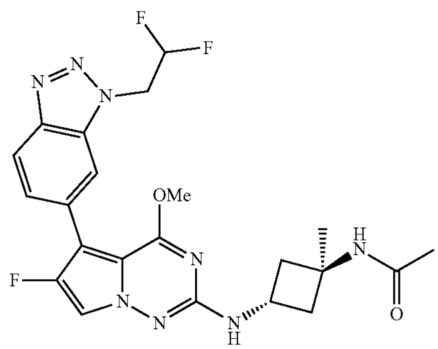 [SMILES: COc1nc(N[C@H]2C[C@](C)(NC(C)=O)C2)nn2cc(F)c(-c3ccc4nnn(CC(F)F)c4c3)c12]
847
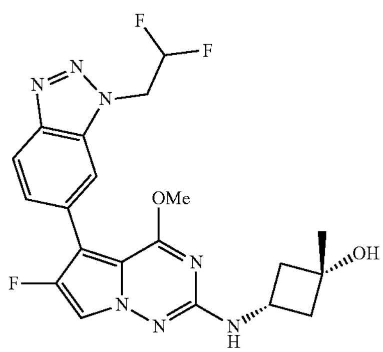 [SMILES: COc1nc(N[C@H]2C[C@@](C)(O)C2)nn2cc(F)c(-c3ccc4nnn(CC(F)F)c4c3)c12]
848
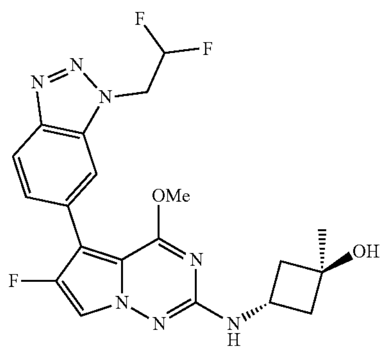 [SMILES: COc1nc(N[C@H]2C[C@](C)(O)C2)nn2cc(F)c(-c3ccc4nnn(CC(F)F)c4c3)c12]
849
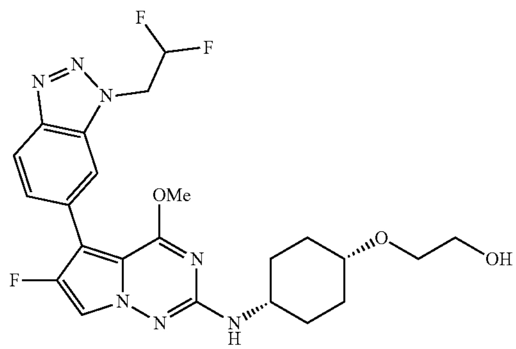 [SMILES: COc1nc(N[C@H]2CC[C@@H](OCCO)CC2)nn2cc(F)c(-c3ccc4nnn(CC(F)F)c4c3)c12]
TABLE 1-continued
850
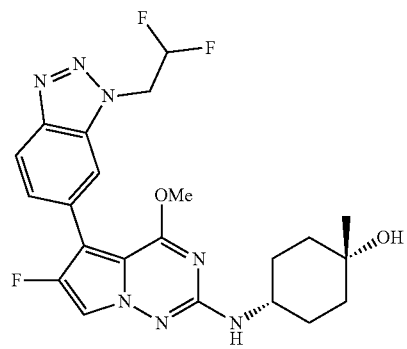 [SMILES: COc1nc(N[C@H]2CC[C@@](C)(O)CC2)nn2cc(F)c(-c3ccc4nnn(CC(F)F)c4c3)c12]
851
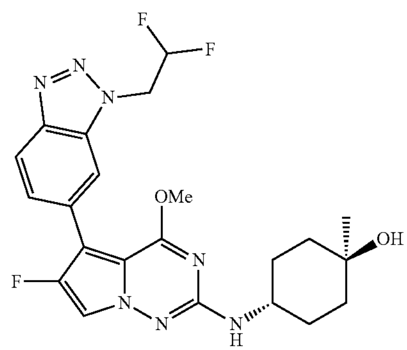 [SMILES: COc1nc(N[C@H]2CC[C@](C)(O)CC2)nn2cc(F)c(-c3ccc4nnn(CC(F)F)c4c3)c12]
852
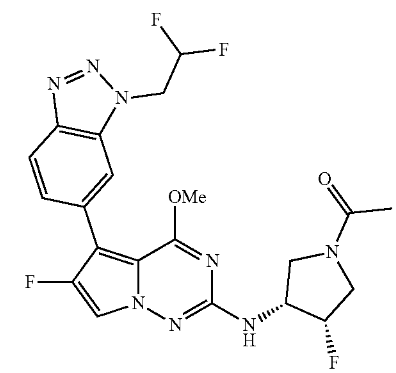 [SMILES: COc1nc(N[C@@H]2CN(C(C)=O)C[C@@H]2F)nn2cc(F)c(-c3ccc4nnn(CC(F)F)c4c3)c12]
853
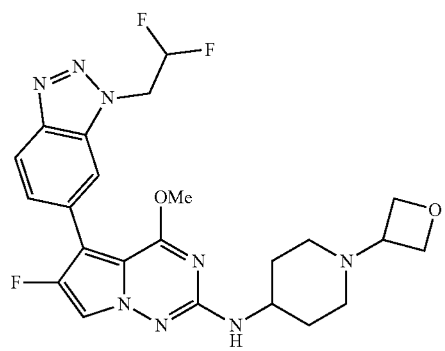 [SMILES: COc1nc(NC2CCN(C3COC3)CC2)nn2cc(F)c(-c3ccc4nnn(CC(F)F)c4c3)c12]

TABLE 1-continued
854
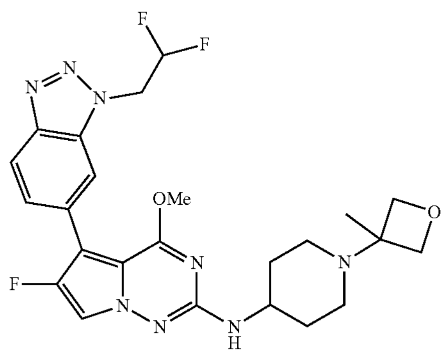 [SMILES: COc1nc(NC2CCN(C3(C)COC3)CC2)nn2cc(F)c(-c3ccc4nnn(CC(F)F)c4c3)c12]
855
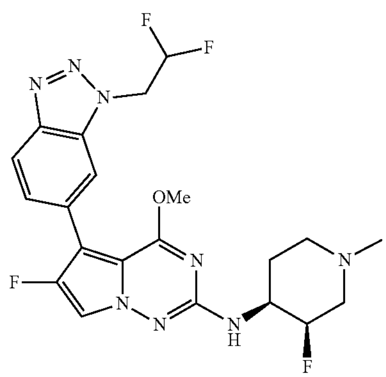 [SMILES: COc1nc(N[C@H]2CCN(C)C[C@H]2F)nn2cc(F)c(-c3ccc4nnn(CC(F)F)c4c3)c12]
856
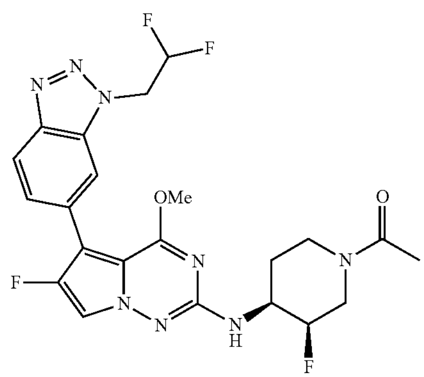 [SMILES: COc1nc(N[C@H]2CCN(C(C)=O)C[C@H]2F)nn2cc(F)c(-c3ccc4nnn(CC(F)F)c4c3)c12]
857
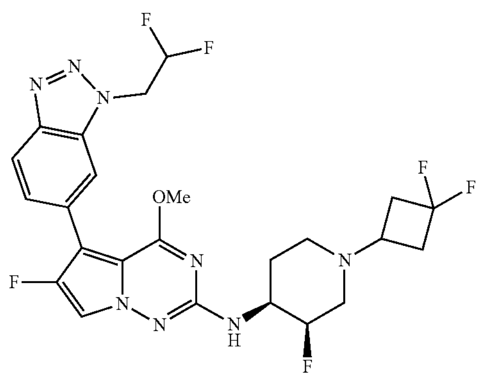 [SMILES: COc1nc(N[C@H]2CCN(C3CC(F)(F)C3)C[C@H]2F)nn2cc(F)c(-c3ccc4nnn(CC(F)F)c4c3)c12]
TABLE 1-continued
858
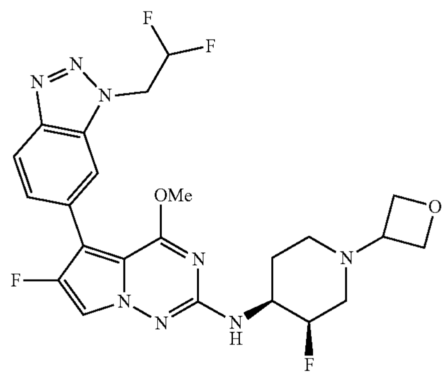 [SMILES: COc1nc(N[C@H]2CCN(C3COC3)C[C@H]2F)nn2cc(F)c(-c3ccc4nnn(CC(F)F)c4c3)c12]
859
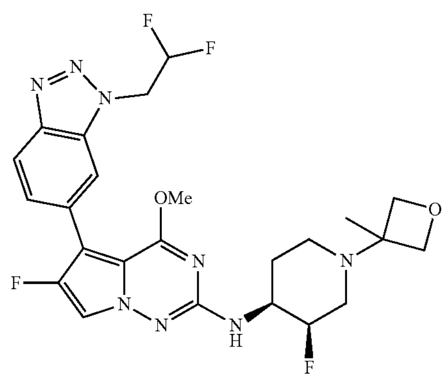 [SMILES: COc1nc(N[C@H]2CCN(C3(C)COC3)C[C@H]2F)nn2cc(F)c(-c3ccc4nnn(CC(F)F)c4c3)c12]
860
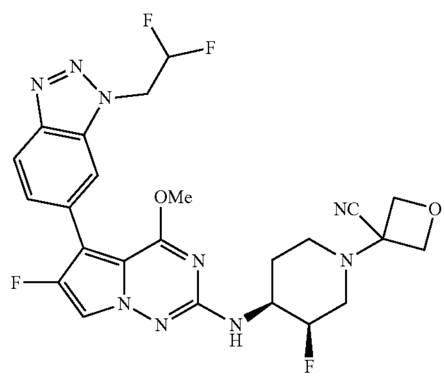 [SMILES: COc1nc(N[C@H]2CCN(C3(C#N)COC3)C[C@H]2F)nn2cc(F)c(-c3ccc4nnn(CC(F)F)c4c3)c12]
861
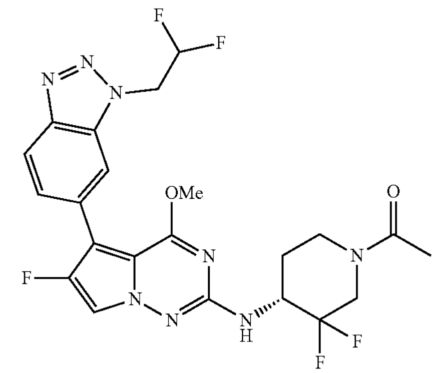 [SMILES: COc1nc(N[C@@H]2CCN(C(C)=O)CC2(F)F)nn2cc(F)c(-c3ccc4nnn(CC(F)F)c4c3)c12]

TABLE 1-continued
862
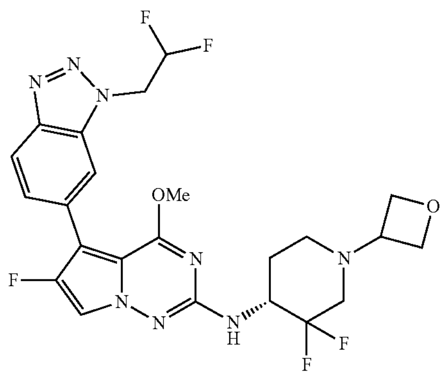 [SMILES: COc1nc(N[C@@H]2CCN(C3COC3)CC2(F)F)nn2cc(F)c(-c3ccc4nnn(CC(F)F)c4c3)c12]
863
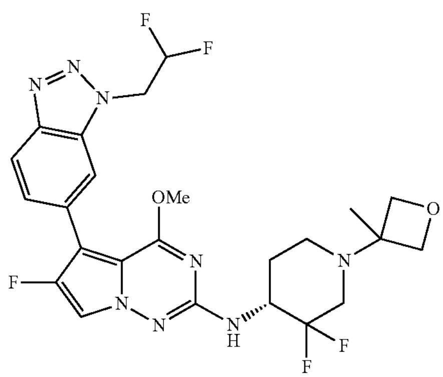 [SMILES: COc1nc(N[C@@H]2CCN(C3(C)COC3)CC2(F)F)nn2cc(F)c(-c3ccc4nnn(CC(F)F)c4c3)c12]
864
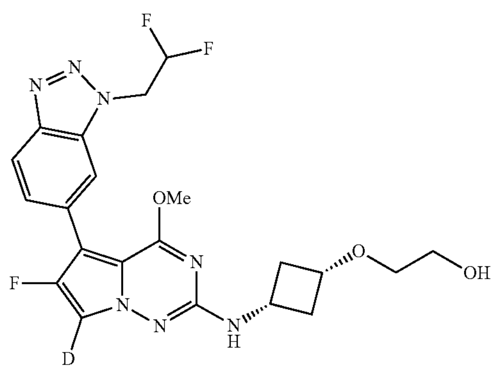 [SMILES: [2H]c1c(F)c(-c2ccc3nnn(CC(F)F)c3c2)c2c(OC)nc(N[C@H]3C[C@@H](OCCO)C3)nn12]
865
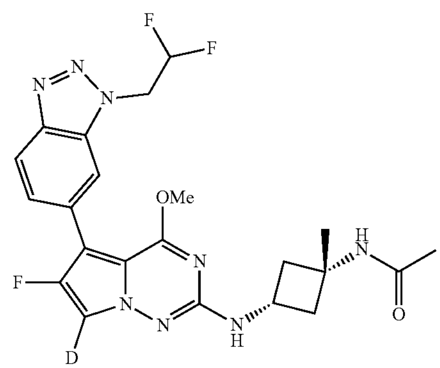 [SMILES: [2H]c1c(F)c(-c2ccc3nnn(CC(F)F)c3c2)c2c(OC)nc(N[C@H]3C[C@@](C)(NC(C)=O)C3)nn12]
TABLE 1-continued
866
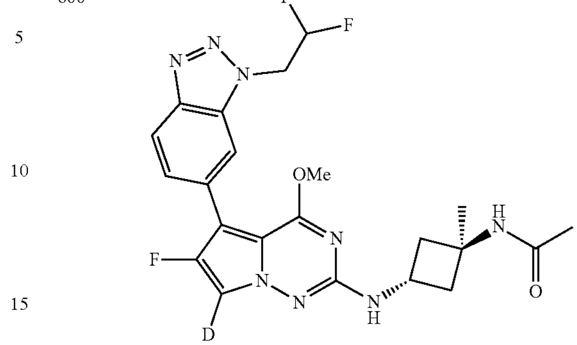
867
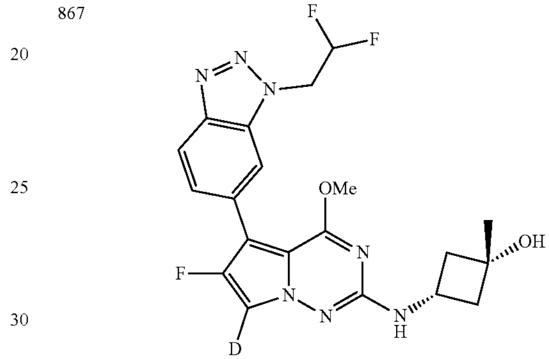
868
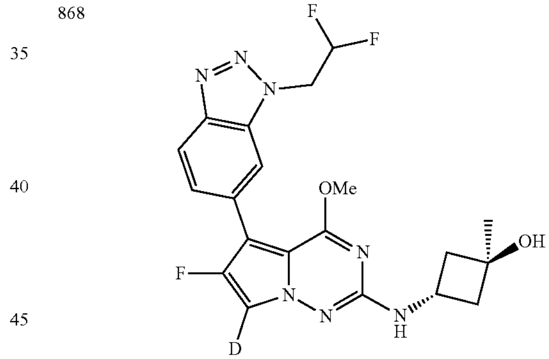
869
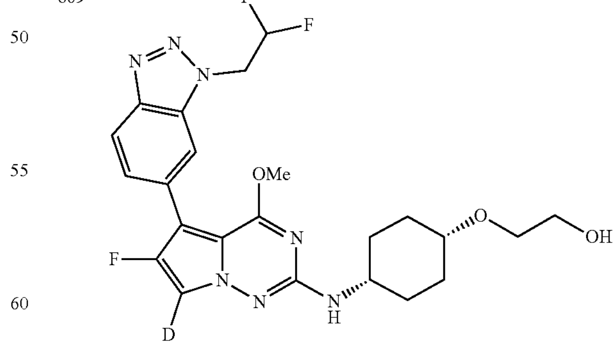

TABLE 1-continued
870
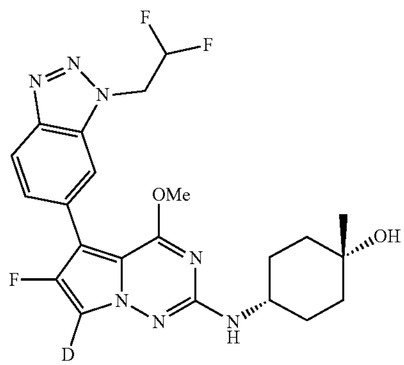 [SMILES: [2H]c1c(F)c(-c2ccc3nnn(CC(F)F)c3c2)c2c(OC)nc(N[C@H]3CC[C@@](C)(O)CC3)nn12]
871
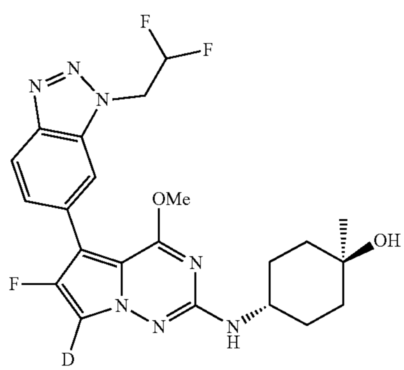 [SMILES: [2H]c1c(F)c(-c2ccc3nnn(CC(F)F)c3c2)c2c(OC)nc(N[C@H]3CC[C@](C)(O)CC3)nn12]
872
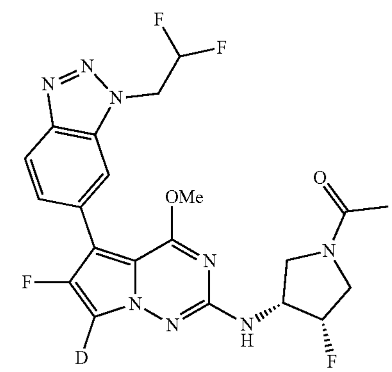 [SMILES: [2H]c1c(F)c(-c2ccc3nnn(CC(F)F)c3c2)c2c(OC)nc(N[C@@H]3CN(C(C)=O)C[C@@H]3F)nn12]
873
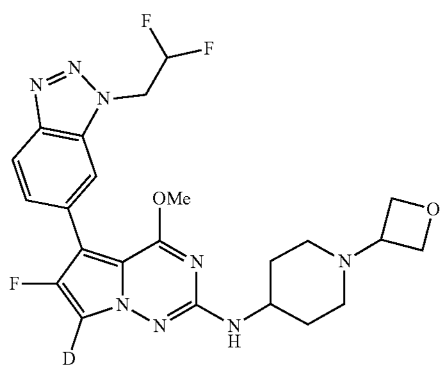 [SMILES: [2H]c1c(F)c(-c2ccc3nnn(CC(F)F)c3c2)c2c(OC)nc(NC3CCN(C4COC4)CC3)nn12]
TABLE 1-continued
874
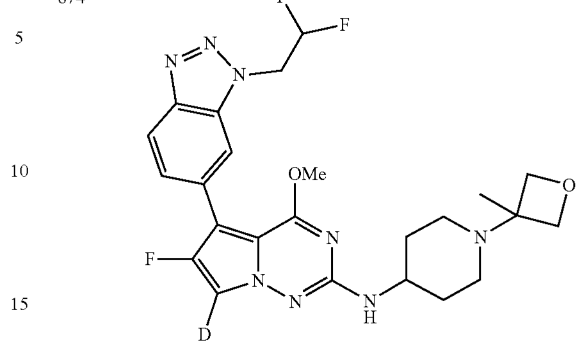
875
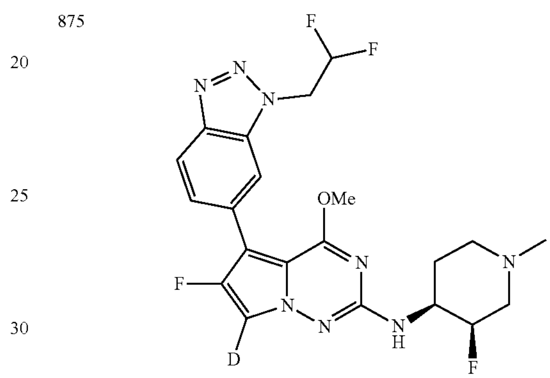
876
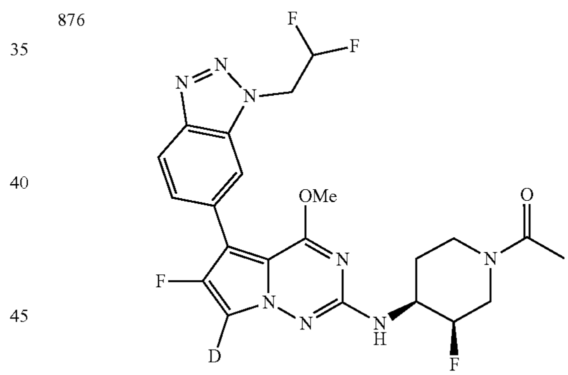
877
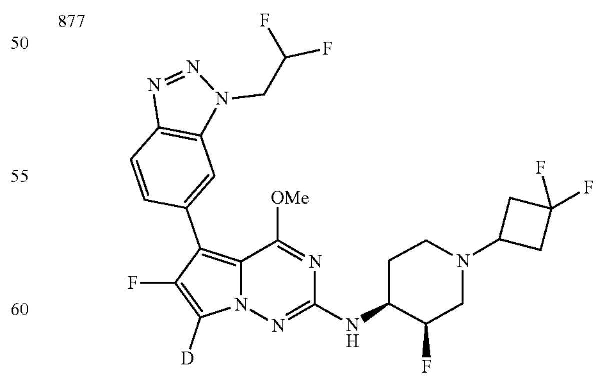

878
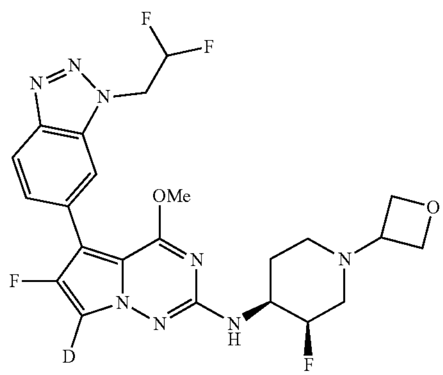 [SMILES: [2H]c1c(F)c(-c2ccc3nnn(CC(F)F)c3c2)c2c(OC)nc(N[C@H]3CCN(C4COC4)C[C@H]3F)nn12]
879
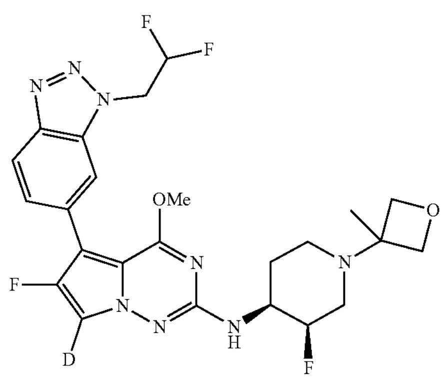 [SMILES: [2H]c1c(F)c(-c2ccc3nnn(CC(F)F)c3c2)c2c(OC)nc(N[C@H]3CCN(C4(C)COC4)C[C@H]3F)nn12]
880
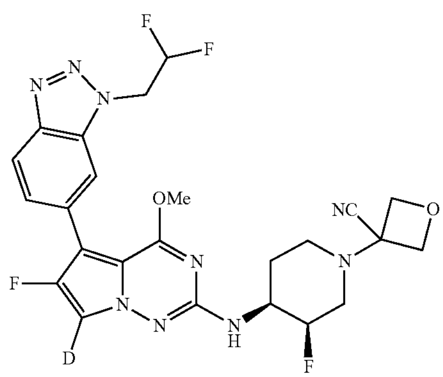 [SMILES: [2H]c1c(F)c(-c2ccc3nnn(CC(F)F)c3c2)c2c(OC)nc(N[C@H]3CCN(C4(C#N)COC4)C[C@H]3F)nn12]
881
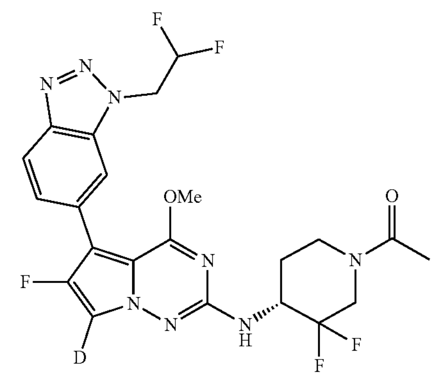 [SMILES: [2H]c1c(F)c(-c2ccc3nnn(CC(F)F)c3c2)c2c(OC)nc(N[C@@H]3CCN(C(C)=O)CC3(F)F)nn12]
882
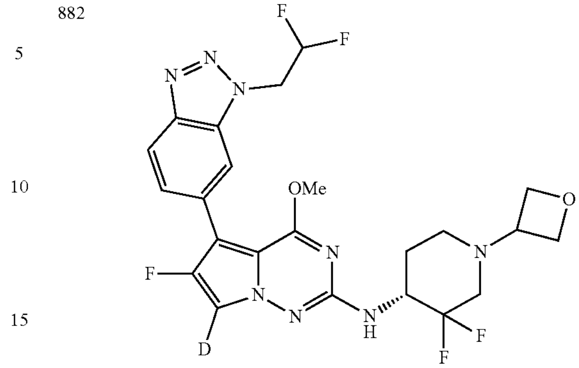
883
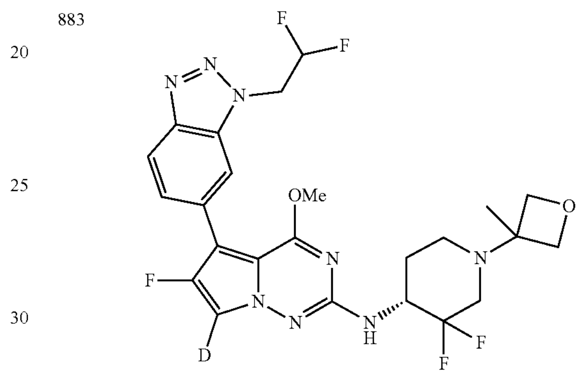
884
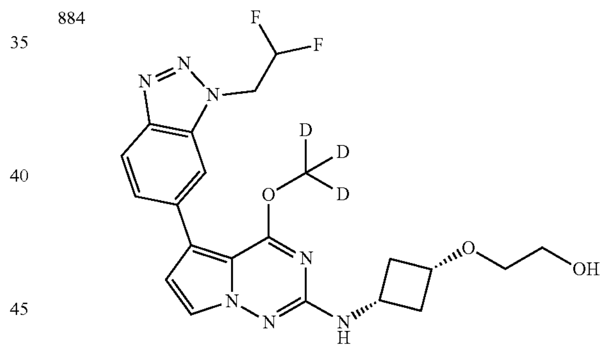
885
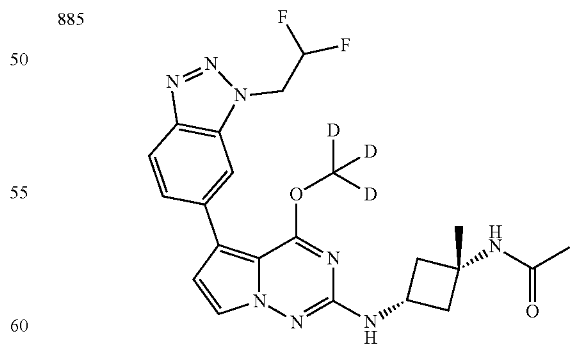

886
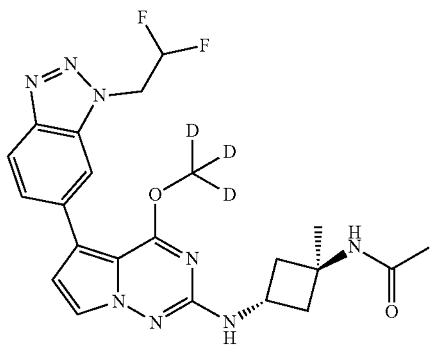 [SMILES: [2H]C([2H])([2H])Oc1nc(N[C@H]2C[C@](C)(NC(C)=O)C2)nn2ccc(-c3ccc4nnn(CC(F)F)c4c3)c12]
887
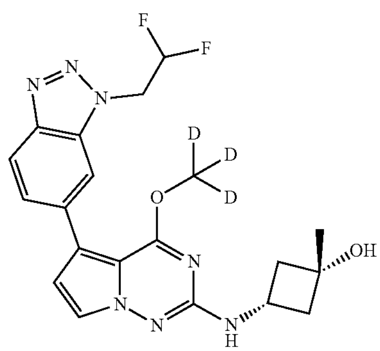 [SMILES: [2H]C([2H])([2H])Oc1nc(N[C@H]2C[C@@](C)(O)C2)nn2ccc(-c3ccc4nnn(CC(F)F)c4c3)c12]
888
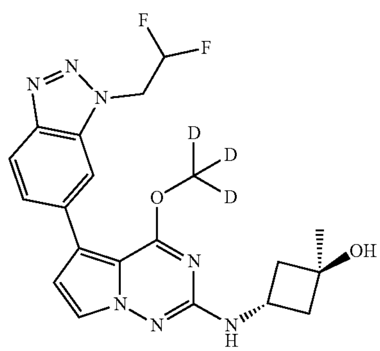 [SMILES: [2H]C([2H])([2H])Oc1nc(N[C@H]2C[C@](C)(O)C2)nn2ccc(-c3ccc4nnn(CC(F)F)c4c3)c12]
889
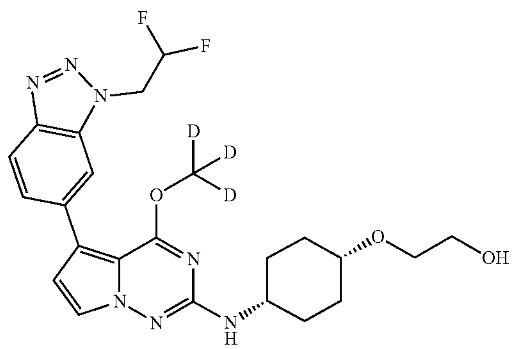 [SMILES: [2H]C([2H])([2H])Oc1nc(N[C@H]2CC[C@@H](OCCO)CC2)nn2ccc(-c3ccc4nnn(CC(F)F)c4c3)c12]
890
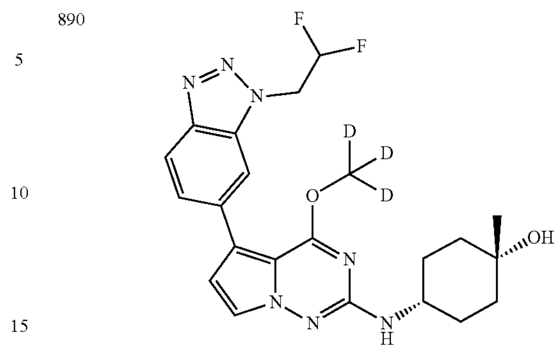
891
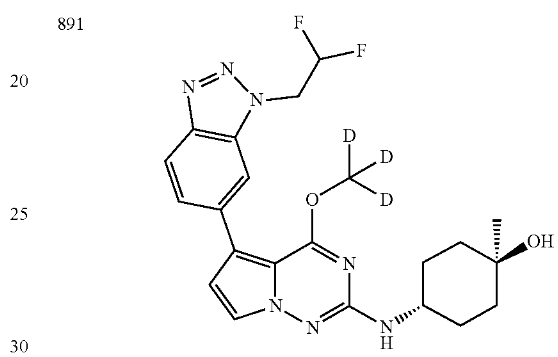
892
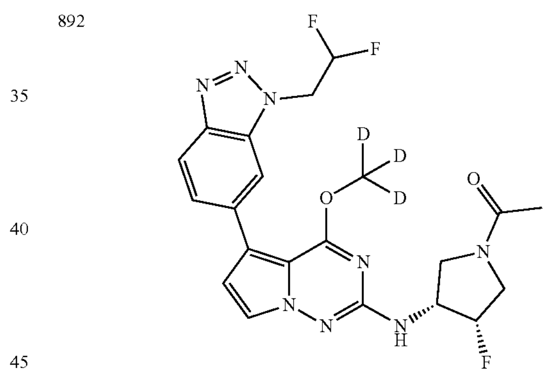
893
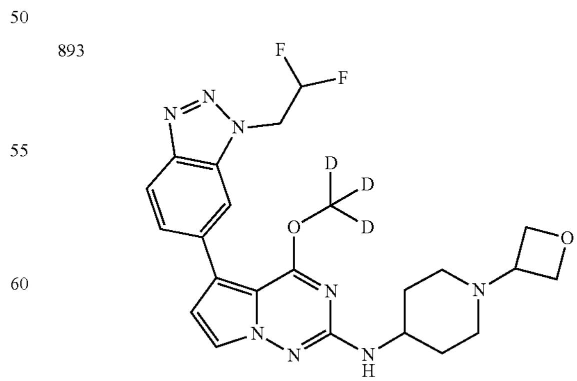

TABLE 1-continued
894
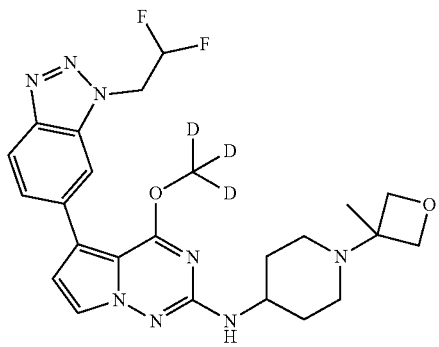 [SMILES: [2H]C([2H])([2H])Oc1nc(NC2CCN(C3(C)COC3)CC2)nn2ccc(-c3ccc4nnn(CC(F)F)c4c3)c12]
895
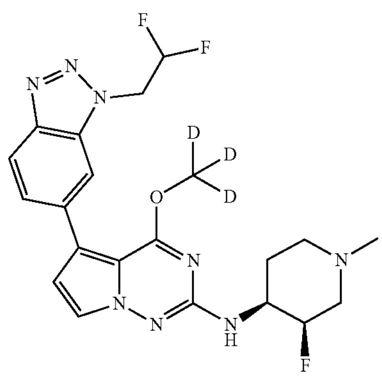 [SMILES: [2H]C([2H])([2H])Oc1nc(N[C@H]2CCN(C)C[C@H]2F)nn2ccc(-c3ccc4nnn(CC(F)F)c4c3)c12]
896
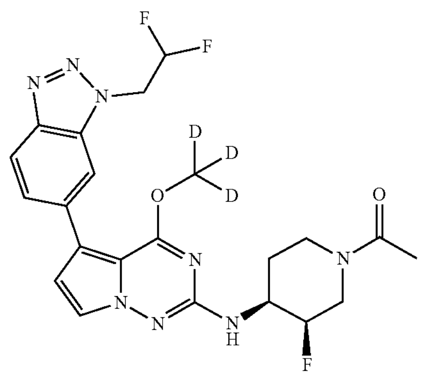 [SMILES: [2H]C([2H])([2H])Oc1nc(N[C@H]2CCN(C(C)=O)C[C@H]2F)nn2ccc(-c3ccc4nnn(CC(F)F)c4c3)c12]
897
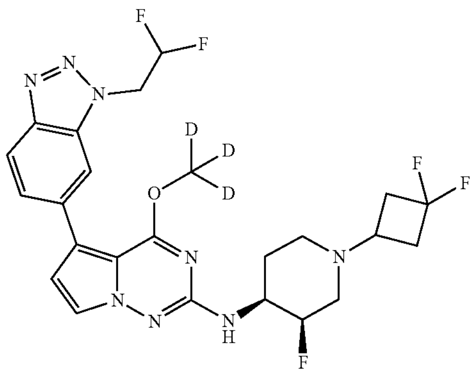 [SMILES: [2H]C([2H])([2H])Oc1nc(N[C@H]2CCN(C3CC(F)(F)C3)C[C@H]2F)nn2ccc(-c3ccc4nnn(CC(F)F)c4c3)c12]
TABLE 1-continued
898
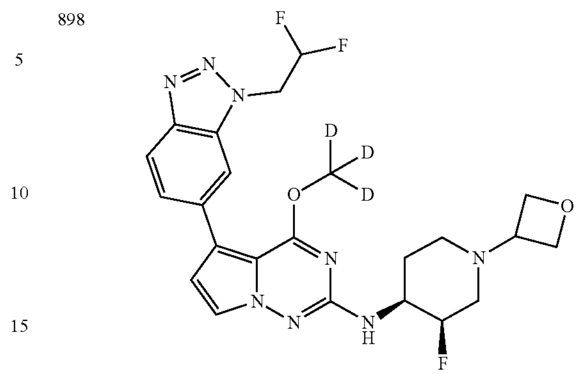
899
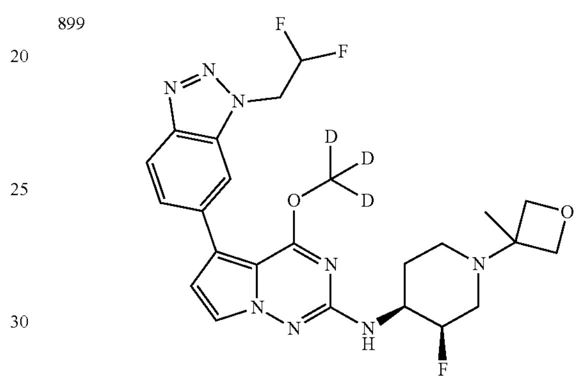
900
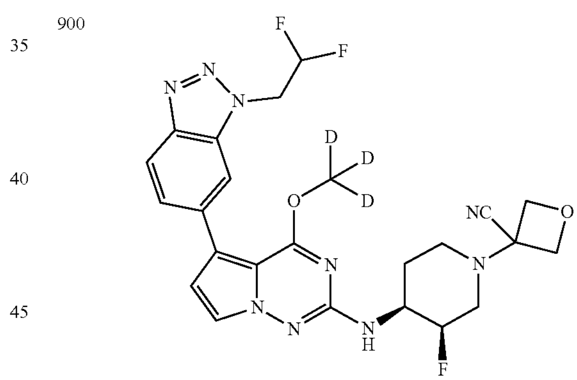
901
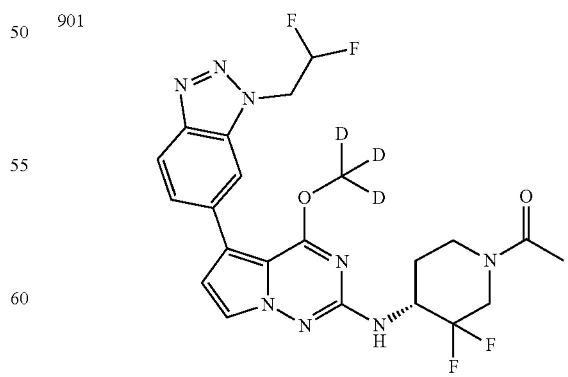

902
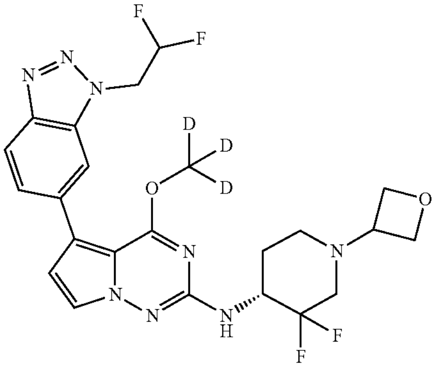 [SMILES: [2H]C([2H])([2H])Oc1nc(N[C@@H]2CCN(C3COC3)CC2(F)F)nn2ccc(-c3ccc4nnn(CC(F)F)c4c3)c12]
903
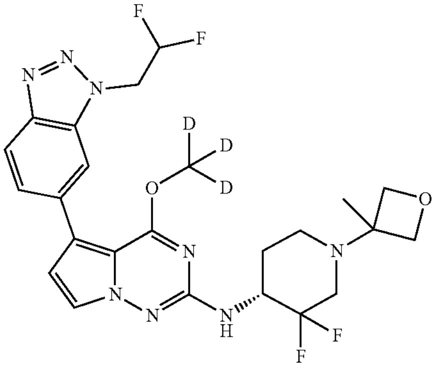 [SMILES: [2H]C([2H])([2H])Oc1nc(N[C@@H]2CCN(C3(C)COC3)CC2(F)F)nn2ccc(-c3ccc4nnn(CC(F)F)c4c3)c12]
904
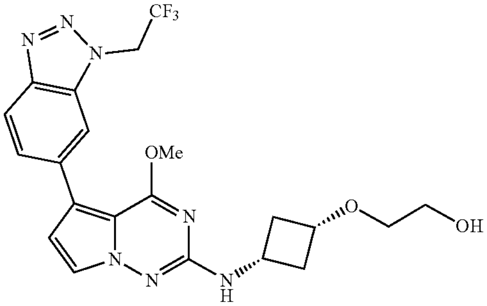 [SMILES: COc1nc(N[C@H]2C[C@@H](OCCO)C2)nn2ccc(-c3ccc4nnn(CC(F)(F)F)c4c3)c12]
905
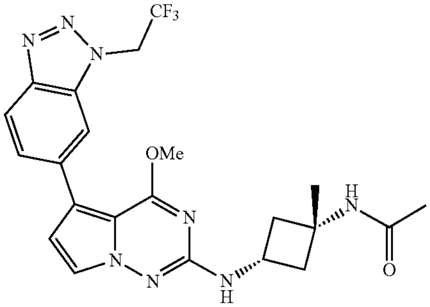 [SMILES: COc1nc(N[C@H]2C[C@@](C)(NC(C)=O)C2)nn2ccc(-c3ccc4nnn(CC(F)(F)F)c4c3)c12]
906
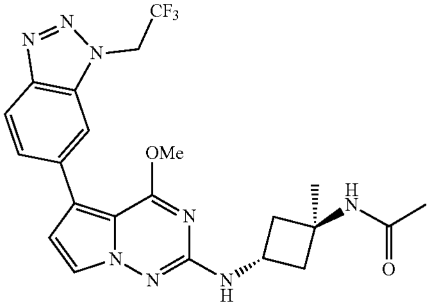 [SMILES: COc1nc(N[C@H]2C[C@](C)(NC(C)=O)C2)nn2ccc(-c3ccc4nnn(CC(F)(F)F)c4c3)c12]
907
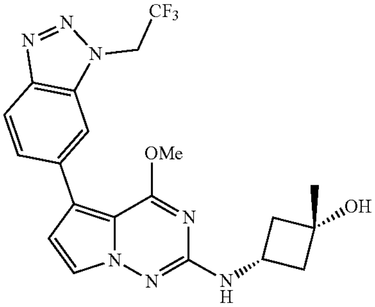 [SMILES: COc1nc(N[C@H]2C[C@@](C)(O)C2)nn2ccc(-c3ccc4nnn(CC(F)(F)F)c4c3)c12]
908
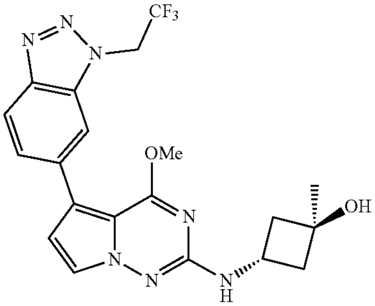 [SMILES: COc1nc(N[C@H]2C[C@](C)(O)C2)nn2ccc(-c3ccc4nnn(CC(F)(F)F)c4c3)c12]
909
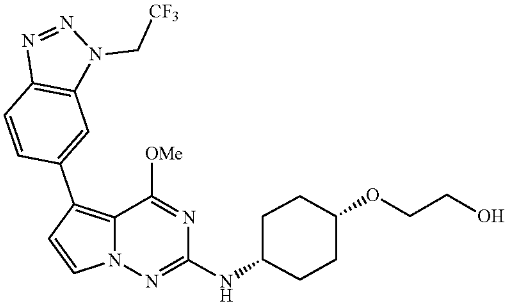 [SMILES: COc1nc(N[C@H]2CC[C@@H](OCCO)CC2)nn2ccc(-c3ccc4nnn(CC(F)(F)F)c4c3)c12]
910
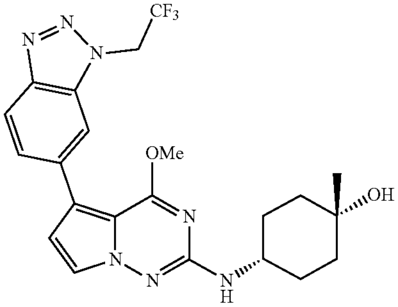 [SMILES: COc1nc(N[C@H]2CC[C@@](C)(O)CC2)nn2ccc(-c3ccc4nnn(CC(F)(F)F)c4c3)c12]

TABLE 1-continued
911
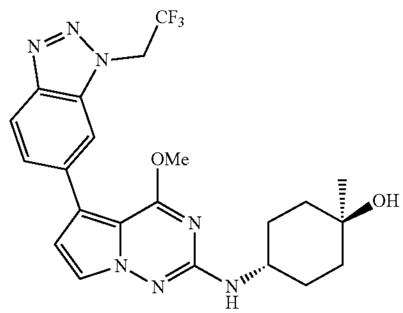 [SMILES: COc1nc(N[C@H]2CC[C@](C)(O)CC2)nn2ccc(-c3ccc4nnn(CC(F)(F)F)c4c3)c12]
912
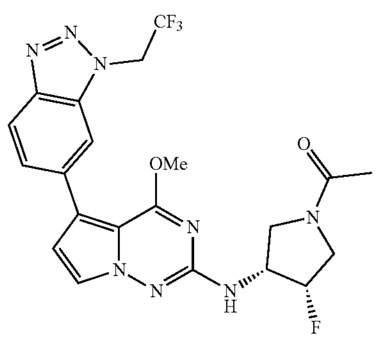 [SMILES: COc1nc(N[C@@H]2CN(C(C)=O)C[C@@H]2F)nn2ccc(-c3ccc4nnn(CC(F)(F)F)c4c3)c12]
913
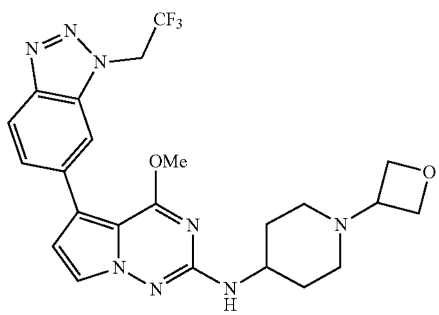 [SMILES: COc1nc(NC2CCN(C3COC3)CC2)nn2ccc(-c3ccc4nnn(CC(F)(F)F)c4c3)c12]
914
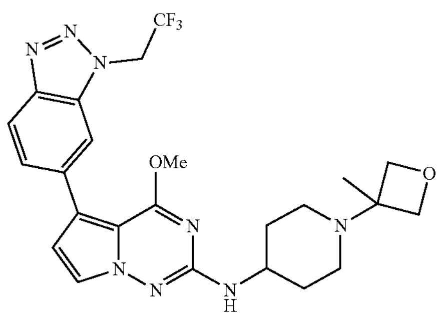 [SMILES: COc1nc(NC2CCN(C3(C)COC3)CC2)nn2ccc(-c3ccc4nnn(CC(F)(F)F)c4c3)c12]
915
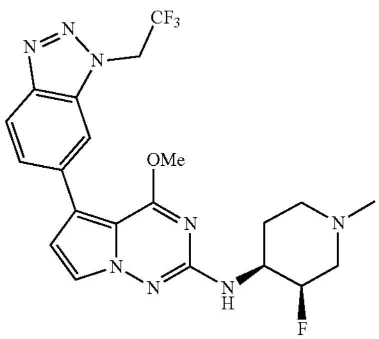 [SMILES: COc1nc(N[C@H]2CCN(C)C[C@H]2F)nn2ccc(-c3ccc4nnn(CC(F)(F)F)c4c3)c12]
TABLE 1-continued
916
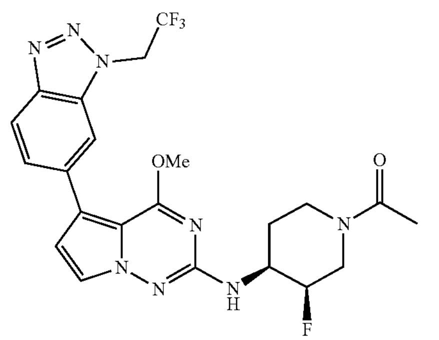 [SMILES: COc1nc(N[C@H]2CCN(C(C)=O)C[C@H]2F)nn2ccc(-c3ccc4nnn(CC(F)(F)F)c4c3)c12]
917
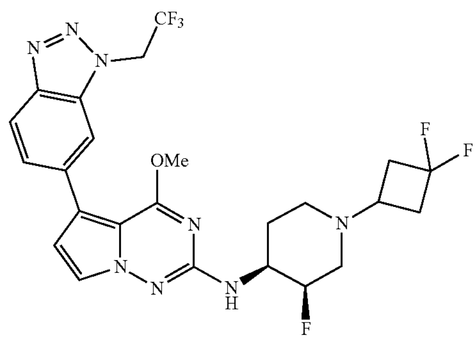 [SMILES: COc1nc(N[C@H]2CCN(C3CC(F)(F)C3)C[C@H]2F)nn2ccc(-c3ccc4nnn(CC(F)(F)F)c4c3)c12]
918
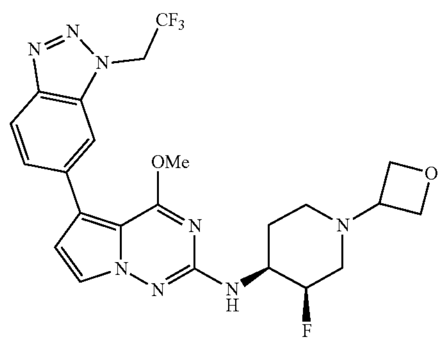 [SMILES: COc1nc(N[C@H]2CCN(C3COC3)C[C@H]2F)nn2ccc(-c3ccc4nnn(CC(F)(F)F)c4c3)c12]
919
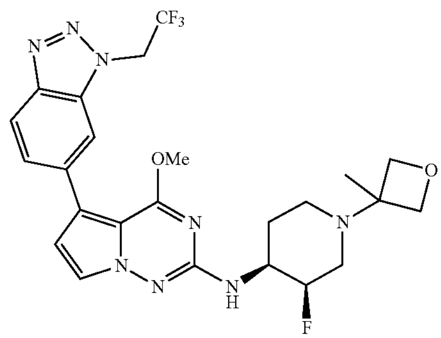 [SMILES: COc1nc(N[C@H]2CCN(C3(C)COC3)C[C@H]2F)nn2ccc(-c3ccc4nnn(CC(F)(F)F)c4c3)c12]

TABLE 1-continued
920
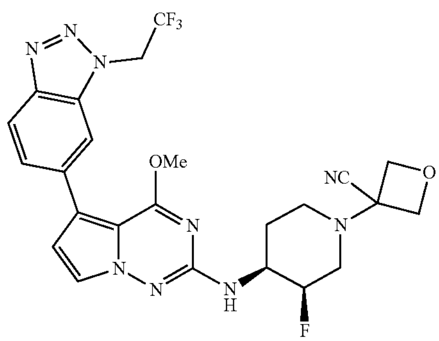 [SMILES: COc1nc(N[C@H]2CCN(C3(C#N)COC3)C[C@H]2F)nn2ccc(-c3ccc4nnn(CC(F)(F)F)c4c3)c12]
921
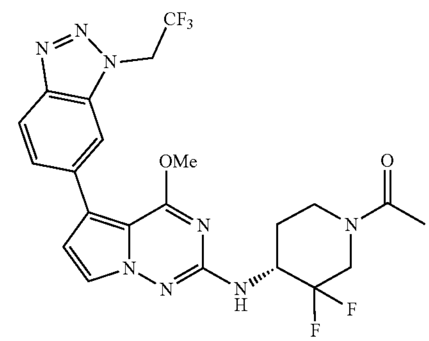 [SMILES: COc1nc(N[C@@H]2CCN(C(C)=O)CC2(F)F)nn2ccc(-c3ccc4nnn(CC(F)(F)F)c4c3)c12]
922
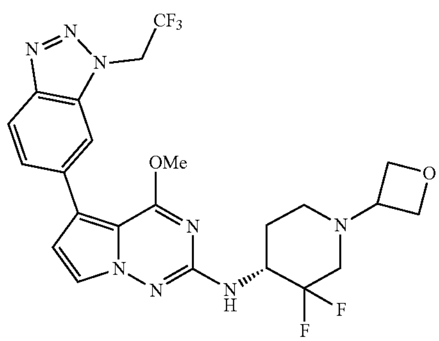 [SMILES: COc1nc(N[C@@H]2CCN(C3COC3)CC2(F)F)nn2ccc(-c3ccc4nnn(CC(F)(F)F)c4c3)c12]
923
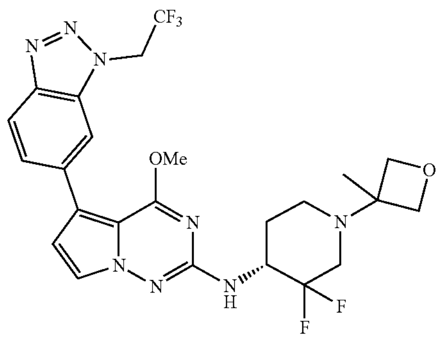 [SMILES: COc1nc(N[C@@H]2CCN(C3(C)COC3)CC2(F)F)nn2ccc(-c3ccc4nnn(CC(F)(F)F)c4c3)c12]
TABLE 1-continued
924
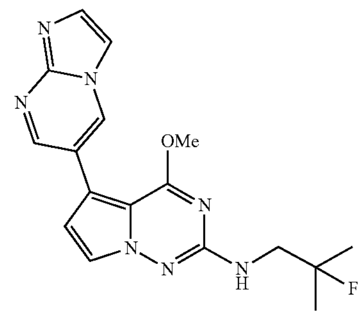 [SMILES: COc1nc(NCC(C)(C)F)nn2ccc(-c3cnc4nccn4c3)c12]
925
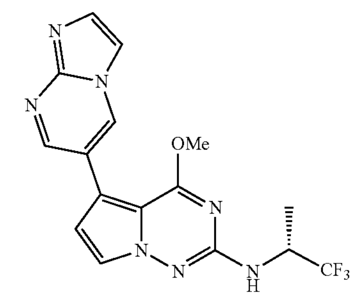 [SMILES: COc1nc(N[C@H](C)C(F)(F)F)nn2ccc(-c3cnc4nccn4c3)c12]
926
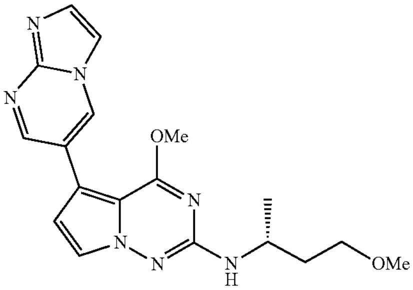 [SMILES: COCC[C@@H](C)Nc1nc(OC)c2c(-c3cnc4nccn4c3)ccn2n1]
927
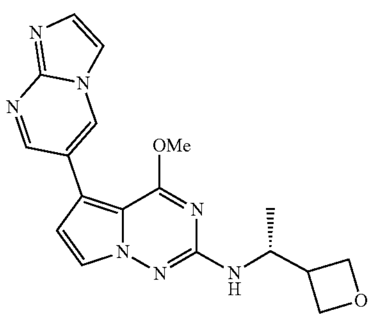 [SMILES: COc1nc(N[C@H](C)C2COC2)nn2ccc(-c3cnc4nccn4c3)c12]
928
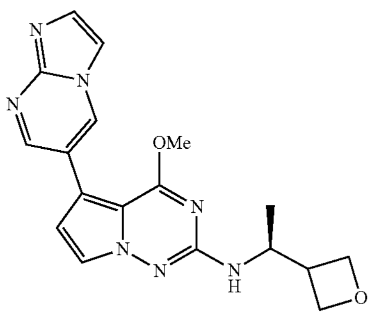 [SMILES: COc1nc(N[C@@H](C)C2COC2)nn2ccc(-c3cnc4nccn4c3)c12]

929
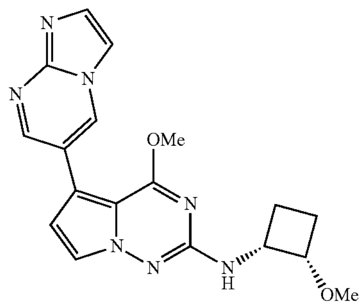 [SMILES: COc1nc(N[C@@H]2CC[C@@H]2OC)nn2ccc(-c3cnc4nccn4c3)c12]
930
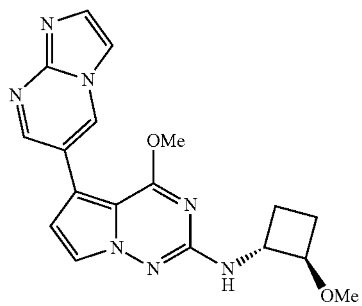 [SMILES: COc1nc(N[C@@H]2CC[C@H]2OC)nn2ccc(-c3cnc4nccn4c3)c12]
931
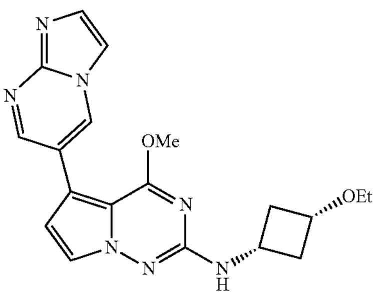 [SMILES: CCO[C@H]1C[C@@H](Nc2nc(OC)c3c(-c4cnc5nccn5c4)ccn3n2)C1]
932
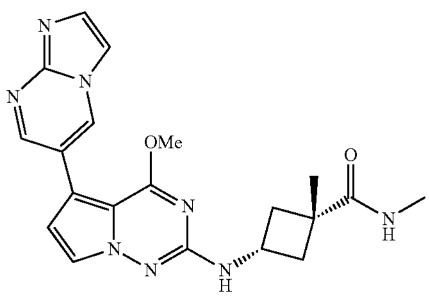 [SMILES: CNC(=O)[C@]1(C)C[C@H](Nc2nc(OC)c3c(-c4cnc5nccn5c4)ccn3n2)C1]
933
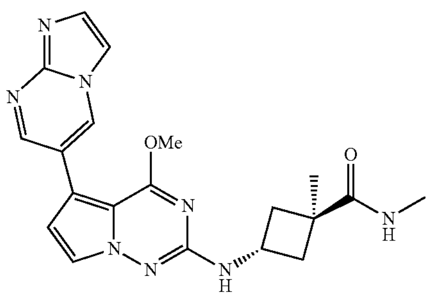 [SMILES: CNC(=O)[C@]1(C)C[C@@H](Nc2nc(OC)c3c(-c4cnc5nccn5c4)ccn3n2)C1]
934
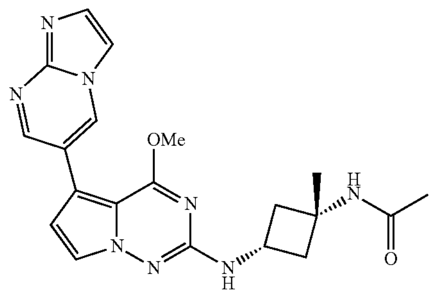 [SMILES: COc1nc(N[C@H]2C[C@@](C)(NC(C)=O)C2)nn2ccc(-c3cnc4nccn4c3)c12]
935
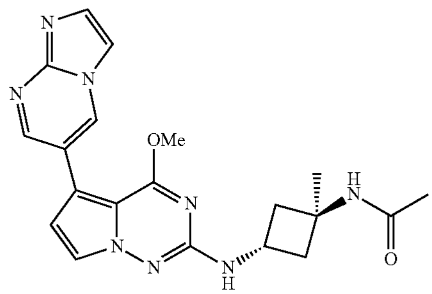 [SMILES: COc1nc(N[C@H]2C[C@](C)(NC(C)=O)C2)nn2ccc(-c3cnc4nccn4c3)c12]
936
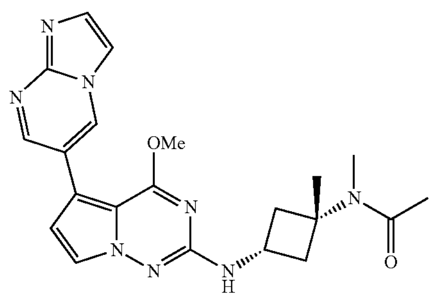 [SMILES: COc1nc(N[C@H]2C[C@@](C)(N(C)C(C)=O)C2)nn2ccc(-c3cnc4nccn4c3)c12]
937
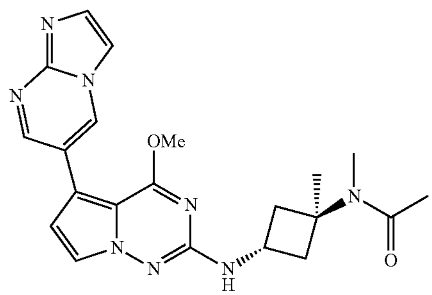 [SMILES: COc1nc(N[C@H]2C[C@](C)(N(C)C(C)=O)C2)nn2ccc(-c3cnc4nccn4c3)c12]
938
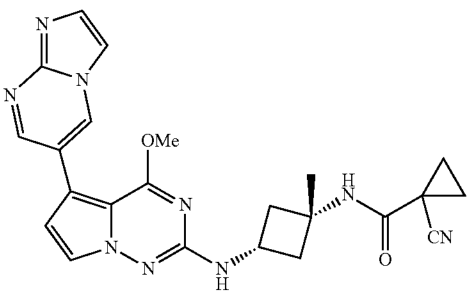 [SMILES: COc1nc(N[C@H]2C[C@@](C)(NC(=O)C3(C#N)CC3)C2)nn2ccc(-c3cnc4nccn4c3)c12]

TABLE 1-continued
939
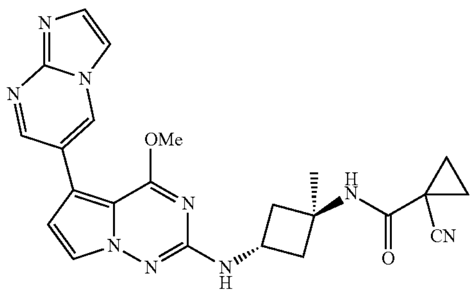 [SMILES: COc1nc(N[C@H]2C[C@](C)(NC(=O)C3(C#N)CC3)C2)nn2ccc(-c3cnc4nccn4c3)c12]
940
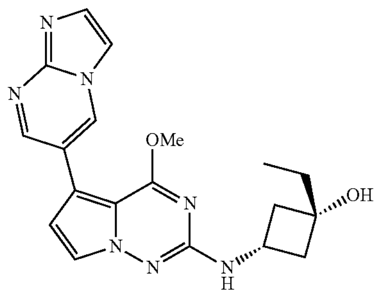 [SMILES: CC[C@]1(O)C[C@@H](Nc2nc(OC)c3c(-c4cnc5nccn5c4)ccn3n2)C1]
941
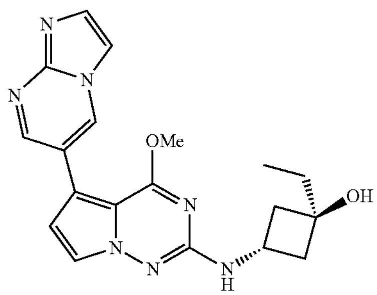 [SMILES: CC[C@]1(O)C[C@H](Nc2nc(OC)c3c(-c4cnc5nccn5c4)ccn3n2)C1]
942
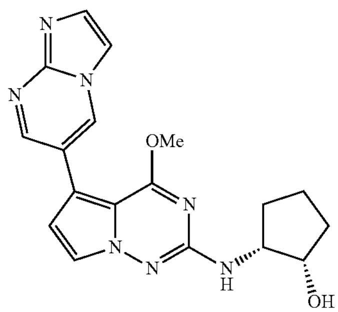 [SMILES: COc1nc(N[C@@H]2CCC[C@@H]2O)nn2ccc(-c3cnc4nccn4c3)c12]
943
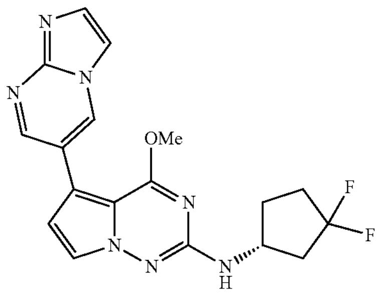 [SMILES: COc1nc(N[C@@H]2CCC(F)(F)C2)nn2ccc(-c3cnc4nccn4c3)c12]
TABLE 1-continued
944
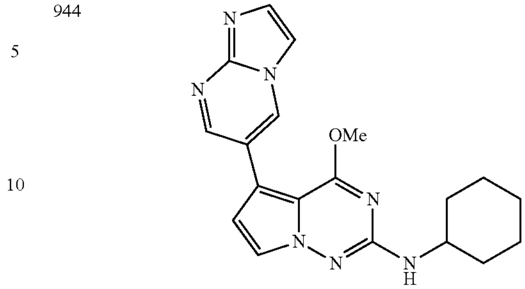
945
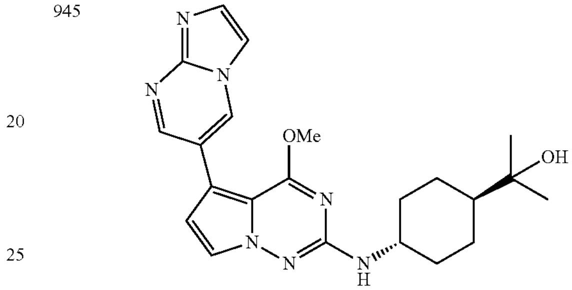
946
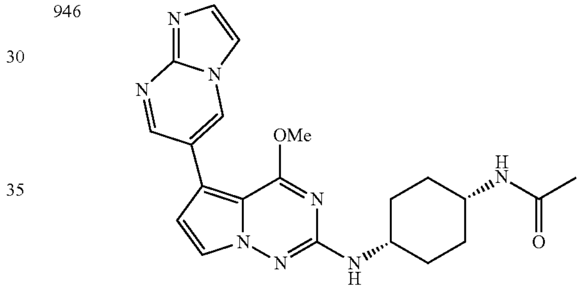
947
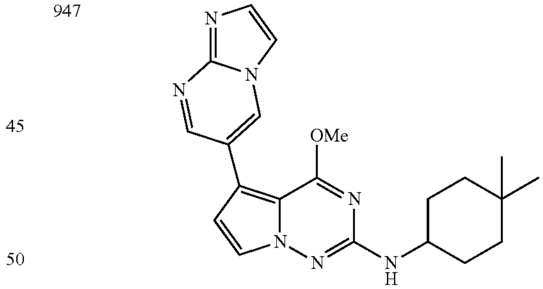
948
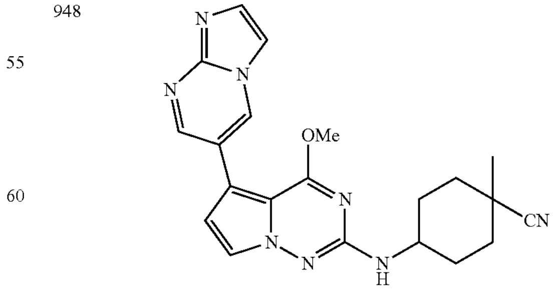

949
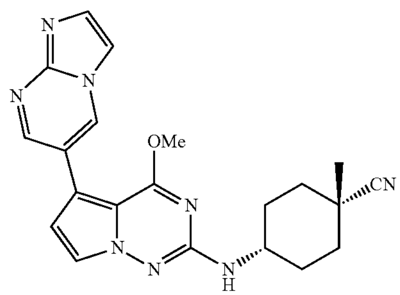 [SMILES: COc1nc(N[C@H]2CC[C@@](C)(C#N)CC2)nn2ccc(-c3cnc4nccn4c3)c12]
950
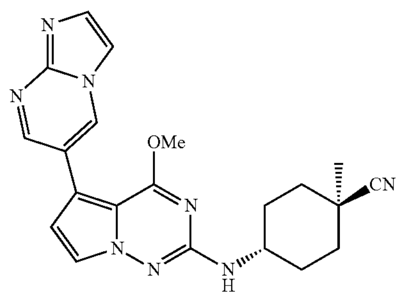 [SMILES: COc1nc(N[C@H]2CC[C@](C)(C#N)CC2)nn2ccc(-c3cnc4nccn4c3)c12]
951
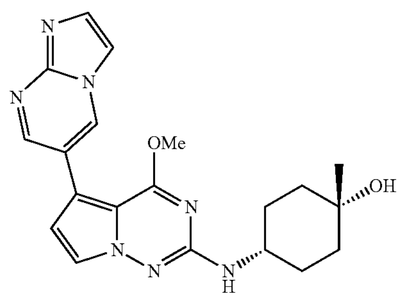
952
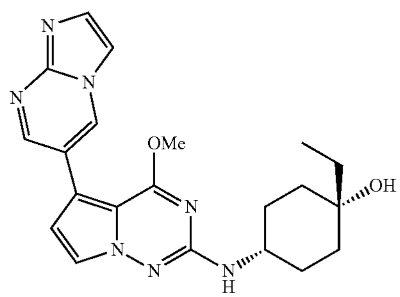 [SMILES: CC[C@]1(O)CC[C@@H](Nc2nc(OC)c3c(-c4cnc5nccn5c4)ccn3n2)CC1]
953
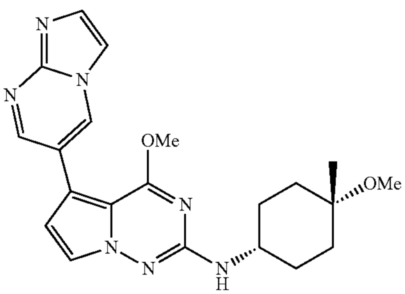 [SMILES: COc1nc(N[C@H]2CC[C@@](C)(OC)CC2)nn2ccc(-c3cnc4nccn4c3)c12]
954
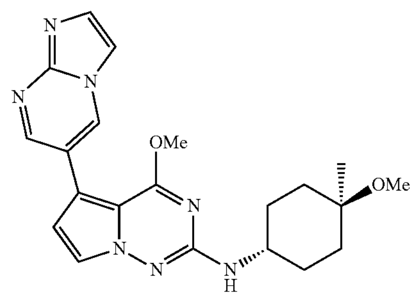 [SMILES: COc1nc(N[C@H]2CC[C@](C)(OC)CC2)nn2ccc(-c3cnc4nccn4c3)c12]
955
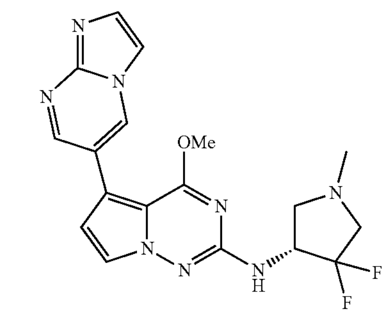 [SMILES: COc1nc(N[C@@H]2CN(C)CC2(F)F)nn2ccc(-c3cnc4nccn4c3)c12]
956
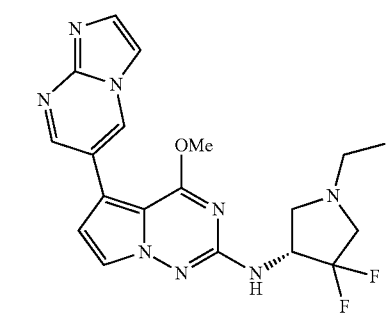 [SMILES: CCN1C[C@@H](Nc2nc(OC)c3c(-c4cnc5nccn5c4)ccn3n2)C(F)(F)C1]
957
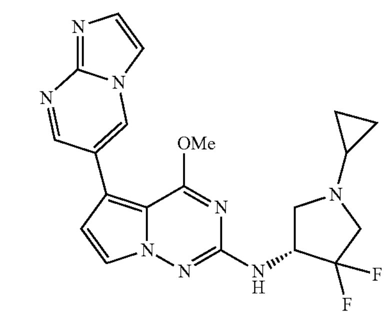 [SMILES: COc1nc(N[C@@H]2CN(C3CC3)CC2(F)F)nn2ccc(-c3cnc4nccn4c3)c12]
958
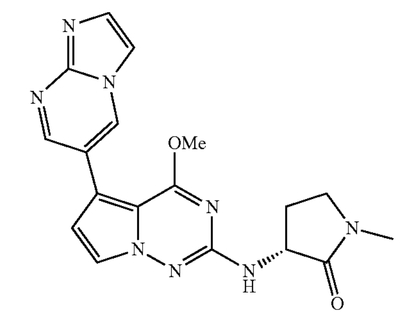 [SMILES: COc1nc(N[C@@H]2CCN(C)C2=O)nn2ccc(-c3cnc4nccn4c3)c12]

TABLE 1-continued
959
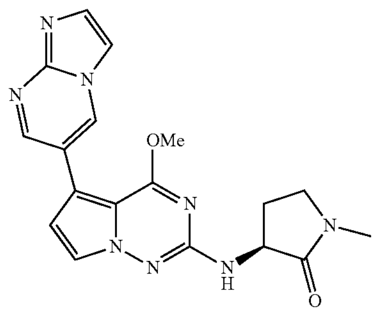 [SMILES: COc1nc(N[C@H]2CCN(C)C2=O)nn2ccc(-c3cnc4nccn4c3)c12]
960
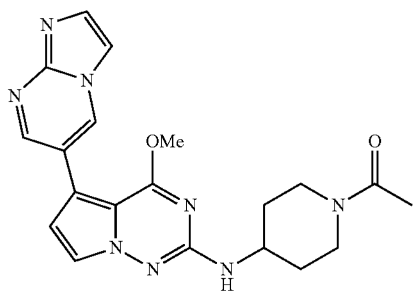 [SMILES: COc1nc(NC2CCN(C(C)=O)CC2)nn2ccc(-c3cnc4nccn4c3)c12]
961
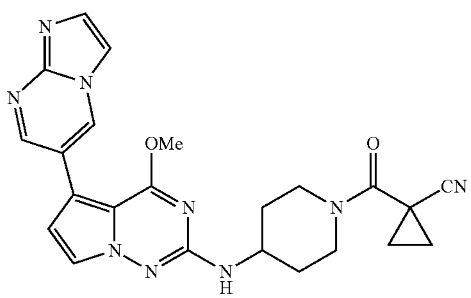 [SMILES: COc1nc(NC2CCN(C(=O)C3(C#N)CC3)CC2)nn2ccc(-c3cnc4nccn4c3)c12]
962
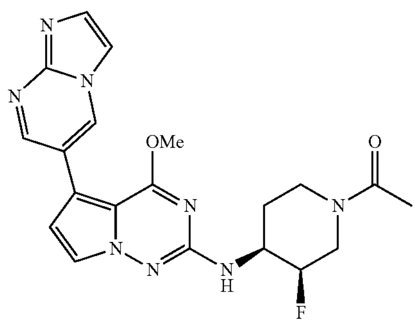 [SMILES: COc1nc(N[C@H]2CCN(C(C)=O)C[C@H]2F)nn2ccc(-c3cnc4nccn4c3)c12]
963
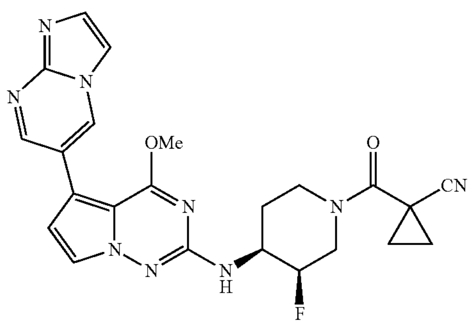 [SMILES: COc1nc(N[C@H]2CCN(C(=O)C3(C#N)CC3)C[C@H]2F)nn2ccc(-c3cnc4nccn4c3)c12]
TABLE 1-continued
964
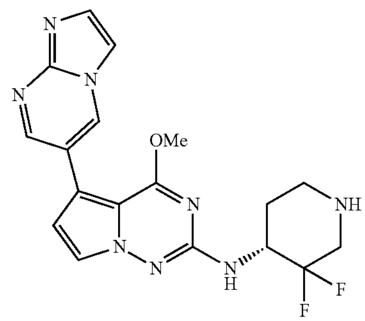 [SMILES: COc1nc(N[C@@H]2CCNCC2(F)F)nn2ccc(-c3cnc4nccn4c3)c12]
965
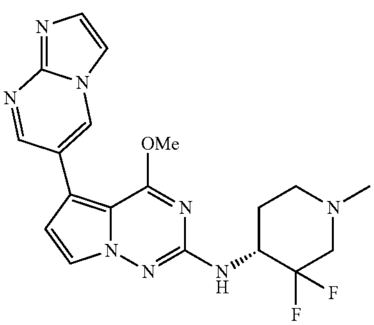 [SMILES: COc1nc(N[C@@H]2CCN(C)CC2(F)F)nn2ccc(-c3cnc4nccn4c3)c12]
966
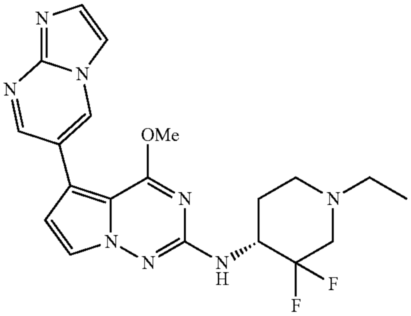 [SMILES: CCN1CC[C@@H](Nc2nc(OC)c3c(-c4cnc5nccn5c4)ccn3n2)C(F)(F)C1]
967
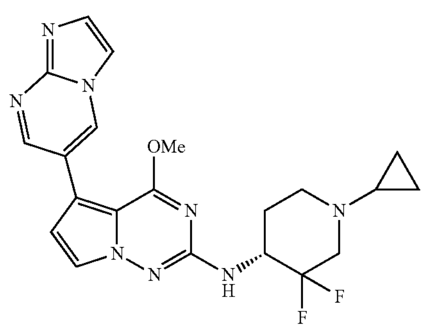 [SMILES: COc1nc(N[C@@H]2CCN(C3CC3)CC2(F)F)nn2ccc(-c3cnc4nccn4c3)c12]
968
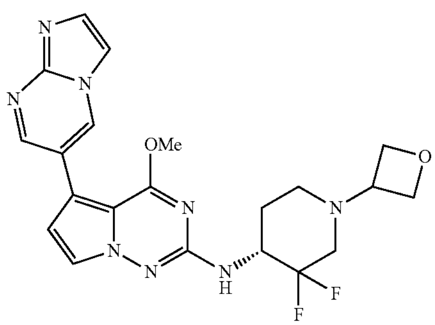 [SMILES: COc1nc(N[C@@H]2CCN(C3COC3)CC2(F)F)nn2ccc(-c3cnc4nccn4c3)c12]

TABLE 1-continued
969
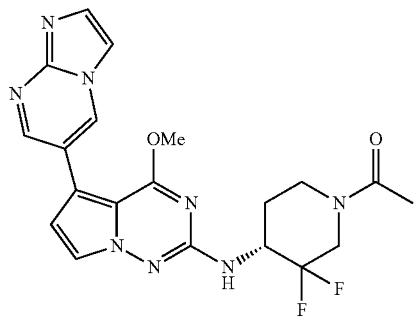 [SMILES: COc1nc(N[C@@H]2CCN(C(C)=O)CC2(F)F)nn2ccc(-c3cnc4nccn4c3)c12]
970
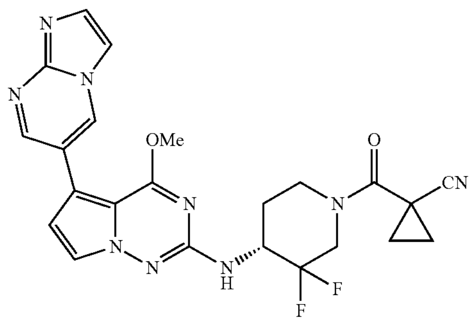 [SMILES: COc1nc(N[C@@H]2CCN(C(=O)C3(C#N)CC3)CC2(F)F)nn2ccc(-c3cnc4nccn4c3)c12]
971
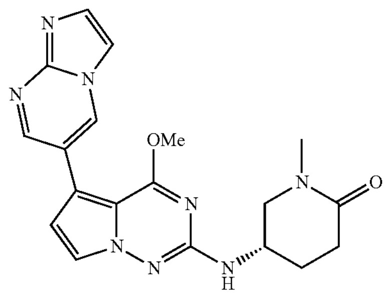 [SMILES: COc1nc(N[C@H]2CCC(=O)N(C)C2)nn2ccc(-c3cnc4nccn4c3)c12]
972
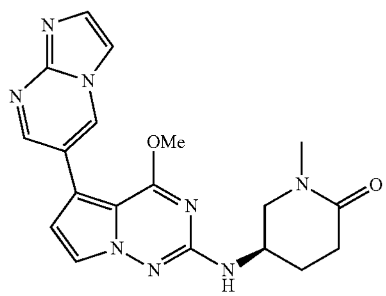 [SMILES: COc1nc(N[C@@H]2CCC(=O)N(C)C2)nn2ccc(-c3cnc4nccn4c3)c12]
973
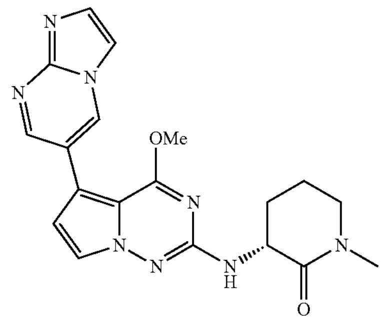 [SMILES: COc1nc(N[C@@H]2CCCN(C)C2=O)nn2ccc(-c3cnc4nccn4c3)c12]
TABLE 1-continued
974
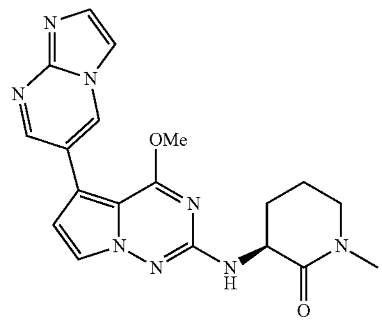 [SMILES: COc1nc(N[C@H]2CCCN(C)C2=O)nn2ccc(-c3cnc4nccn4c3)c12]
975
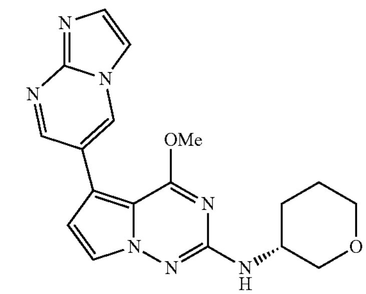 [SMILES: COc1nc(N[C@@H]2CCCOC2)nn2ccc(-c3cnc4nccn4c3)c12]
976
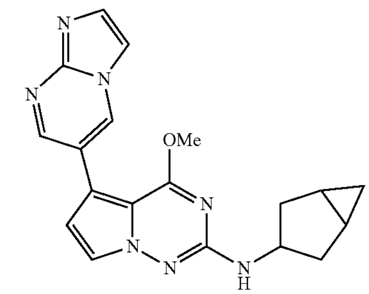 [SMILES: COc1nc(NC2CC3CC3C2)nn2ccc(-c3cnc4nccn4c3)c12]
977
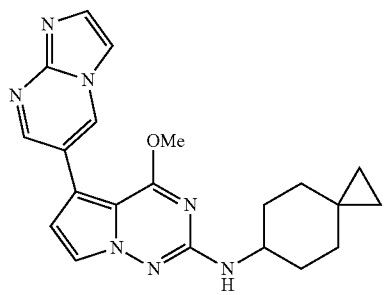 [SMILES: COc1nc(NC2CCC3(CC2)CC3)nn2ccc(-c3cnc4nccn4c3)c12]
978
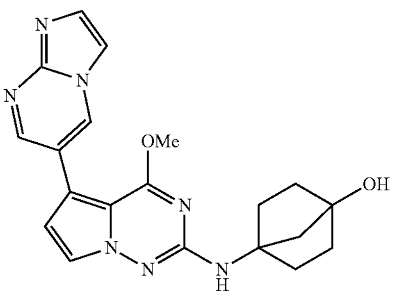 [SMILES: COc1nc(NC23CCC(O)(CC2)C3)nn2ccc(-c3cnc4nccn4c3)c12]

TABLE 1-continued
979
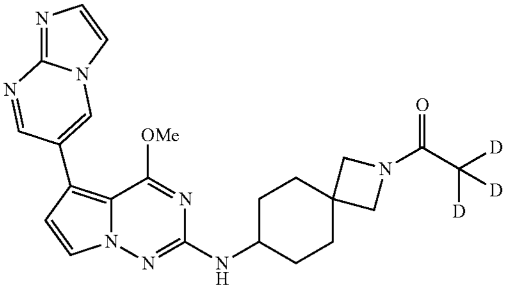 [SMILES: [2H]C([2H])([2H])C(=O)N1CC2(CCC(Nc3nc(OC)c4c(-c5cnc6nccn6c5)ccn4n3)CC2)C1]
980
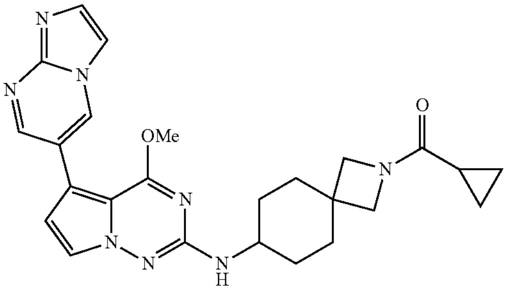 [SMILES: COc1nc(NC2CCC3(CC2)CN(C(=O)C2CC2)C3)nn2ccc(-c3cnc4nccn4c3)c12]
981
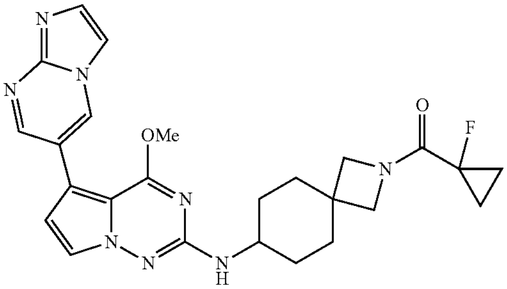 [SMILES: COc1nc(NC2CCC3(CC2)CN(C(=O)C2(F)CC2)C3)nn2ccc(-c3cnc4nccn4c3)c12]
982
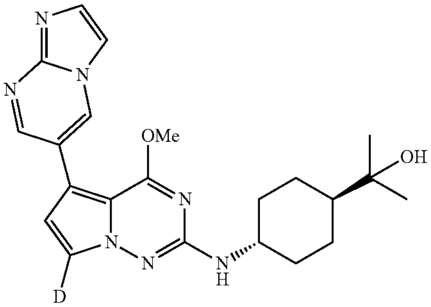 [SMILES: [2H]c1cc(-c2cnc3nccn3c2)c2c(OC)nc(N[C@H]3CC[C@H](C(C)(C)O)CC3)nn12]
983
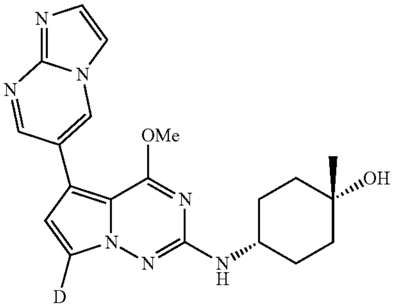 [SMILES: [2H]c1cc(-c2cnc3nccn3c2)c2c(OC)nc(N[C@H]3CC[C@@](C)(O)CC3)nn12]
TABLE 1-continued
984
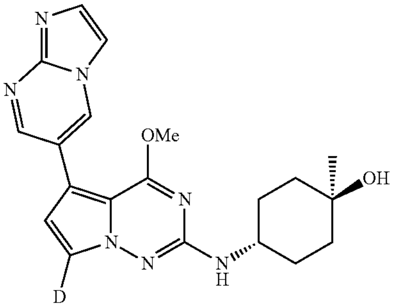 [SMILES: [2H]c1cc(-c2cnc3nccn3c2)c2c(OC)nc(N[C@H]3CC[C@](C)(O)CC3)nn12]
985
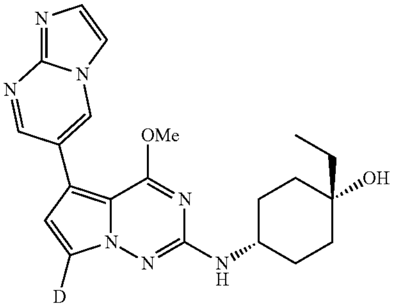 [SMILES: [2H]c1cc(-c2cnc3nccn3c2)c2c(OC)nc(N[C@H]3CC[C@](O)(CC)CC3)nn12]
986
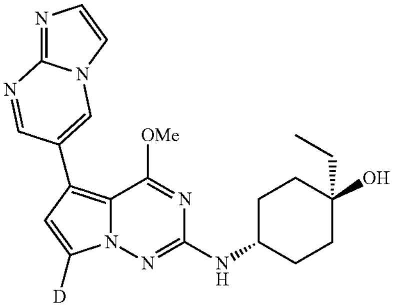 [SMILES: [2H]c1cc(-c2cnc3nccn3c2)c2c(OC)nc(N[C@H]3CC[C@@](O)(CC)CC3)nn12]
987
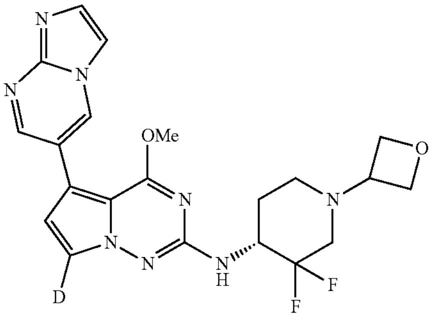 [SMILES: [2H]c1cc(-c2cnc3nccn3c2)c2c(OC)nc(N[C@@H]3CCN(C4COC4)CC3(F)F)nn12]
988
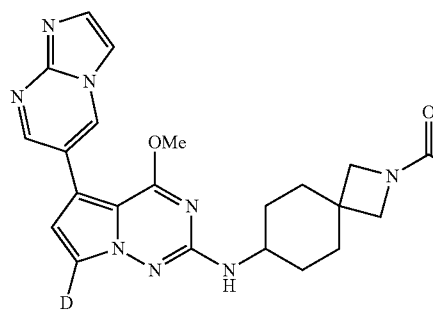

TABLE 1-continued
989
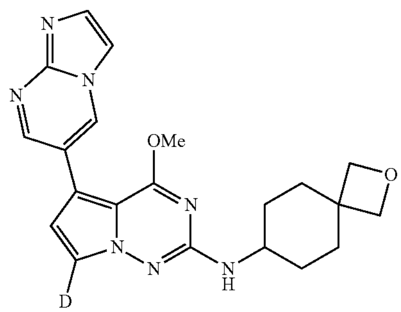 [SMILES: [2H]c1cc(-c2cnc3nccn3c2)c2c(OC)nc(NC3CCC4(CC3)COC4)nn12]
990
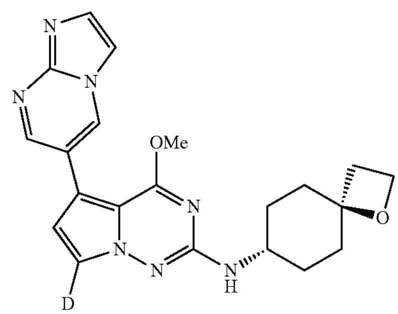 [SMILES: [2H]c1cc(-c2cnc3nccn3c2)c2c(OC)nc(N[C@H]3CC[C@@]4(CCO4)CC3)nn12]
991
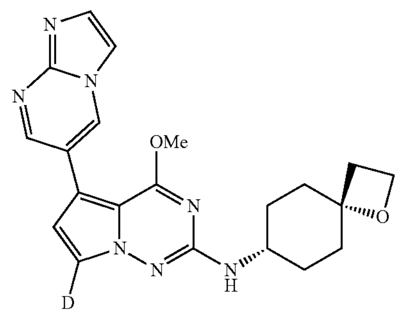 [SMILES: [2H]c1cc(-c2cnc3nccn3c2)c2c(OC)nc(N[C@H]3CC[C@]4(CCO4)CC3)nn12]
992
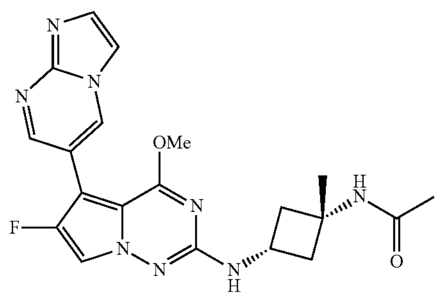 [SMILES: COc1nc(N[C@H]2C[C@@](C)(NC(C)=O)C2)nn2cc(F)c(-c3cnc4nccn4c3)c12]
993
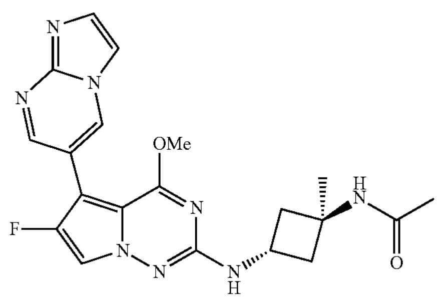 [SMILES: COc1nc(N[C@H]2C[C@](C)(NC(C)=O)C2)nn2cc(F)c(-c3cnc4nccn4c3)c12]
TABLE 1-continued
994
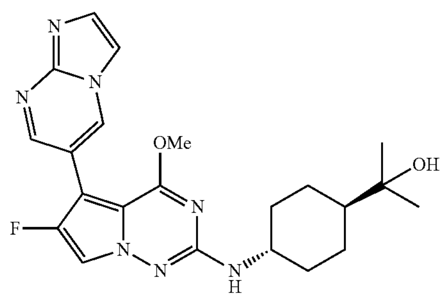 [SMILES: COc1nc(N[C@H]2CC[C@H](C(C)(C)O)CC2)nn2cc(F)c(-c3cnc4nccn4c3)c12]
995
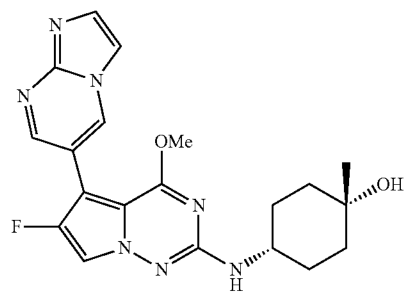 [SMILES: COc1nc(N[C@H]2CC[C@@](C)(O)CC2)nn2cc(F)c(-c3cnc4nccn4c3)c12]
996
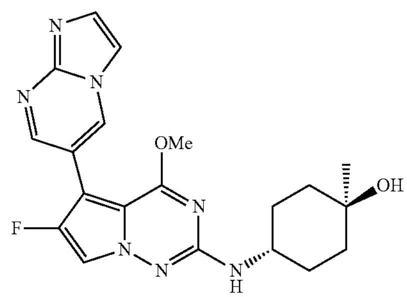 [SMILES: COc1nc(N[C@H]2CC[C@](C)(O)CC2)nn2cc(F)c(-c3cnc4nccn4c3)c12]
997
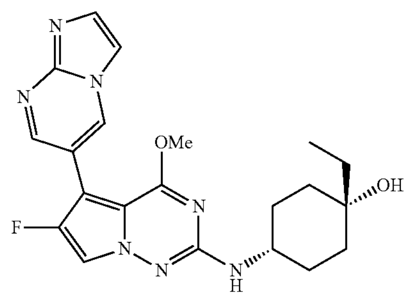 [SMILES: CC[C@]1(O)CC[C@@H](Nc2nc(OC)c3c(-c4cnc5nccn5c4)c(F)cn3n2)CC1]
998
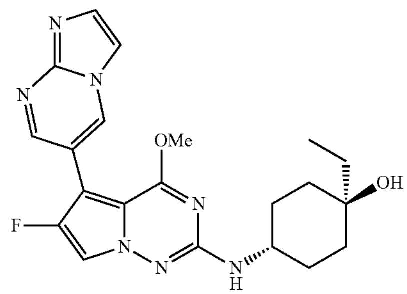 [SMILES: CC[C@]1(O)CC[C@H](Nc2nc(OC)c3c(-c4cnc5nccn5c4)c(F)cn3n2)CC1]

999
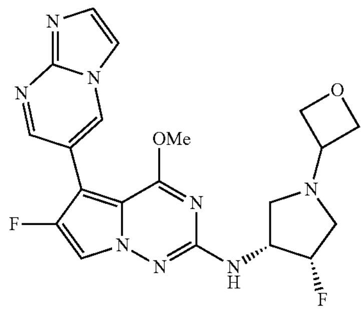 [SMILES: COc1nc(N[C@@H]2CN(C3COC3)C[C@@H]2F)nn2cc(F)c(-c3cnc4nccn4c3)c12]
1000
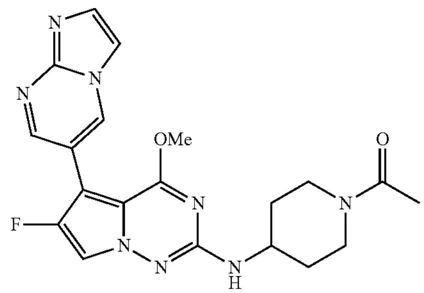 [SMILES: COc1nc(NC2CCN(C(C)=O)CC2)nn2cc(F)c(-c3cnc4nccn4c3)c12]
1001
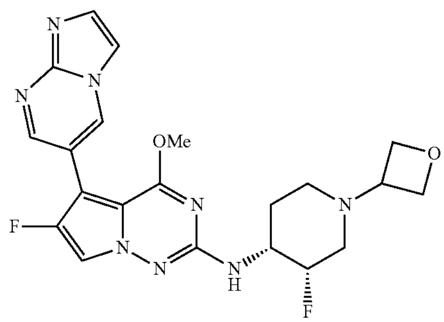 [SMILES: COc1nc(N[C@@H]2CCN(C3COC3)C[C@@H]2F)nn2cc(F)c(-c3cnc4nccn4c3)c12]
1002
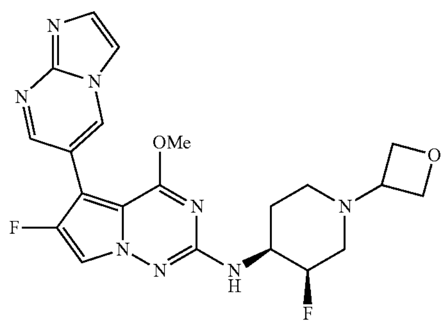 [SMILES: COc1nc(N[C@H]2CCN(C3COC3)C[C@H]2F)nn2cc(F)c(-c3cnc4nccn4c3)c12]
1003
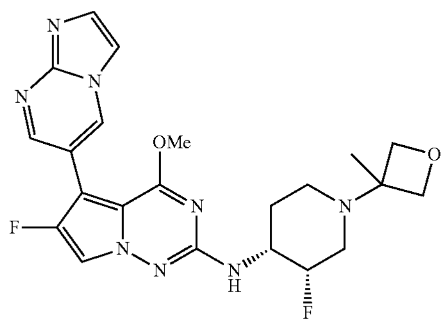 [SMILES: COc1nc(N[C@@H]2CCN(C3(C)COC3)C[C@@H]2F)nn2cc(F)c(-c3cnc4nccn4c3)c12]
1004
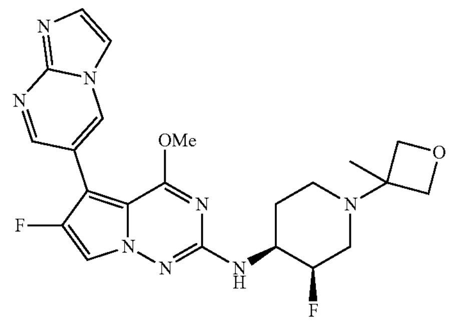 [SMILES: COc1nc(N[C@H]2CCN(C3(C)COC3)C[C@H]2F)nn2cc(F)c(-c3cnc4nccn4c3)c12]
1005
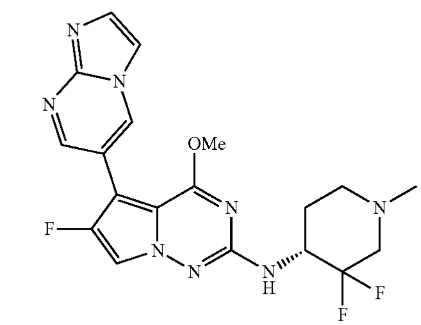 [SMILES: COc1nc(N[C@@H]2CCN(C)CC2(F)F)nn2cc(F)c(-c3cnc4nccn4c3)c12]
1006
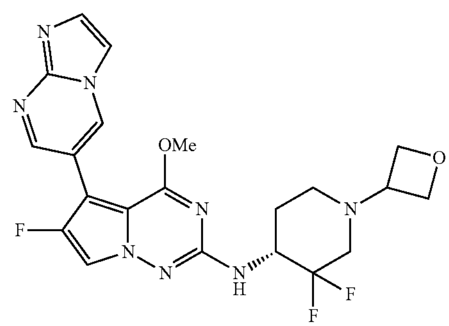 [SMILES: COc1nc(N[C@@H]2CCN(C3COC3)CC2(F)F)nn2cc(F)c(-c3cnc4nccn4c3)c12]
1007
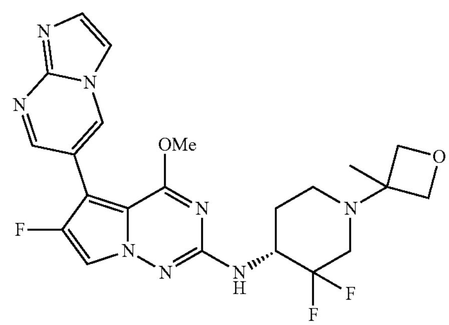 [SMILES: COc1nc(N[C@@H]2CCN(C3(C)COC3)CC2(F)F)nn2cc(F)c(-c3cnc4nccn4c3)c12]
1008
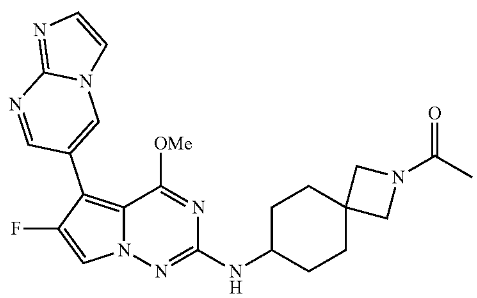 [SMILES: COc1nc(NC2CCC3(CC2)CN(C(C)=O)C3)nn2cc(F)c(-c3cnc4nccn4c3)c12]

1009
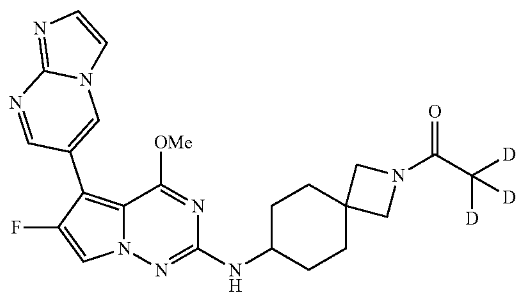 [SMILES: [2H]C([2H])([2H])C(=O)N1CC2(CCC(Nc3nc(OC)c4c(-c5cnc6nccn6c5)c(F)cn4n3)CC2)C1]
1010
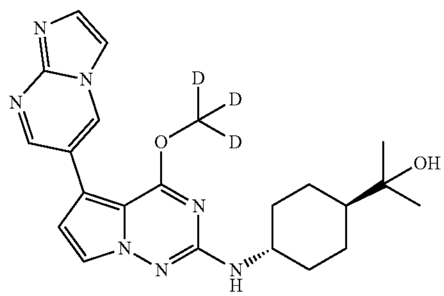 [SMILES: [2H]C([2H])([2H])Oc1nc(N[C@H]2CC[C@H](C(C)(C)O)CC2)nn2ccc(-c3cnc4nccn4c3)c12]
1011
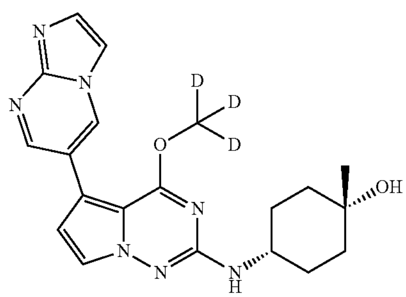 [SMILES: [2H]C([2H])([2H])Oc1nc(N[C@H]2CC[C@@](C)(O)CC2)nn2ccc(-c3cnc4nccn4c3)c12]
1012
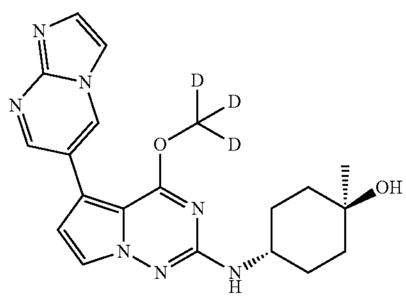 [SMILES: [2H]C([2H])([2H])Oc1nc(N[C@H]2CC[C@](C)(O)CC2)nn2ccc(-c3cnc4nccn4c3)c12]
1013
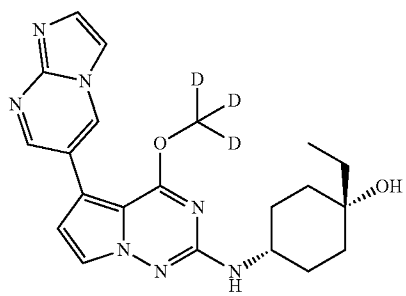 [SMILES: [2H]C([2H])([2H])Oc1nc(N[C@H]2CC[C@](O)(CC)CC2)nn2ccc(-c3cnc4nccn4c3)c12]
1014
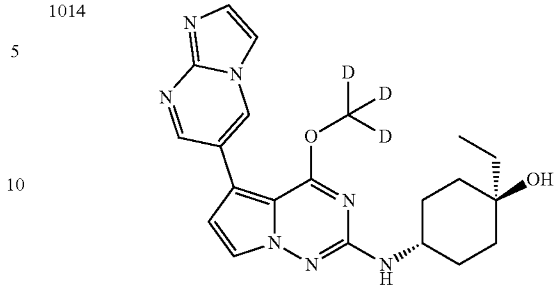
1015
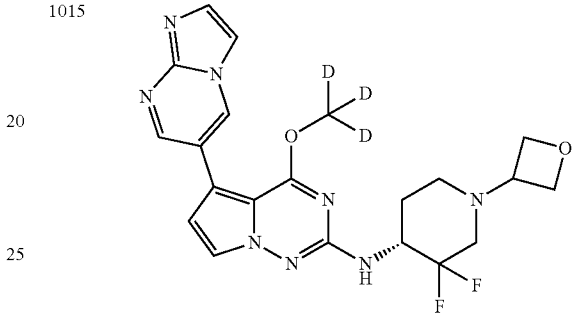
1016
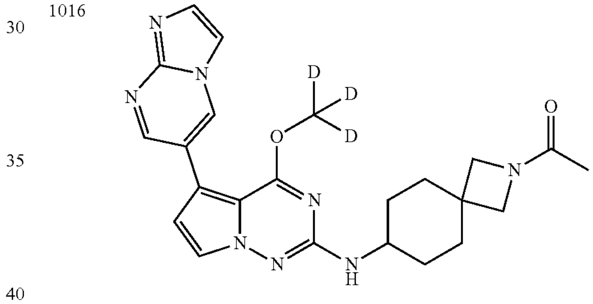
1017
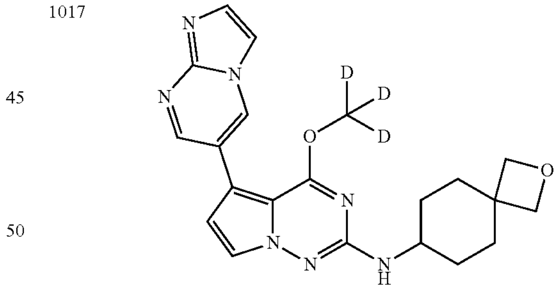
1018
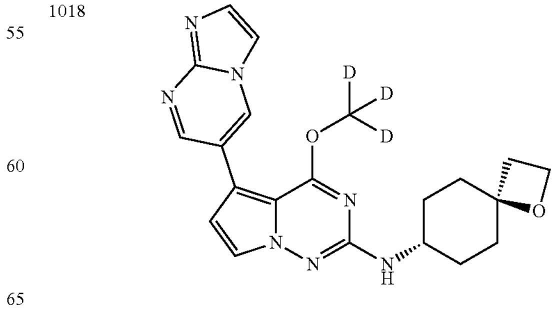

TABLE 1-continued
1019
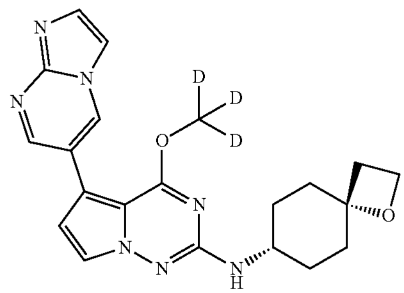 [SMILES: [2H]C([2H])([2H])Oc1nc(N[C@H]2CC[C@]3(CCO3)CC2)nn2ccc(-c3cnc4nccn4c3)c12]
1020
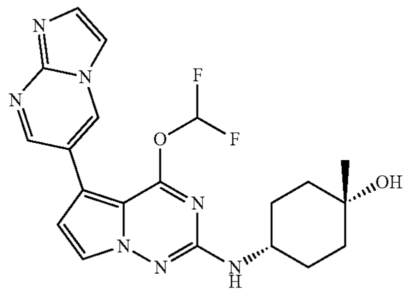 [SMILES: C[C@]1(O)CC[C@@H](Nc2nc(OC(F)F)c3c(-c4cnc5nccn5c4)ccn3n2)CC1]
1021
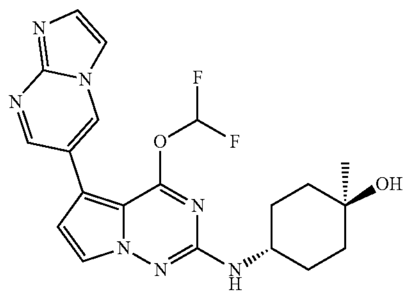 [SMILES: C[C@]1(O)CC[C@H](Nc2nc(OC(F)F)c3c(-c4cnc5nccn5c4)ccn3n2)CC1]
1022
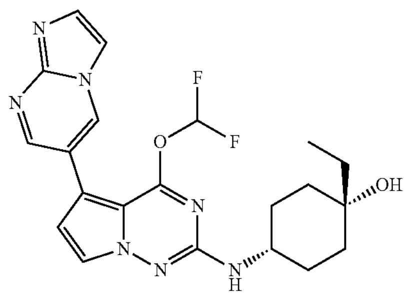 [SMILES: CC[C@]1(O)CC[C@@H](Nc2nc(OC(F)F)c3c(-c4cnc5nccn5c4)ccn3n2)CC1]
1023
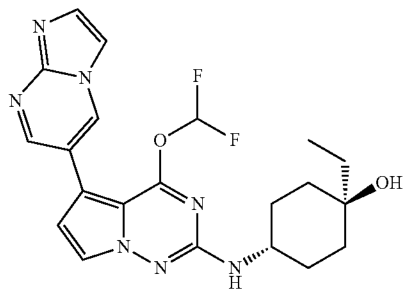 [SMILES: CC[C@]1(O)CC[C@H](Nc2nc(OC(F)F)c3c(-c4cnc5nccn5c4)ccn3n2)CC1]
TABLE 1-continued
1024
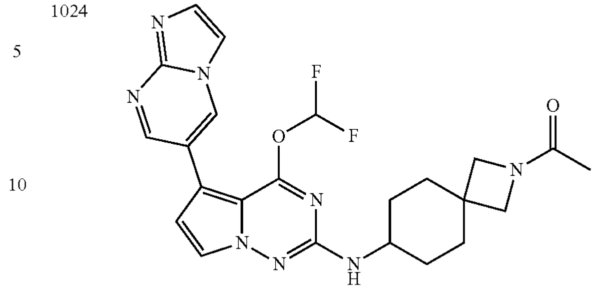
1025
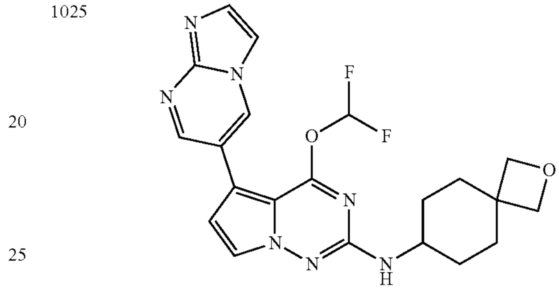
1026
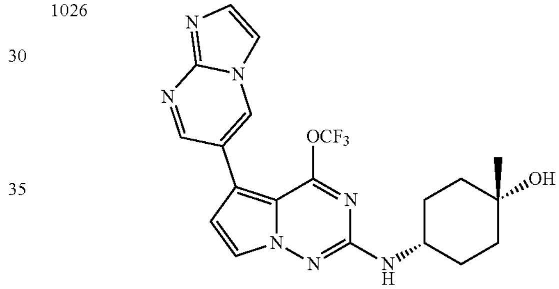
1027
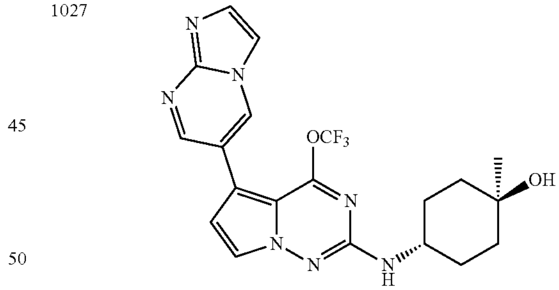
1028
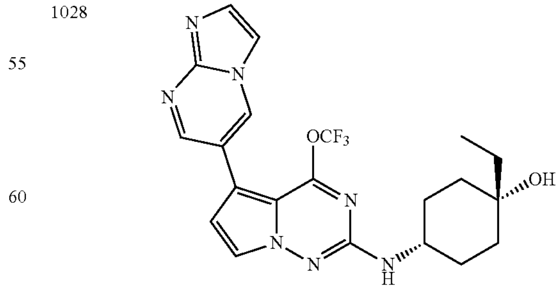

1029
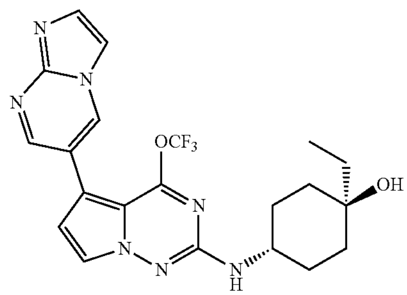 [SMILES: CC[C@]1(O)CC[C@H](Nc2nc(OC(F)(F)F)c3c(-c4cnc5nccn5c4)ccn3n2)CC1]
1030
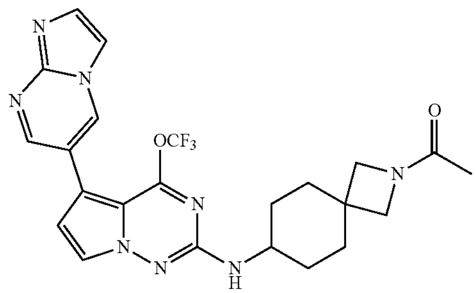 [SMILES: CC(=O)N1CC2(CCC(Nc3nc(OC(F)(F)F)c4c(-c5cnc6nccn6c5)ccn4n3)CC2)C1]
1031
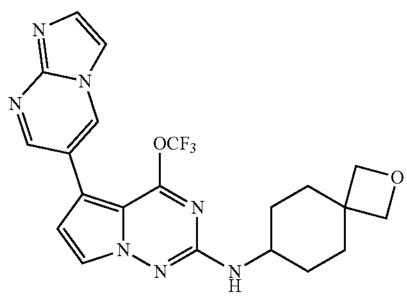 [SMILES: FC(F)(F)Oc1nc(NC2CCC3(CC2)COC3)nn2ccc(-c3cnc4nccn4c3)c12]
1032
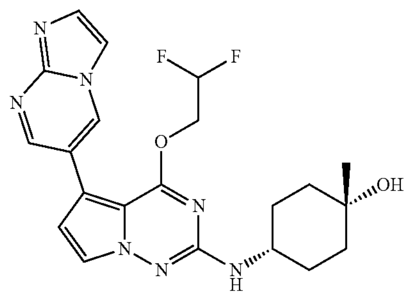 [SMILES: C[C@]1(O)CC[C@@H](Nc2nc(OCC(F)F)c3c(-c4cnc5nccn5c4)ccn3n2)CC1]
1033
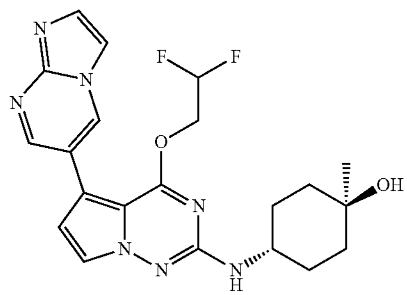 [SMILES: C[C@]1(O)CC[C@H](Nc2nc(OCC(F)F)c3c(-c4cnc5nccn5c4)ccn3n2)CC1]
1034
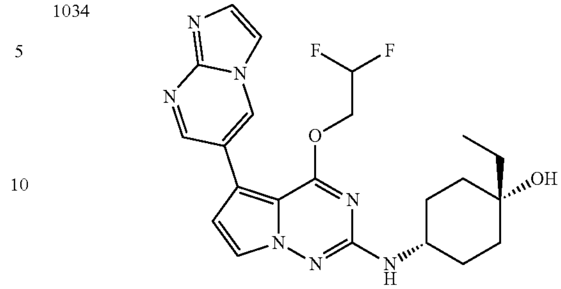
1035
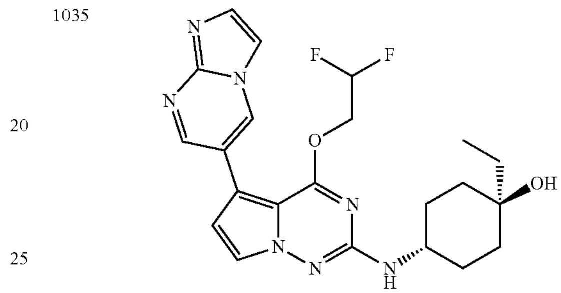
1036
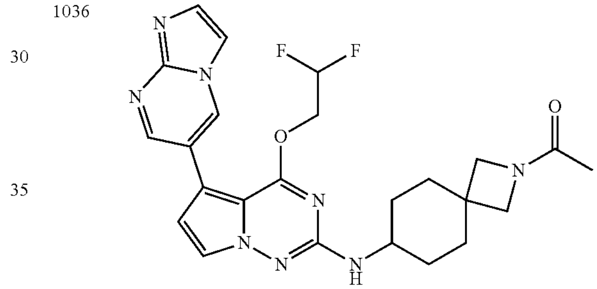
1037
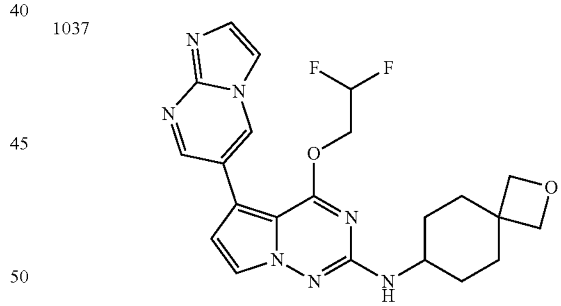
1038
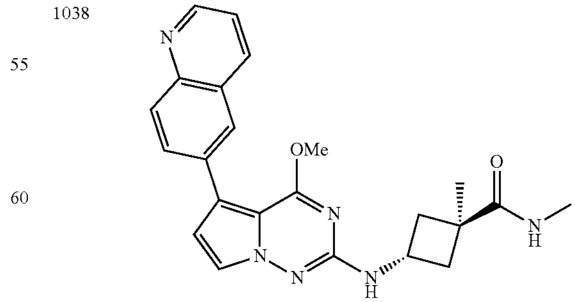

TABLE 1-continued
1039
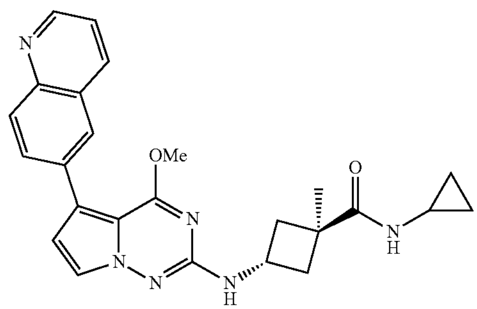 [SMILES: COc1nc(N[C@H]2C[C@](C)(C(=O)NC3CC3)C2)nn2ccc(-c3ccc4ncccc4c3)c12]
1040
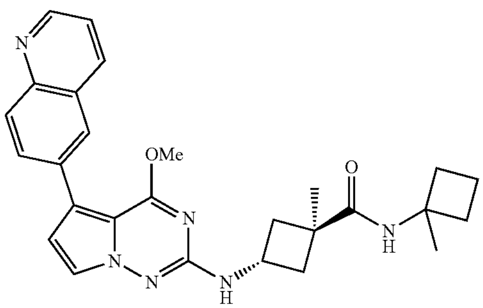 [SMILES: COc1nc(N[C@H]2C[C@](C)(C(=O)NC3(C)CCC3)C2)nn2ccc(-c3ccc4ncccc4c3)c12]
1041
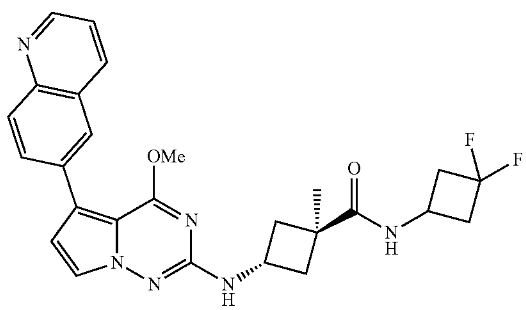 [SMILES: COc1nc(N[C@H]2C[C@](C)(C(=O)NC3CC(F)(F)C3)C2)nn2ccc(-c3ccc4ncccc4c3)c12]
1042
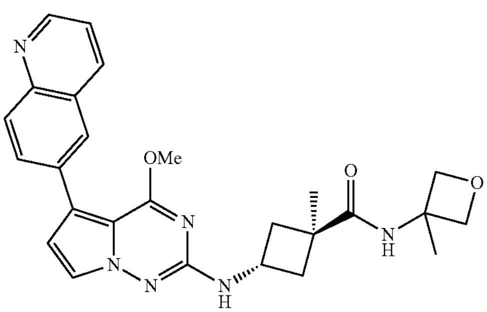 [SMILES: COc1nc(N[C@H]2C[C@](C)(C(=O)NC3(C)COC3)C2)nn2ccc(-c3ccc4ncccc4c3)c12]
1043
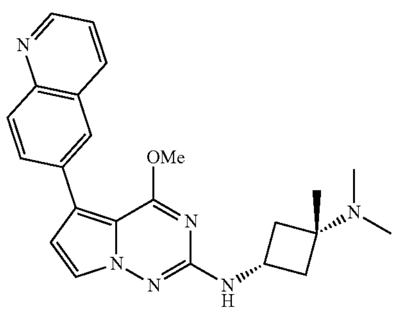 [SMILES: COc1nc(N[C@H]2C[C@@](C)(N(C)C)C2)nn2ccc(-c3ccc4ncccc4c3)c12]
TABLE 1-continued
1044
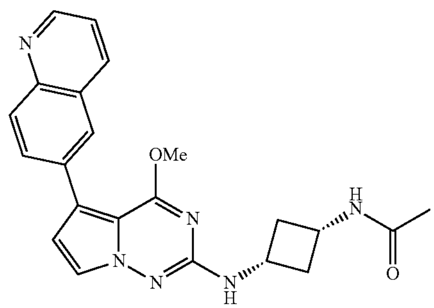 [SMILES: COc1nc(N[C@H]2C[C@@H](NC(C)=O)C2)nn2ccc(-c3ccc4ncccc4c3)c12]
1045
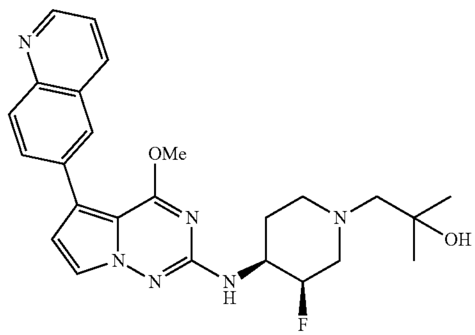 [SMILES: COc1nc(N[C@H]2CCN(CC(C)(C)O)C[C@H]2F)nn2ccc(-c3ccc4ncccc4c3)c12]
1046
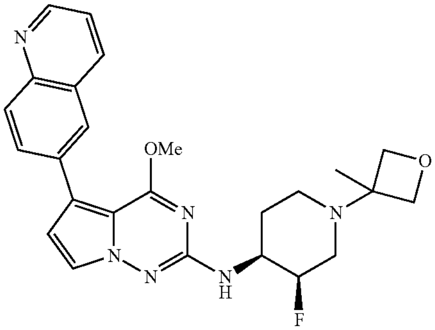 [SMILES: COc1nc(N[C@H]2CCN(C3(C)COC3)C[C@H]2F)nn2ccc(-c3ccc4ncccc4c3)c12]
1047
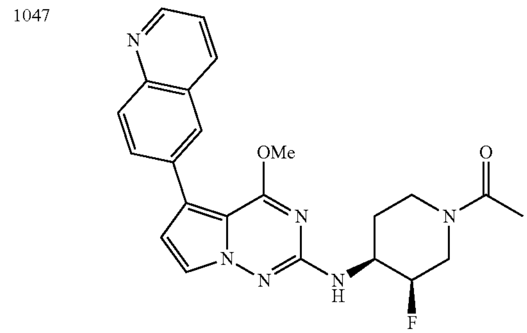
1048
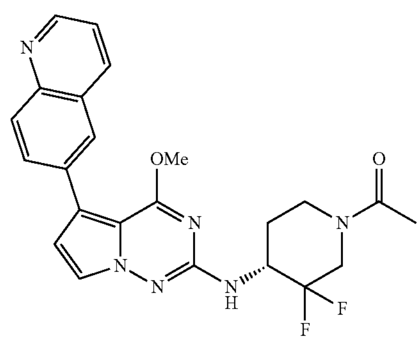 [SMILES: COc1nc(N[C@@H]2CCN(C(C)=O)CC2(F)F)nn2ccc(-c3ccc4ncccc4c3)c12]

TABLE 1-continued
1049
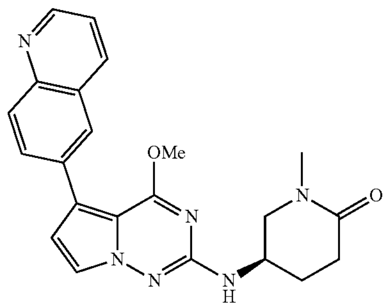 [SMILES: COc1nc(N[C@@H]2CCC(=O)N(C)C2)nn2ccc(-c3ccc4ncccc4c3)c12]
1050
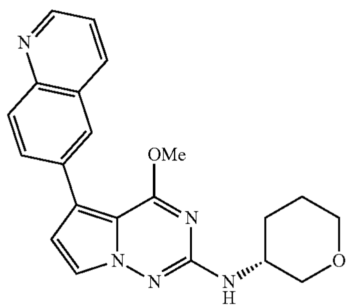 [SMILES: COc1nc(N[C@@H]2CCCOC2)nn2ccc(-c3ccc4ncccc4c3)c12]
1051
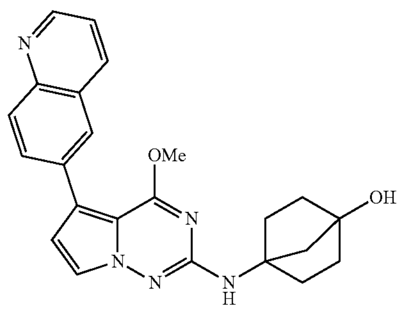 [SMILES: COc1nc(NC23CCC(O)(CC2)C3)nn2ccc(-c3ccc4ncccc4c3)c12]
1052
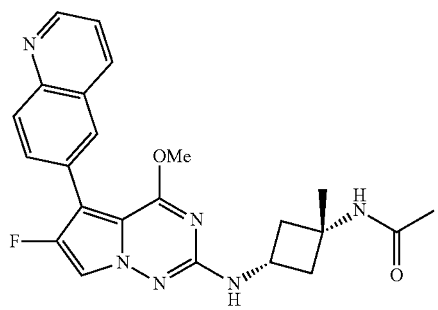 [SMILES: COc1nc(N[C@H]2C[C@@](C)(NC(C)=O)C2)nn2cc(F)c(-c3ccc4ncccc4c3)c12]
1053
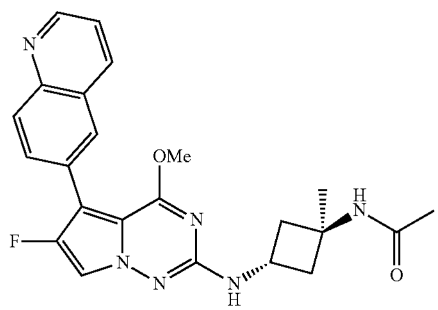 [SMILES: COc1nc(N[C@H]2C[C@](C)(NC(C)=O)C2)nn2cc(F)c(-c3ccc4ncccc4c3)c12]
1054
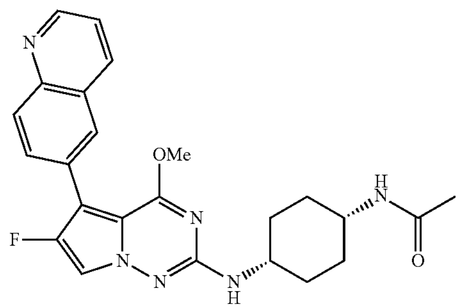 [SMILES: COc1nc(N[C@H]2CC[C@@H](NC(C)=O)CC2)nn2cc(F)c(-c3ccc4ncccc4c3)c12]
1055
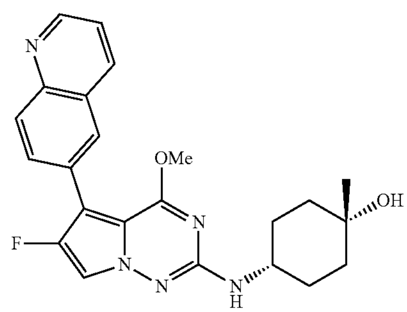 [SMILES: COc1nc(N[C@H]2CC[C@@](C)(O)CC2)nn2cc(F)c(-c3ccc4ncccc4c3)c12]
1056
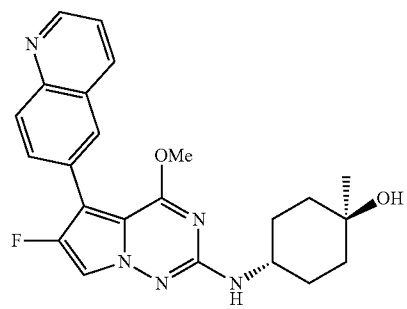 [SMILES: COc1nc(N[C@H]2CC[C@](C)(O)CC2)nn2cc(F)c(-c3ccc4ncccc4c3)c12]
1057
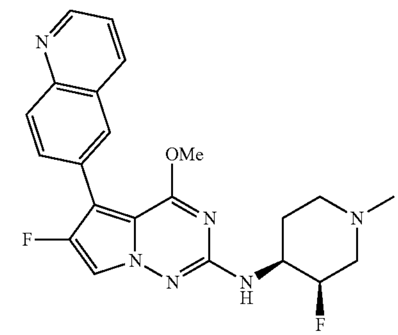 [SMILES: COc1nc(N[C@H]2CCN(C)C[C@H]2F)nn2cc(F)c(-c3ccc4ncccc4c3)c12]
1058
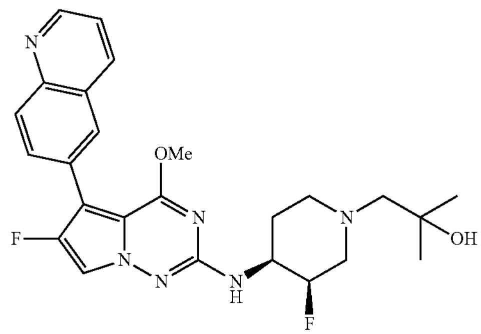 [SMILES: COc1nc(N[C@H]2CCN(CC(C)(C)O)C[C@H]2F)nn2cc(F)c(-c3ccc4ncccc4c3)c12]

TABLE 1-continued
1059
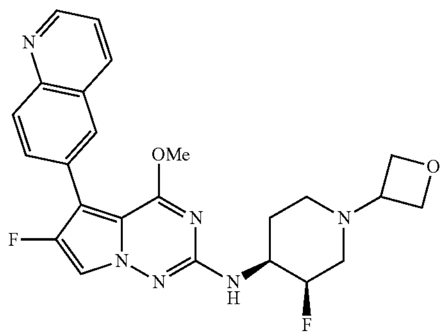 [SMILES: COc1nc(N[C@H]2CCN(C3COC3)C[C@H]2F)nn2cc(F)c(-c3ccc4ncccc4c3)c12]
1060
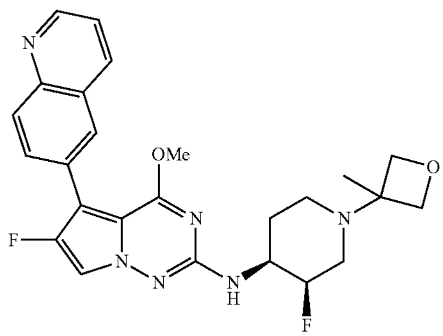 [SMILES: COc1nc(N[C@H]2CCN(C3(C)COC3)C[C@H]2F)nn2cc(F)c(-c3ccc4ncccc4c3)c12]
1061
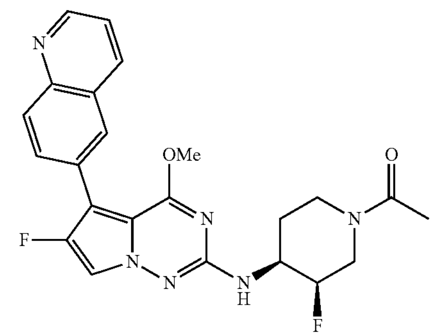 [SMILES: COc1nc(N[C@H]2CCN(C(C)=O)C[C@H]2F)nn2cc(F)c(-c3ccc4ncccc4c3)c12]
1062
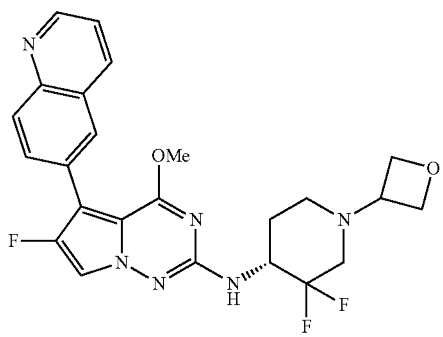 [SMILES: COc1nc(N[C@@H]2CCN(C3COC3)CC2(F)F)nn2cc(F)c(-c3ccc4ncccc4c3)c12]
TABLE 1-continued
1063
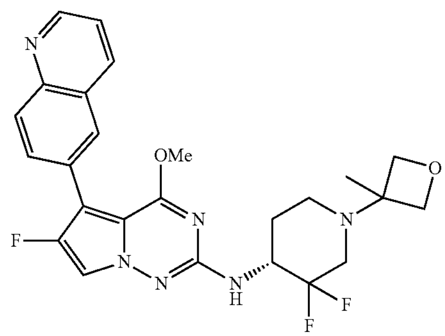 [SMILES: COc1nc(N[C@@H]2CCN(C3(C)COC3)CC2(F)F)nn2cc(F)c(-c3ccc4ncccc4c3)c12]
1064
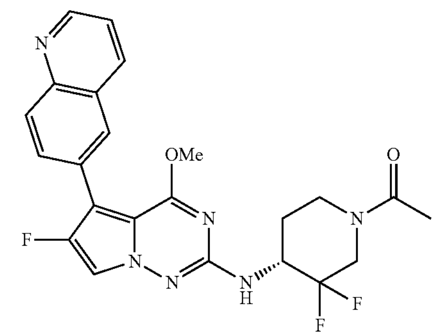 [SMILES: COc1nc(N[C@@H]2CCN(C(C)=O)CC2(F)F)nn2cc(F)c(-c3ccc4ncccc4c3)c12]
1065
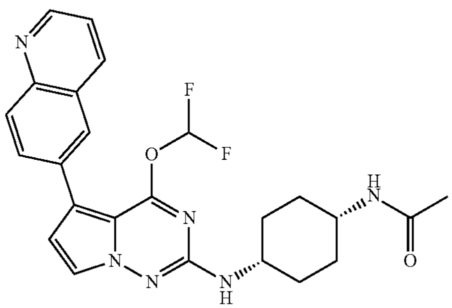 [SMILES: CC(=O)N[C@H]1CC[C@@H](Nc2nc(OC(F)F)c3c(-c4ccc5ncccc5c4)ccn3n2)CC1]
1066
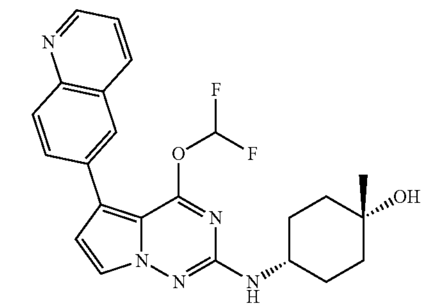 [SMILES: C[C@]1(O)CC[C@@H](Nc2nc(OC(F)F)c3c(-c4ccc5ncccc5c4)ccn3n2)CC1]
1067
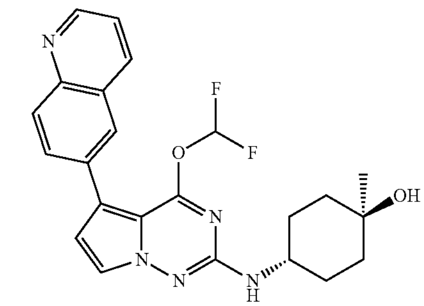 [SMILES: C[C@]1(O)CC[C@H](Nc2nc(OC(F)F)c3c(-c4ccc5ncccc5c4)ccn3n2)CC1]

TABLE 1-continued
1068
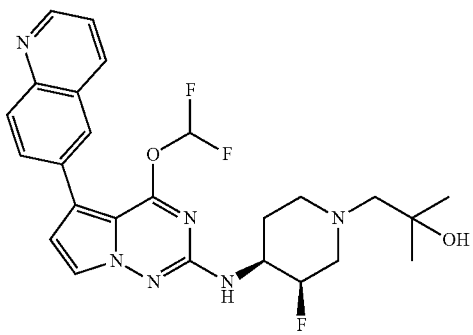 [SMILES: CC(C)(O)CN1CC[C@H](Nc2nc(OC(F)F)c3c(-c4ccc5ncccc5c4)ccn3n2)[C@H](F)C1]
1069
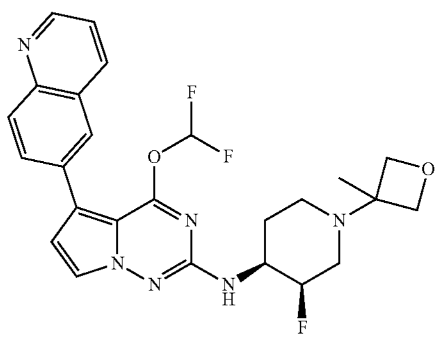 [SMILES: CC1(N2CC[C@H](Nc3nc(OC(F)F)c4c(-c5ccc6ncccc6c5)ccn4n3)[C@H](F)C2)COC1]
1070
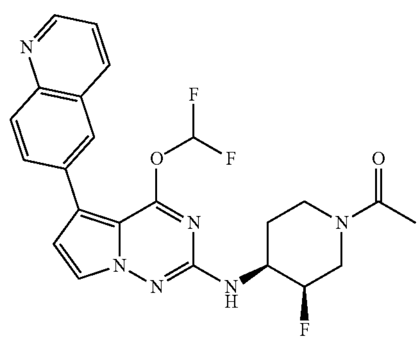 [SMILES: CC(=O)N1CC[C@H](Nc2nc(OC(F)F)c3c(-c4ccc5ncccc5c4)ccn3n2)[C@H](F)C1]
1071
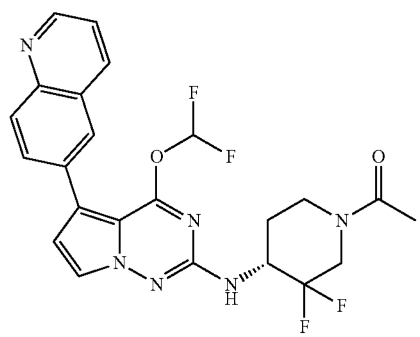 [SMILES: CC(=O)N1CC[C@@H](Nc2nc(OC(F)F)c3c(-c4ccc5ncccc5c4)ccn3n2)C(F)(F)C1]
1072
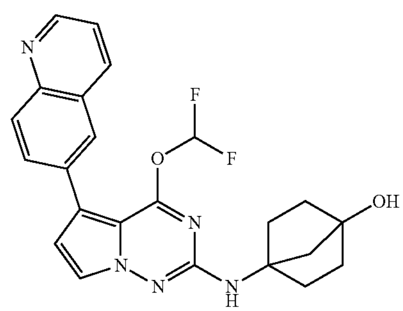 [SMILES: OC12CCC(Nc3nc(OC(F)F)c4c(-c5ccc6ncccc6c5)ccn4n3)(CC1)C2]
TABLE 1-continued
1073
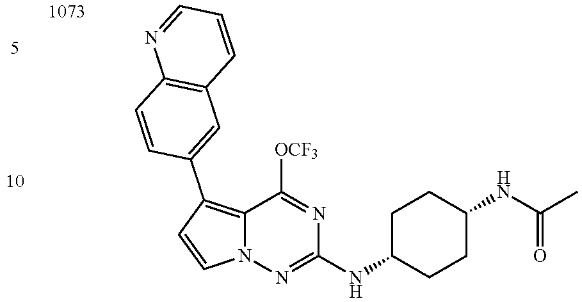
1074
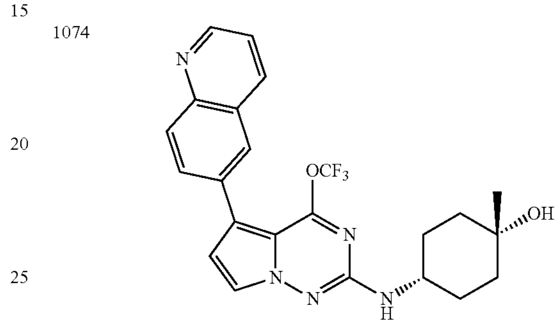
1075
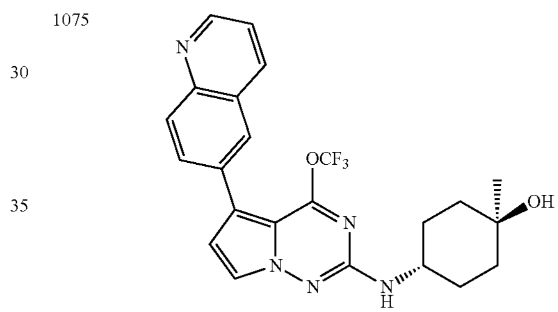
1076
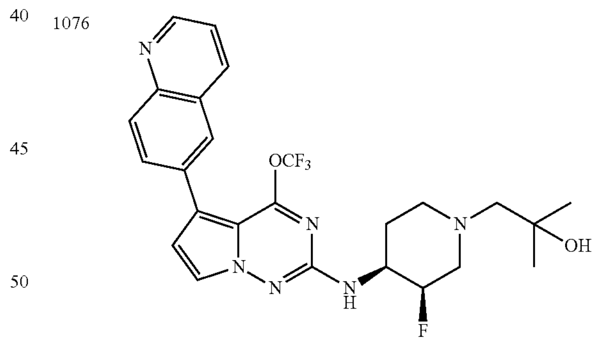
1077
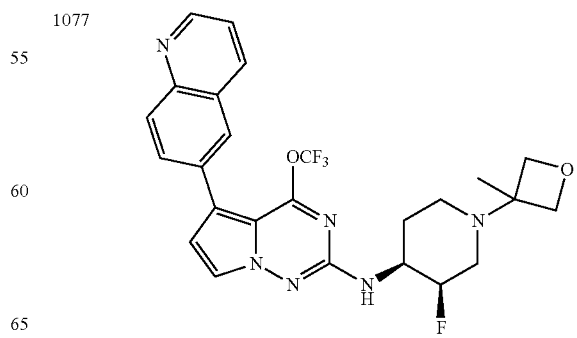

TABLE 1-continued
1078
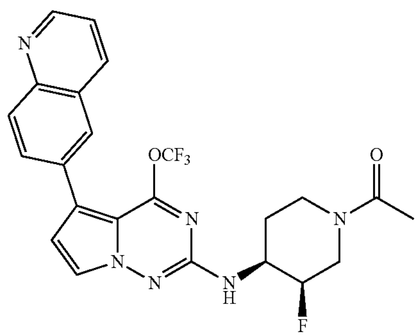 [SMILES: CC(=O)N1CC[C@H](Nc2nc(OC(F)(F)F)c3c(-c4ccc5ncccc5c4)ccn3n2)[C@H](F)C1]
1079
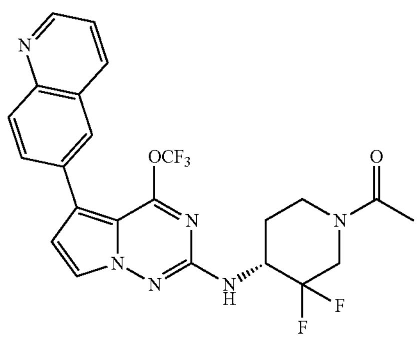 [SMILES: CC(=O)N1CC[C@@H](Nc2nc(OC(F)(F)F)c3c(-c4ccc5ncccc5c4)ccn3n2)C(F)(F)C1]
1080
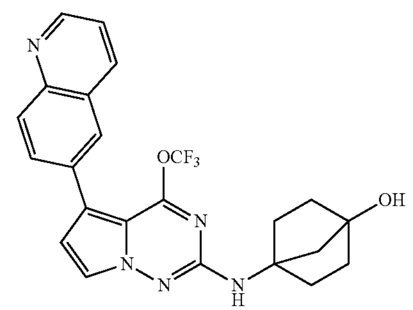
1081
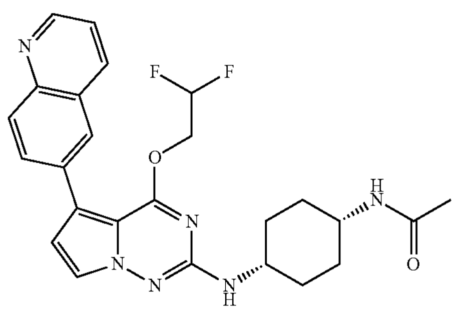 [SMILES: CC(=O)N[C@H]1CC[C@@H](Nc2nc(OCC(F)F)c3c(-c4ccc5ncccc5c4)ccn3n2)CC1]
1082
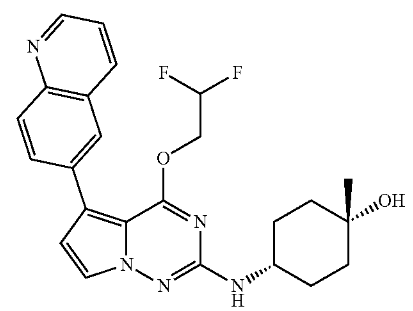
TABLE 1-continued
1083
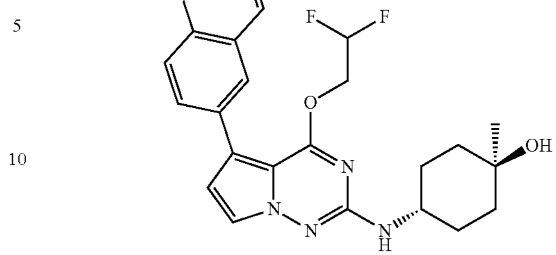
1084
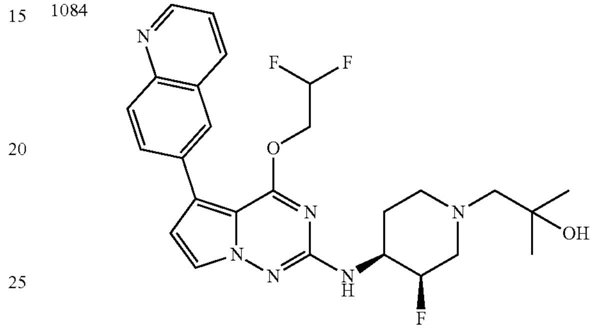
1085
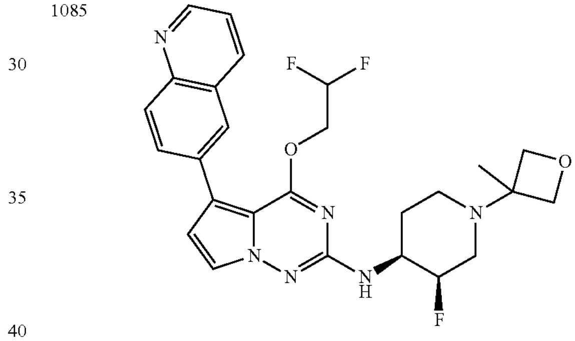
1086
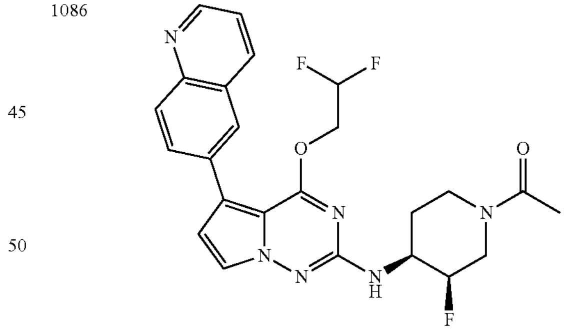
1087
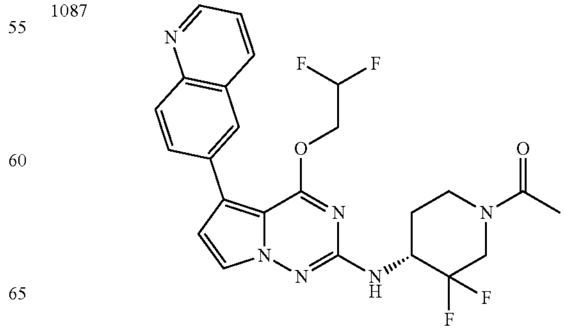

TABLE 1-continued
1088
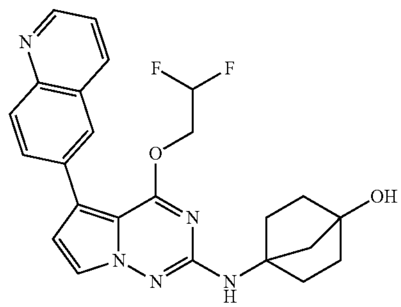
1089
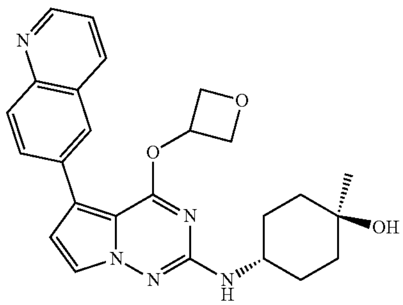 [SMILES: C[C@]1(O)CC[C@H](Nc2nc(OC3COC3)c3c(-c4ccc5ncccc5c4)ccn3n2)CC1]
1090
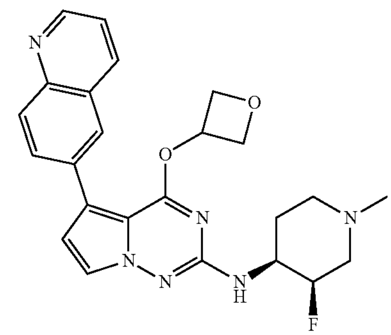 [SMILES: CN1CC[C@H](Nc2nc(OC3COC3)c3c(-c4ccc5ncccc5c4)ccn3n2)[C@H](F)C1]
1091
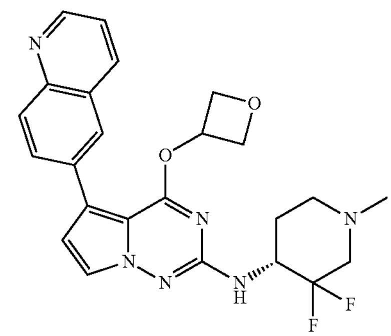 [SMILES: CN1CC[C@@H](Nc2nc(OC3COC3)c3c(-c4ccc5ncccc5c4)ccn3n2)C(F)(F)C1]
1092
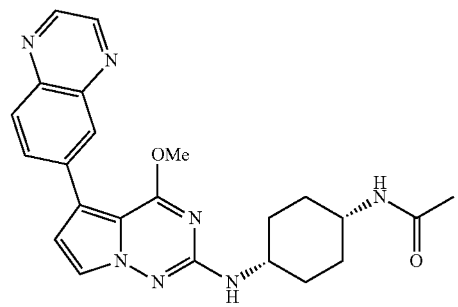
TABLE 1-continued
1093
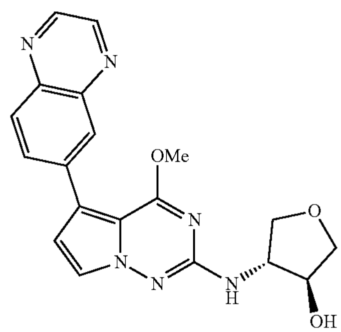 [SMILES: COc1nc(N[C@@H]2COC[C@H]2O)nn2ccc(-c3ccc4nccnc4c3)c12]
1094
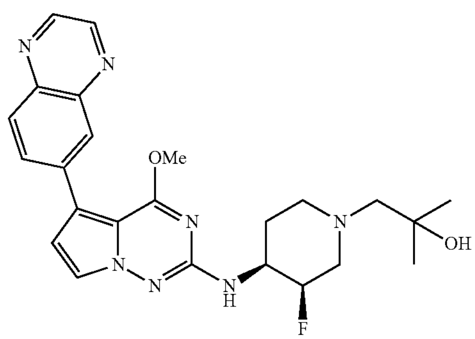 [SMILES: COc1nc(N[C@H]2CCN(CC(C)(C)O)C[C@H]2F)nn2ccc(-c3ccc4nccnc4c3)c12]
1095
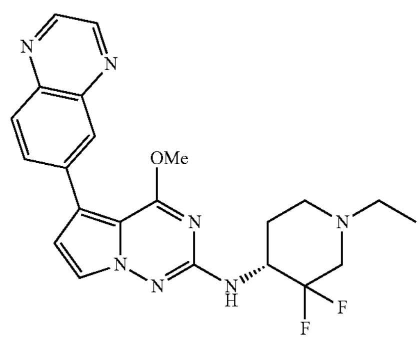 [SMILES: CCN1CC[C@@H](Nc2nc(OC)c3c(-c4ccc5nccnc5c4)ccn3n2)C(F)(F)C1]
1096
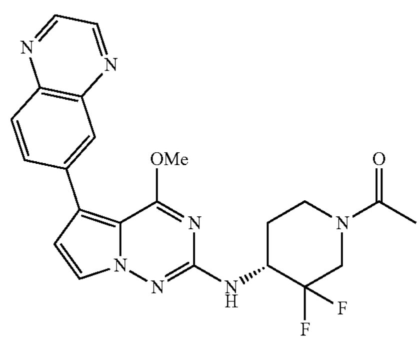 [SMILES: COc1nc(N[C@@H]2CCN(C(C)=O)CC2(F)F)nn2ccc(-c3ccc4nccnc4c3)c12]
1097
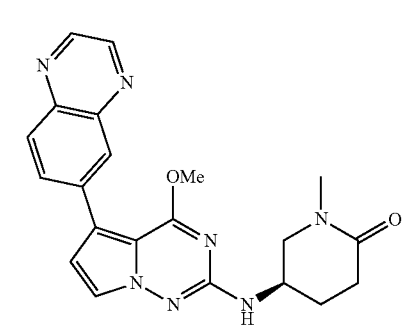 [SMILES: COc1nc(N[C@@H]2CCC(=O)N(C)C2)nn2ccc(-c3ccc4nccnc4c3)c12]

TABLE 1-continued
1098
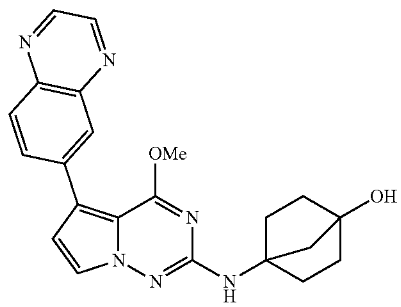
1099
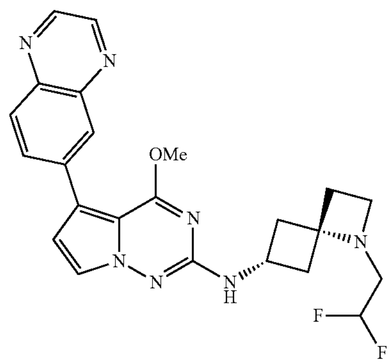 [SMILES: COc1nc(N[C@H]2C[C@]3(CCN3CC(F)F)C2)nn2ccc(-c3ccc4nccnc4c3)c12]
1100
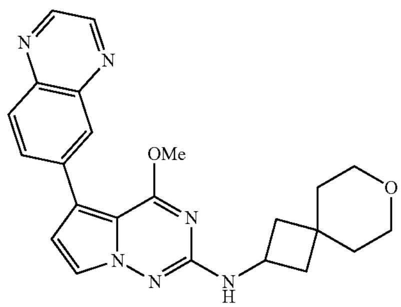 [SMILES: COc1nc(NC2CC3(CCOCC3)C2)nn2ccc(-c3ccc4nccnc4c3)c12]
1101
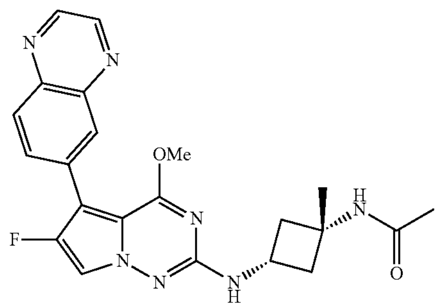 [SMILES: COc1nc(N[C@H]2C[C@@](C)(NC(C)=O)C2)nn2cc(F)c(-c3ccc4nccnc4c3)c12]
1102
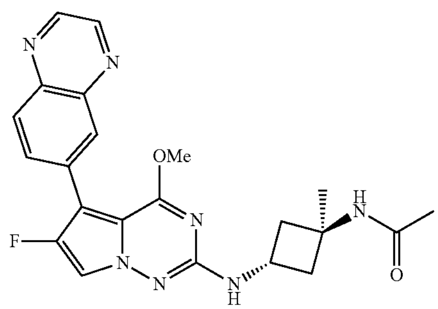
TABLE 1-continued
1103
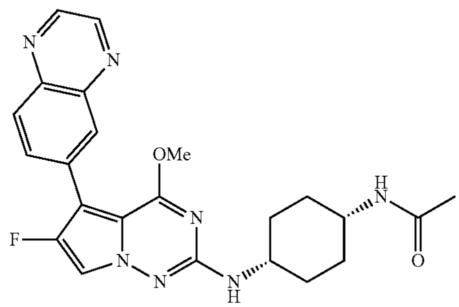 [SMILES: COc1nc(N[C@H]2CC[C@@H](NC(C)=O)CC2)nn2cc(F)c(-c3ccc4nccnc4c3)c12]
1104
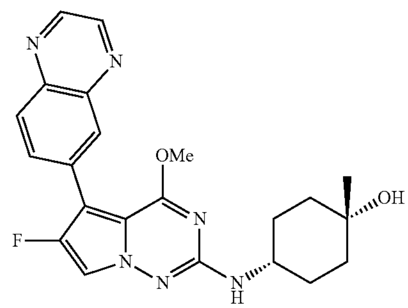 [SMILES: COc1nc(N[C@H]2CC[C@@](C)(O)CC2)nn2cc(F)c(-c3ccc4nccnc4c3)c12]
1105
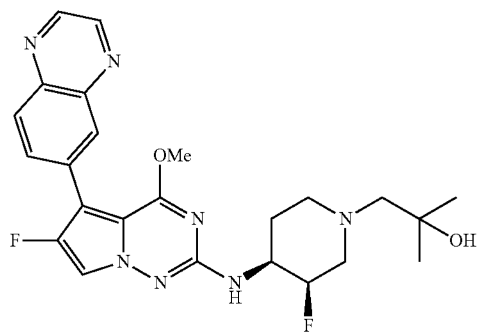
1106
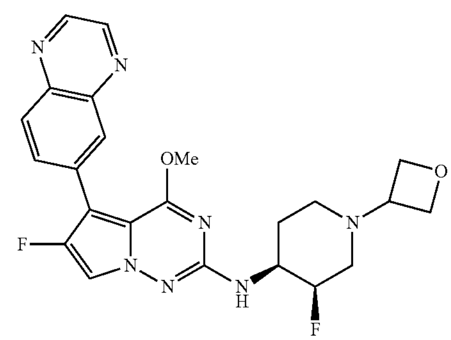
1107
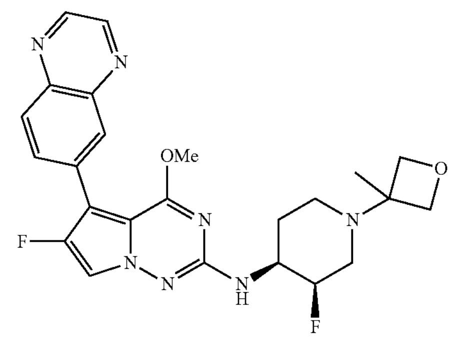 [SMILES: COc1nc(N[C@H]2CCN(C3(C)COC3)C[C@H]2F)nn2cc(F)c(-c3ccc4nccnc4c3)c12]

TABLE 1-continued
1108
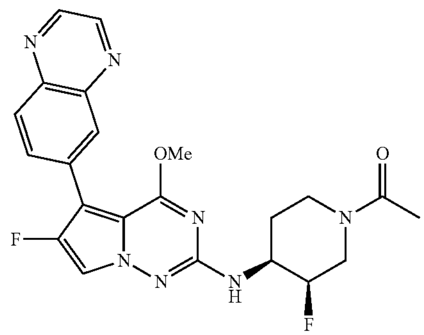
1109
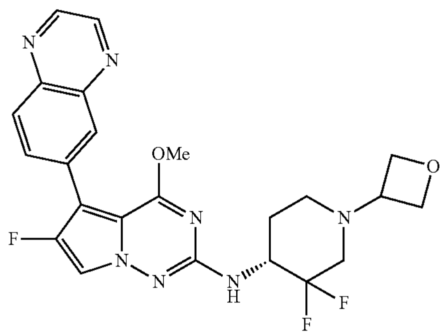
1110
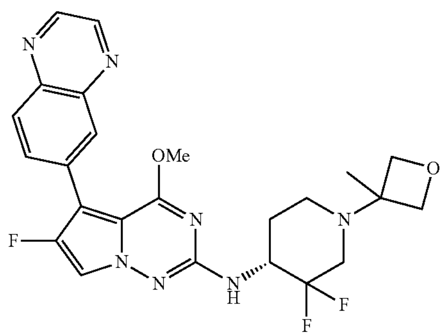 [SMILES: COc1nc(N[C@@H]2CCN(C3(C)COC3)CC2(F)F)nn2cc(F)c(-c3ccc4nccnc4c3)c12]
1111
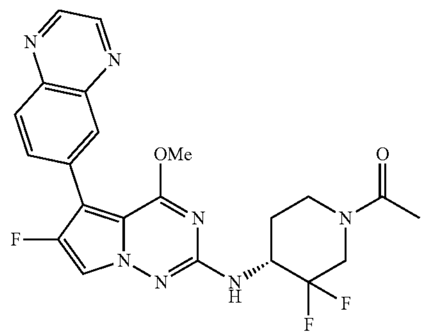
1112
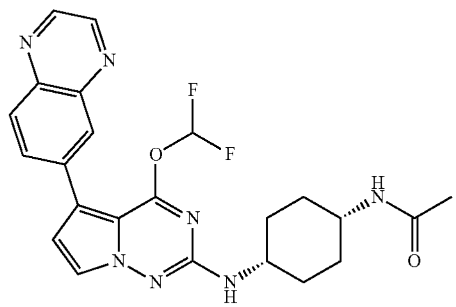 [SMILES: CC(=O)N[C@H]1CC[C@@H](Nc2nc(OC(F)F)c3c(-c4ccc5nccnc5c4)ccn3n2)CC1]
1113
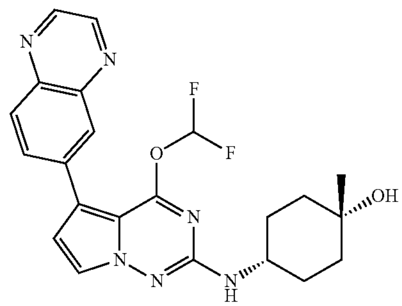 [SMILES: C[C@]1(O)CC[C@@H](Nc2nc(OC(F)F)c3c(-c4ccc5nccnc5c4)ccn3n2)CC1]
1114
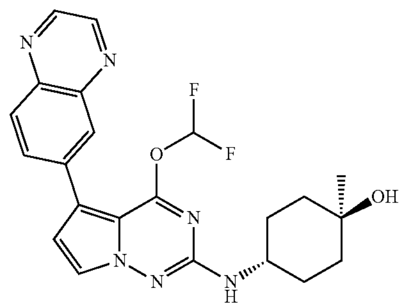 [SMILES: C[C@]1(O)CC[C@H](Nc2nc(OC(F)F)c3c(-c4ccc5nccnc5c4)ccn3n2)CC1]
1115
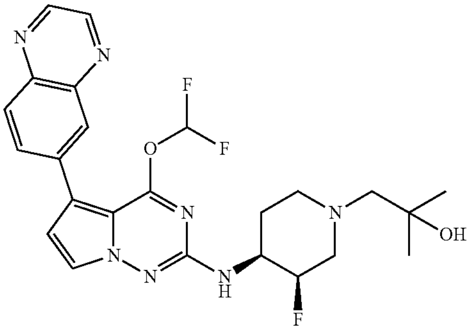
1116
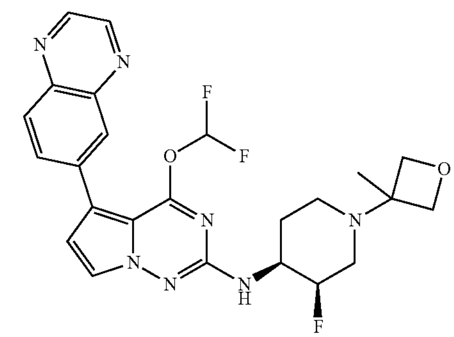
1117
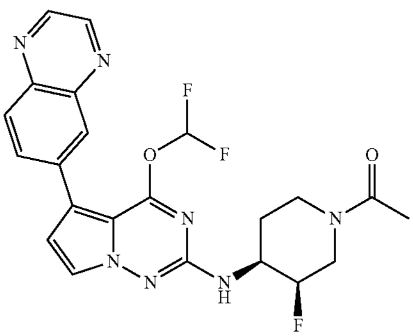 [SMILES: CC(=O)N1CC[C@H](Nc2nc(OC(F)F)c3c(-c4ccc5nccnc5c4)ccn3n2)[C@H](F)C1]

TABLE 1-continued
| | |
|---|---|
| 1118 | 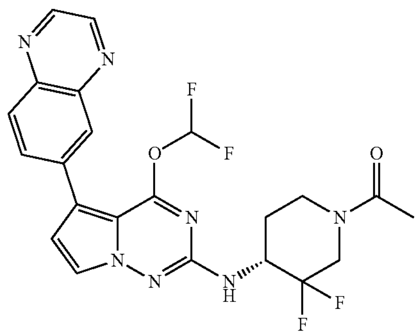 [SMILES: CC(=O)N1CC[C@@H](Nc2nc(OC(F)F)c3c(-c4ccc5nccnc5c4)ccn3n2)C(F)(F)C1] |
| 1119 | 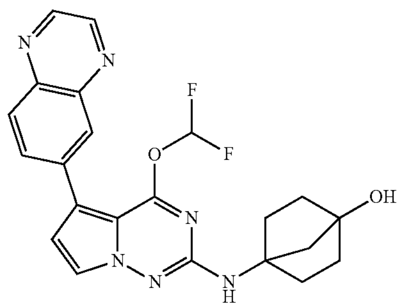 [SMILES: OC12CCC(Nc3nc(OC(F)F)c4c(-c5ccc6nccnc6c5)ccn4n3)(CC1)C2] |
| 1120 | 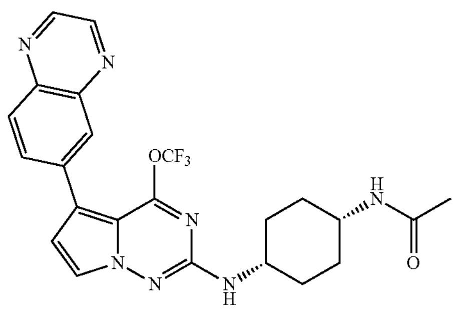 [SMILES: CC(=O)N[C@H]1CC[C@@H](Nc2nc(OC(F)(F)F)c3c(-c4ccc5nccnc5c4)ccn3n2)CC1] |
| 1121 | 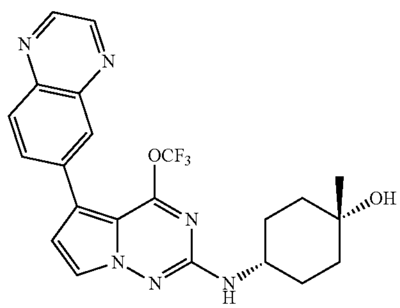 [SMILES: C[C@]1(O)CC[C@@H](Nc2nc(OC(F)(F)F)c3c(-c4ccc5nccnc5c4)ccn3n2)CC1] |
| 1122 | 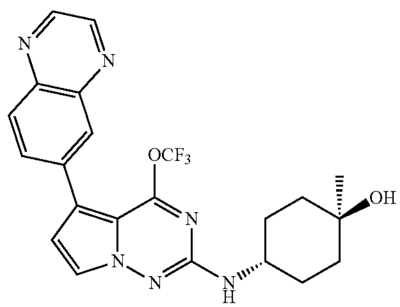 [SMILES: C[C@]1(O)CC[C@H](Nc2nc(OC(F)(F)F)c3c(-c4ccc5nccnc5c4)ccn3n2)CC1] |
TABLE 1-continued
| | |
|---|---|
| 1123 | 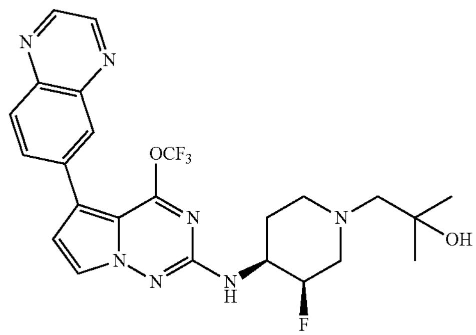 |
| 1124 | 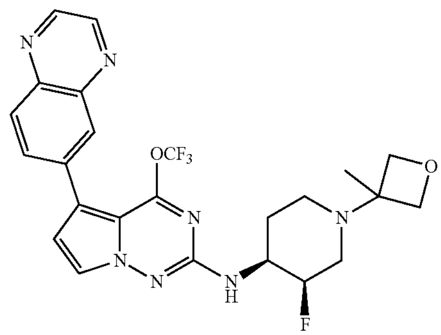 |
| 1125 | 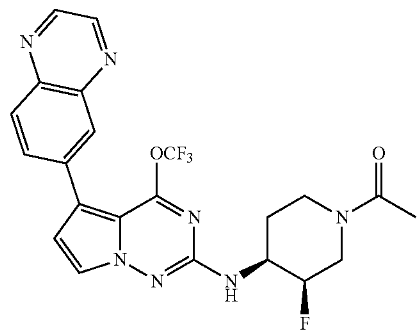 [SMILES: CC(=O)N1CC[C@H](Nc2nc(OC(F)(F)F)c3c(-c4ccc5nccnc5c4)ccn3n2)[C@H](F)C1] |
| 1126 | 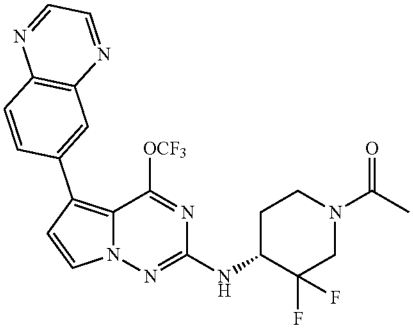 |
| 1127 | 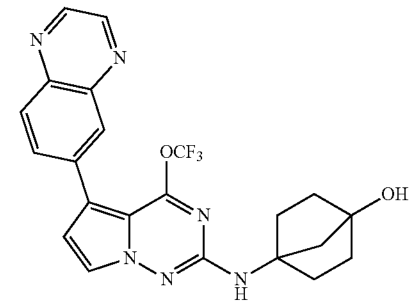 [SMILES: OC12CCC(Nc3nc(OC(F)(F)F)c4c(-c5ccc6nccnc6c5)ccn4n3)(CC1)C2] |

TABLE 1-continued
1128
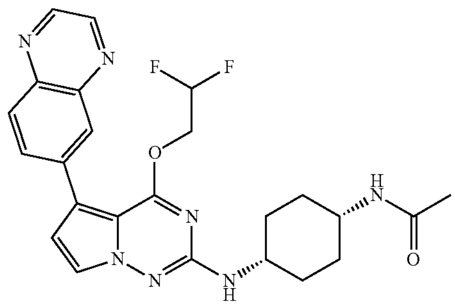 [SMILES: CC(=O)N[C@H]1CC[C@@H](Nc2nc(OCC(F)F)c3c(-c4ccc5nccnc5c4)ccn3n2)CC1]
1129
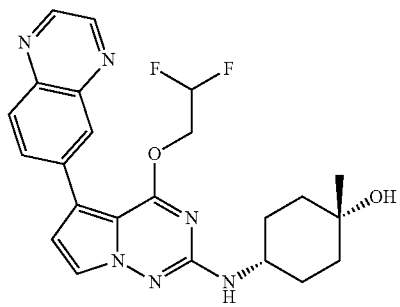 [SMILES: C[C@]1(O)CC[C@@H](Nc2nc(OCC(F)F)c3c(-c4ccc5nccnc5c4)ccn3n2)CC1]
1130
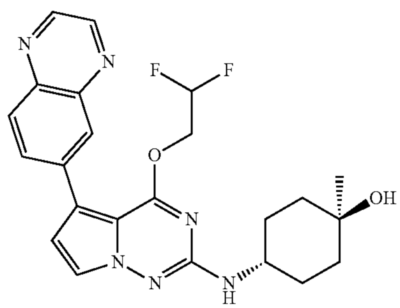 [SMILES: C[C@]1(O)CC[C@H](Nc2nc(OCC(F)F)c3c(-c4ccc5nccnc5c4)ccn3n2)CC1]
1131
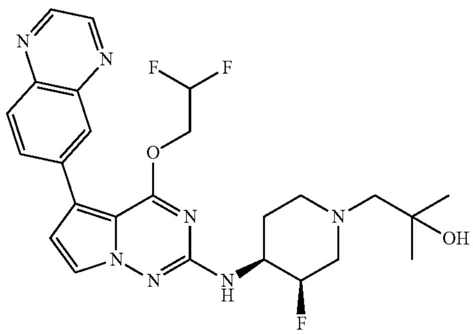 [SMILES: CC(C)(O)CN1CC[C@H](Nc2nc(OCC(F)F)c3c(-c4ccc5nccnc5c4)ccn3n2)[C@H](F)C1]
1132
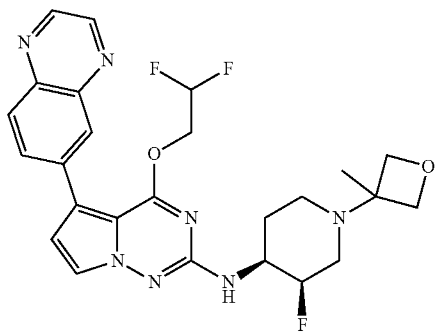 [SMILES: CC1(N2CC[C@H](Nc3nc(OCC(F)F)c4c(-c5ccc6nccnc6c5)ccn4n3)[C@H](F)C2)COC1]
TABLE 1-continued
1133
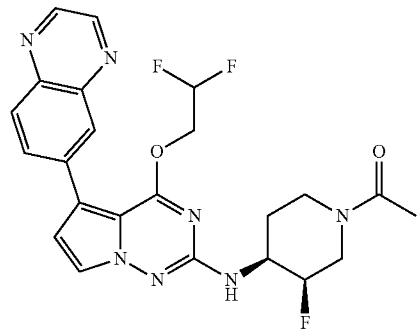 [SMILES: CC(=O)N1CC[C@H](Nc2nc(OCC(F)F)c3c(-c4ccc5nccnc5c4)ccn3n2)[C@H](F)C1]
1134
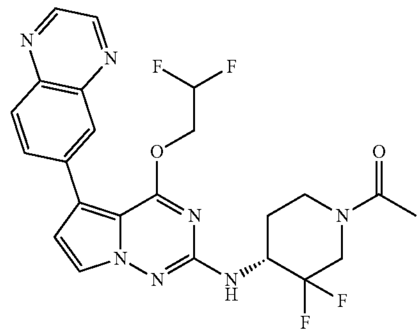
1135
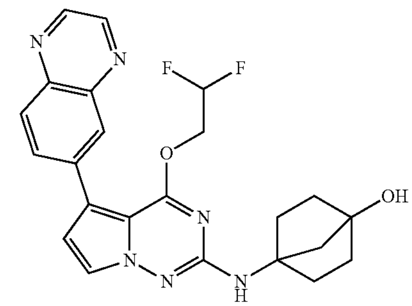 [SMILES: OC12CCC(Nc3nc(OCC(F)F)c4c(-c5ccc6nccnc6c5)ccn4n3)(CC1)C2]
1136
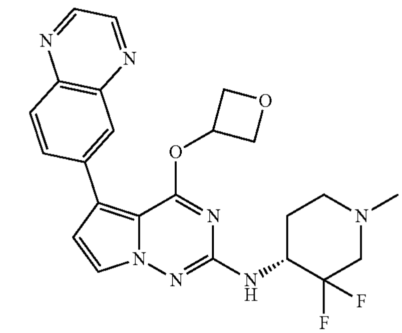 [SMILES: CN1CC[C@@H](Nc2nc(OC3COC3)c3c(-c4ccc5nccnc5c4)ccn3n2)C(F)(F)C1]
1137
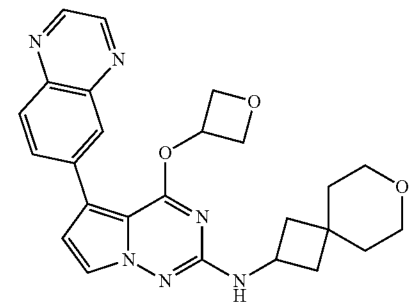 [SMILES: c1cnc2cc(-c3ccn4nc(NC5CC6(CCOCC6)C5)nc(OC5COC5)c34)ccc2n1]

TABLE 1-continued
1138
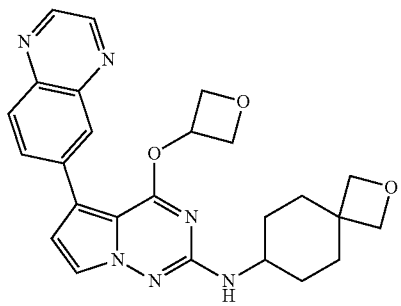 [SMILES: c1cnc2cc(-c3ccn4nc(NC5CCC6(CC5)COC6)nc(OC5COC5)c34)ccc2n1]
1139
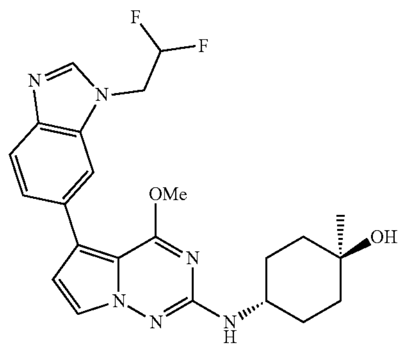 [SMILES: COc1nc(N[C@H]2CC[C@](C)(O)CC2)nn2ccc(-c3ccc4ncn(CC(F)F)c4c3)c12]
1140
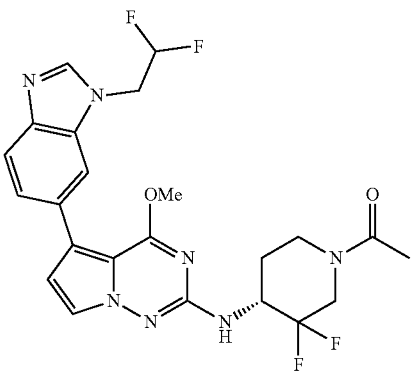 [SMILES: COc1nc(N[C@@H]2CCN(C(C)=O)CC2(F)F)nn2ccc(-c3ccc4ncn(CC(F)F)c4c3)c12]
1141
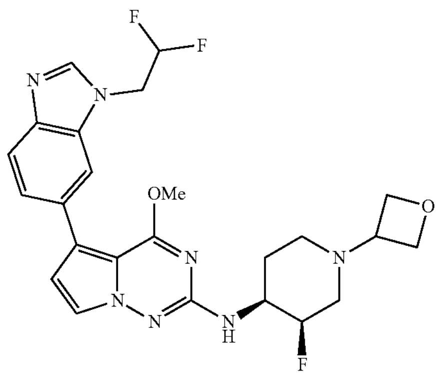 [SMILES: COc1nc(N[C@H]2CCN(C3COC3)C[C@H]2F)nn2ccc(-c3ccc4ncn(CC(F)F)c4c3)c12]
TABLE 1-continued
1142
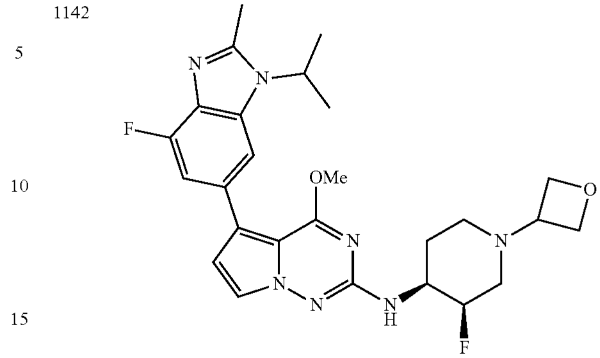
1143
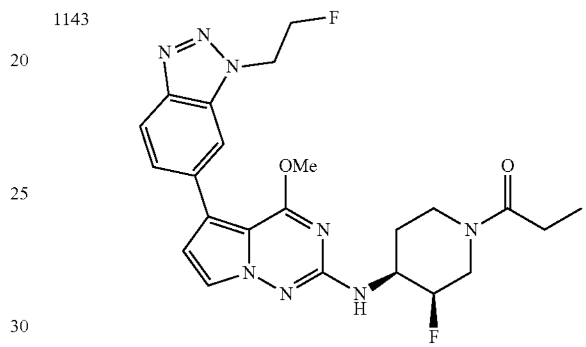
1144
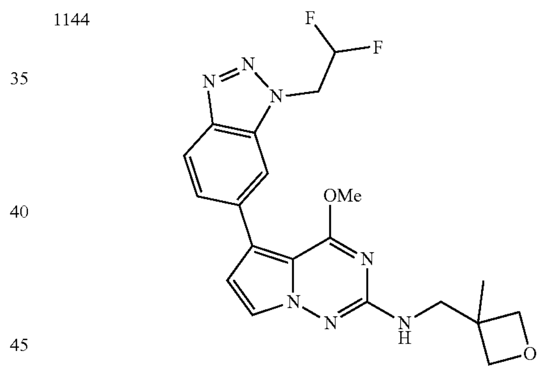
1145
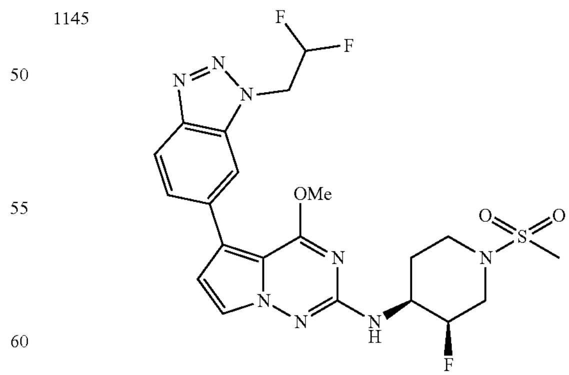

TABLE 1-continued

1146

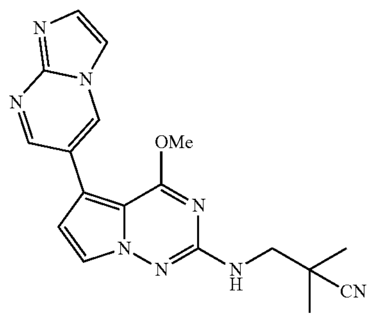 [SMILES: COc1nc(NCC(C)(C)C#N)nn2ccc(-c3cnc4nccn4c3)c12]

1147

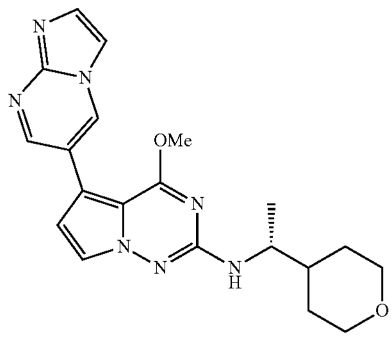 [SMILES: COc1nc(N[C@H](C)C2CCOCC2)nn2ccc(-c3cnc4nccn4c3)c12]

1148

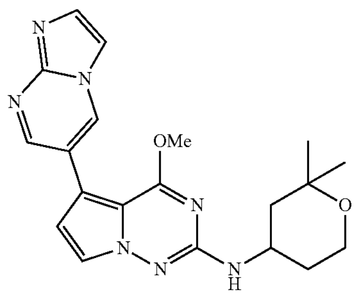 [SMILES: COc1nc(NC2CCOC(C)(C)C2)nn2ccc(-c3cnc4nccn4c3)c12]

1149

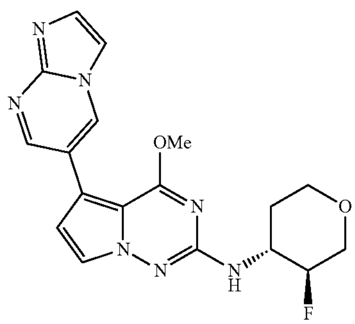 [SMILES: COc1nc(N[C@@H]2CCOC[C@H]2F)nn2ccc(-c3cnc4nccn4c3)c12]

1150

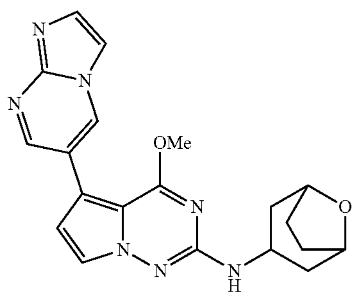 [SMILES: COc1nc(NC2CC3CCC(C2)O3)nn2ccc(-c3cnc4nccn4c3)c12]

TABLE 1-continued

1151

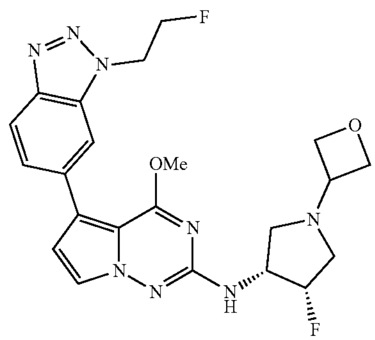 [SMILES: COc1nc(N[C@@H]2CN(C3COC3)C[C@@H]2F)nn2ccc(-c3ccc4nnn(CCF)c4c3)c12]

1152

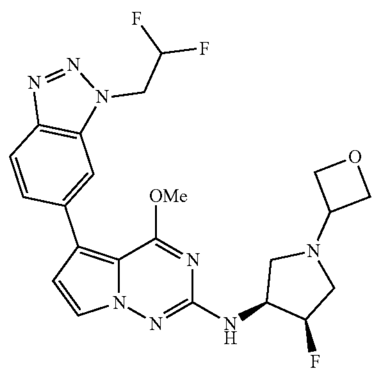 [SMILES: COc1nc(N[C@H]2CN(C3COC3)C[C@H]2F)nn2ccc(-c3ccc4nnn(CC(F)F)c4c3)c12]

1153

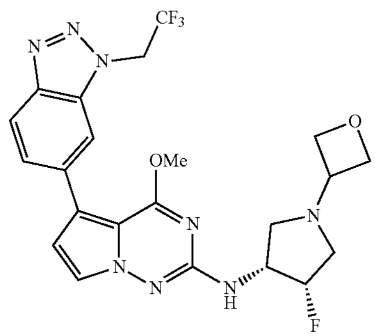 [SMILES: COc1nc(N[C@@H]2CN(C3COC3)C[C@@H]2F)nn2ccc(-c3ccc4nnn(CC(F)(F)F)c4c3)c12]

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula I and another active agent are colorectal cancer, ovarian cancer, hepatocellular carcinoma, head and neck squamous cell carcinoma, acute lymphoblastic leukemia (ALL), pancreatic cancer, brain tumors, acute megakaryoblastic leukemia (AMKL), and osteoarthritis. For example, a compound of Formula I can be combined with one or more chemotherapeutic compounds.

In some embodiments, hepatocellular carcinoma can be treated with a combination of a compound of Formula I and one or more of the following drugs/therapies: sorafenib (Nexavar®); regorafenib (Stivarga®, Regonix®), nivolumab (Opdivo®); lenvatinib (Lenvima®); pembrolizumab (Keytruda®); cabozantinib (Cometriq®, Cabometyx®); 5-fluorouracil (5-FU®); ramucirumab (Cyramza®); combination of gemcitabine and oxaliplatin (GEMOX). Other therapies that can be performed in combination with a compound of Formula I are i) transcatheter arterial chemoembolization (TACE) in combination with doxorubicin (DOXIL®), cisplatin, or mitomycin C (Mitosol®, Mutamycin®, Jelmyto®); ii) low-dose brachytherapy.

In some embodiments, head and neck squamous cell carcinoma can be treated with a combination of a compound of Formula I and one or more of the following drugs/therapies: TransOral Robotic Surgery (TORS); TORS with radiation therapy; larotrectinib (Vitrakvi®); EGFR inhibitors, e.g., erlotinib (Tarceva®), osimertinib (Tagrisso®), neratinib (Nerlynx®), gefitinib (Iressa®), cetuximab (Erbitux®), panitumumab (Vectibix®), dacomitinib (Vizimpro®), lapatinib (Tykerb®), necitumumab (Portrazza), and vandetanib (Caprelsa®).

In some embodiments, acute lymphoblastic leukemia (ALL) can be treated with a combination of a compound of Formula I and one or more of the following drugs/therapies: remission induction therapy; consolidation therapy; nelarabine (Arranon®); asparaginase *Erwinia chrysanthemi* (Erwinaze®); asparaginase *Erwinia chrysanthemi* (recombinant)-rywn (Rylaze®); calaspargase Pegol-mknl (Asparlas®); inotuzumab ozogamicin (Besponsa®); blinatumomab (Blincyto®); daunorubicin hydrochloride (Cerubidine®); clofarabine (Clolar®); cyclophosphamide; methotrexate sodium (Trexall®); cytarabine (Cytosar-U®); dasatinib (Sprycel®); dexamethasone; imatinib mesylate (Gleevec®); ponatinib hydrochloride (Iclusig®); mercaptopurine (Purinethol®, Purixan®); tisagenlecleucel (Kymriah®); vincristine sulfate liposome (Marqibo®); pegaspargase (Oncaspar®); prednisone; daunorubicin hydrochloride (Rubidomycin®); and vincristine sulfate.

In some embodiments, pancreatic cancer can be treated with a combination of a compound of Formula I and one or more of the following drugs/therapies: ablation and embolization treatment; gemcitabine (Gemzar®); 5-fluorouracil (5-FU®); oxaliplatin (Eloxatin®); albumin-bound paclitaxel (Abraxane®); capecitabine (Xeloda®); cisplatin; irinotecan (Camptosar®); liposomal irinotecan (Onivyde®); paclitaxel (Taxol®), and docetaxel (Taxotere®).

In some embodiments, brain tumors can be treated with a combination of a compound of Formula I and one or more of the following drugs/therapies: carmustine can be administered by way of a gliadel wafer; for glioblastoma and high-grade glioma, radiation therapy with daily low-dose temozolomide (Temodar®) followed by monthly doses of temozolomide after radiation therapy for 6 months to 1 year; lomustine (Gleostine®), procarbazine (Matulane®), and vincristine (Vincasar®), have been used along with radiation therapy; anti-angiogenesis therapy with bevacizumab (Avastin®, Mvasi®); and targeted therapy using larotrectinib (Vitrakvi®).

In some embodiments, acute megakaryoblastic leukemia (AMKL) can be treated with a combination of a compound of Formula I and one or more of the following drugs/therapies: cytarabine (Cytosar-U®), etoposide (Vepesid®), and anthracycline drugs. Anthracyclines include daunorubicin (Cerubidine®), idarubicin (Idamycin®), and mitoxantrone (Novantrone®).

In some embodiments, acute myeloid leukemia (AML) can be treated with a combination of a compound of Formula I and one or more of the following drugs/therapies: venetoclax and hypomethylating agents (e.g., decitabine, azacitidine), induction chemotherapy (cytarabine and an anthracycline (e.g., daunorubicin or idarubicin), all-trans-retinoic acid (ATRA) and either arsenic trioxide (ATO) monotherapy or an anthracycline), consolidation therapy (cytarabine).

In some embodiments, myelodysplastic syndrome (MDS) can be treated with a combination of a compound of Formula I and one or more of the following drugs/therapies: 5-azacytidine, decitabine, lenalidomide, and decitabine/cedazuridine (Ingovi®).

In some embodiments, colorectal cancer can be treated with a combination of a compound of Formula I and one or more of the following drugs: 5-fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula I are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula I and one or more of the following drugs: topotecan, liposomal doxorubicin (DOXIL®), gemcitabine (GEMZAR®), cyclophosphamide (CYTOXAN®), vinorelbine (NAVELBINE®), ifosfamide (IFEX®), etoposide (VP-16), altretamine (HEXALEN®), capecitabine (XELODA®), irinotecan (CPT-11, CAMPTOSAR®), melphalan, pemetrexed (ALIMTA®) and albumin bound paclitaxel (nab-paclitaxel, ABRAXANE®). Examples of combinations of these drugs which could be further combined with a compound of Formula I are TIP (paclitaxel [Taxol], ifosfamide, and cisplatin), VeIP (vinblastine, ifosfamide, and cisplatin) and VIP (etoposide [VP-16], ifosfamide, and cisplatin). Ovarian cancer can also be treated with a combination of a compound of Formula I and immune checkpoint blockade (ICB) therapy.

In some embodiments, a compound of Formula I can be used to treat cancer in combination with any of the following methods: (a) hormone therapy such as aromatase inhibitors, LHRH [luteinizing hormone-releasing hormone] analogs and inhibitors, and others; (b) ablation or embolization procedures such as radiofrequency ablation (RFA), ethanol (alcohol) ablation, microwave thermotherapy and cryosurgery (cryotherapy); (c) chemotherapy using alkylating agents such as cisplatin and carboplatin, oxaliplatin, mechlorethamine, cyclophosphamide, chlorambucil and ifosfamide; (d) chemotherapy using anti-metabolites such as azathioprine and mercaptopurine; (e) chemotherapy using plant alkaloids and terpenoids such as vinca alkaloids (i.e., vincristine, vinblastine, vinorelbine and vindesine) and taxanes; (f) chemotherapy using podophyllotoxin, etoposide, teniposide and docetaxel; (g) chemotherapy using topoisomerase inhibitors such as irinotecan, topotecan, amsacrine, etoposide, etoposide phosphate, and teniposide; (h) chemotherapy using cytotoxic antibiotics such as actinomycin, anthracyclines, doxorubicin, daunorubicin, valrubicin, idarubicin, epirubicin, bleomycin, plicamycin and mitomycin; (i) chemotherapy using tyrosine-kinase inhibitors such as imatinib mesylate (GLEEVEC®, also known as STI-571), gefitinib (Iressa, also known as ZD1839), erlotinib (marketed as TARCEVA®), bortezomib (VELCADE®), tamoxifen, tofacitinib, crizotinib, Bcl-2 inhibitors (e.g., obatoclax, navitoclax (ABT-263), oblimersen (G3139), venetoclax (ABT-199), Gossypol), PARP inhibitors (e.g., iniparib, olaparib, rucaparib, niraparib, talazoparib), PI3K inhibitors (e.g., perifosine in a phase III trial), VEGF receptor 2 inhibitors (e.g., apatinib), AN-152, (AEZS-108), BRAF inhibitors (e.g., vemurafenib, dabrafenib and LGX818), MEK inhibitors (e.g., trametinib and MEK162), CDK inhibitors (e.g., PD-0332991), salinomycin and sorafenib; (j) chemotherapy using monoclonal antibodies such as rituximab (marketed as MABTHERA® or RITUXAN®), trastuzumab (Herceptin also known as ErbB2), cetuximab (marketed as ERBITUX®), and bevacizumab (marketed as AVASTIN®); (k) chemotherapy using KRAS G12C inhibitors such as sotorasib (Lumakras® and Lumykras®), adagrasib (MRTX849), and ARS-3248 (Wellspring Biosciences); (l) chemotherapy using checkpoint inhibitor therapy such as ipilimumab (Yervoy®), nivolumab (Opdivo®), pembrolizumab (Keytruda®), atezolizumab (Tecentriq®), avelumab (Bavencio), durvalumab (Imfinzi), cemiplimab (Libtayo®), and spartalizumab (PDR001); (m) chemotherapy using antibody-drug conjugates (ADC) such as gemtuzumab ozogamicin, brentuximab vedotin, trastuzumab emtansine, inotuzumab ozogamicin, polatuzumab vedotin, enfortumab vedotin, trastuzumab deruxtecan, sacituzumab govitecan, belantamab mafodotin, moxetumomab pasudotox, and loncastuximab tesirine; (n) chemotherapy using proteasome inhibitors such as carfilzomib, lactacystin, disulfiram, salinosporamide A (marizomib), oprozomib, delanzomib, epoxomicin, MG132, β-hydroxy β-methylbutyric acid (HMB), bortezomib, ixazomib (alone or in in combination with lenalidomide and dexamethasone); and (o) radiation therapy.

In some embodiments, a compound of Formula I, can be used to treat diabetes mellitus in combination with any of the following methods: (a) injections of insulin; (b) biguanides such as metformin (Glucophage), phenformin (DBI), and buformin; (c) thiazolidinediones (TZDs) such as rosiglitazone (Avandia), pioglitazone (Actos), and yroglitazone (Rezulin); (d) lyn kinase activators such as glimepiride (Amaryl®) and tolimidone (MLR-1023); (e) secretagogues such as sulfonylureas (non-limiting examples are acetohexamide, carbutamide, chlorpropamide, glycyclamide (tolcyclamide), metahexamide, tolazamide, tolbutamide, glibenclamide (glyburide), glibornuride, gliclazide, glipizide, gliquidone, glisoxepide, glyclopyramide, and glimepiride) and meglitinides (nonlimiting examples are repaglinide (Prandin), nateglinide (Starlix), and mitiglinide (Glufast)); (f) alpha-glucosidase inhibitors such as acarbose (Glucobay, Precose, Prandase), miglitol (Glyset), and voglibose; (g) injectable incretin mimetics such as glucagon-like peptide-1 (GLP-1) and gastric inhibitory peptide (glucose-dependent insulinotropic peptide, GIP), nonlimiting examples of injectable glucagon-like peptide (GLP) analogs and agonists are exenatide (Exendin-4, marketed as Byetta), liraglutide (Victoza, Saxenda), taspoglutide, lixisenatide (Lyxumia), Semaglutide (Ozempic, Rybelsus), dulaglutide (Trulicity), albiglutide (Tanzeum), nonlimiting examples of dipeptidyl peptidase-4 (DPP-4) inhibitors are sitagliptin (Januvia), vildagliptin (Galvus), saxagliptin (Onglyza), linagliptin (Tradjenta), gemigliptin (Zemiglo), anagliptin (Suiny), teneligliptin (Tenelia), alogliptin (Nesina, Vipidia, Kazano, Vipidomet (with metformin), Oseni, Incresync (with pioglitazone)), trelagliptin (Zafatek, Wedica), omarigliptin (MK-3102), evogliptin (Suganon, Evodine), gosogliptin (Saterex), and dutogliptin; (h) injectable amylin analogues such as pramlintide (Symlin); (i) glycosurics (SGLT2 inhibitors) such as canagliflozin (Invokana, Sulisent, Prominad), dapagliflozin (Forxiga, Farxiga, Edistride), empagliflozin (Jardiance, Sciampa-M), ertugliflozin (Steglatro), ipragliflozin (Suglat), luseogliflozin (Lusefi), remogliflozin etabonate (pro-drug of remogliflozin), sergliflozin etabonate (GW869682X), sotagliflozin (Zynquista), and tofogliflozin (CSG452).

In some embodiments, a compound of Formula I can be used to treat osteoarthritis in combination with any of the following methods: (d) injections of a Wnt signaling pathway inhibitor (e.g., lorecivivint); (a) nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g., Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, a compound of Formula I can be used to treat Alzheimer's disease in combination with aducanumab (Aduhelm™); acetylcholinesterase inhibitors, e.g., tacrine, rivastigmine (Exelon®), galantamine (Razadyne® and GalantaMind™), and donepezil (Aricept®); and memantine (Axura®, Ebixa®, Namenda®).

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release, or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants, and the like, for prolonged and/or timed, pulsed administration at a predetermined rate.

The compounds can be administered either alone or in combination with a conventional pharmaceutical carrier, excipient, or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives, or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol, or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula I is about 0.25 mg/Kg to about 50 mg/Kg in humans.

In some embodiments, the unit dosage of compounds of Formula I is about 0.25 mg/Kg to about 20 mg/Kg in humans.

In some embodiments, the unit dosage of compounds of Formula I is about 0.50 mg/Kg to about 19 mg/Kg in humans.

In some embodiments, the unit dosage of compounds of Formula I is about 0.75 mg/Kg to about 18 mg/Kg in humans.

In some embodiments, the unit dosage of compounds of Formula I is about 1.0 mg/Kg to about 17 mg/Kg in humans.

In some embodiments, the unit dosage of compounds of Formula I is about 1.25 mg/Kg to about 16 mg/Kg in humans.

In some embodiments, the unit dosage of compounds of Formula I is about 1.50 mg/Kg to about 15 mg/Kg in humans.

In some embodiments, the unit dosage of compounds of Formula I is about 1.75 mg/Kg to about 14 mg/Kg in humans.

In some embodiments, the unit dosage of compounds of Formula I is about 2.0 mg/Kg to about 13 mg/Kg in humans.

In some embodiments, the unit dosage of compounds of Formula I is about 3.0 mg/Kg to about 12 mg/Kg in humans.

In some embodiments, the unit dosage of compounds of Formula I is about 4.0 mg/Kg to about 11 mg/Kg in humans.

In some embodiments, the unit dosage of compounds of Formula I is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable and could be higher if the composition is a solid or suspension, which could be subsequently diluted to the above percentages.

In some embodiments, the composition comprises about 0.1-10% of the active agent in solution.

In some embodiments, the composition comprises about 0.1-5% of the active agent in solution.

In some embodiments, the composition comprises about 0.1-4% of the active agent in solution.

In some embodiments, the composition comprises about 0.15-3% of the active agent in solution.

In some embodiments, the composition comprises about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 $mg/m^2$ to about 300 $mg/m^2$.

In some embodiments, these compositions can be administered by intravenous infusion to humans at doses of about 5 $mg/m^2$ to about 200 $mg/m^2$.

In some embodiments, these compositions can be administered by intravenous infusion to humans at doses of about 5 $mg/m^2$ to about 100 $mg/m^2$.

In some embodiments, these compositions can be administered by intravenous infusion to humans at doses of about 10 $mg/m^2$ to about 50 $mg/m^2$.

In some embodiments, these compositions can be administered by intravenous infusion to humans at doses of about 50 $mg/m^2$ to about 200 $mg/m^2$.

In some embodiments, these compositions can be administered by intravenous infusion to humans at doses of about 75 $mg/m^2$ to about 175 $mg/m^2$.

In some embodiments, these compositions can be administered by intravenous infusion to humans at doses of about 100 $mg/m^2$ to about 150 $mg/m^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula I disclosed herein intended for respiratory delivery (either systemic or local) can be administered as aqueous formulations, as non-aqueous solutions, or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula I disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula I disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula I can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula I are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of glioblastoma, ovarian, breast, pancreatic cancers, acute lymphoblastic leukemia, acute megakaryoblastic leukemia, chronic myeloid leukemia, Alzheimer's disease, amyotrophic lateral sclerosis, CDKL5 deficiency disorder, Down syndrome, frontotemporal dementia with parkinsonism-17 (FTDP-17), Lewy body dementia, Parkinson's disease, Pick's disease, autism, dementia, epilepsy, Huntington's disease, and multiple sclerosis.

Methods of Treatment

The compounds and compositions provided herein can be used as inhibitors of DYRK1A, and thus can be used to treat a variety of disorders and diseases in which over expression of DYRK1A is implicated, such as cancer and neurological conditions/disorders/diseases. Non-limiting examples of diseases which can be treated with the compounds and compositions provided herein include a variety of cancers, Alzheimer's disease, amyotrophic lateral sclerosis, CDKL5 deficiency disorder, Down Syndrome, frontotemporal dementia with parkinsonism-17 (FTDP-17), Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, stroke, tauopathies (e.g., Pick's disease, progressive supranuclear palsy, corticobasal degeneration, argyrophilic grain disease, globular glial tauopathies, primary age-related tauopathy, which includes neurofibrillary tangle dementia, chronic traumatic encephalopathy (CTE), frontotemporal lobar degeneration with tau inclusions (FTLD-tau), and aging-related tau astrogliopathy. Clinical symptoms include frontotemporal dementia, corticobasal syndrome, Richardson syndrome, parkinsonism, pure akinesia with gait freezing and, rarely, motor neuron symptoms or cerebellar ataxia, diabetes, psoriasis, knee osteoarthritis, tendinopathy, human immunodeficiency virus type 1 (HIV-1), human cytomegalovirus (HCMV), hepatitis C virus (HCV), and herpes simplex virus 1 (HSV-1).

The gene encoding DYRK1A is located on chromosome 21, within the Down syndrome critical region (DSCR), the triploidy of which is responsible for most Down syndrome-associated deficiencies (*FEBS Journal* (2011), 278, 246-256). There is considerable genetical and pharmacological evidence showing that the mere 1.5-fold overexpression of DYRK1A is responsible for most cognitive deficits observed in Down syndrome patients (*Pharmacology & Therapeutics* (2019), 194, 199-221 and *Brain Science* (2018), 8(10), 187). Genetical normalization of DYRK1A levels or pharmacological inhibition of its catalytic activity restores cognitive functions. The development of pharmacological inhibitors of DYRK1A is a major avenue for the treatment of cognitive deficits associated with Down syndrome.

DYRK1A and DYRK1B are utilized during human cytomegalovirus (HCMV) placental replication. Inhibition of DYRKs prevent replication of various viruses, including hepatitis C virus (HCV), human cytomegalovirus (HCMV), human immunodeficiency virus type 1 (HIV-1), and herpes simplex virus 1 (HSV-1) (*Journal of Virology* (2020), 94(6) and *PLoS ONE* (2015), 10, e0144229).

There is a growing body of evidence showing that DYRK1A/1B inhibitors induce the proliferation of insulin-producing pancreatic β-cells, making DYRK1A/1B kinases attractive therapeutic targets for β-cell regeneration for both type 1 and type 2 diabetes mellitus and gestational diabetes (*Nature Communications* (2015), 6(8372); *Diabetes* (2016), 65(6), 1660-1671; *JCI Insight* (2020), 5(1), e132594; *Science Translational Medicine* (2020), 12(530); *International Journal of Molecular Sciences* (2021), 22(16), 9083; and *Journal of Medicinal Chemistry* (2021), 64(6), 2901-2922). Other forms of diabetes that may be treated with DYRK inhibitors are maturity onset diabetes of the young (MODY, monogenic diabetes), cases of diabetes that are caused by the body's tissue receptors not responding to insulin, double diabetes (when a type 1 diabetic becomes insulin resistant), diabetes associated with excessive secretion of insulin-antagonistic hormones, malnutrition-related diabetes mellitus (ICD-10 code E12), and diabetes caused by any genetic mutations (autosomal or mitochondrial) that leads to defects in beta cell function.

There is abundant literature linking DYRK1A with solid cancers and leukemias (*Pharmacology & Therapeutics* (2015), 151, 87-98; *Cancers* (2020), 12(8), 2106; and *Cellular and Molecular Life Sciences* (2021), 78, 603-619). The most prominent examples are pancreatic cancer (*Gut* (2019), 68(8), 1465-1476 and *Gene* (2020), 758, 144960), brain tumors, glioblastoma (*Journal of Clinical Investigation* (2013), 123(6), 2475-2487), acute megakaryoblastic leukemia (AMKL) (*Journal of Clinical Investigation* (2012), 122(3), 948-962), and acute lymphoblastic leukemia (ALL) (*Journal of Clinical Investigation* (2021), 131(1), e135937). Other cancers linked to DYRK1A are ovarian (*Frontiers in Oncology* (2021), 11, 637193), head and neck squamous cell carcinoma (*Scientific Reports* (2016), 6, 36132), hepatocellular carcinoma (*Cell Death & Disease* (2021), 12, 125), DYRK1A regulates DNA damage response (*Scientific Reports* (2019), 9, 6014 and *Scientific Reports* (2019), 9, 6539). In some situations, DYRK1A appears to function as a tumor-suppressor protein (*Molecular & Cellular Oncology* (2015), 2(1), e970048 and *Nature* (2016), 529, 172-177).

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her^{2-}$ breast cancer, $her^{2+}$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; chemoresistant breast cancers (TNBC), and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her^{2-}$). In some embodiments, the breast cancer may have a high risk Oncotype score.
2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.
3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; chemoresistant small cell lung cancer (SCLC), and mesothelioma.
4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; colon cancers with APC gene mutations; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.
5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.
6) Liver cancers, including, for example, hepatoma, e.g., hepatocellular carcinoma; cholangiocarcinoma; hepatoblastoma; angiosarcoma; hepatocellular adenoma; and hemangioma.
7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.
8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, oligodendrocytoma, schwannoma, retinoblastoma, and congenital tumors; and cancers of the spinal cord, e.g., neurofibroma, meningioma, glioma, and sarcoma.
9) Gynecological cancers, including, for example, cancers of the uterus, e.g., endometrial cancers (e.g., carcinoma, endometrioid adenocarcinoma, serous carcinoma, clear cell carcinoma, mucinous carcinomas, mixed or undifferentiated carcinoma (including mixed Müllerian tumor), endometrial stromal sarcoma, squamous cell carcinoma of the endometrium, urothelial carcinoma, endometrial cancer with CTNNB1 mutations); cancers of the cervix, e.g., cervical carcinoma, and pre tumor cervical dysplasia; cancers of the ovaries, e.g., BRCA-mutant ovarian cancer, surface epithelial-stromal tumors (epithelial ovarian cancer (Type 1 (endometroid, mucinous, clear cell, low grade serous) or Type 2 (poorly differentiated, carcinosarcoma, and high grade serous))), ovarian carcinoma, including serous cystadenocarcinoma, mucinous cystadenocarcinoma, endometrioid tumors, small cell ovarian cancer (small cell ovarian cancer of hypercalcemic type, small cell ovarian cancer of pulmonary type) unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma, primary fallopian tube cancer; Primary peritoneal cancer (also known as serous surface papillary carcinoma, primary peritoneal carcinoma, extra-ovarian serous carcinoma, primary serous papillary carcinoma, and psammomacarcinoma).

10) Hematologic cancers, including, for example, cancers of the blood, e.g., acute myeloid leukemia, chronic myeloid leukemia, myelodysplastic syndromes (refractory cytopenia with unilineage dysplasia (refractory anemia, refractory neutropenia, and refractory thrombocytopenia), refractory anemia with ring sideroblasts, refractory cytopenia with multilineage dysplasia, refractory anemias with excess blasts I and II, refractory cytopenia of childhood), and myeloproliferative neoplasms, acute lymphoblastic leukemia, chronic lymphocytic leukemia, myeloproliferative diseases, multiple myeloma, myelodysplastic syndrome, myelodysplastic-myeloproliferative diseases, Hodgkin's lymphoma, non-Hodgkin's lymphoma (malignant lymphoma) and Waldenstrom's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

13) Soft-tissue sarcomas (STS) such as fibrosarcoma, malignant fibrous histiocytoma, dermatofibrosarcoma, liposarcoma, rhabdomyosarcoma, leiomyosarcoma, hemangiosarcoma, Kaposi's sarcoma, lymphangiosarcoma, synovial sarcoma, malignant peripheral nerve sheath tumors (also called neurofibrosarcomas, malignant schwannomas, and neurogenic sarcomas), neurofibrosarcoma, extraskeletal chondrosarcoma, extraskeletal osteosarcoma, extraskeletal myxoid chondrosarcoma, extraskeletal mesenchymal, embryonal, alveolar soft part sarcoma, and infantile hemangiopericytoma.

More particularly, tumors of the central nervous system that may be treated by the compounds, compositions and methods described herein include:

1) Astrocytic tumors, e.g., diffuse astrocytoma (fibrillary, protoplasmic, gemistocytic, mixed), anaplastic (malignant) astrocytoma, glioblastoma multiforme (giant cell glioblastoma and gliosarcoma), pilocytic astrocytoma (pilomyxoid astrocytoma), pleomorphic xanthoastrocytoma, subependymal giant cell astrocytoma, and gliomatosis cerebri.

2) Oligodendroglial tumors, e.g., oligodendroglioma and anaplastic oligodendroglioma.

3) Oligoastrocytic tumors, e.g., oligoastrocytoma and anaplastic oligoastrocytoma.

4) Ependymal tumors, e.g., subependymoma, myxopapillary ependymoma, ependymoma, (cellular, papillary, clear cell, tanycytic), and anaplastic (malignant) ependymoma.

5) Choroid plexus tumors, e.g., choroid plexus papilloma, atypical choroid plexus papilloma, and choroid plexus carcinoma.

6) Neuronal and mixed neuronal-glial tumors, e.g., gangliocytoma, ganglioglioma, dysembryoplastic neuroepithelial tumor (DNET), dysplastic gangliocytoma of the cerebellum (Lhermitte-Duclos), desmoplastic infantile astrocytoma/ganglioglioma, central neurocytoma, anaplastic ganglioglioma, extraventricular neurocytoma, cerebellar liponeurocytoma, Papillary glioneuronal tumor, Rosette-forming glioneuronal tumor of the fourth ventricle, and paraganglioma of the filum terminale.

7) Pineal tumors, e.g., pineocytoma, pineoblastoma, papillary tumors of the pineal region, and pineal parenchymal tumor of intermediate differentiation.

8) Embryonal tumors, e.g., medulloblastoma (medulloblastoma with extensive nodularity, anaplastic medulloblastoma, desmoplastic, large cell, melanotic, medullomyoblastoma), medulloepithelioma, supratentorial primitive neuroectodermal tumors, and primitive neuroectodermal tumors (PNETs) such as neuroblastoma, ganglioneuroblastoma, ependymoblastoma, and atypical teratoid/rhabdoid tumor.

9) Neuroblastic tumors, e.g., olfactory (esthesioneuroblastoma), olfactory neuroepithelioma, and neuroblastomas of the adrenal gland and sympathetic nervous system.

10) Glial tumors, e.g., astroblastoma, chordoid glioma of the third ventricle, and angiocentric glioma.

11) Tumors of cranial and paraspinal nerves, e.g., schwannoma, neurofibroma Perineurioma, and malignant peripheral nerve sheath tumor.

12) Tumors of the meninges such as tumors of meningothelial cells, e.g., meningioma (atypical meningioma and anaplastic meningioma); mesenchymal tumors, e.g., lipoma, angiolipoma, hibernoma, liposarcoma, solitary fibrous tumor, fibrosarcoma, malignant fibrous histiocytoma, leiomyoma, leiomyosarcoma, rhabdomyoma, rhabdomyosarcoma, chondroma, chondrosarcoma, osteoma, osteosarcoma, osteochondroma, haemangioma, epithelioid hemangioendothelioma, haemangiopericytoma, anaplastic haemangiopericytoma, angiosarcoma, Kaposi Sarcoma, and Ewing Sarcoma; primary melanocytic lesions, e.g., diffuse melanocytosis, melanocytoma, malignant melanoma, meningeal melanomatosis; and hemangioblastomas.

13) Tumors of the hematopoietic system, e.g., malignant Lymphomas, plasmocytoma, and granulocytic sarcoma.

14) Germ cell tumors, e.g., germinoma, embryonal carcinoma, yolk sac tumor, choriocarcinoma, teratoma, and mixed germ cell tumors.

15) Tumors of the sellar region, e.g., craniopharyngioma, granular cell tumor, pituicytoma, and spindle cell oncocytoma of the adenohypophysis.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

There is mounting evidence for a role of DYRK1A in the onset of Alzheimer's Disease (*Future Medicinal Chemistry* (2016), 8(6), 681-696 and *European Journal of Medicinal Chemistry* (2018), 158, 559-592). DYRK1A phosphorylates key substrates involved in Alzheimer's Disease and dementia: Tau, septin 4, amyloid precursor protein (APP), presenilin 1, neprilysin, Munc18-1, α-synuclein, RCAN1, and β-tubulin. By modulating alternative splicing of Tau exon 10, DYRK1A favors the production of the 3R-Tau splice isoform (characteristic for DS/AD/tauopathy) over the 4R-Tau isoform (*Journal of Biological Chemistry* (2015), 290, 15219-15237).

Genome-wide association studies (GWAS) have revealed that DYRK1A is a risk factor for Parkinson's Disease (The Lancet Neurology (2019), 18(12), 1091-1102). DYRK1A phosphorylates key factors for Parkinson's Disease such as parkin, septin 4, and α-synuclein. Upregulation of microRNAs specific for Parkinson's Disease targets DYRK1A expression. There is further evidence that DYRK1A expression is increased in Parkinson's Disease and in Pick's disease (*Neurobiology of Disease* (2005), 20(2), 392-400).

The compounds and compositions provided herein can be used as inhibitors and/or modulators of the enzyme DYRK1A, and thus can be used to treat a variety of disorders and diseases associated with tau protein, including, but not limited to, Alzheimer's disease, amyotrophic lateral sclerosis (ALS), down syndrome, frontotemporal dementia (FTD) including FTD with parkinsonism-17 (FTDP-17), behavioural variant frontotemporal dementia (bvFTD), FTD in patients with motor neuron disease (MND) (typically amyotrophic lateral sclerosis, also called FTD-ALS), corticobasal degeneration (CBD) (also called corticobasal ganglionic degeneration), progressive supranuclear palsy, primary progressive aphasia (PPA), globular glial tauopathy (GGT), myotonic dystrophy type 1 (DM1) (also called Steinert disease), myotonic dystrophy type 2 (DM2) (also called proximal myotonic myopathy), Guam complex, argyrophilic grain disease, dementia pugilistica, post-encephalitic parkinsonism, Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the pharmaceutical composition comprises a therapeutically effective amount of a compound of Formula I, or a pharmaceutically acceptable salt thereof, and a pharmaceutically acceptable excipient.

In some embodiments, the disorder or disease is cancer.

In some embodiments, the disorder or disease is metastatic melanoma.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is a viral infection.

In some embodiments, the disorder or disease is a neurological disorder.

In some embodiments, the disorder or disease is Alzheimer's disease.

In some embodiments, the disorder or disease is osteoarthritis.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma, and ovarian cancer.

In some embodiments, the cancer is chosen from: lung cancer-non-small cell, lung cancer-small cell, multiple myeloma, nasopharyngeal cancer, neuroblastoma, osteosarcoma, penile cancer, pituitary tumors, prostate cancer, retinoblastoma, synovial sarcoma, rhabdomyosarcoma, salivary gland cancer, skin cancer-basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma; in some embodiments, the cancer is colon cancer; in some embodiments, the cancer is colorectal cancer; in some embodiments, the cancer is breast cancer; in some embodiments, the cancer is pancreatic cancer; in some embodiments, the cancer is chronic myeloid leukemia (CML); in some embodiments, the cancer is chronic myelomonocytic leukemia; in some embodiments, the cancer is chronic lymphocytic leukemia (CLL); in some embodiments, the cancer is acute myeloid leukemia; in some embodiments, the cancer is acute lymphocytic leukemia; in some embodiments, the cancer is Hodgkin lymphoma; in some embodiments, the cancer is lymphoma; in some embodiments, the cancer is sarcoma; in some embodiments, the cancer is ovarian cancer; in some embodiments, the cancer is lung cancer-non-small cell; in some embodiments, the cancer is lung cancer-small cell; in some embodiments, the cancer is multiple myeloma; in some embodiments, the cancer is nasopharyngeal cancer; in some embodiments, the cancer is neuroblastoma; in some embodiments, the cancer is osteosarcoma; in some embodiments, the cancer is penile cancer; in some embodiments, the cancer is pituitary tumors; in some embodiments, the cancer is prostate cancer; in some embodiments, the cancer is retinoblastoma; in some embodiments, the cancer is rhabdomyosarcoma; in some embodiments, the cancer is salivary gland cancer; in some embodiments, the cancer is skin cancer-basal and squamous cell; in some embodiments, the cancer is skin cancer-melanoma; in some embodiments, the cancer is small intestine cancer; in some embodiments, the cancer is stomach (gastric) cancers; in some embodiments, the cancer is testicular cancer; in some embodiments, the cancer is thymus cancer; in some embodiments, the cancer is thyroid cancer; in some embodiments, the cancer is uterine sarcoma; in some embodiments, the cancer is vaginal cancer; in some embodiments, the cancer is vulvar cancer; in some embodiments, the cancer is Wilms tumor; in some embodiments, the cancer is laryngeal or hypopharyngeal cancer; in some embodiments, the cancer is kidney cancer; in some embodiments, the cancer is Kaposi sarcoma; in some embodiments, the cancer is gestational trophoblastic disease; in some embodiments, the cancer is gastrointestinal stromal tumor; in some embodiments, the cancer is gastrointestinal carcinoid tumor; in some embodiments, the cancer is gallbladder cancer; in some embodiments, the cancer is eye cancer (melanoma and lymphoma); in some embodiments, the cancer is Ewing tumor; in some embodiments, the cancer is esophagus cancer; in some embodiments, the cancer is endometrial cancer; in some embodiments, the cancer is colorectal cancer; in some embodiments, the cancer is cervical cancer; in some embodiments, the cancer is brain or spinal cord tumor; in some embodiments, the cancer is bone metastasis; in some embodiments, the cancer is bone cancer; in some embodiments, the cancer is bladder cancer; in some embodiments, the cancer is bile duct cancer; in some embodiments, the cancer is anal cancer; and in some embodiments, the cancer is adrenal cortical cancer.

In some embodiments, the disorder or disease is a neurological condition, disorder, or disease, wherein the neurological disease is selected from: Alzheimer's disease, frontotemporal dementias, Parkinson's disease, Huntington's disease, progressive supranuclear palsy, corticobasal degeneration, multiple system atrophy, amyotrophic lateral sclerosis (ALS), inclusion body myositis, autism, degenerative myopathies.

In some embodiments, the disorder or disease is selected from the group consisting of: Alzheimer's disease, amyotrophic lateral sclerosis, Down syndrome, frontotemporal dementia with parkinsonism-17 (FTDP-17), Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

In some embodiments, a compound of Formula I inhibits DYRK1A.

In some embodiments, the method treats a disease or disorder mediated by kinase activity in a patient, the method comprises administering to the patient a therapeutically effective amount of a compound (or compounds) of Formula I, or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula I, or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula I, or a pharmaceutically acceptable salt thereof.

In some embodiments, the method prevents or reduces abnormal cellular proliferation in a patient; the method comprises administering to the patient a therapeutically effective amount of a compound (or compounds) of Formula I, or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Evaluation of Biological Activity

The biological activity of the compounds described herein can be tested using any suitable assay known to those of skill in the art. For example, the activity of a compound may be tested using one or more of the test methods outlined below.

For example, in vitro assays for DYRK1A biological activity may be used, e.g., regulation of microtubule-associated protein tau (MAPT/Tau) phosphorylation in neuronal cell lines such as the human SH-SY5Y neuroblastoma cell line. Assays for DYRK1A-regulated level of phosphorylation can include monitoring levels of basal pSer396 Tau, which can be measured, for example, by serial dilutions of a candidate inhibitor composition using a ten micromolar top concentration and detected by ELISA or Western Blotting. An exemplary assay for DYRK-1A-regulated phosphorylation uses the SH-SY5Y cells cultured in a 96 well plate format for a period of time sufficient to stabilize microtubules and Tau phosphorylation, usually at least 2 days, then treated with a 1/3 serial dilution of compounds overnight and lysed. The cell lysate is resolved by SDS PAGE, then transferred to nitrocellulose and probed with an antibody specific for pSer396 Tau. The chemiluminescence signal for HRP-linked antibodies used in western blotting is detected using a Carestream Image Station and blot densitometry for pSer396 and beta-actin are analyzed using ImageJ (NIH).

In a further example, the activity of a candidate compound can be measured by phosphoTau (Thr212) AlphaLISA by adding the lysate mentioned above onto total Tau-coated plates and detected with a specific pThr212Tau antibody. Colorimetric detection of AlphaLISA signal is performed by EnVision Multilabel Plate Reader (Perkin Elmer).

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described and claimed herein. The reader will recognize that the skilled artisan, armed with the present disclosure, and skill in the art is able to prepare and use the disclosure without exhaustive examples.

Examples

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* $7^{th}$ Ed., John Wiley & Sons (2013), Carey and Sundberg, *Advanced Organic Chemistry* $5^{th}$ Ed., Springer (2007), *Comprehensive Organic Transformations: A Guide to Functional Group Transformations,* $2^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts *Greene's Protective Groups in Organic Synthesis,* 5th Ed., John Wiley & Sons (2014), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:

$Ac_2O$=acetic anhydride
Boc=tert-butyloxycarbonyl
$B(OiPr)_3$=Triisopropyl borate
BrettPhos=dicyclohexyl(2',4',6'-triisopropyl-3,6-dimethoxy-[1,1'-biphenyl]-2-yl) phosphine
BrettPhos Pd G3=[(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate
brine=saturated aqueous sodium chloride
nBuLi=n-butyl lithium
$CDCl_3$=deuterated chloroform
$(COCl)_2$=oxalyl chloride
$Cs_2CO_3$=cesium carbonate
DCE=1,2-dichloroethane
DCM=dichloromethane
DIPEA=N,N-diisopropylethylamine
DME=1,2-dimethoxyethane, or glyme, or monoglyme
DMF=N,N-dimethylformamide
DMPU=N,N'-dimethylpropyleneurea
DMSO-$d_6$=deuterated dimethylsulfoxide
ESIMS=electron spray mass spectrometry
EtOAc=ethyl acetate
HATU=1-[bis(dimethylamino)methylene]-1H-1,2,3-triazolo[4,5-b]pyridinium 3-oxid hexafluorophosphate
HCl=hydrochloric acid
HOAc=acetic acid
IPA=isopropyl alcohol
ISCO=Teledyne ISCO, Inc brand CombiFlash® Rf 200
KOAc=potassium acetate
LCMS=liquid chromatography-mass spectrometry
LiHMDS=lithium bis(trimethylsilyl)amide
MeCN=acetonitrile
MeOH=methanol
MeTHF=2-methyltetrahydrofuran
$MgSO_4$=magnesium sulfate
MsCl=methanesulfonyl chloride or mesyl chloride
MTBE=methyl tert-butyl ether
MW=microwave irradiation
NaO$^t$Bu=sodium tert-butoxide
$NaHCO_3$=sodium bicarbonate
$NaBH(OAc)_3$=Sodium triacetoxyborohydride
$Na_2SO_4$=sodium sulfate
NMR=nuclear magnetic resonance
ON=overnight
Pd/C=palladium on carbon
Pd(dppf)$Cl_2$=1,1'-bis(diphenylphosphino)ferrocene-palladium(II)dichloride
$Pd(OH)_2$/C=palladium hydroxide on carbon
PE=petroleum ether
PPTS=pyridinium p-toluenesulfonate
prep-TLC=preparative thin layer chromatography
QPhos=1,2,3,4,5-pentaphenyl-1'-(di-tert-butylphosphino) ferrocene
r.t.=room temperature
TBDMSCl=tert-butyldimethylsilyl chloride
TEA=triethylamine
TFA=trifluoroacetic acid
THF=tetrahydrofuran
TLC=thin layer chromatography
TMSOK=potassium trimethylsilanolate
XPhos=dicyclohexyl[2',4',6'-tris(propan-2-yl)[1,1'-biphenyl]-2-yl]phosphane The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only and should not be construed as or confused with same numberings in other sections of the application. Unless otherwise indicated, all variables are as defined above.

GENERAL PROCEDURES

Compounds of Formula I of the present disclosure can be prepared as depicted in Scheme 1.

Scheme 1

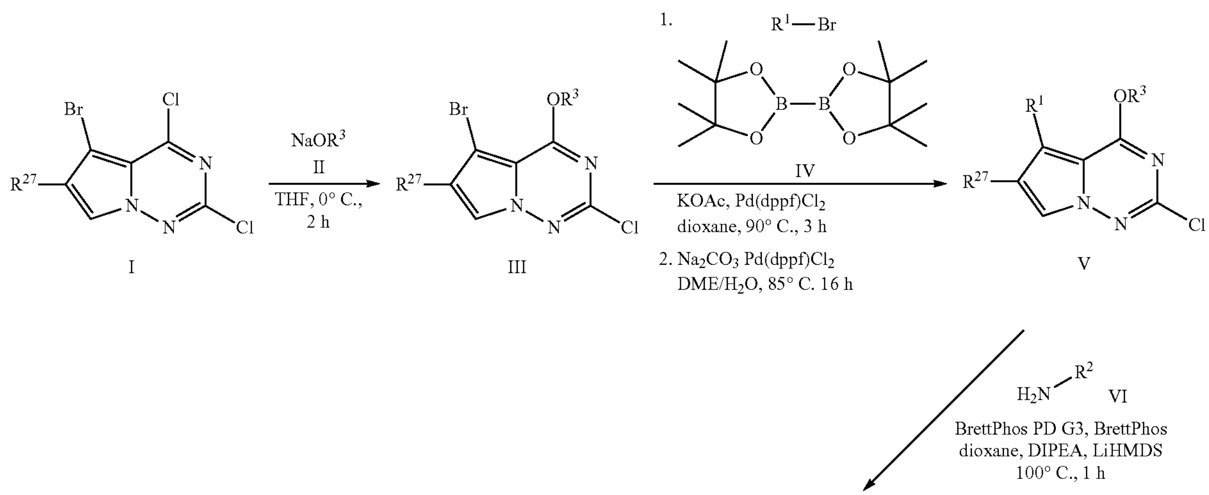

I

III

V

-continued

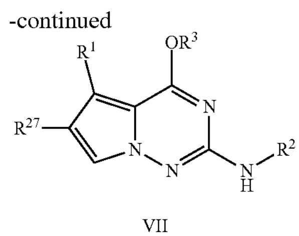

VII

Scheme 1 describes a method for preparation of 4-alkoxypyrrolo[2,1-f][1,2,4]triazine derivatives (VII) by first displacing the 4-chloride (I) with a variety of alkoxys (II) to produce 2-chloro-5-bromo-4-alkoxypyrrolo[2,1-f][1,2,4]triazine III. Formation of a variety of boronic acid pinacol esters by reacting various bromides (IV) with bis(pinacolato)diboron followed by Suzuki coupling with bromide (III) produces 2-chloro-4-alkoxypyrrolo[2,1-f][1,2,4]triazine (V). The chloro is then displaced with a variety of amines (VI) to produce the final 4-alkoxypyrrolo[2,1-f][1,2,4]triazine (VII).

Illustrative Compound Examples

Preparation of intermediate 5-bromo-2-chloro-4-methoxypyrrolo[2,1-f][1,2,4]triazine (XII) is depicted below in Scheme 2.

filtrate was diluted with MTBE (2 L) and washed with brine (2 L×3). The above reaction was performed six times.

The combined organics of five batches were combined, dried over $MgSO_4$, filtered, and concentrated under vacuum to give the crude product. The crude product was purified by column chromatography on silica gel (DCM/PE=0-50%, then EtOAc/PE=20%) to give methyl 1-amino-3-bromo-1H-pyrrole-2-carboxylate (IX) (380 g, 1.62 mol, 55.1% yield, 93.3% purity) as a yellow solid. $^1H$ NMR (400 MHz, DMSO-$d_6$) δ ppm 3.84 (3H, s), 6.24 (1H, d, J=2.8 Hz), 6.38 (2H, br s), 7.12 (1H, d, J=2.8 Hz).

Steps 2-3

To a solution of methyl 1-amino-3-bromo-1H-pyrrole-2-carboxylate (IX) (190 g, 867.44 mmol, 1 eq.) in THF (1900 mL) was added dropwise 2,2,2-trichloroacetyl isocyanate (179.76 g, 954.18 mmol, 113.06 mL, 1.1 eq.) at 0~5° C., then warmed to room temperature for 1 h. The reaction was Scheme 2

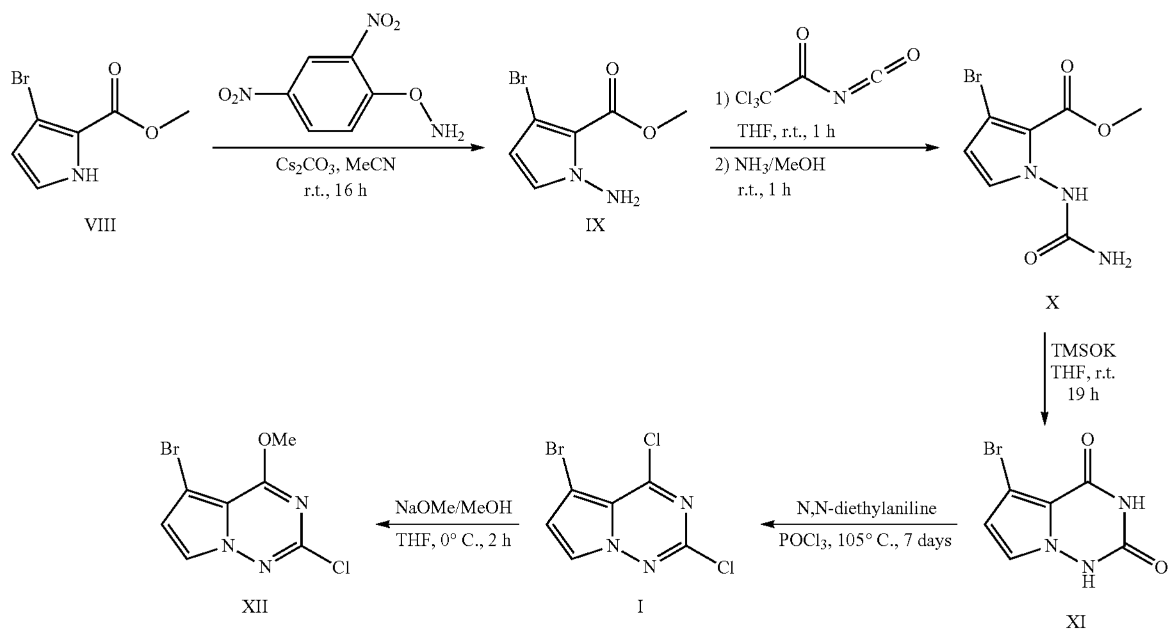

VIII IX X XI I XII

Step 1

To a solution of methyl 3-bromo-1H-pyrrole-2-carboxylate (VIII) (100 g, 490.15 mmol, 1 eq.) in MeCN (2 L) was added $Cs_2CO_3$ (255.52 g, 784.23 mmol, 1.6 eq.) in one portion at 20° C. (no exothermic). The reaction was stirred at room temperature for 5 h. A solution of O-(2,4-dinitrophenyl)hydroxylamine (146.40 g, 735.22 mmol, 1.5 eq.) in MeCN (2 L) was then added dropwise at 0-5° C. under $N_2$. After addition, the reaction was warmed to room temperature for 16 h. The reaction mixture was filtered, and the then added dropwise to $NH_3$/MeOH (7 M, 1.24 L, 10 eq) at room temperature, stirred at room temperature for 1 h to give a yellow suspension. The above reaction was performed twice.

The two reactions were combined and concentrated under vacuum. The residue was triturated with MTBE (4 L) at room temperature for 30 min, filtered. The filter cake was washed with MTBE (500 mL×3), dried under vacuum to give methyl 3-bromo-1-ureido-1H-pyrrole-2-carboxylate (X) (402 g, 1.53 mol, 88.2% yield, 99.78% purity) as an off-white solid. $^1H$ NMR (400 MHz, DMSO-$d_6$) δ ppm 3.75 (3H, s), 6.27 (2H, br s), 6.28 (1H, d, J=2.8 Hz), 7.10 (1H, d, J=2.8 Hz), 9.27 (1H, br s); ESIMS found for $C_7H_8BrN_3O_3$ m/z 262.1 ($^{79}$BrM+H).

Step 4

To a solution of methyl 3-bromo-1-ureido-1H-pyrrole-2-carboxylate (X) (67 g, 255.67 mmol, 1 eq.) in THF (4 L) was added TMSOK (65.60 g, 511.33 mmol, 2 eq.) in portions at 0~5° C. under $N_2$. After stirring for 5 min, the reaction became a thick slurry. The reaction mixture was stirred vigorously at room temperature for 16 h. LCMS showed ~25.8% of starting material remained. An additional portion of TMSOK (16.40 g, 127.83 mmol, 0.5 eq.) was added at room temperature and stirred for 3 h. LCMS showed the reaction was complete. The reaction was concentrated. The residue was diluted with $H_2O$ (1.6 L), cooled with ice-bath, added dropwise HCl (4 M, 160 mL) to pH 2-3, and filtered. The filter cake was washed with $H_2O$ (600 mL×3). The above reaction was performed six times.

The filter cakes of six reactions were combined, triturated with $H_2O$ (6 L) at room temperature, for 2 h and then filtered. The filter cake was dried in a vacuum drying oven at 60° C. for 24 h to give 5-bromopyrrolo[2,1-f][1,2,4]triazine-2,4(1H,3H)-dione (XI) (320 g, 1.28 mol, 83.4% yield, 91.95% purity) as a white solid. $^1H$ NMR (400 MHz, DMSO-$d_6$) δ ppm 6.49 (1H, d, J=2.8 Hz), 7.17 (1H, d, J=2.8 Hz), 11.30 (1H, br s); ESIMS found for $C_6H_4BrN_3O_2$ m/z 232.0 ($^{81}$BrM+H).

Step 5

To a solution of $POCl_3$ (1500 mL) was added 5-bromopyrrolo[2,1-f][1,2,4]triazine-2,4(1H,3H)-dione (XI) (180 g, 782.55 mmol, 1 eq.) in portions at room temperature. N,N-Diethylaniline (291.95 g, 1.96 mol, 312.92 mL, 2.5 eq.) was then added dropwise at room temperature (a little exothermic). After addition, the reaction was heated to 105° C. for 48 h. LCMS showed the starting material was consumed but the intermediate remained, ~4.3% of desired product was formed. The reaction was cooled to 90° C., added an additional $POCl_3$ (500 mL) in one portion, then heated to reflux gently for 24 h. LCMS showed most of intermediate remained, ~11.9% of desired product was formed. The reaction was heated to reflux gently for another 4 days. LCMS showed ~7.4% of intermediate remained, ~55.5% of desired product was formed. The reaction was cooled to 40° C. and distilled under reduced pressure to remove most of $POCl_3$. The residue was diluted with MeTHF (5 L), poured into ice-$H_2O$ (2 L), the added brine (1 L), and separated. The aqueous layer was extracted with MeTHF (1.5 L×2). The combined organic were washed with brine (1.5 L×2), dried over $MgSO_4$, filtered, and concentrated under vacuum to give the crude product. The crude product was purified by column chromatography on silica gel (4 kg, 100~200 mesh, DCM/PE=0-20%) and triturated with n-heptane (500 mL) at room temperature for 3 h, then filtered to afford 5-bromo-2,4-dichloropyrrolo[2,1-f][1,2,4]triazine (I) (150 g, 556.14 mmol, 71.1% yield, 98.96% purity) as a yellow solid. $^1H$ NMR (400 MHz, $CDCl_3$) δ ppm 7.02 (1H, d, J=2.4 Hz), 7.79 (1H, d, J=2.4 Hz); ESIMS found for $C_6H_2BrCl_2N_3$ m/z 266.1 ($^{79}$BrM+H).

Step 6

To a stirred solution of 5-bromo-2,4-dichloropyrrolo[2,1-f][1,2,4]triazine (I) (8.0 g, 29.97 mmol) in THF (10 mL) was added sodium methoxide (66 mL, 33 mmol) in MeOH dropwise at 0° C. and the mixture was stirred for 2 h. The reaction mixture was quenched with saturated aqueous $NH_4Cl$, taken into EtOAc, washed with water and brine. The organics were separated, dried over anhydrous $Na_2SO_4$, concentrated, and dried under high vacuo to obtain 5-bromo-2-chloro-4-methoxypyrrolo[2,1-f][1,2,4]triazine (XII) (6 g, 22.86 mmol, 76.3% yield) as an off-white solid which was used for the next step without purification. $^1H$ NMR (499 MHz, DMSO-$d_6$) δ ppm 4.12 (3H, s), 7.00 (1H, d, J=3.01 Hz), 8.01 (1H, d, J=3.01 Hz); ESIMS found for $C_7H_5BrClN_3O$ m/z 261.1 ($^{79}$BrM+H).

Preparation of intermediate 5-bromo-2-chloro-6-fluoro-4-methoxypyrrolo[2,1-f][1,2,4]triazine (XXII) is depicted below in Scheme 3.

Scheme 3

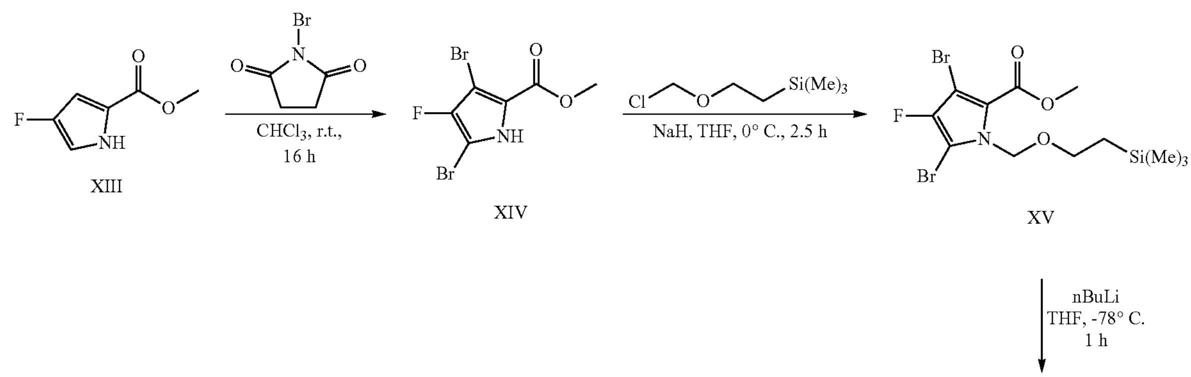

XIII XIV XV

-continued

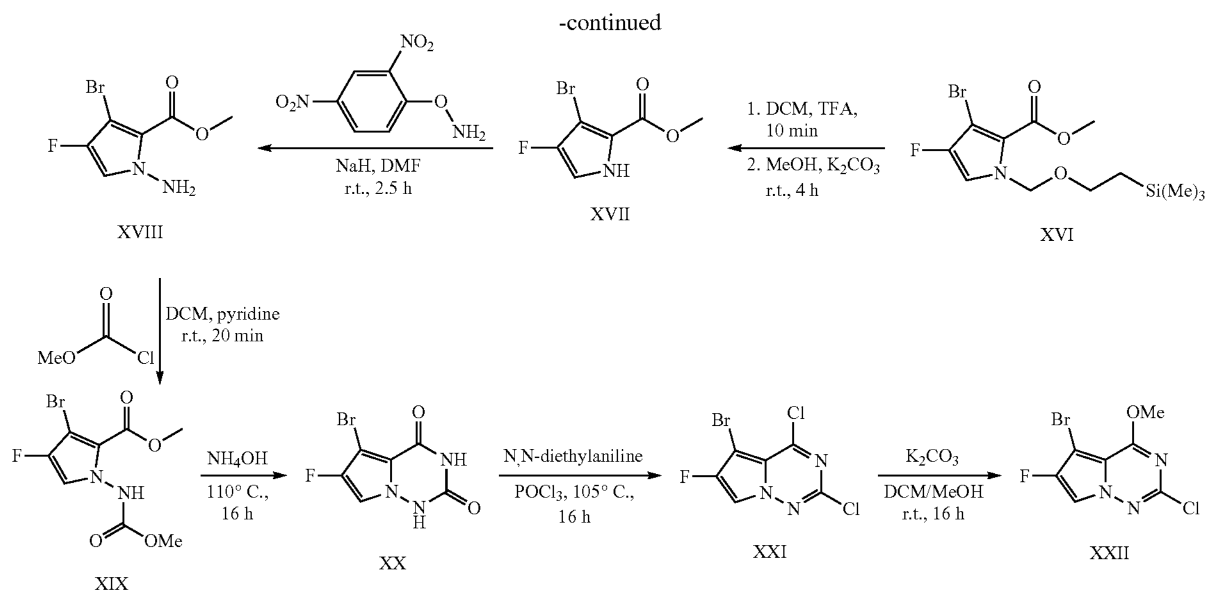

XVIII XVII XVI

XIX XX XXI XXII

Step 1

To a solution of methyl 4-fluoro-1H-pyrrole-2-carboxylate (XIII) (commercially available from PharmaBlock (USA), Inc.) (1 g, 6.99 mmol) in $CHCl_3$ (9 mL) at 0° C. was added N-bromosuccinimide (2.64 g, 14.68 mmol). The reaction was stirred at room temperature for 16 h. The reaction mixture was quenched with 10% sodium thiosulfate (50 mL) and extracted with $CHC_3$ (3×30 mL). The organic layers were combined and washed with aqueous saturated NaCl (50 ml) and evaporated under reduced pressure to produce methyl 3,5-dibromo-4-fluoro-1H-pyrrole-2-carboxylate (XIV) (2.1 g, 6.979 mmol, 99.9% yield) as a beige solid. The product was used as is without further purification. ESIMS found for $C_6H_4Br_2FNO_2$ m/z 299.9 (M+H).

Step 2

To a solution of methyl 3,5-dibromo-4-fluoro-1H-pyrrole-2-carboxylate (XIV) (2.1 g, 6.98 mmol) in dry THF (25 mL) at 0° C. under $N_2$ was added slowly NaH (0.43 g, 10.63 mmol) in small portions. The suspension was stirred at 0° C. for 30 min. To the suspension was added (2-(chloromethoxy)ethyl)trimethylsilane (1.9 mL, 10.74 mmol) at 0° C. under $N_2$. The reaction mixture was stirred at 0° C. for 2 h before quenching with ice-water (20 mL) and extracted with EtOAc (3×30 mL). The EtOAc layer was evaporated under reduced pressure and purified by silica gel column chromatography (100% hexanes) to produce methyl 3,5-dibromo-4-fluoro-1-((2-(trimethylsilyl)ethoxy)methyl)-1H-pyrrole-2-carboxylate (XV) (2.76 g, 6.401 mmol, 91.7% yield) as an amber liquid. $^1$H NMR (499 MHz, DMSO-$d_6$) δ ppm −0.07 (9H, s), 0.81 (2H, t, J=7.80 Hz), 3.50 (2H, t, J=7.80 Hz), 3.82 (3H, s), 5.69 (2H, s).

Step 3

To solution of methyl 3,5-dibromo-4-fluoro-1-((2-(trimethylsilyl)ethoxy)methyl)-1H-pyrrole-2-carboxylate (XV) (2.76 g, 6.4 mmol) in dry THF (60 mL) at −78° C. under $N_2$ was added nBuLi (2.4 mL, 6. mmol). The reaction mixture was stirred at −78° C. for 1 h. The mixture was carefully quenched with ice water (20 mL), warmed to room temperature, and extracted with EtOAc (3×20 mL). The organics were dried over anhydrous $Na_2SO_4$, filtered and evaporated onto Celite® and purified by silica gel column chromatography (0→6% EtOAc/hexanes) to produce methyl 3-bromo-4-fluoro-1-((2-(trimethylsilyl) ethoxy) methyl)-1H-pyrrole-2-carboxylate (XVI) (760 mg, 2.157 mmol, 33.7% yield) as a clear oil. $^1$H NMR (500 MHz, DMSO-$d_6$) δ ppm −0.06 (9H, s), 0.80 (2H, t, J=7.96 Hz), 3.41-3.50 (2H, m), 3.80 (3H, s), 5.56 (2H, s), 7.52 (1H, d, J=3.29 Hz).

Step 4

To a stirred solution of methyl 3-bromo-4-fluoro-1-((2-(trimethylsilyl)ethoxy)methyl)-1H-pyrrole-2-carboxylate (XVI) (881 mg, 2.5 mmol) in DCM (23 mL) was added TFA (23 mL) and the mixture was stirred at room temperature for 10 min. The solvents were concentrated, the residue taken in a mixture of MeOH (12 mL)/water (6 mL). To this mixture was added $K_2CO_3$ (1.75 g, 12.66 mmol) and stirred at room temperature for 4 h. Water (10 mL) was added, and the solution was neutralized with 1H HCl and washed with $CHCl_3$ (3×10 mL). The organic layer was stripped onto Celite® and purified by silica gel column chromatography (0→5% MeOH/$CHCl_3$ (7 N $NH_3$)) to produce methyl 3-bromo-4-fluoro-1H-pyrrole-2-carboxylate (XVII) (450 mg, 2.027 mmol, 81.0% yield) as an off white solid. $^1$H NMR (499 MHz, DMSO-$d_6$) δ ppm 3.80 (3H, s), 7.15 (1H, d, J=3.56 Hz), 12.29 (1H, br s); ESIMS found for $C_6H_5BrFNO_2$ m/z 222.0 (M+H).

Step 5

To a solution of methyl 3-bromo-4-fluoro-1H-pyrrole-2-carboxylate (XVII) (500 mg, 2.25 mmol) in dry DMF (7 mL) at 0° C. was slowly added NaH (120 mg, 2.93 mmol). After 30 min, 0-(2,4-dinitrophenyl)hydroxylamine (490 mg, 2.48 mmol)) was added in one portion and the reaction was stirred in the ice bath for 1 h and at room temperature for 1 h. LC/MS showed the reaction was incomplete so addition O-(2,4-dinitrophenyl)hydroxylamine (490 mg, 2.48 mmol) and stirred at room temperature for 15 min. The reaction was diluted with water (100 mL) and extracted with EtOAc (3×75 mL). The combined extracts were stripped onto Celite® and purified by silica gel column chromatography (100% $CHCl_3$) to produce methyl 1-amino-3-bromo-4-fluoro-1H-pyrrole-2-carboxylate (XVIII) (501 mg, 2.114 mmol, 93.9% yield) as an off-white solid. $^1$H NMR (499 MHz, DMSO-$d_6$) δ ppm 3.80 (3H, s), 6.36 (2H, s), 7.25 (1H, d, J=3.29 Hz); ESIMS found for $C_6H_6BrFN_2O_2$ m/z 237.0 (M+H).

Step 6

To a solution of methyl 1-amino-3-bromo-4-fluoro-1H-pyrrole-2-carboxylate (XVIII) (500 mg, 2.11 mmol) in DCM (10 mL) was added pyridine (210 μL, 2.6 mmol) and methyl carbonochloridate (180 μL, 2.33 mmol) dropwise. The reaction was stirred at room temperature for 20 min. DCM (100 mL) was added and washed with 1 N HCl (2×50 mL), stripped onto Celite® and purified by silica gel column chromatography (0->100% EtOAc/hexanes) to produce methyl 3-bromo-4-fluoro-1-((methoxycarbonyl) amino)-1H-pyrrole-2-carboxylate (XIX) (560 mg, 1.898 mmol, 89.8% yield) as a clear oil. $^1$H NMR (499 MHz, DMSO-$d_6$) δ ppm 3.69 (3H, br s), 3.76 (3H, s), 7.48 (1H, br d, J=1.92 Hz), 10.76 (1H, br s); ESIMS found for $C_6H_5BrFN_2O_4$ m/z 295.0 (M+H).

Step 7

To $NH_4OH$ (35 mL, 263.7 mmol) in a sealed tube was added methyl 3-bromo-4-fluoro-1-((methoxycarbonyl) amino)-1H-pyrrole-2-carboxylate (XIX) (560 mg, 1.9 mmol). The reaction was sealed and heated to 110° C. for 16 h. The solvent was removed under vacuum and the residue was dissolved in MeCN. The solvent was stripped (3× to remove water) and placed under high vacuum for 1 h, to produce 5-bromo-6-fluoropyrrolo[2,1-f][1,2,4]triazine-2,4 (1H,3H)-dione (XX) (440 mg, 1.774 mmol, 93.5% yield) as a light brown solid. The product was used as is without further purification. $^1$H NMR (499 MHz, DMSO-$d_6$) δ ppm 7.04 (1H, d, J=3.29 Hz), 7.13 (1H, br s), 9.58 (1H, br s); ESIMS found for $C_6H_3BrFN_3O_2$ m/z 247.9 (M+H).

Step 8

To a solution of neat $POCl_3$ (3 mL, 32.19 mmol) was added 5-bromo-6-fluoropyrrolo[2,1-f][1,2,4]triazine-2,4 (1H,3H)-dione (XX) (440 mg, 1.77 mmol) in portions at room temperature. N,N-Diethylaniline (0.7 mL, 4.4 mmol) was then added dropwise at room temperature. The reaction was heated at 105° C. for 16 h. The solvent was removed under vacuum before adding water (20 mL) and extracting with EtOAc. The organic layer was stripped onto Celite® and purified by silica gel column chromatography (0->100% EtOAc/hexanes) to produce 5-bromo-2,4-dichloro-6-fluoro-pyrrolo[2,1-f][1,2,4]triazine (XXI) (175 mg, 0.614 mmol, 34.6% yield) as an off-white solid. $^1$H NMR (499 MHz, DMSO-$d_6$) δ ppm 7.92 (1H, d, J=3.29 Hz); ESIMS found for $C_6HBrCl_2FN_3$ m/z 283.9 (M+H).

Step 9

To a solution of 5-bromo-2,4-dichloro-6-fluoropyrrolo[2,1-f][1,2,4]triazine (XXI) (175 mg, 0.61 mmol) in MeOH (664 μL) and DCM (2 mL) was added $K_2CO_3$ (254.1 mg, 1.84 mmol). The flask was capped and the reaction and stirred at room temperature for 16 h. Water (50 mL) was added and extracted with DCM (3×50 mL). The organic layers were separated and washed with water (2×50 mL) and brine (50 mL). The solvent was removed under vacuum to produce 5-bromo-2-chloro-6-fluoro-4-methoxypyrrolo[2,1-f][1,2,4]triazine (XXII) (163 mg, 0.581 mmol, 94.6% yield) as a beige solid. $^1$H NMR (500 MHz, DMSO-$d_6$) δ ppm 4.12 (3H, s), 8.34 (1H, d, J=3.29 Hz); ESIMS found for $C_7H_4BrClFN_3O$ m/z 279.95 (M+H).

Preparation of intermediate 2,5-dichloro-4-methoxypyrrolo[2,1-f][1,2,4]triazine (XXIV) is depicted below in Scheme 4.

Scheme 4

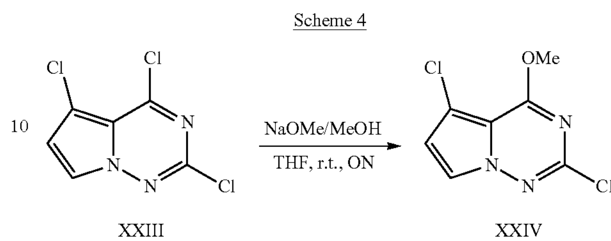

XXIII XXIV

Step 1

To a stirred solution of 2,4,5-trichloropyrrolo[2,1-f][1,2,4]triazine (XXIII) (commercially available from PharmaBlock Sciences Inc.) (202 mg, 0.910 mmol) in THF (4 mL) was added sodium methoxide (2 mL, 1 mmol) in MeOH dropwise at 0° C. and the mixture was stirred at room temperature overnight. The reaction mixture was quenched with water, taken into EtOAc, and washed with brine. The organics were separated, dried over anhydrous $Na_2SO_4$, concentrated, and the crude mixture was purified on ISCO (0->100% EtOAc/hexanes). Fractions were collected and concentrated under reduced pressure and dried under high vacuo to obtain 5-bromo-2-chloro-4-methoxypyrrolo[2,1-f][1,2,4]triazine (XXIV) (140 mg, 0.642 mmol, 70.7% yield) as a pale-yellow solid. $^1$H NMR (499 MHz, DMSO-$d_6$) δ ppm 4.12 (3H, s), 6.95 (1H, d, J=3.01 Hz), 8.02 (1H, d, J=3.01 Hz).

The following intermediate was prepared in accordance with the procedure described in the above Scheme 4.

XXV

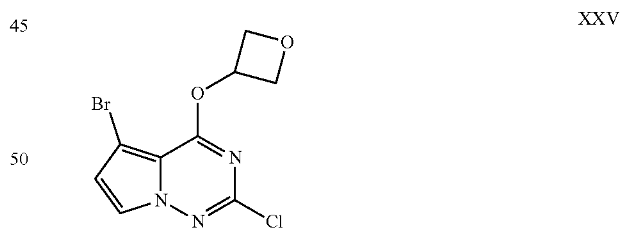

5-Bromo-2-chloro-4-(oxetan-3-yloxy)pyrrolo[2,1-f][1,2,4]triazine (XXV): Off-white solid (558.8 mg, 1.84 mmol, 98.0% yield). $^1$H NMR (499 MHz, DMSO-$d_6$) δ ppm 4.70 (2H, ddd, J=7.94, 4.65, 1.10 Hz), 4.95 (2H, ddd, J=7.73, 6.37, 0.96 Hz), 5.80 (1H, tt, J=6.09, 4.86 Hz), 7.05 (1H, d, J=3.01 Hz), 8.05 (1H, d, J=3.01 Hz); ESIMS found $C_9H_7BrClN_3O_2$ m/z 303.95 (M+H).

Preparation of intermediate 6-bromo-1-(2,2-difluoroethyl)-4-fluoro-2-methyl-1H-benzo[d]imidazole (XXX) is depicted below in Scheme 5.

Scheme 5

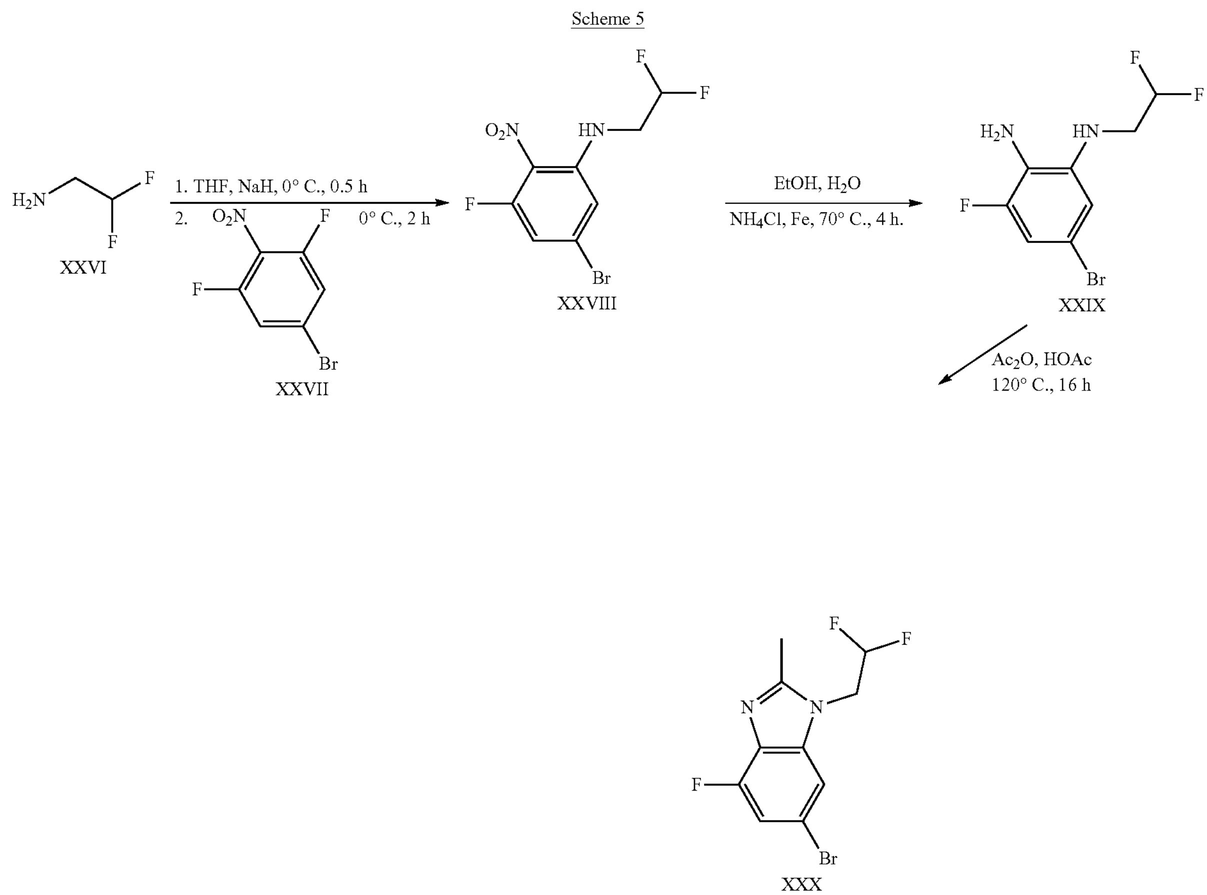

XXVI XXVII XXVIII XXIX XXX

Step 1

To an ice-cold suspension of sodium hydride (222 mg, 9.2 mmol) in THF (20 mL) was added 2,2-difluoroethylamine (XXVI) (746 mg, 9.32 mmol). The reaction mixture was allowed to stir at 0° C. for 30 min before adding an ice-cold solution of 5-bromo-1,3-difluoro-2-nitrobenzene (XXVII) (2.0 g, 8.4 mmol) in THF (20 mL). Reaction mixture was stirred at 0° C. for 2 h. The reaction was quenched with water. The aqueous layer was extracted with EtOAc, the organics were washed with brine, dried over anhydrous $Na_2SO_4$, filtered and concentrated. The crude product was purified via column chromatography (40 g of silica gel) (0->20% EtOAc/hexanes) to give 5-bromo-N-(2,2-difluoroethyl)-3-fluoro-2-nitroaniline (XXVIII) (500 mg, 0.836 mmol, 19.9% yield) as a yellow solid. ESIMS found for $C_8H_6BrF_3N_2O_2$ m/z 299.0 ($^{79}$BrM+H).

Step 2

A mixture of 5-bromo-N-(2,2-difluoroethyl)-3-fluoro-2-nitroaniline (XXVIII) (500 mg, 1.67 mmol), Fe (1.09 g, 16.72 mmol) and $NH_4Cl$ (1.34 g, 25.1 mmol) in a mixture of EtOH (6 mL) and water (2.5 mL) was heated to 70° C. for 4 h. The reaction mixture was cooled and filtered through Celite®. Filtrates were dissolved in EtOAc, washed water and brine, dried over anhydrous $Na_2SO_4$, filtered, and concentrated under reduced pressure to obtain 5-bromo-$N^1$-(2,2-difluoroethyl)-3-fluorobenzene-1,2-diamine (XXIX) (420 mg, 1.561 mmol, 93.4% yield) as a brown solid which was used for next reaction without further purification. ESIMS found for $C_8H_8BrF_3N_2$ m/z 269.0 (M+H).

Step 3

A solution of 5-bromo-$N^1$-(2,2-difluoroethyl)-3-fluorobenzene-1,2-diamine (XXIX) (420 mg, 1.56 mmol) and $Ac_2O$ (175 μL, 1.85 mmol) in HOAc (8 mL) was heated to 120° C. for 16 h. The reaction mixture was concentrated, the residue partitioned between EtOAc/1 N NaOH, organics separated and washed with water and brine. The organics were dried over anhydrous $Na_2SO_4$ and concentrated to yield 6-bromo-1-(2,2-difluoroethyl)-4-fluoro-2-methyl-1H-benzo[d]imidazole (XXX) (380 mg, 1.297 mmol, 83.1% yield) as a light brown solid. ESIMS found for $C_{10}H_{10}BrF_3N_2$ m/z 295.0 (M+H).

Preparation of intermediate 6-bromo-1-(2,2-difluoroethyl)-2-methyl-1H-imidazo[4,5-b]pyridine (XXXIV) is depicted below in Scheme 6.

Scheme 6

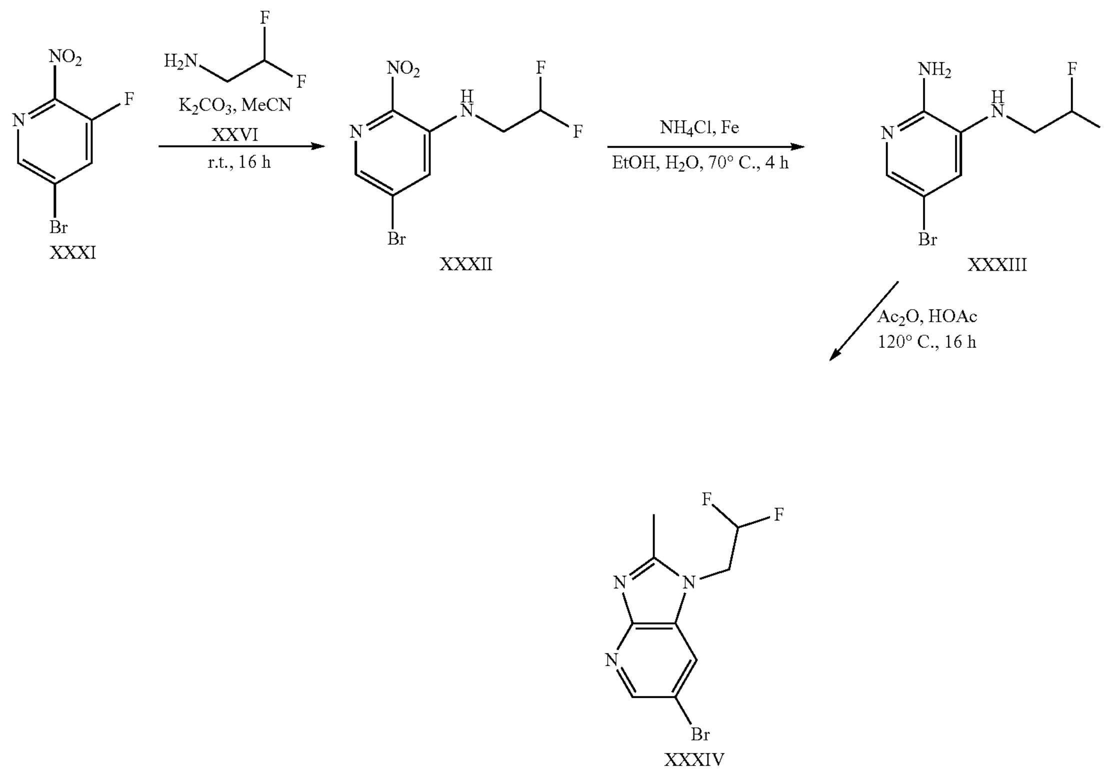

XXXI XXXII XXXIII XXXIV

Step 1

A mixture of 2,2-difluoroethan-1-amine (XXVI) (410 mg, 5.02 mmol), 5-bromo-3-fluoro-2-nitropyridine (XXXI) (commercially available from Ark Pharma Scientific Limited) (1.0 g, 4.53 mmol) and $K_2CO_3$ (1.38 g, 9.95 mmol) in MeCN (20 mL) was stirred at room temperature for 16 h. The reaction was filtered and concentrated under high vacuum. The residue was taken up in water, stirred for 1 hour and the solids were collected by filtration and dried in vacuo to obtain 5-bromo-N-(2,2-difluoroethyl)-2-nitropyridin-3-amine (XXXII) (1.066 g, 3.780 mmol, 83.5% yield) as a yellow solid which was used for next step without purification. ESIMS found for $C_7H_6BrF_2N_3O_2$ m/z 282.0 ($^{79}$BrM+H).

Step 2

A mixture of 5-bromo-N-(2,2-difluoroethyl)-2-nitropyridin-3-amine (XXXII) (1.32 g, 4.69 mmol), Fe (3.07 g, 46.95 mmol) and $NH_4Cl$ (3.77 g, 70.48 mmol) was taken in a mixture of EtOH (18 mL), and water (6 mL) and the mixture was heated to 70° C. for 4 h. The reaction mixture was cooled and filtered through Celite®. The filtrates were taken up in EtOAc, washed with water and brine, dried over anhydrous $Na_2SO_4$, filtered, and concentrated under reduced pressure to obtain 5-bromo-N$^3$-(2,2-difluoroethyl)pyridine-2,3-diamine (XXXIII) (630 mg, 2.499 mmol, 53.2% yield) as a grey solid which was used for next reaction without further purification. ESIMS found for $C_7H_8BrF_2N_3$ m/z 252.0 ($^{79}$BrM+H).

Step 3

A solution of 5-bromo-N$^3$-(2,2-difluoroethyl)pyridine-2,3-diamine (XXXIII) (630 mg, 2.5 mmol) and acetic anhydride (0.28 mL, 2.97 mmol) in HOAc (15 mL) was heated to 120° C. for 16 h. The reaction mixture was concentrated, the residue partitioned between EtOAc/1 N NaOH, organics separated, and washed with water and brine. The organics were dried over anhydrous $Na_2SO_4$, and solvents were concentrated under high vacuum. The residue was triturated with diethyl ether, sonicated and the solids were collected by filtration and dried under high vacuo to obtain 6-bromo-1-(2,2-difluoroethyl)-2-methylimidazo[4,5-b]pyridine (XXXIV) (325 mg, 1.177 mmol, 47.1% yield) as a grey solid which was used for next step without purification. ESIMS found for $C_9H_8BrF_2N_3$ m/z 276.0 ($^{79}$BrM+H).

The following intermediates were prepared in accordance with the procedure described in the above Scheme 6.

XXXV

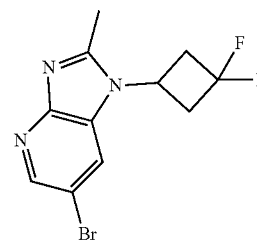

6-Bromo-1-(3,3-difluorocyclobutyl)-2-methyl-1H-imidazo[4,5-b] pyridine (XXXV): Grey solid (1.57 g, 6.178 mmol, 68.3% yield). ESIMS found $C_{11}H_{10}BrF_2N_3$ m/z 302.1 (M+H).

XXXVI

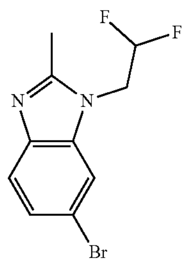

6-Bromo-1-(2,2-difluoroethyl)-2-methyl-1H-benzo[d]imidazole (XXXVI): Beige solid (970 mg, 3.526 mmol, 79.0% yield). ESIMS found $C_{10}H_9BrF_2N_2$ m/z 275.0 (M+H).

Preparation of intermediate 6-bromo-1-isopropyl-2-methyl-1H-imidazo[4,5-b]pyridine (XL) is depicted below in Scheme 7.

Scheme 7

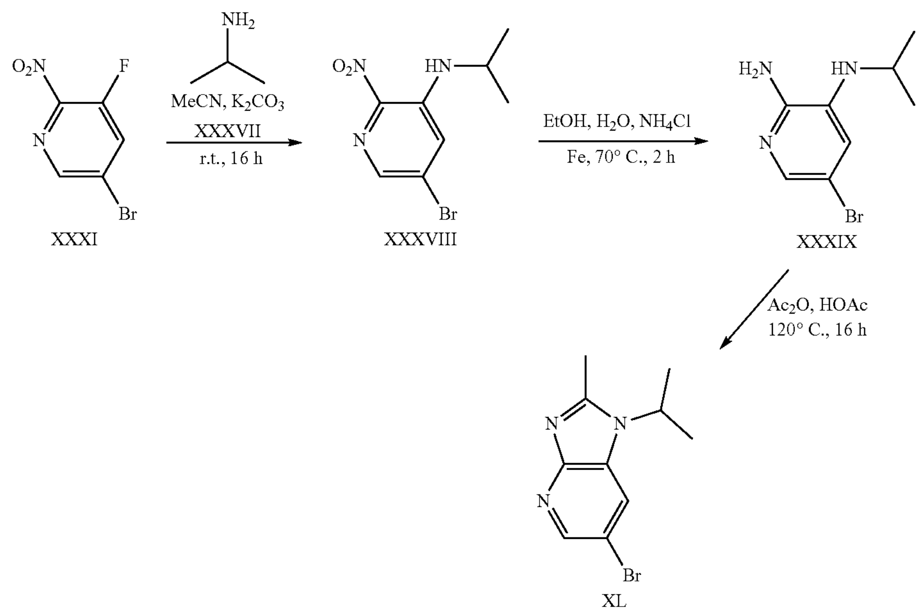

XXXI XXXVIII XXXIX XL

Step 1

A mixture of 2-aminopropane (XXXVII) (0.86 mL, 9.96 mmol), 5-bromo-3-fluoro-2-nitropyridine (XXXI) (2 g, 9.05 mmol) and $K_2CO_3$ (2.5 g, 18.1 mmol) in MeCN (40 mL) was stirred at room temperature for 16 h. The reaction mixture was added to water (200 mL), stirred for 1 h and the resulting solids were collected by filtration and dried under high vacuo to obtain 5-bromo-N-isopropyl-2-nitropyridin-3-amine (XXXVIII) (2.36 g, 9.074 mmol, 100.3% yield) as a yellow solid which was used for next step without purification. ESIMS found for $C_8H_{10}BrN_3O_2$ m/z 260.0 (M+H).

Step 2

The mixture of 5-bromo-N-isopropyl-2-nitropyridin-3-amine (XXXVIII) (2.35 g, 9.04 mmol) Fe (5.91 g, 90.35 mmol) and $NH_4Cl$ (7.25 g, 135.53 mmol) was taken in a mixture of EtOH (30 mL), and water (10 mL) and the mixture was heated to 70° C. for 2 h. The reaction mixture was cooled, filtered through Celite®, filtrates were taken into EtOAc, washed with water then brine, dried over anhydrous $Na_2SO_4$, filtered, and concentrated under reduced pressure to obtain 5-bromo-$N^3$-isopropylpyridine-2,3-diamine (XXXIX) (2.2 g, 9.561 mmol, 105.8% yield) as a dark brown solid which was used for next step without purification. ESIMS found for $C_8H_{12}BrN_3$ m/z 230.05 (M+H).

Step 3

A solution of 5-bromo-$N^3$-isopropylpyridine-2,3-diamine (XXXIX) (2.08 g, 9.04 mmol) and $Ac_2O$ (1.05 mL, 10.84 mmol) in HOAc (20 mL) was heated to 120° C. for 16 h. The reaction mixture was concentrated, the residue partitioned between EtOAc/1 N NaOH, organics separated, washed with water and brine. The organics were dried over anhydrous $Na_2SO_4$, concentrated, and dried under high vacuo to give 6-bromo-1-isopropyl-2-methyl-1H-imidazo[4,5-b]pyridine (XL) (1.57 g, 6.178 mmol, 68.3% yield) as a dark brown solid which was used for next step without purification. ESIMS found for $C_{10}H_{12}BrN_3$ m/z 254.0 (M+H).

The following intermediate was prepared in accordance with the procedure described in the above Scheme 7.

XLI

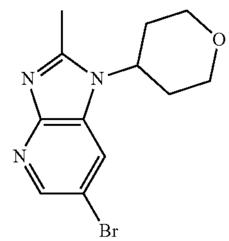

6-Bromo-2-methyl-1-(tetrahydro-2H-pyran-4-yl)-1H-imidazo[4,5-b]pyridine (XLI): Grey solid (722 mg, 2.438 mmol, 66.3% yield). ESIMS found $C_{12}H_{14}BrN_3O$ m/z 296.0 (M+H).

Preparation of intermediate 6-bromo-1-(2,2-difluoroethyl)-1H-benzo[d]imidazole (XLIII) is depicted below in Scheme 8.

Scheme 8

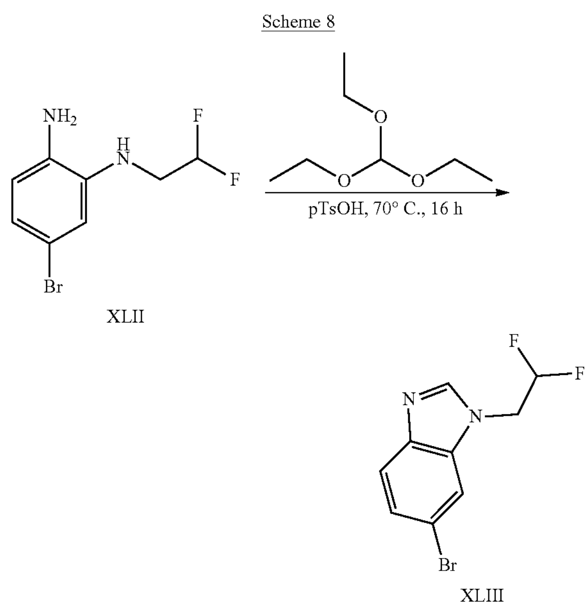

XLII

XLIII

Step 1

To a solution of 5-bromo-N1-(2,2-difluoroethyl)benzene-1,2-diamine (XLII) (3.0 g, 11.95 mmol) in triethoxymethane (60 mL) at room temperature was added p-toluenesulfonic acid (0.23 g, 1.20 mmol). The reaction mixture was stirred at 70° C. for 16 h, then cooled to room temperature. The reaction mixture was concentrated. The reaction mixture was diluted with water (200 mL) and extracted with EtOAc (2×300 mL). The organic layers were concentrated, dried over $Na_2SO_4$, filtered, and concentrated. The mixture was purified by reverse-phase column chromatography (Regular C18 20-40 um, acetonitrile/0.10% $NH_4HCO_3$ aqueous solution, gradient: 40%→60% MeCN) to afford 6-bromo-1-(2,2-difluoroethyl)-1H-benzo[d]imidazole (XLIII) (1.5 g, 5.746 mmol, 48.1% yield) as a yellow solid. $^1$H NMR (400 MHz, DMSO-$d_6$) δ 8.26 (s 1H), 7.98 (d, J=1.6 Hz, 1H), 7.64 (d, J=8.4 Hz, 1H), 7.38 (dd, J=8.8, 2 Hz, 1H), 6.46 (tt, J=54.3, 3.0 Hz, 1H), 5.36 (td, J=16.4, 3.2 Hz, 2H); ESIMS found for $C_9H_7BrF_2N_2$ m/z 260.9 (M+H).

Preparation of intermediate 5-chloro-3-ethyl-2-methyl-3H-imidazo[4,5-b]pyridine (XLV) is depicted below in Scheme 9.

Scheme 9

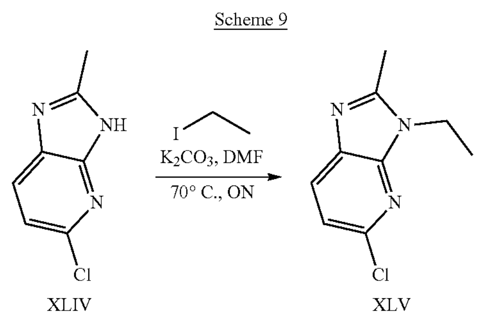

XLIV

XLV

Step 1

A mixture of 5-chloro-2-methyl-3H-imidazo[4,5-b]pyridine (XLIV) (commercially available from eNovation Chemicals, LLC) (0.5 g, 2.98 mmol), iodoethane (0.56 g, 3.58 mmol) and $K_2CO_3$ (0.83 g, 5.97 mmol) in DMF (10 mL) was heated to 70° C. overnight. The reaction mixture was cooled, solvents concentrated, the residue partitioned between EtOAc/water, the organic layers were separated, washed with brine, dried over anhydrous $MgSO_4$ and the solvents were concentrated under vacuo and dried to obtain 5-chloro-3-ethyl-2-methylimidazo[4,5-b]pyridine (XLV) (466 mg, 2.382 mmol, 79.8% yield) as a dark brown solid which was used for next step without purification. ESIMS found for $C_9H_{10}ClN_3$ m/z 196.05 (M+H).

The following intermediates were prepared in accordance with the procedure described in the above Scheme 9.

XLVI

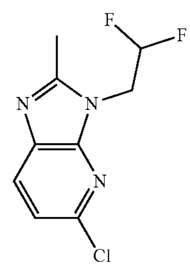

5-Chloro-3-(2,2-difluoroethyl)-2-methyl-3H-imidazo[4,5-b]pyridine (XLVI): Beige solid (830 mg, 3.583 mmol, 60.1% yield). ESIMS found $C_9H_8ClF_2N_3$ m/z 232.0 (M+H).

XLVII

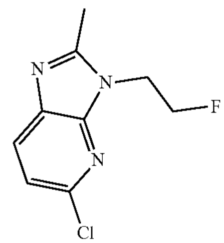

5-Chloro-3-(2-fluoroethyl)-2-methyl-3H-imidazo[4,5-b]pyridine (XLVII): Beige solid (220 mg, 1.030 mmol, 57.5% yield). ESIMS found $C_9H_9ClFN_3$ m/z 214.05 (M+H).

XLVIII

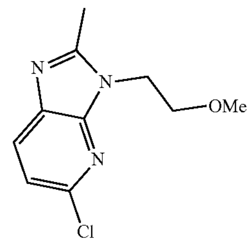

5-Chloro-3-(2-methoxyethyl)-2-methyl-3H-imidazo[4,5-b]pyridine (XLVIII): Beige solid (195 mg, 0.864 mmol, 48.3% yield). ESIMS found $C_{10}H_{12}C_1N_3O$ m/z 226.1 (M+H).

XLIX

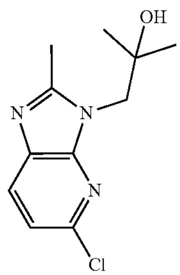

1-(5-Chloro-2-methyl-3H-imidazo[4,5-b]pyridin-3-yl)-2-methylpropan-2-ol (XLIX): White solid (229.9 mg, 0.959 mmol, 39.7% yield). $^1$H NMR (499 MHz, DMSO-$d_6$) δ ppm 1.13 (6H, s), 2.63 (3H, s), 4.11 (2H, s), 4.80 (1H, s), 7.25 (1H, d, J=8.21 Hz), 7.96 (1H, d, J=8.21 Hz); ESIMS found $C_{11}H_{14}ClN_3O$ m/z 240.1 (M+H).

L

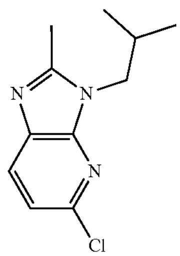

5-Chloro-3-isobutyl-2-methyl-3H-imidazo[4,5-b]pyridine (L): White solid (206.8 mg, 0.925 mmol, 38.7% yield). $^1$H NMR (499 MHz, DMSO-$d_6$) δ ppm 0.87 (6H, d, J=6.57 Hz), 2.22 (1H, dquin, J=13.89, 7.07, 7.07, 7.07, 7.07 Hz), 2.58 (3H, s), 4.01 (2H, d, J=7.67 Hz), 7.26 (1H, d, J=8.21 Hz), 7.98 (1H, d J=8.21 Hz); ESIMS found $C_{11}H_{14}ClN_3$ m/z 224.1 (M+H).

LI

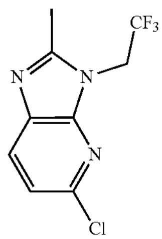

5-Chloro-2-methyl-3-(2,2,2-trifluoroethyl)-3H-imidazo [4,5-b]pyridine (LI): Beige solid (372 mg, 1.490 mmol, 50.0% yield). ESIMS found $C_9H_7ClF_3N_3$ m/z 250.0 (M+H).

LII

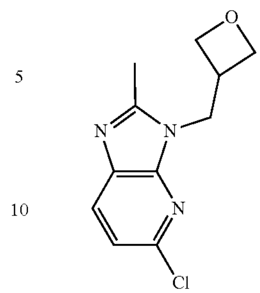

5-Chloro-2-methyl-3-(oxetan-3-ylmethyl)-3H-imidazo[4,5-b]pyridine (LII): Light brown solid (289.7 mg, 1.219 mmol, 40.4% yield). $^1$H NMR (499 MHz, DMSO-$d_6$) δ ppm 2.59 (3H, s), 3.43-3.56 (1H, m), 4.47 (2H, t, J=6.02 Hz), 4.52 (2H, d, J=7.67 Hz), 4.62 (2H, dd, J=7.67, 6.02 Hz), 7.27 (1H, d, J=8.21 Hz), 7.98 (1H, d, J=8.21 Hz); ESIMS found $C_{11}H_{12}ClN_3O$ m/z 238.1 (M+H).

LIII

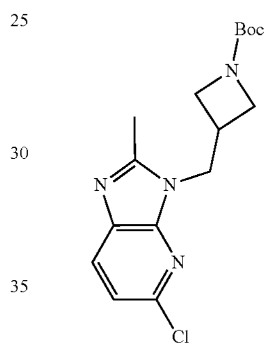

tert-Butyl 3-((5-chloro-2-methyl-3H-imidazo[4,5-b]pyridin-3-yl)methyl) azetidine-1-carboxylate (LIII): Off-white amorphous solid (532.6 mg, 1.581 mmol, 52.1% yield). ESIMS found $C_{16}H_{21}ClN_4O_2$ m/z 337.1 (M+H).

LIV

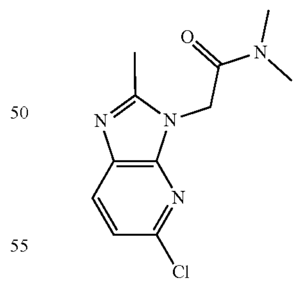

2-(5-Chloro-2-methyl-3H-imidazo[4,5-b]pyridin-3-yl)-N,N-dimethylacetamide (LIV): Off-white solid (474.4 mg, 1.877 mmol, 62.6% yield). ESIMS found $C_{12}H_{13}ClN_4O$ m/z 253.1 (M+H).

LV

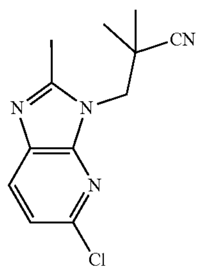

3-(5-Chloro-2-methyl-3H-imidazo[4,5-b]pyridin-3-yl)-2,2-dimethylpropanenitrile (LV): Off-white amorphous solid (59.1 mg, 0.238 mmol, 7.9% yield). ESIMS found $C_{12}H_{13}C_1N_4$ m/z 249.1 (M+H).

Preparation of intermediate 6-bromo-1-(2-((tert-butyldimethylsilyl)oxy)ethyl)-2-methyl-1H-benzo[d]imidazole (LXII) is depicted below in Scheme 10.

Step 2

To a solution of 2-((5-bromo-2-nitrophenyl)amino)ethan-1-ol (LVIII) (1.31 g, 5.02 mmol) in MeOH (50 mL) was added tin(II) chloride (0.96 mL, 20.09 mmol) at room temperature. The reaction mixture was heated to 64° C. for 6 h, then cooled to room temperature. The solvent was removed under vacuum, and the residue was dissolved in water and basified by addition of $Na_2CO_3$ to pH=9. The mixture was extracted with DCM, and the combined organic phase was washed with water, brine, and dried over anhydrous $Na_2SO_4$. The solvent was removed under vacuum before adding HOAc (15.6 mL, 271.49 mmol). The solution was heated to reflux for 30 min. The acetic acid was removed under reduced pressure and the residue was purified using silica gel column chromatography (0->50% 7 N $NH_3$ in $MeOH/CHCl_3$) to produce 2-(6-bromo-2-methyl-1H-benzo[d]imidazol-1-yl)ethyl acetate (LIX) and 2-(6-bromo-2-methyl-1H-benzo[d]imidazol-1-yl)ethan-1-ol (LX) (1.45 g, 4.880 mmol, 97.2% yield), as an 80/20 mixture as an off-white solid. ESIMS found for $C_{12}H_{13}BrN_2O_2$ m/z 297.0 (M+H).

Scheme 10

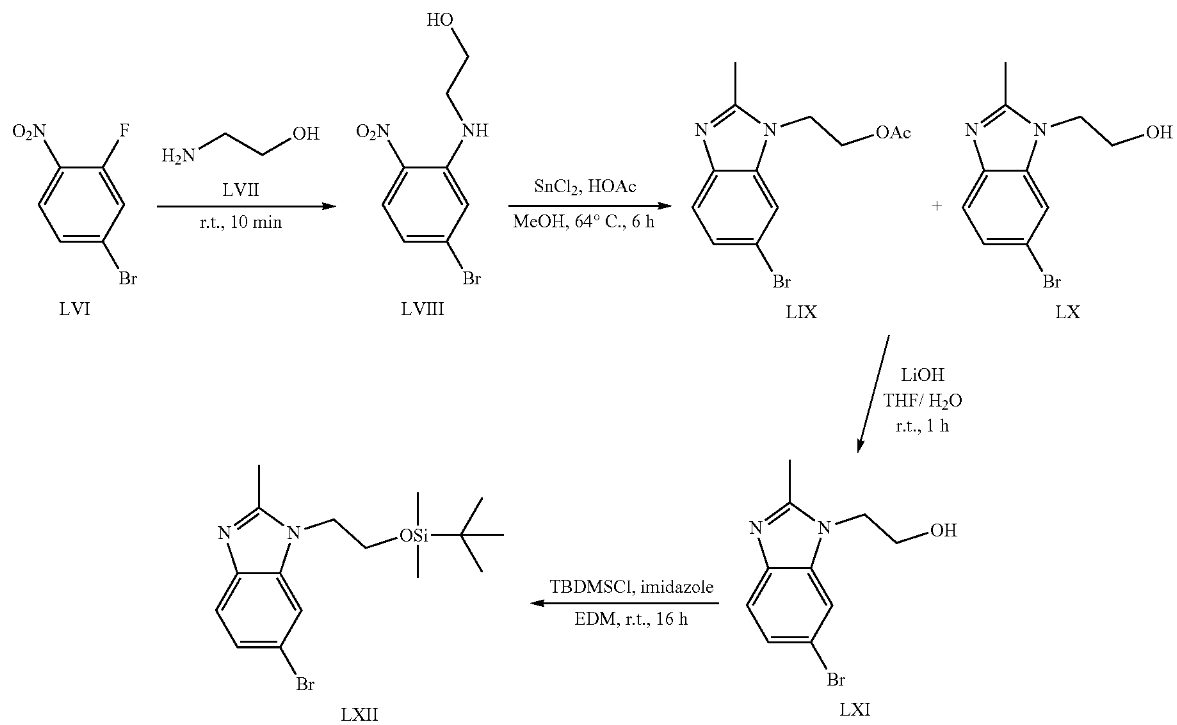

LVI LVIII LIX LX LXI LXII

Step 1

A solution of 4-bromo-2-fluoro-1-nitrobenzene (LVI) (2.0 g, 9.09 mmol) dissolved in 2-aminoethanol (LVII) (2.8 mL, 46.39 mmol) was stirred at room temperature for 10 min. Water (50 mL) was added and extracted with EtOAc and dried onto Celite®. The residue was purified by silica gel column chromatography (0->100% EtOAc/hexanes) to produce 2-((5-bromo-2-nitrophenyl)amino)ethan-1-ol (LVIII) (2.349 g, 8.998 mmol, 99.0% yield) as a yellow solid. $^1H$ NMR (499 MHz, DMSO-$d_6$) δ ppm 3.41 (2H, q, J=5.48 Hz), 3.63 (2H, q, J=5.48 Hz), 5.00 (1H, t, J=5.34 Hz), 6.83 (1H, dd, J=9.17, 2.05 Hz), 7.30 (1H, d, J=1.92 Hz), 7.98 (1H, d, J=9.03 Hz), 8.29 (1H, br t, J=5.06 Hz); ESIMS found for $C_8H_9BrN_2O_3$ m/z 260.96 (M+H).

Step 3

To a solution of LiOH (3.2 mL, 9.6 mmol) in THF (27 mL)/water (6 mL) was added a mixture of 2-(6-bromo-2-methyl-1H-benzo[d]imidazol-1-yl)ethyl acetate (LIX) and 2-(6-bromo-2-methyl-1H-benzo[d]imidazol-1-yl)ethan-1-ol (LX) (1.45 g, 4.88 mmol). The reaction was stirred at room temperature for 1 h. The solution was neutralized with 1 N HCl and stripped onto Celite®, then purified using silica gel column chromatography (0→10% 7 N $NH_3$ in $MeOH/CHCl_3$) to produce 2-(6-bromo-2-methyl-1H-benzo[d]imidazol-1-yl)ethan-1-ol (LXI) (1.02 g, 3.998 mmol, 81.9% yield) as a white solid. ESIMS found for $C_{10}H_{11}BrN_2O$ m/z 255.0 (M+H).

Step 4

2-(6-Bromo-2-methyl-1H-benzo[d]imidazol-1-yl)ethan-1-ol (LXI) (1.02 g, 4. mmol) was dissolved in DCM (8 mL) under a $N_2$ atmosphere. Imidazole (0.55 g, 8.1 mmol) and TBDMSCl (0.9 mL, 4.84 mmol) were then added. The reaction mixture was stirred at room temperature for 16 h. The solution was diluted with EtOAc and washed with saturated aqueous $NaHCO_3$ (400 mL). The aqueous layer was back-extracted twice with EtOAc, the organic layer was stripped onto Celite®, then purified using silica gel column chromatography (0→5% MeOH/$CHCl_3$) to produce 6-bromo-1-(2-((tert-butyldimethylsilyl)oxy)ethyl)-2-methyl-1H-benzo[d]imidazole (LXII) (1.44 g, 3.899 mmol, 97.5% yield) as a white solid. ESIMS found for $C_{16}H_{25}BrN_2OSi$ m/z 369.1 (M+H).

Preparation of intermediate 6-bromo-1-(2,2-difluoro-ethyl)-1H-benzo[d][1,2,3]triazole (LXV) is depicted below in Scheme 11.

Scheme 11

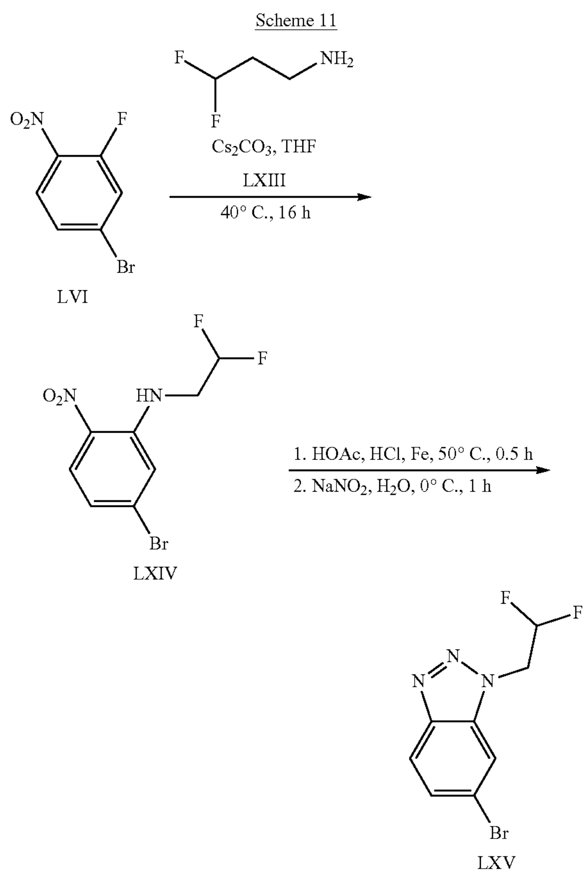

LVI

LXIV

LXV

Step 1

A solution of 4-bromo-2-fluoro-1-nitrobenzene (LVI) (20.0 g, 98.03 mmol) in THF (500.0 mL) was cooled to 0° C. $Cs_2CO_3$ (63.9 g, 196.06 mmol) was added, 2,2-difluoro-ethan-1-amine (LXIII) (36.6 g, 183.81 mmol) was added at 0° C. The reaction was warmed to 40° C. for 16 h. The reaction mixture was extracted with EtOAc (500 L×3). The combined organics were washed with brine (500 mL×3). The combined organic layers were dried with $Na_2SO_4$, filtered, and concentrated to give the crude product. The crude was purified by column chromatography on silica gel (10% EtOAc/PE→20% EtOAc/PE) to give 5-bromo-N-(2,2-difluoroethyl)-2-nitroaniline (LXIV) (23 g, 81.83 mmol, 83.5% yield) as a yellow solid. $^1$H NMR (400 MHz, DMSO-$d_6$) δ 3.99 (tdd, J=15.6, 6.6, 3.8 Hz, 2H), 6.29 (tt, J=55.4, 3.7 Hz, 1H), 6.96 (dd, J=9.2, 2.0 Hz, 1H), 7.51 (d, J=1.6 Hz, 1H), 8.05 (d, J=9.2 Hz, 1H), 8.33 (t, J=6.4 Hz, 1H); ESIMS found for $C_8H_7BrF_2N_2O_2$ m/z 280.9 (M+H).

Step 2

To a solution of 5-bromo-N-(2,2-difluoroethyl)-2-nitroaniline (LXIV) (12.0 g, 42.86 mmol) in HOAc/HCl (500/50 mL) was added Fe (30.0 g, 428.62 mmol). The reaction mixture was stirred at 50° C. for 30 minutes, then cooled to room temperature and filtered. $NaNO_2$ (3.0 g, 53.58 mmol) in water (20 mL) was then added dropwise into the above acid solution at 0° C. The reaction solution was stirred for 1 h at 0° C. The reaction mixture was concentrated to dryness, the reaction mixture was poured into EtOAc (300 mL) and $H_2O$ (300 mL). The pH was adjusted >7 with $NaHCO_3$. The reaction mixture was extracted with EtOAc (500 mL×3). The combined organics were washed with brine (500 mL×3). The organic layers was concentrated, dried over $Na_2SO_4$, filtered, and concentrated to give the crude. The crude was purified by column chromatography on silica gel (10% EtOAc/PE->50% EtOAc/PE) to give 6-bromo-1-(2,2-difluoroethyl)-1H-benzo[d][1,2,3]triazole (LXV) (5 g, 19.08 mmol, 44.5%) as a brown solid. $^1$H NMR (400 MHz, DMSO-$d_6$) δ 5.41-5.29 (m, 2H), 6.61 (tt, J=54.2, 3.2 Hz, 1H), 7.60 (dd, J=8.8, 1.7 Hz, 1H), 8.08 (d, J=8.8 Hz, 1H), 8.31 (d, J=1.0 Hz, 1H); ESIMS found for $C_8H_6BrF_2N_3$ m/z 261.9 (M+H).

The following intermediates were prepared in accordance with the procedure described in the above Scheme 11.

LXVI

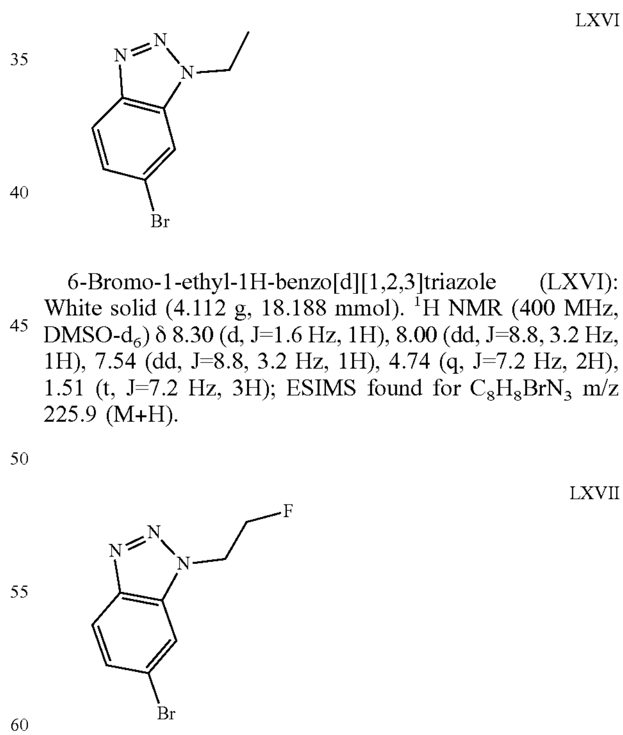

6-Bromo-1-ethyl-1H-benzo[d][1,2,3]triazole (LXVI): White solid (4.112 g, 18.188 mmol). $^1$H NMR (400 MHz, DMSO-$d_6$) δ 8.30 (d, J=1.6 Hz, 1H), 8.00 (dd, J=8.8, 3.2 Hz, 1H), 7.54 (dd, J=8.8, 3.2 Hz, 1H), 4.74 (q, J=7.2 Hz, 2H), 1.51 (t, J=7.2 Hz, 3H); ESIMS found for $C_8H_8BrN_3$ m/z 225.9 (M+H).

LXVII

6-Bromo-1-(2-fluoroethyl)-1H-benzo[d][1,2,3]triazole (LXVII): White solid (4.163 g, 17.057 mmol). $^1$H NMR (400 MHz, DMSO-$d_6$) δ 8.29 (s 1H), 8.05 (d, J=8.4 Hz, 1H), 7.57 (dd, J=8.4, 1.6 Hz, 1H), 5.11 (dt, J=28, 4 Hz, 2H), 4.92 (dt, J=48, 4 Hz, 2H); ESIMS found for $C_8H_7BrFN_3$ m/z 244.0 (M+H).

LXVIII

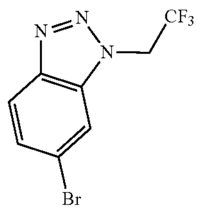

6-Bromo-1-(2,2,2-trifluoroethyl)-1H-benzo[d][1,2,3]triazole (LXVIII): White solid (5.05 g, 18.032 mmol). $^1$H NMR (400 MHz, DMSO-$d_6$) δ 8.38 (s 1H), 8.11 (d, J=8.8 Hz, 1H), 7.63 (dd, J=8.4, 1.6 Hz, 1H), 5.90 (q, J=9.2 Hz, 2H); ESIMS found for $C_8H_5BrF_3N_3$ m/z 280.0 (M+H).

LXIX

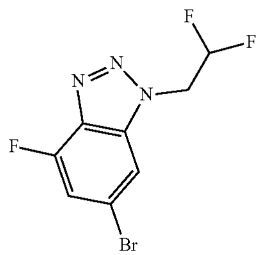

6-Bromo-1-(2,2-difluoroethyl)-4-fluoro-1H-benzo[d][1,2,3]triazole (LXIX): White solid (4.112 g, 14.683 mmol). $^1$H NMR (400 MHz, DMSO-$d_6$) δ 8.19 (s 1H), 7.61 (d, J=10.0 Hz, 1H), 6.60 (tt, J=54.3, 3.0 Hz, 1H), 5.36 (td, J=15.81, 2.87 Hz, 2H); ESIMS found for $C_8H_5BrF_3N_3$ m/z 280.0 (M+H).

LXX

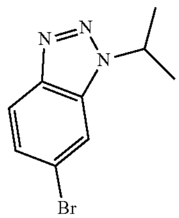

6-Bromo-1-isopropyl-1H-benzo[d][1,2,3]triazole (LXX): White solid (10.58 g, 44.065 mmol). $^1$H NMR (400 MHz, DMSO-$d_6$) δ 8.32 (d, J=1.2 Hz, 1H), 8.03 (d, J=9.2 Hz, 1H), 7.54 (dd, J=8.4, 1.6 Hz, 1H), 5.26 (sep, J=6.8 Hz, 1H), 5.26 (d, J=6.8 Hz, 6H); ESIMS found for $C_9H_{10}BrN_3$ m/z 240.1 (M+H).

Preparation of intermediate 6-bromo-8-fluoro-2-methylimidazo[1,2-a]pyridine (LXXIII) is depicted below in Scheme 12.

Scheme 12

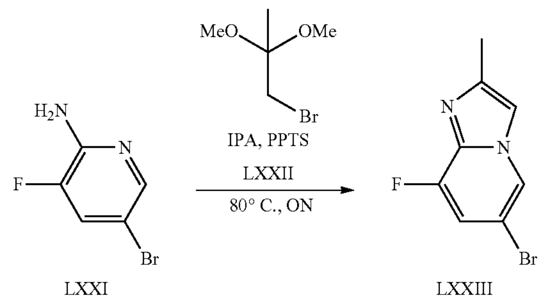

LXXI LXXIII

Step 1

A mixture of 5-bromo-3-fluoropyridin-2-amine (LXXI) (2 g, 10.47 mmol), 1-bromo-2,2-dimethoxypropane (LXXII) (2.11 g, 11.53 mmol) and PPTS (260 mg, 1.05 mmol) in IPA (25 mL) was heated to 80° C. overnight. The reaction mixture was cooled to room temperature, added to water (200 mL) and stirred for 1 h. The resulting solids were collected and dried under high vacuo to obtain 6-bromo-8-fluoro-2-methylimidazo[1,2-a]pyridine (LXXIII) (2.61 g, 11.40 mmol, 108.8% yield) as beige solid which was used for the next step without further purification. ESIMS found for $C_8H_6BrFN_2$ m/z 229.0 (M+H).

The following intermediate was prepared in accordance with the procedure described in the above Scheme 12.

LXXIV

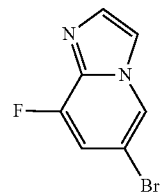

6-Bromo-8-fluoroimidazo[1,2-a]pyridine (LXXIV): Beige solid (909.0 mg, 4.228 mmol, 80.7% yield). ESIMS found for $C_7H_4BrFN_2$ m/z 214.9 (M+H).

Preparation of intermediate (6-bromoimidazo[1,2-a]pyridin-3-yl)(pyrrolidin-1-yl)methanone (LXXVII) is depicted below in Scheme 13.

Scheme 13

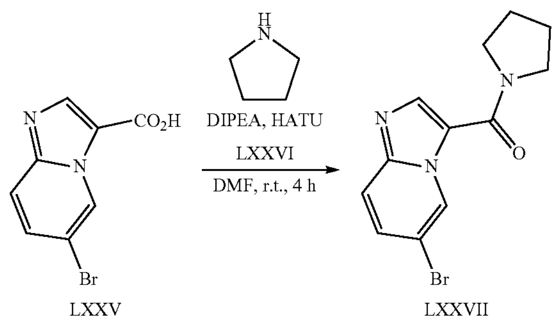

LXXV LXXVII

Step 1

A mixture of 6-bromoimidazo[1,2-a]pyridine-3-carboxylic acid (LXXV) (0.5 g, 2.07 mmol), DIPEA (0.9 mL, 5.17 mmol) and HATU (0.79 g, 2.07 mmol) in DMF (4 mL) was stirred for 5 min. Pyrrolidine (LXXVI) (0.32 mL, 3.18 mmol) was then added, and the reaction mixture was continued to stir at room temperature for 4 h. The solvent were concentrated, the residue partitioned between EtOAc and saturated aqueous $NaHCO_3$, the organic layer was separated, washed with water and brine. The organic layer was dried over anhydrous $Na_2SO_4$, concentrated and dried under high vacuo to obtain (6-bromoimidazo[1,2-a]pyridin-3-yl)-pyrrolidin-1-ylmethanone (LXXVII) (577 mg, 1.962 mmol, 94.6% yield) as a beige solid. ESIMS found for $C_{12}H_{12}BrN_3O$ m/z 294.0 (M+H).

The following intermediates were prepared in accordance with the procedure described in the above Scheme 13.

LXXVIII

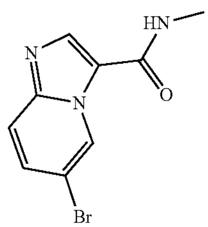

6-Bromo-N-methylimidazo[1,2-a]pyridine-3-carboxamide (LXXVIII): Off-white solid (530 mg, 2.086 mmol, 83.8% yield). ESIMS found for $C_9HsBrN_3O$ m/z 254.0 (M+H).

LXXIX

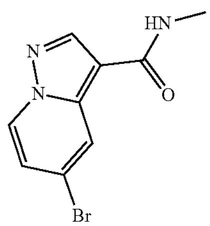

5-Bromo-N-methylpyrazolo[1,5-a]pyridine-3-carboxamide (LXXIX): Off-white solid (290 mg, 1.141 mmol, 91.7% yield). ESIMS found for $C_9HsBrN_3O$ m/z 253.95 (M+H).

Preparation of intermediate imidazo[1,2-a]pyrimidin-6-ylboronic acid (LXXXII) is depicted below in Scheme 14.

Scheme 14

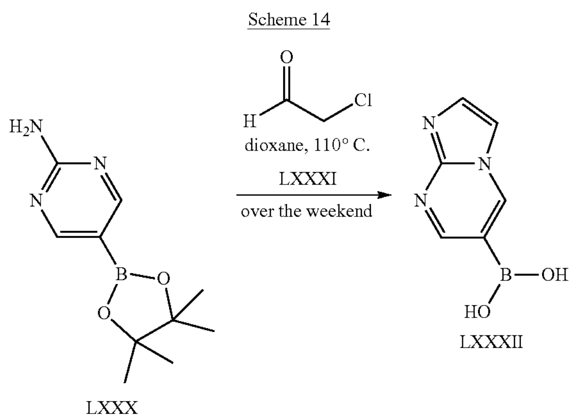

LXXX

LXXXII

Step 1

A mixture of 5-(4,4,5,5-tetramethyl-1,3,2-dioxaborolan-2-yl)pyrimidin-2-amine (LXXX) (1 g, 4.52 mmol) and chloroacetaldehyde (LXXXI) (0.92 mL, 5.39 mmol) was dissolved in 1,4-dioxane (20 mL) and heated to 110° C. over the weekend. The reaction mixture was cooled, and the solids were collected by filtration and dried under high vacuo to obtain imidazo[1,2-a]pyrimidin-6-ylboronic acid (LXXXII) (650 mg, 3.989 mmol, 88.2% yield) as a brown solid which was used for next step without purification. ESIMS found for $C_6H_6BN_3O_2$ m/z 164.1 (M+H).

Preparation of intermediate 6-bromo-3-methylimidazo[1,2-a]pyrimidine (LXXXVII) is depicted below in Scheme 15.

Scheme 15

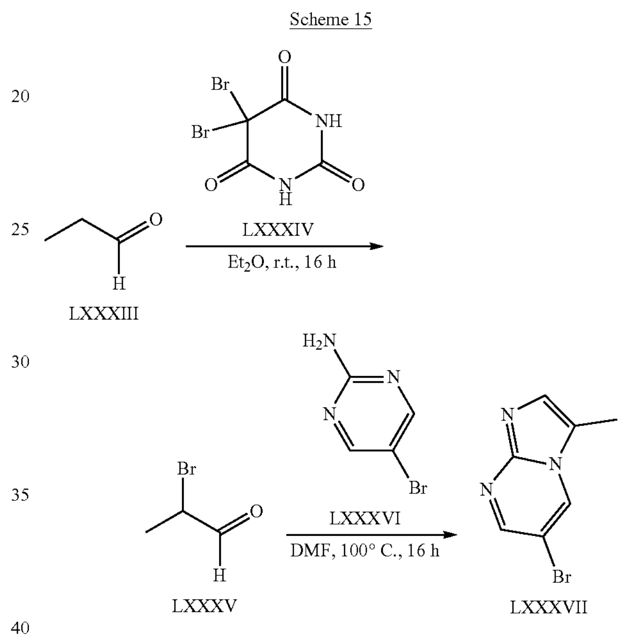

LXXXIII

LXXXV

LXXXVII

Step 1

To a mixture of propionaldehyde (LXXXIII) (5 g, 70 mmol) in $Et_2O$ (150 mL) was added 5,5-dibromopyrimidine-2,4,6(1H,3H,5H)-trione (LXXXIV) (9.91 g, 35 mmol) and the resulting mixture was stirred at room temperature for 16 h. After completion, the mixture was washed by petroleum ether (80 mL×2). The organic layer was filtered and concentrated to give 2-bromopropanal (LXXXV) (2.0 g, 14.6 mmol, 20.9% yield) as a yellow oil.

Step 2

To a solution of 2-bromopropanal (LXXXV) (0.7 g, 5.11 mol) in DMF (20 mL) was added 5-bromopyrimidin-2-amine (LXXXVI) (0.97 g, 5.56 mmol) at room temperature under Ar. The mixture was stirred at 100° C. for 16 h. After completion, the mixture was diluted with EtOAc and washed with brine (20 mL×3). The organic layer was dried over anhydrous $Na_2SO_4$, filtered and concentrated. The crude residue was purified by silica gel column chromatography (0%→20% EtOAc/petroleum ether) to give 6-bromo-3-methylimidazo[1,2-a]pyrimidine (LXXXVII) (80 mg, 0.377 mmol, 7.4% yield) as a white solid. ESIMS found for $C_7H_6BrN_3$ m/z 212.1 (M+H).

The following intermediate was prepared in accordance with the procedure described in the above Scheme 15.

LXXXVIII

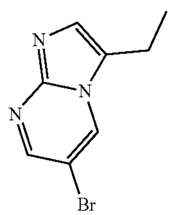

6-Bromo-3-ethylimidazo[1,2-a]pyrimidine (LXXXVIII): White solid (200 mg, 0.885 mmol, 19.1% yield). ESIMS found $C_8H_8BrN_3$ m/z 226.0 (M+H).

Preparation of intermediate (1-((2-(trimethylsilyl)ethoxy)methyl)-1H-pyrrolo[3,2-c]pyridin-2-yl)boronic acid (XCII) is depicted below in Scheme 16.

Scheme 16

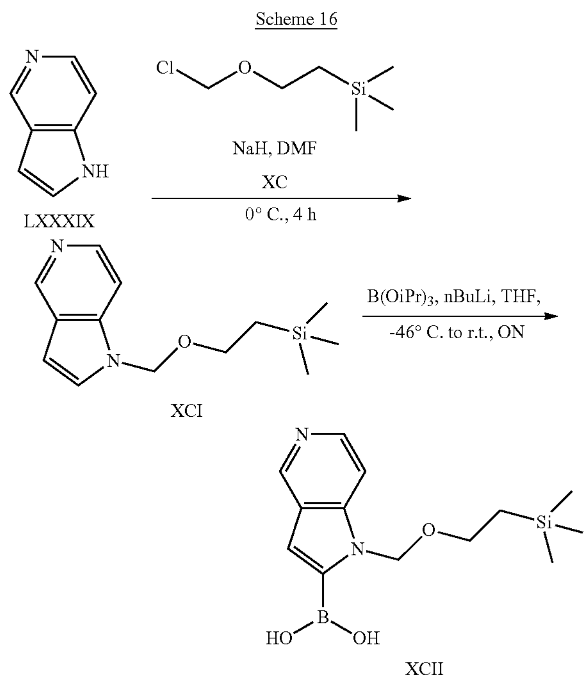

LXXXIX

XCI

XCII

Step 1

To a solution of 5-azaindole (LXXXIX) (commercially available from Combi-Blocks Inc.) (2.0 g, 16.93 mmol) in DMF (20 mL) under $N_2$ was added NaH (0.81 g, 20.18 mmol). The mixture was stirred at 0° C. for 1 h. (2-(Chloromethoxy)ethyl)trimethylsilane (XC) (commercially available from Combi-Blocks Inc.) (3.6 mL, 20.34 mmol) was then added and the mixture was stirred at 0° C. for 4 h. After concentrating in vacuo to remove DMF, ice cold saturated aqueous $NH_3Cl$ was added, and the mixture was extracted with EtOAc. The organic layer was washed with water, brine, and the solvent was concentrated onto Celite® under vacuum. The crude product was purified using column chromatography (0→100% EtOAc/hexanes) to produce 1-((2-(trimethylsilyl)ethoxy)methyl)-1H-pyrrolo[3,2-c]pyridine (XCI) (2.32 g, 9.340 mmol, 55.2% yield) as an amber liquid. $^1H$ NMR (499 MHz, DMSO-$d_6$) δ ppm −0.11 (9H, s), 0.75-0.84 (2H, m), 3.40-3.48 (2H, m), 5.58 (2H, s), 6.64 (1H, dd, J=3.29, 0.82 Hz), 7.55-7.60 (2H, m), 8.23 (1H, d, J=5.75 Hz), 8.84 (1H, d, J=0.82 Hz); ESIMS found for $Cl_3H_{20}N_2OSi$ m/z 249.1 (M+H).

Step 2

A hexane solution of n-butyllithium (1.21 mL, 3.02 mmol) was added slowly to a solution of 1-((2-(trimethylsilyl)ethoxy)methyl)-1H-pyrrolo[3,2-c]pyridine (XCI) (0.5 g, 2.01 mmol) in dry THF (4.0 mL) at −78° C. under $N_2$. The mixture was stirred at −46° C. for 2 h. Triisopropyl borate (0.93 mL, 4.03 mmol) was added, and the mixture was stirred overnight warming to room temperature. The reaction mixture was quenched with 1 M aqueous HCl and neutralized to pH 8 with 4 N NaOH. The solvent was evaporated onto Celite® and purified by reverse phase (C18) silica gel column chromatography (0→40% MeCN/water (0.1% formic acid as modifier)). LC/MS shows a mixture (40/60) of starting material and [1-(2-trimethylsilylethoxymethyl)pyrrolo[3,2-c]pyridin-2-yl]boronic acid (XCII) (200 mg, 0.684 mmol, 34.0% yield) as an off-white solid. The mixture was used as is without further purification. ESIMS found for $C_{13}H_{21}BN_2O_3Si$ m/z 293.1 (M+H).

The following intermediates were prepared in accordance with the procedure described in the above Scheme 16.

XCIII

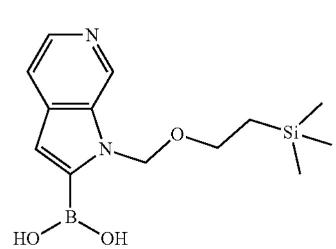

(1-((2-(Trimethylsilyl)ethoxy)methyl)-1H-pyrrolo[2,3-c]pyridin-2-yl)boronic acid (XCIII): Tan solid (796 mg, 2.861 mmol, 71.1% yield). ESIMS found $C_{13}H_{21}BN_2O_3Si$ m/z 293.15 (M+H).

XCIV

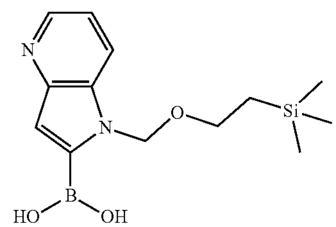

(1-((2-(Trimethylsilyl)ethoxy)methyl)-1H-pyrrolo[3,2-b]pyridin-2-yl)boronic acid (XCIV): Tan solid (831 mg, 2.844 mmol, 70.6% yield). ESIMS found $C_{13}H_{21}BN_2O_3Si$ m/z 293.1 (M+H).

Preparation of intermediate cis-4-(methoxy-$d_3$)cyclohexan-1-amine (C) is depicted below in Scheme 17.

Scheme 17

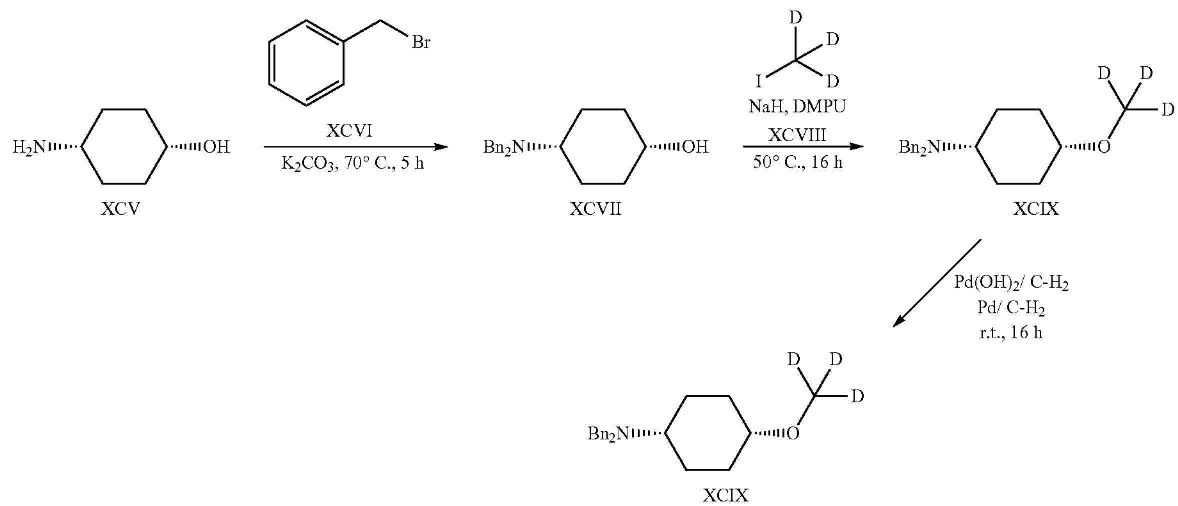

XCV XCVII XCIX XCIX

Step 1

To a solution of cis-4-aminocyclohexan-1-ol (XCV) (5 g, 32.9 mmol), (bromomethyl)benzene (XCVI) (11.25 g, 65.8 mmol) in MeCN (80 mL) was added $K_2CO_3$ (13.64 g, 98.7 mmol). The mixture was stirred at 70° C. for 5 h. The reaction mixture was concentrated under reduced pressure to remove MeCN. The mixture was diluted with EtOAc and then extracted with EtOAc (100 mL×3) and $H_2O$. The combined organic layers were concentrated, and the crude residue was purified by silica gel column chromatography (0%→30% EtOAc/PE) to give the cis-4-(dibenzylamino)cyclohexan-1-ol (XCVII) (8.0 g, 27.08 mmol, 82.3% yield) as a white solid. ESIMS found for $C_{20}H_{25}NO$ m/z 296.4 (M+H).

Step 2

To a solution of cis-4-(dibenzylamino)cyclohexan-1-ol (XCVII) (8.0 g, 27.08 mmol) in DMPU (80 mL) was added slowly NaH (5.98 g, 149.7 mmol) under nitrogen atmosphere with continuous stirring. The reaction mixture was stirred at room temperature for 1 h. Then iodomethane-$d_3$ (XCVIII) (10.85 g, 74.86 mmol) was added at room temperature over a period of 10 min. After complete addition, the reaction mixture was stirred for 16 h at 50° C. The reaction mixture was then quenched with saturated aqueous $NH_4Cl$ (300 mL) and stirred for 10 min. The mixture was diluted with EtOAc and then extracted with EtOAc (300 mL×3) and $H_2O$. The crude residue was purified by silica gel column chromatography (0%->20% EtOAc/PE) to yield cis-N,N-dibenzyl-4-(methoxy-$d_3$)cyclohexan-1-amine (XCIX) (6 g, 19.202 mmol, 70.9% yield) as a colorless oil. ESIMS found for $C_{21}H_{24}D_3NO$ m/z 313.0 (M+H).

Step 3

To a solution of cis-N,N-dibenzyl-4-(methoxy-$d_3$)cyclohexan-1-amine (XCIX) (200 mg, 0.64 mmol) in EtOH (5 mL) was added $Pd(OH)_2$/C (50 mg) and Pd/C (50 mg). The mixture was stirred at room temperature for 16 h. The mixture was filtered through Celite® and washed with EtOH. The reaction mixture was concentrated under reduced pressure to give the cis-4-(methoxy-$d_3$)cyclohexan-1-amine (C) (76.4 mg, 0.578 mmol, 90.3% yield) as a colorless oil. $^1H$ NMR (400 MHz, DMSO-$d_6$) δ ppm 1.51-1.40 (m, 4H), 1.67-1.56 (m, 4H), 1.86 (td, J=9.8, 4.6 Hz, 2H), 2.71 (tt, J=10.8, 5.4 Hz, 1H), 3.34 (td, J=4.8, 2.4 Hz, 1H); ESIMS found for $C_7H_{12}D_3NO$ m/z 133.0 (M+H).

The following intermediates were prepared in accordance with the procedure described in the above Scheme 17.

CI

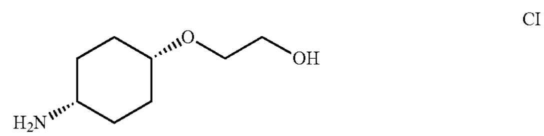 [SMILES: N[C@H]1CC[C@@H](OCCO)CC1]

2-((cis-4-Aminocyclohexyl)oxy)ethan-1-ol (CI): Colorless oil (0.5 g, 3.14 mmol, 67.4% yield). ESIMS found for $C_8H_{17}NO_2$ m/z 160. (M+H).

CII

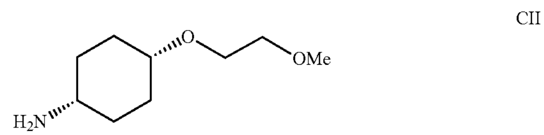 [SMILES: COCCO[C@H]1CC[C@@H](N)CC1]

cis-4-(2-Methoxyethoxy)cyclohexan-1-amine (CII): Colorless oil (1.5 g, 8.65 mmol, 76.6% yield). ESIMS found for $C_9H_{19}NO_2$ m/z 174.1 (M+H).

CIII

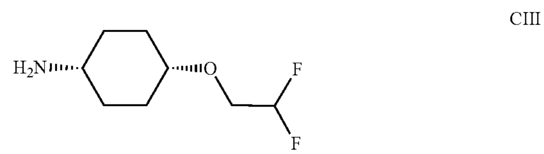 [SMILES: N[C@H]1CC[C@@H](OCC(F)F)CC1]

cis-4-(2,2-Difluoroethoxy)cyclohexan-1-amine (CIII): White solid (1.352 g, 7.54 mmol, 90.3% yield). ESIMS found for $C_8H_{15}F_2NO$ m/z 180.1 (M+H).

CIV

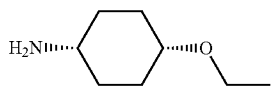

cis-4-Ethoxycyclohexan-1-amine (CIV): Colorless oil (2 g, 13.96 mmol, 64.4% yield). $^1$H NMR (400 MHz, $CDCl_3$) δ 1.19 (t, J=7.0 Hz, 3H), 1.49-1.44 (m, 6H), 1.62-1.55 (m, 2H), 1.86-1.79 (m, 2H), 2.4-2.723 (m, 1H), 3.49-3.41 (m, 3H).

CV

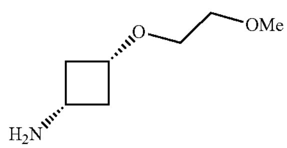

cis-3-(2-Methoxyethoxy)cyclobutan-1-amine (CV): Colorless oil. $^1$H NMR (400 MHz, DMSO-$d_6$) δ 1.51 (dd, J=13.4, 5.2 Hz, 2H), 2.49-2.40 (m, 2H), 2.89-2.75 (m, 1H), 3.23 (s, 3H), 3.37-3.35 (m, 3H), 3.47 (s, 2H), 3.54-3.48 (m, 1H).

CVI

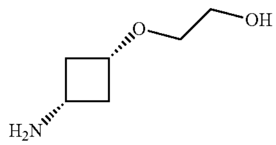

2-(cis-3-Aminocyclobutoxy)ethan-1-ol (CVI): Colorless oil. $^1$H NMR (400 MHz, DMSO-$d_6$) δ 1.79-1.72 (m, 2H), 2.50-2.45 (m, 2H), 3.08-2.97 (m, 1H), 3.29 (t, J=5.4 Hz, 2H), 3.46 (t, J=5.4 Hz, 2H), 3.73-3.57 (m, 1H).

Preparation of intermediate cis-4-(difluoromethoxy)cyclohexan-1-amine (CIX) is depicted below in Scheme 18.

Scheme 18

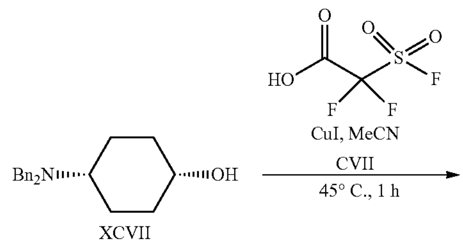

XCVII

-continued

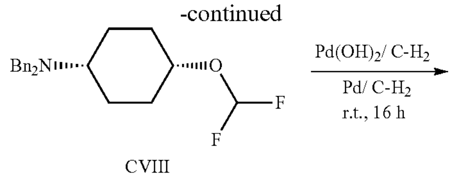

CVIII

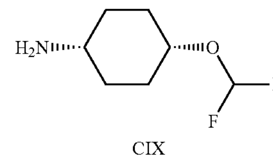

CIX

Step 1

A solution of cis-4-(dibenzylamino)cyclohexan-1-ol (XCVII) (50 mg, 0.170 mmol), CuI (6.5 mg, 0.034 mmol) in MeCN (5 mL) was heated to 45° C. under nitrogen atmosphere for 5 min. To this mixture was added a solution of 2,2-difluoro-2-(fluorosulfonyl)acetic acid (CVII) (60 mg, 0.339 mmol) in (2 mL) MeCN over 10 min. Then the mixture was stirred at 45° C. for 1 h. Volatile components were then removed via evaporation and the residue was diluted with EtOAc (100 mL) and 100 mL of a 1:1 mixture of water and saturated aqueous $NaHCO_3$. The resulting biphasic mixture containing solids was filtered through a sintered glass Buchner funnel. The filtrate layers were separated, and the aqueous layer was extracted with EtOAc (50 mL). The combined EtOAc layers were washed with 50 mL of a 1:1 mixture of brine and water, dried over anhydrous $MgSO_4$, filtered, and concentrated to an oil. The crude oil was purified by silica gel chromatography (100% hexanes→30% EtOAc/hexanes). Product containing fractions were combined and concentrated to afford the cis-N,N-dibenzyl-4-(difluoromethoxy)cyclohexan-1-amine (CVIII) (25 mg, 0.072 mmol, 42.3% yield) as an oil that solidified to an off-white solid. ESIMS found for $C_{21}H_{25}F_2NO$ m/z 346.1 (M+H).

Step 2

To a solution of cis-N,N-dibenzyl-4-(difluoromethoxy)cyclohexan-1-amine (CVIII) (2.8 g, 8.11 mmol) in THF (60 mL) was added $Pd(OH)_2/C$ (1.4 g) and Pd/C (1.4 g). The mixture was stirred at room temperature for 16 h. The mixture was filtered through Celite® and washed with THF. The reaction mixture was concentrated under reduced pressure to afford cis-4-(difluoromethoxy)cyclohexan-1-amine (CIX) (1.05 g, 6.36 mmol, 78.4% yield) as a colorless oil. ESIMS found for $C_7H_{13}F_2NO$ m/z 166.1 (M+H).

Preparation of intermediate trans-4-amino-1-ethylcyclohexan-1-ol (CXIV) is depicted below in Scheme 19.

Scheme 19

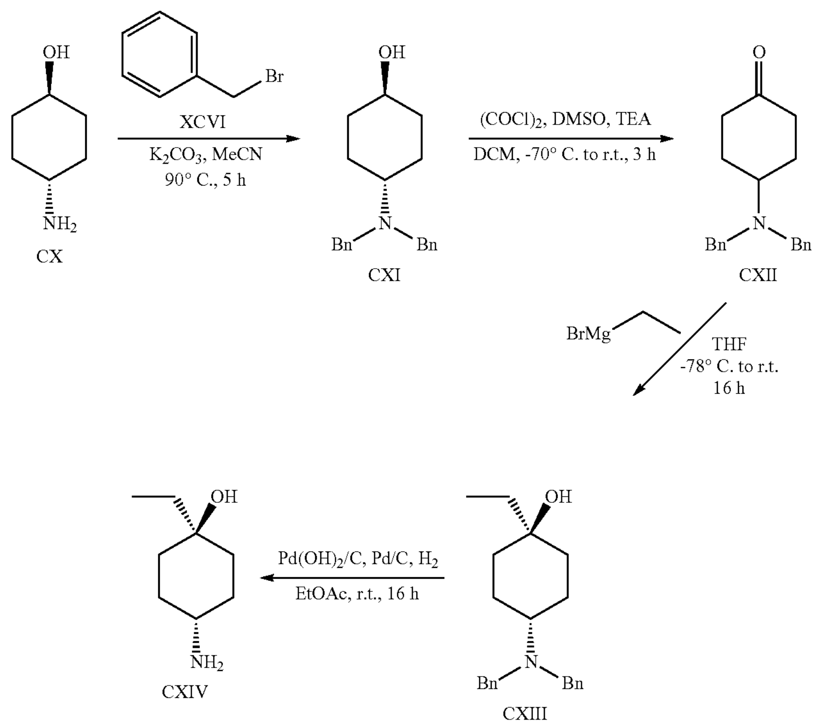

CX

CXI

CXII

CXIII

CXIV

Step 1

To a solution of trans-4-aminocyclohexan-1-ol (CX) (25 g, 0.217 mmol) and benzyl bromide (XCVI) (74.2 g, 0.434 mmol) in MeCN (500 mL) was added $K_2CO_3$ (90 g, 0.6512 mmol). The mixture was stirred at 90° C. for 5 h. The reaction mixture was concentrated under reduced pressure to remove MeCN. The mixture was diluted with EtOAc and then extracted with EtOAc (100 mL×3) and $H_2O$. The organic layers were dried over anhydrous $Na_2SO_4$ and evaporated under high vacuum to produce trans-4-(dibenzylamino)cyclohexan-1-ol (CXI) (32 g, 108.3 mmol, 49.9% yield) as a white solid. The product was directly used in the next step without further purification. ESIMS found for $C_{20}H_{25}NO$ m/z 296.3 (M+H).

Step 2

To a solution of $(COCl)_2$ (12.89 g, 101.55 mmol) in DCM (150 mL) at −70° C. under $N_2$ was slowly added DMSO (10.6 g, 135.4 mmol) in DCM (50 mL). trans-4-(dibenzylamino)cyclohexan-1-ol (CXI) (20.0 g, 67.7 mmol) in DMF (50 mL) was added at −70° C. under $N_2$ and stirred for 30 min. TEA (21.92 g, 216.64 mmol) was then added and the mixture was stirred at −70° C. warming to room temperature over 3 h. The reaction mixture was diluted with $H_2O$ (800 mL) and extracted with DCM (800 mL). The combined organic layers were dried over anhydrous $Na_2SO_4$ and concentrated to give a residue. The residue was purified by column chromatography on silica gel (9->25% EtOAc/PE) to afford 4-(dibenzylamino)cyclohexan-1-one (CXII) (18.0 g, 61.3 mmol, 90.6% yield) as a white solid. ESIMS found for $C_{20}H_{23}NO$ m/z 294.2 (M+H).

Step 3

4-(Dibenzylamino)cyclohexan-1-one (CXII) (5.0 g, 17.04 mmol) was added to THF (50 mL) at −78° C. under $N_2$ and stirred for 1 h. Ethylmagnesium bromide (17 mL, 34.08 mmol) was added and the reaction was stirred at −78° C. warming to room temperature over 16 h. The reaction mixture was diluted with $NH_4Cl$ (100 mL), filtered, and extracted with EtOAc (200 mL×3 mL). The combined organic layers were dried over anhydrous $Na_2SO_4$ and concentrated under high vacuum to give a residue. LC/MS showed two products. The residue was purified by column chromatography on silica gel (2->3% EtOAc/PE) to afford only the trans-4-(dibenzylamino)-1-ethylcyclohexan-1-ol (CXIII) (1.5 g, 4.637 mmol, 27.2% yield) as a white solid. $^1H$ NMR (400 MHz, DMSO-$d_6$) δ 0.80 (t, J=7.4 Hz, 3H), 1.17-1.10 (m, 2H), 1.47-1.37 (m, 4H), 1.65 (t, J=11.4 Hz, 4H), 2.41 (s, 1H), 3.57 (s, 4H), 3.91 (s, 1H), 7.21-7.17 (m, 2H), 7.34-7.27 (m, 8H); ESIMS found for $C_{22}H_{29}NO$ m/z 324.2 (M+H).

Step 4

To a solution of trans-4-(dibenzylamino)-1-ethylcyclohexan-1-ol (CXIII) (1.5 g, 4.6 mmol) in EtOAc (50.0 mL), 10% Pd/C (0.4 g), 20% $Pd(OH)_2/C$ (0.4 g) was purged with $H_2$. The mixture was stirred under a $H_2$ atm at room temperature for 16 h. The reaction mixture was filter through Celite® and concentrated under high vacuum to give trans-4-amino-1-ethylcyclohexan-1-ol (CXIV) (390 mg, 2.723 mmol, 58.7% yield) as a white solid. $^1H$ NMR (400 MHz, DMSO-$d_6$) δ 0.80 (t, J=7.4 Hz, 3H), 1.14-1.03 (m, 2H), 1.29-1.20 (m, 2H), 1.40 (q, J=7.4 Hz, 2H), 1.59-1.49 (m, 2H), 1.67-1.61 (m, 2H), 2.70-2.61 (m, 1H), 3.84 (br s, 1H); ESIMS found for $C_8H_{17}NO$ m/z 144.1 (M+H).

Preparation of intermediate 1-(3,3,3-trifluoropropyl)piperidin-4-amine (CXVIII) is depicted below in Scheme 20.

Scheme 20

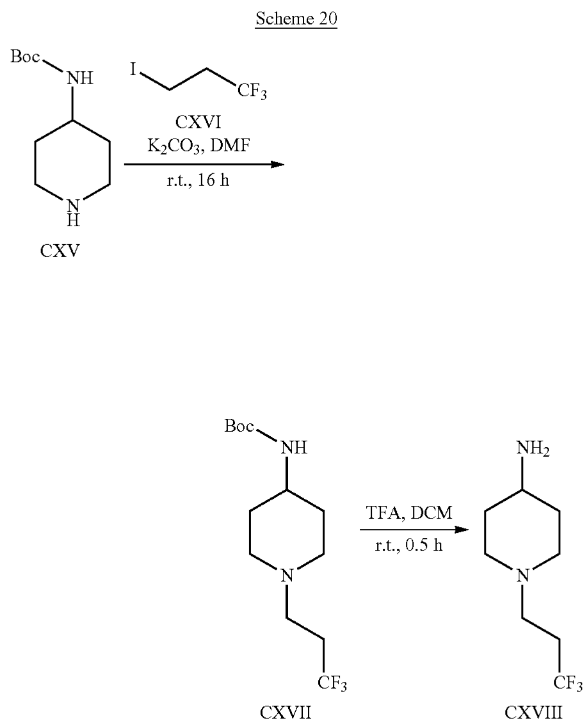

CXV CXVI CXVII CXVIII

Step 1 tert-Butyl piperidin-4-ylcarbamate (CXV) (Commercially available from Combi-Blocks Inc.) (1 g, 4.99 mmol) and $K_2CO_3$ (1.73 g, 12.52 mmol) were dissolved in DMF (15 mL) and 1-iodo-3,3,3-trifluoropropane (CXVI) (878 μL, 7.49 mmol) was added and the reaction was stirred at room temperature for 16 h. The reaction mixture was poured in EtOAc, and the aqueous layer was separated. The aqueous layer was extracted with EtOAc (×3) and then the combined organic layers were acidified to pH 4.5 with 1 M citric acid. The organic layer was washed three times with small volumes of water to remove unreacted SM. Sufficient amounts of the product remained in the organic layer which was dried using anhydrous $MgSO_4$ and reduced in vacuo to give the product tert-butyl N-[1-(3,3,3-trifluoropropyl)piperidin-4-yl]carbamate (CXVII) (861 mg, 2.906 mmol, 58.2% yield) as a white solid. ESIMS found for $Cl_3H_{23}F_3N_2O_2$ m/z 297.2 (M+H).

Step 2 tert-Butyl N-[1-(3,3,3-trifluoropropyl)piperidin-4-yl]carbamate (CXVII) (200 mg, 0.670 mmol) was dissolved in DCE (3.2 mL) and TFA (800 μL, 10.38 mmol) was added and the reaction was stirred at room temperature for 30 m. The reaction mixture was blown dry and excess TFA removed by high vacuum to give the crude intermediate 1-(3,3,3-trifluoropropyl)piperidin-4-amine (CXVIII) (209 mg, 0.674 mmol, 99.8% yield) as a white semi-solid which was used without further purification. ESIMS found for $C_8H_{15}F_3N_2$ m/z 197.1 (M+H).

Preparation of intermediate N-(trans-4-aminocyclohexyl) acetamide (CXXI) is depicted below in Scheme 21.

Scheme 21

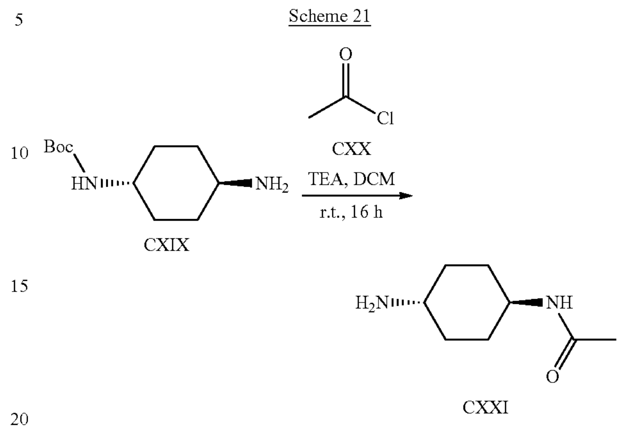

CXIX CXX CXXI

Step 1

To a stirring solution of tert-butyl N-(4-aminocyclohexyl) carbamate (CXIX) (Commercially available from Combi-Blocks Inc.) (0.6 g, 2.8 mmol) in DCM (6 mL) was added TEA (1.2 mL, 8.61 mmol). Acetyl chloride (CXX) (0.22 mL, 3.09 mmol) was then slowly and the reaction mixture was stirred at room temperature for 16 h. The solvent was removed, and the crude material was dissolved in EtOAc, washed with 1 M NaOH, brine, and dried over anhydrous $MgSO_4$ and finally concentrated. The product was dissolved in EtOH (2 mL) and 4 M HCl (1 mL). The solution was stirred at room temperature for 2 h before evaporating to dryness to give the HCl salt of N-(4-aminocyclohexyl) acetamide (CXXI) (480 mg, 2.49 mmol, 89.0% yield) as a white solid. ESIMS found for $C_8H_{16}N_{20}$ m/z 157.05 (M+H).

Preparation of intermediate cis-4-amino-N,N-dimethylcyclohexane-1-carboxamide (CXXIII) is depicted below in Scheme 22.

Scheme 22

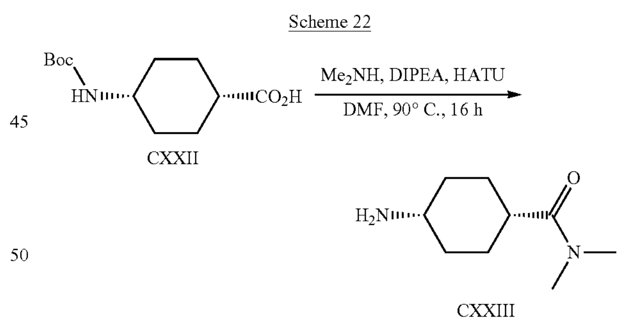

CXXII CXXIII

Step 1

To a stirring solution of 4-(tert-butoxycarbonylamino) cyclohexanecarboxylic acid (CXXII) (Commercially available from Combi-Blocks Inc.) (0.3 g, 1.23 mmol) in DMF (6 mL) was added DIPEA (0.65 mL, 3.73 mmol) and HATU (0.7 g, 1.85 mmol). Reaction was stirred for 5 min at room temperature. Dimethylamine (0.92 mL, 1.84 mmol) was added, and the reaction was heated to 90° C. for 16 h. The reaction was concentrated and dissolved in EtOH (2 mL) and 4 M HCl in dioxane (1 mL). The mixture was stirred for 2 h at room temperature, concentrated under vacuum to yield the HCl salt of 4-amino-N,N-dimethylcyclohexane-1-carboxamide (CXXIII) (280 mg, 1.355 mmol, 109.9% yield) as a light brown viscous solid. ESIMS found for $C_9H_{18}N_2O$ m/z 171.15 (M+H).

The following intermediate was prepared in accordance with the procedure described in the above Scheme 22.

CXXIV

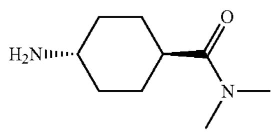

trans-4-Amino-N,N-dimethylcyclohexane-1-carboxamide (CXXIV): Light brown viscous solid (290 mg, 1.403 mmol, 113.8% yield). ESIMS found for $C_9H_{18}N_2O$ m/z 171.1 (M+H).

Preparation of intermediate 3-amino-N-methylbicyclo[1.1.1]pentane-1-carboxamide (CXXVII) is depicted below in Scheme 23.

Scheme 23

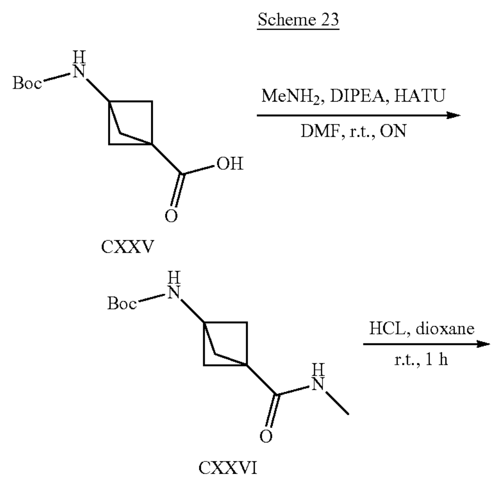

CXXV

CXXVI

-continued

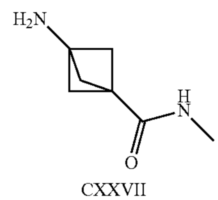

CXXVII

Step 1

To a solution of 3-((tert-butoxycarbonyl)amino)bicyclo[1.1.1]pentane-1-carboxylic acid (CXXV) (commercially available from AmBeed, Inc.) (0.5 g, 2.2 mmol) and HATU (0.8 g, 2.09 mmol) in DMF was added DIPEA (0.8 mL, 4.59 mmol) and the mixture was stirred for 5 min. Methanamine HCL (1.49 g, 22.07 mmol) was then added at −78° C. followed by additional DIPEA (4 mL). The reaction mixture was left stirred at room temperature overnight. The solvents were concentrated, the residue dissolved in EtOAc, washed with saturated aqueous $NaHCO_3$, water and brine. The organics were dried over anhydrous $Na_2SO_4$, concentrated, and the residue was dried under high vacuum to obtain tert-butyl (3-(methylcarbamoyl)bicyclo[1.1.1]pentan-1-yl) carbamate (CXXVI) (244 mg, 1.015 mmol, 46.2% yield) as off-white solids. ESIMS found for $C_{12}H_{20}N_2O_3$ m/z 241.1 (M+H).

Step 2

A solution of tert-butyl (3-(methylcarbamoyl)bicyclo[1.1.1]pentan-1-yl)carbamate (CXXVI) (240 mg, 1.0 mmol) in 4 M HCl in dioxane (1.25 mL, 5.0 mmol) was stirred at room temperature for 1 h. The solvents were concentrated and dried under high vacuum overnight to obtain 3-amino-N-methylbicyclo[1.1.1]pentane-1-carboxamide HCL (CXXVII) (177 mg, 1.002 mmol, 100.3% yield) which was used for next step without purification. ESIMS found for $C_7H_{12}N_2O$ m/z 141.15 (M+H).

Example 1

Preparation of N-(cis-4-((4-methoxy-5-(pyrazolo[1,5-a]pyridin-5-yl)pyrrolo[2,1-f][1,2,4]triazin-2-yl)amino)cyclohexyl)acetamide (17) is depicted below in Scheme 24.

Scheme 24

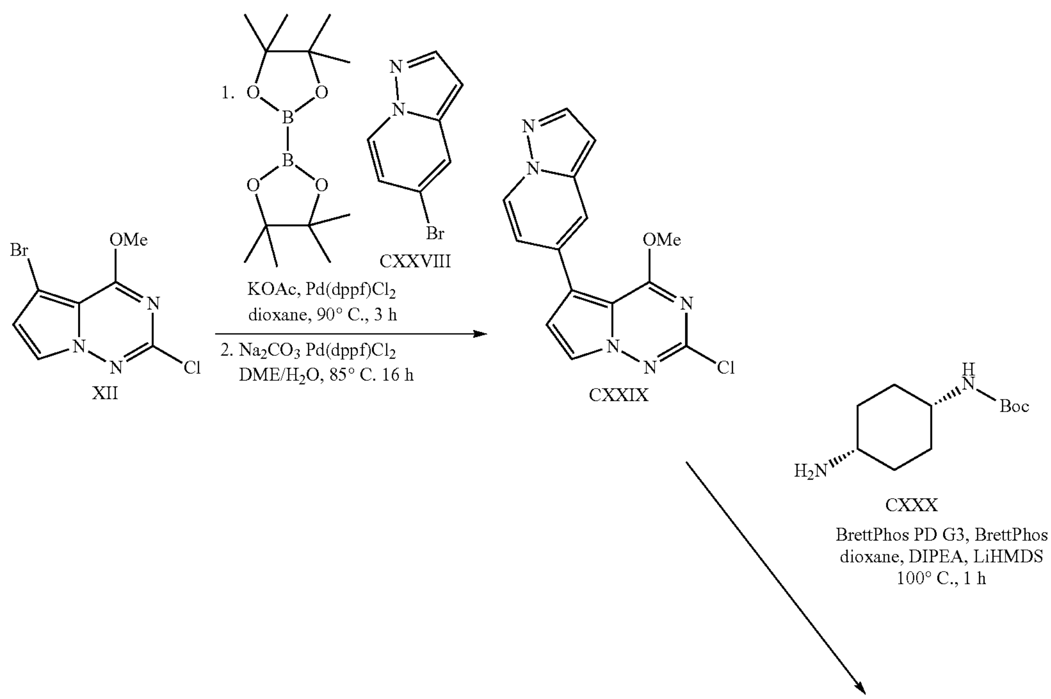

XII

CXXVIII

CXXIX

CXXX

-continued

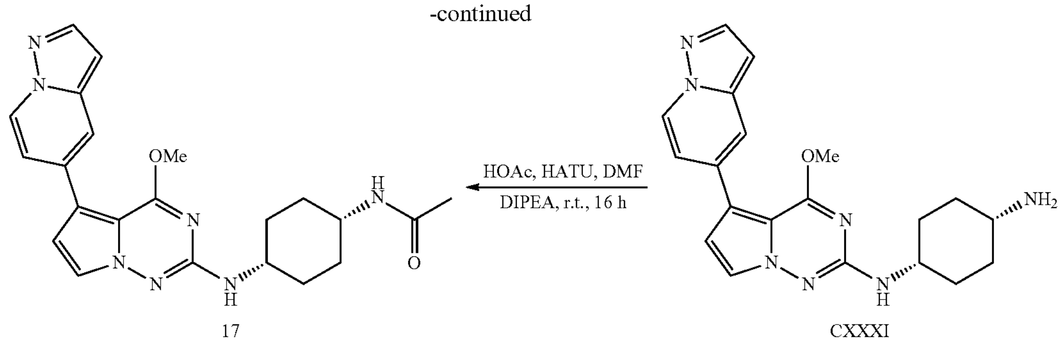

17

CXXXI

Steps 1-2

A mixture of 5-bromopyrazolo[1,5-a]pyridine (CXXVIII) (1.8 g, 9.14 mmol), Pd(dppf)$Cl_2$ (311 mg, 0.380 mmol), bis(pinacolato)diboron (2.9 g, 11.42 mmol), and KOAc (2.24 g, 22.82 mmol) in 1,4-dioxane (15 mL) in a sealed tube, it was degassed with $N_2$ and heated to 90° C. for 3 h. This reaction was cooled to room temperature to which was added 5-bromo-2-chloro-4-methoxypyrrolo[2,1-f][1,2,4]triazine (XII) (2 g, 7.62 mmol), Pd(dppf)$Cl_2$ (311 mg, 0.380 mmol), $Na_2CO_3$ (15 mL, 15 mmol) and DME (15 mL). The reaction was then degassed with $N_2$ and heated to 85° C. for 16 h. Water (100 mL) was added and extracted with EtOAc (100 mL×3). The organic layer was evaporated onto Celite® and purified by silica gel column (0→100% EtOAc/hexanes). The tubes which contained pure sample were collected and the solvent removed under vacuum. The impure fractions were combined and re-purified by silica gel column (0→100% EtOAc/hexanes). The tubes which contained pure sample were collected and the solvent removed under vacuum, the impure fractions were combined and re-purified by silica gel column (0→100% EtOAc/hexanes). The three pure fractions were combined and placed under high vacuum to produce 2-chloro-4-methoxy-5-pyrazolo[1,5-a]pyridin-5-ylpyrrolo[2,1-f][1,2,4]triazine (CXXIX) (660 mg, 2.202 mmol, 28.9% yield) as a beige solid. ESIMS found for $C_{14}H_{10}ClN_5O$ m/z 300.1 (M+H).

Step 3

To a stirred solution of 2-chloro-4-methoxy-5-pyrazolo[1,5-a]pyridin-5-ylpyrrolo[2,1-f][1,2,4]triazine (CXXIX) (100 mg, 0.330 mmol) in 1,4-dioxane (2 mL) were added BrettPhos (19 mg, 0.040 mmol), BrettPhos PD G3 (25 mg, 0.030 mmol), DIPEA (0.13 mL, 0.720 mmol), tert-butyl N-(4-aminocyclohexyl)carbamate (CXXX) (commercially available from Combi-Blocks Inc.) (90 mg, 0.420 mmol) and LiHMDS (1 mL, 1 mmol) at room temperature. The mixture was purged with $N_2$ and stirred at 100° C. for 1 h. The reaction mixture was concentrated and purified by ISCO (0->6% 7 N $NH_3$MeOH/$CHCl_3$). The pure fractions were collected, concentrated under reduced pressure, and dried under high vacuo to obtain cis-$N^1$-(4-methoxy-5-(pyrazolo[1,5-a]pyridin-5-yl)pyrrolo[2,1-f][1,2,4]triazin-2-yl)cyclohexane-1,4-diamine (CXXXI) (70 mg, 0.186 mmol, 55.6% yield) as an off-white gummy solid. ESIMS found for $C_{20}H_{23}N_7O$ m/z 378.2 (M+H).

Step 4

To a solution of HOAc (11 μL, 0.190 mmol), HATU (79 mg, 0.210 mmol) in DMF (0.2 mL) was added DIPEA (85 μL, 0.490 mmol) and the mixture was stirred for 5 min. cis-$N^1$-(4-methoxy-5-(pyrazolo[1,5-a]pyridin-5-yl)pyrrolo[2,1-f][1,2,4]triazin-2-yl)cyclohexane-1,4-diamine (CXXXI) (60 mg, 0.160 mmol) in DMF (0.3 mL) was then added and the reaction mixture was stirred at room temperature for 16 h. Water (10 mL) was added, and the solution was extracted with EtOAc. The organics were separated, concentrated, absorbed on silica gel, and purified by preparative TLC (4% MeOH/$CHCl_3$) to give N-(cis-4-((4-methoxy-5-(pyrazolo[1,5-a]pyridin-5-yl)pyrrolo[2,1-f][1,2,4]triazin-2-yl)amino) cyclohexyl)acetamide (17) (22 mg, 0.052 mmol, 33.0% yield) as a yellow solid. $^1H$ NMR (499 MHz, DMSO-$d_6$) δ ppm 1.50-1.59 (2H, m), 1.60-1.72 (4H, m), 1.74-1.81 (2H, m), 1.81 (3H, s), 3.64-3.71 (2H, m), 3.99 (3H, s), 6.47 (1H, d, J=6.30 Hz), 6.58 (1H, d, J=1.64 Hz), 6.76 (1H, d, J=2.74 Hz), 7.11 (1H, dd, J=7.26, 1.78 Hz), 7.63 (1H, d, J=2.74 Hz), 7.70 (1H, br d, J=6.84 Hz), 7.81 (1H, s), 7.97 (1H, d, J=2.19 Hz), 8.62 (1H, d, J=7.12 Hz); ESIMS found for $C_{22}H_{25}N_7O_2$ m/z 420.2 (M+1).

Example 2

Preparation of 4-methoxy-5-pyrazolo[1,5-a]pyridin-5-yl-N-(3R,4S)-3-fluoropiperidin-4-yl]pyrrolo[2,1-f][1,2,4]triazin-2-amine (29) and N-((3S,4R)-3-fluoro-1-methylpiperidin-4-yl)-4-methoxy-5-(pyrazolo[1,5-a]pyridin-5-yl)pyrrolo[2,1-f][1,2,4]triazin-2-amine (31) are depicted below in Scheme 25.

Scheme 25

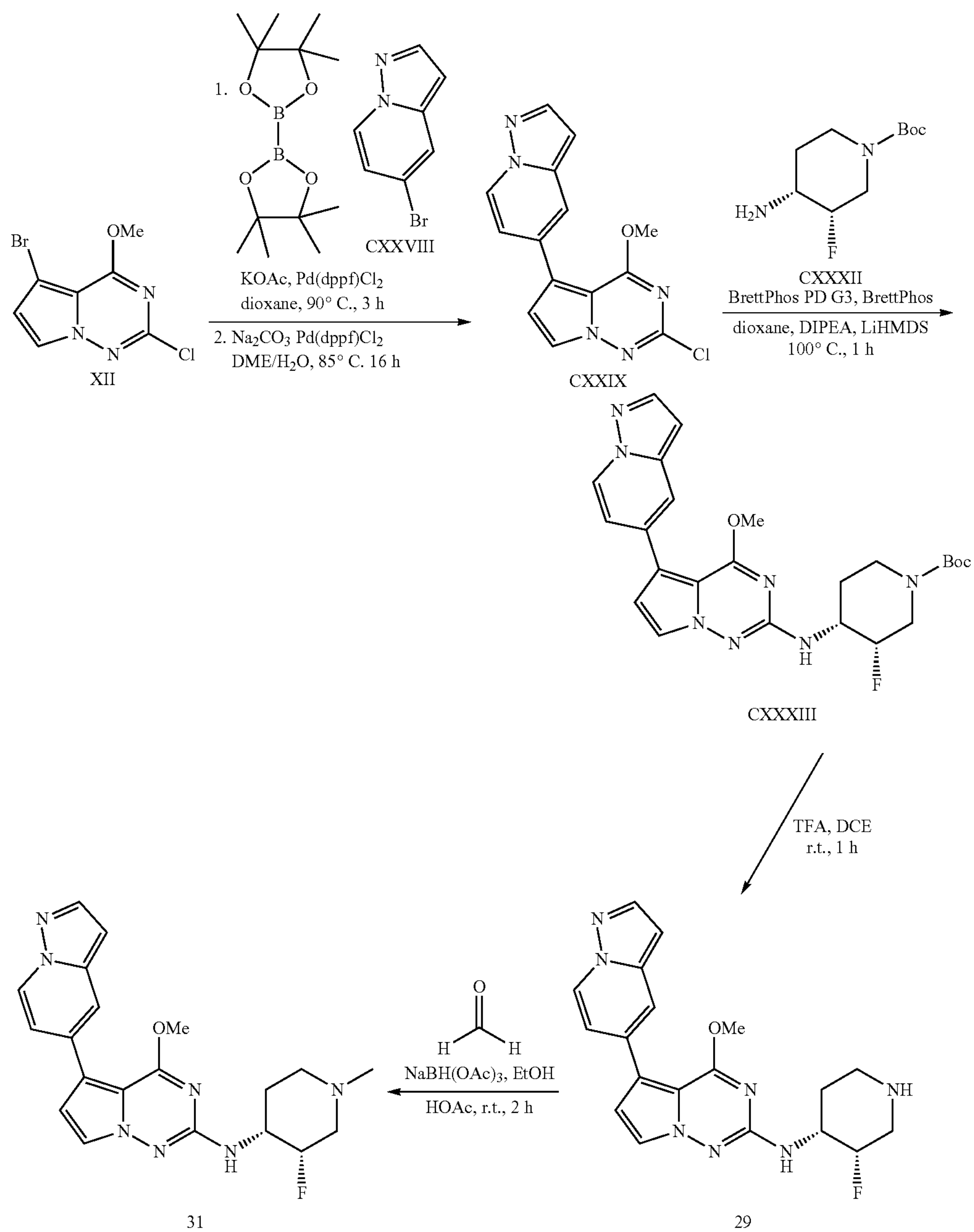

XII CXXVIII CXXIX CXXXII CXXXIII 29 31

Steps 1-2

A mixture of 5-bromopyrazolo[1,5-a]pyridine (CXXVIII) (1.8 g, 9.14 mmol), $Pd(dppf)Cl_2$ (311 mg, 0.380 mmol), bis(pinacolato)diboron (2.9 g, 11.42 mmol), and KOAc (2.24 g, 22.82 mmol) in 1,4-dioxane (15 mL) in a sealed tube, it was degassed with $N_2$ and heated to 90° C. for 3 h. This reaction was cooled to room temperature to which was added 5-bromo-2-chloro-4-methoxypyrrolo[2,1-f][1,2,4]triazine (XII) (2 g, 7.62 mmol), $Pd(dppf)Cl_2$ (311 mg, 0.380 mmol), $Na_2CO_3$ (15 mL, 15 mmol) and DME (15 mL). The reaction was then degassed with $N_2$ and heated to 85° C. for 16 h. Water (100 mL) was added and extracted with EtOAc (100 mL×3). The organic layer was evaporated onto Celite® and purified by silica gel column (0→100% EtOAc/hexanes). The tubes which contained pure sample were collected and the solvent removed under vacuum. The impure fractions were combined and re-purified by silica gel column (0→100% EtOAc/hexanes). The tubes which contained pure sample were collected and the solvent removed under vacuum, the impure fractions were combined and re-purified by silica gel column (0→100% EtOAc/hexanes). The three pure fractions were combined and placed under high vacuum to produce 2-chloro-4-methoxy-5-pyrazolo[1,5-a]pyridin-5-ylpyrrolo[2,1-f][1,2,4]triazine (CXXIX) (660 mg, 2.202 mmol, 28.9% yield) as a beige solid. ESIMS found for $C_{14}H_{10}ClN_5O$ m/z 300.1 (M+H).

Step 3

To a stirred solution of 2-chloro-4-methoxy-5-pyrazolo[1,5-a]pyridin-5-ylpyrrolo[2,1-f][1,2,4]triazine (CXXIX) (100 mg, 0.330 mmol) in 1,4-dioxane (3 mL) were added BrettPhos (19 mg, 0.040 mmol), BrettPhos PD G3 (25 mg, 0.030 mmol), DIPEA (0.13 mL, 0.720 mmol), 2-methyl-2-propanyl (3S,4R)-4-amino-3-fluoro-1-piperidinecarboxylate (CXXXII) (100 mg, 0.460 mmol) and LiHMDS (1 mL, 1 mmol) at room temperature. The mixture was purged with $N_2$ and stirred at 100° C. for 1 h. The reaction mixture was concentrated and purified by ISCO (0->100% EtOAc/hexanes). The pure fractions were collected, concentrated under reduced pressure, and dried under high vacuum to obtain tert-butyl (3R,4S)-3-fluoro-4-[(4-methoxy-5-pyrazolo[1,5-a]pyridin-5-ylpyrrolo[2,1-f][1,2,4]triazin-2-yl)amino]piperidine-1-carboxylate (CXXXIII) (65 mg, 0.135 mmol, 40.5% yield) as a white solid. ESIMS found for $C_{24}H_{28}FN_7O_3$ m/z 482.25 (M+H).

Step 4

To a stirred solution of tert-butyl (3R,4S)-3-fluoro-4-[(4-methoxy-5-pyrazolo[1,5-a]pyridin-5-ylpyrrolo[2,1-f][11,2,4]triazin-2-yl)amino]piperidine-1-carboxylate (CXXXIII) (65 mg, 0.130 mmol) in DCM (1 mL) was added TFA (0.5 mL, 6.49 mmol) and stirred at room temperature for 1 h. The reaction mixture was concentrated, treated with 7 N $NH_3$/MeOH, absorbed on silica gel and purified by ISCO (0->100% $CHCl_3$/MeOH). The pure fractions were collected, concentrated under reduced pressure, and dried under high vacuo to give 4-methoxy-5-pyrazolo[1,5-a]pyridin-5-yl-N-(3R,4S)-3-fluoropiperidin-4-yl]pyrrolo[2,1-f][1,2,4]triazin-2-amine (29) (45 mg, 0.118 mmol, 87.4% yield) as an off-white solid. $^1H$ NMR (499 MHz, DMSO-$d_6$) δ ppm 1.58-1.65 (1H, m), 1.73 (1H, qd, J=12.37, 4.24 Hz), 2.56 (1H, br t, J=12.46 Hz), 2.70 (1H, dd, J=38.70, 14.30 Hz), 2.96 (1H, br d, J=13.14 Hz), 3.13 (1H, br t, J=11.50 Hz), 3.78-3.93 (1H, m), 4.00 (3H, s), 4.80 (1H, d, J=50.75 Hz), 6.59 (1H, d, J=1.64 Hz), 6.64 (1H, d, J=7.94 Hz), 6.78 (1H, d, J=2.74 Hz), 7.11 (1H, dd, J=7.39, 1.92 Hz), 7.63 (1H, d, J=2.46 Hz), 7.81 (1H, d, J=1.10 Hz), 7.97 (1H, d, J=2.19 Hz), 8.63 (1H, d, J=7.12 Hz); ESIMS found for $C_{19}H_{20}FN_7O$ m/z 382.2 (M+H).

Step 5

4-Methoxy-5-pyrazolo[1,5-a]pyridin-5-yl-N-(3R,4S)-3-fluoropiperidin-4-yl]pyrrolo[2,1-f][1,2,4]triazin-2-amine (29) (40 mg, 0.100 mmol) was dissolved in EtOH (1 mL) and HOAc (15 μL, 0.260 mmol) and formaldehyde (18 μL, 0.320 mmol) were added and the reaction was stirred at room temperature for 20 min. $NaBH(OAc)_3$ (56 mg, 0.260 mmol) was added and the reaction was stirred for 2 h. TLC showed completion of the starting material. The reaction mixture was absorbed on silica gel and purified by ISCO (0->8% 7N $NH_3MeOH/CHCl_3$). The pure fractions were concentrated, and the residue was dried under high vacuo to yield N-((3S,4R)-3-fluoro-1-methylpiperidin-4-yl)-4-methoxy-5-(pyrazolo[1,5-a]pyridin-5-yl)pyrrolo [2,1-f][1,2,4]triazin-2-amine (31) (30 mg, 0.076 mmol, 72.3% yield) as an off-white solid. $^1H$ NMR (499 MHz, DMSO-$d_6$) δ ppm 1.68 (1H, br dd, J=12.59, 3.01 Hz), 1.92 (1H, qd, J=12.23, 3.56 Hz), 2.01-2.09 (1H, m), 2.17 (1H, dd, J=37.55, 13.20 Hz), 2.19 (3H, s), 2.79 (1H, br d, J=11.23 Hz), 3.00-3.09 (1H, m), 3.67-3.83 (1H, m), 4.00 (3H, s), 4.91 (1H, d, J=50.20 Hz), 6.59 (1H, d, J=1.64 Hz), 6.64 (1H, d, J=7.67 Hz), 6.78 (1H, d, J=2.74 Hz), 7.11 (1H, dd, J=7.12, 1.92 Hz), 7.63 (1H, d, J=2.74 Hz), 7.81 (1H, d, J=0.82 Hz), 7.97 (1H, d, J=2.19 Hz), 8.63 (1H, d, J=7.39 Hz); ESIMS found for $C_{20}H_{22}FN_7O$ m/z 396.2 (M+1).

Example 3

Preparation of 6-(2-((trans-4-hydroxy-4-methylcyclohexyl)amino)-4-methoxypyrrolo[2,1-f][1,2,4]triazin-5-yl)imidazo[1,2-a]pyridine-3-carboxamide (104) and 6-(2-((trans-4-hydroxy-4-methylcyclohexyl)amino)-4-methoxypyrrolo[2,1-f][1,2,4]triazin-5-yl)imidazo[1,2-a]pyridine-3-carbonitrile (103) are depicted below in Scheme 26.

Scheme 26

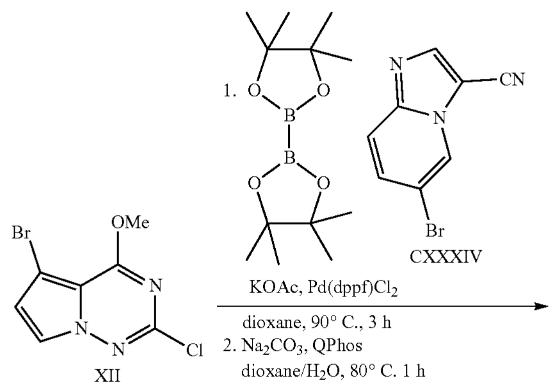

XII

CXXXIV

-continued

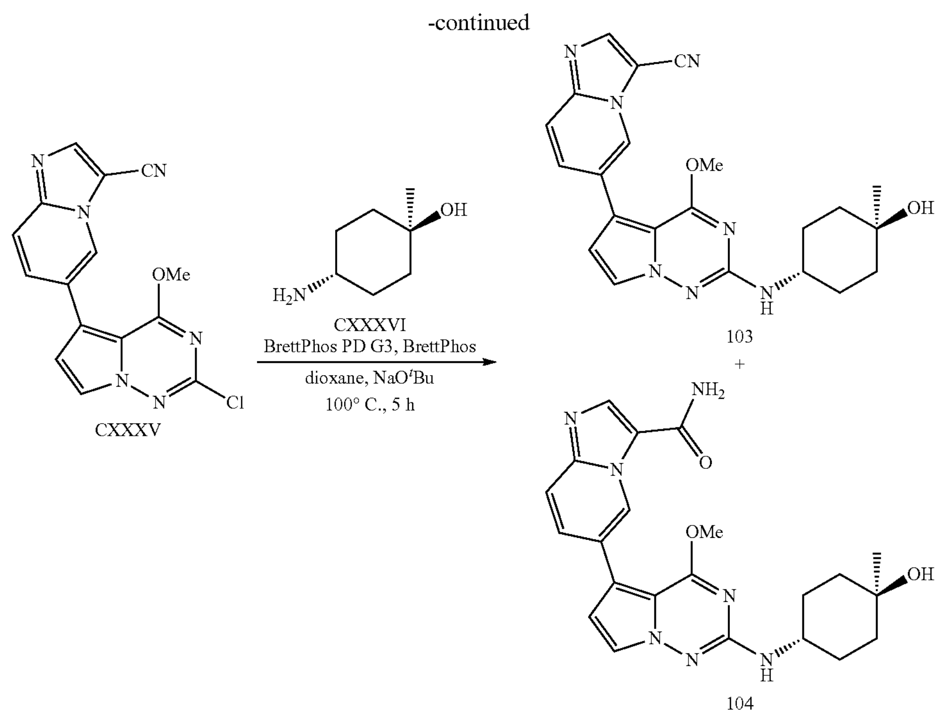

CXXXV

103

+

104

Steps 1-2

A mixture of 6-bromoimidazo[1,2-a]pyridine-3-carbonitrile (CXXXIV) (commercially available from Combi-Blocks Inc) (888 mg, 4.0 mmol), bis(pinacolato)diboron (1.016 g, 4.0 mmol), KOAc (1.18 g, 12.02 mmol) and Pd(dppf)$Cl_2$ (123 mg, 0.15 mmol) were dissolved in 1,4-dioxane (12 mL) and the reaction mixture was purged with $N_2$ gas for 5 min. The vial was sealed and heated at 95° C. for 3 h. To the above reaction mixture was added 5-bromo-2-chloro-4-methoxypyrrolo[2,1-f][1,2,4] triazine (XII) (525 mg, 2.0 mmol), QPhos (143 mg, 0.2 mmol), and a solution of $Na_2CO_3$ (1.27 g, 12. mmol) in water (3 mL). The reaction mixture was purged with $N_2$ gas for 5 min, the vial was sealed and heated for 80° C. for 1 h. The organic layer was separated, absorbed on silica, and purified on ISCO (0->20% MeOH/$CHCl_3$) to obtain 6-(2-chloro-4-methoxypyrrolo[2,1-f][1,2,4]triazin-5-yl)imidazo[1,2-a]pyridine-3-carbonitrile (CXXXV) (116 mg, 0.357 mmol, 17.9% yield) as a beige solid. ESIMS found for $C_{15}H_9ClN_6O$ m/z 325.1 (M+H).

Step 3

To a stirred solution of 6-(2-chloro-4-methoxypyrrolo[2,1-f][1,2,4]triazin-5-yl)imidazo[1,2-a]pyridine-3-carbonitrile (CXXXV) (116. mg, 0.36 mmol), trans-4-amino-1-methylcyclohexan-1-ol (CXXXVI) (commercially available from PharmaBlock (USA), Inc.) (56. mg, 0.43 mmol), BrettPhos Pd G3 (24. mg, 0.03 mmol) and BrettPhos (19. mg, 0.04 mmol) in 1,4-dioxane (3 mL) was added NaO$^t$Bu (110 mg, 1.14 mmol) at room temperature. The reaction mixture was purged for 5 min with $N_2$ then heated to 100° C. for 5 h. The reaction mixture concentrated and purified by ISCO (0->20% 7 N $NH_3$ in MeOH/$CHCl_3$) to obtain two products, 6-(2-((trans-4-hydroxy-4-methylcyclohexyl)amino)-4-methoxypyrrolo[2,1-f][1,2,4]triazin-5-yl)imidazo[1,2-a]pyridine-3-carbonitrile (103) (12 mg, 0.029 mmol, 8.0% yield) as a beige solid. $^1$H NMR (499 MHz, DMSO-$d_6$) δ ppm 1.14 (3H, s), 1.38-1.53 (4H, m), 1.56-1.66 (3H, m), 1.83-1.93 (2H, m), 3.60-3.71 (1H, m), 4.01 (3H, s), 4.23 (1H, s), 6.56 (1H, d, J=7.94 Hz), 6.89 (1H, d, J=2.74 Hz), 7.67 (1H, d, J=2.74 Hz), 7.81-7.92 (2H, m), 8.44 (1H, s), 8.77-8.86 (1H, m); ESIMS found for $C_{22}H_{23}N_7O_2$ m/z 418.2 (M+1) and 6-(2-((trans-4-hydroxy-4-methylcyclohexyl)amino)-4-methoxypyrrolo[2,1-f][1,2,4]triazin-5-yl)imidazo[1,2-a]pyridine-3-carboxamide (104) (2.2 mg, 0.005 mmol, 1.4% yield) as a beige solid. $^1$H NMR (499 MHz, DMSO-$d_6$) δ ppm 1.14 (3H, s), 1.39-1.48 (4H, m), 1.57-1.63 (2H, m), 1.85-1.91 (2H, m), 3.60-3.72 (1H, m), 3.99 (3H, s), 4.23 (1H, s), 6.49 (1H, d, J=7.94 Hz), 6.75 (1H, d, J=2.46 Hz), 7.34 (1H, br s), 7.65 (1H, d, J=2.74 Hz), 7.69 (2H, s), 7.95 (1H, br s), 8.33 (1H, s), 9.84 (1H, s); ESIMS found for $C_{22}H_{25}N_7O_3$ m/z 436.25 (M+1).

Example 4

Preparation of 1-(7-((5-(1-(2-hydroxyethyl)-2-methyl-1H-benzo[d]imidazol-6-yl)-4-methoxypyrrolo[2,1-f][1,2,4]triazin-2-yl)amino)-2-azaspiro[3.5]nonan-2-yl)ethan-1-one (173) is depicted below in Scheme 27.

Scheme 27

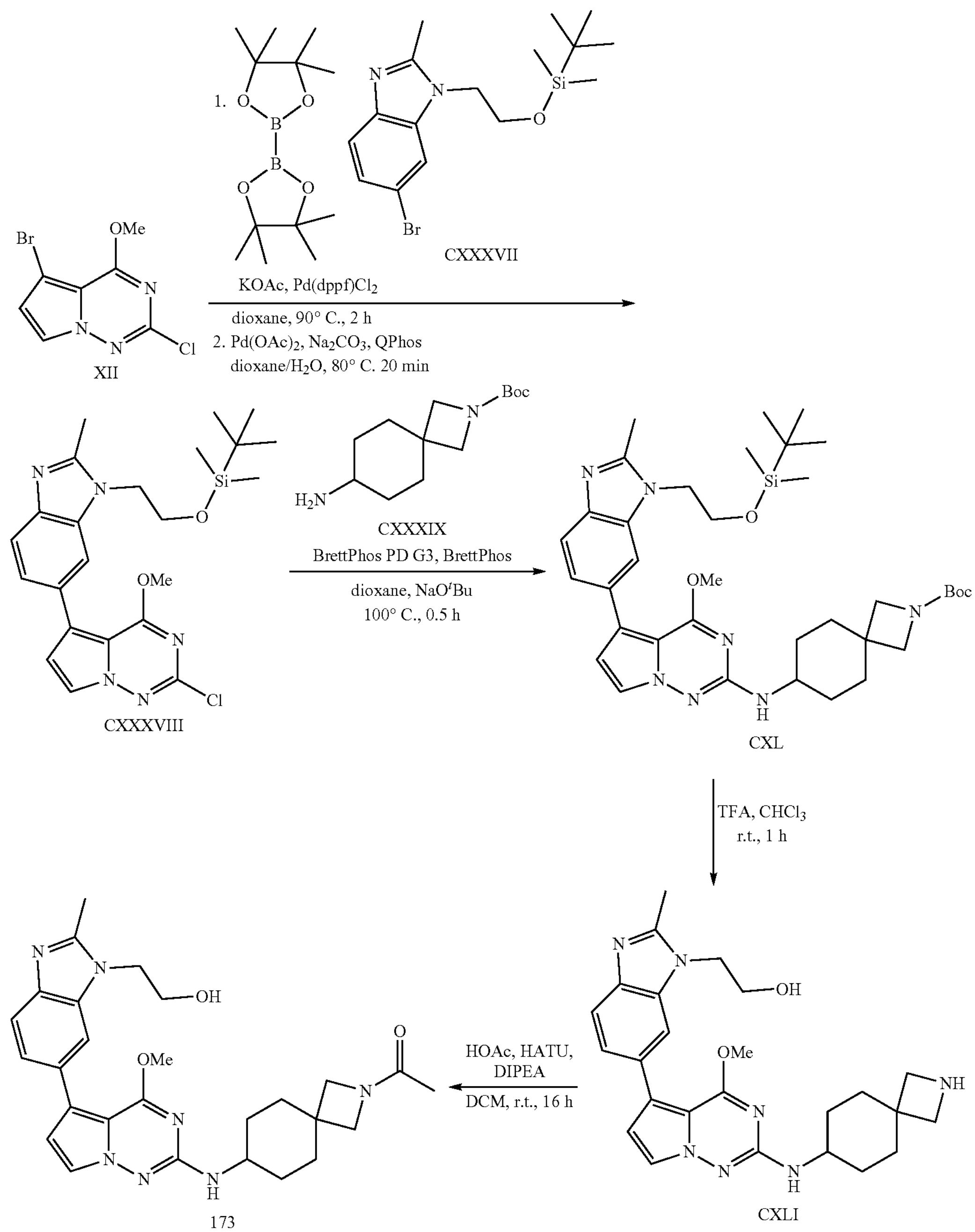

Steps 1-2

A mixture of 6-bromo-1-(2-((tert-butyldimethylsilyl)oxy)ethyl)-2-methyl-1H-benzo[d]imidazole (CXXXVII) (950 mg, 2.57 mmol), $Pd(dppf)Cl_2$ (99 mg, 0.12 mmol), bis(pinacolato)diboron (960 mg, 3.78 mmol) and KOAc (748 mg, 7.62 mmol) in 1,4-dioxane (10 mL) in a sealed tube, it was purged with $N_2$, sealed, and then heated to 90° C. for 2 h. The LCMS shows a mixture of the boronic acid and the boronic ester.

This reaction was cooled to room temperature then to this mixture was added 5-bromo-2-chloro-4-methoxypyrrolo[2,1-f][1,2,4]triazine (XII) (660 mg, 2.51 mmol), QPhos (178 mg, 0.25 mmol), $Pd(OAc)_2$ (28 mg, 0.12 mmol), and an aqueous solution of $Na_2CO_3$ (5 mL, 5.0 mmol). The reaction was purged with $N_2$, sealed, and then heated to 80° C. for 20 min. Water (100 mL) was added and extracted with EtOAc (3×100 mL). The solvent was reduced onto Celite® and purified by silica gel column chromatography (0→100%

EtOAc/hexanes) to produce 5-(1-(2-((tert-butyldimethylsilyl)oxy)ethyl)-2-methyl-1H-benzo[d]imidazol-6-yl)-2-chloro-4-methoxypyrrolo[2,1-f][1,2,4]triazine (CXXXVIII) (460 mg, 0.975 mmol, 38.8% yield) as an off-white solid. ESIMS found for $C_{23}H_{30}ClN_5O_2Si$ m/z 472.2 (M+H).

Step 3

To a stirred solution of tert-butyl 7-amino-2-azaspiro[3.5]nonane-2-carboxylate HCl (CXXXIX) (commercially available from J&W Pharmlab, LLC) (70 mg, 0.25 mmol), 5-(1-(2-((tert-butyldimethylsilyl)oxy)ethyl)-2-methyl-1H-benzo[d]imidazol-6-yl)-2-chloro-4-methoxypyrrolo[2,1-f][1,2,4]triazine (CXXXVIII) (100 mg, 0.21 mmol), BrettPhos (12 mg, 0.02 mmol), and BrettPhos PD G3 (10 mg, 0.01 mmol) in dioxane (1.6 mL) was added $NaO^tBu$ (62 mg, 0.65 mmol). The solution was purged with $N_2$, sealed and then heated at 100° C. for 30 min. The solvent reaction was reduced onto Celite® and purified by silica bel column chromatography (0->30% 7 N $NH_3$ in MeOH/$CHCl_3$) to produce tert-butyl 7-((5-(1-(2-((tert-butyldimethylsilyl)oxy)ethyl)-2-methyl-1H-benzo[d]imidazol-6-yl)-4-methoxypyrrolo[2,1-f][1,2,4]triazin-2-yl)amino)-2-azaspiro[3.5]nonane-2-carboxylate (CXL) (17 mg, 0.025 mmol, 11.9% yield) as an off-white solid. ESIMS found for $C_{36}H_{53}N_7O_4Si$ m/z 676.4 (M+H).

Step 4

To a solution of tert-butyl 7-((5-(1-(2-((tert-butyldimethylsilyl)oxy)ethyl)-2-methyl-1H-benzo[d]imidazol-6-yl)-4-methoxypyrrolo[2,1-f][1,2,4]triazin-2-yl)amino)-2-azaspiro[3.5]nonane-2-carboxylate (CXL) (17. mg, 0.03 mmol) in $CHCl_3$ (3 mL) was added TFA (1 mL). The reaction was stirred at room temperature for 1 h. The solvent was removed under reduced pressure and the residue was purified by silica gel column chromatography (0->15% 7 N $NH_3$ in MeOH/$CHCl_3$) to produce 2-(6-(2-((2-azaspiro[3.5]nonan-7-yl)amino)-4-methoxypyrrolo[2,1-f][1,2,4]triazin-5-yl)-2-methyl-1H-benzo[d]imidazol-1-yl)ethan-1-ol (CXLI) (11 mg, 0.024 mmol, 94.8% yield) as an amber glass. ESIMS found for $C_{25}H_{31}N_7O_2$ m/z 462.3 (M+H).

Step 5

A solution of HATU (10 mg, 0.03 mmol), HOAc (1.5 μL, 0.03 mmol) and DIPEA (12 μL, 0.07 mmol) in DCM (2 mL) was stirred at room temperature for 30 min, then 2-(6-(2-((2-azaspiro[3.5]nonan-7-yl)amino)-4-methoxypyrrolo[2,1-f][1,2,4]triazin-5-yl)-2-methyl-1H-benzo[d]imidazol-1-yl)ethan-1-ol (CXLI) (11 mg, 0.024 mmol) was added and the solution was stirred at room temperature for 16 h. The solvent was reduced onto Celite® and purified by silica gel column chromatography (0→10% 7 N $NH_3$ in MeOH/$CHCl_3$) to yield 1-(7-((5-(1-(2-hydroxyethyl)-2-methyl-1H-benzo[d]imidazol-6-yl)-4-methoxypyrrolo[2,1-f][1,2,4]triazin-2-yl)amino)-2-azaspiro[3.5]nonan-2-yl)ethan-1-one (173) (6 mg, 0.012 mmol, 50.0% yield) as an off-white solid. $^1H$ NMR (499 MHz, DMSO-$d_6$) δ ppm 1.28-1.39 (2H, m), 1.48-1.60 (2H, m), 1.72-1.79 (3H, in), 1.83-1.94 (4H, m), 2.60 (3H, s), 3.47 (1H, s), 3.52 (1H, s), 3.57 (1H, dt, J=10.20, 6.95 Hz), 3.74 (1H, s), 3.75-3.79 (2H, m), 3.80 (1H, s), 3.93 (3H, d, J=1.10 Hz), 4.28 (2H, br t, J=5.20 Hz), 4.99 (1H, t, J=5.48 Hz), 6.43 (1H, dd, J=16.43, 7.94 Hz), 6.62 (1H, d, J=2.46 Hz), 7.37 (1H, dd, J=8.21, 1.37 Hz), 7.51 (1H, d, J=8.49 Hz), 7.58 (1H, t, J=2.74 Hz), 7.69 (1H, s); ESIMS found for $C_{27}H_{33}N_7O_3$ m/z 504.3 (M+1).

Example 5

Preparation of trans-$N^1$-(4-methoxy-5-(1-methyl-1H-benzo[d][1,2,3]triazol-6-yl)pyrrolo[2,1-f][1,2,4]triazin-2-yl)-3-methylcyclobutane-1,3-diamine (203) and 1-(trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)pyrrolidin-2-one (223) are depicted below in Scheme 28.

Scheme 28

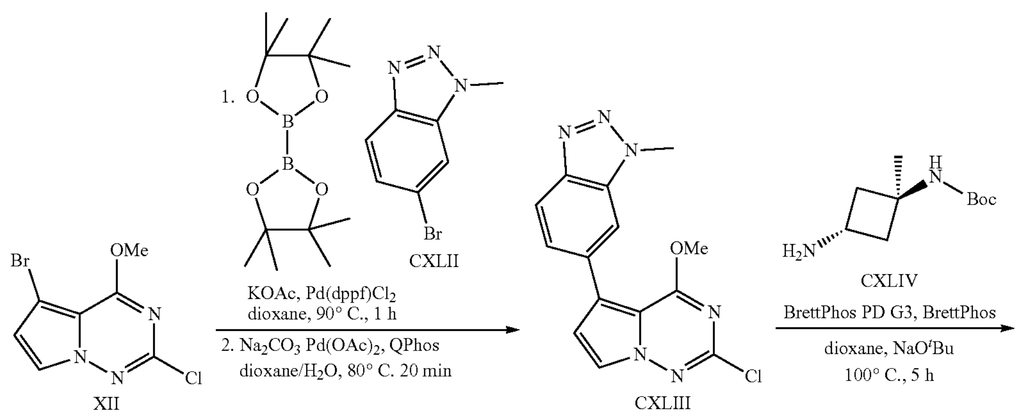

-continued

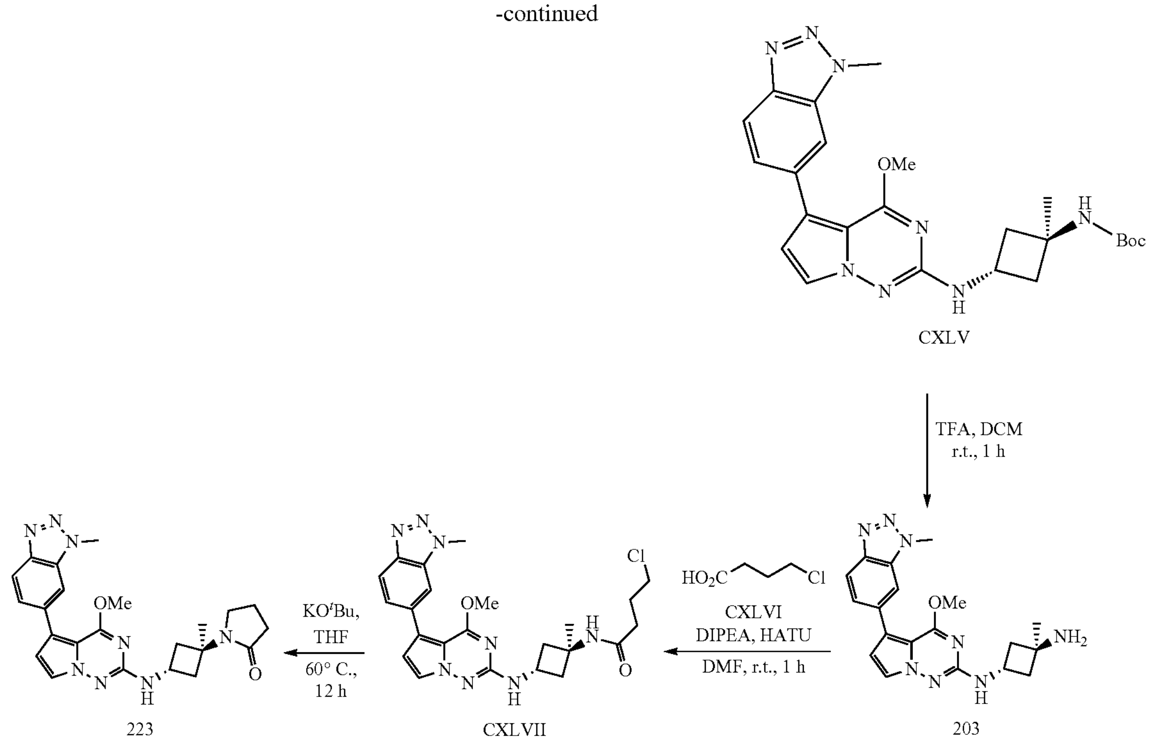

CXLV

223 CXLVII 203

Steps 1-2

A mixture of 6-bromo-1-methyl-1H-benzo[d][1,2,3]triazole (CXLII) (commercially available from Combi-Blocks Inc.) (0.93 g, 4.39 mmol), Pd(dppf)$Cl_2$ (0.17 g, 0.21 mmol), bis(pinacolato)diboron (1.68 g, 6.62 mmol), and KOAc (1.3 g, 13.25 mmol) in 1,4-dioxane (11 mL) in a sealed tube, it was purged with $N_2$, sealed, and heated to 90° C. for 1 h. The LCMS shows a mixture of the boronic acid and the boronic ester.

The reaction was cooled to room temperature and then to this mixture was added 5-bromo-2-chloro-4-methoxypyrrolo[2,1-f][1,2,4]triazine (XII) (1.15 g, 4.38 mmol), $Pd(OAc)_2$ (0.05 g, 0.22 mmol), QPhos (0.32 g, 0.45 mmol), an aqueous solution of $Na_2CO_3$ (9.2 mL, 9.2 mmol) and 1,4-dioxane (11 mL). The reaction was purged with $N_2$, sealed, and heated to 80° C. for 20 min. Water (100 mL) was added and extracted with EtOAc (3×100 mL). The solvent was reduced onto Celite® and purified by silica gel column chromatography (0->100% EtOAc/hexanes) to produce 6-(2-chloro-4-methoxypyrrolo[2,1-f][1,2,4]triazin-5-yl)-1-methyl-1H-benzo[d][1,2,3]triazole (CXLIII) (0.763 g, 2.424 mmol, 55.3% yield) as an off-white solid. ESIMS found for $C_{14}H_{11}ClN_6O$ m/z 315.1 (M+H).

Step 3

To a stirred solution of 6-(2-chloro-4-methoxypyrrolo[2,1-f][1,2,4]triazin-5-yl)-1-methyl-1H-benzo[d][1,2,3]triazole (CXLIII) (212 mg, 0.67 mmol), tert-butyl (trans-3-amino-1-methylcyclobutyl)carbamate (CXLIV) (commercially available from PharmaBlock (USA), Inc.) (160 mg, 0.8 mmol), BrettPhos PD G3, (46 mg, 0.05 mmol) and BrettPhos (37 mg, 0.07 mmol) in 1,4-dioxane (4 mL) was added NaO$^t$Bu (195 mg, 2.03 mmol). The reaction mixture was purged for 5 min then heated to 100° C. for 30 min. The reaction mixture was concentrated and purified on ISCO (0→10% MeOH/$CHCl_3$) to obtain tert-butyl (trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)carbamate (CXLV) (188 mg, 0.393 mmol, 58.3% yield) as a colorless gum. ESIMS found for $C_{24}H_{30}N_8O_3$ m/z 479.3 (M+H).

Step 4

To a stirred solution of tert-butyl (trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)carbamate (CXLV) (188 mg, 0.39 mmol) in DCM (2 mL) was added TFA (1.2 mL, 15.58 mmol) and stirred at room temperature for 1 h. The reaction mixture was concentrated, treated with saturated aqueous $Na_2CO_3$ solution, washed with EtOAc, dried over anhydrous $Na_2SO_4$, concentrated under vacuum, then absorbed on silica gel, and purified by ISCO (0-20% 7 N $NH_3$ in MeOH/$CHCl_3$) to give trans-$N_1$-(4-methoxy-5-(1-methyl-1H-benzo[d][1,2,3]triazol-6-yl)pyrrolo[2,1-f][1,2,4]triazin-2-yl)-3-methylcyclobutane-1,3-diamine (203) (110 mg, 0.291 mmol, 74.0% yield) as an off-white foam. $^1$H NMR (499 MHz, DMSO-$d_6$) δ ppm 1.22 (3H, s), 1.80 (2H, br s), 1.88-1.98 (2H, m), 2.13-2.22 (2H, m), 3.95 (3H, s), 4.23-4.33 (1H, m), 4.31 (3H, s), 6.74 (1H, d, J=2.46 Hz), 6.90 (1H, d, J=7.12 Hz), 7.60 (1H, dd, J=8.76, 1.37 Hz), 7.63 (1H, d, J=2.46 Hz), 7.93 (1H, s), 7.95-8.00 (1H, m); ESIMS found for $C_{19}H_{22}N_8O$ m/z 379.2 (M+1).

Step 5

To a solution of 4-chlorobutanoic acid (CXLVI) (16 μL, 0.16 mmol) and HATU (70 mg, 0.18 mmol) in DMF (0.5 mL) was added DIPEA (74 μL, 0.42 mmol) and the mixture was stirred for 10 min. trans-$N_1$-(4-Methoxy-5-(1-methyl-1H-benzo[d][1,2,3]triazol-6-yl)pyrrolo[2,1-f][1,2,4]triazin-2-yl)-3-methylcyclobutane-1,3-diamine (203) (50 mg, 0.13 mmol) in DMF (0.5 mL) was added and the reaction mixture was stirred at room temperature for 1 h. The reaction mixture was quenched with a saturated aqueous $NaHCO_3$ solution and extracted with EtOAc. The organic layer was separated, concentrated, absorbed on silica gel and purified by ISCO (0->10% $MeOH/CHCl_3$) to obtain 4-chloro-N-(trans-3-((4-methoxy-5-(1-methyl-1H-benzo[d][1,2,3]triazol-6-yl)pyrrolo[2,1-f][1,2,4]triazin-2-yl)amino)-1-methylcyclobutyl) butanamide (CXLVII) (53 mg, 0.110 mmol, 83.1% yield) as an off-white solid. ESIMS found for $C_{23}H_{27}ClN_8O_2$ m/z 483.2 (M+H).

Step 6

To a solution of 4-chloro-N-(trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)butanamide (CXLVII) (53 mg, 0.11 mmol) in THF (5 mL) was added $KO^tBu$ (37 mg, 0.33 mmol) and the reaction mixture was heated at 60° C. for 12 h. The reaction mixture was quenched with a saturated aqueous $NaHCO_3$ solution and extracted with EtOAc. The organic layer was separated, concentrated, absorbed on silica gel, and purified by ISCO (0->10% $MeOH/CHCl_3$) to yield 1-(trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)pyrrolidin-2-one (223) (23 mg, 0.052 mmol, 46.9% yield) as an off-white solid. $^1H$ NMR (499 MHz, DMSO-$d_6$) δ ppm 1.36 (3H, s), 1.92 (2H, quin, J=7.53 Hz), 2.00-2.08 (2H, m), 2.23 (2H, t, J=8.08 Hz), 2.82-2.92 (2H, m), 3.40 (2H, t, J=6.84 Hz), 3.96 (3H, s), 4.04-4.12 (1H, m), 4.31 (3H, s), 6.74 (1H, d, J=2.46 Hz), 7.06 (1H, d, J=6.30 Hz), 7.60 (1H, dd, J=8.62, 1.51 Hz), 7.64 (1H, d, J=2.46 Hz), 7.94 (1H, s), 7.97 (1H, d, J=8.76 Hz); ESIMS found for $C_{23}H_{26}N_8O_2$ m/z 447.3 (M+1).

Example 6

Preparation of cis-$N^3$-(4-methoxy-5-(1-methyl-1H-benzo[d][1,2,3]triazol-6-yl)pyrrolo[2,1-f][1,2,4]triazin-2-yl)-$N^1$,$N^1$,1-trimethylcyclobutane-1,3-diamine (204) is depicted below in Scheme 29.

Scheme 29

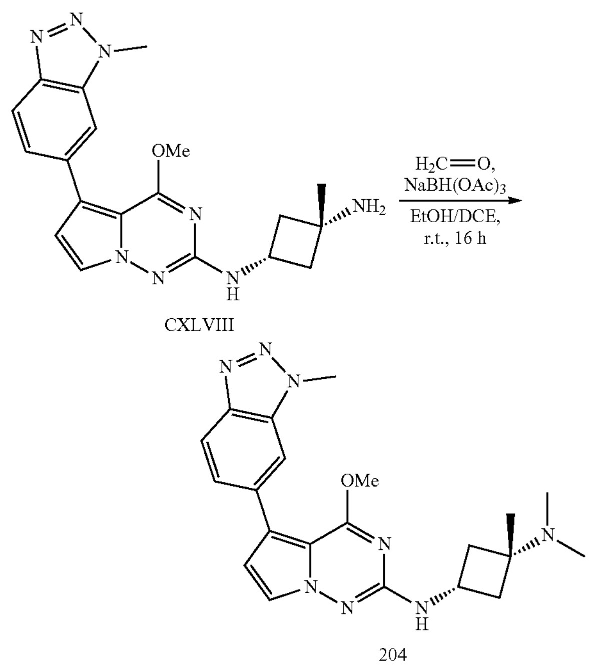

CXLVIII

204

Step 1

To a stirred solution of (cis-$N_1$-(4-methoxy-5-(1-methyl-1H-benzo[d][1,2,3]triazol-6-yl)pyrrolo[2,1-f][1,2,4]triazin-2-yl)-3-methylcyclobutane-1,3-diamine (CXLVIII) (prepared by the method shown in Example 5, steps 1-4) (25 mg, 0.07 mmol) in EtOH (1 mL) and DCE (4 mL) were added formaldehyde (13 µL, 0.17 mmol). The reaction was stirred at room temperature for 30 min before adding $NaBH(OAc)_3$ (70 mg, 0.33 mmol). The reaction was further stirred at room temperature for 16 h. A saturated aqueous $Na_2CO_3$ solution was added and extracted with DCM. The organic layer was separated and dried over anhydrous $Na_2SO_4$. The solvent under reduced pressure and the residue purified by ISCO silica gel column chromatography (0->20% 7 N $NH_3$ in $MeOH/CHCl_3$) to obtain cis-$N^3$-(4-methoxy-5-(1-methyl-1H-benzo[d][1,2,3]triazol-6-yl)pyrrolo[2,1-f][1,2,4]triazin-2-yl)-$N^1$,$N^1$,1-trimethylcyclobutane-1,3-diamine (204) (18 mg, 0.044 mmol, 67.0% yield) as a white solid. $^1H$ NMR (499 MHz, DMSO-$d_6$) δ ppm 1.06 (3H, s), 1.82-1.92 (2H, m), 2.03 (6H, s), 2.19 (2H, td, J=8.15, 2.60 Hz), 3.91-4.01 (1H, m), 3.95 (3H, s), 4.31 (3H, s), 6.74 (1H, d, J=2.46 Hz), 6.95 (1H, d, J=7.12 Hz), 7.60 (1H, dd, J=8.62, 1.51 Hz), 7.64 (1H, d, J=2.74 Hz), 7.93 (1H, s), 7.97 (1H, d, J=8.76 Hz); ESIMS found for $C_{21}H_{26}N_8O$ m/z 407.3 (M+1).

Example 7

Preparation of (trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)(pyrrolidin-1-yl)methanone (222) is depicted below in Scheme 30.

Scheme 30

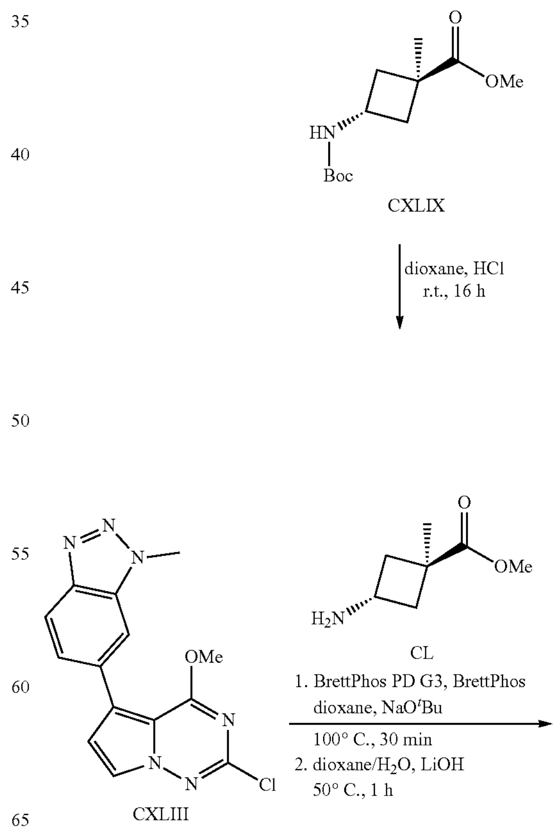

CXLIX

CL

CXLIII

-continued

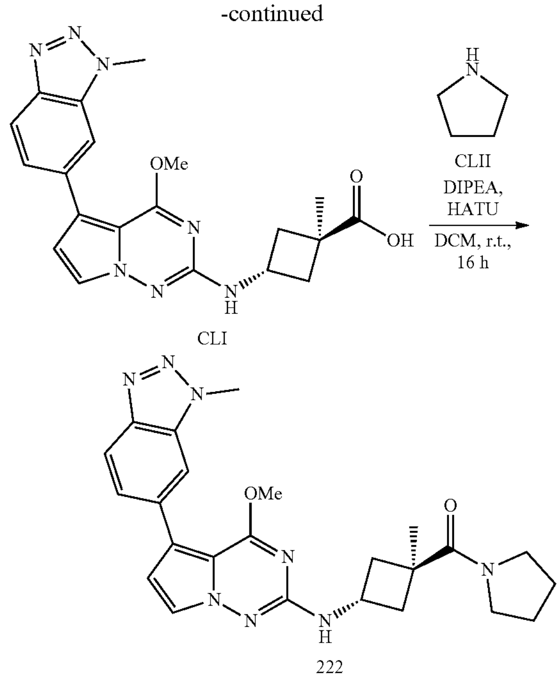

CLI

222

Steps 1-3

To a microwave vial was added methyl trans-3-{[(tert-butoxy)carbonyl]amino}-1-methylcyclobutane-1-carboxylate (CXLIX) (255.1 mg, 1.05 mmol), MeOH (5 mL) and a 4 M solution of HCl in dioxane (0.5 mL, 2. mmol). The vial was sealed, and the solution was stirred at room temperature for 16 h. The solvent was blown off with stream of $N_2$ while heating to 50° C. The residue was dissolved in MeCN (5 mL), and the solvent was blown off with stream of $N_2$ while heating to 50° C. This was repeated 2 more times to produce methyl trans-3-amino-1-methylcyclobutane-1-carboxylate (CL) as a white solid, To the white residue was added 6-(2-chloro-4-methoxy-pyrrolo[2,1-f][1,2,4]triazin-5-yl)-1-methyl-1H-benzo[d][1,2,3]triazole (CXLIII) (300 mg, 0.95 mmol), 1,4-dioxane (4.8 mL), BrettPhos (50 mg, 0.09 mmol), NaO$^t$Bu (366.4 mg, 3.81 mmol), BrettPhos PD G3 (44 mg, 0.05 mmol). The reaction mixture was purged with $N_2$, the vial sealed and heated to 100° C. for 30 min. The LC/MS showed a mixture of the methyl ester and the acid.

To the above solution was added water (2 mL) followed by a 2 M aqueous solution of LiOH (0.48 mL, 0.96 mmol). The reaction was heated at 50° C. for 1 h. The reaction was poured into water (5 mL), neutralized with 1 N HCl and extracted with DCM (3×50 mL). The DCM layer was reduced onto Celite® and purified by silica gel column chromatography (0→50% EtOAc/hexanes) to produce 3-[[4-methoxy-5-(3-methylbenzotriazol-5-yl)pyrrolo[2,1-f][1,2,4]triazin-2-yl]amino]-1-methylcyclobutane-1-carboxylic acid (CLI) (104 mg, 0.2553 mmol, 26.779% yield) as an off white solid. ESIMS found for $C_{20}H_{21}N_7O_3$ m/z 408.2 (M+H).

Step 4

A solution of HATU (34.5 mg, 0.09 mmol), trans-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxylic acid (CLI) (34. mg, 0.08 mmol) and DIPEA (30.9 μL, 0.18 mmol) in DCM (2 mL) was stirred at room temperature for 30 min before adding pyrrolidine (CLII) (10 μL, 0.12 mmol). The reaction was stirred at room temperature for 16 h. The solvent was reduced onto Celite® and purified by silica gel column chromatography (0→10% 7N $NH_3$ in MeOH/$CHCl_3$) to obtain (trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)(pyrrolidin-1-yl)methanone (222) (36 mg, 0.078 mmol, 93.7% yield) as a white solid. $^1H$ NMR (499 MHz, DMSO-$d_6$) δ ppm 1.38 (3H, s), 1.73-1.80 (2H, m), 1.81-1.87 (2H, m), 1.91-1.99 (2H, m), 2.86-2.93 (2H, m), 3.30-3.34 (4H, m), 3.87-3.94 (1H, m), 3.96 (3H, s), 4.31 (3H, s), 6.74 (1H, d, J=2.46 Hz), 7.07 (1H, d, J=6.57 Hz), 7.60 (1H, dd, J=8.62, 1.51 Hz), 7.64 (1H, d, J=2.74 Hz), 7.93 (1H, s), 7.97 (1H, d, J=8.76 Hz); ESIMS found for $C_{24}H_{28}N_8O_2$ m/z 461.3 (M+1).

Example 8

Preparation of 2-(((3R,4S)-4-fluoro-1-(oxetan-3-yl)pyrrolidin-3-yl)amino)-5-(imidazo[1,2-a]pyrimidin-6-yl)pyrrolo[2,1-f][1,2,4]triazin-4-ol (265) is depicted below in Scheme 31.

Scheme 31

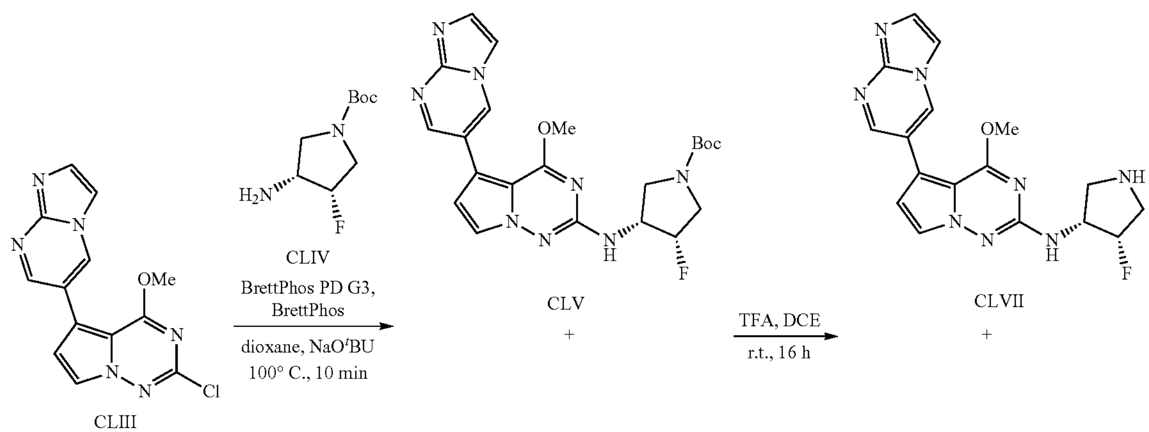

CLIII

CLV

+

CLVII

+

-continued

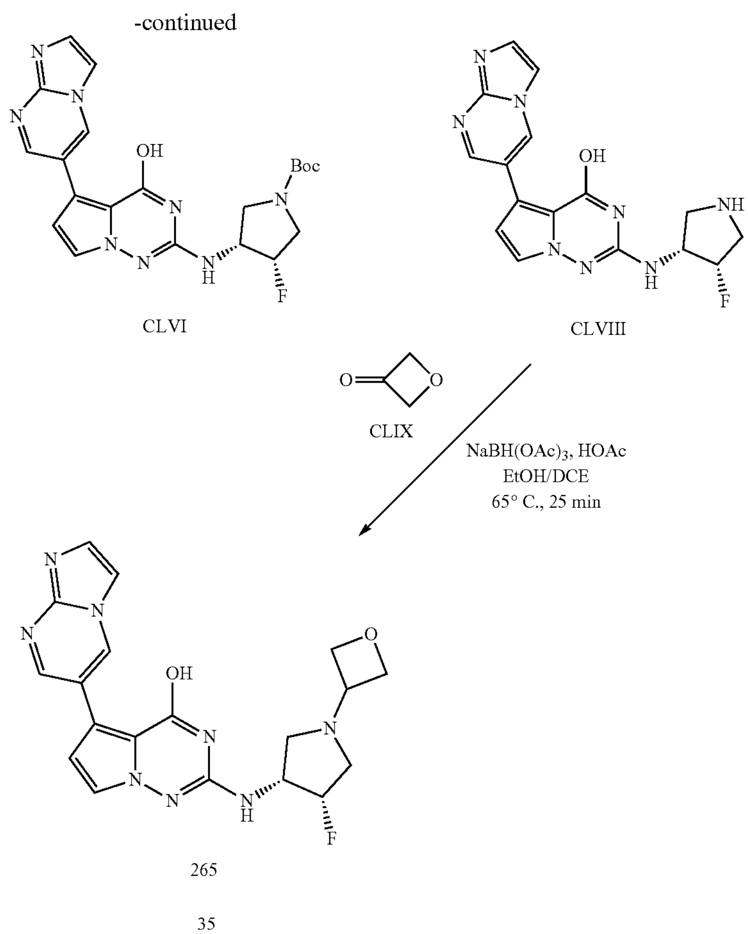

CLVI

CLVIII

CLIX

265

Step 1

2-Chloro-5-(imidazo[1,2-a]pyrimidin-6-yl)-4-methoxy-pyrrolo[2,1-f][1,2,4]triazine (CLIII) (prepared by the method presented in Example 3, steps 1-2) (200 mg, 0.67 mmol), tert-butyl (3R,4S)-3-amino-4-fluoropyrrolidine-1-carboxylate (CLIV) (commercially available from PharmaBlock (USA), Inc.) (177 mg, 0.87 mmol), BrettPhos Pd G3 (51 mg, 0.06 mmol), BrettPhos (31 mg, 0.06 mmol) and $NaO^tBu$ (192 mg, 2.0 mmol) were suspended in dry 1,4-dioxane (4 mL). The mixture is purged with Ar for 5 min, followed by heating at 100° C. for 10 min. The reaction mixture was added to a saturated aqueous $NH_4Cl$ solution and DCM, and the organic layer was separated. The aqueous layer was extracted with DCM (×2) and the combined organic layers were dried (anhydrous $MgSO_4$) and reduced in vacuo to give a mixture of products tert-butyl (3S,4R)-3-fluoro-4-((5-(imidazo[1,2-a]pyrimidin-6-yl)-4-methoxy-pyrrolo[2,1-f][1,2,4]triazin-2-yl)amino)pyrrolidine-1-carboxylate (CLV) (220 mg, 0.470 mmol, 70.6% yield) and tert-butyl (3S,4R)-3-fluoro-4-((4-hydroxy-5-(imidazo[1,2-a]pyrimidin-6-yl)pyrrolo[2,1-f][1,2,4]triazin-2-yl)amino) pyrrolidine-1-carboxylate (CLVI) (91 mg, 0.200 mmol, 30.1% yield) as an orange fluffy solid which was used without purification. Amounts and yields calculated by LCMS. ESIMS found for $C_{22}H_{25}FN_8O_3$ m/z 469.3 (M+H) and $C_{21}H_{23}FN_8O_3$ m/z 455.2 (M+H).

Step 2

The mixture of tert-butyl (3S,4R)-3-fluoro-4-((5-(imidazo[1,2-a]pyrimidin-6-yl)-4-methoxypyrrolo[2,1-f][1,2,4]triazin-2-yl)amino)pyrrolidine-1-carboxylate (CLV) (220 mg, 0.470 mmol) and tert-butyl (3S,4R)-3-fluoro-4-((4-hydroxy-5-(imidazo[1,2-a]pyrimidin-6-yl)pyrrolo[2,1-f][1,2,4]triazin-2-yl)amino)pyrrolidine-1-carboxylate (CLVI) (91 mg, 0.200 mmol) was dissolved in DCE (9 mL) at 0° C. TFA (1 mL) was added and the reaction was stirred at room temperature for 16 h. The reaction mixture was evaporated and excess TFA was removed via high vacuum. The crude product was purified by column chromatography (0->8% 7.0 $NH_3$ in MeOH/$CHCl_3$) followed by (8->20% 7.0 $NH_3$ in MeOH/$CHCl_3$) to separate the two compounds, N-((3R,4S)-4-fluoropyrrolidin-3-yl)-5-(imidazo[1,2-a]pyrimidin-6-yl)-4-methoxypyrrolo[2,1-f][1,2,4]triazin-2-amine (CLVII) (100 mg, 0.272 mmol, 57.8% yield) was collected as a pale-yellow semi-solid. ESIMS found for $C_{17}H_{17}FN_8O$ m/z 369.2 (M+H). The product 2-(((3R,4S)-4-fluoropyrrolidin-3-yl)amino)-5-(imidazo[1,2-a]pyrimidin-6-yl)pyrrolo[2,1-f][1,2,4]triazin-4-ol (CLVIII) (171 mg, 0.483 mmol, 102.8% yield) was collected as a yellow solid. ESIMS found for $C_{16}H_{15}FN_8O$ m/z 355.2 (M+H). Additional demethylation accorded during TFA Boc deprotection.

Step 3

2-(((3R,4S)-4-Fluoropyrrolidin-3-yl)amino)-5-(imidazo[1,2-a]pyrimidin-6-yl)pyrrolo[2,1-f][1,2,4]triazin-4-ol (CLVIII) (40 mg, 0.11 mmol) was suspended in EtOH (1 mL) and DCE (1 mL). HOAc (19 μL, 0.33 mmol) and oxetan-3-one (CLIX) (33 μL, 0.56 mmol) were then added and the reaction was stirred at 65° C. for 15 min. NaBH$(OAc)_3$ (48 mg, 0.23 mmol) was added and the reaction was stirred for another 10 min. LC/MS showed unreacted starting material therefore additional oxetan-3-one (23 μL, 0.36 mmol) was added and stirred for 10 min at 65° C. followed by additional NaBH$(OAc)_3$ (48 mg, 0.23 mmol). The reaction was stirred for 10 min at 65° C. LC/MS showed minor starting material and the reaction was stopped. The reaction mixture was loaded onto Celite® and purified by silica column chromatography (0→9% 7.0 M $NH_3$ in MeOH/$CHCl_3$). The product was further purified by HPLC (0→15% $MeCN/H_2O$ (0.1% formic acid)) to produce 2-(((3R,4S)-4-fluoro-1-(oxetan-3-yl)pyrrolidin-3-yl)amino)-5-(imidazo[1,2-a]pyrimidin-6-yl)pyrrolo[2,1-f][1,2,4]triazin-4-ol (265) (4 mg, 0.010 mmol, 8.6% yield) as an off-white solid. $^1H$ NMR (499 MHz, DMSO-$d_6$) δ ppm 2.56 (1H, t, J=8.49 Hz), 2.79-2.91 (1H, m), 2.96-3.09 (1H, m), 2.98-3.03 (1H, m), 3.76 (1H, quin, J=6.09 Hz), 4.22-4.37 (1H, m), 4.46 (2H, t, J=6.02 Hz), 4.58 (2H, t, J=6.57 Hz), 5.25 (1H, dtd, J=55.95, 4.65, 4.65, 1.00 Hz), 6.29 (1H, br d, J=6.30 Hz), 6.81 (1H, d, J=2.74 Hz), 7.48 (1H, d, J=2.74 Hz), 7.71 (1H, d, J=1.10 Hz), 7.93 (1H, d, J=1.09 Hz), 8.90 (1H, d, J=2.46 Hz), 9.41 (1H, d, J=2.19 Hz), 10.78 (1H, br s); ESIMS found for $C_{19}H_{19}FN_8O_2$ m/z 411.2 (M+1).

Example 9

Preparation of (1r,4r)-4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexan-1-ol (725) and (1r,4r)-4-((5-(1-((E)-2-fluorovinyl)-1H-benzo[d][1,2,3]triazol-6-yl)-4-methoxypyrrolo[2,1-f][1,2,4]triazin-2-yl)amino)-1-methylcyclohexan-1-ol (672) are depicted below in Scheme 32.

Scheme 32

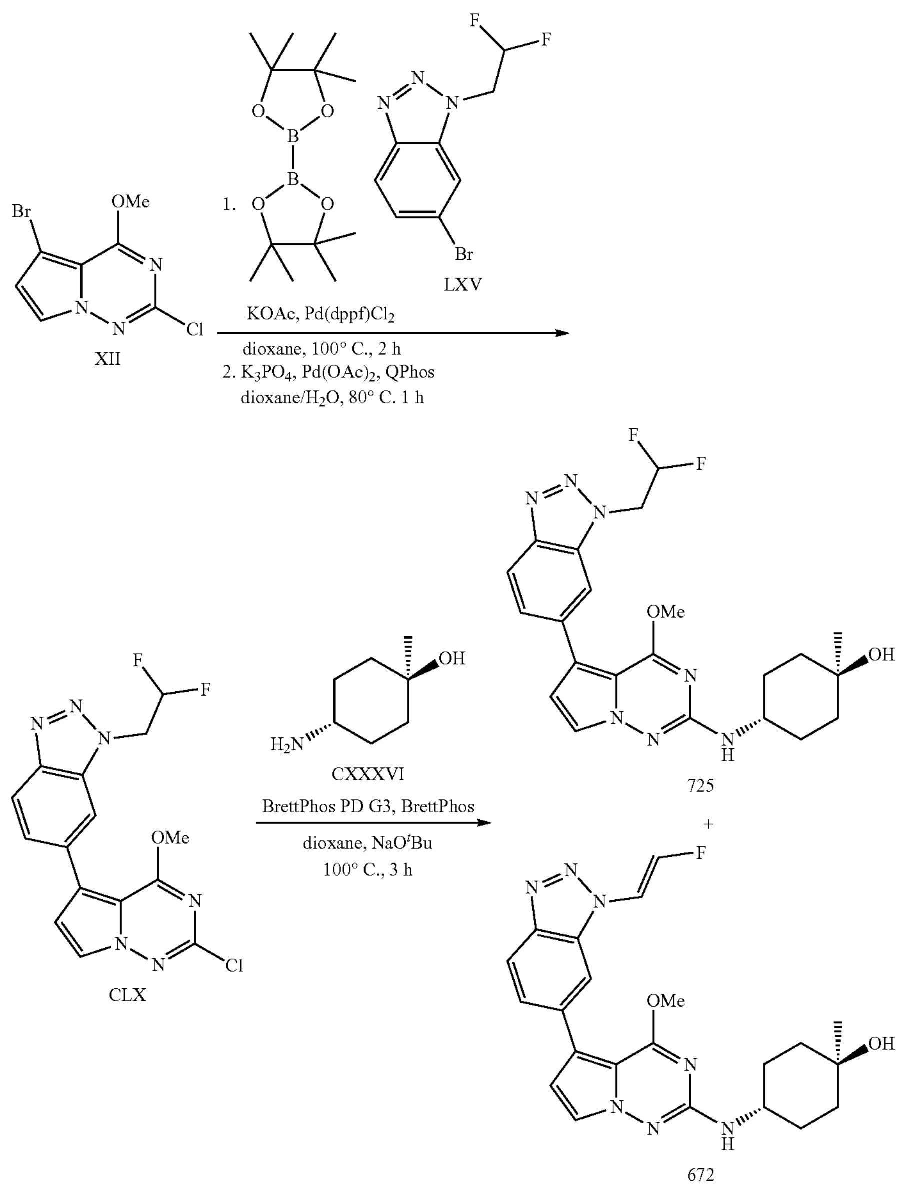

XII

LXV

CLX

CXXXVI

725

+

672

Steps 1-2

6-Bromo-1-(2,2-difluoroethyl)-1H-benzo[d][1,2,3]triazole (LXV) (500 mg, 1.91 mmol), bis(pinacolato)diboron (650 mg, 2.56 mmol), Pd(dppf)$Cl_2$ (75 mg, 0.09 mmol) and KOAc (500 mg, 5.09 mmol) were suspended in dry 1,4-dioxane (12 mL). The reaction was sonicated and degassed for 5 min before heating at 100° C. for 2 h. The reaction mixture was cooled to room temperature and a 2 M aqueous solution of $K_3PO_4$ (2.52 mL, 5.04 mmol) was added and the reaction was stirred for 5 min. 5-Bromo-2-chloro-4-methoxypyrrolo[2,1-f][1,2,4]triazine (XII) (443 mg, 1.69 mmol), $Pd(OAc)_2$ (19 mg, 0.08 mmol) and QPhos (84 mg, 0.12 mmol) were added and the reaction was purged with Ar for 5 min. The reaction was heated to 80° C. for 1 h. The reaction mixture was reduced in vacuo and the crude product was purified by column chromatography (100% $CHCl_3$). The product was further purified by column chromatography (0→50% EtOAc/hexanes hold followed by 50→100% EtOAc/hexanes) to give a solid which was triturated with MeOH and filtered washing with MeOH to give 6-(2-chloro-4-methoxypyrrolo[2,1-f][1,2,4]triazin-5-yl)-1-(2,2-difluoroethyl)-1H-benzo[d][1,2,3]triazole (CLX) (295 mg, 0.809 mmol, 47.9% yield) as a beige solid. ESIMS found for $C_{15}H_{11}ClF_2N_6O$ m/z 365.1 (M+H).

Step 3

6-(2-Chloro-4-methoxypyrrolo[2,1-f][1,2,4]triazin-5-yl)-1-(2,2-difluoroethyl)-1H-benzo[d][1,2,3]triazole (CLX) (25 mg, 0.07 mmol), trans-4-amino-1-methylcyclohexan-1-ol (CXXXVI) (commercially available from PharmaBlock (USA), Inc.) (9 mg, 0.07 mmol), BrettPhos PD G3 (5. mg, 0.01 mmol), BrettPhos (4. mg, 0.01 mmol) and NaO$^t$Bu (21. mg, 0.22 mmol) were dissolved in dry 1,4-dioxane (0.7 mL) in a microwave vial. The suspension was purged with Ar for 5 min and then the reaction was heated to 100° C. for 3 h. The reaction was reduced in vacuo and loaded onto Celite® and purified by column chromatography (0→90% EtOAc/hexanes). The isolated product was further purified by HPLC (0→35% hold followed by 5% stepwise increases to 80% MeOH/$H_2O$ in 0.1% formic acid). Appropriate fractions were collected and neutralized with saturated aqueous $NaHCO_3$ and extracted with DCM (×2). The combined organic layers were dried over anhydrous $MgSO_4$ and reduced in vacuo to give (1r,4r)-4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexan-1-ol (725) as a yellow solid (3 mg, 0.007 mmol, 9.6% yield). $^1$H NMR (499 MHz, DMSO-$d_6$) δ ppm 1.15 (3H, s), 1.40-1.50 (4H, m), 1.57-1.65 (2H, m), 1.84-1.92 (2H, m), 3.60-3.69 (1H, m), 3.94 (3H, s), 4.23 (1H, s), 5.30 (2H, td, J=15.81, 2.87 Hz), 6.50 (1H, d, J=7.94 Hz), 6.60 (1H, tt, J=54.30, 3.00 Hz), 6.72 (1H, d, J=2.46 Hz), 7.62-7.65 (1H, m), 7.65 (1H, d, J=2.74 Hz), 8.00-8.05 (2H, m); ESIMS found for $C_{22}H_{25}F_2N_7O_2$ m/z 458.2 (M+1). The elimination side-product, (1r,4r)-4-((5-(1-((E)-2-fluorovinyl)-1H-benzo[d][1,2,3]triazol-6-yl)-4-methoxypyrrolo[2,1-f][1,2,4]triazin-2-yl)amino)-1-methylcyclohexan-1-ol (672) (7 mg, 0.016 mmol, 23.3% yield) was also obtained as a yellow solid. $^1$H NMR (499 MHz, DMSO-$d_6$) δ ppm 1.15 (3H, s), 1.38-1.51 (4H, m), 1.57-1.66 (2H, m), 1.82-1.93 (2H, m), 3.59-3.71 (1H, m), 3.94 (3H, s), 4.23 (1H, s), 6.51 (1H, d, J=7.94 Hz), 6.74 (1H, d, J=2.74 Hz), 7.34 (1H, dd, J=60.90, 4.10 Hz), 7.45 (1H, dd, J=18.62, 3.83 Hz), 7.65 (1H, d, J=2.46 Hz), 7.69 (1H, d, J=9.03 Hz), 7.92 (1H, s), 8.08 (1H, d, J=8.76 Hz); ESIMS found for $C_{22}H_{24}FN_7O_2$ m/z 438.2 (M+1).

Example 10

Preparation of N-((3R,4S)-3-fluoro-1-(oxetan-3-yl)piperidin-4-yl)-5-(1-isopropyl-1H-benzo[d][1,2,3]triazol-6-yl)-4-methoxypyrrolo[2,1-f][1,2,4]triazin-2-amine (688) and 3-((3R,4S)-3-fluoro-4-((5-(1-isopropyl-1H-benzo[d][1,2,3]triazol-6-yl)-4-methoxypyrrolo[2,1-f][1,2,4]triazin-2-yl)amino)piperidin-1-yl)oxetane-3-carbonitrile (690) are depicted below in Scheme 33.

Scheme 33

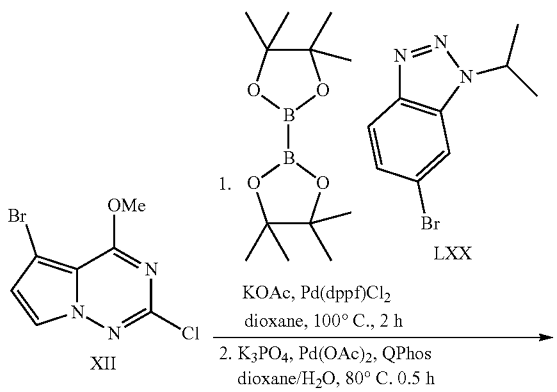

XII LXX

-continued

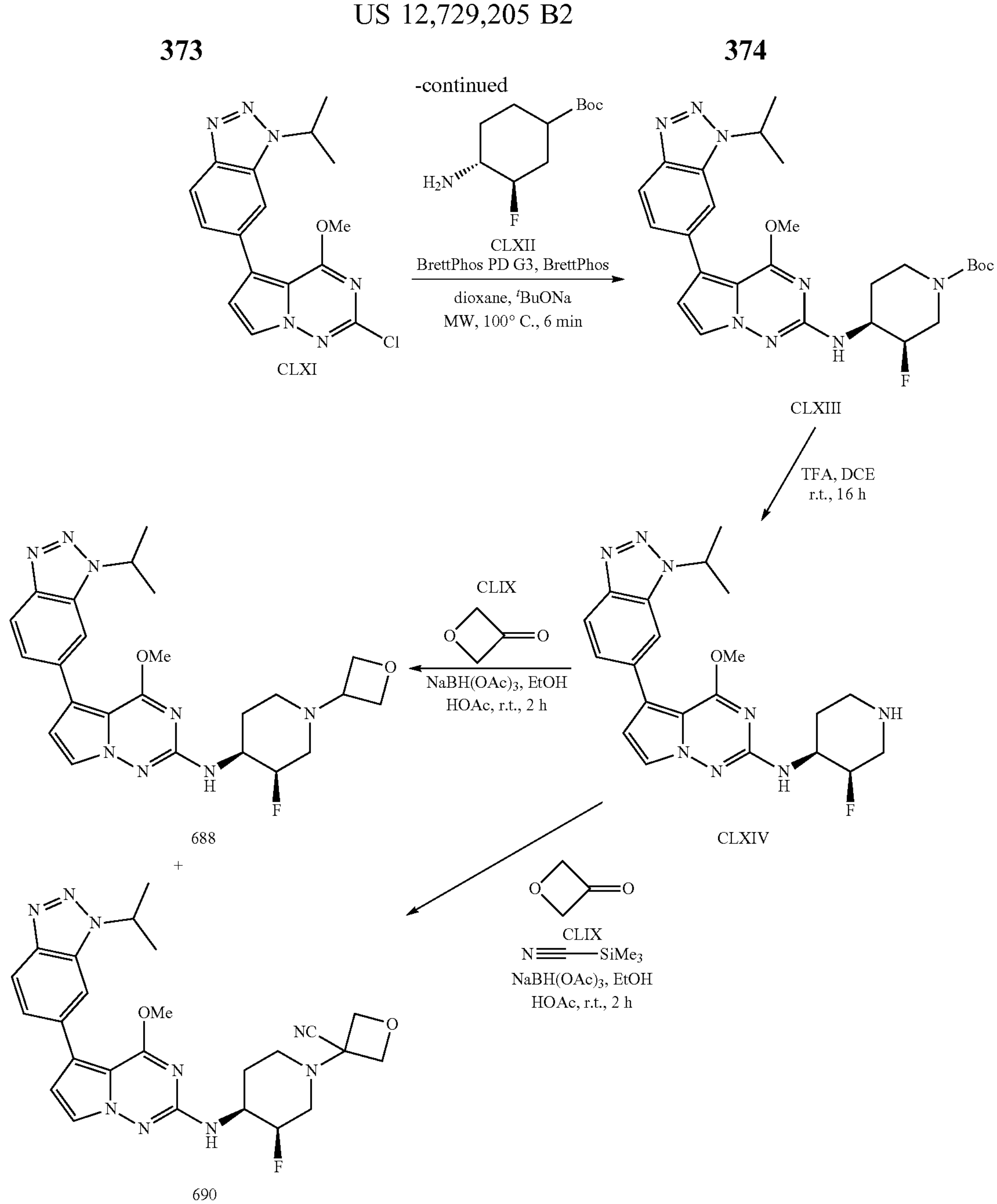

Steps 1-2

Used procedure described in Example 9, Scheme 32, steps 1-2 to produce 6-(2-chloro-4-methoxypyrrolo[2,1-f][1,2,4]triazin-5-yl)-1-isopropyl-1H-benzo[d][1,2,3]triazole (CLXI) (1.022 g, 2.982 mmol, 97.8% yield) as a fluffy red solid. ESIMS found for $C_{16}H_{15}ClN_6O$ m/z 343.1 (M+H).

Step 3

Used procedure described in Example 9, Scheme 32, step 3 to produce tert-butyl (3R,4S)-3-fluoro-4-((5-(1-isopropyl-1H-benzo[d][1,2,3]triazol-6-yl)-4-methoxypyrrolo[2,1-f][1,2,4] triazin-2-yl)amino)piperidine-1-carboxylate (CLXIII) (184 mg, 0.351 mmol, 100.19% yield) as a brown semi-solid. ESIMS found for $C_{26}H_{33}FN_8O_3$ m/z 525.15 (M+H).

Step 4

Used procedure described in Example 8, Scheme 31, step 2 to produce N-((3R,4S)-3-fluoropiperidin-4-yl)-5-(1-isopropyl-1H-benzo[d][1,2,3]triazol-6-yl)-4-methoxypyrrolo[2,1-f][1,2,4]triazin-2-amine (CLXIV) (148 mg, 0.349 mmol, 99.4% yield) as a brown solid. ESIMS found for $C_{21}H_{25}FN_8O$ m/z 425.2 (M+H).

Step 5a and 5b

N-((3R,4S)-3-Fluoropiperidin-4-yl)-5-(1-isopropyl-1H-benzo[d][1,2,3]triazol-6-yl)-4-methoxypyrrolo[2,1-f][1,2,4] triazin-2-amine (CLXIV) (40 mg, 0.09 mmol) was suspended in dry DCE (0.9 mL) followed by EtOH (0.1 mL) to aid dissolution. Acetic acid (16 μL, 0.28 mmol), oxetan-3-one (CLIX) (17 μL, 0.29 mmol), and 3A MS (5 beads) were added before the reaction was heated to 65° C. for 1 h. The reaction was cooled to room temperature and 400 μL of the reaction mixture was removed (leaving 600 μL behind) and was added to a separate vial and both were heated to 65° C. To the first vial was added $NaBH(OAc)_3$ (41 mg, 0.19 mmol) and the reaction was stirred for 10 minutes. To the second vial was added trimethylsilyl cyanide (24 μL, 0.19 mmol) and the reaction was stirred for 10 minutes. Both reactions were loaded onto Celite® separately and were purified by column chromatography (0→2% MeOH/$CHCl_3$). Compound 688 was further purified by HPLC (0→50% MeCN/$H_2O$ with 0.1% formic acid). Compound 690 was further purified by HPLC (0→80% MeCN/$H_2O$ with 0.1% formic acid). N-((3R,4S)-3-Fluoro-1-(oxetan-3-yl)piperidin-4-yl)-5-(1-isopropyl-1H-benzo[d][1,2,3]triazol-6-yl)-4-methoxy-pyrrolo [2,1-f][1,2,4]triazin-2-amine (688) (11 mg, 0.023 mmol, 24.3% yield) as a fluffy white solid. $^1H$ NMR (499 MHz, DMSO-$d_6$) δ ppm 1.67 (6H, d, J=6.57 Hz), 1.70-1.77 (1H, m), 1.88-1.97 (1H, m), 1.99-2.06 (1H, m), 2.16 (1H, dd, J=37.00, 12.59 Hz), 2.71-2.80 (1H, m), 2.95-3.04 (1H, m), 3.49 (1H, quin, J=6.37 Hz), 3.74-3.90 (1H, m), 3.96 (3H, s), 4.40 (1H, t, J=6.16 Hz), 4.46 (1H, t, J=6.16 Hz), 4.54 (2H, td, J=6.43, 3.01 Hz), 4.94 (1H, d, J=49.90 Hz), 5.24 (1H, spt, J=6.75 Hz), 6.69 (1H, d, J=7.94 Hz), 6.77 (1H, d, J=2.74 Hz), 7.59 (1H, dd, J=8.76, 1.37 Hz), 7.64 (1H, d, J=2.46 Hz), 7.99 (1H, d, J=8.76 Hz), 8.02 (1H, s); ESIMS found for $C_{24}H_{29}FN_8O_2$ m/z 481.25 (M+1) and 3-((3R,4S)-3-Fluoro-4-((5-(1-isopropyl-1H-benzo[d][1,2,3]triazol-6-yl)-4-methoxypyrrolo[2,1-f][1,2,4]triazin-2-yl)amino)piperidin-1-yl)oxetane-3-carbonitrile (690) (10 mg, 0.020 mmol, 21.0% yield) as a fluffy white solid. $^1H$ NMR (499 MHz, DMSO-$d_6$) δ ppm 1.67 (6H, d, J=6.84 Hz), 1.82 (1H, br dd, J=12.32, 3.01 Hz), 2.00 (1H, qd, J=12.37, 3.70 Hz), 2.09-2.18 (1H, m), 2.26 (1H, dd, J=36.20, 12.32 Hz), 2.78-2.86 (1H, m), 3.00-3.11 (1H, m), 3.79-3.95 (1H, in), 3.97 (3H, s), 4.52 (1H, d, J=6.84 Hz), 4.65 (1H, d, J=7.12 Hz), 4.76 (2H, t, J=6.84 Hz), 5.04 (1H, d, J=49.35 Hz), 5.24 (1H, spt, J=6.75 Hz), 6.78 (1H, d, J=2.46 Hz), 6.81 (1H, d, J=7.67 Hz), 7.59 (1H, dd, J=8.76, 1.37 Hz), 7.66 (1H, d, J=2.46 Hz), 7.99 (1H, d, J=8.49 Hz), 8.02 (1H, s); ESIMS found for $C_{25}H_{28}FN_9O_2$ m/z 506.2 (M+1).

Example 11

Preparation of 5-(1-(2,2-difluoroethyl)-1H-benzo[d][1,2,3]triazol-6-yl)-N-((3R,4S)-3-fluoro-1-(methylsulfonyl)piperidin-4-yl)-4-methoxypyrrolo[2,1-f][1,2,4]triazin-2-amine (1145) is depicted below in Scheme 34.

Scheme 34

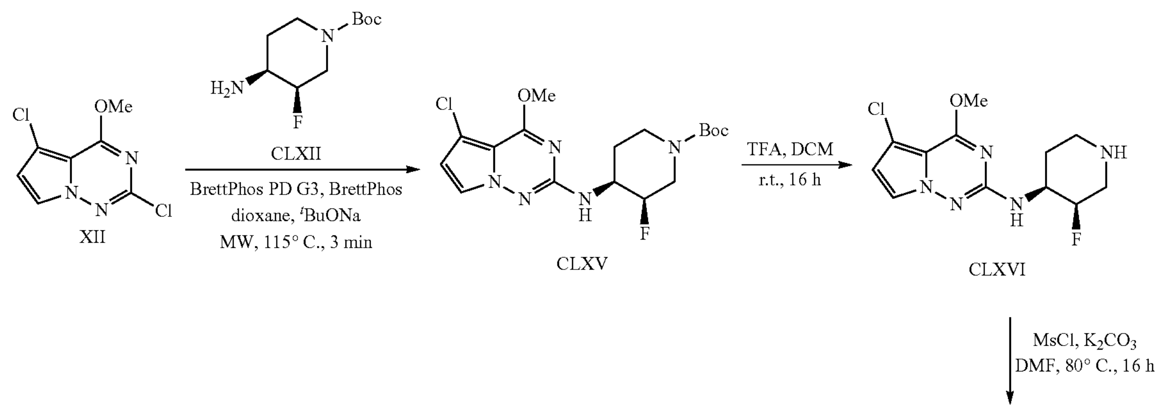

XII CLXV CLXVI

-continued

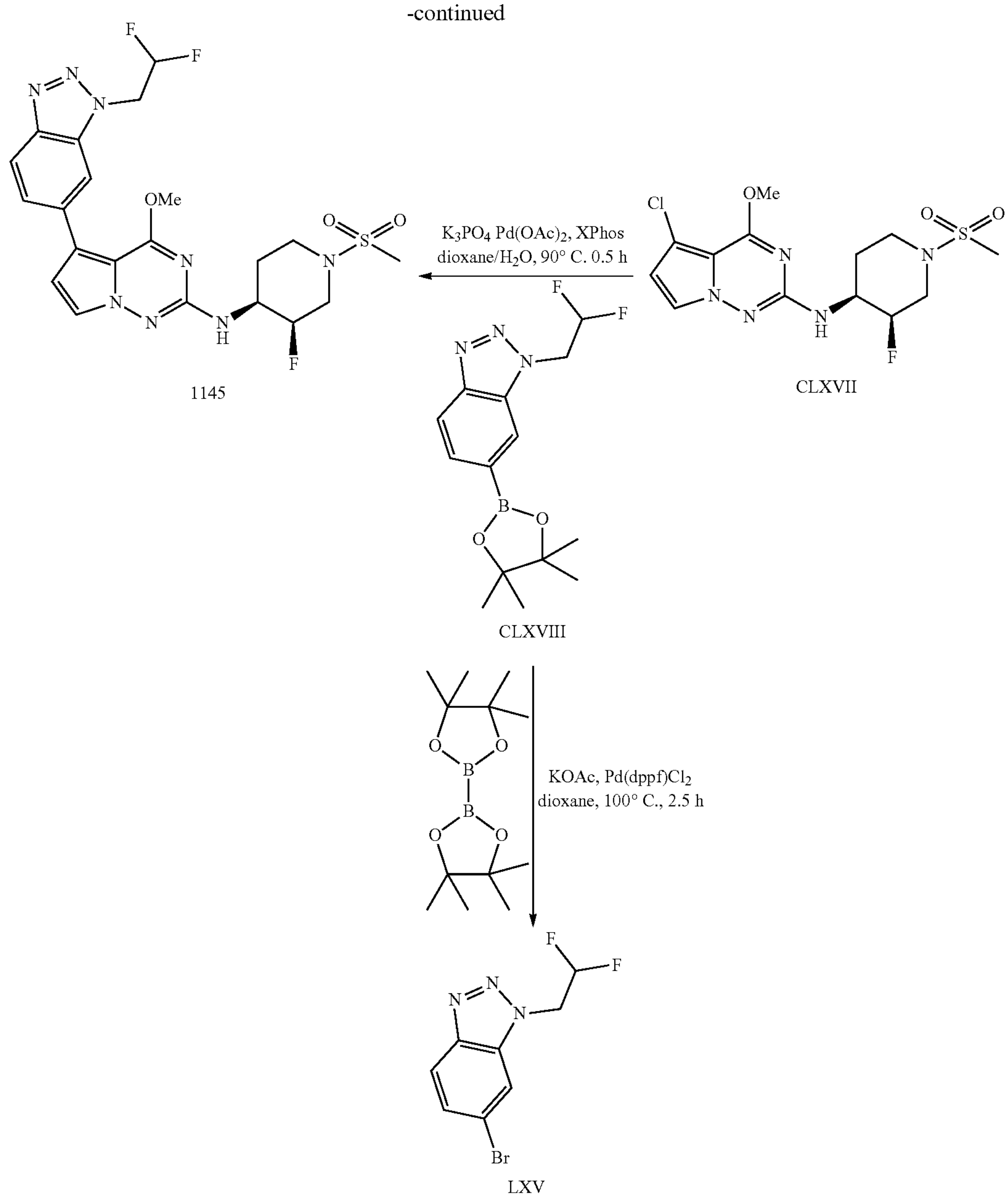

1145

CLXVII

CLXVIII

LXV

Step 1

2,5-Dichloro-4-methoxypyrrolo[2,1-f][1,2,4]triazine (XII) (700 mg, 3.21 mmol), tert-butyl (3R,4S)-4-amino-3-fluoropiperidine-1-carboxylate (CLXII) (commercially available from Advanced ChemBlocks Inc.) (771 mg, 3.53 mmol), BrettPhos Pd G3 (146 mg, 0.16 mmol), BrettPhos (86 mg, 0.16 mmol) and $^{t}$BuONa (770 mg, 8.01 mmol) were charged in a microwave vial and dry 1,4-dioxane (20 mL) was added. 3A MS (8 beads) were added and the reaction was stirred for 1 h at room temperature. The sieves were removed quickly, and the reaction was sealed and purged with Ar for 5 min followed by microwave irradiation to 115° C. for 3 min. The reaction mixture poured into DCM and water and the organic layer was separated. The aqueous layer was extracted with DCM (×2) and the combined organic layers were dried ($MgSO_4$) and reduced in vacuo to give the crude product tert-butyl (3R,4S)-4-((5-chloro-4-methoxypyrrolo[2,1-f][1,2,4]triazin-2-yl)amino)-3-fluoropiperidine-1-carboxylate (CLXV) (1,284 g, 3.211 mmol, 100.0% yield), assuming quantitative yield, as a brown semi-solid which was used without further purification. ESIMS found for $C_{17}H_{23}ClFN_5O_3$ m/z 344.10 (M+H-$^{t}$Bu).

Step 2

Used procedure described in Example 8, Scheme 31, step 2 to produce 5-chloro-N-((3R,4S)-3-fluoropiperidin-4-yl)-4-methoxypyrrolo[2,1-f][1,2,4]triazin-2-amine (CLXVI) (381 mg, 1.271 mmol, 39.6% yield) as a pale-yellow solid. ESIMS found for $C_{12}H_{15}ClFN_5O$ m/z 300.1 (M+H).

Step 3

$K_2CO_3$ (115 mg, 0.83 mmol) and MsCl (45 mg, 0.39 mmol) were suspended in DMF (1 mL) and 5-chloro-N-((3R,4S)-3-fluoropiperidin-4-yl)-4-methoxypyrrolo[2,1-f][1,2,4]triazin-2-amine (CLXVI) (50 mg, 0.17 mmol) was added, and the reaction was heated to 80° C. for 16 h. The reaction was loaded onto Celite® and purified by column chromatography (0→45% EtOAc/hexanes) to give 5-chloro-N-((3R,4S)-3-fluoro-1-(methylsulfonyl)piperidin-4-yl)-4-methoxypyrrolo[2,1-f][1,2,4]triazin-2-amine (CLXVII) (13 mg, 0.034 mmol, 20.6% yield) as a pearlescent white solid. ESIMS found for $C_{13}H_{17}ClFN_5O_3S$ m/z 378.1 (M+H).

Step 4

6-Bromo-1-(2,2-difluoroethyl)-1H-benzo[d][1,2,3]triazole (LXV) (5.16 g, 19.69 mmol), bis(pinacolato)diboron (7.51 g, 29.57 mmol), Pd(dppf)$Cl_2$ (803 mg, 0.98 mmol) and KOAc (5.8 g, 59.1 mmol) were suspended in dry 1,4-dioxane (100 mL). The reaction was sonicated and degassed for 5 minutes before heating at 100° C. for 2.5 h. The reaction mixture was loaded onto Celite® and purified by column chromatography (0→50% EtOAc/hexanes) to produce 1-(2,2-difluoroethyl)-6-(4,4,5,5-tetramethyl-1,3,2-dioxaborolan-2-yl)-1H-benzo[d][1,2,3]triazole (CLXVIII) (5.654 g, 18.291 mmol, 92.9% yield) as a fluffy pale-orange solid. ESIMS found for $C_{14}H_{18}BF_2N_3O_2$ m/z 310.15 (M+H).

Step 5

5-Chloro-N-((3R,4S)-3-fluoro-1-(methylsulfonyl)piperidin-4-yl)-4-methoxypyrrolo [2,1-f][1,2,4]triazin-2-amine (CLXVII) (13 mg, 0.03 mmol), 1-(2,2-difluoroethyl)-6-(4,4,5,5-tetramethyl-1,3,2-dioxaborolan-2-yl)-1H-benzo[d][1,2,3]triazole (CLXVIII) (17 mg, 0.05 mmol), Pd$(OAc)_2$ (2 mg, 0.01 mmol), and XPhos (3 mg, 0.01 mmol) were suspended in dry 1,4-dioxane (0.5 mL). $K_2PO_4$ (52 μL, 0.1 mmol) was added and the reaction was sonicated and bubbled with Ar for 5 min. The reaction was then heated to 90° C. for 30 min. The reaction mixture was loaded onto Celite® and purified by column chromatography (0→1.5% MeOH/$CHCl_3$). The product was further purified by HPLC (0→35% MeCN/$H_2O$ with 0.1% formic acid) to yield 5-(1-(2,2-difluoroethyl)-1H-benzo[d][1,2,3]triazol-6-yl)-N-((3R,4S)-3-fluoro-1-(methylsulfonyl)piperidin-4-yl)-4-methoxypyrrolo[2,1-f][1,2,4]triazin-2-amine (1145) (6 mg, 0.011 mmol, 33.2% yield) as a fluffy white solid after lyophilization. $^1$H NMR (499 MHz, DMSO-$d_6$) δ ppm 1.77-1.88 (1H, m), 1.96 (1H, qd, J=12.50, 4.38 Hz), 2.93 (3H, s), 3.02 (1H, td, J=12.25, 2.60 Hz), 3.20 (1H, dd, J=37.55, 12.59 Hz), 3.61-3.70 (1H, m), 3.80-3.89 (1H, m), 3.90-4.04 (1H, m), 3.96 (3H, s), 5.05 (1H, d, J=49.10 Hz), 5.30 (2H, td, J=15.95, 2.87 Hz), 6.61 (1H, tt, J=54.30, 3.00 Hz), 6.76 (1H, d, J=2.74 Hz), 6.88 (1H, d, J=7.94 Hz), 7.63 (1H, d, J=2.46 Hz), 7.64-7.66 (1H, m), 8.02-8.05 (2H, m); ESIMS found for $C_{21}H_{23}F_3N_8O_3S$ m/z 525.15 (M+1).

The following compounds were prepared in accordance with the procedures described in the above Schemes 1-34.

1

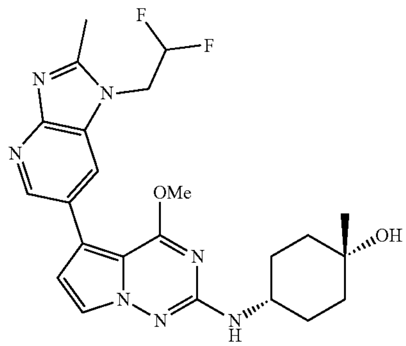

cis-4-((5-(1-(2,2-Difluoroethyl)-2-methyl-1H-imidazo[4,5-b]pyridin-6-yl)-4-methoxypyrrolo[2,1-f][1,2,4]triazin-2-yl)amino)-1-methylcyclohexan-1-ol 1

Beige solid (2.8 mg, 0.005 mmol, 2.5% yield). $^1$H NMR (499 MHz, CHLOROFORM-d) δ ppm 1.29 (3H, s), 1.58-1.68 (4H, m), 1.75 (2H, br d, J=10.68 Hz), 1.99-2.06 (2H, m), 2.72 (3H, s), 3.66-3.74 (1H, m), 3.95 (3H, s), 4.50 (2H, td, J=14.80, 2.50 Hz), 6.12 (1H, tt, J=54.60, 3.00 Hz), 6.60 (1H, d, J=2.46 Hz), 7.47 (1H, d, J=2.19 Hz), 7.81 (1H, br s), 8.73 (1H, br s); ESIMS found for $C_{23}H_{27}F_2N_7O_2$ m/z 472.2 (M+1).

3

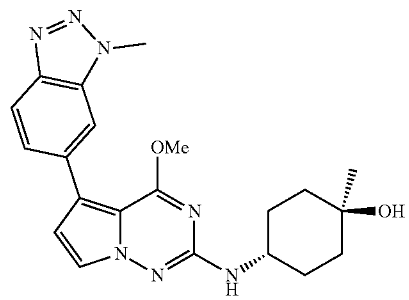

trans-4-((4-Methoxy-5-(1-methyl-1H-benzo[d][1,2,3]triazol-6-yl)pyrrolo[2,1-f][1,2,4]triazin-2-yl)amino)-1-methylcyclohexan-1-ol 3

Beige solid (10 mg, 0.025 mmol, 10.0% yield). $^1$H NMR (499 MHz, DMSO-$d_6$) δ ppm 1.15 (3H, s), 1.38-1.53 (4H, m), 1.56-1.65 (2H, m), 1.84-1.93 (2H, m), 3.59-3.71 (1H, m), 3.95 (3H, s), 4.24 (1H, s), 4.31 (3H, s), 6.48 (1H, d, J=7.94 Hz), 6.73 (1H, d, J=2.74 Hz), 7.61 (1H, dd, J=8.49, 1.37 Hz), 7.64 (1H, d, J=2.74 Hz), 7.93 (1H, s), 7.97 (1H, d, J=8.76 Hz); ESIMS found for $C_{21}H_{25}N_7O_2$ m/z 408.25 (M+1).

4

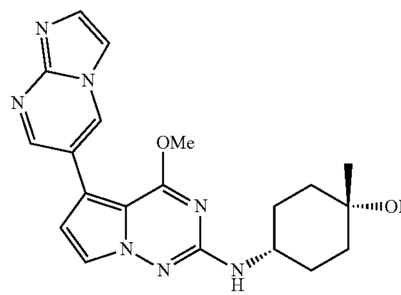

cis-4-((5-(Imidazo[1,2-a]pyrimidin-6-yl)-4-methoxypyrrolo[2,1-f][1,2,4]triazin-2-yl)amino)-1-methylcyclohexan-1-ol 4

Off-white solid (15 mg, 0.038 mmol, 22.9% yield). $^1$H NMR (499 MHz, DMSO-$d_6$) δ ppm 1.12 (3H, s), 1.36 (2H, td, J=13.00, 4.11 Hz), 1.58 (2H, br d, J=12.32 Hz), 1.61-1.75 (4H, m), 3.45-3.60 (1H, m), 3.97 (3H, s), 4.00 (1H, s), 6.57 (1H, d, J=7.94 Hz), 6.76 (1H, d, J=2.46 Hz), 7.64 (1H, d, J=2.46 Hz), 7.72 (1H, d, J=1.37 Hz), 7.93 (1H, d, J=1.37

Hz), 8.73 (1H, d, J=2.46 Hz), 9.08 (1H, d, J=2.46 Hz); ESIMS found for $C_{20}H_{23}N_7O_2$ m/z 394.2 (M+1).

6

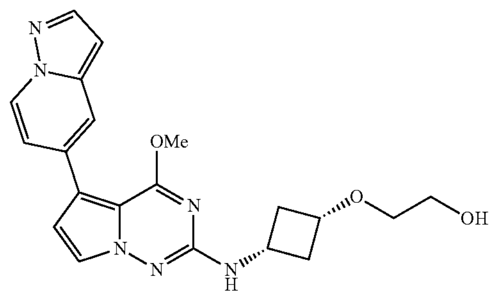

2-(cis-3-((4-Methoxy-5-(pyrazolo[1,5-a]pyridin-5-yl)pyrrolo[2,1-f][1,2,4]triazin-2-yl)amino)cyclobutoxy)ethan-1-ol 6

White solid (28 mg, 0.071 mmol, 35.5% yield). $^1$H NMR (499 MHz, DMSO-$d_6$) δ ppm 1.82-1.93 (2H, m), 2.60-2.69 (2H, m), 3.30-3.33 (2H, m), 3.48 (2H, q, J=5.48 Hz), 3.68-3.74 (1H, m), 3.74-3.81 (1H, m), 3.98 (3H, s), 4.60 (1H, t, J=5.61 Hz), 6.58 (1H, d, J=1.92 Hz), 6.77 (1H, d, J=2.46 Hz), 7.04 (1H, d, J=7.39 Hz), 7.10 (1H, dd, J=7.26, 1.78 Hz), 7.60 (1H, d, J=2.46 Hz), 7.80 (1H, d, J=0.82 Hz), 7.97 (1H, d, J=2.19 Hz), 8.62 (1H, d, J=7.12 Hz); ESIMS found for $C_{20}H_{22}N_6O_3$ m/z 395.2 (M+1).

7

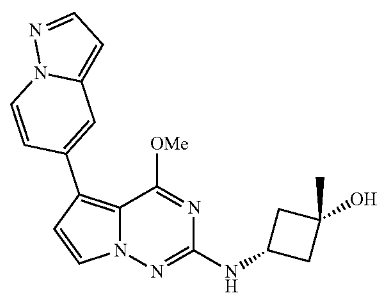

cis-3-((4-Methoxy-5-(pyrazolo[1,5-a]pyridin-5-yl)pyrrolo[2,1-f][1,2,4]triazin-2-yl)amino)-1-methylcyclobutan-1-ol 7

Off-white solid (53 mg, 0.145 mmol, 54.5% yield). $^1$H NMR (499 MHz, DMSO-$d_6$) δ ppm 1.27 (3H, s), 2.02 (2H, td, J=8.90, 2.19 Hz), 2.31-2.41 (2H, m), 3.72 (1H, dq, J=15.16, 7.72 Hz), 3.98 (3H, s), 4.92 (1H, s), 6.58 (1H, d, J=1.64 Hz), 6.76 (1H, d, J=2.74 Hz), 6.95 (1H, d, J=6.57 Hz), 7.10 (1H, dd, J=7.39, 1.92 Hz), 7.63 (1H, d, J=2.74 Hz), 7.80 (1H, d, J=1.10 Hz), 7.97 (1H, d, J=2.19 Hz), 8.62 (1H, d, J=7.39 Hz); ESIMS found for $C_{19}H_{20}N_6O_2$ m/z 365.2 (M+1).

8

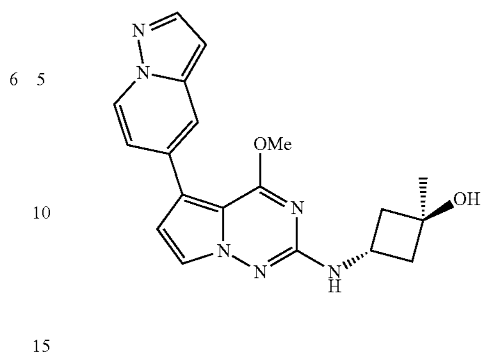

trans-3-((4-Methoxy-5-(pyrazolo[1,5-a]pyridin-5-yl)pyrrolo[2,1-f][1,2,4]triazin-2-yl)amino)-1-methylcyclobutan-1-ol 8

White solid (16 mg, 0.044 mmol, 16.5% yield). $^1$H NMR (499 MHz, DMSO-$d_6$) δ ppm 1.28 (3H, s), 1.93-2.05 (2H, m), 2.27-2.35 (2H, m), 3.98 (3H, s), 4.25 (1H, sxt, J=7.34 Hz), 4.79 (1H, s), 6.58 (1H, d, J=1.92 Hz), 6.76 (1H, d, J=2.74 Hz), 6.95 (1H, d, J=6.57 Hz), 7.10 (1H, dd, J=7.12, 1.92 Hz), 7.62 (1H, d, J=2.46 Hz), 7.80 (1H, d, J=0.82 Hz), 7.97 (1H, d, J=2.19 Hz), 8.62 (1H, d, J=7.39 Hz); ESIMS found for $C_{19}H_{20}N_6O_2$ m/z 365.2 (M+1).

9

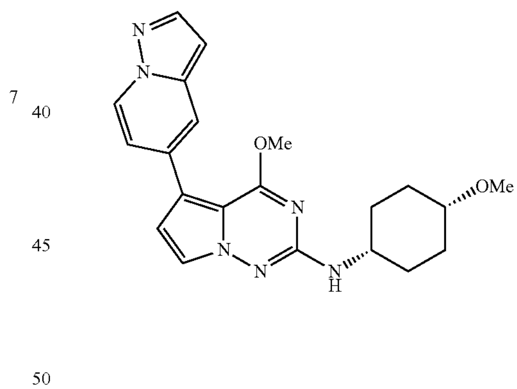

4-Methoxy-N-(cis-4-methoxycyclohexyl)-5-(pyrazolo[1,5-a]pyridin-5-yl)pyrrolo[2,1-f][1,2,4]triazin-2-amine 9

Off-white solid (25 mg, 0.064 mmol, 31.8% yield). $^1$H NMR (499 MHz, DMSO-$d_6$) δ ppm 1.45-1.54 (2H, m), 1.55-1.65 (2H, m), 1.65-1.73 (2H, m), 1.80-1.88 (2H, m), 3.22 (3H, s), 3.34 (1H, br d, J=2.19 Hz), 3.59-3.70 (1H, m), 3.98 (3H, s), 6.56-6.58 (1H, m), 6.58 (1H, s), 6.75 (1H, d, J=2.46 Hz), 7.10 (1H, dd, J=7.26, 2.05 Hz), 7.61 (1H, d, J=2.74 Hz), 7.80 (1H, d, J=1.09 Hz), 7.96 (1H, d, J=2.19 Hz), 8.62 (1H, d, J=7.39 Hz); ESIMS found for $C_{21}H_{24}N_6O_2$ m/z 393.2 (M+1).

10

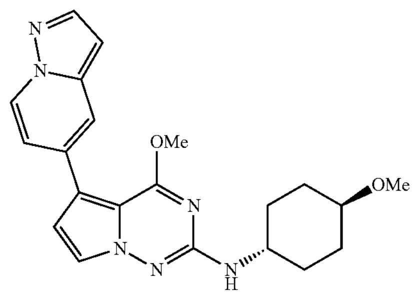

4-Methoxy-N-(trans-4-methoxycyclohexyl)-5-(pyrazolo[1,5-a]pyridin-5-yl)pyrrolo[2,1-f][1,2,4]triazin-2-amine 10

Off-white solid (40 mg, 0.102 mmol, 50.9% yield). $^1H$ NMR (499 MHz, DMSO-$d_6$) δ ppm 1.14-1.26 (2H, m), 1.27-1.40 (2H, m), 2.01 (4H, br t, J=10.81 Hz), 3.12 (1H, tt, J=10.23, 3.73 Hz), 3.24 (3H, s), 3.51-3.63 (1H, m), 3.98 (3H, s), 6.57 (1H, d, J=7.94 Hz), 6.58 (1H, d, J=1.64 Hz), 6.75 (1H, d, J=2.46 Hz), 7.10 (1H, dd, J=7.39, 1.92 Hz), 7.63 (1H, d, J=2.74 Hz), 7.80 (1H, d, J=0.82 Hz), 7.97 (1H, d, J=2.19 Hz), 8.62 (1H, d, J=7.12 Hz); ESIMS found for $C_{21}H_{24}N_6O_2$ m/z 393.2 (M+1).

13

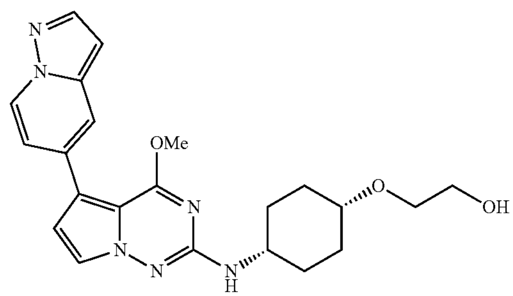

2-((cis-4-((4-Methoxy-5-(pyrazolo[1,5-a]pyridin-5-yl)pyrrolo[2,1-f][1,2,4]triazin-2-yl)amino)cyclohexyl)oxy)ethan-1-ol 13

Off-white semi-solid. (10 mg, 0.024 mmol, 14.2% yield). $^1H$ NMR (499 MHz, DMSO-$d_6$) δ ppm 1.45-1.55 (2H, m), 1.60-1.73 (4H, m), 1.78-1.88 (2H, m), 3.38-3.42 (2H, m), 3.47 (1H, br s), 3.50 (2H, q, J=5.48 Hz), 3.57-3.69 (1H, m), 3.98 (3H, s), 4.51 (1H, t, J=5.48 Hz), 6.55 (1H, d, J=7.67 Hz), 6.58 (1H, d, J=1.37 Hz), 6.75 (1H, d, J=2.46 Hz), 7.10 (1H, dd, J=7.39, 1.64 Hz), 7.61 (1H, d, J=2.74 Hz), 7.80 (1H, s), 7.97 (1H, d, J=1.92 Hz), 8.62 (1H, d, J=7.39 Hz); ESIMS found for $C_{22}H_{26}N_6O_3$ m/z 423.3 (M+1).

15

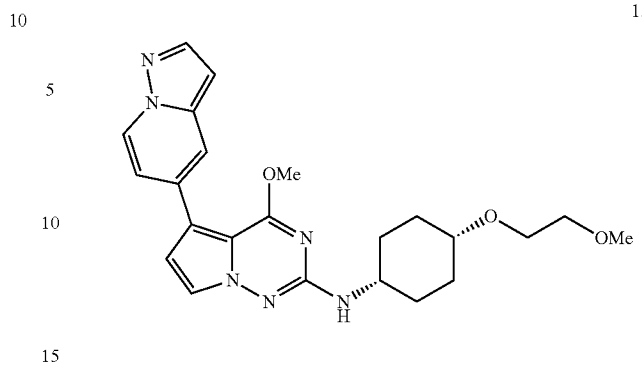

4-Methoxy-N-(cis-4-(2-methoxyethoxy)cyclohexyl)-5-(pyrazolo[1,5-a]pyridin-5-yl)pyrrolo[2,1-f][1,2,4]triazin-2-amine 15

Fluffy off-white solid (33 mg, 0.0756 mmol, 45.3% yield). $^1H$ NMR (499 MHz, DMSO-$d_6$) δ ppm 1.45-1.55 (2H, m), 1.59-1.73 (4H, m), 1.78-1.88 (2H, m), 3.27 (3H, s), 3.43-3.46 (2H, m), 3.46-3.48 (1H, m), 3.48-3.52 (2H, m), 3.57-3.69 (1H, m), 3.98 (3H, s), 6.58 (1H, d, J=2.19 Hz), 6.59 (1H, d, J=7.85 Hz), 6.75 (1H, d, J=2.46 Hz), 7.10 (1H, dd, J=7.39, 1.92 Hz), 7.61 (1H, d, J=2.74 Hz), 7.80 (1H, d, J=0.82 Hz), 7.97 (1H, d, J=2.19 Hz), 8.62 (1H, d, J=7.12 Hz); ESIMS found for $C_{23}H_{28}N_6O_3$ m/z 437.25 (M+1).

16

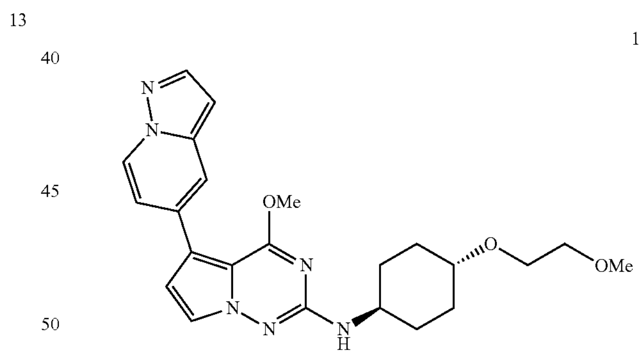

4-Methoxy-N-(trans-4-(2-methoxyethoxy)cyclohexyl)-5-(pyrazolo[1,5-a]pyridin-5-yl)pyrrolo[2,1-f][1,2,4]triazin-2-amine 16

White solid (31 mg, 0.071 mmol, 35.5% yield). $^1H$ NMR (499 MHz, DMSO-$d_6$) δ ppm 1.18-1.37 (4H, m), 2.00 (4H, br d, J=10.95 Hz), 3.20-3.27 (1H, m), 3.25 (3H, s), 3.40-3.45 (2H, m), 3.53 (2H, t, J=4.93 Hz), 3.54-3.60 (1H, m), 3.97 (3H, s), 6.56 (1H, d, J=8.21 Hz), 6.58 (1H, d, J=1.64 Hz), 6.75 (1H, d, J=2.46 Hz), 7.10 (1H, dd, J=7.39, 1.64 Hz), 7.63 (1H, d, J=2.74 Hz), 7.80 (1H, s), 7.96 (1H, d, J=2.19 Hz), 8.62 (1H, d, J=7.12 Hz); ESIMS found for $C_{23}H_{28}N_6O_3$ m/z 437.2 (M+1).

17

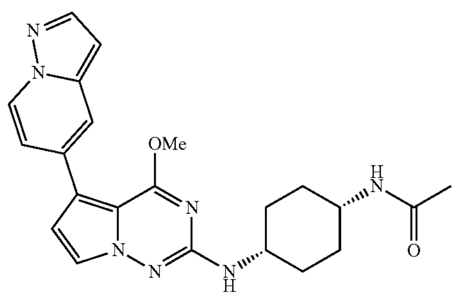

N-(cis-4-((4-Methoxy-5-(pyrazolo[1,5-a]pyridin-5-yl)pyrrolo[2,1-f][1,2,4]triazin-2-yl)amino)cyclohexyl)acetamide 17

White solid (22 mg, 0.052 mmol, 33.0% yield). $^1$H NMR (499 MHz, DMSO-$d_6$) δ ppm 1.50-1.59 (2H, m), 1.60-1.72 (4H, m), 1.74-1.81 (2H, m), 1.81 (3H, s), 3.64-3.71 (2H, m), 3.99 (3H, s), 6.47 (1H, d, J=6.30 Hz), 6.58 (1H, d, J=1.64 Hz), 6.76 (1H, d, J=2.74 Hz), 7.11 (1H, dd, J=7.26, 1.78 Hz), 7.63 (1H, d, J=2.74 Hz), 7.70 (1H, br d, J=6.84 Hz), 7.81 (1H, s), 7.97 (1H, d, J=2.19 Hz), 8.62 (1H, d, J=7.12 Hz); ESIMS found for $C_{22}H_{25}N_7O_2$ m/z 420.2 (M+1).

18

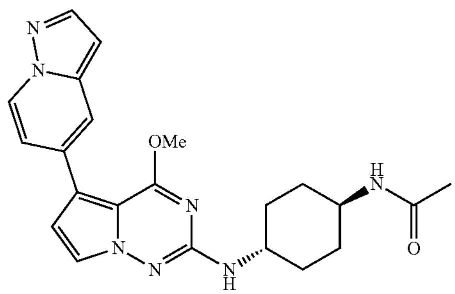

N-(trans-4-((4-Methoxy-5-(pyrazolo[1,5-a]pyridin-5-yl)pyrrolo[2,1-f][1,2,4]triazin-2-yl)amino)cyclohexyl)acetamide 18

White solid (2 mg, 0.005 mmol, 2.9% yield). $^1$H NMR (499 MHz, DMSO-$d_6$) δ ppm 1.19-1.29 (2H, m), 1.30-1.40 (2H, m), 1.78 (3H, s), 1.81 (2H, br d, J=11.50 Hz), 1.99 (2H, br d, J=10.13 Hz), 3.45-3.51 (1H, m), 3.52-3.59 (1H, m), 3.97 (3H, s), 6.56 (1H, d, J=8.21 Hz), 6.58 (1H, d, J=1.64 Hz), 6.76 (1H, d, J=2.74 Hz), 7.10 (1H, dd, J=7.26, 2.05 Hz), 7.63 (1H, d, J=2.46 Hz), 7.74 (1H, d, J=7.67 Hz), 7.80 (1H, d, J=1.09 Hz), 7.97 (1H, d, J=2.46 Hz), 8.62 (1H, d, J=7.39 Hz); ESIMS found for $C_{22}H_{25}N_7O_2$ m/z 420.2 (M+1).

19

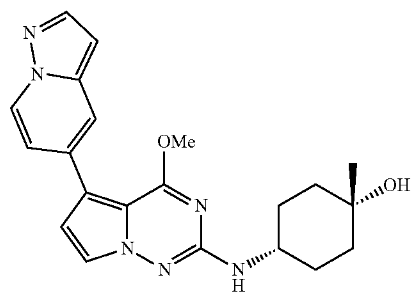

cis-4-((4-Methoxy-5-(pyrazolo[1,5-a]pyridin-5-yl)pyrrolo[2,1-f][1,2,4]triazin-2-yl)amino)-1-methylcyclohexan-1-ol 19

Off-white solid (20 mg, 0.051 mmol, 42.4% yield). $^1$H NMR (499 MHz, DMSO-$d_6$) δ ppm 1.12 (3H, s), 1.36 (2H, td, J=13.00, 4.38 Hz), 1.58 (2H, br d, J=12.05 Hz), 1.61-1.68 (2H, m), 1.69-1.75 (2H, m), 3.45-3.59 (1H, m), 3.98 (3H, s), 3.99 (1H, s), 6.52 (1H, d, J=7.94 Hz), 6.58 (1H, d, J=1.64 Hz), 6.74 (1H, d, J=2.74 Hz), 7.10 (1H, dd, J=7.12, 1.92 Hz), 7.60 (1H, d, J=2.74 Hz), 7.80 (1H, d, J=1.09 Hz), 7.96 (1H, d, J=2.19 Hz), 8.62 (1H, d, J=7.39 Hz); ESIMS found for $C_{21}H_{24}N_6O_2$ m/z 393.2 (M+1).

20

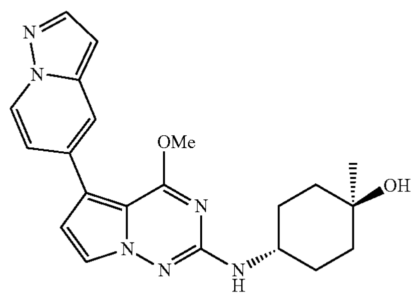

trans-4-((4-Methoxy-5-(pyrazolo[1,5-a]pyridin-5-yl)pyrrolo[2,1-f][1,2,4]triazin-2-yl)amino)-1-methylcyclohexan-1-ol 20

Beige solid (5 mg, 0.013 mmol, 8.3% yield). $^1$H NMR (499 MHz, CHLOROFORM-d) δ ppm 1.32 (3H, s), 1.47-1.58 (2H, m), 1.60-1.68 (2H, m), 1.71-1.79 (2H, m), 2.09-2.18 (2H, m), 3.86 (1H, br d, J=3.83 Hz), 4.01 (3H, s), 4.12 (1H, s), 6.53 (1H, br s), 6.64 (1H, d, J=2.46 Hz), 7.04 (1H, br d, J=5.75 Hz), 7.47 (1H, d, J=2.46 Hz), 7.71 (1H, br s), 7.96 (1H, br s), 8.50 (1H, br d, J=6.57 Hz); ESIMS found for $C_{21}H_{24}N_6O_2$ m/z 393.2 (M+1).

24

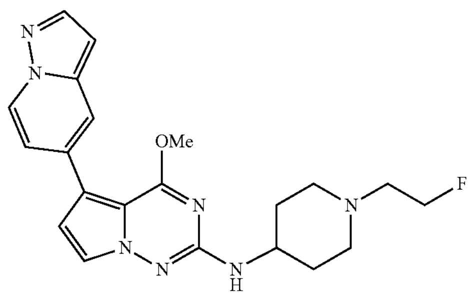

N-(1-(2-Fluoroethyl)piperidin-4-yl)-4-methoxy-5-(pyrazolo[1,5-a]pyridin-5-yl)pyrrolo[2,1-f][1,2,4]triazin-2-amine 24

Off-white solid (17 mg, 0.042 mmol, 20.7% yield). $^1H$ NMR (499 MHz, DMSO-$d_6$) δ ppm 1.46-1.60 (2H, m), 1.85-1.96 (2H, m), 2.11 (2H, br t, J=11.09 Hz), 2.61 (2H, dt, J=28.25, 4.95 Hz), 2.84-2.93 (2H, m), 3.53-3.66 (1H, m), 3.98 (3H, s), 4.53 (2H, dt, J=47.70, 4.95 Hz), 6.58 (1H, d, J=1.64 Hz), 6.62 (1H, d, J=7.94 Hz), 6.76 (1H, d, J=2.74 Hz), 7.10 (1H, dd, J=7.39, 1.92 Hz), 7.62 (1H, d, J=2.46 Hz), 7.81 (1H, d, J=1.10 Hz), 7.97 (1H, d, J=2.46 Hz), 8.62 (1H, d, J=7.39 Hz); ESIMS found for $C_{21}H_{24}FN_7O$ m/z 410.2 (M+1).

26

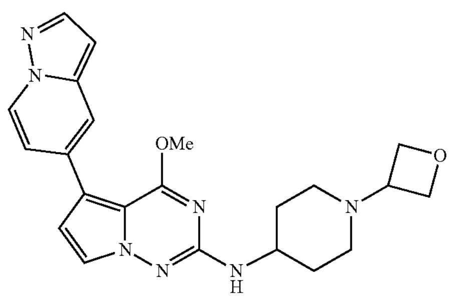

4-Methoxy-N-(1-(oxetan-3-yl)piperidin-4-yl)-5-(pyrazolo[1,5-a]pyridin-5-yl)pyrrolo[2,1-f][1,2,4]triazin-2-amine 26

Off-white solid (2 mg, 0.005 mmol, 1.2% yield). $^1H$ NMR (499 MHz, METHANOL-$d_4$) δ ppm 1.57-1.70 (2H, m), 2.06 (2H, br t, J=11.77 Hz), 2.09-2.15 (2H, m), 2.80 (2H, br d, J=11.77 Hz), 3.53 (1H, quin, J=6.43 Hz), 3.67-3.77 (1H, m), 4.03 (3H, s), 4.62 (2H, t, J=6.30 Hz), 4.69-4.75 (2H, m), 6.54-6.61 (1H, m), 6.70 (1H, d, J=2.46 Hz), 7.14 (1H, dd, J=7.39, 1.92 Hz), 7.47 (1H, d, J=2.46 Hz), 7.79 (1H, d, J=1.10 Hz), 7.92 (1H, d, J=2.19 Hz), 8.46 (1H, d, J=7.12 Hz); ESIMS found for $C_{22}H_{25}N_7O_2$ m/z 420.2 (M+1).

27

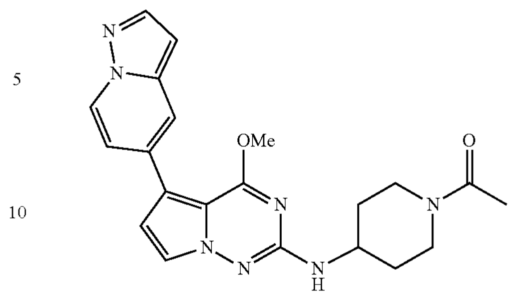

1-(4-((4-Methoxy-5-(pyrazolo[1,5-a]pyridin-5-yl)pyrrolo[2,1-f][1,2,4]triazin-2-yl)amino)piperidin-1-yl)ethan-1-one 27

Beige solid (11 mg, 0.027 mmol, 13.6% yield). $^1H$ NMR (499 MHz, DMSO-$d_6$) δ ppm 1.27-1.39 (1H, m), 1.40-1.52 (1H, m), 1.87-1.94 (1H, m), 1.94-2.00 (1H, m), 2.01 (3H, s), 2.70-2.81 (1H, m), 3.12-3.19 (1H, m), 3.78-3.87 (2H, m), 3.99 (3H, s), 4.24-4.34 (1H, m), 6.59 (1H, dd, J=2.19, 0.82 Hz), 6.73 (1H, d, J=7.94 Hz), 6.77 (1H, d, J=2.74 Hz), 7.11 (1H, dd, J=7.12, 1.92 Hz), 7.63 (1H, d, J=2.74 Hz), 7.81 (1H, d, J=1.10 Hz), 7.97 (1H, d, J=2.19 Hz), 8.62 (1H, d, J=7.12 Hz); ESIMS found for $C_{21}H_{23}N_7O_2$ m/z 406.2 (M+1).

29

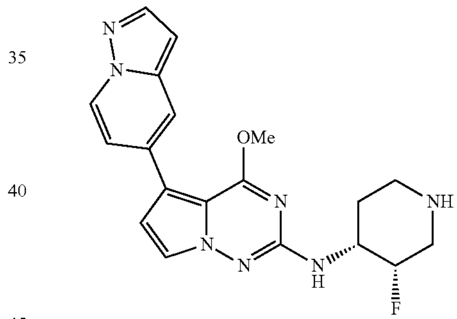

N-((3S,4R)-3-Fluoropiperidin-4-yl)-4-methoxy-5-(pyrazolo[1,5-a]pyridin-5-yl)pyrrolo[2,1-f][1,2,4]triazin-2-amine 29

Off-white solid (45 mg, 0.118 mmol, 87.4% yield). $^1H$ NMR (499 MHz, DMSO-$d_6$) δ ppm 1.57-1.65 (1H, m), 1.73 (1H, qd, J=12.37, 4.24 Hz), 2.56 (1H, br t, J=12.46 Hz), 2.71 (1H, dd, J=39.25, 14.30 Hz), 2.96 (1H, br d, J=13.14 Hz), 3.13 (1H, br t, J=11.50 Hz), 3.77-3.94 (1H, m), 4.00 (3H, s), 4.80 (1H, d, J=50.75 Hz), 6.59 (1H, d, J=1.64 Hz), 6.64 (1H, d, J=7.94 Hz), 6.78 (1H, d, J=2.74 Hz), 7.11 (1H, dd, J=7.39, 1.92 Hz), 7.63 (1H, d, J=2.46 Hz), 7.81 (1H, d, J=1.10 Hz), 7.97 (1H, d, J=2.19 Hz), 8.63 (1H, d, J=7.12 Hz); ESIMS found for $C_{19}H_{20}FN_7O$ m/z 382.2 (M+1).

30

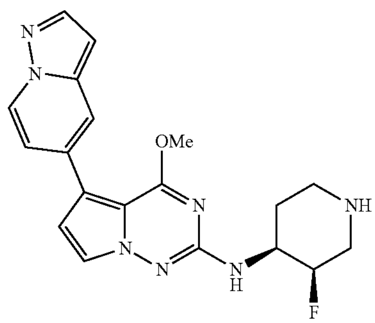

N-((3R,4S)-3-Fluoropiperidin-4-yl)-4-methoxy-5-(pyrazolo[1,5-a]pyridin-5-yl)pyrrolo[2,1-f][1,2,4]triazin-2-amine 30

Brown solid (109 mg, 0.286 mmol, 99.0% yield). $^1$H NMR (499 MHz, DMSO-$d_6$) δ ppm 1.89-1.96 (1H, m), 2.07 (1H, qd, J=13.23, 4.11 Hz), 2.75 (1H, s), 3.11-3.18 (1H, m), 3.27-3.38 (1H, m), 3.58-3.66 (1H, m), 4.01 (3H, s), 4.05-4.18 (1H, m), 5.20 (1H, d, J=47.45 Hz), 6.60 (1H, d, J=1.92 Hz), 6.81 (1H, d, J=2.46 Hz), 7.06 (1H, d, J=7.39 Hz), 7.11 (1H, dd, J=7.12, 1.92 Hz), 7.59 (1H, d, J=2.74 Hz), 7.82 (1H, d, J=1.37 Hz), 7.98 (1H, d, J=2.19 Hz), 8.64 (1H, br d, J=7.39 Hz); ESIMS found for $C_{19}H_{20}FN_7O$ m/z 382.2 (M+1).

31

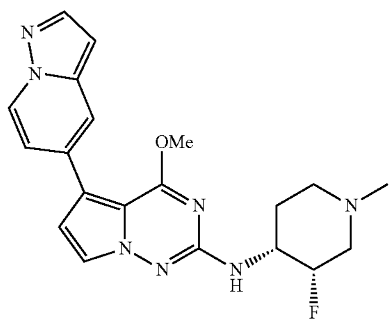

N-((3S,4R)-3-Fluoro-1-methylpiperidin-4-yl)-4-methoxy-5-(pyrazolo[1,5-a]pyridin-5-yl)pyrrolo[2,1-f][1,2,4]triazin-2-amine 31

Off-white solid (30 mg, 0.076 mmol, 72.3% yield). $^1$H NMR (499 MHz, DMSO-$d_6$) δ ppm 1.68 (1H, br dd, J=12.59, 3.01 Hz), 1.92 (1H, qd, J=12.23, 3.56 Hz), 2.01-2.09 (1H, m), 2.17 (1H, dd, J=37.55, 13.20 Hz), 2.19 (3H, s), 2.79 (1H, br d, J=11.23 Hz), 3.00-3.09 (1H, m), 3.67-3.83 (1H, m), 4.00 (3H, s), 4.91 (1H, d, J=50.20 Hz), 6.59 (1H, d, J=1.64 Hz), 6.64 (1H, d, J=7.67 Hz), 6.78 (1H, d, J=2.74 Hz), 7.11 (1H, dd, J=7.12, 1.92 Hz), 7.63 (1H, d, J=2.74 Hz), 7.81 (1H, d, J=0.82 Hz), 7.97 (1H, d, J=2.19 Hz), 8.63 (1H, d, J=7.39 Hz); ESIMS found for $C_{20}H_{22}FN_7O$ m/z 396.2 (M+1).

34

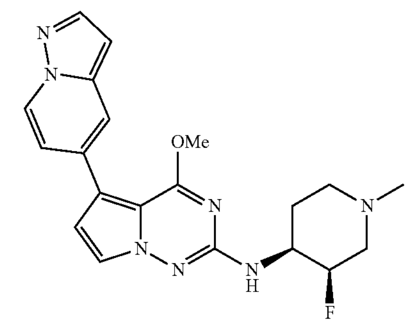

N-((3R,4S)-3-Fluoro-1-methylpiperidin-4-yl)-4-methoxy-5-(pyrazolo[1,5-a]pyridin-5-yl)pyrrolo[2,1-f][1,2,4]triazin-2-amine 34

Off-white solid (43 mg, 0.109 mmol, 38.1% yield). $^1$H NMR (499 MHz, DMSO-$d_6$) δ ppm 1.65-1.72 (1H, m), 1.92 (1H, qd, J=12.27, 3.70 Hz), 2.01-2.09 (1H, m), 2.17 (1H, dd, J=37.55, 13.20 Hz), 2.19 (3H, s), 2.80 (1H, br d, J=11.77 Hz), 3.01-3.07 (1H, m), 3.67-3.83 (1H, m), 4.00 (3H, s), 4.91 (1H, d, J=49.90 Hz), 6.59 (1H, d, J=1.37 Hz), 6.65 (1H, d, J=7.67 Hz), 6.78 (1H, d, J=2.74 Hz), 7.11 (1H, dd, J=7.26, 2.05 Hz), 7.63 (1H, d, J=2.74 Hz), 7.81 (1H, d, J=1.10 Hz), 7.97 (1H, d, J=2.19 Hz), 8.63 (1H, d, J=7.12 Hz); ESIMS found for $C_{20}H_{22}FN_7O$ m/z 396.3 (M+1).

36

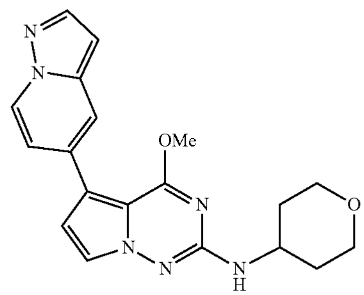

4-Methoxy-5-(pyrazolo[1,5-a]pyridin-5-yl)-N-(tetrahydro-2H-pyran-4-yl)pyrrolo[2,1-f][1,2,4]triazin-2-amine 36

Off-white solid (8 mg, 0.022 mmol, 6.6% yield). $^1$H NMR (499 MHz, DMSO-$d_6$) δ ppm 1.47-1.60 (2H, m), 1.89 (2H, br dd, J=12.46, 2.05 Hz), 3.36-3.45 (2H, m), 3.73-3.85 (1H, m), 3.85-3.92 (2H, m), 3.99 (3H, s), 6.58 (1H, d, J=1.92 Hz), 6.71 (1H, d, J=7.94 Hz), 6.76 (1H, d, J=2.46 Hz), 7.10 (1H, dd, J=7.26, 1.78 Hz), 7.63 (1H, d, J=2.74 Hz), 7.81 (1H, d, J=0.82 Hz), 7.97 (1H, d, J=2.19 Hz), 8.62 (1H, d, J=7.12 Hz); ESIMS found for $C_{19}H_{20}N_6O_2$ m/z 365.2 (M+1).

37

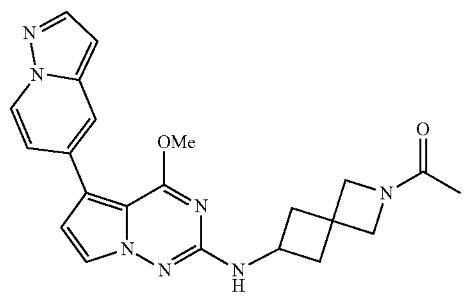

1-(6-((4-Methoxy-5-(pyrazolo[1,5-a]pyridin-5-yl) pyrrolo[2,1-f][1,2,4]triazin-2-yl)amino)-2-azaspiro [3.3]heptan-2-yl)ethan-1-one 37

White solid (28 mg, 0.067 mmol, 38.7% yield). $^1$H NMR (499 MHz, DMSO-$d_6$) δ ppm 1.69-1.76 (3H, m), 2.13-2.25 (2H, m), 2.52-2.60 (2H, m), 3.77 (1H, s), 3.89 (1H, s), 3.98 (3H, s), 4.04-4.11 (1H, m), 4.05 (1H, s), 4.17 (1H, s), 6.58 (1H, d, J=1.92 Hz), 6.77 (1H, d, J=2.46 Hz), 7.03 (1H, t, J=6.98 Hz), 7.10 (1H, dd, J=7.39, 1.92 Hz), 7.62 (1H, dd, J=4.79, 2.60 Hz), 7.80 (1H, d, J=0.82 Hz), 7.97 (1H, d, J=2.19 Hz), 8.62 (1H, d, J=7.39 Hz); ESIMS found for $C_{22}H_{23}N_7O_2$ m/z 418.2 (M+1).

39

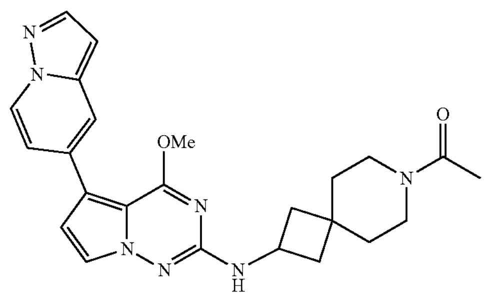

1-(2-((4-Methoxy-5-(pyrazolo[1,5-a]pyridin-5-yl) pyrrolo[2,1-f][1,2,4]triazin-2-yl)amino)-7-azaspiro [3.5]nonan-7-yl)ethan-1-one 39

Off-white solid (50 mg, 0.112 mmol, 79.4% yield). $^1$H NMR (499 MHz, DMSO-$d_6$) δ ppm 1.40-1.46 (1H, m), 1.49-1.56 (2H, m), 1.57-1.64 (1H, m), 1.74-1.84 (2H, m), 1.95-2.01 (3H, m), 2.26 (2H, br dd, J=9.86, 8.21 Hz), 3.26-3.30 (1H, m), 3.30-3.32 (1H, m), 3.35-3.39 (1H, m), 3.39-3.44 (1H, m), 3.98 (3H, s), 4.14-4.25 (1H, m), 6.58 (1H, d, J=1.64 Hz), 6.76 (1H, d, J=2.74 Hz), 7.02 (1H, t, J=7.12 Hz), 7.10 (1H, dd, J=7.12, 1.92 Hz), 7.59-7.66 (1H, m), 7.80 (1H, d, J=1.09 Hz), 7.97 (1H, d, J=2.19 Hz), 8.62 (1H, d, J=7.39 Hz); ESIMS found for $C_{24}H_{27}N_7O_2$ m/z 446.2 (M+1).

40

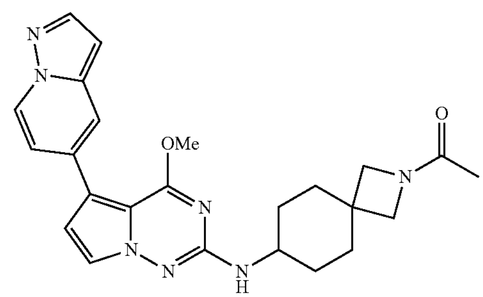

1-(7-((4-Methoxy-5-(pyrazolo[1,5-a]pyridin-5-yl) pyrrolo[2,1-f][1,2,4]triazin-2-yl)amino)-2-azaspiro [3.5]nonan-2-yl)ethan-1-one 40

Off-white solid (75 mg, 0.168 mmol, 95.7% yield). $^1$H NMR (499 MHz, DMSO-$d_6$) δ ppm 1.26-1.39 (2H, m), 1.48-1.60 (2H, m), 1.73-1.78 (3H, m), 1.83-1.93 (4H, m), 3.47 (1H, s), 3.52 (1H, s), 3.57 (1H, br dd, J=7.53, 3.15 Hz), 3.74 (1H, s), 3.80 (1H, s), 3.98 (3H, d, J=1.10 Hz), 6.54 (1H, dd, J=16.15, 7.94 Hz), 6.58 (1H, d, J=1.64 Hz), 6.76 (1H, d, J=2.74 Hz), 7.10 (1H, dd, J=7.39, 1.92 Hz), 7.62 (1H, t, J=2.87 Hz), 7.80 (1H, d, J=1.09 Hz), 7.97 (1H, d, J=2.19 Hz), 8.62 (1H, d, J=7.39 Hz); ESIMS found for $C_{24}H_{27}N_7O_2$ m/z 446.2 (M+1).

43

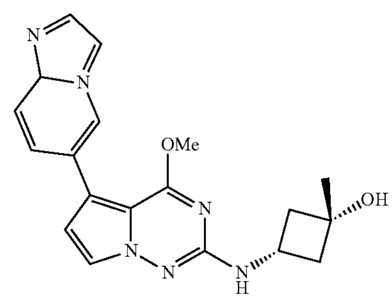

cis-3-((5-(Imidazo[1,2-a]pyridin-6-yl)-4-methoxy-pyrrolo[2,1-f][1,2,4]triazin-2-yl)amino)-1-methylcy-clobutan-1-ol 43

White solid (19 mg, 0.052 mmol, 31.3% yield). $^1$H NMR (499 MHz, DMSO-$d_6$) δ ppm 1.27 (3H, s), 1.96-2.07 (2H, m), 2.31-2.41 (2H, m), 3.71 (1H, dq, J=15.16, 7.72 Hz), 3.96 (3H, s), 4.91 (1H, s), 6.67 (1H, d, J=2.74 Hz), 6.92 (1H, d, J=6.84 Hz), 7.43 (1H, dd, J=9.31, 1.64 Hz), 7.54 (1H, d, J=9.31 Hz), 7.56 (1H, d, J=0.82 Hz), 7.62 (1H, d, J=2.46 Hz), 7.95 (1H, s), 8.68 (1H, s); ESIMS found for $C_{19}H_{20}N_6O_2$ m/z 365.2 (M+1).

44

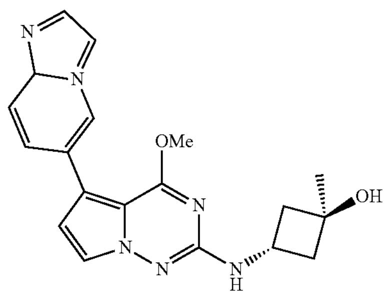

trans-3-((5-(Imidazo[1,2-a]pyridin-6-yl)-4-methoxy-pyrrolo[2,1-f][1,2,4]triazin-2-yl)amino)-1-methylcyclobutan-1-ol 44

Off-white semi-solid (10 mg, 0.027 mmol, 16.5% yield). $^1$H NMR (499 MHz, DMSO-$d_6$) δ ppm 1.28 (3H, s), 1.94-2.03 (2H, m), 2.28-2.35 (2H, m), 3.96 (3H, s), 4.25 (1H, sxt, J=7.39 Hz), 4.78 (1H, br s), 6.68 (1H, d, J=2.74 Hz), 6.93 (1H, d, J=6.84 Hz), 7.43 (1H, dd, J=9.31, 1.64 Hz), 7.54 (1H, d, J=9.58 Hz), 7.56 (1H, s), 7.61 (1H, d, J=2.74 Hz), 7.95 (1H, s), 8.68 (1H, s); ESIMS found for $C_{19}H_{20}N_6O_2$ m/z 365.2 (M+1).

45

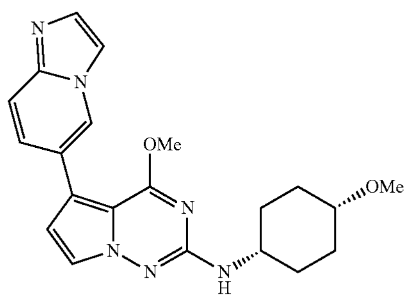

5-(Imidazo[1,2-a]pyridin-6-yl)-4-methoxy-N-(cis-4-methoxycyclohexyl)pyrrolo[2,1-f][1,2,4]triazin-2-amine 45

Off-white solid (2.6 mg, 0.007 mmol, 4.7% yield). $^1$H NMR (499 MHz, DMSO-$d_6$) δ ppm 1.45-1.54 (2H, m), 1.55-1.65 (2H, m), 1.69 (2H, dt, J=8.35, 4.04 Hz), 1.80-1.88 (2H, m), 3.22 (3H, s), 3.29-3.37 (1H, m), 3.56-3.71 (1H, m), 3.96 (3H, s), 6.54 (1H, d, J=7.67 Hz), 6.67 (1H, d, J=2.46 Hz), 7.43 (1H, dd, J=9.31, 1.37 Hz), 7.54 (1H, d, J=9.31 Hz), 7.56 (1H, s), 7.61 (1H, d, J=2.46 Hz), 7.95 (1H, s), 8.68 (1H, s); ESIMS found for $C_{21}H_{24}N_6O_2$ m/z 393.2 (M+1).

49

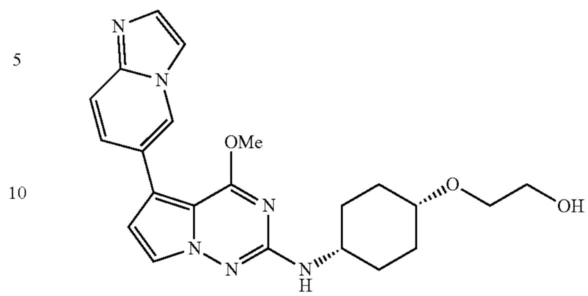

2-((cis-4-((5-(Imidazo[1,2-a]pyridin-6-yl)-4-methoxypyrrolo[2,1-f][1,2,4]triazin-2-yl)amino)cyclohexyl)oxy)ethan-1-ol 49

Orange semi-solid. (6 mg, 0.014 mmol, 6.1% yield). $^1$H NMR (499 MHz, DMSO-$d_6$) δ ppm 1.45-1.56 (2H, m), 1.60-1.74 (4H, m), 1.78-1.88 (2H, m), 3.38-3.42 (2H, m), 3.47 (1H, br s), 3.50 (2H, q, J=5.20 Hz), 3.58-3.70 (1H, m), 3.96 (3H, s), 4.51 (1H, br t, J=5.34 Hz), 6.52 (1H, d, J=7.67 Hz), 6.67 (1H, d, J=2.46 Hz), 7.47 (1H, br d, J=9.03 Hz), 7.56 (1H, br d, J=9.03 Hz), 7.58-7.60 (1H, m), 7.61 (1H, d, J=2.46 Hz), 7.98 (1H, br s), 8.70 (1H, br s); ESIMS found for $C_{22}H_{26}N_6O_3$ m/z 423.25 (M+1).

51

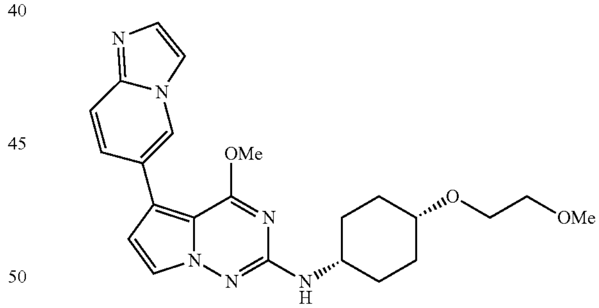

5-(Imidazo[1,2-a]pyridin-6-yl)-4-methoxy-N-(cis-4-(2-methoxyethoxy) cyclohexyl)pyrrolo[2,1-f][1,2,4]triazin-2-amine 51

White solid (3 mg, 0.007 mmol, 4.1% yield). $^1$H NMR (499 MHz, DMSO-$d_6$) δ ppm 1.44-1.56 (2H, m), 1.58-1.74 (4H, m), 1.77-1.88 (2H, m), 3.27 (3H, s), 3.43-3.46 (2H, m), 3.47 (1H, br s), 3.48-3.52 (2H, m), 3.62 (1H, ddt, J=12.53, 8.56, 4.52, 4.52 Hz), 3.96 (3H, s), 6.56 (1H, d, J=7.67 Hz), 6.67 (1H, d, J=2.46 Hz), 7.43 (1H, dd, J=9.45, 1.78 Hz), 7.54 (1 H, d, J=9.31 Hz), 7.56 (1H, d, J=1.09 Hz), 7.61 (1H, d, J=2.74 Hz), 7.95 (1H, s), 8.68 (1H, d, J=1.64 Hz); ESIMS found for $C_{23}H_{28}N_6O_3$ m/z 437.2 (M+1).

52

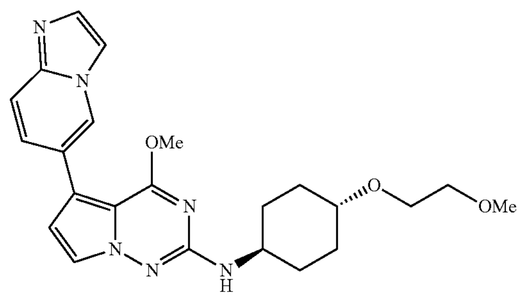

5-(Imidazo[1,2-a]pyridin-6-yl)-4-methoxy-N-(trans-4-(2-methoxyethoxy) cyclohexyl)pyrrolo[2,1-f][1,2,4]triazin-2-amine 52

White solid (5 mg, 0.012 mmol, 5.7% yield). $^1$H NMR (499 MHz, DMSO-$d_6$) δ ppm 1.18-1.26 (2H, m), 1.27-1.36 (2H, m), 2.00 (4H, br d, J=10.95 Hz), 3.20-3.26 (1H, m), 3.25 (3H, s), 3.42 (2H, dd, J=5.75, 3.83 Hz), 3.53 (2H, dd, J=5.75, 3.83 Hz), 3.55-3.60 (1H, m), 3.95 (3H, s), 6.52 (1H, d, J=7.94 Hz), 6.67 (1H, d, J=2.46 Hz), 7.43 (1H, dd, J=9.45, 1.78 Hz), 7.54 (1H, d, J=9.31 Hz), 7.56 (1H, d, J=1.09 Hz), 7.63 (1H, d, J=2.46 Hz), 7.95 (1H, s), 8.64-8.70 (1H, m); ESIMS found for $C_{23}H_{28}N_6O_3$ m/z 437.2 (M+1).

53

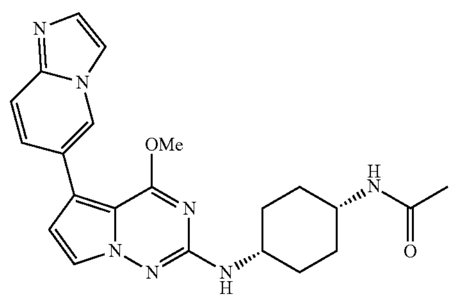

N-(cis-4-((5-(Imidazo[1,2-a]pyridin-6-yl)-4-methoxypyrrolo[2,1-f][1,2,4]triazin-2-yl)amino) cyclohexyl)acetamide 53

Off-white solid (8 mg, 0.019 mmol, 37.9% yield). $^1$H NMR (499 MHz, DMSO-$d_6$) δ ppm 1.50-1.59 (2H, m), 1.60-1.71 (4H, m), 1.73-1.81 (2H, m), 1.81 (3H, s), 3.67 (2H, br d, J=3.56 Hz), 3.97 (3H, s), 6.43 (1H, d, J=6.30 Hz), 6.68 (1H, d, J=2.74 Hz), 7.44 (1H, dd, J=9.31, 1.64 Hz), 7.54 (1H, d, J=9.31 Hz), 7.57 (1H, s), 7.62 (1H, d, J=2.46 Hz), 7.70 (1H, br d, J=7.12 Hz), 7.95 (1H, s), 8.68 (1H, s); ESIMS found for $C_{22}H_{25}N_7O_2$ m/z 420.2 (M+1).

54

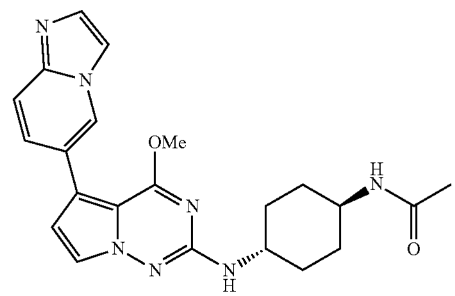

N-(trans-4-((5-(Imidazo[1,2-a]pyridin-6-yl)-4-methoxypyrrolo[2,1-f][1,2,4]triazin-2-yl)amino) cyclohexyl)acetamide 54

Off-white solid (17 mg, 0.041 mmol, 24.3% yield). $^1$H NMR (499 MHz, DMSO-$d_6$) δ ppm 1.19-1.29 (2H, m), 1.29-1.39 (2H, m), 1.78 (3H, s), 1.79-1.85 (2H, m), 1.99 (2H, br d, J=10.95 Hz), 3.44-3.59 (2H, m), 3.95 (3H, s), 6.53 (1H, d, J=8.21 Hz), 6.67 (1H, d, J=2.46 Hz), 7.43 (1H, dd, J=9.45, 1.51 Hz), 7.54 (1H, d, J=9.31 Hz), 7.56 (1H, s), 7.63 (1H, d, J=2.46 Hz), 7.74 (1H, d, J=7.67 Hz), 7.95 (1H, s), 8.68 (1H, s); ESIMS found for $C_{22}H_{25}N_7O_2$ m/z 420.2 (M+1).

55

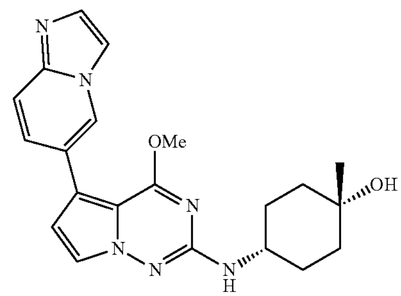

cis-4-((5-(Imidazo[1,2-a]pyridin-6-yl)-4-methoxy-pyrrolo[2,1-f][1,2,4]triazin-2-yl)amino)-1-methylcyclohexan-1-ol 55

Off-white solid (7.9 mg, 0.020 mmol, 14.4% yield). $^1$H NMR (499 MHz, DMSO-$d_6$) δ ppm 1.12 (3H, s), 1.36 (2H, td, J=13.00, 4.11 Hz), 1.58 (2H, br d, J=12.32 Hz), 1.60-1.68 (2H, m), 1.68-1.74 (2H, m), 3.45-3.57 (1H, m), 3.96 (3H, s), 4.00 (1H, s), 6.49 (1H, d, J=7.94 Hz), 6.66 (1H, d, J=2.46 Hz), 7.43 (1H, dd, J=9.58, 1.64 Hz), 7.54 (1H, d, J=9.31 Hz), 7.56 (1H, d, J=0.82 Hz), 7.60 (1H, d, J=2.74 Hz), 7.95 (1H, s), 8.68 (1H, s); ESIMS found for $C_{21}H_{24}N_6O_2$ m/z 393.2 (M+1).

56

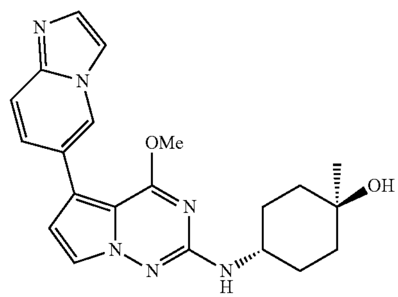

trans-4-((5-(Imidazo[1,2-a]pyridin-6-yl)-4-methoxy-pyrrolo[2,1-f][1,2,4]triazin-2-yl)amino)-1-methylcyclohexan-1-ol 56

Beige solid (16 mg, 0.041 mmol, 20.4% yield). $^1$H NMR (499 MHz, DMSO-$d_6$) δ ppm 1.14 (3H, s), 1.37-1.52 (4H, m), 1.56-1.64 (2H, m), 1.81-1.93 (2H, m), 3.57-3.70 (1H, m), 3.96 (3H, s), 4.24 (1H, s), 6.47 (1H, d, J=7.94 Hz), 6.67 (1H, d, J=2.46 Hz), 7.43 (1H, dd, J=9.31, 1.64 Hz), 7.54 (1H, d, J=9.31 Hz), 7.56 (1H, s), 7.62 (1H, d, J=2.46 Hz), 7.95 (1H, s), 8.68 (1H, s); ESIMS found for $C_{21}H_{24}N_6O_2$ m/z 393.2 (M+1).

61

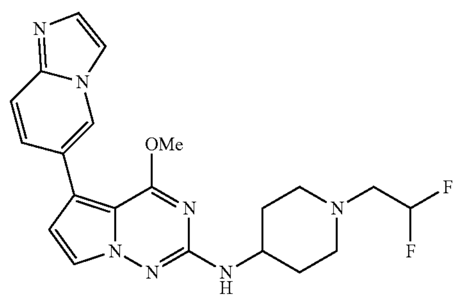

N-(1-(2,2-Difluoroethyl)piperidin-4-yl)-5-(imidazo[1,2-a]pyridin-6-yl)-4-methoxypyrrolo[2,1-f][1,2,4]triazin-2-amine 61

White solid (5 mg, 0.012 mmol, 5.8% yield). H NMR (499 MHz, DMSO-$d_6$) δ ppm 1.48-1.62 (2H, m), 1.89 (2H, br d, J=10.95 Hz), 2.22-2.31 (2H, m), 2.72 (2H, td, J=15.74, 4.38 Hz), 2.90 (2H, br d, J=11.77 Hz), 3.53-3.65 (1H, m), 3.96 (3H, s), 6.13 (1H, tt, J=55.95, 4.40 Hz), 6.59 (1H, d, J=7.94 Hz), 6.68 (1H, d, J=2.74 Hz), 7.43 (1H, dd, J=9.45, 1.78 Hz), 7.54 (1H, d, J=9.58 Hz), 7.56 (1H, d, J=0.82 Hz), 7.62 (1H, d, J=2.74 Hz), 7.95 (1H, s), 8.65-8.70 (1H, m); ESIMS found for $C_{21}H_{23}F_2N_7O$ m/z 428.2 (M+1).

62

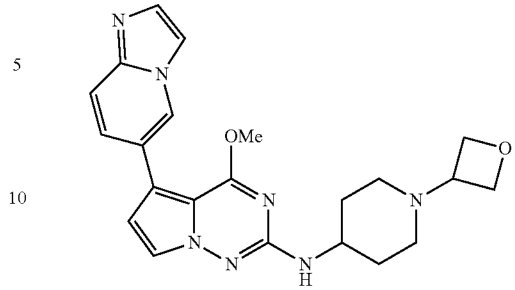

5-(Imidazo[1,2-a]pyridin-6-yl)-4-methoxy-N-(1-(oxetan-3-yl)piperidin-4-yl)pyrrolo[2,1-f][1,2,4]triazin-2-amine 62

Colorless semi-solid. (10 mg, 0.024 mmol, 14.3% yield). $^1$H NMR (499 MHz, DMSO-$d_6$) δ ppm 1.48-1.61 (2H, m), 1.84-1.98 (4H, m), 2.71 (2H, br d, J=11.22 Hz), 3.41 (1H, br s), 3.54-3.65 (1H, m), 3.96 (3H, s), 4.43 (2H, t, J=6.16 Hz), 4.54 (2H, t, J=6.57 Hz), 6.63 (1H, d, J=7.94 Hz), 6.68 (1H, d, J=2.46 Hz), 7.44 (1H, dd, J=9.31, 1.37 Hz), 7.55 (1H, br d, J=9.31 Hz), 7.57 (1H, br s), 7.62 (1H, d, J=2.46 Hz), 7.96 (1H, s), 8.68 (1H, s); ESIMS found for $C_{22}H_{25}N_7O_2$ m/z 420.2 (M+1).

63

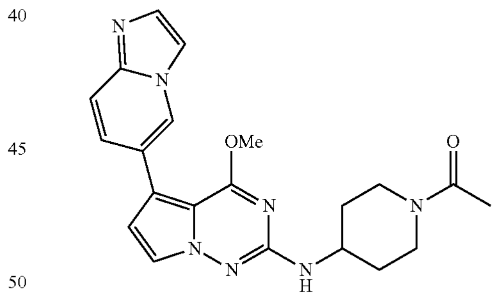

1-(4-((5-(Imidazo[1,2-a]pyridin-6-yl)-4-methoxypyrrolo[2,1-f][1,2,4]triazin-2-yl)amino)piperidin-1-yl)ethan-1-one 63

Beige solid (9 mg, 0.022 mmol, 13.3% yield). $^1$H NMR (499 MHz, DMSO-$d_6$) δ ppm 1.29-1.38 (1H, m), 1.39-1.50 (1H, m), 1.88-1.95 (1H, m), 1.97 (1H, br d, J=13.14 Hz), 2.01 (3H, s), 2.69-2.82 (1H, m), 3.11-3.20 (1H, m), 3.77-3.87 (2H, m), 3.97 (3H, s), 4.28 (1H, br d, J=12.59 Hz), 6.68-6.72 (2H, m), 7.47 (1H, d, J=9.31 Hz), 7.56 (1H, d, J=9.31 Hz), 7.59 (1H, s), 7.63 (1H, d, J=2.46 Hz), 7.97 (1H, s), 8.70 (1H, s); ESIMS found for $C_{21}H_{23}N_7O_2$ m/z 406.2 (M+1).

67

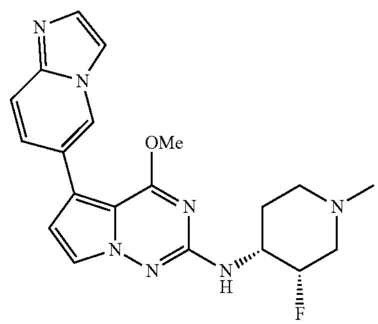

N-((3S,4R)-3-Fluoro-1-methylpiperidin-4-yl)-5-(imidazo[1,2-a]pyridin-6-yl)-4-methoxypyrrolo[2,1-f][1,2,4]triazin-2-amine 67

White solid (5.5 mg, 0.014 mmol, 10.6% yield). $^1$H NMR (499 MHz, DMSO-$d_6$) δ ppm 1.63-1.74 (1H, m), 1.92 (1H, qd, J=12.27, 3.70 Hz), 2.06 (1H, br t, J=11.09 Hz), 2.11-2.24 (1H, m), 2.19 (3H, s), 2.80 (1H, br d, J=10.95 Hz), 3.00-3.07 (1H, m), 3.66-3.83 (1H, m), 3.98 (3H, s), 4.91 (1H, d, J=49.90 Hz), 6.61 (1H, d, J=7.94 Hz), 6.70 (1H, d, J=2.74 Hz), 7.44 (1H, dd, J=9.45, 1.78 Hz), 7.55 (1H, d, J=9.31 Hz), 7.57 (1H, s), 7.62 (1H, d, J=2.46 Hz), 7.95 (1H, s), 8.69 (1H, s); ESIMS found for $C_{20}H_{22}FN_7O$ m/z 396.2 (M+1).

74

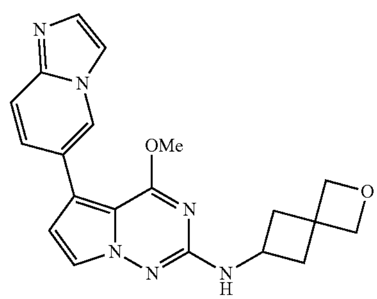

5-(Imidazo[1,2-a]pyridin-6-yl)-4-methoxy-N-(2-oxaspiro[3.3]heptan-6-yl)pyrrolo[2,1-f][1,2,4]triazin-2-amine 74

White solid (4.0 mg, 0.011 mmol, 4.0% yield). $^1$H NMR (499 MHz, DMSO-$d_6$) δ ppm 2.12-2.23 (2H, m), 2.61 (2H, ddd, J=9.86, 7.53, 2.87 Hz), 3.95-4.04 (1H, m), 3.97 (3H, s), 4.51 (2H, s), 4.63 (2H, s), 6.58 (1H, d, J=1.92 Hz), 6.76 (1H, d, J=2.46 Hz), 7.00 (1H, d, J=7.12 Hz), 7.10 (1H, dd, J=7.26, 1.78 Hz), 7.61 (1H, d, J=2.74 Hz), 7.80 (1H, s), 7.97 (1H, d, J=1.92 Hz), 8.62 (1H, d, J=7.39 Hz); ESIMS found for $C_{20}H_{20}N_6O_2$ m/z 377.2 (M+1).

80

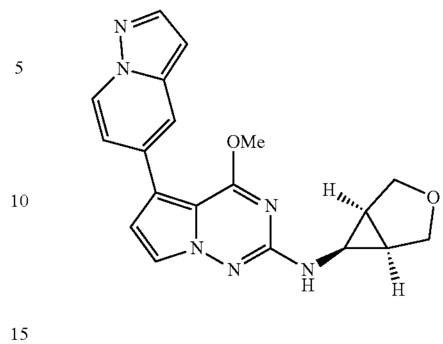

N-((1R,5S,6s)-3-Oxabicyclo[3.1.0]hexan-6-yl)-4-methoxy-5-(pyrazolo[1,5-a]pyridin-5-yl)pyrrolo[2,1-f][1,2,4]triazin-2-amine 80

Off-white solid (16 mg, 0.044 mmol, 13.2% yield). $^1$H NMR (499 MHz, DMSO-$d_6$) δ ppm 1.95-2.04 (2H, m), 2.86 (1H, td, J=6.78, 3.15 Hz), 3.81-3.88 (4H, m), 4.00 (3H, s), 6.39 (1H, d, J=3.01 Hz), 6.59 (1H, d, J=1.64 Hz), 6.78 (1H, d, J=2.74 Hz), 7.11 (1H, dd, J=7.39, 1.92 Hz), 7.65 (1H, d, J=2.46 Hz), 7.82 (1H, d, J=0.82 Hz), 7.97 (1H, d, J=2.19 Hz), 8.62 (1H, d, J=7.12 Hz); ESIMS found for $C_{1-9}H_{18}N_6O_2$ m/z 363.2 (M+1).

91

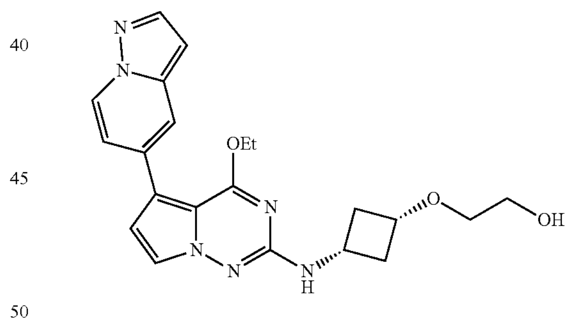

2-(cis-3-((4-Ethoxy-5-(pyrazolo[1,5-a]pyridin-5-yl)pyrrolo[2,1-f][1,2,4]triazin-2-yl)amino)cyclobutoxy)ethan-1-ol 91

Off-white solid (4 mg, 0.010 mmol, 4.9% yield). $^1$H NMR (499 MHz, DMSO-$d_6$) δ ppm 1.33 (3H, t, J=7.12 Hz), 1.87 (2H, qd, J=8.53, 2.87 Hz), 2.58-2.68 (2H, m), 3.30-3.33 (2H, m), 3.48 (2H, q, J=5.20 Hz), 3.68-3.73 (1H, m), 3.74-3.81 (1H, m), 4.47 (2H, q, J=7.12 Hz), 4.60 (1H, t, J=5.48 Hz), 6.57 (1H, d, J=1.37 Hz), 6.78 (1H, d, J=2.46 Hz), 6.98 (1H, d, J=7.39 Hz), 7.13 (1H, dd, J=7.26, 1.78 Hz), 7.59 (1H, d, J=2.46 Hz), 7.86 (1H, s), 7.96 (1H, d, J=2.19 Hz), 8.63 (1H, d, J=7.39 Hz); ESIMS found for $C_{21}H_{24}N_6O_3$ m/z 409.2 (M+1).

92

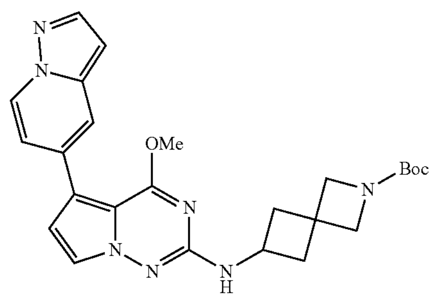

tert-Butyl 6-((4-methoxy-5-(pyrazolo[1,5-a]pyridin-5-yl)pyrrolo[2,1-f][1,2,4]triazin-2-yl)amino)-2-azaspiro[3.3]heptane-2-carboxylate 92

Off-white solid (103 mg, 0.217 mmol, 64.9% yield). $^1H$ NMR (499 MHz, DMSO-$d_6$) δ ppm 1.37 (9H, s), 2.11-2.21 (2H, m), 2.51-2.57 (2H, m), 3.79 (2H, br s), 3.91 (2H, br s), 3.97 (3H, s), 4.01-4.09 (1H, m), 6.58 (1H, d, J=1.64 Hz), 6.77 (1H, d, J=2.74 Hz), 7.01 (1H, d, J=7.12 Hz), 7.10 (1H, dd, J=7.39, 1.92 Hz), 7.62 (1H, d, J=2.74 Hz), 7.80 (1H, d, J=1.10 Hz), 7.97 (1H, d, J=2.19 Hz), 8.62 (1H, d, J=7.12 Hz); ESIMS found for $C_{25}H_{29}N_7O_3$ m/z 476.2 (M+1).

93

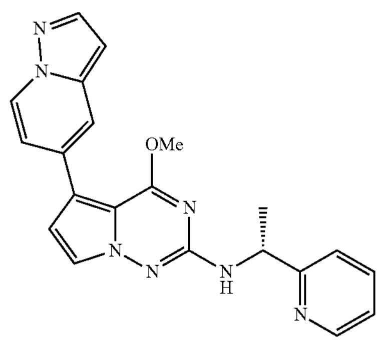

(R)-4-Methoxy-5-(pyrazolo[1,5-a]pyridin-5-yl)-N-(1-(pyridin-2-yl)ethyl)pyrrolo[2,1-f][1,2,4]triazin-2-amine 93

Beige solid (18 mg, 0.047 mmol, 17.5% yield). $^1H$ NMR (499 MHz, DMSO-$d_6$) δ ppm 1.49 (3H, d, J=7.12 Hz), 3.98 (3H, s), 5.00 (1H, quin, J=7.19 Hz), 6.58 (1H, d, J=2.19 Hz), 6.74 (1H, d, J=2.74 Hz), 7.09 (1H, dd, J=7.12, 1.92 Hz), 7.19 (1H, d, J=7.94 Hz), 7.23 (1H, ddd, J=7.46, 4.86, 0.82 Hz), 7.46 (1H, d, J=7.94 Hz), 7.55 (1H, d, J=2.74 Hz), 7.74 (1H, td, J=7.67, 1.64 Hz), 7.79 (1H, d, J=1.10 Hz), 7.96 (1H, d, J=2.19 Hz), 8.48-8.56 (1H, m), 8.61 (1H, d, J=7.12 Hz); ESIMS found for $C_{21}H_{19}N_7O$ m/z 386.2 (M+1).

94

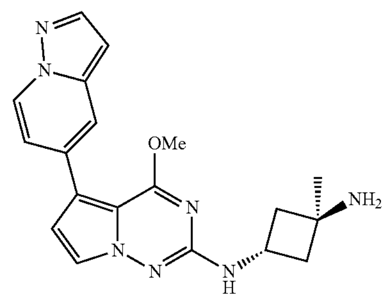

trans-$N_1$-(4-Methoxy-5-(pyrazolo[1,5-a]pyridin-5-yl)pyrrolo[2,1-f][1,2,4]triazin-2-yl)-3-methylcyclobutane-1,3-diamine 94

Off-white solid (67 mg, 0.184 mmol, 85.5% yield). $^1H$ NMR (499 MHz, DMSO-$d_6$) δ ppm 1.22 (3H, s), 1.82 (2H, br s), 1.89-1.97 (2H, m), 2.12-2.22 (2H, m), 3.98 (3H, s), 4.27 (1H, sxt, J=7.56 Hz), 6.58 (1H, d, J=1.64 Hz), 6.76 (1H, d, J=2.74 Hz), 6.92 (1H, d, J=7.12 Hz), 7.10 (1H, dd, J=7.39, 1.92 Hz), 7.61 (1H, d, J=2.74 Hz), 7.80 (1H, d, J=1.09 Hz), 7.97 (1H, d, J=2.19 Hz), 8.62 (1H, d, J=7.39 Hz); ESIMS found for $C_{1-9}H_{21}N_7O$ m/z 364.2 (M+1).

95

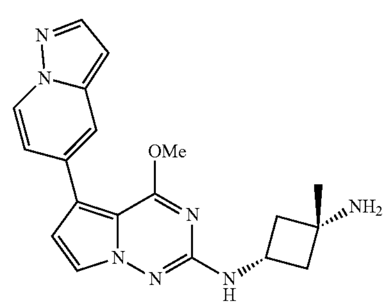

cis-$N_1$-(4-Methoxy-5-(pyrazolo[1,5-a]pyridin-5-yl)pyrrolo[2,1-f][1,2,4]triazin-2-yl)-3-methylcyclobutane-1,3-diamine 95

Off-white foam (157 mg, 0.432 mmol, 69.1% yield). $^1H$ NMR (499 MHz, DMSO-$d_6$) δ ppm 1.19 (3H, s), 1.76 (2H, br s), 1.86 (2H, td, J=8.90, 2.46 Hz), 2.33 (2H, ddd, J=9.03, 7.53, 2.60 Hz), 3.85 (1H, dq, J=15.50, 7.79 Hz), 3.97 (3H, s), 6.58 (1H, d, J=1.64 Hz), 6.76 (1H, d, J=2.46 Hz), 6.81 (1H, d, J=7.12 Hz), 7.10 (1H, dd, J=7.12, 1.92 Hz), 7.63 (1H, d, J=2.74 Hz), 7.80 (1H, d, J=1.10 Hz), 7.96 (1H, d, J=2.19 Hz), 8.62 (1H, d, J=7.12 Hz); ESIMS found for $C_{19}H_{21}N_7O$ m/z 364.2 (M+1).

96

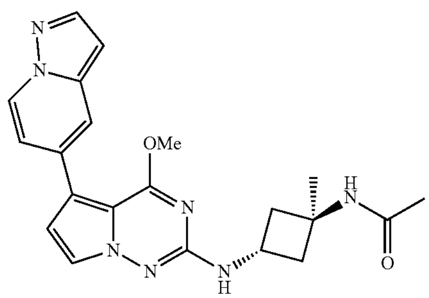

N-(trans-3-((4-Methoxy-5-(pyrazolo[1,5-a]pyridin-5-yl)pyrrolo[2,1-f][1,2,4]triazin-2-yl)amino)-1-methylcyclobutyl)acetamide 96

Off-white solid (34 mg, 0.084 mmol, 45.5% yield). $^1$H NMR (499 MHz, DMSO-$d_6$) δ ppm 1.36 (3H, s), 1.81 (3H, s), 1.92-1.98 (2H, m), 2.63 (2H, ddd, J=10.27, 7.80, 2.74 Hz), 3.98 (3H, s), 4.19 (1H, sxt, J=7.78 Hz), 6.58 (1H, d, J=1.64 Hz), 6.76 (1H, d, J=2.74 Hz), 7.01 (1H, d, J=7.12 Hz), 7.10 (1H, dd, J=7.26, 2.05 Hz), 7.61 (1H, d, J=2.74 Hz), 7.80 (1H, d, J=1.10 Hz), 7.93 (1H, s), 7.97 (1H, d, J=2.19 Hz), 8.62 (1H, d, J=7.39 Hz); ESIMS found for $C_{21}H_{23}N_7O_2$ m/z 406.2 (M+1).

97

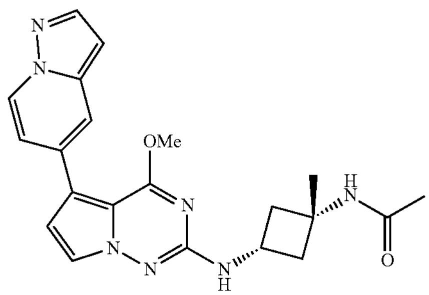

N-(cis-3-((4-Methoxy-5-(pyrazolo[1,5-a]pyridin-5-yl)pyrrolo[2,1-f][1,2,4]triazin-2-yl)amino)-1-methylcyclobutyl)acetamide 97

Off-white solid (27 mg, 0.067 mmol, 96.8% yield). $^1$H NMR (499 MHz, DMSO-$d_6$) δ ppm 1.38 (3H, s), 1.76 (3H, s), 2.10-2.21 (2H, m), 2.42 (2H, ddd, J=9.65, 7.46, 2.60 Hz), 3.98 (3H, s), 3.99-4.07 (1H, m), 6.58 (1H, d, J=1.92 Hz), 6.76 (1H, d, J=2.74 Hz), 7.00 (1H, d, J=6.84 Hz), 7.10 (1H, dd, J=7.26, 2.05 Hz), 7.63 (1H, d, J=2.46 Hz), 7.80 (1H, d, J=1.09 Hz), 7.97 (1H, d, J=2.19 Hz), 8.02 (1H, s), 8.62 (1H, d, J=7.39 Hz); ESIMS found for $C_{21}H_{23}N_7O_2$ m/z 406.2 (M+1).

98

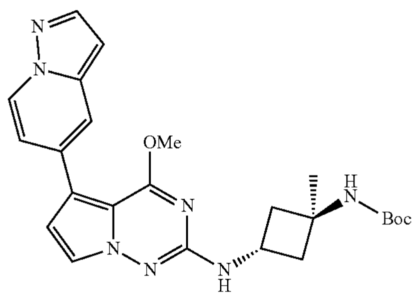

tert-Butyl (trans-3-((4-methoxy-5-(pyrazolo[1,5-a]pyridin-5-yl)pyrrolo[2,1-f][1,2,4]triazin-2-yl)amino)-1-methylcyclobutyl)carbamate 98

Off-white solid (107 mg, 0.231 mmol, 46.1% yield). $^1$H NMR (499 MHz, DMSO-$d_6$) δ ppm 1.33 (3H, s), 1.41 (9H, s), 1.86-1.96 (2H, m), 2.56-2.67 (2H, m), 3.97 (3H, s), 4.17 (1H, sxt, J=7.83 Hz), 6.58 (1H, d, J=1.37 Hz), 6.76 (1H, d, J=2.74 Hz), 7.00 (2H, d, J=7.39 Hz), 7.10 (1H, dd, J=7.39, 1.92 Hz), 7.63 (1H, d, J=2.46 Hz), 7.80 (1H, d, J=1.09 Hz), 7.97 (1H, d, J=2.46 Hz), 8.62 (1H, d, J=7.39 Hz); ESIMS found for $C_{24}H_{29}N_7O_3$ m/z 464.2 (M+1).

99

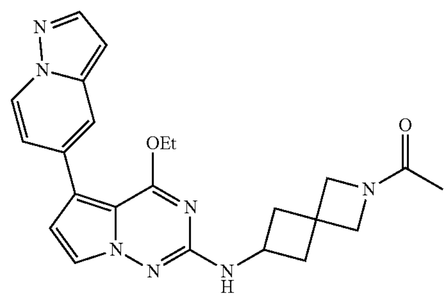

1-(6-((4-Ethoxy-5-(pyrazolo[1,5-a]pyridin-5-yl)pyrrolo[2,1-f][1,2,4]triazin-2-yl)amino)-2-azaspiro[3.3]heptan-2-yl)ethan-1-one 99

White solid (5 mg, 0.012 mmol, 6.7% yield). $^1$H NMR (499 MHz, DMSO-$d_6$) δ ppm 1.33 (3H, t, J=7.12 Hz), 1.69-1.77 (3H, m), 2.13-2.25 (2H, m), 2.51-2.60 (2H, m), 3.77 (1H, s), 3.89 (1H, s), 4.05 (1H, s), 4.05-4.10 (1H, m), 4.17 (1H, s), 4.46 (2H, q, J=7.12 Hz), 6.57 (1H, d, J=1.92 Hz), 6.78 (1H, d, J=2.46 Hz), 6.98 (1H, t, J=6.57 Hz), 7.13 (1H, dd, J=7.26, 1.78 Hz), 7.61 (1H, dd, J=4.52, 2.60 Hz), 7.85 (1H, s), 7.96 (1H, d, J=2.19 Hz), 8.63 (1H, d, J=7.39 Hz); ESIMS found for $C_{23}H_{25}N_7O_2$ m/z 432.2 (M+1).

102

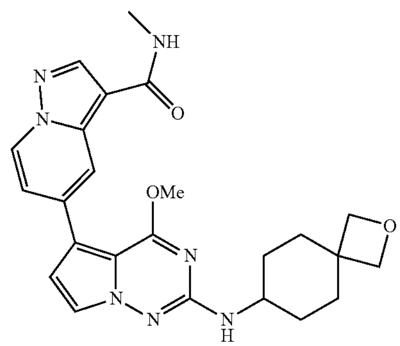

5-(2-((2-Oxaspiro[3.5]nonan-7-yl)amino)-4-methoxypyrrolo[2,1-f][1,2,4]triazin-5-yl)-N-methylpyrazolo[1,5-a]pyridine-3-carboxamide 102

Beige solid (30 mg, 0.065 mmol, 42.0% yield). $^1$H NMR (499 MHz, DMSO-$d_6$) δ ppm 1.20-1.34 (2H, m), 1.52 (2H, td, J=12.94, 3.42 Hz), 1.82-1.93 (2H, m), 2.07 (2H, br d, J=13.14 Hz), 2.79 (3H, d, J=4.65 Hz), 3.49-3.61 (1H, m), 4.01 (3H, s), 4.24 (2H, s), 4.32 (2H, s), 6.57 (1H, d, J=7.94 Hz), 6.83 (1H, d, J=2.74 Hz), 7.28 (1H, dd, J=7.26, 2.05 Hz), 7.64 (1H, d, J=2.46 Hz), 8.10 (1H, q, J=4.56 Hz), 8.45 (1H, s), 8.52 (1H, dd, J=1.92, 0.82 Hz), 8.64-8.73 (1H, m); ESIMS found for $C_{24}H_{27}N_7O_3$ m/z 462.2 (M+1).

103

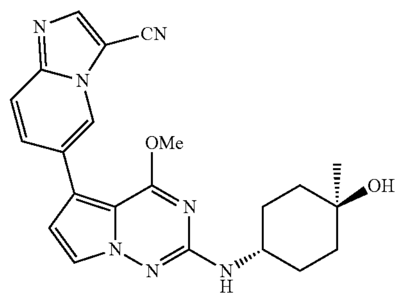

6-(2-((trans-4-Hydroxy-4-methylcyclohexyl)amino)-4-methoxypyrrolo[2,1-f][1,2,4]triazin-5-yl)imidazo[1,2-a]pyridine-3-carbonitrile 103

Beige solid (12 mg, 0.029 mmol, 8.0% yield). $^1$H NMR (499 MHz, DMSO-$d_6$) δ ppm 1.14 (3H, s), 1.38-1.53 (4H, m), 1.56-1.66 (3H, m), 1.83-1.93 (2H, m), 3.60-3.71 (1H, m), 4.01 (3H, s), 4.23 (1H, s), 6.56 (1H, d, J=7.94 Hz), 6.89 (1H, d, J=2.74 Hz), 7.67 (1H, d, J=2.74 Hz), 7.81-7.92 (2H, m), 8.44 (1H, s), 8.77-8.86 (1H, m); ESIMS found for $C_{22}H_{23}N_7O_2$ m/z 418.2 (M+1).

104

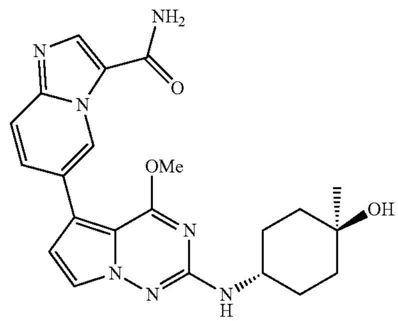

6-(2-((trans-4-Hydroxy-4-methylcyclohexyl)amino)-4-methoxypyrrolo[2,1-f][1,2,4]triazin-5-yl)imidazo[1,2-a]pyridine-3-carboxamide 104

Beige solid (2.2 mg, 0.005 mmol, 1.4% yield). $^1$H NMR (499 MHz, DMSO-$d_6$) δ ppm 1.14 (3H, s), 1.39-1.48 (4H, m), 1.57-1.63 (2H, m), 1.85-1.91 (2H, m), 3.60-3.72 (1H, m), 3.99 (3H, s), 4.23 (1H, s), 6.49 (1H, d, J=7.94 Hz), 6.75 (1H, d, J=2.46 Hz), 7.34 (1H, br s), 7.65 (1H, d, J=2.74 Hz), 7.69 (2H, s), 7.95 (1H, br s), 8.33 (1H, s), 9.84 (1H, s); ESIMS found for $C_{22}H_{25}N_7O_3$ m/z 436.25 (M+1).

107

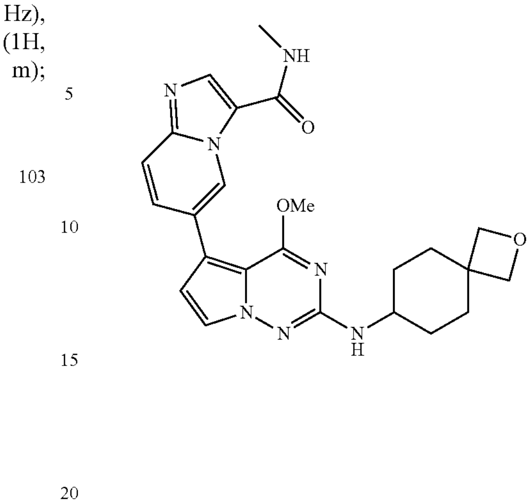

6-(2-((2-Oxaspiro[3.5]nonan-7-yl)amino)-4-methoxypyrrolo[2,1-f][1,2,4]triazin-5-yl)-N-methylimidazo[1,2-a]pyridine-3-carboxamide 107

Off-white solid (37 mg, 0.080 mmol, 32.3% yield). $^1$H NMR (499 MHz, DMSO-$d_6$) δ ppm 1.17-1.37 (2H, m), 1.52 (2H, td, J=12.87, 3.29 Hz), 1.81-1.91 (2H, m), 2.07 (2H, br d, J=13.14 Hz), 2.82 (3H, d, J=4.65 Hz), 3.48-3.61 (1H, m), 4.00 (3H, s), 4.24 (2H, s), 4.32 (2H, s), 6.52 (1H, d, J=7.94 Hz), 6.75 (1H, d, J=2.46 Hz), 7.63 (1H, d, J=2.46 Hz), 7.68 (2H, d, J=1.37 Hz), 8.26 (1H, s), 8.43 (1H, q, J=4.38 Hz), 9.80 (1H, t, J=1.37 Hz); ESIMS found for $C_{24}H_{27}N_7O_3$ m/z 462.2 (M+1).

108

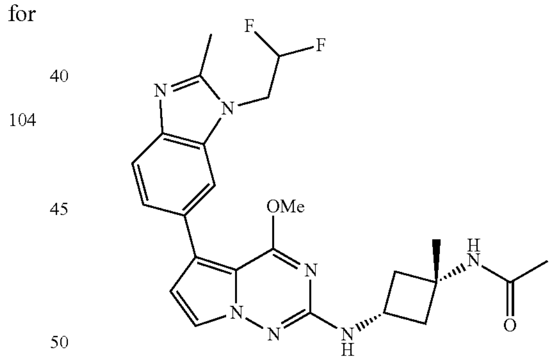

N-(cis-3-((5-(1-(2,2-Difluoroethyl)-2-methyl-1H-benzo[d]imidazol-6-yl)-4-methoxypyrrolo[2,1-f][1,2,4]triazin-2-yl)amino)-1-methylcyclobutyl)acetamide 108

White solid (5 mg, 0.0103 mmol, 28.5% yield). $^1$H NMR (499 MHz, DMSO-$d_6$) δ ppm 1.38 (3H, s), 1.76 (3H, s), 2.10-2.21 (2H, m), 2.42 (2H, ddd, J=9.65, 7.46, 2.60 Hz), 2.56 (3H, s), 3.91 (3H, s), 3.96-4.10 (1H, m), 4.69-4.81 (2H, m), 6.47 (1H, tt, J=54.40, 3.00 Hz), 6.61 (1H, d, J=2.74 Hz), 6.90 (1H, d, J=7.12 Hz), 7.35 (1H, dd, J=8.21, 1.64 Hz), 7.49 (1H, d, J=8.21 Hz), 7.59 (1H, d, J=2.74 Hz), 7.69 (1H, s), 8.02 (1H, s); ESIMS found for $C_{24}H_{27}F_2N_7O_2$ m/z 484.2 (M+1).

109

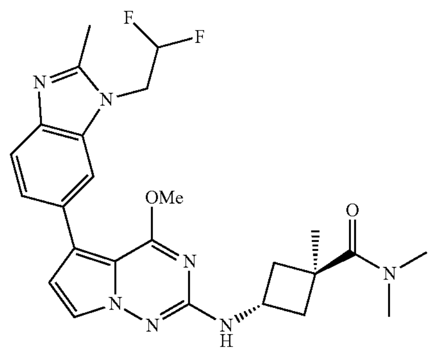

trans-3-((5-(1-(2,2-Difluoroethyl)-2-methyl-1H-benzo[d]imidazol-6-yl)-4-methoxypyrrolo[2,1-f][1,2,4]triazin-2-yl)amino)-N,N,1-trimethylcyclobutane-1-carboxamide 109

White solid (20 mg, 0.040 mmol, 75.6% yield). $^1$H NMR (499 MHz, DMSO-$d_6$) δ ppm 1.39 (3H, s), 1.94-2.02 (2H, m), 2.56 (3H, s), 2.81-2.94 (8H, m), 3.85-3.95 (1H, m), 3.92 (3H, s), 4.68-4.80 (2H, m), 6.47 (1H, tt, J=54.30, 3.00 Hz), 6.60 (1H, d, J=2.46 Hz), 6.98 (1H, d, J=6.57 Hz), 7.35 (1H, dd, J=8.35, 1.51 Hz), 7.49 (1H, d, J=8.21 Hz), 7.59 (1H, d, J=2.46 Hz), 7.69 (1H, s); ESIMS found for $C_{25}H_{29}F_2N_7O_2$ m/z 498.3 (M+1).

112

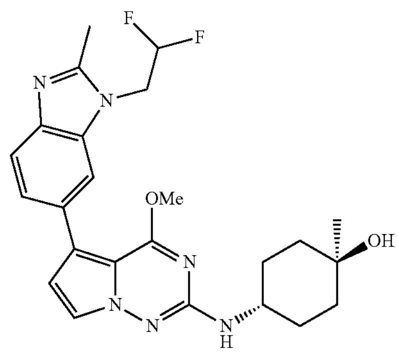

trans-4-((5-(1-(2,2-Difluoroethyl)-2-methyl-1H-benzo[d]imidazol-6-yl)-4-methoxypyrrolo[2,1-f][1,2,4]triazin-2-yl)amino)-1-methylcyclohexan-1-ol 112

White solid (8 mg, 0.020 mmol, 6.4% yield). $^1$H NMR (499 MHz, DMSO-$d_6$) δ ppm 1.15 (3H, s), 1.38-1.51 (4H, m), 1.57-1.64 (2H, m), 1.83-1.92 (2H, m), 2.56 (3H, s), 3.59-3.70 (1H, m), 3.92 (3H, s), 4.23 (1H, br s), 4.74 (2H, td, J=16.02, 2.46 Hz), 6.47 (1H, tt, J=54.50, 3.00 Hz), 6.38 (1H, d, J=7.94 Hz), 6.60 (1H, d, J=2.46 Hz), 7.35 (1H, dd, J=8.35, 1.51 Hz), 7.49 (1H, d, J=8.49 Hz), 7.59 (1H, d, J=2.74 Hz), 7.69 (1H, s); ESIMS found for $C_{24}H_{28}F_2N_6O_2$ m/z 471.25 (M+1).

113

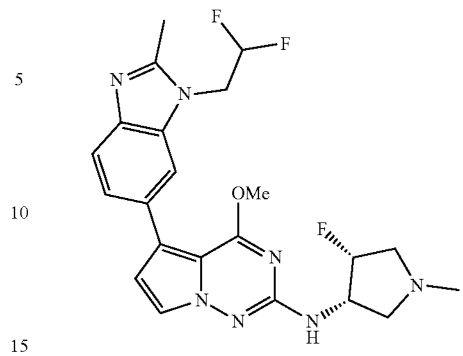

5-(1-(2,2-Difluoroethyl)-2-methyl-1H-benzo[d]imidazol-6-yl)-N-((3S,4R)-4-fluoro-1-methylpyrrolidin-3-yl)-4-methoxypyrrolo[2,1-f][1,2,4]triazin-2-amine 113

White fluffy solid (13 mg, 0.028 mmol, 84.0% yield). $^1$H NMR (499 MHz, DMSO-$d_6$) δ ppm 2.31 (3H, s), 2.56 (3H, s), 2.57-2.65 (2H, m), 2.88-2.96 (1H, m), 3.16 (1H, ddd, J=29.35, 11.64, 4.79 Hz), 3.94 (3H, s), 4.19-4.35 (1H, m), 4.74 (2H, td, J=16.08, 2.60 Hz), 5.21 (1H, dtd, J=55.95, 5.07, 5.07, 1.92 Hz), 6.47 (1H, tt, J=54.30, 3.00 Hz), 6.64 (1H, d, J=2.46 Hz), 6.65 (1H, d, J=7.94 Hz), 7.36 (1H, dd, J=8.21, 1.64 Hz), 7.50 (1H, d, J=8.21 Hz), 7.61 (1H, d, J=2.74 Hz), 7.70 (1H, s); ESIMS found for $C_{22}H_{24}F_3N_7O$ m/z 460.2 (M+1).

114

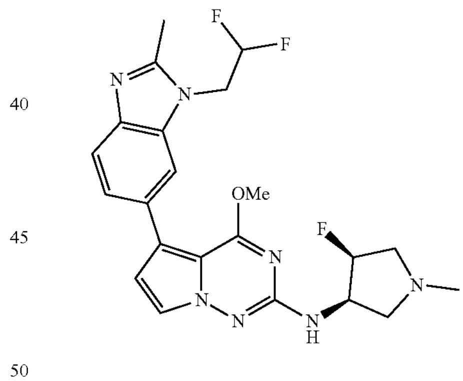

5-(1-(2,2-Difluoroethyl)-2-methyl-1H-benzo[d]imidazol-6-yl)-N-((3R,4S)-4-fluoro-1-methylpyrrolidin-3-yl)-4-methoxypyrrolo[2,1-f][1,2,4]triazin-2-amine 114

White fluffy solid (13 mg, 0.028 mmol, 84.0% yield). $^1$H NMR (499 MHz, DMSO-$d_6$) δ ppm 2.31 (3H, s), 2.56 (3H, s), 2.58-2.65 (2H, m), 2.88-2.96 (1H, m), 3.16 (1H, ddd, J=29.60, 11.77, 4.93 Hz), 3.94 (3H, s), 4.20-4.35 (1H, m), 4.75 (2H, td, J=16.02, 2.46 Hz), 5.21 (1H, dtd, J=55.95, 5.00, 5.00, 2.05 Hz), 6.47 (1H, tt, J=54.30, 3.00 Hz), 6.64 (1H, d, J=2.46 Hz), 6.66 (1H, d, J=7.94 Hz), 7.36 (1H, dd, J=8.21, 1.64 Hz), 7.50 (1H, d, J=8.21 Hz), 7.61 (1H, d, J=2.46 Hz), 7.70 (1H, s); ESIMS found for $C_{22}H_{24}F_3N_7O$ m/z 460.2 (M+1).

122

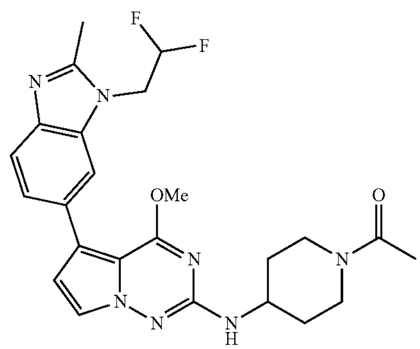

1-(4-((5-(1-(2,2-Difluoroethyl)-2-methyl-1H-benzo[d]imidazol-6-yl)-4-methoxypyrrolo[2,1-f][1,2,4]triazin-2-yl)amino)piperidin-1-yl)ethan-1-one 122

White solid (5 mg, 0.010 mmol, 3.9% yield). $^1$H NMR (499 MHz, DMSO-$d_6$) δ ppm 1.28-1.38 (1H, m), 1.39-1.51 (1H, m), 1.89-1.95 (1H, m), 1.95-2.00 (1H, m), 2.01 (3H, s), 2.56 (3H, s), 2.70-2.80 (1H, m), 3.09-3.21 (1H, m), 3.77-3.87 (2H, m), 3.92 (3H, s), 4.28 (1H, br d, J=14.51 Hz), 4.69-4.81 (2H, m), 6.47 (1H, tt, J=54.50, 3.00 Hz), 6.60-6.63 (2 H, m), 7.35 (1H, dd, J=8.21, 1.64 Hz), 7.50 (1H, d, J=8.49 Hz), 7.59 (1H, d, J=2.46 Hz), 7.69 (1H, s); ESIMS found for $C_{24}H_{27}F_2N_7O_2$ m/z 484.25 (M+1).

124

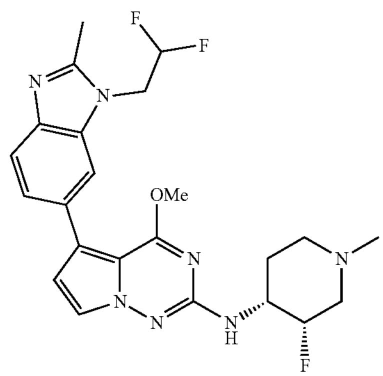

5-(1-(2,2-Difluoroethyl)-2-methyl-1H-benzo[d]imidazol-6-yl)-N-((3S,4R)-3-fluoro-1-methylpiperidin-4-yl)-4-methoxypyrrolo[2,1-f][1,2,4]triazin-2-amine 124

White solid (17 mg, 0.036 mmol, 33.9% yield). $^1$H NMR (499 MHz, DMSO-$d_6$) δ ppm 1.64-1.74 (1H, m), 1.85-1.99 (1H, m), 2.06 (1H, br t, J=11.36 Hz), 2.18 (1H, dd, J=37.85, 12.60 Hz), 2.19 (3H, s), 2.56 (3H, s), 2.80 (1H, br d, J=10.13 Hz), 3.01-3.11 (1H, m), 3.67-3.84 (1H, m), 3.93 (3H, s), 4.74 (2H, td, J=16.08, 2.60 Hz), 4.91 (1H, d, J=50.20 Hz), 6.47 (1H, tt, J=54.30, 3.00 Hz), 6.51 (1H, d, J=7.94 Hz), 6.63 (1H, d, J=2.46 Hz), 7.36 (1H, dd, J=8.49, 1.64 Hz), 7.50 (1H, d, J=8.49 Hz), 7.59 (1H, d, J=2.46 Hz), 7.70 (1H, s); ESIMS found for $C_{23}H_{26}F_3N_7O$ m/z 474.3 (M+1).

127

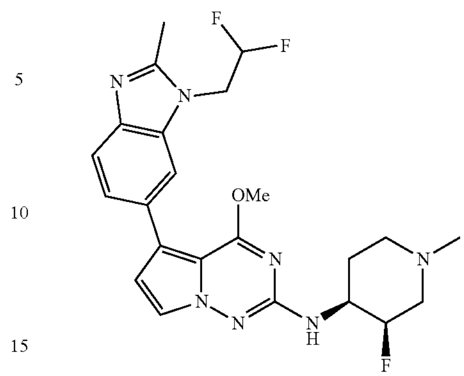

5-(1-(2,2-Difluoroethyl)-2-methyl-1H-benzo[d]imidazol-6-yl)-N-((3R,4S)-3-fluoro-1-methylpiperidin-4-yl)-4-methoxypyrrolo[2,1-f][1,2,4]triazin-2-amine 127

White solid (6 mg, 0.013 mmol, 38.8% yield). $^1$H NMR (499 MHz, DMSO-$d_6$) δ ppm 1.23 (3H, s), 1.65-1.74 (1H, m), 1.92 (1H, qd, J=12.23, 4.11 Hz), 2.03-2.12 (1H, m), 2.13-2.29 (1H, m), 2.20 (3H, s), 2.56 (3H, s), 2.81 (1H, br d, J=9.86 Hz), 3.06 (1H, br t, J=10.40 Hz), 3.68-3.83 (1H, m), 3.93 (3H, s), 4.74 (2H, td, J=16.08, 2.60 Hz), 4.92 (1H, d, J=49.65 Hz), 6.47 (1H, tt, J=54.40, 3.00 Hz), 6.51 (1H, d, J=7.94 Hz), 6.63 (1H, d, J=2.46 Hz), 7.36 (1H, dd, J=8.35, 1.51 Hz), 7.50 (1H, d, J=8.21 Hz), 7.59 (1H, d, J=2.74 Hz), 7.69 (1H, s); ESIMS found for $C_{23}H_{26}F_3N_7O$ m/z 474.3 (M+1).

129

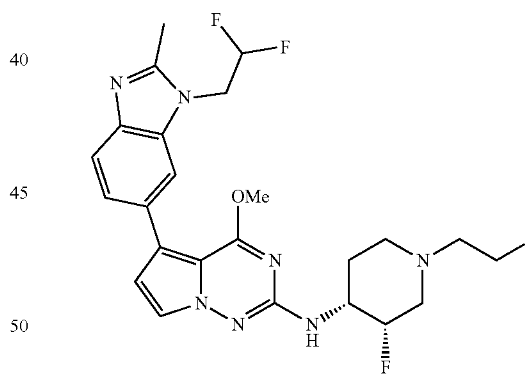

5-(1-(2,2-Difluoroethyl)-2-methyl-1H-benzo[d]imidazol-6-yl)-N-((3S,4R)-3-fluoro-1-(2-fluoroethyl)piperidin-4-yl)-4-methoxypyrrolo[2,1-f][1,2,4]triazin-2-amine 129

White fluffy solid (28 mg, 0.055 mmol, 82.1% yield). $^1$H NMR (499 MHz, DMSO-$d_6$) δ ppm 1.65-1.75 (1H, m), 1.92 (1H, qd, J=12.32, 4.11 Hz), 2.25 (1H, br t, J=11.23 Hz), 2.38 (1H, dd, J=37.60, 12.90 Hz), 2.56 (3H, s), 2.63-2.74 (2H, m), 2.88-2.97 (1H, m), 3.13-3.21 (1H, m), 3.71-3.87 (1H, m), 3.93 (3H, s), 4.54 (2H, dt, J=48.00, 4.95 Hz), 4.74 (2H, td, J=16.02, 2.19 Hz), 4.92 (1H, d, J=49.40 Hz), 6.47 (1H, tt, J=54.30, 3.00 Hz), 6.53 (1H, d, J=7.94 Hz), 6.63 (1H, d, J=2.74 Hz), 7.36 (1H, dd, J=8.35, 1.51 Hz), 7.50 (1H, d, J=8.21 Hz), 7.59 (1H, d, J=2.46 Hz), 7.70 (1H, s); ESIMS found for $C_{24}H_{27}F_4N_7O$ m/z 506.3 (M+1).

137

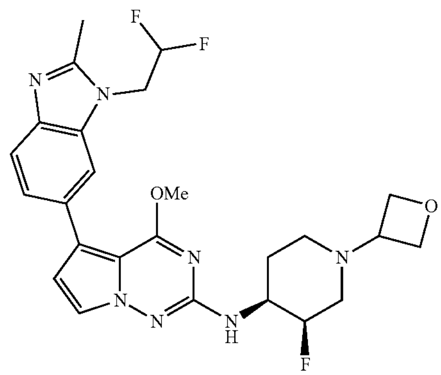

5-(1-(2,2-Difluoroethyl)-2-methyl-1H-benzo[d]imidazol-6-yl)-N-((3R,4S)-3-fluoro-1-(oxetan-3-yl)piperidin-4-yl)-4-methoxypyrrolo[2,1-f][1,2,4]triazin-2-amine 137

White solid (27 mg, 0.052 mmol, 48.1% yield). $^1H$ NMR (499 MHz, DMSO-$d_6$) δ ppm 1.69-1.77 (1H, m), 1.91 (1H, qd, J=12.09, 3.42 Hz), 1.98-2.06 (1H, m), 2.09-2.22 (1H, m), 2.56 (3H, s), 2.76 (1H, br d, J=10.40 Hz), 2.94-3.04 (1H, m), 3.49 (1H, quin, J=6.43 Hz), 3.74-3.89 (1H, m), 3.94 (3H, s), 4.40 (1H, t, J=6.16 Hz), 4.46 (1H, t, J=6.16 Hz), 4.54 (2H, td, J=6.43, 3.01 Hz), 4.74 (2H, td, J=16.08, 2.60 Hz), 4.94 (1H, d, J=49.65 Hz), 6.47 (1H, tt, J=54.60, 3.00 Hz), 6.57 (1H, d, J=7.94 Hz), 6.63 (1H, d, J=2.46 Hz), 7.36 (1H, dd, J=8.49, 1.64 Hz), 7.50 (1H, d, J=8.21 Hz), 7.58 (1H, d, J=2.74 Hz), 7.69 (1H, s); ESIMS found for $C_{25}H_{28}F_3N_7O_2$ m/z 516.3 (M+1).

138

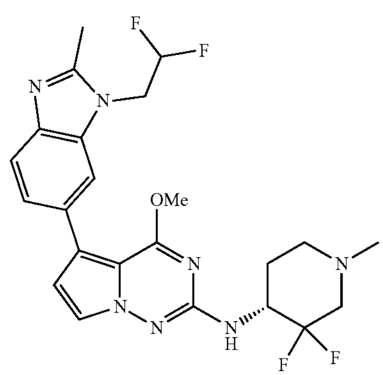

(R)—N-(3,3-Difluoro-1-methylpiperidin-4-yl)-5-(1-(2,2-difluoroethyl)-2-methyl-1H-benzo[d]imidazol-6-yl)-4-methoxypyrrolo[2,1-f][1,2,4]triazin-2-amine 138

White fluffy solid (9 mg, 0.018 mmol, 58.3% yield). $^1H$ NMR (499 MHz, DMSO-$d_6$) δ ppm 1.74-1.89 (2H, m), 2.13-2.22 (1H, m), 2.26 (3H, s), 2.32-2.45 (1H, m), 2.56 (3H, s), 2.78 (1H, br d, J=11.50 Hz), 3.00-3.10 (1H, m), 3.95 (3H, s), 4.16-4.32 (1H, m), 4.74 (2H, td, J=15.88, 2.46 Hz), 6.47 (1H, tt, J=54.55, 3.25 Hz), 6.64 (1H, d, J=2.74 Hz), 6.72 (1H, d, J=9.58 Hz), 7.36 (1H, dd, J=8.35, 1.51 Hz), 7.50 (1H, d, J=8.21 Hz), 7.60 (1H, d, J=2.46 Hz), 7.70 (1H, s); ESIMS found for $C_{23}H_{25}F_4N_7O$ m/z 492.2 (M+1).

139

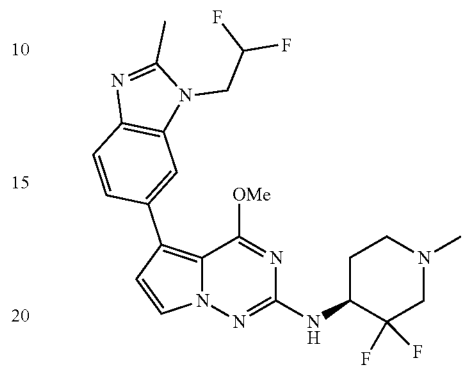

(S)—N-(3,3-Difluoro-1-methylpiperidin-4-yl)-5-(1-(2,2-difluoroethyl)-2-methyl-1H-benzo[d]imidazol-6-yl)-4-methoxypyrrolo[2,1-f][1,2,4]triazin-2-amine 139

White fluffy solid (8 mg, 0.016 mmol, 45.7% yield). $^1H$ NMR (499 MHz, DMSO-$d_6$) δ ppm 1.74-1.90 (2H, m), 2.13-2.22 (1H, m), 2.26 (3H, s), 2.32-2.45 (1H, m), 2.56 (3H, s), 2.78 (1H, br d, J=11.50 Hz), 3.00-3.10 (1H, m), 3.95 (3H, s), 4.16-4.32 (1H, m), 4.74 (2H, td, J=16.02, 2.46 Hz), 6.47 (1H, tt, J=54.40, 3.25 Hz), 6.64 (1H, d, J=2.46 Hz), 6.72 (1H, d, J=9.31 Hz), 7.36 (1H, dd, J=8.35, 1.51 Hz), 7.50 (1H, d, J=8.21 Hz), 7.60 (1H, d, J=2.74 Hz), 7.70 (1H, s); ESIMS found for $C_{23}H_{25}F_4N_7O$ m/z 492.2 (M+1).

140

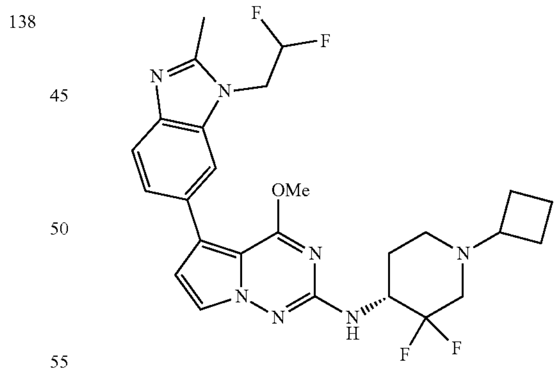

(R)—N-(1-Cyclobutyl-3,3-difluoropiperidin-4-yl)-5-(1-(2,2-difluoroethyl)-2-methyl-1H-benzo[d]imidazol-6-yl)-4-methoxypyrrolo[2,1-f][1,2,4]triazin-2-amine 140

White fluffy solid (10 mg, 0.019 mmol, 56.1% yield). $^1H$ NMR (499 MHz, DMSO-$d_6$) δ ppm 1.56-1.69 (2H, m), 1.71-1.92 (4H, m), 2.00 (3H, br s), 2.58 (3H, s), 2.71-2.94 (2H, m), 2.95-3.09 (1H, m), 3.95 (3H, s), 4.18-4.38 (1H, m), 4.76 (2H, td, J=15.90, 2.45 Hz), 6.48 (1H, tt, J=54.40, 3.00

Hz), 6.65 (1H, d, J=2.46 Hz), 6.76 (1H, br s), 7.38 (1H, dd, J=8.35, 1.51 Hz), 7.52 (1H, d, J=8.21 Hz), 7.60 (1H, d, J=2.46 Hz), 7.72 (1H, s); ESIMS found for $C_{26}H_{29}F_4N_7O$ m/z 532.3 (M+1).

141

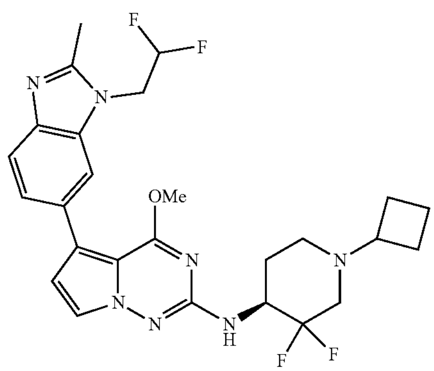

(S)—N-(1-Cyclobutyl-3,3-difluoropiperidin-4-yl)-5-(1-(2,2-difluoroethyl)-2-methyl-1H-benzo[d]imidazol-6-yl)-4-methoxypyrrolo[2,1-f][1,2,4]triazin-2-amine 141

White fluffy solid (11 mg, 0.021 mmol, 58.1% yield). $^1$H NMR (499 MHz, DMSO-$d_6$) δ ppm 1.76-1.85 (1H, m), 1.86-1.93 (1H, m), 2.16 (1H, br t, J=10.27 Hz), 2.33-2.47 (1H, m), 2.58 (3H, s), 2.76 (1H, br d, J=11.22 Hz), 2.96-3.07 (1H, m), 3.60 (1H, quin, J=6.30 Hz), 3.95 (3H, s), 4.23-4.37 (1H, m), 4.44 (2H, dt, J=15.06, 6.16 Hz), 4.55 (2H, td, J=6.57, 3.56 Hz), 4.77 (2H, td, J=15.90, 2.40 Hz), 6.48 (1H, tt, J=54.40, 3.00 Hz), 6.65 (1H, d, J=2.46 Hz), 6.80 (1H, d, J=9.31 Hz), 7.39 (1H, dd, J=8.35, 1.51 Hz), 7.52 (1H, d, J=8.21 Hz), 7.60 (1H, d, J=2.46 Hz), 7.73 (1H, s); ESIMS found for $C_{26}H_{29}F_4N_7O$ m/z 532.3 (M+1).

142

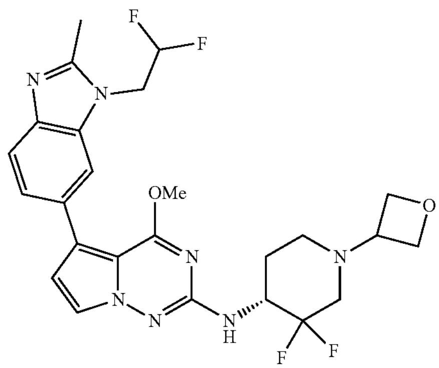

(R)—N-(3,3-Difluoro-1-(oxetan-3-yl)piperidin-4-yl)-5-(1-(2,2-difluoroethyl)-2-methyl-1H-benzo[d]imidazol-6-yl)-4-methoxypyrrolo[2,1-f][1,2,4]triazin-2-amine 142

White fluffy solid (14 mg, 0.026 mmol, 50.1% yield). $^1$H NMR (499 MHz, DMSO-$d_6$) δ ppm 1.76-1.85 (1H, m), 1.86-1.93 (1H, m), 2.16 (1H, br t, J=10.27 Hz), 2.33-2.47 (1H, m), 2.58 (3H, s), 2.76 (1H, br d, J=11.22 Hz), 2.96-3.07 (1H, m), 3.60 (1H, quin, J=6.30 Hz), 4.23-4.37 (1H, m), 4.44 (2H, dt, J=15.06, 6.16 Hz), 4.55 (2H, td, J=6.57, 3.56 Hz), 4.77 (2H, td, J=15.90, 2.40 Hz), 6.48 (1H, tt, J=54.40, 3.00 Hz), 6.65 (1H, d, J=2.46 Hz), 6.80 (1H, d, J=9.31 Hz), 7.39 (1H, dd, J=8.35, 1.51 Hz), 7.52 (1H, d, J=8.21 Hz), 7.60 (1H, d, J=2.46 Hz), 7.73 (1H, s); ESIMS found for $C_{25}H_{27}F_4N_7O_2$ m/z 534.3 (M+1).

143

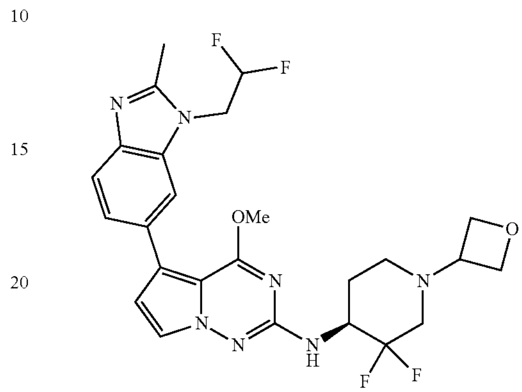

(S)—N-(3,3-Difluoro-1-(oxetan-3-yl)piperidin-4-yl)-5-(1-(2,2-difluoroethyl)-2-methyl-1H-benzo[d]imidazol-6-yl)-4-methoxypyrrolo[2,1-f][1,2,4]triazin-2-amine 143

White fluffy solid (11 mg, 0.021 mmol, 39.4% yield). $^1$H NMR (499 MHz, DMSO-$d_6$) δ ppm 1.75-1.85 (1H, m), 1.86-1.93 (1H, m), 2.12-2.22 (1H, m), 2.33-2.46 (1H, m), 2.58 (3H, s), 2.76 (1H, br d, J=11.50 Hz), 2.97-3.07 (1H, m), 3.60 (1H, quin, J=6.23 Hz), 3.95 (3H, s), 4.23-4.36 (1H, m), 4.44 (2H, dt, J=14.92, 6.23 Hz), 4.55 (2H, td, J=6.57, 3.56 Hz), 4.77 (2H, td, J=16.00, 2.45 Hz), 6.48 (1H, tt, J=54.40, 3.00 Hz), 6.65 (1H, d, J=2.74 Hz), 6.80 (1H, d, J=9.31 Hz), 7.39 (1H, dd, J=8.35, 1.51 Hz), 7.52 (1H, d, J=8.21 Hz), 7.60 (1H, d, J=2.74 Hz), 7.73 (1H, s); ESIMS found for $C_{25}H_{27}F_4N_7O_2$ m/z 534.3 (M+1).

148

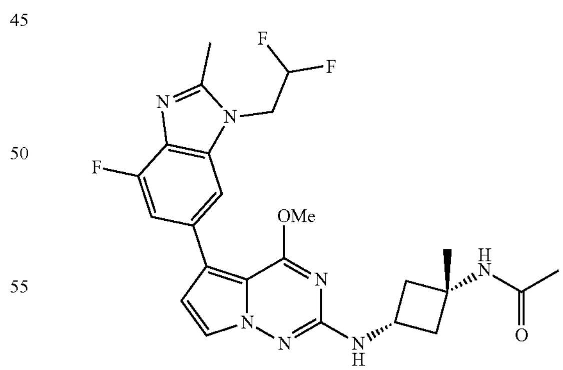

N-((1s,3s)-3-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-1-methylcyclobutyl)acetamide 148

White solid (15 mg, 0.030 mmol, 24.2% yield). $^1$H NMR (499 MHz, DMSO-$d_6$) δ ppm 1.38 (3H, s), 1.76 (3H, s), 2.15

(2H, br dd, J=11.50, 8.76 Hz), 2.37-2.45 (2H, m), 2.57 (3H, s), 3.93 (3H, s), 4.02 (1H, sxt, J=7.72 Hz), 4.77 (2H, td, J=16.02, 2.46 Hz), 6.48 (1H, tt, J=54.30, 3.00 Hz), 6.66 (1H, d, J=2.74 Hz), 6.94 (1H, d, J=6.84 Hz), 7.19 (1H, dd, J=12.18, 1.23 Hz), 7.57 (1H, s), 7.60 (1H, d, J=2.74 Hz), 8.02 (1H, s); ESIMS found for $C_{24}H_{26}F_3N_7O_2$ m/z 502.2 (M+1).

149

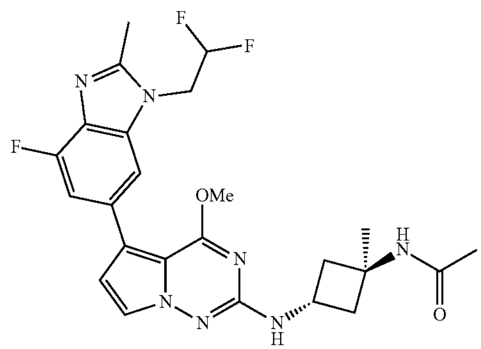

N-((1r,3r)-3-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-1-methylcyclobutyl)acetamide 149

White solid (15 mg, 0.030 mmol, 22.9% yield). $^1$H NMR (499 MHz, DMSO-$d_6$) δ ppm 1.36 (3H, s), 1.81 (3H, s), 1.90-2.00 (2H, m), 2.58 (3H, s), 2.60-2.66 (2H, m), 3.93 (3H, s), 4.18 (1H, sxt, J=7.72 Hz), 4.77 (2H, td, J=16.08, 2.33 Hz), 6.48 (1H, tt, J=54.30, 3.00 Hz), 6.66 (1H, d, J=2.46 Hz), 6.95 (1H, d, J=7.39 Hz), 7.19 (1H, dd, J=12.18, 1.23 Hz), 7.57 (1H, s), 7.58 (1H, d, J=2.46 Hz), 7.93 (1H, s); ESIMS found for $C_{24}H_{26}F_3N_7O_2$ m/z 502.2 (M+1).

151

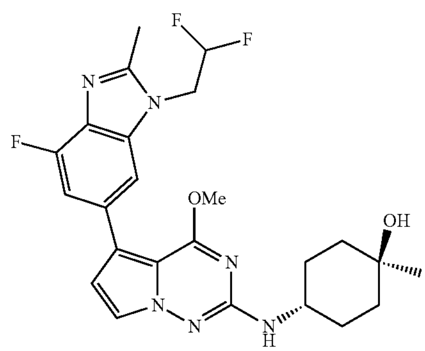

trans-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylcyclohexan-1-ol 151

White solid (5 mg, 0.010 mmol, 6.8% yield). $^1$H NMR (499 MHz, DMSO-$d_6$) δ ppm 1.14 (3H, s), 1.36-1.53 (4H, m), 1.56-1.65 (2H, m), 1.83-1.92 (2H, m), 2.58 (3H, s), 3.59-3.70 (1H, m), 3.94 (3H, s), 4.23 (1H, s), 4.70-4.84 (2H, m), 6.48 (1H, tt, J=54.30, 3.00 Hz), 6.42 (1H, d, J=7.94 Hz), 6.65 (1H, d, J=2.74 Hz), 7.19 (1H, dd, J=12.18, 1.23 Hz), 7.57 (1H, s), 7.60 (1H, d, J=2.74 Hz); ESIMS found for $C_{24}H_{27}F_3N_6O_2$ m/z 489.3 (M+1).

159

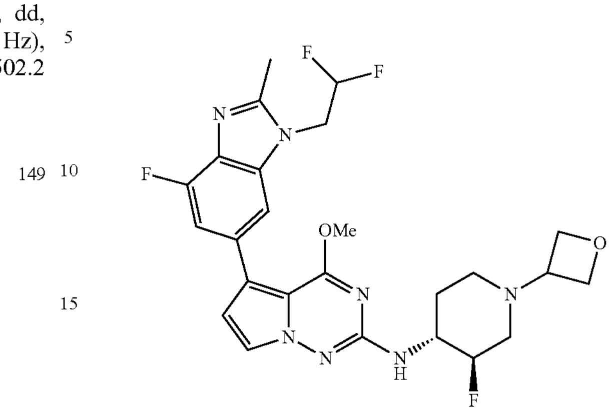

5-(1-(2,2-Difluoroethyl)-4-fluoro-2-methyl-1H-benzo[d]imidazol-6-yl)-N-((3R,4R)-3-fluoro-1-(oxetan-3-yl)piperidin-4-yl)-4-methoxypyrrolo[2,1-f][1,2,4]triazin-2-amine 159

Fluffy white solid (6 mg, 0.011 mmol, 17.4% yield). $^1$H NMR (499 MHz, DMSO-$d_6$) δ ppm 1.67-1.76 (1H, m), 1.91 (1H, qd, J=12.05, 3.56 Hz), 1.98-2.06 (1H, m), 2.15 (1H, dd, J=36.75, 12.87 Hz), 2.58 (3H, s), 2.76 (1H, br d, J=11.77 Hz), 2.98 (1H, br t, J=10.54 Hz), 3.49 (1H, quin, J=6.37 Hz), 3.75-3.89 (1H, m), 3.96 (3H, s), 4.40 (1H, t, J=6.16 Hz), 4.46 (1H, t, J=6.16 Hz), 4.54 (2H, td, J=6.57, 3.01 Hz), 4.77 (2H, td, J=16.02, 2.74 Hz), 4.93 (1H, d, J=49.10 Hz), 6.48 (1H, tt, J=54.30, 3.00 Hz), 6.62 (1H, d, J=7.67 Hz), 6.68 (1H, d, J=2.46 Hz), 7.20 (1H, dd, J=12.32, 1.10 Hz), 7.58 (1H, s), 7.59 (1H, d, J=2.74 Hz); ESIMS found for $C_{25}H_{27}F_4N_7O_2$ m/z 534.2 (M+1).

161

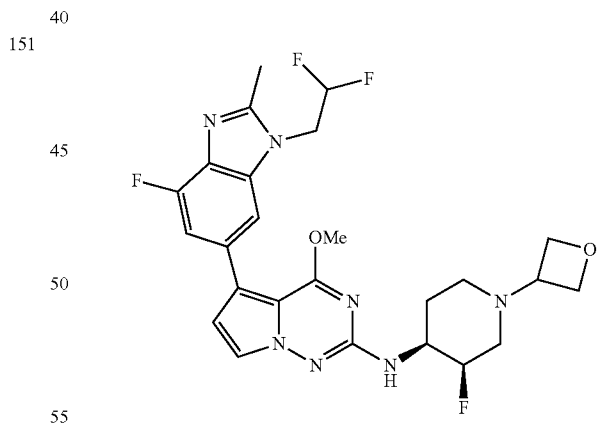

5-(1-(2,2-Difluoroethyl)-4-fluoro-2-methyl-1H-benzo[d]imidazol-6-yl)-N-((3R,4S)-3-fluoro-1-(oxetan-3-yl)piperidin-4-yl)-4-methoxypyrrolo[2,1-f][1,2,4]triazin-2-amine 161

White solid (11 mg, 0.021 mmol, 35.2% yield). $^1$H NMR (499 MHz, DMSO-$d_6$) δ ppm 1.68-1.77 (1H, m), 1.85-1.97 (1H, m), 1.98-2.06 (1H, m), 2.15 (1H, dd, J=37.05, 12.59 Hz), 2.58 (3H, s), 2.71-2.81 (1H, m), 2.94-3.04 (1H, m), 3.49 (1H, quin, J=6.43 Hz), 3.73-3.89 (1H, m), 3.96 (3H, s), 4.40 (1H, t, J=6.16 Hz), 4.46 (1H, t, J=6.16 Hz), 4.54 (2H, td, J=6.57, 3.01 Hz), 4.78 (2H, td, J=16.02, 2.46 Hz), 4.93 (1H, d, J=49.90 Hz), 6.49 (1H, tt, J=54.30, 3.00 Hz), 6.63 (1H, d, J=7.94 Hz), 6.68 (1H, d, J=2.46 Hz), 7.20 (1H, dd, J=12.32, 1.37 Hz), 7.58 (1H, s), 7.60 (1H, d, J=2.46 Hz); ESIMS found for $C_{25}H_{27}F_4N_7O_2$ m/z 534.2 (M+1).

164

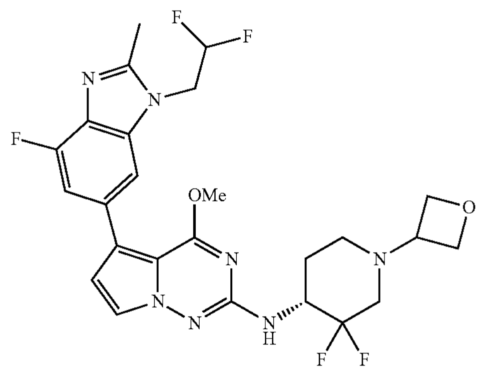

(R)—N-(3,3-Difluoro-1-(oxetan-3-yl)piperidin-4-yl)-5-(1-(2,2-difluoroethyl)-4-fluoro-2-methyl-1H-benzo[d]imidazol-6-yl)-4-methoxypyrrolo[2,1-f][1,2,4]triazin-2-amine 164

Yellowish-white solid (8 mg, 0.015 mmol, 14.4% yield). $^1$H NMR (499 MHz, DMSO-$d_6$) δ ppm 1.76-1.85 (1H, m), 1.86-1.93 (1H, m), 2.13-2.22 (1H, m), 2.40 (1H, dd, J=27.15, 11.38 Hz), 2.58 (3H, s), 2.76 (1H, br d, J=11.23 Hz), 2.94-3.08 (1H, m), 3.60 (1H, quin, J=6.23 Hz), 3.93-4.01 (3H, m), 4.23-4.37 (1H, m), 4.44 (2H, dt, J=15.06, 6.16 Hz), 4.55 (2H, td, J=6.57, 3.56 Hz), 4.77 (2H, td, J=16.08, 2.33 Hz), 6.48 (1H, tt, J=54.30, 3.00 Hz), 6.70 (1H, d, J=2.46 Hz), 6.83 (1H, d, J=9.58 Hz), 7.17-7.24 (1H, m), 7.58 (1H, s), 7.60 (1H, d, J=2.74 Hz); ESIMS found for $C_{25}H_{26}F_5N_7O_2$ m/z 552.2 (M+1).

168

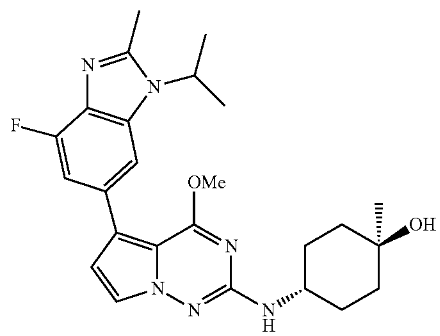

trans-4-((5-(4-Fluoro-1-isopropyl-2-methyl-1H-benzo[d]imidazol-6-yl)-4-methoxypyrrolo[2,1-f][1,2,4]triazin-2-yl)amino)-1-methylcyclohexan-1-ol 168

White solid (20 mg, 0.043 mmol, 16.0% yield). $^1$H NMR (499 MHz, DMSO-$d_6$) δ ppm 1.14 (3H, s), 1.38-1.50 (4H, m), 1.56-1.62 (2H, m), 1.59 (6H, d, J=6.84 Hz), 1.83-1.91 (2H, m), 2.58 (3H, s), 3.59-3.70 (1H, m), 3.94 (3H, s), 4.23 (1H, s), 4.76 (1H, spt, J=6.94 Hz), 6.42 (1H, d, J=7.94 Hz), 6.66 (1H, d, J=2.74 Hz), 7.11 (1H, dd, J=12.18, 1.23 Hz), 7.59 (1H, d, J=2.46 Hz), 7.63 (1H, d, J=1.09 Hz); ESIMS found for $C_{25}H_{31}FN_6O_2$ m/z 467.3 (M+1).

169

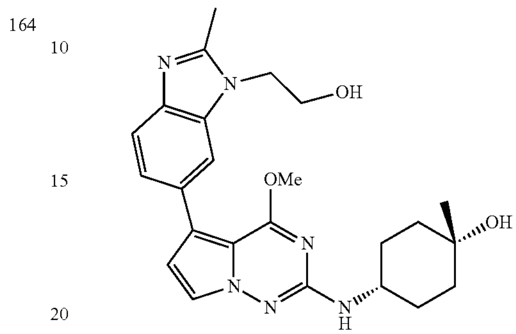

cis-3-((5-(1-(2-Hydroxyethyl)-2-methyl-1H-benzo[d]imidazol-6-yl)-4-methoxypyrrolo[2,1-f][1,2,4]triazin-2-yl)amino)-1-methylcyclobutan-1-ol 169

White solid (7 mg, 0.017 mmol, 49.4% yield). $^1$H NMR (499 MHz, DMSO-$d_6$) δ ppm 1.27 (3H, s), 2.01 (2H, td, J=8.90, 2.19 Hz), 2.35 (2H, ddd, J=8.90, 7.26, 2.74 Hz), 2.55 (3H, s), 3.67-3.73 (1H, m), 3.75 (2H, q, J=5.38 Hz), 3.93 (3H, s), 4.24 (2H, t, J=5.34 Hz), 4.91 (1H, s), 4.96 (1H, t, J=5.48 Hz), 6.60 (1H, d, J=2.74 Hz), 6.81 (1H, d, J=6.57 Hz), 7.30 (1H, dd, J=8.35, 1.51 Hz), 7.47 (1H, d, J=8.21 Hz), 7.58 (1H, d, J=2.46 Hz), 7.62 (1H, d, J=1.37 Hz); ESIMS found for $C_{22}H_{26}N_6O_3$ m/z 423.2 (M+1).

170

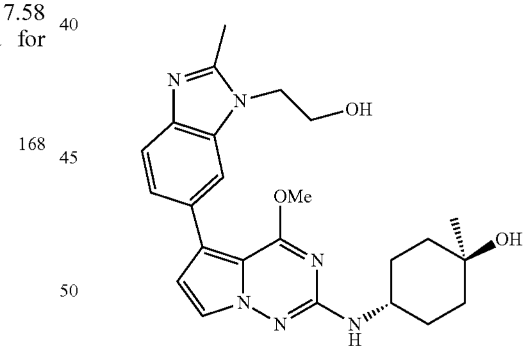

trans-3-((5-(1-(2-Hydroxyethyl)-2-methyl-1H-benzo[d]imidazol-6-yl)-4-methoxypyrrolo[2,1-f][1,2,4]triazin-2-yl)amino)-1-methylcyclobutan-1-ol 170

White solid (3 mg, 0.007 mmol, 127.0% yield). $^1$H NMR (499 MHz, DMSO-$d_6$) δ ppm 1.28 (3H, s), 1.96-2.01 (2H, m), 2.27-2.34 (2H, m), 2.61 (3H, s), 3.76 (2H, q, J=5.20 Hz), 3.93 (3H, s), 4.20-4.27 (1H, m), 4.29 (2H, br t, J=5.06 Hz), 4.78 (1H, s), 4.99 (1H, t, J=5.34 Hz), 6.62 (1H, d, J=2.46 Hz), 6.85 (1H, d, J=6.84 Hz), 7.38 (1H, br d, J=8.49 Hz), 7.52 (1H, d, J=8.21 Hz), 7.58 (1H, d, J=2.74 Hz), 7.70 (1H, s); ESIMS found for $C_{22}H_{26}N_6O_3$ m/z 423.2 (M+1).

171

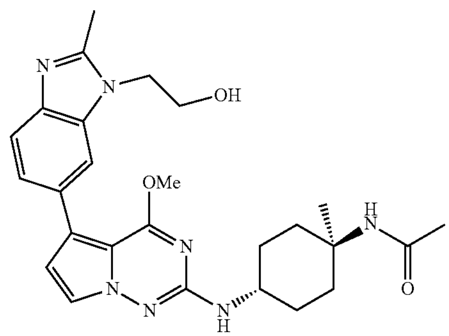

N-(trans-3-((5-(1-(2-Hydroxyethyl)-2-methyl-1H-benzo[d]imidazol-6-yl)-4-methoxypyrrolo[2,1-f][1,2,4]triazin-2-yl)amino)-1-methylcyclobutyl)acetamide 171

White solid (6 mg, 0.0130 mmol, 62.3% yield). $^1$H NMR (499 MHz, DMSO-$d_6$) δ ppm 1.36 (3H, s), 1.81 (3H, s), 1.91-1.99 (2H, m), 2.55 (3H, s), 2.59-2.67 (2H, m), 3.75 (2H, br d, J=3.83 Hz), 3.93 (3H, s), 4.14-4.21 (1H, m), 4.24 (2H, br t, J=5.34 Hz), 4.96 (1H, br s), 6.60 (1H, d, J=2.46 Hz), 6.89 (1H, d, J=7.12 Hz), 7.30 (1H, dd, J=8.08, 1.23 Hz), 7.47 (1H, br d, J=7.94 Hz), 7.56 (1H, d, J=2.46 Hz), 7.61 (1H, s), 7.93 (1H, s); ESIMS found for $C_{24}H_{29}N_7O_3$ m/z 464.3 (M+1).

172

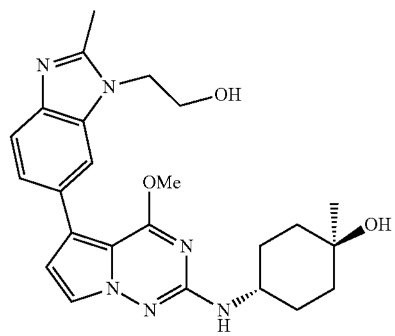

trans-4-((5-(1-(2-Hydroxyethyl)-2-methyl-1H-benzo[d]imidazol-6-yl)-4-methoxypyrrolo[2,1-f][1,2,4]triazin-2-yl)amino)-1-methylcyclohexan-1-ol 172

White solid (14 mg, 0.031 mmol, 54.8% yield). $^1$H NMR (499 MHz, DMSO-$d_6$) δ ppm 1.15 (3H, s), 1.37-1.51 (4H, m), 1.59 (2H, br d, J=10.95 Hz), 1.83-1.93 (2H, m), 2.55 (3H, s), 3.60-3.69 (1H, m), 3.75 (2H, q, J=5.48 Hz), 3.93 (3H, s), 4.20-4.27 (3H, m), 4.95 (1H, t, J=5.34 Hz), 6.36 (1H, d, J=7.94 Hz), 6.59 (1H, d, J=2.46 Hz), 7.30 (1H, dd, J=8.35, 1.51 Hz), 7.46 (1H, d, J=8.21 Hz), 7.58 (1H, d, J=2.74 Hz), 7.61 (1H, s); ESIMS found for $C_{24}H_{30}N_6O_3$ m/z 451.3 (M+1).

173

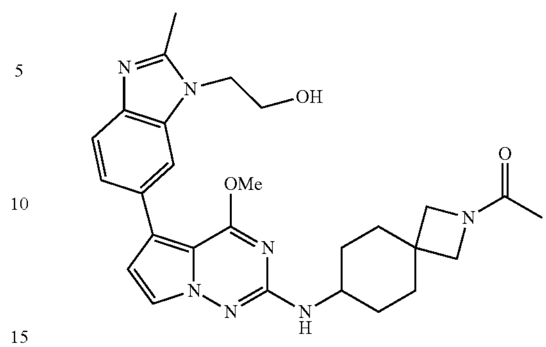

1-(7-((5-(1-(2-Hydroxyethyl)-2-methyl-1H-benzo[d]imidazol-6-yl)-4-methoxypyrrolo[2,1-f][1,2,4]triazin-2-yl)amino)-2-azaspiro[3.5]nonan-2-yl)ethan-1-one 173

Off-white solid (6 mg, 0.012 mmol, 50.0% yield). $^1$H NMR (499 MHz, DMSO-$d_6$) δ ppm 1.28-1.39 (2H, m), 1.48-1.60 (2H, m), 1.72-1.79 (3H, m), 1.83-1.94 (4H, m), 2.60 (3H, s), 3.47 (1H, s), 3.52 (1H, s), 3.57 (1H, dt, J=10.20, 6.95 Hz), 3.74 (1H, s), 3.75-3.79 (2H, m), 3.80 (1H, s), 3.93 (3H, d, J=1.10 Hz), 4.28 (2H, br t, J=5.20 Hz), 4.99 (1H, t, J=5.48 Hz), 6.43 (1H, dd, J=16.43, 7.94 Hz), 6.62 (1H, d, J=2.46 Hz), 7.37 (1H, dd, J=8.21, 1.37 Hz), 7.51 (1H, d, J=8.49 Hz), 7.58 (1H, t, J=2.74 Hz), 7.69 (1H, s); ESIMS found for $C_{27}H_{33}N_7O_3$ m/z 504.3 (M+1).

174

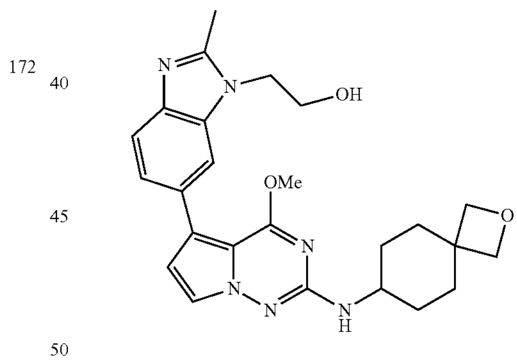

2-(6-(2-((2-Oxaspiro[3.5]nonan-7-yl)amino)-4-methoxypyrrolo[2,1-f][1,2,4]triazin-5-yl)-2-methyl-1H-benzo[d]imidazol-1-yl)ethan-1-ol 174

White solid (6 mg, 0.013 mmol, 57.8% yield). $^1$H NMR (499 MHz, DMSO-$d_6$) δ ppm 1.20-1.33 (2H, m), 1.52 (2H, td, J=12.87, 3.29 Hz), 1.83-1.93 (2H, m), 2.06 (2H, br d, J=12.87 Hz), 2.55 (3H, s), 3.48-3.60 (1H, m), 3.74 (2H, q, J=5.38 Hz), 3.92 (3H, s), 4.21-4.25 (2H, m), 4.24 (2H, s), 4.32 (2H, s), 4.95 (1H, t, J=5.34 Hz), 6.38 (1H, d, J=7.94 Hz), 6.59 (1H, d, J=2.74 Hz), 7.30 (1H, dd, J=8.21, 1.64 Hz), 7.46 (1H, d, J=8.21 Hz), 7.57 (1H, d, J=2.46 Hz), 7.61 (1H, d, J=1.37 Hz); ESIMS found for $C_{25}H_{30}N_6O_3$ m/z 463.3 (M+1).

187

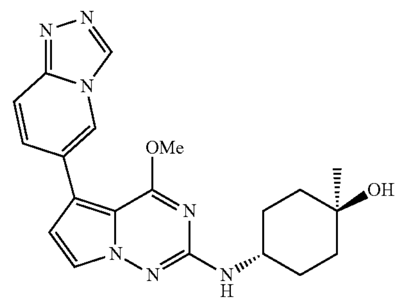

trans-4-((5-([1,2,4]Triazolo[4,3-a]pyridin-6-yl)-4-methoxypyrrolo[2,1-f][1,2,4]triazin-2-yl)amino)-1-methylcyclohexan-1-ol 187

Off-white solid (9 mg, 0.023 mmol, 13.8% yield). $^1$H NMR (499 MHz, DMSO-$d_6$) δ ppm 1.14 (3H, s), 1.37-1.53 (4H, m), 1.56-1.64 (2H, m), 1.83-1.92 (2H, m), 3.64 (1H, br dd, J=8.08, 3.70 Hz), 3.97 (3H, s), 4.23 (1H, s), 6.52 (1H, d, J=7.67 Hz), 6.72 (1H, d, J=2.74 Hz), 7.61 (1H, dd, J=9.45, 1.51 Hz), 7.65 (1H, d, J=2.46 Hz), 7.76 (1H, d, J=9.58 Hz), 8.69 (1H, s), 9.26 (1H, s); ESIMS found for $C_{20}H_{23}N_7O_2$ m/z 394.2 (M+1).

188

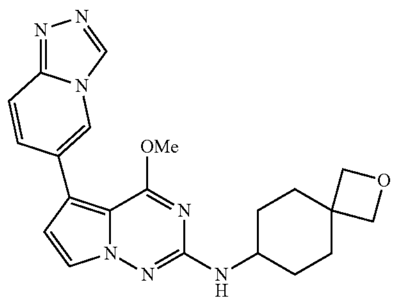

5-([1,2,4]Triazolo[4,3-a]pyridin-6-yl)-4-methoxy-N-(2-oxaspiro[3.5]nonan-7-yl)pyrrolo[2,1-f][1,2,4]triazin-2-amine 188

Beige solid (17 mg, 0.042 mmol, 21.0% yield). $^1$H NMR (499 MHz, DMSO-$d_6$) δ ppm 1.20-1.32 (2H, m), 1.52 (2H, td, J=12.94, 3.42 Hz), 1.82-1.92 (2H, m), 2.06 (2H, br d, J=13.14 Hz), 3.48-3.63 (1H, m), 3.97 (3H, s), 4.23 (2H, s), 4.31 (2H, s), 6.54 (1H, d, J=7.94 Hz), 6.72 (1H, d, J=2.74 Hz), 7.60 (1H, dd, J=9.58, 1.64 Hz), 7.64 (1H, d, J=2.74 Hz), 7.76 (1H, d, J=9.58 Hz), 8.69 (1H, t, J=1.23 Hz), 9.26 (1H, s); ESIMS found for $C_{21}H_{23}N_7O_2$ m/z 406.2 (M+1).

189

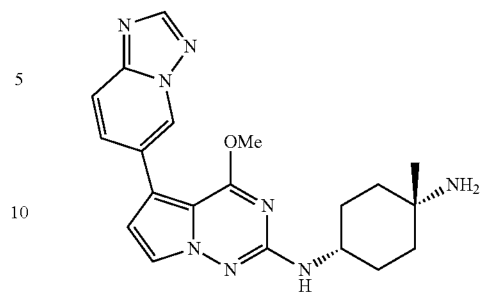

cis-$N_1$-(5-([1,2,4]Triazolo[1,5-a]pyridin-6-yl)-4-methoxypyrrolo[2,1-f][1,2,4]triazin-2-yl)-3-methyl-cyclobutane-1,3-diamine 189

White foam (108 mg, 0.296 mmol, 62.6% yield). $^1$H NMR (499 MHz, DMSO-$d_6$) δ ppm 1.19 (3H, s), 1.76 (2H, br s), 1.86 (2H, td, J=8.76, 2.46 Hz), 2.27-2.38 (2H, m), 3.85 (1H, sxt, J=7.78 Hz), 3.96 (3H, s), 6.80 (1H, d, J=2.46 Hz), 6.84 (1H, d, J=7.12 Hz), 7.66 (1H, d, J=2.74 Hz), 7.81-7.86 (1H, m), 7.87-7.92 (1H, m), 8.49 (1H, s), 9.06 (1H, dd, J=1.64, 0.82 Hz); ESIMS found for $C_{18}H_2O$ $N_8O$ m/z 365.2 (M+1).

190

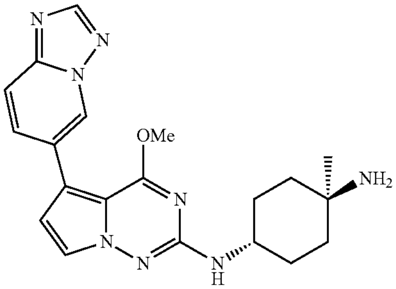

trans-$N^1$-(5-([1,2,4]Triazolo[1,5-a]pyridin-6-yl)-4-methoxypyrrolo[2,1-f][1,2,4]triazin-2-yl)-3-methyl-cyclobutane-1,3-diamine 190

White foam (83 mg, 0.228 mmol, 65.3% yield). $^1$H NMR (499 MHz, DMSO-$d_6$) δ ppm 1.22 (3H, s), 1.74 (2H, br s), 1.88-1.98 (2H, m), 2.12-2.22 (2H, m), 3.96 (3H, s), 4.27 (1H, sxt, J=7.50 Hz), 6.80 (1H, d, J=2.46 Hz), 6.93 (1H, d, J=7.12 Hz), 7.64 (1H, d, J=2.46 Hz), 7.82-7.86 (1H, m), 7.87-7.91 (1H, m), 8.49 (1H, s), 9.03-9.10 (1H, m); ESIMS found for $C_{18}H_2O$ $N_8O$ m/z 365.2 (M+1).

191

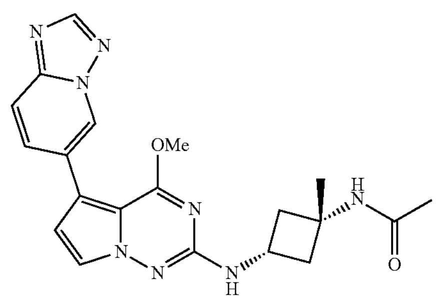

N-(cis-3-((5-([1,2,4]Triazolo[1,5-a]pyridin-6-yl)-4-methoxypyrrolo[2,1-f][1,2,4]triazin-2-yl)amino)-1-methylcyclobutyl)acetamide 191

Off-white solid (27 mg, 0.066 mmol, 96.8% yield). $^1$H NMR (499 MHz, DMSO-$d_6$) δ ppm 1.38 (3H, s), 1.76 (3H, s), 2.10-2.22 (2H, m), 2.42 (2H, ddd, J=9.65, 7.46, 2.60 Hz), 3.96 (3H, s), 4.02 (1H, sxt, J=7.83 Hz), 6.80 (1H, d, J=2.74 Hz), 7.03 (1H, d, J=6.84 Hz), 7.66 (1H, d, J=2.46 Hz), 7.82-7.85 (1H, m), 7.87-7.91 (1H, m), 8.02 (1H, s), 8.49 (1H, s), 9.06 (1H, d, J=1.10 Hz); ESIMS found for $C_{20}H_{22}N_8O_2$ m/z 407.2 (M+1).

192

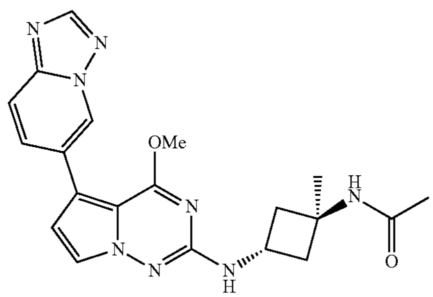

N-(trans-3-((5-([1,2,4]Triazolo[1,5-a]pyridin-6-yl)-4-methoxypyrrolo[2,1-f][1,2,4]triazin-2-yl)amino)-1-methylcyclobutyl)acetamide 192

Off-white solid (27 mg, 0.066 mmol, 96.8% yield). $^1$H NMR (499 MHz, DMSO-$d_6$) δ ppm 1.36 (3H, s), 1.81 (3H, s), 1.89-2.01 (2H, m), 2.64 (2H, ddd, J=10.13, 7.94, 2.74 Hz), 3.96 (3H, s), 4.13-4.27 (1H, m), 6.80 (1H, d, J=2.74 Hz), 7.03 (1H, d, J=7.12 Hz), 7.64 (1H, d, J=2.74 Hz), 7.81-7.86 (1H, m), 7.87-7.91 (1H, m), 7.93 (1H, s), 8.49 (1H, s), 9.06 (1H, s); ESIMS found for $C_{20}H_{22}N_8O_2$ m/z 407.2 (M+1).

193

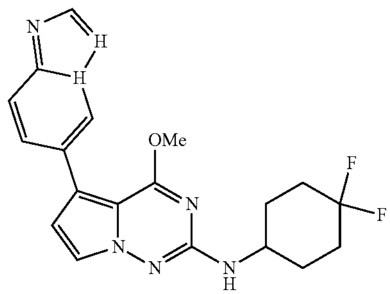

5-([1,2,4]Triazolo[1,5-a]pyridin-6-yl)-N-(4,4-difluorocyclohexyl)-4-methoxypyrrolo[2,1-f][1,2,4]triazin-2-amine 193

Off-white solid (15 mg, 0.038 mmol, 18.8% yield). $^1$H NMR (499 MHz, CHLOROFORM-d) δ ppm 1.62-1.75 (2H, m), 1.88-2.06 (2H, m), 2.11-2.27 (4H, m), 3.87 (1 H, br dd, J=5.07, 1.78 Hz), 4.02 (3H, s), 6.64 (1H, d, J=2.74 Hz), 7.50 (1H, d, J=2.74 Hz), 7.82 (2H, s), 8.09 (1H, d, J=7.67 Hz), 8.40 (1H, s), 8.82 (1H, s); ESIMS found for $C_{19}H_{19}F_2N_7O$ m/z 400.2 (M+1).

194

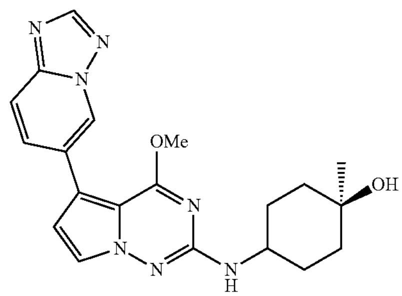

trans-4-((5-([1,2,4]Triazolo[1,5-a]pyridin-6-yl)-4-methoxypyrrolo[2,1-f][1,2,4]triazin-2-yl)amino)-1-methylcyclohexan-1-ol 194

Off-white solid (41 mg, 0.104 mmol, 44.8% yield). $^1$H NMR (499 MHz, DMSO-$d_6$) δ ppm 1.14 (3H, s), 1.37-1.52 (4H, m), 1.55-1.65 (2H, m), 1.82-1.93 (2H, m), 3.64 (1H, br dd, J=8.08, 3.70 Hz), 3.96 (3H, s), 4.24 (1H, s), 6.52 (1H, d, J=7.94 Hz), 6.79 (1H, d, J=2.46 Hz), 7.66 (1H, d, J=2.46 Hz), 7.80-7.86 (1H, m), 7.87-7.94 (1H, m), 8.49 (1H, s), 9.02-9.10 (1H, m); ESIMS found for $C_{20}H_{23}N_7O_2$ m/z 394.2 (M+1).

195

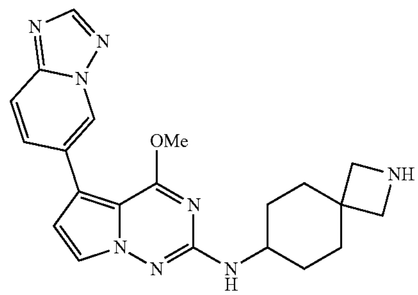

5-([1,2,4]Triazolo[1,5-a]pyridin-6-yl)-4-methoxy-N-(2-azaspiro[3.5]nonan-7-yl)pyrrolo[2,1-f][1,2,4]triazin-2-amine 195

Off-white foam (55 mg, 0.136 mmol, 71.5% yield). $^1$H NMR (499 MHz, DMSO-$d_6$) δ ppm 1.25-1.34 (2H, m), 1.37-1.49 (2H, m), 1.84 (3H, br d, J=10.13 Hz), 1.96 (2H, br d, J=12.87 Hz), 3.14 (2H, br s), 3.20 (2H, br s), 3.46-3.62 (2H, m), 3.95 (3H, s), 6.51 (1H, d, J=7.94 Hz), 6.79 (1H, d, J=2.74 Hz), 7.64 (1H, d, J=2.74 Hz), 7.81-7.85 (1H, m), 7.87-7.91 (1H, m), 8.49 (1H, s), 9.06 (1H, s); ESIMS found for $C_{21}H_{24}N_8O$ m/z 405.3 (M+1).

196

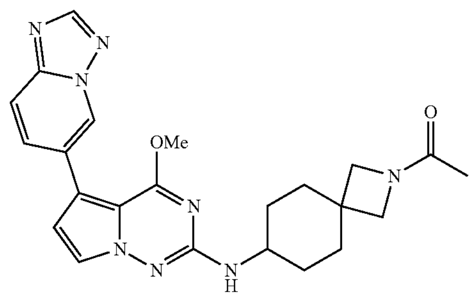

1-(7-((5-([1,2,4]Triazolo[1,5-a]pyridin-6-yl)-4-methoxypyrrolo[2,1-f][1,2,4]triazin-2-yl)amino)-2-azaspiro[3.5]nonan-2-yl)ethan-1-one 196

Off-white solid (46 mg, 0.103 mmol, 83.3% yield). $^1$H NMR (499 MHz, DMSO-$d_6$) δ ppm 1.26-1.41 (2H, m), 1.48-1.60 (2H, m), 1.72-1.80 (3H, m), 1.83-1.93 (4H, m), 3.47 (1H, s), 3.52 (1H, s), 3.57 (1H, br dd, J=6.98, 2.87 Hz), 3.74 (1H, s), 3.80 (1H, s), 3.96 (3H, d, J=1.10 Hz), 6.56 (1H, dd, J=16.02, 7.80 Hz), 6.80 (1H, d, J=2.74 Hz), 7.65 (1H, t, J=2.87 Hz), 7.80-7.86 (1H, m), 7.86-7.93 (1H, m), 8.49 (1H, s), 9.04-9.10 (1H, m); ESIMS found for $C_{23}H_{26}N_8O_2$ m/z 447.3 (M+1).

197

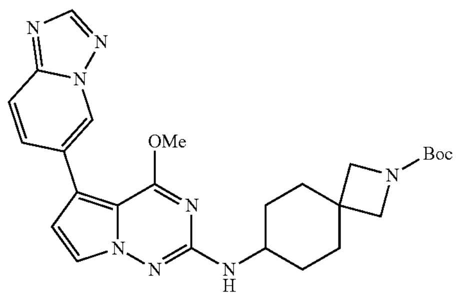

tert-Butyl 7-((5-([1,2,4]triazolo[1,5-a]pyridin-6-yl)-4-methoxypyrrolo[2,1-f][1,2,4]triazin-2-yl)amino)-2-azaspiro[3.5]nonane-2-carboxylate 197

Off-white foam (98 mg, 0.194 mmol, 58.4% yield). $^1$H NMR (499 MHz, DMSO-$d_6$) δ ppm 1.27-1.36 (2H, m), 1.38 (9H, s), 1.46-1.58 (2H, m), 1.86 (4H, br d, J=10.40 Hz), 3.55 (5H, br s), 3.96 (3H, s), 6.52 (1H, br d, J=7.39 Hz), 6.80 (1H, d, J=2.46 Hz), 7.64 (1H, d, J=2.74 Hz), 7.82-7.85 (1H, m), 7.87-7.91 (1H, m), 8.49 (1H, s), 9.06 (1H, s); ESIMS found for $C_{26}H_{32}N_8O_3$ m/z 505.3 (M+1).

198

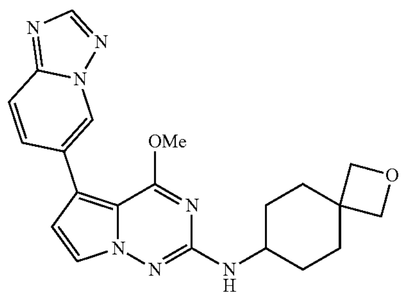

5-([1,2,4]Triazolo[1,5-a]pyridin-6-yl)-4-methoxy-N-(2-oxaspiro[3.5]nonan-7-yl)pyrrolo[2,1-f][1,2,4]triazin-2-amine 198

Off-white solid (46 mg, 0.114 mmol, 56.9% yield). $^1$H NMR (499 MHz, DMSO-$d_6$) δ ppm 1.19-1.31 (2H, m), 1.52 (2H, td, J=12.87, 3.29 Hz), 1.87 (2H, brdd, J=13.14, 3.29 Hz), 2.06 (2H, br d, J=13.14 Hz), 3.48-3.60 (1H, m), 3.95 (3H, s), 4.23 (2H, s), 4.32 (2H, s), 6.54 (1H, d, J=7.94 Hz), 6.79 (1H, d, J=2.74 Hz), 7.64 (1H, d, J=2.74 Hz), 7.80-7.85 (1H, m), 7.87-7.92 (1H, m), 8.49 (1H, s), 9.06 (1H, s); ESIMS found for $C_{21}H_{23}N_7O_2$ m/z 406.2 (M+1).

199

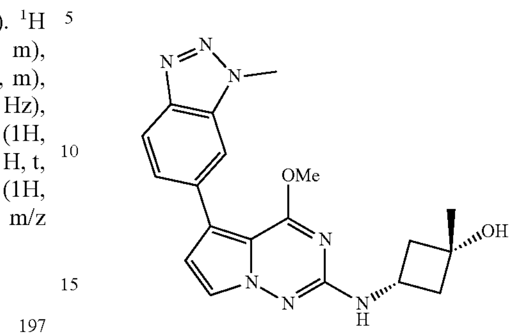

cis-3-((4-Methoxy-5-(1-methyl-1H-benzo[d][1,2,3]triazol-6-yl)pyrrolo[2,1-f][1,2,4]triazin-2-yl)amino)-1-methylcyclobutan-1-ol 199

Off-white solid (12 mg, 0.032 mmol, 16.6% yield). $^1$H NMR (499 MHz, DMSO-$d_6$) δ ppm 1.27 (3H, s), 2.02 (2H, td, J=8.83, 2.33 Hz), 2.31-2.40 (2H, m), 3.72 (1H, dq, J=15.09, 7.75 Hz), 3.95 (3H, s), 4.31 (3H, s), 4.92 (1H, s), 6.74 (1H, d, J=2.46 Hz), 6.93 (1H, d, J=6.57 Hz), 7.60 (1H, dd, J=8.76, 1.37 Hz), 7.64 (1H, d, J=2.46 Hz), 7.93 (1H, s), 7.97 (1H, d, J=8.49 Hz); ESIMS found for $C_{19}H_{21}N_7O_2$ m/z 380.2 (M+1).

200

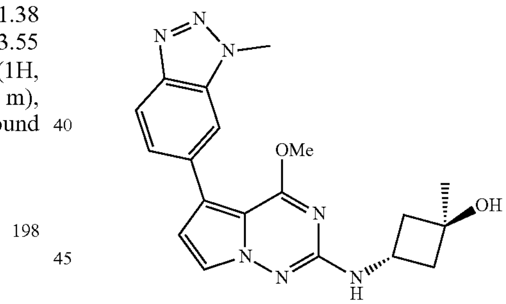

trans-3-((4-Methoxy-5-(1-methyl-1H-benzo[d][1,2,3]triazol-6-yl)pyrrolo[2,1-f][1,2,4]triazin-2-yl)amino)-1-methylcyclobutan-1-ol 200

White solid (5 mg, 0.013 mmol, 8.3% yield). $^1$H NMR (499 MHz, DMSO-$d_6$) δ ppm 1.28 (3H, s), 1.95-2.03 (2H, m), 2.28-2.35 (2H, m), 3.95 (3H, s), 4.21-4.29 (1H, m), 4.31 (3H, s), 4.79 (1H, s), 6.74 (1H, d, J=2.74 Hz), 6.94 (1H, d, J=6.84 Hz), 7.60 (1H, dd, J=8.62, 1.51 Hz), 7.63 (1H, d, J=2.74 Hz), 7.93 (1H, s), 7.97 (1H, d, J=8.76 Hz); ESIMS found for $C_{1-9}H_{21}N_7O_2$ m/z 380.2 (M+1).

201

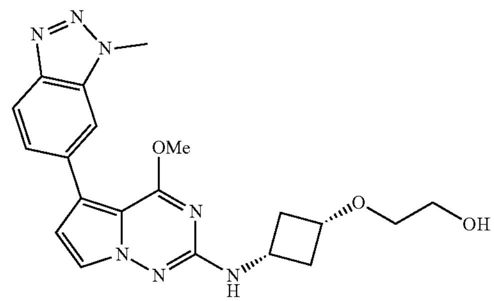

2-(cis-3-((4-Methoxy-5-(1-methyl-1H-benzo[d][1,2,3]triazol-6-yl)pyrrolo[2,1-f][1,2,4]triazin-2-yl)amino)cyclobutoxy)ethan-1-ol 201

Off-white solid (27 mg, 0.066 mmol, 25.9% yield). $^1$H NMR (499 MHz, DMSO-$d_6$) δ ppm 1.82-1.94 (2H, m), 2.60-2.71 (2H, m), 3.29-3.34 (2H, m), 3.48 (2H, q, J=5.48 Hz), 3.68-3.75 (1H, m), 3.75-3.83 (1H, m), 3.95 (3H, s), 4.31 (3H, s), 4.60 (1H, t, J=5.61 Hz), 6.75 (1H, d, J=2.74 Hz), 7.02 (1H, d, J=7.39 Hz), 7.60 (1H, dd, J=8.76, 1.37 Hz), 7.62 (1H, d, J=2.46 Hz), 7.94 (1H, s), 7.97 (1H, d, J=8.76 Hz); ESIMS found for $C_{20}H_{23}N_7O_3$ m/z 410.2 (M+1).

202

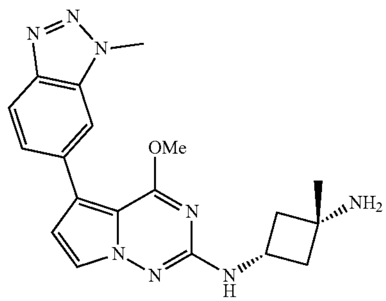

cis-N$^1$-(4-Methoxy-5-(1-methyl-1H-benzo[d][1,2,3]triazol-6-yl)pyrrolo[2,1-f][1,2,4]triazin-2-yl)-3-methylcyclobutane-1,3-diamine 202

Off-white solid (155 mg, 0.410 mmol, 70.0% yield). $^1$H NMR (499 MHz, DMSO-$d_6$) δ ppm 1.19 (3H, s), 1.77 (2H, br s), 1.86 (2H, td, J=8.83, 2.33 Hz), 2.33 (2H, ddd, J=8.97, 7.46, 2.74 Hz), 3.86 (1H, dq, J=15.50, 7.79 Hz), 3.95 (3H, s), 4.31 (3H, s), 6.74 (1H, d, J=2.46 Hz), 6.80 (1H, d, J=7.12 Hz), 7.60 (1H, dd, J=8.76, 1.64 Hz), 7.64 (1H, d, J=2.74 Hz), 7.93 (1H, d, J=1.37 Hz), 7.97 (1H, d, J=8.76 Hz); ESIMS found for $C_{19}H_{22}N_8O$ m/z 379.25 (M+1).

203

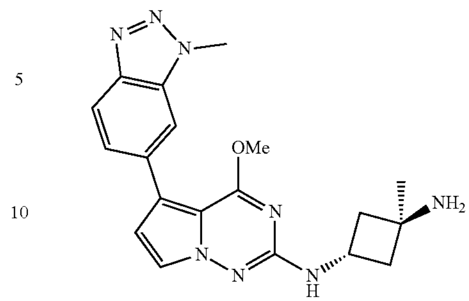

trans-N$_1$-(4-Methoxy-5-(1-methyl-1H-benzo[d][1,2,3]triazol-6-yl)pyrrolo[2,1-f][1,2,4]triazin-2-yl)-3-methylcyclobutane-1,3-diamine 203

Off-white foam (110 mg, 0.291 mmol, 74.0% yield). $^1$H NMR (499 MHz, DMSO-$d_6$) δ ppm 1.22 (3H, s), 1.80 (2H, br s), 1.88-1.98 (2H, m), 2.13-2.22 (2H, m), 3.95 (3H, s), 4.23-4.33 (1H, m), 4.31 (3H, s), 6.74 (1H, d, J=2.46 Hz), 6.90 (1H, d, J=7.12 Hz), 7.60 (1H, dd, J=8.76, 1.37 Hz), 7.63 (1H, d, J=2.46 Hz), 7.93 (1H, s), 7.95-8.00 (1H, m); ESIMS found for $C_{1-9}H_{22}N_8O$ m/z 379.2 (M+1).

204

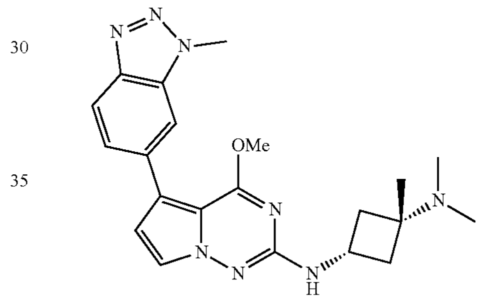

cis-N$^3$-(4-Methoxy-5-(1-methyl-1H-benzo[d][1,2,3]triazol-6-yl)pyrrolo[2,1-f][1,2,4]triazin-2-yl)-N$^1$,N$^1$,1-trimethylcyclobutane-1,3-diamine 204

White solid (18 mg, 0.044 mmol, 67.0% yield). $^1$H NMR (499 MHz, DMSO-$d_6$) δ ppm 1.06 (3H, s), 1.82-1.92 (2H, m), 2.03 (6H, s), 2.19 (2H, td, J=8.15, 2.60 Hz), 3.91-4.01 (1H, m), 3.95 (3H, s), 4.31 (3H, s), 6.74 (1H, d, J=2.46 Hz), 6.95 (1H, d, J=7.12 Hz), 7.60 (1H, dd, J=8.62, 1.51 Hz), 7.64 (1H, d, J=2.74 Hz), 7.93 (1H, s), 7.97 (1H, d, J=8.76 Hz); ESIMS found for $C_{21}H_{26}N_8O$ m/z 407.3 (M+1).

205

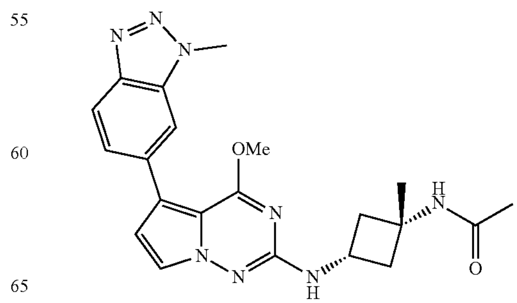

N-(cis-3-((4-Methoxy-5-(1-methyl-1H-benzo[d][1,2,3]triazol-6-yl)pyrrolo[2,1-f][1,2,4]triazin-2-yl)amino)-1-methylcyclobutyl)acetamide 205

Off-white solid (25 mg, 0.060 mmol, 90.0% yield). $^1$H NMR (499 MHz, DMSO-$d_6$) δ ppm 1.38 (3H, s), 1.76 (3H, s), 2.11-2.21 (2H, m), 2.42 (2H, ddd, J=9.58, 7.39, 2.46 Hz), 3.95 (3H, s), 3.99-4.08 (1H, m), 4.31 (3H, s), 6.74 (1H, d, J=2.46 Hz), 6.99 (1H, d, J=6.84 Hz), 7.60 (1H, dd, J=8.76, 1.64 Hz), 7.65 (1H, d, J=2.46 Hz), 7.93 (1H, s), 7.97 (1H, d, J=9.03 Hz), 8.02 (1H, s); ESIMS found for $C_{21}H_{24}N_8O_2$ m/z 421.2 (M+1).

206

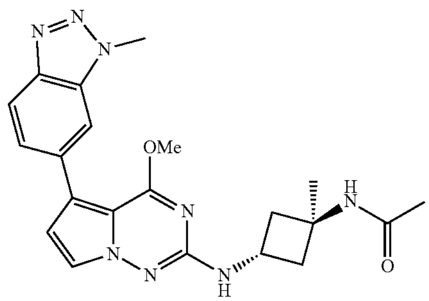

N-(trans-3-((4-Methoxy-5-(1-methyl-1H-benzo[d][1,2,3]triazol-6-yl)pyrrolo[2,1-f][1,2,4]triazin-2-yl)amino)-1-methylcyclobutyl)acetamide 206

Off-white solid (84 mg, 0.200 mmol, 92.2% yield). $^1$H NMR (499 MHz, DMSO-$d_6$) δ ppm 1.36 (3H, s), 1.82 (3H, s), 1.90-2.00 (2H, m), 2.64 (2H, ddd, J=10.20, 7.87, 2.46 Hz), 3.95 (3H, s), 4.19 (1H, sxt, J=7.78 Hz), 4.31 (3H, s), 6.74 (1H, d, J=2.46 Hz), 6.99 (1H, d, J=7.39 Hz), 7.60 (1H, dd, J=8.62, 1.51 Hz), 7.62 (1H, d, J=2.74 Hz), 7.93 (2H, s), 7.97 (1H, d, J=8.49 Hz); ESIMS found for $C_{21}H_{24}N_8O_2$ m/z 421.2 (M+1).

207

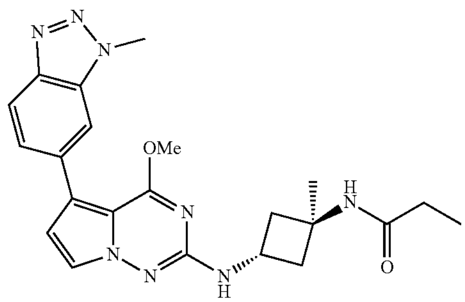

N-(trans-3-((4-Methoxy-5-(1-methyl-1H-benzo[d][1,2,3]triazol-6-yl)pyrrolo[2,1-f][1,2,4]triazin-2-yl)amino)-1-methylcyclobutyl)propionamide 207

Off-white solid (30 mg, 0.069 mmol, 96.8% yield). $^1$H NMR (499 MHz, DMSO-$d_6$) δ ppm 1.00 (3H, t, J=7.53 Hz), 1.36 (3H, s), 1.92-2.00 (2H, m), 2.08 (2H, q, J=7.57 Hz), 2.64 (2H, ddd, J=10.27, 7.94, 2.60 Hz), 3.95 (3H, s), 4.19 (1H, sxt, J=7.78 Hz), 4.31 (3H, s), 6.74 (1H, d, J=2.46 Hz), 6.99 (1H, d, J=7.12 Hz), 7.60 (1H, dd, J=8.62, 1.51 Hz), 7.62 (1H, d, J=2.46 Hz), 7.83 (1H, s), 7.93 (1H, s), 7.97 (1H, d, J=8.76 Hz), 8.31 (1H, s); ESIMS found for $C_{22}H_{26}N_8O_2$ m/z 435.3 (M+1).

208

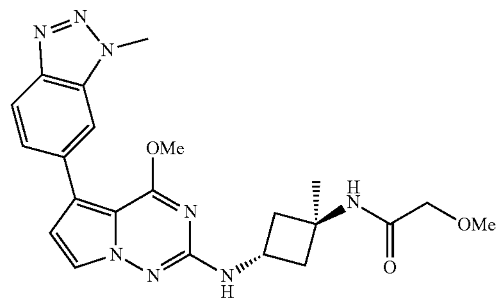

2-Methoxy-N-(trans-3-((4-methoxy-5-(1-methyl-1H-benzo[d][1,2,3]triazol-6-yl)pyrrolo[2,1-f][1,2,4]triazin-2-yl)amino)-1-methylcyclobutyl)acetamide 208

Off-white solid (15 mg, 0.033 mmol, 63.0% yield). $^1$H NMR (499 MHz, DMSO-$d_6$) δ ppm 1.39 (3H, s), 1.95-2.05 (2H, m), 2.69-2.78 (2H, m), 3.78 (2H, s), 3.95 (3H, s), 4.13-4.24 (1H, m), 4.31 (3H, s), 6.74 (1H, d, J=2.74 Hz), 7.01 (1H, d, J=7.39 Hz), 7.60 (1H, dd, J=8.76, 1.37 Hz), 7.63 (1H, d, J=2.74 Hz), 7.72 (1H, s), 7.93 (1H, s), 7.97 (1H, d, J=8.76 Hz); ESIMS found for $C_{22}H_{26}N_8O_3$ m/z 451.3 (M+1).

209

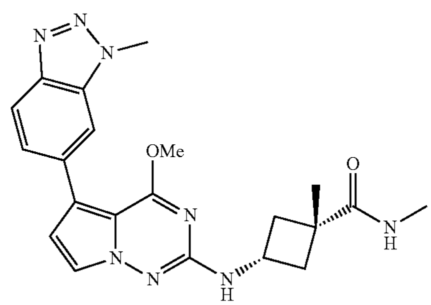

cis-3-((4-Methoxy-5-(1-methyl-1H-benzo[d][1,2,3]triazol-6-yl)pyrrolo[2,1-f][1,2,4]triazin-2-yl)amino)-N,1-dimethylcyclobutane-1-carboxamide 209

Off-white solid (7.3 mg, 0.017 mmol, 9.4% yield). $^1$H NMR (499 MHz, DMSO-$d_6$) δ ppm 1.34 (3H, s), 2.14-2.22 (2H, m), 2.22-2.31 (2H, m), 2.58 (3H, d, J=4.38 Hz), 3.94 (3H, s), 4.20 (1H, sxt, J=7.88 Hz), 4.31 (3H, s), 6.75 (1H, d, J=2.74 Hz), 6.93 (1H, d, J=7.12 Hz), 7.47 (1H, q, J=4.29 Hz), 7.60 (1H, dd, J=8.76, 1.37 Hz), 7.65 (1H, d, J=2.46 Hz), 7.93 (1H, s), 7.96-8.00 (1H, m); ESIMS found for $C_{21}H_{24}N_8O_2$ m/z 421.2 (M+1).

210

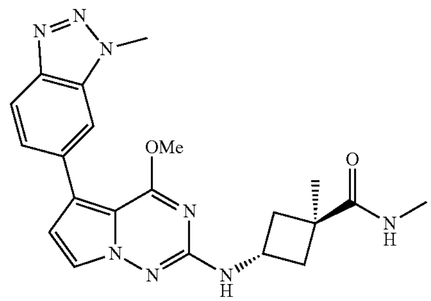

trans-3-((4-Methoxy-5-(1-methyl-1H-benzo[d][1,2,3]triazol-6-yl)pyrrolo[2,1-f][1,2,4]triazin-2-yl)amino)-N,1-dimethylcyclobutane-1-carboxamide 210

White solid (35 mg, 0.083 mmol, 99.7% yield). $^1$H NMR (499 MHz, DMSO-$d_6$) δ ppm 1.32 (3H, s), 1.86-1.94 (2H, m), 2.62 (3H, d, J=4.38 Hz), 2.70-2.79 (2H, m), 3.95 (3H, s), 4.04 (1H, sxt, J=7.99 Hz), 4.31 (3H, s), 6.74 (1H, d, J=2.74 Hz), 6.98 (1H, d, J=7.39 Hz), 7.60 (1H, dd, J=8.62, 1.51 Hz), 7.60-7.64 (1H, m), 7.66 (1H, d, J=2.46 Hz), 7.93 (1H, s), 7.97 (1H, d, J=8.76 Hz); ESIMS found for $C_{21}H_{24}N_8O_2$ m/z 421.2 (M+1).

211

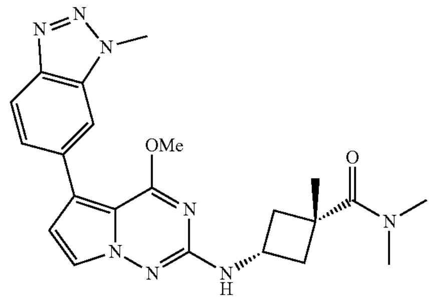

cis-3-((4-Methoxy-5-(1-methyl-1H-benzo[d][1,2,3]triazol-6-yl)pyrrolo[2,1-f][1,2,4]triazin-2-yl)amino)-N,N,1-trimethylcyclobutane-1-carboxamide 211

White solid (4.4 mg, 0.010 mmol, 5.5% yield). $^1$H NMR (499 MHz, DMSO-$d_6$) δ ppm 1.38 (3H, s), 2.27-2.40 (4H, m), 2.80 (3H, s), 2.87 (3H, s), 3.94 (3H, s), 4.18 (1H, dq, J=15.74, 7.89 Hz), 4.31 (3H, s), 6.75 (1H, d, J=2.74 Hz), 6.94 (1H, d, J=7.12 Hz), 7.60 (1H, dd, J=8.76, 1.64 Hz), 7.65 (1H, d, J=2.46 Hz), 7.93 (1H, s), 7.97 (1H, d, J=8.76 Hz); ESIMS found for $C_{22}H_{26}N_8O_2$ m/z 435.3 (M+1).

212

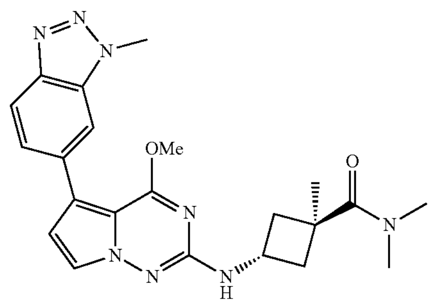

trans-3-((4-Methoxy-5-(1-methyl-1H-benzo[d][1,2,3]triazol-6-yl)pyrrolo[2,1-f][1,2,4]triazin-2-yl)amino)-N,N,1-trimethylcyclobutane-1-carboxamide 212

White solid (35 mg, 0.081 mmol, 96.5% yield). $^1$H NMR (499 MHz, DMSO-$d_6$) δ ppm 1.40 (3H, s), 1.94-2.03 (2H, m), 2.84 (3H, br s), 2.89 (3H, s), 2.89-2.94 (2H, m), 3.86-3.94 (1H, m), 3.96 (3H, s), 4.31 (3H, s), 6.74 (1H, d, J=2.74 Hz), 7.08 (1H, d, J=6.30 Hz), 7.60 (1H, dd, J=8.76, 1.37 Hz), 7.64 (1H, d, J=2.74 Hz), 7.93 (1H, d, J=1.10 Hz), 7.97 (1H, d, J=8.76 Hz); ESIMS found for $C_{22}H_{26}N_8O_2$ m/z 435.3 (M+1).

214

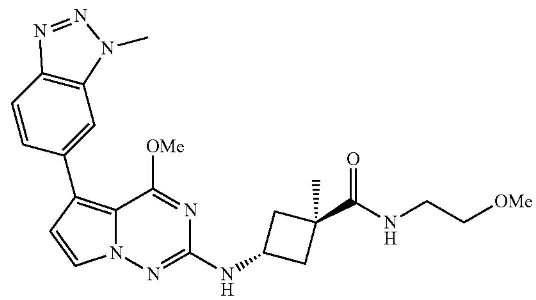

trans-3-((4-Methoxy-5-(1-methyl-1H-benzo[d][1,2,3]triazol-6-yl)pyrrolo[2,1-f][1,2,4]triazin-2-yl)amino)-N-(2-methoxyethyl)-1-methylcyclobutane-1-carboxamide 214

White solid (39 mg, 0.084 mmol, 45.6% yield). $^1$H NMR (499 MHz, DMSO-$d_6$) δ ppm 1.32 (3H, s), 1.84-1.94 (2H, m), 2.70-2.80 (2H, m), 3.22-3.28 (2H, m), 3.26 (3H, s), 3.35-3.39 (2H, m), 3.95 (3H, s), 4.03 (1H, sxt, J=7.94 Hz), 4.31 (3H, s), 6.74 (1H, d, J=2.74 Hz), 6.98 (1H, d, J=7.39 Hz), 7.60 (1H, dd, J=8.76, 1.37 Hz), 7.65 (1H, d, J=2.46 Hz), 7.69 (1H, t, J=5.61 Hz), 7.93 (1H, s), 7.97 (1H, d, J=8.76 Hz); ESIMS found for $C_{23}H_{28}N_8O_3$ m/z 465.3 (M+1).

217

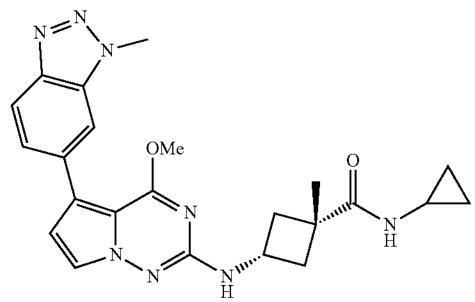

cis-N-Cyclopropyl-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide 217

Off-white solid (7 mg, 0.016 mmol, 8.5% yield). $^1$H NMR (499 MHz, DMSO-$d_6$) δ ppm 0.39-0.46 (2H, m), 0.56-0.64 (2H, m), 1.32 (3H, s), 2.13-2.20 (2H, m), 2.20-2.29 (2H, m), 2.58-2.67 (1H, m), 3.94 (3H, s), 4.17 (1H, sxt, J=7.88 Hz), 4.31 (3H, s), 6.74 (1H, d, J=2.46 Hz), 6.92 (1H, d, J=7.12 Hz), 7.49 (1H, d, J=4.11 Hz), 7.60 (1H, dd, J=8.62, 1.51 Hz), 7.65 (1H, d, J=2.74 Hz), 7.93 (1H, s), 7.97 (1H, d, J=8.76 Hz); ESIMS found for $C_{23}H_{26}N_8O_2$ m/z 447.2 (M+1).

218

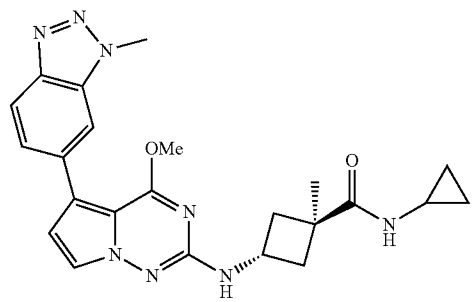

trans-N-Cyclopropyl-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide 218

White solid (44 mg, 0.099 mmol, 53.5% yield). $^1$H NMR (499 MHz, DMSO-$d_6$) δ ppm 0.42-0.49 (2H, m), 0.58-0.65 (2H, m), 1.30 (3H, s), 1.82-1.92 (2H, m), 2.67 (1H, tq, J=7.46, 3.88 Hz), 2.74 (2H, ddd, J=9.92, 7.87, 2.46 Hz), 3.95 (3H, s), 3.97-4.04 (1H, m), 4.31 (3H, s), 6.74 (1H, d, J=2.74 Hz), 6.98 (1H, d, J=7.39 Hz), 7.60 (1H, dd, J=8.62, 1.51 Hz), 7.62 (1H, d, J=4.38 Hz), 7.66 (1H, d, J=2.46 Hz), 7.93 (1H, s), 7.97 (1H, d, J=8.76 Hz); ESIMS found for $C_{23}H_{26}N_8O_2$ m/z 447.25 (M+1).

222

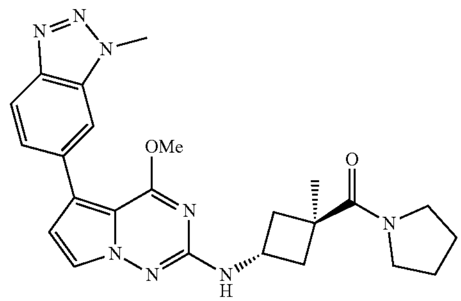

(trans-3-((4-Methoxy-5-(1-methyl-1H-benzo[d][1,2,3]triazol-6-yl)pyrrolo[2,1-f][1,2,4]triazin-2-yl)amino)-1-methylcyclobutyl)(pyrrolidin-1-yl)methanone 222

White solid (36 mg, 0.078 mmol, 93.7% yield). $^1$H NMR (499 MHz, DMSO-$d_6$) δ ppm 1.38 (3H, s), 1.73-1.80 (2H, m), 1.81-1.87 (2H, m), 1.91-1.99 (2H, m), 2.86-2.93 (2H, m), 3.30-3.34 (4H, m), 3.87-3.94 (1H, m), 3.96 (3H, s), 4.31 (3H, s), 6.74 (1H, d, J=2.46 Hz), 7.07 (1H, d, J=6.57 Hz), 7.60 (1H, dd, J=8.62, 1.51 Hz), 7.64 (1H, d, J=2.74 Hz), 7.93 (1H, s), 7.97 (1H, d, J=8.76 Hz); ESIMS found for $C_{24}H_{28}N_8O_2$ m/z 461.3 (M+1).

223

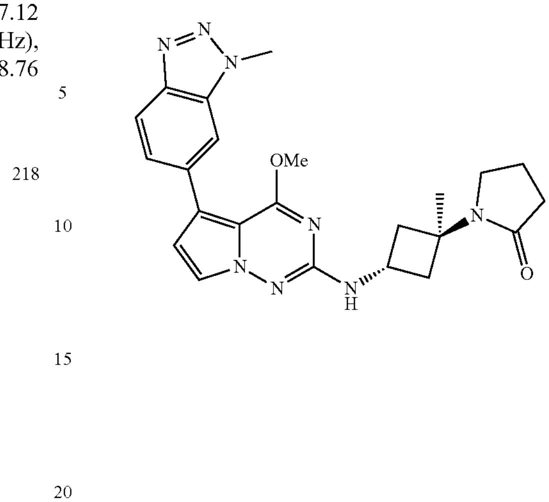

1-(trans-3-((4-Methoxy-5-(1-methyl-1H-benzo[d][1,2,3]triazol-6-yl)pyrrolo[2,1-f][1,2,4]triazin-2-yl)amino)-1-methylcyclobutyl)pyrrolidin-2-one 223

Off-white solid (23 mg, 0.052 mmol, 46.9% yield). $^1$H NMR (499 MHz, DMSO-$d_6$) δ ppm 1.36 (3H, s), 1.92 (2H, quin, J=7.53 Hz), 2.00-2.08 (2H, m), 2.23 (2H, t, J=8.08 Hz), 2.82-2.92 (2H, m), 3.40 (2H, t, J=6.84 Hz), 3.96 (3H, s), 4.04-4.12 (1H, m), 4.31 (3H, s), 6.74 (1H, d, J=2.46 Hz), 7.06 (1H, d, J=6.30 Hz), 7.60 (1H, dd, J=8.62, 1.51 Hz), 7.64 (1H, d, J=2.46 Hz), 7.94 (1H, s), 7.97 (1H, d, J=8.76 Hz); ESIMS found for $C_{23}H_{26}N_8O_2$ m/z 447.3 (M+1).

224

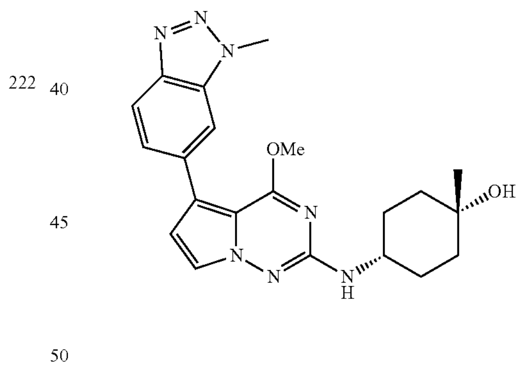

cis-4-((4-Methoxy-5-(1-methyl-1H-benzo[d][1,2,3]triazol-6-yl)pyrrolo[2,1-f][1,2,4]triazin-2-yl)amino)-1-methylcyclohexan-1-ol 224

Off-white solid (36 mg, 0.088 mmol, 34.8% yield). $^1$H NMR (499 MHz, DMSO-$d_6$) δ ppm 1.12 (3H, s), 1.37 (2H, td, J=13.00, 4.38 Hz), 1.58 (2H, br d, J=12.32 Hz), 1.61-1.69 (2H, m), 1.69-1.75 (2H, m), 3.47-3.58 (1H, m), 3.95 (3H, s), 4.00 (1H, s), 4.31 (3H, s), 6.50 (1H, d, J=7.94 Hz), 6.72 (1H, d, J=2.46 Hz), 7.59-7.63 (2H, m), 7.93 (1H, s), 7.97 (1H, d, J=8.49 Hz); ESIMS found for $C_{21}H_{25}N_7O_2$ m/z 408.2 (M+1).

225

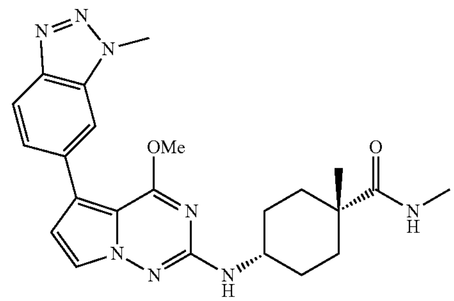

cis-4-((4-Methoxy-5-(1-methyl-1H-benzo[d][1,2,3]triazol-6-yl)pyrrolo[2,1-f][1,2,4]triazin-2-yl)amino)-N,1-dimethylcyclohexane-1-carboxamide 225

Off-white solid (10 mg, 0.022 mmol, 31.3% yield). $^1$H NMR (499 MHz, DMSO-$d_6$) δ ppm 1.03 (3H, s), 1.15-1.27 (2H, m), 1.27-1.37 (2H, m), 1.77-1.87 (2H, m), 2.18 (2H, br d, J=12.32 Hz), 2.61 (3H, d, J=4.38 Hz), 3.49-3.61 (1H, m), 3.93 (3H, s), 4.31 (3H, s), 6.51 (1H, d, J=7.94 Hz), 6.73 (1H, d, J=2.46 Hz), 7.53 (1H, q, J=4.38 Hz), 7.59-7.61 (1H, m), 7.62 (1H, d, J=2.46 Hz), 7.93 (1H, d, J=0.82 Hz), 7.97 (1H, d, J=8.76 Hz); ESIMS found for $C_{23}H_{28}N_8O_2$ m/z 449.3 (M+1).

226

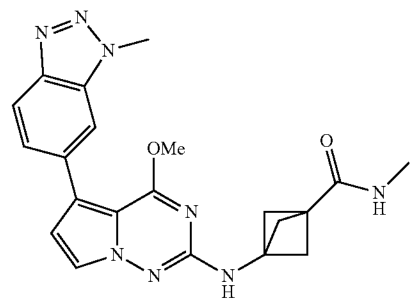

3-((4-Methoxy-5-(1-methyl-1H-benzo[d][1,2,3]triazol-6-yl)pyrrolo[2,1-f][1,2,4]triazin-2-yl)amino)-N-methylbicyclo[1.1.1]pentane-1-carboxamide 226

Off-white solid (5 mg, 0.012 mmol, 5.0% yield). $^1$H NMR (499 MHz, DMSO-$d_6$) δ ppm 2.23 (6H, s), 2.55-2.59 (3H, m), 3.96 (3H, s), 4.31 (3H, s), 6.79 (1H, d, J=2.46 Hz), 7.47 (1H, s), 7.61 (1H, dd, J=8.76, 1.37 Hz), 7.64 (1H, d, J=2.46 Hz), 7.73 (1H, q, J=4.47 Hz), 7.95 (1H, s), 7.98 (1H, d, J=8.76 Hz); ESIMS found for $C_{21}H_{22}N_8O_2$ m/z 419.2 (M+1).

227

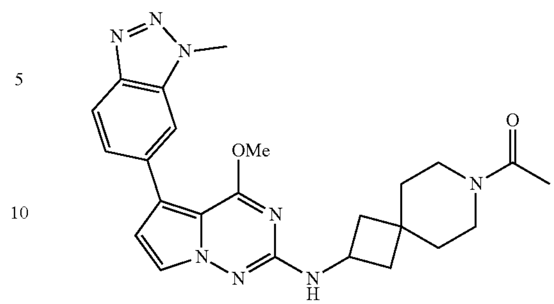

1-(2-((4-Methoxy-5-(1-methyl-1H-benzo[d][1,2,3]triazol-6-yl)pyrrolo[2,1-f][1,2,4]triazin-2-yl)amino)-7-azaspiro[3.5]nonan-7-yl)ethan-1-one 227

Off-white solid (23 mg, 0.050 mmol, 69.7% yield). $^1$H NMR (499 MHz, DMSO-$d_6$) δ ppm 1.41-1.46 (1H, m), 1.52 (2H, br t, J=10.27 Hz), 1.57-1.63 (1H, m), 1.76-1.85 (2H, m), 1.95-2.00 (3H, m), 2.23-2.32 (2H, m), 3.26-3.30 (1H, m), 3.31-3.35 (1H, m), 3.35-3.39 (1H, m), 3.40-3.44 (1H, m), 3.95 (3H, s), 4.15-4.26 (1H, m), 4.31 (3H, s), 6.74 (1H, d, J=2.46 Hz), 7.00 (1H, t, J=7.12 Hz), 7.60 (1H, dd, J=8.76, 1.37 Hz), 7.63-7.65 (1H, m), 7.93 (1H, s), 7.97 (1H, d, J=8.76 Hz); ESIMS found for $C_{24}H_{28}N_8O_2$ m/z 461.3 (M+1).

228

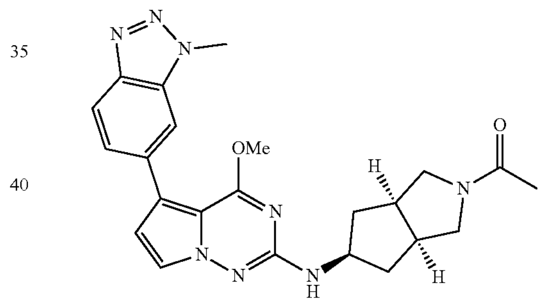

1-((3aR,5r,6aS)-5-((4-Methoxy-5-(1-methyl-1H-benzo[d][1,2,3]triazol-6-yl)pyrrolo[2,1-f][1,2,4]triazin-2-yl)amino)hexahydrocyclopenta[c]pyrrol-2(1H)-yl)ethan-1-one 228

Off-white solid (74 mg, 0.166 mmol, 89.4% yield). $^1$H NMR (499 MHz, DMSO-$d_6$) δ ppm 1.34-1.49 (2H, m), 1.94 (3H, s), 2.24-2.36 (2H, m), 2.57 (1H, quind, J=8.01, 8.01, 8.01, 8.01, 4.65 Hz), 2.62-2.72 (1H, m), 3.35-3.46 (3H, m), 3.59 (1H, dd, J=10.68, 7.94 Hz), 3.95 (3H, s), 4.07-4.20 (1H, m), 4.31 (3H, s), 6.74 (1H, d, J=2.74 Hz), 6.82 (1H, d, J=7.39 Hz), 7.60 (1H, dd, J=8.76, 1.37 Hz), 7.63 (1H, d, J=2.46 Hz), 7.93 (1H, s), 7.97 (1H, d, J=9.03 Hz); ESIMS found for $C_{23}H_{26}N_8O_2$ m/z 447.2 (M+1).

229

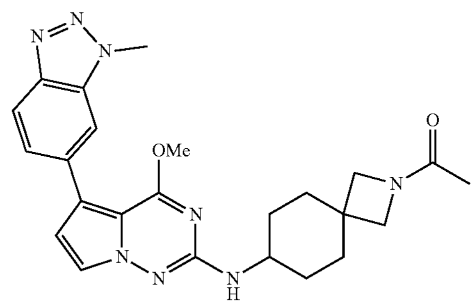

1-(7-((4-Methoxy-5-(1-methyl-1H-benzo[d][1,2,3]triazol-6-yl)pyrrolo[2,1-f][1,2,4]triazin-2-yl)amino)-2-azaspiro[3.5]nonan-2-yl)ethan-1-one 229

Off-white solid (12 mg, 0.026 mmol, 72.7% yield). $^1$H NMR (499 MHz, DMSO-$d_6$) δ ppm 1.27-1.39 (2H, m), 1.49-1.61 (2H, m), 1.72-1.78 (3H, m), 1.82-1.94 (4H, m), 3.47 (1H, s), 3.52 (1H, s), 3.54-3.65 (1H, m), 3.75 (1H, s), 3.80 (1H, s), 3.95 (3H, d, J=1.10 Hz), 4.31 (3H, s), 6.52 (1H, dd, J=16.43, 7.94 Hz), 6.74 (1H, d, J=2.74 Hz), 7.61 (1H, dd, J=8.62, 1.51 Hz), 7.63 (1H, t, J=2.87 Hz), 7.93 (1H, s), 7.97 (1H, d, J=8.76 Hz); ESIMS found for $C_{24}H_{28}N_8O_2$ m/z 461.3 (M+1).

230

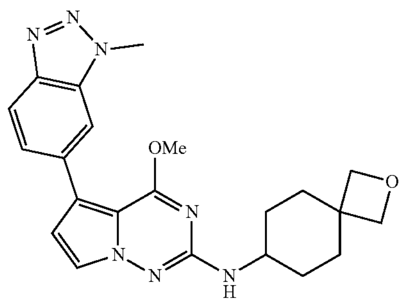

4-Methoxy-5-(1-methyl-1H-benzo[d][1,2,3]triazol-6-yl)-N-(2-oxaspiro[3.5]nonan-7-yl)pyrrolo[2,1-f][1,2,4]triazin-2-amine 230

Beige solid (28 mg, 0.067 mmol, 35.0% yield). $^1$H NMR (499 MHz, DMSO-$d_6$) δ ppm 1.21-1.33 (2H, m), 1.53 (2H, td, J=12.87, 3.29 Hz), 1.82-1.93 (2H, m), 2.07 (2H, br d, J=13.14 Hz), 3.51-3.61 (1H, m), 3.94 (3H, s), 4.24 (2H, s), 4.31 (3H, s), 4.32 (2H, s), 6.50 (1H, d, J=7.94 Hz), 6.73 (1H, d, J=2.74 Hz), 7.60 (1H, dd, J=8.76, 1.37 Hz), 7.63 (1H, d, J=2.46 Hz), 7.93 (1H, s), 7.97 (1H, d, J=8.76 Hz); ESIMS found for $C_{22}H_{25}N_7O_2$ m/z 420.2 (M+1).

231

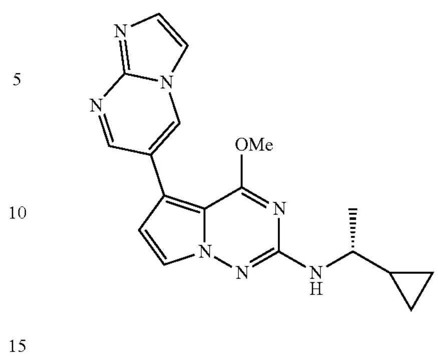

(R)—N-(1-Cyclopropylethyl)-5-(imidazo[1,2-a]pyrimidin-6-yl)-4-methoxypyrrolo[2,1-f][1,2,4]triazin-2-amine 231

Beige solid (4 mg, 0.011 mmol, 6.9% yield). $^1$H NMR (499 MHz, DMSO-$d_6$) δ ppm 0.16-0.24 (1H, m), 0.33-0.40 (2H, m), 0.47 (1H, s), 0.97-1.07 (1H, m), 1.23 (3H, d, J=6.57 Hz), 3.33-3.38 (1H, m), 3.97 (3H, s), 6.66 (1H, d, J=8.49 Hz), 6.76 (1H, d, J=2.46 Hz), 7.63 (1H, d, J=2.46 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{18}H_{19}N_7O$ m/z 350.2 (M+1).

233

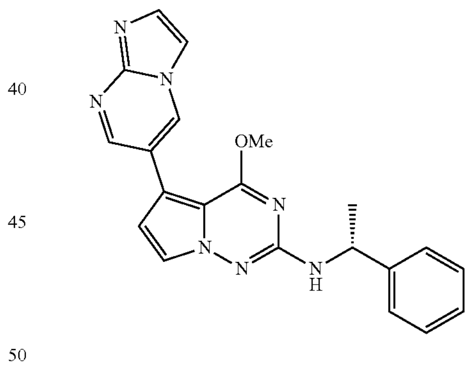

(R)-5-(Imidazo[1,2-a]pyrimidin-6-yl)-4-methoxy-N-(1-phenylethyl)pyrrolo[2,1-f][1,2,4]triazin-2-amine 233

Off-white solid (10 mg, 0.026 mmol, 15.6% yield). $^1$H NMR (499 MHz, DMSO-$d_6$) δ ppm 1.46 (3H, d, J=7.12 Hz), 3.98 (3H, s), 4.95 (1H, quin, J=7.39 Hz), 6.74 (1H, d, J=2.46 Hz), 7.17-7.22 (1H, m), 7.28-7.33 (3H, m), 7.43 (2H, d, J=7.39 Hz), 7.58 (1H, d, J=2.74 Hz), 7.71 (1H, d, J=1.10 Hz), 7.91 (1H, d, J=1.09 Hz), 8.71 (1H, d, J=2.46 Hz), 9.06 (1H, d, J=2.46 Hz); ESIMS found for $C_{21}H_{19}N_7O$ m/z 386.2 (M+1).

236

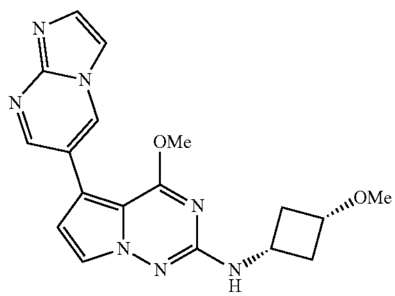

5-(Imidazo[1,2-a]pyrimidin-6-yl)-4-methoxy-N-(cis-3-methoxycyclobutyl)pyrrolo[2,1-f][1,2,4]triazin-2-amine 236

White solid (65 mg, 0.178 mmol, 53.5% yield). $^1$H NMR (499 MHz, DMSO-$d_6$) δ ppm 1.78-1.91 (2H, m), 2.59-2.70 (2H, m), 3.14 (3H, s), 3.61 (1H, quin, J=7.12 Hz), 3.73-3.87 (1H, m), 3.97 (3H, s), 6.78 (1H, d, J=2.46 Hz), 7.07 (1H, d, J=7.39 Hz), 7.65 (1H, d, J=2.74 Hz), 7.72 (1H, d, J=1.09 Hz), 7.92 (1H, d, J=1.09 Hz), 8.73 (1H, d, J=2.46 Hz), 9.09 (1H, d, J=2.46 Hz); ESIMS found for $C_{18}H_{19}N_7O_2$ m/z 366.2 (M+1).

239

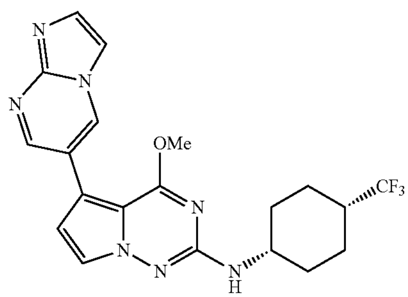

5-(Imidazo[1,2-a]pyrimidin-6-yl)-4-methoxy-N-(cis-4-(trifluoromethyl)cyclohexyl)pyrrolo[2,1-f][1,2,4]triazin-2-amine 239

Off-white solid (31 mg, 0.072 mmol, 36.0% yield). $^1$H NMR (499 MHz, DMSO-$d_6$) δ ppm 1.59-1.69 (4H, m), 1.69-1.80 (2H, m), 1.95-2.06 (2H, m), 2.23-2.35 (1H, m), 3.87-3.95 (1H, m), 4.00 (3H, s), 6.78 (1H, d, J=2.46 Hz), 6.80 (1H, d, J=6.30 Hz), 7.66 (1H, d, J=2.46 Hz), 7.72 (1H, d, J=1.10 Hz), 7.93 (1H, d, J=1.37 Hz), 8.74 (1H, d, J=2.46 Hz), 9.09 (1H, d, J=2.46 Hz); ESIMS found for $C_{20}H_{20}F_3N_7O$ m/z 432.2 (M+1).

242

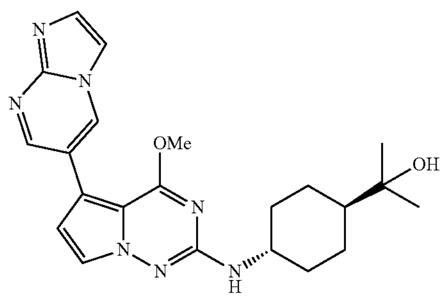

2-(trans-4-((5-(Imidazo[1,2-a]pyrimidin-6-yl)-4-methoxypyrrolo[2,1-f][1,2,4]triazin-2-yl)amino)cyclohexyl)propan-2-ol 242

White solid (1 mg, 0.002 mmol, 1.4% yield). $^1$H NMR (499 MHz, CHLOROFORM-d) δ ppm 1.22 (6H, s), 1.24-1.30 (3H, m), 1.31-1.41 (2H, m), 1.95 (2H, br d, J=12.05 Hz), 2.30 (2H, br d, J=10.95 Hz), 3.66 (1H, tdt, J=11.21, 11.21, 7.63, 3.87, 3.87 Hz), 4.00 (3H, s), 4.37 (1H, d, J=7.94 Hz), 6.59 (1H, d, J=2.46 Hz), 7.49 (1H, d, J=2.46 Hz), 7.57 (1H, br s), 7.85 (1H, br s), 8.42-8.66 (2H, m), 8.79 (1H, br s); ESIMS found for $C_{22}H_{27}N_7O_2$ m/z 422.2 (M+1).

243

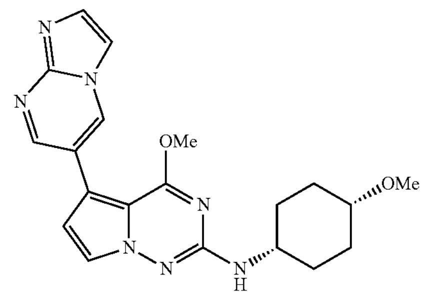

5-(imidazo[1,2-a]pyrimidin-6-yl)-4-methoxy-N-(cis-4-methoxycyclohexyl)pyrrolo[2,1-f][1,2,4]triazin-2-amine 243

White solid (71 mg, 0.181 mmol, 54.3% yield). $^1$H NMR (499 MHz, DMSO-$d_6$) δ ppm 1.45-1.54 (2H, m), 1.56-1.65 (2H, m), 1.66-1.73 (2H, m), 1.80-1.89 (2H, m), 3.22 (3H, s), 3.34-3.37 (1H, m), 3.55-3.70 (1H, m), 3.97 (3H, s), 6.62 (1H, d, J=7.67 Hz), 6.76 (1H, d, J=2.46 Hz), 7.65 (1H, d, J=2.74 Hz), 7.72 (1H, d, J=1.10 Hz), 7.93 (1H, d, J=1.37 Hz), 8.73 (1H, d, J=2.46 Hz), 9.08 (1H, d, J=2.46 Hz); ESIMS found for $C_{20}H_{23}N_7O_2$ m/z 394.2 (M+1).

245

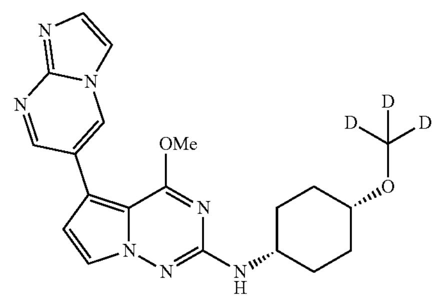

5-(Imidazo[1,2-a]pyrimidin-6-yl)-4-methoxy-N-(cis-4-(methoxy-$d_3$)cyclohexyl)pyrrolo[2,1-f][1,2,4]triazin-2-amine 245

Off-white solid (49 mg, 0.124 mmol, 41.3% yield). $^1$H NMR (499 MHz, DMSO-$d_6$) δ ppm 1.44-1.54 (2H, m), 1.55-1.65 (2H, m), 1.65-1.73 (2H, m), 1.80-1.88 (2H, m), 3.33-3.38 (1H, m), 3.58-3.71 (1H, m), 3.97 (3H, s), 6.62 (1H, d, J=7.67 Hz), 6.76 (1H, d, J=2.46 Hz), 7.65 (1H, d, J=2.74 Hz), 7.72 (1H, d, J=1.37 Hz), 7.93 (1H, d, J=1.37

Hz), 8.73 (1H, d, J=2.46 Hz), 9.08 (1H, d, J=2.46 Hz) ESIMS found for $C_{20}H_{20}[^2H_3]N_7O_2$ m/z 397.2 (M+1).

250

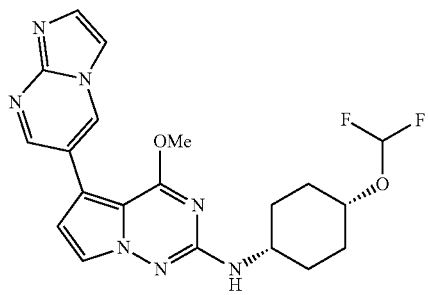

N-(cis-4-(Difluoromethoxy)cyclohexyl)-5-(imidazo[1,2-a]pyrimidin-6-yl)-4-methoxypyrrolo[2,1-f][1,2,4]triazin-2-amine 250

Beige solid (21 mg, 0.049 mmol, 21.0% yield). $^1H$ NMR (499 MHz, DMSO-$d_6$) δ ppm 1.61-1.72 (4H, m), 1.74-1.82 (2H, m), 1.87 (2H, dt, J=9.58, 4.79 Hz), 3.68 (1H, br dd, J=8.08, 3.97 Hz), 3.98 (3H, s), 4.29 (1H, br s), 6.72 (1H, t, J=77.05 Hz), 6.73 (1H, d, J=7.67 Hz), 6.77 (1H, d, J=2.46 Hz), 7.65 (1H, d, J=2.46 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{20}H_{21}F_2N_702$ m/z 430.2 (M+1).

252

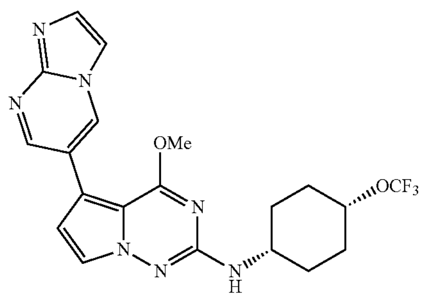

5-(Imidazo[1,2-a]pyrimidin-6-yl)-4-methoxy-N-(cis-4-(trifluoromethoxy)cyclohexyl)pyrrolo[2,1-f][1,2,4]triazin-2-amine 252

Off-white solid (31 mg, 0.069 mmol, 34.7% yield). $^1H$ NMR (499 MHz, DMSO-$d_6$) δ ppm 1.61-1.71 (2H, m), 1.71-1.79 (2H, m), 1.83 (2H, td, J=8.42, 3.97 Hz), 1.91-1.99 (2H, m), 3.65-3.77 (1H, m), 3.98 (3H, s), 4.60 (1H, dt, J=5.00, 2.29 Hz), 6.76 (1H, d, J=7.67 Hz), 6.77 (1H, d, J=2.74 Hz), 7.66 (1H, d, J=2.46 Hz), 7.72 (1H, d, J=1.37 Hz), 7.93 (1H, d, J=1.37 Hz), 8.74 (1H, d, J=2.46 Hz), 9.09 (1H, d, J=2.74 Hz); ESIMS found for $C_{20}H_{20}F_3N_7O_2$ m/z 448.2 (M+1).

254

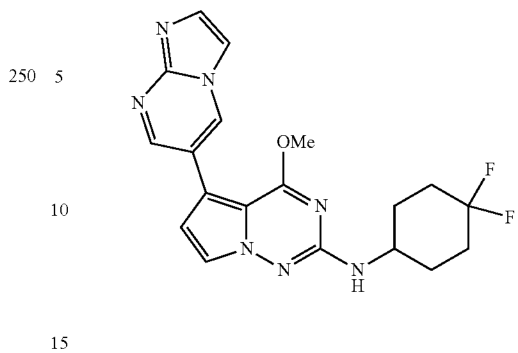

N-(4,4-Difluorocyclohexyl)-5-(imidazo[1,2-a]pyrimidin-6-yl)-4-methoxypyrrolo[2,1-f][1,2,4]triazin-2-amine 254

Off-white solid (68 mg, 0.170 mmol, 56.9% yield). $^1H$ NMR (499 MHz, DMSO-$d_6$) δ ppm 1.54-1.69 (2H, m), 1.85-2.02 (4H, m), 2.03-2.16 (2H, m), 3.74-3.86 (1H, m), 3.98 (3H, s), 6.78 (1H, d, J=2.46 Hz), 6.80 (1H, d, J=7.67 Hz), 7.67 (1H, d, J=2.74 Hz), 7.72 (1H, d, J=1.37 Hz), 7.93 (1H, d, J=1.09 Hz), 8.74 (1H, d, J=2.46 Hz), 9.09 (1H, d, J=2.46 Hz); ESIMS found for $C_{19}H_{19}F_2N_7O$ m/z 400.2 (M+1).

257

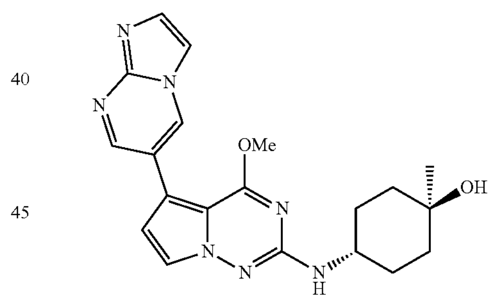

trans-4-((5-(Imidazo[1,2-a]pyrimidin-6-yl)-4-methoxypyrrolo[2,1-f][1,2,4]triazin-2-yl)amino)-1-methylcyclohexan-1-ol 257

Off-white solid (25 mg, 0.064 mmol, 29.4% yield). $^1H$ NMR (499 MHz, DMSO-$d_6$) δ ppm 1.14 (3H, s), 1.36-1.52 (4H, m), 1.55-1.68 (2H, m), 1.82-1.93 (2H, m), 3.58-3.72 (1H, m), 3.97 (3H, s), 4.24 (1H, s), 6.54 (1H, d, J=7.94 Hz), 6.76 (1H, d, J=2.46 Hz), 7.67 (1H, d, J=2.74 Hz), 7.72 (1H, d, J=1.37 Hz), 7.92 (1H, d, J=1.10 Hz), 8.73 (1H, d, J=2.46 Hz), 9.08 (1H, d, J=2.46 Hz); ESIMS found for $C_{20}H_{23}N_7O_2$ m/z 394.2 (M+1).

258

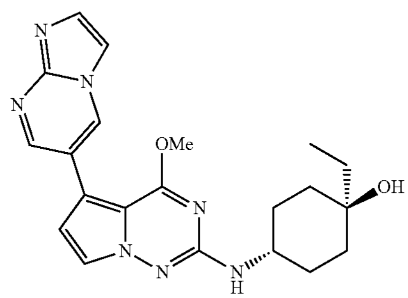

trans-1-Ethyl-4-((5-(imidazo[1,2-a]pyrimidin-6-yl)-4-methoxypyrrolo[2,1-f][1,2,4]triazin-2-yl)amino) cyclohexan-1-ol 258

Off-white solid (13 mg, 0.032 mmol, 24.0% yield). $^1$H NMR (499 MHz, DMSO-$d_6$) δ ppm 0.83 (3H, t, J=7.39 Hz), 1.31-1.39 (2H, m), 1.40-1.49 (4H, m), 1.64 (2H, br d, J=10.68 Hz), 1.85 (2H, br dd, J=12.05, 6.30 Hz), 3.68 (1H, dt, J=8.01, 3.80 Hz), 3.97 (3H, s), 3.98 (1H, br s), 6.53 (1H, d, J=7.67 Hz), 6.76 (1H, d, J=2.46 Hz), 7.67 (1H, d, J=2.46 Hz), 7.72 (1H, s), 7.92 (1H, s), 8.73 (1H, d, J=2.46 Hz), 9.08 (1H, d, J=2.46 Hz); ESIMS found for $C_{21}H_{25}N_7O_2$ m/z 408.2 (M+1).

261

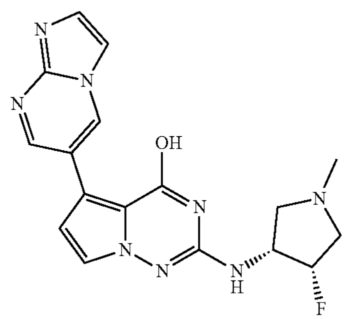

2-(((3R,4S)-4-Fluoro-1-methylpyrrolidin-3-yl) amino)-5-(imidazo[1,2-a]pyrimidin-6-yl)pyrrolo[2,1-f][1,2,4]triazin-4-ol 261

Pale-yellow semi-solid (11 mg, 0.030 mmol, 26.5% yield). $^1$H NMR (499 MHz, DMSO-$d_6$) δ ppm 2.29 (3H, s), 2.47-2.52 (16H, m), 2.71 (1H, ddd, J=30.45, 12.05, 1.10 Hz), 2.88 (1H, dd, J=9.17, 7.26 Hz), 2.96 (1H, ddd, J=31.85, 12.10, 4.70 Hz), 4.19-4.34 (1H, m), 5.22 (1H, dtd, J=55.95, 5.20, 5.20, 1.35 Hz), 6.17 (1H, br d, J=7.39 Hz), 6.81 (1H, d, J=2.74 Hz), 7.48 (1H, d, J=2.74 Hz), 7.71 (1H, d, J=1.37 Hz), 7.93 (1H, d, J=1.37 Hz), 8.90 (1H, d, J=2.46 Hz), 9.41 (1H, d, J=2.46 Hz), 10.69 (1H, br s); ESIMS found for $C_{17}H_{17}FN_8O$ m/z 369.2 (M+1).

262

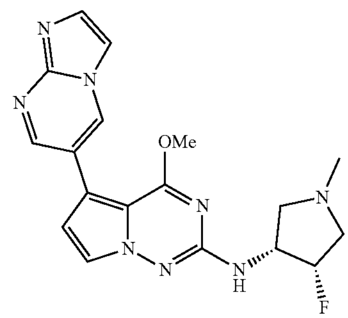

N-((3R,4S)-4-Fluoro-1-methylpyrrolidin-3-yl)-5-(imidazo[1,2-a]pyrimidin-6-yl)-4-methoxypyrrolo[2,1-f][1,2,4]triazin-2-amine 262

Pale-yellow semi-solid (12 mg, 0.031 mmol, 39.9% yield). $^1$H NMR (499 MHz, DMSO-$d_6$) δ ppm 2.31 (3H, s), 2.55-2.66 (2H, m), 2.92 (1H, t, J=8.08 Hz), 3.17 (1H, ddd, J=29.35, 11.80, 4.95 Hz), 4.00 (3H, s), 4.20-4.35 (1H, m), 5.21 (1H, dtd, J=55.95, 5.20, 5.20, 1.95 Hz), 6.81 (1H, d, J=2.46 Hz), 6.84 (1H, d, J=7.67 Hz), 7.69 (1H, d, J=2.74 Hz), 7.73 (1H, d, J=1.09 Hz), 7.93 (1H, d, J=1.09 Hz), 8.74 (1H, d, J=2.46 Hz), 9.10 (1H, d, J=2.46 Hz); ESIMS found for $C_{18}H_{19}FN_8O$ m/z 383.2 (M+1).

263

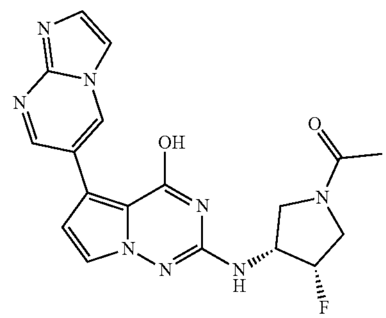

1-((3S,4R)-3-Fluoro-4-((4-hydroxy-5-(imidazo[1,2-a]pyrimidin-6-yl)pyrrolo[2,1-f][1,2,4]triazin-2-yl) amino)pyrrolidin-1-yl)ethan-1-one 263

Pale yellow solid (7 mg, 0.018 mmol, 15.6% yield). $^1$H NMR (499 MHz, DMSO-$d_6$) δ ppm 1.91-2.03 (3H, m), 3.48-3.76 (2H, m), 3.79-3.93 (1H, m), 3.99-4.09 (1H, m), 4.28-4.61 (1H, m), 5.22-5.49 (1H, m), 6.30-6.43 (1H, m), 6.83 (1H, br s), 7.48 (1H, d, J=2.19 Hz), 7.71 (1H, s), 7.94 (1H, s), 8.91 (1H, d, J=1.64 Hz), 9.41 (1H, s), 10.77 (1H, br s); ESIMS found for $C_{18}H_{17}FN_8O_2$ m/z 397.2 (M+1).

264

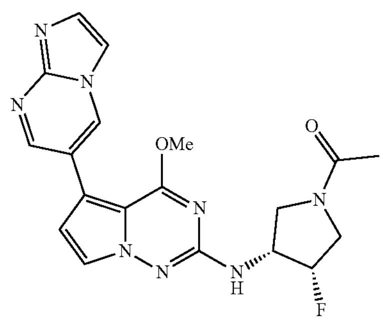

1-((3S,4R)-3-Fluoro-4-((5-(imidazo[1,2-a]pyrimidin-6-yl)-4-methoxypyrrolo[2,1-f][1,2,4]triazin-2-yl)amino)pyrrolidin-1-yl)ethan-1-one 264

Yellow solid (24 mg, 0.059 mmol, 74.3% yield). $^1$H NMR (499 MHz, DMSO-$d_6$) δ ppm 1.93-2.01 (3H, m), 3.47-3.57 (1H, m), 3.58-3.76 (1H, m), 3.78-3.97 (2H, m), 4.01 (3H, d, J=1.37 Hz), 4.28-4.59 (1H, m), 5.24-5.50 (1H, m), 6.83 (1H, t, J=2.33 Hz), 7.15 (1H, dd, J=7.12, 4.65 Hz), 7.70 (1H, dd, J=3.83, 2.74 Hz), 7.73 (1H, s), 7.94 (1H, d, J=0.82 Hz), 8.75 (1H, d, J=2.46 Hz), 9.11 (1H, d, J=2.46 Hz); ESIMS found for $C_{19}H_{19}FN_8O_2$ m/z 411.2 (M+1).

265

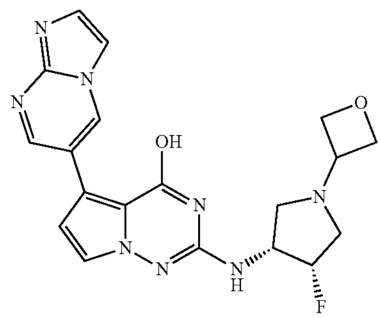

2-(((3R,4S)-4-Fluoro-1-(oxetan-3-yl)pyrrolidin-3-yl)amino)-5-(imidazo[1,2-a]pyrimidin-6-yl)pyrrolo[2,1-f][1,2,4]triazin-4-ol 265

Off-white solid (4 mg, 0.010 mmol, 8.6% yield). $^1$H NMR (499 MHz, DMSO-$d_6$) δ ppm 2.56 (1H, t, J=8.49 Hz), 2.79-2.91 (1H, m), 2.96-3.09 (1H, m), 2.98-3.03 (1H, m), 3.76 (1H, quin, J=6.09 Hz), 4.22-4.37 (1H, m), 4.46 (2H, t, J=6.02 Hz), 4.58 (2H, t, J=6.57 Hz), 5.25 (1H, dtd, J=55.95, 4.65, 4.65, 1.00 Hz), 6.29 (1H, br d, J=6.30 Hz), 6.81 (1H, d, J=2.74 Hz), 7.48 (1H, d, J=2.74 Hz), 7.71 (1H, d, J=1.10 Hz), 7.93 (1H, d, J=1.09 Hz), 8.90 (1H, d, J=2.46 Hz), 9.41 (1H, d, J=2.19 Hz), 10.78 (1H, br s); ESIMS found for $C_{19}H_{19}FN_8O_2$ m/z 411.2 (M+1).

266

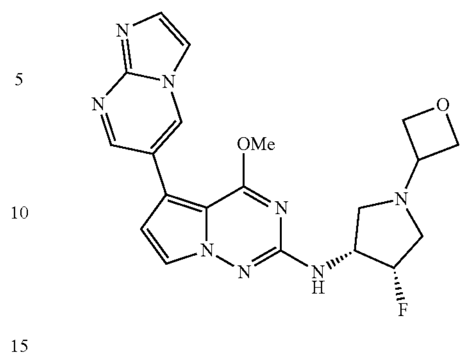

N-((3R,4S)-4-Fluoro-1-(oxetan-3-yl)pyrrolidin-3-yl)-5-(imidazo[1,2-a]pyrimidin-6-yl)-4-methoxypyrrolo[2,1-f][1,2,4]triazin-2-amine 266

Off-white solid (15 mg, 0.035 mmol, 33.4% yield). $^1$H NMR (499 MHz, DMSO-$d_6$) δ ppm 2.69 (1H, t, J=9.17 Hz), 2.77 (1H, ddd, J=29.65, 12.10, 1.10 Hz), 3.01 (1H, t, J=8.35 Hz), 3.18 (1H, ddd, J=32.95, 12.05, 4.40 Hz), 3.74-3.84 (1H, m), 4.00 (3H, s), 4.23-4.38 (1H, m), 4.47 (2H, t, J=6.02 Hz), 4.60 (2H, t, J=6.57 Hz), 5.25 (1H, dtd, J=55.65, 4.65, 4.65, 1.65 Hz), 6.82 (1H, d, J=2.46 Hz), 6.90 (1H, d, J=7.67 Hz), 7.69 (1H, d, J=2.74 Hz), 7.73 (1H, d, J=1.10 Hz), 7.93 (1H, d, J=1.37 Hz), 8.74 (1H, d, J=2.46 Hz), 9.10 (1H, d, J=2.46 Hz); ESIMS found for $C_{20}H_{21}FN_8O_2$ m/z 425.2 (M+1).

267

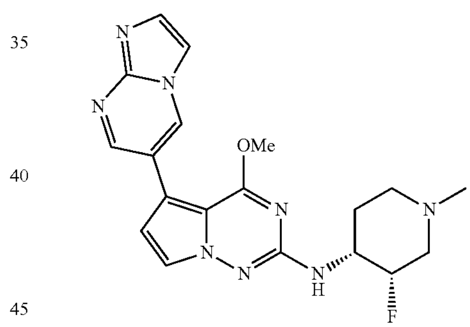

N-((3S,4R)-3-Fluoro-1-methylpiperidin-4-yl)-5-(imidazo[1,2-a]pyrimidin-6-yl)-4-methoxypyrrolo[2,1-f][1,2,4]triazin-2-amine 267

White solid (14 mg, 0.035 mmol, 67.5% yield). $^1$H NMR (499 MHz, DMSO-$d_6$) δ ppm 1.65-1.72 (1H, m), 1.92 (1H, qd, J=12.18, 3.70 Hz), 2.02-2.10 (1H, m), 2.11-2.25 (1H, m), 2.19 (3H, s), 2.80 (1H, br d, J=12.32 Hz), 3.00-3.12 (1H, m), 3.67-3.84 (1H, m), 3.99 (3H, s), 4.55 (4H, s), 4.91 (1H, d, J=50.20 Hz), 6.70 (1H, d, J=7.94 Hz), 6.79 (1H, d, J=2.74 Hz), 7.67 (1H, d, J=2.74 Hz), 7.73 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{19}H_{21}FN_8O$ m/z 397.2 (M+1).

268

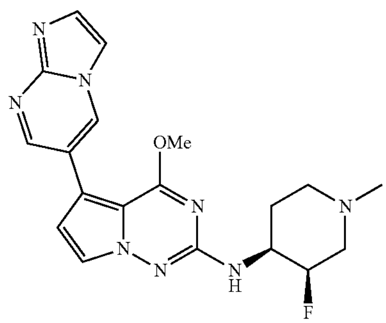

N-((3R,4S)-3-Fluoro-1-methylpiperidin-4-yl)-5-(imidazo[1,2-a]pyrimidin-6-yl)-4-methoxypyrrolo[2,1-f][1,2,4]triazin-2-amine 268

White solid (15 mg, 0.038 mmol, 72.3% yield). $^1$H NMR (499 MHz, DMSO-$d_6$) δ ppm 1.62-1.74 (1H, m), 1.92 (1H, qd, J=12.09, 3.70 Hz), 2.01-2.10 (1H, m), 2.11-2.24 (1H, m), 2.18 (3H, s), 2.79 (1H, br d, J=11.23 Hz), 3.00-3.11 (1H, m), 3.68-3.83 (1H, m), 3.99 (3H, s), 4.91 (1H, d, J=50.20 Hz), 6.69 (1H, d, J=7.94 Hz), 6.79 (1H, d, J=2.46 Hz), 7.67 (1H, d, J=2.74 Hz), 7.72 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{19}H_{21}FN_8O$ m/z 397.2 (M+1).

269

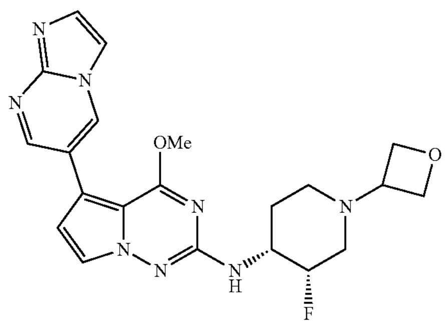

N-((3S,4R)-3-Fluoro-1-(oxetan-3-yl)piperidin-4-yl)-5-(imidazo[1,2-a]pyrimidin-6-yl)-4-methoxypyrrolo[2,1-f][1,2,4]triazin-2-amine 269

White solid (13 mg, 0.030 mmol, 36.6% yield). $^1$H NMR (499 MHz, DMSO-$d_6$) δ ppm 1.66-1.78 (1H, m), 1.92 (1H, qd, J=12.14, 3.56 Hz), 1.98-2.06 (1H, m), 2.10-2.25 (1H, m), 2.76 (1H, br d, J=10.13 Hz), 2.93-3.06 (1H, m), 3.49 (1H, quin, J=6.30 Hz), 3.74-3.90 (1H, m), 3.99 (3H, s), 4.40 (1H, t, J=6.16 Hz), 4.46 (1H, t, J=6.16 Hz), 4.54 (2H, td, J=6.57, 3.01 Hz), 4.94 (1H, d, J=49.35 Hz), 6.76 (1H, d, J=7.67 Hz), 6.79 (1H, d, J=2.46 Hz), 7.67 (1H, d, J=2.74 Hz), 7.73 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{21}H_{23}FN_8O_2$ m/z 439.2 (M+1).

270

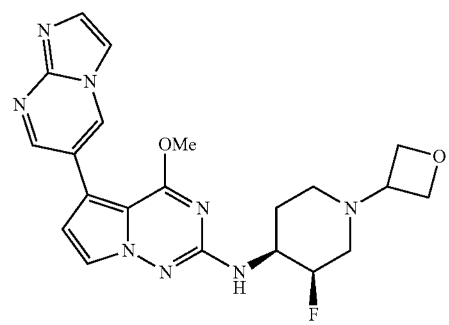

N-((3R,4S)-3-Fluoro-1-(oxetan-3-yl)piperidin-4-yl)-5-(imidazo[1,2-a]pyrimidin-6-yl)-4-methoxypyrrolo[2,1-f][1,2,4]triazin-2-amine 270

White solid (23 mg, 0.053 mmol, 37.8% yield). $^1$H NMR (499 MHz, DMSO-$d_6$) δ ppm 1.69-1.76 (1H, m), 1.92 (1H, qd, J=12.14, 3.29 Hz), 1.98-2.06 (1H, m), 2.08-2.24 (1H, m), 2.71-2.80 (1H, m), 2.94-3.05 (1H, m), 3.49 (1H, quin, J=6.50 Hz), 3.74-3.91 (1H, m), 3.99 (3H, s), 4.40 (1H, t, J=6.02 Hz), 4.46 (1H, t, J=6.16 Hz), 4.54 (2H, td, J=6.50, 3.15 Hz), 4.93 (1H, d, J=49.35 Hz), 6.76 (1H, d, J=7.94 Hz), 6.79 (1H, d, J=2.74 Hz), 7.67 (1H, d, J=2.46 Hz), 7.73 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{21}H_{23}FN_8O_2$ m/z 439.2 (M+1).

271

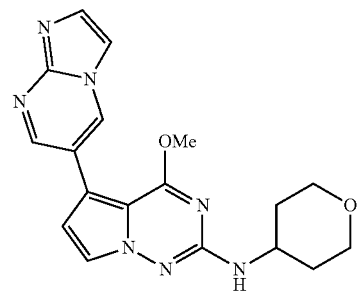

5-(Imidazo[1,2-a]pyrimidin-6-yl)-4-methoxy-N-(tetrahydro-2H-pyran-4-yl)pyrrolo[2,1-f][1,2,4]triazin-2-amine 271

Beige solid (4 mg, 0.011 mmol, 6.6% yield). $^1$H NMR (499 MHz, DMSO-$d_6$) δ ppm 1.48-1.61 (2H, m), 1.90 (2H, br dd, J=12.59, 2.19 Hz), 3.40 (2H, td, J=11.64, 1.92 Hz), 3.76-3.84 (1H, m), 3.85-3.91 (2H, m), 3.98 (3H, s), 6.74 (1H, d, J=7.94 Hz), 6.77 (1H, d, J=2.46 Hz), 7.67 (1H, d, J=2.46 Hz), 7.72 (1H, d, J=1.09 Hz), 7.93 (1H, d, J=1.37 Hz), 8.73 (1H, d, J=2.46 Hz), 9.09 (1H, d, J=2.46 Hz) ESIMS found for $C_{18}H_{19}N_7O_2$ m/z 366.2 (M+1).

272

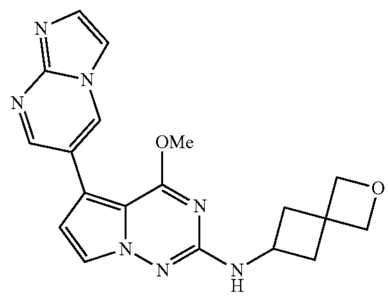

5-(Imidazo[1,2-a]pyrimidin-6-yl)-4-methoxy-N-(2-oxaspiro[3.3]heptan-6-yl)pyrrolo[2,1-f][1,2,4]triazin-2-amine 272

Off-white solid (6 mg, 0.016 mmol, 6.0% yield). $^1$H NMR (499 MHz, DMSO-$d_6$) δ ppm 2.12-2.23 (2H, m), 2.61 (2H, ddd, J=9.99, 7.53, 2.74 Hz), 3.92-4.05 (1H, m), 3.96 (3H, s), 4.51 (2H, s), 4.63 (2H, s), 6.78 (1H, d, J=2.74 Hz), 7.03 (1H, d, J=7.12 Hz), 7.66 (1H, d, J=2.46 Hz), 7.72 (1H, d, J=1.37 Hz), 7.92 (1H, d, J=1.37 Hz), 8.72 (1H, d, J=2.46 Hz), 9.08 (1H, d, J=2.46 Hz); ESIMS found for $C_{19}H_{19}N_7O_2$ m/z 378.2 (M+1).

273

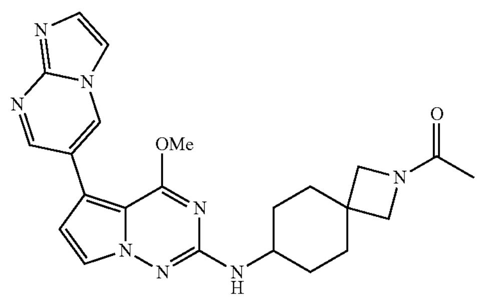

1-(7-((5-(Imidazo[1,2-a]pyrimidin-6-yl)-4-methoxy-pyrrolo[2,1-f][1,2,4]triazin-2-yl)amino)-2-azaspiro[3.5]nonan-2-yl)ethan-1-one 273

Colorless gum (10 mg, 0.022 mmol, 21.6% yield). $^1$H NMR (499 MHz, DMSO-$d_6$) δ ppm 1.26-1.40 (2H, m), 1.49-1.61 (2H, m), 1.74-1.77 (3H, m), 1.83-1.93 (4H, m), 3.47 (1H, s), 3.52 (1H, s), 3.53-3.63 (1H, m), 3.75 (1H, s), 3.80 (1H, s), 3.97 (3H, s), 6.59 (1H, dd, J=16.70, 7.94 Hz), 6.77 (1H, d, J=2.74 Hz), 7.67 (1H, t, J=2.87 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{23}H_{26}N_8O_2$ m/z 447.3 (M+1).

274

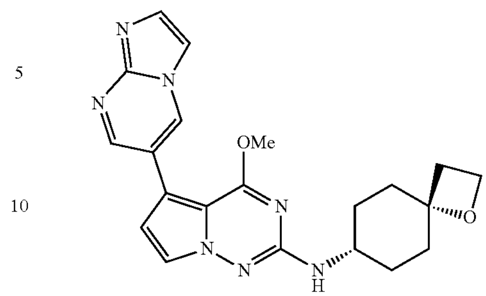

5-(Imidazo[1,2-a]pyrimidin-6-yl)-4-methoxy-N-((4s, 7s)-1-oxaspiro[3.5]nonan-7-yl)pyrrolo[2,1-f][1,2,4]triazin-2-amine 274

White solid (4.2 mg, 0.0104 mmol). $^1$H NMR (400 MHz, DMSO-$d_6$) δ ppm 1.28-1.41 (2H, m), 1.52 (2H, td, J=12.38, 3.38 Hz), 1.85-1.98 (2H, m), 2.05 (2H, br d, J=12.88 Hz), 2.34 (2H, t, J=7.69 Hz), 3.50-3.64 (1H, m), 3.97 (3H, s), 4.37 (2H, t, J=7.69 Hz), 6.58 (1H, d, J=7.75 Hz), 6.76 (1H, d, J=2.63 Hz), 7.67 (1H, d, J=2.63 Hz), 7.72 (1H, s), 7.92 (1H, d, J=1.00 Hz), 8.73 (1H, d, J=2.38 Hz), 9.08 (1H, d, J=2.38 Hz); ESIMS found for $C_{21}H_{23}N_7O_2$ m/z 406.0 (M+1).

275

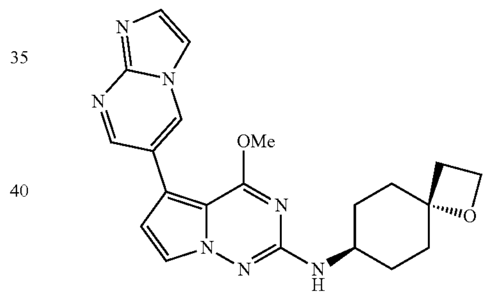

5-(Imidazo[1,2-a]pyrimidin-6-yl)-4-methoxy-N-((4r, 7r)-1-oxaspiro[3.5]nonan-7-yl)pyrrolo[2,1-f][1,2,4]triazin-2-amine 275

White solid (4.20 mg, 0.010 mmol). $^1$H NMR (400 MHz, DMSO-$d_6$) δ ppm 1.29-1.43 (2H, m), 1.47-1.60 (2H, m), 1.86-1.97 (2H, m), 2.05 (2H, br d, J=12.88 Hz), 2.34 (2H, t, J=7.69 Hz), 3.51-3.63 (1H, m), 3.97 (3H, s), 4.37 (2H, t, J=7.69 Hz), 6.58 (1H, d, J=7.75 Hz), 6.76 (1H, d, J=2.63 Hz), 7.67 (1H, d, J=2.63 Hz), 7.72 (1H, s), 7.92 (1H, d, J=1.00 Hz), 8.73 (1H, d, J=2.38 Hz), 9.08 (1H, d, J=2.38 Hz); ESIMS found for $C_{21}H_{23}N_7O_2$ m/z 406.0 (M+1).

276

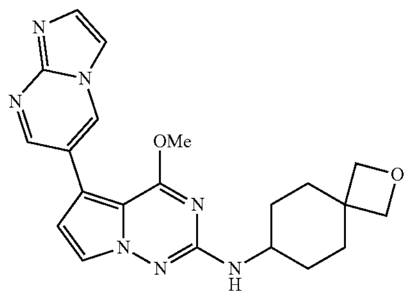

5-(Imidazo[1,2-a]pyrimidin-6-yl)-4-methoxy-N-(2-oxaspiro[3.5]nonan-7-yl)pyrrolo[2,1-f][1,2,4]triazin-2-amine 276

Beige solid (32 mg, 0.079 mmol, 29.7% yield). $^1$H NMR (499 MHz, DMSO-$d_6$) δ ppm 1.20-1.32 (2H, m), 1.52 (2H, td, J=12.87, 3.29 Hz), 1.87 (2H, br dd, J=13.14, 3.29 Hz), 2.07 (2H, br d, J=13.14 Hz), 3.48-3.62 (1H, m), 3.96 (3H, s), 4.24 (2H, s), 4.32 (2H, s), 6.55 (1H, d, J=7.94 Hz), 6.76 (1H, d, J=2.46 Hz), 7.66 (1H, d, J=2.46 Hz), 7.73 (1H, s), 7.93 (1H, s), 8.73 (1H, d, J=2.19 Hz), 9.08 (1H, d, J=2.46 Hz); ESIMS found for $C_{21}H_{23}N_7O_2$ m/z 406.2 (M+1).

277

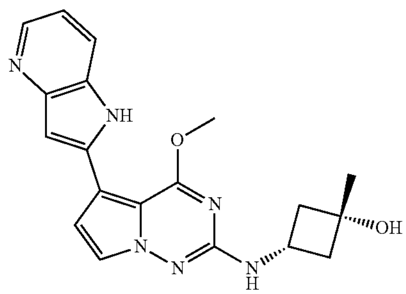

cis-3-((4-Methoxy-5-(1H-pyrrolo[3,2-b]pyridin-2-yl) pyrrolo[2,1-f][1,2,4]triazin-2-yl)amino)-1-methylcyclobutan-1-ol 277

Beige solid (39 mg, 0.107 mmol, 46.0% yield). $^1$H NMR (499 MHz, DMSO-$d_6$) δ ppm 1.27 (3H, s), 1.99-2.07 (2H, m), 2.31-2.40 (2H, m), 3.72 (1H, dq, J=15.09, 7.75 Hz), 4.11 (3H, s), 4.92 (1H, s), 6.94 (1H, dd, J=2.19, 0.82 Hz), 6.99 (1H, d, J=2.74 Hz), 7.00 (1H, d, J=6.57 Hz), 7.03 (1H, dd, J=7.95, 4.65 Hz), 7.65 (1H, d, J=2.74 Hz), 7.70 (1H, dt, J=8.01, 1.20 Hz), 8.25 (1H, dd, J=4.65, 1.37 Hz), 11.18 (1H, d, J=1.92 Hz); ESIMS found for $C_{1-9}H_2O$ $N_6O_2$ m/z 365.2 (M+1).

280

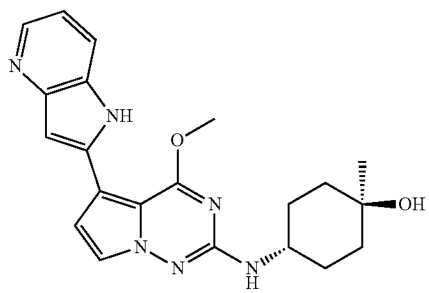

trans-4-((4-Methoxy-5-(1H-pyrrolo[3,2-b]pyridin-2-yl)pyrrolo[2,1-f][1,2,4]triazin-2-yl)amino)-1-methylcyclohexan-1-ol 280

Yellow solid (37 mg, 0.094 mmol, 39.4% yield). $^1$H NMR (499 MHz, DMSO-$d_6$) δ ppm 1.15 (3H, s), 1.33-1.52 (4H, m), 1.54-1.63 (2H, m), 1.82-1.91 (2H, m), 3.64 (1H, dt, J=8.08, 4.18 Hz), 4.12 (3H, s), 4.23 (1H, s), 6.55 (1H, d, J=7.94 Hz), 6.93 (1H, d, J=1.37 Hz), 6.98 (1H, d, J=2.74 Hz), 7.03 (1H, dd, J=7.95, 4.65 Hz), 7.65 (1H, d, J=2.74 Hz), 7.69-7.72 (1H, m), 8.25 (1H, dd, J=4.65, 1.37 Hz), 11.18 (1H, d, J=1.92 Hz); ESIMS found for $C_{21}H_{24}N_6O_2$ m/z 393.2 (M+1).

281

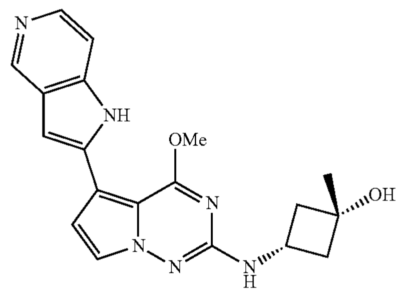

cis-3-((4-Methoxy-5-(1H-pyrrolo[3,2-c]pyridin-2-yl) pyrrolo[2,1-f][1,2,4]triazin-2-yl)amino)-1-methylcyclobutan-1-ol 281

Off-white solid (2 mg, 0.006 mmol, 9.1% yield). $^1$H NMR (499 MHz, DMSO-$d_6$) δ ppm 1.27 (3H, s), 1.97-2.07 (2H, m), 2.30-2.41 (2H, m), 3.71 (1H, dq, J=15.09, 7.65 Hz), 4.10 (3H, s), 4.93 (1H, s), 6.93 (1H, d, J=1.10 Hz), 6.95 (1H, d, J=2.74 Hz), 6.98 (1H, d, J=6.57 Hz), 7.34 (1H, d, J=5.48 Hz), 7.64 (1H, d, J=2.74 Hz), 8.11 (1H, d, J=5.48 Hz), 8.76 (1H, s), 11.41 (1H, s); ESIMS found for $C_{1-9}H_2O$ $N_6O_2$ m/z 365.2 (M+1).

282

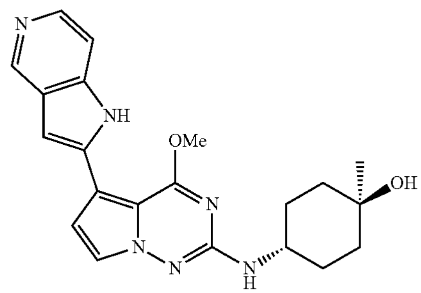

trans-4-((4-Methoxy-5-(1H-pyrrolo[3,2-c]pyridin-2-yl)pyrrolo[2,1-f][1,2,4]triazin-2-yl)amino)-1-methylcyclohexan-1-ol 282

White solid (7 mg, 0.018 mmol, 31.7% yield). $^1$H NMR (499 MHz, DMSO-$d_6$) δ ppm 1.15 (3H, s), 1.36-1.52 (4H, m), 1.57-1.65 (2H, m), 1.83-1.92 (2H, m), 3.63 (1H, br dd, J=7.80, 3.70 Hz), 4.11 (3H, s), 4.24 (1H, s), 6.53 (1H, d, J=7.94 Hz), 6.93 (1H, d, J=1.10 Hz), 6.95 (1H, d, J=2.74 Hz), 7.34 (1H, d, J=5.75 Hz), 7.64 (1H, d, J=2.46 Hz), 8.12

(1H, br d, J=5.48 Hz), 8.76 (1H, s), 11.41 (1H, d, J=0.82 Hz); ESIMS found for $C_{21}H_{24}N_6O_2$ m/z 393.2 (M+1).

283

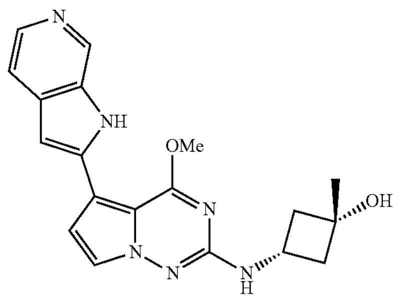

cis-3-((4-Methoxy-5-(1H-pyrrolo[2,3-c]pyridin-2-yl)pyrrolo[2,1-f][1,2,4]triazin-2-yl)amino)-1-methylcyclobutan-1-ol 283

Tan solid (6 mg, 0.017 mmol, 40.7% yield). $^1$H NMR (499 MHz, DMSO-$d_6$) δ ppm 1.27 (3H, s), 1.96-2.07 (2H, m), 2.30-2.41 (2H, m), 3.66-3.78 (1H, m), 4.11 (3H, s), 4.93 (1H, s), 6.86 (1H, d, J=1.64 Hz), 6.99 (1H, d, J=2.74 Hz), 7.02 (1H, d, J=6.57 Hz), 7.45 (1H, br d, J=5.20 Hz), 7.65 (1H, d, J=2.74 Hz), 8.04 (1H, br d, J=4.93 Hz), 8.70 (1H, br s), 11.42 (1H, s); ESIMS found for $C_{19}H_{20}N_6O_2$ m/z 365.2 (M+1).

284

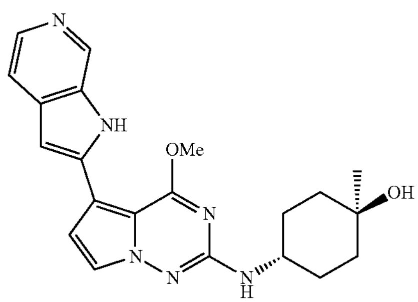

trans-4-((4-Methoxy-5-(1H-pyrrolo[2,3-c]pyridin-2-yl)pyrrolo[2,1-f][1,2,4]triazin-2-yl)amino)-1-methylcyclohexan-1-ol 284

Beige solid (12 mg, 0.031 mmol, 66.6% yield). $^1$H NMR (499 MHz, DMSO-$d_6$) δ ppm 1.15 (3H, s), 1.30-1.53 (4H, m), 1.54-1.63 (2H, m), 1.63-1.77 (2H, m), 3.47-3.70 (1H, m), 4.11 (3H, d, J=1.64 Hz), 6.58 (1H, dd, J=14.51, 7.94 Hz), 6.86 (1H, d, J=1.64 Hz), 6.98 (1H, t, J=2.87 Hz), 7.45 (1H, br d, J=5.48 Hz), 7.64 (1H, dd, J=14.78, 2.46 Hz), 8.04 (1H, br d, J=4.93 Hz), 8.70 (1H, s), 11.41 (1H, br s); ESIMS found for $C_{21}H_{24}N_6O_2$ m/z 393.2 (M+1).

287

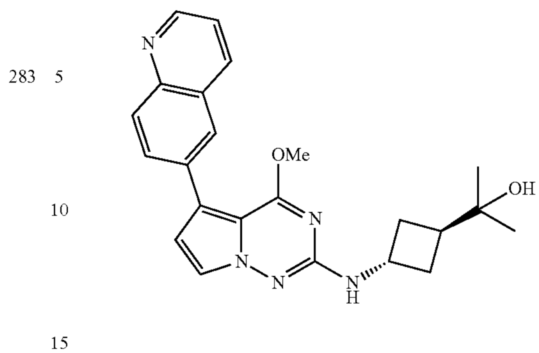

2-(trans-3-((4-methoxy-5-(quinolin-6-yl)pyrrolo[2,1-f][1,2,4]triazin-2-yl)amino)cyclobutyl)propan-2-ol 287

Yellow solid (36 mg, 0.089 mmol, 46.2% yield). $^1$H NMR (499 MHz, DMSO-$d_6$) δ ppm 1.05 (6H, s), 1.98 (2H, ddd, J=12.39, 9.65, 5.89 Hz), 2.16-2.27 (1H, m), 2.27-2.36 (2H, m), 3.96 (3H, s), 4.09 (1H, dq, J=13.62, 6.96 Hz), 4.19 (1H, s), 6.76 (1H, d, J=2.74 Hz), 6.96 (1H, d, J=6.84 Hz), 7.52 (1H, dd, J=8.21, 4.11 Hz), 7.64 (1H, d, J=2.46 Hz), 7.94-8.01 (2H, m), 8.10 (1H, s), 8.36 (1H, dd, J=8.35, 1.51 Hz), 8.86 (1H, dd, J=4.24, 1.78 Hz); ESIMS found for $C_{23}H_{25}N_5O_2$ m/z 404.2 (M+1).

288

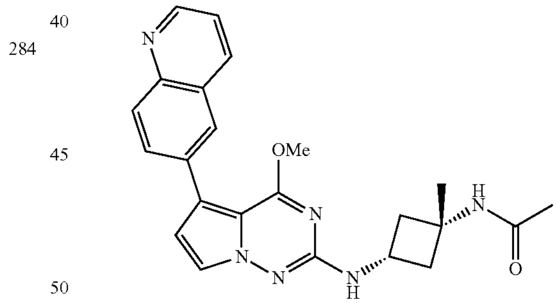

N-(cis-3-((4-Methoxy-5-(quinolin-6-yl)pyrrolo[2,1-f][1,2,4]triazin-2-yl)amino)-1-methylcyclobutyl)acetamide 288

Off-white solid (39 mg, 0.094 mmol, 97.4% yield). $^1$H NMR (499 MHz, DMSO-$d_6$) δ ppm 1.38 (3H, s), 1.76 (3H, s), 2.10-2.21 (2H, m), 2.43 (2H, ddd, J=9.58, 7.39, 2.46 Hz), 3.96 (3H, s), 4.04 (1H, sxt, J=7.72 Hz), 6.77 (1H, d, J=2.46 Hz), 7.00 (1H, d, J=6.84 Hz), 7.52 (1H, dd, J=8.35, 4.24 Hz), 7.66 (1H, d, J=2.74 Hz), 7.95-8.01 (2H, m), 8.03 (1H, s), 8.11 (1H, s), 8.36 (1H, dd, J=8.35, 1.51 Hz), 8.86 (1H, dd, J=4.11, 1.64 Hz); ESIMS found for $C_{23}H_{24}N_6O_2$ m/z 417.2 (M+1).

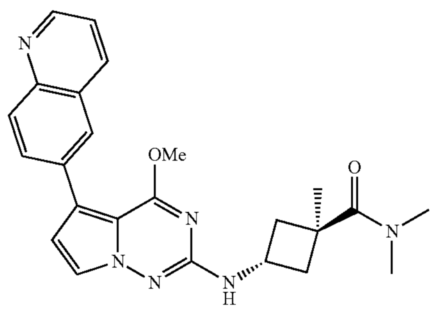

290 trans-3-((4-Methoxy-5-(quinolin-6-yl)pyrrolo[2,1-f][1,2,4]triazin-2-yl)amino)-N,N,1-trimethylcyclobutane-1-carboxamide 290

Light yellow solid (32 mg, 0.074 mmol, 60.0% yield). $^1$H NMR (499 MHz, DMSO-$d_6$) δ ppm 1.40 (3H, s), 1.95-2.05 (2H, m), 2.80-2.95 (8H, m), 3.91 (1H, dq, J=14.78, 7.30 Hz), 3.97 (3H, s), 6.78 (1H, d, J=2.74 Hz), 7.08 (1H, d, J=6.57 Hz), 7.56 (1H, dd, J=8.35, 4.24 Hz), 7.66 (1H, d, J=2.46 Hz), 8.00 (2H, s), 8.13 (1H, s), 8.40 (1H, d, J=7.39 Hz), 8.88 (1H, br d, J=3.01 Hz); ESIMS found for $C_{24}H_{26}N_6O_2$ m/z 431.2 (M+1).

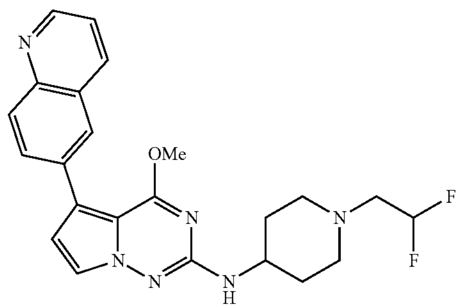

304

N-(1-(2,2-Difluoroethyl)piperidin-4-yl)-4-methoxy-5-(quinolin-6-yl)pyrrolo[2,1-f][1,2,4]triazin-2-amine 304

Yellow solid (42 mg, 0.096 mmol, 37.7% yield). $^1$H NMR (499 MHz, DMSO-$d_6$) δ ppm 1.47-1.62 (2H, m), 1.85-1.95 (2H, m), 2.21-2.32 (2H, m), 2.72 (2H, td, J=15.61, 4.38 Hz), 2.91 (2H, br d, J=11.77 Hz), 3.54-3.66 (1H, m), 3.96 (3H, s), 6.14 (1H, tt, J=55.95, 4.38 Hz), 6.61 (1H, d, J=7.94 Hz), 6.77 (1H, d, J=2.46 Hz), 7.47-7.57 (1H, m), 7.65 (1H, d, J=2.74 Hz), 7.94-8.03 (2H, m), 8.11 (1H, s), 8.36 (1H, dd, J=8.35, 1.51 Hz), 8.86 (1H, dd, J=4.11, 1.64 Hz); ESIMS found for $C_{23}H_{24}F_2N_6O$ m/z 439.2 (M+1).

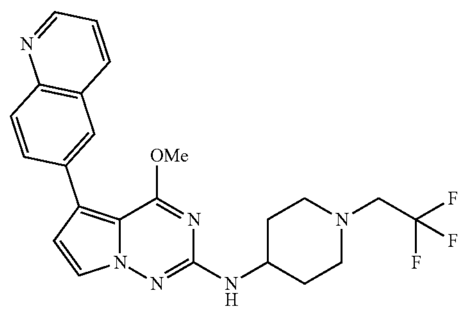

305

4-Methoxy-5-(quinolin-6-yl)-N-(1-(2,2,2-trifluoroethyl)piperidin-4-yl)pyrrolo[2,1-f][1,2,4]triazin-2-amine 305

Off-white solid (30 mg, 0.066 mmol, 26.5% yield). $^1$H NMR (499 MHz, DMSO-$d_6$) δ ppm 1.49-1.61 (2H, m), 1.91 (2H, br d, J=9.86 Hz), 2.39-2.48 (2H, m), 2.93 (2H, br d, J=11.77 Hz), 3.17 (2H, q, J=10.40 Hz), 3.55-3.66 (1H, m), 3.96 (3H, s), 6.62 (1H, d, J=7.94 Hz), 6.77 (1H, d, J=2.46 Hz), 7.52 (1H, dd, J=8.21, 4.11 Hz), 7.65 (1H, d, J=2.74 Hz), 7.94-8.03 (2H, m), 8.11 (1H, s), 8.36 (1H, dd, J=8.49, 1.64 Hz), 8.86 (1H, dd, J=4.38, 1.64 Hz); ESIMS found for $C_{23}H_{23}F_3N_6O$ m/z 457.2 (M+1).

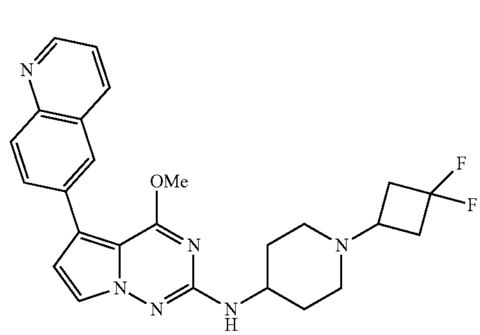

306

N-(1-(3,3-Difluorocyclobutyl)piperidin-4-yl)-4-methoxy-5-(quinolin-6-yl)pyrrolo[2,1-f][1,2,4]triazin-2-amine 306

White solid (4 mg, 0.009 mmol, 4.6% yield). $^1$H NMR (499 MHz, DMSO-$d_6$) δ ppm 1.45-1.59 (2H, m), 1.86-1.97 (4H, m), 2.32-2.46 (2H, m), 2.59-2.73 (3H, m), 2.80 (2H, br d, J=11.50 Hz), 3.56-3.66 (1H, m), 3.96 (3H, s), 6.63 (1H, d, J=7.94 Hz), 6.77 (1H, d, J=2.46 Hz), 7.52 (1H, dd, J=8.35, 4.24 Hz), 7.65 (1H, d, J=2.74 Hz), 7.94-8.03 (2H, m), 8.11 (1H, s), 8.36 (1H, dd, J=8.35, 1.51 Hz), 8.86 (1H, dd, J=4.11, 1.64 Hz); ESIMS found for $C_{25}H_{26}F_2N_6O$ m/z 465.2 (M+1).

310

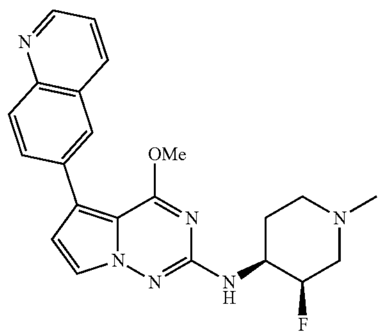

N-((3R,4S)-3-Fluoro-1-methylpiperidin-4-yl)-4-methoxy-5-(quinolin-6-yl)pyrrolo[2,1-f][1,2,4]triazin-2-amine 310

Off-white solid (11 mg, 0.027 mmol, 88.5% yield). $^1$H NMR (499 MHz, DMSO-$d_6$) δ ppm 1.69 (1H, br dd, J=13.00, 3.42 Hz), 1.93 (1H, qd, J=12.18, 3.70 Hz), 2.06 (1H, br t, J=10.95 Hz), 2.12-2.25 (1H, m), 2.19 (3H, s), 2.74-2.86 (1H, m), 3.00-3.11 (1H, m), 3.69-3.85 (1H, m), 3.98 (3H, s), 4.92 (1H, d, J=49.90 Hz), 6.63 (1H, d, J=7.67 Hz), 6.79 (1H, d, J=2.46 Hz), 7.53 (1H, dd, J=8.21, 4.38 Hz), 7.65 (1H, d, J=2.46 Hz), 7.95-8.04 (2H, m), 8.12 (1H, s), 8.36 (1H, dd, J=8.35, 1.51 Hz), 8.86 (1H, dd, J=4.11, 1.64 Hz); ESIMS found for $C_{22}H_{23}FN_6O$ m/z 407.2 (M+1).

314

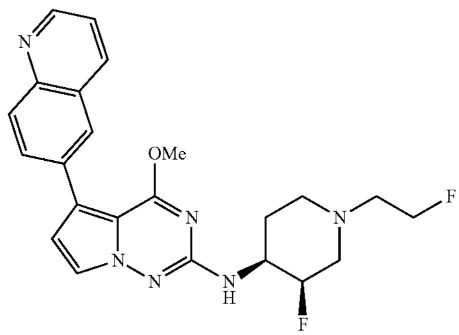

N-((3R,4S)-3-Fluoro-1-(2-fluoroethyl)piperidin-4-yl)-4-methoxy-5-(quinolin-6-yl)pyrrolo[2,1-f][1,2,4]triazin-2-amine 314

Off-white fluffy solid (16 mg, 0.037 mmol, 47.7% yield). $^1$H NMR (500 MHz, DMSO-$d_6$) δ ppm 1.66-1.77 (1H, m), 1.93 (1H, qd, J=12.21, 3.43 Hz), 2.26 (1H, br t, J=11.25 Hz), 2.39 (1H, dd, J=37.60, 12.90 Hz), 2.68 (2H, dt, J=28.60, 5.25 Hz), 2.93 (1H, br d, J=10.70 Hz), 3.13-3.22 (1H, m), 3.73-3.89 (1H, m), 3.98 (3H, s), 4.55 (2H, dt, J=47.75, 4.95 Hz), 4.93 (1H, d, J=49.70 Hz), 6.64 (1H, d, J=7.68 Hz), 6.79 (1H, d, J=2.47 Hz), 7.53 (1H, dd, J=8.23, 4.39 Hz), 7.65 (1H, d, J=2.47 Hz), 7.94-8.04 (2H, m), 8.12 (1H, s), 8.36 (1H, dd, J=8.23, 1.37 Hz), 8.86 (1H, dd, J=4.12, 1.37 Hz); ESIMS found for $C_{23}H_{24}F_2N_6O$ m/z 439.2 (M+1).

318

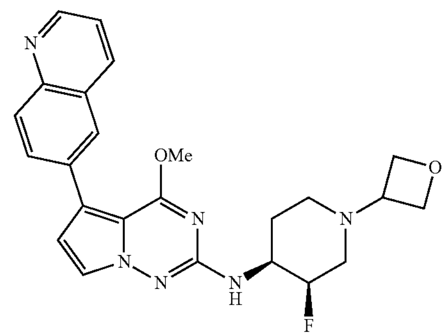

N-((3R,4S)-3-Fluoro-1-(oxetan-3-yl)piperidin-4-yl)-4-methoxy-5-(quinolin-6-yl)pyrrolo[2,1-f][1,2,4]triazin-2-amine 318

Beige solid (15 mg, 0.033 mmol, 72.9% yield). $^1$H NMR (499 MHz, DMSO-$d_6$) δ ppm 1.68-1.79 (1H, m), 1.93 (1H, qd, J=12.18, 3.15 Hz), 1.98-2.08 (1H, m), 2.16 (1H, dd, J=37.00, 12.60 Hz), 2.76 (1H, br d, J=11.23 Hz), 2.95-3.05 (1H, m), 3.50 (1H, quin, J=6.43 Hz), 3.75-3.92 (1H, m), 3.98 (3H, s), 4.40 (1H, t, J=6.16 Hz), 4.46 (1H, t, J=6.16 Hz), 4.54 (2H, td, J=6.57, 3.01 Hz), 4.95 (1H, d, J=49.65 Hz), 6.69 (1H, d, J=7.94 Hz), 6.79 (1H, d, J=2.74 Hz), 7.49-7.57 (1H, m), 7.65 (1H, d, J=2.74 Hz), 7.95-8.04 (2H, m), 8.12 (1H, s), 8.36 (1H, dd, J=8.21, 1.64 Hz), 8.86 (1H, dd, J=4.11, 1.64 Hz); ESIMS found for $C_{24}H_{25}FN_6O_2$ m/z 449.3 (M+1).

319

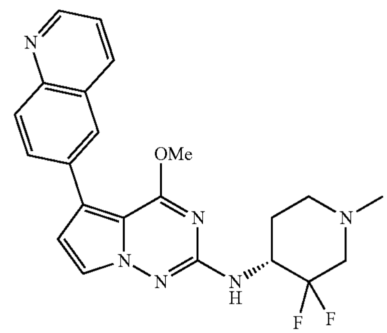

(R)—N-(3,3-Difluoro-1-methylpiperidin-4-yl)-4-methoxy-5-(quinolin-6-yl)pyrrolo[2,1-f][1,2,4]triazin-2-amine 319

Off-white solid (17 mg, 0.040 mmol, 74.7% yield). $^1$H NMR (499 MHz, DMSO-$d_6$) δ ppm 1.76-1.91 (2H, m), 2.12-2.23 (1H, m), 2.26 (3H, s), 2.33-2.46 (1H, m), 2.79 (1H, br d, J=11.77 Hz), 2.99-3.11 (1H, m), 3.99 (3H, s), 4.18-4.33 (1H, m), 6.81 (1H, d, J=2.46 Hz), 6.83 (1H, d, J=9.31 Hz), 7.53 (1H, dd, J=8.21, 4.11 Hz), 7.67 (1H, d, J=2.46 Hz), 7.99 (2H, s), 8.12 (1H, s), 8.33-8.40 (1H, m), 8.86 (1H, dd, J=4.24, 1.51 Hz); ESIMS found for $C_{22}H_{22}F_2N_6O$ m/z 425.2 (M+1).

320

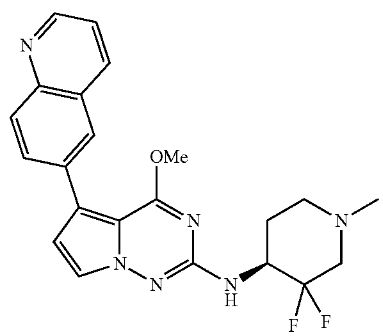

(S)—N-(3,3-Difluoro-1-methylpiperidin-4-yl)-4-methoxy-5-(quinolin-6-yl)pyrrolo[2,1-f][1,2,4]triazin-2-amine 320

Yellow solid (11 mg, 0.026 mmol, 88.6% yield). $^1$H NMR (499 MHz, DMSO-$d_6$) δ ppm 1.77-1.92 (2H, m), 2.13-2.22 (1H, m), 2.26 (3H, s), 2.34-2.45 (1H, m), 2.79 (1H, br d, J=11.23 Hz), 2.99-3.12 (1H, m), 3.99 (3H, s), 4.17-4.33 (1H, m), 6.81 (1H, d, J=2.46 Hz), 6.83 (1H, d, J=9.31 Hz), 7.53 (1H, dd, J=8.21, 4.11 Hz), 7.67 (1H, d, J=2.46 Hz), 7.99 (2H, s), 8.12 (1H, s), 8.36 (1H, d, J=8.21 Hz), 8.86 (1H, d, J=4.11 Hz); ESIMS found for $C_{22}H_{22}F_2N_6O$ m/z 425.2 (M+1).

321

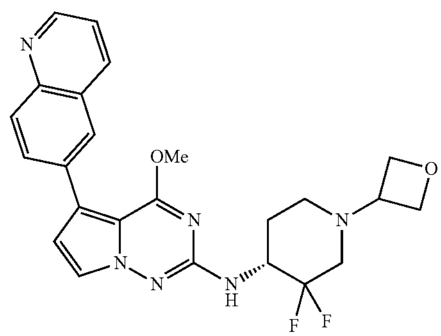

(R)—N-(3,3-Difluoro-1-(oxetan-3-yl)piperidin-4-yl)-4-methoxy-5-(quinolin-6-yl)pyrrolo[2,1-f][1,2,4]triazin-2-amine 321

Off-white solid (15 mg, 0.033 mmol, 72.9% yield). $^1$H NMR (499 MHz, CHLOROFORM-d) δ ppm 1.77-1.87 (1H, m), 2.19-2.30 (2H, m), 2.31-2.45 (1H, m), 2.82-2.90 (1H, m), 3.05-3.15 (1H, m), 3.70 (1H, quin, J=6.43 Hz), 4.01 (3H, s), 4.25-4.41 (1H, m), 4.63-4.67 (1H, m), 4.68 (1H, d, J=6.30 Hz), 4.69-4.71 (2H, m), 4.71-4.73 (1H, m), 6.70 (1H, d, J=2.46 Hz), 7.41 (1H, dd, J=8.35, 4.24 Hz), 7.48 (1H, d, J=2.74 Hz), 7.94-7.99 (2H, m), 8.10 (1H, d, J=8.49 Hz), 8.18 (1H, d, J=7.39 Hz), 8.90 (1H, dd, J=4.11, 1.64 Hz); ESIMS found for $C_{24}H_{24}F_2N_6O_2$ m/z 467.2 (M+1).

322

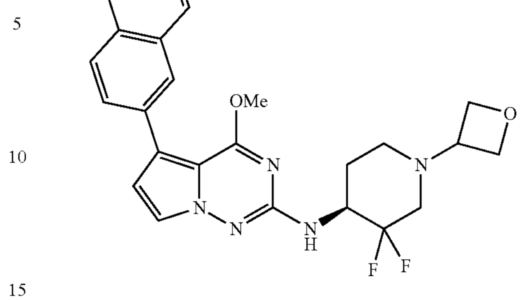

(S)—N-(3,3-Difluoro-1-(oxetan-3-yl)piperidin-4-yl)-4-methoxy-5-(quinolin-6-yl)pyrrolo[2,1-f][1,2,4]triazin-2-amine 322

Off-white solid (15 mg, 0.033 mmol, 72.9% yield). $^1$H NMR (499 MHz, DMSO-$d_6$) δ ppm 1.77-1.86 (1H, m), 1.87-1.94 (1H, m), 2.13-2.20 (1H, m), 2.37-2.46 (1H, m), 2.76 (1H, br d, J=11.50 Hz), 2.97-3.07 (1H, m), 3.61 (1H, quin, J=6.37 Hz), 4.00 (3H, s), 4.24-4.39 (1H, m), 4.44 (2H, dt, J=15.06, 6.16 Hz), 4.55 (2H, td, J=6.57, 3.83 Hz), 6.81 (1H, d, J=2.74 Hz), 6.89 (1H, d, J=9.58 Hz), 7.53 (1H, dd, J=8.21, 4.11 Hz), 7.66 (1H, d, J=2.74 Hz), 7.96-8.04 (2H, m), 8.12 (1H, s), 8.36 (1H, dd, J=8.49, 1.64 Hz), 8.86 (1H, dd, J=4.11, 1.64 Hz); ESIMS found for $C_{24}H_{24}F_2N_6O_2$ m/z 467.3 (M+1).

326

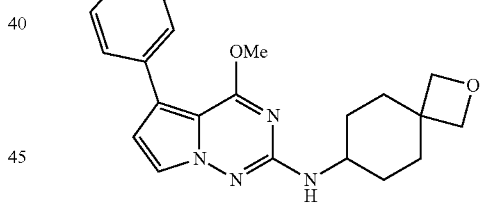

4-Methoxy-5-(quinolin-6-yl)-N-(2-oxaspiro[3.5]nonan-7-yl)pyrrolo[2,1-f][1,2,4]triazin-2-amine 326

Off-white solid (61 mg, 0.147 mmol, 53.7% yield). $^1$H NMR (499 MHz, DMSO-$d_6$) δ ppm 1.21-1.34 (2H, m), 1.53 (2H, td, J=12.87, 3.29 Hz), 1.82-1.94 (2H, m), 2.07 (2H, br d, J=13.42 Hz), 3.49-3.61 (1H, m), 3.95 (3H, s), 4.24 (2H, s), 4.32 (2H, s), 6.50 (1H, d, J=7.94 Hz), 6.76 (1H, d, J=2.74 Hz), 7.52 (1H, dd, J=8.21, 4.11 Hz), 7.64 (1H, d, J=2.74 Hz), 7.94-8.03 (2H, m), 8.10 (1H, d, J=1.37 Hz), 8.35 (1H, dd, J=8.49, 1.64 Hz), 8.86 (1H, dd, J=4.24, 1.78 Hz); ESIMS found for $C_{24}H_{25}N_5O_2$ m/z 416.2 (M+1).

328

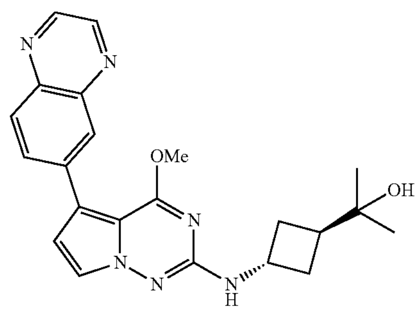

2-(trans-3-((4-Methoxy-5-(quinoxalin-6-yl)pyrrolo [2,1-f][1,2,4]triazin-2-yl)amino)cyclobutyl)propan-2-ol 328

Yellow solid (36 mg, 0.089 mmol, 46.2% yield). $^1$H NMR (499 MHz, DMSO-$d_6$) δ ppm 1.05 (6H, s), 1.93-2.04 (2H, m), 2.16-2.26 (1H, m), 2.28-2.36 (2H, m), 3.97 (3H, s), 4.05-4.15 (1H, m), 4.19 (1H, s), 6.86 (1H, d, J=2.74 Hz), 7.01 (1H, d, J=6.84 Hz), 7.66 (1 H, d, J=2.46 Hz), 8.04-8.08 (1H, m), 8.09-8.13 (1H, m), 8.23 (1H, d, J=1.92 Hz), 8.89 (1H, d, J=1.64 Hz), 8.93 (1H, d, J=1.92 Hz); ESIMS found for $C_{22}H_{24}N_6O_2$ m/z 405.2 (M+1).

329

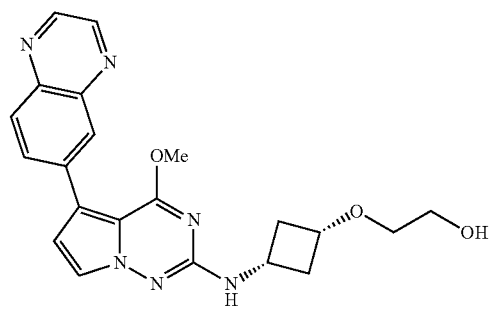

2-(cis-3-((4-Methoxy-5-(quinoxalin-6-yl)pyrrolo[2,1-f][1,2,4]triazin-2-yl)amino)cyclobutoxy)ethan-1-ol 329

Yellow solid (25 mg, 0.062 mmol, 24.0% yield). $^1$H NMR (499 MHz, DMSO-$d_6$) δ ppm 1.82-1.95 (2H, m), 2.58-2.72 (2H, m), 3.31-3.34 (2H, m), 3.49 (2H, q, J=5.48 Hz), 3.69-3.76 (1H, m), 3.76-3.84 (1H, m), 3.97 (3H, s), 4.60 (1H, t, J=5.48 Hz), 6.88 (1H, d, J=2.74 Hz), 7.07 (1H, d, J=7.39 Hz), 7.66 (1H, d, J=2.74 Hz), 8.05-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{21}H_{22}N_6O_3$ m/z 407.2 (M+1).

330

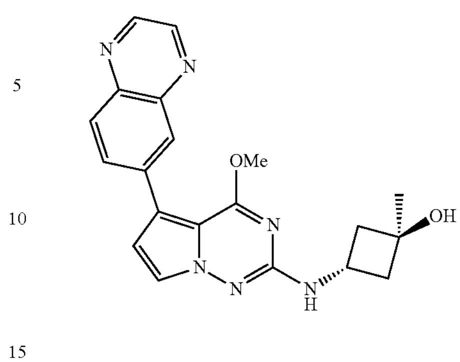

trans-3-((4-Methoxy-5-(quinoxalin-6-yl)pyrrolo[2,1-f][1,2,4]triazin-2-yl)amino)-1-methylcyclobutan-1-ol 330

Light yellow solid (5 mg, 0.013 mmol, 6.9% yield). $^1$H NMR (499 MHz, DMSO-$d_6$) δ ppm 1.28 (3H, s), 1.95-2.05 (2H, m), 2.27-2.37 (2H, m), 3.97 (3H, s), 4.27 (1H, dq, J=14.78, 7.39 Hz), 4.80 (1H, s), 6.87 (1H, d, J=2.74 Hz), 6.99 (1H, d, J=6.84 Hz), 7.67 (1H, d, J=2.46 Hz), 8.05-8.08 (1H, m), 8.09-8.13 (1H, m), 8.23 (1H, d, J=1.92 Hz), 8.89 (1H, d, J=1.64 Hz), 8.93 (1H, d, J=1.92 Hz); ESIMS found for $C_{20}H_{20}N_6O_2$ m/z 377.2 (M+1).

331

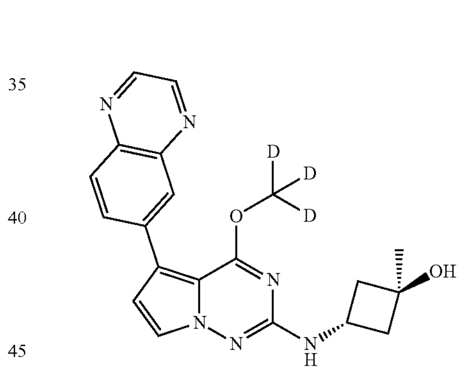

trans-3-((4-(Methoxy-$d_3$)-5-(quinoxalin-6-yl)pyrrolo [2,1-f][1,2,4]triazin-2-yl)amino)-1-methylcyclobutan-1-ol 331

Yellow solid (5 mg, 0.013 mmol, 5.2% yield). $^1$H NMR (499 MHz, DMSO-$d_6$) δ ppm 1.28 (3H, s), 1.95-2.06 (2H, m), 2.28-2.38 (2H, m), 4.27 (1H, dq, J=14.54, 7.29 Hz), 4.80 (1H, s), 6.87 (1H, d, J=2.46 Hz), 6.99 (1H, d, J=6.84 Hz), 7.67 (1H, d, J=2.74 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.64 Hz); ESIMS found for $C_{20}H_{17}[^2H_3]N_6O_2$ m/z 380.2 (M+1).

332

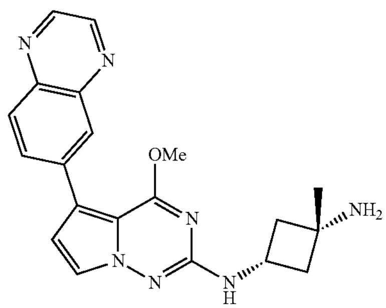

cis-$N_1$-(4-Methoxy-5-(quinoxalin-6-yl)pyrrolo[2,1-f][1,2,4]triazin-2-yl)-3-methylcyclobutane-1,3-diamine 332

Yellow solid (64 mg, 0.171 mmol, 70.5% yield). $^1$H NMR (499 MHz, DMSO-$d_6$) δ ppm 1.20 (3H, s), 1.77 (2H, br s), 1.87 (2H, br dd, J=11.23, 8.76 Hz), 2.29-2.39 (2H, m), 3.87 (1H, dq, J=15.50, 7.79 Hz), 3.97 (3H, s), 6.85 (1H, d, J=7.12 Hz), 6.86 (1H, d, J=2.74 Hz), 7.68 (1H, d, J=2.74 Hz), 8.04-8.08 (1H, m), 8.09-8.12 (1H, m), 8.23 (1H, d, J=1.92 Hz), 8.89 (1H, d, J=1.64 Hz), 8.93 (1H, d, J=1.64 Hz); ESIMS found for $C_{20}H_{21}N_7O$ m/z 376.3 (M+1).

333

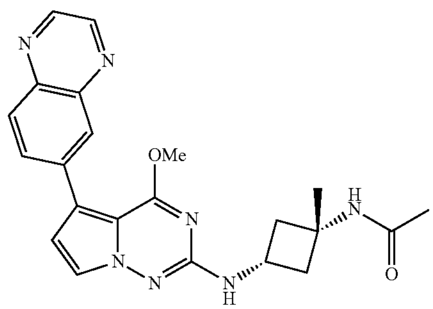

N-(cis-3-((4-Methoxy-5-(quinoxalin-6-yl)pyrrolo[2,1-f][1,2,4]triazin-2-yl)amino)-1-methylcyclobutyl)acetamide 333

Yellow solid (24 mg, 0.058 mmol, 98.1% yield). $^1$H NMR (499 MHz, DMSO-$d_6$) δ ppm 1.38 (3H, s), 1.76 (3H, s), 2.12-2.22 (2H, m), 2.43 (2H, ddd, J=9.58, 7.39, 2.74 Hz), 3.97 (3H, s), 4.04 (1H, dq, J=15.40, 7.83 Hz), 6.87 (1H, d, J=2.46 Hz), 7.05 (1H, d, J=7.12 Hz), 7.69 (1H, d, J=2.46 Hz), 8.03 (1H, s), 8.04-8.08 (1H, m), 8.09-8.12 (1H, m), 8.23 (1H, d, J=1.92 Hz), 8.89 (1H, d, J=1.92 Hz), 8.93 (1H, d, J=1.64 Hz); ESIMS found for $C_{22}H_{23}N_7O_2$ m/z 418.2 (M+1).

334

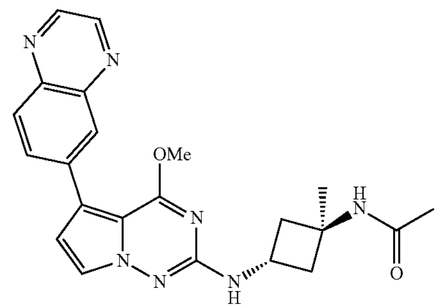

N-(trans-3-((4-Methoxy-5-(quinoxalin-6-yl)pyrrolo[2,1-f][1,2,4]triazin-2-yl)amino)-1-methylcyclobutyl)acetamide 334

Yellow solid (96 mg, 0.230 mmol, 90.9% yield). $^1$H NMR (499 MHz, DMSO-$d_6$) δ ppm 1.36 (3H, s), 1.82 (3H, s), 1.90-2.03 (2H, m), 2.58-2.71 (2H, m), 3.97 (3H, s), 4.20 (1H, sxt, J=7.83 Hz), 6.87 (1H, d, J=2.74 Hz), 7.05 (1H, d, J=7.39 Hz), 7.66 (1H, d, J=2.74 Hz), 7.94 (1H, s), 8.04-8.08 (1H, m), 8.08-8.13 (1H, m), 8.23 (1H, d, J=1.64 Hz), 8.89 (1H, d, J=1.92 Hz), 8.93 (1H, d, J=1.92 Hz); ESIMS found for $C_{22}H_{23}N_7O_2$ m/z 418.2 (M+1).

335

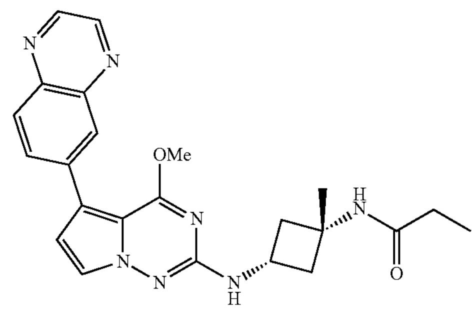

N-(cis-3-((4-Methoxy-5-(quinoxalin-6-yl)pyrrolo[2,1-f][1,2,4]triazin-2-yl)amino)-1-methylcyclobutyl)propionamide 335

Yellow solid (27 mg, 0.063 mmol, 83.9% yield). $^1$H NMR (499 MHz, DMSO-$d_6$) δ ppm 0.98 (3H, t, J=7.67 Hz), 1.38 (3H, s), 2.02 (2H, q, J=7.57 Hz), 2.13-2.23 (2H, m), 2.43 (2H, ddd, J=9.65, 7.46, 2.60 Hz), 3.97 (3H, s), 4.04 (1H, dq, J=15.30, 7.77 Hz), 6.87 (1H, d, J=2.46 Hz), 7.04 (1H, d, J=6.84 Hz), 7.69 (1H, d, J=2.74 Hz), 7.93 (1H, s), 8.05-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{23}H_{25}N_7O_2$ m/z 432.2 (M+1).

336

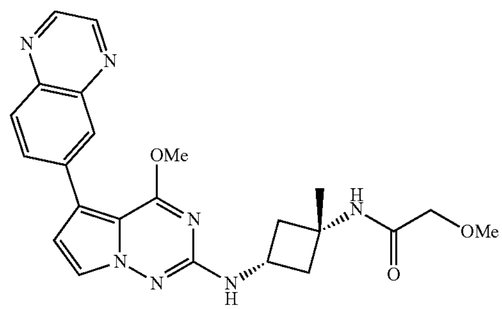

2-Methoxy-N-(cis-3-((4-methoxy-5-(quinoxalin-6-yl)pyrrolo[2,1-f][1,2,4]triazin-2-yl)amino)-1-methylcyclobutyl)acetamide 336

Yellow solid (27 mg, 0.060 mmol, 75.5% yield). $^1$H NMR (499 MHz, DMSO-$d_6$) δ ppm 1.41 (3H, s), 2.14-2.26 (2H, m), 2.44-2.49 (2H, m), 3.31 (3H, s), 3.73 (2H, s), 3.97 (3H, s), 4.05 (1H, dq, J=15.33, 7.85 Hz), 6.88 (1H, d, J=2.46 Hz), 7.06 (1H, d, J=7.12 Hz), 7.69 (1H, d, J=2.74 Hz), 7.87 (1H, s), 8.05-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{23}H_{25}N_7O_3$ m/z 448.2 (M+1).

337

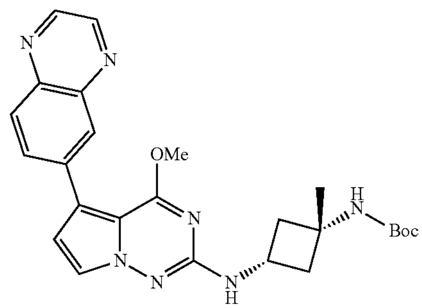

tert-Butyl (cis-3-((4-methoxy-5-(quinoxalin-6-yl) pyrrolo[2,1-f][1,2,4]triazin-2-yl)amino)-1-methylcyclobutyl)carbamate 337

Amber solid (118 mg, 0.248 mmol, 51.6% yield). $^1$H NMR (499 MHz, DMSO-$d_6$) δ ppm 1.35 (3H, s), 1.38 (9H, s), 2.17 (2H, br s), 2.32-2.42 (2H, m), 3.97 (3H, s), 3.98-4.05 (1H, m), 6.87 (1H, d, J=2.46 Hz), 6.98-7.09 (2H, m), 7.68 (1H, d, J=2.74 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.64 Hz); ESIMS found for $C_{25}H_{29}N_7O_3$ m/z 476.3 (M+1).

338

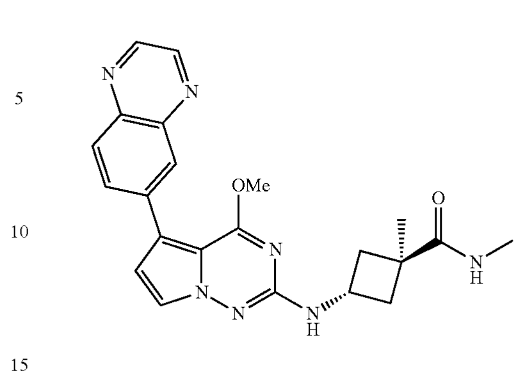

trans-3-((4-Methoxy-5-(quinoxalin-6-yl)pyrrolo[2,1-f][1,2,4]triazin-2-yl)amino)-N,1-dimethylcyclobutane-1-carboxamide 338

Yellow solid (27 mg, 0.065 mmol, 81.7% yield). $^1$H NMR (499 MHz, DMSO-$d_6$) δ ppm 1.32 (3H, s), 1.85-1.96 (2H, m), 2.63 (3H, d, J=4.65 Hz), 2.71-2.81 (2H, m), 3.97 (3H, s), 4.05 (1H, sxt, J=7.99 Hz), 6.87 (1H, d, J=2.74 Hz), 7.04 (1H, d, J=7.39 Hz), 7.62 (1H, q, J=4.29 Hz), 7.69 (1H, d, J=2.46 Hz), 8.04-8.08 (1H, m), 8.08-8.12 (1H, m), 8.23 (1H, d, J=1.92 Hz), 8.89 (1H, d, J=1.92 Hz), 8.93 (1H, d, J=1.64 Hz); ESIMS found for $C_{22}H_{23}N_7O_2$ m/z 418.2 (M+1).

339

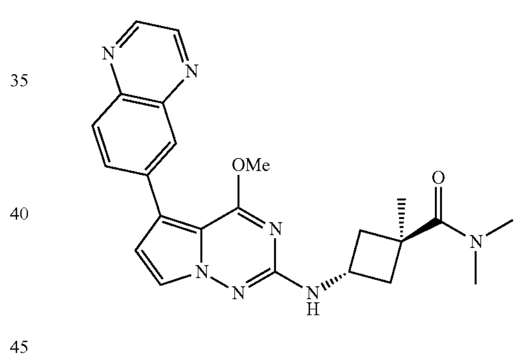

trans-3-((4-Methoxy-5-(quinoxalin-6-yl)pyrrolo[2,1-f][1,2,4]triazin-2-yl)amino)-N,N,1-trimethylcyclobutane-1-carboxamide 339

Beige solid (24 mg, 0.056 mmol, 70.3% yield). $^1$H NMR (499 MHz, DMSO-$d_6$) δ ppm 1.40 (3H, s), 1.93-2.05 (2H, m), 2.84 (3H, br s), 2.89 (3H, br s), 2.90-2.94 (2H, m), 3.86-3.95 (1H, m), 3.97 (3H, s), 6.87 (1H, d, J=2.46 Hz), 7.13 (1H, d, J=6.57 Hz), 7.68 (1H, d, J=2.74 Hz), 8.04-8.08 (1H, m), 8.08-8.13 (1H, m), 8.23 (1H, d, J=1.92 Hz), 8.89 (1H, d, J=1.92 Hz), 8.93 (1H, d, J=1.92 Hz); ESIMS found for $C_{23}H_{25}N_7O_2$ m/z 432.2 (M+1).

341

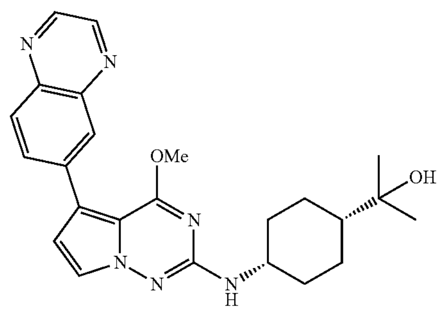

2-(cis-4-((4-methoxy-5-(quinoxalin-6-yl)pyrrolo[2,1-f][1,2,4]triazin-2-yl)amino)cyclohexyl)propan-2-ol 341

Yellow solid (30 mg, 0.069 mmol, 36.0% yield). $^1$H NMR (499 MHz, DMSO-$d_6$) δ ppm 1.06 (6H, s), 1.18-1.23 (1H, m), 1.33-1.43 (2H, m), 1.43-1.52 (2H, m), 1.57 (2H, br d, J=10.40 Hz), 1.96-2.07 (2H, m), 3.92-3.97 (1H, m), 4.00 (1H, s), 4.00 (3H, s), 6.48 (1H, d, J=6.30 Hz), 6.87 (1H, d, J=2.46 Hz), 7.66 (1H, d, J=2.74 Hz), 8.04-8.08 (1H, m), 8.09-8.14 (1H, m), 8.23 (1H, d, J=1.92 Hz), 8.89 (1H, d, J=1.64 Hz), 8.93 (1H, d, J=1.92 Hz); ESIMS found for $C_{24}H_{28}N_6O_2$ m/z 433.2 (M+1).

342

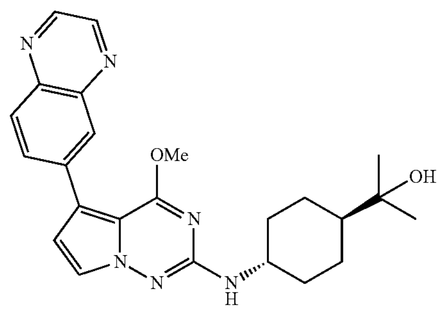

2-(trans-4-((4-Methoxy-5-(quinoxalin-6-yl)pyrrolo[2,1-f][1,2,4]triazin-2-yl)amino)cyclohexyl)propan-2-ol 342

Yellow solid (16 mg, 0.037 mmol, 19.2% yield). $^1$H NMR (499 MHz, DMSO-$d_6$) δ ppm 1.05 (6H, s), 1.07-1.15 (2H, m), 1.16-1.30 (3H, m), 1.83 (2H, br d, J=12.05 Hz), 2.04 (2H, br d, J=9.86 Hz), 3.47-3.59 (1H, m), 3.97 (3H, s), 4.03 (1H, s), 6.55 (1H, d, J=8.21 Hz), 6.86 (1H, d, J=2.74 Hz), 7.67 (1H, d, J=2.74 Hz), 8.05-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{24}H_{28}N_6O_2$ m/z 433.3 (M+1).

343

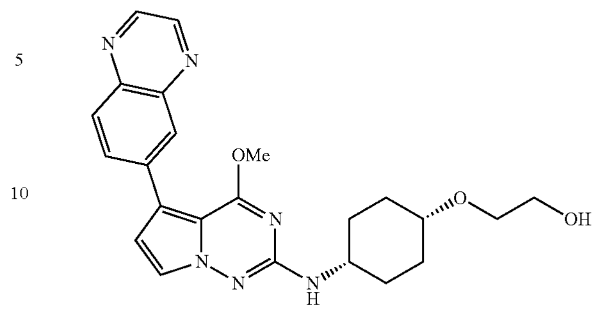

2-((cis-4-((4-Methoxy-5-(quinoxalin-6-yl)pyrrolo[2,1-f][1,2,4]triazin-2-yl)amino)cyclohexyl)oxy)ethan-1-ol 343

White solid (8.0 mg, 0.018 mmol, 7.7% yield). $^1$H NMR (499 MHz, DMSO-$d_6$) δ ppm 1.45-1.57 (2H, m), 1.60-1.75 (4H, m), 1.80-1.89 (2H, m), 3.40 (2H, t, J=5.47 Hz), 3.48 (1H, br d, J=2.19 Hz), 3.51 (2H, q, J=5.57 Hz), 3.65 (1H, tt, J=8.25, 4.21 Hz), 3.97 (3H, s), 4.52 (1H, t, J=5.61 Hz), 6.59 (1H, d, J=7.67 Hz), 6.86 (1H, d, J=2.46 Hz), 7.66 (1H, d, J=2.74 Hz), 8.04-8.08 (1H, m), 8.09-8.13 (1H, m), 8.23 (1H, d, J=1.92 Hz), 8.89 (1H, d, J=1.64 Hz), 8.93 (1H, d, J=1.64 Hz); ESIMS found for $C_{23}H_{26}N_6O_3$ m/z 435.2 (M+1).

344

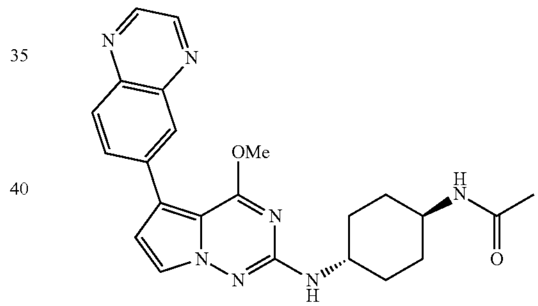

N-(trans-4-((4-Methoxy-5-(quinoxalin-6-yl)pyrrolo[2,1-f][1,2,4]triazin-2-yl)amino)cyclohexyl)acetamide 344

Yellow solid (5 mg, 0.012 mmol, 4.5% yield). $^1$H NMR (499 MHz, DMSO-$d_6$) δ ppm 1.20-1.30 (2H, m), 1.31-1.41 (2H, m), 1.79 (3H, s), 1.82 (2H, br d, J=10.40 Hz), 2.01 (2H, br d, J=10.13 Hz), 3.45-3.53 (1H, m), 3.53-3.61 (1H, m), 3.97 (3H, s), 6.60 (1H, d, J=8.21 Hz), 6.86 (1H, d, J=2.74 Hz), 7.68 (1H, d, J=2.46 Hz), 7.75 (1H, d, J=7.67 Hz), 8.04-8.08 (1H, m), 8.09-8.13 (1H, m), 8.23 (1H, d, J=1.92 Hz), 8.89 (1H, d, J=1.64 Hz), 8.93 (1H, d, J=1.92 Hz); ESIMS found for $C_{23}H_{25}N_7O_2$ m/z 432.2 (M+1).

345

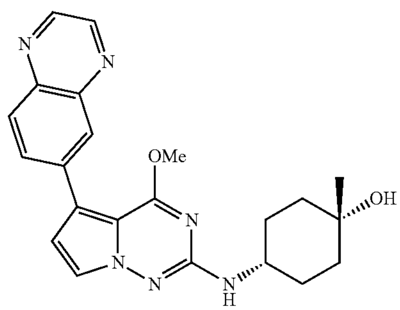

cis-4-((4-Methoxy-5-(quinoxalin-6-yl)pyrrolo[2,1-f][1,2,4]triazin-2-yl)amino)-1-methylcyclohexan-1-ol 345

Yellow solid (16 mg, 0.040 mmol, 15.4% yield). $^1$H NMR (499 MHz, DMSO-$d_6$) δ ppm 1.13 (3H, s), 1.37 (2H, td, J=13.07, 4.24 Hz), 1.58 (2H, br d, J=12.05 Hz), 1.61-1.69 (2H, m), 1.70-1.75 (2H, m), 3.47-3.60 (1H, m), 3.97 (3H, s), 4.01 (1H, s), 6.56 (1H, d, J=7.94 Hz), 6.85 (1H, d, J=2.46 Hz), 7.65 (1H, d, J=2.46 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{22}H_{24}N_6O_2$ m/z 405.2 (M+1).

346

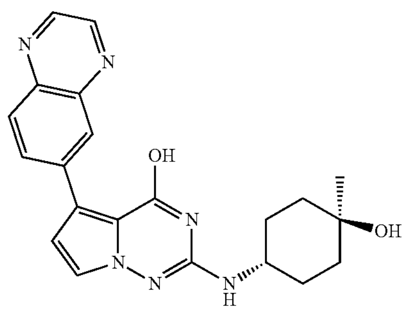

2-((trans-4-Hydroxy-4-methylcyclohexyl)amino)-5-(quinoxalin-6-yl)pyrrolo[2,1-f][11,2,4]triazin-4-ol 346

Yellow solid (10 mg, 0.026 mmol, 10.0% yield). $^1$H NMR (499 MHz, DMSO-$d_6$) δ ppm 1.14 (3H, s), 1.40-1.48 (4H, m), 1.49-1.56 (2H, m), 1.85-1.96 (2H, m), 3.63-3.74 (1H, m), 4.23 (1H, s), 5.92 (1H, br s), 6.85 (1H, d, J=2.74 Hz), 7.47 (1H, d, J=2.74 Hz), 8.03 (1H, d, J=9.31 Hz), 8.34 (1H, dd, J=9.03, 1.92 Hz), 8.59 (1H, d, J=1.64 Hz), 8.87 (1H, d, J=2.19 Hz), 8.91 (1H, d, J=2.19 Hz); ESIMS found for $C_{21}H_{22}N_6O_2$ m/z 391.2 (M+1).

347

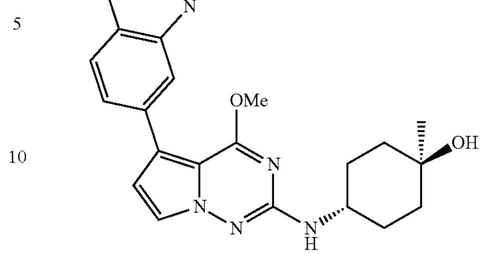

trans-4-((4-Methoxy-5-(quinoxalin-6-yl)pyrrolo[2,1-f][1,2,4]triazin-2-yl)amino)-1-methylcyclohexan-1-ol 347

Yellow solid (26 mg, 0.064 mmol, 40.1% yield). $^1$H NMR (499 MHz, DMSO-$d_6$) δ ppm 1.15 (3H, s), 1.38-1.54 (4H, m), 1.56-1.65 (2H, m), 1.85-1.93 (2H, m), 3.65 (1H, br dd, J=7.94, 3.56 Hz), 3.97 (3H, s), 4.24 (1H, s), 6.54 (1H, d, J=7.94 Hz), 6.86 (1H, d, J=2.46 Hz), 7.68 (1H, d, J=2.74 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.64 Hz); ESIMS found for $C_{22}H_{24}N_6O_2$ m/z 405.2 (M+1).

348

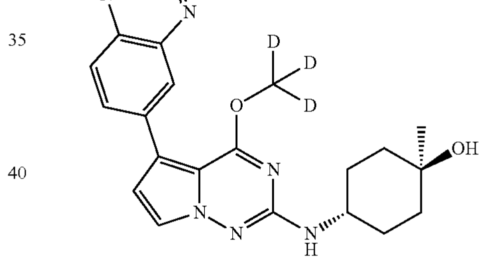

trans-4-((4-(Methoxy-$d_3$)-5-(quinoxalin-6-yl)pyrrolo[2,1-f][1,2,4]triazin-2-yl)amino)-1-methylcyclohexan-1-ol 348

Yellow solid (38 mg, 0.093 mmol, 36.7% yield). $^1$H NMR (499 MHz, DMSO-$d_6$) δ ppm 1.15 (3H, s), 1.37-1.53 (4H, m), 1.55-1.65 (2H, m), 1.84-1.92 (2H, m), 3.66 (1H, br dd, J=8.21, 3.83 Hz), 4.24 (1H, s), 6.53 (1H, d, J=7.94 Hz), 6.86 (1H, d, J=2.74 Hz), 7.68 (1H, d, J=2.74 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{22}H_{21}[^2H_3]N_6O_2$ m/z 408.2 (M+1).

349

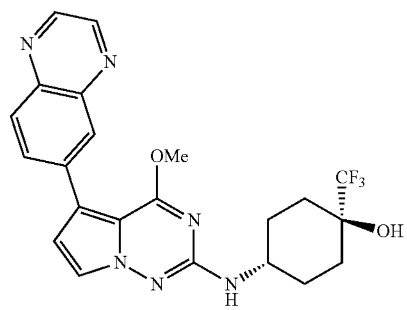

trans-4-((4-Methoxy-5-(quinoxalin-6-yl)pyrrolo[2,1-f][1,2,4]triazin-2-yl)amino)-1-(trifluoromethyl)cyclohexan-1-ol 349

Off-white solid (18 mg, 0.039 mmol, 16.3% yield). $^1$H NMR (499 MHz, DMSO-$d_6$) δ ppm 1.53 (2H, br d, J=12.59 Hz), 1.82-1.90 (4H, m), 1.90-1.99 (2H, m), 3.87-3.94 (1H, m), 4.00 (3H, s), 5.70 (1H, s), 6.83 (1H, d, J=5.75 Hz), 6.87 (1H, d, J=2.46 Hz), 7.68 (1H, d, J=2.46 Hz), 8.05-8.08 (1H, m), 8.09-8.13 (1H, m), 8.23 (1H, d, J=1.92 Hz), 8.89 (1H, d, J=1.92 Hz), 8.93 (1H, d, J=1.92 Hz); ESIMS found for $C_{22}H_{21}F_3N_6O_2$ m/z 459.2 (M+1).

350

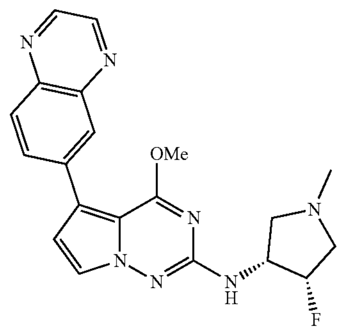

N-((3R,4S)-4-Fluoro-1-methylpyrrolidin-3-yl)-4-methoxy-5-(quinoxalin-6-yl)pyrrolo[2,1-f][1,2,4]triazin-2-amine 350

Yellow solid (33 mg, 0.084 mmol, 86.0% yield). $^1$H NMR (499 MHz, DMSO-$d_6$) δ ppm 2.31 (3H, s), 2.55-2.66 (1H, m), 2.61-2.64 (1H, m), 2.92 (1H, t, J=8.08 Hz), 3.17 (1H, ddd, J=29.85, 11.50, 4.65 Hz), 3.99 (3H, s), 4.21-4.36 (1H, m), 5.22 (1H, dtd, J=55.95, 4.95, 4.95, 1.90 Hz), 6.82 (1H, d, J=7.67 Hz), 6.91 (1H, d, J=2.74 Hz), 7.70 (1H, d, J=2.74 Hz), 8.05-8.09 (1H, m), 8.10-8.14 (1H, m), 8.24 (1H, d, J=1.92 Hz), 8.90 (1H, d, J=1.64 Hz), 8.94 (1H, d, J=1.92 Hz); ESIMS found for $C_{20}H_{20}FN_7O$ m/z 394.2 (M+1).

351

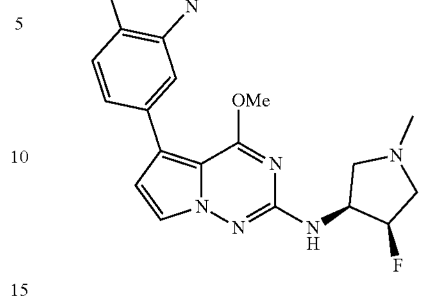

N-((3S,4R)-4-Fluoro-1-methylpyrrolidin-3-yl)-4-methoxy-5-(quinoxalin-6-yl)pyrrolo[2,1-f][1,2,4]triazin-2-amine 351

Yellow solid (21 mg, 0.053 mmol, 29.9% yield). $^1$H NMR (499 MHz, DMSO-$d_6$) δ ppm 2.31 (3H, s), 2.56-2.68 (2H, m), 2.93 (1H, t, J=8.08 Hz), 3.17 (1H, ddd, J=29.65, 11.80, 4.65 Hz), 3.99 (3H, s), 4.20-4.37 (1H, m), 5.22 (1H, dtd, J=55.95, 4.95, 4.95, 1.90 Hz), 6.83 (1H, d, J=7.67 Hz), 6.91 (1H, d, J=2.74 Hz), 7.70 (1H, d, J=2.74 Hz), 8.05-8.09 (1H, m), 8.10-8.14 (1H, m), 8.24 (1H, d, J=1.64 Hz), 8.90 (1H, d, J=1.92 Hz), 8.94 (1H, d, J=1.64 Hz); ESIMS found for $C_{20}H_{20}FN_7O$ m/z 394.2 (M+1).

352

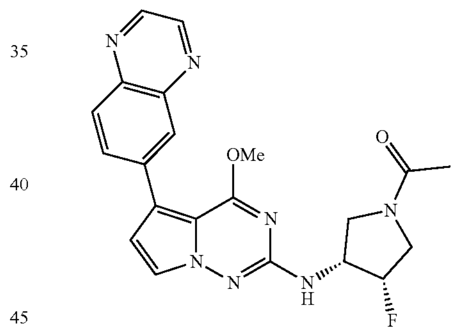

1-((3S,4R)-3-Fluoro-4-((4-methoxy-5-(quinoxalin-6-yl)pyrrolo[2,1-f][1,2,4]triazin-2-yl)amino)pyrrolidin-1-yl)ethan-1-one 352

Yellow solid (43 mg, 0.102 mmol, 70.4% yield). $^1$H NMR (499 MHz, DMSO-$d_6$) δ ppm 1.92-2.02 (3H, m), 3.48-3.57 (1H, m), 3.58-3.76 (1H, m), 3.79-3.98 (2H, m), 4.01 (3H, d, J=1.64 Hz), 4.30-4.61 (1H, m), 5.26-5.51 (1H, m), 6.93 (1H, t, J=2.46 Hz), 7.14 (1H, t, J=6.71 Hz), 7.71 (1H, dd, J=4.11, 2.74 Hz), 8.06-8.10 (1H, m), 8.10-8.14 (1H, m), 8.25 (1H, d, J=1.92 Hz), 8.90 (1H, d, J=1.92 Hz), 8.94 (1H, d, J=1.64 Hz); ESIMS found for $C_{21}H_2O$ $FN_702$ m/z 422.2 (M+1).

353

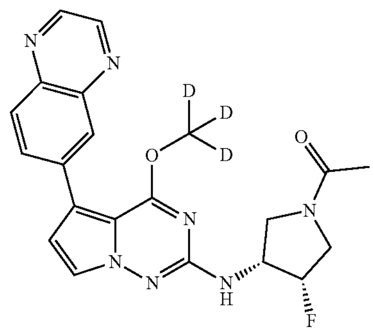

1-((3S,4R)-3-Fluoro-4-((4-(methoxy-d$_3$)-5-(quinoxalin-6-yl)pyrrolo[2,1-f][1,2,4]triazin-2-yl)amino)pyrrolidin-1-yl)ethan-1-one 353

Yellow solid (66 mg, 0.156 mmol, 71.6% yield). $^1$H NMR (499 MHz, DMSO-d$_6$) δ ppm 1.90-2.03 (3H, m), 3.47-3.57 (1H, m), 3.59-3.77 (1H, m), 3.79-3.99 (2H, m), 4.28-4.62 (1H, m), 5.38 (1H, ddt, J=54.30, 37.55, 3.05, 3.05 Hz), 6.93 (1H, t, J=2.46 Hz), 7.14 (1H, t, J=6.71 Hz), 7.71 (1H, dd, J=3.97, 2.60 Hz), 8.06-8.10 (1H, m), 8.10-8.15 (1H, m), 8.25 (1H, d, J=1.64 Hz), 8.90 (1H, d, J=1.64 Hz), 8.94 (1H, d, J=1.64 Hz); ESIMS found for $C_{21}H_{17}[^2H_3]FN_7O_2$ m/z 425.2 (M+1).

355

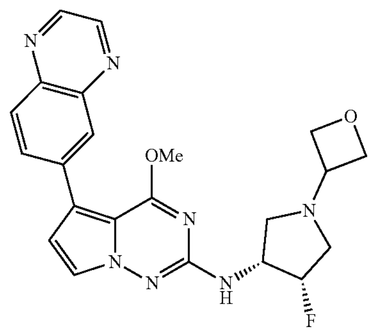

N-((3R,4S)-4-Fluoro-1-(oxetan-3-yl)pyrrolidin-3-yl)-4-methoxy-5-(quinoxalin-6-yl)pyrrolo[2,1-f][1,2,4]triazin-2-amine 355

Yellow solid (7 mg, 0.016 mmol, 11.7% yield). $^1$H NMR (499 MHz, DMSO-d$_6$) δ ppm 2.70 (1H, t, J=9.03 Hz), 2.78 (1H, ddd, J=29.90, 12.10, 1.40 Hz), 3.02 (1H, t, J=8.35 Hz), 3.18 (1H, ddd, J=33.20, 12.05, 4.40 Hz), 3.75-3.85 (1H, m), 4.00 (3H, s), 4.24-4.40 (1H, m), 4.47 (2H, t, J=6.02 Hz), 4.60 (2H, t, J=6.57 Hz), 5.26 (1H, dtd, J=55.65, 4.65, 4.65, 1.10 Hz), 6.89 (1H, d, J=7.67 Hz), 6.91 (1H, d, J=2.74 Hz), 7.70 (1H, d, J=2.74 Hz), 8.05-8.09 (1H, m), 8.10-8.14 (1H, m), 8.25 (1H, d, J=1.92 Hz), 8.90 (1H, d, J=1.92 Hz), 8.94 (1H, d, J=1.92 Hz); ESIMS found for $C_{22}H_{22}FN_7O_2$ m/z 436.2 (M+1).

356

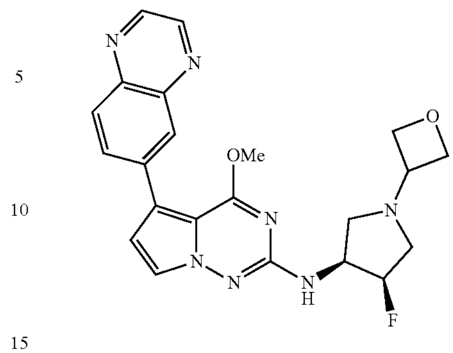

N-((3S,4R)-4-Fluoro-1-(oxetan-3-yl)pyrrolidin-3-yl)-4-methoxy-5-(quinoxalin-6-yl)pyrrolo[2,1-f][1,2,4]triazin-2-amine 356

Yellow solid (25 mg, 0.057 mmol, 49.5% yield). $^1$H NMR (499 MHz, DMSO-d$_6$) δ ppm 2.70 (1H, t, J=9.03 Hz), 2.78 (1H, ddd, J=30.15, 12.35, 1.40 Hz), 3.02 (1H, t, J=8.35 Hz), 3.18 (1H, ddd, J=32.90, 12.10, 4.40 Hz), 3.74-3.84 (1H, m), 4.00 (3H, s), 4.26-4.38 (1H, m), 4.47 (2H, t, J=6.02 Hz), 4.60 (2H, t, J=6.57 Hz), 5.26 (1H, dtd, J=55.65, 4.40, 4.40, 1.10 Hz), 6.89 (1H, d, J=7.67 Hz), 6.91 (1H, d, J=2.46 Hz), 7.70 (1H, d, J=2.46 Hz), 8.06-8.09 (1H, m), 8.10-8.14 (1H, m), 8.25 (1H, d, J=1.64 Hz), 8.90 (1H, d, J=1.92 Hz), 8.94 (1H, d, J=1.64 Hz); ESIMS found for $C_{22}H_{22}FN_7O_2$ m/z 436.2 (M+1).

362

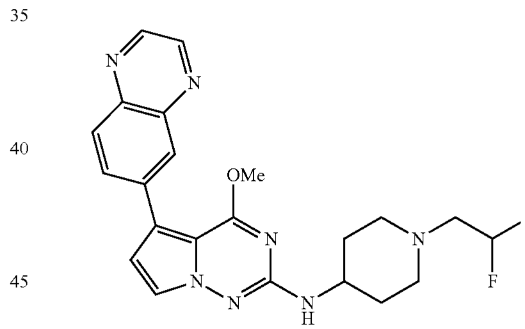

N-(1-(2,2-Difluoroethyl)piperidin-4-yl)-4-methoxy-5-(quinoxalin-6-yl)pyrrolo[2,1-f][1,2,4]triazin-2-amine 362

Yellow solid (27 mg, 0.061 mmol, 25.5% yield). H NMR (499 MHz, DMSO-d$_6$) δ ppm 1.48-1.62 (2H, m), 1.85-1.96 (2H, m), 2.20-2.33 (2H, m), 2.72 (2H, td, J=15.74, 4.38 Hz), 2.91 (2H, br d, J=11.77 Hz), 3.55-3.67 (1H, m), 3.97 (3H, s), 6.14 (1H, tt, J=55.95, 4.24 Hz), 6.67 (1H, d, J=7.94 Hz), 6.87 (1H, d, J=2.46 Hz), 7.68 (1H, d, J=2.74 Hz), 8.04-8.08 (1H, m), 8.08-8.13 (1H, m), 8.23 (1H, d, J=1.92 Hz), 8.89 (1H, d, J=1.64 Hz), 8.93 (1H, d, J=1.64 Hz); ESIMS found for $C_{22}H_{23}F_2N_7O$ m/z 440.2 (M+1).

363

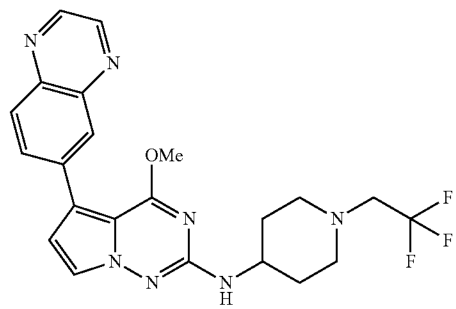

4-Methoxy-5-(quinoxalin-6-yl)-N-(1-(2,2,2-trifluoroethyl)piperidin-4-yl)pyrrolo[2,1-f][1,2,4]triazin-2-amine 363

Yellow solid (13 mg, 0.028 mmol, 12.7% yield). $^1$H NMR (499 MHz, DMSO-$d_6$) δ ppm 1.47-1.63 (2H, m), 1.91 (2H, br d, J=10.13 Hz), 2.39-2.49 (2H, m), 2.93 (2H, br d, J=11.77 Hz), 3.16 (2H, q, J=10.31 Hz), 3.55-3.68 (1H, m), 3.97 (3H, s), 6.67 (1H, d, J=7.94 Hz), 6.87 (1H, d, J=2.74 Hz), 7.68 (1H, d, J=2.46 Hz), 8.05-8.08 (1H, m), 8.09-8.12 (1H, m), 8.23 (1H, d, J=1.64 Hz), 8.89 (1H, d, J=1.92 Hz), 8.93 (1H, d, J=1.92 Hz); ESIMS found for $C_{22}H_{22}F_3N_7O$ m/z 458.2 (M+1).

365

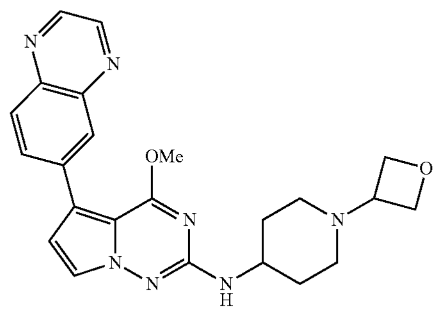

4-Methoxy-N-(1-(oxetan-3-yl)piperidin-4-yl)-5-(quinoxalin-6-yl)pyrrolo[2,1-f][1,2,4]triazin-2-amine 365

Yellow solid (6 mg, 0.0140 mmol, 4.3% yield). $^1$H NMR (499 MHz, DMSO-$d_6$) δ ppm 1.55 (2H, qd, J=11.64, 3.15 Hz), 1.87 (2H, br t, J=11.36 Hz), 1.93 (2H, br d, J=11.50 Hz), 2.70 (2H, br d, J=11.23 Hz), 3.36-3.42 (1H, m), 3.56-3.68 (1H, m), 3.97 (3H, s), 4.42 (2H, t, J=6.16 Hz), 4.53 (2H, t, J=6.57 Hz), 6.69 (1H, d, J=7.94 Hz), 6.86 (1H, d, J=2.46 Hz), 7.67 (1H, d, J=2.46 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.64 Hz); ESIMS found for $C_{23}H_{25}N_7O_2$ m/z 432.2 (M+1).

366

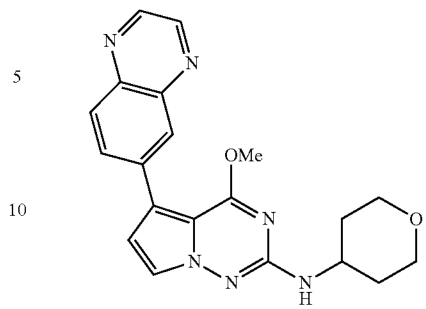

4-Methoxy-5-(quinoxalin-6-yl)-N-(tetrahydro-2H-pyran-4-yl)pyrrolo[2,1-f][1,2,4]triazin-2-amine 366

Yellow solid (34 mg, 0.090 mmol, 46.9% yield). $^1$H NMR (499 MHz, DMSO-$d_6$) δ ppm 1.48-1.61 (2H, m), 1.91 (2H, br dd, J=12.59, 2.46 Hz), 3.40 (2H, td, J=11.57, 1.78 Hz), 3.76-3.86 (1H, m), 3.86-3.92 (2H, m), 3.98 (3H, s), 6.74 (1H, d, J=7.94 Hz), 6.87 (1H, d, J=2.74 Hz), 7.68 (1H, d, J=2.46 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.64 Hz); ESIMS found for $C_{20}H_{20}N_6O_2$ m/z 377.2 (M+1).

367

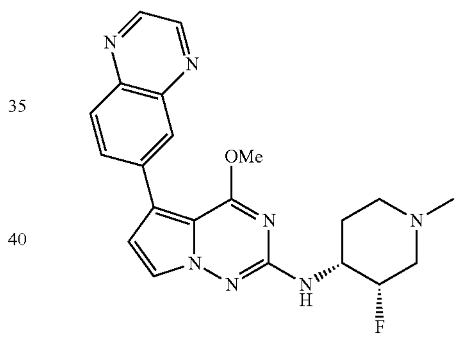

N-((3S,4R)-3-Fluoro-1-methylpiperidin-4-yl)-4-methoxy-5-(quinoxalin-6-yl)pyrrolo[2,1-f][1,2,4]triazin-2-amine 367

Pale yellow solid (34 mg, 0.083 mmol, 65.7% yield). $^1$H NMR (499 MHz, DMSO-$d_6$) δ ppm 1.66-1.74 (1H, m), 1.89-1.99 (1H, m), 2.02-2.11 (1H, m), 2.12-2.25 (1H, m), 2.19 (3H, s), 2.80 (1H, br d, J=11.22 Hz), 3.05 (1H, br t, J=10.95 Hz), 3.69-3.84 (1H, m), 3.99 (3H, s), 4.92 (1H, d, J=49.65 Hz), 6.68 (1H, d, J=7.94 Hz), 6.89 (1H, d, J=2.74 Hz), 7.68 (1H, d, J=2.46 Hz), 8.05-8.09 (1H, m), 8.09-8.14 (1H, m), 8.24 (1H, d, J=1.64 Hz), 8.90 (1H, d, J=1.92 Hz), 8.94 (1H, d, J=1.64 Hz); ESIMS found for $C_{21}H_{22}FN_7O$ m/z 408.2 (M+1).

368

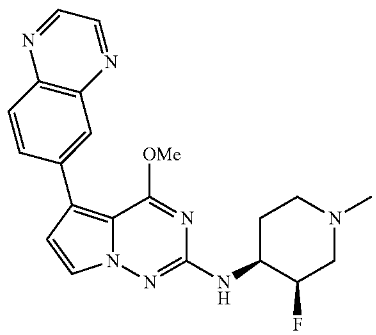

N-((3R,4S)-3-Fluoro-1-methylpiperidin-4-yl)-4-methoxy-5-(quinoxalin-6-yl)pyrrolo[2,1-f][1,2,4]triazin-2-amine 368

Yellow solid (45 mg, 0.110 mmol, 43.0% yield). $^1$H NMR (499 MHz, DMSO-$d_6$) δ ppm 1.76 (1H, br d, J=9.86 Hz), 1.98 (1H, qd, J=12.41, 3.56 Hz), 2.33 (3H, br s), 2.34-2.38 (1H, m), 2.88-3.03 (1H, m), 3.14-3.27 (1H, m), 3.27-3.30 (1H, m), 3.75-3.93 (1H, m), 3.99 (3H, s), 5.00 (1H, d, J=49.65 Hz), 6.78 (1H, br d, J=6.30 Hz), 6.90 (1H, d, J=2.46 Hz), 7.67 (1H, d, J=2.46 Hz), 8.05-8.09 (1H, m), 8.09-8.14 (1H, m), 8.24 (1H, d, J=1.92 Hz), 8.90 (1H, d, J=1.92 Hz), 8.94 (1H, d, J=1.92 Hz); ESIMS found for $C_{21}H_{22}FN_7O$ m/z 408.2 (M+1).

372

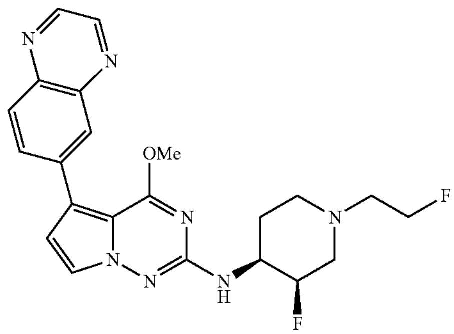

N-((3R,4S)-3-Fluoro-1-(2-fluoroethyl)piperidin-4-yl)-4-methoxy-5-(quinoxalin-6-yl)pyrrolo[2,1-f][1,2,4]triazin-2-amine 372

Pale-yellow solid (20 mg, 0.046 mmol, 59.7% yield). $^1$H NMR (499 MHz, DMSO-$d_6$) δ ppm 1.66-1.76 (1H, m), 1.93 (1H, qd, J=12.23, 3.83 Hz), 2.26 (1H, br t, J=10.95 Hz), 2.39 (1H, dd, J=37.85, 12.38 Hz), 2.64-2.73 (2H, m), 2.94 (1H, br d, J=11.23 Hz), 3.13-3.23 (1H, m), 3.74-3.90 (1H, m), 3.99 (3H, s), 4.55 (2H, dt, J=48.00, 4.95 Hz), 4.93 (1H, d, J=49.95 Hz), 6.71 (1H, d, J=7.67 Hz), 6.89 (1H, d, J=2.74 Hz), 7.68 (1H, d, J=2.74 Hz), 8.05-8.09 (1H, m), 8.09-8.14 (1H, m), 8.24 (1H, d, J=1.92 Hz), 8.90 (1H, d, J=1.92 Hz), 8.94 (1H, d, J=1.92 Hz); ESIMS found for $C_{22}H_{23}F_2N_7O$ m/z 440.2 (M+1).

373

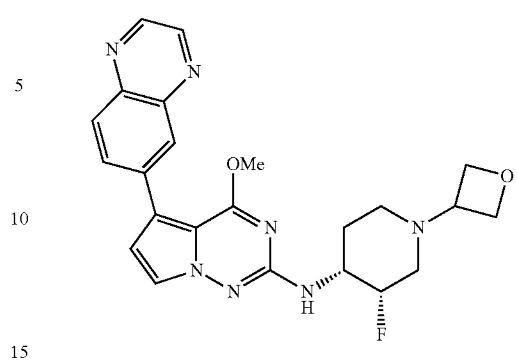

N-((3S,4R)-3-Fluoro-1-(oxetan-3-yl)piperidin-4-yl)-4-methoxy-5-(quinoxalin-6-yl)pyrrolo[2,1-f][1,2,4]triazin-2-amine 373

Yellow solid (39 mg, 0.087 mmol, 68.3% yield). $^1$H NMR (499 MHz, DMSO-$d_6$) δ ppm 1.68-1.79 (1H, m), 1.93 (1H, qd, J=12.09, 3.15 Hz), 1.99-2.08 (1H, m), 2.10-2.25 (1H, m), 2.76 (1H, br d, J=10.40 Hz), 2.95-3.06 (1H, m), 3.50 (1H, quin, J=6.37 Hz), 3.77-3.91 (1H, m), 3.99 (3H, s), 4.40 (1H, t, J=6.16 Hz), 4.44-4.49 (1H, m), 4.54 (2H, td, J=6.57, 3.01 Hz), 4.95 (1H, d, J=49.65 Hz), 6.75 (1H, d, J=7.67 Hz), 6.89 (1H, d, J=2.46 Hz), 7.67 (1H, d, J=2.46 Hz), 8.05-8.09 (1H, m), 8.10-8.13 (1H, m), 8.24 (1H, d, J=1.92 Hz), 8.90 (1H, d, J=1.92 Hz), 8.94 (1H, d, J=1.64 Hz); ESIMS found for $C_{23}H_{24}FN_7O_2$ m/z 450.2 (M+1).

374

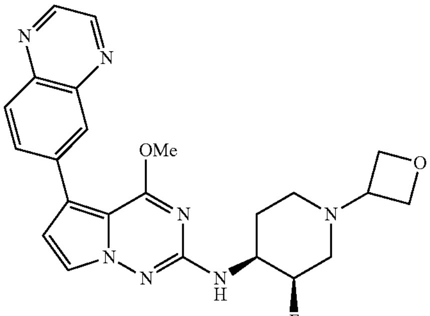

N-((3R,4S)-3-Fluoro-1-(oxetan-3-yl)piperidin-4-yl)-4-methoxy-5-(quinoxalin-6-yl)pyrrolo[2,1-f][1,2,4]triazin-2-amine 374

Yellow solid (51 mg, 0.114 mmol, 74.4% yield). $^1$H NMR (499 MHz, DMSO-$d_6$) δ ppm 1.69-1.79 (1H, m), 1.93 (1H, qd, J=12.14, 3.56 Hz), 2.00-2.07 (1H, m), 2.09-2.25 (1H, m), 2.76 (1H, br d, J=9.86 Hz), 2.95-3.06 (1H, m), 3.50 (1H, quin, J=6.30 Hz), 3.75-3.94 (1H, m), 3.99 (3H, s), 4.40 (1H, t, J=6.16 Hz), 4.46 (1H, t, J=6.16 Hz), 4.54 (2H, td, J=6.57, 3.01 Hz), 4.95 (1H, d, J=49.65 Hz), 6.76 (1H, d, J=7.67 Hz), 6.89 (1H, d, J=2.74 Hz), 7.67 (1H, d, J=2.46 Hz), 8.06-8.09 (1H, m), 8.09-8.13 (1H, m), 8.24 (1H, d, J=1.92 Hz), 8.90 (1H, d, J=1.92 Hz), 8.94 (1H, d, J=1.92 Hz); ESIMS found for $C_{23}H_{24}FN_7O_2$ m/z 450.25 (M+1).

375

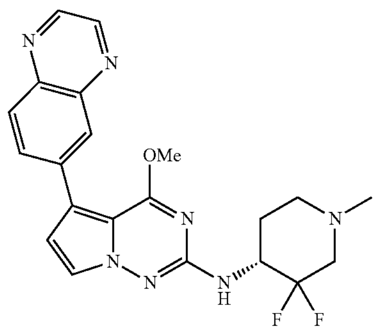

(R)—N-(3,3-Difluoro-1-methylpiperidin-4-yl)-4-methoxy-5-(quinoxalin-6-yl)pyrrolo[2,1-f][1,2,4]triazin-2-amine 375

Yellow solid (14 mg, 0.033 mmol, 67.7% yield). $^1$H NMR (499 MHz, DMSO-$d_6$) δ ppm 1.78-1.92 (2H, m), 2.18 (1H, td, J=11.02, 2.60 Hz), 2.26 (3H, s), 2.34-2.44 (1H, m), 2.79 (1H, br d, J=12.05 Hz), 3.06 (1H, td, J=9.86, 7.94 Hz), 4.00 (3H, s), 4.18-4.33 (1H, m), 6.89 (1H, d, J=9.31 Hz), 6.91 (1H, d, J=2.74 Hz), 7.69 (1H, d, J=2.74 Hz), 8.06-8.09 (1H, m), 8.10-8.13 (1H, m), 8.24 (1H, d, J=1.64 Hz), 8.90 (1H, d, J=1.92 Hz), 8.94 (1H, d, J=1.92 Hz); ESIMS found for $C_{21}H_{21}F_2N_7O$ m/z 426.2 (M+1).

379

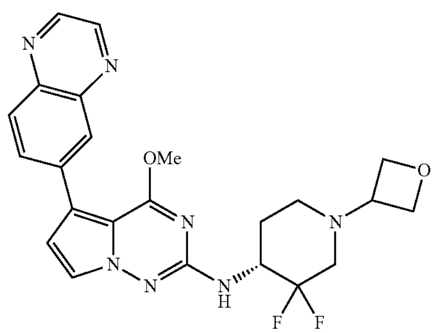

(R)—N-(3,3-Difluoro-1-(oxetan-3-yl)piperidin-4-yl)-4-methoxy-5-(quinoxalin-6-yl)pyrrolo[2,1-f][1,2,4]triazin-2-amine 379

Red brown fluffy solid (14 mg, 0.028 mmol, 67.2% yield). $^1$H NMR (499 MHz, DMSO-$d_6$) δ ppm 1.81-1.93 (1H, m), 1.94-2.03 (1H, m), 2.18-2.44 (1H, m), 2.78-2.98 (1H, m), 3.07-3.28 (1H, m), 3.60-3.68 (1H, m), 3.68-3.84 (1H, m), 4.01 (3H, s), 4.29-4.44 (1H, m), 4.45-4.56 (2H, m), 4.59 (2H, br s), 6.92 (1H, d, J=2.74 Hz), 6.98-7.08 (1H, m), 7.68 (1H, d, J=2.46 Hz), 8.06-8.09 (1H, m), 8.10-8.14 (1H, m), 8.25 (1H, d, J=1.64 Hz), 8.90 (1H, d, J=1.92 Hz), 8.94 (1H, d, J=1.64 Hz); ESIMS found for $C_{23}H_{23}F_2N_7O_2$ m/z 469.2 (M+1).

381

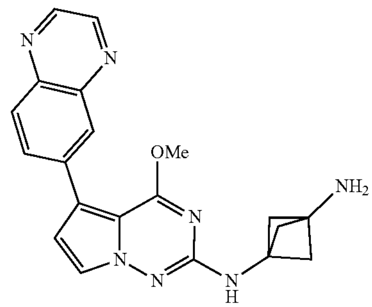

$N_1$-(4-Methoxy-5-(quinoxalin-6-yl)pyrrolo[2,1-f][1,2,4]triazin-2-yl)bicyclo[1.1.1]pentane-1,3-diamine 381

Yellow foam (14 mg, 0.038 mmol, 42.3% yield). $^1$H NMR (499 MHz, DMSO-$d_6$) δ ppm 2.02 (6H, s), 2.24 (2H, br s), 3.97 (3H, s), 6.90 (1H, d, J=2.74 Hz), 7.34 (1H, s), 7.66 (1H, d, J=2.74 Hz), 8.04-8.09 (1H, m), 8.09-8.13 (1H, m), 8.24 (1H, d, J=1.92 Hz), 8.89 (1H, d, J=1.92 Hz), 8.93 (1H, d, J=1.92 Hz); ESIMS found for $C_{20}H_{19}N_7O$ m/z 374.2 (M+1).

382

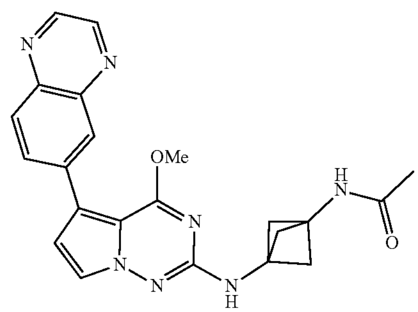

N-(3-((4-Methoxy-5-(quinoxalin-6-yl)pyrrolo[2,1-f][1,2,4]triazin-2-yl)amino)bicyclo[1.1.1]pentan-1-yl)acetamide 382

Yellow solid (10 mg, 0.024 mmol, 89.9% yield). $^1$H NMR (499 MHz, DMSO-$d_6$) δ ppm 1.78 (3H, s), 2.28 (6H, s), 3.97 (3H, s), 6.91 (1H, d, J=2.74 Hz), 7.48 (1H, s), 7.69 (1H, d, J=2.46 Hz), 8.05-8.09 (1H, m), 8.09-8.14 (1H, m), 8.24 (1H, d, J=1.64 Hz), 8.43 (1H, s), 8.90 (1H, d, J=1.92 Hz), 8.93 (1H, d, J=1.64 Hz); ESIMS found for $C_{22}H_{21}N_7O_2$ m/z 416.2 (M+1).

383

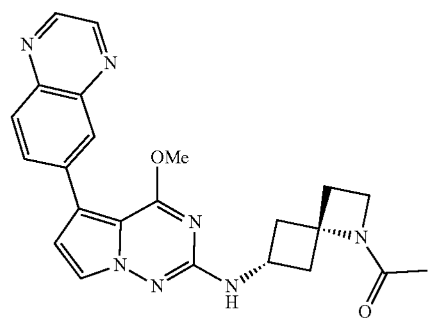

1-((4s,6r)-6-((4-Methoxy-5-(quinoxalin-6-yl)pyrrolo[2,1-f][1,2,4]triazin-2-yl)amino)-1-azaspiro[3.3]heptan-1-yl)ethan-1-one 383

Yellow solid (20 mg, 0.047 mmol, 60.1% yield). $^1$H NMR (500 MHz, DMSO-$d_6$) δ ppm 1.74 (3H, s), 2.27-2.44 (2H, m), 2.52-2.60 (2H, m), 2.62-2.70 (2H, m), 2.84-2.97 (2H, m), 3.70 (1H, br s), 4.00 (3H, s), 6.85 (2H, br d, J=2.20 Hz), 7.63 (1H, d, J=2.20 Hz), 8.04-8.08 (1H, m), 8.08-8.12 (1H, m), 8.24 (1H, d, J=1.92 Hz), 8.87 (1H, d, J=1.65 Hz), 8.91 (1H, d, J=1.92 Hz); ESIMS found for $C_{23}H_{23}N_7O_2$ m/z 430.2 (M+1).

385

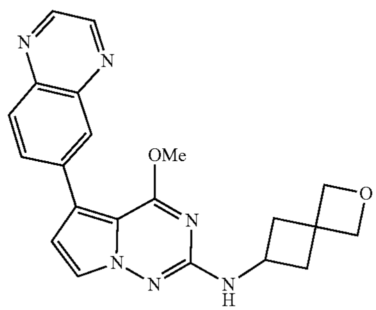

4-Methoxy-5-(quinoxalin-6-yl)-N-(2-oxaspiro[3.3]heptan-6-yl)pyrrolo[2,1-f][11,2,4]triazin-2-amine 385

Pale yellow solid (22 mg, 0.057 mmol, 26.8% yield). $^1$H NMR (499 MHz, DMSO-$d_6$) δ ppm 2.14-2.24 (2H, m), 2.62 (2H, ddd, J=9.99, 7.53, 2.74 Hz), 3.96 (3H, s), 3.97-4.06 (1H, m), 4.51 (2H, s), 4.64 (2H, s), 6.87 (1H, d, J=2.74 Hz), 7.03 (1H, d, J=7.12 Hz), 7.67 (1H, d, J=2.74 Hz), 8.04-8.08 (1H, m), 8.08-8.13 (1H, m), 8.23 (1H, d, J=1.64 Hz), 8.89 (1H, d, J=1.64 Hz), 8.93 (1H, d, J=1.64 Hz); ESIMS found for $C_{21}H_2O$ $N_6O_2$ m/z 389.2 (M+1).

386

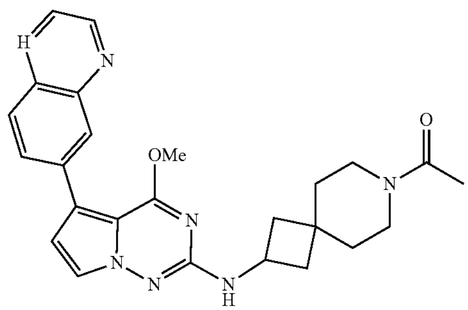

1-(2-((4-Methoxy-5-(quinoxalin-6-yl)pyrrolo[2,1-f][1,2,4]triazin-2-yl)amino)-7-azaspiro[3.5]nonan-7-yl)ethan-1-one 386

Off-white solid (32 mg, 0.070 mmol, 41.5% yield). $^1$H NMR (499 MHz, DMSO-$d_6$) δ ppm 1.40-1.47 (1H, m), 1.52 (2H, br t, J=10.13 Hz), 1.57-1.65 (1H, m), 1.76-1.86 (2H, m), 1.94-2.01 (3H, m), 2.23-2.33 (2H, m), 3.26-3.33 (2H, m), 3.36-3.39 (1H, m), 3.40-3.44 (1H, m), 3.97 (3H, s), 4.15-4.27 (1H, m), 6.87 (1H, d, J=2.74 Hz), 7.05 (1H, t, J=7.12 Hz), 7.65-7.71 (1H, m), 8.05-8.08 (1H, m), 8.09-8.13 (1H, m), 8.23 (1H, d, J=1.92 Hz), 8.89 (1H, d, J=1.64 Hz), 8.93 (1H, d, J=1.92 Hz); ESIMS found for $C_{25}H_{27}N_7O_2$ m/z 458.2 (M+1).

387

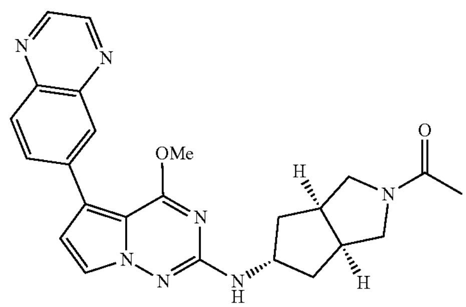

1-((3aR,5s,6aS)-5-((4-Methoxy-5-(quinoxalin-6-yl)pyrrolo[2,1-f][1,2,4]triazin-2-yl)amino)hexahydrocyclopenta[c]pyrrol-2 (1H)-yl)ethan-1-one 387

White solid (53 mg, 0.120 mmol, 99.95% yield). $^1$H NMR (499 MHz, DMSO-$d_6$) δ ppm 1.82-1.91 (4H, m), 1.95 (3H, s), 2.73-2.81 (1H, m), 2.82-2.91 (1H, m), 3.15 (1H, dd, J=12.32, 4.93 Hz), 3.26 (1H, br dd, J=10.81, 4.79 Hz), 3.52 (1H, dd, J=12.18, 8.62 Hz), 3.65 (1H, dd, J=10.95, 8.21 Hz), 3.94-3.99 (3H, m), 4.25 (1H, sxt, J=6.63 Hz), 6.83 (1H, d, J=6.84 Hz), 6.87 (1H, d, J=2.46 Hz), 7.68 (1H, d, J=2.74 Hz), 8.04-8.08 (1H, m), 8.09-8.13 (1H, m), 8.23 (1H, d, J=1.92 Hz), 8.89 (1H, d, J=1.92 Hz), 8.93 (1H, d, J=1.64 Hz); ESIMS found for $C_{24}H_{25}N_7O_2$ m/z 444.2 (M+1).

388

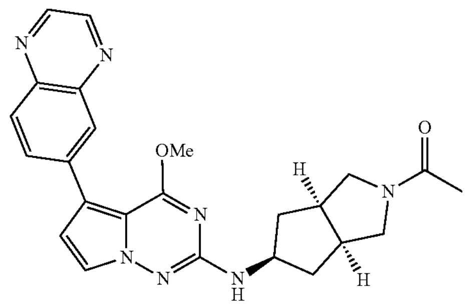

1-((3aR,5r,6aS)-5-((4-Methoxy-5-(quinoxalin-6-yl)pyrrolo[2,1-f][1,2,4]triazin-2-yl)amino)hexahydrocyclopenta[c]pyrrol-2 (1H)-yl)ethan-1-one 388

Off-white solid (55 mg, 0.124 mmol, 90.5% yield). $^1$H NMR (499 MHz, DMSO-$d_6$) δ ppm 1.34-1.48 (2H, m), 1.95 (3H, s), 2.24-2.38 (2H, m), 2.54-2.62 (1H, m), 2.62-2.72 (1H, m), 3.35-3.45 (3H, m), 3.59 (1H, dd, J=10.68, 7.94 Hz), 3.97 (3H, s), 4.08-4.21 (1H, m), 6.85-6.90 (2H, m), 7.66 (1H, d, J=2.74 Hz), 8.05-8.08 (1H, m), 8.09-8.13 (1 H, m), 8.23 (1H, d, J=1.64 Hz), 8.89 (1H, d, J=1.92 Hz), 8.93 (1H, d, J=1.92 Hz); ESIMS found for $C_{24}H_{25}N_7O_2$ m/z 444.2 (M+1).

389

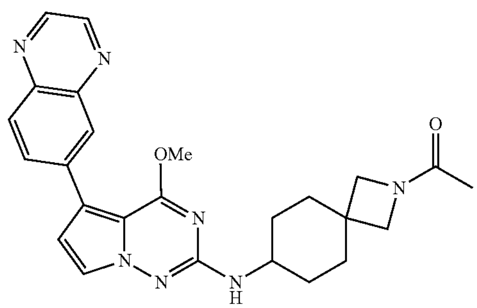

1-(7-((4-Methoxy-5-(quinoxalin-6-yl)pyrrolo[2,1-f][1,2,4]triazin-2-yl)amino)-2-azaspiro[3.5]nonan-2-yl)ethan-1-one 389

Off-white solid (60 mg, 0.131 mmol, 82.6% yield). $^1$H NMR (499 MHz, DMSO-$d_6$) δ ppm 1.29-1.41 (2H, m), 1.49-1.62 (2H, m), 1.73-1.78 (3H, m), 1.88 (4H, br dd, J=9.58, 4.11 Hz), 3.47 (1H, s), 3.52 (1H, s), 3.56-3.67 (1H, m), 3.75 (1H, s), 3.81 (1H, s), 3.97 (3H, d, J=1.10 Hz), 6.58 (1H, dd, J=16.15, 7.94 Hz), 6.87 (1H, d, J=2.74 Hz), 7.67 (1H, t, J=2.87 Hz), 8.04-8.08 (1H, m), 8.09-8.13 (1H, m), 8.23 (1H, d, J=1.64 Hz), 8.89 (1H, d, J=1.64 Hz), 8.93 (1H, d, J=1.64 Hz); ESIMS found for $C_{25}H_{27}N_7O_2$ m/z 458.2 (M+1).

390

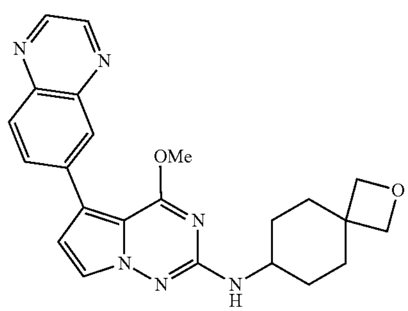

4-Methoxy-5-(quinoxalin-6-yl)-N-(2-oxaspiro[3.5]nonan-7-yl)pyrrolo[2,1-f][1,2,4]triazin-2-amine 390

Yellow solid (39 mg, 0.094 mmol, 48.7% yield). $^1$H NMR (499 MHz, DMSO-$d_6$) δ ppm 1.20-1.36 (2H, m), 1.53 (2H, td, J=12.87, 3.29 Hz), 1.88 (2H, br dd, J=13.14, 3.29 Hz), 2.07 (2H, br d, J=12.87 Hz), 3.48-3.63 (1H, m), 3.96 (3H, s), 4.24 (2H, s), 4.32 (2H, s), 6.56 (1H, d, J=8.21 Hz), 6.86 (1H, d, J=2.74 Hz), 7.67 (1H, d, J=2.74 Hz), 8.04-8.08 (1H, m), 8.08-8.13 (1H, m), 8.23 (1H, d, J=1.92 Hz), 8.89 (1H, d, J=1.64 Hz), 8.93 (1H, d, J=1.64 Hz); ESIMS found for $C_{23}H_{24}N_6O_2$ m/z 417.2 (M+1).

391

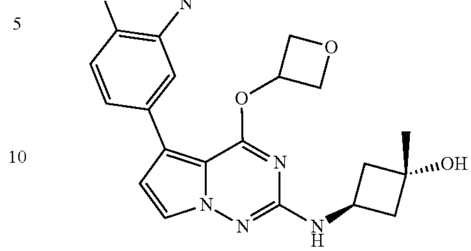

cis-1-Methyl-3-((4-(oxetan-3-yloxy)-5-(quinoxalin-6-yl)pyrrolo[2,1-f][1,2,4]triazin-2-yl)amino)cyclobutan-1-ol 391

Yellow solid (10 mg, 0.024 mmol, 11.3% yield). $^1$H NMR (499 MHz, DMSO-$d_6$) δ ppm 1.27 (3H, s), 1.96-2.04 (2H, m), 2.28-2.40 (2H, m), 3.64-3.76 (1H, m), 4.61 (2H, dd, J=7.94, 5.20 Hz), 4.86 (2H, t, J=7.26 Hz), 4.93 (1H, s), 5.65-5.73 (1H, m), 6.92-6.95 (2H, m), 7.71 (1H, d, J=2.74 Hz), 8.10 (1H, d, J=8.76 Hz), 8.19 (1H, dd, J=8.76, 1.92 Hz), 8.38 (1H, d, J=1.92 Hz), 8.90 (1H, d, J=1.92 Hz), 8.95 (1H, d, J=1.92 Hz); ESIMS found for $C_{22}H_{22}N_6O_3$ m/z 419.2 (M+1).

392

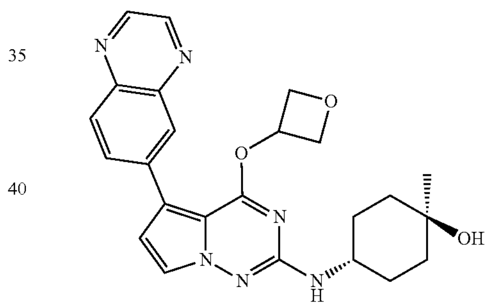

trans-1-Methyl-4-((4-(oxetan-3-yloxy)-5-(quinoxalin-6-yl)pyrrolo[2,1-f][1,2,4]triazin-2-yl)amino)cyclohexan-1-ol 392

Yellow solid (17 mg, 0.038 mmol, 14.8% yield). $^1$H NMR (499 MHz, DMSO-$d_6$) δ ppm 1.15 (3H, s), 1.36-1.50 (4H, m), 1.54-1.64 (2H, m), 1.80-1.93 (2H, m), 3.61 (1H, br d, J=3.56 Hz), 4.25 (1H, s), 4.62 (2H, dd, J=7.53, 5.34 Hz), 4.86 (2H, t, J=6.98 Hz), 5.72 (1H, quin, J=5.75 Hz), 6.50 (1H, d, J=7.94 Hz), 6.93 (1H, d, J=2.46 Hz), 7.71 (1H, d, J=2.46 Hz), 8.10 (1H, d, J=8.76 Hz), 8.20 (1H, dd, J=8.76, 1.92 Hz), 8.39 (1H, d, J=1.92 Hz), 8.90 (1H, d, J=1.64 Hz), 8.94 (1H, d, J=1.64 Hz); ESIMS found for $C_{24}H_{26}N_6O_3$ m/z 447.2 (M+1).

393

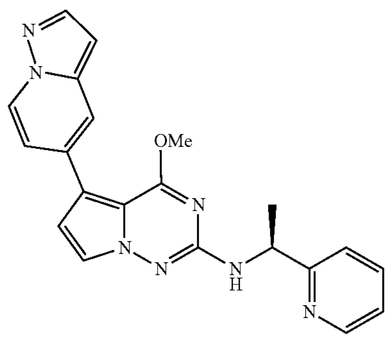

(S)-4-Methoxy-5-(pyrazolo[1,5-a]pyridin-5-yl)-N-(1-(pyridin-2-yl)ethyl)pyrrolo[2,1-f][1,2,4]triazin-2-amine 393

Off-white solid (14 mg, 0.036 mmol, 18.1% yield). $^1$H NMR (499 MHz, DMSO-$d_6$) δ ppm 1.49 (3H, d, J=7.12 Hz), 3.98 (3H, s), 5.00 (1H, quin, J=7.19 Hz), 6.58 (1H, d, J=1.64 Hz), 6.74 (1H, d, J=2.46 Hz), 7.09 (1H, dd, J=7.39, 1.92 Hz), 7.19 (1H, d, J=7.94 Hz), 7.23 (1H, ddd, J=7.46, 4.86, 0.82 Hz), 7.46 (1H, d, J=7.94 Hz), 7.55 (1H, d, J=2.74 Hz), 7.74 (1 H, td, J=7.73, 1.78 Hz), 7.79 (1H, d, J=1.10 Hz), 7.96 (1H, d, J=2.19 Hz), 8.50-8.54 (1H, m), 8.61 (1H, d, J=7.12 Hz); ESIMS found for $C_{21}H_{19}N_7O$ m/z 386.2 (M+1).

394

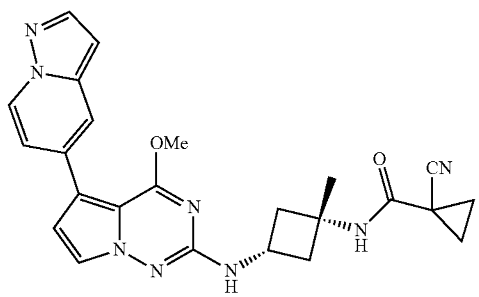

1-Cyano-N-((1s,3s)-3-((4-methoxy-5-(pyrazolo[1,5-a]pyridin-5-yl)pyrrolo[2,1-f][1,2,4]triazin-2-yl)amino)-1-methylcyclobutyl)cyclopropane-1-carboxamide 394

Beige solid (8 mg, 0.018 mmol, 25.5% yield). $^1$H NMR (499 MHz, DMSO-$d_6$) δ ppm 1.37 (3H, s), 1.44-1.49 (2H, m), 1.49-1.54 (2H, m), 2.13-2.22 (2H, m), 2.45 (2H, ddd, J=9.72, 7.39, 2.60 Hz), 3.98 (3H, s), 4.03 (1H, sxt, J=7.78 Hz), 6.58 (1H, dd, J=2.19, 0.82 Hz), 6.77 (1H, d, J=2.46 Hz), 7.01 (1H, d, J=6.84 Hz), 7.10 (1H, dd, J=7.26, 2.05 Hz), 7.64 (1H, d, J=2.46 Hz), 7.78-7.85 (1H, m), 7.97 (1H, d, J=2.19 Hz), 8.29 (1H, s), 8.62 (1H, d, J=7.39 Hz); ESIMS found for $C_{24}H_{24}N_8O_2$ m/z 457.2 (M+1).

395

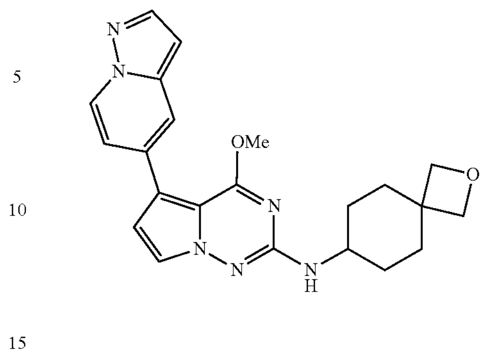

4-Methoxy-5-(pyrazolo[1,5-a]pyridin-5-yl)-N-(2-oxaspiro[3.5]nonan-7-yl)pyrrolo[2,1-f][1,2,4]triazin-2-amine 395

Beige solid (74 mg, 0.18 mmol, 54.8% yield). $^1$H NMR (499 MHz, DMSO-$d_6$) δ ppm 1.24-1.31 (2H, m), 1.52 (2H, td, J=12.94, 3.42 Hz), 1.80-1.92 (2H, m), 2.02-2.11 (2H, m), 3.48-3.61 (1H, m), 3.97 (3H, s), 4.23 (2H, s), 4.32 (2H, s), 6.51 (1H, d, J=7.94 Hz), 6.56-6.61 (1H, m), 6.75 (1H, d, J=2.74 Hz), 7.10 (1H, dd, J=7.26, 2.05 Hz), 7.62 (1H, d, J=2.74 Hz), 7.80 (1H, dd, J=1.92, 0.82 Hz), 7.96 (1H, d, J=2.19 Hz), 8.62 (1H, d, J=7.12 Hz); ESIMS found for $C_{22}H_{24}N_6O_2$ m/z 405.2 (M+1).

399

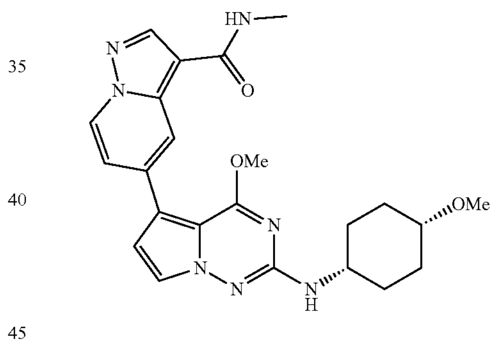

5-(4-Methoxy-2-((cis-4-methoxycyclohexyl)amino)pyrrolo[2,1-f][1,2,4]triazin-5-yl)-N-methylpyrazolo[1,5-a]pyridine-3-carboxamide 399

Beige solid (40 mg, 0.089 mmol, 55.3% yield). $^1$H NMR (499 MHz, DMSO-$d_6$) δ ppm 1.45-1.54 (2H, m), 1.54-1.65 (2H, m), 1.66-1.74 (2H, m), 1.80-1.90 (2H, m), 2.79 (3H, d, J=4.38 Hz), 3.22 (3H, s), 3.33-3.38 (1H, m), 3.58-3.71 (1H, m), 4.02 (3H, s), 6.63 (1H, d, J=7.67 Hz), 6.83 (1H, d, J=2.74 Hz), 7.29 (1H, dd, J=7.26, 2.05 Hz), 7.64 (1H, d, J=2.46 Hz), 8.10 (1H, q, J=4.20 Hz), 8.45 (1H, s), 8.49-8.55 (1H, m), 8.68 (1H, d, J=7.39 Hz); ESIMS found for $C_{23}H_{27}N_7O_3$ m/z 450.2 (M+1).

401

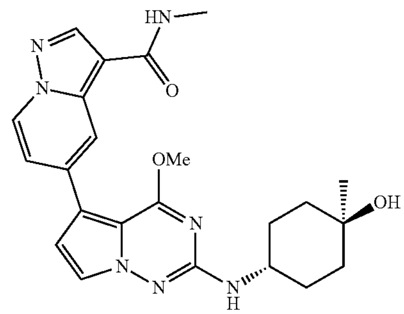

5-(2-(((1r,4r)-4-Hydroxy-4-methylcyclohexyl)amino)-4-methoxypyrrolo[2,1-f][1,2,4]triazin-5-yl)-N-methylpyrazolo[1,5-a]pyridine-3-carboxamide 401

Beige solid (58 mg, 0.129 mmol, 80.2% yield). $^1$H NMR (499 MHz, DMSO-$d_6$) δ ppm 1.15 (3H, s), 1.37-1.54 (4H, m), 1.57-1.66 (2H, m), 1.83-1.93 (2H, m), 2.79 (3H, d, J=4.65 Hz), 3.65 (1H, dt, J=7.87, 3.87 Hz), 4.02 (3H, s), 4.23 (1H, s), 6.56 (1H, d, J=7.94 Hz), 6.83 (1H, d, J=2.74 Hz), 7.29 (1H, dd, J=7.26, 2.05 Hz), 7.65 (1H, d, J=2.74 Hz), 8.10 (1H, q, J=4.56 Hz), 8.45 (1H, s), 8.52 (1H, d, J=1.37 Hz), 8.68 (1H, d, J=7.67 Hz); ESIMS found for $C_{23}H_{27}N_7O_3$ m/z 450.25 (M+1).

405

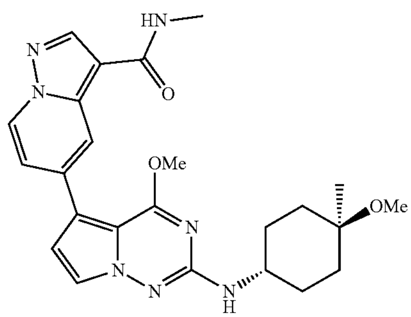

5-(4-Methoxy-2-(((1r,4r)-4-methoxy-4-methylcyclohexyl)amino)pyrrolo[2,1-f][1,2,4]triazin-5-yl)-N-methylpyrazolo[1,5-a]pyridine-3-carboxamide 405

Off-white solid (47 mg, 0.101 mmol, 63.3% yield). $^1$H NMR (499 MHz, DMSO-$d_6$) δ ppm 1.14 (3H, s), 1.43-1.58 (4H, m), 1.63-1.73 (2H, m), 1.79-1.90 (2H, m), 2.79 (3H, d, J=4.65 Hz), 3.11 (3H, s), 3.66-3.77 (1H, m), 4.03 (3H, s), 6.61 (1H, d, J=7.94 Hz), 6.83 (1H, d, J=2.74 Hz), 7.29 (1H, dd, J=7.26, 2.05 Hz), 7.65 (1H, d, J=2.74 Hz), 8.10 (1H, q, J=4.56 Hz), 8.45 (1H, s), 8.52 (1H, dd, J=2.19, 0.82 Hz), 8.65-8.72 (1H, m); ESIMS found for $C_{24}H_{29}N_7O_3$ m/z 464.2 (M+1).

431

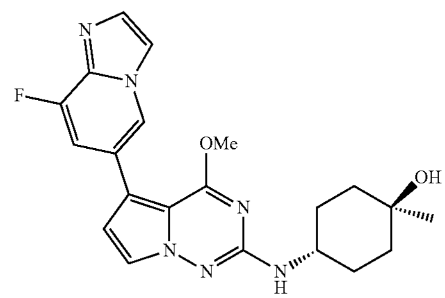

(1r,4r)-4-((5-(8-Fluoroimidazo[1,2-a]pyridin-6-yl)-4-methoxypyrrolo[2,1-f][1,2,4]triazin-2-yl)amino)-1-methylcyclohexan-1-ol 431

Off-white solid (42 mg, 0.102 mmol, 32.5% yield). $^1$H NMR (499 MHz, DMSO-$d_6$) δ ppm 1.14 (3H, s), 1.37-1.52 (4H, m), 1.57-1.65 (2H, m), 1.82-1.93 (2H, m), 3.58-3.72 (1H, m), 3.98 (3H, s), 4.23 (1H, s), 6.50 (1H, d, J=7.94 Hz), 6.71 (1H, d, J=2.46 Hz), 7.38 (1H, d, J=12.59 Hz), 7.62 (1H, s), 7.63 (1H, d, J=2.74 Hz), 8.09 (1H, d, J=2.74 Hz), 8.59 (1H, s); ESIMS found for $C_21H_{23}FN_6O_2$ m/z 411.2 (M+1).

433

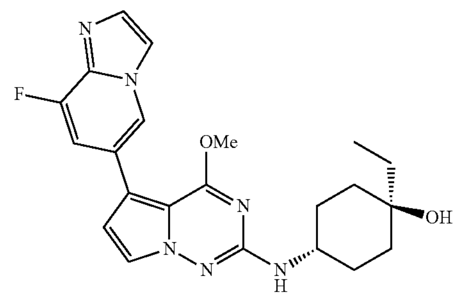

(1r,4r)-1-Ethyl-4-((5-(8-fluoroimidazo[1,2-a]pyridin-6-yl)-4-methoxypyrrolo[2,1-f][1,2,4]triazin-2-yl)amino)cyclohexan-1-ol 433

White solid (10.1 mg, 0.024 mmol, 11.6% yield). $^1$H NMR (499 MHz, DMSO-$d_6$) δ ppm 0.83 (3H, t, J=7.53 Hz), 1.31-1.39 (2H, m), 1.39-1.50 (4H, m), 1.60-1.70 (2H, m), 1.80-1.89 (2H, m), 3.68 (1H, tt, J=8.18, 4.14 Hz), 3.98 (3H, s), 6.50 (1H, d, J=7.94 Hz), 6.71 (1H, d, J=2.74 Hz), 7.38 (1H, dd, J=12.59, 1.37 Hz), 7.62 (1H, d, J=1.37 Hz), 7.63 (1H, d, J=2.46 Hz), 8.09 (1H, dd, J=3.01, 1.10 Hz), 8.59 (1H, d, J=1.37 Hz); ESIMS found for $C_{22}H_{25}FN_6O_2$ m/z 425.2 (M+1).

434

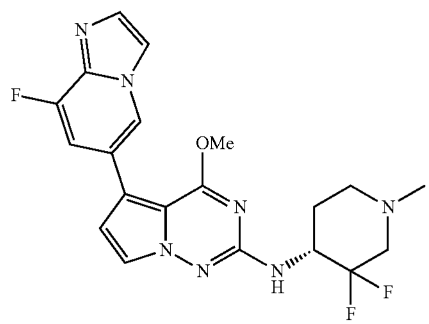

(R)—N-(3,3-Difluoro-1-methylpiperidin-4-yl)-5-(8-fluoroimidazo[1,2-a]pyridin-6-yl)-4-methoxypyrrolo[2,1-f][1,2,4]triazin-2-amine 434

Tan solid (33 mg, 0.077 mmol, 32.4% yield). $^1$H NMR (499 MHz, DMSO-$d_6$) δ ppm 1.77-1.89 (2H, m), 2.14-2.25 (1H, m), 2.28 (3H, br s), 2.35-2.47 (1H, m), 2.76-2.88 (1H, m), 3.01-3.15 (1H, m), 4.01 (3H, s), 4.19-4.32 (1H, m), 6.76 (1H, d, J=2.74 Hz), 6.86 (1H, br d, J=9.31 Hz), 7.40 (1H, dd, J=12.59, 1.37 Hz), 7.63 (1H, s), 7.64 (1H, d, J=2.46 Hz), 8.10 (1H, d, J=2.46 Hz), 8.61 (1H, d, J=1.10 Hz); ESIMS found for $C_{20}H_{20}F_3N_7O$ m/z 432.2 (M+1).

435

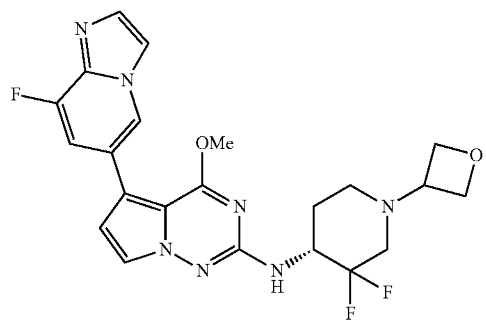

(R)—N-(3,3-Difluoro-1-(oxetan-3-yl)piperidin-4-yl)-5-(8-fluoroimidazo[1,2-a]pyridin-6-yl)-4-methoxypyrrolo[2,1-f][1,2,4]triazin-2-amine 435

Tan solid (10 mg, 0.021 mmol, 48.4% yield). $^1$H NMR (499 MHz, DMSO-$d_6$) δ ppm 1.76-1.85 (1H, m), 1.86-1.92 (1H, m), 2.12-2.22 (1H, m), 2.35-2.45 (1H, m), 2.76 (1H, br d, J=11.50 Hz), 2.95-3.07 (1H, m), 3.60 (1H, quin, J=6.30 Hz), 4.02 (3H, s), 4.22-4.37 (1H, m), 4.44 (2H, dt, J=15.26, 6.19 Hz), 4.55 (2H, td, J=6.64, 3.70 Hz), 6.76 (1H, d, J=2.74 Hz), 6.92 (1H, d, J=9.31 Hz), 7.40 (1H, dd, J=12.59, 1.37 Hz), 7.62 (1H, d, J=1.09 Hz), 7.64 (1H, d, J=2.46 Hz), 8.10 (1H, dd, J=3.01, 1.09 Hz), 8.61 (1H, d, J=1.37 Hz); ESIMS found for $C_{22}H_{22}F_3N_7O_2$ m/z 474.2 (M+1).

439

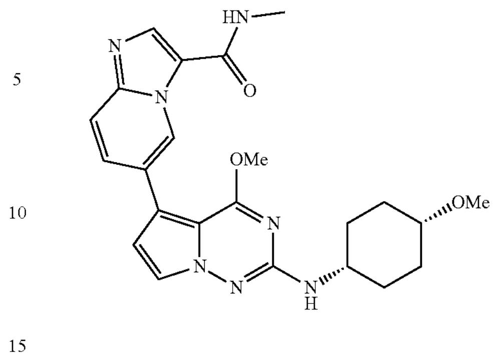

6-(4-Methoxy-2-((cis-4-methoxycyclohexyl)amino)pyrrolo[2,1-f][1,2,4]triazin-5-yl)-N-methylimidazo[1,2-a]pyridine-3-carboxamide 439

Beige solid (38 mg, 0.085 mmol, 52.5% yield). $^1$H NMR (499 MHz, DMSO-$d_6$) δ ppm 1.45-1.54 (2H, m), 1.55-1.65 (2H, m), 1.66-1.74 (2H, m), 1.79-1.89 (2H, m), 2.82 (3H, d, J=4.65 Hz), 3.22 (3H, s), 3.33-3.37 (1H, m), 3.57-3.72 (1H, m), 4.00 (3H, s), 6.58 (1H, d, J=7.67 Hz), 6.74 (1H, d, J=2.74 Hz), 7.63 (1H, d, J=2.46 Hz), 7.68 (2H, d, J=1.37 Hz), 8.27 (1H, s), 8.43 (1H, q, J=4.56 Hz), 9.80 (1H, t, J=1.37 Hz); ESIMS found for $C_{23}H_{27}N_7O_3$ m/z 450.2

441

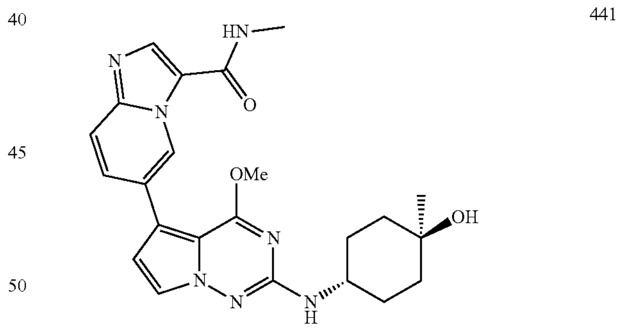

6-(2-(((1r,4r)-4-Hydroxy-4-methylcyclohexyl)amino)-4-methoxypyrrolo[2,1-f][1,2,4]triazin-5-yl)-N-methylimidazo[1,2-a]pyridine-3-carboxamide 441

Off-white solid (23 mg, 0.051 mmol, 31.8% yield). $^1$H NMR (499 MHz, DMSO-$d_6$) δ ppm 1.14 (3H, s), 1.34-1.52 (4H, m), 1.56-1.66 (2H, m), 1.82-1.94 (2H, m), 2.82 (3H, d, J=4.38 Hz), 3.59-3.71 (1H, m), 4.00 (3H, s), 4.23 (1H, br s), 6.51 (1H, d, J=7.94 Hz), 6.75 (1H, d, J=2.46 Hz), 7.64 (1H, d, J=2.74 Hz), 7.68 (2H, d, J=1.10 Hz), 8.26 (1H, s), 8.43 (1H, q, J=4.20 Hz), 9.80 (1H, s); ESIMS found for $C_{23}H_{27}N_7O_3$ m/z 450.2 (M+1).

445

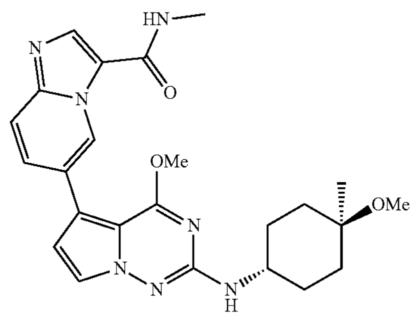

6-(4-Methoxy-2-(((1r,4r)-4-methoxy-4-methylcyclohexyl)amino)pyrrolo[2,1-f][1,2,4]triazin-5-yl)-N-methylimidazo[1,2-a]pyridine-3-carboxamide 445

Brown solid (33 mg, 0.071 mmol, 44.5% yield). $^1$H NMR (499 MHz, DMSO-$d_6$) δ ppm 1.14 (3H, s), 1.41-1.58 (4H, m), 1.62-1.74 (2H, m), 1.78-1.91 (2H, m), 2.82 (3H, d, J=4.38 Hz), 3.11 (3H, s), 3.71 (1H, br d, J=3.56 Hz), 4.01 (3H, s), 6.56 (1H, d, J=7.67 Hz), 6.75 (1H, d, J=2.46 Hz), 7.64 (1H, d, J=2.46 Hz), 7.68 (2H, d, J=1.37 Hz), 8.27 (1H, s), 8.43 (1H, q, J=4.11 Hz), 9.81 (1H, t, J=1.37 Hz); ESIMS found for $C_{24}H_{29}N_7O_3$ m/z 464.25 (M+1).

502

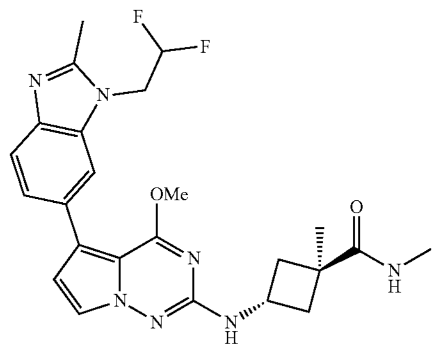

trans-3-((5-(1-(2,2-Difluoroethyl)-2-methyl-1H-benzo[d]imidazol-6-yl)-4-methoxypyrrolo[2,1-f][1,2,4]triazin-2-yl)amino)-N,1-dimethylcyclobutane-1-carboxamide 502

White solid (18 mg, 0.037 mmol, 70.1% yield). $^1$H NMR (499 MHz, DMSO-$d_6$) δ ppm 1.31 (3H, s), 1.84-1.94 (2H, m), 2.57 (3H, s), 2.62 (3H, d, J=4.38 Hz), 2.73 (2H, ddd, J=9.86, 7.80, 2.60 Hz), 3.91 (3H, s), 3.99-4.08 (1H, m), 4.69-4.84 (2H, m), 6.48 (1H, tt, J=54.30, 3.00 Hz), 6.61 (1H, d, J=2.74 Hz), 6.90 (1H, d, J=7.39 Hz), 7.37 (1H, dd, J=8.21, 1.37 Hz), 7.51 (1H, d, J=8.21 Hz), 7.58-7.64 (2H, m), 7.71 (1H, s); ESIMS found for $C_{24}H_{27}F_2N_7O_2$ m/z 484.2 (M+1).

503

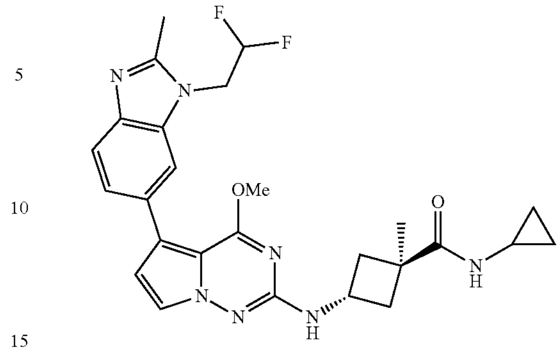

trans-N-Cyclopropyl-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutane-1-carboxamide 503

White solid (21 mg, 0.041 mmol, 77.6% yield). $^1$H NMR (499 MHz, DMSO-$d_6$) δ ppm 0.42-0.49 (2H, m), 0.58-0.65 (2H, m), 1.29 (3H, s), 1.82-1.91 (2H, m), 2.56 (3H, s), 2.64-2.70 (1H, m), 2.71-2.77 (2H, m), 3.91 (3H, s), 3.95-4.04 (1H, m), 4.74 (2H, td, J=16.02, 2.19 Hz), 6.47 (1H, tt, J=54.30, 3.00 Hz), 6.60 (1H, d, J=2.46 Hz), 6.88 (1H, d, J=7.39 Hz), 7.35 (1H, dd, J=8.21, 1.64 Hz), 7.49 (1H, d, J=8.21 Hz), 7.61 (1H, d, J=2.46 Hz), 7.62 (1H, d, J=4.38 Hz), 7.68 (1H, s); ESIMS found for $C_{26}H_{29}F_2N_7O_2$ m/z 510.3 (M+1).

504

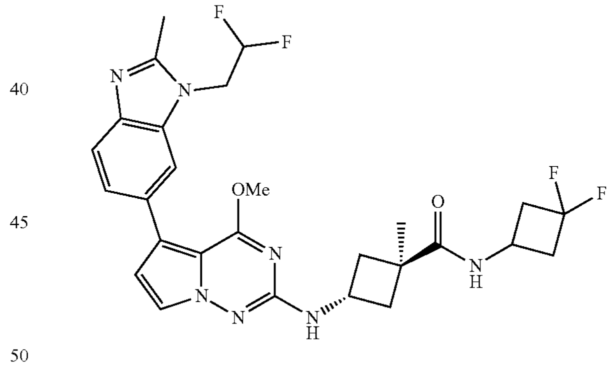

trans-N-(3,3-Difluorocyclobutyl)-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutane-1-carboxamide 504

White solid (23 mg, 0.041 mmol, 77.4% yield). $^1$H NMR (499 MHz, DMSO-$d_6$) δ ppm 1.34 (3H, s), 1.86-1.95 (2H, m), 2.56 (3H, s), 2.58-2.71 (2H, m), 2.76 (2H, ddd, J=10.06, 8.01, 2.46 Hz), 2.83-2.94 (2H, m), 3.91 (3H, s), 4.01 (1H, sxt, J=7.94 Hz), 4.10 (1H, dt, J=14.85, 7.49 Hz), 4.68-4.80 (2H, m), 6.47 (1H, tt, J=54.30, 3.00 Hz), 6.60 (1H, d, J=2.46 Hz), 6.91 (1H, d, J=7.12 Hz), 7.35 (1H, dd, J=8.21, 1.64 Hz), 7.49 (1H, d, J=8.21 Hz), 7.60 (1H, d, J=2.46 Hz), 7.68 (1H, s), 8.03 (1H, d, J=6.84 Hz); ESIMS found for $C_{27}H_{29}F_4N_7O_2$ m/z 560.25 (M+1).

505

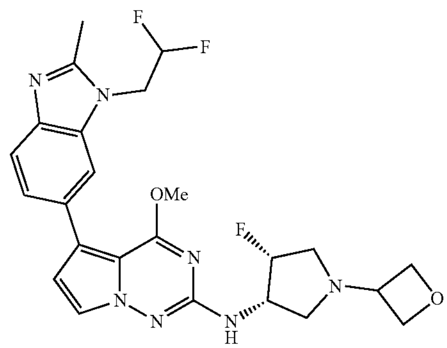

5-(1-(2,2-Difluoroethyl)-2-methyl-1H-benzo[d]imidazol-6-yl)-N-((3S,4R)-4-fluoro-1-(oxetan-3-yl)pyrrolidin-3-yl)-4-methoxypyrrolo[2,1-f][1,2,4]triazin-2-amine 505

White fluffy solid (14 mg, 0.028 mmol, 49.7% yield). $^1$H NMR (499 MHz, DMSO-$d_6$) δ ppm 2.56 (3H, s), 2.68 (1H, t, J=9.03 Hz), 2.77 (1H, ddd, J=30.20, 12.10, 1.40 Hz), 3.01 (1H, t, J=8.35 Hz), 3.18 (1H, ddd, J=33.20, 11.91, 4.52 Hz), 3.79 (1H, quin, J=6.23 Hz), 3.94 (3H, s), 4.23-4.38 (1H, m), 4.47 (2H, t, J=6.02 Hz), 4.60 (2H, t, J=6.57 Hz), 4.75 (2H, td, J=16.02, 2.46 Hz), 5.25 (1H, dtd, J=55.65, 4.70, 4.70, 1.35 Hz), 6.47 (1H, tt, J=54.30, 3.00 Hz), 6.65 (1H, d, J=2.74 Hz), 6.72 (1H, d, J=7.67 Hz), 7.36 (1H, dd, J=8.35, 1.51 Hz), 7.50 (1H, d, J=8.21 Hz), 7.61 (1H, d, J=2.46 Hz), 7.70 (1H, s); ESIMS found for $C_{24}H_{26}F_3N_7O_2$ m/z 502.3 (M+1).

506

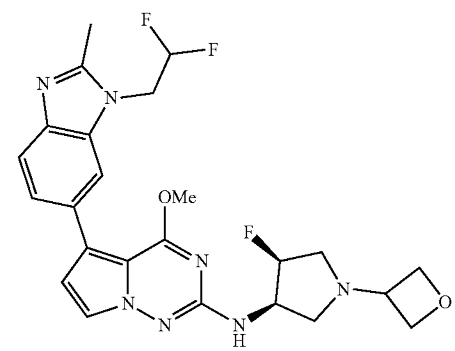

5-(1-(2,2-Difluoroethyl)-2-methyl-1H-benzo[d]imidazol-6-yl)-N-((3R,4S)-4-fluoro-1-(oxetan-3-yl)pyrrolidin-3-yl)-4-methoxypyrrolo[2,1-f][1,2,4]triazin-2-amine 506

White fluffy solid (17 mg, 0.034 mmol, 60.4% yield). $^1$H NMR (499 MHz, DMSO-$d_6$) δ ppm 2.56 (3H, s), 2.68 (1H, t, J=9.03 Hz), 2.77 (1H, ddd, J=29.90, 12.05, 1.37 Hz), 3.01 (1H, t, J=8.35 Hz), 3.18 (1H, ddd, J=33.20, 11.91, 4.52 Hz), 3.73-3.84 (1H, m), 3.94 (3H, s), 4.23-4.37 (1H, m), 4.47 (2H, t, J=6.02 Hz), 4.60 (2H, t, J=6.57 Hz), 4.70-4.81 (2H, m), 5.25 (1H, dtd, J=55.65, 4.45, 4.45, 1.23 Hz), 6.47 (1H, tt, J=54.30, 3.00 Hz), 6.65 (1H, d, J=2.74 Hz), 6.72 (1H, d, J=7.67 Hz), 7.36 (1H, dd, J=8.35, 1.51 Hz), 7.50 (1H, d, J=8.21 Hz), 7.61 (1H, d, J=2.46 Hz), 7.70 (1H, s); ESIMS found for $C_{24}H_{26}F_3N_7O_2$ m/z 502.3 (M+1).

507

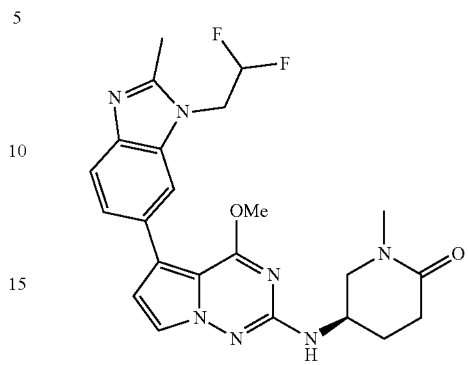

5-((5-(1-(2,2-Difluoroethyl)-2-methyl-1H-benzo[d]imidazol-6-yl)-4-methoxypyrrolo[2,1-f][1,2,4]triazin-2-yl)amino)-1-methylpiperidin-2-one 507

White solid (25 mg, 0.053 mmol, 40.2% yield). $^1$H NMR (499 MHz, DMSO-$d_6$) δ ppm 1.86-1.96 (1H, m), 1.96-2.04 (1H, m), 2.26-2.35 (1H, m), 2.35-2.43 (1H, m), 2.56 (3H, s), 2.81 (3H, s), 3.25 (1H, dd, J=11.77, 7.67 Hz), 3.57 (1H, dd, J=11.77, 4.93 Hz), 3.94 (3H, s), 4.04-4.15 (1H, m), 4.75 (2H, td, J=16.02, 2.46 Hz), 6.47 (1H, tt, J=54.30, 3.00 Hz), 6.63 (1H, d, J=2.74 Hz), 6.83 (1H, d, J=7.39 Hz), 7.36 (1H, dd, J=8.35, 1.51 Hz), 7.50 (1H, d, J=8.21 Hz), 7.62 (1H, d, J=2.46 Hz), 7.70 (1H, s); ESIMS found for $C_{23}H_{25}F_2N_7O_2$ m/z 470.2 (M+1).

508

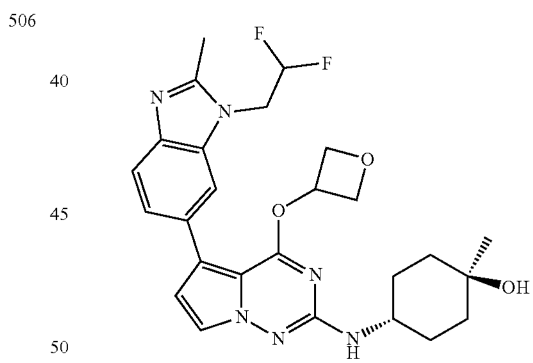

(1r,4r)-4-((5-(1-(2,2-Difluoroethyl)-2-methyl-1H-benzo[d]imidazol-6-yl)-4-(oxetan-3-yloxy)pyrrolo[2,1-f][1,2,4]triazin-2-yl)amino)-1-methylcyclohexan-1-ol 508

White solid (14 mg, 0.027 mmol, 38.5% yield). $^1$H NMR (499 MHz, DMSO-$d_6$) δ ppm 1.14 (3H, s), 1.36-1.50 (4H, m), 1.54-1.64 (2H, m), 1.80-1.90 (2H, m), 2.56 (3H, s), 3.59 (1H, br s), 4.25 (1H, s), 4.51 (2H, dd, J=7.67, 5.20 Hz), 4.74 (2H, td, J=15.61, 2.19 Hz), 4.84 (2H, t, J=6.98 Hz), 5.67 (1H, quin, J=5.68 Hz), 6.35 (1H, d, J=7.94 Hz), 6.47 (1H, tt, J=54.30, 3.00 Hz), 6.64 (1H, d, J=2.46 Hz), 7.45-7.50 (1H, m), 7.51-7.55 (1H, m), 7.62 (1H, d, J=2.46 Hz), 7.72 (1H, s); ESIMS found for $C_{26}H_{30}F_2N_6O_3$ m/z 513.3 (M+1).

509

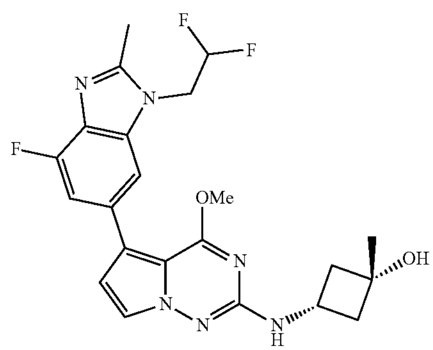

cis-3-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-1-methylcyclobutan-1-ol 509

White solid (8 mg, 0.017 mmol, 11.5% yield). $^1$H NMR (499 MHz, DMSO-d$_6$) δ ppm 1.27 (3H, s), 1.97-2.07 (2H, m), 2.31-2.40 (2H, m), 2.58 (3H, s), 3.71 (1H, sxt, J=7.67 Hz), 3.93 (3H, s), 4.78 (2H, td, J=16.02, 2.46 Hz), 4.91 (1H, s), 6.48 (1H, tt, J=54.30, 3.00 Hz), 6.66 (1H, d, J=2.46 Hz), 6.88 (1H, d, J=6.57 Hz), 7.19 (1H, dd, J=12.32, 1.10 Hz), 7.57 (1H, s), 7.60 (1H, d, J=2.74 Hz); ESIMS found for $C_{22}H_{23}F_3N_6O_2$ m/z 461.2 (M+1).

513

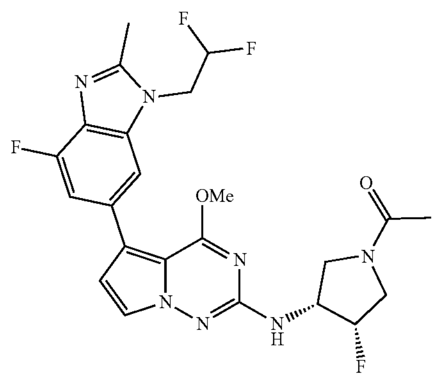

1-((3R,4S)-3-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-4-fluoropyrrolidin-1-yl)ethan-1-one 513

White solid (30 mg, 0.059 mmol, 32.4% yield). $^1$H NMR (499 MHz, DMSO-d$_6$) δ ppm 1.93-2.01 (3H, m), 2.58 (3H, s), 3.47-3.61 (1H, m), 3.61-3.76 (1H, m), 3.78-3.85 (1H, m), 3.86-3.96 (1H, m), 3.97-3.98 (3H, m), 4.31-4.58 (1H, m), 4.78 (2H, td, J=16.08, 2.60 Hz), 5.23-5.48 (1H, m), 6.49 (1H, tt, J=54.30, 3.00 Hz), 6.72 (1H, t, J=2.33 Hz), 7.03 (1H, t, J=6.98 Hz), 7.21 (1H, dd, J=12.18, 1.23 Hz), 7.59 (1H, s), 7.63 (1H, dd, J=4.11, 2.46 Hz); ESIMS found for $C_{23}H_{23}F_4N_7O_2$ m/z 506.2 (M+1).

519

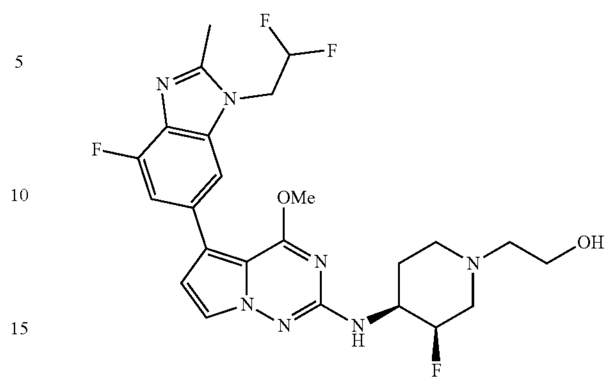

2-((3R,4S)-4-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-3-fluoropiperidin-1-yl)ethan-1-ol 519

White solid (13 mg, 0.025 mmol, 23.8% yield). $^1$H NMR (499 MHz, DMSO-d$_6$) δ ppm 1.64-1.72 (1H, m), 1.90 (1H, qd, J=12.23, 3.83 Hz), 2.17 (1H, br t, J=11.23 Hz), 2.32 (1H, dd, J=37.55, 12.59 Hz), 2.44 (2H, t, J=6.16 Hz), 2.58 (3H, s), 2.91 (1H, br d, J=10.95 Hz), 3.15 (1H, br t, J=9.72 Hz), 3.46-3.55 (2H, m), 3.69-3.86 (1H, m), 3.95 (3H, s), 4.41 (1H, t, J=5.34 Hz), 4.78 (2H, td, J=16.08, 2.33 Hz), 4.89 (1H, d, J=49.65 Hz), 6.48 (1H, tt, J=54.30, 3.00 Hz), 6.56 (1H, d, J=7.94 Hz), 6.68 (1H, d, J=2.46 Hz), 7.20 (1H, dd, J=12.18, 1.23 Hz), 7.58 (1H, s), 7.60 (1H, d, J=2.46 Hz); ESIMS found for $C_{24}H_{27}F_4N_7O_2$ m/z 522.3 (M+1).

520

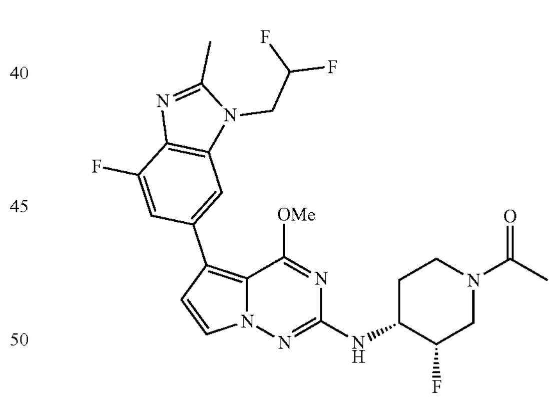

1-((3S,4R)-4-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-3-fluoropiperidin-1-yl)ethan-1-one 520

Fluffy white solid (5 mg, 0.010 mmol, 19.4% yield). $^1$H NMR (499 MHz, DMSO-d$_6$) δ ppm 1.66-1.73 (1H, m), 1.74-1.90 (1H, m), 1.98-2.06 (3H, m), 2.58 (3H, s), 2.66-2.97 (1H, m), 3.17-3.25 (1H, m), 3.87-4.02 (1H, m), 3.96 (3H, s), 4.03-4.16 (1H, m), 4.39-4.72 (1H, m), 4.78 (2H, td, J=15.88, 2.19 Hz), 4.99 (1H, d, J=49.65 Hz), 6.49 (1H, tt, J=54.30, 3.00 Hz), 6.69 (1H, d, J=2.74 Hz), 6.73 (1H, dd, J=7.80, 1.78 Hz), 7.20 (1H, dd, J=12.18, 1.23 Hz), 7.58 (1H, s), 7.60 (1H, d, J=2.46 Hz); ESIMS found for $C_{24}H_{25}F_4N_7O_2$ m/z 520.2 (M+1).

521

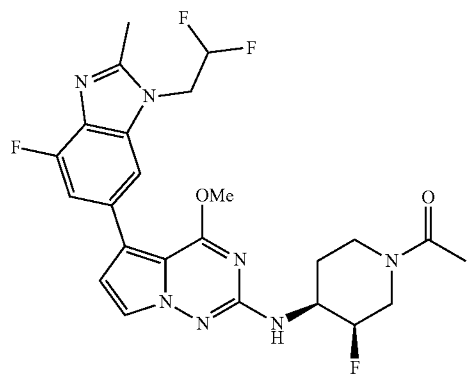

1-((3R,4S)-4-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-3-fluoropiperidin-1-yl)ethan-1-one 521

White solid (25 mg, 0.048 mmol, 46.0% yield). $^1H$ NMR (499 MHz, DMSO-$d_6$) δ ppm 1.66-1.73 (1H, m), 1.74-1.90 (1H, m), 1.98-2.06 (3H, m), 2.58 (3H, s), 2.65-2.97 (1H, m), 3.15-3.26 (1H, m), 3.86-4.01 (1H, m), 3.96 (3H, s), 4.02-4.18 (1H, m), 4.39-4.73 (1H, m), 4.78 (2H, td, J=16.02, 2.46 Hz), 4.99 (1H, d, J=49.55 Hz), 6.49 (1H, tt, J=54.30, 3.00 Hz), 6.69 (1H, d, J=2.46 Hz), 6.73 (1H, dd, J=7.67, 1.92 Hz), 7.20 (1H, dd, J=12.18, 1.23 Hz), 7.58 (1H, s), 7.60 (1H, d, J=2.46 Hz); ESIMS found for $C_{24}H_{25}F_4N_7O_2$ m/z 520.2 (M+1).

525

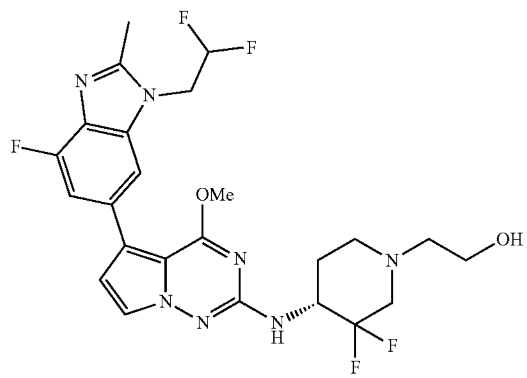

(R)-2-(4-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-3,3-difluoropiperidin-1-yl)ethan-1-ol 525

White solid (15 mg, 0.028 mmol, 27.6% yield). $^1H$ NMR (499 MHz, DMSO-$d_6$) δ ppm 1.73-1.88 (2H, m), 2.25-2.34 (1H, m), 2.51-2.54 (2H, m), 2.58 (3H, s), 2.90 (1H, br d, J=11.50 Hz), 3.13-3.23 (1H, m), 3.30-3.32 (1H, m), 3.52 (2H, q, J=5.84 Hz), 3.97 (3H, s), 4.17-4.32 (1H, m), 4.49 (1H, t, J=5.20 Hz), 4.78 (2H, td, J=16.02, 2.19 Hz), 6.48 (1H, tt, J=54.30, 3.00 Hz), 6.70 (1H, d, J=2.74 Hz), 6.77 (1H, d, J=9.31 Hz), 7.20 (1H, dd, J=12.18, 1.23 Hz), 7.58 (1H, s), 7.61 (1H, d, J=2.74 Hz); ESIMS found for $C_{24}H_{26}F_5N_7O_2$ m/z 540.2 (M+1).

526

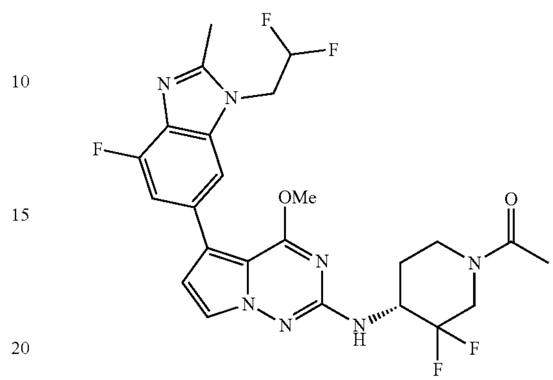

(R)-1-(4-((5-(1-(2,2-Difluoroethyl)-4-fluoro-2-methyl-1H-benzo[d]imidazol-6-yl)-4-methoxypyrrolo[2,1-f][1,2,4]triazin-2-yl)amino)-3,3-difluoropiperidin-1-yl)ethan-1-one 526

White solid (20 mg, 0.037 mmol, 36.9% yield). $^1H$ NMR (499 MHz, DMSO-$d_6$) δ ppm 1.58-1.83 (1H, m), 1.84-1.99 (1H, m), 2.03-2.09 (3H, m), 2.58 (3H, s), 2.92-3.05 (1H, m), 3.63-3.92 (1H, m), 3.98 (3H, s), 4.10-4.30 (1H, m), 4.45-4.60 (2H, m), 4.78 (2H, td, J=16.08, 2.33 Hz), 6.49 (1H, tt, J=54.30, 3.00 Hz), 6.71 (1H, d, J=2.46 Hz), 6.95 (1H, d, J=9.31 Hz), 7.21 (1H, dd, J=12.18, 1.23 Hz), 7.59 (1H, s), 7.61 (1H, dd, J=2.46, 1.37 Hz); ESIMS found for $C_{24}H_{24}F_5N_7O_2$ m/z 538.2 (M+1).

542

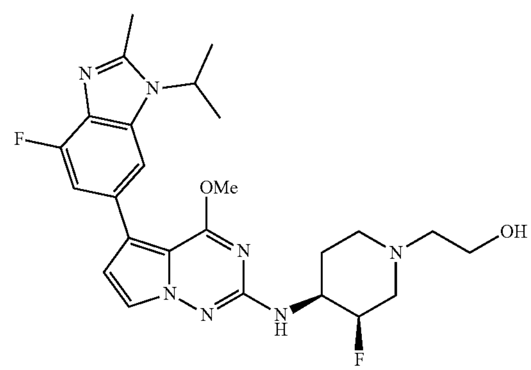

2-((3R,4S)-3-Fluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-ol 542

White solid (6 mg, 0.012 mmol, 18.2% yield). $^1H$ NMR (499 MHz, DMSO-$d_6$) δ ppm 1.59 (6H, d, J=6.84 Hz), 1.64-1.72 (1H, m), 1.90 (1H, qd, J=12.27, 3.70 Hz), 2.17 (1H, br t, J=10.68 Hz), 2.32 (1H, dd, J=37.25, 12.87 Hz), 2.44 (2H, t, J=6.30 Hz), 2.58 (3H, s), 2.91 (1H, br d, J=10.95

Hz), 3.15 (1H, br t, J=10.13 Hz), 3.46-3.54 (2H, m), 4.41 (1H, t, J=5.34 Hz), 4.76 (1H, spt, J=6.84 Hz), 4.89 (1H, d, J=49.90 Hz), 6.55 (1H, d, J=7.67 Hz), 6.69 (1H, d, J=2.74 Hz), 7.12 (1H, d, J=12.05 Hz), 7.59 (1H, d, J=2.46 Hz), 7.64 (1H, s); ESIMS found for $C_{25}H_{31}F_2N_7O_2$ m/z 500.3 (M+1).

544

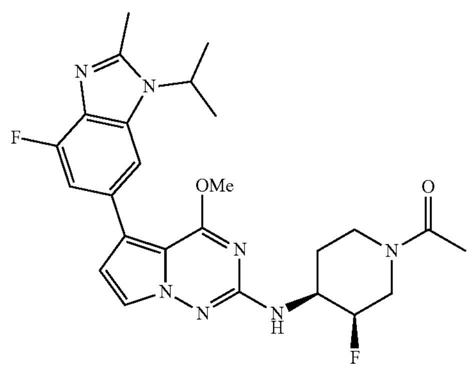

1-((3R,4S)-3-Fluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-one 544

White solid (15 mg, 0.030 mmol, 45.8% yield). $^1$H NMR (499 MHz, DMSO-$d_6$) δ ppm 1.59 (6H, d, J=6.57 Hz), 1.64-1.89 (2H, m), 1.97-2.07 (3H, m), 2.58 (3H, s), 2.66-2.96 (1H, m), 3.17-3.26 (1H, m), 3.83-4.17 (2H, m), 3.96 (3H, s), 4.39-4.72 (1H, m), 4.73-4.81 (1H, m), 4.92-5.06 (1H, m), 6.70 (1H, d, J=2.74 Hz), 6.72 (1H, d, J=7.94 Hz), 7.12 (1H, dd, J=12.18, 1.23 Hz), 7.59 (1H, d, J=2.46 Hz), 7.64 (1H, d, J=1.10 Hz); ESIMS found for $C_{25}H_{29}F_2N_7O_2$ m/z 498.25 (M+1).

549

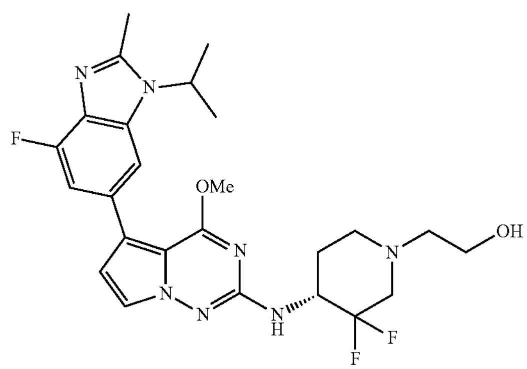

(R)-2-(3,3-Difluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-ol 549

White solid (5 mg, 0.010 mmol, 15.2% yield). $^1$H NMR (499 MHz, DMSO-$d_6$) δ ppm 1.59 (6H, dd, J=6.84, 2.19 Hz), 1.72-1.88 (2H, m), 2.25-2.34 (1H, m), 2.44-2.55 (1H, m), 2.58 (3H, s), 2.90 (1H, br d, J=11.50 Hz), 3.11-3.22 (1H, m), 3.52 (2H, q, J=5.84 Hz), 3.97 (3H, s), 4.17-4.32 (1H, m), 4.49 (1H, t, J=5.34 Hz), 4.76 (1H, spt, J=6.89 Hz), 6.70 (1H, d, J=2.74 Hz), 6.76 (1H, d, J=9.31 Hz), 7.12 (1H, dd, J=12.05, 1.10 Hz), 7.61 (1H, d, J=2.74 Hz), 7.65 (1H, d, J=1.10 Hz); ESIMS found for $C_{25}H_{30}F_3N_7O_2$ m/z 518.3 (M+1).

550

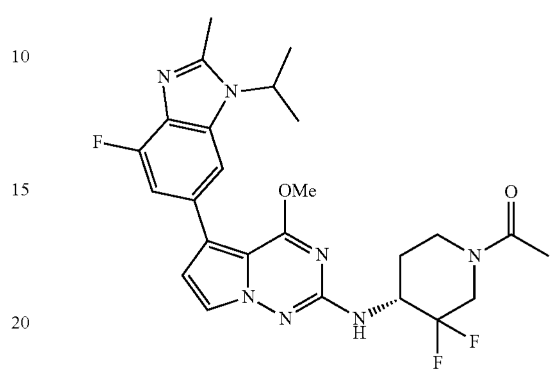

(R)-1-(3,3-Difluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-one 550

White solid (6 mg, 0.012 mmol, 18.4% yield). $^1$H NMR (499 MHz, DMSO-$d_6$) δ ppm 1.57-1.61 (6H, m), 1.62-1.83 (1H, m), 1.84-1.98 (1H, m), 2.02-2.10 (3H, m), 2.58 (3H, s), 2.93-3.05 (1H, m), 3.63-3.77 (1H, m), 3.82-4.21 (1H, m), 3.98 (3H, s), 4.22-4.61 (2H, m), 4.76 (1H, spt, J=6.89 Hz), 6.72 (1H, d, J=2.74 Hz), 6.93 (1H, d, J=9.31 Hz), 7.12 (1H, dd, J=12.05, 1.10 Hz), 7.60 (1H, dd, J=2.46, 1.37 Hz), 7.65 (1H, d, J=1.10 Hz); ESIMS found for $C_{25}H_{28}F_3N_7O_2$ m/z 516.2 (M+1).

551

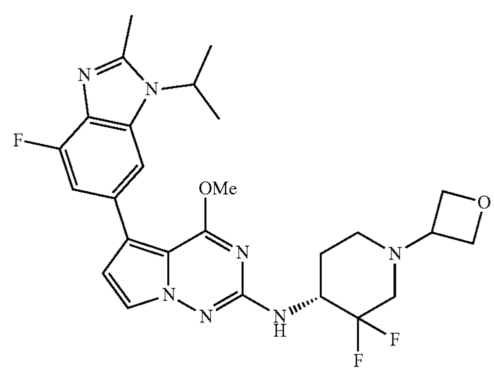

(R)—N-(3,3-Difluoro-1-(oxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine 551

White solid (8 mg, 0.015 mmol, 23.8% yield). $^1$H NMR (499 MHz, DMSO-$d_6$) δ ppm 1.59 (6H, dd, J=6.98, 2.05 Hz), 1.75-1.85 (1H, m), 1.85-1.93 (1H, m), 2.16 (1H, br t, J=10.40 Hz), 2.34-2.47 (1H, m), 2.58 (3H, s), 2.76 (1H, br d, J=11.77 Hz), 2.96-3.07 (1H, m), 3.60 (1H, quin, J=6.23

Hz), 3.97 (3H, s), 4.24-4.37 (1H, m), 4.44 (2H, dt, J=14.92, 6.23 Hz), 4.55 (2H, td, J=6.64, 3.42 Hz), 4.76 (1H, spt, J=6.89 Hz), 6.71 (1H, d, J=2.74 Hz), 6.83 (1H, d, J=9.58 Hz), 7.12 (1H, dd, J=12.18, 0.96 Hz), 7.60 (1H, d, J=2.74 Hz), 7.65 (1H, d, J=1.10 Hz); ESIMS found for $C_{26}H_{30}F_3N_7O_2$ m/z 530.25 (M+1).

554

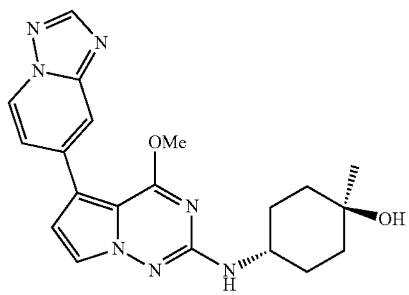

(1r,4r)-4-((5-([1,2,4]Triazolo[1,5-a]pyridin-7-yl)-4-methoxypyrrolo[2,1-f][1,2,4]triazin-2-yl)amino)-1-methylcyclohexan-1-ol 554

White solid (6.4 mg, 0.016 mmol, 8.9% yield). $^1$H NMR (499 MHz, DMSO-$d_6$) δ ppm 1.15 (3H, s), 1.37-1.53 (4H, m), 1.57-1.65 (2H, m), 1.84-1.93 (2H, m), 3.65 (1H, br dd, J=8.08, 3.70 Hz), 3.99 (3H, s), 4.23 (1H, s), 6.58 (1H, d, J=7.94 Hz), 6.88 (1H, d, J=2.74 Hz), 7.44 (1H, dd, J=7.12, 1.64 Hz), 7.67 (1H, d, J=2.74 Hz), 7.95 (1H, dd, J=1.92, 0.82 Hz), 8.46 (1H, s), 8.89 (1H, dd, J=7.12, 0.82 Hz); ESIMS found for $C_{20}H_{23}N_7O_2$ m/z 394.2 (M+1).

555

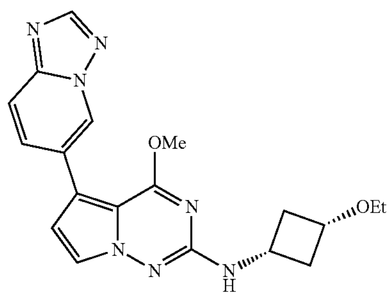

5-([1,2,4]Triazolo[1,5-a]pyridin-6-yl)-N-(cis-3-ethoxycyclobutyl)-4-methoxypyrrolo[2,1-f][1,2,4]triazin-2-amine 555

Off-white solid (9 mg, 0.024 mmol, 32.4% yield). $^1$H NMR (499 MHz, DMSO-$d_6$) δ ppm 1.10 (3H, t, J=6.98 Hz), 1.80-1.91 (2H, m), 2.59-2.70 (2H, m), 3.34 (2H, q, J=7.10 Hz), 3.65-3.72 (1H, m), 3.74-3.84 (1H, m), 3.96 (3H, s), 6.81 (1H, d, J=2.74 Hz), 7.05 (1H, d, J=7.39 Hz), 7.63 (1H, d, J=2.74 Hz), 7.80-7.86 (1H, m), 7.87-7.92 (1H, m), 8.49 (1H, s), 9.03-9.10 (1H, m); ESIMS found for $C_{1-9}H_{21}N_7O_2$ m/z 380.2 (M+1).

562

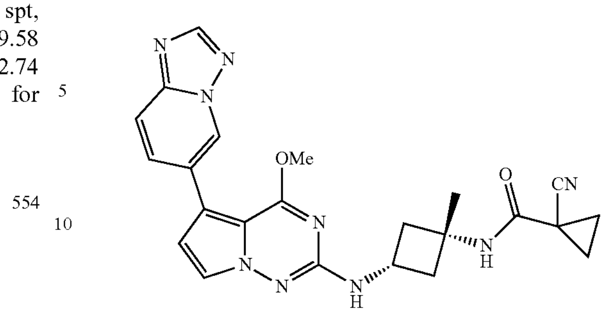

N-((1s,3s)-3-((5-([1,2,4]Triazolo[1,5-a]pyridin-6-yl)-4-methoxypyrrolo[2,1-f][1,2,4]triazin-2-yl)amino)-1-methylcyclobutyl)-1-cyanocyclopropane-1-carboxamide 562

Beige solid (8 mg, 0.018 mmol, 25.5% yield). $^1$H NMR (499 MHz, DMSO-$d_6$) δ ppm 1.37 (3H, s), 1.43-1.49 (2H, m), 1.49-1.55 (2H, m), 2.18 (2H, br dd, J=11.64, 9.17 Hz), 2.45 (2H, ddd, J=9.86, 7.39, 2.46 Hz), 3.96 (3H, s), 4.03 (1H, sxt, J=7.78 Hz), 6.81 (1H, d, J=2.74 Hz), 7.03 (1H, d, J=7.12 Hz), 7.67 (1H, d, J=2.46 Hz), 7.82-7.86 (1H, m), 7.87-7.92 (1H, m), 8.29 (1H, s), 8.49 (1H, s), 9.04-9.11 (1H, m); ESIMS found for $C_{23}H_{23}N_9O_2$ m/z 458.2 (M+1).

563

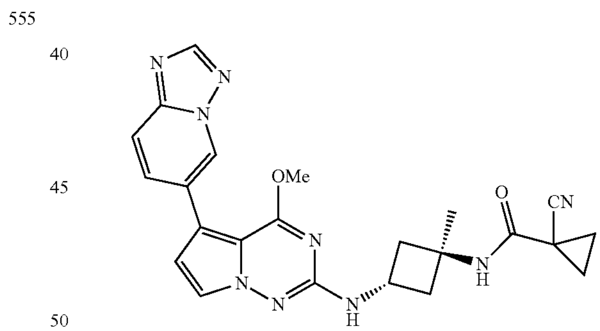

N-((1r,3r)-3-((5-([1,2,4]Triazolo[1,5-a]pyridin-6-yl)-4-methoxypyrrolo[2,1-f][1,2,4]triazin-2-yl)amino)-1-methylcyclobutyl)-1-cyanocyclopropane-1-carboxamide 563

Beige solid (7 mg, 0.015 mmol, 22.3% yield). $^1$H NMR (499 MHz, DMSO-$d_6$) δ ppm 1.37 (3H, s), 1.48-1.57 (4H, m), 1.93-2.06 (2H, m), 2.67-2.78 (2H, m), 3.96 (3H, s), 4.18 (1H, sxt, J=7.72 Hz), 6.80 (1H, d, J=2.74 Hz), 7.05 (1H, d, J=6.84 Hz), 7.67 (1H, d, J=2.74 Hz), 7.81-7.86 (1H, m), 7.87-7.92 (1H, m), 8.05 (1H, s), 8.49 (1H, s), 9.02-9.10 (1H, m); ESIMS found for $C_{23}H_{23}N_9O_2$ m/z 458.2 (M+1).

567

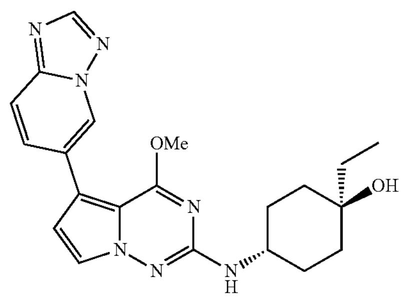

(1r,4r)-4-((5-([1,2,4]Triazolo[1,5-a]pyridin-6-yl)-4-methoxypyrrolo[2,1-f][1,2,4]triazin-2-yl)amino)-1-ethylcyclohexan-1-ol 567

Off-white solid (25 mg, 0.061 mmol, 36.9% yield). $^1$H NMR (499 MHz, DMSO-$d_6$) δ ppm 0.83 (3H, t, J=7.39 Hz), 1.31-1.39 (2H, m), 1.40-1.45 (2H, m), 1.46 (2H, q, J=7.57 Hz), 1.58-1.69 (2H, m), 1.80-1.90 (2H, m), 3.68 (1H, tt, J=8.01, 4.04 Hz), 3.96 (3H, s), 3.99 (1H, s), 6.51 (1H, d, J=7.67 Hz), 6.79 (1H, d, J=2.46 Hz), 7.65 (1H, d, J=2.74 Hz), 7.81-7.85 (1H, m), 7.87-7.91 (1H, m), 8.49 (1H, s), 9.06 (1H, s); ESIMS found for $C_{21}H_{25}N_7O_2$ m/z 408.2 (M+1).

575

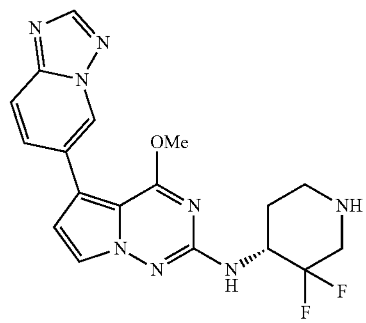

(R)-5-([1,2,4]Triazolo[1,5-a]pyridin-6-yl)-N-(3,3-difluoropiperidin-4-yl)-4-methoxypyrrolo[2,1-f][1,2,4]triazin-2-amine 575

Off-white solid (86 mg, 0.215 mmol, 53.8% yield). $^1$H NMR (499 MHz, DMSO-$d_6$) δ ppm 1.69 (1H, qd, J=11.82, 3.70 Hz), 1.80-1.89 (1H, m), 2.60 (1H, br t, J=11.64 Hz), 2.81 (1H, dd, J=29.65, 13.46 Hz), 2.93 (1H, br d, J=12.87 Hz), 3.06-3.19 (1H, m), 4.00 (3H, s), 4.25-4.42 (1H, m), 6.83 (1H, d, J=2.46 Hz), 6.89 (1H, d, J=9.31 Hz), 7.67 (1H, d, J=2.46 Hz), 7.82-7.87 (1H, m), 7.88-7.93 (1H, m), 8.50 (1H, s), 9.08 (1H, s); ESIMS found for $C_{18}H_{18}F_2N_8O$ m/z 401.2 (M+1).

576

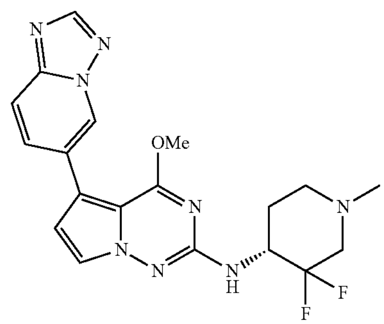

(R)-5-([1,2,4]Triazolo[1,5-a]pyridin-6-yl)-N-(3,3-difluoro-1-methylpiperidin-4-yl)-4-methoxypyrrolo[2,1-f][1,2,4]triazin-2-amine 576

Fluffy white solid (12 mg, 0.027 mmol, 71.0% yield). $^1$H NMR (499 MHz, DMSO-$d_6$) δ ppm 1.76-1.94 (2H, m), 2.10-2.47 (5H, m), 2.73-2.94 (1H, m), 3.00-3.20 (1H, m), 4.00 (3H, s), 4.21-4.41 (1H, m), 6.84 (1H, d, J=2.74 Hz), 6.89-6.99 (1H, m), 7.67 (1H, d, J=2.74 Hz), 7.80-7.87 (1H, m), 7.88-7.94 (1H, m), 8.50 (1H, s), 9.05-9.12 (1H, m); ESIMS found for $C_{1-9}H_2O$ $F_2N_8O$ m/z 415.2 (M+1).

577

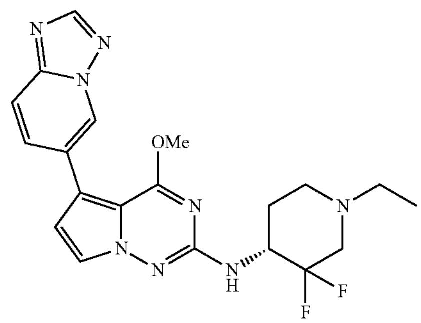

(R)-5-([1,2,4]Triazolo[1,5-a]pyridin-6-yl)-N-(1-ethyl-3,3-difluoropiperidin-4-yl)-4-methoxypyrrolo[2,1-f][1,2,4]triazin-2-amine 577

Fluffy white solid (16 mg, 0.034 mmol, 55.1% yield). $^1$H NMR (499 MHz, DMSO-$d_6$) δ ppm 1.01 (3H, br s), 1.71-1.94 (2H, m), 2.10-2.24 (1H, m), 2.29-2.48 (3H, m), 2.80-2.94 (1H, m), 3.01-3.18 (1H, m), 4.00 (3H, s), 4.18-4.36 (1H, m), 6.79-6.94 (2H, m), 7.66 (1H, br s), 7.82-7.87 (1H, m), 7.88-7.95 (1H, m), 8.50 (1H, s), 9.09 (1H, s); ESIMS found for $C_{20}H_{22}F_2N_8O$ m/z 429.2 (M+1).

578

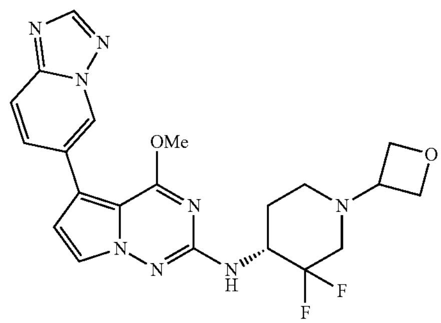

(R)-5-([1,2,4]Triazolo[1,5-a]pyridin-6-yl)-N-(3,3-difluoro-1-(oxetan-3-yl)piperidin-4-yl)-4-methoxy-pyrrolo[2,1-f][1,2,4]triazin-2-amine 578

Fluffy white solid (18 mg, 0.039 mmol, 63.2% yield). $^1$H NMR (499 MHz, DMSO-$d_6$) δ ppm 1.76-1.86 (1H, m), 1.86-1.93 (1H, m), 2.10-2.22 (1H, m), 2.40 (1H, dd, J=26.30, 11.77 Hz), 2.76 (1H, br d, J=11.22 Hz), 2.95-3.08 (1H, m), 3.60 (1H, quin, J=6.30 Hz), 4.00 (3H, s), 4.23-4.37 (1H, m), 4.44 (2H, dt, J=15.19, 6.23 Hz), 4.55 (2H, td, J=6.57, 3.83 Hz), 6.84 (1H, d, J=2.74 Hz), 6.94 (1H, d, J=9.31 Hz), 7.66 (1H, d, J=2.74 Hz), 7.80-7.87 (1H, m), 7.88-7.95 (1H, m), 8.50 (1H, s), 9.08 (1H, s); ESIMS found for $C_{21}H_{22}F_2N_8O_2$ m/z 457.2 (M+1).

582

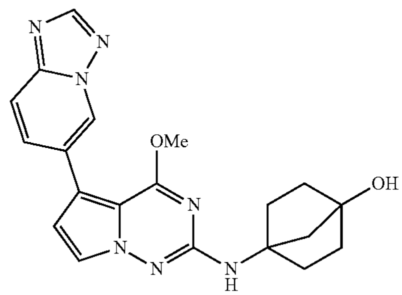

4-((5-([1,2,4]Triazolo[1,5-a]pyridin-6-yl)-4-methoxypyrrolo[2,1-f][1,2,4]triazin-2-yl)amino)bicyclo[2.2.1]heptan-1-ol 582

Off-white solid (3 mg, 0.008 mmol, 4.6% yield). $^1$H NMR (499 MHz, DMSO-$d_6$) δ ppm 1.51-1.63 (2H, m), 1.66-1.79 (2H, m), 1.85 (2H, s), 1.86-1.92 (2H, m), 1.98-2.11 (2H, m), 3.96 (3H, s), 4.89 (1H, s), 6.77 (1H, s), 6.80 (1H, d, J=2.74 Hz), 7.62 (1H, d, J=2.74 Hz), 7.80-7.86 (1H, m), 7.87-7.91 (1H, m), 8.49 (1H, s), 9.03-9.10 (1H, m); ESIMS found for $C_{20}H_{21}N_7O_2$ m/z 392.2 (M+1).

585

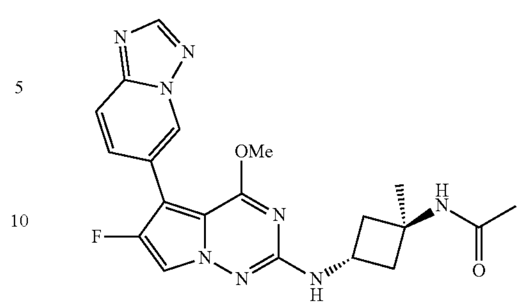

N-((1r,3r)-3-((5-([1,2,4]Triazolo[1,5-a]pyridin-6-yl)-6-fluoro-4-methoxypyrrolo[2,1-f][1,2,4]triazin-2-yl)amino)-1-methylcyclobutyl)acetamide 585

Off-white solid (6 mg, 0.014 mmol, 27.0% yield). $^1$H NMR (499 MHz, DMSO-$d_6$) δ ppm 1.35 (3H, s), 1.81 (3H, s), 1.89-2.00 (2H, m), 2.58-2.70 (2H, m), 3.92 (3H, s), 4.17 (1H, sxt, J=7.72 Hz), 7.13 (1H, d, J=7.12 Hz), 7.77-7.82 (1H, m), 7.83 (1H, d, J=3.01 Hz), 7.88 (1H, d, J=9.86 Hz), 7.93 (1H, s), 8.53 (1H, s), 9.05 (1H, s); ESIMS found for $C_{20}H_{21}FN_8O_2$ m/z 425.2 (M+1).

589

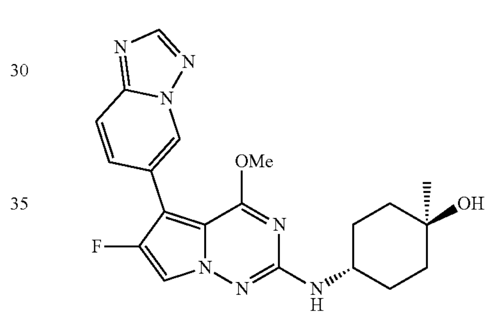

(1r,4r)-4-((5-([1,2,4]Triazolo[1,5-a]pyridin-6-yl)-6-fluoro-4-methoxypyrrolo-[2,1-f][1,2,4]triazin-2-yl)amino)-1-methylcyclohexan-1-ol 589

Off-white solid (7 mg, 0.017 mmol, 23.6% yield). $^1$H NMR (499 MHz, DMSO-$d_6$) δ ppm 1.14 (3H, s), 1.36-1.51 (4H, m), 1.55-1.65 (2H, m), 1.81-1.90 (2H, m), 3.58-3.68 (1H, m), 3.92 (3H, s), 4.25 (1H, s), 6.63 (1H, d, J=7.94 Hz), 7.78-7.82 (1H, m), 7.86 (1H, d, J=3.01 Hz), 7.88 (1H, dd, J=9.31, 0.82 Hz), 8.53 (1H, s), 9.05 (1H, s); ESIMS found for $C_{20}H_{22}FN_7O_2$ m/z 412.2 (M+1).

616

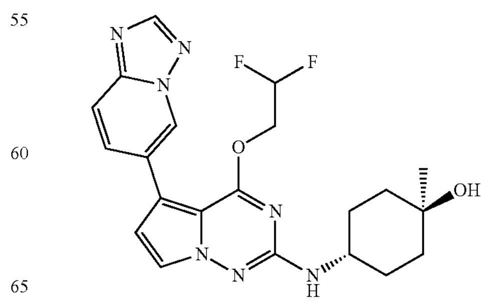

(1r,4r)-4-((5-([1,2,4]Triazolo[1,5-a]pyridin-6-yl)-4-(2,2-difluoroethoxy)pyrrolo[2,1-f][1,2,4]triazin-2-yl)amino)-1-methylcyclohexan-1-ol 616

White solid (2.92 mg, 0.007 mmol). $^1$H NMR (400 MHz, Solvent) 6 ppm 1.28 (3H, s), 1.46-1.66 (4H, m), 1.69-1.80 (2H, m), 1.99-2.10 (2H, m), 3.68-3.82 (1H, m), 4.69 (2H, td, J=14.07, 3.75 Hz), 6.18 (1H, tt, J=55.00, 3.76 Hz), 6.77 (1H, d, J=2.63 Hz), 7.57 (1H, d, J=2.50 Hz), 7.75 (1H, d, J=9.13 Hz), 7.96 (1H, dd, J=9.26, 1.38 Hz), 8.41 (1H, s), 8.94 (1H, s); ESIMS found for $C_{21}H_{23}F_2N_7O_2$ m/z 444.3 (M+1).

621

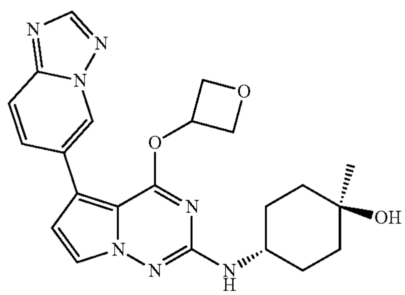

(1r,4r)-4-((5-([1,2,4]Triazolo[1,5-a]pyridin-6-yl)-4-(oxetan-3-yloxy)pyrrolo[2,1-f][1,2,4]triazin-2-yl)amino)-1-methylcyclohexan-1-ol 621

White solid (11 mg, 0.025 mmol, 35.6% yield). $^1$H NMR (499 MHz, DMSO-$d_6$) δ ppm 1.14 (3H, s), 1.36-1.48 (4H, m), 1.55-1.64 (2H, m), 1.80-1.90 (2H, m), 3.59 (1H, br d, J=3.83 Hz), 4.25 (1H, s), 4.61 (2H, dd, J=7.53, 5.34 Hz), 4.86 (2H, t, J=7.12 Hz), 5.69 (1H, quin, J=5.75 Hz), 6.48 (1H, d, J=7.94 Hz), 6.86 (1H, d, J=2.74 Hz), 7.69 (1H, d, J=2.74 Hz), 7.88 (1H, d, J=9.31 Hz), 7.98 (1H, dd, J=9.31, 1.64 Hz), 8.51 (1H, s), 9.21 (1H, s); ESIMS found for $C_{22}H_{25}N_7O_3$ m/z 436.2 (M+1).

622

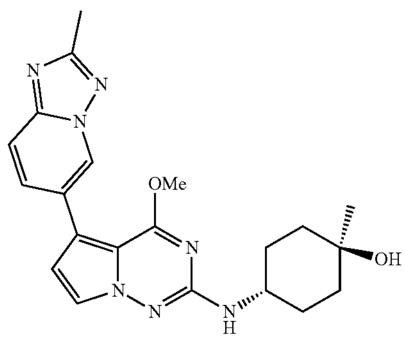

(1r,4r)-4-((4-Methoxy-5-(2-methyl-[1,2,4]triazolo[1,5-a]pyridin-6-yl)pyrrolo[2,1-f][1,2,4]triazin-2-yl)amino)-1-methylcyclohexan-1-ol 622

White solid (34 mg, 0.083 mmol, 35.0% yield). $^1$H NMR (499 MHz, DMSO-$d_6$) δ ppm 1.14 (3H, s), 1.37-1.52 (4H, m), 1.55-1.66 (2H, m), 1.82-1.93 (2H, m), 2.48 (3H, s), 3.64 (1H, br d, J=4.11 Hz), 3.96 (3H, s), 4.23 (1H, s), 6.51 (1H, d, J=7.67 Hz), 6.76 (1H, d, J=2.74 Hz), 7.65 (1H, d, J=2.74 Hz), 7.68 (1H, d, J=9.03 Hz), 7.82 (1H, dd, J=9.31, 1.64 Hz), 8.94 (1H, s); ESIMS found for $C_{21}H_{25}N_7O_2$ m/z 408.2 (M+1).

623

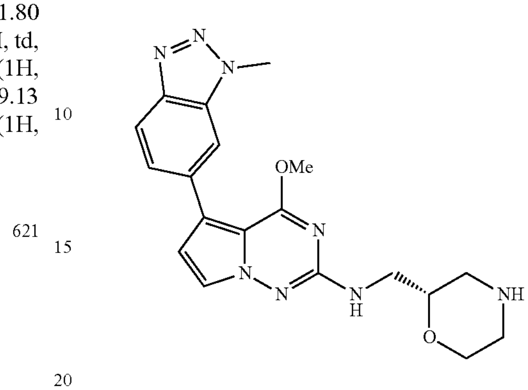

(S)-4-Methoxy-5-(1-methyl-1H-benzo[d][1,2,3]triazol-6-yl)-N-(morpholin-2-ylmethyl)pyrrolo[2,1-f][1,2,4]triazin-2-amine 623

White solid (54 mg, 0.137 mmol, 94.0% yield). $^1$H NMR (499 MHz, DMSO-$d_6$) δ ppm 2.59 (1H, dd, J=12.32, 10.68 Hz), 2.80 (1H, td, J=12.05, 3.56 Hz), 2.86-2.94 (1H, m), 3.06 (1H, br d, J=11.77 Hz), 3.20-3.26 (1H, m), 3.28-3.32 (1H, m), 3.54 (1H, td, J=11.64, 2.46 Hz), 3.75 (1H, dtd, J=10.23, 6.04, 6.04, 2.05 Hz), 3.85 (1H, dd, J=11.77, 2.19 Hz), 3.96 (3H, s), 4.31 (3H, s), 6.74 (1H, t, J=6.02 Hz), 6.76 (1H, d, J=2.46 Hz), 7.61 (1H, dd, J=8.76, 1.37 Hz), 7.65 (1H, d, J=2.74 Hz), 7.94 (1H, s), 7.98 (1H, d, J=8.76 Hz); ESIMS found for $C_{1-9}H_{22}N_8O_2$ m/z 395.2 (M+1).

624

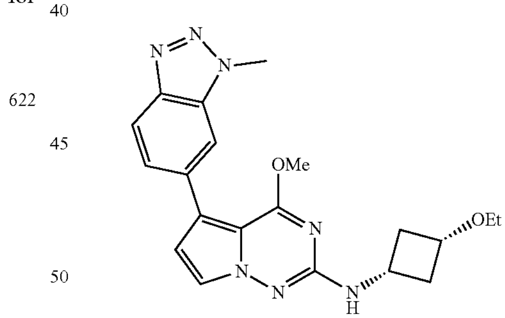

N-(cis-3-Ethoxycyclobutyl)-4-methoxy-5-(1-methyl-1H-benzo[d][1,2,3]triazol-6-yl)pyrrolo[2,1-f][1,2,4]triazin-2-amine 624

Beige solid (23 mg, 0.059 mmol, 30.7% yield). $^1$H NMR (499 MHz, DMSO-$d_6$) δ ppm 1.10 (3H, t, J=6.98 Hz), 1.81-1.93 (2H, m), 2.64 (2H, tdt, J=9.02, 9.02, 6.74, 2.53, 2.53 Hz), 3.34 (2H, q, J=6.85 Hz), 3.65-3.73 (1H, m), 3.74-3.84 (1H, m), 3.95 (3H, s), 4.31 (3H, s), 6.75 (1H, d, J=2.46 Hz), 7.01 (1H, d, J=7.39 Hz), 7.58-7.62 (1H, m), 7.62 (1H, d, J=2.74 Hz), 7.94 (1H, s), 7.95-7.99 (1H, m); ESIMS found for $C_{20}H_{23}N_7O_2$ m/z 394.2 (M+1).

625

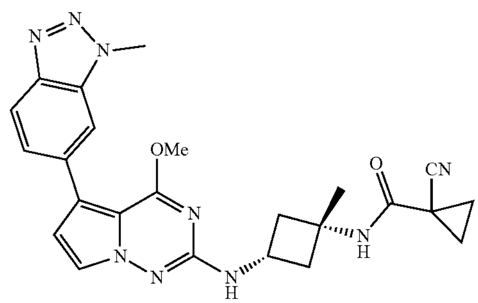

1-Cyano-N-((1s,3s)-3-((4-methoxy-5-(1-methyl-1H-benzo[d][1,2,3]triazol-6-yl)pyrrolo[2,1-f][1,2,4]triazin-2-yl)amino)-1-methylcyclobutyl)cyclopropane-1-carboxamide 625

Off-white solid (9 mg, 0.019 mmol, 28.9% yield). $^{1}$H NMR (499 MHz, DMSO-d$_6$) δ ppm 1.38 (3H, s), 1.43-1.49 (2H, m), 1.49-1.54 (2H, m), 2.14-2.23 (2H, m), 2.45 (2H, ddd, J=9.79, 7.46, 2.74 Hz), 3.95 (3H, s), 4.04 (1H, sxt, J=7.78 Hz), 4.31 (3H, s), 6.75 (1H, d, J=2.46 Hz), 6.99 (1H, d, J=7.12 Hz), 7.60 (1H, dd, J=8.76, 1.64 Hz), 7.65 (1H, d, J=2.46 Hz), 7.94 (1H, s), 7.97 (1H, dd, J=8.62, 0.68 Hz), 8.29 (1H, s); ESIMS found for $C_{24}H_{25}N_9O_2$ m/z 472.2 (M+1).

626

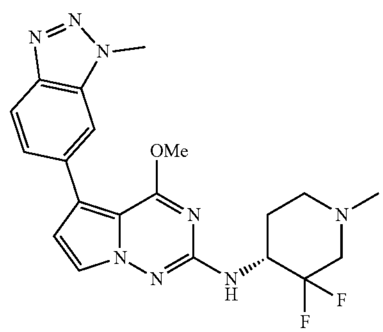

(R)—N-(3,3-Difluoro-1-methylpiperidin-4-yl)-4-methoxy-5-(1-methyl-1H-benzo[d][1,2,3]triazol-6-yl)pyrrolo[2,1-f][1,2,4]triazin-2-amine 626

Fluffy white solid (6 mg, 0.013 mmol, 35.7% yield). $^{1}$H NMR (499 MHz, DMSO-d$_6$) δ ppm 1.77-1.90 (2H, m), 2.12-2.23 (1H, m), 2.28 (3H, br s), 2.34-2.46 (1H, m), 2.75-2.88 (1H, m), 3.01-3.15 (1H, m), 3.98 (3H, s), 4.19-4.30 (1H, m), 4.31 (3H, s), 6.78 (1H, d, J=2.46 Hz), 6.84 (1H, br d, J=6.84 Hz), 7.62 (1H, dd, J=8.62, 1.51 Hz), 7.66 (1H, d, J=2.46 Hz), 7.95 (1H, s), 7.98 (1H, d, J=8.76 Hz); ESIMS found for $C_{20}H_{22}F_2N_8O$ m/z 429.2 (M+1).

627

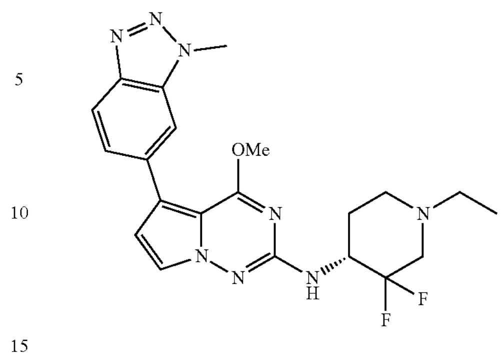

(R)—N-(1-Ethyl-3,3-difluoropiperidin-4-yl)-4-methoxy-5-(1-methyl-1H-benzo[d][1,2,3]triazol-6-yl)pyrrolo[2,1-f][1,2,4]triazin-2-amine 627

Fluffy white solid (14 mg, 0.032 mmol, 52.4% yield). $^{1}$H NMR (499 MHz, DMSO-d$_6$) δ ppm 1.01 (3H, t, J=7.26 Hz), 1.72-1.83 (1H, m), 1.84-1.92 (1H, m), 2.18 (1H, br t, J=10.40 Hz), 2.33-2.42 (1H, m), 2.45 (2H, q, J=7.12 Hz), 2.88 (1H, br d, J=11.77 Hz), 3.07-3.18 (1H, m), 3.98 (3H, s), 4.20-4.30 (1H, m), 4.31 (3H, s), 6.78 (1H, d, J=2.46 Hz), 6.83 (1H, d, J=9.31 Hz), 7.60-7.63 (1H, m), 7.66 (1H, d, J=2.46 Hz), 7.95 (1H, s), 7.98 (1H, d, J=8.49 Hz); ESIMS found for $C_{21}H_{24}F_2N_8O$ m/z 443.2 (M+1).

628

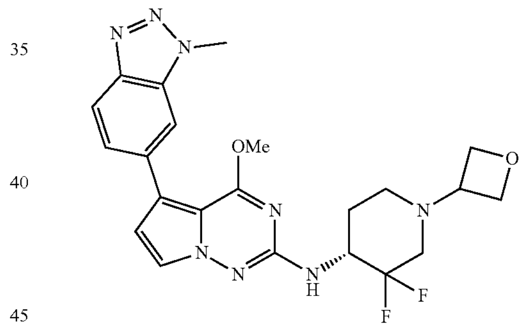

(R)—N-(3,3-Difluoro-1-(oxetan-3-yl)piperidin-4-yl)-4-methoxy-5-(1-methyl-1H-benzo[d][1,2,3]triazol-6-yl)pyrrolo[2,1-f][1,2,4]triazin-2-amine 628

Fluffy white solid (22 mg, 0.047 mmol, 52.4% yield). $^{1}$H NMR (499 MHz, DMSO-d$_6$) δ ppm 1.75-1.86 (1H, m), 1.87-1.94 (1H, m), 2.11-2.22 (1H, m), 2.41 (1H, dd, J=27.15, 11.55 Hz), 2.76 (1H, br d, J=11.23 Hz), 2.96-3.07 (1H, m), 3.60 (1H, quin, J=6.23 Hz), 3.99 (3H, s), 4.25-4.37 (1H, m), 4.31 (3H, s), 4.44 (2H, dt, J=15.06, 6.16 Hz), 4.55 (2H, td, J=6.64, 3.70 Hz), 6.78 (1H, d, J=2.46 Hz), 6.89 (1H, d, J=9.31 Hz), 7.62 (1H, dd, J=8.76, 1.64 Hz), 7.65 (1H, d, J=2.46 Hz), 7.95 (1H, s), 7.98 (1H, d, J=8.76 Hz); ESIMS found for $C_{22}H_{24}F_2N_8O_2$ m/z 471.2 (M+1).

629

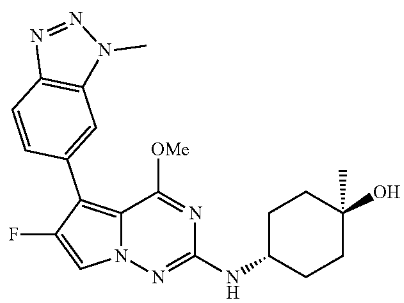

trans-4-((6-Fluoro-4-methoxy-5-(1-methyl-1H-benzo[d][1,2,3]triazol-6-yl)pyrrolo[2,1-f][1,2,4]triazin-2-yl)amino)-1-methylcyclohexan-1-ol 629

Off-white solid (10.5 mg, 0.025 mmol, 27.4% yield). $^1$H NMR (499 MHz, DMSO-$d_6$) δ ppm 1.14 (3H, s), 1.37-1.52 (4H, m), 1.56-1.66 (2H, m), 1.82-1.92 (2H, m), 3.63 (1H, dt, J=8.21, 4.11 Hz), 3.90 (3H, s), 4.24 (1H, s), 4.31 (3H, s), 6.59 (1H, d, J=7.94 Hz), 7.52 (1H, d, J=8.76 Hz), 7.84 (1H, d, J=2.74 Hz), 7.90 (1H, s), 8.02 (1H, d, J=8.76 Hz); ESIMS found for $C_{21}H_{24}FN_7O_2$ m/z 426.2 (M+1).

630

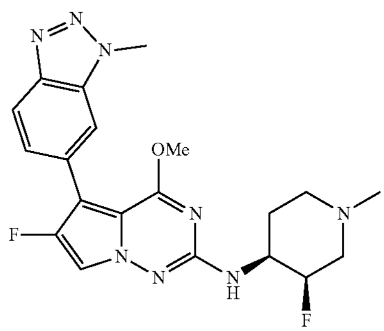

6-Fluoro-N-((3R,4S)-3-fluoro-1-methylpiperidin-4-yl)-4-methoxy-5-(1-methyl-1H-benzo[d][1,2,3]triazol-6-yl)pyrrolo[2,1-f][1,2,4]triazin-2-amine 630

White solid (7.6 mg, 0.018 mmol, 19.7% yield). $^1$H NMR (499 MHz, DMSO-$d_6$) δ ppm 1.63-1.72 (1H, m), 1.86-1.98 (1H, m), 2.01-2.10 (1H, m), 2.17 (1H, dd, J=37.55, 12.87 Hz), 2.19 (3H, s), 2.80 (1H, br d, J=10.95 Hz), 3.00-3.11 (1H, m), 3.66-3.83 (1H, m), 3.92 (3H, s), 4.32 (3H, s), 4.89 (1H, d, J=50.20 Hz), 6.74 (1H, d, J=7.67 Hz), 7.52 (1H, d, J=8.76 Hz), 7.83 (1H, d, J=3.01 Hz), 7.91 (1H, s), 8.03 (1H, d, J=8.49 Hz); ESIMS found for $C_{20}H_{22}F_2N_8O$ m/z 429.2 (M+1).

631

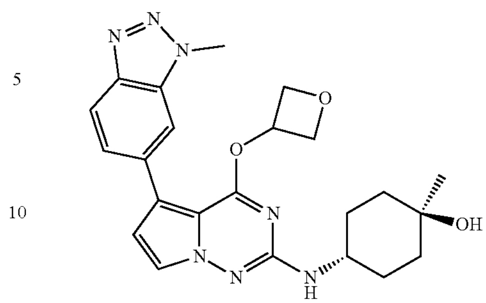

(1r,4r)-1-Methyl-4-((5-(1-methyl-1H-benzo[d][1,2,3]triazol-6-yl)-4-(oxetan-3-yloxy)pyrrolo[2,1-f][1,2,4]triazin-2-yl)amino)cyclohexan-1-ol 631

Off-white solid (11 mg, 0.025 mmol, 34.5% yield). $^1$H NMR (499 MHz, DMSO-$d_6$) δ ppm 1.15 (3H, s), 1.36-1.52 (4H, m), 1.54-1.65 (2H, m), 1.79-1.93 (2H, m), 3.60 (1H, br s), 4.25 (1H, s), 4.32 (3H, s), 4.56 (2H, dd, J=7.39, 5.20 Hz), 4.85 (2H, t, J=6.98 Hz), 5.70 (1H, quin, J=5.61 Hz), 6.45 (1H, br d, J=7.67 Hz), 6.79 (1H, d, J=2.46 Hz), 7.68 (1H, d, J=2.46 Hz), 7.69-7.73 (1H, m), 8.01 (1H, d, J=8.76 Hz), 8.04 (1H, s); ESIMS found for $C_{23}H_{27}N_7O_3$ m/z 450.2 (M+1).

639

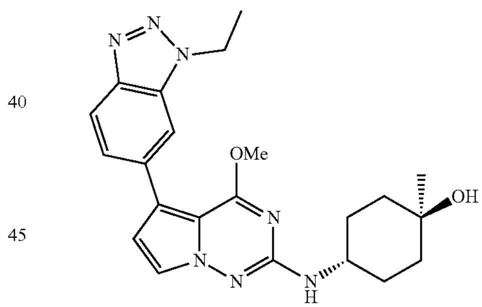

(1r,4r)-4-((5-(1-Ethyl-1H-benzo[d][1,2,3]triazol-6-yl)-4-methoxypyrrolo[2,1-f][1,2,4]triazin-2-yl)amino)-1-methylcyclohexan-1-ol 639

Fluffy white solid (6 mg, 0.014 mmol, 29.5% yield). $^1$H NMR (499 MHz, DMSO-$d_6$) δ ppm 1.15 (3H, s), 1.38-1.50 (4H, m), 1.54 (3H, t, J=7.26 Hz), 1.57-1.63 (2H, m), 1.84-1.93 (2H, m), 3.65 (1H, dt, J=8.08, 3.90 Hz), 3.95 (3H, s), 4.23 (1H, s), 4.75 (2H, q, J=7.12 Hz), 6.49 (1H, d, J=7.94 Hz), 6.74 (1H, d, J=2.46 Hz), 7.57-7.62 (1H, m), 7.64 (1H, d, J=2.46 Hz), 7.97-7.99 (2H, m); ESIMS found for $C_{22}H_{27}N_7O_2$ m/z 422.2 (M+1).

646

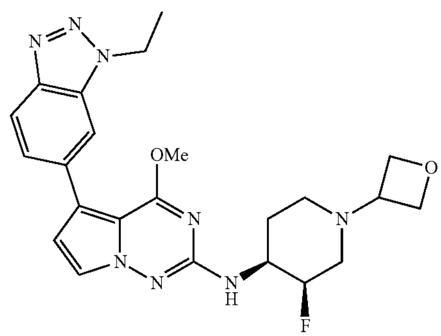

5-(1-Ethyl-1H-benzo[d][1,2,3]triazol-6-yl)-N-((3R, 4S)-3-fluoro-1-(oxetan-3-yl)piperidin-4-yl)-4-methoxypyrrolo[2,1-f][1,2,4]triazin-2-amine 646

Off-white solid (2 mg, 0.004 mmol, 25.0% yield). $^1$H NMR (499 MHz, DMSO-$d_6$) δ ppm 1.54 (3H, t, J=7.39 Hz), 1.68-1.78 (1H, m), 1.92 (1H, qd, J=12.14, 3.29 Hz), 1.98-2.06 (1H, m), 2.16 (1H, dd, J=37.30, 12.59 Hz), 2.76 (1H, br d, J=10.68 Hz), 2.99 (1H, br t, J=10.13 Hz), 3.49 (1H, quin, J=6.30 Hz), 3.74-3.91 (1H, m), 3.97 (3H, s), 4.40 (1H, t, J=6.16 Hz), 4.46 (1H, t, J=6.16 Hz), 4.54 (2H, td, J=6.57, 3.01 Hz), 4.75 (2H, q, J=7.12 Hz), 4.94 (1H, d, J=49.60 Hz), 6.69 (1H, d, J=7.67 Hz), 6.77 (1H, d, J=2.74 Hz), 7.59-7.62 (1H, m), 7.64 (1H, d, J=2.74 Hz), 7.97-8.00 (2H, m); ESIMS found for $C_{23}H_{27}FN_8O_2$ m/z 467.25 (M+1).

653

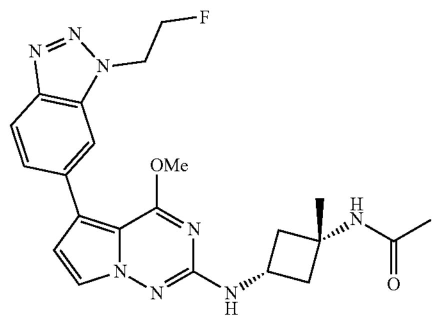

N-((1s,3s)-3-((5-(1-(2-Fluoroethyl)-1H-benzo[d][1,2,3]triazol-6-yl)-4-methoxypyrrolo[2,1-f][1,2,4]triazin-2-yl)amino)-1-methylcyclobutyl)acetamide 653

White solid (12 mg, 0.027 mmol, 21.5% yield). $^1$H NMR (499 MHz, DMSO-$d_6$) δ ppm 1.38 (3H, s), 1.76 (3H, s), 2.11-2.21 (2H, m), 2.42 (2H, ddd, J=9.58, 7.39, 2.46 Hz), 3.93 (3H, s), 4.03 (1H, sxt, J=7.78 Hz), 4.94 (3H, dt, J=47.15, 4.65 Hz), 5.08 (2H, dt, J=27.70, 4.70 Hz), 6.73 (1H, d, J=2.46 Hz), 6.99 (1H, d, J=6.84 Hz), 7.61 (1H, dd, J=8.76, 1.37 Hz), 7.65 (1H, d, J=2.46 Hz), 7.98-8.04 (3H, m); ESIMS found for $C_{22}H_{25}FN_8O_2$ m/z 453.2 (M+1).

658

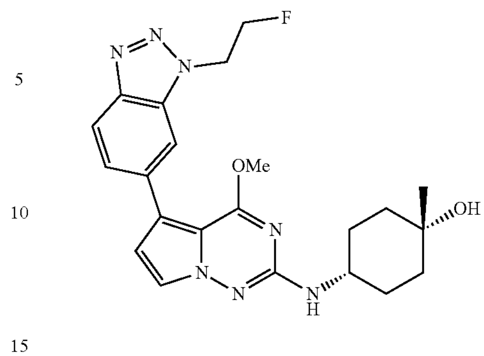

(1s,4s)-4-((5-(1-(2-Fluoroethyl)-1H-benzo[d][1,2,3]triazol-6-yl)-4-methoxypyrrolo[2,1-f][1,2,4]triazin-2-yl)amino)-1-methylcyclohexan-1-ol 658

White solid (10 mg, 0.023 mmol, 23.6% yield). $^1$H NMR (499 MHz, DMSO-$d_6$) δ ppm 1.12 (3H, s), 1.37 (2H, td, J=13.00, 4.38 Hz), 1.58 (2H, br d, J=12.05 Hz), 1.61-1.74 (4H, m), 3.46-3.58 (1H, m), 3.93 (3H, s), 4.00 (1H, s), 4.94 (2H, dt, J=47.20, 4.65 Hz), 5.07 (2H, dt, J=27.95, 4.65 Hz), 6.50 (1H, d, J=7.94 Hz), 6.71 (1H, d, J=2.74 Hz), 7.61 (1H, dd, J=8.62, 1.51 Hz), 7.61 (1H, d, J=2.46 Hz), 7.99 (1H, s), 8.00 (1H, d, J=8.49 Hz); ESIMS found for $C_{22}H_{26}FN_7O_2$ m/z 440.2 (M+1).

659

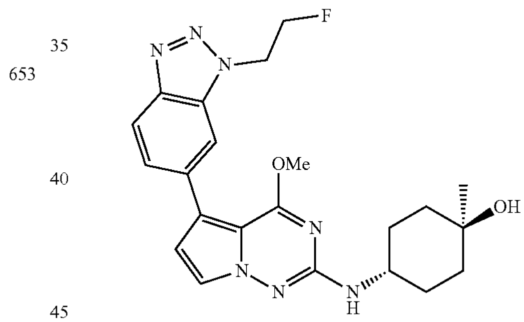

(1r,4r)-4-((5-(1-(2-Fluoroethyl)-1H-benzo[d][1,2,3]triazol-6-yl)-4-methoxypyrrolo[2,1-f][1,2,4]triazin-2-yl)amino)-1-methylcyclohexan-1-ol 659

Fluffy white solid (3 mg, 0.007 mmol, 14.1% yield). $^1$H NMR (499 MHz, DMSO-$d_6$) δ ppm 1.15 (3H, s), 1.38-1.51 (4H, m), 1.56-1.65 (2H, m), 1.82-1.92 (2H, m), 3.65 (1H, dt, J=7.73, 3.94 Hz), 3.94 (3H, s), 4.23 (1H, s), 4.94 (2H, dt, J=47.20, 4.65 Hz), 5.07 (2H, dt, J=27.70, 4.65 Hz), 6.49 (1H, d, J=7.94 Hz), 6.72 (1H, d, J=2.46 Hz), 7.61 (1H, dd, J=8.62, 1.51 Hz), 7.64 (1H, d, J=2.46 Hz), 7.99 (1H, s), 8.00 (1H, d, J=8.76 Hz); ESIMS found for $C_{22}H_{26}FN_7O_2$ m/z 440.2 (M+1).

660

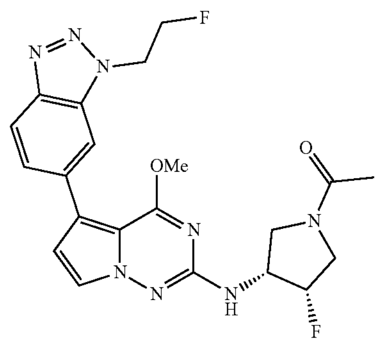

1-((3S,4R)-3-Fluoro-4-((5-(1-(2-fluoroethyl)-1H-benzo[d][1,2,3]triazol-6-yl)-4-methoxypyrrolo[2,1-f][1,2,4]triazin-2-yl)amino)pyrrolidin-1-yl)ethan-1-one 660

White solid (17 mg, 0.037 mmol, 20.3% yield). $^1$H NMR (499 MHz, DMSO-d$_6$) δ ppm 1.93-2.01 (3H, m), 3.46-3.58 (1H, m), 3.59-3.76 (1H, m), 3.77-3.85 (1H, m), 3.85-3.96 (1H, m), 3.96-3.99 (3H, m), 4.29-4.59 (1H, m), 4.94 (2H, dt, J=47.15, 4.65 Hz), 5.08 (2H, dt, J=27.95, 4.65 Hz), 5.24-5.50 (1H, m), 6.79 (1H, t, J=2.46 Hz), 7.09 (1H, dd, J=7.12, 5.75 Hz), 7.61-7.65 (1H, m), 7.68 (1H, dd, J=3.97, 2.60 Hz), 8.00-8.04 (2H, m); ESIMS found for $C_{21}H_{22}F_2N_8O_2$ m/z 457.2 (M+1).

664

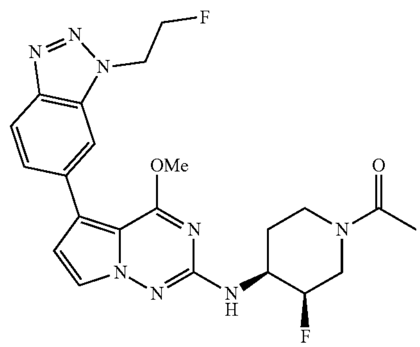

1-((3R,4S)-3-Fluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)ethan-1-one 664

Fluffy white solid (15 mg, 0.032 mmol, 64.1% yield). $^1$H NMR (499 MHz, DMSO-d$_6$) δ ppm 1.66-1.92 (2H, m), 1.97-2.06 (3H, m), 2.66-3.00 (1H, m), 3.36-3.52 (1H, m), 3.86-4.18 (2H, m), 3.96 (3H, s), 4.41-4.75 (1H, m), 4.94 (2H, dt, J=47.20, 4.65 Hz), 4.94 (1H, br s), 5.08 (2H, dt, J=27.95, 4.65 Hz), 6.76 (1H, d, J=2.74 Hz), 6.80 (1H, dd, J=7.80, 3.15 Hz), 7.62 (1H, dd, J=8.62, 1.51 Hz), 7.65 (1H, d, J=2.74 Hz), 7.99-8.03 (2H, m); ESIMS found for $C_{22}H_{24}F_2N_8O_2$ m/z 471.2 (M+1).

666

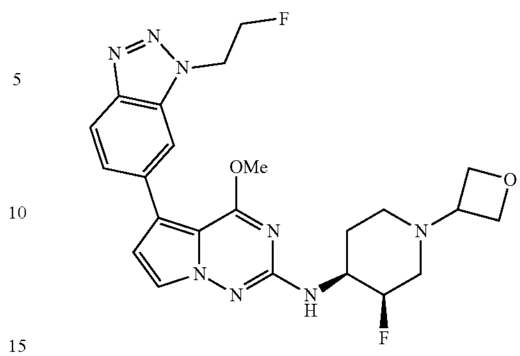

N-((3R,4S)-3-Fluoro-1-(oxetan-3-yl)piperidin-4-yl)-5-(1-(2-fluoroethyl)-1H-benzo[d][1,2,3]triazol-6-yl)-4-methoxypyrrolo[2,1-f][1,2,4]triazin-2-amine 666

Off-white solid (2 mg, 0.004 mmol, 14.9% yield). $^1$H NMR (499 MHz, DMSO-d$_6$) δ ppm 1.67-1.78 (1H, m), 1.87-1.97 (1H, m), 1.99-2.05 (1H, m), 2.16 (1H, dd, J=37.00, 12.59 Hz), 2.72-2.79 (1H, m), 2.99 (1H, br t, J=10.54 Hz), 3.49 (1H, quin, J=6.30 Hz), 3.76-3.91 (1H, m), 3.96 (3H, s), 4.40 (1H, t, J=6.16 Hz), 4.46 (1H, t, J=6.16 Hz), 4.54 (2H, td, J=6.43, 3.01 Hz), 4.94 (2H, dt, J=47.45, 4.65 Hz), 5.08 (2H, dt, J=28.00, 4.65 Hz), 6.70 (1H, d, J=7.67 Hz), 6.75 (1H, d, J=2.46 Hz), 7.62 (1H, dd, J=8.62, 1.51 Hz), 7.64 (1H, d, J=2.74 Hz), 7.99-8.03 (2H, m); ESIMS found for $C_{23}H_{26}F_2N_8O_2$ m/z 485.2 (M+1).

669

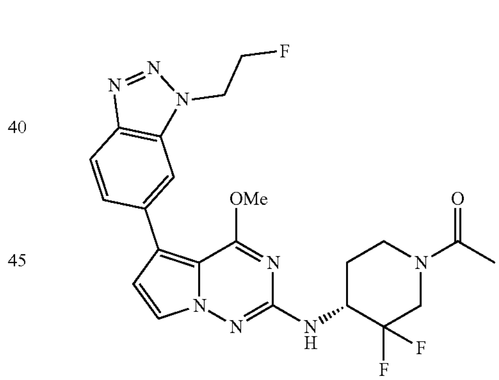

(R)-1-(3,3-Difluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)ethan-1-one 669

Fluffy white solid (7 mg, 0.014 mmol, 32.2% yield). $^1$H NMR (499 MHz, DMSO-d$_6$) δ ppm 1.58-1.84 (1H, m), 1.85-2.00 (1H, m), 2.02-2.10 (3H, m), 2.99 (1H, br t, J=11.09 Hz), 3.63-3.92 (1H, m), 3.98 (3H, s), 4.10-4.31 (1H, m), 4.46-4.63 (2H, m), 4.94 (2H, dt, J=47.20, 4.65 Hz), 5.08 (2H, dt, J=28.00, 4.65 Hz), 6.78 (1H, d, J=2.74 Hz), 7.00 (1H, d, J=9.31 Hz), 7.61-7.64 (1H, m), 7.65 (1H, dd, J=2.46, 1.37 Hz), 8.00-8.04 (2H, m); ESIMS found for $C_{22}H_{23}F_3N_8O_2$ m/z 489.2 (M+1).

670

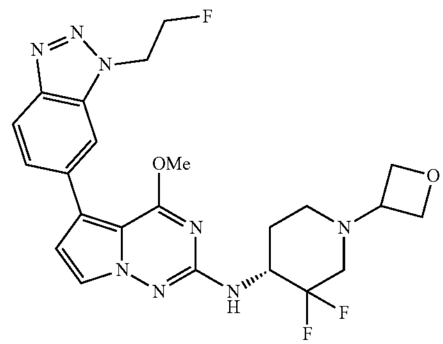

(R)—N-(3,3-Difluoro-1-(oxetan-3-yl)piperidin-4-yl)-5-(1-(2-fluoroethyl)-1H-benzo[d][1,2,3]triazol-6-yl)-4-methoxypyrrolo[2,1-f][1,2,4]triazin-2-amine 670

Pale yellow solid (8 mg, 0.016 mmol, 33.1% yield). $^1$H NMR (499 MHz, DMSO-$d_6$) δ ppm 1.76-1.86 (1H, m), 1.86-1.93 (1H, m), 2.12-2.23 (1H, m), 2.34-2.47 (1H, m), 2.76 (1H, br d, J=11.77 Hz), 2.97-3.06 (1H, m), 3.60 (1H, quin, J=6.30 Hz), 3.97 (3H, s), 4.24-4.38 (1H, m), 4.44 (2H, dt, J=15.13, 6.26 Hz), 4.55 (2H, td, J=6.57, 3.83 Hz), 4.94 (2H, dt, J=46.90, 4.65 Hz), 5.08 (2H, dt, J=27.70, 4.65 Hz), 6.77 (1H, d, J=2.74 Hz), 6.90 (1H, d, J=9.31 Hz), 7.61-7.64 (1H, m), 7.65 (1H, d, J=2.46 Hz), 8.00-8.03 (2H, m); ESIMS found for $C_{23}H_{25}F_3N_8O_2$ m/z 503.2 (M+1).

672

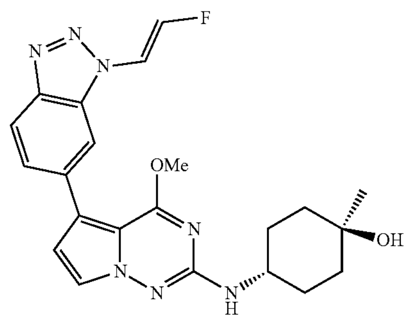

(1r,4r)-4-((5-(1-((E)-2-Fluorovinyl)-1H-benzo[d][1,2,3]triazol-6-yl)-4-methoxypyrrolo[2,1-f][1,2,4]triazin-2-yl)amino)-1-methylcyclohexan-1-ol 672

Yellow solid (7 mg, 0.016 mmol, 23.3% yield). $^1$H NMR (499 MHz, DMSO-$d_6$) δ ppm 1.15 (3H, s), 1.38-1.51 (4H, m), 1.57-1.66 (2H, m), 1.82-1.93 (2H, m), 3.59-3.71 (1H, m), 3.94 (3H, s), 4.23 (1H, s), 6.51 (1H, d, J=7.94 Hz), 6.74 (1H, d, J=2.74 Hz), 7.34 (1H, dd, J=60.90, 4.10 Hz), 7.45 (1H, dd, J=18.62, 3.83 Hz), 7.65 (1H, d, J=2.46 Hz), 7.69 (1H, d, J=9.03 Hz), 7.92 (1H, s), 8.08 (1H, d, J=8.76 Hz); ESIMS found for $C_{22}H_{24}FN_7O_2$ m/z 438.2 (M+1).

673

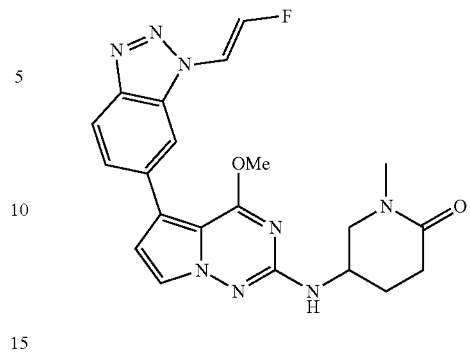

(E)-5-((5-(1-(2-Fluorovinyl)-1H-benzo[d][1,2,3]triazol-6-yl)-4-methoxypyrrolo[2,1-f][1,2,4]triazin-2-yl)amino)-1-methylpiperidin-2-one 673

White solid (2 mg, 0.005 mmol, 4.2% yield). $^1$H NMR (499 MHz, DMSO-$d_6$) δ ppm 1.82-2.06 (2H, m), 2.23-2.43 (2H, m), 2.81 (3H, br s), 3.20-3.28 (1H, m), 3.56 (1H, br s), 3.96 (3H, br s), 4.10 (1H, br s), 6.78 (1H, br s), 6.95 (1H, br s), 7.34 (1H, d, J=63.35 Hz), 7.45 (1H, br d, J=17.25 Hz), 7.68 (2H, br s), 7.93 (1H, br s), 8.08 (1H, br d, J=3.01 Hz); ESIMS found for $C_{21}H_{21}FN_8O_2$ m/z 437.2 (M+1).

681

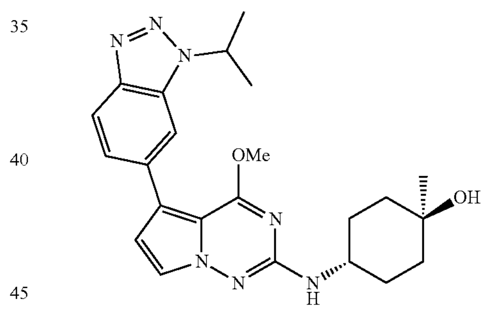

(1r,4r)-4-((5-(1-Isopropyl-1H-benzo[d][1,2,3]triazol-6-yl)-4-methoxypyrrolo[2,1-f][1,2,4]triazin-2-yl)amino)-1-methylcyclohexan-1-ol 681

Fluffy white solid (2.7 mg, 0.006 mmol, 10.6% yield). $^1$H NMR (499 MHz, DMSO-$d_6$) δ ppm 1.15 (3H, s), 1.39-1.51 (4H, m), 1.57-1.63 (2H, m), 1.67 (6H, d, J=6.57 Hz), 1.84-1.91 (2H, m), 3.65 (1H, br dd, J=7.80, 3.97 Hz), 3.94 (3H, s), 4.23 (1H, s), 5.24 (1H, spt, J=6.71 Hz), 6.48 (1H, d, J=7.94 Hz), 6.74 (1H, d, J=2.46 Hz), 7.58 (1H, dd, J=8.76, 1.37 Hz), 7.64 (1H, d, J=2.46 Hz), 7.98 (1H, d, J=8.49 Hz), 8.00 (1H, s); ESIMS found for $C_{23}H_{29}N_7O_2$ m/z 436.2 (M+1).

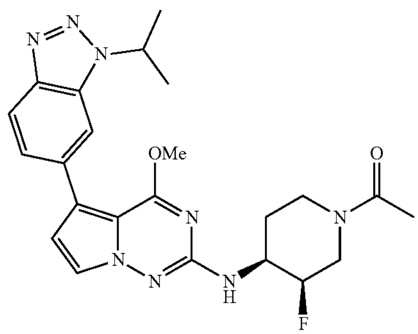 [SMILES: COc1nc(N[C@H]2CCN(C(C)=O)C[C@H]2F)nn2ccc(-c3ccc4nnn(C(C)C)c4c3)c12]

1-((3R,4S)-3-Fluoro-4-((5-(1-isopropyl-1H-benzo[d][1,2,3]triazol-6-yl)-4-methoxypyrrolo[2,1-f][1,2,4]triazin-2-yl)amino)piperidin-1-yl)ethan-1-one 686

Fluffy white solid (9 mg, 0.019 mmol, 54.6% yield). $^1$H NMR (499 MHz, DMSO-$d_6$) δ ppm 1.67 (6H, d, J=6.84 Hz), 1.69-1.74 (1H, m), 1.74-1.92 (1H, m), 1.97-2.06 (3H, m), 2.67-2.98 (1H, m), 3.18-3.51 (1H, m), 3.86-4.18 (2H, m), 3.96 (3H, s), 4.38-4.76 (1H, m), 4.99 (1H, d, J=49.90 Hz), 5.24 (1H, spt, J=6.71 Hz), 6.78 (1H, d, J=2.74 Hz), 6.78-6.81 (1H, m), 7.59 (1H, dd, J=8.62, 1.51 Hz), 7.64 (1H, d, J=2.46 Hz), 7.99 (1H, d, J=8.76 Hz), 8.02 (1H, s); ESIMS found for $C_{23}H_{27}FN_8O_2$ m/z 467.3 (M+1).

688

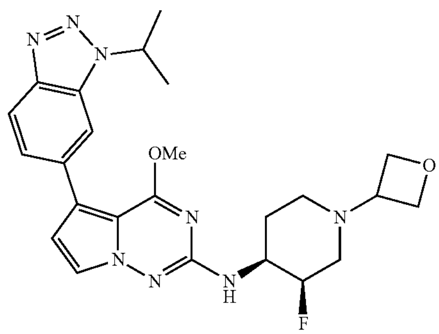

N-((3R,4S)-3-Fluoro-1-(oxetan-3-yl)piperidin-4-yl)-5-(1-isopropyl-1H-benzo[d][1,2,3]triazol-6-yl)-4-methoxypyrrolo[2,1-f][1,2,4]triazin-2-amine 688

Fluffy white solid (11 mg, 0.023 mmol, 24.3% yield). $^1$H NMR (499 MHz, DMSO-$d_6$) δ ppm 1.67 (6H, d, J=6.57 Hz), 1.70-1.77 (1H, m), 1.88-1.97 (1H, m), 1.99-2.06 (1H, m), 2.16 (1H, dd, J=37.00, 12.59 Hz), 2.71-2.80 (1H, m), 2.95-3.04 (1H, m), 3.49 (1H, quin, J=6.37 Hz), 3.74-3.90 (1H, m), 3.96 (3H, s), 4.40 (1H, t, J=6.16 Hz), 4.46 (1H, t, J=6.16 Hz), 4.54 (2H, td, J=6.43, 3.01 Hz), 4.94 (1H, d, J=49.90 Hz), 5.24 (1H, spt, J=6.75 Hz), 6.69 (1 H, d, J=7.94 Hz), 6.77 (1H, d, J=2.74 Hz), 7.59 (1H, dd, J=8.76, 1.37 Hz), 7.64 (1H, d, J=2.46 Hz), 7.99 (1H, d, J=8.76 Hz), 8.02 (1H, s); ESIMS found for $C_{24}H_{29}FN_8O_2$ m/z 481.25 (M+1).

690

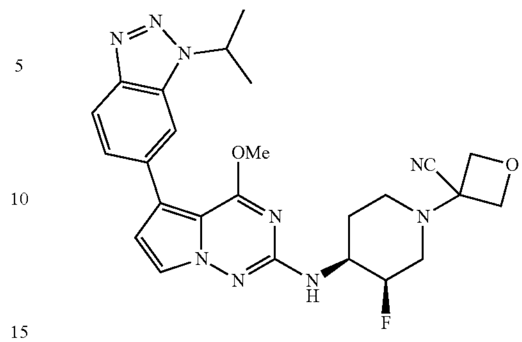

3-((3R,4S)-3-Fluoro-4-((5-(1-isopropyl-1H-benzo[d][1,2,3]triazol-6-yl)-4-methoxypyrrolo[2,1-f][1,2,4]triazin-2-yl)amino)piperidin-1-yl)oxetane-3-carbonitrile 690

Fluffy white solid (10 mg, 0.020 mmol, 21.0% yield). $^1$H NMR (499 MHz, DMSO-$d_6$) δ ppm 1.67 (6H, d, J=6.84 Hz), 1.82 (1H, br dd, J=12.32, 3.01 Hz), 2.00 (1H, qd, J=12.37, 3.70 Hz), 2.09-2.18 (1H, m), 2.26 (1H, dd, J=36.20, 12.32 Hz), 2.78-2.86 (1H, m), 3.00-3.11 (1H, m), 3.79-3.95 (1H, m), 3.97 (3H, s), 4.52 (1H, d, J=6.84 Hz), 4.65 (1H, d, J=7.12 Hz), 4.76 (2H, t, J=6.84 Hz), 5.04 (1H, d, J=49.35 Hz), 5.24 (1H, spt, J=6.75 Hz), 6.78 (1H, d, J=2.46 Hz), 6.81 (1H, d, J=7.67 Hz), 7.59 (1H, dd, J=8.76, 1.37 Hz), 7.66 (1H, d, J=2.46 Hz), 7.99 (1H, d, J=8.49 Hz), 8.02 (1H, s); ESIMS found for $C_{25}H_{28}FN_9O_2$ m/z 506.2 (M+1).

691

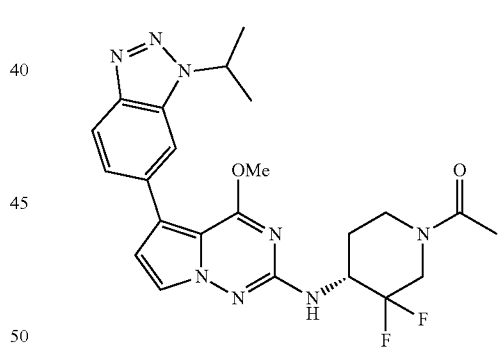

(R)-1-(3,3-Difluoro-4-((5-(1-isopropyl-1H-benzo[d][1,2,3]triazol-6-yl)-4-methoxypyrrolo[2,1-f][1,2,4]triazin-2-yl)amino)piperidin-1-yl)ethan-1-one 691

Fluffy white solid (11 mg, 0.023 mmol, 67.0% yield). $^1$H NMR (499 MHz, DMSO-$d_6$) δ ppm 1.67 (6H, d, J=6.84 Hz), 1.72-1.84 (1H, m), 1.85-2.00 (1H, m), 2.02-2.10 (3H, m), 2.95-3.43 (2H, m), 3.64-3.91 (1H, m), 4.10-4.31 (1H, m), 4.46-4.61 (1H, m), 5.24 (1H, spt, J=6.71 Hz), 6.80 (1H, d, J=2.74 Hz), 7.00 (1H, d, J=9.31 Hz), 7.60 (1H, dd, J=8.76, 1.37 Hz), 7.65 (1H, dd, J=2.46, 1.37 Hz), 7.99 (1H, d, J=8.76 Hz), 8.03 (1H, s); ESIMS found for $C_{23}H_{26}F_2N_8O_2$ m/z 485.2 (M+1).

695

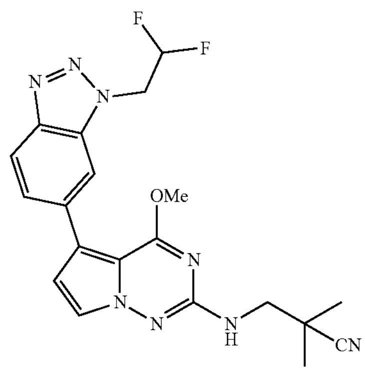

3-((5-(1-(2,2-Difluoroethyl)-1H-benzo[d][1,2,3]triazol-6-yl)-4-methoxypyrrolo[2,1-f][1,2,4]triazin-2-yl)amino)-2,2-dimethylpropanenitrile 695

Off-white solid (30 mg, 0.070 mmol, 35.1% yield). $^1$H NMR (499 MHz, DMSO-$d_6$) δ ppm 1.36 (6H, s), 3.49 (2H, d, J=6.57 Hz), 3.98 (3H, s), 5.30 (2H, td, J=15.88, 2.74 Hz), 6.61 (1H, tt, J=54.30, 3.00 Hz), 6.76 (1H, d, J=2.74 Hz), 7.14 (1H, t, J=6.71 Hz), 7.63-7.66 (1H, m), 7.67 (1H, d, J=2.46 Hz), 8.04 (1H, d, J=8.21 Hz), 8.04 (1H, s); ESIMS found for $C_{20}H_{20}F_2N_8O$ m/z 427.2 (M+1).

696

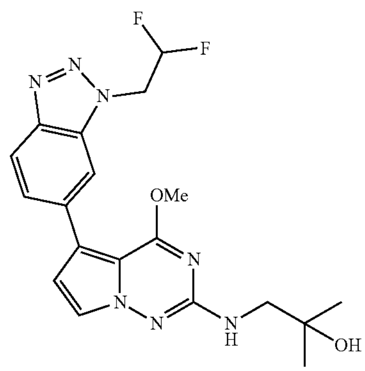

1-((5-(1-(2,2-Difluoroethyl)-1H-benzo[d][1,2,3]triazol-6-yl)-4-methoxypyrrolo[2,1-f][1,2,4]triazin-2-yl)amino)-2-methylpropan-2-ol 696

Off-white solid (6 mg, 0.014 mmol, 15.6% yield). $^1$H NMR (499 MHz, DMSO-$d_6$) δ ppm 1.16 (6H, s), 3.23 (2H, d, J=6.02 Hz), 3.96 (3H, s), 4.56 (1H, s), 5.30 (2H, td, J=15.95, 2.87 Hz), 6.21 (1H, br t, J=5.89 Hz), 6.60 (1H, tt, J=54.30, 3.00 Hz), 6.74 (1H, d, J=2.74 Hz), 7.63-7.65 (1H, m), 7.64 (1H, d, J=2.74 Hz), 8.02 (1H, s), 8.03-8.05 (1H, m); ESIMS found for $C_{1-9}H_{21}F_2N_7O_2$ m/z 418.1 (M+1).

699

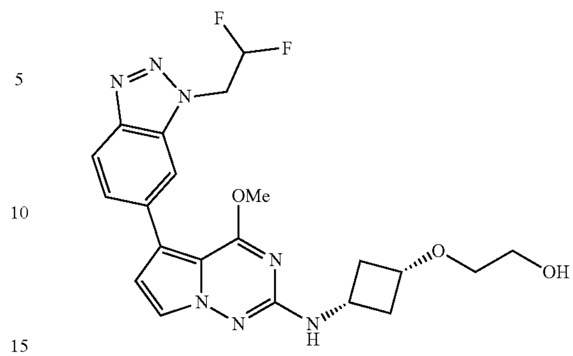

2-(cis-3-((5-(1-(2,2-Difluoroethyl)-1H-benzo[d][1,2,3]triazol-6-yl)-4-methoxypyrrolo[2,1-f][1,2,4]triazin-2-yl)amino)cyclobutoxy)ethan-1-ol 699

Fluffy white solid (3.5 mg, 0.008 mmol, 19.9% yield). $^1$H NMR (499 MHz, DMSO-$d_6$) δ ppm 1.81-1.94 (2H, m), 2.59-2.70 (2H, m), 3.33-3.35 (2H, m), 3.48 (2H, q, J=5.29 Hz), 3.70-3.75 (1H, m), 3.75-3.82 (1H, m), 3.94 (3H, s), 4.60 (1H, t, J=5.48 Hz), 5.30 (2H, td, J=15.88, 2.74 Hz), 6.60 (2H, tt, J=54.30, 3.00 Hz), 6.73 (1H, d, J=2.46 Hz), 7.03 (1H, d, J=7.39 Hz), 7.63 (1H, d, J=2.46 Hz), 7.62-7.65 (1H, m), 8.01-8.04 (2H, m); ESIMS found for $C_{21}H_{23}F_2N_7O_3$ m/z 460.2 (M+1).

702

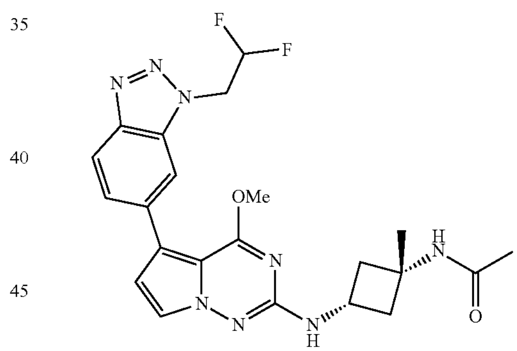

N-((1s,3s)-3-((5-(1-(2,2-Difluoroethyl)-1H-benzo[d][1,2,3]triazol-6-yl)-4-methoxypyrrolo[2,1-f][1,2,4]triazin-2-yl)amino)-1-methylcyclobutyl)acetamide 702

White solid (16 mg, 0.034 mmol, 27.5% yield). $^1$H NMR (499 MHz, DMSO-$d_6$) δ ppm 1.38 (3H, s), 1.76 (3H, s), 2.12-2.23 (2H, m), 2.42 (2H, ddd, J=9.58, 7.39, 2.74 Hz), 3.93 (3H, s), 4.03 (1H, sxt, J=7.78 Hz), 5.30 (2H, td, J=15.95, 2.87 Hz), 6.60 (1H, tt, J=54.30, 3.00 Hz), 6.73 (1H, d, J=2.74 Hz), 7.00 (1H, d, J=6.84 Hz), 7.63 (1H, dd, J=8.62, 1.51 Hz), 7.66 (1H, d, J=2.74 Hz), 7.99-8.05 (3H, m); ESIMS found for $C_{22}H_{24}F_2N_8O_2$ m/z 471.2 (M+1).

710

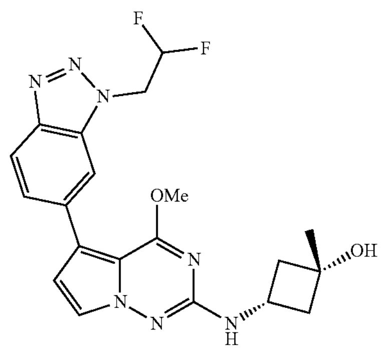

(1s,3s)-3-((5-(1-(2,2-Difluoroethyl)-1H-benzo[d][1,2,3]triazol-6-yl)-4-methoxypyrrolo[2,1-f][1,2,4]triazin-2-yl)amino)-1-methylcyclobutan-1-ol 710

Fluffy white solid (18 mg, 0.042 mmol, 39.5% yield). $^1$H NMR (499 MHz, DMSO-$d_6$) δ ppm 1.27 (3H, s), 2.02 (2H, td, J=8.90, 2.46 Hz), 2.32-2.40 (2H, m), 3.72 (1H, dq, J=15.16, 7.72 Hz), 3.93 (3H, s), 4.91 (1H, s), 5.30 (2H, td, J=15.95, 2.87 Hz), 6.60 (1H, tt, J=54.30, 3.00 Hz), 6.72 (1H, d, J=2.74 Hz), 6.94 (1H, d, J=6.57 Hz), 7.63 (1H, dd, J=8.76, 1.64 Hz), 7.65 (1H, d, J=2.74 Hz), 7.99-8.06 (2H, m); ESIMS found for $C_{20}H_{21}F_2N_7O_2$ m/z 430.15

711

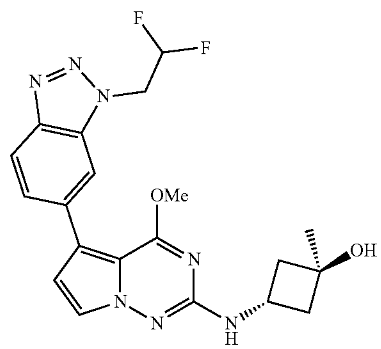

(1r,3r)-3-((5-(1-(2,2-Difluoroethyl)-1H-benzo[d][1,2,3]triazol-6-yl)-4-methoxypyrrolo[2,1-f][1,2,4]triazin-2-yl)amino)-1-methylcyclobutan-1-ol 711

Fluffy white solid (20 mg, 0.047 mmol, 43.9% yield). $^1$H NMR (499 MHz, DMSO-$d_6$) δ ppm 1.28 (3H, s), 1.95-2.05 (2H, m), 2.27-2.35 (2H, m), 3.93 (3H, s), 4.26 (1H, dq, J=14.82, 7.38 Hz), 4.79 (1H, s), 5.30 (2H, td, J=15.95, 2.87 Hz), 6.60 (1H, tt, J=54.30, 3.00 Hz), 6.72 (1H, d, J=2.74 Hz), 6.95 (1H, d, J=6.84 Hz), 7.63 (1H, dd, J=8.80, 1.35 Hz), 7.64 (1H, d, J=2.74 Hz), 8.01-8.04 (2H, m); ESIMS found for $C_{20}H_{21}F_2N_7O_2$ m/z 430.2 (M+1).

717

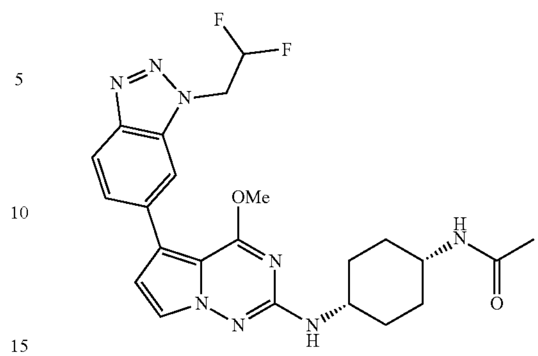

N-(cis-4-((5-(1-(2,2-Difluoroethyl)-1H-benzo[d][1,2,3]triazol-6-yl)-4-methoxypyrrolo[2,1-f][1,2,4]triazin-2-yl)amino)cyclohexyl)acetamide 717

White solid (5.83 mg, 0.012 mmol). $^1$H NMR (400 MHz, DMSO-$d_6$) δ ppm 1.50-1.59 (2H, m), 1.60-1.72 (4H, m), 1.73-1.80 (2H, m), 1.81 (3H, s), 3.68 (2H, br s), 3.95 (3H, s), 5.30 (2H, td, J=15.85, 2.69 Hz), 6.46 (1H, d, J=6.38 Hz), 6.60 (1H, tt, J=54.30, 3.00 Hz), 6.73 (1H, d, J=2.63 Hz), 7.62-7.66 (2H, m), 7.70 (1H, br d, J=7.00 Hz), 8.00-8.05 (2H, m); ESIMS found for $C_{23}H_{26}F_2N_8O_2$ m/z 485.0 (M+1).

718

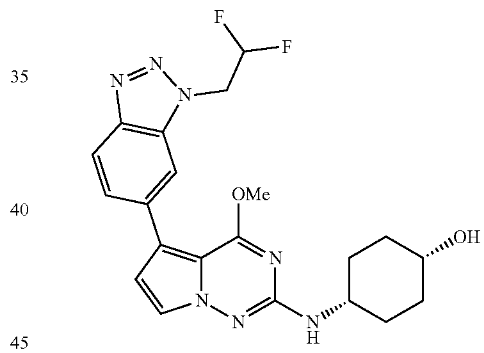

cis-4-((5-(1-(2,2-Difluoroethyl)-1H-benzo[d][1,2,3]triazol-6-yl)-4-methoxypyrrolo[2,1-f][1,2,4]triazin-2-yl)amino)cyclohexan-1-ol 718

Fluffy white solid (9 mg, 0.020 mmol, 14.7% yield). $^1$H NMR (499 MHz, DMSO-$d_6$) δ ppm 1.46-1.54 (2H, m), 1.61-1.69 (4H, m), 1.70-1.79 (2H, m), 3.56-3.67 (1H, m), 3.73 (1H, br d, J=2.19 Hz), 3.94 (3H, s), 4.34 (1H, d, J=3.01 Hz), 5.30 (2H, td, J=15.95, 2.87 Hz), 6.60 (1H, tt, J=54.30, 3.00 Hz), 6.53 (1H, d, J=7.39 Hz), 6.71 (1H, d, J=2.46 Hz), 7.64 (1H, dd, J=8.50, 1.65 Hz), 7.63 (1H, d, J=2.46 Hz), 8.01-8.05 (2H, m); ESIMS found for $C_{21}H_{23}F_2N_7O_2$ m/z 444.2 (M+1).

719

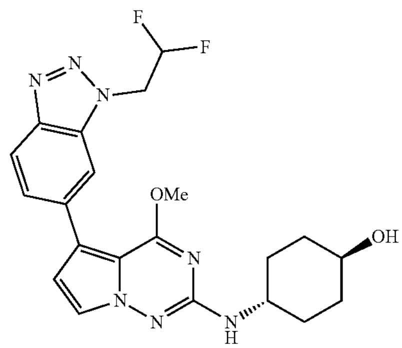

trans-4-((5-(1-(2,2-Difluoroethyl)-1H-benzo[d][1,2,3]triazol-6-yl)-4-methoxypyrrolo[2,1-f][1,2,4]triazin-2-yl)amino)cyclohexan-1-ol 719

Fluffy white solid (7 mg, 0.016 mmol, 11.4% yield). $^1$H NMR (499 MHz, DMSO-$d_6$) δ ppm 1.17-1.40 (4H, m), 1.79-1.89 (2H, m), 1.92-2.01 (2H, m), 3.35-3.46 (1H, m), 3.49-3.59 (1H, m), 3.93 (3H, s), 4.55 (1H, d, J=4.38 Hz), 5.30 (2H, td, J=15.95, 2.87 Hz), 6.60 (1H, tt, J=54.30, 3.00 Hz), 6.51 (1H, d, J=8.21 Hz), 6.71 (1H, d, J=2.46 Hz), 7.64 (1H, dd, J=8.76, 1.64 Hz), 7.65 (1H, d, J=2.46 Hz), 8.02 (1H, d, J=9.86 Hz), 8.02 (1H, s); ESIMS found for $C_{21}H_{23}F_2N_7O_2$ m/z 444.2 (M+1).

720

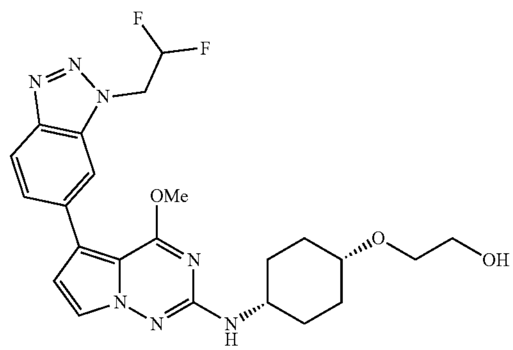

2-((cis-4-((5-(1-(2,2-Difluoroethyl)-1H-benzo[d][1,2,3]triazol-6-yl)-4-methoxypyrrolo[2,1-f][1,2,4]triazin-2-yl)amino)cyclohexyl)oxy)ethan-1-ol 720

White solid (7.47 mg, 0.015 mmol). $^1$H NMR (400 MHz, DMSO-$d_6$) δ ppm 1.46-1.57 (2H, m), 1.62-1.73 (4H, m), 1.78-1.89 (2H, m), 3.40 (2H, t, J=5.50 Hz), 3.48-3.54 (2H, m), 3.58-3.72 (2H, m), 3.94 (3H, s), 4.52 (1H, t, J=5.50 Hz), 5.30 (2H, td, J=15.86, 2.51 Hz), 6.60 (1H, tt, J=54.30, 3.00 Hz), 6.54 (1H, d, J=7.70 Hz), 6.71 (1H, d, J=2.57 Hz), 7.61-7.66 (2H, m), 7.99-8.05 (2H, m); ESIMS found for $C_{23}H_{27}F_2N_7O_3$ m/z 488.2 (M+1).

721

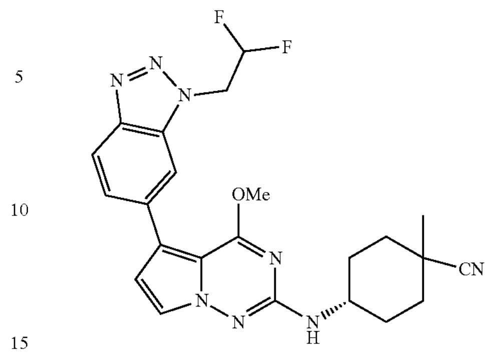

4-((5-(1-(2,2-Difluoroethyl)-1H-benzo[d][1,2,3]triazol-6-yl)-4-methoxypyrrolo[2,1-f][1,2,4]triazin-2-yl)amino)-1-methylcyclohexane-1-carbonitrile 721

White solid (15 mg, 0.032 mmol, 51.4% yield). $^1$H NMR (499 MHz, DMSO-$d_6$) δ ppm 1.34 (3H, s), 1.45-1.63 (4H, m), 1.95 (2H, br d, J=10.68 Hz), 1.99-2.08 (2H, m), 3.56-3.63 (1H, m), 3.94 (3H, s), 5.30 (2H, td, J=15.88, 2.74 Hz), 6.61 (1H, tt, J=54.30, 3.00 Hz), 6.72 (1H, d, J=2.46 Hz), 6.78 (1H, d, J=7.94 Hz), 7.62 (1H, d, J=2.74 Hz), 7.63-7.66 (1H, m), 8.01-8.05 (2H, m); ESIMS found for $C_{23}H_{24}F_2N_8O$ m/z 467.2 (M+1).

724

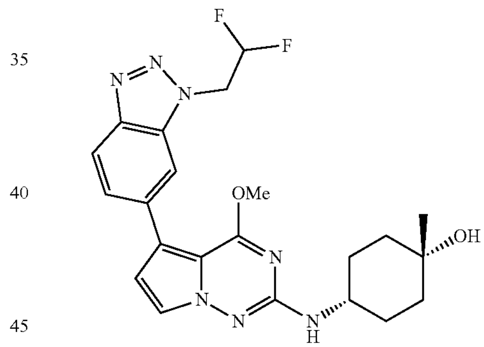

(1s,4s)-4-((5-(1-(2,2-Difluoroethyl)-1H-benzo[d][1,2,3]triazol-6-yl)-4-methoxypyrrolo[2,1-f][1,2,4]triazin-2-yl)amino)-1-methylcyclohexan-1-ol 724

Fluffy white solid (15 mg, 0.033 mmol, 34.0% yield). $^1$H NMR (499 MHz, DMSO-$d_6$) δ ppm 1.12 (3H, s), 1.37 (2H, td, J=13.07, 4.52 Hz), 1.58 (2H, br d, J=12.32 Hz), 1.61-1.69 (2H, m), 1.69-1.75 (2H, m), 3.46-3.59 (1H, m), 3.93 (3H, s), 4.00 (1H, s), 5.30 (2H, td, J=15.88, 2.74 Hz), 6.60 (1H, tt, J=54.30, 3.00 Hz), 6.51 (1H, d, J=7.94 Hz), 6.71 (1H, d, J=2.74 Hz), 7.62 (1H, d, J=2.46 Hz), 7.62-7.65 (1H, m), 8.00-8.04 (2H, m); ESIMS found for $C_{22}H_{25}F_2N_7O_2$ m/z 458.2 (M+1).

725

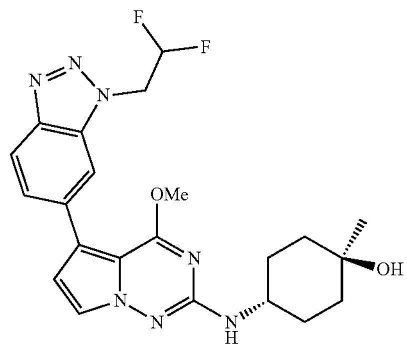

(1r,4r)-4-((5-(1-(2,2-Difluoroethyl)-1H-benzo[d][1,2,3]triazol-6-yl)-4-methoxypyrrolo[2,1-f][1,2,4]triazin-2-yl)amino)-1-methylcyclohexan-1-ol 725

Fluffy white solid (9 mg, 0.020 mmol, 55.6% yield). $^1$H NMR (499 MHz, DMSO-$d_6$) δ ppm 1.15 (3H, s), 1.38-1.53 (4H, m), 1.56-1.65 (2H, m), 1.81-1.93 (2H, m), 3.60-3.72 (1H, m), 3.94 (3H, s), 4.23 (1H, s), 5.30 (2H, td, J=15.88, 2.74 Hz), 6.50 (1H, d, J=7.94 Hz), 6.60 (1H, tt, J=54.30, 3.00 Hz), 6.72 (1H, s), 7.62-7.65 (1H, m), 7.65 (1H, d, J=2.74 Hz), 8.01-8.04 (2H, m); ESIMS found for $C_{22}H_{25}F_2N_7O_2$ m/z 458.2 (M+1).

726

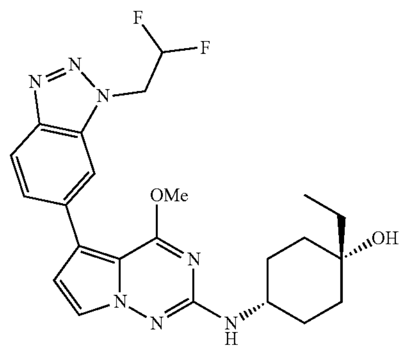

(1s,4s)-4-((5-(1-(2,2-Difluoroethyl)-1H-benzo[d][1,2,3]triazol-6-yl)-4-methoxypyrrolo[2,1-f][1,2,4]triazin-2-yl)amino)-1-ethylcyclohexan-1-ol 726

Fluffy white solid (24 mg, 0.051 mmol, 36.7% yield). $^1$H NMR (499 MHz, DMSO-$d_6$) δ ppm 0.85 (3H, t, J=7.53 Hz), 1.30 (2H, td, J=13.21, 3.97 Hz), 1.37 (2H, q, J=7.39 Hz), 1.56 (2H, br d, J=12.32 Hz), 1.60-1.70 (2H, m), 1.71-1.77 (2H, m), 3.45-3.59 (1H, m), 3.80 (1H, s), 3.93 (3H, s), 5.30 (2H, td, J=15.81, 2.87 Hz), 6.60 (1H, tt, J=54.30, 3.00 Hz), 6.54 (1H, d, J=7.94 Hz), 6.71 (1H, d, J=2.74 Hz), 7.62 (1H, d, J=2.46 Hz), 7.64 (1H, dd, J=8.76, 1.64 Hz), 8.00-8.04 (2H, m); ESIMS found for $C_{23}H_{27}F_2N_7O_2$ m/z 472.2 (M+1).

727

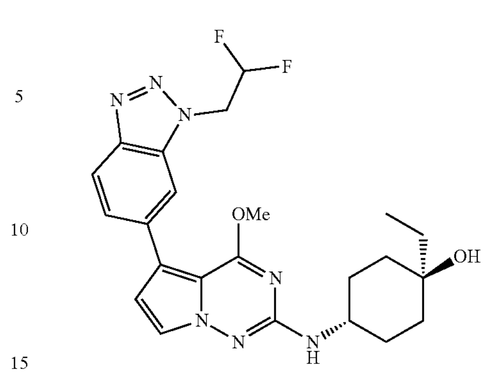

(1r,4r)-4-((5-(1-(2,2-Difluoroethyl)-1H-benzo[d][1,2,3]triazol-6-yl)-4-methoxypyrrolo[2,1-f][1,2,4]triazin-2-yl)amino)-1-ethylcyclohexan-1-ol 727

Fluffy white solid (28 mg, 0.059 mmol, 42.9% yield). $^1$H NMR (499 MHz, DMSO-$d_6$) δ ppm 0.83 (3H, t, J=7.39 Hz), 1.32-1.39 (2H, m), 1.40-1.46 (2H, m), 1.47 (2H, q, J=7.39 Hz), 1.60-1.71 (2H, m), 1.80-1.91 (2H, m), 3.69 (1H, tt, J=8.08, 4.11 Hz), 3.94 (3H, s), 3.98 (1H, s), 5.30 (2H, td, J=15.95, 2.87 Hz), 6.49 (1H, d, J=7.94 Hz), 6.60 (1H, tt, J=54.30, 3.00 Hz), 6.72 (1H, d, J=2.46 Hz), 7.64 (1H, dd, J=8.50, 1.65 Hz), 7.65 (1H, d, J=2.74 Hz), 8.00-8.06 (2H, m); ESIMS found for $C_{23}H_{27}F_2N_7O_2$ m/z 472.2 (M+1).

730

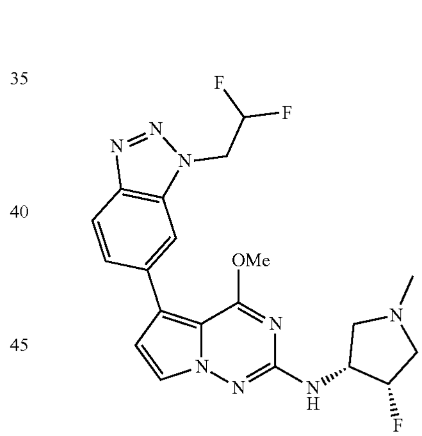

5-(1-(2,2-Difluoroethyl)-1H-benzo[d][1,2,3]triazol-6-yl)-N-((3R,4S)-4-fluoro-1-methylpyrrolidin-3-yl)-4-methoxypyrrolo[2,1-f][1,2,4]triazin-2-amine 730

Fluffy white solid (12 mg, 0.027 mmol, 58.1% yield). $^1$H NMR (499 MHz, DMSO-$d_6$) δ ppm 2.31 (3H, s), 2.60 (1H, ddd, J=31.55, 11.64, 2.05 Hz), 2.61 (1H, br t, J=8.90 Hz), 2.92 (1H, t, J=8.08 Hz), 3.17 (1H, ddd, J=29.35, 11.50, 4.93 Hz), 3.96 (3H, s), 4.20-4.36 (1H, m), 5.14-5.28 (1H, m), 5.25-5.35 (2H, m), 6.61 (1H, tt, J=54.30, 3.00 Hz), 6.76 (1H, d, J=2.74 Hz), 6.78 (1H, d, J=7.67 Hz), 7.64 (1H, dd, J=8.90, 0.96 Hz), 7.67 (1H, d, J=2.74 Hz), 8.04 (1H, d, J=8.21 Hz), 8.03 (1H, s); ESIMS found for $C_{20}H_{21}F_3N_8O$ m/z 447.2 (M+1).

732

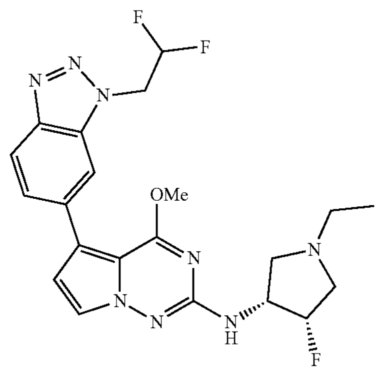

5-(1-(2,2-Difluoroethyl)-1H-benzo[d][1,2,3]triazol-6-yl)-N-((3R,4S)-1-ethyl-4-fluoropyrrolidin-3-yl)-4-methoxypyrrolo[2,1-f][1,2,4]triazin-2-amine 732

Fluffy white solid (2 mg, 0.004 mmol, 6.3% yield). $^1$H NMR (499 MHz, DMSO-$d_6$) δ ppm 1.03 (3H, t, J=7.26 Hz), 2.47-2.54 (2H, m), 2.59-2.70 (2H, m), 2.97 (1H, t, J=8.21 Hz), 3.18 (1H, ddd, J=30.95, 11.91, 4.79 Hz), 3.96 (3H, s), 4.19-4.33 (1H, m), 5.13-5.27 (1H, m), 5.27-5.35 (2H, m), 6.61 (1H, tt, J=54.30, 3.00 Hz), 6.75-6.77 (1H, m), 6.76 (1H, d, J=2.74 Hz), 7.63-7.66 (1H, m), 7.67 (1H, d, J=2.46 Hz), 8.04 (1H, d, J=7.94 Hz), 8.03 (1H, s); ESIMS found for $C_{21}H_{23}F_3N_8O$ m/z 461.2 (M+1).

734

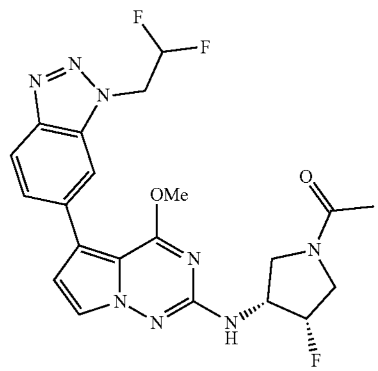

1-((3R,4S)-3-((5-(1-(2,2-Difluoroethyl)-1H-benzo[d][1,2,3]triazol-6-yl)-4-methoxypyrrolo[2,1-f][1,2,4]triazin-2-yl)amino)-4-fluoropyrrolidin-1-yl)ethan-1-one 734

Fluffy white solid (19 mg, 0.040 mmol, 69.3% yield). $^1$H NMR (499 MHz, DMSO-$d_6$) δ ppm 1.92-2.02 (3H, m), 3.47-3.75 (2H, m), 3.78-3.96 (2H, m), 3.97 (3H, d, J=1.37 Hz), 4.30-4.59 (1H, m), 5.25-5.48 (3H, m), 6.61 (1H, tt, J=54.30, 3.00 Hz), 6.78 (1H, t, J=2.46 Hz), 7.10 (1H, dd, J=7.12, 5.20 Hz), 7.63-7.67 (1H, m), 7.68 (1H, dd, J=3.97, 2.60 Hz), 8.03-8.06 (2H, m); ESIMS found for $C_{21}H_{21}F_3N_8O_2$ m/z 475.2 (M+1).

739

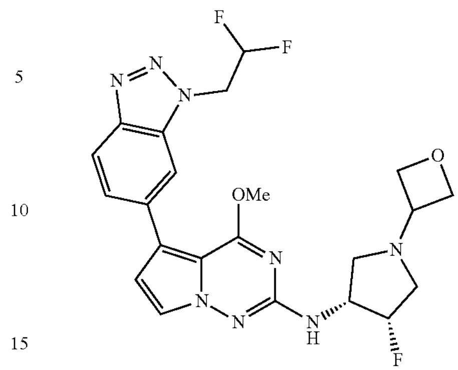

5-(1-(2,2-Difluoroethyl)-1H-benzo[d][1,2,3]triazol-6-yl)-N-((3R,4S)-4-fluoro-1-(oxetan-3-yl)pyrrolidin-3-yl)-4-methoxypyrrolo[2,1-f][1,2,4]triazin-2-amine 739

Fluffy white solid (14 mg, 0.029 mmol, 27.5% yield). $^1$H NMR (499 MHz, DMSO-$d_6$) δ ppm 2.69 (1H, t, J=9.17 Hz), 2.77 (1H, ddd, J=30.20, 12.10, 1.40 Hz), 3.02 (1H, t, J=8.35 Hz), 3.18 (1H, ddd, J=32.90, 12.05, 4.38 Hz), 3.79 (1H, quin, J=6.16 Hz), 3.96 (3H, s), 4.23-4.37 (1H, m), 4.47 (2H, t, J=6.02 Hz), 4.60 (2H, t, J=6.57 Hz), 5.18-5.32 (1H, m), 5.31 (2H, td, J=15.95, 2.87 Hz), 6.61 (1H, tt, J=54.30, 3.00 Hz), 6.77 (1H, d, J=2.46 Hz), 6.84 (1H, d, J=7.67 Hz), 7.63-7.66 (1H, m), 7.67 (1H, d, J=2.46 Hz), 8.04 (1H, d, J=8.21 Hz), 8.04 (1H, s); ESIMS found for $C_{22}H_{23}F_3N_8O_2$ m/z 489.2 (M+1).

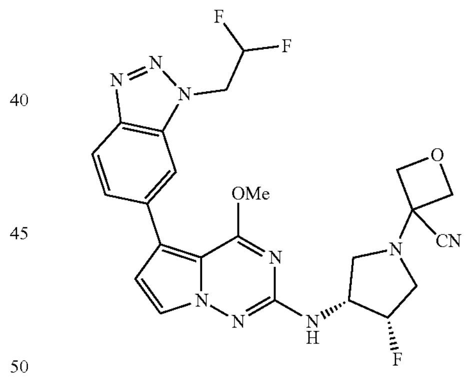

3-((3R,4S)-3-((5-(1-(2,2-Difluoroethyl)-1H-benzo[d][1,2,3]triazol-6-yl)-4-methoxypyrrolo[2,1-f][1,2,4]triazin-2-yl)amino)-4-fluoropyrrolidin-1-yl)oxetane-3-carbonitrile 741

Fluffy white solid (14 mg, 0.027 mmol, 26.2% yield). $^1$H NMR (499 MHz, DMSO-$d_6$) δ ppm 2.82 (1H, t, J=9.05 Hz), 2.88 (1H, ddd, J=29.60, 11.77, 0.82 Hz), 3.09 (1H, t, J=8.35 Hz), 3.26 (1H, ddd, J=34.05, 12.05, 4.38 Hz), 3.97 (3H, s), 4.32-4.46 (1H, m), 4.58 (1H, d, J=6.84 Hz), 4.62 (1H, d, J=6.84 Hz), 4.81 (2H, d, J=6.84 Hz), 5.26-5.41 (3H, m), 6.61 (1H, tt, J=54.30, 3.00 Hz), 6.78 (1H, d, J=2.46 Hz), 7.02 (1H, d, J=7.39 Hz), 7.63-7.67 (1H, m), 7.69 (1H, d, J=2.74 Hz), 8.04 (1H, br d, J=8.21 Hz), 8.04 (1H, s); ESIMS found for $C_{23}H_{22}F_3N_902$ m/z 514.2 (M+1).

750

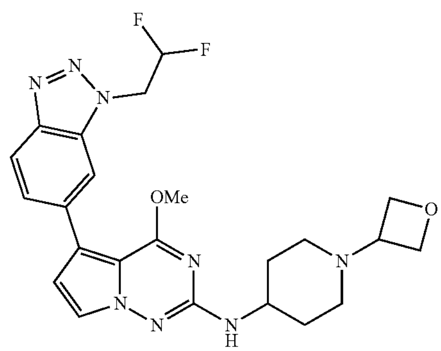

5-(1-(2,2-Difluoroethyl)-1H-benzo[d][1,2,3]triazol-6-yl)-4-methoxy-N-(1-(oxetan-3-yl)piperidin-4-yl)pyrrolo[2,1-f][1,2,4]triazin-2-amine 750

Fluffy white solid (4 mg, 0.008 mmol, 6.1% yield). $^1H$ NMR (499 MHz, DMSO-$d_6$) δ ppm 1.54 (2H, qd, J=11.64, 3.42 Hz), 1.86 (2H, br t, J=11.50 Hz), 1.92 (2H, br d, J=11.50 Hz), 2.69 (2H, br d, J=11.50 Hz), 3.35-3.42 (1H, m), 3.54-3.66 (1H, m), 3.94 (3H, s), 4.42 (2H, t, J=6.02 Hz), 4.50-4.57 (2H, m), 5.30 (2H, td, J=15.95, 2.87 Hz), 6.60 (1H, tt, J=54.30, 3.00 Hz), 6.65 (1H, d, J=7.94 Hz), 6.72 (1H, d, J=2.46 Hz), 7.64 (1H, br dd, J=8.50, 1.65 Hz), 7.64 (1H, d, J=2.74 Hz), 8.03 (1H, d, J=10.40 Hz), 8.02 (1H, s); ESIMS found for $C_{23}H_{26}F_2N_8O_2$ m/z 485.2 (M+1).

754

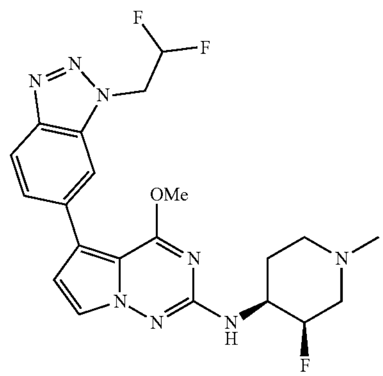

5-(1-(2,2-Difluoroethyl)-1H-benzo[d][1,2,3]triazol-6-yl)-N-((3R,4S)-3-fluoro-1-methylpiperidin-4-yl)-4-methoxypyrrolo[2,1-f][1,2,4]triazin-2-amine 754

Fluffy white solid (3 mg, 0.007 mmol, 19.4% yield). $^1H$ NMR (499 MHz, DMSO-$d_6$) δ ppm 1.64-1.74 (1H, m), 1.93 (1H, qd, J=12.32, 3.56 Hz), 2.02-2.10 (1H, m), 2.18 (1H, dd, J=37.85, 12.32 Hz), 2.19 (3H, s), 2.80 (1H, br d, J=11.23 Hz), 3.00-3.10 (1H, m), 3.69-3.85 (1H, m), 3.95 (3H, s), 4.92 (1H, d, J=50.20 Hz), 5.30 (2H, td, J=15.95, 2.87 Hz), 6.60 (1H, tt, J=54.30, 3.00 Hz), 6.64 (1H, d, J=7.67 Hz), 6.75 (1H, d, J=2.74 Hz), 7.63-7.66 (1H, m), 7.65 (1H, d, J=2.46 Hz), 8.01-8.05 (2H, m); ESIMS found for $C_{21}H_{23}F_3N_8O$ m/z 461.2 (M+1).

755

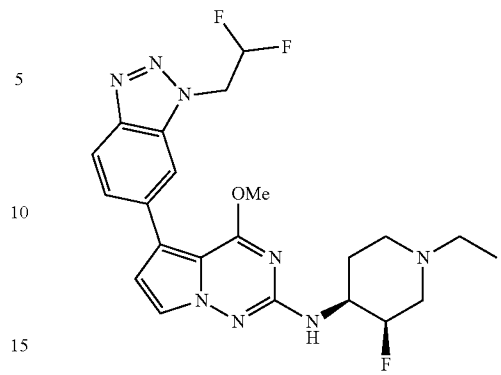

5-(1-(2,2-Difluoroethyl)-1H-benzo[d][1,2,3]triazol-6-yl)-N-((3R,4S)-1-ethyl-3-fluoropiperidin-4-yl)-4-methoxypyrrolo[2,1-f][1,2,4]triazin-2-amine 755

Fluffy white solid (2.6 mg, 0.006 mmol, 12.2% yield). $^1H$ NMR (499 MHz, DMSO-$d_6$) δ ppm 1.00 (3H, t, J=7.12 Hz), 1.66-1.75 (1H, m), 1.90 (1H, qd, J=12.23, 3.56 Hz), 2.06 (1H, br t, J=11.09 Hz), 2.19 (1H, dd, J=37.85, 12.32 Hz), 2.37 (2H, q, J=7.30 Hz), 2.89 (1H, br d, J=10.95 Hz), 3.08-3.17 (1H, m), 3.71-3.86 (1H, m), 3.95 (3H, s), 4.92 (1H, d, J=49.90 Hz), 5.30 (2H, td, J=15.95, 2.87 Hz), 6.60 (1H, tt, J=54.30, 3.00 Hz), 6.63 (1H, d, J=7.94 Hz), 6.75 (1H, d, J=2.74 Hz), 7.63-7.65 (1H, m), 7.65 (1H, d, J=2.74 Hz), 8.01-8.05 (2H, m); ESIMS found for $C_{22}H_{25}F_3N_8O$ m/z 475.2 (M+1).

756

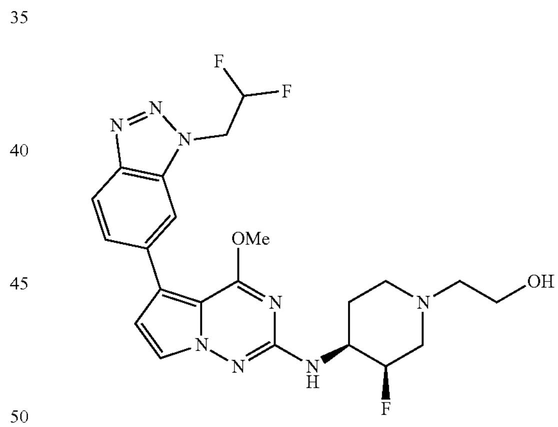

2-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-ol 756

Fluffy white solid (8 mg, 0.016 mmol, 37.4% yield). $^1H$ NMR (499 MHz, DMSO-$d_6$) δ ppm 1.63-1.72 (1H, m), 1.85-1.97 (1H, m), 2.14-2.22 (1H, m), 2.32 (1H, dd, J=37.55, 12.59 Hz), 2.44 (2H, t, J=6.30 Hz), 2.91 (1H, br d, J=11.77 Hz), 3.16 (1H, br dd, J=11.23, 10.13 Hz), 3.50 (2H, t, J=6.30 Hz), 3.71-3.88 (1H, m), 3.95 (3H, s), 4.42 (1H, br s), 4.90 (1H, d, J=50.15 Hz), 5.30 (2H, td, J=15.95, 2.87 Hz), 6.60 (2H, tt, J=54.30, 3.00 Hz), 6.63 (1H, d, J=7.94 Hz), 6.74 (1H, d, J=2.74 Hz), 7.62-7.66 (2H, m), 8.01-8.05 (2H, m); ESIMS found for $C_{22}H_{25}F_3N_8O_2$ m/z 491.2 (M+1).

757

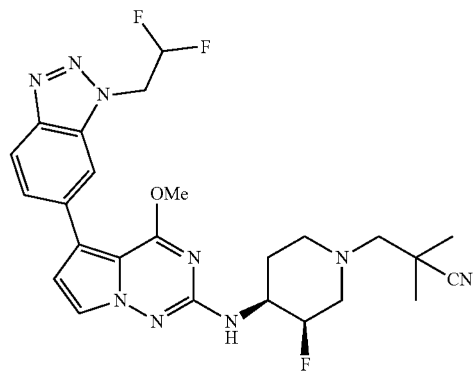

3-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)-2,2-dimethylpropanenitrile 757

Fluffy white solid (2 mg, 0.004 mmol, 20.6% yield). $^1$H NMR (499 MHz, DMSO-$d_6$) δ ppm 1.16 (6H, s), 1.65-1.74 (1H, m), 1.86-1.98 (1H, m), 2.02-2.10 (1H, m), 2.13-2.25 (1H, m), 2.19 (2H, s), 2.75-2.83 (1H, m), 2.99-3.08 (1H, m), 3.70-3.86 (1H, m), 4.46 (3H, s), 4.91 (1H, d, J=50.20 Hz), 5.29 (2H, td, J=15.67, 3.15 Hz), 6.59 (1H, tt, J=54.30, 3.00 Hz), 6.70 (1H, d, J=7.67 Hz), 6.74 (1H, d, J=2.46 Hz), 7.70 (1H, d, J=2.74 Hz), 7.71 (1H, dd, J=8.50, 1.65 Hz), 7.98 (1H, s), 8.00 (1H, d, J=8.49 Hz); ESIMS found for $C_{25}H_{28}F_3N_90$ m/z 528.3 (M+1).

758

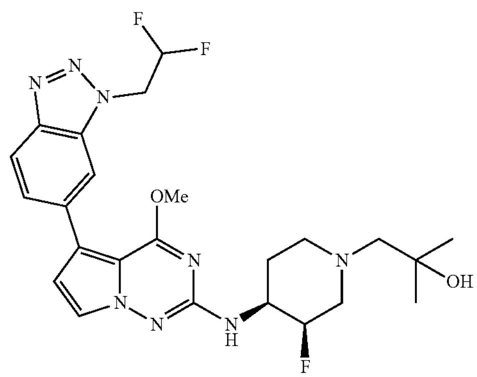

1-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)-2-methylpropan-2-ol 758

Fluffy white solid (2 mg, 0.004 mmol, 26.6% yield). $^1$H NMR (499 MHz, DMSO-$d_6$) δ ppm 1.09 (6H, s), 1.60-1.69 (1H, m), 1.95 (1H, qd, J=12.46, 3.70 Hz), 2.26-2.32 (1H, m), 2.33-2.46 (1H, m), 2.98 (1H, br d, J=10.13 Hz), 3.25-3.29 (1H, m), 3.33 (2H, s), 3.70-3.85 (1H, m), 3.95 (3H, s), 4.08 (1H, br s), 4.86 (1H, d, J=49.65 Hz), 5.30 (2H, td, J=16.02, 2.74 Hz), 6.60 (1H, tt, J=54.30, 3.00 Hz), 6.61 (1H, d, J=7.94 Hz), 6.74 (1H, d, J=2.46 Hz), 7.63-7.66 (1H, m), 7.65 (1H, d, J=2.46 Hz), 8.01-8.05 (2H, m); ESIMS found for $C_{24}H_{29}F_3N_8O_2$ m/z 519.2 (M+1).

761

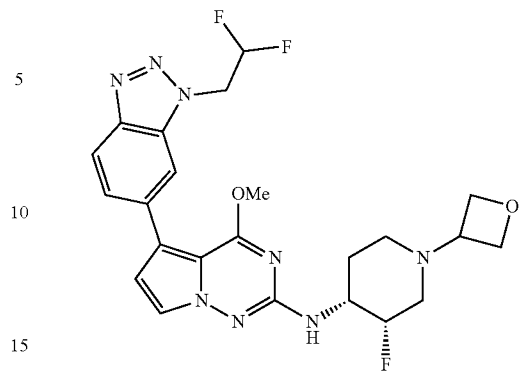

5-(1-(2,2-Difluoroethyl)-1H-benzo[d][1,2,3]triazol-6-yl)-N-((3S,4R)-3-fluoro-1-(oxetan-3-yl)piperidin-4-yl)-4-methoxypyrrolo[2,1-f][1,2,4]triazin-2-amine 761

Fluffy white solid (11 mg, 0.022 mmol, 32.5% yield). $^1$H NMR (499 MHz, DMSO-$d_6$) δ ppm 1.68-1.78 (1H, m), 1.92 (1H, qd, J=12.18, 3.42 Hz), 1.99-2.06 (1H, m), 2.16 (1H, dd, J=37.05, 12.59 Hz), 2.76 (1H, br d, J=9.31 Hz), 2.94-3.05 (1H, m), 3.50 (1H, quin, J=6.30 Hz), 3.74-3.91 (1H, m), 3.96 (3H, s), 4.40 (1H, t, J=6.16 Hz), 4.46 (1H, t, J=6.16 Hz), 4.54 (2H, td, J=6.57, 3.01 Hz), 4.94 (1H, d, J=49.65 Hz), 5.30 (2H, td, J=15.88, 2.74 Hz), 6.60 (1H, tt, J=54.30, 3.00 Hz), 6.70 (1H, d, J=7.94 Hz), 6.75 (1H, d, J=2.74 Hz), 7.64 (1H, dd, J=8.76, 1.64 Hz), 7.64 (1H, d, J=2.74 Hz), 8.01-8.05 (2H, m); ESIMS found for $C_{23}H_{25}F_3N_8O_2$ m/z 503.2 (M+1).

762

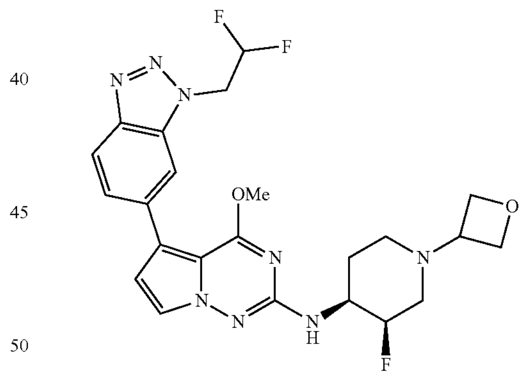

5-(1-(2,2-Difluoroethyl)-1H-benzo[d][1,2,3]triazol-6-yl)-N-((3R,4S)-3-fluoro-1-(oxetan-3-yl)piperidin-4-yl)-4-methoxypyrrolo[2,1-f][1,2,4]triazin-2-amine 762

Fluffy white solid (12 mg, 0.024 mmol, 18.7% yield). $^1$H NMR (499 MHz, DMSO-$d_6$) δ ppm 1.68-1.78 (1H, m), 1.92 (1H, qd, J=12.09, 3.42 Hz), 1.99-2.06 (1H, m), 2.16 (1H, dd, J=37.05, 12.59 Hz), 2.76 (1H, br d, J=9.86 Hz), 2.94-3.04 (1H, m), 3.50 (1H, quin, J=6.43 Hz), 3.75-3.91 (1H, m), 3.96 (3H, s), 4.40 (1H, t, J=6.16 Hz), 4.46 (1H, t, J=6.16 Hz), 4.54 (2H, td, J=6.57, 3.01 Hz), 4.94 (1H, d, J=49.90 Hz), 5.30 (2H, td, J=15.95, 2.87 Hz), 6.61 (1H, tt, J=54.30, 3.00 Hz), 6.70 (1H, d, J=7.94 Hz), 6.75 (1H, d, J=2.74 Hz), 7.64 (1H, dd, J=8.50, 1.35 Hz), 7.64 (1H, d, J=2.74 Hz), 8.01-8.05 (2H, m); ESIMS found for $C_{23}H_{25}F_3N_8O_2$ m/z 503.2 (M+1).

764

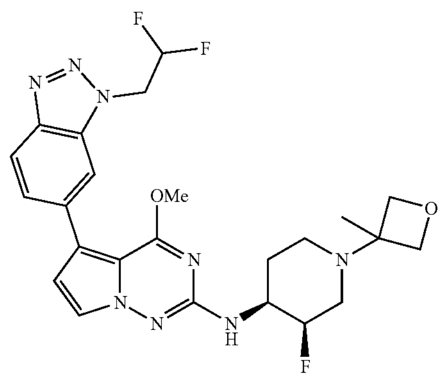

5-(1-(2,2-difluoroethyl)-1H-benzo[d][1,2,3]triazol-6-yl)-N-((3R,4S)-3-fluoro-1-(3-methyloxetan-3-yl)piperidin-4-yl)-4-methoxypyrrolo[2,1-f][1,2,4]triazin-2-amine 764

Fluffy white solid (1 mg, 0.002 mmol, 5.3% yield). $^1$H NMR (499 MHz, DMSO-$d_6$) δ ppm 1.29 (3H, s), 1.69-1.78 (1H, m), 1.91 (1H, qd, J=11.96, 3.83 Hz), 2.20 (1H, br t, J=10.81 Hz), 2.35 (1H, dd, J=35.35, 11.77 Hz), 2.54-2.59 (1H, m), 2.75-2.84 (1H, m), 3.74-3.90 (1H, m), 3.96 (3H, s), 4.13 (2H, dd, J=7.26, 5.61 Hz), 4.34 (1H, d, J=5.48 Hz), 4.42 (1H, d, J=5.75 Hz), 4.93 (1H, d, J=49.90 Hz), 5.30 (2H, td, J=15.95, 2.87 Hz), 6.61 (1H, tt, J=54.30, 3.00 Hz), 6.70 (1H, d, J=7.94 Hz), 6.75 (1H, d, J=2.74 Hz), 7.64 (1H, dd, J=8.80, 1.35 Hz), 7.64 (1H, d, J=2.74 Hz), 8.01-8.05 (2H, m); ESIMS found for $C_{24}H_{27}F_3N_8O_2$ m/z 517.25 (M+1).

769

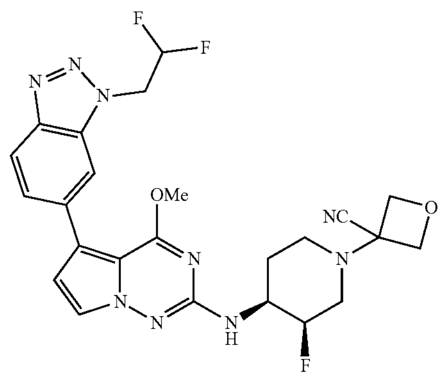

3-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)oxetane-3-carbonitrile 769

Fluffy white solid (14 mg, 0.027 mmol, 20.8% yield). $^1$H NMR (499 MHz, DMSO-$d_6$) δ ppm 1.82 (1H, br dd, J=13.00, 3.15 Hz), 2.00 (1H, qd, J=12.32, 3.83 Hz), 2.10-2.17 (1H, m), 2.26 (1H, dd, J=36.20, 12.05 Hz), 2.77-2.86 (1H, m), 3.00-3.11 (1H, m), 3.79-3.94 (1H, m), 3.97 (3H, s), 4.52 (1H, d, J=7.12 Hz), 4.65 (1H, d, J=7.12 Hz), 4.76 (2H, t, J=6.84 Hz), 5.04 (1H, d, J=49.90 Hz), 5.30 (2H, td, J=15.95, 2.87 Hz), 6.61 (1H, tt, J=54.30, 3.00 Hz), 6.76 (1H, d, J=2.46 Hz), 6.82 (1H, d, J=7.67 Hz), 7.63-7.66 (1H, m), 7.67 (1H, d, J=2.46 Hz), 8.02-8.05 (2H, m); ESIMS found for $C_{24}H_{24}F_3N_9O_2$ m/z 528.2 (M+1).

770

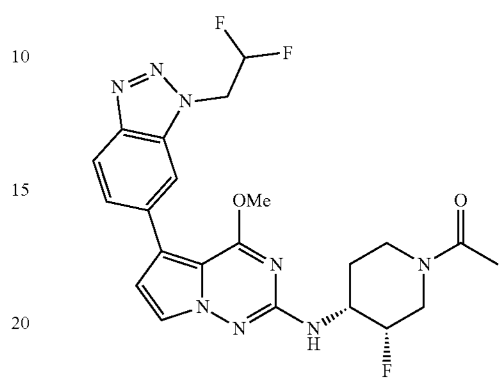

1-((3S,4R)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-one 770

Fluffy white solid (8 mg, 0.016 mmol, 32.9% yield). $^1$H NMR (499 MHz, DMSO-$d_6$) δ ppm 1.65-1.74 (1H, m), 1.75-1.92 (1H, m), 1.98-2.06 (3H, m), 2.67-2.98 (1H, m), 3.17-3.26 (1H, m), 3.87-4.04 (1H, m), 3.96 (3H, s), 4.04-4.17 (1H, m), 4.42-4.74 (1H, m), 4.99 (1H, d, J=48.80 Hz), 5.30 (2H, td, J=15.95, 2.87 Hz), 6.61 (2H, tt, J=54.30, 3.00 Hz), 6.76 (1H, d, J=2.74 Hz), 6.80 (1H, dd, J=7.80, 2.60 Hz), 7.63-7.66 (1H, m), 7.65 (1H, d, J=2.46 Hz), 8.02-8.05 (2H, m); ESIMS found for $C_{22}H_{23}F_3N_8O_2$ m/z 489.2 (M+1).

771

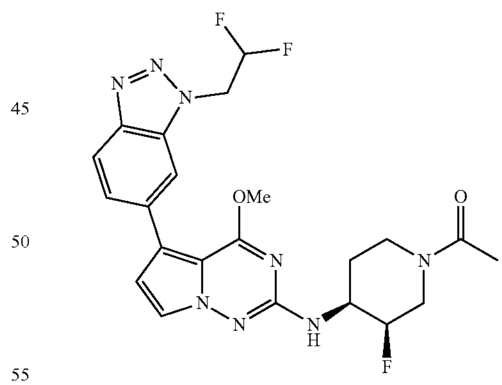

1-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-one 771

Fluffy white solid (7 mg, 0.014 mmol, 53.3% yield). $^1$H NMR (499 MHz, DMSO-$d_6$) δ ppm 1.64-1.90 (2H, m), 1.97-2.08 (3H, m), 2.66-3.28 (1H, m), 2.82-3.50 (1H, m), 3.86-4.02 (1H, m), 3.96 (3H, s), 4.02-4.17 (1H, m), 4.41-4.75 (1H, m), 5.00 (1H, d, J=49.90 Hz), 5.30 (2H, td, J=15.88, 2.74 Hz), 6.61 (1H, tt, J=54.30, 3.00 Hz), 6.76 (1H, d, J=2.74 Hz), 6.81 (1H, dd, J=7.80, 3.42 Hz), 7.63-7.66 (1H, m), 7.65 (1H, d, J=2.74 Hz), 8.02-8.05 (2H, m); ESIMS found for $C_{22}H_{23}F_3N_8O_2$ m/z 489.2 (M+1).

772

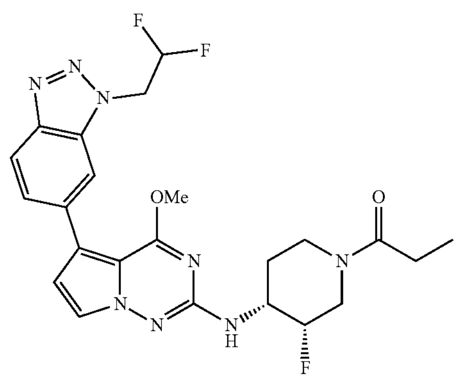

1-((3S,4R)-4-((5-(1-(2,2-Difluoroethyl)-1H-benzo[d][1,2,3]triazol-6-yl)-4-methoxypyrrolo[2,14][1,2,4]triazin-2-yl)amino)-3-fluoropiperidin-1-yl)propan-1-one 772

Fluffy white solid (7 mg, 0.014 mmol, 27.5% yield). $^1$H NMR (499 MHz, DMSO-$d_6$) δ ppm 1.00 (3H, t, J=7.39 Hz), 1.66-1.89 (2H, m), 2.26-2.41 (2H, m), 2.67-2.98 (1H, m), 3.14-3.23 (1H, m), 3.90-4.05 (1H, m), 3.96 (3H, s), 4.05-4.22 (1H, m), 4.43-4.79 (1H, m), 4.99 (1H, d, J=49.65 Hz), 5.30 (2H, td, J=15.88, 2.74 Hz), 6.61 (2H, tt, J=54.30, 3.00 Hz), 6.76 (1H, d, J=2.46 Hz), 6.79 (1H, d, J=7.67 Hz), 7.64 (1H, dd, J=6.30, 1.35 Hz), 7.65 (1H, s), 8.01-8.06 (2H, m); ESIMS found for $C_{23}H_{25}F_3N_8O_2$ m/z 503.2 (M+1).

773

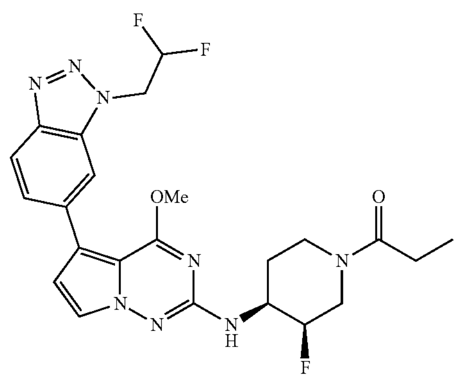

1-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidin-1-yl)propan-1-one 773

Fluffy white solid (9.1 mg, 0.018 mmol, 46.0% yield). $^1$H NMR (499 MHz, DMSO-$d_6$) δ ppm 1.00 (3H, t, J=7.39 Hz), 1.66-1.90 (2H, m), 2.24-2.42 (2H, m), 2.69-3.00 (1H, m), 3.12-3.24 (1H, m), 3.91-4.00 (1H, m), 3.96 (3H, s), 4.04-4.22 (1H, m), 4.43-4.78 (1H, m), 4.99 (1H, d, J=49.35 Hz), 5.30 (2H, td, J=15.88, 2.74 Hz), 6.61 (1H, tt, J=54.30, 3.00 Hz), 6.76 (1H, d, J=2.74 Hz), 6.79 (1H, d, J=7.94 Hz), 7.63-7.66 (2H, m), 8.02-8.05 (2H, m); ESIMS found for $C_{23}H_{25}F_3N_8O_2$ m/z 503.2 (M+1).

776

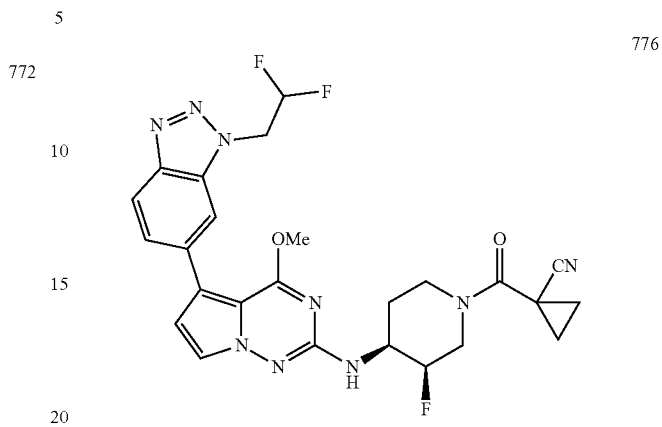

1-((3R,4S)-4-((5-(1-(2,2-Difluoroethyl)-1H-benzo[d][1,2,3]triazol-6-yl)-4-methoxypyrrolo[2,1-f][1,2,4]triazin-2-yl)amino)-3-fluoropiperidine-1-carbonyl)cyclopropane-1-carbonitrile 776

Beige solid (4 mg, 0.007 mmol, 23.6% yield). $^1$H NMR (499 MHz, DMSO-$d_6$) δ ppm 1.23 (2H, s), 1.35-1.52 (1H, m), 1.52-1.65 (2H, m), 1.63-1.75 (1H, m), 1.75-1.94 (1H, in), 1.94-2.12 (1H, m), 3.96 (3H, s), 4.05-4.17 (1H, m), 4.26-4.38 (1H, m), 4.51-4.62 (1H, m), 5.09 (1H, d, J=48.55 Hz), 5.30 (2H, td, J=15.81, 2.87 Hz), 6.61 (1H, tt, J=54.30, 3.00 Hz), 6.76 (1H, d, J=2.74 Hz), 6.88 (1H, br s), 7.63-7.67 (2H, m), 8.02-8.06 (2H, m); ESIMS found for $C_{25}H_{24}F_3N_9O_2$ m/z 540.2 (M+1).

777

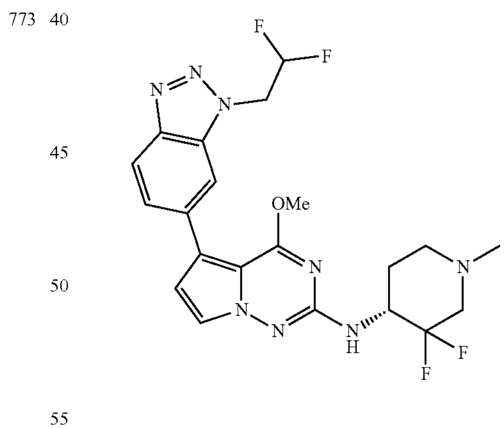

(R)—N-(3,3-Difluoro-1-methylpiperidin-4-yl)-5-(1-(2,2-difluoroethyl)-1H-benzo[d][1,2,3]triazol-6-yl)-4-methoxypyrrolo[2,1-f][1,2,4]triazin-2-amine 777

Off-white solid (7 mg, 0.015 mmol, 31.3% yield). $^1$H NMR (499 MHz, DMSO-$d_6$) δ ppm 1.75-1.89 (2H, m), 2.18 (1H, td, J=11.16, 2.87 Hz), 2.26 (3H, s), 2.38 (1H, ddd, J=27.15, 11.50, 1.40 Hz), 2.79 (1H, br d, J=11.77 Hz), 2.99-3.12 (1H, m), 3.97 (3H, s), 4.17-4.32 (1H, m), 5.30 (2H, td, J=15.95, 2.87 Hz), 6.61 (1H, tt, J=54.30, 3.00 Hz), 6.76 (1H, d, J=2.46 Hz), 6.84 (1H, d, J=9.31 Hz), 7.63-7.66

(1H, m), 7.66 (1H, d, J=2.46 Hz), 8.03 (1H, s), 8.04 (1H, d, J=6.57 Hz); ESIMS found for $C_{21}H_{22}F_4N_8O$ m/z 479.2 (M+1).

780

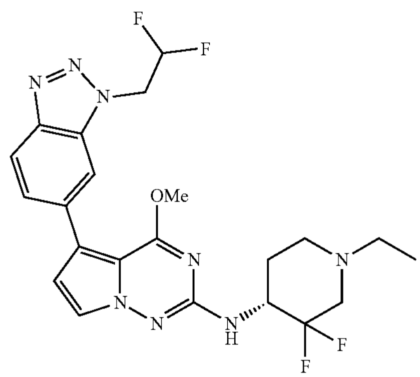

(R)-5-(1-(2,2-Difluoroethyl)-1H-benzo[d][1,2,3]triazol-6-yl)-N-(1-ethyl-3,3-difluoropiperidin-4-yl)-4-methoxypyrrolo[2,1-f][1,2,4]triazin-2-amine 780

Off-white solid (8 mg, 0.016 mmol, 36.1% yield). $^1H$ NMR (499 MHz, DMSO-$d_6$) δ ppm 1.01 (3H, t, J=7.26 Hz), 1.73-1.83 (1H, m), 1.84-1.90 (1H, m), 2.12-2.24 (1H, m), 2.34-2.43 (1H, m), 2.45 (2H, q, J=7.12 Hz), 2.88 (1H, br d, J=12.05 Hz), 3.05-3.17 (1H, m), 3.97 (3H, s), 4.19-4.35 (1H, m), 5.30 (2H, td, J=15.88, 2.74 Hz), 6.61 (1H, tt, J=54.30, 3.00 Hz), 6.76 (1H, d, J=2.74 Hz), 6.85 (1H, d, J=9.58 Hz), 7.63-7.66 (1H, m), 7.66 (1H, d, J=2.74 Hz), 8.03 (1H, s), 8.04 (1H, d, J=6.55 Hz); ESIMS found for $C_{22}H_{24}F_4N_8O$ m/z 493.25 (M+1).

785

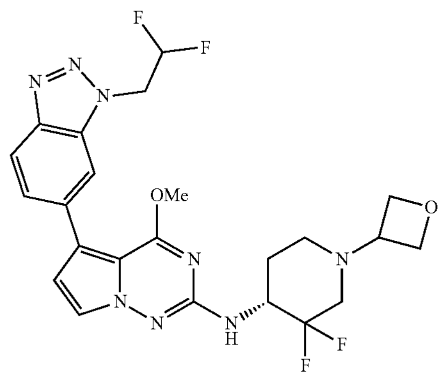

(R)—N-(3,3-Difluoro-1-(oxetan-3-yl)piperidin-4-yl)-5-(1-(2,2-difluoroethyl)-1H-benzo[d][1,2,3]triazol-6-yl)-4-methoxypyrrolo[2,1-f][1,2,4]triazin-2-amine 785

Off-white solid (8 mg, 0.015 mmol, 22.2% yield). $^1H$ NMR (499 MHz, DMSO-$d_6$) δ ppm 1.77-1.86 (1H, m), 1.86-1.93 (1H, m), 2.12-2.22 (1H, m), 2.41 (1H, ddd, J=26.60, 11.50, 1.65 Hz), 2.76 (1H, br d, J=11.50 Hz), 2.95-3.08 (1H, m), 3.60 (1H, quin, J=6.30 Hz), 3.97 (3H, s), 4.24-4.37 (1H, m), 4.44 (2H, dt, J=15.06, 6.16 Hz), 4.55 (2H, td, J=6.57, 3.56 Hz), 5.30 (2H, td, J=15.88, 2.74 Hz), 6.61 (1H, tt, J=54.30, 3.00 Hz), 6.76 (1H, d, J=2.46 Hz), 6.91 (1H, d, J=9.31 Hz), 7.63-7.66 (1H, m), 7.66 (1H, d, J=2.46 Hz), 8.03 (1H, s), 8.04 (1H, d, J=6.30 Hz); ESIMS found for $C_{23}H_{24}F_4N_8O_2$ m/z 521.2 (M+1).

788

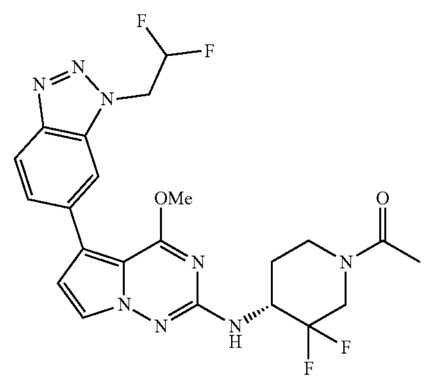

(R)-1-(4-((5-(1-(2,2-Difluoroethyl)-1H-benzo[d][1,2,3]triazol-6-yl)-4-methoxypyrrolo[2,1-f][1,2,4]triazin-2-yl)amino)-3,3-difluoropiperidin-1-yl)ethan-1-one 788

Fluffy white solid (20 mg, 0.040 mmol, 79.7% yield). $^1H$ NMR (499 MHz, DMSO-$d_6$) δ ppm 1.58-1.84 (1H, m), 1.85-2.00 (1H, m), 2.02-2.10 (3H, m), 3.32 (1H, s), 3.39-3.78 (1H, m), 3.84-4.30 (1H, m), 3.98 (3H, s), 4.10-4.61 (2H, m), 5.30 (2H, td, J=15.81, 2.87 Hz), 6.61 (1H, tt, J=54.30, 3.00 Hz), 6.77 (1H, d, J=2.74 Hz), 7.01 (1H, d, J=9.31 Hz), 7.63-7.67 (2H, m), 8.02-8.06 (2H, m); ESIMS found for $C_{22}H_{22}F_4N_8O_2$ m/z 507.2 (M+1).

791

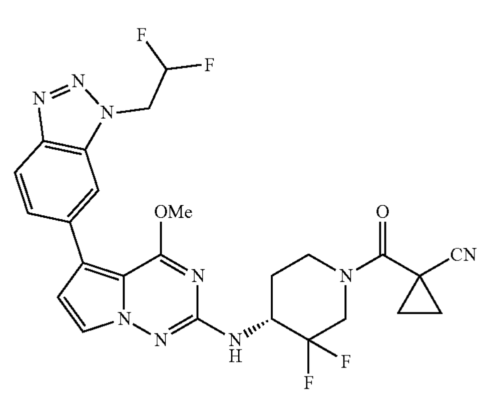

(R)-1-(4-((5-(1-(2,2-Difluoroethyl)-1H-benzo[d][1,2,3]triazol-6-yl)-4-methoxypyrrolo[2,1-f][1,2,4]triazin-2-yl)amino)-3,3-difluoropiperidine-1-carbonyl)cyclopropane-1-carbonitrile 791

Off-white solid (3 mg, 0.005 mmol, 13.5% yield). $^1H$ NMR (499 MHz, DMSO-$d_6$) δ ppm 1.36-1.52 (2H, m), 1.61-1.81 (3H, m), 1.86-2.08 (2H, m), 3.04-3.11 (1H, m), 3.98 (3H, s), 4.18-4.31 (1H, m), 4.38-4.49 (1H, m), 4.56-4.70 (1H, m), 5.30 (2H, td, J=15.74, 2.74 Hz), 6.61 (1H, tt, J=54.30, 3.00 Hz), 6.78 (1H, d, J=2.46 Hz), 7.08 (1H, br d, J=9.31 Hz), 7.64-7.66 (1H, m), 7.67 (1H, d, J=2.74 Hz), 8.03 (1H, s), 8.04-8.06 (1H, m); ESIMS found for $C_{25}H_{23}F_4N_9O_2$ m/z 558.2 (M+1).

793

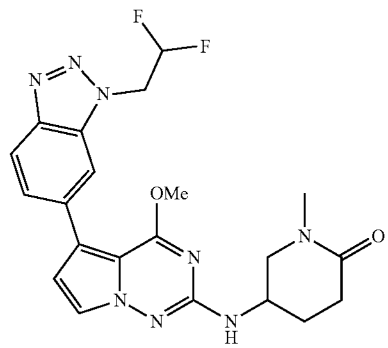

5-((5-(1-(2,2-Difluoroethyl)-1H-benzo[d][1,2,3]triazol-6-yl)-4-methoxypyrrolo[2,1-f][1,2,4]triazin-2-yl)amino)-1-methylpiperidin-2-one 793

White solid (11 mg, 0.024 mmol, 22.0% yield). $^1$H NMR (499 MHz, DMSO-d$_6$) δ ppm 1.87-1.96 (1H, m), 1.97-2.04 (1H, m), 2.27-2.35 (1H, m), 2.36-2.44 (1H, m), 2.81 (3H, s), 3.26 (1H, dd, J=11.77, 7.67 Hz), 3.57 (1H, dd, J=11.91, 4.52 Hz), 3.96 (3H, s), 4.05-4.15 (1H, m), 5.30 (2H, td, J=15.95, 2.60 Hz), 6.61 (1H, tt, J=54.30, 3.00 Hz), 6.76 (1H, d, J=2.46 Hz), 6.94 (1H, d, J=7.12 Hz), 7.63-7.66 (1H, m), 7.68 (1H, d, J=2.74 Hz), 8.02-8.05 (2H, m); ESIMS found for $C_{21}H_{22}F_2N_8O_2$ m/z 457.2 (M+1).

798

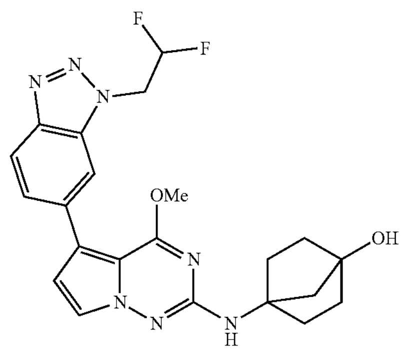

4-((5-(1-(2,2-Difluoroethyl)-1H-benzo[d][1,2,3]triazol-6-yl)-4-methoxypyrrolo[2,1-f][1,2,4]triazin-2-yl)amino)bicyclo[2.2.1]heptan-1-ol 798

Fluffy white solid (2.4 mg, 0.005 mmol, 3.8% yield). $^1$H NMR (499 MHz, DMSO-d$_6$) δ ppm 1.52-1.63 (2H, m), 1.65-1.77 (2H, m), 1.86 (2H, s), 1.87-1.93 (2H, m), 1.99-2.09 (2H, m), 3.93 (3H, s), 4.88 (1H, s), 5.30 (2H, td, J=16.02, 3.01 Hz), 6.60 (1H, tt, J=54.30, 3.00 Hz), 6.73 (1H, d, J=2.74 Hz), 6.75 (1H, s), 7.61 (1H, d, J=2.46 Hz), 7.64 (1H, dd, J=8.62, 1.51 Hz), 8.01-8.04 (2H, m); ESIMS found for $C_{22}H_{23}F_2N_7O_2$ m/z 456.2 (M+1).

799

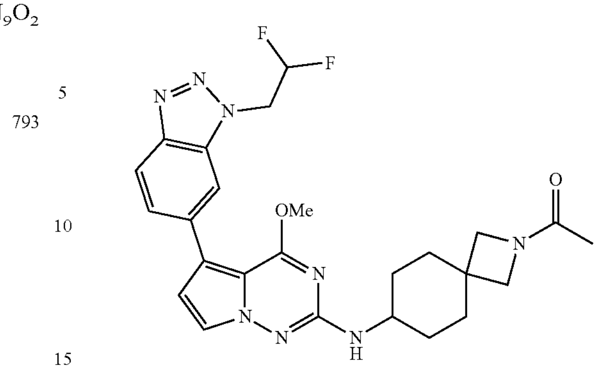

1-(7-((5-(1-(2,2-Difluoroethyl)-1H-benzo[d][1,2,3]triazol-6-yl)-4-methoxypyrrolo[2,1-f][1,2,4]triazin-2-yl)amino)-2-azaspiro[3.5]nonan-2-yl)ethan-1-one 799

White solid (8 mg, 0.016 mmol, 8.4% yield). $^1$H NMR (499 MHz, DMSO-d$_6$) δ ppm 1.27-1.41 (2H, m), 1.50-1.61 (2H, m), 1.73-1.78 (3H, m), 1.82-1.94 (4H, m), 3.45-3.54 (2H, m), 3.55-3.64 (1H, m), 3.72-3.82 (2H, m), 3.93 (3H, d, J=1.10 Hz), 5.30 (2H, td, J=15.74, 2.46 Hz), 6.60 (1H, tt, J=54.30, 3.00 Hz), 6.53 (1H, dd, J=16.43, 7.94 Hz), 6.72 (1H, d, J=2.46 Hz), 7.62-7.65 (2H, m), 8.00-8.05 (2H, m); ESIMS found for $C_{25}H_{28}F_2N_8O_2$ m/z 511.2

801

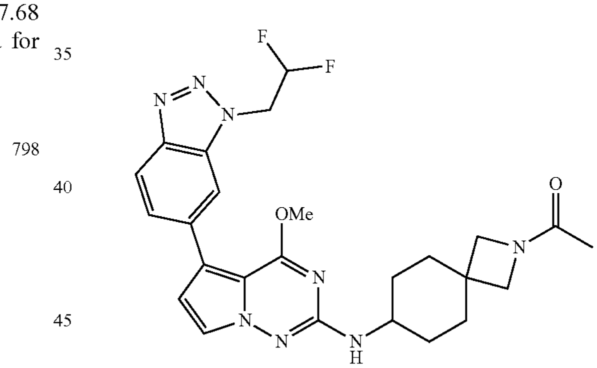

5-(1-(2,2-Difluoroethyl)-1H-benzo[d][1,2,3]triazol-6-yl)-4-methoxy-N-(2-oxaspiro[3.5]nonan-7-yl)pyrrolo[2,1-f][1,2,4]triazin-2-amine 801

Colorless semi-solid (2 mg, 0.004 mmol, 4.6% yield). $^1$H NMR (499 MHz, DMSO-d$_6$) δ ppm 1.41-1.49 (1H, m), 1.53 (2H, td, J=12.94, 3.42 Hz), 1.83-1.92 (2H, m), 1.96-2.03 (1H, m), 2.07 (2H, br d, J=12.87 Hz), 3.49-3.61 (1H, m), 3.93 (3H, s), 4.24 (2H, s), 4.32 (2H, s), 5.30 (2H, td, J=15.88, 3.01 Hz), 6.60 (1H, tt, J=54.30, 3.00 Hz), 6.51 (1H, d, J=8.21 Hz), 6.72 (1H, d, J=2.74 Hz), 7.63 (1H, dd, J=8.80, 1.35 Hz), 7.64 (1H, d, J=2.74 Hz), 8.02 (1H, d, J=9.86 Hz), 8.02 (1H, s); ESIMS found for $C_{23}H_{25}F_2N_7O_2$ m/z 470.2 (M+1).

805

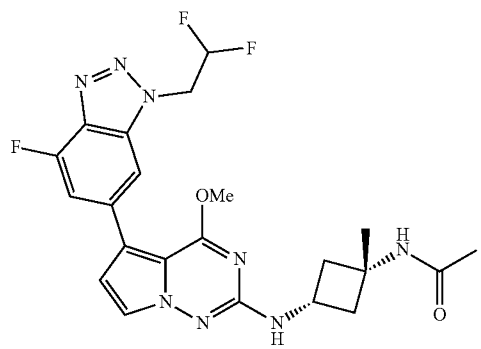

N-((1s,3s)-3-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-1-methylcyclobutyl)acetamide 805

White solid (16 mg, 0.033 mmol, 26.5% yield). $^1$H NMR (499 MHz, DMSO-$d_6$) δ ppm 1.38 (3H, s), 1.76 (3H, s), 2.12-2.21 (2H, m), 2.42 (2H, ddd, J=9.65, 7.32, 2.46 Hz), 3.96 (3H, s), 4.03 (1H, sxt, J=7.72 Hz), 5.34 (2H, td, J=15.88, 2.74 Hz), 6.62 (1H, tt, J=54.30, 3.00 Hz), 6.78 (1H, d, J=2.46 Hz), 7.05 (1H, d, J=6.84 Hz), 7.50 (1H, dd, J=12.18, 0.96 Hz), 7.66 (1H, d, J=2.46 Hz), 7.90 (1H, s), 8.02 (1H, s); ESIMS found for $C_{22}H_{23}F_3N_8O_2$ m/z 489.2 (M+1).

806

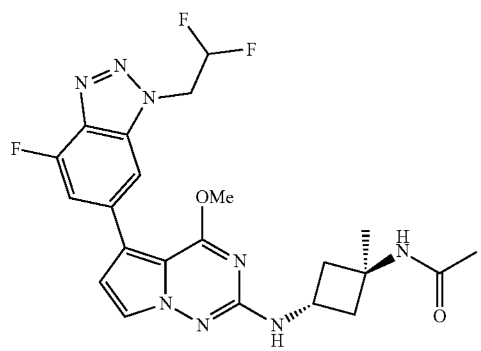

N-((1r,3r)-3-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-1-methylcyclobutyl)acetamide 806

White solid (5 mg, 0.010 mmol, 13.1% yield). $^1$H NMR (499 MHz, DMSO-$d_6$) δ ppm 1.36 (3H, s), 1.81 (3H, s), 1.91-2.00 (2H, m), 2.59-2.68 (2H, m), 3.95 (3H, s), 4.19 (1H, sxt, J=7.78 Hz), 5.34 (2H, td, J=15.88, 2.74 Hz), 6.62 (1H, tt, J=54.30, 3.00 Hz), 6.78 (1H, d, J=2.74 Hz), 7.05 (1H, d, J=7.39 Hz), 7.50 (1H, dd, J=12.18, 0.96 Hz), 7.64 (1H, d, J=2.46 Hz), 7.89 (1H, s), 7.93 (1H, s); ESIMS found for $C_{22}H_{23}F_3N_8O_2$ m/z 489.2 (M+1).

810

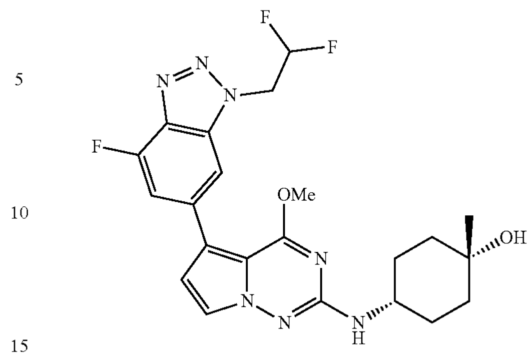

(1s,4s)-4-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-1-methylcyclohexan-1-ol 810

White solid (15 mg, 0.032 mmol, 32.7% yield). $^1$H NMR (499 MHz, DMSO-$d_6$) δ ppm 1.12 (3H, s), 1.37 (2H, td, J=13.00, 4.38 Hz), 1.53-1.62 (2H, m), 1.63-1.74 (4H, m), 3.47-3.57 (1H, m), 3.96 (3H, s), 4.00 (1H, s), 5.34 (2H, td, J=15.88, 2.74 Hz), 6.62 (1H, tt, J=54.30, 3.00 Hz), 6.56 (1H, d, J=8.21 Hz), 6.76 (1H, d, J=2.46 Hz), 7.50 (1H, dd, J=12.05, 1.10 Hz), 7.63 (1H, d, J=2.46 Hz), 7.90 (1H, s); ESIMS found for $C_{22}H_{24}F_3N_7O_2$ m/z 476.2 (M+1).

811

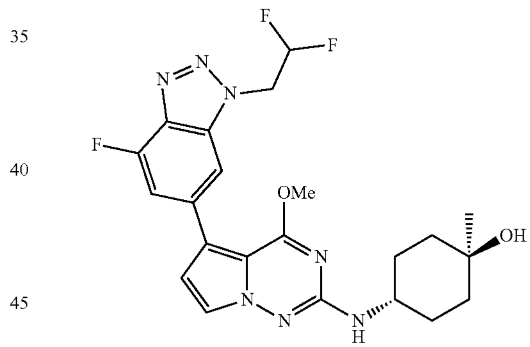

(1r,4r)-4-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-1-methylcyclohexan-1-ol 811

Fluffy white solid (14 mg, 0.029 mmol, 61.0% yield). $^1$H NMR (499 MHz, DMSO-$d_6$) δ ppm 1.15 (3H, s), 1.38-1.52 (4H, m), 1.56-1.64 (2H, m), 1.83-1.92 (2H, m), 3.64 (1H, br dd, J=8.62, 3.97 Hz), 3.96 (3H, s), 4.23 (1H, s), 5.34 (2H, td, J=15.95, 2.60 Hz), 6.62 (1H, tt, J=54.30, 3.00 Hz), 6.54 (1H, d, J=7.94 Hz), 6.77 (1H, d, J=2.46 Hz), 7.50 (1H, dd, J=12.05, 0.82 Hz), 7.66 (1H, d, J=2.74 Hz), 7.90 (1H, s); ESIMS found for $C_{22}H_{24}F_3N_7O_2$ m/z 476.2 (M+1).

812

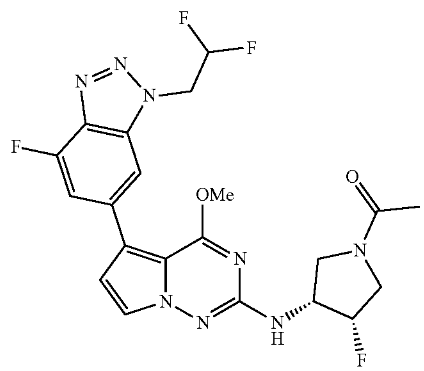

1-((3R,4S)-3-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-4-fluoropyrrolidin-1-yl)ethan-1-one 812

White solid (30 mg, 0.061 mmol, 33.3% yield). $^1$H NMR (499 MHz, DMSO-d$_6$) δ ppm 1.93-2.01 (3H, m), 3.47-3.64 (1H, m), 3.65-3.77 (1H, m), 3.78-3.85 (1H, m), 3.86-3.97 (1H, m), 3.98-4.01 (3H, m), 4.36-4.56 (1H, m), 5.25-5.48 (1H, m), 5.35 (2H, td, J=16.02, 3.01 Hz), 6.62 (1H, tt, J=54.30, 3.00 Hz), 6.84 (1H, t, J=2.46 Hz), 7.14 (1H, dd, J=7.26, 4.24 Hz), 7.52 (1H, dd, J=12.18, 0.96 Hz), 7.69 (1H, dd, J=3.83, 2.74 Hz), 7.92 (1H, s); ESIMS found for $C_{21}H_2O F_4N_8O_2$ m/z 493.2 (M+1).

816

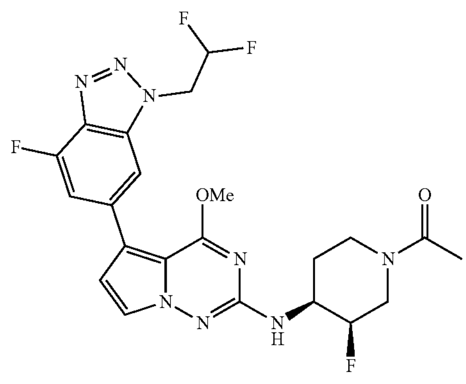

1-((3R,4S)-4-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-3-fluoropiperidin-1-yl)ethan-1-one 816

Fluffy white solid (10 mg, 0.020 mmol, 39.7% yield). $^1$H NMR (499 MHz, DMSO-d$_6$) δ ppm 1.66-1.73 (1H, m), 1.74-1.93 (1H, m), 1.98-2.06 (3H, m), 2.67-2.98 (1H, m), 3.17-3.26 (1H, m), 3.87-4.04 (1H, m), 3.98 (3H, s), 4.04-4.17 (1H, m), 4.41-4.76 (1H, m), 4.99 (1H, d, J=49.65 Hz), 5.34 (2H, td, J=15.88, 2.74 Hz), 6.62 (1H, tt, J=54.30, 3.00 Hz), 6.81 (1H, d, J=2.46 Hz), 6.85 (1H, dd, J=7.67, 3.29 Hz), 7.51 (1H, dd, J=12.05, 1.10 Hz), 7.66 (1H, d, J=2.74 Hz), 7.91 (1H, s); ESIMS found for $C_{22}H_{22}F_4N_8O_2$ m/z 507.2 (M+1).

818

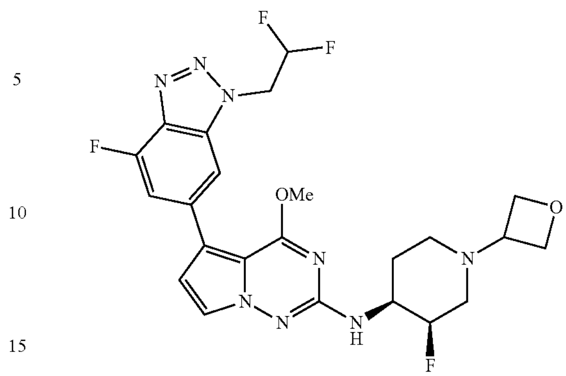

5-(1-(2,2-Difluoroethyl)-4-fluoro-1H-benzo[d][1,2,3]triazol-6-yl)-N-((3R,4S)-3-fluoro-1-(oxetan-3-yl)piperidin-4-yl)-4-methoxypyrrolo[2,1-f][1,2,4]triazin-2-amine 818

Fluffy white solid (4 mg, 0.008 mmol, 23.8% yield). $^1$H NMR (499 MHz, DMSO-d$_6$) δ ppm 1.68-1.77 (1H, m), 1.92 (1H, qd, J=12.00, 3.42 Hz), 1.98-2.06 (1H, m), 2.16 (1H, dd, J=37.30, 12.05 Hz), 2.76 (1H, br d, J=10.13 Hz), 2.94-3.03 (1H, m), 3.49 (1H, quin, J=6.23 Hz), 3.74-3.91 (1H, m), 3.98 (3H, s), 4.40 (1H, t, J=6.16 Hz), 4.46 (1H, t, J=6.16 Hz), 4.54 (2H, td, J=6.50, 3.15 Hz), 4.93 (1H, d, J=49.35 Hz), 5.34 (2H, td, J=15.95, 2.87 Hz), 6.62 (1H, tt, J=54.30, 3.00 Hz), 6.76 (1H, d, J=7.94 Hz), 6.80 (1H, d, J=2.74 Hz), 7.51 (1H, dd, J=12.18, 0.96 Hz), 7.65 (1H, d, J=2.46 Hz), 7.91 (1H, s); ESIMS found for $C_{23}H_{24}F_4N_8O_2$ m/z 521.2 (M+1).

821

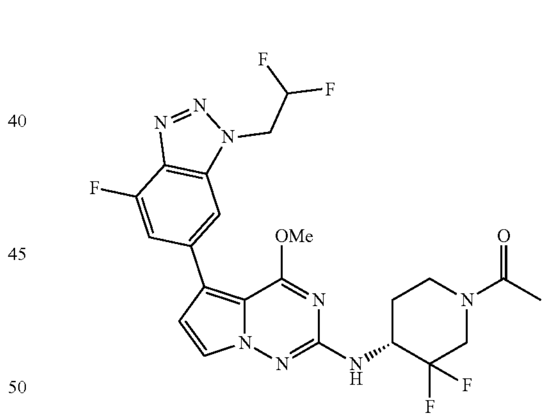

(R)-1-(4-((5-(1-(2,2-Difluoroethyl)-4-fluoro-1H-benzo[d][1,2,3]triazol-6-yl)-4-methoxypyrrolo[2,1-f][1,2,4]triazin-2-yl)amino)-3,3-difluoropiperidin-1-yl)ethan-1-one 821

Fluffy white solid (11 mg, 0.021 mmol, 44.4% yield). $^1$H NMR (499 MHz, DMSO-d$_6$) δ ppm 1.58-1.84 (1H, m), 1.85-1.99 (1H, m), 2.03-2.09 (3H, m), 2.94-3.04 (1H, m), 3.64-3.92 (1H, m), 4.00 (3H, s), 4.09-4.31 (1H, m), 4.46-4.61 (2H, m), 5.34 (2H, td, J=15.88, 2.46 Hz), 6.62 (1H, tt, J=54.30, 3.00 Hz), 6.83 (1H, d, J=2.74 Hz), 7.06 (1H, d, J=9.31 Hz), 7.52 (1H, dd, J=12.18, 0.96 Hz), 7.67 (1H, dd, J=2.46, 1.37 Hz), 7.92 (1H, s); ESIMS found for $C_{22}H_{21}F_5N_8O_2$ m/z 525.2 (M+1).

822

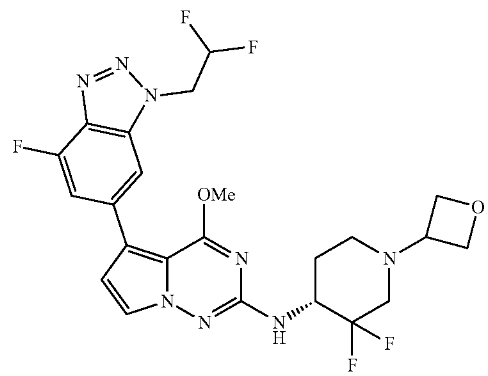

(R)—N-(3,3-Difluoro-1-(oxetan-3-yl)piperidin-4-yl)-5-(1-(2,2-difluoroethyl)-4-fluoro-1H-benzo[d][1,2,3]triazol-6-yl)-4-methoxypyrrolo[2,1-f][1,2,4]triazin-2-amine 822

Fluffy white solid (3 mg, 0.006 mmol, 11.0% yield). $^1$H NMR (499 MHz, DMSO-$d_6$) δ ppm 1.77-1.86 (1H, m), 1.86-1.93 (1H, m), 2.12-2.21 (1H, m), 2.40 (1H, dd, J=26.90, 11.88 Hz), 2.76 (1H, br d, J=11.50 Hz), 2.96-3.07 (1H, m), 3.60 (1H, quin, J=6.23 Hz), 4.00 (3H, s), 4.23-4.37 (1H, m), 4.44 (2H, dt, J=15.19, 6.23 Hz), 4.55 (2H, td, J=6.64, 3.70 Hz), 5.34 (2H, td, J=15.88, 2.74 Hz), 6.62 (2H, tt, J=54.30, 3.00 Hz), 6.82 (1H, d, J=2.74 Hz), 6.96 (1H, d, J=9.31 Hz), 7.52 (1H, dd, J=12.05, 1.10 Hz), 7.67 (1H, d, J=2.46 Hz), 7.91 (1H, s); ESIMS found for $C_{23}H_{23}F_5N_8O_2$ m/z 539.2 (M+1).

856

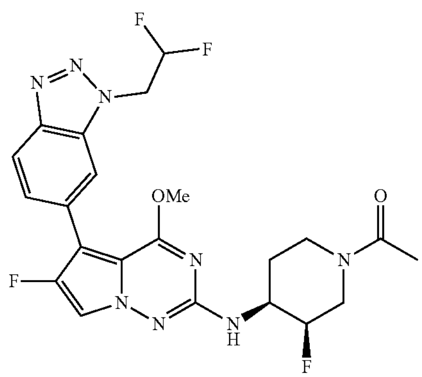

1-((3R,4S)-4-((5-(1-(2,2-Difluoroethyl)-1H-benzo[d][1,2,3]triazol-6-yl)-6-fluoro-4-methoxypyrrolo[2,1-f][1,2,4]triazin-2-yl)amino)-3-fluoropiperidin-1-yl)ethan-1-one 856

White solid (4 mg, 0.008 mmol, 21.6% yield). $^1$H NMR (499 MHz, DMSO-$d_6$) δ ppm 1.67-1.73 (1H, m), 1.74-1.90 (1H, m), 1.98-2.06 (3H, m), 2.66-2.98 (1H, m), 3.13-3.26 (1H, m), 3.87-4.01 (1H, m), 3.91 (3H, s), 4.02-4.16 (1H, m), 4.39-4.76 (1H, m), 4.97 (1H, d, J=49.40 Hz), 5.32 (2H, td, J=16.02, 2.74 Hz), 6.59 (1H, tt, J=54.30, 3.00 Hz), 6.91 (1H, dd, J=7.67, 4.11 Hz), 7.57 (1H, d, J=8.76 Hz), 7.83 (1H, d, J=3.01 Hz), 7.99 (1H, s), 8.09 (1H, d, J=8.76 Hz); ESIMS found for $C_{22}H_{22}F_4N_8O_2$ m/z 507.2 (M+1).

904

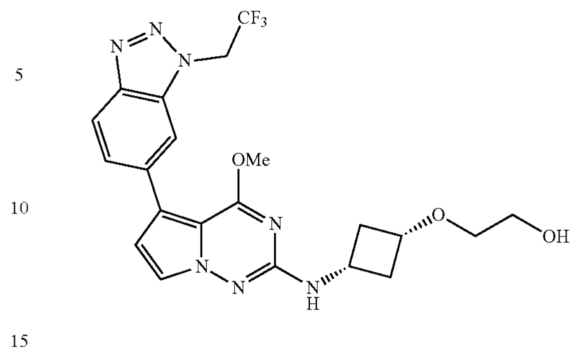

2-(cis-3-((4-Methoxy-5-(1-(2,2,2-trifluoroethyl)-1H-benzo[d][1,2,3]triazol-6-yl)pyrrolo[2,1-f][1,2,4]triazin-2-yl)amino)cyclobutoxy)ethan-1-ol 904

Fluffy white solid (1.8 mg, 0.004 mmol, 9.8% yield). $^1$H NMR (499 MHz, DMSO-$d_6$) δ ppm 1.81-1.95 (2H, m), 2.59-2.71 (2H, m), 3.36-3.43 (2H, m), 3.48 (2H, br s), 3.69-3.75 (1H, m), 3.75-3.81 (1H, m), 3.93 (3H, s), 5.87 (2H, q, J=9.13 Hz), 6.73 (1H, d, J=2.46 Hz), 7.05 (1H, d, J=7.39 Hz), 7.63 (1H, d, J=2.46 Hz), 7.65-7.69 (1H, m), 8.07 (1H, d, J=8.76 Hz), 8.09 (1H, s); ESIMS found for $C_{21}H_{22}F_3N_7O_3$ m/z 478.2 (M+1).

905

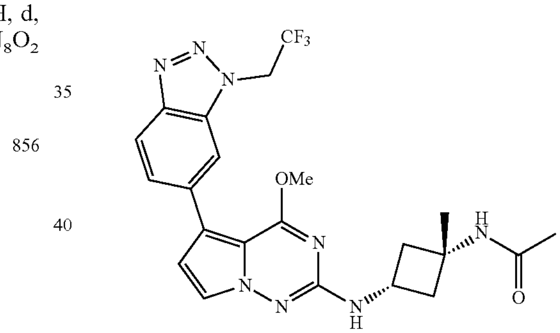

N-((1s,3s)-3-((4-Methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclobutyl)acetamide 905

White solid (18 mg, 0.037 mmol, 29.8% yield). $^1$H NMR (499 MHz, DMSO-$d_6$) δ ppm 1.38 (3H, s), 1.76 (3H, s), 2.12-2.22 (2H, m), 2.42 (2H, ddd, J=9.58, 7.39, 2.46 Hz), 3.93 (3H, s), 4.03 (1H, sxt, J=7.72 Hz), 5.87 (2H, q, J=9.03 Hz), 6.73 (1H, d, J=2.46 Hz), 7.02 (1H, d, J=6.84 Hz), 7.67 (1H, dd, J=8.50, 1.65 Hz), 7.66 (1H, d, J=2.74 Hz), 8.02 (1H, s), 8.07 (1H, d, J=8.76 Hz), 8.09 (1H, s); ESIMS found for $C_{22}H_{23}F_3N_8O_2$ m/z 489.2 (M+1).

909

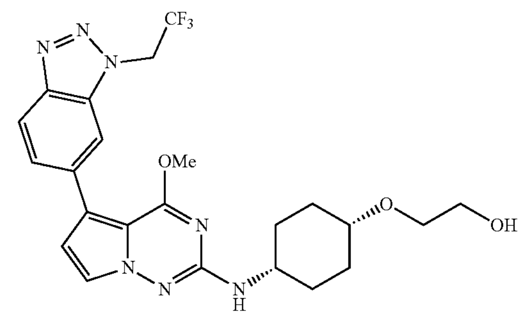

2-((cis-4-((4-Methoxy-5-(1-(2,2,2-trifluoroethyl)-1H-benzo[d][1,2,3]triazol-6-yl)pyrrolo[2,1-f][1,2,4]triazin-2-yl)amino)cyclohexyl)oxy)ethan-1-ol 909

White solid (14.88 mg, 0.029 mmol, % yield). $^1$H NMR (400 MHz, DMSO-$d_6$) δ ppm 1.40-1.57 (2H, m), 1.61-1.76 (4H, m), 1.78-1.90 (2H, m), 3.38-3.43 (2H, m), 3.48-3.54 (2H, m), 3.57-3.71 (2H, m), 3.93 (3H, s), 4.52 (1H, t, J=5.44 Hz), 5.87 (2H, q, J=9.01 Hz), 6.56 (1H, br d, J=7.46 Hz), 6.71 (1H, d, J=2.57 Hz), 7.64 (1H, d, J=2.57 Hz), 7.67 (1H, dd, J=8.68, 1.22 Hz), 8.07 (1H, d, J=8.68 Hz), 8.09 (1H, s); ESIMS found for $C_{23}H_{26}F_3N_7O_3$ m/z 506.2 (M+1).

910

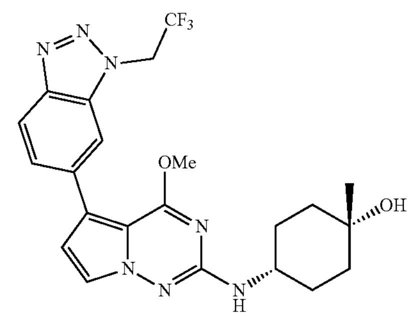

(1s,4s)-4-((4-Methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclohexan-1-ol 910

White solid (15 mg, 0.032 mmol, 32.7% yield). $^1$H NMR (499 MHz, DMSO-$d_6$) δ ppm 1.12 (3H, s), 1.37 (2H, td, J=13.07, 4.24 Hz), 1.58 (2H, br d, J=12.05 Hz), 1.61-1.75 (4H, m), 3.45-3.56 (1H, m), 3.92 (3H, s), 4.00 (1H, s), 5.87 (2H, q, J=8.94 Hz), 6.53 (1H, d, J=7.94 Hz), 6.71 (1H, d, J=2.74 Hz), 7.63 (1H, d, J=2.46 Hz), 7.67 (1H, dd, J=8.76, 1.37 Hz), 8.06 (1H, d, J=8.76 Hz), 8.09 (1H, s); ESIMS found for $C_{22}H_{24}F_3N_7O_2$ m/z 476.2 (M+1).

911

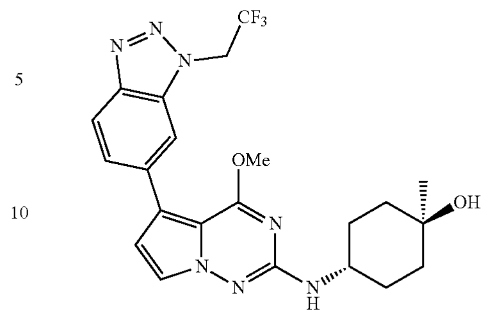

(1r,4r)-4-((4-Methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclohexan-1-ol 911

Fluffy white solid (15 mg, 0.032 mmol, 65.4% yield). $^1$H NMR (499 MHz, DMSO-$d_6$) δ ppm 1.15 (3H, s), 1.38-1.51 (4H, m), 1.56-1.66 (2H, m), 1.83-1.93 (2H, m), 3.65 (1H, dt, J=7.87, 3.87 Hz), 3.93 (3H, s), 4.24 (1H, s), 5.87 (2H, q, J=8.94 Hz), 6.51 (1H, d, J=7.94 Hz), 6.71 (1H, d, J=2.74 Hz), 7.66 (1H, d, J=2.46 Hz), 7.66-7.68 (1H, m), 8.07 (1H, d, J=8.76 Hz), 8.09 (1H, s); ESIMS found for $C_{22}H_{24}F_3N_7O_2$ m/z 476.2 (M+1).

912

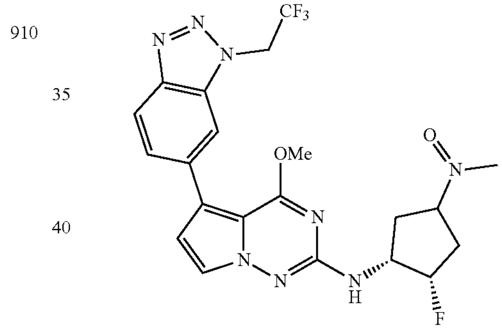

1-((3S,4R)-3-Fluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)pyrrolidin-1-yl)ethan-1-one 912

White solid (18 mg, 0.037 mmol, 20.0% yield). $^1$H NMR (499 MHz, DMSO-$d_6$) δ ppm 1.92-2.02 (3H, m), 3.47-3.56 (1H, m), 3.58-3.75 (1H, m), 3.79-3.86 (1H, m), 3.86-3.95 (1H, m), 3.95-3.98 (3H, m), 4.28-4.60 (1H, m), 5.22-5.51 (1H, m), 5.88 (2H, q, J=8.94 Hz), 6.78 (1H, t, J=2.46 Hz), 7.11 (1H, dd, J=7.12, 5.20 Hz), 7.67-7.70 (2H, m), 8.08 (1H, d, J=8.76 Hz), 8.11 (1H, s); ESIMS found for $C_{21}H_2O F_4N_8O_2$ m/z 493.2 (M+1).

916

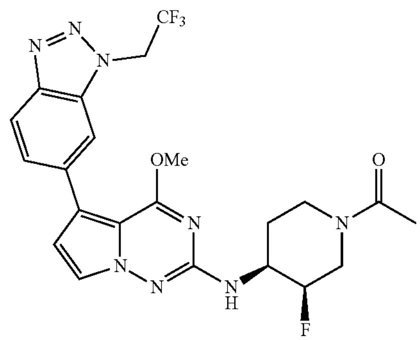

1-((3R,4S)-3-Fluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)piperidin-1-yl)ethan-1-one 916

Fluffy white solid (12 mg, 0.024 mmol, 47.6% yield). $^1$H NMR (499 MHz, DMSO-$d_6$) δ ppm 1.67-1.74 (1H, m), 1.74-1.91 (1H, m), 1.98-2.06 (3H, m), 2.67-2.99 (1H, m), 3.16-3.26 (1H, m), 3.88-4.02 (1H, m), 3.95 (3H, s), 4.03-4.17 (1H, m), 4.40-4.75 (1H, m), 5.00 (1H, d, J=49.65 Hz), 5.88 (2H, q, J=9.22 Hz), 6.75 (1H, d, J=2.74 Hz), 6.82 (1H, dd, J=7.67, 3.01 Hz), 7.66 (1H, d, J=2.46 Hz), 7.68 (1H, dd, J=8.76, 1.64 Hz), 8.08 (1H, d, J=8.76 Hz), 8.10 (1H, s); ESIMS found for $C_{22}H_{22}F_4N_8 02$ m/z 507.2 (M+1).

918

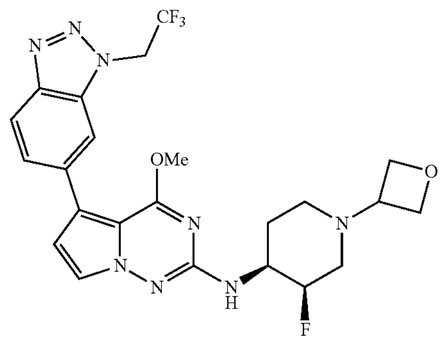

N-((3R,4S)-3-Fluoro-1-(oxetan-3-yl)piperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine 918

Fluffy white solid (10 mg, 0.019 mmol, 45.6% yield). $^1$H NMR (499 MHz, DMSO-$d_6$) δ ppm 1.68-1.78 (1H, m), 1.87-1.97 (1H, m), 1.99-2.06 (1H, m), 2.16 (1H, dd, J=37.00, 12.59 Hz), 2.76 (1H, br d, J=10.95 Hz), 2.94-3.05 (1H, m), 3.49 (1H, quin, J=6.30 Hz), 3.73-3.90 (1H, m), 3.95 (3H, s), 4.40 (1H, t, J=6.16 Hz), 4.46 (1H, t, J=6.16 Hz), 4.54 (2H, td, J=6.43, 3.01 Hz), 4.94 (1H, d, J=49.60 Hz), 5.87 (2H, q, J=8.94 Hz), 6.73 (1H, d, J=7.94 Hz), 6.74 (1H, d, J=2.74 Hz), 7.65 (1H, d, J=2.46 Hz), 7.67 (1H, dd, J=8.49, 1.37 Hz), 8.07 (1H, d, J=8.76 Hz), 8.10 (1H, s); ESIMS found for $C_{23}H_{24}F_4N_8O_2$ m/z 521.2 (M+1).

921

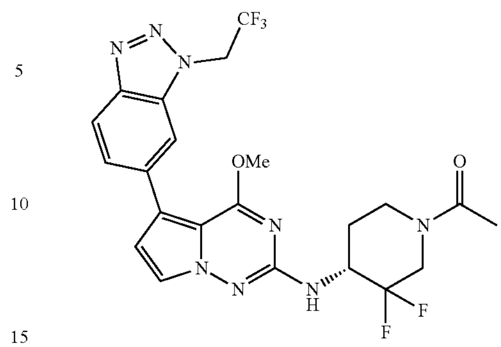

(R)-1-(3,3-Difluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)piperidin-1-yl)ethan-1-one 921

Fluffy white solid (7 mg, 0.013 mmol, 43.7% yield). $^1$H NMR (499 MHz, DMSO-$d_6$) δ ppm 1.58-1.84 (1H, m), 1.84-2.01 (1H, m), 2.03-2.09 (3H, m), 2.99 (1H, br t, J=11.36 Hz), 3.61-3.90 (1H, m), 3.97 (3H, s), 4.10-4.31 (1H, m), 4.45-4.63 (2H, m), 5.88 (2H, q, J=9.22 Hz), 6.77 (1H, d, J=2.46 Hz), 7.03 (1H, d, J=9.03 Hz), 7.67 (1H, dd, J=2.60, 1.23 Hz), 7.67-7.70 (1H, m), 8.08 (1H, d, J=8.76 Hz), 8.11 (1H, s); ESIMS found for $C_{22}H_{21}F_5N_8O_2$ m/z 525.2 (M+1).

922

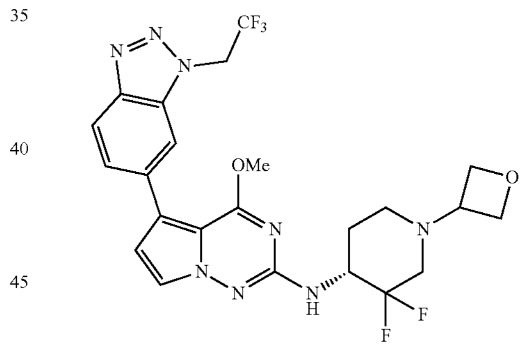

(R)—N-(3,3-Difluoro-1-(oxetan-3-yl)piperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine 922

Fluffy white solid (3 mg, 0.006 mmol, 11.0% yield). $^1$H NMR (499 MHz, DMSO-$d_6$) δ ppm 1.76-1.86 (1H, m), 1.86-1.93 (1H, m), 2.12-2.20 (1H, m), 2.41 (1H, dd, J=27.15, 11.23 Hz), 2.76 (1H, br d, J=11.77 Hz), 2.95-3.08 (1H, m), 3.61 (1H, quin, J=6.09 Hz), 3.96 (3H, s), 4.22-4.37 (1H, m), 4.44 (2H, dt, J=15.19, 6.09 Hz), 4.55 (2H, td, J=6.57, 3.56 Hz), 5.87 (2H, q, J=9.03 Hz), 6.76 (1H, d, J=2.74 Hz), 6.93 (1H, d, J=9.31 Hz), 7.66 (1H, d, J=2.74 Hz), 7.68 (1H, dd, J=8.80, 1.35 Hz), 8.08 (1H, d, J=8.76 Hz), 8.11 (1H, s); ESIMS found for $C_{23}H_{23}F_5N_8O_2$ m/z 539.2 (M+1).

924

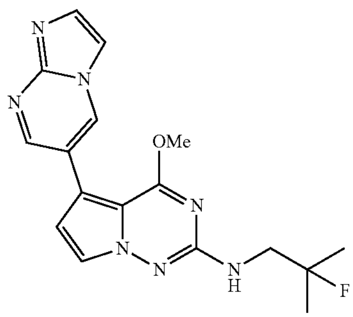

N-(2-Fluoro-2-methylpropyl)-5-(imidazo[1,2-a]pyrimidin-6-yl)-4-methoxypyrrolo[2,1-f][1,2,4]triazin-2-amine 924

Beige solid (6 mg, 0.017 mmol, 8.5% yield). $^1$H NMR (499 MHz, DMSO-$d_6$) δ ppm 1.37 (6H, d, J=21.40 Hz), 3.47 (2H, dd, J=18.89, 6.57 Hz), 4.00 (3H, s), 6.79 (1H, d, J=2.74 Hz), 6.86 (1H, t, J=6.43 Hz), 7.67 (1H, d, J=2.46 Hz), 7.73 (1H, d, J=1.10 Hz), 7.93 (1H, d, J=1.37 Hz), 8.74 (1H, d, J=2.46 Hz), 9.10 (1H, d, J=2.46 Hz); ESIMS found for $C_{17}H_{18}FN_7O$ m/z 356.2 (M+1).

926

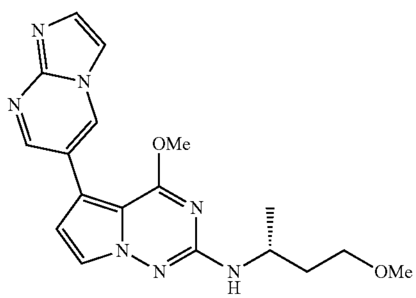

(R)-5-(Imidazo[1,2-a]pyrimidin-6-yl)-4-methoxy-N-(4-methoxybutan-2-yl)pyrrolo[2,1-f][1,2,4]triazin-2-amine 926

Beige solid (4 mg, 0.011 mmol, 5.5% yield). $^1$H NMR (499 MHz, DMSO-$d_6$) δ ppm 1.16 (3H, d, J=6.57 Hz), 1.63-1.73 (1H, m), 1.77-1.88 (1H, m), 3.22 (3H, s), 3.36-3.45 (2H, m), 3.88-3.96 (1H, m), 3.97 (3H, s), 6.58 (1H, d, J=8.49 Hz), 6.77 (1H, d, J=2.46 Hz), 7.66 (1H, d, J=2.46 Hz), 7.75 (1H, br s), 7.95 (1H, br s), 8.74 (1H, d, J=2.19 Hz), 9.10 (1H, d, J=1.64 Hz); ESIMS found for $C_{18}H_{21}N_7O_2$ m/z 368.2 (M+1).

927

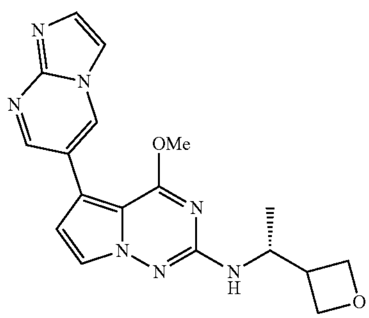

(R)-5-(Imidazo[1,2-a]pyrimidin-6-yl)-4-methoxy-N-(1-(oxetan-3-yl)ethyl)pyrrolo[2,1-f][1,2,4]triazin-2-amine 927

Beige solid (13 mg, 0.036 mmol, 17.8% yield). $^1$H NMR (499 MHz, DMSO-$d_6$) δ ppm 1.10 (3H, d, J=6.57 Hz), 3.04-3.14 (1H, m), 3.98 (3H, s), 4.14-4.26 (1H, m), 4.35 (1H, t, J=6.30 Hz), 4.43 (1H, t, J=6.16 Hz), 4.58-4.65 (2H, m), 6.70 (1H, d, J=8.76 Hz), 6.78 (1H, d, J=2.46 Hz), 7.69 (1H, d, J=2.46 Hz), 7.72 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{18}H_{19}N_7O_2$ m/z 366.2 (M+1).

928

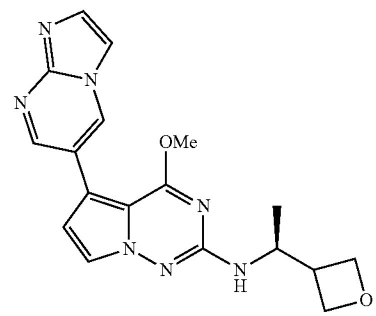

(S)-5-(Imidazo[1,2-a]pyrimidin-6-yl)-4-methoxy-N-(1-(oxetan-3-yl)ethyl)pyrrolo[2,1-f][1,2,4]triazin-2-amine 928

Off-white solid (14 mg, 0.038 mmol, 19.2% yield). $^1$H NMR (499 MHz, DMSO-$d_6$) δ ppm 1.10 (3H, d, J=6.57 Hz), 3.04-3.17 (1H, m), 4.15-4.26 (1H, m), 4.35 (1H, t, J=6.16 Hz), 4.43 (1H, t, J=6.16 Hz), 4.55-4.66 (2H, m), 6.70 (1H, d, J=8.49 Hz), 6.78 (1H, d, J=2.46 Hz), 7.69 (1H, d, J=2.74 Hz), 7.72 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{18}H_{19}N_7O_2$ m/z 366.2 (M+1).

929

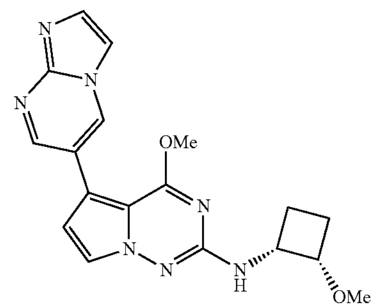

5-(Imidazo[1,2-a]pyrimidin-6-yl)-4-methoxy-N-((1R,2S)-2-methoxycyclobutyl)pyrrolo[2,1-f][1,2,4]triazin-2-amine 929

White solid (10 mg, 0.027 mmol, 27.4% yield). $^1$H NMR (499 MHz, DMSO-$d_6$) δ ppm 1.92-2.05 (3H, m), 2.05-2.12 (1H, m), 3.19 (3H, s), 4.00 (3H, s), 4.00-4.04 (1H, m), 4.30-4.41 (1H, m), 6.59 (1H, d, J=7.67 Hz), 6.79 (1H, d, J=2.74 Hz), 7.68 (1H, d, J=2.46 Hz), 7.73 (1H, d, J=1.37

Hz), 7.93 (1H, d, J=1.37 Hz), 8.74 (1H, d, J=2.46 Hz), 9.10 (1H, d, J=2.46 Hz); ESIMS found for $C_{18}H_{19}N_7O_2$ m/z 366.2 (M+1).

930

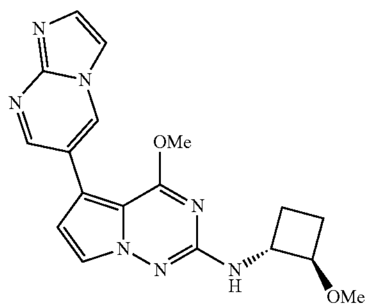

5-(Imidazo[1,2-a]pyrimidin-6-yl)-4-methoxy-N-((1R,2R)-2-methoxycyclobutyl)pyrrolo[2,1-f][1,2,4]triazin-2-amine 930

Off-white solid (25 mg, 0.068 mmol, 41.1% yield). $^1$H NMR (499 MHz, DMSO-$d_6$) δ ppm 1.38-1.48 (2H, m), 1.95-2.02 (1H, m), 2.02-2.10 (1H, m), 3.22 (3H, s), 3.81 (1H, q, J=7.48 Hz), 3.98 (3H, s), 4.06-4.16 (1H, m), 6.79 (1H, d, J=2.46 Hz), 7.19 (1H, d, J=8.76 Hz), 7.68 (1H, d, J=2.46 Hz), 7.72 (1H, d, J=1.37 Hz), 7.93 (1H, d, J=1.10 Hz), 8.73 (1H, d, J=2.46 Hz), 9.09 (1H, d, J=2.46 Hz); ESIMS found for $C_{18}H_{19}N_7O_2$ m/z 366.2 (M+1).

931

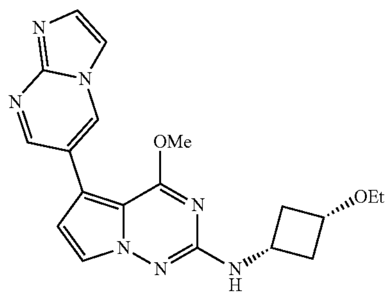

N-(cis-3-Ethoxycyclobutyl)-5-(imidazo[1,2-a]pyrimidin-6-yl)-4-methoxypyrrolo[2,1-f][1,2,4]triazin-2-amine 931

Off-white solid (10 mg, 0.026 mmol, 13.2% yield). $^1$H NMR (499 MHz, DMSO-$d_6$) δ ppm 1.10 (3H, t, J=6.98 Hz), 1.79-1.92 (2H, m), 2.57-2.69 (2H, m), 3.33-3.37 (2H, m), 3.64-3.72 (1H, m), 3.74-3.83 (1H, m), 3.97 (3H, s), 6.78 (1H, d, J=2.46 Hz), 7.07 (1H, d, J=7.39 Hz), 7.65 (1H, d, J=2.74 Hz), 7.72 (1H, d, J=1.37 Hz), 7.93 (1H, d, J=1.37 Hz), 8.73 (1H, d, J=2.46 Hz), 9.09 (1H, d, J=2.74 Hz); ESIMS found for $C_{1-9}H_{21}N_7O_2$ m/z 380.2 (M+1).

934

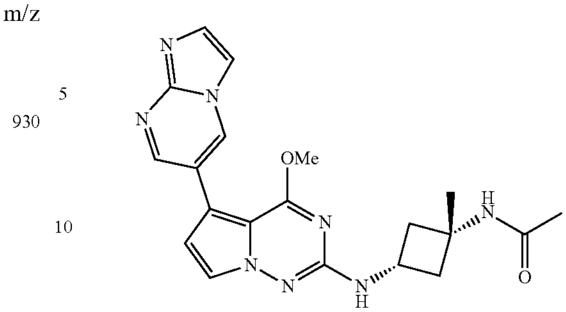

N-((1s,3s)-3-((5-(Imidazo[1,2-a]pyrimidin-6-yl)-4-methoxypyrrolo[2,1-f][1,2,4]triazin-2-yl)amino)-1-methylcyclobutyl)acetamide 934

Beige solid (26 mg, 0.064 mmol, 93.2% yield). $^1$H NMR (499 MHz, DMSO-$d_6$) δ ppm 1.38 (3H, s), 1.76 (3H, s), 2.12-2.21 (2H, m), 2.42 (2H, ddd, J=9.58, 7.39, 2.74 Hz), 3.97 (3H, s), 3.98-4.07 (1H, m), 6.77 (1H, d, J=2.74 Hz), 7.05 (1H, d, J=7.12 Hz), 7.68 (1H, d, J=2.46 Hz), 7.72 (1H, d, J=1.37 Hz), 7.93 (1H, d, J=1.37 Hz), 8.02 (1H, s), 8.73 (1H, d, J=2.46 Hz), 9.08 (1H, d, J=2.46 Hz); ESIMS found for $C_{20}H_{22}N_8O_2$ m/z 407.2 (M+1).

935

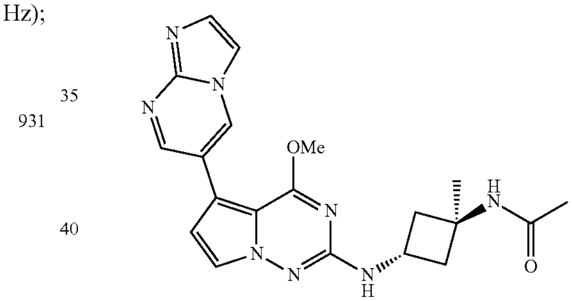

N-((1r,3r)-3-((5-(Imidazo[1,2-a]pyrimidin-6-yl)-4-methoxypyrrolo[2,1-f][1,2,4]triazin-2-yl)amino)-1-methylcyclobutyl)acetamide 935

Off-white solid (26 mg, 0.064 mmol, 93.2% yield). $^1$H NMR (499 MHz, DMSO-$d_6$) δ ppm 1.36 (3H, s), 1.81 (3H, s), 1.90-2.00 (2H, m), 2.58-2.69 (2H, m), 3.97 (3H, s), 4.19 (1H, sxt, J=7.78 Hz), 6.77 (1H, d, J=2.46 Hz), 7.05 (1H, d, J=7.12 Hz), 7.65 (1H, d, J=2.74 Hz), 7.72 (1H, d, J=1.37 Hz), 7.93 (1H, d, J=1.37 Hz), 7.94 (1H, s), 8.73 (1H, d, J=2.46 Hz), 9.08 (1H, d, J=2.46 Hz); ESIMS found for $C_{20}H_{22}N_8O_2$ m/z 407.2 (M+1).

942

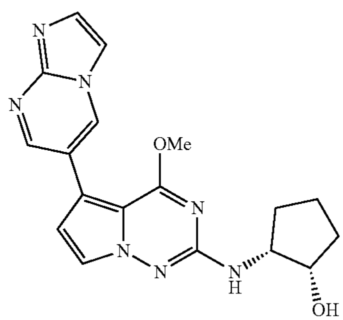

(1S,2R)-2-((5-(Imidazo[1,2-a]pyrimidin-6-yl)-4-methoxypyrrolo[2,1-f][1,2,4]triazin-2-yl)amino)cyclopentan-1-ol 942

Beige solid (16 mg, 0.044 mmol, 26.3% yield). $^1$H NMR (499 MHz, DMSO-$d_6$) δ ppm 1.46-1.56 (1H, m), 1.57-1.67 (2H, m), 1.69-1.77 (1H, m), 1.77-1.86 (1H, m), 1.92-2.01 (1H, m), 3.79-3.91 (1H, m), 3.98 (3H, s), 4.09-4.19 (1H, m), 4.74 (1H, d, J=4.38 Hz), 5.98 (1H, d, J=7.67 Hz), 6.79 (1H, d, J=2.46 Hz), 7.68 (1H, d, J=2.46 Hz), 7.73 (1H, s), 7.93 (1H, s), 8.73 (1H, d, J=2.46 Hz), 9.09 (1H, d, J=2.46 Hz); ESIMS found for $C_{18}H_{19}N_7O_2$ m/z 366.15 (M+1).

943

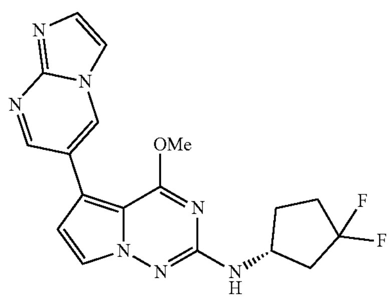

(R)—N-(3,3-Difluorocyclopentyl)-5-(imidazo[1,2-a]pyrimidin-6-yl)-4-methoxypyrrolo[2,1-f][1,2,4]triazin-2-amine 943

White solid (17 mg, 0.044 mmol, 26.5% yield). $^1$H NMR (499 MHz, DMSO-$d_6$) δ ppm 1.82 (1H, dq, J=12.25, 8.42 Hz), 2.02-2.23 (3H, m), 2.23-2.35 (1H, m), 2.54-2.62 (1H, m), 3.98 (3H, s), 4.23 (1H, sxt, J=7.34 Hz), 6.80 (1H, d, J=2.46 Hz), 7.07 (1H, d, J=6.84 Hz), 7.70 (1H, d, J=2.46 Hz), 7.73 (1H, s), 7.93 (1H, s), 8.74 (1H, d, J=2.46 Hz), 9.09 (1H, d, J=2.46 Hz); ESIMS found for $C_{18}H_{17}F_2N_7O$ m/z 386.2 (M+1).

944

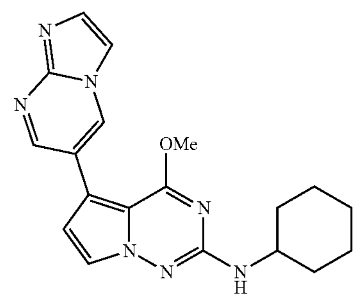

N-Cyclohexyl-5-(imidazo[1,2-a]pyrimidin-6-yl)-4-methoxypyrrolo[2,1-f][1,2,4]triazin-2-amine 944

Beige solid (43 mg, 0.118 mmol, 59.3% yield). $^1$H NMR (499 MHz, DMSO-$d_6$) δ ppm 1.08-1.19 (1H, m), 1.21-1.38 (4H, m), 1.54-1.65 (1H, m), 1.70-1.78 (2H, m), 1.95 (2H, br d, J=10.40 Hz), 3.53-3.65 (1H, m), 3.97 (3H, s), 6.58 (1H, d, J=8.21 Hz), 6.76 (1H, d, J=2.74 Hz), 7.66 (1H, d, J=2.46 Hz), 7.72 (1H, d, J=1.37 Hz), 7.92 (1H, d, J=1.10 Hz), 8.73 (1H, d, J=2.46 Hz), 9.08 (1H, d, J=2.46 Hz); ESIMS found for $C_{19}H_{21}N_7O$ m/z 364.15 (M+1).

947

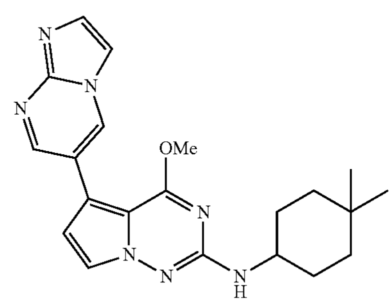

N-(4,4-Dimethylcyclohexyl)-5-(imidazo[1,2-a]pyrimidin-6-yl)-4-methoxypyrrolo[2,1-f][1,2,4]triazin-2-amine 947

Off-white solid (12 mg, 0.031 mmol, 15.4% yield). $^1$H NMR (499 MHz, DMSO-$d_6$) δ ppm 0.93 (3H, s), 0.93 (3H, s), 1.26 (2H, td, J=13.21, 3.70 Hz), 1.35-1.43 (1H, m), 1.44-1.54 (1H, m), 1.62-1.72 (1H, m), 1.73-1.83 (2H, m), 1.90 (1H, br d, J=3.56 Hz), 3.48-3.61 (1H, m), 3.97 (3H, s), 6.56 (1H, d, J=8.21 Hz), 6.76 (1H, d, J=2.74 Hz), 7.65 (1H, d, J=2.46 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{21}H_{25}N_7O$ m/z 392.2 (M+1).

948

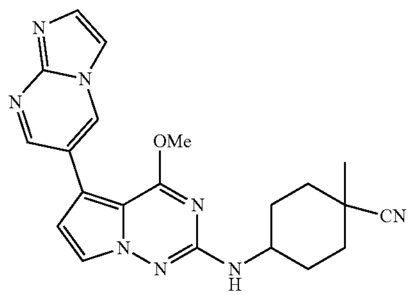

4-((5-(Imidazo[1,2-a]pyrimidin-6-yl)-4-methoxypyrrolo[2,1-f][1,2,4]triazin-2-yl)amino)-1-methylcyclohexane-1-carbonitrile 948

Off-white solid (34 mg, 0.085 mmol, 42.3% yield). $^1$H NMR (499 MHz, DMSO-$d_6$) δ ppm 1.34 (3H, s), 1.45-1.60 (4H, m), 1.95 (2H, br d, J=10.68 Hz), 2.00-2.07 (2H, m), 3.52-3.65 (1H, m), 3.98 (3H, s), 6.77 (1H, d, J=2.46 Hz), 6.83 (1H, d, J=7.94 Hz), 7.65 (1H, d, J=2.74 Hz), 7.72 (1H, d, J=1.10 Hz), 7.93 (1H, d, J=1.37 Hz), 8.73 (1H, d, J=2.46 Hz), 9.09 (1H, d, J=2.46 Hz); ESIMS found for $C_{21}H_{22}N_8O$ m/z 403.2 (M+1).

954

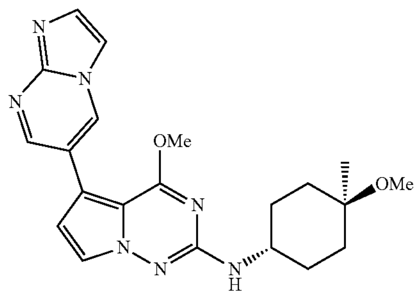

5-(Imidazo[1,2-a]pyrimidin-6-yl)-4-methoxy-N-((1r, 4r)-4-methoxy-4-methylcyclohexyl)pyrrolo[2,1-f][1,2,4]triazin-2-amine 954

Off-white solid (22 mg, 0.054 mmol, 27.1% yield). $^1$H NMR (499 MHz, DMSO-$d_6$) δ ppm 1.14 (3H, s), 1.42-1.57 (4H, m), 1.63-1.74 (2H, m), 1.78-1.90 (2H, m), 3.11 (3H, s), 3.65-3.77 (1H, m), 3.98 (3H, s), 6.60 (1H, d, J=7.94 Hz), 6.77 (1H, d, J=2.74 Hz), 7.67 (1H, d, J=2.74 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{21}H_{25}N_7O_2$ m/z 408.2 (M+1).

964

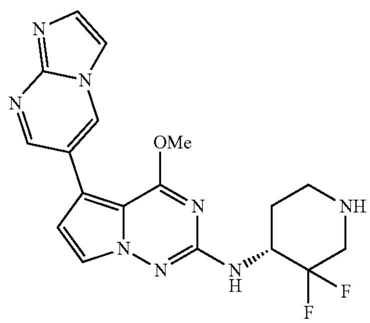

(R)—N-(3,3-Difluoropiperidin-4-yl)-5-(imidazo[1,2-a]pyrimidin-6-yl)-4-methoxypyrrolo[2,1-f][1,2,4]triazin-2-amine 964

Beige solid (18 mg, 0.045 mmol, 75.0% yield). $^1$H NMR (499 MHz, DMSO-$d_6$) δ ppm 1.69 (1H, qd, J=11.96, 3.56 Hz), 1.79-1.90 (1H, m), 2.55-2.67 (1H, m), 2.81 (1H, dd, J=29.35, 14.00 Hz), 2.93 (1H, br d, J=12.05 Hz), 3.06-3.15 (1H, m), 4.01 (3H, s), 4.26-4.41 (1H, m), 6.80 (1H, d, J=2.74 Hz), 6.91 (1H, d, J=9.31 Hz), 7.68 (1H, d, J=2.46 Hz), 7.73 (1H, d, J=1.37 Hz), 7.93 (1H, d, J=1.37 Hz), 8.74 (1H, d, J=2.46 Hz), 9.10 (1H, d, J=2.46 Hz); ESIMS found for $C_{18}H_{18}F_2N_8O$ m/z 401.2 (M+1).

968

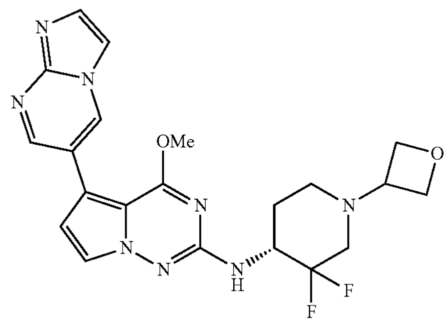

(R)—N-(3,3-Difluoro-1-(oxetan-3-yl)piperidin-4-yl)-5-(imidazo[1,2-a]pyrimidin-6-yl)-4-methoxypyrrolo[2,1-f][1,2,4]triazin-2-amine 968

Off-white solid (15 mg, 0.033 mmol, 72.9% yield). $^1$H NMR (499 MHz, DMSO-$d_6$) δ ppm 1.76-1.86 (1H, m), 1.86-1.92 (1H, m), 2.12-2.22 (1H, m), 2.35-2.46 (1H, m), 2.76 (1H, br d, J=11.50 Hz), 2.96-3.08 (1H, m), 3.60 (1H, quin, J=6.30 Hz), 4.01 (3H, s), 4.23-4.37 (1H, m), 4.44 (2H, dt, J=15.19, 6.23 Hz), 4.55 (2H, td, J=6.57, 3.83 Hz), 6.81 (1H, d, J=2.46 Hz), 6.96 (1H, d, J=9.31 Hz), 7.68 (1H, d, J=2.46 Hz), 7.73 (1H, d, J=1.37 Hz), 7.93 (1H, d, J=1.37 Hz), 8.74 (1H, d, J=2.46 Hz), 9.10 (1H, d, J=2.46 Hz); ESIMS found for $C_{21}H_{22}F_2N_8O_2$ m/z 457. (M+1).

975

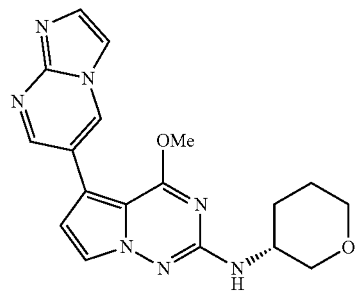

(R)-5-(Imidazo[1,2-a]pyrimidin-6-yl)-4-methoxy-N-(tetrahydro-2H-pyran-3-yl)pyrrolo[2,1-f][1,2,4]triazin-2-amine 975

White solid (7 mg, 0.019 mmol, 11.5% yield). $^1$H NMR (499 MHz, DMSO-$d_6$) δ ppm 1.53-1.65 (2H, m), 1.67-1.76 (1H, m), 1.99 (1H, br d, J=7.39 Hz), 3.11 (1H, t, J=9.99 Hz), 3.23-3.30 (1H, m), 3.70-3.80 (2H, m), 3.94 (1H, br dd, J=10.54, 3.15 Hz), 3.98 (3H, s), 6.66 (1H, d, J=7.94 Hz), 6.78 (1H, d, J=2.46 Hz), 7.69 (1H, d, J=2.46 Hz), 7.72 (1H, d, J=0.82 Hz), 7.93 (1H, d, J=1.10 Hz), 8.73 (1H, d, J=2.46 Hz), 9.09 (1H, d, J=2.46 Hz); ESIMS found for $C_{18}H_{19}N_7O_2$ m/z 366.2 (M+1).

976

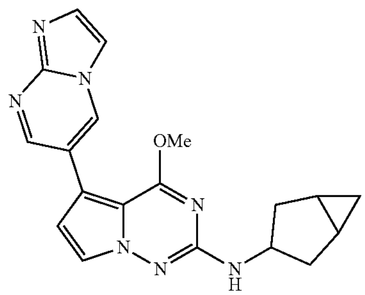

N-(Bicyclo[3.1.0]hexan-3-yl)-5-(imidazo[1,2-a]pyrimidin-6-yl)-4-methoxypyrrolo[2,1-f][1,2,4]triazin-2-amine 976

Beige solid (18 mg, 0.050 mmol, 25.0% yield). $^1$H NMR (499 MHz, DMSO-d$_6$) δ ppm 0.39 (1H, q, J=4.11 Hz), 0.55 (1H, td, J=8.08, 4.93 Hz), 1.26-1.30 (2H, m), 1.74 (2H, dd, J=13.69, 3.01 Hz), 2.18-2.28 (2H, m), 3.97 (3H, s), 4.18 (1H, tdt, J=8.30, 8.30, 5.51, 2.91, 2.91 Hz), 6.62 (1H, d, J=5.48 Hz), 6.76 (1H, d, J=2.46 Hz), 7.65 (1H, d, J=2.74 Hz), 7.72 (1H, d, J=1.37 Hz), 7.92 (1H, d, J=1.37 Hz), 8.73 (1H, d, J=2.46 Hz), 9.08 (1H, d, J=2.46 Hz); ESIMS found for $C_{19}H_{19}N_7O$ m/z 362.2 (M+1).

977

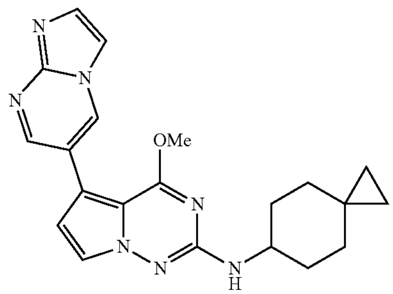

5-(Imidazo[1,2-a]pyrimidin-6-yl)-4-methoxy-N-(spiro[2.5]octan-6-yl)pyrrolo[2,1-f][1,2,4]triazin-2-amine 977

Off-white solid (8 mg, 0.021 mmol, 10.3% yield). $^1$H NMR (499 MHz, DMSO-d$_6$) δ ppm 0.17-0.25 (2H, m), 0.26-0.35 (2H, m), 0.98 (2H, br d, J=13.42 Hz), 1.45 (2H, qd, J=11.65, 3.30 Hz), 1.67-1.79 (2H, m), 1.88-1.97 (2H, m), 3.57-3.73 (1H, m), 3.98 (3H, s), 6.64 (1H, d, J=8.21 Hz), 6.76 (1H, d, J=2.46 Hz), 7.67 (1H, d, J=2.74 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{21}H_{23}N_7O$ m/z 390.2 (M+1).

978

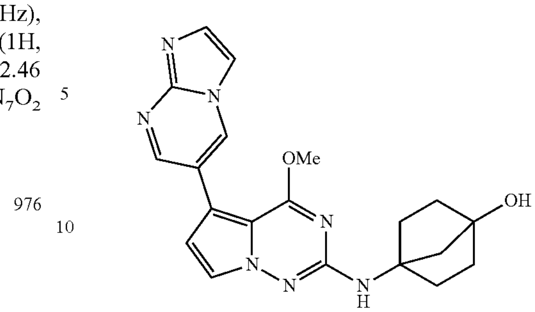

4-((5-(Imidazo[1,2-a]pyrimidin-6-yl)-4-methoxypyrrolo[2,1-f][1,2,4]triazin-2-yl)amino)bicyclo[2.2.1]heptan-1-ol 978

Beige solid (17 mg, 0.043 mmol, 21.8% yield). $^1$H NMR (499 MHz, DMSO-d$_6$) δ ppm 1.57 (2H, td, J=9.79, 3.70 Hz), 1.65-1.77 (2H, m), 1.85 (2H, s), 1.87-1.93 (2H, m), 1.97-2.07 (2H, m), 3.97 (3H, s), 4.89 (1H, s), 6.77 (1H, d, J=2.46 Hz), 6.79 (1H, s), 7.63 (1H, d, J=2.46 Hz), 7.72 (1H, d, J=1.10 Hz), 7.93 (1H, d, J=1.10 Hz), 8.73 (1H, d, J=2.46 Hz), 9.08 (1H, d, J=2.46 Hz); ESIMS found for $C_{20}H_{21}N_7O_2$ m/z 392.2 (M+1).

996

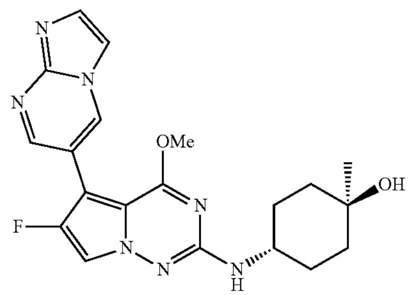

(1r,4r)-4-((6-Fluoro-5-(imidazo[1,2-a]pyrimidin-6-yl)-4-methoxypyrrolo[2,1-f][1,2,4]triazin-2-yl)amino)-1-methylcyclohexan-1-ol 996

Off-white solid (1 mg, 0.002 mmol, 4.3% yield). $^1$H NMR (499 MHz, METHANOL-d$_4$) δ ppm 1.28 (3H, s), 1.48-1.56 (2H, m), 1.56-1.63 (2H, m), 1.68-1.78 (2H, m), 1.98-2.09 (2H, m), 3.74 (1H, tt, J=8.80, 4.21 Hz), 4.01 (3H, s), 4.58 (1H, br s), 7.54 (1H, d, J=3.01 Hz), 7.75 (1H, s), 7.88 (1H, s), 8.72 (1H, d, J=2.19 Hz), 9.00 (1H, d, J=2.19 Hz); ESIMS found for $C_{20}H_{22}FN_7O_2$ m/z 412.2 (M+1).

1038

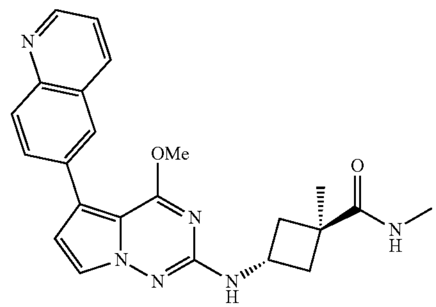

trans-3-((4-Methoxy-5-(quinolin-6-yl)pyrrolo[2,1-f][1,2,4]triazin-2-yl)amino)-N,1-dimethylcyclobutane-1-carboxamide 1038

Yellow solid (23 mg, 0.055 mmol, 44.6% yield). $^1$H NMR (499 MHz, DMSO-$d_6$) δ ppm 1.32 (3H, s), 1.85-1.95 (2H, m), 2.63 (3H, d, J=4.65 Hz), 2.71-2.80 (2H, m), 3.95 (3H, s), 4.05 (1H, sxt, J=7.94 Hz), 6.77 (1H, d, J=2.46 Hz), 6.99 (1H, d, J=7.39 Hz), 7.52 (1H, dd, J=8.21, 4.11 Hz), 7.62 (1H, q, J=4.11 Hz), 7.66 (1H, d, J=2.74 Hz), 7.94-8.03 (2H, m), 8.10 (1H, d, J=1.37 Hz), 8.36 (1H, dd, J=8.35, 1.51 Hz), 8.86 (1H, br d, J=2.74 Hz); ESIMS found for $C_{23}H_{24}N_6O_2$ m/z 417.2 (M+1).

1039

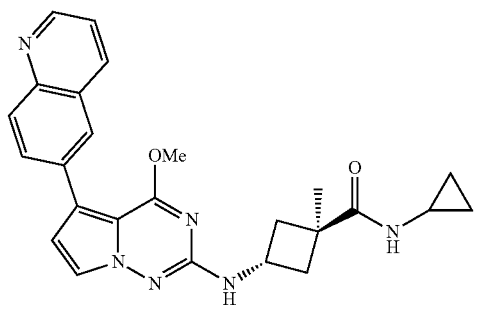

trans-N-Cyclopropyl-3-((4-methoxy-5-(quinolin-6-yl)pyrrolo[2,1-f][1,2,4]triazin-2-yl)amino)-1-methyl-cyclobutane-1-carboxamide 1039

Light yellow solid (20 mg, 0.045 mmol, 36.5% yield). $^1$H NMR (499 MHz, DMSO-$d_6$) δ ppm 0.42-0.48 (2H, m), 0.58-0.64 (2H, m), 1.30 (3H, s), 1.84-1.90 (2H, m), 2.68 (1H, tq, J=7.41, 3.91 Hz), 2.72-2.78 (2H, m), 3.95 (3H, s), 3.96-4.06 (1H, m), 6.77 (1H, d, J=2.74 Hz), 6.98 (1H, d, J=7.39 Hz), 7.53 (1H, dd, J=8.35, 4.24 Hz), 7.63 (1H, d, J=4.11 Hz), 7.67 (1H, d, J=2.46 Hz), 7.94-8.04 (2H, m), 8.11 (1H, s), 8.37 (1H, dd, J=8.21, 1.37 Hz), 8.87 (1H, br d, J=2.46 Hz); ESIMS found for $C_{25}H_{26}N_6O_2$ m/z 443.2 (M+1).

1040

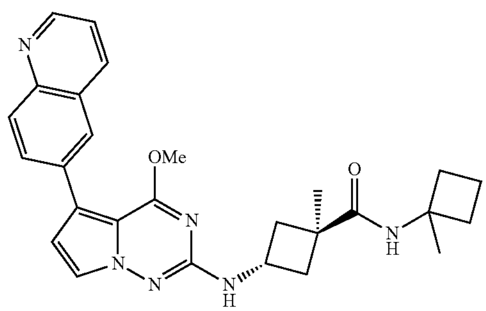

trans-3-((4-Methoxy-5-(quinolin-6-yl)pyrrolo[2,1-f][1,2,4]triazin-2-yl)amino)-1-methyl-N-(1-methylcyclobutyl)cyclobutane-1-carboxamide 1040

Tan solid (21 mg, 0.045 mmol, 36.0% yield). $^1$H NMR (499 MHz, DMSO-$d_6$) δ ppm 1.33 (3H, s), 1.39 (3H, s), 1.71-1.82 (2H, m), 1.83-1.97 (4H, m), 2.16-2.28 (2H, m), 2.71-2.82 (2H, m), 3.96 (3H, s), 3.97-4.04 (1H, m), 6.77 (1H, d, J=2.74 Hz), 6.97 (1H, br d, J=7.12 Hz), 7.51-7.56 (2H, m), 7.67 (1H, d, J=2.74 Hz), 7.95-8.04 (2H, m), 8.12 (1H, s), 8.38 (1H, br d, J=7.94 Hz), 8.84-8.92 (1H, m); ESIMS found for $C_{27}H_{30}N_6O_2$ m/z 471.3 (M+1).

1041

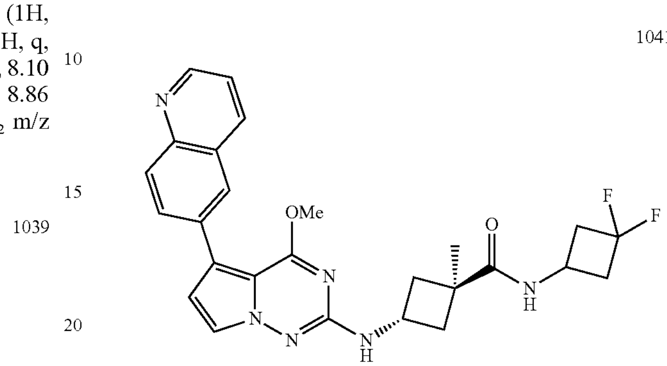

trans-N-(3,3-Difluorocyclobutyl)-3-((4-methoxy-5-(quinolin-6-yl)pyrrolo[2,1-f][1,2,4]triazin-2-yl)amino)-1-methylcyclobutane-1-carboxamide ?1041

Yellow solid (33 mg, 0.067 mmol, 54.1% yield). $^1$H NMR (499 MHz, DMSO-$d_6$) δ ppm 1.34 (3H, s), 1.87-1.98 (2H, m), 2.58-2.71 (2H, m), 2.77 (2H, ddd, J=9.99, 7.80, 2.46 Hz), 2.83-2.96 (2H, m), 3.96 (3H, s), 3.99-4.06 (1H, m), 4.07-4.15 (1H, m), 6.78 (1H, d, J=2.74 Hz), 7.02 (1H, br d, J=7.12 Hz), 7.59 (1H, dd, J=8.21, 4.11 Hz), 7.67 (1H, d, J=2.46 Hz), 8.02 (2H, s), 8.04 (1H, d, J=6.84 Hz), 8.14 (1H, s), 8.45 (1H, br d, J=7.94 Hz), 8.91 (1H, br d, J=3.01 Hz); ESIMS found for $C_{26}H_{26}F_2N_6O_2$ m/z 493.25 (M+1).

1042

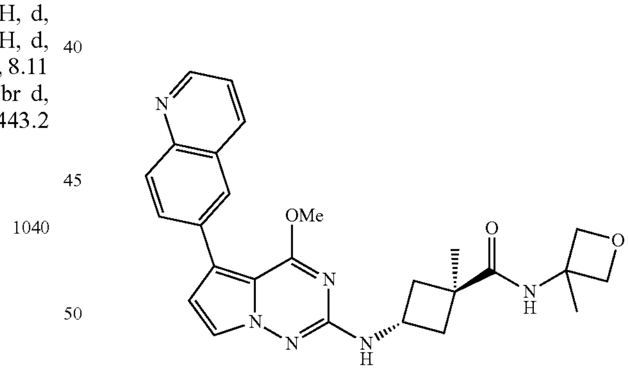

trans-3-((4-Methoxy-5-(quinolin-6-yl)pyrrolo[2,1-f][1,2,4]triazin-2-yl)amino)-1-methyl-N-(3-methyl-oxetan-3-yl)cyclobutane-1-carboxamide 1042

Tan solid (21 mg, 0.044 mmol, 35.9% yield). $^1$H NMR (499 MHz, DMSO-$d_6$) δ ppm 1.35 (3H, s), 1.52 (3H, s), 1.87-1.98 (2H, m), 2.71-2.80 (2H, m), 3.96 (3H, s), 4.05 (1H, sxt, J=7.94 Hz), 4.31 (2H, d, J=6.30 Hz), 4.60 (2H, d, J=6.30 Hz), 6.77 (1H, d, J=2.74 Hz), 7.00 (1H, d, J=7.39 Hz), 7.46-7.57 (1H, m), 7.67 (1H, d, J=2.46 Hz), 7.93-8.03 (2H, m), 8.08 (1H, s), 8.10 (1H, d, J=1.37 Hz), 8.36 (1H, dd, J=8.21, 1.64 Hz), 8.86 (1H, dd, J=4.24, 1.78 Hz); ESIMS found for $C_{26}H_{28}N_6O_3$ m/z 473.3 (M+1).

1043

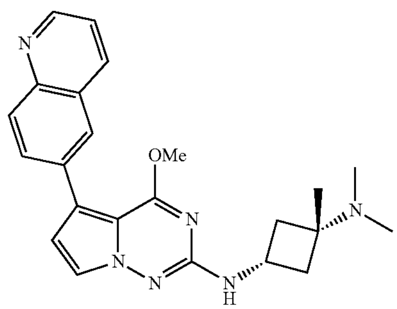

cis-$N_3$-(4-Methoxy-5-(quinolin-6-yl)pyrrolo[2,1-f][1,2,4]triazin-2-yl)-$N_1$,$N_{1,1}$-trimethylcyclobutane-1,3-diamine 1043

Beige solid (28 mg, 0.070 mmol, 57.9% yield). $^1$H NMR (499 MHz, DMSO-$d_6$) δ ppm 1.07 (3H, s), 1.82-1.92 (2H, m), 2.03 (6H, s), 2.15-2.25 (2H, m), 3.92-4.03 (1H, m), 3.96 (3H, s), 6.77 (1H, d, J=2.74 Hz), 6.96 (1H, d, J=7.12 Hz), 7.52 (1H, dd, J=8.35, 4.24 Hz), 7.65 (1H, d, J=2.46 Hz), 7.94-8.03 (2H, m), 8.11 (1H, s), 8.36 (1H, dd, J=8.35, 1.51 Hz), 8.86 (1H, dd, J=4.38, 1.64 Hz); ESIMS found for $C_{23}H_{26}N_{60}$ m/z 403.25 (M+1).

1044

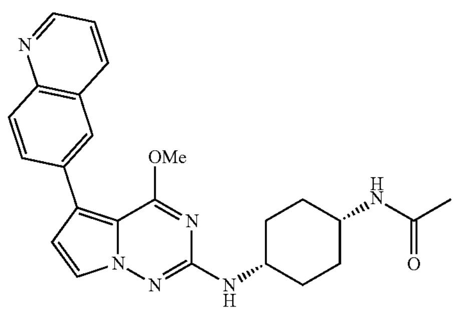

N-(cis-4-((4-Methoxy-5-(quinolin-6-yl)pyrrolo[2,1-f][1,2,4]triazin-2-yl) amino)cyclohexyl)acetamide 1044

White solid (4.16 mg, 0.010 mmol). $^1$H NMR (400 MHz, DMSO-$d_6$) δ ppm 1.50-1.60 (2H, m), 1.60-1.73 (4H, m), 1.73-1.81 (2H, m), 1.81 (3H, s), 3.40-3.47 (1H, m), 3.68 (2H, br s), 3.97 (3H, s), 6.46 (1H, d, J=6.38 Hz), 6.77 (1H, d, J=2.63 Hz), 7.53 (1H, dd, J=8.32, 4.19 Hz), 7.65 (1H, d, J=2.63 Hz), 7.73 (1H, br d, J=7.00 Hz), 7.99 (2H, s), 8.11 (1H, s), 8.36 (1H, dd, J=8.25, 1.50 Hz), 8.86 (1H, dd, J=4.19, 1.69 Hz); ESIMS found for $C_{24}H_{26}N_6O_2$ m/z 431.1 (M+1).

1045

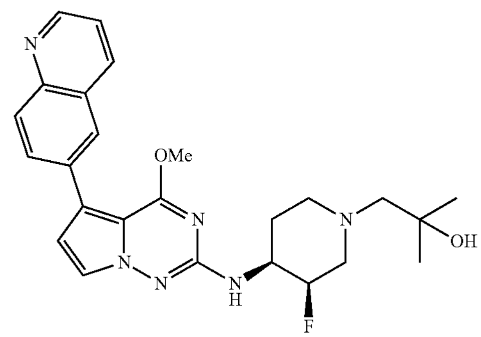

1-((3R,4S)-3-Fluoro-4-((4-methoxy-5-(quinolin-6-yl)pyrrolo[2,1-f][1,2,4]triazin-2-yl)amino)piperidin-1-yl)-2-methylpropan-2-ol 1045

White solid (5 mg, 0.011 mmol, 14.1% yield). $^1$H NMR (499 MHz, DMSO-$d_6$) δ ppm 1.10 (6H, s), 1.61-1.71 (1H, m), 1.95 (1H, qd, J=12.18, 3.42 Hz), 2.20-2.29 (2H, m), 2.29-2.35 (1H, m), 2.43 (1H, dd, J=37.55, 12.87 Hz), 2.98 (1H, br d, J=12.32 Hz), 3.23-3.30 (2H, m), 3.71-3.86 (1H, m), 3.98 (3H, s), 4.08 (1H, br s), 4.87 (1H, d, J=49.90 Hz), 6.59 (1H, d, J=7.94 Hz), 6.79 (1H, d, J=2.74 Hz), 7.53 (1H, dd, J=8.21, 4.11 Hz), 7.65 (1H, d, J=2.46 Hz), 7.95-8.03 (2H, m), 8.11 (1H, d, J=1.37 Hz), 8.36 (1H, dd, J=8.35, 1.78 Hz), 8.86 (1H, dd, J=4.24, 1.78 Hz); ESIMS found for $C_{25}H_{29}FN_6O_2$ m/z 465.3 (M+1).

1047

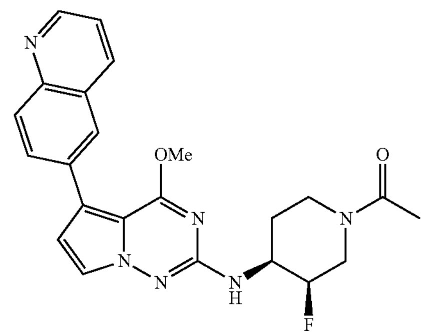

1-((3R,4S)-3-Fluoro-4-((4-methoxy-5-(quinolin-6-yl)pyrrolo[2,1-f][1,2,4]triazin-2-yl)amino)piperidin-1-yl)ethan-1-one 1047

Light orange solid (20 mg, 0.046 mmol, 60.2% yield). $^1$H NMR (499 MHz, DMSO-$d_6$) δ ppm 1.67-1.75 (1H, m), 1.75-1.91 (1H, m), 1.99-2.07 (3H, m), 2.67-2.97 (1H, m), 3.15-3.27 (1H, m), 3.87-3.95 (1H, m), 3.98 (3H, s), 4.03-4.17 (1H, m), 4.40-4.77 (1H, m), 5.00 (1H, d, J=49.35 Hz), 6.80 (2H, d, J=2.46 Hz), 7.53 (1H, dd, J=8.21, 4.11 Hz), 7.65 (1H, d, J=2.74 Hz), 7.96-8.02 (2H, m), 8.12 (1H, s), 8.36 (1H, dd, J=8.21, 1.64 Hz), 8.86 (1H, dd, J=4.38, 1.64 Hz); ESIMS found for $C_{23}H_{23}FN_6O_2$ m/z 435.2 (M+1).

1048

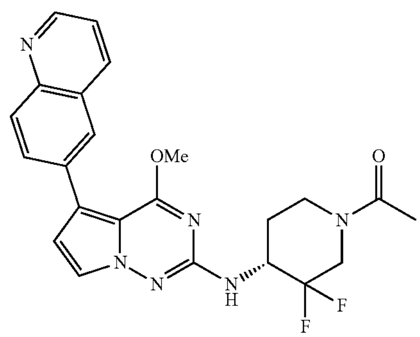

(R)-1-(3,3-Difluoro-4-((4-methoxy-5-(quinolin-6-yl)pyrrolo[2,1-f][1,2,4]triazin-2-yl)amino)piperidin-1-yl)ethan-1-one 1048

Light yellow solid (5 mg, 0.011 mmol, 37.8% yield). $^1$H NMR (499 MHz, DMSO-$d_6$) δ ppm 1.55-1.85 (1H, m), 1.86-2.01 (1H, m), 2.03-2.10 (3H, m), 2.92-3.06 (1H, m), 3.80-3.94 (1H, m), 4.00 (3H, s), 4.11-4.32 (1H, m), 4.46-4.62 (2H, m), 6.82 (1H, d, J=2.74 Hz), 7.00 (1H, d, J=9.31 Hz), 7.53 (1H, dd, J=8.21, 4.11 Hz), 7.66 (1H, dd, J=2.46, 1.37 Hz), 7.94-8.04 (2H, m), 8.12 (1H, s), 8.37 (1H, dd, J=8.35, 1.51 Hz), 8.87 (1H, dd, J=4.24, 1.78 Hz); ESIMS found for $C_{23}H_{22}F_2N_6O_2$ m/z 453.2 (M+1).

1049

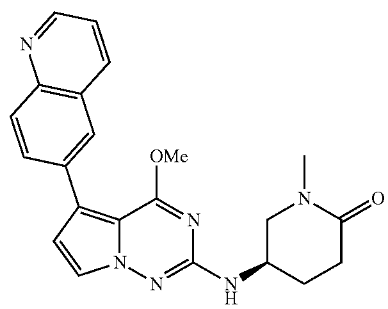

(R)-5-((4-Methoxy-5-(quinolin-6-yl)pyrrolo[2,1-f][1,2,4]triazin-2-yl)amino)-1-methylpiperidin-2-one 1049

Beige solid (23 mg, 0.057 mmol, 44.4% yield). $^1$H NMR (499 MHz, DMSO-$d_6$) δ ppm 1.88-1.97 (1H, m), 1.97-2.04 (1H, m), 2.27-2.36 (1H, m), 2.37-2.44 (1H, m), 2.81 (3H, s), 3.26 (1H, dd, J=12.05, 7.67 Hz), 3.58 (1H, dd, J=12.05, 4.38 Hz), 3.98 (3H, s), 4.05-4.17 (1H, m), 6.80 (1H, d, J=2.74 Hz), 6.92 (1H, d, J=7.39 Hz), 7.53 (1H, dd, J=8.21, 4.11 Hz), 7.69 (1H, d, J=2.74 Hz), 7.94-8.04 (2H, m), 8.12 (1H, s), 8.36 (1H, dd, J=8.35, 1.51 Hz), 8.86 (1H, dd, J=4.11, 1.64 Hz); ESIMS found for $C_{22}H_{22}N_6O_2$ m/z 403.2 (M+1).

1050

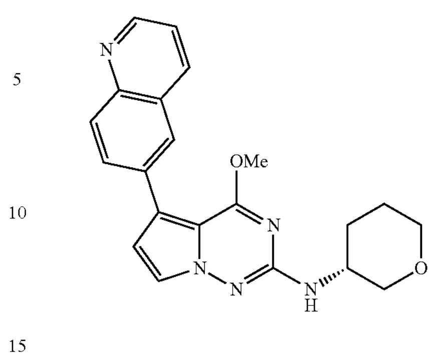

(R)-4-Methoxy-5-(quinolin-6-yl)-N-(tetrahydro-2H-pyran-3-yl)pyrrolo[2,1-f][1,2,4]triazin-2-amine 1050

Off-white solid (59 mg, 0.157 mmol, 46.5% yield). $^1$H NMR (499 MHz, DMSO-$d_6$) δ ppm 1.51-1.63 (2H, m), 1.67-1.76 (1H, m), 1.95-2.04 (1H, m), 3.06-3.17 (1H, m), 3.25-3.32 (1H, m), 3.72-3.81 (2H, m), 3.93-3.98 (1H, m), 3.96 (3H, s), 6.60 (1H, d, J=8.21 Hz), 6.78 (1H, d, J=2.46 Hz), 7.52 (1H, dd, J=8.35, 4.24 Hz), 7.67 (1H, d, J=2.46 Hz), 7.94-8.03 (2H, m), 8.11 (1H, s), 8.36 (1H, dd, J=8.35, 1.51 Hz), 8.86 (1H, dd, J=4.24, 1.78 Hz); ESIMS found for $C_{21}H_{21}N_5O_2$ m/z 376.2 (M+1).

1052

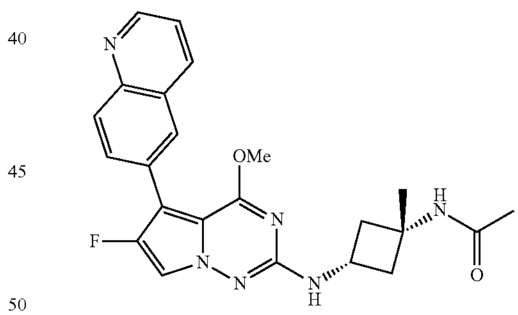

N-(cis-3-((6-Fluoro-4-methoxy-5-(quinolin-6-yl)pyrrolo[2,1-f][1,2,4]triazin-2-yl)amino)-1-methylcyclobutyl)acetamide 1052

Off-white solid (14 mg, 0.032 mmol, 90.3% yield). $^1$H NMR (499 MHz, DMSO-$d_6$) δ ppm 1.38 (3H, s), 1.76 (3H, s), 2.11-2.21 (2H, m), 2.42 (2H, ddd, J=9.65, 7.46, 2.60 Hz), 3.91 (3H, s), 4.01 (1H, sxt, J=7.83 Hz), 7.09 (1H, d, J=6.84 Hz), 7.55 (1H, dd, J=8.35, 4.24 Hz), 7.85 (1H, d, J=2.74 Hz), 7.88 (1H, dd, J=8.76, 1.64 Hz), 8.01-8.05 (2H, m), 8.06 (1H, s), 8.39 (1H, dd, J=8.49, 1.10 Hz), 8.90 (1H, dd, J=4.24, 1.78 Hz); ESIMS found for $C_{23}H_{23}FN_6O_2$ m/z 435.2 (M+1).

1054

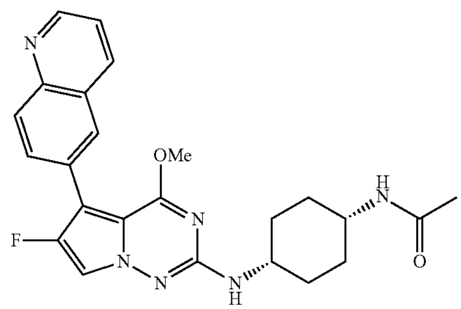

N-(cis-4-((6-Fluoro-4-methoxy-5-(quinolin-6-yl) pyrrolo[2,1-f][1,2,4]triazin-2-yl)amino)cyclohexyl) acetamide 1054

Off-white solid (8.6 mg, 0.019 mmol, 70.2% yield). $^1H$ NMR (499 MHz, DMSO-$d_6$) δ ppm 1.50-1.59 (2H, m), 1.61-1.72 (4H, m), 1.73-1.81 (2H, m), 1.81 (3H, s), 3.67 (2H, br d, J=3.29 Hz), 3.93 (3H, s), 6.56 (1H, d, J=6.30 Hz), 7.50-7.59 (1H, m), 7.70 (1H, d, J=7.12 Hz), 7.84 (1H, d, J=2.74 Hz), 7.89 (1H, dd, J=8.76, 1.64 Hz), 8.03 (1H, d, J=8.76 Hz), 8.07 (1H, s), 8.39 (1H, dd, J=8.35, 1.23 Hz), 8.90 (1H, dd, J=4.11, 1.64 Hz); ESIMS found for $C_{24}H_{25}FN_6O_2$ m/z 449.2 (M+1).

1056

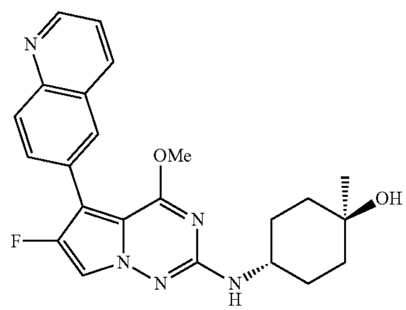

trans-4-((6-Fluoro-4-methoxy-5-(quinolin-6-yl)pyrrolo[2,1-f][1,2,4]triazin-2-yl)amino)-1-methylcyclohexan-1-ol 1056

Off-white solid (9.7 mg, 0.023 mmol, 30.3% yield). $^1H$ NMR (499 MHz, DMSO-$d_6$) δ ppm 1.15 (3H, s), 1.36-1.53 (4H, m), 1.56-1.65 (2H, m), 1.80-1.92 (2H, m), 3.63 (1H, br dd, J=8.21, 3.83 Hz), 3.91 (3H, s), 4.23 (1H, s), 6.59 (1H, d, J=7.94 Hz), 7.55 (1H, dd, J=8.35, 4.24 Hz), 7.85 (1H, d, J=2.74 Hz), 7.89 (1H, dd, J=8.76, 1.64 Hz), 8.03 (1H, d, J=8.76 Hz), 8.06 (1H, s), 8.39 (1H, dd, J=8.49, 1.10 Hz), 8.90 (1H, dd, J=4.11, 1.64 Hz); ESIMS found for $C_{23}H_{24}FN_5O_2$ m/z 422.2 (M+1).

1057

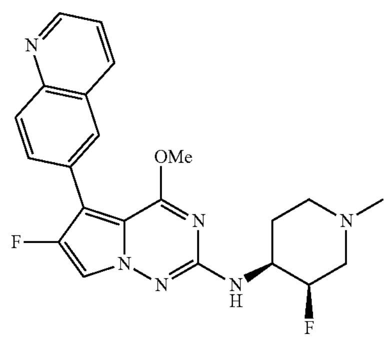

6-Fluoro-N-((3R,4S)-3-fluoro-1-methylpiperidin-4-yl)-4-methoxy-5-(quinolin-6-yl)pyrrolo[2,1-f][1,2,4]triazin-2-amine 1057

White solid (6 mg, 0.014 mmol, 18.6% yield). $^1H$ NMR (499 MHz, DMSO-$d_6$) δ ppm 1.64-1.73 (1H, m), 1.93 (1H, qd, J=12.23, 3.83 Hz), 2.06 (1H, br t, J=11.09 Hz), 2.17 (1H, dd, J=37.60, 12.59 Hz), 2.19 (3H, s), 2.80 (1H, br d, J=11.23 Hz), 3.05 (1H, br t, J=10.54 Hz), 3.69-3.83 (1H, m), 3.93 (3H, s), 4.90 (1H, d, J=49.65 Hz), 6.74 (1H, d, J=7.67 Hz), 7.55 (1H, dd, J=8.35, 4.24 Hz), 7.84 (1H, d, J=2.74 Hz), 7.89 (1H, dd, J=8.62, 1.51 Hz), 8.04 (1H, d, J=8.76 Hz), 8.07 (1H, s), 8.39 (1H, dd, J=8.49, 1.09 Hz), 8.90 (1H, dd, J=4.11, 1.64 Hz); ESIMS found for $C_{22}H_{22}F_2N_6O$ m/z 425.2 (M+1).

1058

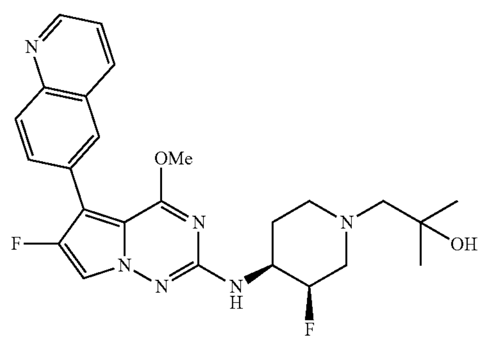

1-((3R,4S)-3-Fluoro-4-((6-fluoro-4-methoxy-5-(quinolin-6-yl)pyrrolo[2,1-f][1,2,4]triazin-2-yl)amino) piperidin-1-yl)-2-methylpropan-2-ol 1058

White solid (3 mg, 0.006 mmol, 23.2% yield). $^1H$ NMR (499 MHz, DMSO-$d_6$) δ ppm 1.09 (6H, s), 1.60-1.70 (1H, m), 1.95 (1H, qd, J=12.18, 3.70 Hz), 2.20-2.28 (2H, m), 2.29-2.35 (1H, m), 2.37-2.48 (1H, m), 2.92-3.03 (1H, m), 3.23-3.31 (1H, m), 3.68-3.85 (1H, m), 3.93 (3H, s), 4.08 (1H, s), 4.85 (1H, d, J=49.60 Hz), 6.71 (1H, d, J=7.67 Hz), 7.55 (1H, dd, J=8.21, 4.11 Hz), 7.84 (1H, d, J=3.01 Hz), 7.89 (1H, dd, J=8.62, 1.78 Hz), 8.04 (1H, d, J=8.76 Hz), 8.07 (1H, s), 8.40 (1H, d, J=8.49 Hz), 8.90 (1H, dd, J=4.11, 1.64 Hz); ESIMS found for $C_{25}H_{28}F_2N_6O_2$ m/z 483.2 (M+1).

1059

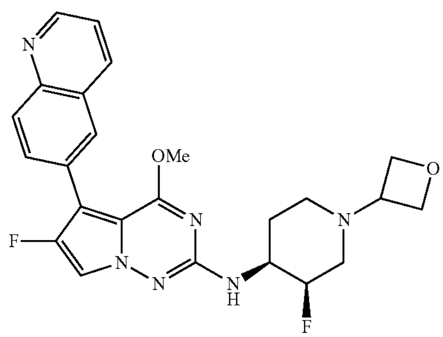

6-Fluoro-N-((3R,4S)-3-fluoro-1-(oxetan-3-yl)piperidin-4-yl)-4-methoxy-5-(quinolin-6-yl)pyrrolo[2,1-f][1,2,4]triazin-2-amine 1059

White solid (14 mg, 0.030 mmol, 21.2% yield). $^1$H NMR (500 MHz, DMSO-$d_6$) δ ppm 1.67-1.77 (1H, m), 1.92 (1H, qd, J=12.21, 3.43 Hz), 1.98-2.06 (1H, m), 2.15 (1H, dd, J=36.80, 12.62 Hz), 2.76 (1H, br d, J=10.15 Hz), 2.99 (1H, br t, J=10.02 Hz), 3.49 (1H, quin, J=6.31 Hz), 3.71-3.88 (1H, m), 3.93 (3H, s), 4.40 (1H, t, J=6.17 Hz), 4.46 (1H, t, J=6.17 Hz), 4.54 (2H, td, J=6.52, 2.88 Hz), 4.92 (1H, d, J=49.45 Hz), 6.81 (1H, d, J=7.96 Hz), 7.55 (1H, dd, J=8.23, 4.12 Hz), 7.84 (1H, d, J=3.02 Hz), 7.89 (1H, dd, J=8.64, 1.51 Hz), 8.04 (1H, d, J=8.78 Hz), 8.07 (1H, s), 8.36-8.43 (1H, m), 8.90 (1H, dd, J=4.12, 1.65 Hz); ESIMS found for $C_{24}H_{24}F_2N_6O_2$ m/z 467.2 (M+1).

1061

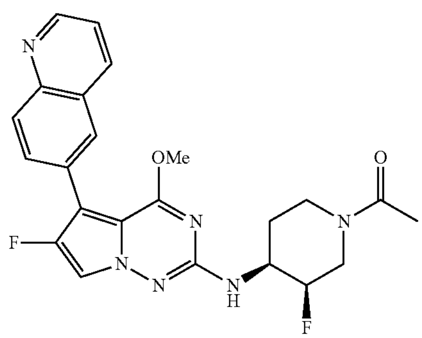

1-((3R,4S)-3-Fluoro-4-((6-fluoro-4-methoxy-5-(quinolin-6-yl)pyrrolo[2,1-f][1,2,4]triazin-2-yl)amino)piperidin-1-yl)ethan-1-one 1061

Tan solid (7 mg, 0.016 mmol, 63.5% yield). $^1$H NMR (499 MHz, DMSO-$d_6$) δ ppm 1.67-1.74 (1H, m), 1.74-1.91 (1H, m), 2.00 (3H, s), 2.66-2.97 (1H, m), 3.86-4.17 (3H, m), 3.93 (3H, s), 4.41-4.76 (1H, m), 4.98 (1H, d, J=49.35 Hz), 6.90 (1H, dd, J=7.80, 3.15 Hz), 7.55 (1H, dd, J=8.35, 4.24 Hz), 7.83 (1H, d, J=3.01 Hz), 7.90 (1H, dd, J=8.62, 1.51 Hz), 8.04 (1H, d, J=8.76 Hz), 8.08 (1H, s), 8.40 (1H, dd, J=8.35, 1.23 Hz), 8.90 (1H, dd, J=4.24, 1.78 Hz); ESIMS found for $C_{23}H_{22}F_2N_6O_2$ m/z 453.2 (M+1).

1062

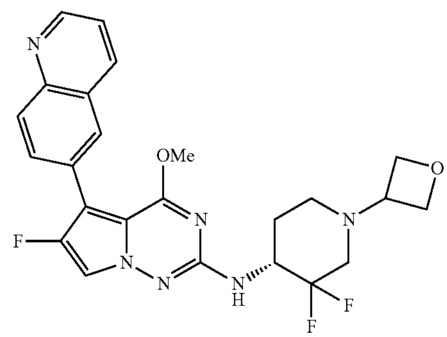

(R)—N-(3,3-Difluoro-1-(oxetan-3-yl)piperidin-4-yl)-6-fluoro-4-methoxy-5-(quinolin-6-yl)pyrrolo[2,1-f][1,2,4]triazin-2-amine 1062

Yellow solid (1.6 mg, 0.003 mmol, 14.1% yield). $^1$H NMR (499 MHz, DMSO-$d_6$) δ ppm 1.75-1.96 (2H, m), 2.13-2.24 (1H, m), 2.74-2.83 (1H, m), 2.98-3.10 (1H, m), 3.62 (1H, br d, J=6.02 Hz), 3.95 (3H, s), 3.96 (1H, s), 4.20-4.37 (1H, m), 4.45 (2H, dt, J=14.99, 6.19 Hz), 4.56 (2H, td, J=6.57, 3.83 Hz), 7.02 (1H, d, J=9.31 Hz), 7.58 (1H, dd, J=8.21, 4.11 Hz), 7.82-7.88 (1H, m), 7.92 (1H, br d, J=8.76 Hz), 8.05 (1H, d, J=8.49 Hz), 8.10 (1H, s), 8.44 (1H, d, J=7.94 Hz), 8.93 (1H, br s); ESIMS found for $C_{24}H_{23}F_3N_6O_2$ m/z 485.2 (M+1).

1064

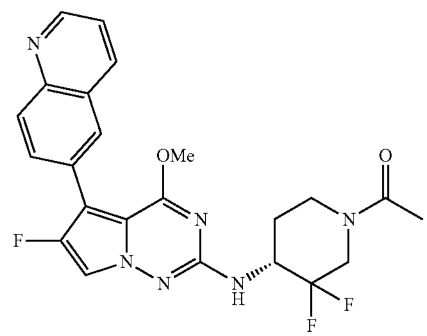

(R)-1-(3,3-Difluoro-4-((6-fluoro-4-methoxy-5-(quinolin-6-yl)pyrrolo[2,1-f][1,2,4]triazin-2-yl)amino)piperidin-1-yl)ethan-1-one 1064

Off-white solid (7.7 mg, 0.016 mmol, 70.1% yield). $^1$H NMR (499 MHz, DMSO-$d_6$) δ ppm 1.55-1.83 (1H, m), 1.85-2.00 (1H, m), 2.03-2.10 (3H, m), 2.92-3.04 (1H, m), 3.61-3.91 (1H, m), 3.95 (3H, s), 4.12-4.31 (1H, m), 4.44-4.60 (2H, m), 7.10 (1H, dd, J=9.31, 1.92 Hz), 7.51-7.60 (1H, m), 7.85 (1H, t, J=2.33 Hz), 7.90 (1H, dd, J=8.76, 1.64 Hz), 8.04 (1H, d, J=8.76 Hz), 8.08 (1H, s), 8.40 (1H, dd, J=8.49, 1.09 Hz), 8.90 (1H, dd, J=4.11, 1.64 Hz); ESIMS found for $C_{23}H_{21}F_3N_6O_2$ m/z 471.2 (M+1).

1089

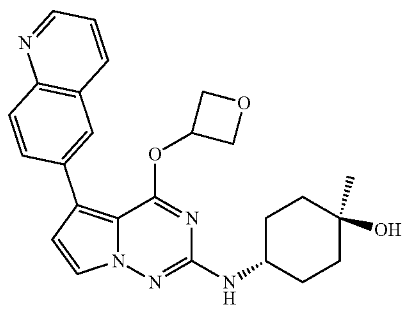

(1r,4r)-1-Methyl-4-((4-(oxetan-3-yloxy)-5-(quinolin-6-yl)pyrrolo[2,1-f][1,2,4]triazin-2-yl)amino)cyclohexan-1-ol 1089

White solid (20 mg, 0.045 mmol, 27.8% yield). $^1$H NMR (499 MHz, DMSO-$d_6$) δ ppm 1.15 (3H, s), 1.37-1.48 (4H, m), 1.55-1.65 (2H, m), 1.81-1.90 (2H, m), 3.55-3.67 (1H, m), 4.25 (1H, s), 4.56 (2H, dd, J=7.80, 5.34 Hz), 4.86 (2H, t, J=7.12 Hz), 5.66-5.74 (1H, m), 6.44 (1H, d, J=7.67 Hz), 6.82 (1H, d, J=2.46 Hz), 7.51-7.57 (1H, m), 7.69 (1H, d, J=2.46 Hz), 7.98-8.05 (1H, m), 8.06-8.12 (1H, m), 8.21 (1H, d, J=1.92 Hz), 8.36 (1H, dd, J=8.35, 1.23 Hz), 8.87 (1H, dd, J=4.11, 1.64 Hz); ESIMS found for $C_{25}H_{27}N_5O_3$ m/z 446.2 (M+1).

1090

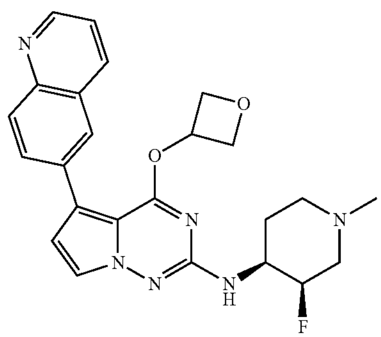

N-((3R,4S)-3-Fluoro-1-methylpiperidin-4-yl)-4-(oxetan-3-yloxy)-5-(quinolin-6-yl)pyrrolo[2,1-f][1,2,4]triazin-2-amine 1090

Off-white solid (19 mg, 0.042 mmol, 21.4% yield). $^1$H NMR (499 MHz, DMSO-$d_6$) δ ppm 1.63-1.75 (1H, m), 1.90 (1H, qd, J=12.23, 3.56 Hz), 2.06 (1H, br t, J=11.36 Hz), 2.18 (1H, dd, J=37.85, 12.87 Hz), 2.19 (3H, s), 2.80 (1H, br d, J=12.05 Hz), 3.00-3.10 (1H, m), 3.64-3.82 (1H, m), 4.57 (2H, dd, J=7.53, 5.34 Hz), 4.87 (1H, d, J=49.60 Hz), 4.85-4.89 (2H, m), 5.71 (1H, quin, J=5.75 Hz), 6.64 (1H, d, J=7.94 Hz), 6.85 (1H, d, J=2.46 Hz), 7.54 (1H, dd, J=8.35, 4.24 Hz), 7.69 (1H, d, J=2.46 Hz), 8.01-8.04 (1H, m), 8.07-8.11 (1H, m), 8.22 (1H, d, J=1.92 Hz), 8.36 (1H, dd, J=8.35, 1.23 Hz), 8.87 (1H, dd, J=4.24, 1.78 Hz); ESIMS found for $C_{24}H_{25}FN_6O_2$ m/z 449.2 (M+1).

1091

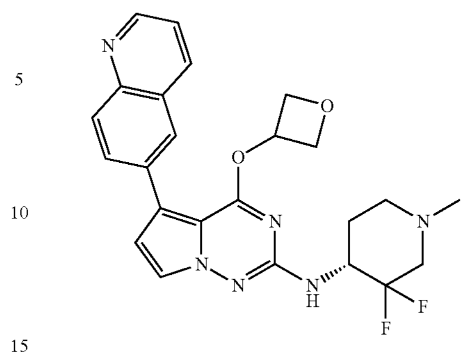

(R)—N-(3,3-Difluoro-1-methylpiperidin-4-yl)-4-(oxetan-3-yloxy)-5-(quinolin-6-yl)pyrrolo[2,1-f][1,2,4]triazin-2-amine 1091

Tan solid (14 mg, 0.030 mmol, 15.1% yield). $^1$H NMR (499 MHz, DMSO-$d_6$) δ ppm 1.72-1.90 (2H, m), 2.12-2.23 (1H, m), 2.26 (3H, s), 2.39 (1H, dd, J=26.90, 12.05 Hz), 2.79 (1H, br d, J=11.50 Hz), 2.99-3.11 (1H, m), 4.09-4.27 (1H, m), 4.57 (2H, ddd, J=12.73, 7.26, 5.48 Hz), 4.88 (2H, q, J=7.12 Hz), 5.73 (1H, quin, J=5.75 Hz), 6.84 (1H, br d, J=9.31 Hz), 6.87 (1H, d, J=2.46 Hz), 7.54 (1H, dd, J=8.21, 4.11 Hz), 7.70 (1H, d, J=2.74 Hz), 7.99-8.06 (1H, m), 8.07-8.14 (1H, m), 8.23 (1H, d, J=2.19 Hz), 8.37 (1H, dd, J=8.35, 1.23 Hz), 8.87 (1H, dd, J=4.11, 1.64 Hz); ESIMS found for $C_{24}H_{24}F_2N_6 02$ m/z 467.2 (M+1).

1093

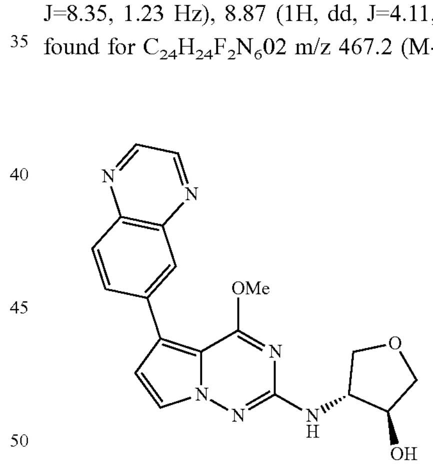

(3S,4R)-4-((4-Methoxy-5-(quinoxalin-6-yl)pyrrolo[2,1-f][1,2,4]triazin-2-yl)amino)tetrahydrofuran-3-ol 1093

Yellow solid (30 mg, 0.079 mmol, 33.0% yield). $^1$H NMR (499 MHz, DMSO-$d_6$) δ ppm 3.55 (1H, dd, J=9.31, 1.92 Hz), 3.66-3.72 (1H, m), 3.92 (1H, dd, J=9.31, 4.65 Hz), 3.99 (3H, s), 4.01-4.06 (2H, m), 4.27 (1H, dt, J=3.76, 2.09 Hz), 5.19 (1H, d, J=3.83 Hz), 6.89 (1H, d, J=2.74 Hz), 6.96 (1H, d, J=5.48 Hz), 7.71 (1H, d, J=2.46 Hz), 8.05-8.09 (1H, m), 8.09-8.13 (1H, m), 8.24 (1H, d, J=1.92 Hz), 8.90 (1H, d, J=1.92 Hz), 8.94 (1H, d, J=1.92 Hz); ESIMS found for $C_{19}H_{18}N_6O_3$ m/z 379.2 (M+1).

1095

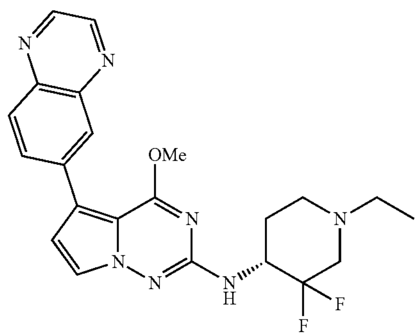

(R)—N-(1-Ethyl-3,3-difluoropiperidin-4-yl)-4-methoxy-5-(quinoxalin-6-yl)pyrrolo[2,1-f][1,2,4]triazin-2-amine 1095

Fluffy yellow solid (8 mg, 0.017 mmol, 49.4% yield). $^{1}$H NMR (499 MHz, DMSO-$d_6$) δ ppm 1.02 (3H, br s), 1.79 (1H, br d, J=10.95 Hz), 1.87 (1H, br s), 2.12-2.25 (1H, m), 2.37-2.49 (3H, m), 2.88 (1H, br d, J=9.58 Hz), 3.12 (1H, br dd, J=4.38, 1.64 Hz), 4.01 (3H, s), 4.20-4.36 (1H, m), 6.85-6.96 (2H, m), 7.69 (1H, br d, J=2.19 Hz), 8.05-8.09 (1H, m), 8.10-8.14 (1H, m), 8.25 (1H, d, J=1.92 Hz), 8.90 (1H, d, J=1.92 Hz), 8.94 (1H, d, J=1.92 Hz); ESIMS found for $C_{22}H_{23}F_2N_7O$ m/z 440.2 (M+1).

1096

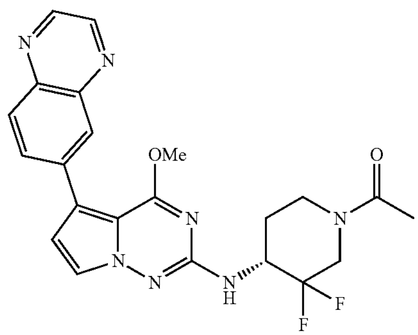

(R)-1-(3,3-Difluoro-4-((4-methoxy-5-(quinoxalin-6-yl)pyrrolo[2,1-f][1,2,4]triazin-2-yl)amino)piperidin-1-yl)ethan-1-one 1096

Fluffy yellow solid (4 mg, 0.009 mmol, 60.5% yield). $^{1}$H NMR (499 MHz, DMSO-$d_6$) δ ppm 1.57-1.85 (1H, m), 1.86-2.02 (1H, m), 2.03-2.11 (3H, m), 3.33-3.43 (1H, m), 3.65-3.94 (1H, m), 3.98-4.05 (3H, m), 4.10-4.64 (3H, m), 6.92 (1H, d, J=2.74 Hz), 7.05 (1H, d, J=9.31 Hz), 7.69 (1H, dd, J=2.46, 1.37 Hz), 8.05-8.09 (1H, m), 8.10-8.14 (1H, m), 8.25 (1H, d, J=1.92 Hz), 8.90 (1H, d, J=1.92 Hz), 8.94 (1H, d, J=1.64 Hz); ESIMS found for $C_{22}H_{21}F_2N_7O_2$ m/z 454.2 (M+1).

1097

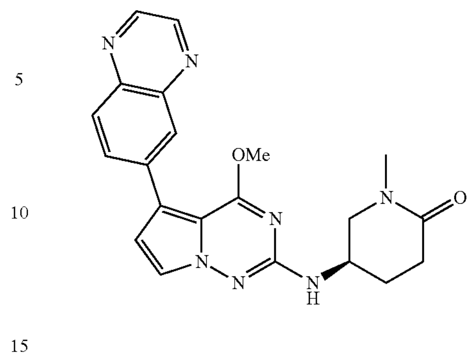

(R)-5-((4-Methoxy-5-(quinoxalin-6-yl)pyrrolo[2,1-f][1,2,4]triazin-2-yl)amino)-1-methylpiperidin-2-one 1097

Yellow solid (26 mg, 0.064 mmol, 33.5% yield). $^{1}$H NMR (499 MHz, DMSO-$d_6$) δ ppm 1.88-1.96 (1H, m), 1.97-2.05 (1H, m), 2.27-2.36 (1H, m), 2.37-2.45 (1H, m), 2.81 (3H, s), 3.26 (1H, dd, J=12.05, 7.67 Hz), 3.58 (1H, dd, J=11.64, 4.79 Hz), 3.99 (3H, s), 4.06-4.17 (1H, m), 6.90 (1H, d, J=2.74 Hz), 6.98 (1H, d, J=7.39 Hz), 7.71 (1H, d, J=2.74 Hz), 8.06-8.09 (1H, m), 8.10-8.13 (1H, m), 8.24 (1H, d, J=1.64 Hz), 8.90 (1H, d, J=1.92 Hz), 8.94 (1H, d, J=1.64 Hz); ESIMS found for $C_{21}H_{21}N_7O_2$ m/z 404.2 (M+1).

1099

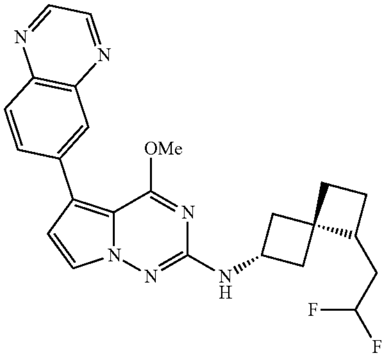

N-((4s,6r)-1-(2,2-Difluoroethyl)-1-azaspiro[3.3]heptan-6-yl)-4-methoxy-5-(quinoxalin-6-yl)pyrrolo[2,1-f][1,2,4]triazin-2-amine 1099

Yellow solid (1 mg, 0.024 mmol, 31.5% yield). $^{1}$H NMR (499 MHz, DMSO-$d_6$) δ ppm 2.11-2.22 (4H, m), 2.41 (2H, ddd, J=9.31, 6.98, 2.87 Hz), 2.83 (2H, td, J=16.08, 4.24 Hz), 3.17 (2H, t, J=6.71 Hz), 3.87-3.96 (1H, m), 3.97 (3H, s), 6.00 (1H, tt, J=56.25, 4.40 Hz), 6.88 (1H, d, J=2.74 Hz), 6.92 (1H, d, J=7.94 Hz), 7.68 (1H, d, J=2.74 Hz), 8.05-8.08 (1H, m), 8.09-8.12 (1H, m), 8.23 (1H, d, J=1.64 Hz), 8.89 (1H, d, J=1.92 Hz), 8.93 (1H, d, J=1.92 Hz); ESIMS found for $C_{23}H_{23}F_2N_7O$ m/z 452.2 (M+1).

1100

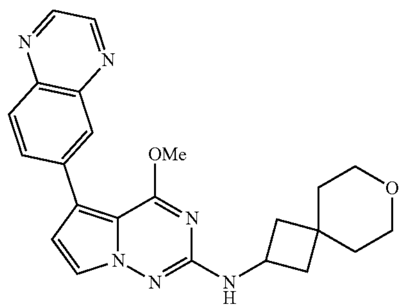

4-Methoxy-5-(quinoxalin-6-yl)-N-(7-oxaspiro[3.5]nonan-2-yl)pyrrolo[2,1-f][1,2,4]triazin-2-amine 1100

Yellow solid (18 mg, 0.043 mmol, 44.9% yield). $^1$H NMR (499 MHz, DMSO-d$_6$) δ ppm 1.48-1.54 (2H, m), 1.56-1.63 (2H, m), 1.76-1.85 (2H, m), 2.24-2.34 (2H, m), 3.42-3.48 (2H, m), 3.51-3.59 (2H, m), 3.97 (3H, s), 4.19 (1H, sxt, J=7.83 Hz), 6.87 (1H, d, J=2.74 Hz), 7.04 (1H, d, J=7.12 Hz), 7.68 (1H, d, J=2.74 Hz), 8.05-8.08 (1H, m), 8.08-8.13 (1H, m), 8.23 (1H, d, J=1.92 Hz), 8.89 (1H, d, J=1.64 Hz), 8.93 (1H, d, J=1.92 Hz); ESIMS found for $C_{23}H_{24}N_6O_2$ m/z 417.2 (M+1).

1130

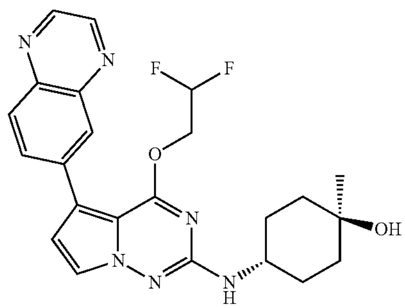

(1r,4r)-4-((4-(2,2-Difluoroethoxy)-5-(quinoxalin-6-yl)pyrrolo[2,1-f][1,2,4]triazin-2-yl)amino)-1-methylcyclohexan-1-ol 1130

White solid (10.45 mg, 0.023 mmol). $^1$H NMR (400 MHz, DMSO-d$_6$) δ ppm 0.47 (3H, s), 0.62-0.85 (4H, m), 0.87-1.01 (2H, m), 1.18-1.31 (2H, m), 2.88-3.02 (1H, m), 3.86 (2H, td, J=13.88, 3.88 Hz), 5.35 (1H, tt, J=55.00, 3.84 Hz), 5.99 (1H, d, J=2.63 Hz), 6.76 (1H, d, J=2.63 Hz), 7.19-7.26 (1H, m), 7.28-7.36 (1H, m), 7.42 (1H, d, J=1.75 Hz), 8.01 (1H, d, J=1.88 Hz), 8.05 (1H, d, J=1.88 Hz); ESIMS found for $C_{23}H_{24}F_2N_6O_2$ m/z 455.1 (M+1).

1136

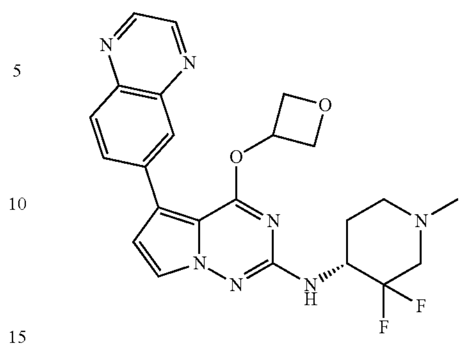

(R)—N-(3,3-Difluoro-1-methylpiperidin-4-yl)-4-(oxetan-3-yloxy)-5-(quinoxalin-6-yl)pyrrolo[2,1-f][1,2,4]triazin-2-amine 1136

Tan solid (16 mg, 0.034 mmol, 15.3% yield). $^1$H NMR (499 MHz, DMSO-d$_6$) δ ppm 1.73-1.90 (2H, m), 2.13-2.24 (1H, m), 2.26 (3H, s), 2.39 (1H, dd, J=27.45, 11.25 Hz), 2.79 (1H, br d, J=11.50 Hz), 3.00-3.12 (1H, m), 4.13-4.29 (1H, m), 4.62 (2H, ddd, J=16.22, 7.60, 5.48 Hz), 4.88 (2H, q, J=6.94 Hz), 5.70-5.80 (1H, m), 6.89 (1H, br d, J=9.31 Hz), 6.97 (1H, d, J=2.46 Hz), 7.73 (1H, d, J=2.74 Hz), 8.11 (1H, d, J=8.76 Hz), 8.21 (1H, dd, J=8.76, 1.92 Hz), 8.40 (1H, d, J=1.92 Hz), 8.91 (1H, d, J=1.92 Hz), 8.95 (1H, d, J=1.92 Hz); ESIMS found for $C_{23}H_{23}F_2N_7O_2$ m/z 468.2 (M+1).

1137

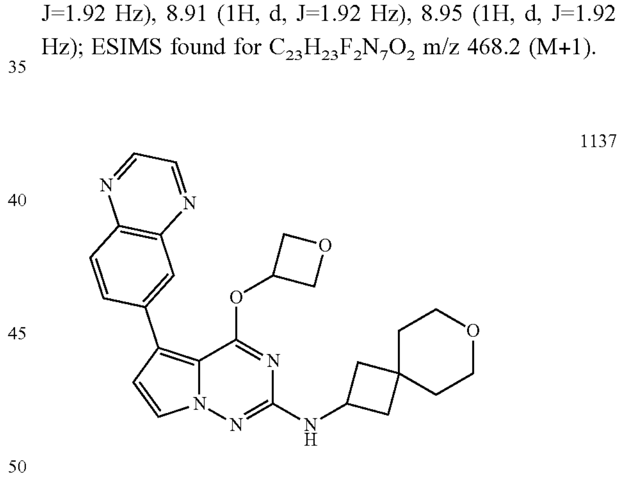

4-(Oxetan-3-yloxy)-5-(quinoxalin-6-yl)-N-(7-oxaspiro[3.5]nonan-2-yl)pyrrolo[2,1-f][1,2,4]triazin-2-amine 1137

Beige solid (20 mg, 0.044 mmol, 40.6% yield). $^1$H NMR (499 MHz, DMSO-d$_6$) δ ppm 1.45-1.55 (2H, m), 1.56-1.63 (2H, m), 1.72-1.84 (2H, m), 2.22-2.33 (2H, m), 3.42-3.49 (2H, m), 3.50-3.59 (2H, m), 4.16 (1H, sxt, J=7.88 Hz), 4.61 (2H, dd, J=7.67, 5.20 Hz), 4.87 (2H, t, J=7.12 Hz), 5.71 (1H, quin, J=5.68 Hz), 6.94 (1H, d, J=2.74 Hz), 6.98 (1H, d, J=7.39 Hz), 7.71 (1H, d, J=2.74 Hz), 8.10 (1H, d, J=8.76 Hz), 8.19 (1H, dd, J=8.76, 1.92 Hz), 8.39 (1 H, d, J=1.92 Hz), 8.90 (1H, d, J=1.92 Hz), 8.95 (1H, d, J=1.92 Hz); ESIMS found for $C_{25}H_{26}N_6O_3$ m/z 459.25 (M+1).

1138

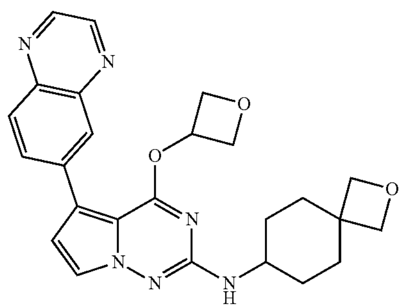

4-(Oxetan-3-yloxy)-5-(quinoxalin-6-yl)-N-(2-oxaspiro[3.5]nonan-7-yl)pyrrolo[2,1-f][1,2,4]triazin-2-amine 1138

Yellow solid (14 mg, 0.031 mmol, 28.4% yield). $^1$H NMR (499 MHz, DMSO-$d_6$) δ ppm 1.18-1.31 (2H, m), 1.53 (2H, td, J=12.87, 3.29 Hz), 1.86 (2H, br dd, J=13.28, 3.15 Hz), 2.07 (2H, br d, J=13.14 Hz), 3.47-3.59 (1H, m), 4.24 (2H, s), 4.32 (2H, s), 4.62 (2H, dd, J=7.67, 5.48 Hz), 4.85 (2H, t, J=7.12 Hz), 5.70 (1H, quin, J=5.75 Hz), 6.50 (1H, d, J=7.94 Hz), 6.93 (1H, d, J=2.74 Hz), 7.70 (1H, d, J=2.74 Hz), 8.10 (1H, d, J=8.76 Hz), 8.19 (1H, dd, J=8.76, 1.92 Hz), 8.39 (1H, d, J=1.92 Hz), 8.90 (1H, d, J=1.92 Hz), 8.94 (1H, d, J=1.92 Hz); ESIMS found for $C_{25}H_{26}N_6O_3$ m/z 459.25 (M+1).

1139

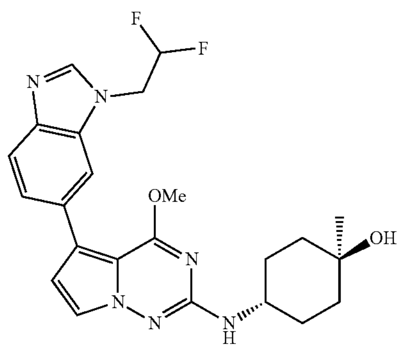

(1r,4r)-4-((5-(1-(2,2-Difluoroethyl)-1H-benzo[d]imidazol-6-yl)-4-methoxypyrrolo[2,1-f][1,2,4]triazin-2-yl)amino)-1-methylcyclohexan-1-ol 1139

Fluffy white solid (11 mg, 0.024 mmol, 49.9% yield). $^1$H NMR (499 MHz, DMSO-$d_6$) δ ppm 1.15 (3H, s), 1.37-1.53 (4H, m), 1.56-1.66 (2H, m), 1.82-1.93 (2H, m), 3.64 (1H, br dd, J=8.21, 3.56 Hz), 3.92 (3H, s), 4.23 (1H, s), 4.81 (2H, td, J=15.95, 2.87 Hz), 6.47 (1H, tt, J=54.30, 3.00 Hz), 6.39 (1H, d, J=7.94 Hz), 6.61 (1H, d, J=2.46 Hz), 7.42 (1H, dd, J=8.35, 1.51 Hz), 7.60 (1H, d, J=2.46 Hz), 7.63 (1H, d, J=8.49 Hz), 7.80 (1H, s), 8.20 (1H, s); ESIMS found for $C_{23}H_{26}F_2N_6O_2$ m/z 457.2 (M+1).

1140

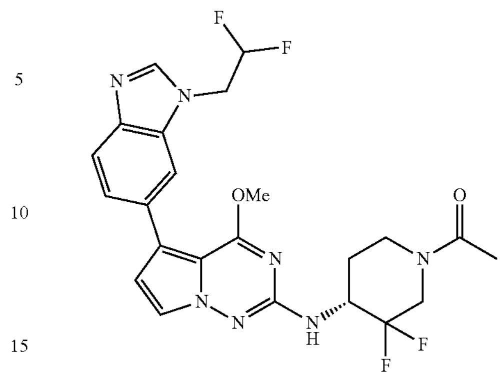

(R)-1-(4-((5-(1-(2,2-Difluoroethyl)-1H-benzo[d]imidazol-6-yl)-4-methoxypyrrolo[2,1-f][1,2,4]triazin-2-yl)amino)-3,3-difluoropiperidin-1-yl)ethan-1-one 1140

Fluffy white solid (5 mg, 0.010 mmol, 32.4% yield). $^1$H NMR (499 MHz, DMSO-$d_6$) δ ppm 1.57-1.83 (1H, m), 1.85-2.00 (1H, m), 2.03-2.09 (3H, m), 2.93-3.06 (1H, m), 3.61-3.92 (2H, m), 3.96 (3H, s), 4.09-4.31 (1H, m), 4.45-4.62 (2H, m), 4.81 (2H, td, J=16.15, 3.01 Hz), 6.48 (1H, tt, J=54.30, 3.00 Hz), 6.67 (1H, d, J=2.46 Hz), 6.91 (1H, d, J=9.31 Hz), 7.43 (1H, dd, J=8.35, 1.51 Hz), 7.61 (1H, dd, J=2.46, 1.37 Hz), 7.64 (1H, d, J=8.21 Hz), 7.82 (1H, s), 8.21 (1H, s); ESIMS found for $C_{23}H_{23}F_4N_7O_2$ m/z 506.2 (M+1).

1141

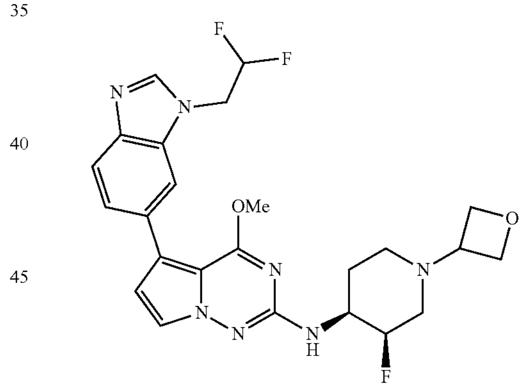

5-(1-(2,2-Difluoroethyl)-1H-benzo[d]imidazol-6-yl)-N-((3R,4S)-3-fluoro-1-(oxetan-3-yl)piperidin-4-yl)-4-methoxypyrrolo[2,1-f][1,2,4]triazin-2-amine 1141

Fluffy white solid (13 mg, 0.026 mmol, 61.5% yield). $^1$H NMR (499 MHz, DMSO-$d_6$) δ ppm 1.68-1.75 (1H, m), 1.91 (1H, qd, J=12.14, 3.56 Hz), 1.98-2.06 (1H, m), 2.16 (1H, dd, J=37.55, 12.32 Hz), 2.76 (1H, br d, J=11.23 Hz), 2.95-3.05 (1H, m), 3.49 (1H, quin, J=6.30 Hz), 3.71-3.89 (1H, m), 3.94 (3H, s), 4.40 (1H, t, J=6.16 Hz), 4.46 (1H, t, J=6.16 Hz), 4.54 (2H, td, J=6.57, 3.01 Hz), 4.81 (2H, td, J=15.95, 2.87 Hz), 4.94 (1H, d, J=50.50 Hz), 6.47 (1H, tt, J=54.85, 3.30 Hz), 6.60 (1H, d, J=7.94 Hz), 6.65 (1H, d, J=2.74 Hz), 7.42 (1H, dd, J=8.49, 1.64 Hz), 7.60 (1H, d, J=2.46 Hz), 7.64 (1H, d, J=8.49 Hz), 7.81 (1H, s), 8.21 (1H, s); ESIMS found for $C_{24}H_{26}F_3N_7O_2$ m/z 502.2 (M+1).

1142

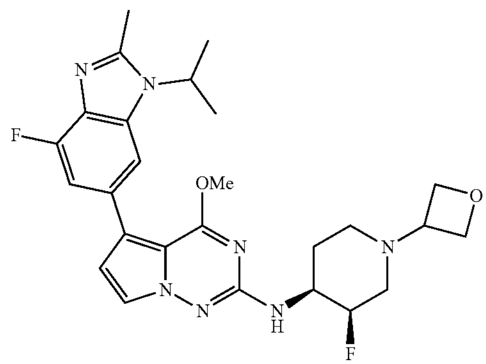

N-((3R,4S)-3-Fluoro-1-(oxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine 1142

White solid (14 mg, 0.027 mmol, 41.6% yield). $^1$H NMR (499 MHz, DMSO-$d_6$) δ ppm 1.59 (6H, d, J=6.84 Hz), 1.69-1.78 (1H, m), 1.85-1.97 (1H, m), 1.97-2.06 (1H, m), 2.15 (1H, dd, J=36.75, 12.59 Hz), 2.58 (3H, s), 2.76 (1H, br d, J=11.22 Hz), 2.94-3.04 (1H, m), 3.49 (1H, quin, J=6.43 Hz), 3.73-3.91 (1H, m), 3.96 (3H, s), 4.40 (1H, t, J=6.16 Hz), 4.46 (1H, t, J=6.16 Hz), 4.54 (2H, td, J=6.57, 3.01 Hz), 4.76 (1H, spt, J=6.94 Hz), 4.93 (1H, d, J=49.65 Hz), 6.62 (1H, d, J=7.94 Hz), 6.69 (1H, d, J=2.46 Hz), 7.12 (1H, dd, J=12.05, 1.10 Hz), 7.59 (1H, d, J=2.74 Hz), 7.64 (1H, d, J=1.09 Hz); ESIMS found for $C_{26}H_{31}F_2N_7O_2$ m/z 512.3 (M+1).

1143

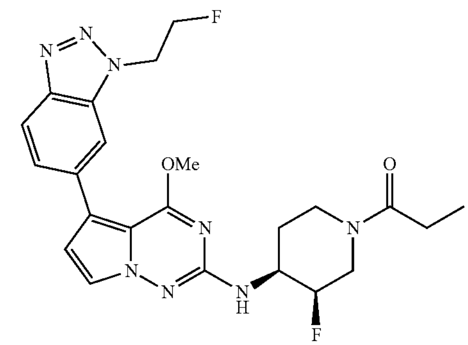

1-((3R,4S)-3-Fluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)propan-1-one 1143

Fluffy white solid (8.8 mg, 0.018 mmol, 46.2% yield). $^1$H NMR (499 MHz, DMSO-$d_6$) δ ppm 1.00 (3H, t, J=7.39 Hz), 1.67-1.90 (2H, m), 2.27-2.42 (2H, m), 2.70-2.99 (1H, m), 3.13-3.22 (1H, m), 3.91-4.00 (1H, m), 3.96 (3H, s), 4.05-4.22 (1H, m), 4.44-4.77 (1H, m), 4.94 (2H, dt, J=47.15, 4.65 Hz), 4.99 (1H, d, J=49.35 Hz), 5.08 (2H, dt, J=27.70, 4.65 Hz), 6.76 (1H, d, J=2.46 Hz), 6.78 (1H, d, J=7.67 Hz), 7.62 (1H, dd, J=8.62, 1.51 Hz), 7.65 (1H, d, J=2.74 Hz), 8.01 (1H, d, J=10.40 Hz), 8.01 (1H, s); ESIMS found for $C_{23}H_{26}F_2N_8O_2$ m/z 485.2 (M+1).

1144

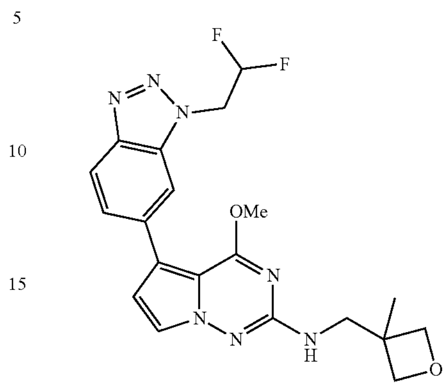

5-(1-(2,2-Difluoroethyl)-1H-benzo[d][1,2,3]triazol-6-yl)-4-methoxy-N-((3-methyloxetan-3-yl)methyl)pyrrolo[2,1-f][1,2,4]triazin-2-amine 1144

White solid (33 mg, 0.077 mmol, 38.1% yield). $^1$H NMR (499 MHz, DMSO-$d_6$) δ ppm 1.30 (3H, s), 3.46 (2H, d, J=6.02 Hz), 3.96 (3H, s), 4.22 (2H, d, J=5.75 Hz), 4.51 (2H, d, J=5.75 Hz), 5.30 (2H, td, J=15.95, 2.87 Hz), 6.60 (1H, tt, J=54.30, 3.00 Hz), 6.73 (1H, d, J=2.74 Hz), 6.95 (1H, t, J=6.16 Hz), 7.63-7.66 (1H, m), 7.64 (1H, d, J=2.46 Hz), 8.01-8.05 (2H, m); ESIMS found for $C_{20}H_{21}F_2N_7O_2$ m/z 430.2 (M+1).

1145

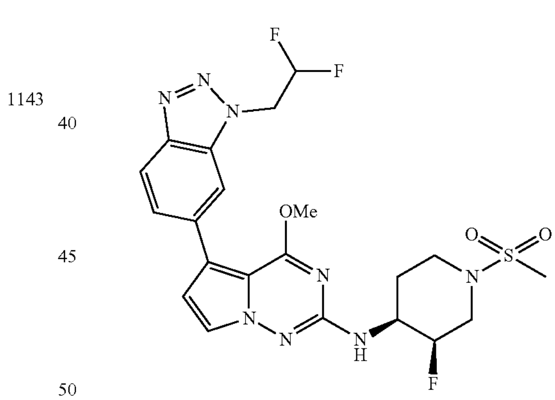

5-(1-(2,2-Difluoroethyl)-1H-benzo[d][1,2,3]triazol-6-yl)-N-((3R,4S)-3-fluoro-1-(methylsulfonyl)piperidin-4-yl)-4-methoxypyrrolo[2,1-f][1,2,4]triazin-2-amine 1145

Fluffy white solid (6 mg, 0.011 mmol, 33.2% yield). $^1$H NMR (499 MHz, DMSO-$d_6$) δ ppm 1.77-1.88 (1H, m), 1.96 (1H, qd, J=12.50, 4.38 Hz), 2.93 (3H, s), 3.02 (1H, td, J=12.25, 2.60 Hz), 3.20 (1H, dd, J=37.55, 12.59 Hz), 3.61-3.70 (1H, m), 3.80-3.89 (1H, m), 3.90-4.04 (1H, m), 3.96 (3H, s), 5.05 (1H, d, J=49.10 Hz), 5.30 (2H, td, J=15.95, 2.87 Hz), 6.61 (1H, tt, J=54.30, 3.00 Hz), 6.76 (1H, d, J=2.74 Hz), 6.88 (1H, d, J=7.94 Hz), 7.63 (1H, d, J=2.46 Hz), 7.64-7.66 (1H, m), 8.02-8.05 (2H, m); ESIMS found for $C_{21}H_{23}F_3N_8O_3S$ m/z 525.15

1146

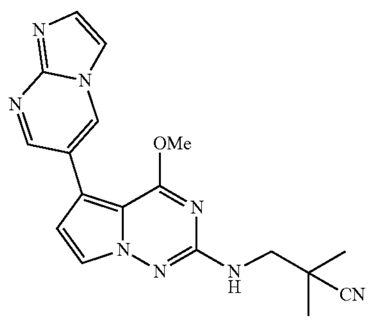

3-((5-(Imidazo[1,2-a]pyrimidin-6-yl)-4-methoxypyrrolo[2,1-f][1,2,4]triazin-2-yl)amino)-2,2-dimethylpropanenitrile 1146

Beige solid (20 mg, 0.055 mmol, 27.7% yield). $^1$H NMR (499 MHz, DMSO-$d_6$) δ ppm 1.36 (6H, s), 3.49 (2H, d, J=6.57 Hz), 4.02 (3H, s), 6.81 (1H, d, J=2.74 Hz), 7.17 (1H, t, J=6.57 Hz), 7.69 (1H, d, J=2.46 Hz), 7.73 (1H, d, J=1.37 Hz), 7.93 (1H, d, J=1.37 Hz), 8.74 (1H, d, J=2.46 Hz), 9.10 (1H, d, J=2.46 Hz); ESIMS found for $C_{18}H_{18}N_8O$ m/z 363.3 (M+1).

1147

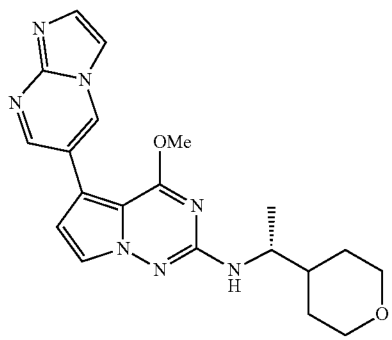

(R)-5-(Imidazo[1,2-a]pyrimidin-6-yl)-4-methoxy-N-(1-(tetrahydro-2H-pyran-4-yl)ethyl)pyrrolo[2,1-f][1,2,4]triazin-2-amine 1147

Beige solid (14 mg, 0.036 mmol, 17.8% yield). $^1$H NMR (499 MHz, DMSO-$d_6$) δ ppm 1.13 (3H, d, J=6.57 Hz), 1.20-1.33 (3H, m), 1.58-1.65 (1H, m), 1.66-1.73 (2H, m), 3.18-3.30 (2H, m), 3.69 (1H, br dd, J=14.92, 7.26 Hz), 3.83-3.92 (2H, m), 3.98 (3H, s), 6.61 (1H, d, J=9.03 Hz), 6.76 (1H, d, J=2.46 Hz), 7.64 (1H, d, J=2.46 Hz), 7.72 (1H, d, J=1.37 Hz), 7.93 (1H, d, J=1.37 Hz), 8.73 (1H, d, J=2.46 Hz), 9.08 (1H, d, J=2.46 Hz); ESIMS found for $C_{20}H_{23}N_7O_2$ m/z 394.2 (M+1).

1148

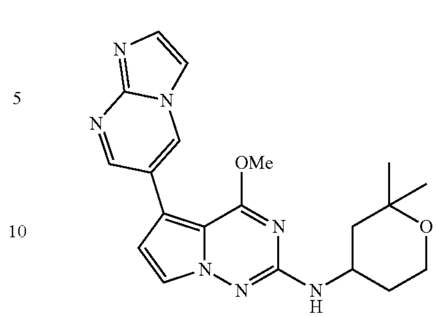

N-(2,2-Dimethyltetrahydro-2H-pyran-4-yl)-5-(imidazo[1,2-a]pyrimidin-6-yl)-4-methoxypyrrolo[2,1-f][1,2,4]triazin-2-amine 1148

Off-white solid (20 mg, 0.051 mmol, 25.5% yield). $^1$H NMR (499 MHz, DMSO-$d_6$) δ ppm 1.16 (3H, s), 1.22 (3H, s), 1.32 (1H, t, J=12.32 Hz), 1.35-1.43 (1H, m), 1.81-1.86 (1H, m), 1.87-1.92 (1H, m), 3.59-3.71 (2H, m), 3.91-4.02 (1H, m), 3.98 (3H, s), 6.64 (1H, d, J=8.21 Hz), 6.77 (1H, d, J=2.46 Hz), 7.66 (1H, d, J=2.46 Hz), 7.72 (1H, d, J=1.37 Hz), 7.93 (1H, d, J=1.37 Hz), 8.73 (1H, d, J=2.46 Hz), 9.09 (1H, d, J=2.46 Hz); ESIMS found for $C_{20}H_{23}N_7O_2$ m/z 394.2 (M+1).

1149

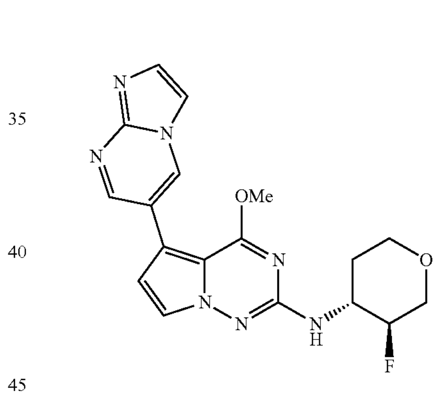

N-((3S,4R)-3-Fluorotetrahydro-2H-pyran-4-yl)-5-(imidazo[1,2-a]pyrimidin-6-yl)-4-methoxypyrrolo[2,1-f][1,2,4]triazin-2-amine 1149

Off-white solid (14 mg, 0.037 mmol, 18.3% yield). $^1$H NMR (499 MHz, DMSO-$d_6$) δ ppm 1.55-1.68 (1H, m), 2.03-2.13 (1H, m), 3.39-3.44 (1H, m), 3.44-3.51 (1H, m), 3.80-3.88 (1H, m), 3.98-4.02 (1H, m), 4.00 (3H, s), 4.05-4.10 (1H, m), 4.58 (1H, dtd, J=48.55, 8.21, 8.21, 4.38 Hz), 6.80 (1H, d, J=2.74 Hz), 7.03 (1H, d, J=8.21 Hz), 7.69 (1H, d, J=2.46 Hz), 7.73 (1H, d, J=1.37 Hz), 7.93 (1H, d, J=1.37 Hz), 8.74 (1H, d, J=2.46 Hz), 9.09 (1H, d, J=2.46 Hz); ESIMS found for $C_{18}H_{18}FN_7O_2$ m/z 384.2 (M+1).

1150

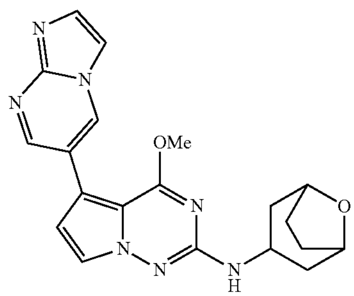

N-(8-Oxabicyclo[3.2.1]octan-3-yl)-5-(imidazo[1,2-a]pyrimidin-6-yl)-4-methoxypyrrolo[2,1-f][1,2,4]triazin-2-amine 1150

Off-white solid (7 mg, 0.018 mmol, 9.0% yield). $^1$H NMR (499 MHz, DMSO-$d_6$) δ ppm 1.76-1.82 (2H, m), 1.87-1.92 (2H, m), 2.00-2.07 (2H, m), 2.11-2.18 (2H, m), 3.78-3.87 (1H, m), 4.00 (3H, s), 4.27 (2H, br s), 6.62 (1H, d, J=4.11 Hz), 6.78 (1H, d, J=2.46 Hz), 7.67 (1H, d, J=2.74 Hz), 7.72 (1H, d, J=1.37 Hz), 7.93 (1H, d, J=1.64 Hz), 8.74 (1H, d, J=2.46 Hz), 9.09 (1H, d, J=2.46 Hz); ESIMS found for $C_{20}H_{21}N_7O_2$ m/z 392.15 (M+1).

1151

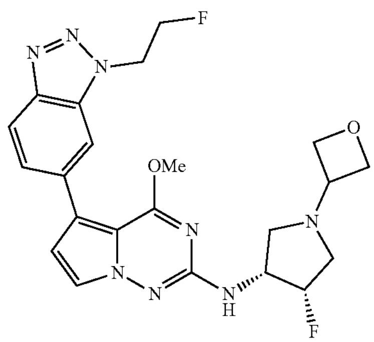

N-((3R,4S)-4-Fluoro-1-(oxetan-3-yl)pyrrolidin-3-yl)-5-(1-(2-fluoroethyl)-1H-benzo[d][1,2,3]triazol-6-yl)-4-methoxypyrrolo[2,1-f][1,2,4]triazin-2-amine 1151

Fluffy white solid (6 mg, 0.013 mmol, 18.2% yield). $^1$H NMR (499 MHz, DMSO-$d_6$) δ ppm 2.68 (1H, t, J=9.03 Hz), 2.77 (1H, ddd, J=29.90, 12.05, 1.10 Hz), 3.02 (1H, t, J=8.35 Hz), 3.18 (1H, ddd, J=33.20, 12.05, 4.38 Hz), 3.79 (1H, quin, J=6.16 Hz), 3.96 (3H, s), 4.22-4.38 (1H, m), 4.47 (2H, t, J=6.02 Hz), 4.60 (2H, t, J=6.57 Hz), 4.94 (2H, dt, J=47.15, 4.65 Hz), 5.08 (2H, dt, J=28.00, 4.65 Hz), 5.25 (1H, dtd, J=55.95, 4.65, 4.65, 1.40 Hz), 6.77 (1H, d, J=2.74 Hz), 6.82 (1H, d, J=7.67 Hz), 7.61-7.64 (1H, m), 7.66 (1H, d, J=2.46 Hz), 8.00-8.03 (2H, m); ESIMS found for $C_{22}H_{24}F_2N_8O_2$ m/z 471.2 (M+1).

1152

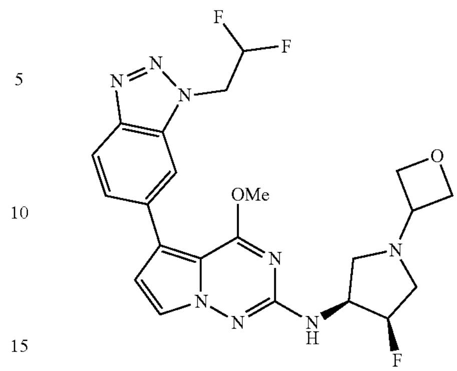

5-(1-(2,2-Difluoroethyl)-1H-benzo[d][1,2,3]triazol-6-yl)-N-((3S,4R)-4-fluoro-1-(oxetan-3-yl)pyrrolidin-3-yl)-4-methoxypyrrolo[2,1-f][1,2,4]triazin-2-amine 1152

Fluffy white solid (15 mg, 0.031 mmol, 43.7% yield). $^1$H NMR (499 MHz, DMSO-$d_6$) δ ppm 2.69 (1H, t, J=9.03 Hz), 2.77 (1H, ddd, J=29.90, 12.05, 1.37 Hz), 3.02 (1H, t, J=8.35 Hz), 3.18 (1H, ddd, J=33.20, 12.05, 4.38 Hz), 3.74-3.84 (1H, m), 3.96 (3H, s), 4.24-4.38 (1H, m), 4.47 (2H, t, J=6.02 Hz), 4.55-4.64 (2H, m), 5.25 (1H, dtd, J=55.95, 4.65, 4.65, 1.40 Hz), 5.31 (2H, td, J=15.81, 2.87 Hz), 6.61 (1H, tt, J=54.30, 3.00 Hz), 6.77 (1H, d, J=2.46 Hz), 6.84 (1H, d, J=7.67 Hz), 7.63-7.66 (1H, m), 7.67 (1H, d, J=2.74 Hz), 8.04 (1H, d, J=7.94 Hz), 8.04 (1H, d, J=1.10 Hz); ESIMS found for $C_{22}H_{23}F_3N_8O_2$ m/z 489.2 (M+1).

1153

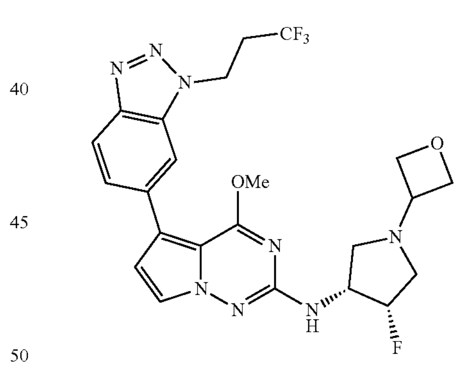

N-((3R,4S)-4-Fluoro-1-(oxetan-3-yl)pyrrolidin-3-yl)-4-methoxy-5-(1-(2,2,2-trifluoroethyl)-1H-benzo[d][1,2,3]triazol-6-yl)pyrrolo[2,1-f][1,2,4]triazin-2-amine 1153

Fluffy white solid (10 mg, 0.020 mmol, 28.1% yield). $^1$H NMR (499 MHz, DMSO-$d_6$) δ ppm 2.69 (1H, t, J=9.03 Hz), 2.77 (1H, ddd, J=29.90, 12.05, 1.37 Hz), 3.02 (1H, t, J=8.35 Hz), 3.18 (1H, ddd, J=32.90, 11.91, 4.52 Hz), 3.74-3.84 (1H, m), 3.95 (3H, s), 4.23-4.39 (1H, m), 4.47 (2H, t, J=6.02 Hz), 4.60 (2H, t, J=6.57 Hz), 5.25 (1H, dtd, J=55.95, 4.65, 4.65, 1.40 Hz), 5.88 (2H, q, J=9.13 Hz), 6.77 (1H, d, J=2.46 Hz), 6.86 (1H, d, J=7.67 Hz), 7.68 (1H, dd, J=8.62, 1.51 Hz), 7.68 (1H, d, J=2.74 Hz), 8.08 (1H, d, J=8.49 Hz), 8.11 (1H, s); ESIMS found for $C_{22}H_{22}F_4N_8O_2$ m/z 507.2 (M+1).

Example 12

Representative compounds were screened using the assay procedure for DYRK1A kinase activity as described below.

Each compound was dissolved in DMSO as a 10 mM stock and used to prepare compound source plates. Serial dilution (1:3, 11-point dose-response curves from 10 μM to 0.00016 μM) and compound transfer was performed using the ECHO 550 (Labcyte, Sunnyvale, CA) into 1536-well black-walled round bottom plates (Corning).

The DYRK1A kinase assay was run using the Ser/Thr 18 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRK1A kinase, ATP and Ser/Thr peptide 18 were prepared in 1× Kinase buffer to final concentrations of 0.25 μg/mL, 15 μM, and 4 μM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: [1−((Em ratio×F100%)−C100%)/((C0%−C100%)+(Em ratio×(F100%−F0%)))]. Dose-response curves were generated, and inhibitory concentration ($IC_{50}$) values were calculated using non-linear regression curve fit in the Dotmatics' Studies Software (Bishops Stortford, UK).

Table 2 shows the measured activity for representative compounds of Formula I as described herein.

TABLE 2

| Compound | $EC_{50}$ (μM) |
|---|---|
| 1 | 0.0224 |
| 3 | 0.0015 |
| 4 | 0.0011 |
| 6 | 0.0011 |
| 7 | 0.0046 |
| 8 | 0.0006 |
| 9 | 9.9633 |
| 10 | 0.0938 |
| 13 | 0.0055 |
| 15 | 0.0337 |
| 16 | 0.0344 |
| 17 | 0.0175 |
| 18 | 0.0074 |
| 19 | 0.0141 |
| 20 | 0.0034 |
| 24 | 0.0143 |
| 26 | 0.0071 |
| 27 | 9.9633 |
| 29 | 0.0092 |
| 30 | 0.0221 |
| 31 | 0.0077 |

TABLE 2-continued

| Compound | $EC_{50}$ (μM) |
|---|---|
| 34 | 0.0062 |
| 36 | 0.0121 |
| 37 | 0.0025 |
| 39 | 0.0029 |
| 40 | 0.0016 |
| 43 | 0.0013 |
| 44 | 0.0032 |
| 45 | 0.0093 |
| 49 | 0.0026 |
| 51 | 0.0067 |
| 52 | 0.0052 |
| 53 | 0.0007 |
| 54 | 0.0012 |
| 55 | 0.0067 |
| 56 | 0.0013 |
| 61 | 0.0049 |
| 62 | 0.0085 |
| 63 | 0.0046 |
| 67 | 0.0056 |
| 74 | 0.0052 |
| 80 | 0.0562 |
| 91 | 0.0016 |
| 92 | 0.0626 |
| 93 | 0.1944 |
| 94 | 0.0041 |
| 95 | 0.0082 |
| 96 | 0.0010 |
| 97 | 0.0011 |
| 98 | 0.0256 |
| 99 | 0.0045 |
| 102 | 0.0019 |
| 103 | 0.0059 |
| 104 | 0.0012 |
| 107 | 0.0009 |
| 108 | 0.0033 |
| 109 | 0.0010 |
| 112 | 0.0026 |
| 113 | 0.0033 |
| 114 | 0.0019 |
| 122 | 0.0016 |
| 124 | 0.0028 |
| 127 | 0.0022 |
| 129 | 0.0026 |
| 137 | 0.0019 |
| 138 | 0.0043 |
| 139 | 0.0069 |
| 140 | 0.0107 |
| 141 | 0.0218 |
| 142 | 0.0027 |
| 143 | 0.0108 |
| 148 | 0.0018 |
| 149 | 0.0015 |
| 151 | 0.0017 |
| 159 | 0.0029 |
| 161 | 0.0030 |
| 164 | 0.0021 |
| 168 | 0.0027 |
| 169 | 0.0021 |
| 170 | 0.0086 |
| 171 | 0.0029 |
| 172 | 0.0025 |
| 173 | 0.0017 |
| 174 | 0.0030 |
| 187 | 0.1003 |
| 188 | 0.0503 |
| 189 | 0.0188 |
| 190 | 0.0115 |
| 191 | 0.0053 |
| 192 | 0.0009 |
| 193 | 0.0199 |
| 194 | 0.0022 |
| 195 | 0.0039 |
| 196 | 0.0011 |
| 197 | 0.0296 |
| 198 | 0.0045 |
| 199 | 0.0057 |
| 200 | 0.0038 |

TABLE 2-continued

| Compound | $EC_{50}$ (μM) |
|---|---|
| 201 | 0.0020 |
| 202 | 0.0109 |
| 203 | 0.0075 |
| 204 | 0.0035 |
| 205 | 0.0043 |
| 206 | 0.0004 |
| 207 | 0.0013 |
| 208 | 0.0005 |
| 209 | 0.0088 |
| 210 | 0.0015 |
| 211 | 0.0066 |
| 212 | 0.0014 |
| 214 | 0.0022 |
| 217 | 0.0093 |
| 218 | 0.0029 |
| 222 | 0.0035 |
| 223 | 0.0016 |
| 224 | 0.0113 |
| 225 | 0.0117 |
| 226 | 0.0032 |
| 227 | 0.0036 |
| 228 | 0.0034 |
| 229 | 0.0019 |
| 230 | 0.0042 |
| 231 | 0.0072 |
| 233 | 0.0068 |
| 236 | 0.0005 |
| 239 | 0.0029 |
| 242 | 0.0044 |
| 243 | 0.0012 |
| 245 | 0.0007 |
| 250 | 0.0006 |
| 252 | 0.0025 |
| 254 | 0.0018 |
| 257 | 0.0004 |
| 258 | 0.0008 |
| 261 | 0.1532 |
| 262 | 0.0032 |
| 263 | 0.1117 |
| 264 | 0.0035 |
| 265 | 0.0589 |
| 266 | 0.0029 |
| 267 | 0.0048 |
| 268 | 0.0050 |
| 269 | 0.0023 |
| 270 | 0.0051 |
| 271 | 0.0038 |
| 272 | 0.0013 |
| 273 | 0.0018 |
| 274 | 0.0010 |
| 275 | 0.0034 |
| 276 | 0.0006 |
| 277 | 0.0633 |
| 280 | 0.0334 |
| 281 | 0.0066 |
| 282 | 0.0136 |
| 283 | 0.1099 |
| 284 | 0.2352 |
| 287 | 0.0022 |
| 288 | 0.0026 |
| 290 | 0.0018 |
| 304 | 0.0143 |
| 305 | 0.0807 |
| 306 | 0.0282 |
| 310 | 0.0047 |
| 314 | 0.0041 |
| 318 | 0.0042 |
| 319 | 0.0022 |
| 320 | 0.0082 |
| 321 | 0.0021 |
| 322 | 0.0066 |
| 326 | 0.0073 |
| 328 | 0.0054 |
| 329 | 0.0019 |
| 330 | 0.0023 |
| 331 | 0.0012 |
| 332 | 0.0028 |

TABLE 2-continued

| Compound | $EC_{50}$ (μM) |
|---|---|
| 333 | 0.0011 |
| 334 | 0.0009 |
| 335 | 0.0020 |
| 336 | 0.0013 |
| 337 | 0.0115 |
| 338 | 0.0012 |
| 339 | 0.0048 |
| 341 | 0.0093 |
| 342 | 0.0032 |
| 343 | 0.0007 |
| 344 | 0.0018 |
| 345 | 0.0037 |
| 346 | 0.0344 |
| 347 | 0.0017 |
| 348 | 0.0023 |
| 349 | 0.0066 |
| 350 | 0.0014 |
| 351 | 0.0081 |
| 352 | 0.0022 |
| 353 | 0.0022 |
| 355 | 0.0027 |
| 356 | 0.0088 |
| 362 | 0.0060 |
| 363 | 0.0401 |
| 365 | 0.0028 |
| 366 | 0.0025 |
| 367 | 0.0033 |
| 368 | 0.0040 |
| 372 | 0.0041 |
| 373 | 0.0029 |
| 374 | 0.0029 |
| 375 | 0.0033 |
| 379 | 0.0033 |
| 381 | 0.0025 |
| 382 | 0.0018 |
| 383 | 0.0014 |
| 385 | 0.0017 |
| 386 | 0.0009 |
| 387 | 0.0007 |
| 388 | 0.0012 |
| 389 | 0.0013 |
| 390 | 0.0030 |
| 391 | 0.0072 |
| 392 | 0.0014 |
| 393 | 0.1779 |
| 394 | 0.0021 |
| 395 | 0.0062 |
| 399 | 0.0035 |
| 401 | 0.0027 |
| 405 | 0.0007 |
| 431 | 0.0023 |
| 433 | 0.0026 |
| 434 | 0.0049 |
| 435 | 0.0089 |
| 439 | 0.0023 |
| 441 | 0.0011 |
| 445 | 0.0021 |
| 502 | 0.0014 |
| 503 | 0.0023 |
| 504 | 0.0014 |
| 505 | 0.0038 |
| 506 | 0.0023 |
| 507 | 0.0031 |
| 508 | 0.0243 |
| 509 | 0.0014 |
| 513 | 0.0028 |
| 519 | 0.0027 |
| 520 | 0.0030 |
| 521 | 0.0026 |
| 525 | 0.0024 |
| 526 | 0.0016 |
| 542 | 0.0011 |
| 544 | 0.0009 |
| 549 | 0.0026 |
| 550 | 0.0016 |
| 551 | 0.0016 |
| 554 | 0.0077 |

TABLE 2-continued

| Compound | $EC_{50}$ (μM) |
|---|---|
| 555 | 0.0050 |
| 562 | 0.0011 |
| 563 | 0.0010 |
| 567 | 0.0037 |
| 575 | 0.0069 |
| 576 | 0.0073 |
| 577 | 0.0064 |
| 578 | 0.0080 |
| 582 | 0.0409 |
| 585 | 0.0022 |
| 589 | 0.0009 |
| 616 | 0.0029 |
| 621 | 0.0354 |
| 622 | 0.0141 |
| 623 | 0.0051 |
| 624 | 0.0086 |
| 625 | 0.0009 |
| 626 | 0.0027 |
| 627 | 0.0039 |
| 628 | 0.0063 |
| 629 | 0.0024 |
| 630 | 0.0049 |
| 631 | 0.0245 |
| 639 | 0.0013 |
| 646 | 0.0034 |
| 653 | 0.0013 |
| 658 | 0.0045 |
| 659 | 0.0009 |
| 660 | <0.0002 |
| 664 | 0.0016 |
| 666 | 0.0011 |
| 669 | 0.0016 |
| 670 | 0.0008 |
| 672 | 0.0059 |
| 673 | 0.0053 |
| 681 | 0.0019 |
| 686 | 0.0034 |
| 688 | 0.0023 |
| 690 | 0.0078 |
| 691 | 0.0014 |
| 695 | 0.0013 |
| 696 | 0.0013 |
| 699 | 0.0014 |
| 702 | 0.0012 |
| 710 | 0.0009 |
| 711 | 0.0005 |
| 717 | 0.0023 |
| 718 | 0.0005 |
| 719 | 0.0003 |
| 721 | 0.0057 |
| 724 | 0.0011 |
| 725 | 0.0006 |
| 726 | 0.0018 |
| 727 | 0.0028 |
| 730 | 0.0046 |
| 732 | 0.0010 |
| 734 | 0.0008 |
| 739 | 0.0046 |
| 741 | 0.0012 |
| 750 | 0.0003 |
| 754 | 0.0017 |
| 755 | 0.0023 |
| 756 | 0.0014 |
| 757 | 0.0367 |
| 758 | 0.0011 |
| 761 | 0.0017 |
| 762 | 0.0013 |
| 764 | 0.0004 |
| 769 | 0.0029 |
| 770 | 0.0015 |
| 771 | 0.0001 |
| 772 | 0.0020 |
| 773 | 0.0007 |
| 776 | 0.0005 |
| 777 | 0.0016 |
| 780 | 0.0019 |
| 785 | 0.0005 |

TABLE 2-continued

| Compound | $EC_{50}$ (μM) |
|---|---|
| 788 | 0.0007 |
| 791 | 0.0022 |
| 793 | 0.0013 |
| 798 | 0.0003 |
| 799 | 0.0017 |
| 801 | 0.0032 |
| 805 | 0.0016 |
| 806 | 0.0014 |
| 810 | 0.0109 |
| 811 | 0.0017 |
| 812 | 0.0028 |
| 816 | 0.0028 |
| 818 | 0.0008 |
| 821 | 0.0019 |
| 822 | 0.0018 |
| 856 | 0.0019 |
| 904 | 0.0018 |
| 905 | 0.0004 |
| 910 | 0.0077 |
| 911 | 0.0021 |
| 912 | 0.0008 |
| 916 | 0.0014 |
| 918 | 0.0007 |
| 921 | 0.0014 |
| 922 | 0.0009 |
| 924 | 0.0021 |
| 926 | 0.0056 |
| 927 | 0.0012 |
| 928 | 0.0020 |
| 929 | 0.0198 |
| 930 | 0.0069 |
| 931 | 0.0015 |
| 934 | 0.0016 |
| 935 | 0.0012 |
| 942 | 0.0189 |
| 943 | 0.0036 |
| 944 | 0.0015 |
| 947 | 0.0022 |
| 948 | 0.0004 |
| 954 | 0.0009 |
| 964 | 0.0043 |
| 968 | 0.0028 |
| 975 | 0.0076 |
| 976 | 0.0025 |
| 977 | 0.0018 |
| 978 | 0.0024 |
| 996 | 0.0029 |
| 1038 | 0.0005 |
| 1039 | 0.0017 |
| 1040 | 0.0027 |
| 1041 | 0.0009 |
| 1042 | 0.0012 |
| 1043 | 0.0028 |
| 1044 | 0.0032 |
| 1045 | 0.0045 |
| 1047 | 0.0021 |
| 1048 | 0.0013 |
| 1049 | 0.0049 |
| 1050 | 0.0135 |
| 1052 | 0.0045 |
| 1054 | 0.0020 |
| 1056 | 0.0011 |
| 1057 | 0.0017 |
| 1058 | 0.0023 |
| 1059 | 0.0019 |
| 1061 | 0.0009 |
| 1062 | 0.0037 |
| 1064 | 0.0020 |
| 1089 | 0.0045 |
| 1090 | 0.0057 |
| 1091 | 0.0018 |
| 1093 | 0.0043 |
| 1095 | 0.0040 |
| 1096 | 0.0030 |
| 1097 | 0.0027 |
| 1099 | 0.0007 |
| 1100 | 0.0067 |

TABLE 2-continued

| Compound | $EC_{50}$ (μM) |
|---|---|
| 1130 | 0.0008 |
| 1136 | 0.0038 |
| 1137 | 0.0048 |
| 1138 | 0.0033 |
| 1139 | 0.0005 |
| 1140 | 0.0013 |
| 1141 | 0.0014 |
| 1142 | 0.0023 |
| 1143 | 0.0018 |
| 1144 | 0.0020 |
| 1145 | 0.0014 |
| 1146 | 0.0020 |
| 1147 | 0.0027 |
| 1148 | 0.0006 |
| 1149 | 0.0045 |
| 1150 | 0.0044 |

Example 13

Representative compounds were screened using the assay procedure for tau phosphorylation activity described below.

HEK293T cells (ATCC, CRL3216) cultured in DMEM (Thermo Fisher Scientific, 10566024) supplemented with 10% FBS (Corning, 35-011-CV) and Penicillin/Streptomycin (Thermo Fisher Scientific, 15140163) were seeded in a 75 $cm^2$ flask at $8.1\times10^6$ cells/flask. The HEK293T cells were then transiently transfected with 5 μg DYRK1A (NM_001396) human untagged clone (OriGene, SC314641) and 2.5 μg MAPT (441 a.a. Tau gene) (NM_005910) human untagged clone (OriGene, TP313312) using Lipofectamine 3000 (Thermo Fisher Scientific, L30000015) and incubated for 20-30 hours in a humidified incubator at 37° C. and 5% $CO^2$. Post-incubation, HEK293T cells transfected with the DYRK1A and MAPT expression vectors were harvested and seeded in BioCoat poly-D lysine coated 96-well plates (Corning, 354461) at $3\times10^4$ cells/well.

The above synthesized compounds were screened using the cell assay procedure to assess decreased Tau phosphorylation at Thr212 (pThr212) described below.

Each compound was dissolved in DMSO (Sigma-Aldrich, D8418-100 mL) as a 10 mM stock. 10 mM stocks were serially diluted 1:3, 10-point dose-response curve and added to the cells with a final concentration ranging from 20 μM to 1.1 nM. Cells were treated with compounds in duplicate and incubated for 18-24 hours in a humidified incubator at 37° C. and 5% $CO^2$.

Following the overnight compound treatment, cells were lysed with 1× Alpha Surefire Ultra Lysis Buffer (Perkin Elmer, ALSU-LB-100ML) complemented with 1× Halt Phosphatase Inhibitor Cocktail (Thermo Fisher Scientific, 78427) and 1× Halt Protease Inhibitor Cocktail (Thermo Fisher Scientific, 78438). Lysates were spun down at 12,000 g for 10 min to remove any cellular debris and 5 μL of lysates were dispensed into a 384-well Opti-Plate (Perkin Elmer, 6007290) for the measurement of Tau phosphorylation in the phosphoTau (Thr212) AlphaLISA assay. Donor antibody, biotinylated HT7Tau (Thermo Fisher Scientific, MN1000B), and acceptor antibody, pThr212Tau (Thermo Fisher Scientific, 44740G) were both added to the cell lysates at a final concentration of 3 nM and incubated for 1 hour at room temperature. Following incubation of the lysates with the donor and acceptor antibodies, anti-rabbit IgG (Fc specific) AlphaLISA acceptor beads (Perkin Elmer, AL104C) were added at a 10 ug/mL final concentration and incubated for 1 hour at room temperature protected from light. Lastly, AlphaScreen streptavidin donor beads (PerkinElmer, 6760002) were added at 40 ug/mL final concentration and incubated for 1 hour at room temperature protected from light. Plates were read at Ex=665 nm, and Em=615 nm on the EnVision Multilabel Plate Reader (Perkin Elmer). The phospho-Tau (Thr212) AlphaLISA signal was used to plot, draw the curve fitting, and determine each compound's $EC_{50}$ in Prism (GraphPad).

Table 3 shows the measured activity for representative compounds of Formula I as described herein.

TABLE 3

| Compound | pTau (Thr212) $EC_{50}$ (μM) |
|---|---|
| 1 | 0.0216 |
| 3 | 0.1966 |
| 20 | 0.1068 |
| 44 | 0.0482 |
| 54 | 0.0257 |
| 56 | 0.0357 |
| 192 | 0.0181 |
| 194 | 0.1071 |
| 200 | 0.1299 |
| 210 | 0.0197 |
| 257 | 0.0151 |
| 258 | 0.0089 |
| 272 | 0.0134 |
| 276 | 0.0101 |
| 310 | 0.1090 |
| 318 | 0.0754 |
| 352 | 0.0394 |
| 392 | 0.0252 |
| 431 | 0.1288 |
| 943 | 0.0575 |

What is claimed is:

1. A compound, or a pharmaceutically acceptable salt thereof, of Formula I:

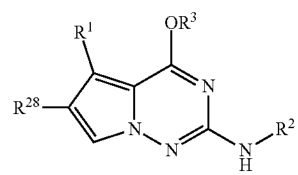

I wherein:

$R^1$ is heteroaryl optionally substituted with 1-10 $R^4$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^5$, —($C_{1-5}$ alkylene)CN, —($C_{1-5}$ alkylene)$_p$heterocyclyl optionally substituted with 1-10 $R^6$, —($C_{1-5}$ alkylene)$_p$aryl optionally substituted with 1-10 $R^{26}$, —($C_{1-5}$ alkylene)$_p$heteroaryl optionally substituted with 1-10 $R^7$, and —($C_{1-5}$ alkylene)$_p$carbocyclyl optionally substituted with 1-12 $R^8$, wherein each —($C_{1-5}$ alkylene) is, independently, optionally substituted with 1-5 halide and/or 1-3 unsubstituted —($C_{1-3}$ alkyl);

$R^3$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and heterocyclyl optionally substituted with 1-10 $R^{18}$;

each $R^4$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), unsubstituted —($C_{2-9}$ haloalkenyl), —($C_{1-5}$ alkylene)$_p$OR$^9$, —($C_{1-5}$ alkylene)$_p$CN, —($C_{1-5}$ alkylene)$_p$heterocyclyl optionally substituted with 1-10 $R^{10}$, -carbocyclyl optionally substituted with 1-12 $R^{11}$, —($C_{1-5}$ alkylene)$_p$heteroaryl optionally substituted with 1-10 $R^{20}$, —($C_{1-5}$ alkylene)$_p$C(═O)N($R^{12}$)$_2$, and —C(═O)$R^{13}$, wherein each —($C_{1-5}$ alkylene) is, independently, optionally substituted with 1-5 halide and/or 1-3 unsubstituted —($C_{1-3}$ alkyl);

each $R^5$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{16}$, -carbocyclyl optionally substituted with 1-12 $R^{17}$, —($C_{1-5}$ alkylene)$_p$OR$^{21}$, —($C_{1-5}$ alkylene)CN, —SO$_2$R$^{23}$, and —C(═O)R$^{24}$, wherein the —($C_{1-5}$ alkylene) is optionally substituted with 1-5 halide and/or 1-3 unsubstituted —($C_{1-3}$ alkyl);

alternatively, two $R^6$ attached to the same carbon atom are taken together to form a carbonyl group;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^8$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{14}$)$_2$, —($C_{1-5}$ alkylene)$_p$OR$^{15}$, —CN, —($C_{1-5}$ alkylene)$_p$heterocyclyl optionally substituted with 1-10 $R^{16}$, —C(═O)R$^{22}$, and —NR$^{14}$C(═O)R$^{23}$, wherein each —($C_{1-5}$ alkylene) is, independently, optionally substituted with 1-5 halide and/or 1-3 unsubstituted —($C_{1-3}$ alkyl);

each $R^9$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{12}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^{21'}$—($C_{1-5}$ alkylene)$_p$carbocyclyl optionally substituted with 1-12 $R^{17}$, -heterocyclyl optionally substituted with 1-10 $R^{18}$, and -heteroaryl optionally substituted with 1-10 $R^{19}$, wherein the —($C_{1-5}$ alkylene) is optionally substituted with 1-5 halide and/or 1-3 unsubstituted —($C_{1-3}$ alkyl);

each $R^{13}$ is -heterocyclyl optionally substituted with 1-10 $R^{18}$;

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{15}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{21}$;

each $R^{16}$ is independently selected from the group consisting of halide, —CN, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{27}$;

alternatively, two $R^{16}$ attached to the same carbon atom are taken together to form a carbonyl group;

each $R^{17}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{22}$ is independently selected from the group consisting of -heterocyclyl optionally substituted with 1-10 $R^{18}$, —N($R^{12}$)$_2$, and —OR$^{21}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^{21}$, and -carbocyclyl optionally substituted with 1-12 $R^{25}$;

each $R^{24}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —OR$^{21}$, and -carbocyclyl optionally substituted with 1-12 $R^{25}$;

each $R^{25}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —CN;

each $R^{26}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{27}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

$R^{28}$ is independently selected from the group consisting of H and halide; and each p is independently 0 or 1;

wherein each H atom is optionally, independently replaced by $^2$H (D) (deuterium).

2. The compound of claim 1, wherein $R^1$ is selected from the group consisting of:

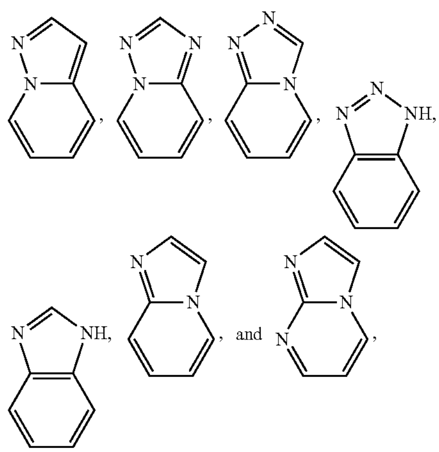

optionally substituted with 1-10 $R^4$.

3. The compound according to claim 2, wherein $R^1$ is selected from the group consisting of:

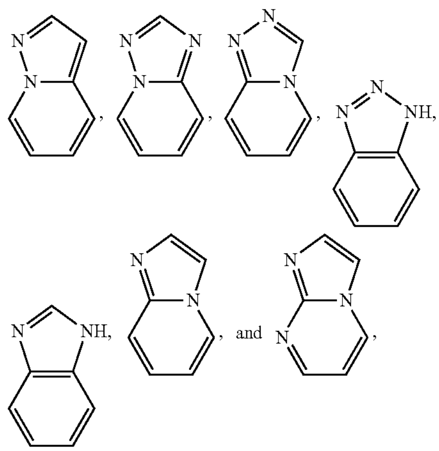

optionally substituted with 1-3 $R^4$.

4. The compound according to claim 3, wherein $R^1$ is selected from the group consisting of:

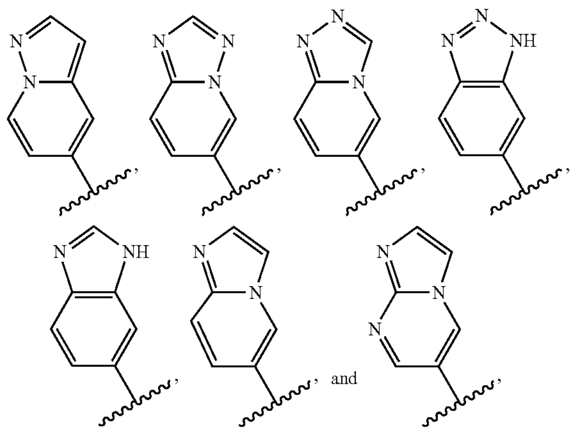

optionally substituted with 1-3 $R^4$.

5. The compound according to claim 4, wherein $R^1$ is selected from the group consisting of:

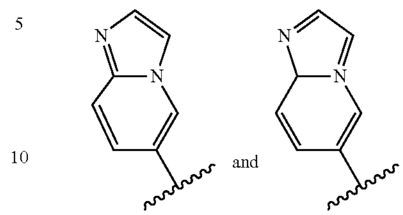

optionally substituted with 1-3 $R^4$.

6. The compound according to claim 5, wherein $R^1$ is selected from the group consisting of:

unsubstituted

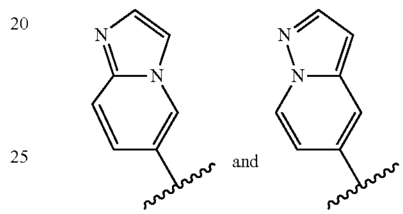

7. The compound according to claim 1, wherein $R^4$ is selected from the group consisting of halide, unsubstituted —($C_{1-3}$ alkyl), unsubstituted —($C_{1-3}$ haloalkyl), —($C_{1-3}$ alkylene)OH, —($C_{1-3}$ alkylene)OMe, —CN, and —C(=O)N($R^{12}$)$_2$.

8. The compound according to claim 1, wherein $R^2$ is selected from the group consisting of -heterocyclyl optionally substituted with 1-3 $R^6$, —($C_{1-2}$ alkylene)$_p$carbocyclyl optionally substituted with 1-3 $R^8$, and —($C_{1-2}$ alkylene)aryl optionally substituted with 1-2 $R^7$ wherein each —($C_{1-2}$ alkylene) is, independently, optionally substituted with 1-2 halide.

9. The compound according to claim 1, wherein $R^3$ is selected from the group consisting of unsubstituted —($C_{1-5}$ alkyl), unsubstituted —($C_{1-s}$ haloalkyl), and -heterocyclyl optionally substituted with 1-2 $R^{18}$.

10. The compound according to claim 9, wherein $R^3$ is selected from the group consisting of unsubstituted —($C_{1-3}$ alkyl) and unsubstituted —($C_{1-3}$ haloalkyl).

11. The compound according to claim 10, wherein $R^3$ is methyl.

12. The compound according to claim 1, wherein the compound of Formula I is selected from the group consisting of:

(1s,4s)-4-((5-(1-(2,2-difluoroethyl)-2-methyl-1H-imidazo[4,5-b]pyridin-6-yl)-4-methoxypyrrolo[2,1-f][1,2,4]triazin-2-yl)amino)-1-methylcyclohexan-1-ol [1];

(1r,4r)-4-((5-(3-(2,2-difluoroethyl)-2-methyl-3H-imidazo[4,5-b]pyridin-5-yl)-4-methoxypyrrolo[2,1-f][1,2,4]triazin-2-yl)amino)-1-methylcyclohexan-1-ol [2];

(1r,4r)-4-((4-methoxy-5-(1-methyl-1H-benzo[d][1,2,3]triazol-6-yl)pyrrolo[2,1-f][1,2,4]triazin-2-yl)amino)-1-methylcyclohexan-1-ol [3];

(1s,4s)-4-((5-(imidazo[1,2-a]pyrimidin-6-yl)-4-methoxypyrrolo[2,1-f][1,2,4]triazin-2-yl)amino)-1-methylcyclohexan-1-ol [4];

1-((4-methoxy-5-(pyrazolo[1,5-a]pyridin-5-yl)pyrrolo[2,1-f][1,2,4]triazin-2-yl)amino)-2-methylpropan-2-ol [5];

2-(cis-3-((4-methoxy-5-(pyrazolo[1,5-a]pyridin-5-yl)pyrrolo[2,1-f][1,2,4]triazin-2-yl)amino)cyclobutoxy)ethan-1-ol [6];

(1s,3s)-3-((4-methoxy-5-(pyrazolo[1,5-a]pyridin-5-yl)pyrrolo[2,1-f][1,2,4]triazin-2-yl)amino)-1-methylcyclobutan-1-ol [7];

(1r,3r)-3-((4-methoxy-5-(pyrazolo[1,5-a]pyridin-5-yl)pyrrolo[2,1-f][1,2,4]triazin-2-yl)amino)-1-methylcyclobutan-1-ol [8];

4-methoxy-N-(cis-4-methoxycyclohexyl)-5-(pyrazolo[1,5-a]pyridin-5-yl)pyrrolo[2,1-f][1,2,4]triazin-2-amine [9];

4-methoxy-N-(trans-4-methoxycyclohexyl)-5-(pyrazolo[1,5-a]pyridin-5-yl)pyrrolo[2,1-f][1,2,4]triazin-2-amine [10];

N-(cis-4-(difluoromethoxy)cyclohexyl)-4-methoxy-5-(pyrazolo[1,5-a]pyridin-5-yl)pyrrolo[2,1-f][1,2,4]triazin-2-amine [11];

N-(trans-4-(difluoromethoxy)cyclohexyl)-4-methoxy-5-(pyrazolo[1,5-a]pyridin-5-yl)pyrrolo[2,1-f][1,2,4]triazin-2-amine [12];

2-((cis-4-((4-methoxy-5-(pyrazolo[1,5-a]pyridin-5-yl)pyrrolo[2,1-f][1,2,4]triazin-2-yl)amino)cyclohexyl)oxy)ethan-1-ol [13];

2-((trans-4-((4-methoxy-5-(pyrazolo[1,5-a]pyridin-5-yl)pyrrolo[2,1-f][1,2,4]triazin-2-yl)amino)cyclohexyl)oxy)ethan-1-ol [14];

4-methoxy-N-(cis-4-(2-methoxyethoxy)cyclohexyl)-5-(pyrazolo[1,5-a]pyridin-5-yl)pyrrolo[2,1-f][1,2,4]triazin-2-amine [15];

4-methoxy-N-(trans-4-(2-methoxyethoxy)cyclohexyl)-5-(pyrazolo[1,5-a]pyridin-5-yl)pyrrolo[2,1-f][1,2,4]triazin-2-amine [16];

N-(cis-4-((4-methoxy-5-(pyrazolo[1,5-a]pyridin-5-yl)pyrrolo[2,1-f][1,2,4]triazin-2-yl)amino)cyclohexyl)acetamide [17];

N-(trans-4-((4-methoxy-5-(pyrazolo[1,5-a]pyridin-5-yl)pyrrolo[2,1-f][1,2,4]triazin-2-yl)amino)cyclohexyl)acetamide [18];

(1s,4s)-4-((4-methoxy-5-(pyrazolo[1,5-a]pyridin-5-yl)pyrrolo[2,1-f][1,2,4]triazin-2-yl)amino)-1-methylcyclohexan-1-ol [19];

(1r,4r)-4-((4-methoxy-5-(pyrazolo[1,5-a]pyridin-5-yl)pyrrolo[2,1-f][1,2,4]triazin-2-yl)amino)-1-methylcyclohexan-1-ol [20];

1-(3-((4-methoxy-5-(pyrazolo[1,5-a]pyridin-5-yl)pyrrolo[2,1-f][1,2,4]triazin-2-yl)amino)azetidin-1-yl)ethan-1-one [21];

N-((3R,4S)-4-fluoro-1-methylpyrrolidin-3-yl)-4-methoxy-5-(pyrazolo[1,5-a]pyridin-5-yl)pyrrolo[2,1-f][1,2,4]triazin-2-amine [22];

N-((3S,4R)-4-fluoro-1-methylpyrrolidin-3-yl)-4-methoxy-5-(pyrazolo[1,5-a]pyridin-5-yl)pyrrolo[2,1-f][1,2,4]triazin-2-amine [23];

N-(1-(2-fluoroethyl)piperidin-4-yl)-4-methoxy-5-(pyrazolo[1,5-a]pyridin-5-yl)pyrrolo[2,1-f][1,2,4]triazin-2-amine [24];

N-(1-(2,2-difluoroethyl)piperidin-4-yl)-4-methoxy-5-(pyrazolo[1,5-a]pyridin-5-yl)pyrrolo[2,1-f][1,2,4]triazin-2-amine [25];

4-methoxy-N-(1-(oxetan-3-yl)piperidin-4-yl)-5-(pyrazolo[1,5-a]pyridin-5-yl)pyrrolo[2,1-f][1,2,4]triazin-2-amine [26];

1-(4-((4-methoxy-5-(pyrazolo[1,5-a]pyridin-5-yl)pyrrolo[2,1-f][1,2,4]triazin-2-yl)amino)piperidin-1-yl)ethan-1-one [27];

4-methoxy-N-(1-(methylsulfonyl)piperidin-4-yl)-5-(pyrazolo[1,5-a]pyridin-5-yl)pyrrolo[2,1-f][1,2,4]triazin-2-amine [28];

N-((3S,4R)-3-fluoropiperidin-4-yl)-4-methoxy-5-(pyrazolo[1,5-a]pyridin-5-yl)pyrrolo[2,1-f][1,2,4]triazin-2-amine [29];

N-((3R,4S)-3-fluoropiperidin-4-yl)-4-methoxy-5-(pyrazolo[1,5-a]pyridin-5-yl)pyrrolo[2,1-f][1,2,4]triazin-2-amine [30];

N-((3S,4R)-3-fluoro-1-methylpiperidin-4-yl)-4-methoxy-5-(pyrazolo[1,5-a]pyridin-5-yl)pyrrolo[2,1-f][1,2,4]triazin-2-amine [31];

N-((3S,4S)-3-fluoro-1-methylpiperidin-4-yl)-4-methoxy-5-(pyrazolo[1,5-a]pyridin-5-yl)pyrrolo[2,1-f][1,2,4]triazin-2-amine [32];

N-((3R,4R)-3-fluoro-1-methylpiperidin-4-yl)-4-methoxy-5-(pyrazolo[1,5-a]pyridin-5-yl)pyrrolo[2,1-f][1,2,4]triazin-2-amine [33];

N-((3R,4S)-3-fluoro-1-methylpiperidin-4-yl)-4-methoxy-5-(pyrazolo[1,5-a]pyridin-5-yl)pyrrolo[2,1-f][1,2,4]triazin-2-amine [34];

(S)-5-((4-methoxy-5-(pyrazolo[1,5-a]pyridin-5-yl)pyrrolo[2,1-f][1,2,4]triazin-2-yl)amino)-1-methylpiperidin-2-one [35];

4-methoxy-5-(pyrazolo[1,5-a]pyridin-5-yl)-N-(tetrahydro-2H-pyran-4-yl)pyrrolo[2,1-f][1,2,4]triazin-2-amine [36];

1-(6-((4-methoxy-5-(pyrazolo[1,5-a]pyridin-5-yl)pyrrolo[2,1-f][1,2,4]triazin-2-yl)amino)-2-azaspiro[3.3]heptan-2-yl)ethan-1-one [37];

4-methoxy-5-(pyrazolo[1,5-a]pyridin-5-yl)-N-(2-oxaspiro[3.3]heptan-6-yl)pyrrolo[2,1-f][1,2,4]triazin-2-amine [38];

1-(2-((4-methoxy-5-(pyrazolo[1,5-a]pyridin-5-yl)pyrrolo[2,1-f][1,2,4]triazin-2-yl)amino)-7-azaspiro[3.5]nonan-7-yl)ethan-1-one [39];

1-(7-((4-methoxy-5-(pyrazolo[1,5-a]pyridin-5-yl)pyrrolo[2,1-f][1,2,4]triazin-2-yl)amino)-2-azaspiro[3.5]nonan-2-yl)ethan-1-one [40];

1-((5-(imidazo[1,2-a]pyridin-6-yl)-4-methoxypyrrolo[2,1-f][1,2,4]triazin-2-yl)amino)-2-methylpropan-2-ol [41];

2-(cis-3-((5-(imidazo[1,2-a]pyridin-6-yl)-4-methoxypyrrolo[2,1-f][1,2,4]triazin-2-yl)amino)cyclobutoxy)ethan-1-ol [42];

(1s,3s)-3-((5-(imidazo[1,2-a]pyridin-6-yl)-4-methoxypyrrolo[2,1-f][1,2,4]triazin-2-yl)amino)-1-methylcyclobutan-1-ol [43];

(1r,3r)-3-((5-(imidazo[1,2-a]pyridin-6-yl)-4-methoxypyrrolo[2,1-f][1,2,4]triazin-2-yl)amino)-1-methylcyclobutan-1-ol [44];

5-(imidazo[1,2-a]pyridin-6-yl)-4-methoxy-N-(cis-4-methoxycyclohexyl)pyrrolo[2,1-f][1,2,4]triazin-2-amine [45];

5-(imidazo[1,2-a]pyridin-6-yl)-4-methoxy-N-(trans-4-methoxycyclohexyl)pyrrolo[2,1-f][1,2,4]triazin-2-amine [46];

N-(cis-4-(difluoromethoxy)cyclohexyl)-5-(imidazo[1,2-a]pyridin-6-yl)-4-methoxypyrrolo[2,1-f][1,2,4]triazin-2-amine [47];

N-(trans-4-(difluoromethoxy)cyclohexyl)-5-(imidazo[1,2-a]pyridin-6-yl)-4-methoxypyrrolo[2,1-f][1,2,4]triazin-2-amine [48];

2-((cis-4-((5-(imidazo[1,2-a]pyridin-6-yl)-4-methoxypyrrolo[2,1-f][1,2,4]triazin-2-yl)amino)cyclohexyl)oxy)ethan-1-ol [49];

2-((trans-4-((5-(imidazo[1,2-a]pyridin-6-yl)-4-methoxy-pyrrolo[2,1-f][1,2,4]triazin-2-yl)amino)cyclohexyl)oxy)ethan-1-ol [50];

5-(imidazo[1,2-a]pyridin-6-yl)-4-methoxy-N-(cis-4-(2-methoxyethoxy)cyclohexyl)pyrrolo[2,1-f][1,2,4]triazin-2-amine [51];

5-(imidazo[1,2-a]pyridin-6-yl)-4-methoxy-N-(trans-4-(2-methoxyethoxy)cyclohexyl)pyrrolo[2,1-f][1,2,4]triazin-2-amine [52];

N-(cis-4-((5-(imidazo[1,2-a]pyridin-6-yl)-4-methoxypyrrolo[2,1-f][1,2,4]triazin-2-yl)amino)cyclohexyl)acetamide [53];

N-(trans-4-((5-(imidazo[1,2-a]pyridin-6-yl)-4-methoxy-pyrrolo[2,1-f][1,2,4]triazin-2-yl)amino)cyclohexyl)acetamide [54];

(1s,4s)-4-((5-(imidazo[1,2-a]pyridin-6-yl)-4-methoxy-pyrrolo[2,1-f][1,2,4]triazin-2-yl)amino)-1-methylcyclohexan-1-ol [55];

(1r,4r)-4-((5-(imidazo[1,2-a]pyridin-6-yl)-4-methoxypyrrolo[2,1-f][1,2,4]triazin-2-yl)amino)-1-methylcyclohexan-1-ol [56];

1-(3-((5-(imidazo[1,2-a]pyridin-6-yl)-4-methoxypyrrolo[2,1-f][1,2,4]triazin-2-yl)amino)azetidin-1-yl)ethan-1-one [57];

N-((3R,4S)-4-fluoro-1-methylpyrrolidin-3-yl)-5-(imidazo[1,2-a]pyridin-6-yl)-4-methoxypyrrolo[2,1-f][1,2,4]triazin-2-amine [58];

N-((3S,4R)-4-fluoro-1-methylpyrrolidin-3-yl)-5-(imidazo[1,2-a]pyridin-6-yl)-4-methoxypyrrolo[2,1-f][1,2,4]triazin-2-amine [59];

N-(1-(2-fluoroethyl)piperidin-4-yl)-5-(imidazo[1,2-a]pyridin-6-yl)-4-methoxypyrrolo[2,1-f][1,2,4]triazin-2-amine [60];

N-(1-(2,2-difluoroethyl)piperidin-4-yl)-5-(imidazo[1,2-a]pyridin-6-yl)-4-methoxypyrrolo[2,1-f][1,2,4]triazin-2-amine [61];

5-(imidazo[1,2-a]pyridin-6-yl)-4-methoxy-N-(1-(oxetan-3-yl)piperidin-4-yl)pyrrolo[2,1-f][1,2,4]triazin-2-amine [62];

1-(4-((5-(imidazo[1,2-a]pyridin-6-yl)-4-methoxypyrrolo[2,1-f][1,2,4]triazin-2-yl)amino)piperidin-1-yl)ethan-1-one [63];

5-(imidazo[1,2-a]pyridin-6-yl)-4-methoxy-N-(1-(methylsulfonyl)piperidin-4-yl)pyrrolo[2,1-f][1,2,4]triazin-2-amine [64];

N-((3S,4R)-3-fluoropiperidin-4-yl)-5-(imidazo[1,2-a]pyridin-6-yl)-4-methoxypyrrolo[2,1-f][1,2,4]triazin-2-amine [65];

N-((3R,4S)-3-fluoropiperidin-4-yl)-5-(imidazo[1,2-a]pyridin-6-yl)-4-methoxypyrrolo[2,1-f][1,2,4]triazin-2-amine [66];

N-((3S,4R)-3-fluoro-1-methylpiperidin-4-yl)-5-(imidazo[1,2-a]pyridin-6-yl)-4-methoxypyrrolo[2,1-f][1,2,4]triazin-2-amine [67];

N-((3R,4R)-3-fluoro-1-methylpiperidin-4-yl)-5-(imidazo[1,2-a]pyridin-6-yl)-4-methoxypyrrolo[2,1-f][1,2,4]triazin-2-amine [68];

N-((3S,4S)-3-fluoro-1-methylpiperidin-4-yl)-5-(imidazo[1,2-a]pyridin-6-yl)-4-methoxypyrrolo[2,1-f][1,2,4]triazin-2-amine [69];

N-((3R,4S)-3-fluoro-1-methylpiperidin-4-yl)-5-(imidazo[1,2-a]pyridin-6-yl)-4-methoxypyrrolo[2,1-f][1,2,4]triazin-2-amine [70];

(S)-5-((5-(imidazo[1,2-a]pyridin-6-yl)-4-methoxypyrrolo[2,1-f][1,2,4]triazin-2-yl)amino)-1-methylpiperidin-2-one [71];

5-(imidazo[1,2-a]pyridin-6-yl)-4-methoxy-N-(tetrahydro-2H-pyran-4-yl)pyrrolo[2,1-f][1,2,4]triazin-2-amine [72];

1-(6-((5-(imidazo[1,2-a]pyridin-6-yl)-4-methoxypyrrolo[2,1-f][1,2,4]triazin-2-yl)amino)-2-azaspiro[3.3]heptan-2-yl)ethan-1-one [73];

5-(imidazo[1,2-a]pyridin-6-yl)-4-methoxy-N-(2-oxaspiro[3.3]heptan-6-yl)pyrrolo[2,1-f][1,2,4]triazin-2-amine [74];

1-(2-((5-(imidazo[1,2-a]pyridin-6-yl)-4-methoxypyrrolo[2,1-f][1,2,4]triazin-2-yl)amino)-7-azaspiro[3.5]nonan-7-yl)ethan-1-one [75];

1-(7-((5-(imidazo[1,2-a]pyridin-6-yl)-4-methoxypyrrolo[2,1-f][1,2,4]triazin-2-yl)amino)-2-azaspiro[3.5]nonan-2-yl)ethan-1-one [76];

1-((1R,5S,6s)-6-((4-methoxy-5-(pyrazolo[1,5-a]pyridin-5-yl)pyrrolo[2,1-f][1,2,4]triazin-2-yl)amino)-3-azabicyclo[3.1.0]hexan-3-yl)ethan-1-one [77];

1-((1R,5S,6r)-6-((4-methoxy-5-(pyrazolo[1,5-a]pyridin-5-yl)pyrrolo[2,1-f][1,2,4]triazin-2-yl)amino)-3-azabicyclo[3.1.0]hexan-3-yl)ethan-1-one [78];

N-((1R,5S,6r)-3-oxabicyclo[3.1.0]hexan-6-yl)-4-methoxy-5-(pyrazolo[1,5-a]pyridin-5-yl)pyrrolo[2,1-f][1,2,4]triazin-2-amine [79];

N-((1R,5S,6s)-3-oxabicyclo[3.1.0]hexan-6-yl)-4-methoxy-5-(pyrazolo[1,5-a]pyridin-5-yl)pyrrolo[2,1-f][1,2,4]triazin-2-amine [80];

1-((1R,5S,6s)-6-((5-(imidazo[1,2-a]pyridin-6-yl)-4-methoxypyrrolo[2,1-f][1,2,4]triazin-2-yl)amino)-3-azabicyclo[3.1.0]hexan-3-yl)ethan-1-one [81];

1-((1R,5S,6r)-6-((5-(imidazo[1,2-a]pyridin-6-yl)-4-methoxypyrrolo[2,1-f][1,2,4]triazin-2-yl)amino)-3-azabicyclo[3.1.0]hexan-3-yl)ethan-1-one [82];

N-((1R,5S,6r)-3-oxabicyclo[3.1.0]hexan-6-yl)-5-(imidazo[1,2-a]pyridin-6-yl)-4-methoxypyrrolo[2,1-f][1,2,4]triazin-2-amine [83];

N-((1R,5S,6s)-3-oxabicyclo[3.1.0]hexan-6-yl)-5-(imidazo[1,2-a]pyridin-6-yl)-4-methoxypyrrolo[2,1-f][1,2,4]triazin-2-amine [84];

N-((1R,5S,6r)-3-oxabicyclo[3.1.0]hexan-6-yl)-5-(1-(2,2-difluoroethyl)-2-methyl-1H-imidazo[4,5-b]pyridin-6-yl)-4-methoxypyrrolo[2,1-f][1,2,4]triazin-2-amine [85];

N-((1R,5S,6s)-3-oxabicyclo[3.1.0]hexan-6-yl)-5-(1-(2,2-difluoroethyl)-2-methyl-1H-imidazo[4,5-b]pyridin-6-yl)-4-methoxypyrrolo[2,1-f][1,2,4]triazin-2-amine [86];

(1s,4s)-4-((4-(difluoromethoxy)-5-(pyrazolo[1,5-a]pyridin-5-yl)pyrrolo[2,1-f][1,2,4]triazin-2-yl)amino)-1-methylcyclohexan-1-ol [87];

(1r,4r)-4-((4-(difluoromethoxy)-5-(pyrazolo[1,5-a]pyridin-5-yl)pyrrolo[2,1-f][1,2,4]triazin-2-yl)amino)-1-methylcyclohexan-1-ol [88];

(1s,4s)-4-((4-(difluoromethoxy)-5-(imidazo[1,2-a]pyridin-6-yl)pyrrolo[2,1-f][1,2,4]triazin-2-yl)amino)-1-methylcyclohexan-1-ol [89];

(1r,4r)-4-((4-(difluoromethoxy)-5-(imidazo[1,2-a]pyridin-6-yl)pyrrolo[2,1-f][1,2,4]triazin-2-yl)amino)-1-methylcyclohexan-1-ol [90];

2-(cis-3-((4-ethoxy-5-(pyrazolo[1,5-a]pyridin-5-yl)pyrrolo[2,1-f][1,2,4]triazin-2-yl)amino)cyclobutoxy)ethan-1-ol [91];

tert-butyl 6-((4-methoxy-5-(pyrazolo[1,5-a]pyridin-5-yl)pyrrolo[2,1-f][1,2,4]triazin-2-yl)amino)-2-azaspiro[3.3]heptane-2-carboxylate [92];

(R)-4-methoxy-5-(pyrazolo[1,5-a]pyridin-5-yl)-N-(1-(pyridin-2-yl)ethyl)pyrrolo[2,1-f][1,2,4]triazin-2-amine [93];

(1r,3r)-$N^1$-(4-methoxy-5-(pyrazolo[1,5-a]pyridin-5-yl)pyrrolo[2,1-f][1,2,4]triazin-2-yl)-3-methylcyclobutane-1,3-diamine [94];

(1s,3s)-$N^1$-(4-methoxy-5-(pyrazolo[1,5-a]pyridin-5-yl)pyrrolo[2,1-f][1,2,4]triazin-2-yl)-3-methylcyclobutane-1,3-diamine [95];

N-((1r,3r)-3-((4-methoxy-5-(pyrazolo[1,5-a]pyridin-5-yl)pyrrolo[2,1-f][11,2,4]triazin-2-yl)amino)-1-methylcyclobutyl)acetamide [96];

N-((1s,3s)-3-((4-methoxy-5-(pyrazolo[1,5-a]pyridin-5-yl)pyrrolo[2,1-f][11,2,4]triazin-2-yl)amino)-1-methylcyclobutyl)acetamide [97];

tert-butyl ((1r,3r)-3-((4-methoxy-5-(pyrazolo[1,5-a]pyridin-5-yl)pyrrolo[2,1-f][1,2,4]triazin-2-yl)amino)-1-methylcyclobutyl)carbamate [98];

1-(6-((4-ethoxy-5-(pyrazolo[1,5-a]pyridin-5-yl)pyrrolo[2,1-f][1,2,4]triazin-2-yl)amino)-2-azaspiro[3.3]heptan-2-yl)ethan-1-one [99]; and 5-(2-(((1s,4s)-4-hydroxy-4-methylcyclohexyl)amino)-4-methoxypyrrolo[2,1-f][1,2,4]triazin-5-yl)pyrazolo[1,5-a]pyridine-3-carboxamide [100];

or a pharmaceutically acceptable salt thereof.

13. The compound according to claim 1, wherein the compound of Formula I is selected from the group consisting of:

5-(2-(((1s,4s)-4-hydroxy-4-methylcyclohexyl)amino)-4-methoxypyrrolo[2,1-f][1,2,4]triazin-5-yl)pyrazolo[1,5-a]pyridine-3-carboxamide [101];

5-(2-((2-oxaspiro[3.5]nonan-7-yl)amino)-4-methoxypyrrolo[2,1-f][1,2,4]triazin-5-yl)-N-methylpyrazolo[1,5-a]pyridine-3-carboxamide [102];

6-(2-(((1r,4r)-4-hydroxy-4-methylcyclohexyl)amino)-4-methoxypyrrolo[2,1-f][1,2,4]triazin-5-yl)imidazo[1,2-a]pyridine-3-carbonitrile [103];

6-(2-(((1r,4r)-4-hydroxy-4-methylcyclohexyl)amino)-4-methoxypyrrolo[2,1-f][1,2,4]triazin-5-yl)imidazo[1,2-a]pyridine-3-carboxamide [104];

6-(2-((4,4-difluorocyclohexyl)amino)-4-methoxypyrrolo[2,1-f][1,2,4]triazin-5-yl)-N-methylimidazo[1,2-a]pyridine-3-carboxamide [105];

6-(2-(((1s,4s)-4-hydroxy-4-methylcyclohexyl)amino)-4-methoxypyrrolo[2,1-f][1,2,4]triazin-5-yl)-N-methylimidazo[1,2-a]pyridine-3-carboxamide [106];

6-(2-((2-oxaspiro[3.5]nonan-7-yl)amino)-4-methoxypyrrolo[2,1-f][1,2,4]triazin-5-yl)-N-methylimidazo[1,2-a]pyridine-3-carboxamide [107];

N-((1s,3s)-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutyl)acetamide [108];

(1r,3r)-3-((5-(1-(2,2-difluoroethyl)-2-methyl-1H-benzo[d]imidazol-6-yl)-4-methoxypyrrolo[2,1-f][1,2,4]triazin-2-yl)amino)-N,N,1-trimethylcyclobutane-1-carboxamide [109];

azetidin-1-yl((1r,3r)-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutyl)methanone [110];

((1r,3r)-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutyl)(pyrrolidin-1-yl)methanone [111];

(1r,4r)-4-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclohexan-1-ol [112];

5-(1-(2,2-difluoroethyl)-2-methyl-1H-benzo[d]imidazol-6-yl)-N-((3S,4R)-4-fluoro-1-methylpyrrolidin-3-yl)-4-methoxypyrrolo[2,1-f][1,2,4]triazin-2-amine [113];

5-(1-(2,2-difluoroethyl)-2-methyl-1H-benzo[d]imidazol-6-yl)-N-((3R,4S)-4-fluoro-1-methylpyrrolidin-3-yl)-4-methoxypyrrolo[2,1-f][1,2,4]triazin-2-amine [114];

1-((3R,4S)-3-((5-(1-(2,2-difluoroethyl)-2-methyl-1H-benzo[d]imidazol-6-yl)-4-methoxypyrrolo[2,1-f][1,2,4]triazin-2-yl)amino)-4-fluoropyrrolidin-1-yl)ethan-1-one [115];

1-((3S,4R)-3-((5-(1-(2,2-difluoroethyl)-2-methyl-1H-benzo[d]imidazol-6-yl)-4-methoxypyrrolo[2,1-f][1,2,4]triazin-2-yl)amino)-4-fluoropyrrolidin-1-yl)ethan-1-one [116];

(S)—N-(4,4-difluoro-1-methylpyrrolidin-3-yl)-5-(1-(2,2-difluoroethyl)-2-methyl-1H-benzo[d]imidazol-6-yl)-4-methoxypyrrolo[2,1-f][1,2,4]triazin-2-amine [117];

(R)—N-(4,4-difluoro-1-methylpyrrolidin-3-yl)-5-(1-(2,2-difluoroethyl)-2-methyl-1H-benzo[d]imidazol-6-yl)-4-methoxypyrrolo[2,1-f][1,2,4]triazin-2-amine [118];

5-(1-(2,2-difluoroethyl)-2-methyl-1H-benzo[d]imidazol-6-yl)-N-(1-(2-fluoroethyl)piperidin-4-yl)-4-methoxypyrrolo[2,1-f][1,2,4]triazin-2-amine [119];

5-(1-(2,2-difluoroethyl)-2-methyl-1H-benzo[d]imidazol-6-yl)-N-(1-(2,2-difluoroethyl)piperidin-4-yl)-4-methoxypyrrolo[2,1-f][1,2,4]triazin-2-amine [120];

5-(1-(2,2-difluoroethyl)-2-methyl-1H-benzo[d]imidazol-6-yl)-4-methoxy-N-(1-(2,2,2-trifluoroethyl)piperidin-4-yl)pyrrolo[2,1-f][1,2,4]triazin-2-amine [121];

1-(4-((5-(1-(2,2-difluoroethyl)-2-methyl-1H-benzo[d]imidazol-6-yl)-4-methoxypyrrolo[2,1-f][1,2,4]triazin-2-yl)amino)piperidin-1-yl)ethan-1-one [122];

N-(1-(3,3-difluorocyclobutyl)piperidin-4-yl)-5-(1-(2,2-difluoroethyl)-2-methyl-1H-benzo[d]imidazol-6-yl)-4-methoxypyrrolo[2,1-f][1,2,4]triazin-2-amine [123];

5-(1-(2,2-difluoroethyl)-2-methyl-1H-benzo[d]imidazol-6-yl)-N-((3S,4R)-3-fluoro-1-methylpiperidin-4-yl)-4-methoxypyrrolo[2,1-f][1,2,4]triazin-2-amine [124];

5-(1-(2,2-difluoroethyl)-2-methyl-1H-benzo[d]imidazol-6-yl)-N-((3R,4R)-3-fluoro-1-methylpiperidin-4-yl)-4-methoxypyrrolo[2,1-f][1,2,4]triazin-2-amine [125];

5-(1-(2,2-difluoroethyl)-2-methyl-1H-benzo[d]imidazol-6-yl)-N-((3S,4S)-3-fluoro-1-methylpiperidin-4-yl)-4-methoxypyrrolo[2,1-f][1,2,4]triazin-2-amine [126];

5-(1-(2,2-difluoroethyl)-2-methyl-1H-benzo[d]imidazol-6-yl)-N-((3R,4S)-3-fluoro-1-methylpiperidin-4-yl)-4-methoxypyrrolo[2,1-f][1,2,4]triazin-2-amine [127];

5-(1-(2,2-difluoroethyl)-2-methyl-1H-benzo[d]imidazol-6-yl)-N-((3R,4S)-1-ethyl-3-fluoropiperidin-4-yl)-4-methoxypyrrolo[2,1-f][1,2,4]triazin-2-amine [128];

5-(1-(2,2-difluoroethyl)-2-methyl-1H-benzo[d]imidazol-6-yl)-N-((3S,4R)-3-fluoro-1-(2-fluoroethyl)piperidin-4-yl)-4-methoxypyrrolo[2,1-f][1,2,4]triazin-2-amine [129];

5-(1-(2,2-difluoroethyl)-2-methyl-1H-benzo[d]imidazol-6-yl)-N-((3R,4R)-3-fluoro-1-(2-fluoroethyl)piperidin-4-yl)-4-methoxypyrrolo[2,1-f][1,2,4]triazin-2-amine [130];

5-(1-(2,2-difluoroethyl)-2-methyl-1H-benzo[d]imidazol-6-yl)-N-((3S,4S)-3-fluoro-1-(2-fluoroethyl)piperidin-4-yl)-4-methoxypyrrolo[2,1-f][1,2,4]triazin-2-amine [131];

5-(1-(2,2-difluoroethyl)-2-methyl-1H-benzo[d]imidazol-6-yl)-N-((3R,4S)-3-fluoro-1-(2-fluoroethyl)piperidin-4-yl)-4-methoxypyrrolo[2,1-f][1,2,4]triazin-2-amine [132];

N-((3R,4S)-1-cyclopropyl-3-fluoropiperidin-4-yl)-5-(1-(2,2-difluoroethyl)-2-methyl-1H-benzo[d]imidazol-6-yl)-4-methoxypyrrolo[2,1-f][1,2,4]triazin-2-amine [133];

5-(1-(2,2-difluoroethyl)-2-methyl-1H-benzo[d]imidazol-6-yl)-N-((3S,4R)-3-fluoro-1-(oxetan-3-yl)piperidin-4-yl)-4-methoxypyrrolo[2,1-f][1,2,4]triazin-2-amine [134];

5-(1-(2,2-difluoroethyl)-2-methyl-1H-benzo[d]imidazol-6-yl)-N-((3R,4R)-3-fluoro-1-(oxetan-3-yl)piperidin-4-yl)-4-methoxypyrrolo[2,1-f][1,2,4]triazin-2-amine [135];

5-(1-(2,2-difluoroethyl)-2-methyl-1H-benzo[d]imidazol-6-yl)-N-((3S,4S)-3-fluoro-1-(oxetan-3-yl)piperidin-4-yl)-4-methoxypyrrolo[2,1-f][1,2,4]triazin-2-amine [136];

5-(1-(2,2-difluoroethyl)-2-methyl-1H-benzo[d]imidazol-6-yl)-N-((3R,4S)-3-fluoro-1-(oxetan-3-yl)piperidin-4-yl)-4-methoxypyrrolo[2,1-f][1,2,4]triazin-2-amine [137];

(R)—N-(3,3-difluoro-1-methylpiperidin-4-yl)-5-(1-(2,2-difluoroethyl)-2-methyl-1H-benzo[d]imidazol-6-yl)-4-methoxypyrrolo[2,1-f][1,2,4]triazin-2-amine [138];

(S)—N-(3,3-difluoro-1-methylpiperidin-4-yl)-5-(1-(2,2-difluoroethyl)-2-methyl-1H-benzo[d]imidazol-6-yl)-4-methoxypyrrolo[2,1-f][1,2,4]triazin-2-amine [139];

(R)—N-(1-cyclobutyl-3,3-difluoropiperidin-4-yl)-5-(1-(2,2-difluoroethyl)-2-methyl-1H-benzo[d]imidazol-6-yl)-4-methoxypyrrolo[2,1-f][1,2,4]triazin-2-amine [140];

(S)—N-(1-cyclobutyl-3,3-difluoropiperidin-4-yl)-5-(1-(2,2-difluoroethyl)-2-methyl-1H-benzo[d]imidazol-6-yl)-4-methoxypyrrolo[2,1-f][1,2,4]triazin-2-amine [141];

(R)—N-(3,3-difluoro-1-(oxetan-3-yl)piperidin-4-yl)-5-(1-(2,2-difluoroethyl)-2-methyl-1H-benzo[d]imidazol-6-yl)-4-methoxypyrrolo[2,1-f][1,2,4]triazin-2-amine [142];

(S)—N-(3,3-difluoro-1-(oxetan-3-yl)piperidin-4-yl)-5-(1-(2,2-difluoroethyl)-2-methyl-1H-benzo[d]imidazol-6-yl)-4-methoxypyrrolo[2,1-f][1,2,4]triazin-2-amine [143];

1-((4s,6r)-6-((5-(1-(2,2-difluoroethyl)-2-methyl-1H-benzo[d]imidazol-6-yl)-4-methoxypyrrolo[2,1-f][1,2,4]triazin-2-yl)amino)-1-azaspiro[3.3]heptan-1-yl)ethan-1-one [144];

1-((4r,6s)-6-((5-(1-(2,2-difluoroethyl)-2-methyl-1H-benzo[d]imidazol-6-yl)-4-methoxypyrrolo[2,1-f][1,2,4]triazin-2-yl)amino)-1-azaspiro[3.3]heptan-1-yl)ethan-1-one [145];

1-(7-((5-(1-(2,2-difluoroethyl)-2-methyl-1H-benzo[d]imidazol-6-yl)-4-methoxypyrrolo[2,1-f][1,2,4]triazin-2-yl)amino)-2-azaspiro[3.5]nonan-2-yl)ethan-1-one [146];

5-(1-(2,2-difluoroethyl)-2-methyl-1H-benzo[d]imidazol-6-yl)-4-methoxy-N-(2-oxaspiro[3.5]nonan-7-yl)pyrrolo[2,1-f][1,2,4]triazin-2-amine [147];

N-((1s,3s)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylcyclobutyl)acetamide [148];

N-((1r,3r)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylcyclobutyl)acetamide [149];

(1s,4s)-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylcyclohexan-1-ol [150];

(1r,4r)-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylcyclohexan-1-ol [151];

(S)—N-(4,4-difluoro-1-methylpyrrolidin-3-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [152];

(R)—N-(4,4-difluoro-1-methylpyrrolidin-3-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [153];

5-(1-(2,2-difluoroethyl)-4-fluoro-2-methyl-1H-benzo[d]imidazol-6-yl)-N-((3S,4R)-3-fluoro-1-methylpiperidin-4-yl)-4-methoxypyrrolo[2,1-f][1,2,4]triazin-2-amine [154];

5-(1-(2,2-difluoroethyl)-4-fluoro-2-methyl-1H-benzo[d]imidazol-6-yl)-N-((3R,4R)-3-fluoro-1-methylpiperidin-4-yl)-4-methoxypyrrolo[2,1-f][1,2,4]triazin-2-amine [155];

5-(1-(2,2-difluoroethyl)-4-fluoro-2-methyl-1H-benzo[d]imidazol-6-yl)-N-((3S,4S)-3-fluoro-1-methylpiperidin-4-yl)-4-methoxypyrrolo[2,1-f][1,2,4]triazin-2-amine [156];

5-(1-(2,2-difluoroethyl)-4-fluoro-2-methyl-1H-benzo[d]imidazol-6-yl)-N-((3R,4S)-3-fluoro-1-methylpiperidin-4-yl)-4-methoxypyrrolo[2,1-f][1,2,4]triazin-2-amine [157];

5-(1-(2,2-difluoroethyl)-4-fluoro-2-methyl-1H-benzo[d]imidazol-6-yl)-N-((3S,4R)-3-fluoro-1-(oxetan-3-yl)piperidin-4-yl)-4-methoxypyrrolo[2,1-f][1,2,4]triazin-2-amine [158];

5-(1-(2,2-difluoroethyl)-4-fluoro-2-methyl-1H-benzo[d]imidazol-6-yl)-N-((3R,4R)-3-fluoro-1-(oxetan-3-yl)piperidin-4-yl)-4-methoxypyrrolo[2,1-f][1,2,4]triazin-2-amine [159];

5-(1-(2,2-difluoroethyl)-4-fluoro-2-methyl-1H-benzo[d]imidazol-6-yl)-N-((3S,4S)-3-fluoro-1-(oxetan-3-yl)piperidin-4-yl)-4-methoxypyrrolo[2,1-f][1,2,4]triazin-2-amine [160];

5-(1-(2,2-difluoroethyl)-4-fluoro-2-methyl-1H-benzo[d]imidazol-6-yl)-N-((3R,4S)-3-fluoro-1-(oxetan-3-yl)piperidin-4-yl)-4-methoxypyrrolo[2,1-f][1,2,4]triazin-2-amine [161];

(R)—N-(3,3-difluoro-1-methylpiperidin-4-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [162];

(S)—N-(3,3-difluoro-1-methylpiperidin-4-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [163];

(R)—N-(3,3-difluoro-1-(oxetan-3-yl)piperidin-4-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [164];

(S)—N-(3,3-difluoro-1-(oxetan-3-yl)piperidin-4-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [165];

1-((4s,6r)-6-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-azaspiro[3.3]heptan-1-yl)ethan-1-one [166];

1-((4r,6s)-6-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-azaspiro[3.3]heptan-1-yl)ethan-1-one [167];

(1r,4r)-4-((5-(4-fluoro-1-isopropyl-2-methyl-1H-benzo[d]imidazol-6-yl)-4-methoxypyrrolo[2,1-f][1,2,4]triazin-2-yl)amino)-1-methylcyclohexan-1-ol [168];

(1s,3s)-3-((5-(1-(2-hydroxyethyl)-2-methyl-1H-benzo[d]imidazol-6-yl)-4-methoxypyrrolo[2,1-f][1,2,4]triazin-2-yl)amino)-1-methylcyclobutan-1-ol [169];

(1r,3r)-3-((5-(1-(2-hydroxyethyl)-2-methyl-1H-benzo[d]imidazol-6-yl)-4-methoxypyrrolo[2,1-f][1,2,4]triazin-2-yl)amino)-1-methylcyclobutan-1-ol [170];

N-((1r,3r)-3-((5-(1-(2-hydroxyethyl)-2-methyl-1H-benzo[d]imidazol-6-yl)-4-methoxypyrrolo[2,1-f][1,2,4]triazin-2-yl)amino)-1-methylcyclobutyl)acetamide [171];

(1r,4r)-4-((5-(1-(2-hydroxyethyl)-2-methyl-1H-benzo[d]imidazol-6-yl)-4-methoxypyrrolo[2,1-f][1,2,4]triazin-2-yl)amino)-1-methylcyclohexan-1-ol [172];

1-(7-((5-(1-(2-hydroxyethyl)-2-methyl-1H-benzo[d]imidazol-6-yl)-4-methoxypyrrolo[2,1-f][1,2,4]triazin-2-yl)amino)-2-azaspiro[3.5]nonan-2-yl)ethan-1-one [173];

2-(6-(2-((2-oxaspiro[3.5]nonan-7-yl)amino)-4-methoxypyrrolo[2,1-f][1,2,4]triazin-5-yl)-2-methyl-1H-benzo[d]imidazol-1-yl)ethan-1-ol [174];

5-([1,2,4]triazolo[1,5-a]pyridin-7-yl)-N-((3S,4R)-3-fluoro-1-methylpiperidin-4-yl)-4-methoxypyrrolo[2,1-f][1,2,4]triazin-2-amine [175];

5-([1,2,4]triazolo[1,5-a]pyridin-7-yl)-N-((3R,4R)-3-fluoro-1-methylpiperidin-4-yl)-4-methoxypyrrolo[2,1-f][1,2,4]triazin-2-amine [176];

5-([1,2,4]triazolo[1,5-a]pyridin-7-yl)-N-((3R,4S)-3-fluoro-1-methylpiperidin-4-yl)-4-methoxypyrrolo[2,1-f][1,2,4]triazin-2-amine [177];

5-([1,2,4]triazolo[1,5-a]pyridin-7-yl)-N-((3S,4S)-3-fluoro-1-methylpiperidin-4-yl)-4-methoxypyrrolo[2,1-f][1,2,4]triazin-2-amine [178];

5-([1,2,4]triazolo[1,5-a]pyridin-7-yl)-N-((3S,4R)-3-fluoro-1-(oxetan-3-yl)piperidin-4-yl)-4-methoxypyrrolo[2,1-f][1,2,4]triazin-2-amine [179];

5-([1,2,4]triazolo[1,5-a]pyridin-7-yl)-N-((3R,4R)-3-fluoro-1-(oxetan-3-yl)piperidin-4-yl)-4-methoxypyrrolo[2,1-f][1,2,4]triazin-2-amine [180];

5-([1,2,4]triazolo[1,5-a]pyridin-7-yl)-N-((3S,4S)-3-fluoro-1-(oxetan-3-yl)piperidin-4-yl)-4-methoxypyrrolo[2,1-f][1,2,4]triazin-2-amine [181];

5-([1,2,4]triazolo[1,5-a]pyridin-7-yl)-N-((3R,4S)-3-fluoro-1-(oxetan-3-yl)piperidin-4-yl)-4-methoxypyrrolo[2,1-f][1,2,4]triazin-2-amine [182];

(R)-5-([1,2,4]triazolo[1,5-a]pyridin-7-yl)-N-(3,3-difluoro-1-methylpiperidin-4-yl)-4-methoxypyrrolo[2,1-f][1,2,4]triazin-2-amine [183];

(S)-5-([1,2,4]triazolo[1,5-a]pyridin-7-yl)-N-(3,3-difluoro-1-methylpiperidin-4-yl)-4-methoxypyrrolo[2,1-f][1,2,4]triazin-2-amine [184];

(R)-5-([1,2,4]triazolo[1,5-a]pyridin-7-yl)-N-(3,3-difluoro-1-(oxetan-3-yl)piperidin-4-yl)-4-methoxypyrrolo[2,1-f][1,2,4]triazin-2-amine [185];

(S)-5-([1,2,4]triazolo[1,5-a]pyridin-7-yl)-N-(3,3-difluoro-1-(oxetan-3-yl)piperidin-4-yl)-4-methoxypyrrolo[2,1-f][1,2,4]triazin-2-amine [186];

(1r,4r)-4-((5-([1,2,4]triazolo[4,3-a]pyridin-6-yl)-4-methoxypyrrolo[2,1-f][1,2,4]triazin-2-yl)amino)-1-methylcyclohexan-1-ol [187];

5-([1,2,4]triazolo[4,3-a]pyridin-6-yl)-4-methoxy-N-(2-oxaspiro[3.5]nonan-7-yl)pyrrolo[2,1-f][1,2,4]triazin-2-amine [188];

(1s,3s)-$N^1$-(5-([1,2,4]triazolo[1,5-a]pyridin-6-yl)-4-methoxypyrrolo[2,1-f][1,2,4]triazin-2-yl)-3-methylcyclobutane-1,3-diamine [189];

(1r,3r)-$N^1$-(5-([1,2,4]triazolo[1,5-a]pyridin-6-yl)-4-methoxypyrrolo[2,1-f][1,2,4]triazin-2-yl)-3-methylcyclobutane-1,3-diamine [190];

N-((1s,3s)-3-((5-([1,2,4]triazolo[1,5-a]pyridin-6-yl)-4-methoxypyrrolo[2,1-f][1,2,4]triazin-2-yl)amino)-1-methylcyclobutyl)acetamide [191];

N-((1r,3r)-3-((5-([1,2,4]triazolo[1,5-a]pyridin-6-yl)-4-methoxypyrrolo[2,1-f][1,2,4]triazin-2-yl)amino)-1-methylcyclobutyl)acetamide [192];

5-([1,2,4]triazolo[1,5-a]pyridin-6-yl)-N-(4,4-difluorocyclohexyl)-4-methoxypyrrolo[2,1-f][1,2,4]triazin-2-amine [193];

(1r,4r)-4-((5-([1,2,4]triazolo[1,5-a]pyridin-6-yl)-4-methoxypyrrolo[2,1-f][1,2,4]triazin-2-yl)amino)-1-methylcyclohexan-1-ol [194];

5-([1,2,4]triazolo[1,5-a]pyridin-6-yl)-4-methoxy-N-(2-azaspiro[3.5]nonan-7-yl)pyrrolo[2,1-f][1,2,4]triazin-2-amine [195];

1-(7-((5-([1,2,4]triazolo[1,5-a]pyridin-6-yl)-4-methoxypyrrolo[2,1-f][1,2,4]triazin-2-yl)amino)-2-azaspiro[3.5]nonan-2-yl)ethan-1-one [196];

tert-butyl 7-((5-([1,2,4]triazolo[1,5-a]pyridin-6-yl)-4-methoxypyrrolo[2,1-f][1,2,4]triazin-2-yl)amino)-2-azaspiro[3.5]nonane-2-carboxylate [197];

5-([1,2,4]triazolo[1,5-a]pyridin-6-yl)-4-methoxy-N-(2-oxaspiro[3.5]nonan-7-yl)pyrrolo[2,1-f][1,2,4]triazin-2-amine [198];

(1s,3s)-3-((4-methoxy-5-(1-methyl-1H-benzo[d][1,2,3]triazol-6-yl)pyrrolo[2,1-f][1,2,4]triazin-2-yl)amino)-1-methylcyclobutan-1-ol [199]; and (1r,3r)-3-((4-methoxy-5-(1-methyl-1H-benzo[d][1,2,3]triazol-6-yl)pyrrolo[2,1-f][1,2,4]triazin-2-yl)amino)-1-methylcyclobutan-1-ol [200];

or a pharmaceutically acceptable salt thereof.

14. The compound according to claim 1, wherein the compound of Formula I is selected from the group consisting of:

2-(cis-3-((4-methoxy-5-(1-methyl-1H-benzo[d][1,2,3]triazol-6-yl)pyrrolo[2,1-f][1,2,4]triazin-2-yl)amino)cyclobutoxy)ethan-1-ol [201];

(1s,3s)-$N^1$-(4-methoxy-5-(1-methyl-1H-benzo[d][1,2,3]triazol-6-yl)pyrrolo[2,1-f][1,2,4]triazin-2-yl)-3-methylcyclobutane-1,3-diamine [202];

(1r,3r)-$N^1$-(4-methoxy-5-(1-methyl-1H-benzo[d][1,2,3]triazol-6-yl)pyrrolo[2,1-f][1,2,4]triazin-2-yl)-3-methylcyclobutane-1,3-diamine [203];

(1s,3s)-$N^3$-(4-methoxy-5-(1-methyl-1H-benzo[d][1,2,3]triazol-6-yl)pyrrolo[2,1-f][1,2,4]triazin-2-yl)-$N^1$,$N^1$,1-trimethylcyclobutane-1,3-diamine [204];

N-((1s,3s)-3-((4-methoxy-5-(1-methyl-1H-benzo[d][1,2,3]triazol-6-yl)pyrrolo[2,1-f][1,2,4]triazin-2-yl)amino)-1-methylcyclobutyl)acetamide [205];

N-((1r,3r)-3-((4-methoxy-5-(1-methyl-1H-benzo[d][1,2,3]triazol-6-yl)pyrrolo[2,1-f][1,2,4]triazin-2-yl)amino)-1-methylcyclobutyl)acetamide [206];

N-((1r,3r)-3-((4-methoxy-5-(1-methyl-1H-benzo[d][1,2,3]triazol-6-yl)pyrrolo[2,1-f][1,2,4]triazin-2-yl)amino)-1-methylcyclobutyl)propionamide [207];

2-methoxy-N-((1r,3r)-3-((4-methoxy-5-(1-methyl-1H-benzo[d][1,2,3]triazol-6-yl)pyrrolo[2,1-f][1,2,4]triazin-2-yl)amino)-1-methylcyclobutyl)acetamide [208];

(1s,3s)-3-((4-methoxy-5-(1-methyl-1H-benzo[d][1,2,3]triazol-6-yl)pyrrolo[2,1-f][1,2,4]triazin-2-yl)amino)-N,1-dimethylcyclobutane-1-carboxamide [209];

(1r,3r)-3-((4-methoxy-5-(1-methyl-1H-benzo[d][1,2,3]triazol-6-yl)pyrrolo[2,1-f][1,2,4]triazin-2-yl)amino)-N,1-dimethylcyclobutane-1-carboxamide [210];

(1s,3s)-3-((4-methoxy-5-(1-methyl-1H-benzo[d][1,2,3]triazol-6-yl)pyrrolo[2,1-f][1,2,4]triazin-2-yl)amino)-N,N,1-trimethylcyclobutane-1-carboxamide [211];

(1r,3r)-3-((4-methoxy-5-(1-methyl-1H-benzo[d][1,2,3]triazol-6-yl)pyrrolo[2,1-f][1,2,4]triazin-2-yl)amino)-N,N,1-trimethylcyclobutane-1-carboxamide [212];

(1s,3s)-3-((4-methoxy-5-(1-methyl-1H-benzo[d][1,2,3]triazol-6-yl)pyrrolo[2,1-f][1,2,4]triazin-2-yl)amino)-N-(2-methoxyethyl)-1-methylcyclobutane-1-carboxamide [213];

(1r,3r)-3-((4-methoxy-5-(1-methyl-1H-benzo[d][1,2,3]triazol-6-yl)pyrrolo[2,1-f][1,2,4]triazin-2-yl)amino)-N-(2-methoxyethyl)-1-methylcyclobutane-1-carboxamide [214];

(1r,3r)-N-(2-fluoroethyl)-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide [215];

(1r,3r)-N-(2,2-difluoroethyl)-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide [216];

(1s,3s)-N-cyclopropyl-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide [217];

(1r,3r)-N-cyclopropyl-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide [218];

(1r,3r)-N-cyclobutyl-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide [219];

(1r,3r)-N-(3,3-difluorocyclobutyl)-3-((4-methoxy-5-(1-methyl-1H-benzo[d][1,2,3]triazol-6-yl)pyrrolo[2,1-f][1,2,4]triazin-2-yl)amino)-1-methylcyclobutane-1-carboxamide [220];

(1r,3r)-3-((4-methoxy-5-(1-methyl-1H-benzo[d][1,2,3]triazol-6-yl)pyrrolo[2,1-f][1,2,4]triazin-2-yl)amino)-1-methyl-N-(oxetan-3-yl)cyclobutane-1-carboxamide [221];

((1r,3r)-3-((4-methoxy-5-(1-methyl-1H-benzo[d][1,2,3]triazol-6-yl)pyrrolo[2,1-f][1,2,4]triazin-2-yl)amino)-1-methylcyclobutyl)(pyrrolidin-1-yl)methanone [222];

1-((1r,3r)-3-((4-methoxy-5-(1-methyl-1H-benzo[d][1,2,3]triazol-6-yl)pyrrolo[2,1-f][1,2,4]triazin-2-yl)amino)-1-methylcyclobutyl)pyrrolidin-2-one [223];

(1s,4s)-4-((4-methoxy-5-(1-methyl-1H-benzo[d][1,2,3]triazol-6-yl)pyrrolo[2,1-f][1,2,4]triazin-2-yl)amino)-1-methylcyclohexan-1-ol [224];

(1s,4s)-4-((4-methoxy-5-(1-methyl-1H-benzo[d][1,2,3]triazol-6-yl)pyrrolo[2,1-f][1,2,4]triazin-2-yl)amino)-N,1-dimethylcyclohexane-1-carboxamide [225];

3-((4-methoxy-5-(1-methyl-1H-benzo[d][1,2,3]triazol-6-yl)pyrrolo[2,1-f][1,2,4]triazin-2-yl)amino)-N-methylbicyclo[1.1.1]pentane-1-carboxamide [226];

1-(2-((4-methoxy-5-(1-methyl-1H-benzo[d][1,2,3]triazol-6-yl)pyrrolo[2,1-f][1,2,4]triazin-2-yl)amino)-7-azaspiro[3.5]nonan-7-yl)ethan-1-one [227];

1-((3aR,5r,6aS)-5-((4-methoxy-5-(1-methyl-1H-benzo[d][1,2,3]triazol-6-yl)pyrrolo[2,1-f][1,2,4]triazin-2-yl)amino)hexahydrocyclopenta[c]pyrrol-2 (1H)-yl)ethan-1-one [228];

1-(7-((4-methoxy-5-(1-methyl-1H-benzo[d][1,2,3]triazol-6-yl)pyrrolo[2,1-f][1,2,4]triazin-2-yl)amino)-2-azaspiro[3.5]nonan-2-yl)ethan-1-one [229];

4-methoxy-5-(1-methyl-1H-benzo[d][1,2,3]triazol-6-yl)-N-(2-oxaspiro[3.5]nonan-7-yl)pyrrolo[2,1-f][1,2,4]triazin-2-amine [230];

(R)—N-(1-cyclopropylethyl)-5-(imidazo[1,2-a]pyrimidin-6-yl)-4-methoxypyrrolo[2,1-f][1,2,4]triazin-2-amine [231];

(S)—N-(1-cyclopropylethyl)-5-(imidazo[1,2-a]pyrimidin-6-yl)-4-methoxypyrrolo[2,1-f][1,2,4]triazin-2-amine [232];

(R)-5-(imidazo[1,2-a]pyrimidin-6-yl)-4-methoxy-N-(1-phenylethyl)pyrrolo[2,1-f][1,2,4]triazin-2-amine [233];

(R)-5-(imidazo[1,2-a]pyrimidin-6-yl)-4-methoxy-N-(1-(pyridin-2-yl)ethyl)pyrrolo[2,1-f][1,2,4]triazin-2-amine [234];

(S)-5-(imidazo[1,2-a]pyrimidin-6-yl)-4-methoxy-N-(1-(pyridin-2-yl)ethyl)pyrrolo[2,1-f][1,2,4]triazin-2-amine [235];

5-(imidazo[1,2-a]pyrimidin-6-yl)-4-methoxy-N-(cis-3-methoxycyclobutyl)pyrrolo[2,1-f][1,2,4]triazin-2-amine [236];

N-((1R,2S)-2-fluorocyclohexyl)-5-(imidazo[1,2-a]pyrimidin-6-yl)-4-methoxypyrrolo[2,1-f][1,2,4]triazin-2-amine [237];

N-((1S,2R)-2-fluorocyclohexyl)-5-(imidazo[1,2-a]pyrimidin-6-yl)-4-methoxypyrrolo[2,1-f][1,2,4]triazin-2-amine [238];

5-(imidazo[1,2-a]pyrimidin-6-yl)-4-methoxy-N-(cis-4-(trifluoromethyl)cyclohexyl)pyrrolo[2,1-f][1,2,4]triazin-2-amine [239];

5-(imidazo[1,2-a]pyrimidin-6-yl)-4-methoxy-N-(trans-4-(trifluoromethyl)cyclohexyl)pyrrolo[2,1-f][1,2,4]triazin-2-amine [240];

2-(cis-4-((5-(imidazo[1,2-a]pyrimidin-6-yl)-4-methoxypyrrolo[2,1-f][1,2,4]triazin-2-yl)amino)cyclohexyl)propan-2-ol [241];

2-(trans-4-((5-(imidazo[1,2-a]pyrimidin-6-yl)-4-methoxypyrrolo[2,1-f][1,2,4]triazin-2-yl)amino)cyclohexyl)propan-2-ol [242];

5-(imidazo[1,2-a]pyrimidin-6-yl)-4-methoxy-N-(cis-4-methoxycyclohexyl)pyrrolo[2,1-f][1,2,4]triazin-2-amine [243];

5-(imidazo[1,2-a]pyrimidin-6-yl)-4-methoxy-N-(trans-4-methoxycyclohexyl)pyrrolo[2,1-f][1,2,4]triazin-2-amine [244];

5-(imidazo[1,2-a]pyrimidin-6-yl)-4-methoxy-N-(cis-4-(methoxy-$d_3$)cyclohexyl)pyrrolo[2,1-f][1,2,4]triazin-2-amine [245];

N-(cis-4-ethoxycyclohexyl)-5-(imidazo[1,2-a]pyrimidin-6-yl)-4-methoxypyrrolo[2,1-f][1,2,4]triazin-2-amine [246];

N-(trans-4-ethoxycyclohexyl)-5-(imidazo[1,2-a]pyrimidin-6-yl)-4-methoxypyrrolo[2,1-f][1,2,4]triazin-2-amine [247];

5-(imidazo[1,2-a]pyrimidin-6-yl)-N-(cis-4-isopropoxy-cyclohexyl)-4-methoxypyrrolo[2,1-f][1,2,4]triazin-2-amine [248];

5-(imidazo[1,2-a]pyrimidin-6-yl)-N-(trans-4-isopropoxy-cyclohexyl)-4-methoxypyrrolo[2,1-f][1,2,4]triazin-2-amine [249];

N-(cis-4-(difluoromethoxy)cyclohexyl)-5-(imidazo[1,2-a]pyrimidin-6-yl)-4-methoxypyrrolo[2,1-f][1,2,4]triazin-2-amine [250];

N-(trans-4-(difluoromethoxy)cyclohexyl)-5-(imidazo[1,2-a]pyrimidin-6-yl)-4-methoxypyrrolo[2,1-f][1,2,4]triazin-2-amine [251];

5-(imidazo[1,2-a]pyrimidin-6-yl)-4-methoxy-N-(cis-4-(trifluoromethoxy)cyclohexyl)pyrrolo[2,1-f][1,2,4]triazin-2-amine [252];

5-(imidazo[1,2-a]pyrimidin-6-yl)-4-methoxy-N-(trans-4-(trifluoromethoxy)cyclohexyl)pyrrolo[2,1-f][1,2,4]triazin-2-amine [253];

N-(4,4-difluorocyclohexyl)-5-(imidazo[1,2-a]pyrimidin-6-yl)-4-methoxypyrrolo[2,1-f][1,2,4]triazin-2-amine [254];

(R)—N-(2,2-difluorocyclohexyl)-5-(imidazo[1,2-a]pyrimidin-6-yl)-4-methoxypyrrolo[2,1-f][1,2,4]triazin-2-amine [255];

(S)—N-(2,2-difluorocyclohexyl)-5-(imidazo[1,2-a]pyrimidin-6-yl)-4-methoxypyrrolo[2,1-f][1,2,4]triazin-2-amine [256];

(1r,4r)-4-((5-(imidazo[1,2-a]pyrimidin-6-yl)-4-methoxypyrrolo[2,1-f][1,2,4]triazin-2-yl)amino)-1-methylcyclohexan-1-ol [257];

(1r,4r)-1-ethyl-4-((5-(imidazo[1,2-a]pyrimidin-6-yl)-4-methoxypyrrolo[2,1-f][1,2,4]triazin-2-yl)amino)cyclohexan-1-ol [258];

1-(3-((5-(imidazo[1,2-a]pyrimidin-6-yl)-4-methoxypyrrolo[2,1-f][1,2,4]triazin-2-yl)amino)azetidin-1-yl)ethan-1-one [259];

5-(imidazo[1,2-a]pyrimidin-6-yl)-4-methoxy-N-(1-(oxetan-3-yl)azetidin-3-yl)pyrrolo[2,1-f][1,2,4]triazin-2-amine [260];

2-(((3R,4S)-4-fluoro-1-methylpyrrolidin-3-yl)amino)-5-(imidazo[1,2-a]pyrimidin-6-yl)pyrrolo[2,1-f][1,2,4]triazin-4-ol [261];

N-((3R,4S)-4-fluoro-1-methylpyrrolidin-3-yl)-5-(imidazo[1,2-a]pyrimidin-6-yl)-4-methoxypyrrolo[2,1-f][1,2,4]triazin-2-amine [262];

1-((3S,4R)-3-fluoro-4-((4-hydroxy-5-(imidazo[1,2-a]pyrimidin-6-yl)pyrrolo[2,1-f][1,2,4]triazin-2-yl)amino)pyrrolidin-1-yl)ethan-1-one [263];

1-((3S,4R)-3-fluoro-4-((5-(imidazo[1,2-a]pyrimidin-6-yl)-4-methoxypyrrolo[2,1-f][1,2,4]triazin-2-yl)amino)pyrrolidin-1-yl)ethan-1-one [264];

2-(((3R,4S)-4-fluoro-1-(oxetan-3-yl)pyrrolidin-3-yl)amino)-5-(imidazo[1,2-a]pyrimidin-6-yl)pyrrolo[2,1-f][1,2,4]triazin-4-ol [265];

N-((3R,4S)-4-fluoro-1-(oxetan-3-yl)pyrrolidin-3-yl)-5-(imidazo[1,2-a]pyrimidin-6-yl)-4-methoxypyrrolo[2,1-f][1,2,4]triazin-2-amine [266];

N-((3S,4R)-3-fluoro-1-methylpiperidin-4-yl)-5-(imidazo[1,2-a]pyrimidin-6-yl)-4-methoxypyrrolo[2,1-f][1,2,4]triazin-2-amine [267];

N-((3R,4S)-3-fluoro-1-methylpiperidin-4-yl)-5-(imidazo[1,2-a]pyrimidin-6-yl)-4-methoxypyrrolo[2,1-f][1,2,4]triazin-2-amine [268];

N-((3S,4R)-3-fluoro-1-(oxetan-3-yl)piperidin-4-yl)-5-(imidazo[1,2-a]pyrimidin-6-yl)-4-methoxypyrrolo[2,1-f][1,2,4]triazin-2-amine [269];

N-((3R,4S)-3-fluoro-1-(oxetan-3-yl)piperidin-4-yl)-5-(imidazo[1,2-a]pyrimidin-6-yl)-4-methoxypyrrolo[2,1-f][1,2,4]triazin-2-amine [270];

5-(imidazo[1,2-a]pyrimidin-6-yl)-4-methoxy-N-(tetrahydro-2H-pyran-4-yl)pyrrolo[2,1-f][1,2,4]triazin-2-amine [271];

5-(imidazo[1,2-a]pyrimidin-6-yl)-4-methoxy-N-(2-oxaspiro[3.3]heptan-6-yl)pyrrolo[2,1-f][1,2,4]triazin-2-amine [272];

1-(7-((5-(imidazo[1,2-a]pyrimidin-6-yl)-4-methoxypyrrolo[2,1-f][1,2,4]triazin-2-yl)amino)-2-azaspiro[3.5]nonan-2-yl)ethan-1-one [273];

5-(imidazo[1,2-a]pyrimidin-6-yl)-4-methoxy-N-((4s,7s)-1-oxaspiro[3.5]nonan-7-yl)pyrrolo[2,1-f][1,2,4]triazin-2-amine [274];

5-(imidazo[1,2-a]pyrimidin-6-yl)-4-methoxy-N-((4r,7r)-1-oxaspiro[3.5]nonan-7-yl)pyrrolo[2,1-f][1,2,4]triazin-2-amine [275];

5-(imidazo[1,2-a]pyrimidin-6-yl)-4-methoxy-N-(2-oxaspiro[3.5]nonan-7-yl)pyrrolo[2,1-f][1,2,4]triazin-2-amine [276];

(1s,3s)-3-((4-methoxy-5-(1H-pyrrolo[3,2-b]pyridin-2-yl)pyrrolo[2,1-f][1,2,4]triazin-2-yl)amino)-1-methylcyclobutan-1-ol [277];

(1r,3r)-3-((4-methoxy-5-(1H-pyrrolo[3,2-b]pyridin-2-yl)pyrrolo[2,1-f][1,2,4]triazin-2-yl)amino)-1-methylcyclobutan-1-ol [278];

(1s,4s)-4-((4-methoxy-5-(1H-pyrrolo[3,2-b]pyridin-2-yl)pyrrolo[2,1-f][1,2,4]triazin-2-yl)amino)-1-methylcyclohexan-1-ol [279];

(1r,4r)-4-((4-methoxy-5-(1H-pyrrolo[3,2-b]pyridin-2-yl)pyrrolo[2,1-f][1,2,4]triazin-2-yl)amino)-1-methylcyclohexan-1-ol [280];

(1s,3s)-3-((4-methoxy-5-(1H-pyrrolo[3,2-c]pyridin-2-yl)pyrrolo[2,1-f][1,2,4]triazin-2-yl)amino)-1-methylcyclobutan-1-ol [281];

(1r,4r)-4-((4-methoxy-5-(1H-pyrrolo[3,2-c]pyridin-2-yl)pyrrolo[2,1-f][1,2,4]triazin-2-yl)amino)-1-methylcyclohexan-1-ol [282];

(1s,3s)-3-((4-methoxy-5-(1H-pyrrolo[2,3-c]pyridin-2-yl)pyrrolo[2,1-f][1,2,4]triazin-2-yl)amino)-1-methylcyclobutan-1-ol [283];

(1r,4r)-4-((4-methoxy-5-(1H-pyrrolo[2,3-c]pyridin-2-yl)pyrrolo[2,1-f][1,2,4]triazin-2-yl)amino)-1-methylcyclohexan-1-ol [284];

(R)-4-methoxy-N-(1-(pyridin-2-yl)ethyl)-5-(quinolin-6-yl)pyrrolo[2,1-f][1,2,4]triazin-2-amine [285];

2-((1s,3s)-3-((4-methoxy-5-(quinolin-6-yl)pyrrolo[2,1-f][1,2,4]triazin-2-yl)amino)cyclobutyl)propan-2-ol [286];

2-((1r,3r)-3-((4-methoxy-5-(quinolin-6-yl)pyrrolo[2,1-f][1,2,4]triazin-2-yl)amino)cyclobutyl)propan-2-ol [287];

N-((1s,3s)-3-((4-methoxy-5-(quinolin-6-yl)pyrrolo[2,1-f][1,2,4]triazin-2-yl)amino)-1-methylcyclobutyl)acetamide [288];

N-((1s,3s)-3-((4-methoxy-5-(quinolin-6-yl)pyrrolo[2,1-f][1,2,4]triazin-2-yl)amino)-1-methylcyclobutyl)-N-methylacetamide [289];

(1r,3r)-3-((4-methoxy-5-(quinolin-6-yl)pyrrolo[2,1-f][1,2,4]triazin-2-yl)amino)-N,N,1-trimethylcyclobutane-1-carboxamide [290];

azetidin-1-yl((1r,3r)-3-((4-methoxy-5-(quinolin-6-yl)pyrrolo[2,1-f][1,2,4]triazin-2-yl)amino)-1-methylcyclobutyl)methanone [291];

((1r,3r)-3-((4-methoxy-5-(quinolin-6-yl)pyrrolo[2,1-f][1,2,4]triazin-2-yl)amino)-1-methylcyclobutyl)(pyrrolidin-1-yl)methanone [292];

(1s,4s)-4-((4-methoxy-5-(quinolin-6-yl)pyrrolo[2,1-f][1,2,4]triazin-2-yl)amino)-1-methylcyclohexan-1-ol [293];

(1r,4r)-4-((4-methoxy-5-(quinolin-6-yl)pyrrolo[2,1-f][1,2,4]triazin-2-yl)amino)-1-methylcyclohexan-1-ol [294];

N-((3S,4R)-4-fluoro-1-methylpyrrolidin-3-yl)-4-methoxy-5-(quinolin-6-yl)pyrrolo[2,1-f][1,2,4]triazin-2-amine [295];

N-((3R,4S)-4-fluoro-1-methylpyrrolidin-3-yl)-4-methoxy-5-(quinolin-6-yl)pyrrolo[2,1-f][1,2,4]triazin-2-amine [296];

1-((3R,4S)-3-fluoro-4-((4-methoxy-5-(quinolin-6-yl)pyrrolo[2,1-f][1,2,4]triazin-2-yl)amino)pyrrolidin-1-yl)ethan-1-one [297];

1-((3S,4R)-3-fluoro-4-((4-methoxy-5-(quinolin-6-yl)pyrrolo[2,1-f][1,2,4]triazin-2-yl)amino)pyrrolidin-1-yl)ethan-1-one [298];

N-((3S,4R)-4-fluoro-1-(oxetan-3-yl)pyrrolidin-3-yl)-4-methoxy-5-(quinolin-6-yl)pyrrolo[2,1-f][1,2,4]triazin-2-amine [299]; and N-((3R,4S)-4-fluoro-1-(oxetan-3-yl)pyrrolidin-3-yl)-4-methoxy-5-(quinolin-6-yl)pyrrolo[2,1-f][1,2,4]triazin-2-amine [300];

or a pharmaceutically acceptable salt thereof.

15. The compound according to claim 1, wherein the compound of Formula I is selected from the group consisting of:

(S)—N-(4,4-difluoro-1-methylpyrrolidin-3-yl)-4-methoxy-5-(quinolin-6-yl)pyrrolo[2,1-f][1,2,4]triazin-2-amine [301];

(R)—N-(4,4-difluoro-1-methylpyrrolidin-3-yl)-4-methoxy-5-(quinolin-6-yl)pyrrolo[2,1-f][1,2,4]triazin-2-amine [302];

N-(1-(2-fluoroethyl)piperidin-4-yl)-4-methoxy-5-(quinolin-6-yl)pyrrolo[2,1-f][1,2,4]triazin-2-amine [303];

N-(1-(2,2-difluoroethyl)piperidin-4-yl)-4-methoxy-5-(quinolin-6-yl)pyrrolo[2,1-f][1,2,4]triazin-2-amine [304];

4-methoxy-5-(quinolin-6-yl)-N-(1-(2,2,2-trifluoroethyl)piperidin-4-yl)pyrrolo[2,1-f][1,2,4]triazin-2-amine [305];

N-(1-(3,3-difluorocyclobutyl)piperidin-4-yl)-4-methoxy-5-(quinolin-6-yl)pyrrolo[2,1-f][1,2,4]triazin-2-amine [306];

N-((3S,4R)-3-fluoro-1-methylpiperidin-4-yl)-4-methoxy-5-(quinolin-6-yl)pyrrolo[2,1-f][1,2,4]triazin-2-amine [307];

N-((3R,4R)-3-fluoro-1-methylpiperidin-4-yl)-4-methoxy-5-(quinolin-6-yl)pyrrolo[2,1-f][1,2,4]triazin-2-amine [308];

N-((3S,4S)-3-fluoro-1-methylpiperidin-4-yl)-4-methoxy-5-(quinolin-6-yl)pyrrolo[2,1-f][1,2,4]triazin-2-amine [309];

N-((3R,4S)-3-fluoro-1-methylpiperidin-4-yl)-4-methoxy-5-(quinolin-6-yl)pyrrolo[2,1-f][1,2,4]triazin-2-amine [310];

N-((3S,4R)-3-fluoro-1-(2-fluoroethyl)piperidin-4-yl)-4-methoxy-5-(quinolin-6-yl)pyrrolo[2,1-f][1,2,4]triazin-2-amine [311];

N-((3R,4R)-3-fluoro-1-(2-fluoroethyl)piperidin-4-yl)-4-methoxy-5-(quinolin-6-yl)pyrrolo[2,1-f][1,2,4]triazin-2-amine [312];

N-((3S,4S)-3-fluoro-1-(2-fluoroethyl)piperidin-4-yl)-4-methoxy-5-(quinolin-6-yl)pyrrolo[2,1-f][1,2,4]triazin-2-amine [313];

N-((3R,4S)-3-fluoro-1-(2-fluoroethyl)piperidin-4-yl)-4-methoxy-5-(quinolin-6-yl)pyrrolo[2,1-f][1,2,4]triazin-2-amine [314];

N-((3S,4R)-3-fluoro-1-(oxetan-3-yl)piperidin-4-yl)-4-methoxy-5-(quinolin-6-yl)pyrrolo[2,1-f][1,2,4]triazin-2-amine [315];

N-((3R,4R)-3-fluoro-1-(oxetan-3-yl)piperidin-4-yl)-4-methoxy-5-(quinolin-6-yl)pyrrolo[2,1-f][1,2,4]triazin-2-amine [316];

N-((3S,4S)-3-fluoro-1-(oxetan-3-yl)piperidin-4-yl)-4-methoxy-5-(quinolin-6-yl)pyrrolo[2,1-f][1,2,4]triazin-2-amine [317];

N-((3R,4S)-3-fluoro-1-(oxetan-3-yl)piperidin-4-yl)-4-methoxy-5-(quinolin-6-yl)pyrrolo[2,1-f][1,2,4]triazin-2-amine [318];

(R)—N-(3,3-difluoro-1-methylpiperidin-4-yl)-4-methoxy-5-(quinolin-6-yl)pyrrolo[2,1-f][1,2,4]triazin-2-amine [319];

(S)—N-(3,3-difluoro-1-methylpiperidin-4-yl)-4-methoxy-5-(quinolin-6-yl)pyrrolo[2,1-f][1,2,4]triazin-2-amine [320];

(R)—N-(3,3-difluoro-1-(oxetan-3-yl)piperidin-4-yl)-4-methoxy-5-(quinolin-6-yl)pyrrolo[2,1-f][1,2,4]triazin-2-amine [321];

(S)—N-(3,3-difluoro-1-(oxetan-3-yl)piperidin-4-yl)-4-methoxy-5-(quinolin-6-yl)pyrrolo[2,1-f][1,2,4]triazin-2-amine [322];

1-((4s,6r)-6-((4-methoxy-5-(quinolin-6-yl)pyrrolo[2,1-f][1,2,4]triazin-2-yl)amino)-1-azaspiro[3.3]heptan-1-yl)ethan-1-one [323];

1-((4r,6s)-6-((4-methoxy-5-(quinolin-6-yl)pyrrolo[2,1-f][1,2,4]triazin-2-yl)amino)-1-azaspiro[3.3]heptan-1-yl)ethan-1-one [324];

1-(7-((4-methoxy-5-(quinolin-6-yl)pyrrolo[2,1-f][1,2,4]triazin-2-yl)amino)-2-azaspiro[3.5]nonan-2-yl)ethan-1-one [325];

4-methoxy-5-(quinolin-6-yl)-N-(2-oxaspiro[3.5]nonan-7-yl)pyrrolo[2,1-f][1,2,4]triazin-2-amine [326];

2-(cis-3-((4-methoxy-5-(quinoxalin-6-yl)pyrrolo[2,1-f][1,2,4]triazin-2-yl)amino)cyclobutyl)propan-2-ol [327];

2-(trans-3-((4-methoxy-5-(quinoxalin-6-yl)pyrrolo[2,1-f][1,2,4]triazin-2-yl)amino)cyclobutyl)propan-2-ol [328];

2-(cis-3-((4-methoxy-5-(quinoxalin-6-yl)pyrrolo[2,1-f][1,2,4]triazin-2-yl)amino)cyclobutoxy)ethan-1-ol [329];

(1r,3r)-3-((4-methoxy-5-(quinoxalin-6-yl)pyrrolo[2,1-f][1,2,4]triazin-2-yl)amino)-1-methylcyclobutan-1-ol [330];

(1r,3r)-3-((4-(methoxy-$d_3$)-5-(quinoxalin-6-yl)pyrrolo[2,1-f][1,2,4]triazin-2-yl)amino)-1-methylcyclobutan-1-ol [331];

(1s,3s)-N -(4-methoxy-5-(quinoxalin-6-yl)pyrrolo[2,1-f][1,2,4]triazin-2-yl)-3-methylcyclobutane-1,3-diamine [332];

N-((1s,3s)-3-((4-methoxy-5-(quinoxalin-6-yl)pyrrolo[2,1-f][1,2,4]triazin-2-yl)amino)-1-methylcyclobutyl)acetamide [333];

N-((1r,3r)-3-((4-methoxy-5-(quinoxalin-6-yl)pyrrolo[2,1-f][1,2,4]triazin-2-yl)amino)-1-methylcyclobutyl)acetamide [334];

N-((1s,3s)-3-((4-methoxy-5-(quinoxalin-6-yl)pyrrolo[2,1-f][1,2,4]triazin-2-yl)amino)-1-methylcyclobutyl)propionamide [335];

2-methoxy-N-((1s,3s)-3-((4-methoxy-5-(quinoxalin-6-yl)pyrrolo[2,1-f][1,2,4]triazin-2-yl)amino)-1-methylcyclobutyl)acetamide [336];

tert-butyl ((1s,3s)-3-((4-methoxy-5-(quinoxalin-6-yl)pyrrolo[2,1-f][1,2,4]triazin-2-yl)amino)-1-methylcyclobutyl)carbamate [337];

(1r,3r)-3-((4-methoxy-5-(quinoxalin-6-yl)pyrrolo[2,1-f][1,2,4]triazin-2-yl)amino)-N,1-dimethylcyclobutane-1-carboxamide [338];

(1r,3r)-3-((4-methoxy-5-(quinoxalin-6-yl)pyrrolo[2,1-f][1,2,4]triazin-2-yl)amino)-N,N,1-trimethylcyclobutane-1-carboxamide [339];

((1r,3r)-3-((4-methoxy-5-(quinoxalin-6-yl)pyrrolo[2,1-f][1,2,4]triazin-2-yl)amino)-1-methylcyclobutyl)(pyrrolidin-1-yl)methanone [340];

2-(cis-4-((4-methoxy-5-(quinoxalin-6-yl)pyrrolo[2,1-f][1,2,4]triazin-2-yl)amino)cyclohexyl)propan-2-ol [341];

2-(trans-4-((4-methoxy-5-(quinoxalin-6-yl)pyrrolo[2,1-f][1,2,4]triazin-2-yl)amino)cyclohexyl)propan-2-ol [342];

2-((cis-4-((4-methoxy-5-(quinoxalin-6-yl)pyrrolo[2,1-f][1,2,4]triazin-2-yl)amino)cyclohexyl)oxy)ethan-1-ol [343];

N-(trans-4-((4-methoxy-5-(quinoxalin-6-yl)pyrrolo[2,1-f][1,2,4]triazin-2-yl)amino)cyclohexyl)acetamide [344];

(1s,4s)-4-((4-methoxy-5-(quinoxalin-6-yl)pyrrolo[2,1-f][1,2,4]triazin-2-yl)amino)-1-methylcyclohexan-1-ol [345];

2-(((1r,4r)-4-hydroxy-4-methylcyclohexyl)amino)-5-(quinoxalin-6-yl)pyrrolo[2,1-f][1,2,4]triazin-4-ol [346];

(1r,4r)-4-((4-methoxy-5-(quinoxalin-6-yl)pyrrolo[2,1-f][1,2,4]triazin-2-yl)amino)-1-methylcyclohexan-1-ol [347];

(1r,4r)-4-((4-(methoxy-$d_3$)-5-(quinoxalin-6-yl)pyrrolo[2,1-f][1,2,4]triazin-2-yl)amino)-1-methylcyclohexan-1-ol [348];

(1r,4r)-4-((4-methoxy-5-(quinoxalin-6-yl)pyrrolo[2,1-f][1,2,4]triazin-2-yl)amino)-1-(trifluoromethyl)cyclohexan-1-ol [349];

N-((3R,4S)-4-fluoro-1-methylpyrrolidin-3-yl)-4-methoxy-5-(quinoxalin-6-yl)pyrrolo[2,1-f][1,2,4]triazin-2-amine [350];

N-((3S,4R)-4-fluoro-1-methylpyrrolidin-3-yl)-4-methoxy-5-(quinoxalin-6-yl)pyrrolo[2,1-f][1,2,4]triazin-2-amine [351];

1-((3S,4R)-3-fluoro-4-((4-methoxy-5-(quinoxalin-6-yl)pyrrolo[2,1-f][1,2,4]triazin-2-yl)amino)pyrrolidin-1-yl)ethan-1-one [352];

1-((3S,4R)-3-fluoro-4-((4-(methoxy-$d_3$)-5-(quinoxalin-6-yl)pyrrolo[2,1-f][1,2,4]triazin-2-yl)amino)pyrrolidin-1-yl)ethan-1-one [353];

1-((3R,4S)-3-fluoro-4-((4-methoxy-5-(quinoxalin-6-yl)pyrrolo[2,1-f][1,2,4]triazin-2-yl)amino)pyrrolidin-1-yl)ethan-1-one [354];

N-((3R,4S)-4-fluoro-1-(oxetan-3-yl)pyrrolidin-3-yl)-4-methoxy-5-(quinoxalin-6-yl)pyrrolo[2,1-f][1,2,4]triazin-2-amine [355];

N-((3S,4R)-4-fluoro-1-(oxetan-3-yl)pyrrolidin-3-yl)-4-methoxy-5-(quinoxalin-6-yl)pyrrolo[2,1-f][1,2,4]triazin-2-amine [356];

(R)—N-(4,4-difluoro-1-methylpyrrolidin-3-yl)-4-methoxy-5-(quinoxalin-6-yl)pyrrolo[2,1-f][1,2,4]triazin-2-amine [357];

(S)—N-(4,4-difluoro-1-methylpyrrolidin-3-yl)-4-methoxy-5-(quinoxalin-6-yl)pyrrolo[2,1-f][1,2,4]triazin-2-amine [358];

(R)—N-(4,4-difluoro-1-(oxetan-3-yl)pyrrolidin-3-yl)-4-methoxy-5-(quinoxalin-6-yl)pyrrolo[2,1-f][1,2,4]triazin-2-amine [359];

(S)—N-(4,4-difluoro-1-(oxetan-3-yl)pyrrolidin-3-yl)-4-methoxy-5-(quinoxalin-6-yl)pyrrolo[2,1-f][1,2,4]triazin-2-amine [360];

N-(1-(2-fluoroethyl)piperidin-4-yl)-4-methoxy-5-(quinoxalin-6-yl)pyrrolo[2,1-f][1,2,4]triazin-2-amine [361];

N-(1-(2,2-difluoroethyl)piperidin-4-yl)-4-methoxy-5-(quinoxalin-6-yl)pyrrolo[2,1-f][1,2,4]triazin-2-amine [362];

4-methoxy-5-(quinoxalin-6-yl)-N-(1-(2,2,2-trifluoroethyl)piperidin-4-yl)pyrrolo[2,1-f][1,2,4]triazin-2-amine [363];

N-(1-(3,3-difluorocyclobutyl)piperidin-4-yl)-4-methoxy-5-(quinoxalin-6-yl)pyrrolo[2,1-f][1,2,4]triazin-2-amine [364];

4-methoxy-N-(1-(oxetan-3-yl)piperidin-4-yl)-5-(quinoxalin-6-yl)pyrrolo[2,1-f][1,2,4]triazin-2-amine [365];

4-methoxy-5-(quinoxalin-6-yl)-N-(tetrahydro-2H-pyran-4-yl)pyrrolo[2,1-f][1,2,4]triazin-2-amine [366];

N-((3S,4R)-3-fluoro-1-methylpiperidin-4-yl)-4-methoxy-5-(quinoxalin-6-yl)pyrrolo[2,1-f][1,2,4]triazin-2-amine [367];

N-((3R,4S)-3-fluoro-1-methylpiperidin-4-yl)-4-methoxy-5-(quinoxalin-6-yl)pyrrolo[2,1-f][1,2,4]triazin-2-amine [368];

N-((3S,4R)-3-fluoro-1-(2-fluoroethyl)piperidin-4-yl)-4-methoxy-5-(quinoxalin-6-yl)pyrrolo[2,1-f][1,2,4]triazin-2-amine [369];

N-((3R,4R)-3-fluoro-1-(2-fluoroethyl)piperidin-4-yl)-4-methoxy-5-(quinoxalin-6-yl)pyrrolo[2,1-f][1,2,4]triazin-2-amine [370];

N-((3S,4S)-3-fluoro-1-(2-fluoroethyl)piperidin-4-yl)-4-methoxy-5-(quinoxalin-6-yl)pyrrolo[2,1-f][1,2,4]triazin-2-amine [371];

N-((3R,4S)-3-fluoro-1-(2-fluoroethyl)piperidin-4-yl)-4-methoxy-5-(quinoxalin-6-yl)pyrrolo[2,1-f][1,2,4]triazin-2-amine [372];

N-((3S,4R)-3-fluoro-1-(oxetan-3-yl)piperidin-4-yl)-4-methoxy-5-(quinoxalin-6-yl)pyrrolo[2,1-f][1,2,4]triazin-2-amine [373];

N-((3R,4S)-3-fluoro-1-(oxetan-3-yl)piperidin-4-yl)-4-methoxy-5-(quinoxalin-6-yl)pyrrolo[2,1-f][1,2,4]triazin-2-amine [374];

(R)—N-(3,3-difluoro-1-methylpiperidin-4-yl)-4-methoxy-5-(quinoxalin-6-yl)pyrrolo[2,1-f][1,2,4]triazin-2-amine [375];

(S)—N-(3,3-difluoro-1-methylpiperidin-4-yl)-4-methoxy-5-(quinoxalin-6-yl)pyrrolo[2,1-f][1,2,4]triazin-2-amine [376];

(R)—N-(1-cyclobutyl-3,3-difluoropiperidin-4-yl)-4-methoxy-5-(quinoxalin-6-yl)pyrrolo[2,1-f][1,2,4]triazin-2-amine [377];

(S)—N-(1-cyclobutyl-3,3-difluoropiperidin-4-yl)-4-methoxy-5-(quinoxalin-6-yl)pyrrolo[2,1-f][1,2,4]triazin-2-amine [378];

(R)—N-(3,3-difluoro-1-(oxetan-3-yl)piperidin-4-yl)-4-methoxy-5-(quinoxalin-6-yl)pyrrolo[2,1-f][1,2,4]triazin-2-amine [379];

(S)—N-(3,3-difluoro-1-(oxetan-3-yl)piperidin-4-yl)-4-methoxy-5-(quinoxalin-6-yl)pyrrolo[2,1-f][1,2,4]triazin-2-amine [380];

N-(4-methoxy-5-(quinoxalin-6-yl)pyrrolo[2,1-f][1,2,4]triazin-2-yl)bicyclo[1.1.1]pentane-1,3-diamine [381];

N-(3-((4-methoxy-5-(quinoxalin-6-yl)pyrrolo[2,1-f][1,2,4]triazin-2-yl)amino)bicyclo[1.1.1]pentan-1-yl)acetamide [382];

1-((4s,6r)-6-((4-methoxy-5-(quinoxalin-6-yl)pyrrolo[2,1-f][1,2,4]triazin-2-yl)amino)-1-azaspiro[3.3]heptan-1-yl)ethan-1-one [383];

1-((4r,6s)-6-((4-methoxy-5-(quinoxalin-6-yl)pyrrolo[2,1-f][1,2,4]triazin-2-yl)amino)-1-azaspiro[3.3]heptan-1-yl)ethan-1-one [384];

4-methoxy-5-(quinoxalin-6-yl)-N-(2-oxaspiro[3.3]heptan-6-yl)pyrrolo[2,1-f][1,2,4]triazin-2-amine [385];

1-(2-((4-methoxy-5-(quinoxalin-6-yl)pyrrolo[2,1-f][1,2,4]triazin-2-yl)amino)-7-azaspiro[3.5]nonan-7-yl)ethan-1-one [386];

1-((3aR,5s,6aS)-5-((4-methoxy-5-(quinoxalin-6-yl)pyrrolo[2,1-f][1,2,4]triazin-2-yl)amino)hexahydrocyclopenta[c]pyrrol-2 (1H)-yl)ethan-1-one [387];

1-((3aR,5r,6aS)-5-((4-methoxy-5-(quinoxalin-6-yl)pyrrolo[2,1-f][1,2,4]triazin-2-yl)amino)hexahydrocyclopenta[c]pyrrol-2 (1H)-yl)ethan-1-one [388];

1-(7-((4-methoxy-5-(quinoxalin-6-yl)pyrrolo[2,1-f][1,2,4]triazin-2-yl)amino)-2-azaspiro[3.5]nonan-2-yl)ethan-1-one [389];

4-methoxy-5-(quinoxalin-6-yl)-N-(2-oxaspiro[3.5]nonan-7-yl)pyrrolo[2,1-f][1,2,4]triazin-2-amine [390];

(1s,3s)-1-methyl-3-((4-(oxetan-3-yloxy)-5-(quinoxalin-6-yl)pyrrolo[2,1-f][1,2,4]triazin-2-yl)amino)cyclobutan-1-ol [391];

(1r,4r)-1-methyl-4-((4-(oxetan-3-yloxy)-5-(quinoxalin-6-yl)pyrrolo[2,1-f][1,2,4]triazin-2-yl)amino)cyclohexan-1-ol [392];

(S)-4-methoxy-5-(pyrazolo[1,5-a]pyridin-5-yl)-N-(1-(pyridin-2-yl)ethyl)pyrrolo[2,1-f][1,2,4]triazin-2-amine [393];

1-cyano-N-((1s,3s)-3-((4-methoxy-5-(pyrazolo[1,5-a]pyridin-5-yl)pyrrolo[2,1-f][1,2,4]triazin-2-yl)amino)-1-methylcyclobutyl)cyclopropane-1-carboxamide [394];

4-methoxy-5-(pyrazolo[1,5-a]pyridin-5-yl)-N-(2-oxaspiro[3.5]nonan-7-yl)pyrrolo[2,1-f][1,2,4]triazin-2-amine [395];

(R)-5-(4-methoxy-2-((1-(oxetan-3-yl)ethyl)amino)pyrrolo[2,1-f][1,2,4]triazin-5-yl)-N-methylpyrazolo[1,5-a]pyridine-3-carboxamide [396];

(S)-5-(4-methoxy-2-((1-(oxetan-3-yl)ethyl)amino)pyrrolo[2,1-f][1,2,4]triazin-5-yl)-N-methylpyrazolo[1,5-a]pyridine-3-carboxamide [397];

5-(2-(cyclohexylamino)-4-methoxypyrrolo[2,1-f][1,2,4]triazin-5-yl)-N-methylpyrazolo[1,5-a]pyridine-3-carboxamide [398];

5-(4-methoxy-2-(((1s,4s)-4-methoxycyclohexyl)amino)pyrrolo[2,1-f][1,2,4]triazin-5-yl)-N-methylpyrazolo[1,5-a]pyridine-3-carboxamide [399]; and 5-(2-((4,4-dimethylcyclohexyl)amino)-4-methoxypyrrolo[2,1-f][1,2,4]triazin-5-yl)-N-methylpyrazolo[1,5-a]pyridine-3-carboxamide [400];

or a pharmaceutically acceptable salt thereof.

16. The compound according to claim 1, wherein the compound of Formula I is selected from the group consisting of:

5-(2-(((1r,4r)-4-hydroxy-4-methylcyclohexyl)amino)-4-methoxypyrrolo[2,1-f][1,2,4]triazin-5-yl)-N-methylpyrazolo[1,5-a]pyridine-3-carboxamide [401];

5-(2-(((1s,4s)-4-ethyl-4-hydroxycyclohexyl)amino)-4-methoxypyrrolo[2,1-f][1,2,4]triazin-5-yl)-N-methylpyrazolo[1,5-a]pyridine-3-carboxamide [402];

5-(2-(((1r,4r)-4-ethyl-4-hydroxycyclohexyl)amino)-4-methoxypyrrolo[2,1-f][1,2,4]triazin-5-yl)-N-methylpyrazolo[1,5-a]pyridine-3-carboxamide [403];

5-(4-methoxy-2-(((1s,4s)-4-methoxy-4-methylcyclohexyl)amino)pyrrolo[2,1-f][1,2,4]triazin-5-yl)-N-methylpyrazolo[1,5-a]pyridine-3-carboxamide [404];

5-(4-methoxy-2-(((1r,4r)-4-methoxy-4-methylcyclohexyl)amino)pyrrolo[2,1-f][1,2,4]triazin-5-yl)-N-methylpyrazolo[1,5-a]pyridine-3-carboxamide [405];

5-(2-(((1s,4s)-4-cyano-4-methylcyclohexyl)amino)-4-methoxypyrrolo[2,1-f][1,2,4]triazin-5-yl)-N-methylpyrazolo[1,5-a]pyridine-3-carboxamide [406];

5-(2-(((1r,4r)-4-cyano-4-methylcyclohexyl)amino)-4-methoxypyrrolo[2,1-f][1,2,4]triazin-5-yl)-N-methylpyrazolo[1,5-a]pyridine-3-carboxamide [407];

5-(2-(bicyclo[3.1.0]hexan-3-ylamino)-4-methoxypyrrolo[2,1-f][1,2,4]triazin-5-yl)-N-methylpyrazolo[1,5-a]pyridine-3-carboxamide [408];

5-(2-((4-hydroxybicyclo[2.2.1]heptan-1-yl)amino)-4-methoxypyrrolo[2,1-f][1,2,4]triazin-5-yl)-N-methylpyrazolo[1,5-a]pyridine-3-carboxamide [409];

5-(4-methoxy-2-(spiro[2.5]octan-6-ylamino)pyrrolo[2,1-f][1,2,4]triazin-5-yl)-N-methylpyrazolo[1,5-a]pyridine-3-carboxamide [410];

(R)-5-(6-fluoro-4-methoxy-2-((1-(oxetan-3-yl)ethyl)amino)pyrrolo[2,1-f][1,2,4]triazin-5-yl)-N-methylpyrazolo[1,5-a]pyridine-3-carboxamide [411];

(S)-5-(6-fluoro-4-methoxy-2-((1-(oxetan-3-yl)ethyl)amino)pyrrolo[2,1-f][1,2,4]triazin-5-yl)-N-methylpyrazolo[1,5-a]pyridine-3-carboxamide [412];

5-(2-(cyclohexylamino)-6-fluoro-4-methoxypyrrolo[2,1-f][1,2,4]triazin-5-yl)-N-methylpyrazolo[1,5-a]pyridine-3-carboxamide [413];

5-(6-fluoro-4-methoxy-2-((cis-4-methoxycyclohexyl)amino)pyrrolo[2,1-f][1,2,4]triazin-5-yl)-N-methylpyrazolo[1,5-a]pyridine-3-carboxamide [414];

5-(2-((4,4-dimethylcyclohexyl)amino)-6-fluoro-4-methoxypyrrolo[2,1-f][1,2,4]triazin-5-yl)-N-methylpyrazolo[1,5-a]pyridine-3-carboxamide [415];

5-(6-fluoro-2-(((1s,4s)-4-hydroxy-4-methylcyclohexyl)amino)-4-methoxypyrrolo[2,1-f][1,2,4]triazin-5-yl)-N-methylpyrazolo[1,5-a]pyridine-3-carboxamide [416];

5-(6-fluoro-2-(((1r,4r)-4-hydroxy-4-methylcyclohexyl)amino)-4-methoxypyrrolo[2,1-f][1,2,4]triazin-5-yl)-N-methylpyrazolo[1,5-a]pyridine-3-carboxamide [417];

5-(2-(((1s,4s)-4-ethyl-4-hydroxycyclohexyl)amino)-6-fluoro-4-methoxypyrrolo[2,1-f][1,2,4]triazin-5-yl)-N-methylpyrazolo[1,5-a]pyridine-3-carboxamide [418];

5-(2-(((1r,4r)-4-ethyl-4-hydroxycyclohexyl)amino)-6-fluoro-4-methoxypyrrolo[2,1-f][1,2,4]triazin-5-yl)-N-methylpyrazolo[1,5-a]pyridine-3-carboxamide [419];

5-(6-fluoro-4-methoxy-2-(((1s,4s)-4-methoxy-4-methylcyclohexyl)amino)pyrrolo[2,1-f][1,2,4]triazin-5-yl)-N-methylpyrazolo[1,5-a]pyridine-3-carboxamide [420];

5-(6-fluoro-4-methoxy-2-(((1r,4r)-4-methoxy-4-methylcyclohexyl)amino)pyrrolo[2,1-f][1,2,4]triazin-5-yl)-N-methylpyrazolo[1,5-a]pyridine-3-carboxamide [421];

5-(2-(((1s,4s)-4-cyano-4-methylcyclohexyl)amino)-6-fluoro-4-methoxypyrrolo[2,1-f][1,2,4]triazin-5-yl)-N-methylpyrazolo[1,5-a]pyridine-3-carboxamide [422];

5-(2-(((1r,4r)-4-cyano-4-methylcyclohexyl)amino)-6-fluoro-4-methoxypyrrolo[2,1-f][1,2,4]triazin-5-yl)-N-methylpyrazolo[1,5-a]pyridine-3-carboxamide [423];

5-(2-(bicyclo[3.1.0]hexan-3-ylamino)-6-fluoro-4-methoxypyrrolo[2,1-f][1,2,4]triazin-5-yl)-N-methylpyrazolo[1,5-a]pyridine-3-carboxamide [424];

5-(6-fluoro-2-((4-hydroxybicyclo[2.2.1]heptan-1-yl)amino)-4-methoxypyrrolo[2,1-f][1,2,4]triazin-5-yl)-N-methylpyrazolo[1,5-a]pyridine-3-carboxamide [425];

5-(6-fluoro-4-methoxy-2-(spiro[2.5]octan-6-ylamino)pyrrolo[2,1-f][1,2,4]triazin-5-yl)-N-methylpyrazolo[1,5-a]pyridine-3-carboxamide [426];

5-(2-((2-oxaspiro[3.5]nonan-7-yl)amino)-6-fluoro-4-methoxypyrrolo[2,1-f][1,2,4]triazin-5-yl)-N-methylpyrazolo[1,5-a]pyridine-3-carboxamide [427];

N-((1s,3s)-3-((5-(8-fluoroimidazo[1,2-a]pyridin-6-yl)-4-methoxypyrrolo[2,1-f][1,2,4]triazin-2-yl)amino)-1-methylcyclobutyl)acetamide [428];

N-((1r,3r)-3-((5-(8-fluoroimidazo[1,2-a]pyridin-6-yl)-4-methoxypyrrolo[2,1-f][1,2,4]triazin-2-yl)amino)-1-methylcyclobutyl)acetamide [429];

(1s,4s)-4-((5-(8-fluoroimidazo[1,2-a]pyridin-6-yl)-4-methoxypyrrolo[2,1-f][1,2,4]triazin-2-yl)amino)-1-methylcyclohexan-1-ol [430];

(1r,4r)-4-((5-(8-fluoroimidazo[1,2-a]pyridin-6-yl)-4-methoxypyrrolo[2,1-f][1,2,4]triazin-2-yl)amino)-1-methylcyclohexan-1-ol [431];

(1s,4s)-1-ethyl-4-((5-(8-fluoroimidazo[1,2-a]pyridin-6-yl)-4-methoxypyrrolo[2,1-f][1,2,4]triazin-2-yl)amino)cyclohexan-1-ol [432];

(1r,4r)-1-ethyl-4-((5-(8-fluoroimidazo[1,2-a]pyridin-6-yl)-4-methoxypyrrolo[2,1-f][1,2,4]triazin-2-yl)amino)cyclohexan-1-ol [433];

(R)—N-(3,3-difluoro-1-methylpiperidin-4-yl)-5-(8-fluoroimidazo[1,2-a]pyridin-6-yl)-4-methoxypyrrolo[2,1-f][1,2,4]triazin-2-amine [434];

(R)—N-(3,3-difluoro-1-(oxetan-3-yl)piperidin-4-yl)-5-(8-fluoroimidazo[1,2-a]pyridin-6-yl)-4-methoxypyrrolo[2,1-f][1,2,4]triazin-2-amine [435];

(R)-6-(4-methoxy-2-((1-(oxetan-3-yl)ethyl)amino)pyrrolo[2,1-f][1,2,4]triazin-5-yl)-N-methylimidazo[1,2-a]pyridine-3-carboxamide [436];

(S)-6-(4-methoxy-2-((1-(oxetan-3-yl)ethyl)amino)pyrrolo[2,1-f][1,2,4]triazin-5-yl)-N-methylimidazo[1,2-a]pyridine-3-carboxamide [437];

6-(2-(cyclohexylamino)-4-methoxypyrrolo[2,1-f][1,2,4]triazin-5-yl)-N-methylimidazo[1,2-a]pyridine-3-carboxamide [438];

6-(4-methoxy-2-((cis-4-methoxycyclohexyl)amino)pyrrolo[2,1-f][1,2,4]triazin-5-yl)-N-methylimidazo[1,2-a]pyridine-3-carboxamide [439];

6-(2-((4,4-dimethylcyclohexyl)amino)-4-methoxypyrrolo[2,1-f][1,2,4]triazin-5-yl)-N-methylimidazo[1,2-a]pyridine-3-carboxamide [440];

6-(2-(((1r,4r)-4-hydroxy-4-methylcyclohexyl)amino)-4-methoxypyrrolo[2,1-f][1,2,4]triazin-5-yl)-N-methylimidazo[1,2-a]pyridine-3-carboxamide [441];

6-(2-(((1s,4s)-4-ethyl-4-hydroxycyclohexyl)amino)-4-methoxypyrrolo[2,1-f][1,2,4]triazin-5-yl)-N-methylimidazo[1,2-a]pyridine-3-carboxamide [442];

6-(2-(((1r,4r)-4-ethyl-4-hydroxycyclohexyl)amino)-4-methoxypyrrolo[2,1-f][1,2,4]triazin-5-yl)-N-methylimidazo[1,2-a]pyridine-3-carboxamide [443];

6-(4-methoxy-2-(((1s,4s)-4-methoxy-4-methylcyclohexyl)amino)pyrrolo[2,1-f][1,2,4]triazin-5-yl)-N-methylimidazo[1,2-a]pyridine-3-carboxamide [444];

6-(4-methoxy-2-(((1r,4r)-4-methoxy-4-methylcyclohexyl)amino)pyrrolo[2,1-f][1,2,4]triazin-5-yl)-N-methylimidazo[1,2-a]pyridine-3-carboxamide [445];

6-(2-(((1s,4s)-4-cyano-4-methylcyclohexyl)amino)-4-methoxypyrrolo[2,1-f][1,2,4]triazin-5-yl)-N-methylimidazo[1,2-a]pyridine-3-carboxamide [446];

6-(2-(((1r,4r)-4-cyano-4-methylcyclohexyl)amino)-4-methoxypyrrolo[2,1-f][1,2,4]triazin-5-yl)-N-methylimidazo[1,2-a]pyridine-3-carboxamide [447];

6-(2-(bicyclo[3.1.0]hexan-3-ylamino)-4-methoxypyrrolo[2,1-f][1,2,4]triazin-5-yl)-N-methylimidazo[1,2-a]pyridine-3-carboxamide [448];

6-(2-((4-hydroxybicyclo[2.2.1]heptan-1-yl)amino)-4-methoxypyrrolo[2,1-f][1,2,4]triazin-5-yl)-N-methylimidazo[1,2-a]pyridine-3-carboxamide [449];

6-(4-methoxy-2-(spiro[2.5]octan-6-ylamino)pyrrolo[2,1-f][1,2,4]triazin-5-yl)-N-methylimidazo[1,2-a]pyridine-3-carboxamide [450];

(R)-8-fluoro-6-(4-methoxy-2-((1-(oxetan-3-yl)ethyl)amino)pyrrolo[2,1-f][1,2,4]triazin-5-yl)-N-methylimidazo[1,2-a]pyridine-3-carboxamide [451];

(S)-8-fluoro-6-(4-methoxy-2-((1-(oxetan-3-yl)ethyl)amino)pyrrolo[2,1-f][1,2,4]triazin-5-yl)-N-methylimidazo[1,2-a]pyridine-3-carboxamide [452];

6-(2-(cyclohexylamino)-4-methoxypyrrolo[2,1-f][1,2,4]triazin-5-yl)-8-fluoro-N-methylimidazo[1,2-a]pyridine-3-carboxamide [453];

8-fluoro-6-(4-methoxy-2-((cis-4-methoxycyclohexyl)amino)pyrrolo[2,1-f][1,2,4]triazin-5-yl)-N-methylimidazo[1,2-a]pyridine-3-carboxamide [454];

6-(2-((4,4-dimethylcyclohexyl)amino)-4-methoxypyrrolo[2,1-f][1,2,4]triazin-5-yl)-8-fluoro-N-methylimidazo[1,2-a]pyridine-3-carboxamide [455];

8-fluoro-6-(2-(((1s,4s)-4-hydroxy-4-methylcyclohexyl)amino)-4-methoxypyrrolo[2,1-f][1,2,4]triazin-5-yl)-N-methylimidazo[1,2-a]pyridine-3-carboxamide [456];

8-fluoro-6-(2-(((1r,4r)-4-hydroxy-4-methylcyclohexyl)amino)-4-methoxypyrrolo[2,1-f][1,2,4]triazin-5-yl)-N-methylimidazo[1,2-a]pyridine-3-carboxamide [457];

6-(2-(((1s,4s)-4-ethyl-4-hydroxycyclohexyl)amino)-4-methoxypyrrolo[2,1-f][1,2,4]triazin-5-yl)-8-fluoro-N-methylimidazo[1,2-a]pyridine-3-carboxamide [458];

6-(2-(((1r,4r)-4-ethyl-4-hydroxycyclohexyl)amino)-4-methoxypyrrolo[2,1-f][1,2,4]triazin-5-yl)-8-fluoro-N-methylimidazo[1,2-a]pyridine-3-carboxamide [459];

8-fluoro-6-(4-methoxy-2-(((1s,4s)-4-methoxy-4-methylcyclohexyl)amino)pyrrolo[2,1-f][1,2,4]triazin-5-yl)-N-methylimidazo[1,2-a]pyridine-3-carboxamide [460];

8-fluoro-6-(4-methoxy-2-(((1r,4r)-4-methoxy-4-methylcyclohexyl)amino)pyrrolo[2,1-f][1,2,4]triazin-5-yl)-N-methylimidazo[1,2-a]pyridine-3-carboxamide [461];

6-(2-(((1s,4s)-4-cyano-4-methylcyclohexyl)amino)-4-methoxypyrrolo[2,1-f][1,2,4]triazin-5-yl)-8-fluoro-N-methylimidazo[1,2-a]pyridine-3-carboxamide [462];

6-(2-(((1r,4r)-4-cyano-4-methylcyclohexyl)amino)-4-methoxypyrrolo[2,1-f][1,2,4]triazin-5-yl)-8-fluoro-N-methylimidazo[1,2-a]pyridine-3-carboxamide [463];

6-(2-(bicyclo[3.1.0]hexan-3-ylamino)-4-methoxypyrrolo[2,1-f][1,2,4]triazin-5-yl)-8-fluoro-N-methylimidazo[1,2-a]pyridine-3-carboxamide [464];

8-fluoro-6-(2-((4-hydroxybicyclo[2.2.1]heptan-1-yl)amino)-4-methoxypyrrolo[2,1-f][1,2,4]triazin-5-yl)-N-methylimidazo[1,2-a]pyridine-3-carboxamide [465];

8-fluoro-6-(4-methoxy-2-(spiro[2.5]octan-6-ylamino)pyrrolo[2,1-f][1,2,4]triazin-5-yl)-N-methylimidazo[1,2-a]pyridine-3-carboxamide [466];

6-(2-((2-oxaspiro[3.5]nonan-7-yl)amino)-4-methoxypyrrolo[2,1-f][1,2,4]triazin-5-yl)-8-fluoro-N-methylimidazo[1,2-a]pyridine-3-carboxamide [467];

(R)-6-(6-fluoro-4-methoxy-2-((1-(oxetan-3-yl)ethyl)amino)pyrrolo[2,1-f][1,2,4]triazin-5-yl)-N-methylimidazo[1,2-a]pyridine-3-carboxamide [468];

(S)-6-(6-fluoro-4-methoxy-2-((1-(oxetan-3-yl)ethyl)amino)pyrrolo[2,1-f][1,2,4]triazin-5-yl)-N-methylimidazo[1,2-a]pyridine-3-carboxamide [469];

6-(2-(cyclohexylamino)-6-fluoro-4-methoxypyrrolo[2,1-f][1,2,4]triazin-5-yl)-N-methylimidazo[1,2-a]pyridine-3-carboxamide [470];

6-(6-fluoro-4-methoxy-2-((cis-4-methoxycyclohexyl)amino)pyrrolo[2,1-f][1,2,4]triazin-5-yl)-N-methylimidazo[1,2-a]pyridine-3-carboxamide [471];

6-(2-((4,4-dimethylcyclohexyl)amino)-6-fluoro-4-methoxypyrrolo[2,1-f][1,2,4]triazin-5-yl)-N-methylimidazo[1,2-a]pyridine-3-carboxamide [472];

6-(6-fluoro-2-(((1s,4s)-4-hydroxy-4-methylcyclohexyl)amino)-4-methoxypyrrolo[2,1-f][1,2,4]triazin-5-yl)-N-methylimidazo[1,2-a]pyridine-3-carboxamide [473];

6-(6-fluoro-2-(((1r,4r)-4-hydroxy-4-methylcyclohexyl)amino)-4-methoxypyrrolo[2,1-f][1,2,4]triazin-5-yl)-N-methylimidazo[1,2-a]pyridine-3-carboxamide [474];

6-(2-(((1s,4s)-4-ethyl-4-hydroxycyclohexyl)amino)-6-fluoro-4-methoxypyrrolo[2,1-f][1,2,4]triazin-5-yl)-N-methylimidazo[1,2-a]pyridine-3-carboxamide [475];

6-(2-(((1r,4r)-4-ethyl-4-hydroxycyclohexyl)amino)-6-fluoro-4-methoxypyrrolo[2,1-f][1,2,4]triazin-5-yl)-N-methylimidazo[1,2-a]pyridine-3-carboxamide [476];

6-(6-fluoro-4-methoxy-2-(((1s,4s)-4-methoxy-4-methylcyclohexyl)amino)pyrrolo[2,1-f][1,2,4]triazin-5-yl)-N-methylimidazo[1,2-a]pyridine-3-carboxamide [477];

6-(6-fluoro-4-methoxy-2-(((1r,4r)-4-methoxy-4-methylcyclohexyl)amino)pyrrolo[2,1-f][1,2,4]triazin-5-yl)-N-methylimidazo[1,2-a]pyridine-3-carboxamide [478];

6-(2-(((1s,4s)-4-cyano-4-methylcyclohexyl)amino)-6-fluoro-4-methoxypyrrolo[2,1-f][1,2,4]triazin-5-yl)-N-methylimidazo[1,2-a]pyridine-3-carboxamide [479];

6-(2-(((1r,4r)-4-cyano-4-methylcyclohexyl)amino)-6-fluoro-4-methoxypyrrolo[2,1-f][1,2,4]triazin-5-yl)-N-methylimidazo[1,2-a]pyridine-3-carboxamide [480];

6-(2-(bicyclo[3.1.0]hexan-3-ylamino)-6-fluoro-4-methoxypyrrolo[2,1-f][1,2,4]triazin-5-yl)-N-methylimidazo[1,2-a]pyridine-3-carboxamide [481];

6-(6-fluoro-2-((4-hydroxybicyclo[2.2.1]heptan-1-yl)amino)-4-methoxypyrrolo[2,1-f][1,2,4]triazin-5-yl)-N-methylimidazo[1,2-a]pyridine-3-carboxamide [482];

6-(6-fluoro-4-methoxy-2-(spiro[2.5]octan-6-ylamino)pyrrolo[2,1-f][1,2,4]triazin-5-yl)-N-methylimidazo[1,2-a]pyridine-3-carboxamide [483];

6-(2-((2-oxaspiro[3.5]nonan-7-yl)amino)-6-fluoro-4-methoxypyrrolo[2,1-f][1,2,4]triazin-5-yl)-N-methylimidazo[1,2-a]pyridine-3-carboxamide [484];

(R)-8-fluoro-6-(6-fluoro-4-methoxy-2-((1-(oxetan-3-yl)ethyl)amino)pyrrolo[2,1-f][1,2,4]triazin-5-yl)-N-methylimidazo[1,2-a]pyridine-3-carboxamide [485];

(S)-8-fluoro-6-(6-fluoro-4-methoxy-2-((1-(oxetan-3-yl)ethyl)amino)pyrrolo[2,1-f][1,2,4]triazin-5-yl)-N-methylimidazo[1,2-a]pyridine-3-carboxamide [486];

6-(2-(cyclohexylamino)-6-fluoro-4-methoxypyrrolo[2,1-f][1,2,4]triazin-5-yl)-8-fluoro-N-methylimidazo[1,2-a]pyridine-3-carboxamide [487];

8-fluoro-6-(6-fluoro-4-methoxy-2-((cis-4-methoxycyclohexyl)amino)pyrrolo[2,1-f][1,2,4]triazin-5-yl)-N-methylimidazo[1,2-a]pyridine-3-carboxamide [488];

6-(2-((4,4-dimethylcyclohexyl)amino)-6-fluoro-4-methoxypyrrolo[2,1-f][1,2,4]triazin-5-yl)-8-fluoro-N-methylimidazo[1,2-a]pyridine-3-carboxamide [489];

8-fluoro-6-(6-fluoro-2-(((1s,4s)-4-hydroxy-4-methylcyclohexyl)amino)-4-methoxypyrrolo[2,1-f][1,2,4]triazin-5-yl)-N-methylimidazo[1,2-a]pyridine-3-carboxamide [490];

8-fluoro-6-(6-fluoro-2-(((1r,4r)-4-hydroxy-4-methylcyclohexyl)amino)-4-methoxypyrrolo[2,1-f][1,2,4]triazin-5-yl)-N-methylimidazo[1,2-a]pyridine-3-carboxamide [491];

6-(2-(((1s,4s)-4-ethyl-4-hydroxycyclohexyl)amino)-6-fluoro-4-methoxypyrrolo[2,1-f][1,2,4]triazin-5-yl)-8-fluoro-N-methylimidazo[1,2-a]pyridine-3-carboxamide [492];

6-(2-(((1r,4r)-4-ethyl-4-hydroxycyclohexyl)amino)-6-fluoro-4-methoxypyrrolo[2,1-f][1,2,4]triazin-5-yl)-8-fluoro-N-methylimidazo[1,2-a]pyridine-3-carboxamide [493];

8-fluoro-6-(6-fluoro-4-methoxy-2-(((1s,4s)-4-methoxy-4-methylcyclohexyl)amino)pyrrolo[2,1-f][1,2,4]triazin-5-yl)-N-methylimidazo[1,2-a]pyridine-3-carboxamide [494];

8-fluoro-6-(6-fluoro-4-methoxy-2-(((1r,4r)-4-methoxy-4-methylcyclohexyl)amino)pyrrolo[2,1-f][1,2,4]triazin-5-yl)-N-methylimidazo[1,2-a]pyridine-3-carboxamide [495];

6-(2-(((1s,4s)-4-cyano-4-methylcyclohexyl)amino)-6-fluoro-4-methoxypyrrolo[2,1-f][1,2,4]triazin-5-yl)-8-fluoro-N-methylimidazo[1,2-a]pyridine-3-carboxamide [496];

6-(2-(((1r,4r)-4-cyano-4-methylcyclohexyl)amino)-6-fluoro-4-methoxypyrrolo[2,1-f][1,2,4]triazin-5-yl)-8-fluoro-N-methylimidazo[1,2-a]pyridine-3-carboxamide [497];

6-(2-(bicyclo[3.1.0]hexan-3-ylamino)-6-fluoro-4-methoxypyrrolo[2,1-f][1,2,4]triazin-5-yl)-8-fluoro-N-methylimidazo[1,2-a]pyridine-3-carboxamide [498];

8-fluoro-6-(6-fluoro-2-((4-hydroxybicyclo[2.2.1]heptan-1-yl)amino)-4-methoxypyrrolo[2,1-f][1,2,4]triazin-5-yl)-N-methylimidazo[1,2-a]pyridine-3-carboxamide [499]; and 8-fluoro-6-(6-fluoro-4-methoxy-2-(spiro[2.5]octan-6-ylamino)pyrrolo[2,1-f][1,2,4]triazin-5-yl)-N-methylimidazo[1,2-a]pyridine-3-carboxamide [500];

or a pharmaceutically acceptable salt thereof.

17. The compound according to claim 1, wherein the compound of Formula I is selected from the group consisting of:

6-(2-((2-oxaspiro[3.5]nonan-7-yl)amino)-6-fluoro-4-methoxypyrrolo[2,1-f][1,2,4]triazin-5-yl)-8-fluoro-N-methylimidazo[1,2-a]pyridine-3-carboxamide [501];

(1r,3r)-3-((5-(1-(2,2-difluoroethyl)-2-methyl-1H-benzo[d]imidazol-6-yl)-4-methoxypyrrolo[2,1-f][1,2,4]triazin-2-yl)amino)-N,1-dimethylcyclobutane-1-carboxamide [502];

(1r,3r)-N-cyclopropyl-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutane-1-carboxamide [503];

(1r,3r)-N-(3,3-difluorocyclobutyl)-3-((5-(1-(2,2-difluoroethyl)-2-methyl-1H-benzo[d]imidazol-6-yl)-4-methoxypyrrolo[2,1-f][1,2,4]triazin-2-yl)amino)-1-methylcyclobutane-1-carboxamide [504];

5-(1-(2,2-difluoroethyl)-2-methyl-1H-benzo[d]imidazol-6-yl)-N-((3S,4R)-4-fluoro-1-(oxetan-3-yl)pyrrolidin-3-yl)-4-methoxypyrrolo[2,1-f][1,2,4]triazin-2-amine [505];

5-(1-(2,2-difluoroethyl)-2-methyl-1H-benzo[d]imidazol-6-yl)-N-((3R,4S)-4-fluoro-1-(oxetan-3-yl)pyrrolidin-3-yl)-4-methoxypyrrolo[2,1-f][1,2,4]triazin-2-amine [506];

5-((5-(1-(2,2-difluoroethyl)-2-methyl-1H-benzo[d]imidazol-6-yl)-4-methoxypyrrolo[2,1-f][1,2,4]triazin-2-yl)amino)-1-methylpiperidin-2-one [507];

(1r,4r)-4-((5-(1-(2,2-difluoroethyl)-2-methyl-1H-benzo[d]imidazol-6-yl)-4-(oxetan-3-yloxy)pyrrolo[2,1-f][1,2,4]triazin-2-yl)amino)-1-methylcyclohexan-1-ol [508];

(1s,3s)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylcyclobutan-1-ol [509];

(1s,3r)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-ethylcyclobutan-1-ol [510];

(1r,3s)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-ethylcyclobutan-1-ol [511];

N-((1s,4s)-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)cyclohexyl)acetamide [512];

1-((3R,4S)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-4-fluoropyrrolidin-1-yl)ethan-1-one [513];

1-((3S,4R)-3-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-4-fluoropyrrolidin-1-yl)ethan-1-one [514];

5-(1-(2,2-difluoroethyl)-4-fluoro-2-methyl-1H-benzo[d]imidazol-6-yl)-N-((3R,4S)-4-fluoro-1-(oxetan-3-yl)pyrrolidin-3-yl)-4-methoxypyrrolo[2,1-f][1,2,4]triazin-2-amine [515];

5-(1-(2,2-difluoroethyl)-4-fluoro-2-methyl-1H-benzo[d]imidazol-6-yl)-N-((3S,4R)-4-fluoro-1-(oxetan-3-yl)pyrrolidin-3-yl)-4-methoxypyrrolo[2,1-f][1,2,4]triazin-2-amine [516];

(R)-1-(4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-3,3-difluoropyrrolidin-1-yl)ethan-1-one [517];

(R)—N-(4,4-difluoro-1-(oxetan-3-yl)pyrrolidin-3-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [518];

2-((3R,4S)-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-3-fluoropiperidin-1-yl)ethan-1-ol [519];

1-((3S,4R)-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-3-fluoropiperidin-1-yl)ethan-1-one [520];

1-((3R,4S)-4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-3-fluoropiperidin-1-yl)ethan-1-one [521];

5-(1-(2,2-difluoroethyl)-4-fluoro-2-methyl-1H-benzo[d]imidazol-6-yl)-N-((3S,4R)-3-fluoro-1-(3-methyloxetan-3-yl)piperidin-4-yl)-4-methoxypyrrolo[2,1-f][1,2,4]triazin-2-amine [522];

5-(1-(2,2-difluoroethyl)-4-fluoro-2-methyl-1H-benzo[d]imidazol-6-yl)-N-((3R,4S)-3-fluoro-1-(3-methyloxetan-3-yl)piperidin-4-yl)-4-methoxypyrrolo[2,1-f][1,2,4]triazin-2-amine [523];

3-((3R,4S)-4-((5-(1-(2,2-difluoroethyl)-4-fluoro-2-methyl-1H-benzo[d]imidazol-6-yl)-4-methoxypyrrolo[2,14][1,2,4]triazin-2-yl)amino)-3-fluoropiperidin-1-yl)oxetane-3-carbonitrile [524];

(R)-2-(4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-3,3-difluoropiperidin-1-yl)ethan-1-ol [525];

(R)-1-(4-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-3,3-difluoropiperidin-1-yl)ethan-1-one [526];

(R)—N-(3,3-difluoro-1-(3-methyloxetan-3-yl)piperidin-4-yl)-5-(1-(2,2-difluoroethyl)-4-fluoro-2-methyl-1H-benzo[d]imidazol-6-yl)-4-methoxypyrrolo[2,1-f][1,2,4]triazin-2-amine [527];

(S)-5-((5-(1-(2,2-difluoroethyl)-4-fluoro-2-methyl-1H-benzo[d]imidazol-6-yl)-4-methoxypyrrolo[2,1-f][1,2,4]triazin-2-yl)amino)-1-methylpiperidin-2-one [528];

N-((1s,3s)-3-((5-(4-fluoro-1-isopropyl-2-methyl-1H-benzo[d]imidazol-6-yl)-4-methoxypyrrolo[2,1-f][1,2,4]triazin-2-yl)amino)-1-methylcyclobutyl)acetamide [529];

N-((1r,3r)-3-((5-(4-fluoro-1-isopropyl-2-methyl-1H-benzo[d]imidazol-6-yl)-4-methoxypyrrolo[2,1-f][1,2,4]triazin-2-yl)amino)-1-methylcyclobutyl)acetamide [530];

(1s,3r)-1-ethyl-3-((5-(4-fluoro-1-isopropyl-2-methyl-1H-benzo[d]imidazol-6-yl)-4-methoxypyrrolo[2,1-f][1,2,4]triazin-2-yl)amino)cyclobutan-1-ol [531];

(1r,3s)-1-ethyl-3-((5-(4-fluoro-1-isopropyl-2-methyl-1H-benzo[d]imidazol-6-yl)-4-methoxypyrrolo[2,1-f][1,2,4]triazin-2-yl)amino)cyclobutan-1-ol [532];

N-((1s,4s)-4-((5-(4-fluoro-1-isopropyl-2-methyl-1H-benzo[d]imidazol-6-yl)-4-methoxypyrrolo[2,1-f][1,2,4]triazin-2-yl)amino)cyclohexyl)acetamide [533];

(1s,4s)-4-((5-(4-fluoro-1-isopropyl-2-methyl-1H-benzo[d]imidazol-6-yl)-4-methoxypyrrolo[2,1-f][1,2,4]triazin-2-yl)amino)-1-methylcyclohexan-1-ol [534];

1-((3S,4R)-3-fluoro-4-((5-(4-fluoro-1-isopropyl-2-methyl-1H-benzo[d]imidazol-6-yl)-4-methoxypyrrolo[2,1-f][1,2,4]triazin-2-yl)amino)pyrrolidin-1-yl)ethan-1-one [535];

1-((3R,4S)-3-fluoro-4-((5-(4-fluoro-1-isopropyl-2-methyl-1H-benzo[d]imidazol-6-yl)-4-methoxypyrrolo[2,1-f][1,2,4]triazin-2-yl)amino)pyrrolidin-1-yl)ethan-1-one [536];

N-((3R,4S)-4-fluoro-1-(oxetan-3-yl)pyrrolidin-3-yl)-5-(4-fluoro-1-isopropyl-2-methyl-1H-benzo[d]imidazol-6-yl)-4-methoxypyrrolo[2,1-f][1,2,4]triazin-2-amine [537];

N-((3S,4R)-4-fluoro-1-(oxetan-3-yl)pyrrolidin-3-yl)-5-(4-fluoro-1-isopropyl-2-methyl-1H-benzo[d]imidazol-6-yl)-4-methoxypyrrolo[2,1-f][1,2,4]triazin-2-amine [538];

(R)-1-(3,3-difluoro-4-((5-(4-fluoro-1-isopropyl-2-methyl-1H-benzo[d]imidazol-6-yl)-4-methoxypyrrolo[2,1-f][1,2,4]triazin-2-yl)amino)pyrrolidin-1-yl)ethan-1-one [539];

(R)—N-(4,4-difluoro-1-(oxetan-3-yl)pyrrolidin-3-yl)-5-(4-fluoro-1-isopropyl-2-methyl-1H-benzo[d]imidazol-6-yl)-4-methoxypyrrolo[2,1-f][1,2,4]triazin-2-amine [540];

5-(4-fluoro-1-isopropyl-2-methyl-1H-benzo[d]imidazol-6-yl)-N-((3R,4S)-3-fluoro-1-methylpiperidin-4-yl)-4-methoxypyrrolo[2,1-f][1,2,4]triazin-2-amine [541];

2-((3R,4S)-3-fluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-ol [542];

1-((3S,4R)-3-fluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-one [543];

1-((3R,4S)-3-fluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-one [544];

N-((3S,4R)-3-fluoro-1-(oxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine [545];

N-((3S,4R)-3-fluoro-1-(3-methyloxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine [546];

N-((3R,4S)-3-fluoro-1-(3-methyloxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine [547];

3-((3R,4S)-3-fluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)oxetane-3-carbonitrile [548];

(R)-2-(3,3-difluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-ol [549];

(R)-1-(3,3-difluoro-4-((5-(4-fluoro-1-isopropyl-2-methyl-1H-benzo[d]imidazol-6-yl)-4-methoxypyrrolo[2,1-f][1,2,4]triazin-2-yl)amino)piperidin-1-yl)ethan-1-one [550];

(R)—N-(3,3-difluoro-1-(oxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine [551];

(R)—N-(3,3-difluoro-1-(3-methyloxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine [552];

(S)-5-((5-(4-fluoro-1-isopropyl-2-methyl-1H-benzo[d]imidazol-6-yl)-4-methoxypyrrolo[2,1-f][1,2,4]triazin-2-yl)amino)-1-methylpiperidin-2-one [553];

(1r,4r)-4-((5-([1,2,4]triazolo[1,5-a]pyridin-7-yl)-4-methoxypyrrolo[2,1-f][1,2,4]triazin-2-yl)amino)-1-methylcyclohexan-1-ol [554];

5-([1,2,4]triazolo[1,5-a]pyridin-6-yl)-N-(cis-3-ethoxycyclobutyl)-4-methoxypyrrolo[2,1-f][1,2,4]triazin-2-amine [555];

2-(cis-3-((5-([1,2,4]triazolo[1,5-a]pyridin-6-yl)-4-methoxypyrrolo[2,1-f][1,2,4]triazin-2-yl)amino)cyclobutoxy)ethan-1-ol [556];

(1s,3s)-3-((5-([1,2,4]triazolo[1,5-a]pyridin-6-yl)-4-methoxypyrrolo[2,1-f][1,2,4]triazin-2-yl)amino)-N,1-dimethylcyclobutane-1-carboxamide [557];

(1r,3r)-3-((5-([1,2,4]triazolo[1,5-a]pyridin-6-yl)-4-methoxypyrrolo[2,1-f][1,2,4]triazin-2-yl)amino)-N,1-dimethylcyclobutane-1-carboxamide [558];

N-((1r,3r)-3-((5-([1,2,4]triazolo[1,5-a]pyridin-6-yl)-4-methoxypyrrolo[2,1-f][1,2,4]triazin-2-yl)amino)-1-methylcyclobutyl)acetamide-2,2,2-$d_3$ [559];

N-((1s,3s)-3-((5-([1,2,4]triazolo[1,5-a]pyridin-6-yl)-4-methoxypyrrolo[2,1-f][1,2,4]triazin-2-yl)amino)-1-methylcyclobutyl)-N-methylacetamide [560];

N-((1r,3r)-3-((5-([1,2,4]triazolo[1,5-a]pyridin-6-yl)-4-methoxypyrrolo[2,1-f][1,2,4]triazin-2-yl)amino)-1-methylcyclobutyl)-N-methylacetamide [561];

N-((1s,3s)-3-((5-([1,2,4]triazolo[1,5-a]pyridin-6-yl)-4-methoxypyrrolo[2,1-f][1,2,4]triazin-2-yl)amino)-1-methylcyclobutyl)-1-cyanocyclopropane-1-carboxamide [562];

N-((1r,3r)-3-((5-([1,2,4]triazolo[1,5-a]pyridin-6-yl)-4-methoxypyrrolo[2,1-f][1,2,4]triazin-2-yl)amino)-1-methylcyclobutyl)-1-cyanocyclopropane-1-carboxamide [563];

(1s,3r)-3-((5-([1,2,4]triazolo[1,5-a]pyridin-6-yl)-4-methoxypyrrolo[2,1-f][1,2,4]triazin-2-yl)amino)-1-ethylcyclobutan-1-ol [564];

(1r,3s)-3-((5-([1,2,4]triazolo[1,5-a]pyridin-6-yl)-4-methoxypyrrolo[2,1-f][1,2,4]triazin-2-yl)amino)-1-ethylcyclobutan-1-ol [565];

2-((cis-4-((5-([1,2,4]triazolo[1,5-a]pyridin-6-yl)-4-methoxypyrrolo[2,1-f][1,2,4]triazin-2-yl)amino)cyclohexyl)oxy)ethan-1-ol [566];

(1r,4r)-4-((5-([1,2,4]triazolo[1,5-a]pyridin-6-yl)-4-methoxypyrrolo[2,1-f][1,2,4]triazin-2-yl)amino)-1-ethylcyclohexan-1-ol [567];

(1s,4s)-4-((5-([1,2,4]triazolo[1,5-a]pyridin-6-yl)-4-methoxypyrrolo[2,1-f][1,2,4]triazin-2-yl)amino)-1-methylcyclohexane-1-carbonitrile [568];

(1r,4r)-4-((5-([1,2,4]triazolo[1,5-a]pyridin-6-yl)-4-methoxypyrrolo[2,1-f][1,2,4]triazin-2-yl)amino)-1-methylcyclohexane-1-carbonitrile [569];

(R)-3-((5-([1,2,4]triazolo[1,5-a]pyridin-6-yl)-4-methoxypyrrolo[2,1-f][1,2,4]triazin-2-yl)amino)-1-methylpyrrolidin-2-one [570];

(S)-3-((5-([1,2,4]triazolo[1,5-a]pyridin-6-yl)-4-methoxypyrrolo[2,1-f][1,2,4]triazin-2-yl)amino)-1-methylpyrrolidin-2-one [571];

1-(4-((5-([1,2,4]triazolo[1,5-a]pyridin-6-yl)-4-methoxypyrrolo[2,1-f][1,2,4]triazin-2-yl)amino)piperidin-1-yl)ethan-1-one [572];

1-(4-((5-([1,2,4]triazolo[1,5-a]pyridin-6-yl)-4-methoxypyrrolo[2,1-f][1,2,4]triazin-2-yl)amino)piperidine-1-carbonyl)cyclopropane-1-carbonitrile [573];

1-((3R,4S)-4-((5-([1,2,4]triazolo[1,5-a]pyridin-6-yl)-4-methoxypyrrolo[2,1-f][1,2,4]triazin-2-yl)amino)-3-fluoropiperidine-1-carbonyl)cyclopropane-1-carbonitrile [574];

(R)-5-([1,2,4]triazolo[1,5-a]pyridin-6-yl)-N-(3,3-difluoropiperidin-4-yl)-4-methoxypyrrolo[2,1-f][1,2,4]triazin-2-amine [575];

(R)-5-([1,2,4]triazolo[1,5-a]pyridin-6-yl)-N-(3,3-difluoro-1-methylpiperidin-4-yl)-4-methoxypyrrolo[2,1-f][1,2,4]triazin-2-amine [576];

(R)-5-([1,2,4]triazolo[1,5-a]pyridin-6-yl)-N-(1-ethyl-3,3-difluoropiperidin-4-yl)-4-methoxypyrrolo[2,1-f][1,2,4]triazin-2-amine [577];

(R)-5-([1,2,4]triazolo[1,5-a]pyridin-6-yl)-N-(3,3-difluoro-1-(oxetan-3-yl)piperidin-4-yl)-4-methoxypyrrolo[2,1-f][1,2,4]triazin-2-amine [578];

(R)-1-(4-((5-([1,2,4]triazolo[1,5-a]pyridin-6-yl)-4-methoxypyrrolo[2,1-f][1,2,4]triazin-2-yl)amino)-3,3-difluoropiperidine-1-carbonyl)cyclopropane-1-carbonitrile [579];

(R)-3-((5-([1,2,4]triazolo[1,5-a]pyridin-6-yl)-4-methoxypyrrolo[2,1-f][1,2,4]triazin-2-yl)amino)-1-methylpiperidin-2-one [580];

(S)-3-((5-([1,2,4]triazolo[1,5-a]pyridin-6-yl)-4-methoxypyrrolo[2,1-f][1,2,4]triazin-2-yl)amino)-1-methylpiperidin-2-one [581];

4-((5-([1,2,4]triazolo[1,5-a]pyridin-6-yl)-4-methoxypyrrolo[2,1-f][1,2,4]triazin-2-yl)amino)bicyclo[2.2.1]heptan-1-ol [582];

5-([1,2,4]triazolo[1,5-a]pyridin-6-yl)-N-(bicyclo[3.1.0]hexan-3-yl)-4-methoxypyrrolo[2,1-f][1,2,4]triazin-2-amine [583];

1-(7-((5-([1,2,4]triazolo[1,5-a]pyridin-6-yl)-4-methoxypyrrolo[2,1-f][1,2,4]triazin-2-yl)amino)-2-azaspiro[3.5]nonan-2-yl)ethan-1-one-2,2,2-$d_3$ [584];

N-((1r,3r)-3-((5-([1,2,4]triazolo[1,5-a]pyridin-6-yl)-6-fluoro-4-methoxypyrrolo[2,1-f][1,2,4]triazin-2-yl)amino)-1-methylcyclobutyl)acetamide [585];

N-((1r,3r)-3-((5-([1,2,4]triazolo[1,5-a]pyridin-6-yl)-6-fluoro-4-methoxypyrrolo[2,1-f][1,2,4]triazin-2-yl)amino)-1-methylcyclobutyl)acetamide-2,2,2-$d_3$ [586];

(1s,3r)-3-((5-([1,2,4]triazolo[1,5-a]pyridin-6-yl)-6-fluoro-4-methoxypyrrolo[2,1-f][1,2,4]triazin-2-yl)amino)-1-ethylcyclobutan-1-ol [587];

(1r,3s)-3-((5-([1,2,4]triazolo[1,5-a]pyridin-6-yl)-6-fluoro-4-methoxypyrrolo[2,1-f][1,2,4]triazin-2-yl)amino)-1-ethylcyclobutan-1-ol [588];

(1r,4r)-4-((5-([1,2,4]triazolo[1,5-a]pyridin-6-yl)-6-fluoro-4-methoxypyrrolo[2,1-f][1,2,4]triazin-2-yl)amino)-1-methylcyclohexan-1-ol [589];

(1r,4r)-4-((5-([1,2,4]triazolo[1,5-a]pyridin-6-yl)-6-fluoro-4-methoxypyrrolo[2,1-f][1,2,4]triazin-2-yl)amino)-1-ethylcyclohexan-1-ol [590];

1-(4-((5-([1,2,4]triazolo[1,5-a]pyridin-6-yl)-6-fluoro-4-methoxypyrrolo[2,1-f][1,2,4]triazin-2-yl)amino)piperidin-1-yl)ethan-1-one [591];

1-(7-((5-([1,2,4]triazolo[1,5-a]pyridin-6-yl)-6-fluoro-4-methoxypyrrolo[2,1-f][1,2,4]triazin-2-yl)amino)-2-azaspiro[3.5]nonan-2-yl)ethan-1-one [592];

1-(7-((5-([1,2,4]triazolo[1,5-a]pyridin-6-yl)-6-fluoro-4-methoxypyrrolo[2,1-f][1,2,4]triazin-2-yl)amino)-2-azaspiro[3.5]nonan-2-yl)ethan-1-one-2,2,2-$d_3$ [593];

N-((1r,3r)-3-((5-([1,2,4]triazolo[1,5-a]pyridin-6-yl)-4-methoxypyrrolo[2,1-f][1,2,4]triazin-2-yl-7-d)amino)-1-methylcyclobutyl)acetamide [594];

N-((1r,3r)-3-((5-([1,2,4]triazolo[1,5-a]pyridin-6-yl)-4-methoxypyrrolo[2,1-f][1,2,4]triazin-2-yl-7-d)amino)-1-methylcyclobutyl)acetamide-2,2,2-$d_3$ [595];

(1s,3r)-3-((5-([1,2,4]triazolo[1,5-a]pyridin-6-yl)-4-methoxypyrrolo[2,1-f][1,2,4]triazin-2-yl-7-d)amino)-1-ethylcyclobutan-1-ol [596];

(1r,3s)-3-((5-([1,2,4]triazolo[1,5-a]pyridin-6-yl)-4-methoxypyrrolo[2,1-f][1,2,4]triazin-2-yl-7-d)amino)-1-ethylcyclobutan-1-ol [597];

(1r,4r)-4-((5-([1,2,4]triazolo[1,5-a]pyridin-6-yl)-4-methoxypyrrolo[2,1-f][1,2,4]triazin-2-yl-7-d)amino)-1-methylcyclohexan-1-ol [598];

(1r,4r)-4-((5-([1,2,4]triazolo[1,5-a]pyridin-6-yl)-4-methoxypyrrolo[2,1-f][1,2,4]triazin-2-yl-7-d)amino)-1-ethylcyclohexan-1-ol [599]; and 1-(4-((5-([1,2,4]triazolo[1,5-a]pyridin-6-yl)-4-methoxypyrrolo[2,1-f][1,2,4]triazin-2-yl-7-d)amino)piperidin-1-yl)ethan-1-one [600];

or a pharmaceutically acceptable salt thereof.

18. The compound according to claim 1, wherein the compound of Formula I is selected from the group consisting of:

1-(7-((5-([1,2,4]triazolo[1,5-a]pyridin-6-yl)-4-methoxypyrrolo[2,1-f][1,2,4]triazin-2-yl-7-d)amino)-2-azaspiro[3.5]nonan-2-yl)ethan-1-one [601];

1-(7-((5-([1,2,4]triazolo[1,5-a]pyridin-6-yl)-4-methoxypyrrolo[2,1-f][1,2,4]triazin-2-yl-7-d)amino)-2-azaspiro[3.5]nonan-2-yl)ethan-1-one-2,2,2-$d_3$ [602];

N-((1r,3r)-3-((5-([1,2,4]triazolo[1,5-a]pyridin-6-yl)-4-(methoxy-d)pyrrolo[2,1-f][1,2,4]triazin-2-yl)amino)-1-methylcyclobutyl)acetamide [603];

N-((1r,3r)-3-((5-([1,2,4]triazolo[1,5-a]pyridin-6-yl)-4-(methoxy-d)pyrrolo[2,1-f][1,2,4]triazin-2-yl)amino)-1-methylcyclobutyl)acetamide-2,2,2-$d_3$ [604];

(1s,3r)-3-((5-([1,2,4]triazolo[1,5-a]pyridin-6-yl)-4-(methoxy-$d_3$)pyrrolo[2,1-f][1,2,4]triazin-2-yl)amino)-1-ethylcyclobutan-1-ol [605];

(1r,3s)-3-((5-([1,2,4]triazolo[1,5-a]pyridin-6-yl)-4-(methoxy-$d_3$)pyrrolo[2,1-f][1,2,4]triazin-2-yl)amino)-1-ethylcyclobutan-1-ol [606];

(1r,4r)-4-((5-([1,2,4]triazolo[1,5-a]pyridin-6-yl)-4-(methoxy-$d_3$)pyrrolo[2,1-f][1,2,4]triazin-2-yl)amino)-1-methylcyclohexan-1-ol [607];

(1r,4r)-4-((5-([1,2,4]triazolo[1,5-a]pyridin-6-yl)-4-(methoxy-$d_3$)pyrrolo[2,1-f][1,2,4]triazin-2-yl)amino)-1-ethylcyclohexan-1-ol [608];

1-(4-((5-([1,2,4]triazolo[1,5-a]pyridin-6-yl)-4-(methoxy-$d_3$)pyrrolo[2,1-f][1,2,4]triazin-2-yl)amino)piperidin-1-yl)ethan-1-one [609];

1-(7-((5-([1,2,4]triazolo[1,5-a]pyridin-6-yl)-4-(methoxy-$d_3$)pyrrolo[2,1-f][1,2,4]triazin-2-yl)amino)-2-azaspiro[3.5]nonan-2-yl)ethan-1-one [610];

1-(7-((5-([1,2,4]triazolo[1,5-a]pyridin-6-yl)-4-(methoxy-$d_3$)pyrrolo[2,1-f][1,2,4]triazin-2-yl)amino)-2-azaspiro[3.5]nonan-2-yl)ethan-1-one-2,2,2-$d_3$ [611];

N-((1r,3r)-3-((5-([1,2,4]triazolo[1,5-a]pyridin-6-yl)-4-(2,2-difluoroethoxy)pyrrolo[2,1-f][1,2,4]triazin-2-yl)amino)-1-methylcyclobutyl)acetamide [612];

N-((1r,3r)-3-((5-([1,2,4]triazolo[1,5-a]pyridin-6-yl)-4-(2,2-difluoroethoxy)pyrrolo[2,1-f][1,2,4]triazin-2-yl)amino)-1-methylcyclobutyl)acetamide-2,2,2-$d_3$ [613];

(1s,3r)-3-((5-([1,2,4]triazolo[1,5-a]pyridin-6-yl)-4-(2,2-difluoroethoxy)pyrrolo[2,1-f][1,2,4]triazin-2-yl)amino)-1-ethylcyclobutan-1-ol [614];

(1r,3s)-3-((5-([1,2,4]triazolo[1,5-a]pyridin-6-yl)-4-(2,2-difluoroethoxy)pyrrolo[2,1-f][1,2,4]triazin-2-yl)amino)-1-ethylcyclobutan-1-ol [615];

(1r,4r)-4-((5-([1,2,4]triazolo[1,5-a]pyridin-6-yl)-4-(2,2-difluoroethoxy)pyrrolo[2,1-f][1,2,4]triazin-2-yl)amino)-1-methylcyclohexan-1-ol [616];

(1r,4r)-4-((5-([1,2,4]triazolo[1,5-a]pyridin-6-yl)-4-(2,2-difluoroethoxy)pyrrolo[2,1-f][1,2,4]triazin-2-yl)amino)-1-ethylcyclohexan-1-ol [617];

1-(4-((5-([1,2,4]triazolo[1,5-a]pyridin-6-yl)-4-(2,2-difluoroethoxy)pyrrolo[2,1-f][1,2,4]triazin-2-yl)amino)piperidin-1-yl)ethan-1-one [618];

1-(7-((5-([1,2,4]triazolo[1,5-a]pyridin-6-yl)-4-(2,2-difluoroethoxy)pyrrolo[2,1-f][1,2,4]triazin-2-yl)amino)-2-azaspiro[3.5]nonan-2-yl)ethan-1-one [619];

1-(7-((5-([1,2,4]triazolo[1,5-a]pyridin-6-yl)-4-(2,2-difluoroethoxy)pyrrolo[2,1-f][1,2,4]triazin-2-yl)amino)-2-azaspiro[3.5]nonan-2-yl)ethan-1-one-2,2,2-$d_3$ [620];

(1r,4r)-4-((5-([1,2,4]triazolo[1,5-a]pyridin-6-yl)-4-(oxetan-3-yloxy)pyrrolo[2,1-f][1,2,4]triazin-2-yl)amino)-1-methylcyclohexan-1-ol [621];

(1r,4r)-4-((4-methoxy-5-(2-methyl-[1,2,4]triazolo[1,5-a]pyridin-6-yl)pyrrolo[2,1-f][1,2,4]triazin-2-yl)amino)-1-methylcyclohexan-1-ol [622];

(S)-4-methoxy-5-(1-methyl-1H-benzo[d][1,2,3]triazol-6-yl)-N-(morpholin-2-ylmethyl)pyrrolo[2,1-f][1,2,4]triazin-2-amine [623];

N-(cis-3-ethoxycyclobutyl)-4-methoxy-5-(1-methyl-1H-benzo[d][1,2,3]triazol-6-yl)pyrrolo[2,1-f][1,2,4]triazin-2-amine [624];

1-cyano-N-((1s,3s)-3-((4-methoxy-5-(1-methyl-1H-benzo[d][1,2,3]triazol-6-yl)pyrrolo[2,1-f][1,2,4]triazin-2-yl)amino)-1-methylcyclobutyl)cyclopropane-1-carboxamide [625];

(R)—N-(3,3-difluoro-1-methylpiperidin-4-yl)-4-methoxy-5-(1-methyl-1H-benzo[d][1,2,3]triazol-6-yl)pyrrolo[2,1-f][1,2,4]triazin-2-amine [626];

(R)—N-(1-ethyl-3,3-difluoropiperidin-4-yl)-4-methoxy-5-(1-methyl-1H-benzo[d][1,2,3]triazol-6-yl)pyrrolo[2,1-f][1,2,4]triazin-2-amine [627];

(R)—N-(3,3-difluoro-1-(oxetan-3-yl)piperidin-4-yl)-4-methoxy-5-(1-methyl-1H-benzo[d][1,2,3]triazol-6-yl)pyrrolo[2,1-f][1,2,4]triazin-2-amine [628];

(1r,4r)-4-((6-fluoro-4-methoxy-5-(1-methyl-1H-benzo[d][1,2,3]triazol-6-yl)pyrrolo[2,1-f][1,2,4]triazin-2-yl)amino)-1-methylcyclohexan-1-ol [629];

6-fluoro-N-((3R,4S)-3-fluoro-1-methylpiperidin-4-yl)-4-methoxy-5-(1-methyl-1H-benzo[d][1,2,3]triazol-6-yl)pyrrolo[2,1-f][1,2,4]triazin-2-amine [630];

(1r,4r)-1-methyl-4-((5-(1-methyl-1H-benzo[d][1,2,3]triazol-6-yl)-4-(oxetan-3-yloxy)pyrrolo[2,1-f][1,2,4]triazin-2-yl)amino)cyclohexan-1-ol [631];

2-(cis-3-((5-(1-ethyl-1H-benzo[d][1,2,3]triazol-6-yl)-4-methoxypyrrolo[2,1-f][1,2,4]triazin-2-yl)amino)cyclobutoxy)ethan-1-ol [632];

N-((1s,3s)-3-((5-(1-ethyl-1H-benzo[d][1,2,3]triazol-6-yl)-4-methoxypyrrolo[2,1-f][1,2,4]triazin-2-yl)amino)-1-methylcyclobutyl)acetamide [633];

N-((1r,3r)-3-((5-(1-ethyl-1H-benzo[d][1,2,3]triazol-6-yl)-4-methoxypyrrolo[2,1-f][1,2,4]triazin-2-yl)amino)-1-methylcyclobutyl)acetamide [634];

(1s,3s)-3-((5-(1-ethyl-1H-benzo[d][1,2,3]triazol-6-yl)-4-methoxypyrrolo[2,1-f][1,2,4]triazin-2-yl)amino)-1-methylcyclobutan-1-ol [635];

(1r,3r)-3-((5-(1-ethyl-1H-benzo[d][1,2,3]triazol-6-yl)-4-methoxypyrrolo[2,1-f][1,2,4]triazin-2-yl)amino)-1-methylcyclobutan-1-ol [636];

2-((cis-4-((5-(1-ethyl-1H-benzo[d][1,2,3]triazol-6-yl)-4-methoxypyrrolo[2,1-f][1,2,4]triazin-2-yl)amino)cyclohexyl)oxy)ethan-1-ol [637];

(1s,4s)-4-((5-(1-ethyl-1H-benzo[d][1,2,3]triazol-6-yl)-4-methoxypyrrolo[2,1-f][1,2,4]triazin-2-yl)amino)-1-methylcyclohexan-1-ol [638];

(1r,4r)-4-((5-(1-ethyl-1H-benzo[d][1,2,3]triazol-6-yl)-4-methoxypyrrolo[2,1-f][1,2,4]triazin-2-yl)amino)-1-methylcyclohexan-1-ol [639];

1-((3R,4S)-3-((5-(1-ethyl-1H-benzo[d][1,2,3]triazol-6-yl)-4-methoxypyrrolo[2,1-f][1,2,4]triazin-2-yl)amino)-4-fluoropyrrolidin-1-yl)ethan-1-one [640];

5-(1-ethyl-1H-benzo[d][1,2,3]triazol-6-yl)-4-methoxy-N-(1-(oxetan-3-yl)piperidin-4-yl)pyrrolo[2,1-f][1,2,4]triazin-2-amine [641];

5-(1-ethyl-1H-benzo[d][1,2,3]triazol-6-yl)-4-methoxy-N-(1-(3-methyloxetan-3-yl)piperidin-4-yl)pyrrolo[2,1-f][1,2,4]triazin-2-amine [642];

5-(1-ethyl-1H-benzo[d][1,2,3]triazol-6-yl)-N-((3R,4S)-3-fluoro-1-methylpiperidin-4-yl)-4-methoxypyrrolo[2,1-f][1,2,4]triazin-2-amine [643];

1-((3R,4S)-4-((5-(1-ethyl-1H-benzo[d][1,2,3]triazol-6-yl)-4-methoxypyrrolo[2,1-f][1,2,4]triazin-2-yl)amino)-3-fluoropiperidin-1-yl)ethan-1-one [644];

N-((3R,4S)-1-(3,3-difluorocyclobutyl)-3-fluoropiperidin-4-yl)-5-(1-ethyl-1H-benzo[d][1,2,3]triazol-6-yl)-4-methoxypyrrolo[2,1-f][1,2,4]triazin-2-amine [645];

5-(1-ethyl-1H-benzo[d][1,2,3]triazol-6-yl)-N-((3R,4S)-3-fluoro-1-(oxetan-3-yl)piperidin-4-yl)-4-methoxypyrrolo[2,1-f][1,2,4]triazin-2-amine [646];

5-(1-ethyl-1H-benzo[d][1,2,3]triazol-6-yl)-N-((3R,4S)-3-fluoro-1-(3-methyloxetan-3-yl)piperidin-4-yl)-4-methoxypyrrolo[2,1-f][1,2,4]triazin-2-amine [647];

3-((3R,4S)-4-((5-(1-ethyl-1H-benzo[d][1,2,3]triazol-6-yl)-4-methoxypyrrolo[2,1-f][1,2,4]triazin-2-yl)amino)-3-fluoropiperidin-1-yl)oxetane-3-carbonitrile [648];

(R)-1-(4-((5-(1-ethyl-1H-benzo[d][1,2,3]triazol-6-yl)-4-methoxypyrrolo[2,1-f][1,2,4]triazin-2-yl)amino)-3,3-difluoropiperidin-1-yl)ethan-1-one [649];

(R)—N-(3,3-difluoro-1-(oxetan-3-yl)piperidin-4-yl)-5-(1-ethyl-1H-benzo[d][1,2,3]triazol-6-yl)-4-methoxypyrrolo[2,1-f][1,2,4]triazin-2-amine [650];

(R)—N-(3,3-difluoro-1-(3-methyloxetan-3-yl)piperidin-4-yl)-5-(1-ethyl-1H-benzo[d][1,2,3]triazol-6-yl)-4-methoxypyrrolo[2,1-f][1,2,4]triazin-2-amine [651];

2-(cis-3-((5-(1-(2-fluoroethyl)-1H-benzo[d][1,2,3]triazol-6-yl)-4-methoxypyrrolo[2,1-f][1,2,4]triazin-2-yl)amino)cyclobutoxy)ethan-1-ol [652];

N-((1s,3s)-3-((5-(1-(2-fluoroethyl)-1H-benzo[d][1,2,3]triazol-6-yl)-4-methoxypyrrolo[2,1-f][1,2,4]triazin-2-yl)amino)-1-methylcyclobutyl)acetamide [653];

N-((1r,3r)-3-((5-(1-(2-fluoroethyl)-1H-benzo[d][1,2,3]triazol-6-yl)-4-methoxypyrrolo[2,1-f][1,2,4]triazin-2-yl)amino)-1-methylcyclobutyl)acetamide [654];

(1s,3s)-3-((5-(1-(2-fluoroethyl)-1H-benzo[d][1,2,3]triazol-6-yl)-4-methoxypyrrolo[2,1-f][1,2,4]triazin-2-yl)amino)-1-methylcyclobutan-1-ol [655];

(1r,3r)-3-((5-(1-(2-fluoroethyl)-1H-benzo[d][1,2,3]triazol-6-yl)-4-methoxypyrrolo[2,1-f][1,2,4]triazin-2-yl)amino)-1-methylcyclobutan-1-ol [656];

2-((cis-4-((5-(1-(2-fluoroethyl)-1H-benzo[d][1,2,3]triazol-6-yl)-4-methoxypyrrolo[2,1-f][1,2,4]triazin-2-yl)amino)cyclohexyl)oxy)ethan-1-ol [657];

(1s,4s)-4-((5-(1-(2-fluoroethyl)-1H-benzo[d][1,2,3]triazol-6-yl)-4-methoxypyrrolo[2,1-f][1,2,4]triazin-2-yl)amino)-1-methylcyclohexan-1-ol [658];

(1r,4r)-4-((5-(1-(2-fluoroethyl)-1H-benzo[d][1,2,3]triazol-6-yl)-4-methoxypyrrolo[2,1-f][1,2,4]triazin-2-yl)amino)-1-methylcyclohexan-1-ol [659];

1-((3S,4R)-3-fluoro-4-((5-(1-(2-fluoroethyl)-1H-benzo[d][1,2,3]triazol-6-yl)-4-methoxypyrrolo[2,1-f][1,2,4]triazin-2-yl)amino)pyrrolidin-1-yl)ethan-1-one [660];

5-(1-(2-fluoroethyl)-1H-benzo[d][1,2,3]triazol-6-yl)-4-methoxy-N-(1-(oxetan-3-yl)piperidin-4-yl)pyrrolo[2,1-f][1,2,4]triazin-2-amine [661];

5-(1-(2-fluoroethyl)-1H-benzo[d][1,2,3]triazol-6-yl)-4-methoxy-N-(1-(3-methyloxetan-3-yl)piperidin-4-yl)pyrrolo[2,1-f][1,2,4]triazin-2-amine [662];

N-((3R,4S)-3-fluoro-1-methylpiperidin-4-yl)-5-(1-(2-fluoroethyl)-1H-benzo[d][1,2,3]triazol-6-yl)-4-methoxypyrrolo[2,1-f][1,2,4]triazin-2-amine [663];

1-((3R,4S)-3-fluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)ethan-1-one [664];

N-((3R,4S)-1-(3,3-difluorocyclobutyl)-3-fluoropiperidin-4-yl)-5-(1-(2-fluoroethyl)-1H-benzo[d][1,2,3]triazol-6-yl)-4-methoxypyrrolo[2,1-f][1,2,4]triazin-2-amine [665];

N-((3R,4S)-3-fluoro-1-(oxetan-3-yl)piperidin-4-yl)-5-(1-(2-fluoroethyl)-1H-benzo[d][1,2,3]triazol-6-yl)-4-methoxypyrrolo[2,1-f][1,2,4]triazin-2-amine [666];

N-((3R,4S)-3-fluoro-1-(3-methyloxetan-3-yl)piperidin-4-yl)-5-(1-(2-fluoroethyl)-1H-benzo[d][1,2,3]triazol-6-yl)-4-methoxypyrrolo[2,1-f][1,2,4]triazin-2-amine [667];

3-((3R,4S)-3-fluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)oxetane-3-carbonitrile [668];

(R)-1-(3,3-difluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)ethan-1-one [669];

(R)—N-(3,3-difluoro-1-(oxetan-3-yl)piperidin-4-yl)-5-(1-(2-fluoroethyl)-1H-benzo[d][1,2,3]triazol-6-yl)-4-methoxypyrrolo[2,1-f][1,2,4]triazin-2-amine [670];

(R)—N-(3,3-difluoro-1-(3-methyloxetan-3-yl)piperidin-4-yl)-5-(1-(2-fluoroethyl)-1H-benzo[d][1,2,3]triazol-6-yl)-4-methoxypyrrolo[2,1-f][1,2,4]triazin-2-amine [671];

(1r,4r)-4-((5-(1-((E)-2-fluorovinyl)-1H-benzo[d][1,2,3]triazol-6-yl)-4-methoxypyrrolo[2,1-f][1,2,4]triazin-2-yl)amino)-1-methylcyclohexan-1-ol [672];

(E)-5-((5-(1-(2-fluorovinyl)-1H-benzo[d][1,2,3]triazol-6-yl)-4-methoxypyrrolo[2,1-f][1,2,4]triazin-2-yl)amino)-1-methylpiperidin-2-one [673];

2-(cis-3-((5-(1-isopropyl-1H-benzo[d][1,2,3]triazol-6-yl)-4-methoxypyrrolo[2,1-f][1,2,4]triazin-2-yl)amino)cyclobutoxy)ethan-1-ol [674];

N-((1s,3s)-3-((5-(1-isopropyl-1H-benzo[d][1,2,3]triazol-6-yl)-4-methoxypyrrolo[2,1-f][1,2,4]triazin-2-yl)amino)-1-methylcyclobutyl)acetamide [675];

N-((1r,3r)-3-((5-(1-isopropyl-1H-benzo[d][1,2,3]triazol-6-yl)-4-methoxypyrrolo[2,1-f][1,2,4]triazin-2-yl)amino)-1-methylcyclobutyl)acetamide [676];

(1s,3s)-3-((5-(1-isopropyl-1H-benzo[d][1,2,3]triazol-6-yl)-4-methoxypyrrolo[2,1-f][1,2,4]triazin-2-yl)amino)-1-methylcyclobutan-1-ol [677];

(1r,3r)-3-((5-(1-isopropyl-1H-benzo[d][1,2,3]triazol-6-yl)-4-methoxypyrrolo[2,1-f][1,2,4]triazin-2-yl)amino)-1-methylcyclobutan-1-ol [678];

2-((cis-4-((5-(1-isopropyl-1H-benzo[d][1,2,3]triazol-6-yl)-4-methoxypyrrolo[2,1-f][1,2,4]triazin-2-yl)amino)cyclohexyl)oxy)ethan-1-ol [679];

(1s,4s)-4-((5-(1-isopropyl-1H-benzo[d][1,2,3]triazol-6-yl)-4-methoxypyrrolo[2,1-f][1,2,4]triazin-2-yl)amino)-1-methylcyclohexan-1-ol [680];

(1r,4r)-4-((5-(1-isopropyl-1H-benzo[d][1,2,3]triazol-6-yl)-4-methoxypyrrolo[2,1-f][1,2,4]triazin-2-yl)amino)-1-methylcyclohexan-1-ol [681];

1-((3S,4R)-3-fluoro-4-((5-(1-isopropyl-1H-benzo[d][1,2,3]triazol-6-yl)-4-methoxypyrrolo[2,1-f][1,2,4]triazin-2-yl)amino)pyrrolidin-1-yl)ethan-1-one [682];

5-(1-isopropyl-1H-benzo[d][1,2,3]triazol-6-yl)-4-methoxy-N-(1-(oxetan-3-yl)piperidin-4-yl)pyrrolo[2,1-f][1,2,4]triazin-2-amine [683];

5-(1-isopropyl-1H-benzo[d][1,2,3]triazol-6-yl)-4-methoxy-N-(1-(3-methyloxetan-3-yl)piperidin-4-yl)pyrrolo[2,1-f][1,2,4]triazin-2-amine [684];

N-((3R,4S)-3-fluoro-1-methylpiperidin-4-yl)-5-(1-isopropyl-1H-benzo[d][1,2,3]triazol-6-yl)-4-methoxypyrrolo[2,1-f][1,2,4]triazin-2-amine [685];

1-((3R,4S)-3-fluoro-4-((5-(1-isopropyl-1H-benzo[d][1,2,3]triazol-6-yl)-4-methoxypyrrolo[2,1-f][1,2,4]triazin-2-yl)amino)piperidin-1-yl)ethan-1-one [686];

N-((3R,4S)-1-(3,3-difluorocyclobutyl)-3-fluoropiperidin-4-yl)-5-(1-isopropyl-1H-benzo[d][1,2,3]triazol-6-yl)-4-methoxypyrrolo[2,1-f][1,2,4]triazin-2-amine [687];

N-((3R,4S)-3-fluoro-1-(oxetan-3-yl)piperidin-4-yl)-5-(1-isopropyl-1H-benzo[d][1,2,3]triazol-6-yl)-4-methoxypyrrolo[2,1-f][1,2,4]triazin-2-amine [688];

N-((3R,4S)-3-fluoro-1-(3-methyloxetan-3-yl)piperidin-4-yl)-5-(1-isopropyl-1H-benzo[d][1,2,3]triazol-6-yl)-4-methoxypyrrolo[2,1-f][1,2,4]triazin-2-amine [689];

3-((3R,4S)-3-fluoro-4-((5-(1-isopropyl-1H-benzo[d][1,2,3]triazol-6-yl)-4-methoxypyrrolo[2,1-f][1,2,4]triazin-2-yl)amino)piperidin-1-yl)oxetane-3-carbonitrile [690];

(R)-1-(3,3-difluoro-4-((5-(1-isopropyl-1H-benzo[d][1,2,3]triazol-6-yl)-4-methoxypyrrolo[2,1-f][1,2,4]triazin-2-yl)amino)piperidin-1-yl)ethan-1-one [691];

(R)—N-(3,3-difluoro-1-(oxetan-3-yl)piperidin-4-yl)-5-(1-isopropyl-1H-benzo[d][1,2,3]triazol-6-yl)-4-methoxypyrrolo[2,1-f][1,2,4]triazin-2-amine [692];

(R)—N-(3,3-difluoro-1-(3-methyloxetan-3-yl)piperidin-4-yl)-5-(1-isopropyl-1H-benzo[d][1,2,3]triazol-6-yl)-4-methoxypyrrolo[2,1-f][1,2,4]triazin-2-amine [693];

5-(1-(2,2-difluoroethyl)-1H-benzo[d][1,2,3]triazol-6-yl)-N-(2-fluoro-2-methylpropyl)-4-methoxypyrrolo[2,1-f][1,2,4]triazin-2-amine [694];

3-((5-(1-(2,2-difluoroethyl)-1H-benzo[d][1,2,3]triazol-6-yl)-4-methoxypyrrolo[2,1-f][1,2,4]triazin-2-yl)amino)-2,2-dimethylpropanenitrile [695];

1-((5-(1-(2,2-difluoroethyl)-1H-benzo[d][1,2,3]triazol-6-yl)-4-methoxypyrrolo[2,1-f][1,2,4]triazin-2-yl)amino)-2-methylpropan-2-ol [696];

(R)-5-(1-(2,2-difluoroethyl)-1H-benzo[d][1,2,3]triazol-6-yl)-4-methoxy-N-(1-(oxetan-3-yl)ethyl)pyrrolo[2,1-f][1,2,4]triazin-2-amine [697];

(S)-5-(1-(2,2-difluoroethyl)-1H-benzo[d][1,2,3]triazol-6-yl)-4-methoxy-N-(1-(oxetan-3-yl)ethyl)pyrrolo[2,1-f][1,2,4]triazin-2-amine [698];

2-(cis-3-((5-(1-(2,2-difluoroethyl)-1H-benzo[d][1,2,3]triazol-6-yl)-4-methoxypyrrolo[2,1-f][1,2,4]triazin-2-yl)amino)cyclobutoxy)ethan-1-ol [699]; and (1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-N,1-dimethylcyclobutane-1-carboxamide [700];

or a pharmaceutically acceptable salt thereof.

19. The compound according to claim 1, wherein the compound of Formula I is selected from the group consisting of:

(1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-N,1-dimethylcyclobutane-1-carboxamide [701];

N-((1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutyl)acetamide [702];

N-((1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutyl)acetamide [703];

N-((1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutyl)-N-methylacetamide [704];

N-((1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutyl)-N-methylacetamide [705];

1-cyano-N-((1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutyl)cyclopropane-1-carboxamide [706];

1-cyano-N-((1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutyl)cyclopropane-1-carboxamide [707];

(1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutane-1-carbonitrile [708];

(1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutane-1-carbonitrile [709];

(1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutan-1-ol [710];

(1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclobutan-1-ol [711];

(1s,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-ethylcyclobutan-1-ol [712];

(1r,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-ethylcyclobutan-1-ol [713];

(1s,3s)-3-((5-(1-(2,2-difluoroethyl)-1H-benzo[d][1,2,3]triazol-6-yl)-4-methoxypyrrolo[2,1-f][1,2,4]triazin-2-yl)amino)-1-(trifluoromethyl)cyclobutan-1-ol [714];

(1r,3r)-3-((5-(1-(2,2-difluoroethyl)-1H-benzo[d][1,2,3]triazol-6-yl)-4-methoxypyrrolo[2,1-f][1,2,4]triazin-2-yl)amino)-1-(trifluoromethyl)cyclobutan-1-ol [715];

2-(trans-4-((5-(1-(2,2-difluoroethyl)-1H-benzo[d][1,2,3]triazol-6-yl)-4-methoxypyrrolo[2,1-f][1,2,4]triazin-2-yl)amino)cyclohexyl)propan-2-ol [716];

N-(cis-4-((5-(1-(2,2-difluoroethyl)-1H-benzo[d][1,2,3]triazol-6-yl)-4-methoxypyrrolo[2,1-f][1,2,4]triazin-2-yl)amino)cyclohexyl)acetamide [717];

cis-4-((5-(1-(2,2-difluoroethyl)-1H-benzo[d][1,2,3]triazol-6-yl)-4-methoxypyrrolo[2,1-f][1,2,4]triazin-2-yl)amino)cyclohexan-1-ol [718];

trans-4-((5-(1-(2,2-difluoroethyl)-1H-benzo[d][1,2,3]triazol-6-yl)-4-methoxypyrrolo[2,1-f][1,2,4]triazin-2-yl)amino)cyclohexan-1-ol [719];

2-((cis-4-((5-(1-(2,2-difluoroethyl)-1H-benzo[d][1,2,3]triazol-6-yl)-4-methoxypyrrolo[2,1-f][1,2,4]triazin-2-yl)amino)cyclohexyl)oxy)ethan-1-ol [720];

4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexane-1-carbonitrile [721];

(1s,4s)-4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexane-1-carbonitrile [722];

(1r,4r)-4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexane-1-carbonitrile [723];

(1s,4s)-4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexan-1-ol [724];

(1r,4r)-4-((5-(1-(2,2-difluoroethyl)-1H-benzo[d][1,2,3]triazol-6-yl)-4-methoxypyrrolo[2,1-f][1,2,4]triazin-2-yl)amino)-1-methylcyclohexan-1-ol [725];

(1s,4s)-4-((5-(1-(2,2-difluoroethyl)-1H-benzo[d][1,2,3]triazol-6-yl)-4-methoxypyrrolo[2,1-f][1,2,4]triazin-2-yl)amino)-1-ethylcyclohexan-1-ol [726];

(1r,4r)-4-((5-(1-(2,2-difluoroethyl)-1H-benzo[d][1,2,3]triazol-6-yl)-4-methoxypyrrolo[2,1-f][1,2,4]triazin-2-yl)amino)-1-ethylcyclohexan-1-ol [727];

(1s,4s)-4-((5-(1-(2,2-difluoroethyl)-1H-benzo[d][1,2,3]triazol-6-yl)-4-methoxypyrrolo[2,1-f][1,2,4]triazin-2-yl)amino)-1-(trifluoromethyl)cyclohexan-1-ol [728];

(1r,4r)-4-((5-(1-(2,2-difluoroethyl)-1H-benzo[d][1,2,3]triazol-6-yl)-4-methoxypyrrolo[2,1-f][1,2,4]triazin-2-yl)amino)-1-(trifluoromethyl)cyclohexan-1-ol [729];

5-(1-(2,2-difluoroethyl)-1H-benzo[d][1,2,3]triazol-6-yl)-N-((3R,4S)-4-fluoro-1-methylpyrrolidin-3-yl)-4-methoxypyrrolo[2,1-f][1,2,4]triazin-2-amine [730];

5-(1-(2,2-difluoroethyl)-1H-benzo[d][1,2,3]triazol-6-yl)-N-((3S,4R)-4-fluoro-1-methylpyrrolidin-3-yl)-4-methoxypyrrolo[2,1-f][1,2,4]triazin-2-amine [731];

5-(1-(2,2-difluoroethyl)-1H-benzo[d][1,2,3]triazol-6-yl)-N-((3R,4S)-1-ethyl-4-fluoropyrrolidin-3-yl)-4-methoxypyrrolo[2,1-f][1,2,4]triazin-2-amine [732];

5-(1-(2,2-difluoroethyl)-1H-benzo[d][1,2,3]triazol-6-yl)-N-((3S,4R)-1-ethyl-4-fluoropyrrolidin-3-yl)-4-methoxypyrrolo[2,1-f][1,2,4]triazin-2-amine [733];

1-((3R,4S)-3-((5-(1-(2,2-difluoroethyl)-1H-benzo[d][1,2,3]triazol-6-yl)-4-methoxypyrrolo[2,1-f][1,2,4]triazin-2-yl)amino)-4-fluoropyrrolidin-1-yl)ethan-1-one [734];

1-((3S,4R)-3-((5-(1-(2,2-difluoroethyl)-1H-benzo[d][1,2,3]triazol-6-yl)-4-methoxypyrrolo[2,1-f][1,2,4]triazin-2-yl)amino)-4-fluoropyrrolidin-1-yl)ethan-1-one [735];

1-((3S,4R)-3-((5-(1-(2,2-difluoroethyl)-1H-benzo[d][1,2,3]triazol-6-yl)-4-methoxypyrrolo[2,1-f][1,2,4]triazin-2-yl)amino)-4-fluoropyrrolidin-1-yl)ethan-1-one-2,2,2-$d_3$ [736];

1-((3S,4R)-3-((5-(1-(2,2-difluoroethyl)-1H-benzo[d][1,2,3]triazol-6-yl)-4-methoxypyrrolo[2,1-f][1,2,4]triazin-2-yl)amino)-4-fluoropyrrolidin-1-yl)propan-1-one [737];

N-((3S,4R)-1-cyclopropyl-4-fluoropyrrolidin-3-yl)-5-(1-(2,2-difluoroethyl)-1H-benzo[d][1,2,3]triazol-6-yl)-4-methoxypyrrolo[2,1-f][1,2,4]triazin-2-amine [738];

5-(1-(2,2-difluoroethyl)-1H-benzo[d][1,2,3]triazol-6-yl)-N-((3R,4S)-4-fluoro-1-(oxetan-3-yl)pyrrolidin-3-yl)-4-methoxypyrrolo[2,1-f][1,2,4]triazin-2-amine [739];

5-(1-(2,2-difluoroethyl)-1H-benzo[d][1,2,3]triazol-6-yl)-N-((3S,4R)-4-fluoro-1-(3-methyloxetan-3-yl)pyrrolidin-3-yl)-4-methoxypyrrolo[2,1-f][1,2,4]triazin-2-amine [740];

3-((3R,4S)-3-((5-(1-(2,2-difluoroethyl)-1H-benzo[d][1,2,3]triazol-6-yl)-4-methoxypyrrolo[2,1-f][1,2,4]triazin-2-yl)amino)-4-fluoropyrrolidin-1-yl)oxetane-3-carbonitrile [741];

(R)—N-(4,4-difluoro-1-methylpyrrolidin-3-yl)-5-(1-(2,2-difluoroethyl)-1H-benzo[d][1,2,3]triazol-6-yl)-4-methoxypyrrolo[2,1-f][1,2,4]triazin-2-amine [742];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropyrrolidin-1-yl)ethan-1-one [743];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropyrrolidin-1-yl)ethan-1-one-2,2,2-$d_3$ [744];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropyrrolidin-1-yl)propan-1-one [745];

(R)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylpyrrolidin-2-one [746];

(S)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylpyrrolidin-2-one [747];

2-(4-((5-(1-(2,2-difluoroethyl)-1H-benzo[d][1,2,3]triazol-6-yl)-4-methoxypyrrolo[2,1-f][1,2,4]triazin-2-yl)amino)piperidin-1-yl)ethan-1-ol [748];

3-(4-((5-(1-(2,2-difluoroethyl)-1H-benzo[d][1,2,3]triazol-6-yl)-4-methoxypyrrolo[2,1-f][1,2,4]triazin-2-yl)amino)piperidin-1-yl)-2,2-dimethylpropanenitrile [749];

5-(1-(2,2-difluoroethyl)-1H-benzo[d][1,2,3]triazol-6-yl)-4-methoxy-N-(1-(oxetan-3-yl)piperidin-4-yl)pyrrolo[2,1-f][1,2,4]triazin-2-amine [750];

5-(1-(2,2-difluoroethyl)-1H-benzo[d][1,2,3]triazol-6-yl)-4-methoxy-N-(1-(3-methyloxetan-3-yl)piperidin-4-yl)pyrrolo[2,1-f][1,2,4]triazin-2-amine [751];

3-(4-((5-(1-(2,2-difluoroethyl)-1H-benzo[d][1,2,3]triazol-6-yl)-4-methoxypyrrolo[2,1-f][1,2,4]triazin-2-yl)amino)piperidin-1-yl)oxetane-3-carbonitrile [752];

1-(4-((5-(1-(2,2-difluoroethyl)-1H-benzo[d][1,2,3]triazol-6-yl)-4-methoxypyrrolo[2,1-f][1,2,4]triazin-2-yl)amino)piperidine-1-carbonyl)cyclopropane-1-carbonitrile [753];

5-(1-(2,2-difluoroethyl)-1H-benzo[d][1,2,3]triazol-6-yl)-N-((3R,4S)-3-fluoro-1-methylpiperidin-4-yl)-4-methoxypyrrolo[2,1-f][1,2,4]triazin-2-amine [754];

5-(1-(2,2-difluoroethyl)-1H-benzo[d][1,2,3]triazol-6-yl)-N-((3R,4S)-1-ethyl-3-fluoropiperidin-4-yl)-4-methoxypyrrolo[2,1-f][1,2,4]triazin-2-amine [755];

2-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-ol [756];

3-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)-2,2-dimethylpropanenitrile [757];

1-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)-2-methylpropan-2-ol [758];

N-((3R,4S)-1-cyclopropyl-3-fluoropiperidin-4-yl)-5-(1-(2,2-difluoroethyl)-1H-benzo[d][1,2,3]triazol-6-yl)-4-methoxypyrrolo[2,1-f][1,2,4]triazin-2-amine [759];

N-((3R,4S)-1-(3,3-difluorocyclobutyl)-3-fluoropiperidin-4-yl)-5-(1-(2,2-difluoroethyl)-1H-benzo[d][1,2,3]triazol-6-yl)-4-methoxypyrrolo[2,1-f][1,2,4]triazin-2-amine [760];

5-(1-(2,2-difluoroethyl)-1H-benzo[d][1,2,3]triazol-6-yl)-N-((3S,4R)-3-fluoro-1-(oxetan-3-yl)piperidin-4-yl)-4-methoxypyrrolo[2,1-f][1,2,4]triazin-2-amine [761];

5-(1-(2,2-difluoroethyl)-1H-benzo[d][1,2,3]triazol-6-yl)-N-((3R,4S)-3-fluoro-1-(oxetan-3-yl)piperidin-4-yl)-4-methoxypyrrolo[2,1-f][1,2,4]triazin-2-amine [762];

5-(1-(2,2-difluoroethyl)-1H-benzo[d][1,2,3]triazol-6-yl)-N-((3S,4R)-3-fluoro-1-(3-methyloxetan-3-yl)piperidin-4-yl)-4-methoxypyrrolo[2,1-f][1,2,4]triazin-2-amine [763];

5-(1-(2,2-difluoroethyl)-1H-benzo[d][1,2,3]triazol-6-yl)-N-((3R,4S)-3-fluoro-1-(3-methyloxetan-3-yl)piperidin-4-yl)-4-methoxypyrrolo[2,1-f][1,2,4]triazin-2-amine [764];

5-(1-(2,2-difluoroethyl)-1H-benzo[d][1,2,3]triazol-6-yl)-N-((3R,4S)-1-(3-ethyloxetan-3-yl)-3-fluoropiperidin-4-yl)-4-methoxypyrrolo[2,1-f][1,2,4]triazin-2-amine [765];

5-(1-(2,2-difluoroethyl)-1H-benzo[d][1,2,3]triazol-6-yl)-N-((3R,4S)-1-(3-ethynyloxetan-3-yl)-3-fluoropiperidin-4-yl)-4-methoxypyrrolo[2,1-f][1,2,4]triazin-2-amine [766];

5-(1-(2,2-difluoroethyl)-1H-benzo[d][1,2,3]triazol-6-yl)-N-((3R,4S)-3-fluoro-1-(3-isopropyloxetan-3-yl)piperidin-4-yl)-4-methoxypyrrolo[2,1-f][1,2,4]triazin-2-amine [767];

N-((3R,4S)-1-(3-cyclopropyloxetan-3-yl)-3-fluoropiperidin-4-yl)-5-(1-(2,2-difluoroethyl)-1H-benzo[d][1,2,3]triazol-6-yl)-4-methoxypyrrolo[2,1-f][1,2,4]triazin-2-amine [768];

3-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)oxetane-3-carbonitrile [769];

1-((3S,4R)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-one [770];

1-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-one [771];

1-((3S,4R)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)propan-1-one [772];

1-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)propan-1-one [773];

1-((3S,4R)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-one-2,2,2-$d_3$ [774];

1-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidin-1-yl)ethan-1-one-2,2,2-$d_3$ [775];

1-((3R,4S)-4-((5-(1-(2,2-difluoroethyl)-1H-benzo[d][1,2,3]triazol-6-yl)-4-methoxypyrrolo[2,1-f][1,2,4]triazin-2-yl)amino)-3-fluoropiperidine-1-carbonyl)cyclopropane-1-carbonitrile [776];

(R)—N-(3,3-difluoro-1-methylpiperidin-4-yl)-5-(1-(2,2-difluoroethyl)-1H-benzo[d][1,2,3]triazol-6-yl)-4-methoxypyrrolo[2,1-f][1,2,4]triazin-2-amine [777];

(R)—N-(3,3-difluoro-1-(methyl-$d_2$)piperidin-4-yl)-5-(1-(2,2-difluoroethyl)-1H-benzo[d][1,2,3]triazol-6-yl)-4-methoxypyrrolo[2,1-f][1,2,4]triazin-2-amine [778];

(R)—N-(3,3-difluoro-1-(methyl-$d_3$)piperidin-4-yl)-5-(1-(2,2-difluoroethyl)-1H-benzo[d][1,2,3]triazol-6-yl)-4-methoxypyrrolo[2,1-f][1,2,4]triazin-2-amine [779];

(R)-5-(1-(2,2-difluoroethyl)-1H-benzo[d][1,2,3]triazol-6-yl)-N-(1-ethyl-3,3-difluoropiperidin-4-yl)-4-methoxypyrrolo[2,1-f][1,2,4]triazin-2-amine [780];

(R)-2-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)ethan-1-ol [781];

(R)-3-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)-2,2-dimethylpropanenitrile [782];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)-2-methylpropan-2-ol [783];

(R)—N-(1-cyclopropyl-3,3-difluoropiperidin-4-yl)-5-(1-(2,2-difluoroethyl)-1H-benzo[d][1,2,3]triazol-6-yl)-4-methoxypyrrolo[2,1-f][1,2,4]triazin-2-amine [784];

(R)—N-(3,3-difluoro-1-(oxetan-3-yl)piperidin-4-yl)-5-(1-(2,2-difluoroethyl)-1H-benzo[d][1,2,3]triazol-6-yl)-4-methoxypyrrolo[2,1-f][1,2,4]triazin-2-amine [785];

(R)—N-(3,3-difluoro-1-(3-methyloxetan-3-yl)piperidin-4-yl)-5-(1-(2,2-difluoroethyl)-1H-benzo[d][1,2,3]triazol-6-yl)-4-methoxypyrrolo[2,1-f][1,2,4]triazin-2-amine [786];

(R)-3-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)oxetane-3-carbonitrile [787];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)ethan-1-one [788];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)ethan-1-one-2,2,2-$d_3$ [789];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)propan-1-one [790];

(R)-1-(4-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidine-1-carbonyl)cyclopropane-1-carbonitrile [791];

(S)-1-(5-((5-(1-(2,2-difluoroethyl)-1H-benzo[d][1,2,3]triazol-6-yl)-4-methoxypyrrolo[2,1-f][1,2,4]triazin-2-yl)amino)-3,3-difluoropiperidin-1-yl)ethan-1-one [792];

5-((5-(1-(2,2-difluoroethyl)-1H-benzo[d][1,2,3]triazol-6-yl)-4-methoxypyrrolo[2,1-f][1,2,4]triazin-2-yl)amino)-1-methylpiperidin-2-one [793];

(S)-5-((5-(1-(2,2-difluoroethyl)-1H-benzo[d][1,2,3]triazol-6-yl)-4-methoxypyrrolo[2,1-f][1,2,4]triazin-2-yl)amino)-1-methylpiperidin-2-one [794];

(R)-5-((5-(1-(2,2-difluoroethyl)-1H-benzo[d][1,2,3]triazol-6-yl)-4-methoxypyrrolo[2,1-f][1,2,4]triazin-2-yl)amino)-1-methylpiperidin-2-one [795];

(R)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylpiperidin-2-one [796];

(S)-3-((5-(1-(2,2-difluoroethyl)-1H-benzo[d][1,2,3]triazol-6-yl)-4-methoxypyrrolo[2,1-f][1,2,4]triazin-2-yl)amino)-1-methylpiperidin-2-one [797];

4-((5-(1-(2,2-difluoroethyl)-1H-benzo[d][1,2,3]triazol-6-yl)-4-methoxypyrrolo[2,1-f][1,2,4]triazin-2-yl)amino)bicyclo[2.2.1]heptan-1-ol [798];

1-(7-((5-(1-(2,2-difluoroethyl)-1H-benzo[d][1,2,3]triazol-6-yl)-4-methoxypyrrolo[2,1-f][1,2,4]triazin-2-yl)amino)-2-azaspiro[3.5]nonan-2-yl)ethan-1-one [799]; and 1-(7-((5-(1-(2,2-difluoroethyl)-1H-benzo[d][1,2,3]triazol-6-yl)-4-methoxypyrrolo[2,1-f][1,2,4]triazin-2-yl)amino)-2-azaspiro[3.5]nonan-2-yl)ethan-1-one-2,2,2-$d_3$ [800];

or a pharmaceutically acceptable salt thereof.

20. The compound according to claim 1, wherein the compound of Formula I is selected from the group consisting of:

5-(1-(2,2-difluoroethyl)-1H-benzo[d][1,2,3]triazol-6-yl)-4-methoxy-N-(2-oxaspiro[3.5]nonan-7-yl)pyrrolo[2,1-f][1,2,4]triazin-2-amine [801];

5-(1-(2,2-difluoroethyl)-1H-benzo[d][1,2,3]triazol-6-yl)-4-methoxy-N-((4r,7r)-1-oxaspiro[3.5]nonan-7-yl)pyrrolo[2,1-f][1,2,4]triazin-2-amine [802];

5-(1-(2,2-difluoroethyl)-1H-benzo[d][1,2,3]triazol-6-yl)-4-methoxy-N-((4s,7s)-1-oxaspiro[3.5]nonan-7-yl)pyrrolo[2,1-f][1,2,4]triazin-2-amine [803];

2-(cis-3-((5-(1-(2,2-difluoroethyl)-4-fluoro-1H-benzo[d][1,2,3]triazol-6-yl)-4-methoxypyrrolo[2,1-f][1,2,4]triazin-2-yl)amino)cyclobutoxy)ethan-1-ol [804];

N-((1s,3s)-3-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-1-methylcyclobutyl)acetamide [805];

N-((1r,3r)-3-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-1-methylcyclobutyl)acetamide [806];

(1s,3s)-3-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-1-methylcyclobutan-1-ol [807];

(1r,3r)-3-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-1-methylcyclobutan-1-ol [808];

2-((cis-4-((5-(1-(2,2-difluoroethyl)-4-fluoro-1H-benzo[d][1,2,3]triazol-6-yl)-4-methoxypyrrolo[2,1-f][1,2,4]triazin-2-yl)amino)cyclohexyl)oxy)ethan-1-ol [809];

(1s,4s)-4-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-1-methylcyclohexan-1-ol [810];

(1r,4r)-4-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-1-methylcyclohexan-1-ol [811];

1-((3R,4S)-3-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-4-fluoropyrrolidin-1-yl)ethan-1-one [812];

5-(1-(2,2-difluoroethyl)-4-fluoro-1H-benzo[d][1,2,3]triazol-6-yl)-4-methoxy-N-(1-(oxetan-3-yl)piperidin-4-yl)pyrrolo[2,1-f][1,2,4]triazin-2-amine [813];

5-(1-(2,2-difluoroethyl)-4-fluoro-1H-benzo[d][1,2,3]triazol-6-yl)-4-methoxy-N-(1-(3-methyloxetan-3-yl)piperidin-4-yl)pyrrolo[2,1-f][1,2,4]triazin-2-amine [814];

5-(1-(2,2-difluoroethyl)-4-fluoro-1H-benzo[d][1,2,3]triazol-6-yl)-N-((3R,4S)-3-fluoro-1-methylpiperidin-4-yl)-4-methoxypyrrolo[2,1-f][1,2,4]triazin-2-amine [815];

1-((3R,4S)-4-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-3-fluoropiperidin-1-yl)ethan-1-one [816];

N-((3R,4S)-1-(3,3-difluorocyclobutyl)-3-fluoropiperidin-4-yl)-5-(1-(2,2-difluoroethyl)-4-fluoro-1H-benzo[d][1,2,3]triazol-6-yl)-4-methoxypyrrolo[2,1-f][1,2,4]triazin-2-amine [817];

5-(1-(2,2-difluoroethyl)-4-fluoro-1H-benzo[d][1,2,3]triazol-6-yl)-N-((3R,4S)-3-fluoro-1-(oxetan-3-yl)piperidin-4-yl)-4-methoxypyrrolo[2,1-f][1,2,4]triazin-2-amine [818];

5-(1-(2,2-difluoroethyl)-4-fluoro-1H-benzo[d][1,2,3]triazol-6-yl)-N-((3R,4S)-3-fluoro-1-(3-methyloxetan-3-yl)piperidin-4-yl)-4-methoxypyrrolo[2,1-f][1,2,4]triazin-2-amine [819];

3-((3R,4S)-4-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-3-fluoropiperidin-1-yl)oxetane-3-carbonitrile [820];

(R)-1-(4-((5-(1-(2,2-difluoroethyl)-4-fluoro-1H-benzo[d][1,2,3]triazol-6-yl)-4-methoxypyrrolo[2,1-f][1,2,4]triazin-2-yl)amino)-3,3-difluoropiperidin-1-yl)ethan-1-one [821];

(R)—N-(3,3-difluoro-1-(oxetan-3-yl)piperidin-4-yl)-5-(1-(2,2-difluoroethyl)-4-fluoro-1H-benzo[d][1,2,3]triazol-6-yl)-4-methoxypyrrolo[2,1-f][1,2,4]triazin-2-amine [822];

(R)—N-(3,3-difluoro-1-(3-methyloxetan-3-yl)piperidin-4-yl)-5-(1-(2,2-difluoroethyl)-4-fluoro-1H-benzo[d][1,2,3]triazol-6-yl)-4-methoxypyrrolo[2,1-f][1,2,4]triazin-2-amine [823];

2-(cis-3-((5-(1-(2,2-difluoroethyl)-1H-benzo[d][1,2,3]triazol-6-yl)-4-methoxypyrrolo[2,1-f][1,2,4]triazin-2-yl-7-d)amino)cyclobutoxy)ethan-1-ol [824];

N-((1s,3s)-3-((5-(1-(2,2-difluoroethyl)-1H-benzo[d][1,2,3]triazol-6-yl)-4-methoxypyrrolo[2,1-f][1,2,4]triazin-2-yl-7-d)amino)-1-methylcyclobutyl)acetamide [825];

N-((1r,3r)-3-((5-(1-(2,2-difluoroethyl)-1H-benzo[d][1,2,3]triazol-6-yl)-4-methoxypyrrolo[2,1-f][1,2,4]triazin-2-yl-7-d)amino)-1-methylcyclobutyl)acetamide [826];

(1s,3s)-3-((5-(1-(2,2-difluoroethyl)-1H-benzo[d][1,2,3]triazol-6-yl)-4-methoxypyrrolo[2,1-f][1,2,4]triazin-2-yl-7-d)amino)-1-methylcyclobutan-1-ol [827];

(1r,3r)-3-((5-(1-(2,2-difluoroethyl)-1H-benzo[d][1,2,3]triazol-6-yl)-4-methoxypyrrolo[2,1-f][1,2,4]triazin-2-yl-7-d)amino)-1-methylcyclobutan-1-ol [828];

2-((cis-4-((5-(1-(2,2-difluoroethyl)-1H-benzo[d][1,2,3]triazol-6-yl)-4-methoxypyrrolo[2,1-f][1,2,4]triazin-2-yl-7-d)amino)cyclohexyl)oxy)ethan-1-ol [829];

(1s,4s)-4-((5-(1-(2,2-difluoroethyl)-1H-benzo[d][1,2,3]triazol-6-yl)-4-methoxypyrrolo[2,1-f][1,2,4]triazin-2-yl-7-d)amino)-1-methylcyclohexan-1-ol [830];

(1r,4r)-4-((5-(1-(2,2-difluoroethyl)-1H-benzo[d][1,2,3]triazol-6-yl)-4-methoxypyrrolo[2,1-f][1,2,4]triazin-2-yl-7-d)amino)-1-methylcyclohexan-1-ol [831];

1-((3R,4S)-3-((5-(1-(2,2-difluoroethyl)-1H-benzo[d][1,2,3]triazol-6-yl)-4-methoxypyrrolo[2,1-f][1,2,4]triazin-2-yl-7-d)amino)-4-fluoropyrrolidin-1-yl)ethan-1-one [832];

5-(1-(2,2-difluoroethyl)-1H-benzo[d][1,2,3]triazol-6-yl)-4-methoxy-N-(1-(oxetan-3-yl)piperidin-4-yl)pyrrolo[2,1-f][1,2,4]triazin-7-d-2-amine [833];

5-(1-(2,2-difluoroethyl)-1H-benzo[d][1,2,3]triazol-6-yl)-4-methoxy-N-(1-(3-methyloxetan-3-yl)piperidin-4-yl)pyrrolo[2,1-f][1,2,4]triazin-7-d-2-amine [834];

5-(1-(2,2-difluoroethyl)-1H-benzo[d][1,2,3]triazol-6-yl)-N-((3R,4S)-3-fluoro-1-methylpiperidin-4-yl)-4-methoxypyrrolo[2,1-f][1,2,4]triazin-7-d-2-amine [835];

1-((3R,4S)-4-((5-(1-(2,2-difluoroethyl)-1H-benzo[d][1,2,3]triazol-6-yl)-4-methoxypyrrolo[2,1-f][1,2,4]triazin-2-yl-7-d)amino)-3-fluoropiperidin-1-yl)ethan-1-one [836];

N-((3R,4S)-1-(3,3-difluorocyclobutyl)-3-fluoropiperidin-4-yl)-5-(1-(2,2-difluoroethyl)-1H-benzo[d][1,2,3]triazol-6-yl)-4-methoxypyrrolo[2,1-f][1,2,4]triazin-7-d-2-amine [837];

5-(1-(2,2-difluoroethyl)-1H-benzo[d][1,2,3]triazol-6-yl)-N-((3R,4S)-3-fluoro-1-(oxetan-3-yl)piperidin-4-yl)-4-methoxypyrrolo[2,1-f][1,2,4]triazin-7-d-2-amine [838];

5-(1-(2,2-difluoroethyl)-1H-benzo[d][1,2,3]triazol-6-yl)-N-((3R,4S)-3-fluoro-1-(3-methyloxetan-3-yl)piperidin-4-yl)-4-methoxypyrrolo[2,1-f][1,2,4]triazin-7-d-2-amine [839];

3-((3R,4S)-4-((5-(1-(2,2-difluoroethyl)-1H-benzo[d][1,2,3]triazol-6-yl)-4-methoxypyrrolo[2,1-f][1,2,4]triazin-2-yl-7-d)amino)-3-fluoropiperidin-1-yl)oxetane-3-carbonitrile [840];

(R)-1-(4-((5-(1-(2,2-difluoroethyl)-1H-benzo[d][1,2,3]triazol-6-yl)-4-methoxypyrrolo[2,1-f][1,2,4]triazin-2-yl-7-d)amino)-3,3-difluoropiperidin-1-yl)ethan-1-one [841];

(R)—N-(3,3-difluoro-1-(oxetan-3-yl)piperidin-4-yl)-5-(1-(2,2-difluoroethyl)-1H-benzo[d][1,2,3]triazol-6-yl)-4-methoxypyrrolo[2,1-f][1,2,4]triazin-7-d-2-amine [842];

(R)—N-(3,3-difluoro-1-(3-methyloxetan-3-yl)piperidin-4-yl)-5-(1-(2,2-difluoroethyl)-1H-benzo[d][1,2,3]triazol-6-yl)-4-methoxypyrrolo[2,1-f][1,2,4]triazin-7-d-2-amine [843];

2-(cis-3-((5-(1-(2,2-difluoroethyl)-1H-benzo[d][1,2,3]triazol-6-yl)-6-fluoro-4-methoxypyrrolo[2,1-f][1,2,4]triazin-2-yl)amino)cyclobutoxy)ethan-1-ol [844];

N-((1s,3s)-3-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-1-methylcyclobutyl)acetamide [845];

N-((1r,3r)-3-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-1-methylcyclobutyl)acetamide [846];

(1s,3s)-3-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-1-methylcyclobutan-1-ol [847];

(1r,3r)-3-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-1-methylcyclobutan-1-ol [848];

2-((cis-4-((5-(1-(2,2-difluoroethyl)-1H-benzo[d][1,2,3]triazol-6-yl)-6-fluoro-4-methoxypyrrolo[2,1-f][1,2,4]triazin-2-yl)amino)cyclohexyl)oxy)ethan-1-ol [849];

(1s,4s)-4-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-1-methylcyclohexan-1-ol [850];

(1r,4r)-4-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-1-methylcyclohexan-1-ol [851];

1-((3R,4S)-3-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-4-fluoropyrrolidin-1-yl)ethan-1-one [852];

5-(1-(2,2-difluoroethyl)-1H-benzo[d][1,2,3]triazol-6-yl)-6-fluoro-4-methoxy-N-(1-(oxetan-3-yl)piperidin-4-yl)pyrrolo[2,1-f][1,2,4]triazin-2-amine [853];

5-(1-(2,2-difluoroethyl)-1H-benzo[d][1,2,3]triazol-6-yl)-6-fluoro-4-methoxy-N-(1-(3-methyloxetan-3-yl)piperidin-4-yl)pyrrolo[2,1-f][1,2,4]triazin-2-amine [854];

5-(1-(2,2-difluoroethyl)-1H-benzo[d][1,2,3]triazol-6-yl)-6-fluoro-N-((3R,4S)-3-fluoro-1-methylpiperidin-4-yl)-4-methoxypyrrolo[2,1-f][1,2,4]triazin-2-amine [855];

1-((3R,4S)-4-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-3-fluoropiperidin-1-yl)ethan-1-one [856];

N-((3R,4S)-1-(3,3-difluorocyclobutyl)-3-fluoropiperidin-4-yl)-5-(1-(2,2-difluoroethyl)-1H-benzo[d][1,2,3]triazol-6-yl)-6-fluoro-4-methoxypyrrolo[2,1-f][1,2,4]triazin-2-amine [857];

5-(1-(2,2-difluoroethyl)-1H-benzo[d][1,2,3]triazol-6-yl)-6-fluoro-N-((3R,4S)-3-fluoro-1-(oxetan-3-yl)piperidin-4-yl)-4-methoxypyrrolo[2,1-f][1,2,4]triazin-2-amine [858];

5-(1-(2,2-difluoroethyl)-1H-benzo[d][1,2,3]triazol-6-yl)-6-fluoro-N-((3R,4S)-3-fluoro-1-(3-methyloxetan-3-yl)piperidin-4-yl)-4-methoxypyrrolo[2,1-f][1,2,4]triazin-2-amine [859];

3-((3R,4S)-4-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-3-fluoropiperidin-1-yl)oxetane-3-carbonitrile [860];

(R)-1-(4-((5-(1-(2,2-difluoroethyl)-1H-benzo[d][1,2,3]triazol-6-yl)-6-fluoro-4-methoxypyrrolo[2,1-f][1,2,4]triazin-2-yl)amino)-3,3-difluoropiperidin-1-yl)ethan-1-one [861];

(R)—N-(3,3-difluoro-1-(oxetan-3-yl)piperidin-4-yl)-5-(1-(2,2-difluoroethyl)-1H-benzo[d][1,2,3]triazol-6-yl)-6-fluoro-4-methoxypyrrolo[2,1-f][1,2,4]triazin-2-amine [862];

(R)—N-(3,3-difluoro-1-(3-methyloxetan-3-yl)piperidin-4-yl)-5-(1-(2,2-difluoroethyl)-1H-benzo[d][1,2,3]triazol-6-yl)-6-fluoro-4-methoxypyrrolo[2,1-f][1,2,4]triazin-2-amine [863];

2-(cis-3-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)cyclobutoxy)ethan-1-ol [864];

N-((1s,3s)-3-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-1-methylcyclobutyl)acetamide [865];

N-((1r,3r)-3-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-1-methylcyclobutyl)acetamide [866];

(1s,3s)-3-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-1-methylcyclobutan-1-ol [867];

(1r,3r)-3-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-1-methylcyclobutan-1-ol [868];

2-((cis-4-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)cyclohexyl)oxy)ethan-1-ol [869];

(1s,4s)-4-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-1-methylcyclohexan-1-ol [870];

(1r,4r)-4-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-1-methylcyclohexan-1-ol [871];

1-((3R,4S)-3-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-4-fluoropyrrolidin-1-yl)ethan-1-one [872];

5-(1-(2,2-difluoroethyl)-1H-benzo[d][1,2,3]triazol-6-yl)-6-fluoro-4-methoxy-N-(1-(oxetan-3-yl)piperidin-4-yl)pyrrolo[2,1-f][1,2,4]triazin-7-d-2-amine [873];

5-(1-(2,2-difluoroethyl)-1H-benzo[d][1,2,3]triazol-6-yl)-6-fluoro-4-methoxy-N-(1-(3-methyloxetan-3-yl)piperidin-4-yl)pyrrolo[2,1-f][1,2,4]triazin-7-d-2-amine [874];

5-(1-(2,2-difluoroethyl)-1H-benzo[d][1,2,3]triazol-6-yl)-6-fluoro-N-((3R,4S)-3-fluoro-1-methylpiperidin-4-yl)-4-methoxypyrrolo[2,1-f][1,2,4]triazin-7-d-2-amine [875];

1-((3R,4S)-4-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-3-fluoropiperidin-1-yl)ethan-1-one [876];

N-((3R,4S)-1-(3,3-difluorocyclobutyl)-3-fluoropiperidin-4-yl)-5-(1-(2,2-difluoroethyl)-1H-benzo[d][1,2,3]triazol-6-yl)-6-fluoro-4-methoxypyrrolo[2,1-f][1,2,4]triazin-7-d-2-amine [877];

5-(1-(2,2-difluoroethyl)-1H-benzo[d][1,2,3]triazol-6-yl)-6-fluoro-N-((3R,4S)-3-fluoro-1-(oxetan-3-yl)piperidin-4-yl)-4-methoxypyrrolo[2,1-f][1,2,4]triazin-7-d-2-amine [878];

5-(1-(2,2-difluoroethyl)-1H-benzo[d][1,2,3]triazol-6-yl)-6-fluoro-N-((3R,4S)-3-fluoro-1-(3-methyloxetan-3-yl)piperidin-4-yl)-4-methoxypyrrolo[2,1-f][1,2,4]triazin-7-d-2-amine [879];

3-((3R,4S)-4-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-3-fluoropiperidin-1-yl)oxetane-3-carbonitrile [880];

(R)-1-(4-((5-(1-(2,2-difluoroethyl)-1H-benzo[d][1,2,3]triazol-6-yl)-6-fluoro-4-methoxypyrrolo[2,1-f][1,2,4]triazin-2-yl-7-d)amino)-3,3-difluoropiperidin-1-yl)ethan-1-one [881];

(R)—N-(3,3-difluoro-1-(oxetan-3-yl)piperidin-4-yl)-5-(1-(2,2-difluoroethyl)-1H-benzo[d][1,2,3]triazol-6-yl)-6-fluoro-4-methoxypyrrolo[2,1-f][1,2,4]triazin-7-d-2-amine [882];

(R)—N-(3,3-difluoro-1-(3-methyloxetan-3-yl)piperidin-4-yl)-5-(1-(2,2-difluoroethyl)-1H-benzo[d][1,2,3]triazol-6-yl)-6-fluoro-4-methoxypyrrolo[2,1-f][1,2,4]triazin-7-d-2-amine [883];

2-(cis-3-((5-(1-(2,2-difluoroethyl)-1H-benzo[d][1,2,3]triazol-6-yl)-4-(methoxy-$d_3$)pyrrolo[2,1-f][1,2,4]triazin-2-yl)amino)cyclobutoxy)ethan-1-ol [884];

N-((1s,3s)-3-((5-(1-(2,2-difluoroethyl)-1H-benzo[d][1,2,3]triazol-6-yl)-4-(methoxy-$d_3$)pyrrolo[2,1-f][1,2,4]triazin-2-yl)amino)-1-methylcyclobutyl)acetamide [885];

N-((1r,3r)-3-((5-(1-(2,2-difluoroethyl)-1H-benzo[d][1,2,3]triazol-6-yl)-4-(methoxy-$d_3$)pyrrolo[2,1-f][1,2,4]triazin-2-yl)amino)-1-methylcyclobutyl)acetamide [886];

(1s,3s)-3-((5-(1-(2,2-difluoroethyl)-1H-benzo[d][1,2,3]triazol-6-yl)-4-(methoxy-$d_3$)pyrrolo[2,1-f][1,2,4]triazin-2-yl)amino)-1-methylcyclobutan-1-ol [887];

(1r,3r)-3-((5-(1-(2,2-difluoroethyl)-1H-benzo[d][1,2,3]triazol-6-yl)-4-(methoxy-d)pyrrolo[2,1-f][1,2,4]triazin-2-yl)amino)-1-methylcyclobutan-1-ol [888];

2-((cis-4-((5-(1-(2,2-difluoroethyl)-1H-benzo[d][1,2,3]triazol-6-yl)-4-(methoxy-d)pyrrolo[2,1-f][1,2,4]triazin-2-yl)amino)cyclohexyl)oxy)ethan-1-ol [889];

(1s,4s)-4-((5-(1-(2,2-difluoroethyl)-1H-benzo[d][1,2,3]triazol-6-yl)-4-(methoxy-$d_3$)pyrrolo[2,1-f][1,2,4]triazin-2-yl)amino)-1-methylcyclohexan-1-ol [890];

(1r,4r)-4-((5-(1-(2,2-difluoroethyl)-1H-benzo[d][1,2,3]triazol-6-yl)-4-(methoxy-d)pyrrolo[2,1-f][1,2,4]triazin-2-yl)amino)-1-methylcyclohexan-1-ol [891];

1-((3R,4S)-3-((5-(1-(2,2-difluoroethyl)-1H-benzo[d][1,2,3]triazol-6-yl)-4-(methoxy-d)pyrrolo[2,1-f][1,2,4]triazin-2-yl)amino)-4-fluoropyrrolidin-1-yl)ethan-1-one [892];

5-(1-(2,2-difluoroethyl)-1H-benzo[d][1,2,3]triazol-6-yl)-4-(methoxy-$d_3$)-N-(1-(oxetan-3-yl)piperidin-4-yl)pyrrolo[2,1-f][1,2,4]triazin-2-amine [893];

5-(1-(2,2-difluoroethyl)-1H-benzo[d][1,2,3]triazol-6-yl)-4-(methoxy-$d_3$)-N-(1-(3-methyloxetan-3-yl)piperidin-4-yl)pyrrolo[2,1-f][1,2,4]triazin-2-amine [894];

5-(1-(2,2-difluoroethyl)-1H-benzo[d][1,2,3]triazol-6-yl)-N-((3R,4S)-3-fluoro-1-methylpiperidin-4-yl)-4-(methoxy-$d_3$)pyrrolo[2,1-f][1,2,4]triazin-2-amine [895];

1-((3R,4S)-4-((5-(1-(2,2-difluoroethyl)-1H-benzo[d][1,2,3]triazol-6-yl)-4-(methoxy-d)pyrrolo[2,1-f][1,2,4]triazin-2-yl)amino)-3-fluoropiperidin-1-yl)ethan-1-one [896];

N-((3R,4S)-1-(3,3-difluorocyclobutyl)-3-fluoropiperidin-4-yl)-5-(1-(2,2-difluoroethyl)-1H-benzo[d][1,2,3]triazol-6-yl)-4-(methoxy-$d_3$)pyrrolo[2,1-f][1,2,4]triazin-2-amine [897];

5-(1-(2,2-difluoroethyl)-1H-benzo[d][1,2,3]triazol-6-yl)-N-((3R,4S)-3-fluoro-1-(oxetan-3-yl)piperidin-4-yl)-4-(methoxy-$d_3$)pyrrolo[2,1-f][1,2,4]triazin-2-amine [898];

5-(1-(2,2-difluoroethyl)-1H-benzo[d][1,2,3]triazol-6-yl)-N-((3R,4S)-3-fluoro-1-(3-methyloxetan-3-yl)piperidin-4-yl)-4-(methoxy-$d_3$)pyrrolo[2,1-f][1,2,4]triazin-2-amine [899]; and 3-((3R,4S)-4-((5-(1-(2,2-difluoroethyl)-1H-benzo[d][1,2,3]triazol-6-yl)-4-(methoxy-d)pyrrolo[2,1-f][1,2,4]triazin-2-yl)amino)-3-fluoropiperidin-1-yl)oxetane-3-carbonitrile [900];

or a pharmaceutically acceptable salt thereof.

21. The compound according to claim 1, wherein the compound of Formula I is selected from the group consisting of:

(R)-1-(4-((5-(1-(2,2-difluoroethyl)-1H-benzo[d][1,2,3]triazol-6-yl)-4-(methoxy-d)pyrrolo[2,1-f][1,2,4]triazin-2-yl)amino)-3,3-difluoropiperidin-1-yl)ethan-1-one [901];

(R)—N-(3,3-difluoro-1-(oxetan-3-yl)piperidin-4-yl)-5-(1-(2,2-difluoroethyl)-1H-benzo[d][1,2,3]triazol-6-yl)-4-(methoxy-$d_3$)pyrrolo[2,1-f][1,2,4]triazin-2-amine [902];

(R)—N-(3,3-difluoro-1-(3-methyloxetan-3-yl)piperidin-4-yl)-5-(1-(2,2-difluoroethyl)-1H-benzo[d][1,2,3]triazol-6-yl)-4-(methoxy-$d_3$)pyrrolo[2,1-f][1,2,4]triazin-2-amine [903];

2-(cis-3-((4-methoxy-5-(1-(2,2,2-trifluoroethyl)-1H-benzo[d][1,2,3]triazol-6-yl)pyrrolo[2,1-f][1,2,4]triazin-2-yl)amino)cyclobutoxy)ethan-1-ol [904];

N-((1s,3s)-3-((4-methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclobutyl)acetamide [905];

N-((1r,3r)-3-((4-methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclobutyl)acetamide [906];

(1s,3s)-3-((4-methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclobutan-1-ol [907];

(1r,3r)-3-((4-methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclobutan-1-ol [908];

2-((cis-4-((4-methoxy-5-(1-(2,2,2-trifluoroethyl)-1H-benzo[d][1,2,3]triazol-6-yl)pyrrolo[2,1-f][1,2,4]triazin-2-yl)amino)cyclohexyl)oxy)ethan-1-ol [909];

(1s,4s)-4-((4-methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclohexan-1-ol [910];

(1r,4r)-4-((4-methoxy-5-(1-(2,2,2-trifluoroethyl)-1H-benzo[d][1,2,3]triazol-6-yl)pyrrolo[2,1-f][1,2,4]triazin-2-yl)amino)-1-methylcyclohexan-1-ol [911];

1-((3S,4R)-3-fluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)pyrrolidin-1-yl)ethan-1-one [912];

4-methoxy-N-(1-(oxetan-3-yl)piperidin-4-yl)-5-(1-(2,2,2-trifluoroethyl)-1H-benzo[d][1,2,3]triazol-6-yl)pyrrolo[2,1-f][1,2,4]triazin-2-amine [913];

4-methoxy-N-(1-(3-methyloxetan-3-yl)piperidin-4-yl)-5-(1-(2,2,2-trifluoroethyl)-1H-benzo[d][1,2,3]triazol-6-yl)pyrrolo[2,1-f][1,2,4]triazin-2-amine [914];

N-((3R,4S)-3-fluoro-1-methylpiperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine [915];

1-((3R,4S)-3-fluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)piperidin-1-yl)ethan-1-one [916];

N-((3R,4S)-1-(3,3-difluorocyclobutyl)-3-fluoropiperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine [917];

N-((3R,4S)-3-fluoro-1-(oxetan-3-yl)piperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine [918];

N-((3R,4S)-3-fluoro-1-(3-methyloxetan-3-yl)piperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine [919];

3-((3R,4S)-3-fluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)piperidin-1-yl)oxetane-3-carbonitrile [920];

(R)-1-(3,3-difluoro-4-((4-methoxy-5-(1-(2,2,2-trifluoroethyl)-1H-benzo[d][1,2,3]triazol-6-yl)pyrrolo[2,1-f][1,2,4]triazin-2-yl)amino)piperidin-1-yl)ethan-1-one [921];

(R)—N-(3,3-difluoro-1-(oxetan-3-yl)piperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine [922];

(R)—N-(3,3-difluoro-1-(3-methyloxetan-3-yl)piperidin-4-yl)-4-methoxy-5-(1-(2,2,2-trifluoroethyl)-1H-benzo[d][1,2,3]triazol-6-yl)pyrrolo[2,1-f][1,2,4]triazin-2-amine [923];

N-(2-fluoro-2-methylpropyl)-5-(imidazo[1,2-a]pyrimidin-6-yl)-4-methoxypyrrolo[2,1-f][1,2,4]triazin-2-amine [924];

(R)-5-(imidazo[1,2-a]pyrimidin-6-yl)-4-methoxy-N-(1,1,1-trifluoropropan-2-yl)pyrrolo[2,1-f][1,2,4]triazin-2-amine [925];

(R)-5-(imidazo[1,2-a]pyrimidin-6-yl)-4-methoxy-N-(4-methoxybutan-2-yl)pyrrolo[2,1-f][1,2,4]triazin-2-amine [926];

(R)-5-(imidazo[1,2-a]pyrimidin-6-yl)-4-methoxy-N-(1-(oxetan-3-yl)ethyl)pyrrolo[2,1-f][1,2,4]triazin-2-amine [927];

(S)-5-(imidazo[1,2-a]pyrimidin-6-yl)-4-methoxy-N-(1-(oxetan-3-yl)ethyl)pyrrolo[2,1-f][1,2,4]triazin-2-amine [928];

5-(imidazo[1,2-a]pyrimidin-6-yl)-4-methoxy-N-((1R,2S)-2-methoxycyclobutyl)pyrrolo[2,1-f][1,2,4]triazin-2-amine [929];

5-(imidazo[1,2-a]pyrimidin-6-yl)-4-methoxy-N-((1R,2R)-2-methoxycyclobutyl)pyrrolo[2,1-f][1,2,4]triazin-2-amine [930];

N-(cis-3-ethoxycyclobutyl)-5-(imidazo[1,2-a]pyrimidin-6-yl)-4-methoxypyrrolo[2,1-f][1,2,4]triazin-2-amine [931];

(1s,3s)-3-((5-(imidazo[1,2-a]pyrimidin-6-yl)-4-methoxypyrrolo[2,1-f][1,2,4]triazin-2-yl)amino)-N,1-dimethylcyclobutane-1-carboxamide [932];

(1r,3r)-3-((5-(imidazo[1,2-a]pyrimidin-6-yl)-4-methoxypyrrolo[2,1-f][1,2,4]triazin-2-yl)amino)-N,1-dimethylcyclobutane-1-carboxamide [933];

N-((1s,3s)-3-((5-(imidazo[1,2-a]pyrimidin-6-yl)-4-methoxypyrrolo[2,1-f][1,2,4]triazin-2-yl)amino)-1-methylcyclobutyl)acetamide [934];

N-((1r,3r)-3-((5-(imidazo[1,2-a]pyrimidin-6-yl)-4-methoxypyrrolo[2,1-f][1,2,4]triazin-2-yl)amino)-1-methylcyclobutyl)acetamide [935];

N-((1s,3s)-3-((5-(imidazo[1,2-a]pyrimidin-6-yl)-4-methoxypyrrolo[2,1-f][1,2,4]triazin-2-yl)amino)-1-methylcyclobutyl)-N-methylacetamide [936];

N-((1r,3r)-3-((5-(imidazo[1,2-a]pyrimidin-6-yl)-4-methoxypyrrolo[2,1-f][1,2,4]triazin-2-yl)amino)-1-methylcyclobutyl)-N-methylacetamide [937];

1-cyano-N-((1s,3s)-3-((5-(imidazo[1,2-a]pyrimidin-6-yl)-4-methoxypyrrolo[2,1-f][1,2,4]triazin-2-yl)amino)-1-methylcyclobutyl)cyclopropane-1-carboxamide [938];

1-cyano-N-((1r,3r)-3-((5-(imidazo[1,2-a]pyrimidin-6-yl)-4-methoxypyrrolo[2,1-f][1,2,4]triazin-2-yl)amino)-1-methylcyclobutyl)cyclopropane-1-carboxamide [939];

(1s,3r)-1-ethyl-3-((5-(imidazo[1,2-a]pyrimidin-6-yl)-4-methoxypyrrolo[2,1-f][1,2,4]triazin-2-yl)amino)cyclobutan-1-ol [940];

(1r,3s)-1-ethyl-3-((5-(imidazo[1,2-a]pyrimidin-6-yl)-4-methoxypyrrolo[2,1-f][1,2,4]triazin-2-yl)amino)cyclobutan-1-ol [941];

(1S,2R)-2-((5-(imidazo[1,2-a]pyrimidin-6-yl)-4-methoxypyrrolo[2,1-f][1,2,4]triazin-2-yl)amino)cyclopentan-1-ol [942];

(R)—N-(3,3-difluorocyclopentyl)-5-(imidazo[1,2-a]pyrimidin-6-yl)-4-methoxypyrrolo[2,1-f][1,2,4]triazin-2-amine [943];

N-cyclohexyl-5-(imidazo[1,2-a]pyrimidin-6-yl)-4-methoxypyrrolo[2,1-f][1,2,4]triazin-2-amine [944];

2-(trans-4-((5-(imidazo[1,2-a]pyrimidin-6-yl)-4-methoxypyrrolo[2,1-f][1,2,4]triazin-2-yl)amino)cyclohexyl)propan-2-ol [945];

N-(cis-4-((5-(imidazo[1,2-a]pyrimidin-6-yl)-4-methoxypyrrolo[2,1-f][1,2,4]triazin-2-yl)amino)cyclohexyl)acetamide [946];

N-(4,4-dimethylcyclohexyl)-5-(imidazo[1,2-a]pyrimidin-6-yl)-4-methoxypyrrolo[2,1-f][1,2,4]triazin-2-amine [947];

4-((5-(imidazo[1,2-a]pyrimidin-6-yl)-4-methoxypyrrolo[2,1-f][1,2,4]triazin-2-yl)amino)-1-methylcyclohexane-1-carbonitrile [948];

(1s,4s)-4-((5-(imidazo[1,2-a]pyrimidin-6-yl)-4-methoxypyrrolo[2,1-f][1,2,4]triazin-2-yl)amino)-1-methylcyclohexane-1-carbonitrile [949];

(1r,4r)-4-((5-(imidazo[1,2-a]pyrimidin-6-yl)-4-methoxypyrrolo[2,1-f][1,2,4]triazin-2-yl)amino)-1-methylcyclohexane-1-carbonitrile [950];

(1s,4s)-4-((5-(imidazo[1,2-a]pyrimidin-6-yl)-4-methoxypyrrolo[2,1-f][1,2,4]triazin-2-yl)amino)-1-methylcyclohexan-1-ol [951];

(1s,4s)-1-ethyl-4-((5-(imidazo[1,2-a]pyrimidin-6-yl)-4-methoxypyrrolo[2,1-f][1,2,4]triazin-2-yl)amino)cyclohexan-1-ol [952];

5-(imidazo[1,2-a]pyrimidin-6-yl)-4-methoxy-N-((1s,4s)-4-methoxy-4-methylcyclohexyl)pyrrolo[2,1-f][1,2,4]triazin-2-amine [953];

5-(imidazo[1,2-a]pyrimidin-6-yl)-4-methoxy-N-((1r,4r)-4-methoxy-4-methylcyclohexyl)pyrrolo[2,1-f][1,2,4]triazin-2-amine [954];

(R)—N-(4,4-difluoro-1-methylpyrrolidin-3-yl)-5-(imidazo[1,2-a]pyrimidin-6-yl)-4-methoxypyrrolo[2,1-f][1,2,4]triazin-2-amine [955];

(R)—N-(1-ethyl-4,4-difluoropyrrolidin-3-yl)-5-(imidazo[1,2-a]pyrimidin-6-yl)-4-methoxypyrrolo[2,1-f][1,2,4]triazin-2-amine [956];

(R)—N-(1-cyclopropyl-4,4-difluoropyrrolidin-3-yl)-5-(imidazo[1,2-a]pyrimidin-6-yl)-4-methoxypyrrolo[2,1-f][1,2,4]triazin-2-amine [957];

(R)-3-((5-(imidazo[1,2-a]pyrimidin-6-yl)-4-methoxypyrrolo[2,1-f][1,2,4]triazin-2-yl)amino)-1-methylpyrrolidin-2-one [958];

(S)-3-((5-(imidazo[1,2-a]pyrimidin-6-yl)-4-methoxypyrrolo[2,1-f][1,2,4]triazin-2-yl)amino)-1-methylpyrrolidin-2-one [959];

1-(4-((5-(imidazo[1,2-a]pyrimidin-6-yl)-4-methoxypyrrolo[2,1-f][1,2,4]triazin-2-yl)amino)piperidin-1-yl)ethan-1-one [960];

1-(4-((5-(imidazo[1,2-a]pyrimidin-6-yl)-4-methoxypyrrolo[2,1-f][1,2,4]triazin-2-yl)amino)piperidine-1-carbonyl)cyclopropane-1-carbonitrile [961];

1-((3R,4S)-3-fluoro-4-((5-(imidazo[1,2-a]pyrimidin-6-yl)-4-methoxypyrrolo[2,1-f][1,2,4]triazin-2-yl)amino)piperidin-1-yl)ethan-1-one [962];

1-((3R,4S)-3-fluoro-4-((5-(imidazo[1,2-a]pyrimidin-6-yl)-4-methoxypyrrolo[2,1-f][1,2,4]triazin-2-yl)amino)piperidine-1-carbonyl)cyclopropane-1-carbonitrile [963];

(R)—N-(3,3-difluoropiperidin-4-yl)-5-(imidazo[1,2-a]pyrimidin-6-yl)-4-methoxypyrrolo[2,1-f][1,2,4]triazin-2-amine [964];

(R)—N-(3,3-difluoro-1-methylpiperidin-4-yl)-5-(imidazo[1,2-a]pyrimidin-6-yl)-4-methoxypyrrolo[2,1-f][1,2,4]triazin-2-amine [965];

(R)—N-(1-ethyl-3,3-difluoropiperidin-4-yl)-5-(imidazo[1,2-a]pyrimidin-6-yl)-4-methoxypyrrolo[2,1-f][1,2,4]triazin-2-amine [966];

(R)—N-(1-cyclopropyl-3,3-difluoropiperidin-4-yl)-5-(imidazo[1,2-a]pyrimidin-6-yl)-4-methoxypyrrolo[2,1-f][1,2,4]triazin-2-amine [967];

(R)—N-(3,3-difluoro-1-(oxetan-3-yl)piperidin-4-yl)-5-(imidazo[1,2-a]pyrimidin-6-yl)-4-methoxypyrrolo[2,1-f][1,2,4]triazin-2-amine [968];

(R)-1-(3,3-difluoro-4-((5-(imidazo[1,2-a]pyrimidin-6-yl)-4-methoxypyrrolo[2,1-f][1,2,4]triazin-2-yl)amino)piperidin-1-yl)ethan-1-one [969];

(R)-1-(3,3-difluoro-4-((5-(imidazo[1,2-a]pyrimidin-6-yl)-4-methoxypyrrolo[2,1-f][1,2,4]triazin-2-yl)amino)piperidine-1-carbonyl)cyclopropane-1-carbonitrile [970];

(S)-5-((5-(imidazo[1,2-a]pyrimidin-6-yl)-4-methoxypyrrolo[2,1-f][1,2,4]triazin-2-yl)amino)-1-methylpiperidin-2-one [971];

(R)-5-((5-(imidazo[1,2-a]pyrimidin-6-yl)-4-methoxypyrrolo[2,1-f][1,2,4]triazin-2-yl)amino)-1-methylpiperidin-2-one [972];

(R)-3-((5-(imidazo[1,2-a]pyrimidin-6-yl)-4-methoxypyrrolo[2,1-f][1,2,4]triazin-2-yl)amino)-1-methylpiperidin-2-one [973];

(S)-3-((5-(imidazo[1,2-a]pyrimidin-6-yl)-4-methoxypyrrolo[2,1-f][1,2,4]triazin-2-yl)amino)-1-methylpiperidin-2-one [974];

(R)-5-(imidazo[1,2-a]pyrimidin-6-yl)-4-methoxy-N-(tetrahydro-2H-pyran-3-yl)pyrrolo[2,1-f][1,2,4]triazin-2-amine [975];

N-(bicyclo[3.1.0]hexan-3-yl)-5-(imidazo[1,2-a]pyrimidin-6-yl)-4-methoxypyrrolo[2,1-f][1,2,4]triazin-2-amine [976];

5-(imidazo[1,2-a]pyrimidin-6-yl)-4-methoxy-N-(spiro[2.5]octan-6-yl)pyrrolo[2,1-f][1,2,4]triazin-2-amine [977];

4-((5-(imidazo[1,2-a]pyrimidin-6-yl)-4-methoxypyrrolo[2,1-f][1,2,4]triazin-2-yl)amino)bicyclo[2.2.1]heptan-1-ol [978];

1-(7-((5-(imidazo[1,2-a]pyrimidin-6-yl)-4-methoxypyrrolo[2,1-f][1,2,4]triazin-2-yl)amino)-2-azaspiro[3.5]nonan-2-yl)ethan-1-one-2,2,2-$d_3$ [979];

cyclopropyl(7-((5-(imidazo[1,2-a]pyrimidin-6-yl)-4-methoxypyrrolo[2,1-f][1,2,4]triazin-2-yl)amino)-2-azaspiro[3.5]nonan-2-yl)methanone [980];

(1-fluorocyclopropyl)(7-((5-(imidazo[1,2-a]pyrimidin-6-yl)-4-methoxypyrrolo[2,1-f][1,2,4]triazin-2-yl)amino)-2-azaspiro[3.5]nonan-2-yl)methanone [981];

2-(trans-4-((5-(imidazo[1,2-a]pyrimidin-6-yl)-4-methoxypyrrolo[2,1-f][1,2,4]triazin-2-yl-7-d)amino)cyclohexyl)propan-2-ol [982];

(1s,4s)-4-((5-(imidazo[1,2-a]pyrimidin-6-yl)-4-methoxypyrrolo[2,1-f][1,2,4]triazin-2-yl-7-d)amino)-1-methylcyclohexan-1-ol [983];

(1r,4r)-4-((5-(imidazo[1,2-a]pyrimidin-6-yl)-4-methoxypyrrolo[2,1-f][1,2,4]triazin-2-yl-7-d)amino)-1-methylcyclohexan-1-ol [984];

(1s,4s)-1-ethyl-4-((5-(imidazo[1,2-a]pyrimidin-6-yl)-4-methoxypyrrolo[2,1-f][1,2,4]triazin-2-yl-7-d)amino)cyclohexan-1-ol [985];

(1r,4r)-1-ethyl-4-((5-(imidazo[1,2-a]pyrimidin-6-yl)-4-methoxypyrrolo[2,1-f][1,2,4]triazin-2-yl-7-d)amino)cyclohexan-1-ol [986];

(R)—N-(3,3-difluoro-1-(oxetan-3-yl)piperidin-4-yl)-5-(imidazo[1,2-a]pyrimidin-6-yl)-4-methoxypyrrolo[2,1-f][1,2,4]triazin-7-d-2-amine [987];

1-(7-((5-(imidazo[1,2-a]pyrimidin-6-yl)-4-methoxypyrrolo[2,1-f][1,2,4]triazin-2-yl-7-d)amino)-2-azaspiro[3.5]nonan-2-yl)ethan-1-one [988];

5-(imidazo[1,2-a]pyrimidin-6-yl)-4-methoxy-N-(2-oxaspiro[3.5]nonan-7-yl)pyrrolo[2,1-f][1,2,4]triazin-7-d-2-amine [989];

5-(imidazo[1,2-a]pyrimidin-6-yl)-4-methoxy-N-((4r,7r)-1-oxaspiro[3.5]nonan-7-yl)pyrrolo[2,1-f][1,2,4]triazin-7-d-2-amine [990];

5-(imidazo[1,2-a]pyrimidin-6-yl)-4-methoxy-N-((4s,7s)-1-oxaspiro[3.5]nonan-7-yl)pyrrolo[2,1-f][1,2,4]triazin-7-d-2-amine [991];

N-((1s,3s)-3-((6-fluoro-5-(imidazo[1,2-a]pyrimidin-6-yl)-4-methoxypyrrolo[2,1-f][1,2,4]triazin-2-yl)amino)-1-methylcyclobutyl)acetamide [992];

N-((1r,3r)-3-((6-fluoro-5-(imidazo[1,2-a]pyrimidin-6-yl)-4-methoxypyrrolo[2,1-f][1,2,4]triazin-2-yl)amino)-1-methylcyclobutyl)acetamide [993];

2-(trans-4-((6-fluoro-5-(imidazo[1,2-a]pyrimidin-6-yl)-4-methoxypyrrolo[2,1-f][1,2,4]triazin-2-yl)amino)cyclohexyl)propan-2-ol [994];

(1s,4s)-4-((6-fluoro-5-(imidazo[1,2-a]pyrimidin-6-yl)-4-methoxypyrrolo[2,1-f][1,2,4]triazin-2-yl)amino)-1-methylcyclohexan-1-ol [995];

(1r,4r)-4-((6-fluoro-5-(imidazo[1,2-a]pyrimidin-6-yl)-4-methoxypyrrolo[2,1-f][1,2,4]triazin-2-yl)amino)-1-methylcyclohexan-1-ol [996];

(1s,4s)-1-ethyl-4-((6-fluoro-5-(imidazo[1,2-a]pyrimidin-6-yl)-4-methoxypyrrolo[2,1-f][1,2,4]triazin-2-yl)amino)cyclohexan-1-ol [997];

(1r,4r)-1-ethyl-4-((6-fluoro-5-(imidazo[1,2-a]pyrimidin-6-yl)-4-methoxypyrrolo[2,1-f][1,2,4]triazin-2-yl)amino)cyclohexan-1-ol [998];

6-fluoro-N-((3R,4S)-4-fluoro-1-(oxetan-3-yl)pyrrolidin-3-yl)-5-(imidazo[1,2-a]pyrimidin-6-yl)-4-methoxypyrrolo[2,1-f][1,2,4]triazin-2-amine [999]; and 1-(4-((6-fluoro-5-(imidazo[1,2-a]pyrimidin-6-yl)-4-methoxypyrrolo[2,1-f][1,2,4]triazin-2-yl)amino)piperidin-1-yl)ethan-1-one [1000]; or a pharmaceutically acceptable salt thereof.

22. The compound according to claim 1, wherein the compound of Formula I is selected from the group consisting of:

6-fluoro-N-((3S,4R)-3-fluoro-1-(oxetan-3-yl)piperidin-4-yl)-5-(imidazo[1,2-a]pyrimidin-6-yl)-4-methoxypyrrolo[2,1-f][1,2,4]triazin-2-amine [1001];

6-fluoro-N-((3R,4S)-3-fluoro-1-(oxetan-3-yl)piperidin-4-yl)-5-(imidazo[1,2-a]pyrimidin-6-yl)-4-methoxypyrrolo[2,1-f][1,2,4]triazin-2-amine [1002];

6-fluoro-N-((3S,4R)-3-fluoro-1-(3-methyloxetan-3-yl)piperidin-4-yl)-5-(imidazo[1,2-a]pyrimidin-6-yl)-4-methoxypyrrolo[2,1-f][1,2,4]triazin-2-amine [1003];

6-fluoro-N-((3R,4S)-3-fluoro-1-(3-methyloxetan-3-yl)piperidin-4-yl)-5-(imidazo[1,2-a]pyrimidin-6-yl)-4-methoxypyrrolo[2,1-f][1,2,4]triazin-2-amine [1004];

(R)—N-(3,3-difluoro-1-methylpiperidin-4-yl)-6-fluoro-5-(imidazo[1,2-a]pyrimidin-6-yl)-4-methoxypyrrolo[2,1-f][1,2,4]triazin-2-amine [1005];

(R)—N-(3,3-difluoro-1-(oxetan-3-yl)piperidin-4-yl)-6-fluoro-5-(imidazo[1,2-a]pyrimidin-6-yl)-4-methoxypyrrolo[2,1-f][1,2,4]triazin-2-amine [1006];

(R)—N-(3,3-difluoro-1-(3-methyloxetan-3-yl)piperidin-4-yl)-6-fluoro-5-(imidazo[1,2-a]pyrimidin-6-yl)-4-methoxypyrrolo[2,1-f][1,2,4]triazin-2-amine [1007];

1-(7-((6-fluoro-5-(imidazo[1,2-a]pyrimidin-6-yl)-4-methoxypyrrolo[2,1-f][1,2,4]triazin-2-yl)amino)-2-azaspiro[3.5]nonan-2-yl)ethan-1-one [1008];

1-(7-((6-fluoro-5-(imidazo[1,2-a]pyrimidin-6-yl)-4-methoxypyrrolo[2,1-f][1,2,4]triazin-2-yl)amino)-2-azaspiro[3.5]nonan-2-yl)ethan-1-one-2,2,2-$d_3$ [1009];

2-(trans-4-((5-(imidazo[1,2-a]pyrimidin-6-yl)-4-(methoxy-$d_3$)pyrrolo[2,1-f][1,2,4]triazin-2-yl)amino)cyclohexyl)propan-2-ol [1010];

(1s,4s)-4-((5-(imidazo[1,2-a]pyrimidin-6-yl)-4-(methoxy-$d_3$)pyrrolo[2,1-f][1,2,4]triazin-2-yl)amino)-1-methylcyclohexan-1-ol [1011];

(1r,4r)-4-((5-(imidazo[1,2-a]pyrimidin-6-yl)-4-(methoxy-$d_3$)pyrrolo[2,1-f][1,2,4]triazin-2-yl)amino)-1-methylcyclohexan-1-ol [1012];

(1s,4s)-1-ethyl-4-((5-(imidazo[1,2-a]pyrimidin-6-yl)-4-(methoxy-$d_3$)pyrrolo[2,1-f][1,2,4]triazin-2-yl)amino)cyclohexan-1-ol [1013];

(1r,4r)-1-ethyl-4-((5-(imidazo[1,2-a]pyrimidin-6-yl)-4-(methoxy-$d_3$)pyrrolo[2,1-f][1,2,4]triazin-2-yl)amino)cyclohexan-1-ol [1014];

(R)—N-(3,3-difluoro-1-(oxetan-3-yl)piperidin-4-yl)-5-(imidazo[1,2-a]pyrimidin-6-yl)-4-(methoxy-$d_3$)pyrrolo[2,1-f][1,2,4]triazin-2-amine [1015];

1-(7-((5-(imidazo[1,2-a]pyrimidin-6-yl)-4-(methoxy-$d_3$)pyrrolo[2,1-f][1,2,4]triazin-2-yl)amino)-2-azaspiro[3.5]nonan-2-yl)ethan-1-one [1016];

5-(imidazo[1,2-a]pyrimidin-6-yl)-4-(methoxy-$d_3$)-N-(2-oxaspiro[3.5]nonan-7-yl)pyrrolo[2,1-f][1,2,4]triazin-2-amine [1017];

5-(imidazo[1,2-a]pyrimidin-6-yl)-4-(methoxy-$d_3$)-N-((4r,7r)-1-oxaspiro[3.5]nonan-7-yl)pyrrolo[2,1-f][1,2,4]triazin-2-amine [1018];

5-(imidazo[1,2-a]pyrimidin-6-yl)-4-(methoxy-$d_3$)-N-((4s,7s)-1-oxaspiro[3.5]nonan-7-yl)pyrrolo[2,1-f][1,2,4]triazin-2-amine [1019];

(1s,4s)-4-((4-(difluoromethoxy)-5-(imidazo[1,2-a]pyrimidin-6-yl)pyrrolo[2,1-f][1,2,4]triazin-2-yl)amino)-1-methylcyclohexan-1-ol [1020];

(1r,4r)-4-((4-(difluoromethoxy)-5-(imidazo[1,2-a]pyrimidin-6-yl)pyrrolo[2,1-f][1,2,4]triazin-2-yl)amino)-1-methylcyclohexan-1-ol [1021];

(1s,4s)-4-((4-(difluoromethoxy)-5-(imidazo[1,2-a]pyrimidin-6-yl)pyrrolo[2,1-f][1,2,4]triazin-2-yl)amino)-1-ethylcyclohexan-1-ol [1022];

(1r,4r)-4-((4-(difluoromethoxy)-5-(imidazo[1,2-a]pyrimidin-6-yl)pyrrolo[2,1-f][1,2,4]triazin-2-yl)amino)-1-ethylcyclohexan-1-ol [1023];

1-(7-((4-(difluoromethoxy)-5-(imidazo[1,2-a]pyrimidin-6-yl)pyrrolo[2,1-f][1,2,4]triazin-2-yl)amino)-2-azaspiro[3.5]nonan-2-yl)ethan-1-one [1024];

4-(difluoromethoxy)-5-(imidazo[1,2-a]pyrimidin-6-yl)-N-(2-oxaspiro[3.5]nonan-7-yl)pyrrolo[2,1-f][1,2,4]triazin-2-amine [1025];

(1s,4s)-4-((5-(imidazo[1,2-a]pyrimidin-6-yl)-4-(trifluoromethoxy)pyrrolo[2,1-f][1,2,4]triazin-2-yl)amino)-1-methylcyclohexan-1-ol [1026];

(1r,4r)-4-((5-(imidazo[1,2-a]pyrimidin-6-yl)-4-(trifluoromethoxy)pyrrolo[2,1-f][1,2,4]triazin-2-yl)amino)-1-methylcyclohexan-1-ol [1027];

(1s,4s)-1-ethyl-4-((5-(imidazo[1,2-a]pyrimidin-6-yl)-4-(trifluoromethoxy)pyrrolo[2,1-f][1,2,4]triazin-2-yl)amino)cyclohexan-1-ol [1028];

(1r,4r)-1-ethyl-4-((5-(imidazo[1,2-a]pyrimidin-6-yl)-4-(trifluoromethoxy)pyrrolo[2,1-f][1,2,4]triazin-2-yl)amino)cyclohexan-1-ol [1029];

1-(7-((5-(imidazo[1,2-a]pyrimidin-6-yl)-4-(trifluoromethoxy)pyrrolo[2,1-f][1,2,4]triazin-2-yl)amino)-2-azaspiro[3.5]nonan-2-yl)ethan-1-one [1030];

5-(imidazo[1,2-a]pyrimidin-6-yl)-N-(2-oxaspiro[3.5]nonan-7-yl)-4-(trifluoromethoxy)pyrrolo[2,1-f][1,2,4]triazin-2-amine [1031];

(1s,4s)-4-((4-(2,2-difluoroethoxy)-5-(imidazo[1,2-a]pyrimidin-6-yl)pyrrolo[2,1-f][1,2,4]triazin-2-yl)amino)-1-methylcyclohexan-1-ol [1032];

(1r,4r)-4-((4-(2,2-difluoroethoxy)-5-(imidazo[1,2-a]pyrimidin-6-yl)pyrrolo[2,1-f][1,2,4]triazin-2-yl)amino)-1-methylcyclohexan-1-ol [1033];

(1s,4s)-4-((4-(2,2-difluoroethoxy)-5-(imidazo[1,2-a]pyrimidin-6-yl)pyrrolo[2,1-f][1,2,4]triazin-2-yl)amino)-1-ethylcyclohexan-1-ol [1034];

(1r,4r)-4-((4-(2,2-difluoroethoxy)-5-(imidazo[1,2-a]pyrimidin-6-yl)pyrrolo[2,1-f][1,2,4]triazin-2-yl)amino)-1-ethylcyclohexan-1-ol [1035];

1-(7-((4-(2,2-difluoroethoxy)-5-(imidazo[1,2-a]pyrimidin-6-yl)pyrrolo[2,1-f][1,2,4]triazin-2-yl)amino)-2-azaspiro[3.5]nonan-2-yl)ethan-1-one [1036];

4-(2,2-difluoroethoxy)-5-(imidazo[1,2-a]pyrimidin-6-yl)-N-(2-oxaspiro[3.5]nonan-7-yl)pyrrolo[2,1-f][1,2,4]triazin-2-amine [1037];

(1r,3r)-3-((4-methoxy-5-(quinolin-6-yl)pyrrolo[2,1-f][1,2,4]triazin-2-yl)amino)-N,1-dimethylcyclobutane-1-carboxamide [1038];

(1r,3r)-N-cyclopropyl-3-((4-methoxy-5-(quinolin-6-yl)pyrrolo[2,1-f][1,2,4]triazin-2-yl)amino)-1-methylcyclobutane-1-carboxamide [1039];

(1r,3r)-3-((4-methoxy-5-(quinolin-6-yl)pyrrolo[2,1-f][1,2,4]triazin-2-yl)amino)-1-methyl-N-(1-methylcyclobutyl)cyclobutane-1-carboxamide [1040];

(1r,3r)-N-(3,3-difluorocyclobutyl)-3-((4-methoxy-5-(quinolin-6-yl)pyrrolo[2,1-f][1,2,4]triazin-2-yl)amino)-1-methylcyclobutane-1-carboxamide [1041];

(1r,3r)-3-((4-methoxy-5-(quinolin-6-yl)pyrrolo[2,1-f][1,2,4]triazin-2-yl)amino)-1-methyl-N-(3-methyloxetan-3-yl)cyclobutane-1-carboxamide [1042];

(1s,3s)-$N^3$-(4-methoxy-5-(quinolin-6-yl)pyrrolo[2,1-f][1,2,4]triazin-2-yl)-$N^1$,$N^1$,1-trimethylcyclobutane-1,3-diamine [1043];

N-(cis-4-((4-methoxy-5-(quinolin-6-yl)pyrrolo[2,1-f][1,2,4]triazin-2-yl)amino)cyclohexyl)acetamide [1044];

1-((3R,4S)-3-fluoro-4-((4-methoxy-5-(quinolin-6-yl)pyrrolo[2,1-f][1,2,4]triazin-2-yl)amino)piperidin-1-yl)-2-methylpropan-2-ol [1045];

N-((3R,4S)-3-fluoro-1-(3-methyloxetan-3-yl)piperidin-4-yl)-4-methoxy-5-(quinolin-6-yl)pyrrolo[2,1-f][1,2,4]triazin-2-amine [1046];

1-((3R,4S)-3-fluoro-4-((4-methoxy-5-(quinolin-6-yl)pyrrolo[2,1-f][1,2,4]triazin-2-yl)amino)piperidin-1-yl)ethan-1-one [1047];

(R)-1-(3,3-difluoro-4-((4-methoxy-5-(quinolin-6-yl)pyrrolo[2,1-f][1,2,4]triazin-2-yl)amino)piperidin-1-yl)ethan-1-one [1048];

(R)-5-((4-methoxy-5-(quinolin-6-yl)pyrrolo[2,1-f][1,2,4]triazin-2-yl)amino)-1-methylpiperidin-2-one [1049];

(R)-4-methoxy-5-(quinolin-6-yl)-N-(tetrahydro-2H-pyran-3-yl)pyrrolo[2,1-f][1,2,4]triazin-2-amine [1050];

4-((4-methoxy-5-(quinolin-6-yl)pyrrolo[2,1-f][1,2,4]triazin-2-yl)amino)bicyclo[2.2.1]heptan-1-ol [1051];

N-((1s,3s)-3-((6-fluoro-4-methoxy-5-(quinolin-6-yl)pyrrolo[2,1-f][1,2,4]triazin-2-yl)amino)-1-methylcyclobutyl)acetamide [1052];

N-((1r,3r)-3-((6-fluoro-4-methoxy-5-(quinolin-6-yl)pyrrolo[2,1-f][1,2,4]triazin-2-yl)amino)-1-methylcyclobutyl)acetamide [1053];

N-(cis-4-((6-fluoro-4-methoxy-5-(quinolin-6-yl)pyrrolo[2,1-f][1,2,4]triazin-2-yl)amino)cyclohexyl)acetamide [1054];

(1s,4s)-4-((6-fluoro-4-methoxy-5-(quinolin-6-yl)pyrrolo[2,1-f][1,2,4]triazin-2-yl)amino)-1-methylcyclohexan-1-ol [1055];

(1r,4r)-4-((6-fluoro-4-methoxy-5-(quinolin-6-yl)pyrrolo[2,1-f][1,2,4]triazin-2-yl)amino)-1-methylcyclohexan-1-ol [1056];

6-fluoro-N-((3R,4S)-3-fluoro-1-methylpiperidin-4-yl)-4-methoxy-5-(quinolin-6-yl)pyrrolo[2,1-f][1,2,4]triazin-2-amine [1057];

1-((3R,4S)-3-fluoro-4-((6-fluoro-4-methoxy-5-(quinolin-6-yl)pyrrolo[2,1-f][1,2,4]triazin-2-yl)amino)piperidin-1-yl)-2-methylpropan-2-ol [1058];

6-fluoro-N-((3R,4S)-3-fluoro-1-(oxetan-3-yl)piperidin-4-yl)-4-methoxy-5-(quinolin-6-yl)pyrrolo[2,1-f][1,2,4]triazin-2-amine [1059];

6-fluoro-N-((3R,4S)-3-fluoro-1-(3-methyloxetan-3-yl)piperidin-4-yl)-4-methoxy-5-(quinolin-6-yl)pyrrolo[2,1-f][1,2,4]triazin-2-amine [1060];

1-((3R,4S)-3-fluoro-4-((6-fluoro-4-methoxy-5-(quinolin-6-yl)pyrrolo[2,1-f][1,2,4]triazin-2-yl)amino)piperidin-1-yl)ethan-1-one [1061];

(R)—N-(3,3-difluoro-1-(oxetan-3-yl)piperidin-4-yl)-6-fluoro-4-methoxy-5-(quinolin-6-yl)pyrrolo[2,1-f][1,2,4]triazin-2-amine [1062];

(R)—N-(3,3-difluoro-1-(3-methyloxetan-3-yl)piperidin-4-yl)-6-fluoro-4-methoxy-5-(quinolin-6-yl)pyrrolo[2,1-f][1,2,4]triazin-2-amine [1063];

(R)-1-(3,3-difluoro-4-((6-fluoro-4-methoxy-5-(quinolin-6-yl)pyrrolo[2,1-f][1,2,4]triazin-2-yl)amino)piperidin-1-yl)ethan-1-one [1064];

N-(cis-4-((4-(difluoromethoxy)-5-(quinolin-6-yl)pyrrolo[2,1-f][1,2,4]triazin-2-yl)amino)cyclohexyl)acetamide [1065];

(1s,4s)-4-((4-(difluoromethoxy)-5-(quinolin-6-yl)pyrrolo[2,1-f][1,2,4]triazin-2-yl)amino)-1-methylcyclohexan-1-ol [1066];

(1r,4r)-4-((4-(difluoromethoxy)-5-(quinolin-6-yl)pyrrolo[2,1-f][1,2,4]triazin-2-yl)amino)-1-methylcyclohexan-1-ol [1067];

1-((3R,4S)-4-((4-(difluoromethoxy)-5-(quinolin-6-yl)pyrrolo[2,1-f][1,2,4]triazin-2-yl)amino)-3-fluoropiperidin-1-yl)-2-methylpropan-2-ol [1068];

4-(difluoromethoxy)-N-((3R,4S)-3-fluoro-1-(3-methyloxetan-3-yl)piperidin-4-yl)-5-(quinolin-6-yl)pyrrolo[2,1-f][1,2,4]triazin-2-amine [1069];

1-((3R,4S)-4-((4-(difluoromethoxy)-5-(quinolin-6-yl)pyrrolo[2,1-f][1,2,4]triazin-2-yl)amino)-3-fluoropiperidin-1-yl)ethan-1-one [1070];

(R)-1-(4-((4-(difluoromethoxy)-5-(quinolin-6-yl)pyrrolo[2,1-f][1,2,4]triazin-2-yl)amino)-3,3-difluoropiperidin-1-yl)ethan-1-one [1071];

4-((4-(difluoromethoxy)-5-(quinolin-6-yl)pyrrolo[2,1-f][1,2,4]triazin-2-yl)amino)bicyclo[2.2.1]heptan-1-ol [1072];

N-(cis-4-((5-(quinolin-6-yl)-4-(trifluoromethoxy)pyrrolo[2,1-f][1,2,4]triazin-2-yl)amino)cyclohexyl)acetamide [1073];

(1s,4s)-1-methyl-4-((5-(quinolin-6-yl)-4-(trifluoromethoxy)pyrrolo[2,1-f][1,2,4]triazin-2-yl)amino)cyclohexan-1-ol [1074];

(1r,4r)-1-methyl-4-((5-(quinolin-6-yl)-4-(trifluoromethoxy)pyrrolo[2,1-f][1,2,4]triazin-2-yl)amino)cyclohexan-1-ol [1075];

1-((3R,4S)-3-fluoro-4-((5-(quinolin-6-yl)-4-(trifluoromethoxy)pyrrolo[2,1-f][1,2,4]triazin-2-yl)amino)piperidin-1-yl)-2-methylpropan-2-ol [1076];

N-((3R,4S)-3-fluoro-1-(3-methyloxetan-3-yl)piperidin-4-yl)-5-(quinolin-6-yl)-4-(trifluoromethoxy)pyrrolo[2,1-f][1,2,4]triazin-2-amine [1077];

1-((3R,4S)-3-fluoro-4-((5-(quinolin-6-yl)-4-(trifluoromethoxy)pyrrolo[2,1-f][1,2,4]triazin-2-yl)amino)piperidin-1-yl)ethan-1-one [1078];

(R)-1-(3,3-difluoro-4-((5-(quinolin-6-yl)-4-(trifluoromethoxy)pyrrolo[2,1-f][1,2,4]triazin-2-yl)amino)piperidin-1-yl)ethan-1-one [1079];

4-((5-(quinolin-6-yl)-4-(trifluoromethoxy)pyrrolo[2,1-f][1,2,4]triazin-2-yl)amino)bicyclo[2.2.1]heptan-1-ol [1080];

N-(cis-4-((4-(2,2-difluoroethoxy)-5-(quinolin-6-yl)pyrrolo[2,1-f][1,2,4]triazin-2-yl)amino)cyclohexyl)acetamide [1081];

(1s,4s)-4-((4-(2,2-difluoroethoxy)-5-(quinolin-6-yl)pyrrolo[2,1-f][1,2,4]triazin-2-yl)amino)-1-methylcyclohexan-1-ol [1082];

(1r,4r)-4-((4-(2,2-difluoroethoxy)-5-(quinolin-6-yl)pyrrolo[2,1-f][1,2,4]triazin-2-yl)amino)-1-methylcyclohexan-1-ol [1083];

1-((3R,4S)-4-((4-(2,2-difluoroethoxy)-5-(quinolin-6-yl)pyrrolo[2,1-f][1,2,4]triazin-2-yl)amino)-3-fluoropiperidin-1-yl)-2-methylpropan-2-ol [1084];

4-(2,2-difluoroethoxy)-N-((3R,4S)-3-fluoro-1-(3-methyloxetan-3-yl)piperidin-4-yl)-5-(quinolin-6-yl)pyrrolo[2,1-f][1,2,4]triazin-2-amine [1085];

1-((3R,4S)-4-((4-(2,2-difluoroethoxy)-5-(quinolin-6-yl)pyrrolo[2,1-f][1,2,4]triazin-2-yl)amino)-3-fluoropiperidin-1-yl)ethan-1-one [1086];

(R)-1-(4-((4-(2,2-difluoroethoxy)-5-(quinolin-6-yl)pyrrolo[2,1-f][1,2,4]triazin-2-yl)amino)-3,3-difluoropiperidin-1-yl)ethan-1-one [1087];

4-((4-(2,2-difluoroethoxy)-5-(quinolin-6-yl)pyrrolo[2,1-f][1,2,4]triazin-2-yl)amino)bicyclo[2.2.1]heptan-1-ol [1088];

(1r,4r)-1-methyl-4-((4-(oxetan-3-yloxy)-5-(quinolin-6-yl)pyrrolo[2,1-f][1,2,4]triazin-2-yl)amino)cyclohexan-1-ol [1089];

N-((3R,4S)-3-fluoro-1-methylpiperidin-4-yl)-4-(oxetan-3-yloxy)-5-(quinolin-6-yl)pyrrolo[2,1-f][1,2,4]triazin-2-amine [1090];

(R)—N-(3,3-difluoro-1-methylpiperidin-4-yl)-4-(oxetan-3-yloxy)-5-(quinolin-6-yl)pyrrolo[2,1-f][1,2,4]triazin-2-amine [1091];

N-(cis-4-((4-methoxy-5-(quinoxalin-6-yl)pyrrolo[2,1-f][1,2,4]triazin-2-yl)amino)cyclohexyl)acetamide [1092];

(3S,4R)-4-((4-methoxy-5-(quinoxalin-6-yl)pyrrolo[2,1-f][1,2,4]triazin-2-yl)amino)tetrahydrofuran-3-ol [1093];

1-((3R,4S)-3-fluoro-4-((4-methoxy-5-(quinoxalin-6-yl)pyrrolo[2,1-f][1,2,4]triazin-2-yl)amino)piperidin-1-yl)-2-methylpropan-2-ol [1094];

(R)—N-(1-ethyl-3,3-difluoropiperidin-4-yl)-4-methoxy-5-(quinoxalin-6-yl)pyrrolo[2,1-f][1,2,4]triazin-2-amine [1095];

(R)-1-(3,3-difluoro-4-((4-methoxy-5-(quinoxalin-6-yl)pyrrolo[2,1-f][1,2,4]triazin-2-yl)amino)piperidin-1-yl)ethan-1-one [1096];

(R)-5-((4-methoxy-5-(quinoxalin-6-yl)pyrrolo[2,1-f][1,2,4]triazin-2-yl)amino)-1-methylpiperidin-2-one [1097];

4-((4-methoxy-5-(quinoxalin-6-yl)pyrrolo[2,1-f][1,2,4]triazin-2-yl)amino)bicyclo[2.2.1]heptan-1-ol [1098];

N-((4s,6r)-1-(2,2-difluoroethyl)-1-azaspiro[3.3]heptan-6-yl)-4-methoxy-5-(quinoxalin-6-yl)pyrrolo[2,1-f][1,2,4]triazin-2-amine [1099]; and 4-methoxy-5-(quinoxalin-6-yl)-N-(7-oxaspiro[3.5]nonan-2-yl)pyrrolo[2,1-f][1,2,4]triazin-2-amine [1100]; or a pharmaceutically acceptable salt thereof.

23. The compound according to claim 1, wherein the compound of Formula I is selected from the group consisting of N-((1s,3s)-3-((6-fluoro-4-methoxy-5-(quinoxalin-6-yl)pyrrolo[2,1-f][1,2,4]triazin-2-yl)amino)-1-methylcyclobutyl)acetamide [1101];

N-((1r,3r)-3-((6-fluoro-4-methoxy-5-(quinoxalin-6-yl)pyrrolo[2,1-f][1,2,4]triazin-2-yl)amino)-1-methylcyclobutyl)acetamide [1102];

N-(cis-4-((6-fluoro-4-methoxy-5-(quinoxalin-6-yl)pyrrolo[2,1-f][1,2,4]triazin-2-yl)amino)cyclohexyl)acetamide [1103];

(1s,4s)-4-((6-fluoro-4-methoxy-5-(quinoxalin-6-yl)pyrrolo[2,1-f][1,2,4]triazin-2-yl)amino)-1-methylcyclohexan-1-ol [1104];

1-((3R,4S)-3-fluoro-4-((6-fluoro-4-methoxy-5-(quinoxalin-6-yl)pyrrolo[2,1-f][1,2,4]triazin-2-yl)amino)piperidin-1-yl)-2-methylpropan-2-ol [1105];

6-fluoro-N-((3R,4S)-3-fluoro-1-(oxetan-3-yl)piperidin-4-yl)-4-methoxy-5-(quinoxalin-6-yl)pyrrolo[2,1-f][1,2,4]triazin-2-amine [1106];

6-fluoro-N-((3R,4S)-3-fluoro-1-(3-methyloxetan-3-yl)piperidin-4-yl)-4-methoxy-5-(quinoxalin-6-yl)pyrrolo[2,1-f][1,2,4]triazin-2-amine [1107];

1-((3R,4S)-3-fluoro-4-((6-fluoro-4-methoxy-5-(quinoxalin-6-yl)pyrrolo[2,1-f][1,2,4]triazin-2-yl)amino)piperidin-1-yl)ethan-1-one [1108];

(R)—N-(3,3-difluoro-1-(oxetan-3-yl)piperidin-4-yl)-6-fluoro-4-methoxy-5-(quinoxalin-6-yl)pyrrolo[2,1-f][1,2,4]triazin-2-amine [1109];

(R)—N-(3,3-difluoro-1-(3-methyloxetan-3-yl)piperidin-4-yl)-6-fluoro-4-methoxy-5-(quinoxalin-6-yl)pyrrolo[2,1-f][1,2,4]triazin-2-amine [1110];

(R)-1-(3,3-difluoro-4-((6-fluoro-4-methoxy-5-(quinoxalin-6-yl)pyrrolo[2,1-f][1,2,4]triazin-2-yl)amino)piperidin-1-yl)ethan-1-one [1111];

N-(cis-4-((4-(difluoromethoxy)-5-(quinoxalin-6-yl)pyrrolo[2,1-f][1,2,4]triazin-2-yl)amino)cyclohexyl)acetamide [1112];

(1s,4s)-4-((4-(difluoromethoxy)-5-(quinoxalin-6-yl)pyrrolo[2,1-f][1,2,4]triazin-2-yl)amino)-1-methylcyclohexan-1-ol [1113];

(1r,4r)-4-((4-(difluoromethoxy)-5-(quinoxalin-6-yl)pyrrolo[2,1-f][1,2,4]triazin-2-yl)amino)-1-methylcyclohexan-1-ol [1114];

1-((3R,4S)-4-((4-(difluoromethoxy)-5-(quinoxalin-6-yl)pyrrolo[2,1-f][1,2,4]triazin-2-yl)amino)-3-fluoropiperidin-1-yl)-2-methylpropan-2-ol [1115];

4-(difluoromethoxy)-N-((3R,4S)-3-fluoro-1-(3-methyloxetan-3-yl)piperidin-4-yl)-5-(quinoxalin-6-yl)pyrrolo[2,1-f][1,2,4]triazin-2-amine [1116];

1-((3R,4S)-4-((4-(difluoromethoxy)-5-(quinoxalin-6-yl)pyrrolo[2,1-f][1,2,4]triazin-2-yl)amino)-3-fluoropiperidin-1-yl)ethan-1-one [1117];

(R)-1-(4-((4-(difluoromethoxy)-5-(quinoxalin-6-yl)pyrrolo[2,1-f][1,2,4]triazin-2-yl)amino)-3,3-difluoropiperidin-1-yl)ethan-1-one [1118];

4-((4-(difluoromethoxy)-5-(quinoxalin-6-yl)pyrrolo[2,1-f][1,2,4]triazin-2-yl)amino)bicyclo[2.2.1]heptan-1-01 [1119];

N-(cis-4-((5-(quinoxalin-6-yl)-4-(trifluoromethoxy)pyrrolo[2,1-f][1,2,4]triazin-2-yl)amino)cyclohexyl)acetamide [1120];

(1s,4s)-1-methyl-4-((5-(quinoxalin-6-yl)-4-(trifluoromethoxy)pyrrolo[2,1-f][1,2,4]triazin-2-yl)amino)cyclohexan-1-ol [1121];

(1r,4r)-1-methyl-4-((5-(quinoxalin-6-yl)-4-(trifluoromethoxy)pyrrolo[2,1-f][1,2,4]triazin-2-yl)amino)cyclohexan-1-ol [1122];

1-((3R,4S)-3-fluoro-4-((5-(quinoxalin-6-yl)-4-(trifluoromethoxy)pyrrolo[2,1-f][1,2,4]triazin-2-yl)amino)piperidin-1-yl)-2-methylpropan-2-ol [1123];

N-((3R,4S)-3-fluoro-1-(3-methyloxetan-3-yl)piperidin-4-yl)-5-(quinoxalin-6-yl)-4-(trifluoromethoxy)pyrrolo[2,1-f][1,2,4]triazin-2-amine [1124];

1-((3R,4S)-3-fluoro-4-((5-(quinoxalin-6-yl)-4-(trifluoromethoxy)pyrrolo[2,1-f][1,2,4]triazin-2-yl)amino)piperidin-1-yl)ethan-1-one [1125];

(R)-1-(3,3-difluoro-4-((5-(quinoxalin-6-yl)-4-(trifluoromethoxy)pyrrolo[2,1-f][1,2,4]triazin-2-yl)amino)piperidin-1-yl)ethan-1-one [1126];

4-((5-(quinoxalin-6-yl)-4-(trifluoromethoxy)pyrrolo[2,1-f][1,2,4]triazin-2-yl)amino)bicyclo[2.2.1]heptan-1-ol [1127];

N-(cis-4-((4-(2,2-difluoroethoxy)-5-(quinoxalin-6-yl)pyrrolo[2,1-f][1,2,4]triazin-2-yl)amino)cyclohexyl)acetamide [1128];

(1s,4s)-4-((4-(2,2-difluoroethoxy)-5-(quinoxalin-6-yl)pyrrolo[2,1-f][1,2,4]triazin-2-yl)amino)-1-methylcyclohexan-1-ol [1129];

(1r,4r)-4-((4-(2,2-difluoroethoxy)-5-(quinoxalin-6-yl)pyrrolo[2,1-f][1,2,4]triazin-2-yl)amino)-1-methylcyclohexan-1-ol [1130];

1-((3R,4S)-4-((4-(2,2-difluoroethoxy)-5-(quinoxalin-6-yl)pyrrolo[2,1-f][1,2,4]triazin-2-yl)amino)-3-fluoropiperidin-1-yl)-2-methylpropan-2-ol [1131];

4-(2,2-difluoroethoxy)-N-((3R,4S)-3-fluoro-1-(3-methyloxetan-3-yl)piperidin-4-yl)-5-(quinoxalin-6-yl)pyrrolo[2,1-f][1,2,4]triazin-2-amine [1132];

1-((3R,4S)-4-((4-(2,2-difluoroethoxy)-5-(quinoxalin-6-yl)pyrrolo[2,1-f][1,2,4]triazin-2-yl)amino)-3-fluoropiperidin-1-yl)ethan-1-one [1133];

(R)-1-(4-((4-(2,2-difluoroethoxy)-5-(quinoxalin-6-yl)pyrrolo[2,1-f][1,2,4]triazin-2-yl)amino)-3,3-difluoropiperidin-1-yl)ethan-1-one [1134];

4-((4-(2,2-difluoroethoxy)-5-(quinoxalin-6-yl)pyrrolo[2,1-f][1,2,4]triazin-2-yl)amino)bicyclo[2.2.1]heptan-1-ol [1135];

(R)—N-(3,3-difluoro-1-methylpiperidin-4-yl)-4-(oxetan-3-yloxy)-5-(quinoxalin-6-yl)pyrrolo[2,1-f][1,2,4]triazin-2-amine [1136];

4-(oxetan-3-yloxy)-5-(quinoxalin-6-yl)-N-(7-oxaspiro[3.5]nonan-2-yl)pyrrolo[2,1-f][1,2,4]triazin-2-amine [1137];

4-(oxetan-3-yloxy)-5-(quinoxalin-6-yl)-N-(2-oxaspiro[3.5]nonan-7-yl)pyrrolo[2,1-f][1,2,4]triazin-2-amine [1138];

(1r,4r)-4-((5-(1-(2,2-difluoroethyl)-1H-benzo[d]imidazol-6-yl)-4-methoxypyrrolo[2,1-f][1,2,4]triazin-2-yl)amino)-1-methylcyclohexan-1-ol [1139];

(R)-1-(4-((5-(1-(2,2-difluoroethyl)-1H-benzo[d]imidazol-6-yl)-4-methoxypyrrolo[2,1-f][1,2,4]triazin-2-yl)amino)-3,3-difluoropiperidin-1-yl)ethan-1-one [1140];

5-(1-(2,2-difluoroethyl)-1H-benzo[d]imidazol-6-yl)-N-((3R,4S)-3-fluoro-1-(oxetan-3-yl)piperidin-4-yl)-4-methoxypyrrolo[2,1-f][1,2,4]triazin-2-amine [1141];

N-((3R,4S)-3-fluoro-1-(oxetan-3-yl)piperidin-4-yl)-5-(4-fluoro-1-isopropyl-2-methyl-1H-benzo[d]imidazol-6-yl)-4-methoxypyrrolo[2,1-f][1,2,4]triazin-2-amine [1142];

1-((3R,4S)-3-fluoro-4-((5-(1-(2-fluoroethyl)-1H-benzo[d][1,2,3]triazol-6-yl)-4-methoxypyrrolo[2,1-f][1,2,4]triazin-2-yl)amino)piperidin-1-yl)propan-1-one [1143];

5-(1-(2,2-difluoroethyl)-1H-benzo[d][1,2,3]triazol-6-yl)-4-methoxy-N-((3-methyloxetan-3-yl)methyl)pyrrolo[2,1-f][1,2,4]triazin-2-amine [1144];

5-(1-(2,2-difluoroethyl)-1H-benzo[d][1,2,3]triazol-6-yl)-N-((3R,4S)-3-fluoro-1-(methylsulfonyl)piperidin-4-yl)-4-methoxypyrrolo[2,1-f][1,2,4]triazin-2-amine [1145];

3-((5-(imidazo[1,2-a]pyrimidin-6-yl)-4-methoxypyrrolo[2,1-f][1,2,4]triazin-2-yl)amino)-2,2-dimethylpropanenitrile [1146];

(R)-5-(imidazo[1,2-a]pyrimidin-6-yl)-4-methoxy-N-(1-(tetrahydro-2H-pyran-4-yl)ethyl)pyrrolo[2,1-f][1,2,4]triazin-2-amine [1147];

N-(2,2-dimethyltetrahydro-2H-pyran-4-yl)-5-(imidazo[1,2-a]pyrimidin-6-yl)-4-methoxypyrrolo[2,1-f][1,2,4]triazin-2-amine [1148];

N-((3S,4R)-3-fluorotetrahydro-2H-pyran-4-yl)-5-(imidazo[1,2-a]pyrimidin-6-yl)-4-methoxypyrrolo[2,1-f][1,2,4]triazin-2-amine [1149];

N-(8-oxabicyclo[3.2.1]octan-3-yl)-5-(imidazo[1,2-a]pyrimidin-6-yl)-4-methoxypyrrolo[2,1-f][1,2,4]triazin-2-amine [1150];

N-((3R,4S)-4-fluoro-1-(oxetan-3-yl)pyrrolidin-3-yl)-5-(1-(2-fluoroethyl)-1H-benzo[d][1,2,3]triazol-6-yl)-4-methoxypyrrolo[2,1-f][1,2,4]triazin-2-amine [1151];

5-(1-(2,2-difluoroethyl)-1H-benzo[d][1,2,3]triazol-6-yl)-N-((3S,4R)-4-fluoro-1-(oxetan-3-yl)pyrrolidin-3-yl)-4-methoxypyrrolo[2,1-f][1,2,4]triazin-2-amine [1152]; and N-((3R,4S)-4-fluoro-1-(oxetan-3-yl)pyrrolidin-3-yl)-4-methoxy-5-(1-(2,2,2-trifluoroethyl)-1H-benzo[d][1,2,3]triazol-6-yl)pyrrolo[2,1-f][1,2,4]triazin-2-amine [1153]; or a pharmaceutically acceptable salt thereof.

24. A pharmaceutical composition comprising a therapeutically effective amount of a compound according to claim 1, or a pharmaceutically acceptable salt thereof, and a pharmaceutically acceptable excipient.

* * * * *